US012729207B2

(12) United States Patent
Lanman et al.

(10) Patent No.: US 12,729,207 B2
(45) Date of Patent: Sep. 8, 2026

(54) HETEROCYCLIC SPIRO COMPOUNDS AND METHODS OF USE

(71) Applicant: AMGEN INC., Thousand Oaks, CA (US)

(72) Inventors: Brian Alan Lanman, Woodland Hills, CA (US); Abhisek Banerjee, Bangalore (IN); Margaret Chu-Moyer, Brookline, MA (US); Dongcheng Dai, Corvallis, OR (US); Josephine Eshon, Ithaca, NY (US); David Huang, Thousand Oaks, CA (US); Matthew R. Kaller, Ventura, CA (US); Heejun Lee, Thousand Oaks, CA (US); Patricia Lopez, Woodland Hills, CA (US); Vu Van Ma, Oak Park, CA (US); Francesco Manoni, Newbury Park, CA (US); Jose M Medina, Thousand Oaks, CA (US); Alexander J. Pickrell, Westlake Village, CA (US); John C. Stellwagen, Newbury Park, CA (US); Zhen Sun, Shanghai (CN); Nuria A. Tamayo, Newbury Park, CA (US); Wenhan Zhang, Thousand Oaks, CA (US); Kai Zhu, Westlake Village, CA (US)

(73) Assignee: AMGEN INC., Thousand Oaks, CA (US)

( * ) Notice: Subject to any disclaimer, the term of this patent is extended or adjusted under 35 U.S.C. 154(b) by 395 days.

(21) Appl. No.: 18/032,548

(22) PCT Filed: Oct. 19, 2021

(86) PCT No.: PCT/CN2021/124598

§ 371 (c)(1),
(2) Date: Apr. 18, 2023

(87) PCT Pub. No.: WO2022/083569

PCT Pub. Date: Apr. 28, 2022

(65) Prior Publication Data

US 2024/0059703 A1 Feb. 22, 2024

(30) Foreign Application Priority Data

Oct. 20, 2020 (WO) ................ PCT/CN2020/122197

(51) Int. Cl.

| | |
|---|---|
| *C07D 487/10* | (2006.01) |
| *A61K 45/06* | (2006.01) |
| *A61P 35/00* | (2006.01) |
| *C07D 519/00* | (2006.01) |

(52) U.S. Cl.
CPC ............ *C07D 487/10* (2013.01); *A61K 45/06* (2013.01); *A61P 35/00* (2018.01); *C07D 519/00* (2013.01)

(58) Field of Classification Search
None
See application file for complete search history.

(56) References Cited

U.S. PATENT DOCUMENTS

| | | | |
|---|---|---|---|
| 10,519,146 | B2 | 12/2019 | Lanman et al. |
| 10,590,090 | B2 | 3/2020 | Koltun et al. |
| 10,640,504 | B2 | 5/2020 | Lanman et al. |
| 2020/0017511 | A1 | 1/2020 | Blank et al. |

(Continued)

FOREIGN PATENT DOCUMENTS

| | | |
|---|---|---|
| CN | 107814792 | 3/2018 |
| JP | 2018-512408 | 5/2008 |

(Continued)

OTHER PUBLICATIONS

"A Phase 1/?2, Study Evaluating the Safety, Tolerability, PK, and Efficacy of Sotorasib (AMG 510) in Subjects With Solid Tumors With a Specific KRAS Mutation (CodeBreak 100)", National Library of Medicine, NCT03600883, Retrieved from Internet: https://clinicaltrials.gov/ct2/show/NCT03600883, pp. 1-37(2018).

(Continued)

*Primary Examiner* — Sarah Pihonak
*Assistant Examiner* — Donna M Nestor
(74) *Attorney, Agent, or Firm* — Kimberly L. Berkowski

(57) ABSTRACT

Provided are compounds of Formula (I) having activity as inhibitors of G12C mutant KRAS protein, pharmaceutical compositions comprising the compounds, and uses and methods of treating certain disorders, such as cancer, including but not limited to lung, pancreatic and colorectal cancers.

(I)

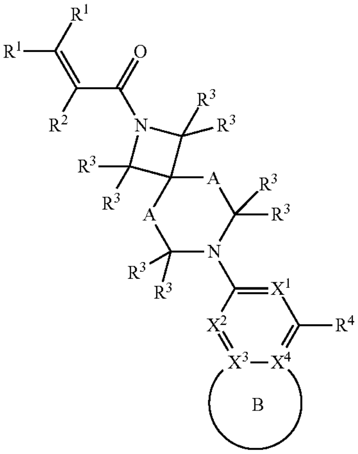

26 Claims, No Drawings

(56) References Cited

U.S. PATENT DOCUMENTS

| | | | |
|---|---|---|---|
| 2020/0017517 A1 | 1/2020 | Gill et al. | |
| 2020/0239441 A1 | 7/2020 | Tamayo et al. | |

FOREIGN PATENT DOCUMENTS

| | | | |
|---|---|---|---|
| JP | 2013-522281 | 6/2013 | |
| WO | 00/44753 | 8/2000 | |
| WO | 2004/043931 | 5/2004 | |
| WO | 2004/052858 | 6/2004 | |
| WO | 2006/004200 | 1/2006 | |
| WO | 2007/092364 | 8/2007 | |
| WO | 2007/146719 | 12/2007 | |
| WO | 2009/062308 | 5/2009 | |
| WO | 2009/073300 | 6/2009 | |
| WO | 2009/109743 | 9/2009 | |
| WO | 2009/125606 | 10/2009 | |
| WO | WO-2011114275 A1 * | 9/2011 | ............. A61P 37/02 |
| WO | 2014/093337 | 6/2014 | |
| WO | 2016/148306 | 9/2016 | |
| WO | 2017/027310 | 2/2017 | |
| WO | 2017/181177 | 10/2017 | |
| WO | 2017/201161 | 11/2017 | |
| WO | 2018/140514 | 8/2018 | |
| WO | 2019/075265 | 4/2019 | |
| WO | 2019/232319 | 12/2019 | |
| WO | 2020/028706 | 2/2020 | |
| WO | 2020/086739 | 4/2020 | |
| WO | 2020/113071 | 6/2020 | |
| WO | 2020/132649 | 6/2020 | |
| WO | 2020/132651 | 6/2020 | |
| WO | 2020/132653 | 6/2020 | |
| WO | 2020/177629 | 9/2020 | |

OTHER PUBLICATIONS

"Phase 1/?2 Study of MRTX849 in Patients With Cancer Having a KRAS G12C Mutation KRYSTAL-1" Retrieved from the internet: https://clinicaltrials.gov/study/NCT03785249, pp. 1-27(2025).

"Sotorasib Activity in Subjects With Advanced Solid Tumors With KRAS p. G12C Mutation (CodeBreak 101)", National Library of Medicine, NCT04185883, Retrieved from Internet: https://clinicaltrials.gov/ct2/show/NCT04185883, pp. 1-35(2019).

Berge et al., "Pharmaceutical salts", Journal of Pharmaceutical Sciences, vol. 66(1), pp. 1-19(1977).

Canon et al., "The clinical KRAS(G12C) inhibitor AMG 510 drives anti-tumour immunity", Nature, vol. 575(7781), pp. 1-26(2019).

Caunt et al., "MEK1 and MEK2 inhibitors and cancer therapy: the long and winding road", Nature Reviews Cancer, vol. 15(10), pp. 577-592(2015).

Cerami et al., "The cBio cancer genomics portal: an open platform for exploring multidimensional cancer genomics data", Cancer Discovery, vol. 2(5), pp. 401-404(2012).

Chandrappa et al., "N-Methyl Morpholine Chlorochromate: An Efficient Reagent for Oxidation of Primary and Secondary Alcohols to Carbonyl Compounds", Synthetic Communications, vol. 38(15), pp. 2638-2645(2008).

Chen et al., "Pd-Catalyzed, ortho C—H Methylation and Fluorination of Benzaldehydes Using Orthanilic Acids as Transient Directing Groups", Journal of the American Chemical Society, vol. 140(8), pp. 2789-2792(2018).

Cox et al., "Drugging the undruggable RAS: Mission possible?", Nature reviews. Drug discovery, vol. 13(11), pp. 1-24(2014).

Der et al., "Transforming genes of human bladder and lung carcinoma cell lines are homologous to the ras genes of Harvey and Kirsten sarcoma viruses", Proceedings of the National Academy of Sciences of the United States of America, vol. 79(11), pp. 3637-3640(1982).

Eliel, "Stereochemistry of Carbon Compounds", Mcgraw-hill Series in Advanced Chemistry, pp. 1-99(1962).

Extended European Search Report and Search Opinion received for European Application No. 21881985.2, mailed on Aug. 13, 2024, 7 pages.

Gao et al., "Integrative analysis of complex cancer genomics and clinical profiles using the cBioPortal", Science Signaling, vol. 6(269), pp. 1-19(2013).

Holderfield et al., "Targeting RAF kinases for cancer therapy: BRAF-mutated melanoma and beyond", Nature reviews. Cancer, vol. 14(7), pp. 455-467(2014).

Hong et al., "KRASG12C Inhibition with Sotorasib in Advanced Solid Tumors", The New England Journal of Medicine, vol. 383(13), pp. 1-11(2020).

International Preliminary Report on Patentability received for PCT Patent Application No. PCT/CN2021/124598, mailed on May 4, 2023, 7 pages.

International Search Report and Written Opinion received for PCT Patent Application No. PCT/CN2021/124598, mailed on Jan. 18, 2022, 10 pages.

Jones et al., "Practical and Scalable Kinetic Resolution of BINOLs Mediated by a Chiral Counterion", Angewandte Chemie, vol. 58(14), pp. 4596-4600(2019).

Kibbe, "Handbook Of Pharmaceutical Excipients", Third Edition, American Pharmaceutical Association, pp. 1-6 (2000).

Lanman et al., "Discovery of a Covalent Inhibitor of KRAS(G12C) (AMG 510) for the Treatment of Solid Tumors." Journal of Medicinal Chemistry, vol. 63(1), pp. 52-65(2020).

Legros et al., "Trifluoromethylcyclohexane as a new solvent? Limits of use", Tetrahedron, vol. 58(20), pp. 4067-4070(2002).

Li et al., "Monodentate Transient Directing Group Enabled Pd-Catalyzed Ortho-C-H Methoxylation and Chlorination of Benzaldehydes", Organic Letters, vol. 21(10), pp. 3692-3695(2019).

Malumbres et al., "RAS oncogenes: the first 30 years", Nature reviews. Cancer, vol. 3(6), pp. 7-13(2003).

Mello et al., "A Simple Protocol for the Generation of Methyl(trifluoromethyl)dioxirane", Synlett, No. 1, pp. 47-50 (2007).

Muñoz et al., "Application of Flow Chemistry to the Selective Reduction of Esters to Aldehydes", European Journal of Organic Chemistry, vol. 2012(2), pp. 260-263(2012).

O'Bryan, "Pharmacological targeting of RAS: Recent success with direct inhibitors", Pharmacological research, vol. 139, pp. 503-511(2019).

Ostrem et al., "K-Ras(G12C) inhibitors allosterically control GTP affinity and effector interactions", Nature, vol. 503(7477), pp. 1-14(2013).

Sanz-Marco et al., "Highly enantioselective copper(I)-catalyzed conjugate addition of 1,3-diynes to a,beta-unsaturated trifluoromethyl ketones", Chemical Communications, vol. 51(43), pp. 8958-8961(2015).

Simanshu et al., "RAS Proteins and Their Regulators in Human Disease", Cell, vol. 170(1), pp. 17-33(2017).

Sridhar et al., "Inhibitors of epidermal-growth-factor receptors: a review of clinical research with a focus on non-small-cell lung cancer", The Lancet. Oncology, vol. 4(7), pp. 397-406(2003).

Turiso et al., "Discovery and in Vivo Evaluation of Dual PI3Kbeta/delta Inhibitors", Journal of Medicinal Chemistry, vol. 55(17), pp. 7667-7685(2012).

Vojtek et al., "Increasing complexity of the Ras signaling pathway", The Journal of biological chemistry, vol. 273 (32), pp. 19925-19928(1998).

Wilen et al., "Strategies in optical resolutions", Tetrahedron, vol. 33(21), pp. 2725-2736(1977).

Wilen, "Tables of Resolving Agents and Optical Resolutions", Univ. of Notre Dame Press, p. A258(1972).

* cited by examiner

HETEROCYCLIC SPIRO COMPOUNDS AND METHODS OF USE

CROSS-REFERENCE TO RELATED APPLICATIONS

This application is a national stage application under 35 U.S.C. § 371 of International Application No. PCT/CN21/124598, filed Oct. 19, 2021, and claims the benefit of International Patent Application No. PCT/CN2020/122197, filed Oct. 20, 2020, each of which is incorporated herein by reference in its entirety, and for all purposes as if fully set forth herein.

FIELD

The present disclosure provides compounds having activity as inhibitors of G12C mutant KRAS protein. This disclosure also provides pharmaceutical compositions comprising the compounds, uses and methods of treating certain disorders, such as cancer, including but not limited to lung, pancreatic and colorectal cancers.

BACKGROUND

From its identification as one of the first human oncogenes in 1982 (Der et al., 1982), KRAS (the Kirsten rat sarcoma viral oncogene homologue) has been the focus of extensive academic and industrial research, as a key node in the MAPK signal transduction pathway, as a transforming factor in a network of parallel effector pathways (e.g., PI3K/AKT) (Vojtek et al., 1998) and as a potential target for anti-cancer agents (Malumbres et al., 2003). Despite progress in the development of inhibitors of upstream and downstream nodes in the MAPK pathway (e.g., EGFR (Sridhar et al., 2003), BRAF (Holderfield et al., 2014), and MEK (Caunt et al., 2015), the KRAS protein has historically proven resistant to direct inhibition.

KRAS is a G-protein that couples extracellular mitogenic signaling to intracellular, pro-proliferative responses. KRAS serves as an intracellular "on/off" switch. Mitogen stimulation induces the binding of GTP to KRAS, bringing about a conformational change which enables the interaction of KRAS with downstream effector proteins, leading to cellular proliferation. Normally, pro-proliferative signaling is regulated by the action of GTPase-activating proteins (GAPs), which return KRAS to its GDP-bound, non-proliferative state. Mutations in KRAS impair the regulated cycling of KRAS between these GDP- and GTP-bound states, leading to the accumulation of the GTP-bound active state and dysregulated cellular proliferation (Simanshu et al., 2017).

Attempts to develop inhibitors of mutated KRAS proteins have historically been thwarted by the absence of druggable pockets on the surface of the protein (Cox et al., 2014). In 2013, Shokat and colleagues identified covalent inhibitors of a common (O'Bryan, 2019) oncogenic mutant of KRAS, $KRAS^{G12C}$, which bound to a previously unrecognized allosteric pocket on GDP-$KRAS^{G12C}$ and prevented its subsequent activation (Ostrem et al., 2013). This discovery brought about significant new efforts in KRAS inhibitor research, which have recently culminated in the entry of MRAS inhibitors into human clinical trials. See, e.g., https://clinicaltrials.gov/: e.g., NCT03600883 & NCT04185883 (AMG 510) and NCT03785249 (MRTX849) (last accessed Aug. 29, 2020).

While some progress has been made, the need for further $KRAS^{G12C}$ inhibitors for the treatment of disorders, such as cancer, remains.

SUMMARY

First, provided herein is a compound of Formula I (I)

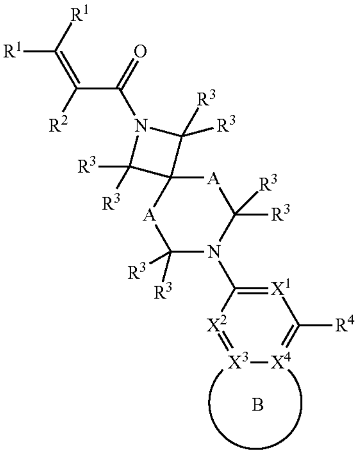

or a pharmaceutically acceptable salt thereof, wherein $R^1$ at each occurrence independently is H, $^2H$, $C_{1-4}$haloalkyl, $C_{1-4}$alkoxy, —$CH_2OH$, —$(CH_2)O(C_{1-4}$alky), —$(CH_2)O(C_{1-4}$haloalkyl), —$(CH_2)$—$C_{1-4}$dialkylamino, aziridin-1-yl-methyl, azetidin-1-yl-methyl, pyrrolidine-1-yl-methyl, piperidin-1-yl-methyl, or morpholin-1-yl-methyl;

$R^2$ is H, $^2H$, halogen, —CN, $C_{1-4}$alkyl, $C_{1-4}$haloalkyl, —$CH_2CN$, —$CH_2OH$, $C_{1-4}$alkoxy, or $C_{1-4}$haloalkoxy;

wherein, optionally, one $R^1$ and $R^2$ together with the carbon atoms to which they are attached form a

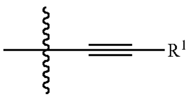

group;

$R^3$ at each occurrence independently is H, halogen, CN, OH, $C_{1-4}$alkyl, $C_{1-4}$haloalkyl, —$CH_2CN$, —$CH_2OH$, $C_{1-4}$alkoxy, or $C_{1-4}$haloalkoxy, wherein two substituents $R^3$ attached to the same carbon atom optionally form together with said carbon atom a $C_{3-6}$cycloalkyl or a carbonyl group;

A at each occurrence independently is $CR^3R^3$ or absent;

$R^4$ is 1,2,3,4-tetrahydro-8-quinolinyl, 6 or 10 membered aryl, or 5 to 10 membered heteroaryl, wherein the aryl or heteroaryl is optionally substituted with 1 to 5 substituents independently selected from OH, halogen, —CN, $NH_2$, $C_{1-4}$alkyl, $C_{1-4}$deuteroalkyl, $C_{1-4}$haloalkyl, $C_{1-4}$alkoxy, $C_{1-4}$haloalkoxy, —$SO_2NH_2$, —$NHSO_2CH_3$, wherein the $C_{1-4}$alkyl is optionally substituted with OH;

$X^1$ is $CR^5$ or N;

$X^2$ is CH, CF, or N;

$X^3$ is C or N;

$X^4$ is C or N;

$R^3$ is H, halogen, CN, —COO($C_{1-4}$alkyl), $C_{1-4}$alkyl, $C_{1-4}$alkenyl, $C_{1-4}$haloalkyl, —$(CH_2)_m$($C_{1-4}$alkoxy), —$(CH_2)_m$($C_{1-4}$haloalkoxy), $C_{3-5}$cycloalkyl, $C_{3-5}$cyclohaloalkyl, or $C_{3-5}$heterocycloalkyl;

B together with the atoms to which it is attached forms a 4 to 7 membered fully saturated, fully unsaturated, or partially unsaturated carbocyclic or heterocyclic ring system,
- wherein the heterocyclic ring system comprises 1 to 5 heteroatoms independently selected from N, O, and S,
- wherein the ring system is optionally substituted with 1 to 5 substituents $R^6$;

$R^6$ at each occurrence independently is halogen, OH, —CN, —$NH_2$, $C_{1-6}$alkyl, $C_{1-6}$haloalkyl, $C_{1-4}$alkoxy, $C_{1-4}$haloalkoxy, —C(═O)$C_{1-6}$alkyl, —$R^7$—($C_{3-5}$cycloalkyl), —$R^7$—($C_{3-5}$ cyclohaloalkyl), —$R^7$—($C_{3-6}$heterocycloalkyl), —$R^7$-(phenyl), or —$R^7$-(5 to 6 membered heteroaryl),
- wherein the $C_{1-6}$alkyl is optionally substituted with $C_{1-4}$alkoxy, $C_{1-4}$alkylamino, $C_{1-4}$dialkylamino, —CO($C_{1-4}$alkylamino) or —CO($C_{1-4}$dialkylamino),
- wherein the $C_{1-6}$haloalkyl is optionally substituted with a OH,
- wherein the $C_{3-6}$heterocycloalkyl is optionally substituted with 1 to 3 substituents independently selected from (═O) and $C_{1-6}$alkyl,
- wherein the phenyl is optionally substituted with 1 to 3 substituents independently selected from halogen and $C_{1-4}$alkoxy,
- wherein the heteroaryl is optionally substituted with 1 to 3 substituents independently selected from halogen, —$(CH_2)_{1-3}$OH, $(CH_2)_{1-3}$O($C_{1-4}$alkyl), —$(CH_2)_{1-3}$O($C_{1-4}$haloalkyl), $C_{1-4}$alkyl, and $C_{1-4}$haloalkyl,
- wherein two substituents $R^6$ together optionally form a —$(CH_2)_n$— group creating a ring together with the ring atom or ring atoms to which the two substituents $R^6$ are attached,
- wherein the —$(CH_2)_n$— group optionally has one —$CH_2$— group substituted with one heteroatom selected from N, O, and S, and
- wherein the —$(CH_2)_n$— group is optionally substituted with 1 to 3 substituents independently selected from halogen and $C_{1-6}$alkyl;

$R^7$ is $(CH_2)_m$ or CO;

n is 1, 2, 3, 4, 5 or 6; and m is 0 or 1.

Second, provided herein is a pharmaceutical composition comprising a compound of Formula I or a pharmaceutically acceptable salt thereof, and a pharmaceutically acceptable excipient.

Third, provided herein is a compound of Formula I or a pharmaceutically acceptable salt thereof, or a pharmaceutical composition as described hereinabove, for use in treating cancer.

Reference will now be made in detail to embodiments of the present disclosure. While certain embodiments of the present disclosure will be described, it will be understood that it is not intended to limit the embodiments of the present disclosure to those described embodiments. To the contrary, reference to embodiments of the present disclosure is intended to cover alternatives, modifications, and equivalents as may be included within the spirit and scope of the embodiments of the present disclosure as defined by the appended claims.

DETAILED DESCRIPTION

Provided herein as Embodiment 1 is a compound of Formula I (I)

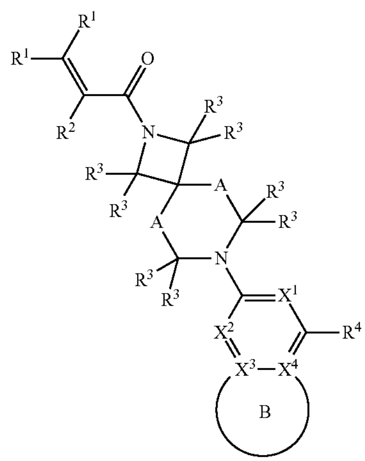

or a pharmaceutically acceptable salt thereof, wherein $R^1$ at each occurrence independently is H, $^2$H, $C_{1-4}$haloalkyl, $C_{1-4}$alkoxy, —$CH_2$OH, —$(CH_2)$O($C_{1-4}$alkyl), —$(CH_2)$O($C_{1-4}$haloalkyl), —$(CH_2)$—$C_{1-4}$dialkylamino, aziridin-1-yl-methyl, azetidin-1-yl-methyl, pyrrolidine-1-yl-methyl, piperidin-1-yl-methyl, or morpholin-1-yl-methyl;

$R^2$ is H, $^2$H, halogen, —CN, $C_{1-4}$alkyl, $C_{1-4}$haloalkyl, —$CH_2$CN, —$CH_2$OH, $C_{1-4}$alkoxy, or $C_{1-4}$haloalkoxy;

wherein, optionally, one $R^1$ and $R^2$ together with the carbon atoms to which they are attached form a

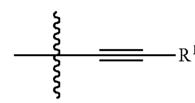

group;

$R^3$ at each occurrence independently is H, halogen, CN, OH, $C_{1-4}$alkyl, $C_{1-4}$haloalkyl, —$CH_2$CN, —$CH_2$OH, $C_{1-4}$alkoxy, or $C_{1-4}$haloalkoxy, wherein two substituents $R^3$ attached to the same carbon atom optionally form together with said carbon atom a $C_{3-6}$cycloalkyl or a carbonyl group;

A at each occurrence independently is $CR^3R^3$ or absent;

$R^4$ is 1,2,3,4-tetrahydro-8-quinolinyl, 6 or 10 membered aryl, or 5 to 10 membered heteroaryl, wherein the aryl or heteroaryl is optionally substituted with 1 to 5 substituents independently selected from OH, halogen, —CN, $NH_2$, $C_{1-4}$alkyl, $C_{1-4}$deuteroalkyl, $C_{1-4}$haloalkyl, $C_{1-4}$alkoxy, $C_{1-4}$haloalkoxy, —$SO_2NH$—$_2$, —$NHSO_2C_3$, wherein the $C_{1-4}$alkyl is optionally substituted with GOH;

$X^1$ is $CR^5$ or N;

$X^2$ is CH, CF, or N;

$X^3$ is C or N;

$X^4$ is C or N;

$R^5$ is H, halogen, CN, —COO($C_{1-4}$alkyl), $C_{1-4}$alkyl, $C_{2-4}$alkenyl, $C_{1-4}$haloalkyl, —$(CH_2)_m$($C_{1-4}$alkoxy), —$(CH_2)_m$($C_{1-4}$haloalkoxy), $C_{3-5}$cycloalkyl, $C_{3-5}$cyclohaloalkyl, or $C_{3-5}$heterocycloalkyl;

B together with the atoms to which it is attached forms a 4 to 7 membered fully saturated, fully unsaturated, or partially unsaturated carbocyclic or heterocyclic ring system, wherein the heterocyclic ring system comprises 1 to 5 heteroatoms independently selected from N, O, and S, wherein the ring system is optionally substituted with 1 to 5 substituents $R^6$;

$R^6$ at each occurrence independently is halogen, OH, —CN, —$NH_2$, $C_{1-6}$alkyl, $C_{1-6}$haloalkyl, $C_{1-4}$alkoxy, $C_{1-4}$haloalkoxy, —C(═O)$C_{1-6}$alkyl, —$R_7$—($C_{3-5}$cycloalkyl), —$R^7$—($C_{3-5}$cyclohaloalkyl), —$R^7$—($C_{3-5}$heterocycloalkyl), —$R^7$-(phenyl), or —$R_7$-(5 to 6 membered heteroaryl), wherein the $C_{1-6}$alkyl is optionally substituted with $C_{1-4}$alkoxy, $C_{1-4}$alkylamino, $C_{1-4}$dialkylamino, —CO($C_{1-4}$akylamino) or —CO($C_{1-4}$dialkylamino), wherein the $C_{1-6}$haloalkyl is optionally substituted with a OH, wherein the $C_{3-6}$heterocycloalkyl is optionally substituted with 1 to 3 substituents independently selected from (═O) and $C_{1-6}$alkyl, wherein the phenyl is optionally substituted with 1 to 3 substituents independently selected from halogen and $C_{1-4}$alkoxy, wherein the heteroaryl is optionally substituted with 1 to 3 substituents independently selected from halogen, —$(CH_2)_{1-3}$OH, $(CH_2)_{1-3}$O($C_{1-4}$alkyl), —($CH_2$)—($C_{1-4}$haloalkyl), $C_{1-4}$alkyl, and $C_{1-4}$haloalkyl, wherein two substituents $R^6$ together optionally form a —$(CH_2)_n$— group creating a ring together with the ring atom or ring atoms to which the two substituents $R^6$ are attached, wherein the —$(CH_2)_n$— group optionally has one —$CH_2$— group substituted with one heteroatom selected from N, O, and S, and wherein the —$(CH_2)_n$— group is optionally substituted with 1 to 3 substituents independently selected from halogen and $C_{1-6}$alkyl;

$R^7$ is $(C_2)_m$ or CO;

n is 1, 2, 3, 4, 5 or 6; and m is 0 or 1.

Provided herein as Embodiment 2 is the compound according to Embodiment 1 or a pharmaceutically acceptable salt thereof, wherein $R^2$ is not methyl; or

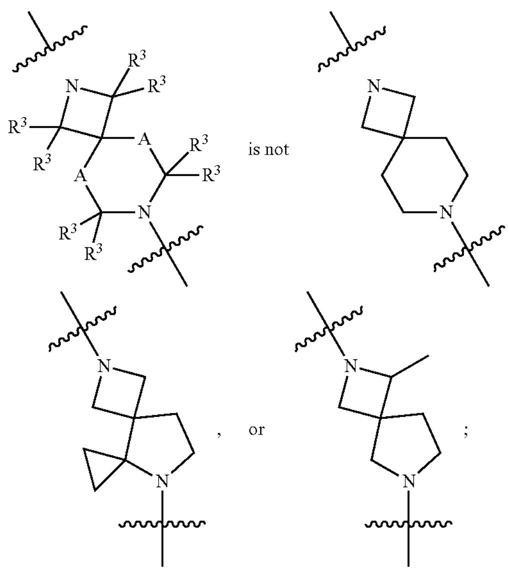

$R^4$ is not 4-cyano-1-methyl-1H-pyrazol-5-yl, 2-fluoro-5-cyano-phenyl, 2-methyl-5-hydroxymethyl-phenyl, 2-chloro-5-(difluoromethoxy)phenyl, 2-methyl-5-(difluoromethyl)-phenyl, 3-methoxy-5-(trifluoromethyl) phenyl, 2-fluoro-3-methoxyphenyl, 5-hydroxy-2-(2-propanyl)phenyl, 3-methyl-4-pyridinyl, 6-amino-3-methyl-pyridin-2-yl, 5-(trifluoromethyl)-3-pyridinyl, 6-oxo-1,6-dihydro-3-pyridinyl, 4-oxo-6-(2-propanyl)-1,4-dihydro-2-pyridinyl, 5-pyrimidinyl, 5-methyl-1,2-benzoxazol-4-yl, 5-methyl-1H-pyrrolo[2,3-b]pyridin-4-yl, imidazo[1,2-a]pyridin-3-yl, pyrazolo[1,5-a]pyridin-3-yl, 1H-pyrrolo[3,2-c]pyridin-7-yl, 6-hydroxy-2-methyl-naphthalen-1-yl, isoquinolin-4-yl, 2-oxo-1,2-dihydroquinolin-4-yl, or 6-hydroxy-8-quinolinyl; or B is not selected from the group consisting of

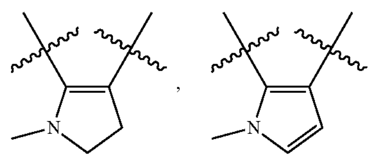

unsubstituted

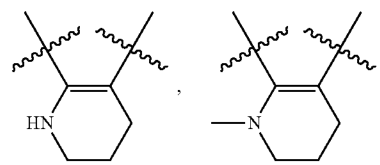

or unsubstituted

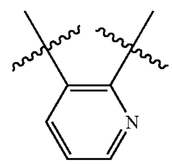

or $R^6$ is not 3-chlorophenyl or 8-methylnaphthalen-1-yl; or wherein the compound is not a compound, wherein $R^4$ is 3-fluoro-2-pyridinyl, $X^1$ is $CCH_3$ and $X^2$ is N.

Provided herein as Embodiment 3 is the compound according to Embodiment 1 or a pharmaceutically acceptable salt thereof, wherein the compound is not 1-(6-(4-(2-fluorophenyl)-7-methyl-7H-pyrrolo[2,3-d]pyrimidin-2-yl)-2,6-diazaspiro[3.4]octan-2-yl)-2-propen-1-one;

1-(6-(4-(2-fluorophenyl)-8-methyl-5,6,7,8-tetrahydropyrido[2,3-d]pyrimidin-2-yl)-2,6-diazaspiro[3.4]octan-2-yl)-2-propen-1-one;

1-(6-(7-methy-4-(5-methyl-1H-indazol-4-yl)-6,7-dihydro-5H-pyrrolo[2,3-d]pyrimidin-2-yl)-2,6-diazaspiro[3.4]octan-2-yl)prop-2-en-1-one:

1-(6-(4-(2-fluorophenyl)-7-(8-methyl-1-naphthalenyl)-6,7-dihydro-5H-pyrrolo[2,3-d]pyrimidin-2-yl)-2,6-diazaspiro[3.4]octan-2-yl)-2-propen-1-one;

2-(2-acryloyl-2,6-diazaspiro[3.4]octan-6-yl)-4-(5-cyano-2-fluorophenyl)quinoline-3-carbonitrile;

1-(6-(4-(2-chloro-5-(difluoromethoxy)phenyl)-5,6,7,8-tetrahydro-2-quinazolinyl)-2,6-diazaspiro[3.4]octan-2-yl)-2-propen-1-one;

1-(6-(4-(2-fluorophenyl)-7-(8-methylnaphthalen-1-yl)-7H-pyrrolo[2,3-d]pyrimidin-2-yl)-2,6-diazaspiro[3.4]octan-2-yl)prop-2-en-1-one;

1-(6-(4-(4-isoquinolinyl)-5,6,7,8-tetrahydro-2-quinazolinyl)-2,6-diazaspiro[3.4]octan-2-yl)-2-propen-1-one;

1-(6-(4-(5-(difluoromethyl)-2-methylphenyl)-5,6,7,8-tetrahydro-2-quinazolinyl)-2,6-diazaspiro[3.4]octan-2-yl)-2-propen-1-one;

1-(6-(4-(5-(hydroxymethyl)-2-methylphenyl)-5,6,7,8-tetrahydro-2-quinazolinyl)-2,6-diazaspiro[3.4]octan-2-yl)-2-propen-1-one;

1-(6-(4-(5-methyl-1H-indazol-4-yl)-5,6,7,8-tetrahydropyrido[2,3-d]pyrimidin-2-yl)-2,6-diazaspiro[3.4]octan-2-yl)-2-propen-1-one;

1-(6-(4-(5-methyl-1H-indazol-4-yl)pyrido[3,2-d]pyrimidin-2-yl)-2,6-diazaspiro[3.4]octan-2-yl)-2-propen-1-one;

1-(6-(4-(6-amino-3-methyl-2-pyridinyl)-5,6,7,8-tetrahydro-2-quinazolinyl)-2,6-diazaspiro[3.4]octan-2-yl)-2-propen-1-one;

1-(6-(4-(6-hydroxy-2-methyl-1-naphthalenyl)-5,6,7,8-tetrahydro-2-quinazolinyl)-2,6-diazaspiro[3.4]octan-2-yl)-2-propen-1-one;

1-(6-(4-(6-hydroxy-8-quinolinyl)-5,6,7,8-tetrahydro-2-quinazolinyl)-2,6-diazaspiro[3.4]octan-2-yl)-2-propen-1-one;

1-(6-(8-(3-chlorophenyl)-4-(2-fluorophenyl)-5,6,7,8-tetrahydropyrido[2,3-d]pyrimidin-2-yl)-2,6-diazaspiro[3.4]octan-2-yl)-2-propen-1-one;

1-(6-(4-(2-fluoro-3-methoxyphenyl)-7-methoxy-2-quinazolinyl)-2,6-diazaspiro[3.4]octan-2-yl)-2-propen-1-one;

1-(6-(8-(2,3-difluorophenyl)-6-quinolinyl)-2,6-diazaspiro[3.4]octan-2-yl)-2-propen-1-one:

4-(5-hydroxy-2-(2-propanyl)phenyl)-2-(2-(2-propenoyl)-2,6-diazaspiro[3.4]octan-6-yl)-3-quinolinecarbonitrile;

1-(6-(4-(2,3-dimethylphenyl)pyrido[3,2-d]pyrimidin-2-yl)-2,6-diazaspiro[3.4]octan-2-yl)-2-propen-1-one;

7,7-dimethyl-2-(2-(2-propanoyl)-2,6-diazaspiro[3.4]octan-6-yl)-4-(5-pyrimidinyl)-7,8-dihydro-5H-pyrano[4,3-b]pyridine-3-carbonitrile;

8-fluoro-4-(5-methyl-1H-indazol-4-yl)-2-(2-(2-methyl-2-propenoyl)-2,6-diazaspiro[3.4]octan-6-yl)-3-quinolinecarbonitrile;

1-(6-(3-methyl-4-(3-methyl-4-pyridinyl)-2-quinolinyl)-2,6-diazaspiro[3.4]octan-2-yl)-2-propen-1-one;

4-(4-cyano-1-methyl-1H-pyrazol-5-yl)-7,7-dimethyl-2-(2-(2-propenoyl)-2,6-diazaspiro[3.4]octan-6-yl)-5,7-dihydrofuro[3,4-b]pyridine-3-carbonitrile;

8-fluoro-4-(5-methyl-1H-indazol-4-yl)-2-((1R,4R)-1-methyl-2-(2-propanoyl)-2,6-diazaspiro[3.4]octan-6-yl)-3-quinolinecarbonitrile;

4-(5-methyl-1,2-benzoxazol-4-yl)-2-(2-(2-propenoyl)-2,6-diazaspiro[3.4]octan-6-yl)-3-quinolinecarbonitrile;

4-(5-methyl-1H-pyrrolo[2,3-b]pyridin-4-yl)-2-(2-(2-propanoyl)-2,6-diazaspiro[3.4]octan-6-yl)-3-quinolinecarbonitrile;

4-(imidazo[1,2-a]pyridin-3-yl)-7,7-dimethyl-2-(2-(2-propenoyl)-2,6-diazaspiro[3.4]octan-6-yl)-7,8-dihydro-51H-pyrano[4,3-b]pyridine-3-carbonitrile;

7,7-dimethyl-2-(2-(2-propenoyl)-2,6-diazaspiro[3.4]octan-6-yl)-4-(pyrazolo[1,5-a]pyridin-3-yl)-7,8-dihydro-5H-pyrano[4,3-b]pyridine-3-carbonitrile;

4-(1,6-dimethyl-1H-indazol-7-yl)-7,7-dimethyl-2-(6-(2-propenoyl)-6,10-diazadispiro[$2.0.3^4.3^3$]decan-10-yl)-7,8-dihydro-5H-pyrano[4,3-b]pyridine-3-carbonitrile;

2'-oxo-2-(2-(2-propenoyl)-2,6-diazaspiro[3.4]octan-6-yl)-1',2'-dihydro[4,4'-biquinoline]-3-carbonitrile;

(1R,9R)-10,10-dimethyl-4-(2-(2-propenoyl)-2,6-diazaspiro[3.4]octan-6-yl)-6-(5-(trifluoromethyl)-3-pyridinyl)-3-azatricyclo[$7.1.1.0^{2,7}$]undeca-2,4,6-triene-5-carbonitrile;

(1R,9R)-6-(3-methoxy-5-(trifluoromethyl)phenyl)-10,10-dimethyl-4-(2-(2-propenoyl)-2,6-diazaspiro[3.4]octan-6-yl)-3-azatricyclo[$7.1.1.0^{2,7}$]undeca-2,4,6-triene-5-carbonitrile;

4-(2,4-difluorophenyl)-7-(2-propanyl)-2-(2-(2-propenoyl)-2,7-diazaspiro[3.5]nonan-7-yl)-5,6,7,8-tetrahydro-1,7-naphthyridine-3-carbonitrile;

(1R,9R)-10,10-dimethyl-4-(2-(2-propenoyl)-2,6-diazaspiro[3.4]octan-6-yl)-6-(1H-pyrrolo[3,2-c]pyridin-7-yl)-3-azatricyclo[$7.1.1.0^{2,7}$]undeca-2,4,6-triene-5-carbonitrile;

(1R,9R)-6-(1-(difluoromethyl)-6-oxo-1,6-dihydro-3-pyridinyl)-10,10-dimethyl-4-(2-(2-propenoyl)-2,6-diazaspiro[3.4]octan-6-yl)-3-azatricyclo[$7.1.1.0^{2,7}$]undeca-2,4,6-triene-5-carbonitrile;

1-(6-(4-(3-fluoro-2-pyridinyl)-3,7,7-trimethyl-7,8-dihydro-5H-pyrano[4,3-b]pyridin-2-yl)-2,6-diazaspiro[3.4]octan-2-yl)-2-propen-1-one; or 7,7-dimethyl-4-(4-oxo-6-(2-propanyl)-1,4-dihydro-2-pyridinyl)-2-(2-(2-propenoyl)-2,6-diazaspiro[3.4]octan-6-yl)-7,8-dihydro-5H-pyrano[4,3-b]pyridine-3-carbonitrile.

Provided herein as Embodiment 4 is the compound according to Embodiment 1 or a pharmaceutically acceptable salt thereof, wherein the compound has an $IC_{50}$ of less than 10 μM in the 2 h coupled exchange assay or the 20 h coupled exchange assay.

Provided herein as Embodiment 5 is the compound according to any one of Embodiments 1-4 or a pharmaceutically acceptable salt thereof, wherein $R^1$ at each occurrence independently is H, $^2H$, $C_{1-4}$haloalkyl, —$CH_2OH$, —$(CH_2)O(C_{1-4}alkyl)$, —$(CH_2)O(C_{1-4}haloalkyl)$, or —$(CH_2)$—$C_{1-4}$dialkylamino.

Provided herein as Embodiment 6 is the compound according to any one of Embodiments 1-4 or a pharmaceutically acceptable salt thereof, wherein $R^1$ at each occurrence independently is H, $^2H$, $C_{1-4}$haloalkyl, or —$(CH_2)$—$C_{1-4}$dialkylamino.

Provided herein as Embodiment 7 is the compound according to any one of Embodiments 1-4 or a pharmaceutically acceptable salt thereof, wherein $R^1$ at each occurrence independently is H, $^2H$, $CH_2F$, $CHF_2$, $CF_3$, —$CH_2OH$, —$CH_2OCH_3$, —$(CH_2)OCHF_2$, or —$(CH_2)$—$N(CH_3)_2$.

Provided herein as Embodiment 8 is the compound according to any one of Embodiments 1-4 or a pharmaceutically acceptable salt thereof, wherein $R^1$ at each occurrence independently is H, $^2H$, $CHF_2$, or —$(CH_2)$—$N(CH_3)$.

Provided herein as Embodiment 9 is the compound according to any one of Embodiments 1-4 or a pharmaceutically acceptable salt thereof, wherein $R^1$ is H.

Provided herein as Embodiment 10 is the compound according to any one of Embodiments 1-4 or a pharmaceutically acceptable salt thereof, wherein one $R^1$ and $R^2$ together with the carbon atoms to which they are attached form a

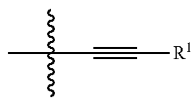

group.

Provided herein as Embodiment 11 is the compound according to Embodiment 10 or a pharmaceutically acceptable salt thereof, wherein the

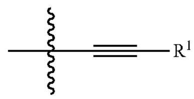

group is

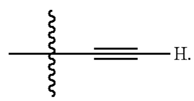

Provided herein as Embodiment 12 is the compound according to any one of Embodiments 1-10 or a pharmaceutically acceptable salt thereof, wherein $R^2$ is H or halogen.

Provided herein as Embodiment 13 is the compound according to any one of Embodiments 1-10 or a pharmaceutically acceptable salt thereof, wherein $R^2$ is Br or Cl.

Provided herein as Embodiment 14 is the compound according to any one of Embodiments 1-10 or a pharmaceutically acceptable salt thereof, wherein $R^2$ is H.

Provided herein as Embodiment 15 is the compound according to any one of Embodiments 1-14 or a pharmaceutically acceptable salt thereof, wherein $R^3$ at each occurrence independently is H, halogen, $C_{1-4}$alkyl, $C_{1-4}$haloalkyl, or —$CH_2OH$.

Provided herein as Embodiment 16 is the compound according to any one of Embodiments 1-14 or a pharmaceutically acceptable salt thereof wherein $R^3$ at each occurrence independently is H, halogen, or $C_{1-4}$alkyl.

Provided herein as Embodiment 17 is the compound according to any one of Embodiments 1-14 or a pharmaceutically acceptable salt thereof, wherein $R^3$ at each occurrence independently is H, F, methyl, $CH_2F$, $CHF_2$, or —$CH_2OH$.

Provided herein as Embodiment 18 is the compound according to any one of Embodiments 1-14 or a pharmaceutically acceptable salt thereof, wherein $R^3$ at each occurrence independently is H, F, methyl, or $CH_3F$.

Provided herein as Embodiment 19 is the compound according to any one of Embodiments 1-14 or a pharmaceutically acceptable salt thereof, wherein $R^7$ is H.

Provided herein as Embodiment 20 is the compound according to any one of Embodiments 1-19 or a pharmaceutically acceptable salt thereof, wherein one A is absent and the other A is $CR^3R^3$.

Provided herein as Embodiment 21 is the compound according to any one of Embodiments 1-19 or a pharmaceutically acceptable salt thereof wherein both A are absent.

Provided herein as Embodiment 22 is the compound according to any one of Embodiments 1-14 or a pharmaceutically acceptable salt thereof wherein

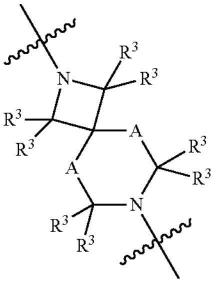

is

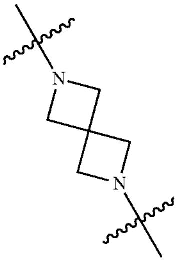

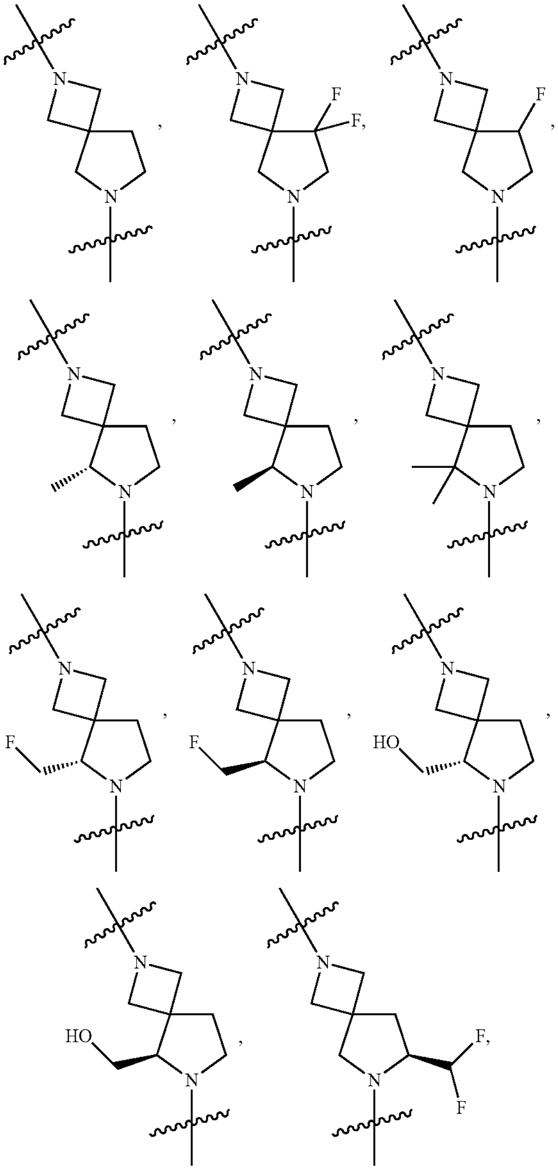

-continued

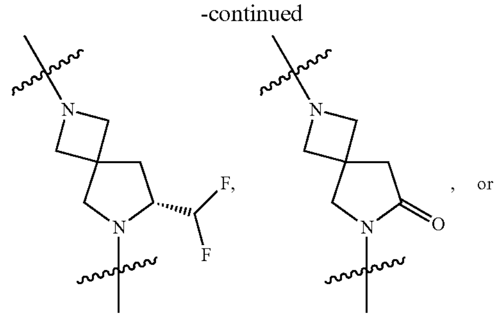

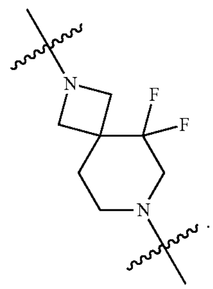 [SMILES: *N1CCC2(CN(*)C2)C(F)(F)C1]

Provided herein as Embodiment 23 is the compound according to any one of Embodiments 1-14 or a pharmaceutically acceptable salt thereof, wherein

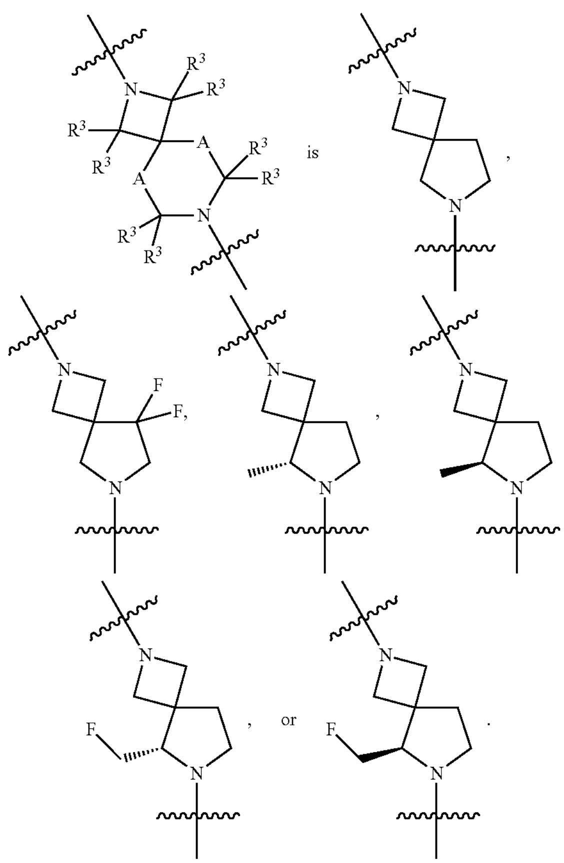

Provided herein as Embodiment 24 is the compound according to any one of Embodiments 1-14 or a pharmaceutically acceptable salt thereof wherein

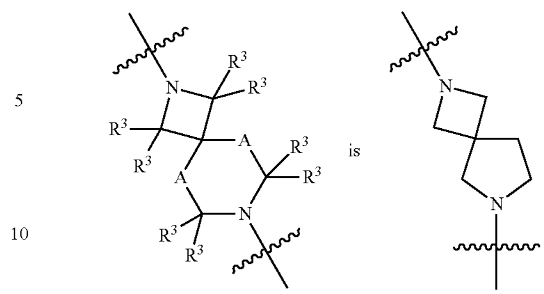

Provided herein as Embodiment 25 is the compound according to any one of Embodiments 1-24 or a pharmaceutically acceptable salt thereof, wherein $R^4$ is 6 or 10 membered aryl or 5 to 10 membered heteroaryl, wherein the aryl or heteroaryl is optionally substituted with 1 to 5 substituents independently selected from OH, halogen, —CN, $NH_2$, $C_{1-4}$alkyl, $C_{1-4}$deuteroalkyl, $C_{1-4}$haloalkyl, $C_{1-4}$alkoxy, —$SO_2NH_2$, —$NHSO_2CH_3$, wherein the $C_{1-4}$alkyl is optionally substituted with OH.

Provided herein as Embodiment 26 is the compound according to any one of Embodiments 1-24 or a pharmaceutically acceptable salt thereof, wherein R is 6 or 10 membered aryl or 5 to 10 membered heteroaryl, wherein the aryl or heteroaryl is optionally substituted with 1 to 3 substituents independently selected from OH, halogen, —CN, $NH_2$, $C_{1-4}$alkyl, or $C_{1-4}$haloalkyl.

Provided herein as Embodiment 27 is the compound according to any one of Embodiments 1-24 or a pharmaceutically acceptable salt thereof, wherein $R^4$ is 6 or 10 membered aryl or 5 to 10 membered heteroaryl, wherein the aryl or heteroaryl is optionally substituted with 1 to 5 substituents independently selected from OH, F, Cl, Br, —CN, $NH_2$, methyl, ethyl, isopropyl, $CD_3$, $CHF_2$, $CF_3$, methoxy, —$SO_2NH_2$, —$NHSO_2CH_3$, —$CH_2OH$, or —$CH(OH)CH_3$.

Provided herein as Embodiment 28 is the compound according to any one of Embodiments 1-24 or a pharmaceutically acceptable salt thereof wherein $R^4$ is 6 or 10 membered aryl or 5 to 10 membered heteroaryl, wherein the aryl or heteroaryl is optionally substituted with 1 to 3 substituents independently selected from OH, F, Cl, —CN, $NH_2$, methyl, or $CF_3$.

Provided herein as Embodiment 29 is the compound according to any one of Embodiments 1-24 or a pharmaceutically acceptable salt thereof, wherein $R^4$ is 6 or 10 membered aryl or 5 to 10 membered heteroaryl, wherein the aryl or heteroaryl is optionally substituted with 1 to 3 substituents independently selected from OH, F, Cl, or methyl.

Provided herein as Embodiment 30 is the compound according to any one of Embodiments 25-29 or a pharmaceutically acceptable salt thereof, wherein the 6 or 10 membered aryl is phenyl.

Provided herein as Embodiment 31 is the compound according to any one of Embodiments 25-29 or a pharmaceutically acceptable salt thereof, wherein the 6 or 10 membered aryl is naphthalenyl.

Provided herein as Embodiment 32 is the compound according to any one of Embodiments 25-29 or a pharmaceutically acceptable salt thereof, wherein the 5 to 10 membered heteroaryl is 1,3-thiazolyl, pyrazolyl, pyridyl, benzothiophenyl, indolyl, indazolyl, 1,3-benzothiazolyl, 1,2,3-benzothiadiazolyl, 2,1,3-benzoxadiazolyl, quinolinyl, isoquinolinyl, quinoxalinyl, imidazo[1,5-a]pyridinyl, or pyrazolo[3,4-b]pyridinyl.

Provided herein as Embodiment 33 is the compound according to any one of Embodiments 25-29 or a pharmaceutically acceptable salt thereof, wherein the 5 to 10 membered heteroaryl is pyridyl, indazolyl, 1,3-benzothiazolyl, or quinolinyl.

Provided herein as Embodiment 34 is the compound according to any one of Embodiments 25-29 or a pharmaceutically acceptable salt thereof, wherein the 5 to 10 membered heteroaryl is indazolyl.

Provided herein as Embodiment 35 is the compound according to any one of Embodiments 1-24 or a pharmaceutically acceptable salt thereof, wherein $R^4$ is

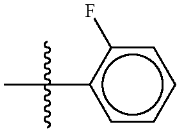 , 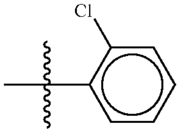 ,

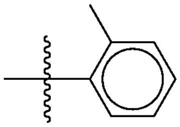 , 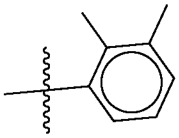 ,

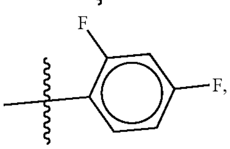 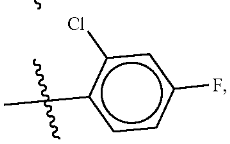

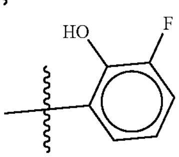 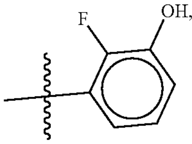

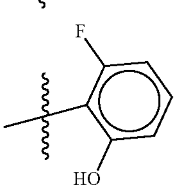 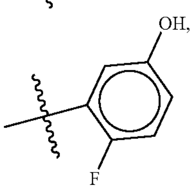

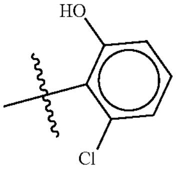 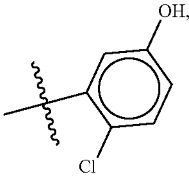

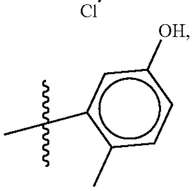 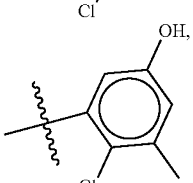

-continued

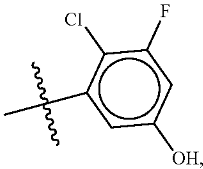 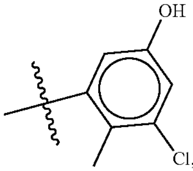

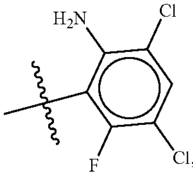 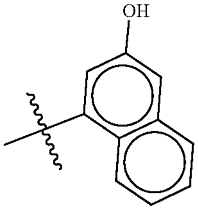

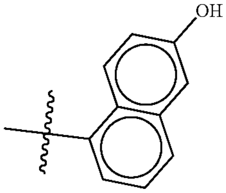 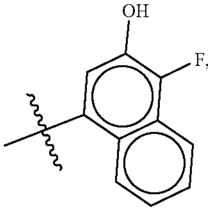

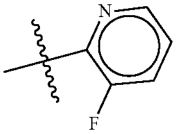 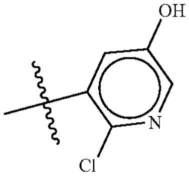

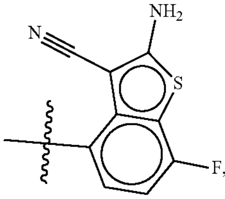 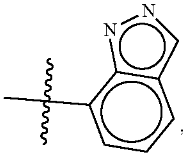

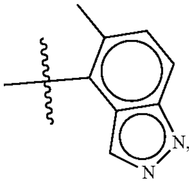 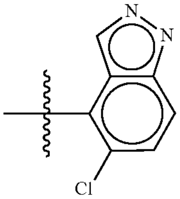

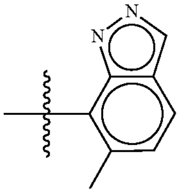 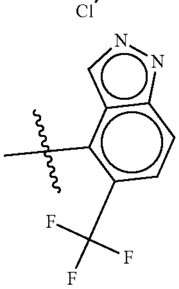

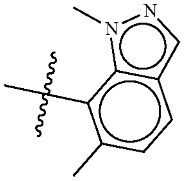 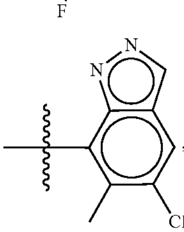

-continued

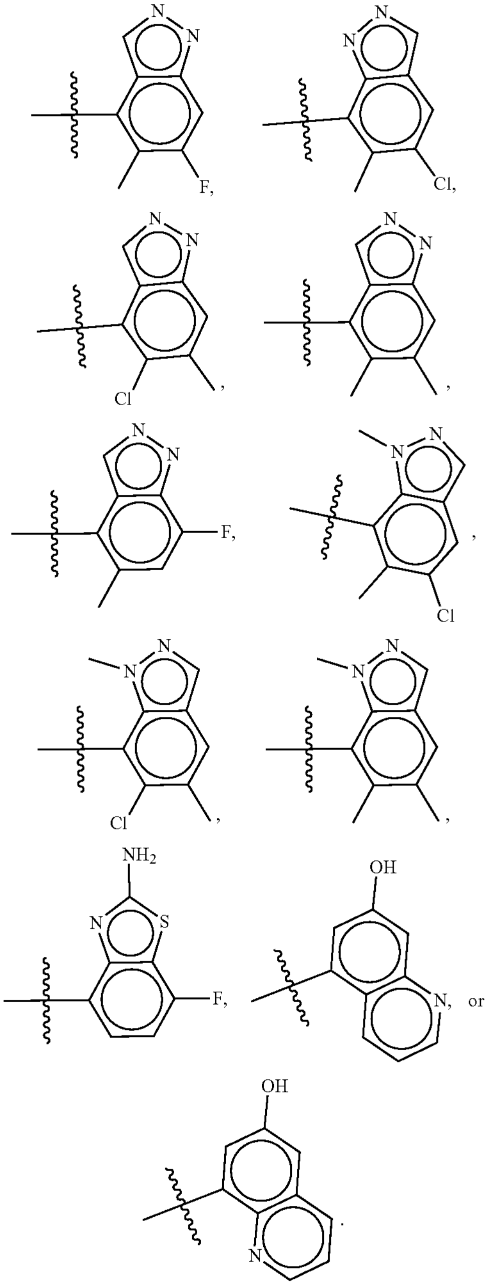

or

.

Provided herein as Embodiment 36 is the compound according to any one of Embodiments 1-24 or a pharmaceutically acceptable salt thereof, wherein $R^4$ is

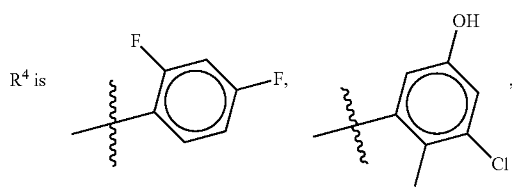

-continued

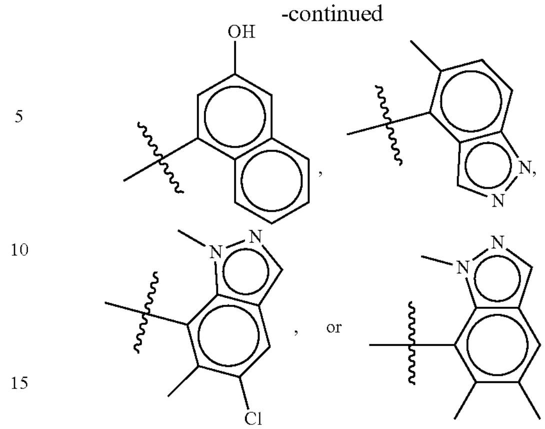

or

.

Provided herein as Embodiment 37 is the compound according to any one of Embodiments 1-36 or a pharmaceutically acceptable salt thereof, wherein $X^1$ is $CR^5$.

Provided herein as Embodiment 38 is the compound according to any one of Embodiments 1-36 or a pharmaceutically acceptable salt thereof, wherein $X^1$ is N.

Provided herein as Embodiment 39 is the compound according to any one of Embodiments 1-38 or a pharmaceutically acceptable salt thereof, wherein $X^2$ is CH.

Provided herein as Embodiment 40 is the compound according to any one of Embodiments 1-38 or a pharmaceutically acceptable salt thereof, wherein $X^2$ is N.

Provided herein as Embodiment 41 is the compound according to any one of Embodiments 1-40 or a pharmaceutically acceptable salt thereof, wherein $X^3$ is C.

Provided herein as Embodiment 42 is the compound according to any one of Embodiments 1-40 or a pharmaceutically acceptable salt thereof, wherein $X^4$ is N.

Provided herein as Embodiment 43 is the compound according to any one of Embodiments 1-42 or a pharmaceutically acceptable salt thereof, wherein $X^4$ is C.

Provided herein as Embodiment 44 is the compound according to any one of Embodiments 1-42 or a pharmaceutically acceptable salt thereof, wherein $X^4$ is N.

Provided herein as Embodiment 45 is the compound according to any one of Embodiments 1-36 or a pharmaceutically acceptable salt thereof, wherein $X^1$ is N, $X^2$ is N, $X^3$ is C, and $X^4$ is C; or
$X^1$ is $CR^5$, $X^2$ is N, $X^3$ is C, and $X^4$ is C; or
$X^1$ is $CR^5$, $X^2$ is CH, $X^3$ is C, and $X^4$ is C; or
$X^1$ is $CR^5$, $X^2$ is CH, $X^3$ is N, and $X^4$ is C; or
$X^1$ is $CR^5$, $X^2$ is CH, $X^3$ is C, and $X^4$ is N.

Provided herein as Embodiment 46 is the compound according to any one of Embodiments 1-36 or a pharmaceutically acceptable salt thereof, wherein $X^1$ is $CR^5$, $X^2$ is N, $X^3$ is C, and $X^4$ is C.

Provided herein as Embodiment 47 is the compound according to any one of Embodiments 1-37, 45, and 46 or a pharmaceutically acceptable salt thereof, wherein $R^5$ is H, halogen, CN, —COO($C_{1-4}$ alkyl), $C_{1-4}$alkyl, $C_{2-4}$alkenyl, $C_{1-4}$haloalkyl, —$(CH_2)_m$($C_{1-4}$alkoxy), or, $C_{3-5}$cycloalkyl.

Provided herein as Embodiment 48 is the compound according to any one of Embodiments 1-37, 45, and 46 or a pharmaceutically acceptable salt thereof, wherein $R^5$ is halogen, CN, or $C_{1-4}$alkyl.

Provided herein as Embodiment 49 is the compound according to any one of Embodiments 1-37, 45, and 46 or a pharmaceutically acceptable salt thereof, wherein $R^5$ is H, F, Cl, CN, —$COOCH_3$, methyl, —$CHCH_2$, $C_{1-4}$haloalkyl, —$CH_2OCH_3$, or cyclopropyl.

Provided herein as Embodiment 50 is the compound according to any one of Embodiments 1-37, 45, and 46 or a pharmaceutically acceptable salt thereof, wherein $R^5$ is F, Cl, CN, or methyl.

Provided herein as Embodiment 51 is the compound according to any one of Embodiments 1-37, 45, and 46 or a pharmaceutically acceptable salt thereof, wherein $R^5$ is F, Cl, or methyl.

Provided herein as Embodiment 52 is the compound according to any one of Embodiments 1-40, 45, and 47-51 or a pharmaceutically acceptable salt thereof, wherein B together with the atoms to which it is attached forms a ring system selected from

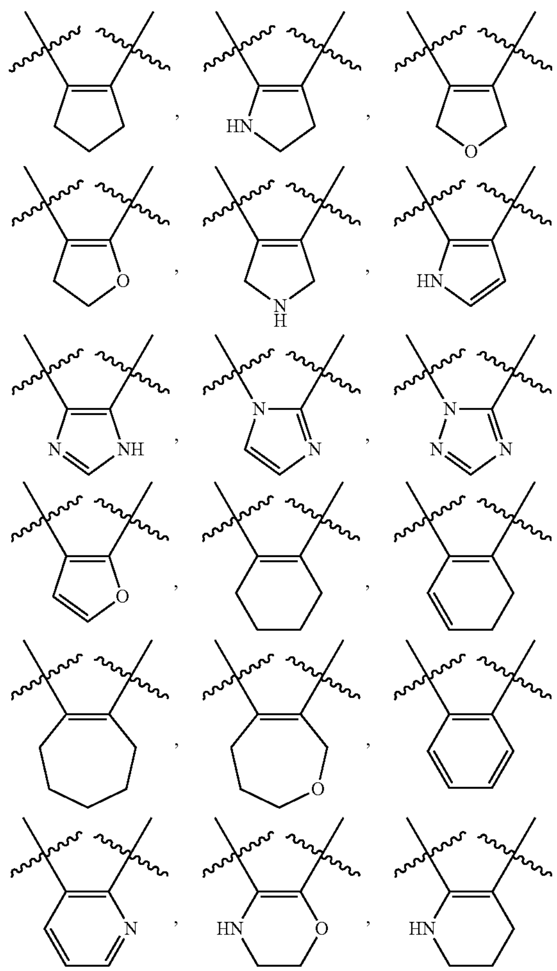

-continued

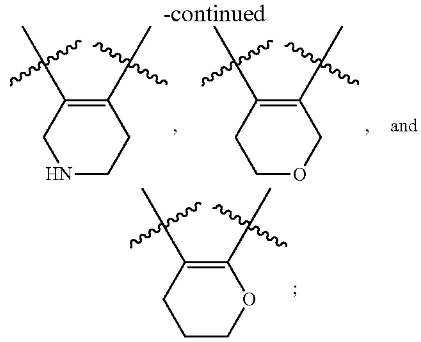

wherein the ring system is optionally substituted with 1 to 5 substituents $R^6$.

Provided herein as Embodiment 53 is the compound according to any one of Embodiments 1-40, 45, and 47-51 or a pharmaceutically acceptable salt thereof, wherein B together with the atoms to which it is attached forms a ring system selected from

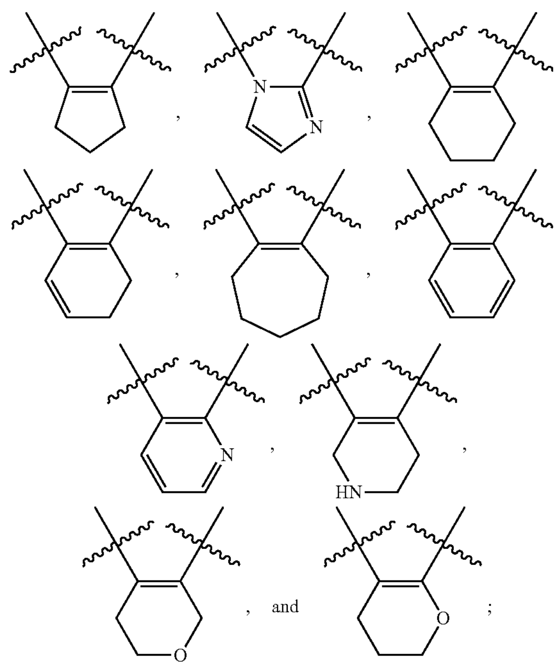

wherein the ring system is optionally substituted with 1 to 5 substituents $R^6$.

Provided herein as Embodiment 54 is the compound according to any one of Embodiments 1-40 and 45-51 or a pharmaceutically acceptable salt thereof, wherein B together with the atoms to which it is attached forms a ring system selected from

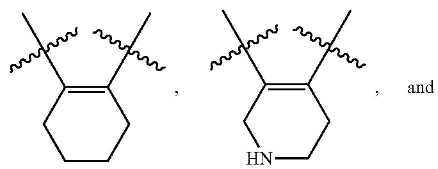

-continued

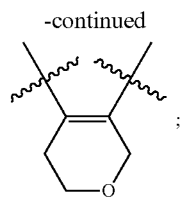

;

wherein the ring system is optionally substituted with 1 to 5 substituents $R^6$.

Provided herein as Embodiment 55 is the compound according to any one of Embodiments 1-40 and 45-51 or a pharmaceutically acceptable salt thereof, wherein B together with the atoms to which it is attached forms a ring system selected from

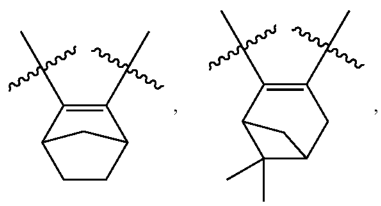

, ,

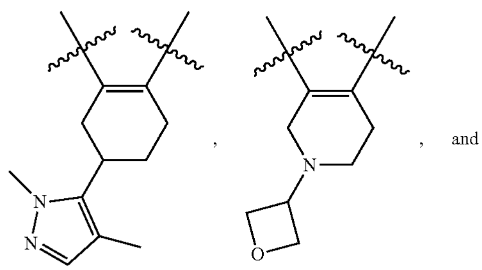

, , and

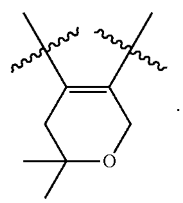

.

Provided herein as Embodiment 56 is the compound according to any one of Embodiments 1-20 and 22-51 or a pharmaceutically acceptable salt thereof, wherein the compound is a compound of Formula II (II)

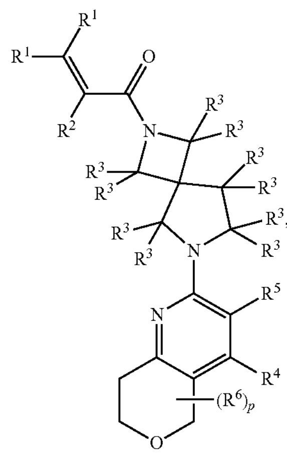

wherein $R^1$ at each occurrence independently, $R^2$, $R^3$ at each occurrence independently, $R^4$, $R^5$, and $R^6$ at each occurrence independently are defined as in the preceding Embodiments; and p is 0 to 5.

Provided herein as Embodiment 57 is the compound according to any one of Embodiments 1-20 and 22-51 or a pharmaceutically acceptable salt thereof, wherein the compound is a compound of Formula III (III)

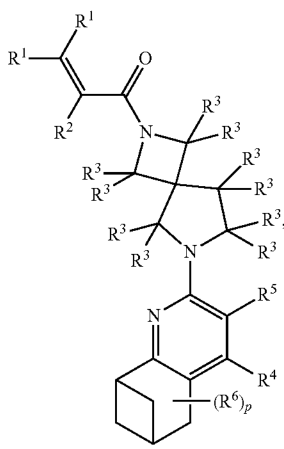

wherein $R^1$ at each occurrence independently, $R^2$, $R^3$ at each occurrence independently, $R^4$, $R^5$, and $R^6$ at each occurrence independently are defined as in the preceding Embodiments; and p is 0 to 3.

Provided herein as Embodiment 58 is the compound according to any one of Embodiments 1-20 and 22-51 or a pharmaceutically acceptable salt thereof, wherein the compound is a compound of Formula IV (IV)

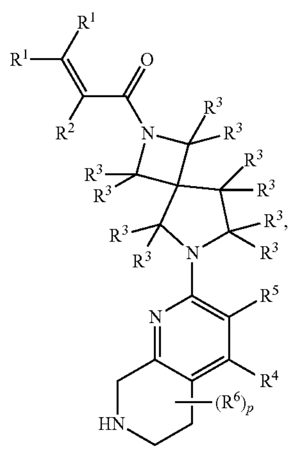

wherein $R^1$ at each occurrence independently, $R^2$, $R^3$ at each occurrence independently, $R^4$, $R^5$, and $R^6$ at each occurrence independently are defined as in the preceding Embodiments; and p is 0 to 5.

Provided herein as Embodiment 59 in the compound according to any one of Embodiments 1-20 and 22-51 or a pharmaceutically acceptable salt thereof, wherein the compound is a compound of Formula V (V)

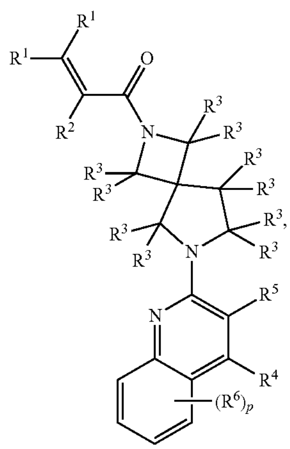

wherein $R^1$ at each occurrence independently, $R^2$, $R^3$ at each occurrence independently, $R^4$, $R^5$, and $R^6$ at each occurrence independently are defined as in the preceding Embodiments; and p is 0 to 4.

Provided herein as Embodiment 60 is the compound according to any one of Embodiments 1-20 and 22-51 or a pharmaceutically acceptable salt thereof, wherein the compound is a compound of Formula VI (VI)

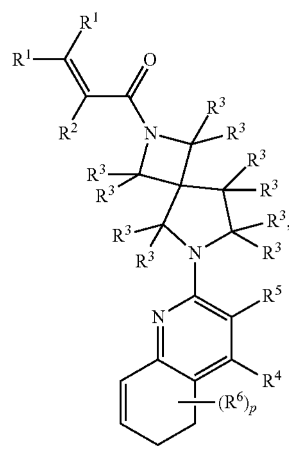

wherein $R^1$ at each occurrence independently, $R^2$, $R^3$ at each occurrence independently, $R^4$, $R^5$, and $R^6$ at each occurrence independently are defined as in the preceding Embodiments; and p is 0 to 5.

Provided herein as Embodiment 61 is the compound according to any one of Embodiments 1-20 and 22-51 or a pharmaceutically acceptable salt thereof, wherein the compound is a compound of Formula VII (VII)

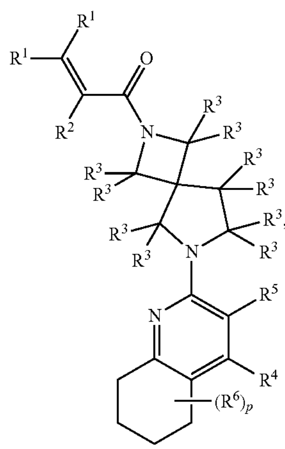

wherein $R^1$ at each occurrence independently, $R^2$, $R^3$ at each occurrence independently, $R^4$, $R^5$, and $R^6$ at each occurrence independently are defined as in the preceding Embodiments; and p is 0 to 5.

Provided herein as Embodiment 62 is the compound according to any one of Embodiments 1-20 and 22-51 or a pharmaceutically acceptable salt thereof, wherein the compound is a compound of Formula VIII (VIII)

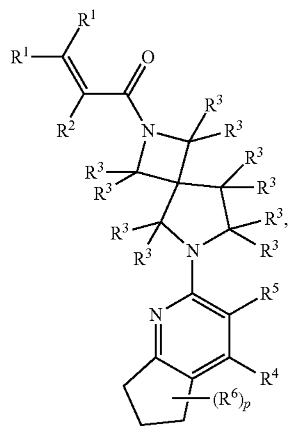

wherein $R^1$ at each occurrence independently, $R^2$, $R^3$ at each occurrence independently, $R^4$, $R^5$, and $R^6$ at each occurrence independently are defined as in the preceding Embodiments; and p is 0 to 5.

Provided herein as Embodiment 63 is the compound according to any one of Embodiments 1-20 and 22-51 or a pharmaceutically acceptable salt thereof, wherein the compound is a compound of Formula IX (IX)

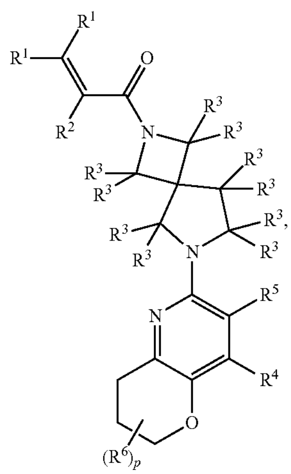

wherein $R^1$ at each occurrence independently, $R^2$, $R^3$ at each occurrence independently, $R^4$, $R^5$, and $R^6$ at each occurrence independently are defined as in the preceding Embodiments; and p is 0 to 5.

Provided herein as Embodiment 64 is the compound according to any one of Embodiments 1-20 and 22-51 or a pharmaceutically acceptable salt thereof, wherein the compound is a compound of Formula X (X)

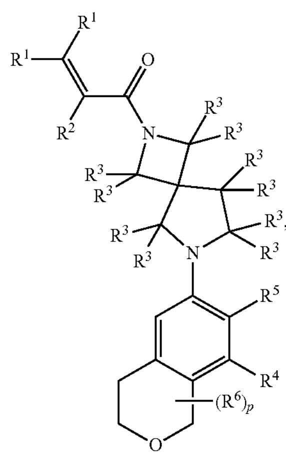

wherein $R^1$ at each occurrence independently, $R^2$, $R^3$ each occurrence independently, $R^4$, $R^5$, and $R^6$ at each occurrence independently are defined as in the preceding Embodiments; and p is 0 to 5.

Provided herein as Embodiment 65 is the compound according to any one of Embodiments 1-20 and 22-51 or a pharmaceutically acceptable salt thereof, wherein the compound is a compound of Formula XI (XI)

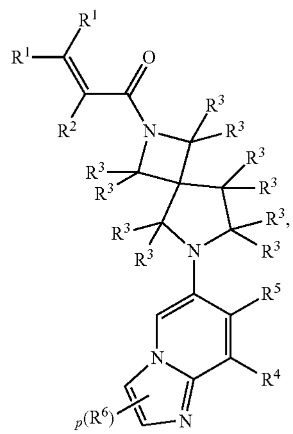

wherein $R^1$ at each occurrence independently, $R^2$, $R^3$ at each occurrence independently, $R^4$, $R^5$, and $R^6$ at each occurrence independently are defined as in the preceding Embodiments; and p is 0 to 2.

Provided herein as Embodiment 66 is the compound according to any one of Embodiments 1-20 and 22-51 or a pharmaceutically acceptable salt thereof, wherein the compound is a compound of Formula XII (XII)

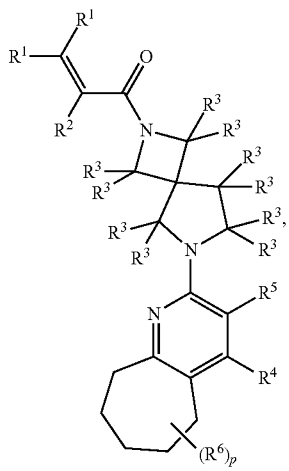

wherein $R^1$ at each occurrence independently, $R^2$, $R^3$ at each occurrence independently, $R^4$, $R^5$, and $R^6$ at each occurrence independently are defined as in the preceding Embodiments; and p is 0 to 5.

Provided herein as Embodiment 67 is the compound according to any one of Embodiments 1-20 and 22-51 or a pharmaceutically acceptable salt thereof, wherein the compound is a compound of Formula XIII (XIII)

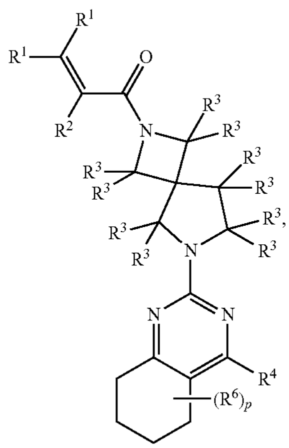

wherein $R^1$ at each occurrence independently, $R^2$, $R^3$ at each occurrence independently, $R^4$, $R^5$, and $R^6$ at each occurrence independently are defined as in the preceding Embodiments; and p is 0 to 5.

Provided herein as Embodiment 68 is the compound according to any one of Embodiments 1-20 and 22-51 or a pharmaceutically acceptable salt thereof, wherein the compound is a compound of Formula XIV (XIV)

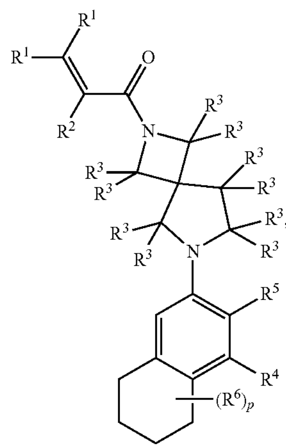

wherein $R^1$ at each occurrence independently, $R^2$, $R^3$ at each occurrence independently, $R^4$, $R^5$, and $R^6$ at each occurrence independently are defined as in the preceding Embodiments; and p is 0 to 5.

Provided herein as Embodiment 69 is the compound according to any one of Embodiments 1-20 and 22-51 or a pharmaceutically acceptable salt thereof, wherein the compound is a compound of Formula XV (XV)

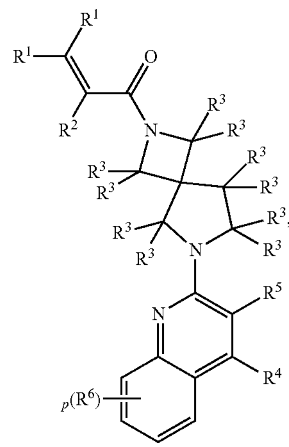

wherein $R^1$ at each occurrence independently, $R^2$, $R^3$ at each occurrence independently, $R^4$, $R^5$, and $R^6$ at each occurrence independently are defined as in the preceding Embodiments; and p is 0 to 3.

Provided herein as Embodiment 70 is the compound according to any one of Embodiments 1-54 and 56-69 or a pharmaceutically acceptable salt thereof, wherein $R^6$ at each occurrence independently is $C_{1-6}$alkyl, $C_{1-6}$haloalkyl, $C_{1-6}$alkoxy, —$R^7$—($C_{3-5}$ cycloalkyl), —$R^7$—($C_{3-6}$heterocycloalkyl), —$R^7$-(phenyl), or —$R^7$-(5 to 6 membered heteroaryl), wherein the $C_{1-6}$alkyl is optionally substituted with $C_{1-4}$alkoxy, wherein the $C_{3-6}$heterocycloalkyl is optionally substituted with $C_{1-6}$alkyl, wherein the phenyl is optionally substituted with $C_{1-4}$alkoxy, wherein the heteroaryl is optionally substituted with 1 to 3 substituents independently selected from halogen, $—(CH_2)^{1-3}OH$ and $C_{1-4}$alkyl, and wherein two substituents $R^6$ together optionally form a $—(CH_2)_n—$ group creating a ring together with the ring atom or ring atoms to which the two substituents $R^6$ are attached, wherein the $—(CH_2)_n—$ group optionally has one $—CH_2—$ group substituted with an —O— atom.

Provided herein as Embodiment 71 is the compound according to any one of Embodiments 1-54 and 56-69 or a pharmaceutically acceptable salt thereof, wherein $R^6$ at each occurrence independently is $C_{1-6}$alkyl $—R^7—$($C_{3-6}$heterocycloalkyl), or $—R^7—$ (5 to 6 membered heteroaryl), wherein the heteroaryl is optionally substituted with 1 to 3 $C_{1-4}$alkyl, and wherein two substituents $R^6$ together optionally form a $—(CH_2)_n—$ group creating a ring together with the ring atom or ring atoms to which the two substituents R& are attached.

Provided herein as Embodiment 72 is the compound according to any one of Embodiments 1-54 and 56-69 or a pharmaceutically acceptable salt thereof, wherein $R^6$ at each occurrence independently is methyl, isopropyl, 1-methoxy-propan-2-yl, $CF_3$, methoxy, cyclopropyl, oxetan-3-yl, 3-methyloxetan-3-yl, 4-methyl-1-piperazinyl, 4-methoxyphenyl, 4-methyl-1,3-thiazol-5-yl, 4-(hydroxymethyl)-1,3-thiazol-5-yl, 2-methyl-1H-imidazol-1-yl, 1-methyl-1H-pyrazol-5-yl, or 1,4-dimethyl-1H-pyrazol-5-yl wherein two substituents $R^6$ together optionally form a $—(CH_2)_n—$ group creating a ring together with the ring atom or ring atoms to which the two substituents $R^6$ are attached, wherein the $—(CH_2)_n—$ group optionally has one $—CH_2—$ group substituted with an —O— atom.

Provided herein as Embodiment 73 is the compound according to any one of Embodiments 1-54 and 56-69 or a pharmaceutically acceptable salt thereof, wherein $R^6$ at each occurrence independently is methyl, oxetan-3-yl, or 1,4-dimethyl-1H-pyrazol-5-yl, wherein two substituents $R^6$ together optionally form a $—(CH_2)_n—$ group creating a ring together with the ring atom or ring atoms to which the two substituents $R^6$ are attached.

Provided herein as Embodiment 74 is the compound according to any one of Embodiments 1-54 and 56-70 or a pharmaceutically acceptable salt thereof, wherein $R^7$ is $(CH_2)_m$.

Provided herein as Embodiment 75 is the compound according to any one of Embodiments 1-54 and 56-73 or a pharmaceutically acceptable salt thereof, wherein n is 1.

Provided herein as Embodiment 76 is the compound according to any one of Embodiments 1-54 and 56-73 or a pharmaceutically acceptable salt thereof, wherein n is 2.

Provided herein as Embodiment 77 is the compound according to any one of Embodiments 1-54 and 56-73 or a pharmaceutically acceptable salt thereof, wherein n is 3.

Provided herein as Embodiment 78 is the compound according to any one of Embodiments 1-54 and 56-73 or a pharmaceutically acceptable salt thereof, wherein n is 4.

Provided herein as Embodiment 79 is the compound according to any one of Embodiments 1-54 and 56-73 or a pharmaceutically acceptable salt thereof, wherein n is 5.

Provided herein as Embodiment 80 is the compound according to any one of Embodiments 1-54 and 56-73 or a pharmaceutically acceptable salt thereof, wherein n is 6.

Provided herein as Embodiment 81 is the compound according to any one of Embodiments 1-37, 45-47, 52-71, and 74-80 or a pharmaceutically acceptable salt thereof, wherein m is 0.

Provided herein as Embodiment 82 is the compound according to any one of Embodiments 1-37, 45-47, 52-71, and 74-80 or a pharmaceutically acceptable salt thereof, wherein m is 1.

Provided herein as Embodiment 83 is the compound according to Embodiment 1 or a pharmaceutically acceptable salt thereof, wherein the compound is 8-fluoro-2-(5-(fluoromethyl)-2-(2-propenoyl)-2,6-diazaspiro[3.4]octan-6-yl)-4-(5-methyl-1H-indazol-4-yl)-3-quinolinecarbonitrile;

8-(5-methyl-1H-indazol-4-yl)-3-(4-methyl-1-piperazinyl)-6-(2-(2-propenoyl)-2,6-diazaspiro[3.4]octan-6-yl)imidazo[1,2-a]pyridine-7-carbonitrile;

8-(5-methyl-1H-indazol-4-yl)-6-(2-(2-propenoyl)-2,6-diazaspiro[3.4]octan-6-yl)-2-(1,3-thiazol-2-yl)imidazo[1,2-a]pyridine-7-carbonitrile;

4-(5-methyl-1H-indazol-4-yl)-2-(2-(2-propenoyl)-2,6-diazaspiro[3.4]octan-6-yl)-6,7,8,9-tetrahydro-5H-cyclohepta[b]pyridine-3-carbonitrile;

(P)-1-(6-(3,7,7-trimethyl-4-(5-methyl-1H-indazol-4-yl)-5,6,7,8-tetrahydro-2-quinolinyl)-2,6-diazaspiro[3.4]octan-2-yl)-2-propen-1-one;

1-(6-(4-(6-hydroxy-1-naphthalenyl)-3,7,7-trimethyl-5,6,7,8-tetrahydro-2-quinolinyl)-2,6-diazaspiro[3.4]octan-2-yl)-2-propen-1-one;

(P)-1-(6-(4-(6-hydroxy-1-naphthalenyl)-3,7,7-trimethyl-5,6,7,8-tetrahydro-2-quinolinyl)-2,6-diazaspiro[3.4]octan-2-yl)-2-propen-1-one;

1-(6-(4-(2-amino-7-fluoro-1,3-benzothiazol-4-yl)-3,7,7-trimethyl-5,6,7,8-tetrahydro-2-quinolinyl)-2,6-diazaspiro[3.4]octan-2-yl)-2-propen-1-one;

(P)-1-(6-(4-(2-amino-7-fluoro-1,3-benzothiazol-4-yl)-3,7,7-trimethyl-5,6,7,8-tetrahydro-2-quinolinyl)-2,6-diazaspiro[3.4]octan-2-yl)-2-propen-1-one;

1-(6-(4-(1,6-dimethyl-1H-indazol-7-yl)-3,7,7-trimethyl-5,6,7,8-tetrahydro-2-quinolinyl)-2,6-diazaspiro[3.4]octan-2-yl)-2-propen-1-one;

(P)-1-(6-(3,7,7-trimethyl-4-(6-methyl-1H-indazol-7-yl)-5,6,7,8-tetrahydro-2-quinolinyl)-2,6-diazaspiro[3.4]octan-2-yl)-2-propen-1-one;

1-(6-(4-(3-hydroxy-1-naphthalenyl)-3,7,7-trimethyl-5,6,7,8-tetrahydro-2-quinolinyl)-2,6-diazaspiro[3.4]octan-2-yl)-2-propen-1-one;

1-(6-(3,7,7-trimethyl-4-(5-methyl-1H-indazol-4-yl)-5,6,7,8-tetrahydro-2-quinolinyl)-2,6-diazaspiro[3.4]octan-2-yl)-2-propen-1-one;

(1R,9R)-10,10-dimethyl-4-(2-(2-propanoyl)-2,6-diazaspiro[3.4]octan-6-yl)-6-(5-(trifluoromethyl)-1H-indazol-4-yl)-3-azatricyclo[7.1.1.0$^{2,7}$]undeca-2,4,6-triene-5-carbonitrile;

1-(6-(4-(6-chloro-5-methyl-1H-indazol-4-yl)-3,7,7-trimethyl-7,8-dihydro-5H-pyrano[4,3-b]pyridin-2-yl)-2,6-diazaspiro[3.4]octan-2-yl)-2-propen-1-one;

(P)-(1R,8S)-6-(3-hydroxy-1-naphthalenyl)-4-(2-(2-propenoyl)-2,6-diazaspiro[3.4]octan-6-yl)-3-azatricyclo[6.2.1.$0^{2,7}$]undeca-2,4,6-triene-5-carbonitrile;

(1R,8S)-6-(3-hydroxy-1-naphthalenyl)-4-(2-(2-propenoyl)-2,6-diazaspiro[3.4]octan-6-yl)-3-azatricyclo[6.2.1.02,7]undeca-2,4,6-triene-5-carbonitrile or (1S,8R)-6-(3-hydroxy-1-naphthalenyl)-4-(2-(2-propenoyl)-2,6-diazaspiro[3.4]octan-6-yl)-3-azatricyclo[6.2.1.$0^{2,7}$]undeca-2,4,6-triene-5-carbonitrile;

(M)-(1R,8S)-6-(3-hydroxy-1-naphthalenyl)-4-(2-(2-propenoyl)-2,6-diazaspiro[3.4]octan-6-yl)-3-azatricyclo[6.2.1.$0^{2,7}$]undeca-2,4,6-triene-5-carbonitrile;

(1R,9R)-6-(6-hydroxy-8-isoquinolinyl)-10,10-dimethyl-4-(2-(2-propenoyl)-2,6-diazaspiro[3.4]octan-6-yl)-3-azatricyclo[7.1.1.$0^{2,7}$]undeca-2,4,6-triene-5-carbonitrile;

(1R,9R)-6-(7-hydroxy-5-quinolinyl)-10,10-dimethyl-4-(2-(2-propenoyl)-2,6-diazaspiro[3.4]octan-6-yl)-3-azatricyclo[7.1.1.$0^{2,7}$]undeca-2,4,6-triene-5-carbonitrile;

(P)-(1R,9R)-6-(6-hydroxy-8-quinolinyl)-10,10-dimethyl-4-(2-(2-propanoyl)-2,6-diazaspiro[3.4]octan-6-yl)-3-azatricyclo[7.1.1.$0^{2,7}$]undeca-2,4,6-triene-5-carbonitrile;

(P)-(1R,9R)-6-(7-hydroxy-5-quinolinyl)-10,10-dimethyl-4-(2-(2-propanoyl)-2,6-diazaspiro[3.4]octan-6-yl)-3-azatricyclo[7.1.1.$0^{2,7}$]undeca-2,4,6-triene-5-carbonitrile;

1-(6-(7-methoxy-3-methyl-4-(5-methyl-1H-indazol-4-yl)-2-quinolinyl)-2,6-diazaspiro[3.4]octan-2-yl)-2-propen-1-one;

8-(3-hydroxy-1-naphthalenyl)-6-(2-(2-propenoyl)-2,6-diazaspiro[3.4]octan-6-yl)-3,4-dihydro-2H-chromene-7-carbonitrile;

(M)-8-(3-hydroxy-1-naphthalenyl)-6-(2-(2-propenoyl)-2,6-diazaspiro[3.4]octan-6-yl)-3,4-dihydro-2H-chromene-7-carbonitrile;

1-((5S)-5-methyl-6-(3-methyl-4-(5-methyl-1H-indazol-4-yl)-2-quinolinyl)-2,6-diazaspiro[3.4]octan-2-yl)-2-propen-1-one;

(P)-1-((5S)-6-(7-fluoro-3-methyl-4-(5-methyl-1H-indazol-4-yl)-2-quinolinyl)-5-methyl-2,6-diazaspiro[3.4]octan-2-yl)-2-propen-1-one;

(1R,9R)-6-(2-chloro-5-hydroxyphenyl)-10,10-dimethyl-4-(2-(2-propenoyl)-2,6-diazaspiro[3.4]octan-6-yl)-3-azatricyclo[7.1.1.$0^{2,7}$]undeca-2,4,6-triene-5-carbonitrile;

(1R,9R)-6-(2-fluoro-5-hydroxyphenyl)-10,10-dimethyl-4-(2-(2-propenoyl)-2,6-diazaspiro[3.4]octan-6-yl)-3-azatricyclo[7.1.1.$0^{2,7}$]undeca-2,4,6-triene-5-carbonitrile;

(1R,9R)-6-(5-hydroxy-2-methylphenyl)-10,10-dimethyl-4-(2-(2-propenoyl)-2,6-diazaspiro[3.4]octan-6-yl)-3-azatricyclo[7.1.1.$0^{2,7}$]undeca-2,4,6-triene-5-carbonitrile;

(P)-(1R,9R)-6-(5-hydroxy-2-methylphenyl)-10,10-dimethyl-4-(2-(2-propenoyl)-2,6-diazaspiro[3.4]octan-6-yl)-3-azatricyclo[7.1.1.$0^{2,7}$]undeca-2,4,6-triene-5-carbonitrile;

(P)-(1R,9R)-6-(2-chloro-5-hydroxyphenyl)-10,10-dimethyl-4-(2-(2-propenoyl)-2,6-diazaspiro[3.4]octan-6-yl)-3-azatricyclo[7.1.1.$0^{2,7}$]undeca-2,4,6-triene-5-carbonitrile;

1-(6-(3-chloro-4-(3-hydroxy-1-napthalenyl)-7,7-dimethyl-7,8-dihydro-5H-pyrano[4,3-b]pyridin-2-yl)-2,6-diazaspiro[3.4]octan-2-yl)-2-propen-1-one;

(P)-1-(6-(3-chloro-4-(3-hydroxy-1-naphthalenyl)-7,7-dimethyl-7,8-dihydro-5H-pyrano[4,3-b]pyridin-2-yl)-2,6-diazaspiro[3.4]octan-2-yl)-2-propen-1-one;

1-(6-(3-chloro-4-(5-hydroxy-2-methylphenyl)-7,7-dimethyl-7,8-dihydro-5H-pyrano[4,3-b]pyridin-2-yl)-2,6-diazaspiro[3.4]octan-2-yl)-2-propen-1-one;

(P)-1-(6-(3-chloro-4-(5-hydroxy-2-methylphenyl)-7,7-dimethyl-7,8-dihydro-5H-pyrano[4,3-b]pyridin-2-yl)-2,6-diazaspiro[3.4]octan-2-yl)-2-propen-1-one;

1-(6-(3-chloro-7,7-dimethyl-4-(5-methy-1H-indazol-4-yl)-7,8-dihydro-5H-pyrano[4,3-b]pyridin-2-yl)-2,6-diazaspiro[3.4]octan-2-yl)-2-propen-1-one;

(M)-1-(6-(3-chloro-4-(1,6-dimethyl-1H-indazol-7-yl)-7,7-dimethyl-7,8-dihydro-5H-pyrano[4,3-b]pyridin-2-yl)-2,6-diazaspiro[3.4]octan-2-yl)-2-propen-1-one;

1-(6-(3-chloro-4-(5-chloro-1,6-dimethyl-1H-indazol-7-yl)-7,7-dimethyl-7,8-dihydro-5H-pyrano[4,3-b]pyridin-2-yl)-2,6-diazaspiro[3.4]octan-2-yl)-2-propen-1-one;

(M)-1-(6-(3-chloro-4-(5-chloro-1,6-dimethyl-1H-indazol-7-yl)-7,7-dimethyl-7,8-dihydro-5H-pyrano[4,3-b]pyridin-2-yl)-2,6-diazaspiro[3.4]octan-2-yl)-2-propen-1-one;

1-(6-(3-chloro-4-(6-chloro-5-methyl-1H-indazol-4-yl)-7,7-dimethyl-7,8-dihydro-5H-pyrano[4,3-b]pyridin-2-yl)-2,6-diazaspiro[3.4]octan-2-yl)-2-propen-1-one;

1-(5-methyl-1H-indazol-4-yl)-3-(2-(2-propenoyl)-2,6-diazaspiro[3.4]octan-6-yl)-5,6,7,8-tetrahydro-2-naphthalenecarbonitrile;

8-(5-methyl-1H-indazol-4-yl)-6-(2-(2-propenoyl)-2,6-diazaspiro[3.4]octan-6-yl)-3,4-dihydro-1H-2-benzopyran-7-carbonitrile;

1-(1,6-dimethyl-1H-indazol-7-yl)-6,6-dimethyl-3-(2-(2-propanoyl)-2,6-diazaspiro[3.4]octan-6-yl)-5,6,7,8-tetrahydro-2-naphthalenecarbonitrile;

3'-hydroxy-6,6-dimethyl-3-(2-(2-propenoyl)-2,6-diazaspiro[3.4]octan-6-yl)-5,6,7,8-tetrahydro[1,1'-binaphthalene]-2-carbonitrile;

(P)-8-(5-methyl-1H-indazol-4-yl)-6-(2-(2-propenoyl)-2,6-diazaspiro[3.4]octan-6-yl)-3,4-dihydro-1H-2-benzopyran-7-carbonitrile;

8-(1,6-dimethyl-1H-indazol-7-yl)-6-(2-(2-propenoyl)-2,6-diazaspiro[3.4]octan-6-yl)-3,4-dihydro-2H-chromene-7-carbonitrile;

1-(6-(7-chloro-8-(1,6-dimethyl-1H-indazol-7-yl)-3,4-dihydro-2H-chromen-6-yl)-2,6-diazaspiro[3.4]octan-2-yl)-2-propen-1-one;

8-(5-chloro-1,6-dimethyl-1H-indazol-7-yl)-6-(2-(2-propenoyl)-2,6-diazaspiro[3.4]octan-6-yl)-3,4-dihydro-2H-chromene-7-carbonitrile;

2-(8,8-difluoro-2-(2-propenoyl)-2,6-diazaspiro[3.4]octan-6-yl)-7,7-dimethyl-4-(5-methyl-1H-indazol-4-yl)-5,6,7,8-tetrahydro-3-quinolinecarbonitrile;

8-(5-chloro-1,6-dimethyl-1H-indazol-7-yl)-6-((5S)-5-methyl-2-(2-propenoyl)-2,6-diazaspiro[3.4]octan-6-yl)-3,4-dihydro-2H-chromene-7-carbonitrile;

(P)-1-(6-(3-chloro-4-(6-chloro-5-methyl-1H-indazol-4-yl)-7,7-dimethyl-7,8-dihydro-5H-pyrano[4,3-b]pyridin-2-yl)-2,6-diazaspiro[3.4]octan-2-yl)-2-propen-1-one;

1-(6-(7-chloro-8-(5-chloro-1,6-dimethyl-1H-indazol-7-yl)-3,4-dihydro-2H-chromen-6-yl)-2,6-diazaspiro[3.4]octan-2-yl)-2-propen-1-one;

(M)-1-(6-((1S,8R)-5-methyl-6-(1,5,6-trimethyl-1H-indazol-7-yl)-3-azatricyclo[6.2.1.02,7]undeca-2,4,6-trien-4-yl)-2,6-diazaspiro[3.4]octan-2-yl)-2-propen-1-one;

1-(6-(4-(3-chloro-5-hydroxy-2-methylphenyl)-3,7,7-trimethyl-7,8-dihydro-5H-pyrano[4,3-b]pyridin-2-yl)-2,6-diazaspiro[3.4]octan-2-yl)-2-propen-1-one;

(1R,9R)-6-(7-fluoro-5-methyl-1H-indazol-4-yl)-10,10-dimethyl-4-(2-(2-propenoyl)-2,6-diazaspiro[3.4]octan-6-yl)-3-azatricyclo[7.1.1.$0^{2,7}$]undeca-2,4,6-triene-5-carbonitrile;

4-(5-chloro-1H-indol-4-yl)-7,7-dimethyl-2-(2-(2-propenoyl)-2,6-diazaspiro[3.4]octan-6-yl)-7,8-dihydro-5H-pyrano[4,3-b]pyridine-3-carbonitrile;

(1R,9R)-6-(5-chloro-6-methyl-1H-indazol-4-yl)-10,10-dimethyl-4-(2-(2-propenoyl)-2,6-diazaspiro[3.4]octan-6-yl)-3-azatricyclo[7.1.1.0$^{2,7}$]undeca-2,4,6-triene-5-carbonitrile;

(1R,9R)-10,10-dimethyl-6-(7-methylimidazo[1,5-a]pyridin-8-yl)-4-(2-(2-propenoyl)-2,6-diazaspiro[3.4]octan-6-yl)-3-azatricyclo[7.1.1.0$^{2,7}$]undeca-2,4,6-triene-5-carbonitrile;

4-(3-chloro-6-methyl-1H-indol-7-yl)-7,7-dimethyl-2-(2-(2-propenoyl)-2,6-diazaspiro[3.4]octan-6-yl)-7,8-dihydro-5H-pyrano[4,3-b]pyridine-3-carbonitrile;

1-(6-(4-(5-chloro-1,6-dimethyl-1H-indazol-7-yl)-3-methyl-7-(2-propanyl)-5,6,7,8-tetrahydro-1,7-naphthyridin-2-yl)-2,6-diazaspiro[3.4]octan-2-yl)-2-propen-1-one;

(M)-1-(6-(4-(5-chloro-1,6-dimethyl-1H-indazol-7-yl)-3-methyl-7-(2-propanyl)-5,6,7,8-tetrahydro-1,7-naphthyridin-2-yl)-2,6-diazaspiro[3.4]octan-2-yl)-2-propen-1-one;

1-(6-(3-methyl-7-(2-propanyl)-4-(1,5,6-trimethyl-1-H-indazol-7-yl)-5,6,7,8-tetrahydro-1,7-naphthyridin-2-yl)-2,6-diazaspiro[3.4]octan-2-yl)-2-propen-1-one;

(1R,9R)-6-(2-chloro-3-fluoro-5-hydroxyphenyl)-10,10-dimethyl-4-(2-(2-propenoyl)-2,6-diazaspiro[3.4]octan-6-yl)-3-azatricyclo[7.1.1.0$^{2,7}$]undeca-2,4,6-triene-5-carbonitrile;

(1R,9R)-6-(2-chloro-5-hydroxy-3-pyridinyl)-10,10-dimethyl-4-(2-(2-propenoyl)-2,6-diazaspiro[3.4]octan-6-yl)-3-azatricyclo[7.1.1.0$^{2,7}$]undeca-2,4,6-triene-5-carbonitrile;

(P)-(1R,9R)-6-(7-hydroxy-5-quinoxalinyl)-10,10-dimethyl-4-(2-(2-propenoyl)-2,6-diazaspiro[3.4]octan-6-yl)-3-azatricyclo[7.1.1.0$^{2,7}$]undeca-2,4,6-triene-5-carbonitrile;

4-(6-hydroxy-1-naphthalenyl)-7,7-dimethyl-2-(2-(2-propenoyl)-2,6-diazaspiro[3.4]octan-6-yl)-7,8-dihydro-5H-pyrano[4,3-b]pyridine-3-carbonitrile;

(M)-1-(6-(4-(3-chloro-5-hydroxy-2-methylphenyl)-3,7,7-trimethyl-7,8-dihydro-5H-pyrano[4,3-b]pyridin-2-yl)-2,6-diazaspiro[3.4]octan-2-yl)-2-propen-1-one;

1-(6-(4-(2-chloro-5-hydroxy-3-methylphenyl)-3,7,7-trimethyl-7,8-dihydro-5H-pyrano[4,3-b]pyridin-2-yl)-2,6-diazaspiro[3.4]octan-2-yl)-2-propen-1-one;

7,7-dimethyl-4-(5-methyl-1H-indazol-4-yl)-2-(2-(($^2H_3$)-2-propenoyl)-2,6-diazaspiro[3.4]octan-6-yl)-5,6,7,8-tetrahydro-3-quinolinecarbonitrile;

2-(2-((2E)-4-(dimethylamino)-2-butenoyl)-2,6-diazaspiro[3.4]octan-6-yl)-7,7-dimethyl-4-(5-methyl-1-H-indazol-4-yl)-5,6,7,8-tetrahydro-3-quinolinecarbonitrile;

2-(2-((2E)-4-(4-difluoro-2-butenoyl)-2,6-diazaspiro[3.4]octan-6-yl)-7,7-dimethyl-4-(5-methyl-1H-indazol-4-yl)-5,6,7,8-tetrahydro-3-quinolinecarbonitrile;

(7R)-4-(5-methyl-1H-indazol-4-yl)-2-(2-(2-propenoyl)-2,6-diazaspiro[3.4]octan-6-yl)-7-(trifluoromethyl)-5,6,7,8-tetrahydro-3-quinolinecarbonitrile or (7S)-4-(5-methyl-1H-indazol-4-yl)-2-(2-(2-propenoyl)-2,6-diazaspiro[3.4]octan-6-yl)-7-(trifluoromethyl)-5,6,7,8-tetrahydro-3-quinolinecarbonitrile;

4'-(5-methyl-1H-indazol-4-yl)-2'-(2-(2-propenoyl)-2,6-diazaspiro[3.4]octan-6-yl)-7',8'-dihydro-5'-1-spiro[cyclopropane-1,6'-quinoline]-3'-carbonitrile;

6,6-dimethyl-4-(5-methyl-1H-indazol-4-yl)-2-(2-(2-propenoyl)-2,6-diazaspiro[3.4]octan-6-yl)-6,7-dihydro-5H-cyclopenta[b]pyridine-3-carbonitrile;

(5R,7S)-5,7-dimethyl-4-(5-methyl-1H-indazol-4-yl)-2-(2-(2-propanoyl)-2,6-diazaspiro[3.4]octan-6-yl)-7,8-dihydro-51H-pyrano[4,3-b]pyridine-3-carbonitrile or (5S,7R)-5,7-dimethyl-4-(5-methyl-1H-indazol-4-yl)-2-(2-(2-propenoyl)-2,6-diazaspiro[3.4]octan-6-yl)-7,8-dihydro-5H-pyrano[4,3-b]pyridine-3-carbonitrile;

4-(5-methyl-1H-indazol-4-yl)-2-(2-(2-propenoyl)-2,6-diazaspiro[3.4]octan-6-yl)-5,7-dihydrospiro[cyclopenta[b]pyridine-6,1'-cyclopropane]-3-carbonitrile;

4-(1,6-dimethyl-1H-indazol-7-yl)-6,6-dimethyl-2-(2-(2-propenoyl)-2,6-diazaspiro[3.4]octan-6-yl)-6,7-dihydro-5H1-cyclopenta[b]pyridine-3-carbonitrile;

(P)-4-(1,6-dimethyl-1H-indazol-7-yl)-6,6-dimethyl-2-(2-(2-propenoyl)-2,6-diazaspiro[3.4]octan-6-yl)-6,7-dihydro-5H-cyclopenta[b]pyridine-3-carbonitrile;

(7R)-4-(2-chlorophenyl)-7-(1-methyl-1H-pyrazol-5-yl)-2-(2-(2-propenoyl)-2,6-diazaspiro[3.4]octan-6-yl)-5,6,7,8-tetrahydro-3-quinolinecarbonitrile or (7S)-4-(2-chlorophenyl)-7-(1-methyl-1H-pyrazol-5-yl)-2-(2-(2-propenoyl)-2,6-diazaspiro[3.4]octan-6-yl)-5,6,7,8-tetrahydro-3-quinolinecarbonitrile;

(7R)-4-(2-chlorophenyl)-7-(1-methyl-1H-pyrazol-5-yl)-2-(2-(2-propenoyl)-2,6-diazaspiro[3.4]octan-6-yl)-5,6,7,8-tetrahydro-3-quinolinecarbonitrile;

(7S)-4-(2-chlorophenyl)-7-(1-methyl-1H-pyrazol-5-yl)-2-(2-(2-propenoyl)-2,6-diazaspiro[3.4]octan-6-yl)-5,6,7,8-tetrahydro-3-quinolinecarbonitrile;

(7R)-4-(2-fluorophenyl)-7-(1-methyl-1H-pyrazol-5-yl)-2-(2-(2-propenoyl)-2,6-diazaspiro[3.4]octan-6-yl)-5,6,7,8-tetrahydro-3-quinolinecarbonitrile or (7S)-4-(2-fluorophenyl)-7-(1-methyl-1H-pyrazol-5-yl)-2-(2-(2-propenoyl)-2,6-diazaspiro[3.4]octan-6-yl)-5,6,7,8-tetrahydro-3-quinolinecarbonitrile;

4-(3-hydroxy-1-naphthalenyl)-7,7-dimethyl-2-(2-(2-propenoyl)-2,6-diazaspiro[3.4]octan-6-yl)-7,8-dihydro-5H-pyrano[4,3-b]pyridine-3-carbonitrile;

(P)-4-(3-hydroxy-1-naphthalenyl)-7,7-dimethyl-2-(2-(2-propanoyl)-2,6-diazaspiro[3.4]octan-6-yl)-7,8-dihydro-5H-pyrano[4,3-b]pyridine-3-carbonitrile;

1-(6-(3-(difluoromethyl)-7,7-dimethyl-4-(5-methyl-1H-indazol-4-yl)-7,8-dihydro-5H-pyrano[4,3-b]pyridin-2-yl)-2,6-diazaspiro[3.4]octan-2-yl)-2-propen-1-one;

4-(1,6-dimethyl-1H-indazol-7-yl)-7,7-dimethyl-2-(2-(2-propenoyl)-2,6-diazaspiro[3.4]octan-6-yl)-7,8-dihydro-5H-pyrano[4,3-b]pyridine-3-carbonitrile;

4'-(5-methyl-1-indazol-4-yl)-2-(2-(2-propenoyl)-2,6-diazaspiro[3.4]octan-6-yl)-2,3,5,5',6,8'-hexahydrospiro[pyran-4,7'-pyrano[4,3-b]pyridine]-3'-carbonitrile;

(3R)-4'-(5-methyl-1H-indazol-4-yl)-2'-(2-(2-propenoyl)-2,6-diazaspiro[3.4]octan-6-yl)-4,5,5',8'-tetrahydrospiro[furan-3,7'-pyrano[4,3-b]pyridine]-3'-carbonitrile or (3S)-4'-(5-methyl-1H-indazol-4-yl)-2'-(2-(2-propenoyl)-2,6-diazaspiro[3.4]octan-6-yl)-4,5,5',8'-tetrahydrospiro[furan-3.7'-pyrano[4,3-b]pyridine]-3'-carbonitrile;

6,6-dimethyl-4-(5-methyl-1-1H-indazol-4-yl)-2-((5R)-5-methyl-2-(2-propenoyl)-2,6-diazaspiro[3.4]octan-6-yl)-6,7-dihydro-5H-cyclopenta[b]pyridine-3-carbonitrile or 6,6-dimethyl-4-(5-methyl-1H-indazol-4-yl)-2-((5S)-5-methyl-2-(2-propenoyl)-2,6-diazaspiro[3.4]octan-6-yl)-6,7-dihydro-5H-cyclopenta[b]pyridine-3-carbonitrile;

(P)-6,6-dimethyl-4-(5-methyl-1H-indazol-4-yl)-2-((5R)-5-methyl-2-(2-propenoyl)-2,6-diazaspiro[3.4]octan-6-yl)-6,7-dihydro-5H-cyclopenta[b]pyridine-3-carbonitrile;

(P)-4-(1,6-dimethyl-1H-indazol-7-yl)-7,7-dimethyl-2-(2-(2-propenoyl)-2,6-diazaspiro[3.4]octan-6-yl)-7,8-dihydro-5H-pyrano[4,3-b]pyridine-3-carbonitrile;

(6aR,7aR)-4-(1,6-dimethyl-1H-indazol-7-yl)-2-((5R)-5-(hydroxymethyl)-2-(2-propenoyl)-2,6-diazaspiro[3.4]octan-6-yl)-6,6a,7,7a-tetrahydro-5H-cyclopropa[h]quinoline-3-carbonitrile or (6aR,7aR)-4-(1,6-dimethyl-1H- indazol-7-yl)-2-((5S)-5-(hydroxymethyl)-2-(2-propenoyl)-2,6-diazaspiro[3.4]octan-6-yl)-6,6a,7,7a-tetrahydro-5H-cyclopropa[h]quinoline-3-carbonitrile or (6aR,7aS)-4-(1,6-dimethyl-1H-indazol-7-yl)-2-((5R)-5-(hydroxymethyl)-2-(2-propenoyl)-2,6-diazaspiro[3.4]octan-6-yl)-6,6a,7,7a-tetrahydro-5H-cyclopropa[h]quinoline-3-carbonitrile or (6aR,7aS)-4-(1,6-dimethyl-1H-indazol-7-yl)-2-((5S)-5-(hydroxymethyl)-2-(2-propenoyl)-2,6-diazaspiro[3.4]octan-6-yl)-6,6a,7,7a-tetrahydro-51H-cyclopropa[h]quinoline-3-carbonitrile or (6aS,7aR)-4-(1,6-dimethyl-1H-indazol-7-yl)-2-((5R)-5-(hydroxymethyl)-2-(2-propenoyl)-2,6-diazaspiro[3.4]octan-6-yl)-6,6a, 7,7a-tetrahydro-5H-cyclopropa[h]quinoline-3-carbonitrile or (6aS,7aR)-4-(1,6-dimethyl-1H-indazol-7-yl)-2-((5S)-5-(hydroxymethyl)-2-(2-propenoyl)-2,6-diazaspiro[3.4]octan-6-yl)-6,6a,7,7a-tetrahydro-5H-cyclopropa[h]quinoline-3-carbonitrile or (6aS,7aS)-4-(1,6-dimethyl-1H-indazol-7-yl)-2-((5R)-5-(hydroxymethyl)-2-(2-propenoyl)-2,6-diazaspiro[3.4]octan-6-yl)-6,6a,7,7a-tetrahydro-5H-cyclopropa[h]quinoline-3-carbonitrile or (6aS,7aS)-4-(1,6-dimethyl-1H-indazol-7-yl)-2-((5S)-5-(hydroxymethyl)-2-(2-propenoyl)-2,6-diazaspiro[3.4]octan-6-yl)-6,6a,7,7a-tetrahydro-5H-cyclopropa[h]quinoline-3-carbonitrile;

4-(3-hydroxy-1-naphthalenyl)-6,6-dimethyl-2-(2-(2-propenoyl)-2,6-diazaspiro[3.4]octan-6-yl)-6,7-dihydro-5H-cyclopenta[b]pyridine-3-carbonitrile:

(P)-4-(3-hydroxy-1-naphthalenyl)-6,6-dimethyl-2-(2-(2-propenoyl)-2,6-diazaspiro[3.4]octan-6-yl)-6,7-dihydro-5H4-cyclopenta[b]pyridine-3-carbonitrile;

(P)-(6aR,7aS)-4-(4-fluoro-3-hydroxy-1-naphthalenyl)-2-(2-(2-propenoyl)-2,6-diazaspiro[3.4]octan-6-yl)-6,6a,7,7a-tetrahydro-5H-cyclopropa[h]quinoline-3-carbonitrile;

(M)-(6aR,7aS)-4-(4-fluoro-3-hydroxy-1-naphthalenyl)-2-(2-(2-propenoyl)-2,6-diazaspiro[3.4]octan-6-yl)-6,6a,7,7a-tetrahydro-5H-cyclopropa[h]quinoline-3-carbonitrile;

(P)-4-(4-fluoro-3-hydroxy-1-naphthalenyl)-7,7-dimethyl-2-(2-(2-propenoyl)-2,6-diazaspiro[3.4]octan-6-yl)-7,8-dihydro-5H-pyrano[4,3-b]pyridine-3-carbonitrile;

(M)-2-((5S)-5-(fluoromethyl)-2-(2-propenoyl)-2,6-diazaspiro[3.4]octan-6-yl)-7,7-dimethyl-4-(5-methyl-1-indazol-4-yl)-5,6,7,8-tetrahydro-3-quinolinecarbonitrile and (P)-2-((5R)-5-(fluoromethyl)-2-(2-propenoyl)-2,6-diazaspiro[3.4]octan-6-yl)-7,7-dimethyl-4-(5-methyl-1H-indazol-4-yl)-5,6,7,8-tetrahydro-3-quinolinecarbonitrile;

(5aR,6aR)-4-(5-methyl-1H-indazol-4-yl)-2-(2-(2-propanoyl)-2,6-diazaspiro[3.4]octan-6-yl)-5,5a,6,6a-tetrahydrocyclopropa[4,5]cyclopenta[1,2-b]pyridine-3-carbonitrile or (5aR,6aS)-4-(5-methyl-1H-indazol-4-yl)-2-(2-(2-propenoyl)-2,6-diazaspiro[3.4]octan-6-yl)-5,5a,6,6a-tetrahydrocyclopropa[4,5]cyclopenta[1,2-b]pyridine-3-carbonitrile or (5aS,6aR)-4-(5-methyl-1H-indazol-4-yl)-2-(2-(2-propenoyl)-2,6-diazaspiro[3.4]octan-6-yl)-5,5a,6,6a-tetrahydrocyclopropa[4,5]cyclopenta[1,2-b]pyridine-3-carbonitrile or (5aS,6aS)-4-(5-methyl-1H-indazol-4-yl)-2-(2-(2-propenoyl)-2,6-diazaspiro[3.4]octan-6-yl)-5,5a,6,6a-tetrahydrocyclopropa[4,5]cyclopenta[1,2-b]pyridine-3-carbonitrile;

(4bR,5aR)-4-(5-methyl-1H-indazol-4-yl)-2-(2-(2-propanoyl)-2,6-diazaspiro[3.4]octan-6-yl)-4b,5,5a,6-tetrahydrocyclopropa[3.4]cyclopenta[1,2-b]pyridine-3-carbonitrile or (4bR,5aS)-4-(5-methyl-1H-indazol-4-yl)-2-(2-(2-propanoyl)-2,6-diazaspiro[3.4]octan-6-yl)-4b,5,5a,6-tetrahydrocyclopropa[3.4]cyclopenta[1,2-b]pyridine-3-carbonitrile or (4bS,5aR)-4-(5-methyl-1H-indazol-4-yl)-2-(2-(2-propenoyl)-2,6-diazaspiro[3.4]octan-6-yl)-4b,5,5a,6-tetrahydrocyclopropa[3.4]cyclopenta[1,2-b]pyridine-3-carbonitrile or (4bS,5aS)-4-(5-methyl-1H-indazol-4-yl)-2-(2-(2-propenoyl)-2,6-diazaspiro[3.4]octan-6-yl)-4b,5,5a,6-tetrahydrocyclopropa[3.4]cyclopenta[1,2-b]pyridine-3-carbonitrile;

(6R)-6-cyclopropyl-4-(5-methyl-1H-indazol-4-yl)-2-(2-(2-propenoyl)-2,6-diazaspiro[3.4]octan-6-yl)-6,7-dihydro-5H-cyclopenta[b]pyridine-3-carbonitrile or (6S)-6-cyclopropyl-4-(5-methyl-1H-indazol-4-yl)-2-(2-(2-propenoyl)-2,6-diazaspiro[3.4]octan-6-yl)-6,7-dihydro-5H-cyclopenta[b]pyridine-3-carbonitrile;

(4bR,5aR)-5,5-dimethyl-4-(5-methyl-1H-indazol-4-yl)-2-(2-(2-propenoyl)-2,6-diazaspiro[3.4]octan-6-yl)-4b,5,5a,6-tetrahydrocyclopropa[3.4]cyclopenta[1,2-b]pyridine-3-carbonitrile or (4bR,5aS)-5,5-dimethyl-4-(5-methyl-1H-indazol-4-yl)-2-(2-(2-propenoyl)-2,6-diazaspiro[3.4]octan-6-yl)-4b,5,5a,6-tetrahydrocyclopropa[3.4]cyclopenta[1,2-b]pyridine-3-carbonitrile or (4bS,5aR)-5,5-dimethyl-4-(5-methyl-1H-indazol-4-yl)-2-(2-(2-propenoyl)-2,6-diazaspiro[3.4]octan-6-yl)-4b,5,5a,6-tetrahydrocyclopropa[3.4]cyclopenta[1,2-b]pyridine-3-carbonitrile or (4bS,5aS)-5,5-dimethyl-4-(5-methyl-1H-indazol-4-yl)-2-(2-(2-propenoyl)-2,6-diazaspiro[3.4]octan-6-yl)-4b,5,5a,6-tetrahydrocyclopropa[3.4]cyclopenta[1,2-b]pyridine-3-carbonitrile;

(P)-(6aR,7aS)-2-(2-((2E)-4-(dimethylamino)-2-butenoyl)-2,6-diazaspiro[3.4]octan-6-yl)-4-(3-hydroxy-1-naphthalenyl)-6,6a,7,7a-tetrahydro-5H-cyclopropa[h]quinoline-3-carbonitrile ($3^{rd}$ eluting isomer);

(P)-(6aS,7aR)-2-(2-((2E)-4-(dimethylamino)-2-butenoyl)-2,6-diazaspiro[3.4]octan-6-yl)-4-(3-hydroxy-1-naphthalenyl)-6,6a,7,7a-tetrahydro-5H-cyclopropa[h]quinoline-3-carbonitrile;

7,7-dimethyl-2-(2-(2-propenoyl)-2,6-diazaspiro[3.4]octan-6-yl)-4-(1,5,6-trimethyl-1H-indazol-7-yl)-5,6,7,8-tetrahydro-3-quinolinecarbonitrile;

7,7-dimethyl-2-(2-(2-propanoyl)-2,6-diazaspiro[3.4]octan-6-yl)-4-(1,5,6-trimethyl-1H-indazol-7-yl)-7,8-dihydro-5H-pyrano[4,3-b]pyridine-3-carbonitrile;

(P)-7,7-dimethyl-2-(2-(2-propenoyl)-2,6-diazaspiro[3.4]octan-6-yl)-4-(1,5,6-trimethyl-1H-indazol-7-yl)-7,8-dihydro-5H-pyrano[4,3-b]pyridine-3-carbonitrile;

(1R,9R)-10,10-dimethyl-6-(5-methyl-1H-indazol-4-yl)-4-(2-(2-propenoyl)-2,6-diazaspiro[3.4]octan-6-yl)-3-azatricyclo[7.1.1.$0^{2,7}$]undeca-2,4,6-triene-5-carbonitrile;

(1R,9R)-10,10-dimethyl-6-(5-methyl-1H-indazol-4-yl)-4-((5R)-5-methyl-2-(2-propenoyl)-2,6-diazaspiro[3.4]octan-6-yl)-3-azatricyclo[7.1.1.$0^{2,7}$]undeca-2,4,6-triene-5-carbonitrile or (1R,9R)-10,10-dimethyl-6-(5-methyl-1H-indazol-4-yl)-4-((5S)-5-methyl-2-(2-propenoyl)-2,6-diazaspiro[3.4]octan-6-yl)-3-azatricyclo[7.1.1.$0^{2,7}$]undeca-2,4,6-triene-5-carbonitrile;

7,7-dimethyl-4-(5-methyl-1H-indazol-4-yl)-2-(2-(2-propenoyl)-2,6-diazaspiro[3.4]octan-6-yl)-7,8-dihydro-5H-pyrano[4,3-b]pyridine-3-carbonitrile;

7,7-dimethyl-4-(5-methyl-1-indazol-4-yl)-2-(2-(2-propenoyl)-2,6-diazaspiro[3.4]octan-6-yl)-6,7-dihydro-5H-cyclopenta[b]pyridine-3-carbonitrile;

4'-(5-methyl-1H-indazol-4-yl)-2'-(2-(2-propenoyl)-2,6-diazaspiro[3.4]octan-6-yl)-5',8'-dihydrospiro[cyclobutane-1,7'-pyrano[4,3-b]pyridine]-3'-carbonitrile;

7,7-dimethyl-4-(5-methyl-1H-indazol-4-yl)-2-(2-(2-propanoyl)-2,6-diazaspiro[3.4]octan-6-yl)-5,7-dihydrofuro[3,4-b]pyridine-3-carbonitrile;

4-(5-methyl-1H-indazol-4-yl)-2-(2-(2-propenoyl)-2,6-diazaspiro[3.4]octan-6-yl)-5,6-dihydrospiro[cyclopenta[b]pyridine-7,1'-cyclopropane]-3-carbonitrile;

(1R,9R)-6-(1,6-dimethyl-1-H-indazol-7-yl)-10,10-dimethyl-4-(2-(2-propenoyl)-2,6-diazaspiro[3.4]octan-6-yl)-3-azatricyclo[7.1.1.$0^{2,7}$]undeca-2,4,6-triene-5-carbonitrile;

(M)-(1R,9R)-6-(1,6-dimethyl-1H-indazol-7-yl)-10,10-dimethyl-4-(2-(2-propenoyl)-2,6-diazaspiro[3.4]octan-6-yl)-3-azatricyclo[7.1.1.$0^{2,7}$]undeca-2,4,6-triene-5-carbonitrile;

(1R,9R)-6-(3-hydroxy-1-naphthalenyl)-10,10-dimethyl-4-(2-(2-propenoyl)-2,6-diazaspiro[3.4]octan-6-yl)-3-azatricyclo[7.1.1.$0^{2,7}$]undeca-2,4,6-triene-5-carbonitrile;

(1s,9s)-6-(1,6-dimethyl-1H-indazol-7-yl)-4-(2-(2-propenoyl)-2,6-diazaspiro[3.4]octan-6-yl)-3-azatricyclo [7.1.1.$0^{2,7}$]undeca-2,4,6-triene-5-carbonitrile;

4-(5-hydroxy-2-methylphenyl)-7,7-dimethyl-2-(2-(2-propanoyl)-2,6-diazaspiro[3.4]octan-6-yl)-7,8-dihydro-5H-pyrano[4,3-b]pyridine-3-carbonitrile;

(1s,9s)-6-(5-hydroxy-2-methylphenyl)-4-(2-(2-propenoyl)-2,6-diazaspiro[3.4]octan-6-yl)-3-azatricyclo[7.1.1.$0^{2,7}$] undeca-2,4,6-triene-5-carbonitrile;

(M)-(1R,9R)-10,10-dimethyl-6-(5-methyl-1H-indazol-4-yl)-4-(2-(2-propenoyl)-2,6-diazaspiro[3.4]octan-6-yl)-3-azatricyclo[7.1.1.$0^{2,7}$]undeca-2,4,6-triene-5-carbonitrile;

(6aR,7aS)-4-(1,6-dimethyl-1H-indazol-7-yl)-2-(2-(2-propenoyl)-2,6-diazaspiro[3.4]octan-6-yl)-6,6a,7,7a-tetrahydro-5H-cyclopropa[h]quinoline-3-carbonitrile or (6aS, 7aR)-4-(1,6-dimethyl-1H-indazol-7-yl)-2-(2-(2-propenoyl)-2,6-diazaspiro[3.4]octan-6-yl)-6,6a,7,7a-tetrahydro-5H-cyclopropa[h]quinoline-3-carbonitrile;

(M)-(1s,9s)-6-(1,6-dimethyl-1H-indazol-7-yl)-4-(2-(2-propanoyl)-2,6-diazaspiro[3.4]octan-6-yl)-3-azatricyclo [7.1.1.$0^{2,7}$]undeca-2,4,6-triene-5-carbonitrile;

(P)-(1s,9s)-6-(5-hydroxy-2-methylphenyl)-4-(2-(2-propenoyl)-2,6-diazaspiro[3.4]octan-6-yl)-3-azatricyclo [7.1.1.$0^{2,7}$]udeca-2,4,6-triene-5-carbonitrile;

(P)-4-(5-hydroxy-2-methylphenyl)-7,7-dimethyl-2-(2-(2-propenoyl)-2,6-diazaspiro[3.4]octan-6-yl)-7,8-dihydro-51H-pyrano[4,3-b]pyridine-3-carbonitrile;

(P)-(1R,9R)-6-(3-hydroxy-1-naphthalenyl)-10,10-dimethyl-4-(2-(2-propenoyl)-2,6-diazaspiro[3.4]octan-6-yl)-3-azatricyclo[7.1.1.$0^{2,7}$]undeca-2,4,6-triene-5-carbonitrile;

(1s,9s)-3-(1,6-dimethyl-1H-indazol-7-yl)-5-(2-(2-propenoyl)-2,6-diazaspiro[3.4]octan-6-yl)-6-azatricyclo [7.1.1.$0^{2,7}$]undeca-2,4,6-triene-4-carbonitrile;

(M)-(1 s,9s)-3-(1,6-dimethyl-1H-indazol-7-yl)-5-(2-(2-propenoyl)-2,6-diazaspiro[3.4]octan-6-yl)-6-azatricyclo [7.1.1.$0^{2,7}$]undeca-2,4,6-triene-4-carbonitrile;

(M)-(6aR,7aS)-4-(1,6-dimethyl-1H-indazol-7-yl)-2-(2-(2-propenoyl)-2,6-diazaspiro[3.4]octan-6-yl)-6,6a,7,7a-tetrahydro-51H-cyclopropa[h]quinoline-3-carbonitrile;

(M)-(6aS,7aR)-4-(1,6-dimethyl-1H-indazol-7-yl)-2-(2-(2-propenoyl)-2,6-diazaspiro[3.4]octan-6-yl)-6,6a,7,7a-tetrahydro-5H-cyclopropa[h]quinoline-3-carbonitrile 4-(1,6-dimethyl-1H-indazol-7-yl)-7,7-dimethyl-2-2(2-propenoyl)-2,6-diazaspiro[3.4]octan-6-yl)-5,6,7,8-tetrahydro-3-quinolinecarbonitrile;

4-(5-chloro-1H-indazol-4-yl)-7,7-dimethyl-2-(2-(2-propenoyl)-2,6-diazaspiro[3.4]octan-6-yl)-5,6,7,8-tetrahydro-3-quinolinecarbonitrile;

(P)-4-(1,6-dimethyl-1H-indazol-7-yl)-7,7-dimethyl-2-(2-(2-propenoyl)-2,6-diazaspiro[3.4]octan-6-yl)-5,6,7,8-tetrahydro-3-quinolinecarbonitrile;

4-(7-fluoro-5-methyl-1H-indazol-4-yl)-7,7-dimethyl-2-(2-(2-propenoyl)-2,6-diazaspiro[3.4]octan-6-yl)-5,6,7,8-tetrahydro-3-quinolinecarbonitrile;

4-(7-fluoro-5-methyl-1H-indazol-4-yl)-7,7-dimethyl-2-(2-(2-propenoyl)-2,6-diazaspiro[3.4]octan-6-yl)-7,8-dihydro-5H-1-pyrano[4,3-b]pyridine-3-carbonitrile;

4-(5-chloro-1H-indazol-4-yl)-7,7-dimethyl-2-(2-(2-propanoyl)-2,6-diazaspiro[3.4]octan-6-yl)-7,8-dihydro-5H-pyrano[4,3-b]pyridine-3-carbonitrile;

7,7-dimethyl-4-(5-methyl-1H-pyrazolo[3,4-b]pyridin-4-yl)-2-(2-(2-propenoyl)-2,6-diazaspiro[3.4]octan-6-yl)-5,6,7,8-tetrahydro-3-quinolinecarbonitrile;

4-(2-chloro-5-hydroxy-3-methylphenyl)-7,7-dimethyl-2-(2-(2-propenoyl)-2,6-diazaspiro[3.4]octan-6-yl)-7,8-dihydro-5H-pyrano[4,3-b]pyridine-3-carbonitrile;

4-(2-amino-3,5-dichloro-6-fluorophenyl)-7,7-dimethyl-2-(2-(2-propenoyl)-2,6-diazaspiro[3.4]octan-6-yl)-7,8-dihydro-5H-pyrano[4,3-b]pyridine-3-carbonitrile;

(P)-4-(2-amino-3,5-dichloro-6-fluorophenyl)-7,7-dimethyl-2-(2-(2-propenoyl)-2,6-diazaspiro[3.4]octan-6-yl)-7,8-dihydro-5H-pyrano[4,3-b]pyridine-3-carbonitrile;

1-(6-((1R,9R)-5-fluoro-6-(3-hydroxy-1-naphthalenyl)-10,10-dimethyl-3-azatricyclo[7.1.1.$0^{2,7}$]undeca-2,4,6-trien-4-yl)-2,6-diazaspiro[3.4]octan-2-yl)-2-propen-1-one;

4-(6-fluoro-5-methyl-1H-indazol-4-yl)-2-(2-(2-propenoyl)-2,6-diazaspiro[3.4]octan-6-yl)-3-quinolinecarbonitrile;

(1 S,8R)-6-(5-methyl-1H-indazol-4-yl)-4-(2-(2-propenoyl)-2,6-diazaspiro[3.4]octan-6-yl)-3-azatricyclo[6.2.$0^{2,7}$]undeca-2,4,6-triene-5-carbonitrile;

(1R,8S)-6-(5-methyl-1H-indazol-4-yl)-4-(2-(2-propenoyl)-2,6-diazaspiro[3.4]octan-6-yl)-3-azatricyclo[6.2.1.$0^{2,7}$] undeca-2,4,6-triene-5-carbonitrile;

(P)-(1S,8R)-6-(5-methyl-1H-indazol-4-yl)-4-(2-(2-propenoyl)-2,6-diazaspiro[3.4]octan-6-yl)-3-azatricyclo [6.2.1.$0^{2,7}$]undeca-2,4,6-triene-5-carbonitrile;

(1R,8S)-6-(5-hydroxy-2-methylphenyl)-4-(2-(2-propenoyl)-2,6-diazaspiro[3.4]octan-6-yl)-3-azatricyclo [6.2.1.$0^{2,7}$]undeca-2,4,6-triene-5-carbonitrile;

(P)-(1 S,8R)-6-(5-hydroxy-2-methylphenyl)-4-(2-(2-propanoyl)-2,6-diazaspiro[3.4]octan-6-yl)-3-azatricyclo [6.2.1.$0^{2,7}$]undeca-2,4,6-triene-5-carbonitrile;

(P)-(1R,8S)-6-(5-hydroxy-2-methylphenyl)-4-(2-(2-propenoyl)-2,6-diazaspiro[3.4]octan-6-yl)-3-azatricyclo [6.2.1.$0^{2,7}$]undeca-2,4,6-triene-5-carbonitrile;

(1 S,8R)-6-(1,6-dimethyl-1H-indazol-7-yl)-4-(2-(2-propenoyl)-2,6-diazaspiro[3.4]octan-6-yl)-3-azatricyclo [6.2.1.$0^{2,7}$]undeca-2,4,6-triene-5-carbonitrile;

(P)-(1S,8R)-6-(1,6-dimethyl-1H-indazol-7-yl)-4-(2-(2-propenoyl)-2,6-diazaspiro[3.4]octan-6-yl)-3-azatricyclo [6.2.1.$0^{2,7}$]undeca-2,4,6-triene-5-carbonitrile;

4-(6-chloro-5-methyl-1H-indazol-4-yl)-2-(2-(2-propenoyl)-2,6-diazaspiro[3.4]octan-6-yl)-3-quinolinecarbonitrile;

7-cyclopropyl-4-(5-methyl-1H-indazol-4-yl)-2-(2-(2-propenoyl)-2,6-diazaspiro[3.4]octan-6-yl)-3-quinolinecarbonitrile;

2-(8,8-difluoro-2-(2-propenoyl)-2,6-diazaspiro[3.4]octan-6-yl)-7-methoxy-4-(5-methyl-1H-indazol-4-yl)-3-quinolinecarbonitrile;

7-methoxy-4-(5-methyl-1H-indazol-4-yl)-2-((5R)-5-methyl-2-(2-propenoyl)-2,6-diazaspiro[3.4]octan-6-yl)-3-quinolinecarbonitrile or 7-methoxy-4-(5-methyl-1H-indazol-4-yl)-2-((5S)-5-methyl-2-(2-propenoyl)-2,6-diazaspiro[3.4]octan-6-yl)-3-quinolinecarbonitrile;

1-(6-(3,7,7-trimethyl-4-(5-methyl-1H-indazol-4-yl)-7,8-dihydro-5H-pyrano[4,3-b]pyridin-2-yl)-2,6-diazaspiro[3.4]octan-2-yl)-2-propen-1-one;

(1R,9R)-6-(1H-indazol-7-yl)-10,10-dimethyl-4-(2-(2-propenoyl)-2,6-diazaspiro[3.4]octan-6-yl)-3-azatricyclo [7.1.1.$0^{2,7}$]undeca-2,4,6-triene-5-carbonitrile;

1-(6-(4-(3-hydroxy-1-naphthalenyl)-3,7,7-trimethyl-7,8-dihydro-5H-pyrano[4,3-b]pyridin-2-yl)-2,6-diazaspiro[3.4]octan-2-yl)-2-propen-1-one;

(P)-(1R,9R)-6-(1H-indazol-7-yl)-10,10-dimethyl-4-(2-(2-propenoyl)-2,6-diazaspiro[3.4]octan-6-yl)-3-azatricyclo[7.1.1.$0^{2,7}$]undeca-2,4,6-triene-5-carbonitrile;

(M)-1-(6-(4-(5-hydroxy-2-methylphenyl)-3,7,7-trimethyl-7,8-dihydro-5H-pyrano[4,3-b]pyridin-2-yl)-2,6-diazaspiro[3.4]octan-2-yl)-2-propen-1-one;

(P)-1-(6-(3,7,7-trimethyl-4-(5-methyl-1H-indazol-4-yl)-7,8-dihydro-5H-pyrano[4,3-b]pyridin-2-yl)-2,6-diazaspiro[3.4]octan-2-yl)-2-propen-1-one;

(P)-1-(6-(4-(2-amino-7-fluoro-1,3-benzothiazol-4-yl)-3,7,7-trimethyl-7,8-dihydro-5H-pyrano[4,3-b]pyridin-2-yl)-2,6-diazaspiro[3.4]octan-2-yl)-2-propen-1-one;

1-(6-(3,7,7-trimethyl-4-(1,5,6-trimethyl-1H-indazol-7-yl)-7,8-dihydro-5H-pyrano[4,3-b]pyridin-2-yl)-2,6-diazaspiro[3.4]octan-2-yl)-2-propen-1-one;

(P)-1-(6-(3,7,7-trimethyl-4-(1,5,6-trimethyl-1H-indazol-7-yl)-7,8-dihydro-5H-pyrano[4,3-b]pyridin-2-yl)-2,6-diazaspiro[3.4]octan-2-yl)-2-propen-1-one;

1-(6-(4-(6-hydroxy-1-naphthalenyl)-3,7,7-trimethyl-7,8-dihydro-5H-pyrano[4,3-b]pyridin-2-yl)-2,6-diazaspiro[3.4]octan-2-yl)-2-propen-1-one;

(P)-1-(6-(4-(6-hydroxy-1-naphthalenyl)-3,7,7-trimethyl-7,8-dihydro-5H-pyrano[4,3-b]pyridin-2-yl)-2,6-diazaspiro[3.4]octan-2-yl)-2-propen-1-one;

4-(2-chlorophenyl)-2-(2-(2-propenoyl)-2,6-diazaspiro[3.4]octan-6-yl)-7-(1,3,5-trimethyl-1H-pyrazol-4-yl)-3-quinolinecarbonitrile;

(1R,9R)-10,10-dimethyl-6-(6-methyl-1H-indazol-7-yl)-4-(2-(2-propenoyl)-2,6-diazaspiro[3.4]octan-6-yl)-3-azatricyclo[7.1.1.$0^{2,7}$]undeca-2,4,6-triene-5-carbonitrile;

1-(6-((1R,9R)-5-fluoro-6-(5-hydroxy-2-methylphenyl)-10,10-dimethyl-3-azatricyclo[7.1.1.$0^{2,7}$]undeca-2,4,6-trien-4-yl)-2,6-diazaspiro[3.4]octan-2-yl)-2-propen-1-one;

(M)-(1R,9R)-10,10-dimethyl-6-(6-methyl-1H-indazol-7-yl)-4-(2-(2-propenoyl)-2,6-diazaspiro[3.4]octan-6-yl)-3-azatricyclo[7.1.1.$0^{2,7}$]undeca-2,4,6-triene-5-carbonitrile;

4-(2-amino-7-fluoro-1,3-benzothiazol-4-yl)-7,7-dimethyl-2-(2-(2-propenoyl)-2,6-diazaspiro[3.4]octan-6-yl)-7,8-dihydro-5H-pyrano[4,3-b]pyridine-3-carbonitrile;

(P)-4-(2-amino-7-fluoro-1,3-benzothiazol-4-yl)-7,7-dimethyl-2-(2-(2-propenoyl)-2,6-diazaspiro[3.4]octan-6-yl)-7,8-dihydro-5H-pyrano[4,3-b]pyridine-3-carbonitrile;

(P)-1-(6-((1R,9R)-5-fluoro-6-(5-hydroxy-2-methylphenyl)-10,10-di methyl-3-azatricyclo[7.1.1.$0^{2,7}$]undeca-2,4,6-trien-4-yl)-2,6-diazaspiro[3.4]octan-2-yl)-2-propen-1-one;

1-(6-(3-fluoro-4-(3-hydroxy-1-naphthalenyl)-7,7-dimethyl-7,8-dihydro-5H-pyrano[4,3-b]pyridin-2-yl)-2,6-diazaspiro[3.4]octan-2-yl)-2-propen-1-one;

(P)-1-(6-(3-fluoro-4-(3-hydroxy-1-naphthalenyl)-7,7-dimethyl-7,8-dihydro-5H-pyrano[4,3-b]pyridin-2-yl)-2,6-diazaspiro[3.4]octan-2-yl)-2-propen-1-one;

1-(6-((1R,9R)-5-fluoro-10,10-dimethyl-6-(5-methyl-1H-indazol-4-yl)-3-azatricyclo[7.1.1.$0^{2,7}$]undeca-2,4,6-trien-4-yl)-2,6-diazaspiro[3.4]octan-2-yl)-2-propen-1-one;

(M)-1-(6-((1R,9R)-5-fluoro-10,10-dimethyl-6-(5-methyl-1H-indazol-4-yl)-3-azatricyclo[7.1.1.$0^{2,7}$]undeca-2,4,6-trien-4-yl)-2,6-diazaspiro[3.4]octan-2-yl)-2-propen-1-one;

(P)-1-(6-((1R,9R)-5-fluoro-6-(3-hydroxy-1-naphthalenyl)-10,10-dimethyl-3-azatricyclo[7.1.1.$0^{2,7}$]undeca-2,4,6-trien-4-yl)-2,6-diazaspiro[3.4]octan-2-yl)-2-propen-1-one;

(M)-1-(6-(4-(5-chloro-1,6-dimethyl-1H-indazol-7-yl)-3-fluoro-7,7-dimethyl-7,8-dihydro-5H-pyrano[4,3-b]pyridin-2-yl)-2,6-diazaspiro[3.4]octan-2-yl)-2-propen-1-one;

7,7-dimethyl-4-(6-methyl-1H-indazol-7-yl)-2-(2-(2-propanoyl)-2,6-diazaspiro[3.4]octan-6-yl)-7,8-dihydro-5H-pyrano[4,3-b]pyridine-3-carbonitrile;

(P)-7,7-dimethyl-4-(6-methyl-1H-indazol-7-yl)-2-(2-(2-propenoyl)-2,6-diazaspiro[3.4]octan-6-yl)-7,8-dihydro-5H-pyrano[4,3-b]pyridine-3-carbonitrile;

(1R,9R)-6-(2-chloro-4-fluoro-5-hydroxyphenyl)-10,10-dimethyl-4-(2-(2-propenoyl)-2,6-diazaspiro[3.4]octan-6-yl)-3-azatricyclo[7.1.1.$0^{2,7}$]undeca-2,4,6-triene-5-carbonitrile;

1-(6-(4-(5-chloro-6-methyl-1H-indazol-7-yl)-3-fluoro-7,7-dimethyl-7,8-dihydro-5H-1-pyrano[4,3-b]pyridin-2-yl)-2,6-diazaspiro[3.4]octan-2-yl)-2-propen-1-one;

4-(5-hydroxy-2-(trifluoromethyl)phenyl)-7,7-dimethyl-2-(2-(2-propenoyl)-2,6-diazaspiro[3.4]octan-6-yl)-7,8-dihydro-5H-pyrano[4,3-b]pyridine-3-carbonitrile;

1-(6-(4-(5-chloro-1,6-dimethyl-1H-indazol-7-yl)-3,7,7-trimethyl-7,8-dihydro-5H-pyrano[4,3-b]pyridin-2-yl)-2,6-diazaspiro[3.4]octan-2-yl)-2-propen-1-one;

(P)-1-(6-(4-(5-chloro-1,6-dimethyl-1H-indazol-7-yl)-3,7,7-trimethyl-7,8-dihydro-5H-pyrano[4,3-b]pyridin-2-yl)-2,6-diazaspiro[3.4]octan-2-yl)-2-propen-1-one;

4-(5-chloro-1,6-dimethyl-1H-indazol-7-yl)-2-(2-(2-propenoyl)-2,6-diazaspiro[3.4]octan-6-yl)-3-quinolinecarbonitrile;

4-(5-chloro-6-methyl-1H-indazol-7-yl)-7,7-dimethyl-2-(2(2-propenoyl)-2,6-diazaspiro[3.4]octan-6-yl)-7,8-dihydro-5H-pyrano[4,3-b]pyridine-3-carbonitrile;

4-(5-chloro-1,6-dimethyl-1H-indazol-7-yl)-7,7-dimethyl-2-(2-(2-propenoyl)-2,6-diazaspiro[3.4]octan-6-yl)-7,8-dihydro-5H-pyrano[4,3-b]pyridine-3-carbonitrile;

1-(6-((7R)-4-(2,4-difluorophenyl)-7-(1,4-dimethyl-1H-pyrazol-5-yl)-3-methyl-5,6,7,8-tetrahydro-2-quinolinyl)-2,6-diazaspiro[3.4]octan-2-yl)-2-propen-1-one;

(P)-1-(6-((7R)-4-(1,6-dimethyl-1H-indazol-7-yl)-7-(1,4-dimethyl-1H-pyrazol-5-yl)-3-methyl-5,6,7,8-tetrahydro-2-quinolinyl)-2,6-diazaspiro[3.4]octan-2-yl)-2-propen-1-one;

(M)-1-(6-(4-(3-hydroxy-1-naphthalenyl)-3,7,7-trimethyl-7,8-dihydro-5H-pyrano[4,3-b]pyridin-2-yl)-2,6-diazaspiro[3.4]octan-2-yl)-2-propen-1-one;

1-(6-(4-(6-chloro-1,5-dimethyl-1H-indazol-7-yl)-3,7,7-trimethyl-7,8-dihydro-5H-pyrano[4,3-b]pyridin-2-yl)-2,6-diazaspiro[3.4]octan-2-yl)-2-propen-1-one;

2-amino-7-fluoro-4-(3,7,7-trimethyl-2-(2-(2-propenoyl)-2,6-diazaspiro[3.4]octan-6-yl)-7,8-dihydro-5H-pyrano[4,3-b]pyridin-4-yl)-1-benzothiophene-3-carbonitrile;

(M)-1-(6-(4-(5-chloro-1,6-dimethyl-1H-indazol-7-yl)-3-fluoro-7-(3-oxetanyl)-5,6,7,8-tetrahydro-1,7-naphthyridin-2-yl)-2,6-diazaspiro[3.4]octan-2-yl)-2-propen-1-one;

(P)-1-(6-(4-(1,6-dimethyl-1H-indazol-7-yl)-3,7,7-trimethyl-7,8-dihydro-5H-pyrano[4,3-b]pyridin-2-yl)-2,6-diazaspiro[3.4]octan-2-yl)-2-propen-1-one;

4-(5-methyl-1H-indazol-4-yl)-7-(1-methyl-1H-pyrazol-5-yl)-2-(2-(2-propenoyl)-2,6-diazaspiro[3.4]octan-6-yl)-3-quinolinecarbonitrile;

1-(6-(3-methyl-4-(5-methyl-1H-indazol-4-yl)-7-(4-methyl-1,3-thiazol-5-yl)-2-quinolinyl)-2,6-diazaspiro[3.4]octan-2-yl)-2-propen-1-one;

4-(2-chlorophenyl)-7-(1-methyl-1H-indazol-2-yl)-2-(2-(2-propenoyl)-2,6-diazaspiro[3.4]octan-6-yl)-3-quinolinecarbonitrile;

1-(6-(4-(2-chloro-5-hydroxyphenyl)-3-methyl-7-(1-methyl-1H-pyrazol-5-yl)-2-quinolinyl)-2,6-diazaspiro[3.4]octan-2-yl)-2-propen-1-one;

4-(2-chlorophenyl)-2-(8,8-difluoro-2-(2-propenoyl)-2,6-diazaspiro[3.4]octan-6-yl)-7-(1-methyl-1H-pyrazol-5-yl)-3-quinolinecarbonitrile;

4-(2-chlorophenyl)-7-(2-methyl-1H-imidazol-1-yl)-2(2-(2-propenoyl)-2,6-diazaspiro[3.4]octan-6-yl)-3-quinolinecarbonitrile;

4-(2-fluorophenyl)-7-(2-methyl-1H-imidazol-1-lv)-2-(2-(2-propenoyl)-2,6-diazaspiro[3.4]octan-6-yl)-3-quinolinecarbonitrile;

4-(2-fluorophenyl)-7-(5-methyl-1H-imidazol-1-yl)-2-(2-(2-propenoyl)-2,6-diazaspiro[3.4]octan-6-yl)-3-quinolinecarbonitrile;

4-(2-chlorophenyl)-7-(5-methyl-1H-imidazol-1-yl)-2-(2-(2-propenoyl)-2,6-diazaspiro[3.4]octan-6-yl)-3-quinolinecarbonitrile;

1-(6-(4-(6-hydroxy-1-naphthalenyl)-3-methyl-7-(2-propanyl)-5,6,7,8-tetrahydro-1,7-naphthyridin-2-yl)-2,6-diazaspiro[3.4]octan-2-yl)-2-propen-1-one;

(P)-1-(6-(4-(6-hydroxy-1-naphthalenyl)-3-methyl-7-(2-propanyl)-5,6,7,8-tetrahydro-1,7-naphthyridin-2-yl)-2,6-diazaspiro[3.4]octan-2-yl)-2-propen-1-one;

1-(6-(4-(6-hydroxy-1-naphthalenyl)-3,7-dimethyl-5,6,7,8-tetrahydro-1,7-naphthyridin-2-yl)-2,6-diazaspiro[3.4]octan-2-yl)-2-propen-1-one;

1-(6-(4-(6-hydroxy-1-naphthalenyl)-3-methyl-7-(3-oxetanyl)-5,6,7,8-tetrahydro-1,7-naphthyridin-2-yl)-2,6-diazaspiro[3.4]octan-2-yl)-2-propen-1-one;

1-(6-(4-(6-hydroxy-1-naphthalenyl)-7-((2R)-1-methoxy-2-propanyl)-3-methyl-5,6,7,8-tetrahydro-1,7-naphthyridin-2-yl)-2,6-diazaspiro[3.4]octan-2-yl)-2-propen-1-one or 1-(6-(4-(6-hydroxy-1-naphthalenyl)-7-((2S)-1-methoxy-2-propanyl)-3-methyl-5,6,7,8-tetrahydro-1,7-naphthyridin-2-yl)-2,6-diazaspiro[3.4]octan-2-yl)-2-propen-1-one;

1-(6-(4-(2-fluoro-5-hydroxyphenyl)-3-methyl-7-(4-methyl-1,3-thiazol-5-yl)-5,6,7,8-tetrahydro-1,7-naphthyridin-2-yl)-2,6-diazaspiro[3.4]octan-2-yl)-2-propen-1-one;

1-(6-(7-cyclopropyl-4-(6-hydroxy-1-naphthalenyl)-3-methyl-5,6,7,8-tetrahydro-1,7-naphthyridin-2-yl)-2,6-diazaspiro[3.4]octan-2-yl)-2-propen-1-one;

1-(6-(4-(6-hydroxy-1-naphthalenyl)-3-methyl-7-((2R)-3,3,3-trifluoro-2-hydroxypropyl)-5,6,7,8-tetrahydro-1,7-naphthyridin-2-yl)-2,6-diazaspiro[3.4]octan-2-yl)-2-propen-1-one or 1-(6-(4-(6-hydroxy-1-naphthalenyl)-3-methyl-7-((2S)-3,3,3-trifluoro-2-hydroxypropyl)-5,6,7,8-tetrahydro-1,7-napthyridine-2-yl)-2,6-diazaspiro[3.4]octan-2-yl)-2-propen-1-one;

1-(6-(3-methyl-4-(5-methyl-1H-indazol-4-yl)-7-(2-propanyl)-5,6,7,8-tetrahydro-1,7-naphthyridin-2-yl)-2,6-diazaspiro[3.4]octan-2-yl)-2-propen-1-one;

4-(2,3-dimethylphenyl)-7-(4-methyl-1,3-thiazol-5-yl)-2-(2-(2-propenoyl)-2,6-diazaspiro[3.4]octan-6-yl)-1,5-naphthyridine-3-carbonitrile;

4-(2-methylphenyl)-7-(4-methyl-1,3-thiazol-5-yl)-2-(2-(2-propanoyl)-2,6-diazaspiro[3.4]octan-6-yl)-3-quinolinecarbonitrile;

4-(2-fluoro-6-hydroxyphenyl)-7-(4-methyl-1,3-thiazol-5-yl)-2-(2-(2-propenoyl)-2,6-diazaspiro[3.4]octan-6-yl)-3-quinolinecarbonitrile;

(P)-4-(2-fluoro-6-hydroxyphenyl)-7-(4-methyl-1,3-thiazol-5-yl)-2-(2-(2-propenoyl)-2,6-diazaspiro[3.4]octan-6-yl)-3-quinolinecarbonitrile;

4-(2,4-difluorophenyl)-7-(4-methyl-1,3-thiazol-5-yl)-2-(2-(2-propenoyl)-2,6-diazaspiro[3.4]octan-6-yl)-1,5-naphthyridine-3-carbonitrile;

4-(2-chlorophenyl)-7-(2-(hydroxymethyl)-4-methyl-1,3-thiazol-5-yl)-2-(2-(2-propenoyl)-2,6-diazaspiro[3.4]octan-6-yl)-1,5-naphthyridine-3-carbonitrile;

4-(2-fluorophenyl)-7-(4-(hydroxyethyl)-1,3-thiazol-5-yl)-2-(2-(2-propenoyl)-2,6-diazaspiro[3.4]octan-6-yl)-1,5-naphthyridine-3-carbonitrile:

(P)-4-(2-methylphenyl)-7-(4-methyl-1,3-thiazol-5-yl)-2-(2-(2-propenoyl)-2,6-diazaspiro[3.4]octan-6-yl)-3-quinolinecarbonitrile;

(M)-4-(2-methylphenyl)-7-(4-methyl-1,3-thiazol-5-yl)-2-(2-(2-propenoyl)-2,6-diazaspiro[3.4]octan-6-yl)-3-quinolinecarbonitrile;

(M)-4-(2,3-dimethylphenyl)-7-(4-methyl-1,3-thiazol-5-yl)-2-(2-(2-propenoyl)-2,6-diazaspiro[3.4]octan-6-yl)-1,5-naphthyridine-3-carbonitrile;

(P)-4-(2,3-dimethylphenyl)-7-(4-methyl-1,3-thiazol-5-yl)-2-(2-(2-propenoyl)-2,6-diazaspiro[3.4]octan-6-yl)-1,5-naphthyridine-3-carbonitrile;

4-(2-chlorophenyl)-7-(4-methyl-1,3-thiazol-5-yl)-2-(2-(2-propenoyl)-2,6-diazaspiro[3.4]octan-6-yl)-3-quinolinecarbonitrile;

4-(2-fluorophenyl)-7-(4-methyl-1,3-thiazol-5-yl)-2-(2-(2-propenoyl)-2,6-diazaspiro[3.4]octan-6-yl)-3-quinolinecarbonitrile;

(P)-4-(2-chlorophenyl)-7-(4-methyl-1,3-thiazol-5-yl)-2-(2-(2-propanoyl)-2,6-diazaspiro[3.4]octan-6-yl)-3-quinolinecarbonitrile;

4-(2,3-dimethylphenyl)-7-(4-methyl-1,3-thiazol-5-yl)-2-(2-(2-propenoyl)-2,6-diazaspiro[3.4]octant-6-yl)-3-quinolinecarbonitrile;

4-(2-chlorophenyl)-7-(4-methyl-1,3-thiazol-5-yl)-2-(2-(2-propenoyl)-2,6-diazaspiro[3.4]octan-6-yl)-1,5-naphthyridine-3-carbonitrile;

(M)-4-(2-chlorophenyl)-7-(4-methyl-1,3-thiazol-5-yl)-2-(2-(2-propenoyl)-2,6-diazaspiro[3.4]octan-6-yl)-1,5-naphthyridine-3-carbonitrile;

(P)-4-(2-chlorophenyl)-7-(4-methyl-1,3-thiazol-5-yl)-2-(2-(2-propenoyl)-2,6-diazaspiro[3.4]octan-6-yl)-1,5-naphthyridine-3-carbonitrile;

4-(2,4-difluorophenyl)-7-(4-methyl-1,3-thiazol-5-yl)-2-(2-(2-propanoyl)-2,6-diazaspiro[3.4]octan-6-yl)-3-quinolinecarbonitrile;

4-(2-fluorophenyl)-7-(4-methyl-1,3-thiazol-5-yl)-2-(2-(2-propenoyl)-2,6-diazaspiro[3.4]octan-6-yl)-1,5-naphthyridine-3-carbonitrile:

4-(2-fluorophenyl)-7-(4-(methoxymethyl)-1,3-thiazol-5-yl)-2-(2-(2-propenoyl)-2,6-diazaspiro[3.4]octan-6-yl)-3-quinolinecarbonitrile;

4-(2-fluorophenyl)-7-(4-(hydroxymethyl)-1,3-thiazol-5-yl)-2-(2-(2-propenoyl)-2,6-diazaspiro[3.4]octan-6-yl)-3-quinolinecarbonitrile;

4-(2-fluorophenyl)-7-(4-methyl-1,3-thiazol-5-yl)-2-(2-(2-propenoyl)-2,6-diazaspiro[3.4]octan-6-yl)-5,6,7,8-tetrahydro-1,7-naphthyridine-3-carbonitrile;

4-(2,4-difluorophenyl)-7-(4-methyl-1,3-thiazol-5-yl)-2-(2-(2-propenoyl)-2,6-diazaspiro[3.4]octan-6-yl)-5,6,7,8-tetrahydro-1,7-naphthyridine-3-carbonitrile;

(8R)-4-(2-fluorophenyl)-8-methyl-7-(4-methyl-1,3-thiazol-5-yl)-2-(2-(2-propenoyl)-2,6-diazaspiro[3.4]octan-6-yl)-5,6,7,8-tetrahydro-1,7-naphthyridine-3-carbonitrile or (8S)-4-(2-fluorophenyl)-8-methyl-7-(4-methyl-1,3-thiazol-5-yl)-2-(2-(2-propanoyl)-2,6-diazaspiro[3.4]octan-6-yl)-5,6,7,8-tetrahydro-1,7-naphthyridine-3-carbonitrile;

(8R)-4-(2-fluorophenyl)-8-methy-7-(4-methyl-1,3-thiazol-5-yl)-2-(2-(2-propenoyl)-2,6-diazaspiro[3.4]octan-6-yl)-5,6,7,8-tetrahydro-1,7-naphthyridine-3-carbonitrile;

4-(2,4-difluorophenyl)-7-(4-methoxyphenyl)-2-(2-(2-propenoyl)-2,6-diazaspiro[3.4]octan-6-yl)-5,6,7,8-tetrahydro-1,7-naphthyridine-3-carbonitrile;

4-(2-chlorophenyl)-7-(4-methyl-1,3-thiazol-5-yl)-2-(2-(2-propanoyl)-2,6-diazaspiro[3.4]octan-6-yl)-5,6,7,8-tetrahydro-1,7-naphthyridine-3-carbonitrile;

4-(2-chloro-5-hydroxyphenyl)-7-(4-methyl-1,3-thiazol-5-yl)-2-(2-(2-propenoyl)-2,6-diazaspiro[3.4]octan-6-yl)-5,6,7,8-tetrahydro-1,7-naphthyridine-3-carbonitrile;

4-(3-fluoro-2-hydroxyphenyl)-7-(4-methyl-1,3-thiazol-5-yl)-2-(2-(2-propenoyl)-2,6-diazaspiro[3.4]octan-6-yl)-5,6,7,8-tetrahydro-1,7-naphthyridine-3-carbonitrile;

4-(2,4-difluorophenyl)-2-((5S)-5-methyl-2-(2-propanoyl)-2,6-diazaspiro[3.4]octan-6-yl)-7-(4-methyl-1,3-thiazol-5-yl)-5,6,7,8-tetrahydro-1,7-naphthyridine-3-carbonitrile;

4-(2,4-difluorophenyl)-2-((5R)-5-methyl-2-(2-propenoyl)-2,6-diazaspiro[3.4]octan-6-yl)-7-(4-methyl-1,3-thiazol-5-yl)-5,6,7,8-tetrahydro-1,7-naphthyridine-3-carbonitrile;

4-(2-fluoro-5-hydroxyphenyl)-7-(4-methyl-1,3-thiazol-5-yl)-2-(2-(2-propenoyl)-2,6-diazaspiro[3.4]octan-6-yl)-5,6,7,8-tetrahydro-1,7-naphthyridine-3-carbonitrile;

(P)-4-(2-chlorophenyl)-7-(4-methyl-1,3-thiazol-5-yl)-2-(2-(2-propenoyl)-2,6-diazaspiro[3.4]octan-6-yl)-5,6,7,8-tetrahydro-1,7-naphthyridine-3-carbonitrile;

(M)-4-(2-chlorophenyl)-7-(4-methyl-1,3-thiazol-5-yl)-2-(2-(2-propenoyl)-2,6-diazaspiro[3.4]octan-6-yl)-5,6,7,8-tetrahydro-1,7-naphthyridine-3-carbonitrile;

(P)-4-(2-chloro-5-hydroxyphenyl)-7-(4-methyl-1,3-thiazol-5-yl)-2-(2-(2-propenoyl)-2,6-diazaspiro[3.4]octan-6-yl)-5,6,7,8-tetrahydro-1,7-naphthyridine-3-carbonitrile 4-(3-fluoro-2-pyridinyl)-7-(4-methyl-1,3-thiazol-5-yl)-2-(2-(($^2H_3$)-2-propenoyl)-2,6-diazaspiro[3.4]octan-6-yl)-5,6,7,8-tetrahydro-1,7-naphthyridine-3-carbonitrile;

7-cyclopropyl-4-(2-fluorophenyl)-2-(2-(2-propenoyl)-2,6-diazaspiro[3.4]octan-6-yl)-5,6,7,8-tetrahydro-1,7-naphthyridine-3-carbonitrile;

1-(6-((7R)-4-(2,3-dimethylphenyl)-7-(4-methyl-1,3-thiazol-5-yl)-5,6,7,8-tetrahydro-2-quinazolinyl)-2,6-diazaspiro[3.4]octan-2-yl)-2-propen-1-one;

(7R)-4-(2-methylphenyl)-7-(4-methyl-1,3-thiazol-5-yl)-2-(2-(2-propenoyl)-2,6-diazaspiro[3.4]octan-6-yl)-5,6,7,8-tetrahydro-3-quinolinecarbonitrile or (7S)-4-(2-methylphenyl)-7-(4-methyl-1,3-thiazol-5-yl)-2-(2-(2-propenoyl)-2,6-diazaspiro[3.4]octan-6-yl)-5,6,7,8-tetrahydro-3-quinolinecarbonitrile;

(M)-(7R)-4-(2-methylphenyl)-7-(4-methyl-1,3-thiazol-5-yl)-2-(2-(2-propenoyl)-2,6-diazaspiro[3.4]octan-6-yl)-5,6,7,8-tetrahydro-3-quinolinecarbonitrile;

(P)-(7S)-4-(2-methylphenyl)-7-(4-methyl-1,3-thiazol-5-yl)-2-(2-(2-propenoyl)-2,6-diazaspiro[3.4]octan-6-yl)-5,6,7,8-tetrahydro-3-quinolinecarbonitrile;

(P)-(7R)-4-(2-methylphenyl)-7-(4-methyl-1,3-thiazol-5-yl)-2-(2-(2-propenoyl)-2,6-diazaspiro[3.4]octan-6-yl)-5,6,7,8-tetrahydro-3-quinolinecarbonitrile;

(M)-(7S)-4-(2-methylphenyl)-7-(4-methyl-1,3-thiazol-5-yl)-2-(2-(2-propanoyl)-2,6-diazaspiro[3.4]octan-6-yl)-5,6,7,8-tetrahydro-3-quinolinecarbonitrile;

4-(2-fluorophenyl)-7-(4-methyl-1,3-thiazol-5-yl)-2-(2-(2-propanoyl)-2,6-diazaspiro[3.4]octan-6-yl)-5,6-dihydro-3-quinolinecarbonitrile;

4-(2-methylphenyl)-7-(4-methyl-1,3-thiazol-5-yl)-2-(2-(2-propenoyl)-2,6-diazaspiro[3.4]octan-6-yl)-5,6-dihydro-3-quinolinecarbonitrile;

(7S)-4-(2-fluorophenyl)-7-methyl-7-(4-methyl-1,3-thiazol-5-yl)-2-(2-(2-propanoyl)-2,6-diazaspiro[3.4]octan-6-yl)-5,6,7,8-tetrahydro-3-quinolinecarbonitrile;

(7R)-4-(2-fluorophenyl)-7-methyl-7-(4-methyl-1,3-thiazol-5-yl)-2-(2-(2-propenoyl)-2,6-diazaspiro[3.4]octan-6-yl)-5,6,7,8-tetrahydro-3-quinolinecarbonitrile;

4-(2-chlorophenyl)-7-(1-methyl-1H-pyrazol-5-yl)-2-(2-(2-propenoyl)-2,6-diazaspiro[3.4]octan-6-yl)-3-quinolinecarbonitrile;

(7R)-4-(2,4-difluorophenyl)-7-(4-methyl-1,3-thiazol-5-yl)-2-(2-(2-propenoyl)-2,6-diazaspiro[3.4]octan-6-yl)-7,8-dihydro-5H-pyrano[4,3-b]pyridine-3-carbonitrile or (7S)-4-(2,4-difluorophenyl)-7-(4-methyl-1,3-thiazol-5-yl)-2-(2-(2-propenoyl)-2,6-diazaspiro[3.4]octan-6-yl)-7,8-dihydro-5H-pyrano[4,3-b]pyridine-3-carbonitrile;

4-(2-chloro-4-fluorophenyl)-7-(4-methyl-1,3-thiazol-5-yl)-2-(2-(2-propenoyl)-2,6-diazaspiro[3.4]octan-6-yl)-5,6-dihydro-3-quinolinecarbonitrile;

4-(2-chlorophenyl)-7-(4-methyl-1,3-thiazol-5-yl)-2-(2-(2-propenoyl)-2,6-diazaspiro[3.4]octan-6-yl)-5,6-dihydro-3-quinolinecarbonitrile;

4-(2,4-difluorophenyl)-7-(4-methyl-1,3-thiazol-5-yl)-2-(2-(2-propenoyl)-2,6-diazaspiro[3.4]octan-6-yl)-5,6-dihydro-3-quinolinecarbonitrile;

(M)-4-(2-methylphenyl)-7-(4-methyl-1,3-thiazol-5-yl)-2-(2-(2-propenoyl)-2,6-diazaspiro[3.4]octan-6-yl)-5,6-dihydro-3-quinolinecarbonitrile;

(P)-4-(2-methylphenyl)-7-(4-methyl-1,3-thiazol-5-yl)-2-(2-(2-propenoyl)-2,6-diazaspiro[3.4]octan-6-yl)-5,6-dihydro-3-quinolinecarbonitrile:

(7R)-4-(2-chloro-4-fluorophenyl)-7-(4-methyl-1,3-thiazol-5-yl)-2-(2-(2-propenoyl)-2,6-diazaspiro[3.4]octan-6-yl)-7,8-dihydro-5H-pyrano[4,3-b]pyridine-3-carbonitrile;

4-(2-fluoro-6-hydroxyphenyl)-7-(4-methyl-1,3-thiazol-5-yl)-2-(2-(2-propenoyl)-2,6-diazaspiro[3.4]octan-6-yl)-5,6-dihydro-3-quinolinecarbonitrile;

4-(4-fluorophenyl)-7-(4-methyl-1,3-triazol-5-yl)-2-(2-(2-propanoyl)-2,6-diazaspiro[3.4]octan-6-yl)-5,6-dihydro-3-quinolinecarbonitrile;

(P)-4-(2-chloro-4-fluorophenyl)-7-(4-methyl-1,3-thiazol-5-yl)-2-(2-(2-propenoyl)-2,6-diazaspiro[3.4]octan-6-yl)-5,6-dihydro-3-quinolinecarbonitrile;

4-(2-chloro-6-hydroxyphenyl)-7-(4-methyl-1,3-thiazol-5-yl)-2-(2-(2-propenoyl)-2,6-diazaspiro[3.4]octan-6-yl)-5,6-dihydro-3-quinolinecarbonitrile;

4-(2-fluoro-5-methoxyphenyl)-7-(4-methyl-1,3-thiazol-5-yl)-2-(2-(2-propenoyl)-2,6-diazaspiro[3.4]octan-6-yl)-5,6-dihydro-3-quinolinecarbonitrile;

4-(2-hydroxyphenyl)-7-(4-methyl-1,3-thiazol-5-yl)-2-(2-(2-propenoyl)-2,6-diazaspiro[3.4]octan-6-yl)-5,6-dihydro-3-quinolinecarbonitrile;

(P)-4-(2-chlorophenyl)-7-(4-methyl-1,3-thiazol-5-yl)-2-(2-(2-propenoyl)-2,6-diazaspiro[3.4]octan-6-yl)-5,6-dihydro-3-quinolinecarbonitrile;

4-(2-chloro-5-hydroxyphenyl)-7-(4-methyl-1,3-thiazol-5-yl)-2-(2-(2-propenoyl)-2,6-diazaspiro[3.4]octan-6-yl)-5,6-dihydro-3-quinolinecarbonitrile;

4-(2,3-difluorophenyl)-7-(4-methyl-1,3-thiazol-5-yl)-2-(2-(2-propanoyl)-2,6-diazaspiro[3.4]octan-6-yl)-5,6-dihydro-3-quinolinecarbonitrile;

4-(2-fluoro-5-hydroxyphenyl)-7-(4-methyl-1,3-thiazol-5-yl)-2-(2-(2-propenoyl)-2,6-diazaspiro[3.4]octan-6-yl)-5,6-dihydro-3-quinolinecarbonitrile;

4-(2-fluoro-6-methylphenyl)-7-(4-methyl-1,3-thiazol-5-yl)-2-(2-(2-propenoyl)-2,6-diazaspiro[3.4]octan-6-yl)-5,6-dihydro-3-quinolinecarbonitrile;

(P)-4-(2-fluoro-6-hydroxyphenyl)-7-(4-methyl-1,3-thiazol-5-yl)-2-(2-(2-propanoyl)-2,6-diazaspiro[3.4]octan-6-yl)-5,6-dihydro-3-quinolinecarbonitrile;

4-(2-fluorophenyl)-7-(4-(methoxymethyl)-1,3-thiazol-5-yl)-2-(2-(2-propanoyl)-2,6-diazaspiro[3.4]octan-6-yl)-5,6-dihydro-3-quinolinecarbonitrile;

4-(3-fluoro-2-hydroxyphenyl)-7-(4-methyl-1,3-thiazol-5-yl)-2-(2-(2-propenoyl)-2,6-diazaspiro[3.4]octan-6-yl)-5,6-dihydro-3-quinolinecarbonitrile;

4-(3-hydroxyphenyl)-7-(4-methyl-1,3-thiazol-5-yl)-2-(2-2propenoyl)-2,6-diazaspiro[3.4]octan-6-yl)-5,6-dihydro-3-quinolinecarbonitrile;

4-(2-fluorophenyl)-7-(4-(hydroxymethyl)-1,3-thiazol-5-yl)-2-(2-(2-propenoyl)-2,6-diazaspiro[3.4]octan-6-yl)-5,6-dihydro-3-quinolinecarbonitrile;

(7R)-4-(3-fluoro-2-pyridinyl)-7-(4-methyl-1,3-thiazol-5-yl)-2-(2-(2-propanoyl)-2,6-diazaspiro[3.4]octan-6-yl)-5,6,7,8-tetrahydro-3-quinolinecarbonitrile or (7S)-4-(3-fluoro-2-pyridinyl)-7-(4-methyl-1,3-thiazol-5-yl)-2-(2-(2-propenoyl)-2,6-diazaspiro[3.4]octan-6-yl)-5,6,7,8-tetrahydro-3-quinolinecarbonitrile;

(7S)-4-(3-fluoro-2-pyridinyl)-7-(4-methyl-1,3-thiazol-5-yl)-2-(2-(2-propenoyl)-2,6-diazaspiro[3.4]octan-6-yl)-5,6,7,8-tetrahydro-3-quinolinecarbonitrile;

4-(2-chloro-5-(difluoromethyl)phenyl)-7-(4-methyl-1,3-thiazol-5-yl)-2-(2-(2-propenoyl)-2,6-diazaspiro[3.4]octan-6-yl)-5,6,7,8-tetrahydro-1,7-naphthyridine-3-carbonitrile;

(6R)-4-(5-methyl-1H-indazol-4-yl)-6-(2-propanyl)-2-(2-(2-propenoyl)-2,6-diazaspiro[3.4]octan-6-yl)-6,7-dihydro-5H-cyclopenta[b]pyridine-3-carbonitrile or (6S)-4-(5-methyl-1H-indazol-4-yl)-6-(2-propanyl)-2-(2-(2-propenoyl)-2,6-diazaspiro[3.4]octan-6-yl)-6,7-dihydro-5H-cyclopenta[b]pyridine-3-carbonitrile;

(P)-1-(6-(3-ethenyl-4-(5-methyl-1H-indazol-4-yl)-2-quinolinyl)-2,6-diazaspiro[3.4]octan-2-yl)-2-propen-1-one;

1-(6-(3-fluoro-7-methoxy-4-(5-methyl-1H-indazol-4-yl)-2-quinolinyl)-2,6-diazaspiro[3.4]octan-2-yl)-2-propen-1-one;

1-(6-(3-chloro-4-(5-methyl-1H-indazol-4-yl)-2-quinolinyl)-2,6-diazaspiro[3.4]octan-2-yl)-2-propen-1-one;

1-(6-(7-chloro-8-(5-methyl-1H-indazol-4-yl)-3,4-dihydro-2H-chromen-6-yl)-2,6-diazaspiro[3.4]octan-2-yl)-2-propen-1-one;

4-(2-fluoro-3-hydroxyphenyl)-7-(4-methyl-1,3-thiazol-5-yl)-2-(2-(2-propenoyl)-2,6-diazaspiro[3.4]octan-6-yl)-5,6,7,8-tetrahydro-1,7-naphthyridine-3-carbonitrile;

(P)-1-(6-(4-(1,6-dimethyl-1H-indazol-7-yl)-3-methyl-7-(3-methyl-3-oxetanyl)-5,6,7,8-tetrahydro-1,7-naphthyridin-2-yl)-2,6-diazaspiro[3.4]octan-2-yl)-2-propen-1-one;

(P)-7,7-dimethyl-4-(5-methyl-1H-indazol-4-yl)-2-(2-(2-propenoyl)-2,6-diazaspiro[3.4]octan-6-yl)-5,6,7,8-tetrahydro-3-quinolinecarbonitrile;

1-(6-(4-(3-hydroxy-1-naphthalenyl)-7,7-dimethyl-5,6,7,8-tetrahydro-2-quinazolinyl)-2,6-diazaspiro[3.4]octan-2-yl)-2-propen-1-one;

8-(5-methyl-1H-indazol-4-yl)-2-phenyl-6-(2-(2-propenoyl)-2,6-diazaspiro[3.4]octan-6-yl)imidazo[1,2-a]pyridine-7-carbonitrile;

7-methoxy-4-(5-methyl-1H-indazol-4-yl)-2-(2-(2-propenoyl)-2,6-diazaspiro[3.4]octan-6-yl)-3-quinolinecarbonitrile;

2-(2-acryloyl-2,6-diazaspiro[3.4]octan-6-yl)-7-methyl-4-(5-methyl-1H-indazol-4-yl)-5,6,7,8-tetrahydroquinoline-3-carbonitrile;

(7)-2-(8,8-difluoro-2-(2-propanoyl)-2,6-diazaspiro[3.4]octan-6-yl)-7-methyl-4-(5-methyl-1H-indazol-4-yl)-5,6,7,8-tetrahydro-3-quinolinecarbonitrile;

4-(5,6-dimethyl-1-H-indazol-4-yl)-2-(2-(2-propenoyl)-2,6-diazaspiro[3.4]octan-6-yl)-3-quinolinecarbonitrile; or 4-(5-methyl-1H-indazol-4-yl)-2-(2-(2-propenoyl)-2,6-diazaspiro[3.4]octan-6-yl)-5,6,7,8-tetrahydro-3-quinolinecarbonitrile.

Provided herein as Embodiment 84 is the compound according to Embodiment 1 or a pharmaceutically acceptable salt thereof, wherein the compound is 1-(6-(4-(3-hydroxy-1-naphthalenyl)-3,7,7-trimethyl-7,8-dihydro-5H-pyrano[4,3-b]pyridin-2-yl)-2,6-diazaspiro[3.4]octan-2-yl)-2-propen-1-one;

1-(6-(5-fluoro-6-(3-hydroxy-1-naphthalenyl)-10,10-dimethyl-3-azatricyclo[7.1.1.0$^{2,7}$]undeca-2,4,6-trien-4-yl)-2,6-diazaspiro[3.4]octan-2-yl)-2-propen-1-one;

1-(6-(3-chloro-4-(3-hydroxy-1-naphthalenyl)-7,7-dimethyl-7,8-dihydro-5H-pyrano[4,3-b]pyridin-2-yl)-2,6-diazaspiro[3.4]octan-2-yl)-2-propen-1-one;

1-(6-(4-(3-chloro-5-hydroxy-2-methylphenyl)-3,7,7-trimethyl-7,8-dihydro-5H-pyrano[4,3-b]pyridin-2-yl)-2,6-diazaspiro[3.4]octan-2-yl)-2-propen-1-one;

1-(6-(5-methyl-6-(1,5,6-trimethyl-1H-indazol-7-yl)-3-azatricyclo[6.2.1.0$^{2,7}$]undeca-2,4,6-trien-4-yl)-2,6-diazaspiro[3.4]octan-2-yl)-2-propen-1-one;

1-(6-(4-(5-chloro-1,6-dimethyl-1H-indazol-7-yl)-3,7,7-trimethyl-7,8-dihydro-5H-pyrano[4,3-b]pyridin-2-yl)-2,6-diazaspiro[3.4]octan-2-yl)-2-propen-1-one;

1-(6-(5-fluoro-10,10-dimethyl-6-(5-methyl-1H-indazol-4-yl)-3-azatricyclo[7.1.1.0]undeca-2,4,6-trien-4-yl)-2,6-diazaspiro[3.4]octan-2-yl)-2-propen-1-one;

1-(6-(3-fluoro-4-(3-hydroxy-1-naphthalenyl)-7,7-dimethyl-7,8-dihydro-5H-pyrano[4,3-b]pyridin-2-yl)-2,6-diazaspiro[3.4]octan-2-yl)-2-propen-1-one;

1-(6-(4-(5-chloro-1,6-dimethyl-1H-indazol-7-yl)-3-fluoro-7-(3-oxetanyl)-5,6,7,8-tetrahydro-1,7-naphthyridin-2-yl)-2,6-diazaspiro[3.4]octan-2-yl)-2-propen-1-one; or 1-(6-(4-(2,4-difluorophenyl)-7-(1,4-dimethyl-1H-pyrazol-5-yl)-3-methyl-5,6,7,8-tetrahydro-2-quinolinyl)-2,6-diazaspiro[3.4]octan-2-yl)-2-propen-1-one.

Provided herein as Embodiment 85 is the compound according to Embodiment 1 or a pharmaceutically acceptable salt thereof, wherein the compound is (M)-1-(6-(4-(3-hydroxy-1-naphthalenyl)-3,7,7-trimethyl-7,8-dihydro-5H-pyrano[4,3-b]pyridin-2-yl)-2,6-diazaspiro[3.4]octan-2-yl)-2-propen-1-one;

(P)-1-(6-((1R,9R)-5-fluoro-6-(3-hydroxy-1-naphthalenyl)-10,10-dimethyl-3-azatricyclo[7.1.1.0$^{2,7}$]undeca-2,4,6-trien-4-yl)-2,6-diazaspiro[3.4]octan-2-yl)-2-propen-1-one;

(P)-1-(6-(3-chloro-4-(3-hydroxy-1-naphthalenyl)-7,7-dimethyl-7,8-dihydro-5H-pyrano[4,3-b]pyridin-2-yl)-2,6-diazaspiro[3.4]octan-2-yl)-2-propen-1-one;

(M)-1-(6-(4-(3-chloro-5-hydroxy-2-methylphenyl)-3,7,7-trimethyl-7,8-dihydro-5H-pyrano[4,3-b]pyridin-2-yl)-2,6-diazaspiro[3.4]octan-2-yl)-2-propen-1-one;

(M)-1-(6-((1 S,8R)-5-methyl-6-(1,5,6-trimethyl-1H-indazol-7-yl)-3-azatricyclo[6.2.1.0$^{2,7}$]undeca-2,4,6-trien-4-yl)-2,6-diazaspiro[3.4]octan-2-yl)-2-propen-1-one;

(P)-1-(6-(4-(5-chloro-1,6-dimethyl-1H-indazol-7-yl)-3,7,7-trimethyl-7,8-dihydro-5H-pyrano[4,3-b]pyridin-2-yl)-2,6-diazaspiro[3.4]octan-2-yl)-2-propen-1-one;

(M)-1-(6-((1R,9R)-5-fluoro-10,10-dimethyl-6-(5-methyl-1H-indazol-4-yl)-3-azatricyclo[7.1.1.0$^{2,7}$]undeca-2,4,6-trien-4-yl)-2,6-diazaspiro[3.4]octan-2-yl)-2-propen-1-one;

(P)-1-(6-(3-fluoro-4-(3-hydroxy-1-naphthalenyl)-7,7-dimethyl-7,8-dihydro-5H-pyrano[4,3-b]pyridin-2-yl)-2,6-diazaspiro[3.4]octan-2-yl)-2-propen-1-one;

(M)-1-(6-(4-(5-chloro-1,6-dimethyl-1H-indazol-7-yl)-3-fluoro-7-(3-oxetanyl)-5,6,7,8-tetrahydro-1,7-naphthyridin-2-yl)-2,6-diazaspiro[3.4]octan-2-yl)-2-propen-1-one; or 1-(6-((7R)-4-(2,4-difluorophenyl)-7-(1,4-dimethyl-1H-pyrazol-5-yl)-3-methyl-5,6,7,8-tetrahydro-2-quinolinyl)-2,6-diazaspiro[3.4]octan-2-yl)-2-propen-1-one.

Provided herein as Embodiment 86 is the compound according to Embodiment 1 or a pharmaceutically acceptable salt thereof, wherein the compound is (P)-1-(6-(4-(3-hydroxy-1-naphthalenyl)-3,7,7-trimethyl-7,8-dihydro-5H-pyrano[4,3-b]pyridin-2-yl)-2,6-diazaspiro[3.4]octan-2-yl)-2-propen-1-one;

(M)-1-(6-((1R,9R)-5-fluoro-6-(3-hydroxy-1-naphthalenyl)-10,10-dimethyl-3-azatricyclo[7.1.1.0$^{2,7}$]undeca-2,4,6-trien-4-yl)-2,6-diazaspiro[3.4]octan-2-yl)-2-propen-1-one;

(P)-1-(6-((1S,9S)-5-fluoro-6-(3-hydroxy-1-naphthalenyl)-10,10-dimethyl-3-azatricyclo[7.1.1.0$^{2,7}$]undeca-2,4,6-trien-4-yl)-2,6-diazaspiro[3.4]octan-2-yl)-2-propen-1-one;

(M)-1-(6-((1 S,9S)-5-fluoro-6-(3-hydroxy-1-naphthalenyl)-10,10-dimethyl-3-azatricyclo[7.1.1.0$^{2,7}$]undeca-2,4,6-trien-4-yl)-2,6-diazaspiro[3.4]octan-2-yl)-2-propen-1-one;

(M)-1-(6-(3-chloro-4-(3-hydroxy-1-naphthalenyl)-7,7-dimethyl-7,8-dihydro-5H-pyrano[4,3-b]pyridin-2-yl)-2,6-diazaspiro[3.4]octan-2-yl)-2-propen-1-one;

(P)-1-(6-(4-(3-chloro-5-hydroxy-2-methylphenyl)-3,7,7-trimethyl-7,8-dihydro-5H-pyrano[4,3-b]pyridin-2-yl)-2,6-diazaspiro[3.4]octan-2-yl)-2-propen-1-one;

(P)-1-(6-((1S,8R)-5-methyl-6-(1,5,6-trimethyl-1H-indazol-7-yl)-3-azatricyclo[6.2.1.0$^{2,7}$]undeca-2,4,6-trien-4-yl)-2,6-diazaspiro[3.4]octan-2-yl)-2-propen-1-one;

(M)-1-(6-((1R,8S)-5-methyl-6-(1,5,6-trimethyl-1H-indazol-7-yl)-3-azatricyclo[6.2.1.0$^{2,7}$]undeca-2,4,6-trien-4-yl)-2,6-diazaspiro[3.4]octan-2-yl)-2-propen-1-one;

(P)-1-(6-((1R,8S)-5-methyl-6-(1,5,6-trimethyl-1H-indazol-7-yl)-3-azatricyclo[6.2.1.0$^{2,7}$]undeca-2,4,6-trien-4-yl)-2,6-diazaspiro[3.4]octan-2-yl)-2-propen-1-one;

(M)-1-(6-(4-(5-chloro-1,6-dimethyl-1H-indazol-7-yl)-3,7,7-trimethyl-7,8-dihydro-5H-pyrano[4,3-b]pyridin-2-yl)-2,6-diazaspiro[3.4]octan-2-yl)-2-propen-1-one;

(P)-1-(6-((1R,9R)-5-fluoro-10,10-di methyl-6-(5-methyl-1H-indazol-4-yl)-3-azatricyclo[7.1.1.0$^{2,7}$]undeca-2,4,6-trien-4-yl)-2,6-diazaspiro[3.4]octan-2-yl)-2-propen-1-one;

(M)-1-(6-((1S,9S)-5-fluoro-10,10-dimethyl-6-(5-methyl-1-indazol-4-yl)-3-azatricyclo[7.1.1.0$^{2,7}$]undeca-2,4,6-trien-4-yl)-2,6-diazaspiro[3.4]octan-2-yl)-2-propen-1-one;

(P)-1-(6-((1 S,9S)-5-fluoro-10,10-dimethyl-6-(5-methyl-1H-indazol-4-yl)-3-azatricyclo[7.1.1.0$^{2,7}$]undeca-2,4,6-trien-4-yl)-2,6-diazaspiro[3.4]octan-2-yl)-2-propen-1-one;

(M)-1-(6-(3-fluoro-4-(3-hydroxy-1-naphthalenyl)-7,7-dimethyl-7,8-dihydro-5H-pyrano[4,3-b]pyridin-2-yl)-2,6-diazaspiro[3.4]octan-2-yl)-2-propen-1-one;

(P)-1-6-4-(5-chloro-1,6-dimethyl-1H-indazol-7-yl)-3-fluoro-7-(3-oxetanyl)-5,6,7,8-tetrahydro-1,7-naphthyridin-2-yl)-2,6-diazaspiro[3.4]octan-2-yl)-2-propen-1-one; or 1-(6-((7S)-4-(2,4-difluorophenyl)-7-(1,4-dimethyl-1H-pyrazol-5-yl)-3-methyl-5,6,7,8-tetrahydro-2-quinolinyl)-2,6-diazaspiro[3.4]octan-2-yl)-2-propen-1-one.

Provided herein as Embodiment 87 is a compound of Formula I (I)

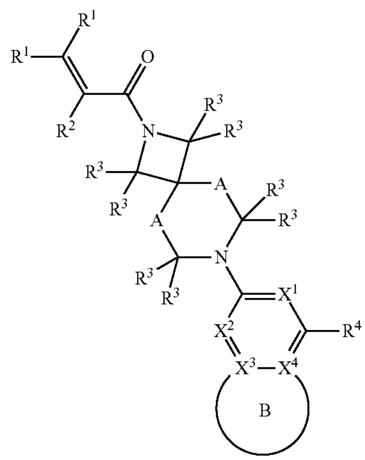

or a pharmaceutically acceptable salt thereof, wherein $R^1$ at each occurrence independently is H, $C_{1-4}$alkoxy, —$(CH_2)$—$C_{1-4}$dialkylamino, aziridin-1-yl-methyl, azetidin-1-yl-methyl, pyrrolidine-1-yl-methyl, piperidin-1-yl-methyl, or morpholin-1-yl-methyl;

$R^2$ is H, halogen, —CN, $C_{1-4}$alkyl, $C_{1-4}$haloalkyl, —$CH_2CN$, —$CH_2OH$, $C_{1-4}$alkoxy, or $C_{1-4}$haloalkoxy;

wherein, optionally, one $R^1$ and $R^2$ together with the carbon atoms to which they are attached form a

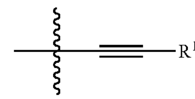

group;

$R^3$ at each occurrence independently is H, halogen, CN, OH, $C_{1-4}$alkyl, $C_{1-4}$haloalkyl, —$CH_2CN$, —$CH_2OH$, $C_{1-4}$alkoxy, or $C_{1-4}$haloalkoxy, wherein two substituents $R^3$ attached to the same carbon atom optionally form together with said carbon atom a $C_{3-6}$cycloalkyl or a carbonyl group;

A at each occurrence independently is $CR^3R^3$ or absent;

$R^4$ is 6 or 10 membered aryl or 5 to 10 membered heteroaryl, wherein the aryl or heteroaryl is optionally substituted with 1 to 3 substituents independently selected from OH, halogen, —CN, $NH_2$, $C_{1-4}$alkyl, $C_{1-4}$haloalkyl, $C_{1-4}$alkoxy, or $C_{1-4}$haloalkoxy;

$X^1$ is $CR^5$ or N;

$X^2$ is CH, CF, or N;

$X^3$ is C or N;

$X^4$ is C or N;

$R^5$ is H, halogen, CN, $C_{1-4}$alkyl, $C_{1-4}$haloalkyl, $C_{1-4}$alkoxy, $C_{1-4}$haloalkoxy, $C_{3-5}$ cycloalkyl, $C_{3-5}$cyclohaloalkyl, or $C_{3-5}$heterocycloalkyl;

B together with the atoms to which it is attached forms a 4 to 7 membered fully saturated, fully unsaturated, or partially unsaturated carbocyclic or heterocyclic ring system, wherein the heterocyclic ring system comprises 1 to 5 heteroatoms independently selected from N, O, and S, wherein the ring system is optionally substituted with 1 to 5 substituents $R^6$;

$R^6$ at each occurrence independently is halogen, OH, —CN, —$NH_2$, $C_{1-6}$alkyl, $C_{1-6}$haloalkyl, $C_{1-4}$alkoxy, $C_{1-4}$haloalkoxy, $C_{3-5}$cycloalkyl, $C_{3-5}$cyclohaloalkyl, phenyl, or 5 to 6 membered heteroaryl, wherein the $C_{1-6}$alkyl is optionally substituted with —CO($C_{1-4}$alkylamino) or —CO($C_{1-4}$dialkylamino), wherein the phenyl is optionally substituted with 1 to 3 independently selected halogens, wherein the heteroaryl is optionally substituted with 1 to 3 substituents selected from halogen, $C_{1-4}$alkyl, and $C_{1-4}$haloalkyl, wherein two substituents $R^6$ together optionally form a —$(CH_2)_n$— group creating a ring together with the ring atom or ring atoms to which the two substituents $R^6$ are attached, wherein the —$(CH_2)_n$— group optionally has one —CH, group substituted with one heteroatom selected from N, O, and S; and n is 1, 2, 3, or 4.

Provided herein as Embodiment 88 is the compound according to Embodiment 87 or a pharmaceutically acceptable salt thereof, wherein $R^4$ is not 2-fluoro-5-cyano-phenyl, 2-methyl-5-hydroxymethyl-phenyl, 2-chloro-5-(difluoromethoxy) phenyl, 2-methyl-5-(difluoromethyl)-phenyl, 6-amino-3-methyl-pyridin-2-yl, 6-hydroxy-2-methyl-naphthalen-1-yl, isoquinolin-4-yl, or 6-hydroxy-8-quinolinyl; or B is not selected from the group consisting of

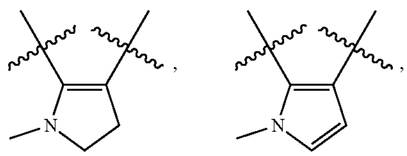

,

, unsubstituted

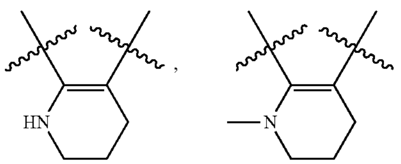

,

, and unsubstituted

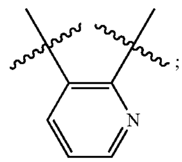 [SMILES: *c1cccnc1*]

;

or $R^6$ is not 3-chlorophenyl or 8-methylnaphthalen-1-yl.

Provided herein as Embodiment 89 is the compound according to Embodiment 87 or a pharmaceutically acceptable salt thereof, wherein the compound is not 1-(6-(4-(2-fluorophenyl)-7-methyl-7H-pyrrolo[2,3-d]pyrimidin-2-yl)-2,6-diazaspiro[3.4]octan-2-yl)-2-propen-1-one;

1-(6-(4-(2-fluorophenyl)-8-methyl-5,6,7,8-tetrahydropyrido[2,3-d]pyrimidin-2-yl)-2,6-diazaspiro[3.4]octan-2-yl)-2-propen-1-one;

1-(6-(7-methyl-4-(5-methyl-1H-indazol-4-yl)-6,7-dihydro-5H-pyrrolo[2,3-d]pyrimidin-2-yl)-2,6-diazaspiro[3.4]octan-2-yl)prop-2-en-1-one;

1-(6-(4-(2-fluorophenyl)-7-(8-methyl-1-naphthalenyl)-6,7-dihydro-5H-pyrrolo[2,3-d]pyrimidin-2-yl)-2,6-diazaspiro[3.4]octan-2-yl)-2-propen-1-one;

2-(2-acryloyl-2,6-diazaspiro[3.4]octan-6-yl)-4-(5-cyano-2-fluorophenyl)quinoline-3-carbonitrile;

1-(6-(4-(2-chloro-5-(difluoromethoxy)phenyl)-5,6,7,8-tetrahydro-2-quinazolinyl)-2,6-diazaspiro[3.4]octan-2-yl)-2-propen-1-one;

1-(6-(4-(2-fluorophenyl)-7-(8-methylnaphthalen-1-yl)-7H-pyrrolo[2,3-d]pyrimidin-2-yl)-2,6-diazaspiro[3.4]octan-2-yl)prop-2-en-1-one;

1-(6-(4-(4-isoquinolinyl)-5,6,7,8-tetrahydro-2-quinazolinyl)-2,6-diazaspiro[3.4]octan-2-yl)-2-propen-1-one;

1-(6-(4-(5-(difluoromethyl)-2-methylphenyl)-5,6,7,8-tetrahydro-2-quinazolinyl)-2,6-diazaspiro[3.4]octan-2-yl)-2-propen-1-one;

1-(6-(4-(5-(hydroxymethyl)-2-methylphenyl)-5,6,7,8-tetrahydro-2-quinazolinyl)-2,6-diazaspiro[3.4]octan-2-yl)-2-propen-1-one;

1-(6-(4-(5-methyl-1H-indazol-4-yl)-5,6,7,8-tetrahydropyrido[2,3-d]pyrimidin-2-yl)-2,6-diazaspiro[3.4]octan-2-yl)-2-propen-1-one;

1-(6-(4-(5-methyl-1-H-indazol-4-yl)pyrido[3,2-d]pyrimidin-2-yl)-2,6-diazaspiro[3.4]octan-2-yl)-2-propen-1-one;

1-(6-(4-(6-amino-3-methyl-2-pyridinyl)-5,6,7,8-tetrahydro-2-quinazolinyl)-2,6-diazaspiro[3.4]octan-2-yl)-2-propen-1-one;

1-(6-(4-(6-hydroxy-2-methyl-1-naphthalenyl)-5,6,7,8-tetrahydro-2-quinazolinyl)-2,6-diazaspiro[3.4]octan-2-yl)-2-propen-1-one;

1-(6-(4-(6-hydroxy-8-quinolinyl)-5,6,7,8-tetrahydro-2-quinazolinyl)-2,6-diazaspiro[3.4]octan-2-yl)-2-propen-1-one; or 1-(6-(8-(3-chlorophenyl)-4-(2-fluorophenyl)-5,6,7,8-tetrahydropyrido[2,3-d]pyrimidin-2-yl)-2,6-diazaspiro[3.4]octan-2-yl)-2-propen-1-one.

Provided herein as Embodiment 90 is the compound according to Embodiment 87 or a pharmaceutically acceptable salt thereof, wherein the compound has an $IC_{50}$ of less than 10 μM in the 2 h coupled exchange assay or the 20 h coupled exchange assay.

Provided herein as Embodiment 91 is the compound according to any one of Embodiments 87-90 or a pharmaceutically acceptable salt thereof, wherein $R^1$ is at each occurrence independently H or —$(CH_2)$—$C_{1-4}$dialkylamino.

Provided herein as Embodiment 92 is the compound according to any one of Embodiments 87-91 or a pharmaceutically acceptable salt thereof, wherein one $R^1$ is H and the other $R^1$ is —$(CH_2)$—$N(CH_3)_2$.

Provided herein as Embodiment 93 is the compound according to any one of Embodiments 87-91 or a pharmaceutically acceptable salt thereof, wherein each $R^1$ is H.

Provided herein as Embodiment 94 is the compound according to any one of Embodiments 87-90 or a pharmaceutically acceptable salt thereof, wherein one $R^1$ and $R^2$ together with the carbon atoms to which they are attached form a

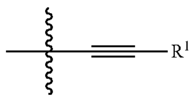

group.

Provided herein as Embodiment 95 is the compound according to any one of Embodiments 87-93 or a pharmaceutically acceptable salt thereof, wherein $R^2$ is H.

Provided herein as Embodiment 96 is the compound according to any one of Embodiments 87-95 or a pharmaceutically acceptable salt thereof, wherein $R^3$ at each occurrence independently is H, halogen, $C_{1-4}$haloalkyl, or two substituents $R^3$ attached to the same carbon atom form together with said carbon atom a carbonyl group.

Provided herein as Embodiment 97 is the compound according to any one of Embodiments 87-95 or a pharmaceutically acceptable salt thereof, wherein $R^3$ at each occurrence independently is H, F, $CHF_2$, or two substituents $R^3$ attached to the same carbon atom form together with said carbon atom a carbonyl group.

Provided herein as Embodiment 98 is the compound according to any one of Embodiments 87-97 or a pharmaceutically acceptable salt thereof, wherein one A is absent and the other A is $CR^3R^3$.

Provided herein as Embodiment 99 is the compound according to any one of Embodiments 87-97 or a pharmaceutically acceptable salt thereof, wherein both A are absent.

Provided herein as Embodiment 100 is the compound according to any one of Embodiments 87-95 or a pharmaceutically acceptable salt thereof, wherein

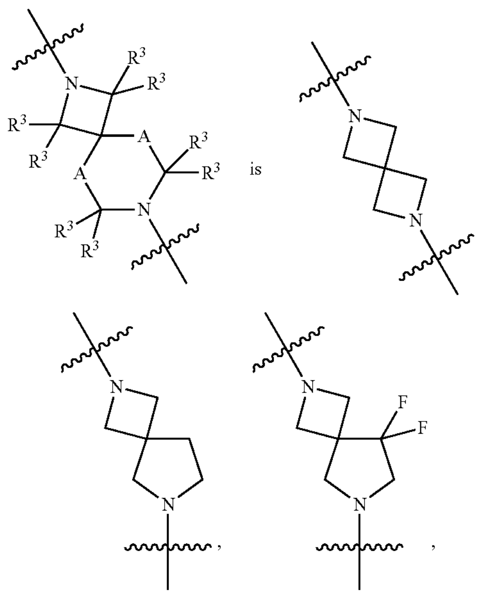

is , , ,

-continued

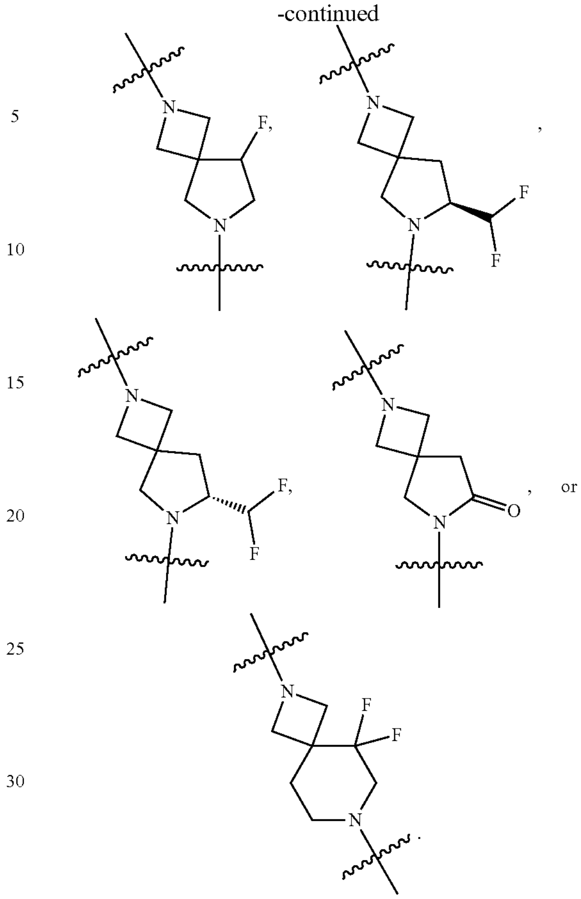

, , , or .

Provided herein as Embodiment 101 is the compound according to any one of Embodiments 87-95 or a pharmaceutically acceptable salt thereof, wherein

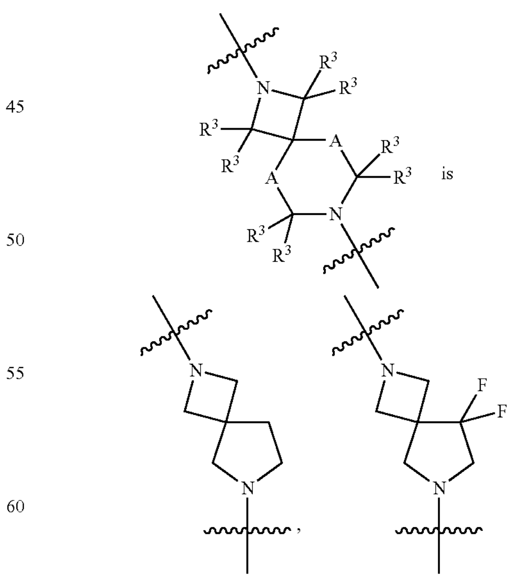

is , .

Provided herein as Embodiment 102 is the compound according to any one of Embodiments 87-101 or a pharmaceutically acceptable salt thereof, wherein $R^4$ is 6 or 10 membered aryl, wherein the aryl is optionally substituted with 1 to 2 substituents independently selected from OH, halogen, or $C_{1-4}$alkyl.

Provided herein as Embodiment 103 is the compound according to any one of Embodiments 87-101 or a pharmaceutically acceptable salt thereof, wherein $R^4$ is 6 or 10 membered aryl, wherein the aryl is optionally substituted with 1 to 2 substituents independently selected from OH, F, Cl, or methyl.

Provided herein as Embodiment 104 is the compound according to any one of Embodiments 87-101 or a pharmaceutically acceptable salt thereof, wherein $R^4$ is 6 or 10 membered aryl, wherein the aryl is optionally substituted with OH.

Provided herein as Embodiment 105 is the compound according to any one of Embodiments 87-101 or a pharmaceutically acceptable salt thereof, wherein $R^4$ is 2-fluorophenyl, 2-fluoro-5-hydroxyphenyl, 2,3-dichlorophenyl, 2-chloro-5-hydroxyphenyl, 2-chloro-3-methylphenyl, 2,3-dimethylphenyl, 5-hydroxy-2-methylphenyl, 3-hydroxynaphthalen-1-yl, 6-hydroxy-1-naphthalenyl, 8-methyl-1-naphthalenyl, 8-chloro-1-naphthalenyl, or 2-methyl-1-naphthalenyl.

Provided herein as Embodiment 106 is the compound according to any one of Embodiments 87-101 or a pharmaceutically acceptable salt thereof, wherein $R^4$ is 3-hydroxynaphthalen-1-yl.

Provided herein as Embodiment 107 is the compound according to any one of Embodiments 87-101 or a pharmaceutically acceptable salt thereof, wherein $R^4$ is 5 to 10 membered heteroaryl, wherein the heteroaryl is optionally substituted with 1 to 2 substituents independently selected from $NH_2$ or $C_{1-4}$alkyl.

Provided herein as Embodiment 108 is the compound according to any one of Embodiments 87-101 or a pharmaceutically acceptable salt thereof, wherein $R^4$ is 5 to 10 membered heteroaryl, wherein the heteroaryl is optionally substituted with 1 to 2 substituents independently selected from $NH_2$, methyl, ethyl, or isopropyl.

Provided herein as Embodiment 109 is the compound according to any one of Embodiments 87-101 or a pharmaceutically acceptable salt thereof, wherein $R^4$ is 5 to 10 membered heteroaryl, wherein the heteroaryl is optionally substituted with 1 or 2 methyl substituents.

Provided herein as Embodiment 110 is the compound according to any one of Embodiments 87-101 or a pharmaceutically acceptable salt thereof, wherein $R^4$ is 5-methyl-1H-indazol-4-yl, 5-ethyl-1-1H-indazol-4-yl, 6-methyl-1H-indazol-7-yl, 1,6-dimethyl-1H-indazol-7-yl, 3,5-dimethyl-1H-indazol-4-yl, 5,6-dimethyl-1H-indazol-4-yl, 5-(2-propanyl)-1H-indazol-4-yl, or 2-amino-1,3-benzothiazol-4-yl.

Provided herein as Embodiment 111 is the compound according to any one of Embodiments 87-101 or a pharmaceutically acceptable salt thereof, wherein $R^4$ is 5-methyl-1H-indazol-4-yl or 5,6-dimethyl-1H-indazol-4-yl.

Provided herein as Embodiment 112 is the compound according to any one of Embodiments 87-111 or a pharmaceutically acceptable salt thereof, wherein $X^1$ is $CR^5$.

Provided herein as Embodiment 113 is the compound according to any one of Embodiments 87-111 or a pharmaceutically acceptable salt thereof, wherein $X^1$ is N.

Provided herein as Embodiment 114 is the compound according to any one of Embodiments 87-113 or a pharmaceutically acceptable salt thereof, wherein $X^1$ is CH.

Provided herein as Embodiment 115 is the compound according to any one of Embodiments 87-113 or a pharmaceutically acceptable salt thereof, wherein $X^2$ is N.

Provided herein as Embodiment 116 is the compound according to any one of Embodiments 87-115 or a pharmaceutically acceptable salt thereof, wherein $X^3$ is C.

Provided herein as Embodiment 117 is the compound according to any one of Embodiments 87-115 or a pharmaceutically acceptable salt thereof, wherein $X^3$ is N.

Provided herein as Embodiment 118 is the compound according to any one of Embodiments 87-117 or a pharmaceutically acceptable salt thereof, wherein $X^4$ is C.

Provided herein as Embodiment 119 is the compound according to any one of Embodiments 87-117 or a pharmaceutically acceptable salt thereof, wherein $X^4$ is N.

Provided herein as Embodiment 120 is the compound according to any one of Embodiments 87-111 or a pharmaceutically acceptable salt thereof, wherein $X^1$ is N, $X^2$ is N, $X^3$ is C, and $X^4$ is C; or
$X^1$ is $CR^5$, $X^2$ is N, $X^3$ is C, and $X^4$ is C; or
$X^1$ is $CR^5$, $X^2$ is CH, $X^3$ is C, and $X^4$ is C; or
$X^1$ is $CR^5$, $X^2$ is CH, $X^3$ is N, and $X^4$ is C; or
$X^1$ is $CR^5$, $X^2$ is CH, $X^3$ is C, and $X^4$ is N.

Provided herein as Embodiment 121 is the compound according to any one of Embodiments 87-112 and 120 or a pharmaceutically acceptable salt thereof, wherein $R^1$ is H, CN, $C_{1-4}$alkyl, or $C_{3-5}$cycloalkyl.

Provided herein as Embodiment 122 is the compound according to any one of Embodiments 87-112 and 120 or a pharmaceutically acceptable salt thereof, wherein $R^1$ is H, CN, methyl, or cyclopropyl.

Provided herein as Embodiment 123 is the compound according to any one of Embodiments 87-112 and 120 or a pharmaceutically acceptable salt thereof, wherein $R^5$ is CN.

Provided herein as Embodiment 124 is the compound according to any one of Embodiments 87-115 and 121-123 or a pharmaceutically acceptable salt thereof, wherein B together with the atoms to which it is attached forms a ring system selected from

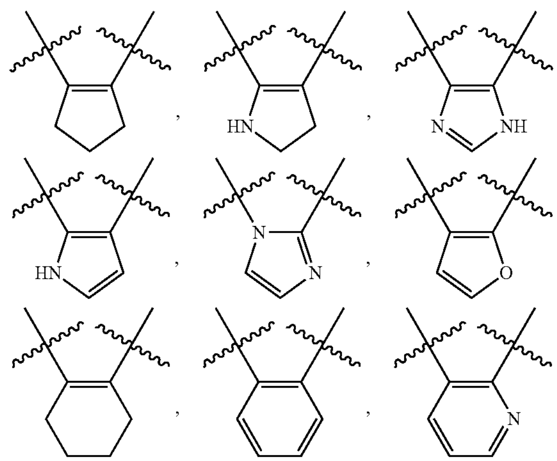

-continued

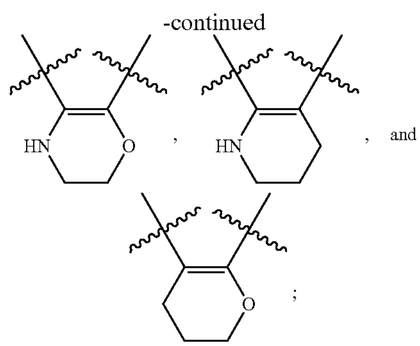

, , and ;

wherein the ring system is optionally substituted with 1 to 5 substituents $R^6$.

Provided herein as Embodiment 125 is the compound according to Embodiment 124 or a pharmaceutically acceptable salt thereof, wherein B together with the atoms to which it is attached forms a ring system selected from

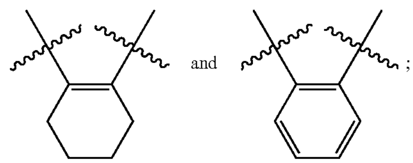 [SMILES: *C1=C(*)CCCC1 ; *c1ccccc1*]

and ;

wherein the ring system is optionally substituted with 1 to 5 substituents $R^6$.

Provided herein as Embodiment 126 is the compound according to Embodiment 125 or a pharmaceutically acceptable salt thereof, wherein B together with the atoms to which it is attached forms a ring system selected from

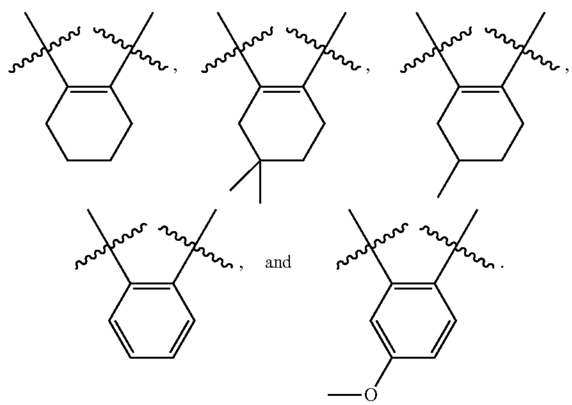

, , , , and .

Provided herein as Embodiment 127 is the compound according to any one of Embodiments 87-115 and 121-125 or a pharmaceutically acceptable salt thereof, wherein wherein the ring system is optionally substituted with 1 to 2 substituents $R^6$;

$R^6$ at each occurrence independently is halogen, $C_{1-6}$alkyl, $C_{1-4}$alkoxy, or phenyl, wherein the $C_{1-6}$alkyl is optionally substituted with —CO($C_{1-4}$alkylamino).

Provided herein as Embodiment 128 is the compound according to any one of Embodiments 87-115 and 121-125 or a pharmaceutically acceptable salt thereof, wherein wherein the ring system is optionally substituted with 1 to 2 substituents $R^6$;

$R^6$ at each occurrence independently is F, Cl, methyl, methoxy, phenyl, or $—CH(CH_2CH(CH_3)_2)(CH_2CONHCH_3)$.

Provided herein as Embodiment 129 is the compound according to any one of Embodiments 87-115 and 121-125 or a pharmaceutically acceptable salt thereof, wherein wherein the ring system is optionally substituted with 1 to 2 substituents $R^6$;

$R^6$ at each occurrence independently is methyl or methoxy.

Provided herein as Embodiment 130 is the compound according to Embodiment 87 or a pharmaceutically acceptable salt thereof, wherein the compound is 1-(6-(4-(3-hydroxynaphthalen-1-yl)-5,6,7,8-tetrahydroquinazolin-2-yl)-2,6-diazaspiro[3.4]octan-2-yl)prop-2-en-1-one;

3-(2-acryloyl-2,6-diazaspiro[3.4]octan-6-yl)-1-(5-methyl-1H-indazol-4-yl)-2-naphtho-nitrile;

4-(5-methyl-1H-indazol-4-yl)-2-(2-(2-propenoyl)-2,6-diazaspiro[3.4]octan-6-yl)-6,7-dihydro-5H-cyclopenta[b]pyridine-3-carbonitrile;

8-fluoro-4-(5-methyl-1H-indazol-4-yl)-2-(2-(2-propenoyl)-2,6-diazaspiro[3.4]octan-6-yl)-3-quinolinecarbonitrile;

8-(5-methyl-1H-indazol-4-yl)-6-(2-(2-propenoyl)-2,6-diazaspiro[3.4]octan-6-yl)imidazo[1,2-a]pyridine-7-carbonitrile;

8-methy-4-(5-methyl-1H-indazol-4-yl)-2-(2-(2-propenoyl)-2,6-diazaspiro[3.4]octan-6-yl)-3-quinolinecarbonitrile;

1-(6-(4-(8-methyl-1-naphthalenyl)-5,6,7,8-tetrahydro-2-quinazolinyl)-2,6-diazaspiro[3.4]octan-2-yl)-2-propen-1-one;

(P)-7,7-dimethyl-4-(5-methyl-1H-indazol-4-yl)-2-(2-(2-propenoyl)-2,6-diazaspiro[3.4]octan-6-yl)-5,6,7,8-tetrahydro-3-quinolinecarbonitrile;

1-(6-(4-(8-chloro-1-naphthalenyl)-5,6,7,8-tetrahydro-2-quinazolinyl)-2,6-diazaspiro[3.4]octan-2-yl)-2-propen-1-one;

(M)-7,7-dimethyl-4-(5-methyl-1H-indazol-4-yl)-2-(2-(2-propenoyl)-2,6-diazaspiro[3.4]octan-6-yl)-5,6,7,8-tetrahydro-3-quinolinecarbonitrile;

1-(6-((7)-7-methyl-4-(5-methyl-1H-indazol-4-yl)-5,6,7,8-tetrahydro-2-quinazolinyl)-2,6-diazaspiro[3.4]octan-2-yl)-2-propen-1-one;

1-(6-(4-(2-methyl-1-naphthalenyl)-5,6,7,8-tetrahydro-2-quinazolinyl)-2,6-diazaspiro[3.4]octan-2-yl)-2-propen-1-one;

8-fluoro-2-((8)-8-fluoro-2-(2-propenoyl)-2,6-diazaspiro[3.4]octan-6-yl)-4-(5-methyl-1H-indazol-4-yl)-3-quinolinecarbonitrile;

8-fluoro-4-(5-methyl-1H-indazol-4-yl)-2-(2-(2-propynoyl)-2,6-diazaspiro[3.4]octan-6-yl)-3-quinolinecarbonitrile;

1-(6-((8)-8-methyl-4-(5-methyl-1H-indazol-4-yl)-5,6,7,8-tetrahydro-2-quinazolinyl)-2,6-diazaspiro[3.4]octan-2-yl)-2-propen-1-one 1-(6-(4-(6-methyl-1H-indazol-7-yl)-5,6,7,8-tetrahydro-2-quinazolinyl)-2,6-diazaspiro[3.4]octan-2-yl)-2-propen-1-one;

1-(6-(4-(5-methyl-1H-indazol-4-yl)-5,6,7,8-tetrahydro-2-quinazolinyl)-2,6-diazaspiro[3.4]octan-2-yl)-2-propen-1-one;

1-(6-(4-(2-chloro-5-hydroxyphenyl)-5,6,7,8-tetrahydro-2-quinazolinyl)-2,6-diazaspiro[3.4]octan-2-yl)-2-propen-1-one;

1-((5S)-5-(difluoromethyl)-6-(4-(3-hydroxy-1-naphthalenyl)-7,7-dimethyl-5,6,7,8-tetrahydro-2-quinazolinyl)-2,6-diazaspiro[3.4]octan-2-yl)-2-propen-1-one;
1-(6-(9-methyl-6-(5-methyl-1H-indazol-4-yl)-9H-purin-2-yl)-2,6-diazaspiro[3.4]octan-2-yl)-2-propen-1-one;
1-(6-(4-(6-hydroxy-1-naphthalenyl)-5,6,7,8-tetrahydro-2-quinazolinyl)-2,6-diazaspiro[3.4]octan-2-yl)-2-propen-1-one;
1-(6-(4-(3-hydroxy-1-naphthalenyl)-7-methylpyrido[3,2-d]pyrimidin-2-yl)-2,6-diazaspiro[3.4]octan-2-yl)-2-propen-1-one;
1-(6-(4-(2-amino-1,3-benzothiazol-4-yl)-5,6,7,8-tetrahydro-2-quinazolinyl)-2,6-diazaspiro[3.4]octan-2-yl)-2-propen-1-one;
1-(6-(4-(2,3-dichlorophenyl)-5,6,7,8-tetrahydro-2-quinazolinyl)-2,6-diazaspiro[3.4]octan-2-yl)-2-propen-1-one;
1-(6-(4-(1,6-dimethyl-1H-indazol-7-yl)-5,6,7,8-tetrahydro-2-quinazolinyl)-2,6-diazaspiro[3.4]octan-2-yl)-2-propen-1-one;
1-(6-(4-(2,3-dimethylphenyl)-5,6,7,8-tetrahydro-2-quinazolinyl)-2,6-diazaspiro[3.4]octan-2-yl)-2-propen-1-one;
1-(6-(4-(2-chloro-3-methylphenyl)-5,6,7,8-tetrahydro-2-quinazolinyl)-2,6-diazaspiro[3.4]octan-2-yl)-2-propen-1-one;
1-(6-(8-methyl-4-(8-methyl-1-naphthalenyl)-7,8-dihydro-6H-pyrimido[5,4-b][1,4]oxazin-2-yl)-2,6-diazaspiro[3.4]octan-2-yl)-2-propen-1-one;
8-(5-hydroxy-2-methylphenyl)-6-(2-(2-propenoyl)-2,6-diazaspiro[3.4]octan-6-yl)imidazo[1,2-a]pyridine-7-carbonitrile;
1-(6-(7,7-dimethyl-4-(8-methyl-1-naphthalenyl)-5,6,7,8-tetrahydro-2-quinazolinyl)-2,6-diazaspiro[3.4]octan-2-yl)-2-propen-1-one
1-(6-(4-(3-hydroxy-1-naphthalenyl)-7,7-dimethyl-5,6,7,8-tetrahydro-2-quinazolinyl)-2,6-diazaspiro[3.4]octan-2-yl)-2-propen-1-one;
1-(5-methyl-1H-indazol-4-yl)-3-(6-(2-propenoyl)-2,6-diazaspiro[3.3]heptan-2-yl)-2-naphthalenecarbonitrile;
1-(6-(4-(5-(2-propanyl)-1H-indazol-4-yl)-5,6,7,8-tetrahydro-2-quinazolinyl)-2,6-diazaspiro[3.4]octan-2-yl)-2-propen-1-one;
1-(6-(4-(3,5-dimethyl-1-J-indazol-4-yl)-5,6,7,8-tetrahydro-2-quinazolinyl)-2,6-diazaspiro[3.4]octan-2-yl)-2-propen-1-one;
3-methyl-8-(5-methyl-1H-indazol-4-yl)-6-(2-(2-propenoyl)-2,6-diazaspiro[3.4]octan-6-yl)imidazo[1,2-a]pyridine-7-carbonitrile;
8-(5-methyl-1H-indazol-4-yl)-2-phenyl-6-(2-(2-propenoyl)-2,6-diazaspiro[3.4]octan-6-yl)imidazo[1,2-a]pyridine-7-carbonitrile;
2-(8,8-difluoro-2-(2-propenoyl)-2,6-diazaspiro[3.4]octan-6-yl)-8-fluoro-4-(5-methyl-1H-indazol-4-yl)-3-quinolinecarbonitrile;
1-(6-(7-methyl-4-(5-methyl-1H-indazol-4-yl)-2-quinazolinyl)-2,6-diazaspiro[3.4]octan-2-yl)-2-propen-1-one;
1-(6-(7-methoxy-4-(5-methyl-1H-indazol-4-yl)-2-quinazolinyl)-2,6-diazaspiro[3.4]octan-2-yl)-2-propen-1-one;
1-(6-(4-(8-methyl-1-naphthalenyl)-7,8-dihydro-6H-pyrano[3,2-d]pyrimidin-2-yl)-2,6-diazaspiro[3.4]octan-2-yl)-2-propen-1-one;
2-(5,5-difluoro-2-(2-propenoyl)-2,7-diazaspiro[3,5]nonan-7-yl)-8-fluoro-4-(5-methyl-1H-indazol-4-yl)-3-quinolinecarbonitrile;
8-fluoro-4-(5-methyl-1H-indazol-4-yl)-2-(5-oxo-2-(2-propenoyl)-2,6-diazaspiro[3.4]octan-6-yl)-3-quinolinecarbonitrile;
7-methoxy-4-(5-methyl-1H-indazol-4-yl)-2-(2-(2-propanoyl)-2,6-diazaspiro[3.4]octan-6-yl)-3-quinolinecarbonitrile;
2-(2-((2E)-4-(dimethylamino)-2-butenoyl)-2,6-diazaspiro[3.4]octan-6-yl)-8-fluoro-4-(5-methyl-1H-indazol-4-yl)-3-quinolinecarbonitrile;
1-((5R)-5-(difluoromethyl)-6-(4-(3-hydroxy-1-naphthalenyl)-7,7-dimethyl-5,6,7,8-tetrahydro-2-quinazolinyl)-2,6-diazaspiro[3.4]octan-2-yl)-2-propen-1-one;
2-(2-acryloyl-2,6-diazaspiro[3.4]octan-6-yl)-7-methyl-4-(5-methyl-1H-indazol-4-yl)-5,6,7,8-tetrahydroquinoline-3-carbonitrile;
4-(6-methyl-1H-indazol-7-yl)-2-(2-(2-propenoyl)-2,6-diazaspiro[3.4]octan-6-yl)-3-quinolinecarbonitrile;
4-(2-amino-1,3-benzothiazol-4-yl)-2-(2-(2-propenoyl)-2,6-diazaspiro[3.4]octan-6-yl)-3-quinolinecarbonitrile;
4-(3-hydroxy-1-naphthalenyl)-2-(2-(2-propenoyl)-2,6-diazaspiro[3.4]octan-6-yl)-3-quinolinecarbonitrile;
2-(8,8-difluoro-2-(2-propenoyl)-2,6-diazaspiro[3.4]octan-6-yl)-7-methyl-4-(5-methyl-1H-indazol-4-yl)-5,6,7,8-tetrahydro-3-quinolinecarbonitrile;
4-(5,6-dimethyl-1H-indazol-4-yl)-2-(2-(2-propenoyl)-2,6-diazaspiro[3.4]octan-6-yl)-3-quinolinecarbonitrile;
4-(2-fluorophenyl)-2-(2-(2-propenoyl)-2,6-diazaspiro[3.4]octan-6-yl)-5,6,7,8-tetrahydro-3-quinolinecarbonitrile;
4-(5-methyl-1H-indazol-4-yl)-2-(2-(2-propenoyl)-2,6-diazaspiro[3.4]octan-6-yl)-5,6,7,8-tetrahydro-3-quinolinecarbonitrile;
4-(2-fluoro-5-hydroxyphenyl)-2-(2-(2-propenoyl)-2,6-diazaspiro[3.4]octan-6-yl)-5,6,7,8-tetrahydro-3-quinolinecarbonitrile;
1-(6-(3-methyl-7-(5-methyl-1H-indazol-4-yl)furo[3,2-b]pyridin-5-yl)-2,6-diazaspiro[3.4]octan-2-yl)prop-2-en-1-one;
2-(2-acryloyl-2,6-diazaspiro[3.4]octan-6-yl)-4-(5-ethyl-1H-indazol-4-yl)quinoline-3-carbonitrile;
1-(6-(3-cyclopropyl-4-(5-methyl-1H-indazol-4-yl)quinolin-2-yl)-2,6-diazaspiro[3.4]octan-2-yl)prop-2-en-1-one;
1-methyl-4-(5-methy-1H-indazol-4-yl)-6-(2-(2-propanoyl)-2,6-diazaspiro[3.4]octan-6-yl)-1H-benzimidazole-5-carbonitrile;
1-(6-(3-methyl-4-(5-methyl-1H-indazol-4-yl)quinolin-2-yl)-2,6-diazaspiro[3.4]octan-2-yl)prop-2-en-1-one;
(S)-3-(2-(2-acryloyl-2,6-diazaspiro[3.4]octan-6-yl)-4-(2-fluorophenyl)-5,6-dihydro-7H-pyrrolo[2,3-d]pyrimidin-7-yl)-N,5-dimethylhexanamide;
(S)-3-(2-(2-acryloyl-2,6-diazaspiro[3.4]octan-6-yl)-4-(2-fluorophenyl)-6,7-dihydropyrido[2,3-d]pyrimidin-8(5H)-yl)-N,5-dimethylhexanamide; or
(S)-3-(2-(2-acryloyl-2,6-diazaspiro[3.4]octan-6-yl)-4-(2-fluorophenyl)-7H-pyrrolo[2,3-d]pyrimidin-7-yl)-N,5-dimethylhexanamide.

Provided herein as Embodiment 131 is the compound according to Embodiment 87 or a pharmaceutically acceptable salt thereof, wherein the compound is
(P)-7,7-dimethyl-4-(5-methyl-1H-indazol-4-yl)-2-(2-(2-propenoyl)-2,6-diazaspiro[3.4]octan-6-yl)-5,6,7,8-tetrahydro-3-quinolinecarbonitrile;
1-(6-(4-(3-hydroxy-1-naphthalenyl)-7,7-dimethyl-5,6,7,8-tetrahydro-2-quinazolinyl)-2,6-diazaspiro[3.4]octan-2-yl)-2-propen-1-one;
7-methoxy-4-(5-methyl-1H-indazol-4-yl)-2-(2-(2-propenoyl)-2,6-diazaspiro[3.4]octan-6-yl)-3-quinolinecarbonitrile;

2-(2-acryloyl-2,6-diazaspiro[3.4]octan-6-yl)-7-methyl-4-(5-methyl-1H-indazol-4-yl)-5,6,7,8-tetrahydroquinoline-3-carbonitrile;

2-(8,8-difluoro-2-(2-propenoyl)-2,6-diazaspiro[3.4]octan-6-yl)-7-methyl-4-(5-methyl-1H-indazol-4-yl)-5,6,7,8-tetrahydro-3-quinolinecarbonitrile;

4-(5,6-dimethyl-1H-indazol-4-yl)-2-(2-(2-propenoyl)-2,6-diazaspiro[3.4]octan-6-yl)-3-quinolinecarbonitrile; or 4-(5-eethyl-1H-indazol-4-yl)-2-(2-(2-propenoyl)-2,6-diazaspiro[3.4]octan-6-yl)-5,6,7,8-tetrahydro-3-quinolinecarbonitrile.

The foregoing merely summarizes certain aspects of this disclosure and is not intended, nor should it be construed, as limiting the disclosure in any way.

Formulation and Route of Administration

While it may be possible to administer a compound disclosed herein alone in the uses described, the compound administered normally will be present as an active ingredient in a pharmaceutical composition. Thus, in one embodiment, provided herein is a pharmaceutical composition comprising a compound disclosed herein in combination with one or more pharmaceutically acceptable excipients and, if desired, other active ingredients. See, e.g., Remington: The Science and Practice of Pharmacy, Volume I and Volume II, twenty-second edition, edited by Loyd V. Allen Jr., Philadelphia, PA, Pharmaceutical Press, 2012; Pharmaceutical Dosage Forms (Vol. 1-3), Liberman et al., Eds., Marcel Dekker. New York, NY, 1992; Handbook of Pharmaceutical Excipients (3rd Ed.), edited by Arthur H. Kibbe, American Pharmaceutical Association, Washington, 2000; Pharmaceutical Formulation: The Science and Technology of Dosage Forms (Drug Discovery), first edition, edited by GD Tovey, Royal Society of Chemistry, 2018. In one embodiment, a pharmaceutical composition comprises a therapeutically effective amount of a compound disclosed herein.

The compound(s) disclosed herein may be administered by any suitable route in the form of a pharmaceutical composition adapted to such a route and in a dose effective for the treatment intended. The compounds and compositions presented herein may, for example, be administered orally, mucosally, topically, transdermally, rectally, pulmonarily, parentally, intranasally, intravascularly, intravenously, intraarterial, intraperitoneally, intrathecally, subcutaneously, sublingually, intramuscularly, intrasternally, vaginally or by infusion techniques, in dosage unit formulations containing conventional pharmaceutically acceptable excipients.

The pharmaceutical composition may be in the form of, for example, a tablet, chewable tablet, minitablet, caplet, pill, bead, hard capsule, soft capsule, gelatin capsule, granule, powder, lozenge, patch, cream, gel, sachet, microneedle array, syrup, flavored syrup, juice, drop, injectable solution, emulsion, microemulsion, ointment, aerosol, aqueous suspension, or oily suspension. The pharmaceutical composition is typically made in the form of a dosage unit containing a particular amount of the active ingredient.

Provided herein as Embodiment 132 is a pharmaceutical composition comprising the compound according to any one of Embodiments 1-131 or a pharmaceutically acceptable salt thereof, and a pharmaceutically acceptable excipient.

Provided herein as Embodiment 133 is a compound according to any one of Embodiments 1-131 or a pharmaceutically acceptable salt thereof, or the pharmaceutical composition according to Embodiment 132 for use as a medicament.

Methods of Use

As discussed herein (see Section entitled "Definitions"), the compounds described herein are to be understood to include all stereoisomers, tautomers, or pharmaceutically acceptable salts of any of the foregoing. Accordingly, the scope of the methods and uses provided in the instant disclosure is to be understood to encompass also methods and uses employing all such forms.

Besides being useful for human treatment, the compounds provided herein may be useful for veterinary treatment of companion animals, exotic animals, and farm animals, including mammals, rodents, and the like. For example, animals including horses, dogs, and cats may be treated with compounds provided herein.

In one embodiment, the disclosure provides methods of using the compounds or pharmaceutical compositions of the present disclosure to treat disease conditions, including but not limited to conditions implicated by KRAS G12C mutation (e.g., cancer). See, e.g., U.S. Pat. No. 10,519,146 B32, issued Dec. 31, 2019; specifically, the section from column 198, line 1, to column 201, line 36, which is herewith incorporated by reference.

Without wishing to be bound by any particular theory, the following is noted: AMG 510 is a small molecule that—similarly to the compounds disclosed herein—specifically and irreversibly inhibits $KRAS^{G12C}$ z (Hong et al., 2020, at 1208). Hong et al. report that "[p]reclinical studies showed that [AMG 510] inhibited nearly all detectable phosphorylation of extracellular signal-regulated kinase (ERK), a key down-stream effector of KRAS, leading to durable complete tumor regression in mice bearing KRAS p.G12C tumors." (id., see also Section entitled "Biological Evaluation" below, Canon et al. 2019, and Lanman et al., 2020).

AMG 510 was evaluated in a Phase 1 dose escalation and expansion trial with 129 subjects having histologically confirmed, locally advanced or metastatic cancer with the KRAS G12C mutation identified by local molecular testing on tumor tissues, including 59 subjects with non-small cell lung cancer, 42 subjects with colorectal cancer, and 28 subjects with other tumor types (Hong et al., 2020, at page 1208-1209). Hong et al. report a disease control rate (95% CI) of 88.1% for non-small cell lung cancer, 73.8% for colorectal cancer and 75.0% for other tumor types (Hong et al., 2020, at page 1213, Table 3). In conclusion, the cancer types showing either stable disease (SD) or partial response (PR) as reported by Hong et al. were non-small cell lung cancer, colorectal cancer, pancreatic cancer, appendiceal cancer, endometrial cancer, esophageal cancer, cancer of unknown primary, ampullary cancer, gastric cancer, small bowel cancer, sinonasal cancer, bile duct cancer, or melanoma (Hong et al., 2020, at page 1212 (Figure A), and Supplementary Appendix (page 59 (Figure S5) and page 63 (Figure S6)).

KRAS G12C mutations occur with the alteration frequencies shown in the table below (Cerami et al., 2012; Gao et al., 2013). For example, the table shows that 11.6% of subjects with non-small cell lung cancer have a cancer, wherein one or more cells express KRAS G12C mutant protein. Accordingly, the compounds provided herein, which specifically and irreversibly bind to $KRAS^{G12C}$ (see Section entitled "Biological Evaluation" below) are useful for treatment of subjects having a cancer, including, but not limited to the cancers listed in the table below.

| Cancer Type | Alteration Frequency |
|---|---|
| Non-Small Cell Lung Cancer | 11.6 |
| Small Bowel Cancer | 4.2 |
| Appendiceal Cancer | 3.6 |
| Colorectal Cancer | 3.0 |
| Cancer of Unknown Primary | 2.9 |
| Endometrial Cancer | 1.3 |
| Mixed Cancer Types | 1.2 |
| Pancreatic Cancer | 1.0 |
| Hepatobiliary Cancer | 0.7 |
| Small Cell Lung Cancer | 0.7 |
| Cervical Cancer | 0.7 |
| Germ Cell Tumor | 0.6 |
| Ovarian Cancer | 0.5 |
| Gastrointestinal Neuroendocrine Tumor | 0.4 |
| Bladder Cancer | 0.4 |
| Myelodysplastic/Myeloproliferative Neoplasms | 0.3 |
| Head and Neck Cancer | 0.3 |
| Esophagogastric Cancer | 0.2 |
| Soft Tissue Sarcoma | 0.2 |
| Mesothelioma | 0.2 |
| Thyroid Cancer | 0.1 |
| Leukemia | 0.1 |
| Melanoma | 0.1 |

Provided herein as Embodiment 134 is a compound according to any one of Embodiments 1-131 or a pharmaceutically acceptable salt thereof, or the pharmaceutical composition according to Embodiment 132 for use in treating cancer.

Provided herein as Embodiment 135 is a compound according to any one of Embodiments 1-131 or a pharmaceutically acceptable salt thereof, or the pharmaceutical composition according to Embodiment 132 for use in treating cancer, wherein one or more cells express KRAS G12C mutant protein.

Provided herein as Embodiment 136 is the compound or pharmaceutical composition for use of Embodiment 134 or 135, wherein the cancer is non-small cell lung cancer, small bowel cancer, appendiceal cancer, colorectal cancer, cancer of unknown primary, endometrial cancer, mixed cancer types, pancreatic cancer, hepatobiliary cancer, small cell lung cancer, cervical cancer, germ cell cancer, ovarian cancer, gastrointestinal neuroendocrine cancer, bladder cancer, myelodysplastic/myeloproliferative neoplasms, head and neck cancer, esophagogastric cancer, soft tissue sarcoma, mesothelioma, thyroid cancer, leukemia, or melanoma.

Provided herein as Embodiment 137 is a use of the compound according to any one of Embodiments 1-131 or a pharmaceutically acceptable salt thereof, or the pharmaceutical composition according to Embodiment 132 in the preparation of a medicament for treating cancer.

Provided herein as Embodiment 138 is a use of the compound according to any one of Embodiments 1-131 or a pharmaceutically acceptable salt thereof, or the pharmaceutical composition according to Embodiment 132 in the preparation of a medicament for treating cancer, wherein one or more cells express KRAS G12C mutant protein.

Provided herein as Embodiment 139 is the use according to Embodiment 137 or 138, wherein the cancer is non-small cell lung cancer, small bowel cancer, appendiceal cancer, colorectal cancer, cancer of unknown primary, endometrial cancer, mixed cancer types, pancreatic cancer, hepatobiliary cancer, small cell lung cancer, cervical cancer, germ cell cancer, ovarian cancer, gastrointestinal neuroendocrine cancer, bladder cancer, myelodysplastic/myeloproliferative neoplasms, head and neck cancer, esophagogastric cancer, soft tissue sarcoma, mesothelioma, thyroid cancer, leukemia, or melanoma.

Provided herein as Embodiment 140 is a method of treating cancer in a subject in need thereof, the method comprising administering to the subject a therapeutically effective amount of the compound according to any one of to any one of Embodiments 1-131 or a pharmaceutically acceptable salt thereof.

Provided herein as Embodiment 141 is a method of treating cancer in a subject in need thereof, the method comprising administering to the subject a therapeutically effective amount of the compound according to any one of to any one of Embodiments 1-131 or a pharmaceutically acceptable salt thereof, wherein one or more cells express KRAS G12C mutant protein.

Provided herein as Embodiment 142 is the method according to Embodiment 140 or 141, wherein the cancer is non-small cell hung cancer, small bowel cancer, appendiceal cancer, colorectal cancer, cancer of unknown primary, endometrial cancer, mixed cancer types, pancreatic cancer, hepatobiliary cancer, small cell lung cancer, cervical cancer, germ cell cancer, ovarian cancer, gastrointestinal neuroendocrine cancer, bladder cancer, myelodysplastic/myeloproliferative neoplasms, head and neck cancer, esophagogastric cancer, soft tissue sarcoma, mesothelioma, thyroid cancer, leukemia, or melanoma.

Provided herein as Embodiment 143 is the method according to Embodiment 140 or 141, wherein the cancer is non-small cell lung cancer, colorectal cancer, pancreatic cancer, appendiceal cancer, endometrial cancer, esophageal cancer, cancer of unknown primary, ampullary cancer, gastric cancer, small bowel cancer, sinonasal cancer, bile duct cancer, or melanoma.

Provided herein as Embodiment 144 is the method according to Embodiment 143, wherein the cancer is non-small cell lung cancer.

Provided herein as Embodiment 145 is the method according to Embodiment 143, wherein the cancer is colorectal cancer.

Provided herein as Embodiment 146 is the method according to Embodiment 143, wherein the cancer is pancreatic cancer.

Provided herein as Embodiment 147 is the method according to anyone of Embodiments 140-146, wherein the subject has a cancer that was determined to have one or more cells expressing the KRAS G12C mutant protein prior to administration of the compound or a pharmaceutically acceptable salt thereof.

Combination Therapy

The present disclosure also provides methods for combination therapies in which an agent known to modulate other pathways, or other components of the same pathway, or even overlapping sets of target enzymes are used in combination with a compound of the present disclosure or a pharmaceutically acceptable salt thereof. In one aspect, such therapy includes but is not limited to the combination of one or more compounds of the disclosure with chemotherapeutic agents, therapeutic antibodies, and radiation treatment, to provide, for example a synergistic or additive therapeutic effect. See, e.g., U.S. Pat. No. 10,519,146 B2, issued Dec. 31, 2019; specifically, the sections from column 201 (line 37) to column 212 (line 46) and column 219 (line 64) to column 220 (line 39), which are herewith incorporated by reference.

Provided herein as Embodiment 148 is the method according to anyone of Embodiments 140-147, which further comprises simultaneous, separate, or sequential administration of an effective amount of a second compound, wherein the second compound is an Aurora kinase A inhibitor, AKT inhibitor, arginase inhibitor, CDK4/6 inhibitor, ErbB3 family inhibitor, ERK inhibitor, FAK inhibitor, FGFR inhibitor, glutaminase inhibitor, IGF-1R inhibitor, KIF18A inhibitor, MCL-1 inhibitor, MEK inhibitor, mTOR inhibitor, PD-1 inhibitor, PD-L1 inhibitor, PI3K inhibitor, Rafkinase inhibitor, SHP2 inhibitor, SOS1 inhibitor, Src kinase inhibitor, or one or more chemotherapeutic agent.

In one embodiment, the second compound is administered as a pharmaceutically acceptable salt. In another embodiment the second compound is administered as a pharmaceutical composition comprising the second compound or a pharmaceutically acceptable salt thereof and a pharmaceutically acceptable excipient.

Aurora Kinase A Inhibitors

Provided herein is the method according to anyone of Embodiments 54-61, which further comprises simultaneous, separate, or sequential administration of an effective amount of a second compound, wherein the second compound is an Aurora kinase A inhibitor.

Exemplary Aurora kinase A inhibitors for use in the methods provided herein include, but are not limited to, alisertib, cenisertib, danusertib, tozasertib, LY3295668 ((2R, 4R)-1-[(3-chloro-2-fluorophenyl)methyl]-4-[[3-fluoro-6-[(5-methyl-1H-pyrazol-3-yl)amino]pyridin-2-yl]methyl]-2-methylpiperidine-4-carboxylic acid), ENMD-2076 (6-(4-methylpiperazin-1-yl)-N-(5-methyl-1H-pyrazol-3-yl)-2-[(E)-2-phenylethenyl]pyrimidin-4-amine), TAK-901 (5-(3-ethylsulfonylphenyl)-3,8-dimethyl-N-(1-methylpiperidin-4-yl)-9H-pyrido[2,3-b]indole-7-carboxamide), TT-00420 (4-[9-(2-chlorophenyl)-6-methyl-2,4,5,8,12-pentazatricyclo [8.4.0.03,7]tetradeca-1(14),3,6,8,10,12-hexaen-13-yl] morpholine), AMG 900 (N-[4-[3-(2-aminopyrimidin-4-yl) pyridin-2-yl]oxyphenyl]-4-(4-methylthiophen-2-yl) phthalazin-1-amine), MLN8054 (4-[[9-chloro-7-(2,6-difluorophenyl)-5H-pyrimido[5,4-d][2]benzazepin-2-yl] amino]benzoic acid), PF-03814735 (N-[2-[(1R,8S)-4-[[4-(cyclobutylamino)-5-(trifluoromethyl)pyrimidin-2-yl] amino]-11-azatricyclo[6.2.1.$0^{2,7}$]undeca-2(7),3,5-trien-1-yl]-2-oxoethyl]acetamide), SNS-314 (1-(3-chlorophenyl)-3-[5-[2-(thieno[3,2-d]pyrimidin-4-ylamino)ethyl]-1,3-thiazol-2-yl]urea), $CYC_{116}$ (4-methyl-5-[2-(4-morpholin-4-ylanilino)pyrimidin-4-yl]-1,3-thiazol-2-amine), TAS-119, BI 811283, and TTP607.

AKT Inhibitors

Provided herein is the method according to anyone of Embodiments 54-61, which further comprises simultaneous, separate, or sequential administration of an effective amount of a second compound, wherein the second compound is an AKT inhibitor.

Exemplary AKT inhibitors for use in the methods provided herein include, but are not limited to, afuresertib, capivasertib, ipatasertib, uprosertib, BAY1125976 (2-[4-(1-aminocyclobutyl)phenyl]-3-phenylimidazo[1,2-b] pyridazine-6-carboxamide), ARQ 092 (3-[3-[4-(1-aminocyclobutyl)phenyl]-5-phenylimidazo[4,5-b]pyridin-2-yl] pyridin-2-amine), MK2206 (8-[4-(1-aminocyclobutyl) phenyl]-9-phenyl-2H-[1,2,4]triazolo[3,4-f][1,6] naphthyridin-3-one), SR13668 (indolo[2,3-b]carbazole-2, 10-dicarboxylic acid, 5,7-dihydro-6-methoxy-2,10-diethyl ester), $ONC_{201}$ (11-benzyl-7-[(2-methylphenyl)methyl]-2,5, 7,11-tetrazatricyclo[7.4.0.02,6]trideca-1(9),5-dien-8-one), ARQ 751 (N-(3-aminopropyl)-N-[(1R)-1-(3-anilino-7-chloro-4-oxoquinazolin-2-yl)but-3-ynyl]-3-chloro-2-fluorobenzamide), RX-0201, and LY2780301.

Arginase Inhibitors

Provided herein is the method according to anyone of Embodiments 54-61, which further comprises simultaneous, separate, or sequential administration of an effective amount of a second compound, wherein the second compound is an arginase inhibitor.

Exemplary arginase inhibitors for use in the methods provided herein include, but are not limited to, numidargistat and CB 280.

CDK4/6 Inhibitors

Provided herein is the method according to anyone of Embodiments 54-61, which further comprises simultaneous, separate, or sequential administration of an effective amount of a second compound, wherein the second compound is a CDK4/6 inhibitor.

The term "CDK 4/6" as used herein refers to cyclin dependent kinases ("CDK") 4 and 6, which are members of the mammalian serine/threonine protein kinases.

The term "CDK 4/6 inhibitor" as used herein refers to a compound that is capable of negatively modulating or inhibiting all or a portion of the enzymatic activity of CDK 4 and/or 6.

Exemplary CDK 4/6 inhibitors for use in the methods provided herein include, but are not limited to, abemaciclib, palbociclib, ribociclib, trilaciclib, and PF-06873600 ((pyrido[2,3-d]pyrimidin-7(8H)-one, 6-(difluoromethyl)-8-[(1R,2R)-2-hydroxy-2-methylcyclopentyl]-2-[[1-(methylsulfonyl)-4-piperidinyl]amino]).

In one embodiment, the CDK4/6 inhibitor is palbociclib.

ErbB Family Inhibitors

Provided herein is the method according to anyone of Embodiments 54-61, which further comprises simultaneous, separate, or sequential administration of an effective amount of a second compound, wherein the second compound is an ErbB family inhibitor.

The term "ErbB family" as used herein refers to a member of a mammalian transmembrane protein tyrosine kinase family including: ErbB1 (EGFR HER1), ErbB2 (HER2), ErbB3 (HER3), and ErbB4 (HER4).

The term "ErbB family inhibitor" as used herein refers to an agent, e.g., a compound or antibody, that is capable of negatively modulating or inhibiting all or a portion of the activity of at least one member of the ErbB family. The modulation or inhibition of one or more ErbB tyrosine kinase may occur through modulating or inhibiting kinase enzymatic activity of one or more ErbB family member or by blocking homodimerization or heterodimerization of ErbB family members.

In one embodiment, the ErbB family inhibitor is an EGFR inhibitor, e.g., an anti-EGFR antibody. Exemplary anti-EGFR antibodies for use in the methods provided herein include, but are not limited to, zalutumumab, nimotuzumab, matuzumab, necitumumab, panitumumab, and cetuximab. In one embodiment, the anti-EGFR antibody is cetuximab. In one embodiment, the anti-EGFR antibody is panitumumab.

In another embodiment the ErbB family inhibitor is a HER2 inhibitor, e.g., an anti-HER2 antibody. Exemplary anti-HER-2 antibodies for use in the methods provided herein include, but are not limited to, pertuzumab, trastuzumab, and trastuzumab emtansine.

In yet another embodiment the ErbB family inhibitor is a HER3 inhibitor, e.g., an anti-HER3 antibody, such as HMBD-001 (Hummingbird Bioscience).

In one embodiment, the ErbB family inhibitor is a combination of an anti-EGFR antibody and anti-HER2 antibody.

In one embodiment, the ErbB family inhibitor is an irreversible inhibitor. Exemplary irreversible ErbB family inhibitors for use in the methods provided herein include, but are not limited to, afatinib, dacomitinib, canertinib, poziotinib, AV 412 ((N-[4-[(3-chloro-4-fluorophenyl) amino]-7-[3-methyl-3-(4-methyl-1-piperazinyl)-1-butyn-1-yl]-6-quinazolinyl]-2-propenamide)), PEF 6274484 ((N-[4-[(3-chloro-4-fluorophenyl)amino]-7-methoxy-6-quinazolinyl]-2-propenamide), and HKI 357 ((E)-N-[4-[3-chloro-4-[(3-fluorophenyl)methoxy]amino]-3-cyano-7-ethoxyquinolin-6-yl]-4-(dimethylamino)but-2-enamide).

In one embodiment, the irreversible ErbB family inhibitor is afatinib. In one embodiment, the irreversible ErbB family inhibitor is dacomitinib.

In one embodiment, the ErbB family inhibitor is a reversible inhibitor. Exemplary reversible ErbB family inhibitors for use in the methods provided herein include, but are not limited to erlotinib, gefitinib, sapitinib, varlitinib, tarloxotinib, TAK-285 (N-(2-(4-((3-chloro-4-(3-(trifluoromethyl) phenoxy)phenyl)amino)-5H-pyrrolo[3,2-d]pyrimidin-5-yl) ethyl)-3-hydroxy-3-methylbutanamide), AEE788 ((S)-6-(4-((4-ethylpiperazin-1-yl)methyl)phenyl)-N-(1-phenylethyl)-7H-pyrrolo[2,3-d]pyrimidin-4-amine), BMS 599626 ((3S)-3-morpholinylmethyl-[4-[[1-[(3-fluorophenyl)methyl]-1H-indazol-5-yl]amino]-5-methylpyrrolo[2,1-f][1,2,4]triazin-6-yl]-carbamate), and GW 583340 (N-[3-chloro-4-[(3-fluorophenyl) methoxy]phenyl]-6-[2-[(2-methylsulfonylethylamino)methyl]-1,3-thiazol-4-yl] quinazolin-4-amine).

In one embodiment, the reversible ErbB family inhibitor is sapitinib. In one embodiment, the reversible ErbB family inhibitor is tarloxotinib.

ERK Inhibitors

Provided herein is the method according to anyone of Embodiments 54-61, which further comprises simultaneous, separate, or sequential administration of an effective amount of a second compound, wherein the second compound is an ERK inhibitor.

Exemplary ERK inhibitors for use in the methods provided herein include, but are not limited to, ulixertinib, ravoxertinib, CC-90003 (N-[2-[[2-[(2-methoxy-5-methylpyridin-4-yl)amino]-5-(trifluoromethyl)pyrimidin-4-yl] amino]-5-methylphenyl]prop-2-enamide), LY3214996 (6,6-dimethyl-2-[2-[(2-methylpyrazol-3-yl)amino]pyrimidin-4-yl]-5-(2-morpholin-4-ylethyl)thieno[2,3-c]pyrrol-4-one), KO-947 (1,5,6,8-tetrahydro-6-(phenylmethyl)-3-(4-pyridinyl)-7-pyrazolo[4,3-g]quinazolin-7-one), ASTX029, LTT462, and JSI-1187.

FAK Inhibitors

Provided herein is the method according to anyone of Embodiments 54-61, which further comprises simultaneous, separate, or sequential administration of an effective amount of a second compound, wherein the second compound is a FAK inhibitor.

Exemplary FAK inhibitors for use in the methods provided herein include, but are not limited to, GSK2256098 (2-[[5-chloro-2-[(5-methyl-2-propan-2-ylpyrazol-3-yl) amino]pyridin-4-yl]amino]-N-methoxybenzamide), PF-00562271 (N-methyl-N-[3-[[[2-[(2-oxo-1,3-dihydroindol-5-yl)amino]-5-(trifluoromethyl)pyrimidin-4-yl]amino] methyl]pyridin-2-yl]methanesulfonamide), VS-4718 (2-[[2-(2-methoxy-4-morpholin-4-ylanilino)-5-(trifluoromethyl) pyridin-4-yl]amino]-N-methylbenzamide), and APG-2449.

FGFR Inhibitors

Provided herein is the method according to anyone of Embodiments 54-61, which further comprises simultaneous, separate, or sequential administration of an effective amount of a second compound, wherein the second compound is an FGFR inhibitor.

Exemplary FGFR inhibitors for use in the methods provided herein include, but are not limited to, futibatinib, pemigatinib, ASP5878 (2-[4-[[5-[(2,6-difluoro-3,5-dimethoxyphenyl)methoxy]pyrimidin-2-yl]amino]pyrazol-1-yl] ethanol), AZD4547 (N-[5-[2-(3,5-dimethoxyphenyl)ethyl]-1H-pyrazol-3-yl]-4-[(3S,5R)-3,5-dimethylpiperazin-1-yl] benzamide), debio 1347 ([5-amino-1-(2-methyl-3H-benzimidazol-5-yl)pyrazol-4-yl]-(1H-indol-2-yl) methanone), INCB062079, H3B-6527 (N-[2-[[6-[(2,6-dichloro-3,5-dimethoxyphenyl)carbamoyl-methylamino] pyrimidin-4-yl]amino]-5-(4-ethylpiperazin-1-yl)phenyl] prop-2-enamide), ICP-105, CPL304110, HMPL-453, and HGS1036.

Glutaminase Inhibitors

Provided herein is the method according to anyone of Embodiments 54-61, which further comprises simultaneous, separate, or sequential administration of an effective amount of a second compound, wherein the second compound is a glutaminase inhibitor.

Exemplary glutaminase inhibitors for use in the methods provided herein include, but are not limited to, telaglenastat, IPN60090, and OP 330.

IGF-1R Inhibitors

Provided herein is the method according to anyone of Embodiments 54-61, which further comprises simultaneous, separate, or sequential administration of an effective amount of a second compound, wherein the second compound is an IGF-1R inhibitor.

Exemplary IGF-1R inhibitors for use in the methods provided herein include, but are not limited to, cixutumumab, dalotuzumab, linsitinib, ganitumab, robatumumab, BMS-754807 ((2S)-1-[4-[(5-cyclopropyl-1H-pyrazol-3-yl) amino]pyrrolo[2,1-f][1,2,4]triazin-2-yl]-N-(6-fluoropyridin-3-yl)-2-methylpyrrolidine-2-carboxamide), KW-2450 (N-[5-[[4-(2-hydroxyacetyl)piperazin-1-yl]methyl]-2-[(E)-2-(1H-indazol-3-yl)ethenyl]phenyl]-3-methylthiophene-2-carboxamide), PL225B, AVE1642, and BIIB022.

KTF18A Inhibitors

Provided herein is the method according to anyone of Embodiments 54-61, which further comprises simultaneous, separate, or sequential administration of an effective amount of a second compound, wherein the second compound is a KIF18A inhibitor.

Exemplary KIF18A inhibitors for use in the methods provided herein include, but are not limited to, the inhibitors disclosed in US 2020/0239441, WO 2020/132649, WO 2020/132651, and WO 2020/132653, each of which is herewith incorporated by reference in its entirety.

MCL-1 Inhibitors

Provided herein is the method according to anyone of Embodiments 54-61, which further comprises simultaneous, separate, or sequential administration of an effective amount of a second compound, wherein the second compound is an MCL-1 inhibitor.

Exemplary MEK inhibitors for use in the methods provided herein include, but are not limited to, murizatoclax, tapotoclax, AZD 5991 ((3aR)-5-chloro-2,11,12,24,27,29-hexahydro-2,3,24,33-tetramethyl-22H-9,4,8-(methenimino methyno)-14,20:26,23-dimetheno-10H,20H-pyrazolo[4,3-1][2,15,22,18,19]benzoxadithiadiazacyclohexacosine-32-carboxylic acid), MIK 665 ((αR)-α-[[(5S)-5-[3-Chloro-2-methyl-4-[2-(4-methyl-1-piperazinyl)ethoxy]phenyl]-6-(4-fluorophenyl)thieno[2,3-d]pyrimidin-4-yl]oxy]-2-[[2-(2-methoxyphenyl)-4-pyrimidinyl]methoxy]benzenepropanoic acid), and ABBV-467.

In one embodiment, the MC-1 inhibitor is murizatoclax. In another embodiment, the MCL-1 inhibitor is tapotoclax.

MEK Inhibitors

Provided herein is the method according to anyone of Embodiments 54-61, which further comprises simultaneous, separate, or sequential administration of an effective amount of a second compound, wherein the second compound is MEK inhibitor.

Exemplary MEK inhibitors for use in the methods provided herein include, but are not limited to, trametinib, cobimetinib, selumetinib, pimasertib, refametinib, PD-325901 (N-[(2R)-2,3-dihydroxypropoxy]-3,4-difluoro-2-(2-fluoro-4-iodoanilino)benzamide), AZD8330 (2-(2-fluoro-4-iodoanilino)-N-(2-hydroxyethoxy)-1,5-dimethyl-6-oxopyridine-3-carboxamide), GDC-0623 (5-(2-fluoro-4-iodoanilino)-N-(2-hydroxyethoxy)imidazo[1,5-a]pyridine-6-carboxamide), RO4987655 (3,4-difluoro-2-(2-fluoro-4-iodoanilino)-N-(2-hydroxyethoxy)-5-[(3-oxooxazinan-2-yl)methyl]benzamide), TAK-733 (3-[(2R)-2,3-dihydroxypropyl]-6-fluoro-5-(2-fluoro-4-iodoanilino)-8-methylpyrido[2,3-d]pyrimidine-4,7-dione), PD0325901 (N-[(2R)-2,3-dihydroxypropoxy]-3,4-difluoro-2-(2-fluoro-4-iodoanilino)benzamide), $C_1$-1040 (2-(2-chloro-4-iodophenylamino)-N-(cyclopropylmethoxy)-3,4-difluorobenzamide), PD318088 (5-bromo-N-(2,3-dihydroxypropoxy)-3,4-difluoro-2-(2-fluoro-4-iodophenylamino)benzamide), PD98059 (2-(2-amino-3-methoxyphenyl)-4H-chromen-4-one), PD334581 (N-[5-[3,4-Difluoro-2-[(2-fluoro-4-iodophenyl)amino]phenyl]-1,3,4-oxadiazol-2-yl]-4-morpholineethanamine), FCN-159, CS3006, HL-085, SHR7390, and WX-554.

In one embodiment, the MEK inhibitor is trametinib.

mTOR Inhibitors

Provided herein is the method according to anyone of Embodiments 54-61, which further comprises simultaneous, separate, or sequential administration of an effective amount of a second compound, wherein the second compound is an mTOR inhibitor.

Exemplary mTOR inhibitors for use in the methods provided herein include, but are not limited to, everolimus, rapamycin, zotarolimus (ABT-578), ridaforolimus (deforolimus, MK-8669), sapanisertib, buparlisib, pictilisib, vistusertib, dactolisib, Torin-1 (1-(4-(4-propionylpiperazin-1-yl)-3-(trifluoromethyl)cyclohexyl)-9-(quinolin-3-yl)benzo[h][1,6]naphthyridin-2(1H)-one), GDC-0349 ((S)-1-ethyl-3-(4-(4-(3-methylmorpholino)-7-(oxetan-3-yl)-5,6,7,8-tetrahydropyrido[3,4-d]pyrimidin-2-yl)phenyl)urea), and VS-5584 (SB2343, (5-(8-methyl-2-morpholin-4-yl-9-propan-2-ylpurin-6-yl)pyrimidin-2-amine).

In one embodiment, the mTOR inhibitor is everolimus.

PD-1 Inhibitors

Provided herein is the method according to anyone of Embodiments 54-61, which further comprises simultaneous, separate, or sequential administration of an effective amount of a second compound, wherein the second compound is a PD-1 inhibitor.

Exemplary PD-1 inhibitors for use in the methods provided herein include, but are not limited to, pembrolizumab, nivolumab, cemiplimab, spartalizumab (PDR001), camrelizumab (SHR1210), sintilimab (IB1308), tislelizumab (BGB-A317), toripalimab (JS 001), dostarlimab (TSR-042, WBP-285), INCMGA00012 (MGA012), AMP-224, AMP-514, and the anti-PD-1 antibody as described in U.S. Pat. No. 10,640,504 B2 (the "Anti-PD-1 Antibody A," column 66, line 56 to column 67, line 24 and column 67, lines 54-57), which is incorporated herein by reference.

In one embodiment, the PD-1 inhibitor is pembrolizumab. In another embodiment the PD-1 inhibitor is the Anti-PD-1 Antibody A.

PD-L1 Inhibitors

Provided herein is the method according to anyone of Embodiments 54-61, which further comprises simultaneous, separate, or sequential administration of an effective amount of a second compound, wherein the second compound is a PD-L1 inhibitor.

Exemplary PD-L1 inhibitors for use in the methods provided herein include, but are not limited to, atezolizumab, avelumab, durvalumab, ZKAB001, TG-1501, SHR-1316, MSB2311, MDX-1105, KN035, IMC-001, HLX20, FAZ053, CS1001, CK-301, CBT-502, BGB-A333, BCD-135, and A167.

In one embodiment, the PD-L1 inhibitor is atezolizumab.

PI3K Inhibitors

Provided herein is the method according to anyone of Embodiments 54-61, which further comprises simultaneous, separate, or sequential administration of an effective amount of a second compound, wherein the second compound is a PI3K inhibitor.

Exemplary PI3K inhibitors for use in the methods provided herein include, but are not limited to, idelalisib, copanlisib, duvelisib, alpelisib, taselisib, perifosine, buparlisib, umbralisib, pictilisib, dactolisib, voxtalisib, sonolisib, tenalisib, serabelisib, acalisib, CUDC-907 (N-hydroxy-2-[[2(6-methoxypyridin-3-yl)-4-morpholin-4-ylthieno[3,2-d]pyrimidin-6-yl]methyl-methylamino]pyrimidine-5-carboxamide), ME-401 (N-[2-methyl-1-[2-(1-methylpiperidin-4-yl)phenyl]propan-2-yl]-4-(2-methylsulfonylbenzimidazol-1-yl)-6-morpholin-4-yl-1,3,5-triazin-2-amine), IPI-549 (2-amino-N-[(1S)-1-[8-[2-(1-methylpyrazol-4-yl)ethynyl]-1-oxo-2-phenylisoquinolin-3-yl]ethyl]pyrazolo[1,5-a]pyrimidine-3-carboxamide), SF1126 ((2S)-2-[[(2S)-3-carboxy-2-[[2-[[(2S)-5-(diaminomethylideneamino)-2-[[4-oxo-4-[[4-(4-oxo-8-phenylchromen-2-yl)morpholin-4-ium-4-yl]methoxy]butanoyl]amino]pentanoyl]amino]acetyl]amino]propanoyl]amino]-3-hydroxypropanoate), XL147 (N-[3-(2,1,3-benzothiadiazol-5-ylamino)quinoxalin-2-yl]-4-methylbenzenesulfonamide), GSK1059615 ((5Z)-5-[(4-pyridin-4-ylquinolin-6-yl)methylidene]-1,3-thiazolidine-2,4-dione), and AMG 319 (N-[(1S)-1-(7-fluoro-2-pyridin-2-yl)quinolin-3-yl)ethyl]-7H-purin-6-anine).

Raf Kinase Inhibitors

Provided herein is the method according to anyone of Embodiments 54-61, which further comprises simultaneous, separate, or sequential administration of an effective amount of a second compound, wherein the second compound is a Raf kinase inhibitor.

The term "RAF kinase" as used herein refers to a member of a mammalian serine/threonine kinases composed of three isoforms (C-Raf, B-Raf and A-Raf) and includes homodimers of each isoform as well as heterodimers between isoforms, e.g., C-Raf/B-Raf heterodimers.

The term "Raf kinase inhibitor" as used herein refers to a compound that is capable of negatively modulating or inhibiting all or a portion of the enzymatic activity of one or more member of the Raf family kinases, or is capable of disrupting Raf homodimer or heterodimer formation to inhibit activity.

In one embodiment, the Rafkinase inhibitor includes, but is not limited to, encorafenib, sorafenib, lifirafenib, vemurafenib, dabrafenib, PLX-8394 (N-(3-(5-(2-cyclopropylpyrimidin-5-yl)-3a,7a-dihydro-1H-pyrrolo[2,3-b]pyridine-3-carbonyl)-2,4-difluorophenyl)-3-fluoropyrrolidine-1-sulfonamide), Raf-709 (N-(2-methyl-5-morpholino-6'-((tetrahydro-2H-pyran-4-yl)oxy)-[3,3'-bipyridin]-5-yl)-3-(trifluoromethyl)benzamide), LXH254 (N-(3-(2-(2-hydroxyethoxy)-6-morpholinopyridin-4-yl)-4- methylphenyl)-2-(trifluoromethyl)isonicotinamide), LY3009120 (1-(3,3-dimethylbutyl)-3-(2-fluoro-4-methyl-5-(7-methyl-2-(methylamino)pyrido[2,3-d]pyrimidin-6-yl) phenyl)urea), Tak-632 (N-(7-cyano-6-(4-fluoro-3-(2-(3-(trifluoromethyl)phenyl)acetamido)phenoxy)benzo[d]thiazol-2-yl)cyclopropanecarboxamide), CEP-32496 (1-(3-((6,7-dimethoxyquinazolin-4-yl)oxy)phenyl)-3-(5-(1,1,1-trifluoro-2-methylpropan-2-yl)isoxazol-3-yl)urea), CCT196969 (1-(3-(tert-butyl)-1-phenyl-1H-pyrazol-5-yl)-3-(2-fluoro-4-((3-oxo-3,4-dihydropyrido[2,3-b]pyrazin-8-yl)oxy)phenyl)urea), and RO5126766 (N-[3-fluoro-4-[[4-methyl-2-oxo-7-(2-pyrimidinyloxy)-2H-1-benzopyran-3-yl] methyl]-2-pyridinyl]-N'-methyl-sulfamide).

In one embodiment, the Raf kinase inhibitor is encorafenib. In one embodiment, the Rafkinase inhibitor is sorafenib. In one embodiment, the Rafkinase inhibitor is lifirafenib.

SHP2 Inhibitors

Provided herein is the method according to anyone of Embodiments 54-61, which further comprises simultaneous, separate, or sequential administration of an effective amount of a second compound, wherein the second compound is a SHP2 inhibitor.

Exemplary SHP2 inhibitors for use in the methods provided herein include, but are not limited to, SHP-099 (6-(4-amino-4-methylpiperidin-1-yl)-3-(2,3-dichlorophenyl)pyrazin-2-amine dihydrochloride), RMC-4550 ([3-[(3S, 4S)-4-amino-3-methyl-2-oxa-8-azaspiro[4.5]decan-8-yl]-6-(2,3-dichlorophenyl)-5-methylpyrazin-2-yl]methanol), TNO155, (3S,4S)-8-[6-amino-5-(2-amino-3-chloropyridin-4-yl)sulfanylpyrazin-2-yl]-3-methyl-2-oxa-8-azaspiro[4.5] decan-4-amine), and RMC-4630 (Revolution Medicine). In one embodiment, the SHP inhibitor for use in the methods provided herein is RMC-4630 (Revolution Medicine).

In another embodiment, exemplary SHP2 inhibitors for use in the methods provided herein include, but are not limited to, 3-[(1R,3R)-1-amino-3-methoxy-8-azaspiro[4.5] dec-8-yl]-6-(2,3-dichlorophenyl)-5-methyl-2-pyrazinemethanol (CAS 2172651-08-8), 3-[(3S,4S)-4-amino-3-methyl-2-oxa-8-azaspiro[4.5]dec-8-yl]-6-[(2,3-dichlorophenyl)thio]-5-methyl-2-pyrazinemethanol (CAS 2172652-13-8), 3-[(3S,4S)-4-amino-3-methyl-2-oxa-8-azaspiro[4.5]dec-8-v]-6-[[3-chloro-2-(3-hydroxy-1-azetidinyl)-4-pyridinyl]thio]-5-methyl-2-pyrazinemethanol (CAS 2172652-38-7), and 6-[(2-amino-3-chloro-4-pyridinyl) thio]-3-[(3S,4S)-4-amino-3-methyl-2-oxa-8-azaspiro[4.5] dec-8-yl]-5-methyl-2-pyrazinemethanol (CAS 2172652-48-9).

In another embodiment, exemplary SHP2 inhibitors for use in the methods provided herein include, but are not limited to, 1-[5-(2,3-dichlorophenyl)-6-methylimidazo[1,5-a]pyrazin-8-yl]-4-methyl-4-piperidinamine (CAS 2240981-75-1), (1R)-8-[5-(2,3-dichlorophenyl)-6-methylimidazo[1, 5-a]pyrazin-8-yl]-8-azaspiro[4.5]decan-1-amine (CAS 2240981-78-4), (3S,4S)-8-[7-(2,3-dichlorophenyl)-6-methylpyrazolo[1,5-a]pyrazin-4-yl]-3-methyl-2-oxa-8-azaspiro [4.5]decan-4-amine (CAS 2240982-45-8), (3S,4S)-8-[7-[(2-amino-3-chloro-4-pyridinyl)thio]pyrazolo[1,5-a]pyrazin-4-yl]-3-methyl-2-oxa-8-azaspiro[4.5]decan-4-amine (CAS 2240982-57-2), 4-[(3S,4S)-4-amino-3-methyl-2-oxa-8-azaspiro[4.5]dec-8-yl]-7-(2,3-dichlorophenyl)-6-methyl-pyrazolo[1,5-a]pyrazine-2-methanol (CAS 2240982-69-6), 7-[(2-amino-3-chloro-4-pyridinyl)thio]-4-[(3S,4S)-4-amino-3-methyl-2-oxa-8-azaspiro[4.5]dec-8-yl]-6-methyl-pyrazolo[1,5-a]pyrazine-2-methanol (CAS 2240982-73-2), and (3S,4S)-8-[7-[(2-amino-3-chloro-4-pyridinyl)thio]-6-methylpyrazolo[1,5-a]pyrazin-4-yl]-3-methyl-2-oxa-8-azaspiro[4.5]decan-4-amine (CAS 2240982-77-6).

In one embodiment, the SHP inhibitor for use in the methods provided herein is (1R)-8-[5-(2,3-dichlorophenyl)-6-methylimidazo[1,5-a]pyrazin-8-yl]-8-azaspiro[4.5]decan-1-amine (CAS 2240981-78-4).

In another embodiment, exemplary SHP2 inhibitors for use in the methods provided herein include, but are not limited to 3[(1R)-1-amino-8-azaspiro[4.5]dec-8-yl]-6-(2,3-dichlorophenyl)-5-hydroxy-2-pyridinemethanol (CAS 2238840-54-3), 3-[(1R)-1-amino-8-azaspiro[4.5]dec-8-yl]-6-[(2,3-dichlorophenyl)thio]-5-hydroxy-2-pyridinemethanol (CAS 2238840-56-5), 5-[(1R)-1-amino-8-azaspiro[4.5] dec-8-yl]-2-(2,3-dichlorophenyl)-3-pyridinol (CAS 2238840-58-7), 3-[(1R)-1-amino-8-azaspiro[4.5]dec-8-yl]-6-(2,3-dichlorophenyl)-5-methyl-2-pyridinemethanol (CAS 2238840-60-1), (1R)-8-[6-(2,3-dichlorophenyl)-5-methyl-3-pyridinyl]-8-azaspiro[4.5]decan-1-amine (CAS 2238840-62-3), 3-[(1R)-1-amino-8-azaspiro[4.5]dec-8-yl]-6-[(2,3-dichlorophenyl)thio]-5-methyl-2-pyridinemethanol (CAS 2238840-63-4), (1R)-8-[6-[(2,3-dichlorophenyl)thio]-5-methyl-3-pyridinyl]-8-azaspiro[4.5]decan-1-amine (CAS 2238840-64-5), 5-(4-amino-4-methyl-1-piperidinyl)-2-[(2, 3-dichlorophenyl)thio]-3-pyridinol (CAS 2238840-65-6), 5-[(1R)-1-amino-8-azaspiro[4.5]dec-8-yl]-2-[(2,3-dichlorophenyl)thio]-3-pyridinol (CAS 2238840-66-7), 6-[(2-amino-3-chloro-4-pyridinyl)thio]-3-[(3S,4S)-4-amino-3-methyl-2-oxa-8-azaspiro[4.5]dec-8-yl]-5-hydroxy-2-pyridinemethanol (CAS 2238840-67-8), 3-(4-amino-4-methyl-1-piperidinyl)-6-(2,3-dichlorophenyl)-5-hydroxy-2-pyridinemethanol (CAS 2238840-68-9), 3-[(3S,4S)-4-amino-3-methyl-2-oxa-8-azaspiro[4.5]dec-8-yl]-6-(2,3-dichlorophenyl)-5-methyl-2-pyridinemethanol (CAS 2238840-69-0), 6-[(2-amino-3-chloro-4-pyridinyl)thio]-3-[(3S,4S)-4-amino-3-methyl-2-oxa-8-azaspiro[4.5]dec-8-yl]-5-methyl-2-pyridinemethanol (CAS 2238840-70-3), 3-(4-amino-4-methyl-1-piperidinyl)-6-(2,3-dichlorophenyl)-5-methyl-2-pyridinemethanol (CAS 2238840-71-4), 6-[(2-amino-3-chloro-4-pyridinyl)thio]-3-(4-amino-4-methyl-1-piperidinyl)-2-pyridinemethanol (AS 2238840-72-5), 5-[(2-amino-3-chloro-4-pyridinyl)thio]-2-[(3S,4S)-4-amino-3-methyl-2-oxa-8-azaspiro[4.5]dec-8-yl]-6-methyl-3-pyridinemethanol (CAS 2238840-73-6), 2-[(3S,4S)-4-amino-3-methyl-2-oxa-8-azaspiro[4.5]dec-8-yl]-5-(2,3-dichlorophenyl)-6-methyl-3-pyridinemethanol (CAS 2238840-74-7), 3-[(3S,4S)-4-amino-3-methyl-2-oxa-8-azaspiro[4.5]dec-8-yl]-6-(2,3-dichlorophenyl)-5-hydroxy-2-pyridinemethanol (CAS 2238840-75-8), and 2-[(2-amino-3-chloro-4-pyridyl)sulfanyl]-5-[(3S,4S)-4-amino-3-methyl-2-oxa-8-azaspiro[4.5]decan-8-yl]-6-(hydroxymethyl) pyridin-3-ol.

In one embodiment, the SHP inhibitor for use in the methods provided herein is 3-[(1R)-1-amino-8-azaspiro[4.5] dec-8-yl]-6-[(2,3-dichlorophenyl)thio]-5-hydroxy-2-pyridinemethanol (CAS 2238840-56-5).

In one embodiment, the SHP2 inhibitor for use in the methods provided herein is an inhibitor disclosed in U.S. Pat. No. 10,590,090 B2, US 2020/017517 A1, US 2020/017511 A1, or WO 2019/075265 A1, each of which is herewith incorporated by reference in its entirety.

SOS1 Inhibitors

Provided herein is the method according to anyone of Embodiments 54-61, which further comprises simultaneous, separate, or sequential administration of an effective amount of a second compound, wherein the second compound is an SOS1 inhibitor.

Exemplary SOS1 inhibitors for use in the methods provided herein include, but are not limited to, BI 3406 (N-[(1R)-1-[3-amino-5-(trifluoromethyl)phenyl]ethyl]-7-methoxy-2-methyl-6-[(3S)-oxolan-3-yl]oxyquinazolin-4-amine), and BI 1701963.

Src Kinase Inhibitors

Provided herein is the method according to anyone of Embodiments 54-61, which further comprises simultaneous, separate, or sequential administration of an effective amount of a second compound, wherein the second compound is a Src kinase inhibitor.

The term "Src kinase" as used herein refers to a member of a mammalian no receptor tyrosine kinase family including: Src, Yes, Fyn, and Fgr (SrcA subfamily); Eck, Hck, Blk, and Lyn (SrcB subfamily), and Frk subfamily.

The term "Src kinase inhibitor" as used herein refers to a compound that is capable of negatively modulating or inhibiting all or a portion of the enzymatic activity of one or more member of the Src kinases.

Exemplary Src kinase inhibitors for use in the methods provided herein include, but are not limited to, dasatinib, ponatinib, vandetanib, bosutinib, saracatinib, KX2-391 (N-benzyl-2-(5-(4-(2-morpholinoethoxy)phenyl)pyridin-2-yl)acetamide), SU6656 ((Z)—N,N-dimethyl-2-oxo-3-((4,5,6,7-tetrahydro-1H-indol-2-yl)methylene)indoline-5-sulfonamide), PP 1 (1-(tert-butyl)-3-(p-tolyl)-1H-pyrazolo[3,4-d]pyrimidin-4-amine), WH-4-023 (2,6-dimethylphenyl(2,4-dimethoxyphenyl)(2-((4-(4-methylpiperazin-1-yl)phenyl)amino)pyrimidin-4-yl)carbamate), and KX-01 (N-benzyl-2-(5-(4-(2-morpholineethoxy)phenyl)pyridin-2-yl)acetamide).

In one embodiment, the Src kinase inhibitor is dasatinib. In one embodiment, the Src kinase inhibitor is saracatinib. In one embodiment, the Src kinase inhibitor is ponatinib. In one embodiment, the Src kinase inhibitor is vandetanib. In one embodiment, the Src kinase inhibitor is KX-01.

Chemotherapeutic Agents

Provided herein is the method according to anyone of Embodiments 54-61, which further comprises simultaneous, separate, or sequential administration of an effective amount of a second compound, wherein the second compound is one or more chemotherapeutic agent.

Exemplary chemotherapeutic agents for use in the methods provided herein include, but are not limited to, leucovorin calcium (calcium folinate), 5-fluorouracil, irinotecan, oxaliplatin, cisplatin, carboplatin, pemetrexed, docetaxel, paclitaxel, gemcitabine, vinorelbine, chlorambucil, cyclophosphamide, and methotrexate.

Definitions

The following definitions are provided to assist in understanding the scope of this disclosure.

Unless otherwise indicated, all numbers expressing quantities of ingredients, reaction conditions, and so forth used in the specification or claims are to be understood as being modified in all instances by the term "about." Accordingly, unless indicated to the contrary, the numerical parameters set forth in the following specification and attached claims are approximations that may vary depending upon the standard deviation found in their respective testing measurements.

As used herein, if any variable occurs more than one time in a chemical formula, its definition on each occurrence is independent of its definition at every other occurrence. If the chemical structure and chemical name conflict, the chemical structure is determinative of the identity of the compound.

Stereoisomers

The compounds of the present disclosure may contain, for example, double bonds, one or more asymmetric carbon atoms, and bonds with a hindered rotation, and therefore, may exist as stereoisomers, such as double-bond isomers (i.e., geometric isomers (E/Z)), enantiomers, diastereomers, and atropoisomers. Accordingly, the scope of the instant disclosure is to be understood to encompass all possible stereoisomers of the illustrated compounds, including the stereoisomerically pure form (for example, geometrically pure, enantiomerically pure, diastereomerically pure, and atropoisomerically pure) and stereoisomeric mixtures (for example, mixtures of geometric isomers, enantiomers, diastereomers, and atropoisomers, or mixture of any of the foregoing) of any chemical structures disclosed herein (in whole or in part), unless the stereochemistry is specifically identified.

If the stereochemistry of a structure or a portion of a structure is not indicated with, for example, bold or dashed lines, the structure or portion of the structure is to be interpreted as encompassing all stereoisomers of it. If the stereochemistry of a structure or a portion of a structure is indicated with, for example, bold or dashed lines, the structure or portion of the structure is to be interpreted as encompassing only the stereoisomer indicated, unless otherwise noted.

For example,

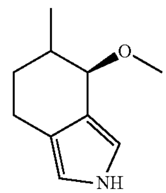

represents

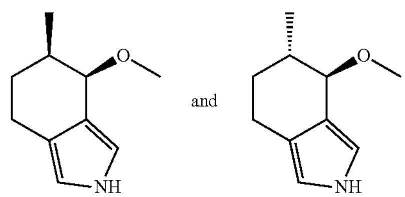

Similarly, for example, the chemical name (4R)-4-methoxy-5-methyl-4,5,6,7-tetrahydro-2H-isoinidole represents (4R,5R)-4-methoxy-5-methyl-4,5,6,7-tetrahydro-2H-isoindole and (4R,5S)-4-methoxy-5-methyl-4,5,6,7-tetrahydro-2H-isoindole.

As a further example

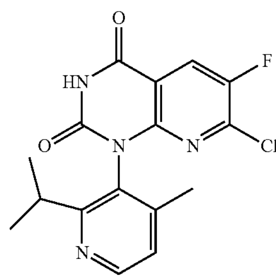 [SMILES: Cc1ccnc(C(C)C)c1-n1c(=O)[nH]c(=O)c2cc(F)c(Cl)nc21]

represents

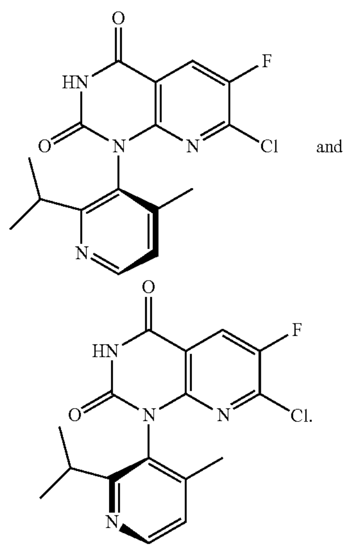

and

Similarly, for example, the chemical name 7-chloro-6-fluoro-1-(2-isopropyl-4-methylpyridin-3-yl)pyrido[2,3-d]pyrimidine-2,4(1H,31)-dione represents (M)-7-chloro-6-fluoro-1-(2-isopropyl-4-methylpyridin-3-yl)pyrido[2,3-d]pyrimidine-2,4(1H,3H)-dione and (P)-7-chloro-6-fluoro-1-(2-isopropyl-4-methylpyridin-3-yl)pyrido[2,3-d]pyrimidine-2,4(1H,3H)-dione.

In certain instances, a bond drawn with a wavy line may be used to indicate that both stereoisomers are encompassed. This is not to be confused with a wavy line drawn perpendicular to a bond which indicates the point of attachment of a group to the rest of the molecule.

The term “stereoisomer” or “stereoisomerically pure” compound as used herein refers to one stereoisomer (for example, geometric isomer, enantiomer, diastereomer and atropisomer) of a compound that is substantially free of other stereoisomers of that compound. For example, a stereoisomerically pure compound having one chiral center will be substantially free of the mirror image enantiomer of the compound and a stereoisomerically pure compound having two chiral centers will be substantially free of the other enantiomer and diastereomers of the compound. A typical stereoisomerically pure compound comprises greater than about 80% by weight of one stereoisomer of the compound and equal or less than about 20% by weight of other stereoisomers of the compound, greater than about 90% by weight of one stereoisomer of the compound and equal or less than about 10% by weight of the other stereoisomers of the compound, greater than about 95% by weight of one stereoisomer of the compound and equal or less than about 5% by weight of the other stereoisomers of the compound, or greater than about 97% by weight of one stereoisomer of the compound and equal or less than about 3% by weight of the other stereoisomers of the compound.

This disclosure also encompasses the pharmaceutical compositions comprising stereoisomerically pure forms and the use of stereoisomerically pure forms of any compounds disclosed herein. Further, this disclosure also encompasses pharmaceutical compositions comprising mixtures of stereoisomers of any compounds disclosed herein and the use of said pharmaceutical compositions or mixtures of stereoisomers. These stereoisomers or mixtures thereof may be synthesized in accordance with methods well known in the art and methods disclosed herein. Mixtures of stereoisomers may be resolved using standard techniques, such as chiral columns or chiral resolving agents. See, for example, Jacques et al., Enantiomers, Racemates and Resolutions (Wiley-Interscience, New York, 1981); Wilen et al., *Tetrahedron* 33:2725; Eliel, Stereochemistry of Carbon Compounds (McGraw-Hill, N Y, 1962); and Wilen, Tables of Resolving Agents and Optical Resolutions, page 268 (Eliel, Ed., Univ. of Notre Dame Press, Notre Dame, IN, 1972).

Tautomers

As known by those skilled in the art, certain compounds disclosed herein may exist in one or more tautomeric forms. Because one chemical structure may only be used to represent one tautomeric form, it will be understood that for convenience, referral to a compound of a given structural formula includes other tautomers of said structural formula. For example,

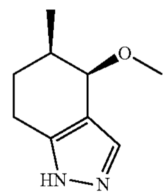

represents

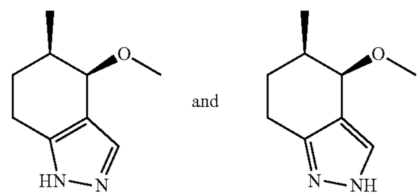

Similarly, for example, the chemical name (4R,5R)-4-methoxy-5-methyl-4,5,6,7-tetrahydro-1-H-indazole represents (4R,5R)-4-methoxy-5-methyl-4,5,6,7-tetrahydro-1H-indazole and (4R,5R)-4-methoxy-5-methyl-4,5,6,7-tetrahydro-2H-indazole.

Accordingly, the scope of the instant disclosure is to be understood to encompass all tautomeric forms of the compounds disclosed herein.

Isotopically-Labelled Compounds

Further, the scope of the present disclosure includes all pharmaceutically acceptable isotopically-labelled compounds of the compounds disclosed herein, such as the compounds of Formula I, wherein one or more atoms are replaced by atoms having the same atomic number, but an atomic mass or mass number different from the atomic mass or mass number usually found in nature. Examples of isotopes suitable for inclusion in the compounds disclosed herein include isotopes of hydrogen, such as $^{2}H$ and $^{3}H$, carbon, such as $^{11}C$, $^{13}C$ and $^{14}C$, chlorine, such as $^{36}Cl$, fluorine, such as $^{18}F$, iodine, such as $^{123}I$ and $^{125}I$ nitrogen, such as $^{13}N$ and $^{15}N$, oxygen, such as $^{15}O$, $^{17}O$ and $^{18}O$, phosphorus, such as $^{32}P$, and sulphur, such as $^{35}S$. Certain isotopically-labelled compounds of Formula I, for example, those incorporating a radioactive isotope, are useful in drug and/or substrate tissue distribution studies. The radioactive isotopes tritium ($^{3}H$) and carbon-14 ($^{14}C$) are particularly useful for this purpose in view of their ease of incorporation and ready means of detection. Substitution with isotopes such as deuterium ($^2H$ or D) may afford certain therapeutic advantages resulting from greater metabolic stability, for example, increased in vivo half-life or reduced dosage requirements, and hence may be advantageous in some circumstances. Substitution with positron emitting isotopes, such as $^{13}C$, $^{18}F$, $^{15}O$ and $^{13}N$, can be useful in Positron Emission Topography (PET) studies, for example, for examining target occupancy. Isotopically-labelled compounds of the compounds disclosed herein can generally be prepared by conventional techniques known to those skilled in the art or by processes analogous to those described in the accompanying General Synthetic Procedures and Examples using an appropriate isotopically-labelled reagent in place of the non-labelled reagent previously employed.

Miscellaneous Definitions

This section will define additional terms used to describe the scope of the compounds, compositions and uses disclosed herein.

The term "2 h coupled exchange assay" or "20 h coupled exchange assay" as used herein refers to the assay described in the Section entitled "BIOLOGICAL EVALUATION."

The term "6 or 10 membered aryl" as used herein refers to a phenyl or napthyl ring.

The term "$C_{2-4}$alkenyl" as used herein refers to a saturated hydrocarbon containing 2 to 4 carbon atoms having at least one carbon-carbon double bond. Alkenyl groups include both straight and branched moieties. Representative examples of $C_{2-4}$alkenyl include, but are not limited to, 1-propenyl, 2-propenyl, 2-methyl-2-propenyl, and butenyl.

The terms "$C_{1-4}$alkyl" and "$C_{1-4}$alkyl" as used herein refer to a straight or branched chain hydrocarbon containing from 1 to 4 and 1 to 6 carbon atoms, respectively. Representative examples of $C_{1-4}$alkyl or $C_{1-6}$alkyl include, but are not limited to, methyl, ethyl, n-propyl, iso-propyl, n-butyl, sec-butyl, iso-butyl, tert-butyl, pentyl, and hexyl.

The term "$C_{1-4}$alkoxy" as used herein refers to —$OR^{\#}$, wherein $R^{\#}$ represents a $C_{1-4}$alkyl group as defined herein. Representative examples of $C_{1-4}$alkoxy include, but are not limited to, methoxy, ethoxy, propoxy, iso-propoxy, and butoxy.

The term "$C_{3-5}$cycloalkyl" and "$C_{3-6}$cycloalkyl" as used herein refers to a saturated carbocyclic molecule wherein the cyclic framework has 3 to 5 and 3 to 6 carbon atoms, respectively. Representative examples of $C_{3-5}$cycloalkyl or $C_{3-5}$cycloalkyl include, but are not limited to, cyclopropyl, cyclobutyl, cyclopentyl, and cyclohexyl.

The term "deutero" as used herein as a prefix to another term for a chemical group refers to a modification of the chemical group, wherein one or more hydrogen atoms are substituted with one or more deuterium atoms. For example, the term "$C_{1-4}$deuteroalkyl" refers to a $C_{1-4}$alkyl as defined herein, wherein one or more hydrogen atoms are substituted with one or more deuterium atoms. Representative examples of $C_{1-4}$deuteroalkyl include, but are not limited to, —$CH_2D$, —$CHD_2$, —$CD_3$, —$CH_2CD_3$, —$CDHCD_3$, —$CD_2CD_3$, —$CH(CD_3)_2$, $CD(CHD_2)_2$, and —$CH(CH_2D)(CD_3)$.

The term "$C_{1-4}$dialkylamino" as used herein refers to —NR*R**, wherein R* and R** independently represent a $C_{1-4}$alkyl as defined herein. Representative examples of $C_{1-4}$dialkylamino include, but are not limited to, —$N(CH_3)_2$, —$N(CH_2CH_3)_2$, —$N(CH_3)(CH_2CH_3)$—. $N(CH_2CH_2CH_3)_2$, and —$N(CH(CH_3)_2)_2$.

The term "$C_{1-4}$alkylamino" as used herein refers to —NHR*, wherein R* represents a $C_{1-4}$alkyl as defined herein. Representative examples of $C_{1-4}$alkylamino include, but are not limited to, —$NH(CH_3)$, —$NH(CH_2CH_3)$, —$NH(CH_2CH_2CH_3)$, and —$NH(CH(CH_3)_2)$.

The term "halogen" as used herein refers to —F, —Cl, —Br, or —I.

The term "halo" as used herein as a prefix to another term for a chemical group refers to a modification of the chemical group, wherein one or more hydrogen atoms are substituted with one or more halogen atoms as defined herein. The halogen is independently selected at each occurrence. For example, the term "$C_{1-4}$haloalkyl" refers to a $C_{1-4}$alkyl as defined herein, wherein one or more hydrogen atoms are substituted with a halogen. Representative examples of $C_{1-4}$haloalkyl include, but are not limited to, —$CH_2F$, —$CHF_2$, —$CF_3$, —CHFCl, —$CH_2CF_3$, —$CFHCF_3$, —$CF_2CF_3$, —$CH(CF_3)_2$, —$CF(CHF_2)_2$, and —$CH(CH_2F)(CF_3)$. Further, for example, the term "$C_{1-4}$haloalkoxy" for example refers to a $C_{1-4}$alkoxy as defined herein, wherein one or more hydrogen atoms are substituted with a halogen. Representative examples of $C_{1-4}$haloalkoxy include, but are not limited to, —$OCH_2F$, —$OCHF_2$, —$OCF_3$, —OCHFCl, —$OCH_2CF_3$, —$OCFHCF_3$, —$OCF_2CF_3$, —$OCH(CF)_2$, —$OCF(CHF_2)_2$, and —$OCH(CH_2F)(CF_3)$.

The terms "5 to 6 membered heteroaryl" and "5 to 10 membered heteroaryl" as used herein refer to a mono or bicyclic ring aromatic ring system containing 1 to 5 and 1 to 10 heteroatoms, respectively, at each occurrence independently selected from N, O, and S with the remaining ring atoms being carbon. Representative examples of 5 to 6 or 5 to 10 membered heteroaryls include, but are not limited to, furanyl, imidazolyl, isothiazolyl, isoxazolyl, oxadiazolyl, oxazolyl, pyrazolyl, pyrrolyl, thiadiazolyl, thiazolyl, thienyl, tetrazolyl, triazinyl, triazolyl, pyridyl, pyridazinyl, pyrazinyl, pyrimidinyl, benzofuranyl, benzimidazolyl, benzoisoxazolyl, benzopyranyl, benzothiadiazolyl, benzothiazolyl, benzothienyl, benzothiophenyl, benzotriazolyl, benzoxazolyl, furopyridyl, imidazopyridinyl, imidazothiazolyl, indolizinyl, indolyl, indazolyl, isobenzofuranyl, isobenzothienyl, isoindolyl, isoquinolinyl, isothiazolyl, naphthyridinyl, oxazolopyridinyl, phthalazinyl, pteridinyl, purinyl, pyridopyridyl, pyrrolopyridyl, quinolinyl, quinoxalinyl, quiazolinyl, thiadiazolopyrimidyl, and thienopyridyl.

The term "$C_{3-5}$heterocycloalkyl" as used herein refers to a saturated carbocyclic molecule wherein the cyclic framework has 3 to 5 carbon atoms and wherein one carbon atom is substituted with a heteroatom selected from N, O, and S. Representative examples of $C_{3-5}$heterocycloalkyl include, but are not limited to, aziridinyl, azetidinyl, oxetanyl, and pyrrolidinyl.

The term "$C_{3-6}$heterocycloalkyl" as used herein refers to a saturated carbocyclic molecule wherein the cyclic framework has 3 to 6 carbon atoms and wherein one or two carbon atoms are substituted with one or two heteroatoms independently selected from N, O, and S. Representative examples of $C_{3-6}$heterocycloalkyl include, but are not limited to, aziridinyl, azetidinyl, oxetanyl, pyrrolidinyl, piperidinyl, piperazinyl, morpholinyl, and thiomorpholinyl.

The term "pharmaceutically acceptable" as used herein refers to generally recognized for use in subjects, particularly in humans.

The term "pharmaceutically acceptable salt" as used herein refers to a salt of a compound that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, and the like; or (2) salts formed when an acidic proton present in the parent compound either is replaced by a metal ion, for example, an alkali metal ion, an alkaline earth ion, or an aluminum ion; or coordinates with an organic base such as ethanolamine, diethanolamine, triethanolamine, N-methylglucamine, dicyclohexylamine, and the like. Additional examples of such salts can be found in Berge et al., *J. Pharm. Sci.* 66(1):1-19 (1977). See also Stahl et al., Pharmaceutical Salts: Properties, Selection, and Use, $2^{nd}$ Revised Edition (2011).

The term "pharmaceutically acceptable excipient" as used herein refers to a broad range of ingredients that may be combined with a compound or salt disclosed herein to prepare a pharmaceutical composition or formulation. Typically, excipients include, but are not limited to, diluents, colorants, vehicles, anti-adherents, glidants, disintegrants, flavoring agents, coatings, binders, sweeteners, lubricants, sorbents, preservatives, and the like.

The term "subject" as used herein refers to humans and mammals, including, but not limited to, primates, cows, sheep, goats, horses, dogs, cats, rabbits, rats, and mice. In one embodiment the subject is a human.

The term "therapeutically effective amount" as used herein refers to that amount of a compound disclosed herein that will elicit the biological or medical response of a tissue, a system, or subject that is being sought by a researcher, veterinarian, medical doctor or other clinician.

General Synthetic Procedures

The compounds provided herein can be synthesized according to the procedures described in this and the following sections. The synthetic methods described herein are merely exemplary, and the compounds disclosed herein may also be synthesized by alternate routes utilizing alternative synthetic strategies, as appreciated by persons of ordinary skill in the art. It should be appreciated that the general synthetic procedures and specific examples provided herein are illustrative only and should not be construed as limiting the scope of the present disclosure in any manner.

Generally, the compounds of Formula I can be synthesized according to the following schemes. Any variables used in the following scheme are the variables as defined for Formula I, unless otherwise noted. All starting materials are either commercially available, for example, from Sigma-Aldrich, Inc., or known in the art or may be synthesized by employing known procedures using ordinary skill. Starting material may also be synthesized via the procedures disclosed herein. Suitable reaction conditions, such as, solvent, reaction temperature, and reagents, for the Schemes discussed in this section, may be found in the examples provided herein.

Scheme 1

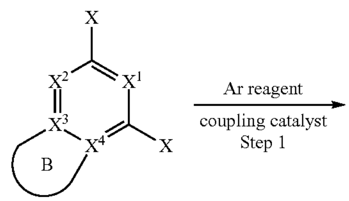
Ar reagent
coupling catalyst
Step 1

-continued

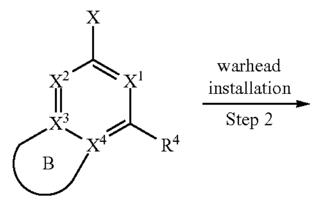

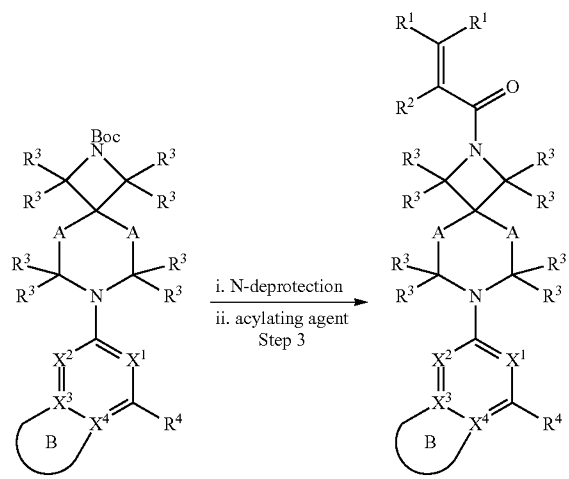

Scheme 2

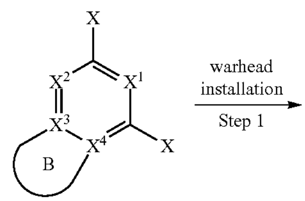

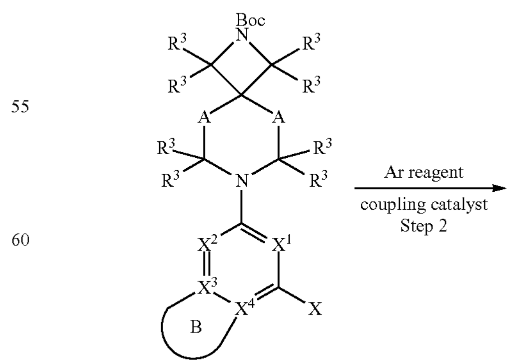

-continued

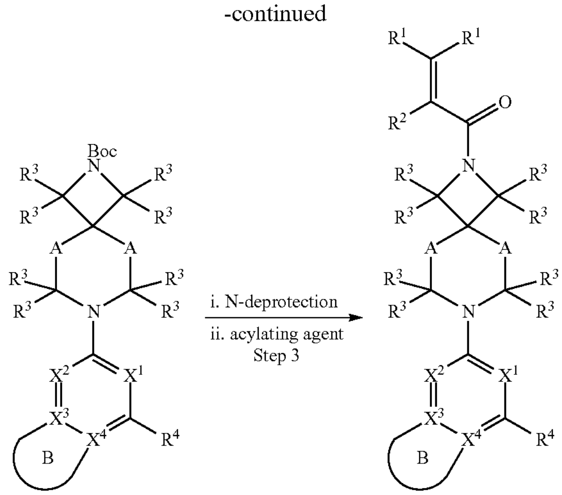

As can be appreciated by the skilled artisan, the above synthetic schemes and representative examples are not intended to comprise a comprehensive list of all means by which the compounds described and claimed in this application may be synthesized. Further methods will be evident to those of ordinary skill in the art. Additionally, the various synthetic steps described above may be performed in an alternate sequence or order to give the desired compounds.

Purification methods for the compounds described herein are known in the art and include, for example, crystallization, chromatography (for example, liquid and gas phase), extraction, distillation, trituration, and reverse phase HPLC.

The disclosure further encompasses "intermediate" compounds, including structures produced from the synthetic procedures described, whether isolated or generated in-situ and not isolated, prior to obtaining the finally desired compound. These intermediates are included in the scope of this disclosure. Exemplary embodiments of such intermediate compounds are set forth in the Examples below.

EXAMPLES

This section provides specific examples of compounds of Formula I and methods of making the same.

List of Abbreviations

TABLE 1

| | |
|---|---|
| AcOH or HOAc | acetic acid |
| $Ac_2O$ | acetic anhydride |
| aq or aq. | aqueous |
| Bn | benzyl |
| BOC or Boc | tert-butyloxycarbonyl |
| CAN | ceric ammonium nitrate |
| DAST | diethylaminosulfur trifluoride |
| DBU | 1,8-diazabicyclo[5.4.0]undec-7-ene |
| DCE | 1,2-dichloroethane |
| DCM | dichloromethane |
| DEAD | diethyl azodicarboxylate |
| DMA | N,N-dimethylacetamide |
| DMAP | 4-dimethylaminopyridine |
| DMF | N,N-dimethylformamide |
| DMSO | dimethyl sulfoxide |
| Dppf, DPPF or dppf | 1,1'-bis(diphenylphosphino)ferrocene |
| EDC or EDCI | 1-ethyl-3-(3-dimethylaminopropyl)carbodiimide |
| ESI or ES | electrospray ionization |
| Et | ethyl |
| EtOH | ethanol |
| $Et_2O$ | diethyl ether |
| EtOAc | ethyl acetate |
| g | gram(s) |
| h | hour(s) |
| HATU | 1-[bis(dimethylamino)methylene]-1H-1,2,3-triazolo[4,5-b]pyridinium 3-oxide hexafluorophosphate |
| HCl | hydrochloric acid |
| HPLC | high pressure liquid chromatography |
| iPr | isopropyl |
| iPrOH | isopropyl alcohol |
| $iPr_2NEt$ or DIPEA or DIEA | N-ethyl diisopropylamine (Hünig's base) |
| $[Ir(1,5\text{-}COD)(OMe)]_2$ | (1,5-Cyclooctadiene)(methoxy)iridium(I) dimer |
| KOAc | potassium acetate |
| $K_3PO_4$ | potassium phosphate |
| LC MS, LCMS, LC-MS or LC/MS | liquid chromatography mass spectroscopy |
| LDA | lithium diisopropylamide |
| LHMDS or LiHMDS | lithium bis(trimethylsilyl)amide |
| m/z | mass divided by charge |
| Me | methyl |
| MeCN | acetonitrile |
| MeOH | methanol |
| μL | microliter |
| m-CPBA | 3-chlorobenzene-1-carboperoxoic acid |
| mg | milligrams |
| min | minutes |
| mL or ml | milliliters |
| MS | mass spectra |
| MTBE | methyl tert-butyl ether |

TABLE 1-continued

| | |
|---|---|
| NBS | N-bromosuccinimide |
| NCS | N-chlorosuccinimide |
| NFSI | N-fluorobenzenesulfonimide |
| NIS | N-iodosuccinimide |
| NsCl | 4-nitrobenzenesulfonyl chloride |
| NMP | N-methyl-2-pyrrolidinone |
| NMR | nuclear magnetic resonance |
| PE | petroleum ether |
| $Pd_2(dba)_3$ | tris(dibenzylideneacetone)dipalladium(0) |
| $Pd(dppf)Cl_2$ | [1,1'-bis(diphenylphosphino)ferrocene]dichloropalladium(II) |
| $Pd(PPh_3)_4$ | tetrakis(triphenylphosphine)palladium(0) |
| PEPPSI-Ipent | [1,3-bis(2,6-di-3-pentylphenyl)imidazol-2-ylidene](3-chloropyridyl)dichloropalladium(II) |
| Ph | phenyl |
| $PPh_3$ | triphenylphosphine |
| PPTS | pyridinium p-toluenesulfonate |
| RBF | round bottomed flask |
| RP | reverse phase |
| RT or rt or r.t. | room temperature |
| RuPhos | 2-dicyclohexylphosphino-2',6'-diisopropoxybiphenyl |
| RuPhos Pd G4 | methanesulfonato(2-dicyclohexylphosphino-2',6'-di-i-propoxy-1,1'-biphenyl)(2'-methylamino-1,1'-biphenyl-2-yl)palladium(II) |
| sat. or satd | saturated |
| SFC | supercritical fluid chromatography |
| SPhos Pd G3 | (2-dicyclohexylphosphino-2',6'-dimethoxybiphenyl) [2-(2'-amino-1,1'-biphenyl)]palladium(II) methanesulfonate |
| T3P | propylphosphonic anhydride |
| TEA or $Et_3N$ | triethylamine |
| TFA | trifluoroacetic acid |
| $Tf_2O$ | trifluoromethanesulfonic anhydride |
| THF | tetrahydrofuran |
| XPhos Pd G2 | chloro(2-dicyclohexylphosphino-2',4',6'-triisopropyl-1,1'-biphenyl)[2-(2'-amino-1,1'-biphenyl)]palladium(II) |

General Analytical and Purification Methods

Provided in this section are descriptions of the general analytical and purification methods used to prepare the specific examples provided herein.

Chromatography:

Unless otherwise indicated, crude product-containing residues were purified by passing the crude material or concentrate through either a Biotage or ISCO brand silica gel column pre-packed with flash silica ($SiO_2$), or reverse phase flash silica ($C_{18}$) and eluting the product off the column with a solvent gradient as indicated. For example, a description of (330 g $SiO_2$, 0-40% EtOAc/hexanes) means the product was obtained by elution from the column packed with 330 grams of silica, with a solvent gradient of 0% to 40% EtOAc in hexanes.

Preparative HPLC Method:

Where so indicated, the compounds described herein were purified via reverse phase HPLC using Waters FractionLynx semi-preparative HPLC-MS system utilizing one of the following two HPLC columns: (a) Phenomenex Gemini column (5 μm, C18, 150×30 mm) or (b) Waters X-select CSH column (5 μm, C18, 100×30 mm).

A typical run through the instrument included: eluting at 45 mL/min with a linear gradient of 10% (v/v) to 100% MeCN (0.1% v/v formic acid) in water (0.1% formic acid) over 10 minutes; conditions can be varied to achieve optimal separations.

Preparative SFC Method:

Where so indicated, the compounds described herein were purified via SFC using Chiral SFC-80 (Thar, Waters) in an AD (20×250 mm, 10 μm) (Daicel) column.

Proton NMR Spectra:

Unless otherwise indicated, all $^1H$ NMR spectra were collected on a Bruker NMR Instrument at 300, 400 or 500 MHz. Where so characterized, all observed protons are reported as parts-per-million (ppm) downfield from tetramethylsilane (TMS) using the internal solvent peak as reference.

Mass Spectra (MS)

Unless otherwise indicated, all mass spectral data for starting materials, intermediates and/or exemplary compounds are reported as mass/charge (m/z), having an $[M+H]^+$ molecular ion. The molecular ion reported was obtained by electrospray detection method (commonly referred to as an ESI MS) utilizing a Waters Acquity UPLC/MS system. Compounds having an isotopic atom, such as bromine and the like, are generally reported according to the detected isotopic pattern, as appreciated by those skilled in the art.

Compound Names

The compounds disclosed and described herein have been named using the IUPAC naming function provided with J Chem for Excel 18.22.1.7 from ChemAxon Ltd.

Specific Examples

Provided in this section are the procedures to synthesize specific examples of the compounds provided herein. All starting materials are either commercially available from Merck Sigma-Aldrich Inc., unless otherwise noted, or known in the art and may be synthesized by employing known procedures using ordinary skill.

Synthesis of Examples

Method 1.

Example 1-1: 1-(6-(4-(3-hydroxynaphthalen-1-yl)-5,6,7,8-tetrahydroquinazolin-2-yl)-2,6-diazaspiro[3.4]octan-2-yl)prop-2-en-1-one

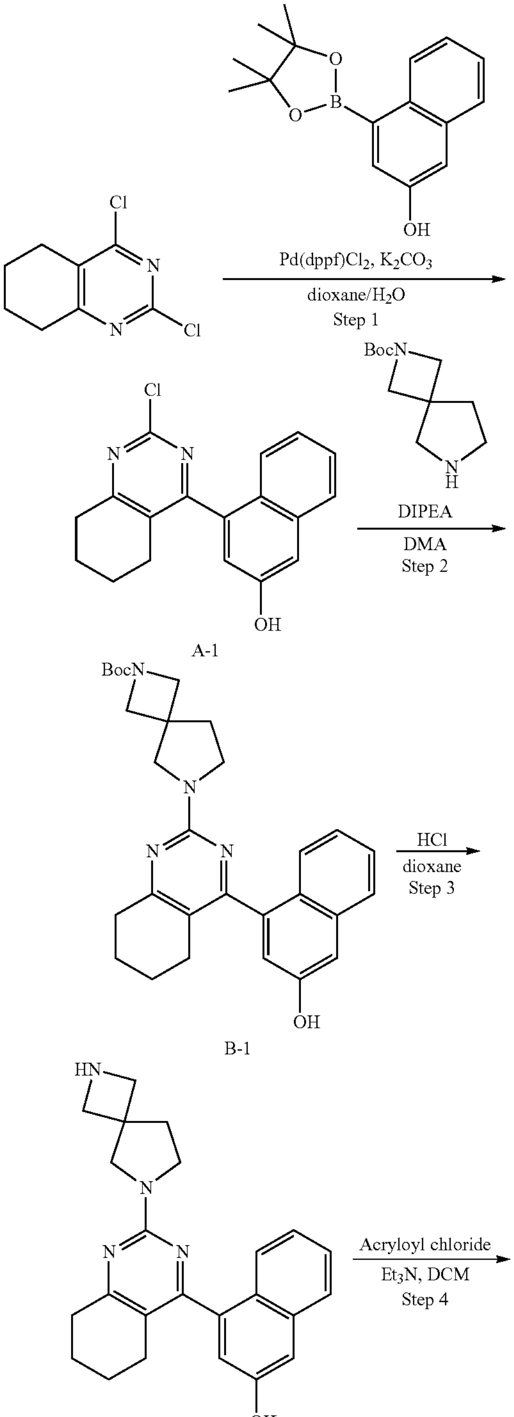

A-1

B-1

C-1

-continued

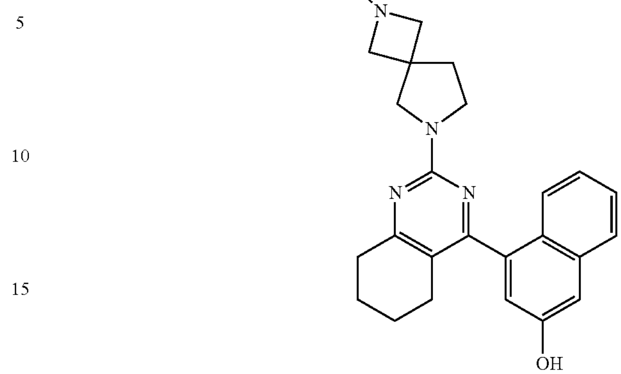

Example 1-1

Step 1: 4-(2-chloro-5,6,7,8-tetrahydroquinazolin-4-yl)naphthalen-2-ol (A-1)

To a degassed solution of 2,4-dichloro-5,6,7,8-tetrahydroquinazoline (0.5 g, 2.462 mmol, Combi-Blocks), 4-(4,4,5,5-tetramethyl-1,3,2-dioxaborolan-2-yl)naphthalen-2-ol (0.665 g, 2.462 mmol, CAS: 2043962-01-0) and $K_2CO_3$ (0.681 g, 4.92 mmol) in 1,4-dioxane (6 mL) and water (1.5 mL), was added $PdCl_2$(dppf)-DCM adduct (0.201 g, 0.246 mmol, Hindustan platinum). The reaction mixture was heated to 90° C. for 16 h. Upon completion, the reaction was allowed to cool to rt and was filtered through celite (washed with EtOAc). The filtrate was washed with water, brine solution, separated, dried over $Na_2SO_4$, filtered and concentrated in vacuo. The residue was further purified by silica gel chromatography eluting with a gradient of 40% to 50% EtOAc in PE, to provide 4-(2-chloro-5,6,7,8-tetrahydroquinazolin-4-yl)naphthalen-2-ol A-1 (0.250 g, 0.804 mmol, 33% yield) as a light yellow liquid. m/z (ESI): 311.1 $(M+H)^+$.

Step 2: tert-butyl 6-(4-(3-hydroxynaphthalen-1-yl)-5,6,7,8-tetrahydroquinazolin-2-yl)-2,6-diazaspiro[3.4]octane-2-carboxylate (B-1)

A solution of 4-(2-chloro-5,6,7,8-tetrahydroquinazolin-4-yl)naphthalen-2-ol A-1 (0.25 g, 0.804 mmol), tert-butyl 2,6-diazaspiro[3.4]octane-2-carboxylate (0.124 g, 0.585 mmol, PharmaBlock), and DIPEA (0.281 mL, 1.61 mmol) in DMA (1.5 mL) was heated to 90° C. for 16 h. Upon completion, the reaction mixture was allowed to cool to rt. The mixture was diluted with water and extracted with EtOAc. The organic extracts were washed with brine solution, separated, dried over $Na_2SO_4$, filtered and concentrated in vacuo. The residue was purified by silica gel chromatography eluting with a gradient of 70% to 90% EtOAc in hexanes, to provide tert-butyl 6-(4-(3-hydroxynaphthalen-1-yl)-5,6,7,8-tetrahydroquinazolin-2-yl)-2,6-diazaspiro[3.4]octane-2-carboxylate B-1 (0.200 g, 0.411 mmol, 52% yield) as a light yellow solid. m/z (ESI): 486.9 $(M+H)^+$.

Step 3: 4-(2-(2,6-diazaspiro[3.4]octan-6-yl)-5,6,7,8-tetrahydroquinazolin-4-yl)naphthalen-2-ol hydrochloride (C-1)

To a solution of tert-butyl 6-(4-(3-hydroxynaphthalen-1-yl)-5,6,7,8-tetrahydroquinazolin-2-yl)-2,6-diazaspiro[3.4]

octane-2-carboxylate B-1 (0.200 g, 0.411 mmol) in 1,4-dioxane (2 mL) was added 4.0 M HCl in 1,4-dioxane (2 mL, 65.8 mmol) at 0° C. The reaction mixture was allowed to stir for 6 h at rt. The reaction mixture was concentrated under reduced pressure and triturated with $Et_2O$ to afford 4-(2-(2,6-diazaspiro[3.4]octan-6-yl)-5,6,7,8-tetrahydroquinazolin-4-yl)naphthalen-2-ol hydrochloride C-1 (0.170 g, 0.402 mmol, 98% yield) as light yellow solid. m/z (ESI): 387.9 $(M+H)^+$.

Step 4: 1-(6-(4-(3-Hydroxynaphthalen-1-yl)-5,6,7,8-tetrahydroquinazolin-2-yl)-2,6-diazaspiro[3.4]octan-2-yl)prop-2-en-1-one (Example 1-1)

To a solution of 4-(2-(2,6-diazaspiro[3.4]octan-6-yl)-5,6,7,8-tetrahydroquinazolin-4-yl)naphthalen-2-ol hydrochloride C-1 (0.15 g, 0.355 mmol) and TEA (0.48 mL, 3.55 mmol) in DCM (2 mL) was added acryloyl chloride (0.021 mL, 0.284 mmol) at −78° C. The resulting reaction mixture was stirred at rt for 10 min. The reaction mixture was then diluted with water and extracted with DCM. The combined organic extracts were dried over $Na_2SO_4$, filtered, and concentrated in vacuo. The residue was purified by preparative HPLC (Phenomenex Gemini $C_{18}$ column, 150×30 mm, 10-100% 0.1% TFA in $MeCN/H_2O$) to afford 1-(6-(4-(3-hydroxynaphthalen-1-yl)-5,6,7,8-tetrahydroquinazolin-2-yl)-2,6-diazaspiro[3.4]octan-2-yl)prop-2-en-1-one Example 1-1 (0.025 g, 0.057 mmol, 16% yield) as a white solid. m/z (ESI): 440.9 $(M+H)^+$. $^1H$ NMR (400 MHz, DMSO-$d_6$) δ ppm 7.77 (d, J=8.3 Hz, 1H), 7.39-7.42 (m, 1H), 7.31 (d, J=8.3 Hz, 1H), 7.17-7.24 (m, 2H), 6.95 (d, J=2.4 Hz, 1H), 6.30 (dd, J=17.0, 10.3 Hz, 1H), 6.10 (dd, J=17.1, 2.3 Hz, 1H), 5.66 (dd, J=10.2, 2.3 Hz, 1H), 4.10-4.27 (m, 2H), 4.07-4.11 (m, 2H), 3.89-3.93 (m, 2H), 3.66-3.69 (m, 2H), 2.76-2.79 (m, 2H), 2.16-2.22 (m, 3H), 205-2.09 (m, 1H), 1.77-1.81 (n, 2H), 1.57-1.61 (m, 2H).

TABLE 2

Examples 1-2 to 1-54 were prepared following the procedure described in Method 1, Steps 1-4, above as follows:

| Ex.# | Chemical Structure | Name | Method changes | Reagent |
|---|---|---|---|---|
| 1-2 | 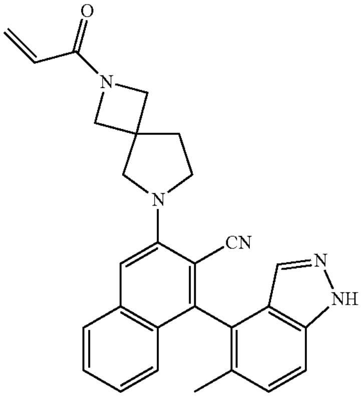 [SMILES: C=CC(=O)N1CC2(CCN(c3cc4ccccc4c(-c4c(C)ccc5[nH]ncc45)c3C#N)C2)C1] | 3-(2-acryloyl-2,6-diazaspiro[3.4]octan-6-yl)-1-(5-methyl-1H-indazol-4-yl)-2-naphthonitrile | See below for alternative Step 2 | Step 1: Intermediate 18 and (5-methyl-1H-indazol-4-yl)boronic acid (CAS: 1245816-10-7, Combi-Blocks). |
| 1-3 | 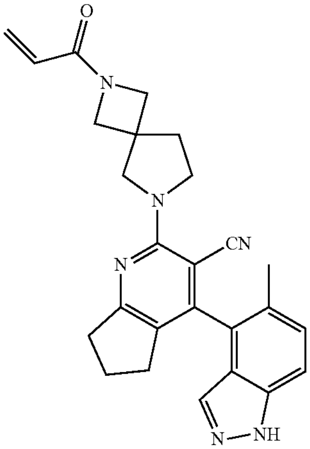 [SMILES: C=CC(=O)N1CC2(CCN(c3nc4c(c(-c5c(C)ccc6[nH]ncc56)c3C#N)CCC4)C2)C1] | 4-(5-methyl-1H-indazol-4-yl)-2-(2-(2-propenoyl)-2,6-diazaspiro[3.4]octan-6-yl)-6,7-dihydro-5H-cyclopenta[b]pyridine-3-carbonitrile | | Step 1: Intermediate 3 and (5-methyl-1H-indazol-4-yl)boronic acid (CAS: 1245816-10-7, Combi-Blocks). |

TABLE 2-continued

| Ex.# | Chemical Structure | Name | Method changes | Reagent |
|---|---|---|---|---|
| Examples 1-2 to 1-54 were prepared following the procedure described in Method 1, Steps 1-4, above as follows: | | | | |
| 1-4 | 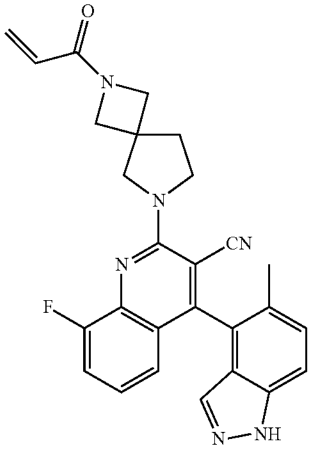 [SMILES: C=CC(=O)N1CC2(CCN(c3nc4c(F)cccc4c(-c4c(C)ccc5[nH]ncc45)c3C#N)C2)C1] | 8-fluoro-4-(5-methyl-1H-indazol-4-yl)-2-(2-(2-propenoyl)-2,6-diazaspiro[3.4]octan-6-yl)-3-quinolinecarbonitrile | | Step 1: Intermediate 4 and (5-methyl-1H-indazol-4-yl)boronic acid (CAS: 1245816-10-7, Combi-Blocks). |
| 1-5 | 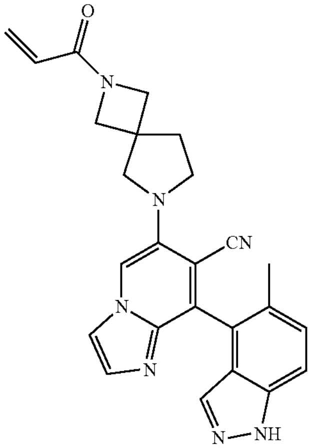 [SMILES: C=CC(=O)N1CC2(CCN(c3cn4ccnc4c(-c4c(C)ccc5[nH]ncc45)c3C#N)C2)C1] | 8-(5-methyl-1H-indazol-4-yl)-6-(2-(2-propenoyl)-2,6-diazaspiro[3.4]octan-6-yl)imidazo[1,2-alpyridine-7-carbonitrile | | Step 1: Intermediate 17 and (5-methyl-1H-indazol-4-yl)boronic acid (CAS: 1245816-10-7, Combi-Blocks). |
| 1-6 | 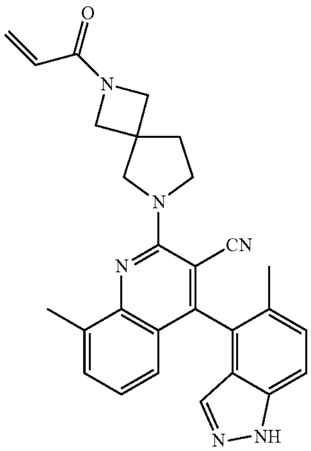 [SMILES: C=CC(=O)N1CC2(CCN(c3nc4c(C)cccc4c(-c4c(C)ccc5[nH]ncc45)c3C#N)C2)C1] | 8-methyl-4-(5-methyl-1H-indazol-4-yl)-2-(2-(2-propenoyl)-2,6-diazaspiro[3.4]octan-6-yl)-3-quinolinecarbonitrile | | Step 1: Intermediate 5 and (5-methyl-1H-indazol-4-yl)boronic acid (CAS: 1245816-10-7, Combi-Blocks). |

TABLE 2-continued

| Ex.# | Chemical Structure | Name | Method changes | Reagent |
|---|---|---|---|---|
| | Examples 1-2 to 1-54 were prepared following the procedure described in Method 1, Steps 1-4, above as follows: | | | |
| 1-7 | 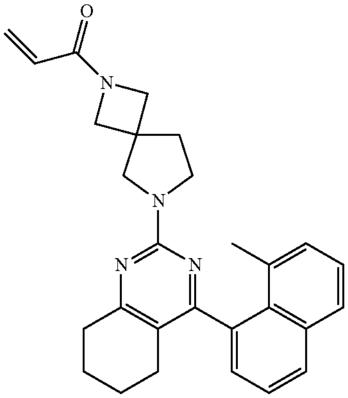 [SMILES: C=CC(=O)N1CC2(CCN(c3nc4c(c(-c5cccc6cccc(C)c56)n3)CCCC4)C2)C1] | 1-(6-(4-(8-methyl-1-naphthalenyl)-5,6,7,8-tetrahydro-2-quinazolinyl)-2,6-diazaspiro[3,4]octan-2-yl)-2-propen-1-one | | Step 1: 2,4-dichloro-5,6,7,8-tetrahydroquinazoline (CAS: 1127-85-1, Combi-Blocks) and (8-methylnaphthalen-1-yl)boronic acid (CAS: 948592-91-4). |
| 1-8 | 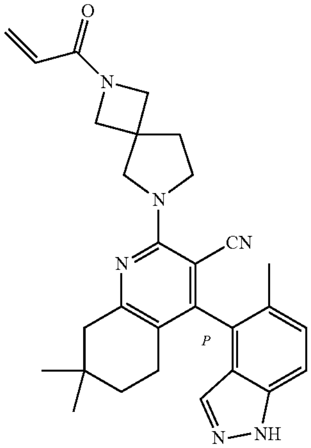 | (P)-7,7-dimethyl-4-(5-methyl-1H-indazol-4-yl)-2-(2-(2-propenoyl)-2,6-diazaspiro[3,4]octan-6-yl)-5,6,7,8-tetrahydro-3-quinolinecarbonitrile, stereochemistry arbitrarily assigned [1st eluting atropisomer | See below for atropisomer separation conditions | Step 1: Intermediate 6 and (5-methyl-1H-indazol-4-yl)boronic acid (CAS: 1245816-10-7, Combi-Blocks). |
| 1-9 | 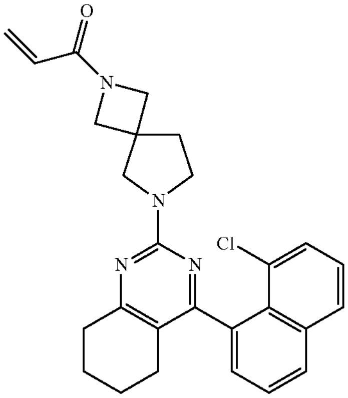 [SMILES: C=CC(=O)N1CC2(CCN(c3nc4c(c(-c5cccc6cccc(Cl)c56)n3)CCCC4)C2)C1] | 1-(6-(4-(8-chloro-1-naphthalenyl)-5,6,7,8-tetrahydro-2-quinazolinyl)-2,6-diazaspiro[3.4]octan-2-yl)-2-propen-1-one | | Step 1: 2,4-dichloro-5,6,7,8-tetrahydroquinazoline (CAS: 1127-85-1, Combi-Blocks) and (8-chloronaphthalen-1-yl)boronic acid (CAS: 2305022-53-9, Enamine). |

TABLE 2-continued

| Ex.# | Chemical Structure | Name | Method changes | Reagent |
|---|---|---|---|---|
| | Examples 1-2 to 1-54 were prepared following the procedure described in Method 1, Steps 1-4, above as follows: | | | |
| 1-10 | 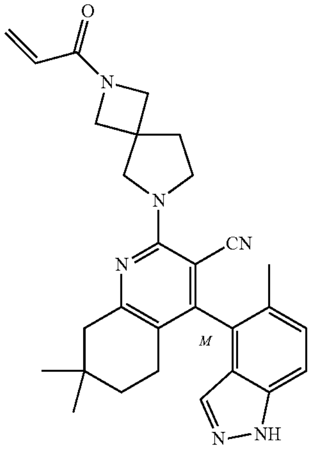 | (M)-7,7-dimethyl-4-(5-methyl-1H-indazol-4-yl)-2-(2-(2-propenoyl)-2,6-diazaspiro[3.4]octan-6-yl)-5,6,7,8-tetrahydro-3-quinolinecarbonitrile, stereochemistry arbitrarily assigned [2nd eluting atropisomer] | See below for atropisomer separation conditions | Step 1: Intermediate 6 and (5-methyl-1H-indazol-4-yl)boronic acid (CAS: 1245816-10-7, Combi-Blocks). |
| 1-11 | 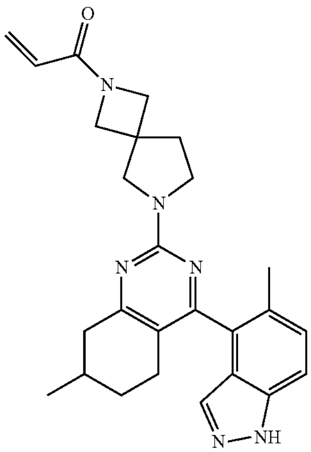 [SMILES: C=CC(=O)N1CC2(CCN(c3nc4c(c(-c5c(C)ccc6[nH]ncc56)n3)CCC(C)C4)C2)C1] | 1-(6-((7)-7-methyl-4-(5-methyl-1H-indazol-4-yl)-5,6,7,8-tetrahydro-2-quinazolinyl)-2,6-diazaspiro[3.4]octan-2-yl)-2-propen-1-one | | Step 1: Intermediate 11 and (5-methyl-1H-indazol-4-yl)boronic acid (CAS: 1245816-10-7, Combi-Blocks). |
| 1-12 | 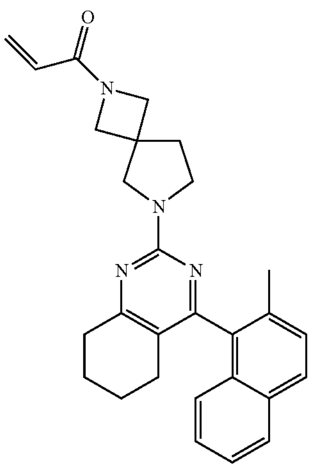 [SMILES: C=CC(=O)N1CC2(CCN(c3nc4c(c(-c5c(C)ccc6ccccc56)n3)CCCC4)C2)C1] | 1-(6-(4-(2-methyl-1-naphthalenyl)-5,6,7,8-tetrahydro-2-quinazolinyl)-2,6-diazaspiro[3.4]octan-2-yl)-2-propen-1-one | | Step 1: 2,4-dichloro-5,6,7,8-tetrahydroquinazoline (CAS: 1127-85-1, Combi-Blocks) and (2-methylnaphthalen-1-yl)boronic acid (CAS: 103989-84-0, Combi-Blocks). |

TABLE 2-continued

| Ex.# | Chemical Structure | Name | Method changes | Reagent |
|---|---|---|---|---|
| Examples 1-2 to 1-54 were prepared following the procedure described in Method 1, Steps 1-4, above as follows: | | | | |
| 1-13 | 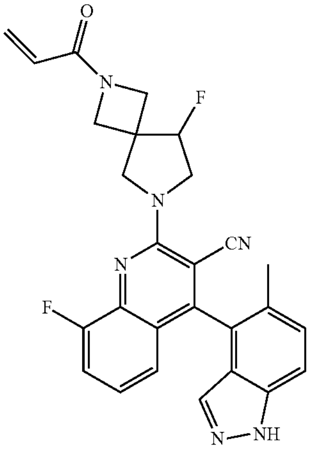 [SMILES: C=CC(=O)N1CC2(C1)CN(c1nc3c(F)cccc3c(-c3c(C)ccc4[nH]ncc34)c1C#N)CC2F] | 8-fluoro-2-((8)-8-fluoro-2-(2-propenoyl)-2,6-diazaspiro[3.4]octan-6-yl)-4-(5-methyl-1H-indazol-4-yl)-3-quinolinecarbonitrile | | Step 1: Intermediate 4 and (5-methyl-1H-indazol-4-yl)boronic acid (CAS: 1245816-10-7, Combi-Blocks). Step 2: Amine 1. |
| 1-14 | 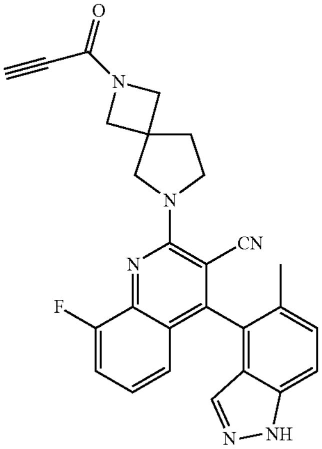 [SMILES: C#CC(=O)N1CC2(CCN(c3nc4c(F)cccc4c(-c4c(C)ccc5[nH]ncc45)c3C#N)C2)C1] | 8-fluoro-4-(5-methyl-1H-indazol-4-yl)-2-(2-(2-propynoyl)-2,6-diazaspiro[3.4]octan-6-yl)-3-quinolinecarbonitrile | See below for alternative Step 4 | Step 1: Intermediate 4 and (5-methyl-1H-indazol-4-yl)boronic acid (CAS: 1245816-10-7, Combi-Blocks). |
| 1-15 | 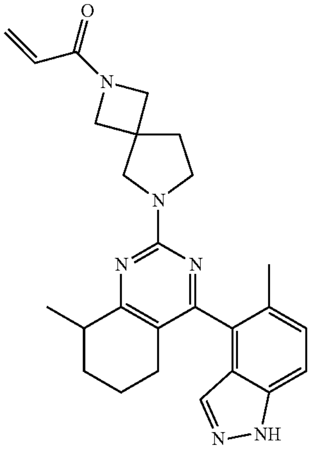 [SMILES: C=CC(=O)N1CC2(CCN(c3nc(-c4c(C)ccc5[nH]ncc45)c4c(n3)C(C)CCC4)C2)C1] | 1-(6-((8)-8-methyl-4-(5-methyl-1H-indazol-4-yl)-5,6,7,8-tetrahydro-2-quinazolinyl)-2,6-diazaspiro[3.4]octan-2-yl)-2-propen-1-one | | Step 1: Intermediate 9 and (5-methyl-1H-indazol-4-yl)boronic acid (CAS: 1245816-10-7, Combi-Blocks). |

TABLE 2-continued

| Ex.# | Chemical Structure | Name | Method changes | Reagent |
|---|---|---|---|---|
| Examples 1-2 to 1-54 were prepared following the procedure described in Method 1, Steps 1-4, above as follows: | | | | |
| 1-16 | 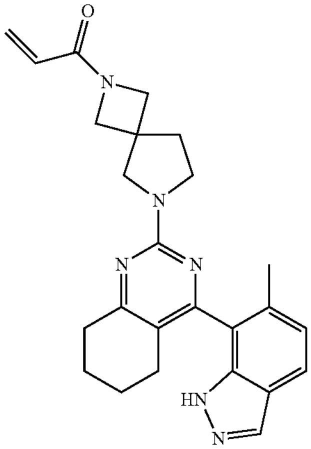 [SMILES: C=CC(=O)N1CC2(CCN(c3nc4c(c(-c5c(C)ccc6cn[nH]c56)n3)CCCC4)C2)C1] | 1-(6-(4-(6-methyl-1H-indazol-7-yl)-5,6,7,8-tetrahydro-2-quinazolinyl)-2,6-diazaspiro[3.4]octan-2-yl)-2-propen-1-one | See additional Step 1a (Example 1-25) for the synthesis of boronic ester | Step 1: 2,4-dichloro-5,6,7,8-tetrahydroquinazoline (CAS: 1127-85-1, Combi-Blocks) and 6-methyl-7-(4,4,5,5-tetramethyl-1,3,2-dioxaborolan-2-yl)-1H-indazole. |
| 1-17 | 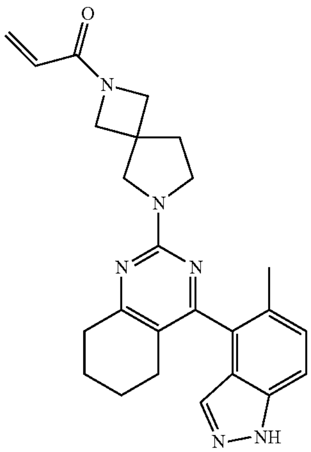 [SMILES: C=CC(=O)N1CC2(CCN(c3nc4c(c(-c5c(C)ccc6[nH]ncc56)n3)CCCC4)C2)C1] | 1-(6-(4-(5-methyl-1H-indazol-4-yl)-5,6,7,8-tetrahydro-2-quinazolinyl)-2,6-diazaspiro[3.4]octan-2-yl)-2-propen-1-one | | Step 1: 2,4-dichloro-5,6,7,8-tetrahydroquinazoline (CAS: 1127-85-1, Combi-Blocks) and (5-methyl-1H-indazol-4-yl)boronic acid (CAS: 1245816-10-7, Combi-Blocks). |
| 1-18 | 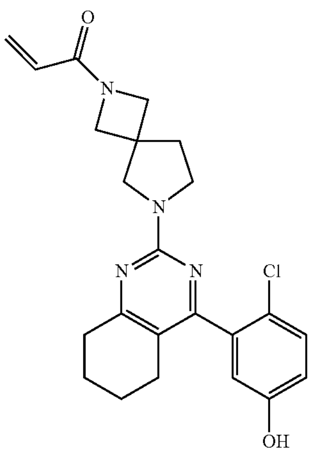 [SMILES: C=CC(=O)N1CC2(CCN(c3nc4c(c(-c5cc(O)ccc5Cl)n3)CCCC4)C2)C1] | 1-(6-(4-(2-chloro-5-hydroxyphenyl)-5,6,7,8-tetrahydro-2-quinazolinyl)-2,6-diazaspiro[3.4]octan-2-yl)-2-propen-1-one | | Step 1: 2,4dichloro-5,6,7,8-tetrahydroquinazoline (CAS: 1127-85-1, Combi-Blocks) and (2-chloro-5-hydroxyphenyl)boronic acid (CAS: 913835-71-9, Combi-Blocks). |

TABLE 2-continued

| Ex.# | Chemical Structure | Name | Method changes | Reagent |
|---|---|---|---|---|
| Examples 1-2 to 1-54 were prepared following the procedure described in Method 1, Steps 1-4, above as follows: | | | | |
| 1-19 | 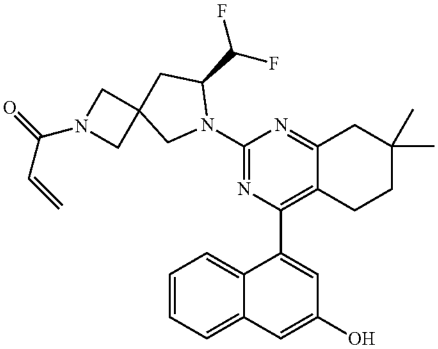 [SMILES: C=CC(=O)N1CC2(C[C@@H](C(F)F)N(c3nc4c(c(-c5cc(O)cc6ccccc56)n3)CCC(C)(C)C4)C2)C1] | 1-((5S)-5-(difluoromethyl)-6-(4-(3-hydroxy-1-naphthalenyl)-7,7-dimethyl-5,6,7,8-tetrahydro-2-quinazolinyl)-2,6-diazaspiro[3.4]octan-2-yl)-2-propen-1-one, stereochemistry arbitrarily assigned | See below for stereoisomer separation conditions of intermediate | Step 1: Intermediate 10 and Step 2: Amine 2. |
| 1-20 | 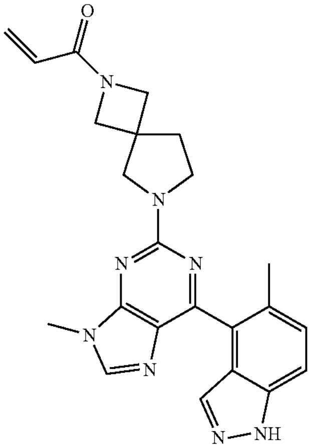 [SMILES: C=CC(=O)N1CC2(CCN(c3nc(-c4c(C)ccc5[nH]ncc45)c4ncn(C)c4n3)C2)C1] | 1-(6-(9-methyl-6-(5-methyl-1H-indazol-4-yl)-9H-purin-2-yl)-2,6-diazaspiro[3.4]octan-2-yl)-2-propen-1-one | | Step 1: 2,6-dichloro-9-methyl-9H-purine (CAS: 2382-10-7, Combi-Blocks) and (5-methyl-1H-indazol-4-yl)boronic acid (CAS: 1245816-10-7, Combi-Blocks). |
| 1-21 | 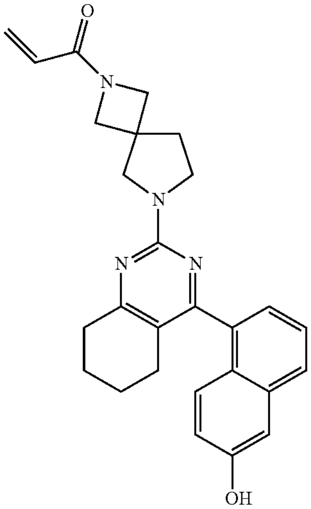 [SMILES: C=CC(=O)N1CC2(CCN(c3nc4c(c(-c5cccc6cc(O)ccc56)n3)CCCC4)C2)C1] | 1-(6-(4-(6-hydroxy-1-naphthalenyl)-5,6,7,8-tetrahydro-2-quinazolinyl)-2,6-diazaspiro[3.4]octan-2-yl)-2-propen-1-one | See below for additional Step 1a for the synthesis of boronic ester | Step 1: 2,4-dichloro-5,6,7,8-tetrahydroquinazoline (CAS: 1127-85-1, Combi-Blocks) and 5-(4,4,5,5-Tetramethyl-1,3,2-dioxaborolan-2-yl)naphthalen-2-ol. |

TABLE 2-continued

| Examples 1-2 to 1-54 were prepared following the procedure described in Method 1, Steps 1-4, above as follows: | | | | |
|---|---|---|---|---|
| Ex.# | Chemical Structure | Name | Method changes | Reagent |
| 1-22 | 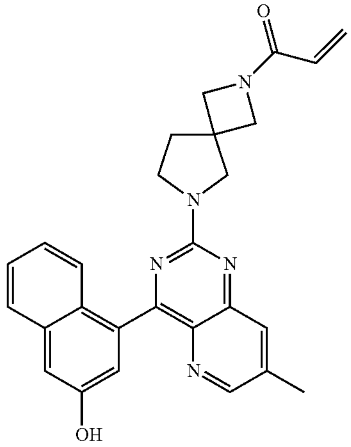 [SMILES: C=CC(=O)N1CC2(CCN(c3nc(-c4cc(O)cc5ccccc45)c4ncc(C)cc4n3)C2)C1] | 1-(6-(4-(3-hydroxy-1-naphthalenyl)-7-methylpyrido[3,2-d]pyrimidin-2-yl)-2,6-diazaspiro[3.4]octan-2-yl)-2-propen-1-one | See below for additional Steps 1a and 3a for the synthesis of boronic ester and late-stage derivatization | Step 1: Intermediate 16. |
| 1-23 | 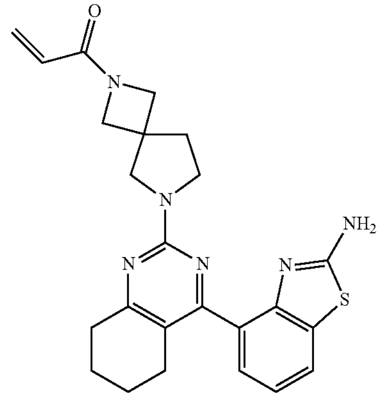 [SMILES: C=CC(=O)N1CC2(CCN(c3nc4c(c(-c5cccc6sc(N)nc56)n3)CCCC4)C2)C1] | 1-(6-(4-(2-amino-1,3-benzothiazol-4-yl)-5,6,7,8-tetrahydro-2-quinazolinyl)-2,6-diazaspiro[3,4]octan-2-yl)-2-propen-1-one | See below for additional Steps 1a-1b for the synthesis of boronic acid | Step 1: 2,4-dichloro-5,6,7,8-tetrahydroquinazoline (CAS: 1127-85-1, Combi-Blocks) and (2-((tert-butoxycarbonyl)amino)benzo[d]thiazol-4-yl)boronic acid. |
| 1-24 | 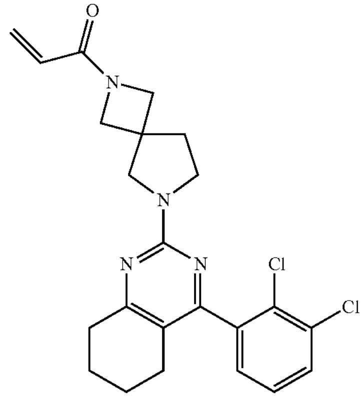 [SMILES: C=CC(=O)N1CC2(CCN(c3nc4c(c(-c5cccc(Cl)c5Cl)n3)CCCC4)C2)C1] | 1-(6-(4-(2,3-dichlorophenyl)-5,6,7,8-tetrahydro-2-quinazolinyl)-2,6-diazaspiro[3.4]octan-2-yl)-2-propen-1-one | | Step 1: 2,4-dichloro-5,6,7,8-tetrahydroquinazoline (CAS: 1127-85-1, Combi-Blocks) and (2,3-dichlorophenyl)boronic acid (CAS: 151169-74-3, Combi-Blocks). |

TABLE 2-continued

| Examples 1-2 to 1-54 were prepared following the procedure described in Method 1, Steps 1-4, above as follows: | | | | |
|---|---|---|---|---|
| Ex.# | Chemical Structure | Name | Method changes | Reagent |
| 1-25 | 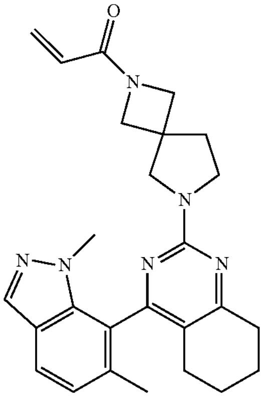 [SMILES: C=CC(=O)N1CC2(CCN(c3nc4c(c(-c5c(C)ccc6cnn(C)c56)n3)CCCC4)C2)C1] | 1-(6-(4-(1,6-dimethyl-1H-indazol-7-yl)-5,6,7,8-tetrahydro-2-quinazolinyl)-2,6-diazaspiro[3.4]octan-2-yl)-2-propen-1-one | See below for additional Steps 1a and 3a for the synthesis of boronic ester and late-stage derivatization | Step 1: 2,4-dichloro-5,6,7,8-tetrahydroquinazolne (CAS: 1127-85-1, Combi-Blocks) and 6-methyl-7-(4,4,5,5-tetramethyl-1,3,2-dioxaborolan-2-yl)-1H-indazole. |
| 1-26 | 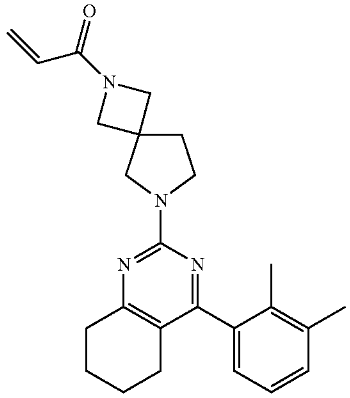 [SMILES: C=CC(=O)N1CC2(CCN(c3nc4c(c(-c5cccc(C)c5C)n3)CCCC4)C2)C1] | 1-(6-(4-(2,3-dimethylphenyl)-5,6,7,8-tetrahydro-2-quinazolinyl)-2,6-diazaspiro[3.4]octan-2-yl)-2-propen-1-one | | Step 1: 2,4-dichloro-5,6,7,8-tetrahydroquinazoline (CAS: 1127-85-1, Combi-Blocks) and 2,3-dimethylphenylboronic acid (CAS: 183158-34-1, Combi-Blocks). |
| 1-27 | 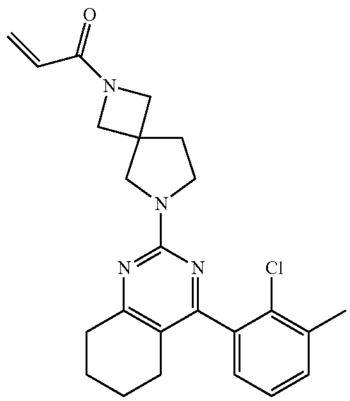 [SMILES: C=CC(=O)N1CC2(CCN(c3nc4c(c(-c5cccc(C)c5Cl)n3)CCCC4)C2)C1] | 1-(6-(4-(2-chloro-3-methylphenyl)-5,6,7,8-tetrahydro-2-quinazolinyl)-2,6-diazaspiro[3.4]octan-2-yl)-2-propen-1-one | | Step 1: 2,4-dichloro-5,6,7,8-tetrahydroquinazoline (CAS: 1127-85-1, Combi-Blocks) and (2-chloro-3-methylphenyl)boronic acid (CAS: 915070-53-0, Combi-Blocks). |

TABLE 2-continued

| Examples 1-2 to 1-54 were prepared following the procedure described in Method 1, Steps 1-4, above as follows: | | | | |
|---|---|---|---|---|
| Ex.# | Chemical Structure | Name | Method changes | Reagent |
| 1-28 | 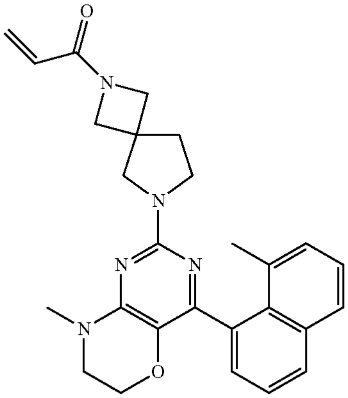 [SMILES: C=CC(=O)N1CC2(CCN(c3nc(-c4cccc5cccc(C)c45)c4c(n3)N(C)CCO4)C2)C1] | 1-(6-(8-methyl-4-(8-methyl-1-naphthalenyl)-7,8-dihydro-6H-pyrimido[5,4-b][1,4]oxazin-2-yl)-2,6-diazaspiro[3.4]octan-2-yl)-2-propen-1-one | | Step 1: Intermediate 13 and (8-methylnaphthalen-1-yl)boronic acid (CAS: 948592-91-4). |
| 1-29 | 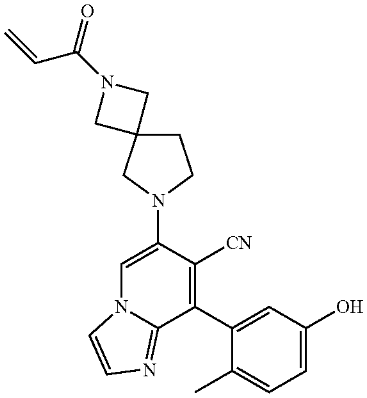 [SMILES: C=CC(=O)N1CC2(CCN(c3cn4ccnc4c(-c4cc(O)ccc4C)c3C#N)C2)C1] | 8-(5-hydroxy-2-methylphenyl)-6-(2-(2-propenoyl)-2,6-diazaspiro[3.4]octan-6-yl)imidazo[1,2-a]pyridine-7-carbonitrile | | Step 1: Intermediate 17 and 4-methyl-3-(4,4,5,5-tetramethyl-1,3,2-dioxaborolan-2-yl)phenol (CAS: 1196985-65-5). |
| 1-30 | 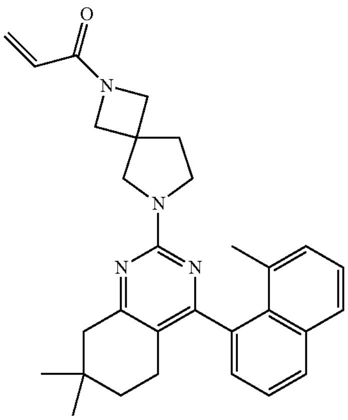 [SMILES: C=CC(=O)N1CC2(CCN(c3nc4c(c(-c5cccc6cccc(C)c56)n3)CCC(C)(C)C4)C2)C1] | 1-(6-(7,7-dimethyl-4-(8-methyl-1-naphthalenyl)-5,6,7,8-tetrahydro-2-quinazolinyl)-2,6-diazaspiro[3.4]octan-2-yl)-2-propen-1-one | | Step 1: Intermediate 10 and (8-methylnaphthalen-1-yl)boronic acid (CAS: 948592-91-4). |

TABLE 2-continued

| Examples 1-2 to 1-54 were prepared following the procedure described in Method 1, Steps 1-4, above as follows: | | | | |
|---|---|---|---|---|
| Ex.# | Chemical Structure | Name | Method changes | Reagent |
| 1-31 | 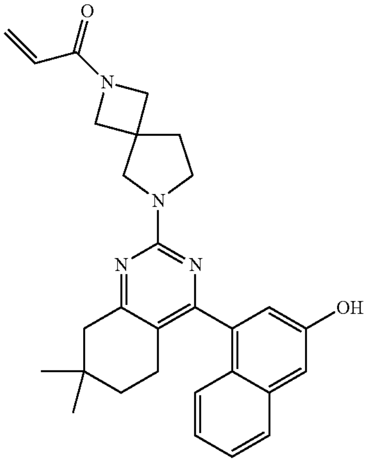 [SMILES: C=CC(=O)N1CC2(CCN(c3nc4c(c(-c5cc(O)cc6ccccc56)n3)CCC(C)(C)C4)C2)C1] | 1-(6-(4-(3-hydroxy-1-naphthalenyl)-7,7-dimethyl-5,6,7,8-tetrahydro-2-quinazolinyl)-2,6-diazaspiro[3.4]octan-2-yl)-2-propen-1-one | | Step 1: Intermediate 10. |
| 1-32 | 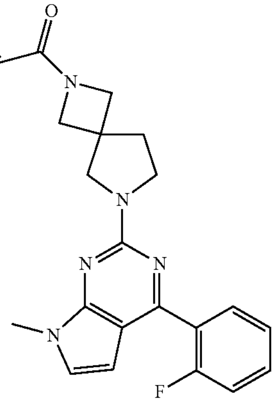 | 1-(6-(4-(2-fluorophenyl)-7-methyl-7H-pyrrolo[2,3-djpyrimidin-2-yl)-2,6-diazaspiro[3.4]octan-2-yl)-2-propen-1-one | Reagent (CAS: 90213-66-4) was methylated prior to Step 1 See below for details. | Step 1: 2,4-dichloro-7-methyl-7H-pyrrolo[2,3-d]pyrimidine (CAS: 90213-67-5) and (2-fluorophenyl)boronic acid (CAS: 1993-03-9, Combi-Blocks). |
| 1-33 | 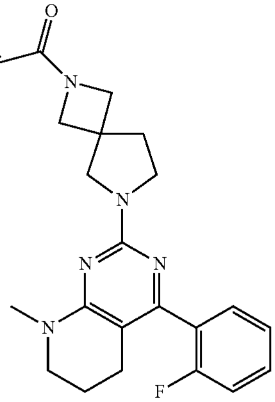 | 1-(6-(4-(2-fluorophenyl)-8-methyl-5,6,7,8-tetrahydropyrido[2,3-d]pyrimidin-2-yl)-2,6-diazaspiro[3,4]octan-2-yl)-2-propen-1-one | Intermediate 15 was methylated prior to Step 1 See below for details. | Step 1: 4-chloro-8-methyl-2-(methylthio)-5,6,7,8-tetrahydropyrido[2,3-d]pyrimidine and (2-fluorophenyl)boronic acid (CAS: 1993-03-9, Combi-Blocks). |

TABLE 2-continued

Examples 1-2 to 1-54 were prepared following the procedure described in Method 1, Steps 1-4, above as follows:

| Ex.# | Chemical Structure | Name | Method changes | Reagent |
|---|---|---|---|---|
| 1-34 | 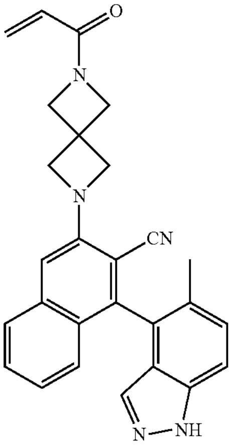 [SMILES: C=CC(=O)N1CC2(C1)CN(c1cc3ccccc3c(-c3c(C)ccc4[nH]ncc34)c1C#N)C2] | 1-(5-methyl-1H-indazol-4-yl)-3-(6-(2-propenoyl)-2,6-diazaspiro[3.3]heptan-2-yl)-2-naphthalenecarbonitrile | See below for alternative Step 2 | Step 1: Intermediate 18 and (5-methyl-1H-indazol-4-yl)boronic acid (CAS: 1245816-10-7, Combi-Blocks). Step 2: tert-butyl 2,6-diazaspiro[3.3]heptane-2-carboxylate (CAS: 1041026-70-3). |
| 1-35 | 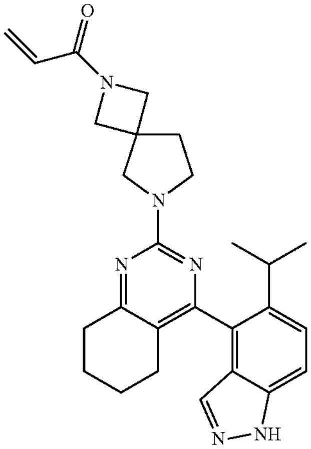 [SMILES: C=CC(=O)N1CC2(CCN(c3nc4c(c(-c5c(C(C)C)ccc6[nH]ncc56)n3)CCCC4)C2)C1] | 1-(6-(4-(5-(2-propanyl)-1H-indazol-4-yl)-5,6,7,8-tetrahydro-2-quinazolinyl)-2,6-diazaspiro[3.4]octan-2-yl)-2-propen-1-one | See below for additional Step 1a-1b for the synthesis of boronic ester | Step 1: 2,4-dichloro-5,6,7,8-tetrahydroquinazoline (CAS: 1127-85-1, Combi-Blocks) and 5-isopropyl-1-(tetrahydro-2H-pyran-2-yl)-4-(4,4,5,5-tetramethyl-1,3,2-dioxaborolan-2-yl)-1H-indazole. |
| 1-36 | 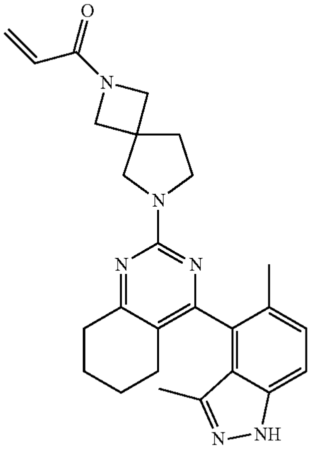 [SMILES: C=CC(=O)N1CC2(CCN(c3nc4c(c(-c5c(C)ccc6[nH]nc(C)c56)n3)CCCC4)C2)C1] | 1-(6-(4-(3,5-dimethyl-1H-indazol-4-yl)-5,6,7,8-tetrahydro-2-quinazolinyl)-2,6-diazaspiro[3.4]octan-2-yl)-2-propen-1-one | See below for additional Step 1a-le for the synthesis of boronic ester | Step 1: 2,4-dichloro-5,6,7,8-tetrahydroquinazoline (CAS: 1127-85-1, Combi-Blocks) and 3,5-dimethyl-1-(tetrahydro-2H-pyran-2-yl)-4-(4,4,5,5-tetramethyl-1,3,2-dioxaborolan-2-yl)-1H-indazole. |

TABLE 2-continued

Examples 1-2 to 1-54 were prepared following the procedure described in Method 1, Steps 1-4, above as follows:

| Ex.# | Chemical Structure | Name | Method changes | Reagent |
|---|---|---|---|---|
| 1-37 | 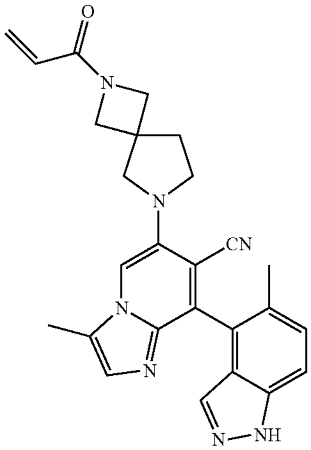 [SMILES: C=CC(=O)N1CC2(CCN(c3cn4c(C)cnc4c(-c4c(C)ccc5[nH]ncc45)c3C#N)C2)C1] | 3-methyl-8-(5-methyl-1H-indazol-4-yl)-6-(2-(2-propenoyl)-2,6-diazaspiro[3.4]octan-6-yl)imidazo[1,2-a]pyridine-7-carbonitrile | | Step 1: Intermediate 19 and (5-methyl-1H-indazol-4-yl)boronic acid (CAS: 1245816-10-7, Combi-Blocks). |
| 1-38 | 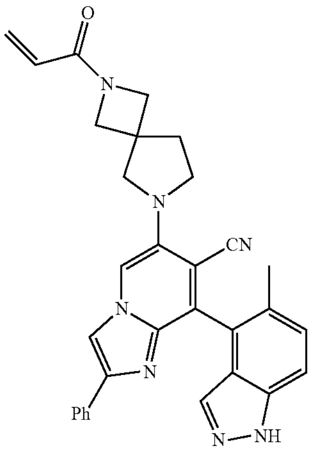 [SMILES: C=CC(=O)N1CC2(CCN(c3cn4cc(-c5ccccc5)nc4c(-c4c(C)ccc5[nH]ncc45)c3C#N)C2)C1] | 8-(5-methyl-1H-indazol-4-yl)-2-phenyl-6-(2-(2-propenoyl)-2,6-diazaspiro[3.4]octan-6-yl)imidazo[1,2-al]yridine-7-carbonitrile | | Step 1: Intermediate 8 and (5-methyl-1H-indazol-4-yl)boronic acid (CAS: 1245816-10-7, Combi-Blocks). |
| 1-39 | 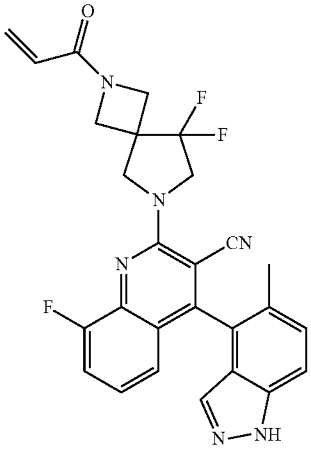 [SMILES: C=CC(=O)N1CC2(C1)CN(c1nc3c(F)cccc3c(-c3c(C)ccc4[nH]ncc34)c1C#N)CC2(F)F] | 2-(8,8-difluoro-2-(2-propenoyl)-2,6-diazaspiro[3.4]octan-6-yl)-8-fluoro-4-(5-methyl-1H-indazol-4-yl)-3-quinolinecarbonitrile | | Step 1: Intermediate 4 and (S-methyl-1H-indazol-4-yl)boronic acid (CAS: 1245816-10-7, Combi-Blocks). Step 2: tert-butyl 8,8-difluoro-2,6-diazaspiro[3.4]octane-2-carboxylate (CAS: 2137997-74-9, PharmaBlock). |

TABLE 2-continued

| Examples 1-2 to 1-54 were prepared following the procedure described in Method 1, Steps 1-4, above as follows: | | | | |
|---|---|---|---|---|
| Ex.# | Chemical Structure | Name | Method changes | Reagent |
| 1-40 | 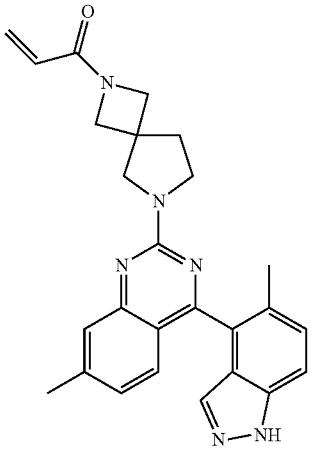 [SMILES: C=CC(=O)N1CC2(CCN(c3nc(-c4c(C)ccc5[nH]ncc45)c4ccc(C)cc4n3)C2)C1] | 1-(6-(7-methyl-4-(5-methyl-1H-indazol-4-yl)-2-quinazolinyl)-2,6-diazaspiro[3.4]octan-2-yl)-2-propen-1-one | | Step 1: 2,4-dichloro-7-methylquinazoline (CAS: 25171-19-1) and (5-methyl-1H-indazol-4-yl)boronic acid (CAS: 1245816-10-7, Combi-Blocks). |
| 1-41 | 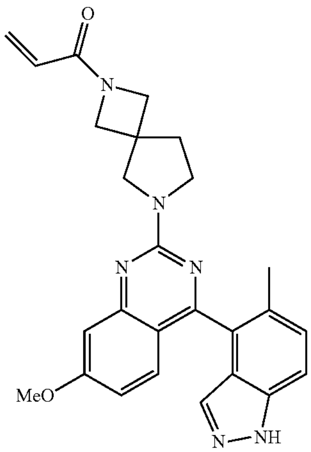 [SMILES: C=CC(=O)N1CC2(CCN(c3nc(-c4c(C)ccc5[nH]ncc45)c4ccc(OC)cc4n3)C2)C1] | 1-(6-(7-methoxy-4-(5-methyl-1H-indazol-4-yl)-2-quinazolinyl)-2,6-diazaspiro[3.4]octan-2-yl)-2-propen-1-one | | Step 1: 2,4-dichloro-7-methoxyquinazoline (CAS: 62484-31-5) and (5-methyl-1H-indazol-4-yl)boronic acid (CAS: 1245816-10-7, Combi-Blocks). |
| 1-42 | 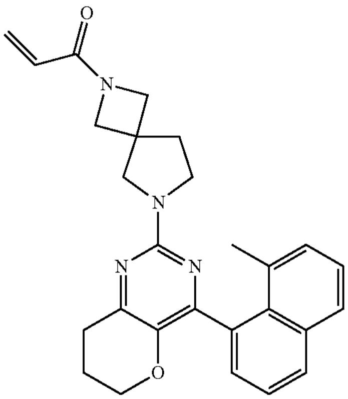 [SMILES: C=CC(=O)N1CC2(CCN(c3nc4c(c(-c5cccc6cccc(C)c56)n3)OCCC4)C2)C1] | 1-(6-(4-(8-methyl-1-naphthalenyl)-7,8-dihydro-6H-pyrano[3,2-d]pyrimidin-2-yl)-2,6-diazaspiro[3,4]octan-2-yl)-2-propen-1-one | | Step 1: Intermediate 14 and (8-methylnaphthalen-1-yl)boronic acid (CAS: 948592-91-4). |

TABLE 2-continued

Examples 1-2 to 1-54 were prepared following the procedure described in Method 1, Steps 1-4, above as follows:

| Ex.# | Chemical Structure | Name | Method changes | Reagent |
|---|---|---|---|---|
| 1-43 | 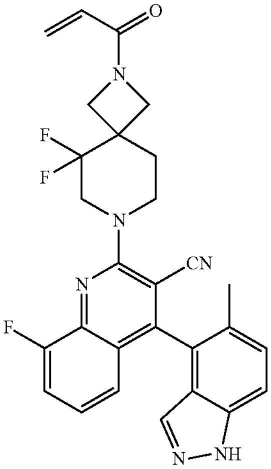 [SMILES: C=CC(=O)N1CC2(CCN(c3nc4c(F)cccc4c(-c4c(C)ccc5[nH]ncc45)c3C#N)CC2(F)F)C1] | 2-(5,5-difluoro-2-(2-propenoyl)-2,7-diazaspiro[3.5]nonan-7-yl)-8-fluoro-4-(5-methyl-1H-indazol-4-yl)-3-quinolinecarbonitrile | | Step 1: Intermediate 4 and (5-methyl-1H-indazol-4-yl)boronic acid (CAS: 1245816-10-7, Combi-Blocks). Step 2: 2.7-Diazaspiro[3.5]nonane-2-carboxylic acid, 5,5-difluoro-, 1,1-dimethylethyl ester (CAS: 2007920-32-1). |
| 1-44 | 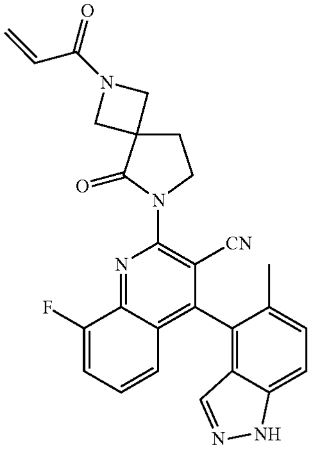 [SMILES: C=CC(=O)N1CC2(CCN(c3nc4c(F)cccc4c(-c4c(C)ccc5[nH]ncc45)c3C#N)C2=O)C1] | 8-fluoro-4-(5-methyl-1H-indazol-4-yl)-2-(5-oxo-2-(2-propenoyl)-2,6-diazaspiro[3,4]octan-6-yl)-3-quinolinecarbonitrile | See below for alternative Step 2 | Step 1: Intermediate 4 and (5-methyl-1H-indazol-4-yl)boronic acid (CAS: 1245816-10-7, Combi-Blocks). Step 2: 2,6-diazaspiro[3.4]octane-2-carboxylic acid, S-oxo-, 1,1-dimethylethyl ester (CAS: 1330765-39-3). |
| 1-45 | 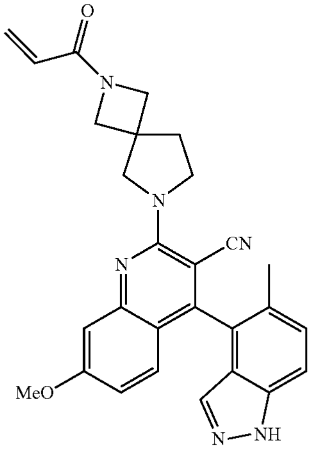 [SMILES: C=CC(=O)N1CC2(CCN(c3nc4cc(OC)ccc4c(-c4c(C)ccc5[nH]ncc45)c3C#N)C2)C1] | 7-methoxy-4-(5-methyl-1H-indazol-4-yl)-2-(2-(2-propenoyl)-2,6-diazaspiro[3.4]octan-6-yl)-3-quinolinecarbonitrile | | Step 1: Intermediate 7 and (5-methyl-1H-indazol-4-yl)boronic acid (CAS: 1245816-10-7, Combi-Blocks). |

TABLE 2-continued

| Examples 1-2 to 1-54 were prepared following the procedure described in Method 1, Steps 1-4, above as follows: | | | | |
|---|---|---|---|---|
| Ex.# | Chemical Structure | Name | Method changes | Reagent |
| 1-46 | 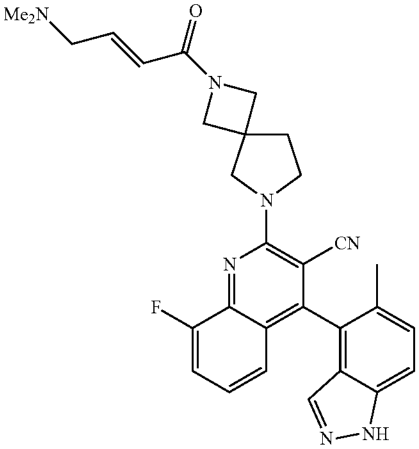 [SMILES: Cc1ccc2[nH]ncc2c1-c1c(C#N)c(N2CCC3(CN(C(=O)/C=C/CN(C)C)C3)C2)nc2c(F)cccc12] | 2-(2-((2E)-4-(dimethylamino)-2-butenoyl)-2,6-diazaspiro[3.4]octan-6-yl)-8-fluoro-4-(5-methyl-1H-indazol-4-yl)-3-quinolinecarbonitrile | See below for alternative Step 4 | Step 1: Intermediate 4 and (5-methyl-1H-indazol-4-yl)boronic acid (CAS: 1245816-10-7, Combi-Blocks). |
| 1-47 | 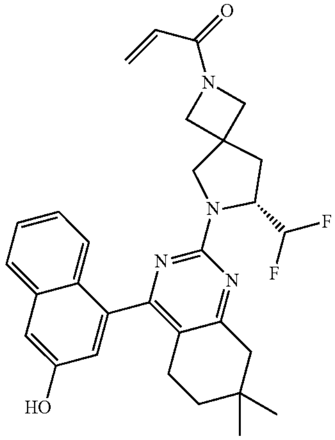 [SMILES: C=CC(=O)N1CC2(C[C@H](C(F)F)N(c3nc4c(c(-c5cc(O)cc6ccccc56)n3)CCC(C)(C)C4)C2)C1] | 1-((5R)-5-(difluoromethyl)-6-(4-(3-hydroxy-1-naphthalenyl)-7,7-dimethyl-5,6,7,8-tetrahydro-2-quinazolinyl)-2,6-diazaspiro[3.4]octan-2-yl)-2-propen-1-one, stereochemistry arbitrarily assigned | See below for stereoisomer separation conditions of intermediate | Step 1: Intermediate 10 and Step 2: Amine 2. |
| 1-48 | 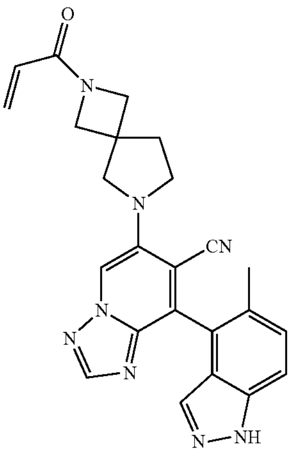 [SMILES: C=CC(=O)N1CC2(CCN(c3cn4ncnc4c(-c4c(C)ccc5[nH]ncc45)c3C#N)C2)C1] | 8-(5-methyl-1H-indazol-4-yl)-6-(2-(2-propenoyl)-2,6-diazaspiro[3.4]octan-6-yl)[1,2,4]triazolo[1,5-a]pyridine-7-carbonitrile | See below for Alternate Step 2. | Step 1: intermediate 53. |

TABLE 2-continued

Examples 1-2 to 1-54 were prepared following the procedure described in Method 1, Steps 1-4, above as follows:

| Ex.# | Chemical Structure | Name | Method changes | Reagent |
|---|---|---|---|---|
| 1-49 | 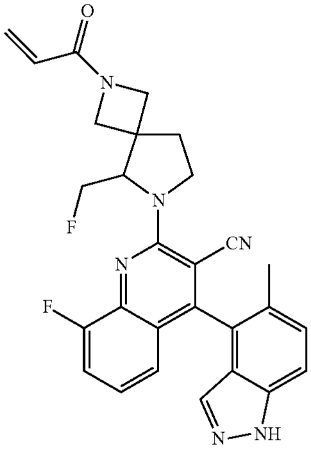 [SMILES: C=CC(=O)N1CC2(CCN(c3nc4c(F)cccc4c(-c4c(C)ccc5[nH]ncc45)c3C#N)C2CF)C1] | 8-fluoro-2-(5-(fluoromethyl)-2-(2-propenoyl)-2,6-diazaspiro[3.4]octan-6-yl)-4-(5-methyl-1H-indazol-4-yl)-3-quinolinecarbonitrile | | Step 1: Intermediate 4 and (5-methyl-1H-indazol-4-yl)boronic acid (CAS: 1245816-10-7, Combi-Blocks). Step 2: tert-butyl 5-(fluoromethyl)-2,6-diazaspiro[3.4]octane-2-carboxylate (LabNetwork). |
| 1-50 | 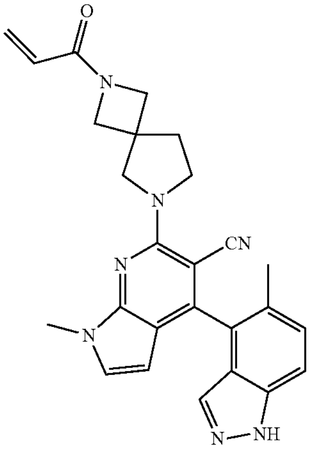 [SMILES: C=CC(=O)N1CC2(CCN(c3nc4c(ccn4C)c(-c4c(C)ccc5[nH]ncc45)c3C#N)C2)C1] | 1-methyl-4-(5-methyl-1H-indazol-4-yl)-6-(2-(2-propenoyl)-2,6-diazaspiro[3.4]octan-6-yl)-1H-pyrrolo[2,3-b]pyridine-5-carbonitrile | Alternative Step 2 done in analogous manner to Example 1-44. Step 3: TFA, DCM instead of HCl, dioxane Step 4: DIPEA replaced TEA. | Step 1: Intermediate 39 and (5-methyl-1-(tetrahydro-2H-pyran-2-yl)-1H-indazol-4-yl)boronic acid (PharmaBlock). |
| 1-51 | 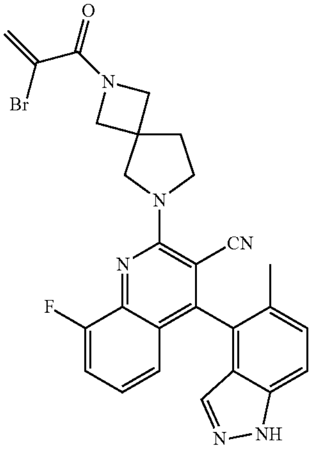 [SMILES: C=C(Br)C(=O)N1CC2(CCN(c3nc4c(F)cccc4c(-c4c(C)ccc5[nH]ncc45)c3C#N)C2)C1] | 2-(2-(2-bromo-2-propenoyl)-2,6-diazaspiro[3.4]octan-6-yl)-8-fluoro-4-(5-methyl-1H-indazol-4-yl)-3-quinolinecarbonitrile | See alternate Step 4 from Example 1-46 | Step 1: Intermediate 4 and (5-methyl-1H-indazol-4-yl)boronic acid (Combi-Blocks). Step 4: 2-bromoacrylic acid (CAS#10443-65-9) |

TABLE 2-continued

Examples 1-2 to 1-54 were prepared following the procedure described in Method 1, Steps 1-4, above as follows:

| Ex.# | Chemical Structure | Name | Method changes | Reagent |
|---|---|---|---|---|
| 1-52 | 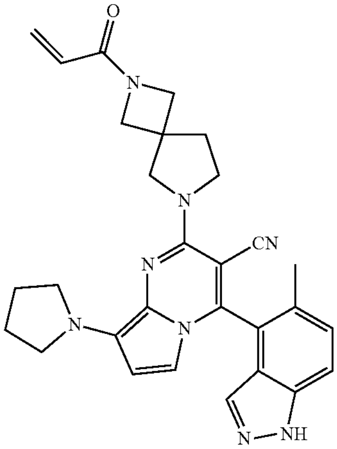 [SMILES: C=CC(=O)N1CC2(CCN(c3nc4c(N5CCCC5)ccn4c(-c4c(C)ccc5[nH]ncc45)c3C#N)C2)C1] | 8-(5-methyl-1H-indazol-4-yl)-6-(2-(2-propenoyl)-2,6-diazaspiro[3.4]octan-6-yl)-3-(1-pyrrolidinyl)imidazo[1,2-alpyridine-7-carbonitrile | Alternative Step 2 done in analogous manner to Example 1-44. Step 3: TFA, DCM instead of HCl, dioxane Step 4: DIPEA replaced TEA. | Step 1: Intermediate 111 and (5-methyl-1-(tetrahydro-2H-pyran-2-yl)-1H-indazol-4-yl)boronic acid (PharmaBlock). |
| 1-53 | 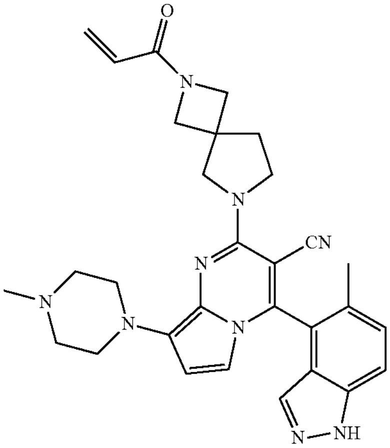 [SMILES: C=CC(=O)N1CC2(CCN(c3nc4c(N5CCN(C)CC5)ccn4c(-c4c(C)ccc5[nH]ncc45)c3C#N)C2)C1] | 8-(5-methyl-1H-indazol-4-yl)-3-(4-methyl-1-piperazinyl)-6-(2-(2-propenoyl)-2,6-diazaspiro[3.4]octan-6-yl)imidazo[1,2-alpyridine-7-carbonitrile | Alternative Step 2 done in analogous manner to Example 1-44, Step 3: TFA, DCM instead of HCl, dioxane Step 4: DIPEA replaced TEA. | Step 1: Intermediate 112 and (5-methyl-1-(tetrahydro-2H-pyran-2-yl)-1H-indazol-4-yl)boronic acid (PharmaBlock). |
| 1-54 | 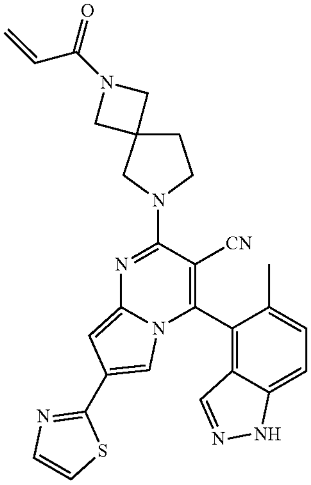 [SMILES: C=CC(=O)N1CC2(CCN(c3nc4cc(-c5nccs5)cn4c(-c4c(C)ccc5[nH]ncc45)c3C#N)C2)C1] | 8-(5-methyl-1H-indazol-4-yl)-6-(2-(2-propenoyl)-2,6-diazaspiro[3.4]octan-6-yl)-2-(1,3-thiazol-2-yl)imidazo[1,2-alpyridine-7-carbonitrile | Alternative Step 2 donein analogous manner to Example 1-44. Step 3: TFA, DCM instead of HCl, dioxane Step 4: DIPEA replaced TEA. | Step 1: Intermediate 113 and (5-methyl-1-(tetrahydro-2H-pyran-2-yl)-1H-indazol-4-yl)boronic acid (PharmaBlock). |

Step 2a Prior to Acrylamide Installation for Examples 1-19 and 1-47

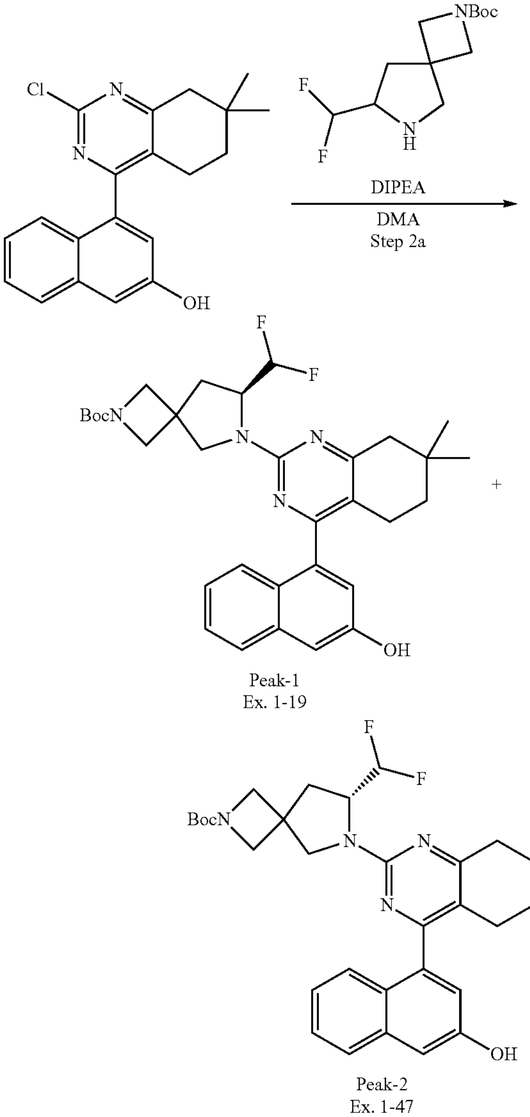

Peak-1
Ex. 1-19

Peak-2
Ex. 1-47

Step 2a: tert-butyl 7-(difluoromethyl)-6-(4-(3-hydroxynaphthalen-1-yl)-7,7-dimethyl-5,6,7,8-tetrahydroquinazolin-2-yl)-2,6-diazaspiro[3.4]octane-2-carboxylate A solution of 4-(2-chloro-7,7-dimethyl-5,6,7,8-tetrahydroquinazolin-4-yl)naphthalen-2-ol (obtained by arylation of Intermediate 10 as in Method 1, step 1) (0.30 g, 0.885 mmol), tert-butyl 7-(difluoromethyl)-2,6-diazaspiro[3.4]octane-2-carboxylate (0.279 g, 1.062 mmol) and DIPEA (0.464 mL, 2.66 mmol) in DMA (1 mL) was heated at 120° C. for 16 h. The reaction mixture was concentrated under reduced pressure. The residue was purified on a Redi-Sep pre-packed silica gel column (12 g), eluting with a gradient of 80-100% EtOAc in PE to provide tert-butyl 7-(difluoromethyl)-6-(4-(3-hydroxynaphthalen-1-yl)-7,7-dimethyl-5,6,7,8-tetrahydroquinazolin-2-yl)-2,6-diazaspiro[3.4]octane-2-carboxylate (0.25 g, 0.443 mmol, 50% yield) as a white solid. $^1$H NMR (400 MHz, DMSO-$d_6$): δ ppm 9.94 (s, 1H), 7.78 (d, J=8.4 Hz, 1H), 7.37-7.47 (m, 1H), 7.13-7.31 (m, 3H), 7.00 (s, 1H), 6.43 (t, J=54.8 Hz, 1H), 4.28-4.52 (br m, 1H), 3.80 (br s, 6H), 2.58 (s, 2H), 1.93-2.43 (m, 6H), 1.37 (s, 9H), 0.97 (br s, 6H). m/z (ESI): 564.8 $(M+H)^+$. The racemic mixture (0.25 g) was separated by Lux $C_4$ Chiral column (250×50 mm, 5μ) using 75% Liquid $CO_2$ and 25% MeOH:MeCN (1:1) to provide tert-butyl (S)-7-(difluoromethyl)-6-(4-(3-hydroxynaphthalen-1-yl)-7,7-dimethyl-5,6,7,8-tetrahydroquinazolin-2-yl)-2,6-diazaspiro[3.4]octane-2-carboxylate (0.10 g) as Peak 1 and tert-butyl (R)-7-(difluoromethyl)-6-(4-(3-hydroxynaphthalen-1-yl)-7,7-dimethyl-5,6,7,8-tetrahydroquinazolin-2-yl)-2,6-diazaspiro[3.4]octane-2-carboxylate (0.10 g) as Peak 2. The stereochemistry of structures was arbitrarily assigned and are not established.

Peak 1: $^1$H NMR (400 MHz, DMSO-$d_6$) δ ppm 9.95 (br s, 1H), 7.8 (d, J=8.3 Hz, 1H), 7.37-7.47 (n, 1H), 7.16-7.31 (m, 3H), 7.00 (s, 1H), 6.43 (br t, J=58.0 Hz, 1H), 4.26-4.53 (br m, 1H), 3.80 (br s, 6H), 2.58 (s, 2H), 1.92-2.44 (m, 6H), 1.37 (s, 9H), 0.97 (s, 6H). $^{19}$F NMR (377 MHz, DMSO-$d_6$) δ ppm −123.12 (d, J=281.3 Hz), −133.79 (d, J=282.0 Hz). m/z (ESI): 564.8 $(M+H)^+$.

Peak 2: $^1$H NMR (400 MHz, DMSO-$d_6$) δ ppm 9.94 (s, 1H), 7.78 (d, J=8.3 Hz, 1H), 7.37-3.45 (m 1H), 7.17-7.33 (m, 3H), 7.00 (d, J=2.5 Hz, 1H), 6.43 (br t, J=58.0 Hz, 1H), 4.26-4.51 (br m, 1H), 3.80 (br s, 6H), 2.58 (s, 2H), 1.87-2.44 (m, 6H), 1.37 (s, 9H), 0.97 (s, 6H), $^{19}$F NMR (377 MHz, DMSO-$d_6$) δ ppm −123.12 (d, J=281.2 Hz), −133.79 (d, J=282.3 Hz), m, (ESI): 564.8 $(M+H)^+$.

Additional Step 1a Prior to Suzuki Coupling for Example 1-21

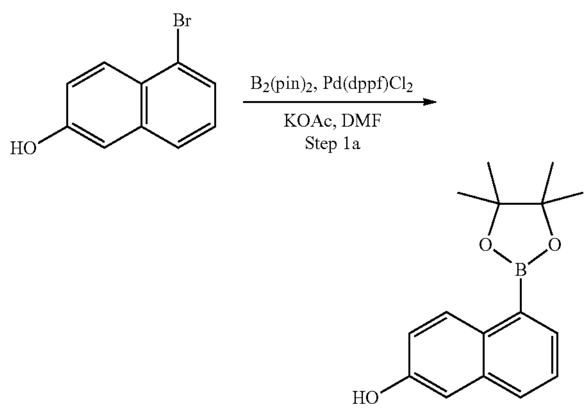

Step 1a: 5-(4,4,5,5-tetramethyl-1,3,2-dioxaborolan-2-yl)naphthalen-2-ol

To a degassed solution of 5-bromonaphthalen-2-ol (1.5 g, 6.7 mmol, synthesized according to ACIE 2019, 58, 4596), bis(pinacolato)diboron (2.56 g, 10.1 mmol) and potassium acetate (1.980 g, 20.2 mmol) in DMF (15 mL) was added $PdCl_2$(dppf)-DCM adduct (0.110 g, 0.134 mmol) and the mixture was heated at 100° C. at for 16 h. Then the reaction mixture was filtered through a pad of celite and washed with EtOAc. The filtrate was concentrated under reduced pressure and the residue was purified on a Redi-Sep pre-packed silica gel column (40 g), eluting with a gradient of 0-10% EtOAc in hexanes to provide 5-(4,4,5,5-tetramethyl-1,3,2-dioxaborolan-2-yl)naphthalen-2-ol (1.5 g, 83% yield) as an off-white solid. $^1$H NMR (400 MHz, $CDCl_3$) δ ppm 8.65-8.75 (m, 1H), 7.95 (dd, J=6.9, 1.4 Hz, 1H), 7.79 (dt, J=8.3, 1.2 Hz, 1H), 7.39-7.49 (m, 1H), 7.14-7.21 (m, 2H), 1.44 (s, 12H). m/z (ESI): 271.1 $(M+H)^+$.

Synthesis of Boronic Ester (Step 1a) and Additional Step 3a for Example 1-22

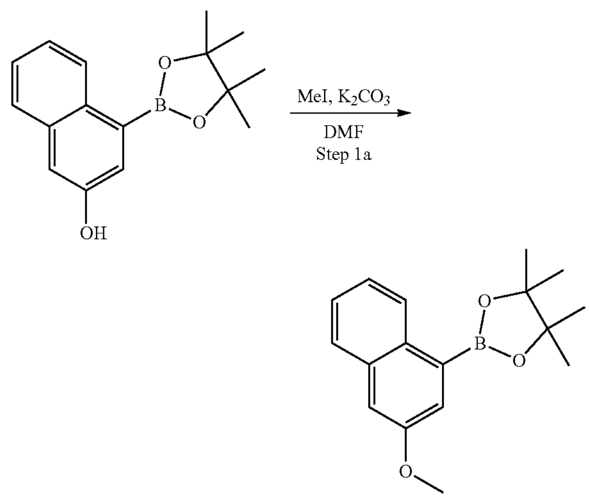

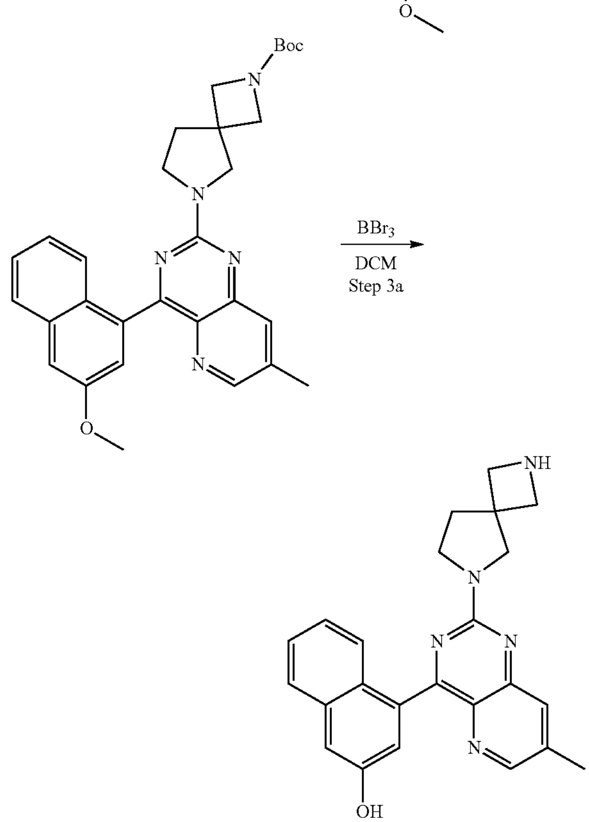

Step 1a: 2-(3-methoxynaphthalen-1-yl)-4,4,5,5-tetramethyl-1,3,2-dioxaborolane

To a solution of 4-(4,4,5,5-tetramethyl-1,3,2-dioxaborolan-2-yl)naphthalen-2-ol (1.0 g, 3.7 mmol) and $K_2CO_3$ (1.54 g, 11.1 mmol) in DMF (10 mL) was added methyl iodide (0.347 mL, 5.55 mmol). The resulting mixture was stirred at rt for 2 h before it was diluted with water and extracted with EtOAc. The combined organic extracts were washed with brine, dried over $Na_2SO_4$, filtered, and concentrated under reduced pressure to provide 2-(3-methoxynaphthalen-1-yl)-4,4,5,5-tetramethyl-1,3,2-dioxaborolane (1.0 g, 95% yield) which was taken to the next step without purification. $^1$H NMR (400 MHz, DMSO-$d_6$) δ ppm 8.54 (dd, J=8.4, 1.3 Hz, 1H), 784 (dd, J=8.2, 1.5 Hz, 1H), 7.56 (d, J=2.8 Hz, 1H), 7.44-7.50 (m, 2H), 7.38-7.42 (m, 1H), 3.88 (s, 3H), 1.37 (s, 12H).

Step 3a: 4-(7-methyl-2-(2,6-diazaspiro[3.4]octan-6-yl)pyrido[3,2-d]pyrimidin-4-yl)naphthalen-2-ol To a solution of tert-butyl 6-(4-(3-methoxynaphthalen-1-yl)-7-methylpyrido[3,2-d]pyrimidin-2-yl-2,6-diazaspiro[3.4]octane-2-carboxylate (0.14 g, 0.274 mmol) in DCM (0.7 mL) was added $BBr_3$ (1M solution in DCM) (0.82 mL, 0.82 mmol, Sigma-Aldrich) at −78° C. The reaction mixture was warmed up to rt and stirred for 1 h before it was quenched with satd $NaHCO_3$ and extracted with 10% MeOH in DCM, The organic extracts were washed with brine, dried over $Na_2SO_4$, filtered and concentrated under reduced pressure to provide 4-(7-methyl-2-(2,6-diazaspiro[3.4]octan-6-yl)pyrido[3,2-d]pyrimidin-4-yl)naphthalen-2-ol which was taken to the next step without purification, m/z (ESI): 398.0 $(M+H)^+$.

Additional Steps 1a-1b Prior to Suzuki Coupling for Example 1-23

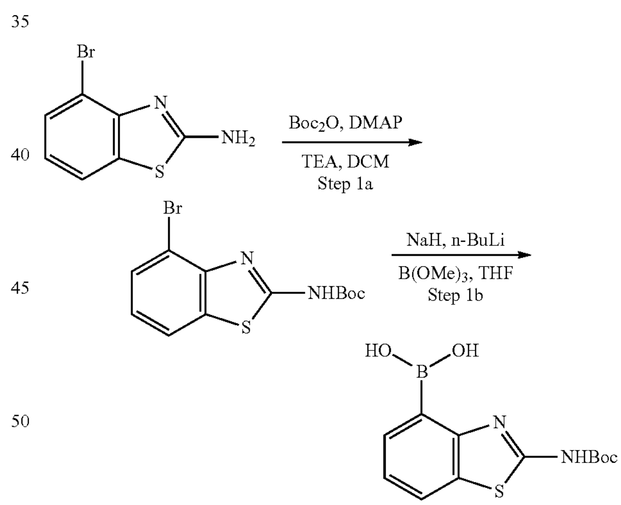

Step 1a: tert-butyl(4-bromobenzo[d]thiazol-2-yl)carbamate

To a solution of 4-bromobenzo[d]thiazol-2-amine (5.0 g, 21.8 mmol, Combi-Blocks) in DCM (50 mL) were added DMAP (2.67 g, 21.8 mmol), TEA (9.13 mL, 65.5 mmol) and $(Boc)_2O$ (5.57 mL, 24.01 mmol). The reaction mixture was stirred at rt for 15 h before it was diluted with water and extracted with DCM. The organic extracts were washed with brine, separated, dried over $Na_2SO_4$, filtered and concentrated. The residue was purified on a Redi-Sep pre-packed silica gel column (40 g), eluting with 10-20% EtOAc in hexanes to afford tert-butyl (4-bromobenzo[d]thiazol-2-yl) carbamate (1.5 g, 21% yield) as an off-white solid. $^1$H NMR (400 MHz, DMSO-$d_6$) δ ppm 12.14 (s, 1H), 7.96 (dd, J=79, 1.1 Hz, 1H), 7.64 (dd, J=7.8, 1.1 Hz, 1H), 7.19 (t, J=7.9 Hz, 1H), 1.51 (s, 9H). m/z (ESI): 330.8 $(M+H)^+$.

Step 1b: (2-((tert-butoxycarbonyl)amino)benzo[d] thiazol-4-yl)boronic acid

To a solution of tert-butyl (4-bromobenzo[d]thiazol-2-yl) carbamate (1.0 g, 3.04 mmol) in THF (15 mL) was added sodium hydride (0.20 g, 4.56 mmol) and stirred for 10 min. Then the reaction mixture was cooled to −78° C. and n-BuLi (1.82 mL, 4.56 mmol, 2.5 M solution in hexanes) was added dropwise. Then the reaction mixture was stirred for 30 min before triisopropyl borate (2.12 mL, 9.11 mmol) was added dropwise. Then the reaction mixture was slowly warmed up to rt over 30 min before it was quenched with a satd aqueous solution of $NH_4Cl$ and extracted with EtOAc. The combined organic extracts were washed with water and brine, separated, dried over $Na_2SO_4$, filtered and concentrated. The residue was purified on a Redi-Sep pre-packed silica gel column (24 g), eluting with 80%14 EtOAc in PE to afford (2-((tert-butoxycarbonyl)amino)benzo[d]thiazol-4-yl)boronic acid (0.3 g, 34% yield) as an off white solid, $^1$H NMR (400 MHz, DMSO-$d_6$) δ ppm 11.98 (s, 1H), 8.60 (s, 2H), 8.03 (d, J=8.8 Hz, 1H), 7.81 (d, J=2.8 Hz, 1H), 7.31 (t, J=8.8 Hz, 1H), 1.53 (s, 9H). m/z (ESI): 295.0 $(M+H)^+$.

Additional Step 1a (Prior to Suzuki Coupling) and Step 3a (Late-Stage Derivatization) for Example 1-25

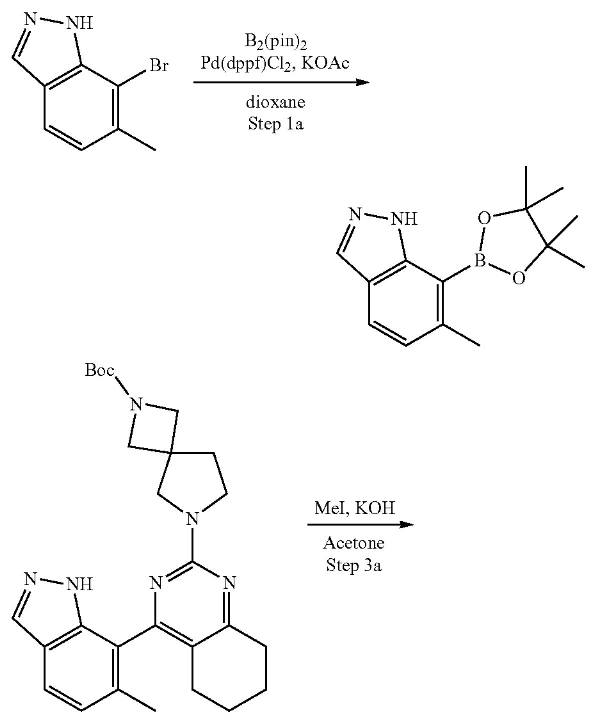

-continued

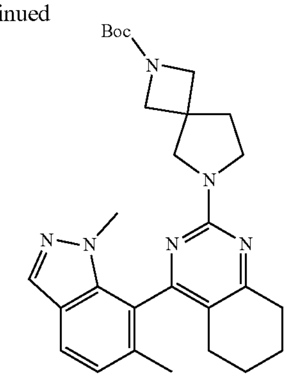

Step 1a: 6-methyl-7-(4,4,5,5-tetramethyl-1,3,2-dioxaborolan-2-yl)-1H-indazole

To a degassed solution of 7-bromo-6-methyl-1H-indazole (3.0 g, 14.21 mmol, BLD Pharma), bis(pinacolato)diboron (5.41 g, 21.3 mmol) and potassium acetate (4.19 g, 42.6 mmol) in 1,4-dioxane (30 mL) was added $PdCl_2$(dppf)-DCM adduct (0.87 g, 1.07 mmol) and the mixture was heated at 100° C. for 16 h. Then the reaction mixture was filtered through a pad of celite and washed with EtOAc. The filtrate was concentrated under reduced pressure and the residue was purified on a Redi-Sep pre-packed silica gel column (40 g), eluting with a gradient of 0-10% EtOAc in hexanes to provide 6-methyl-7-(4,4,5,5-tetramethyl-1,3,2-dioxaborolan-2-yl)-1H-indazole (2.2 g, 60% yield) as an off-white solid. $^1$H NMR (400 MHz, DMSO-$d_6$) δ ppm 12.16 (s, 1H), 8.03 (s, 1H), 7.75 (d, J=8.2 Hz, 1H), 6.98 (d, J=8.2 Hz, 1H), 2.61 (s, 3H), 1.37 (s, 12H). m/z (ESI): 259.0 $(M+H)^+$.

Step 3a: tert-butyl 6-(4-(1,6-dimethyl-1H-indazol-7-yl)-5,6,7,8-tetrahydroquinazolin-2-yl)-2,6-diazaspiro [3.4]octane-2-carboxylate To a solution of tert-butyl 6-(4-(6-methyl-1H-indazol-7-yl)-5,6,7,8-tetrahydroquinazolin-2-yl)-2,6-diazaspiro[3.4] octane-2-carboxylate (0.20 g, 0.421 mmol) in acetone (10 mL) were added KOH (0.071 g, 1.26 mmol) and methyl iodide (0.053 mL, 0.84 mmol) at 0° C. The resulting mixture was stirred at it for 12 h before it was diluted with water and extracted with EtOAc. The combined organic extracts were washed with brine, dried over $Na_2SO_4$, and concentrated under reduced pressure. The residue was purified on a Redi-Sep pre-packed silica gel column (12 g), eluting with a gradient of 0-40% EtOAc in PE to provide tert-butyl 6-(4-(1,6-dimethyl-1H-indazol-7-yl)-5,6,7,8-tetrahydroquinazolin-2-yl)-2,6-diazaspiro[3.4]octane-2-carboxylate as a yellow solid. m/z (ESI): 489.9 $(M+H)^+$.

Step 1a Prior to Suzuki Coupling for Example 1-32

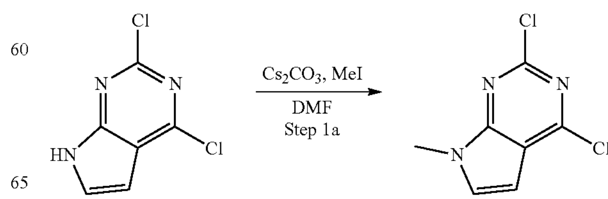

Step 1a: 2,4-dichloro-7-methyl-7H-pyrrolo[2,3-d] pyrimidine

To a solution of 2,4-dichloro-7-H-pyrrolo[2,3-d]pyrimidine (CAS: 90213-66-4, 1.50 g, 7.98 mmol) and $Cs_2CO_3$ (2.60 g, 7.98 mmol) in DMF (20 mL) was added iodomethane (2.27 g, 15.96 mmol). The reaction was allowed to stir for 16 h. The reaction mixture was diluted with water (50 mL) and extracted with EtOAc (3×50 mL). The combined organic extracts were dried over anhydrous $Na_2SO_4$, concentrated and purified by silica gel column chromatography through a Redi-Sep pre-packed silica gel column (40 g), eluting with 0-15% EtOAc in PE to provide 2,4-dichloro-7-methyl-7H-pyrrolo[2,3-d]pyrimidine (1.40 g, 87% yield) as white solid. m/z (ESI): 202.0 $(M+H)^+$.

Step 1a Prior to Suzuki Coupling for Example 1-33

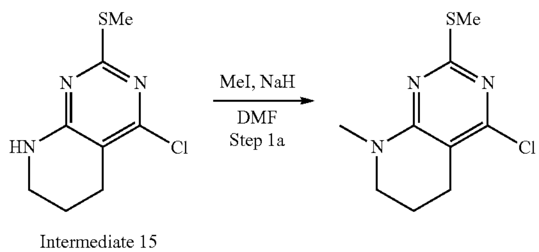

Intermediate 15

Step 1a: 4-chloro-8-methyl-2-(methylthio)-5,6,7,8-tetrahydropyrido[2,3-d]pyrimidine To a stirred solution of 4-chloro-2-(methylthio)-5,6,7,8-tetrahydropyrido[2,3-d]pyrimidine (Intermediate 15, 1.0 g, 4.64 mmol) in DMF (20 mL) was added sodium hydride (0.278 g, 6.95 mmol) at 0° C. The reaction was stirred for 20 min. Then, iodomethane (0.722 mL, 11.59 mmol) was added drop wise at 0° C. and stirred for 3 h. Upon completion, the reaction mixture was slowly quenched with ice. The reaction was extracted with EtOAc (2×75 mL), washed with water (100 mL), brine (100 mL), dried over $Na_2SO_4$ and concentrated in vacuo to provide 4-chloro-8-methyl-2-(methylthio)-5,6,7,8-tetrahydropyrido[2,3-d]pyrimidine (1.0 g, 94% yield) as an off-white solid. m/z (ESI): 230.1 $(M+H)^+$.

Steps 1a-1b for the Synthesis of Boronic Ester for Example 1-35

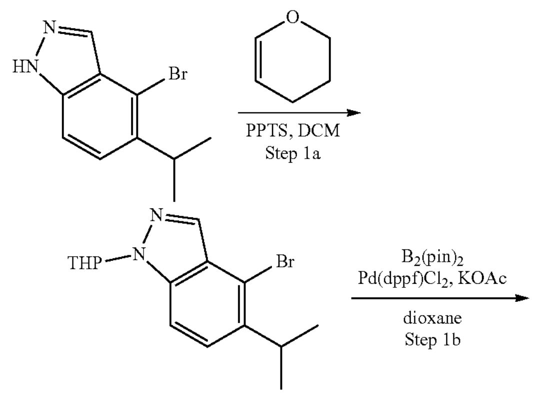

-continued

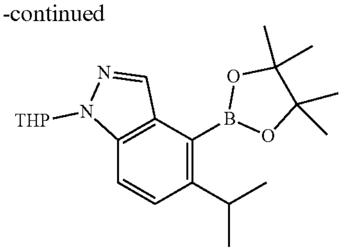

Step 1a: 4-bromo-5-isopropyl-1-(tetrahydro-2H-pyran-2-yl)-1H-indazole

A solution of 4-bromo-3,5-dimethyl-1H-indazole (4.0 g, 16.73 mmol, synthesized according to the procedure described in WO2017201161), 3,4-dihydropyran (6.12 mL, 66.9 mmol) and PPTS (0.84 g, 3.35 mmol, Spectrochem) in DCM (50 mL) was stirred at rt for 16 h. Then the reaction mixture was diluted with water and extracted with DCM. The combined organic extracts were washed with brine, dried over $Na_2SO_4$, filtered, and concentrated under reduced pressure. The residue was purified on a Redi-Sep pre-packed silica gel column (40 g), eluting with a gradient of 10-15% EtOAc in hexanes to provide 4-bromo-5-isopropyl-1-(tetrahydro-2H-pyran-2-yl)-1H-indazole (4.00 g, 74% yield). m/z (ESI): 3228 $(M+H)^+$.

Step 1b: 5-isopropyl-1-(tetrahydro-2H-pyran-2-yl)-4-(4,4,5,5-tetramethyl-1,3,2-dioxaborolan-2-yl)-1H-indazole To a degassed solution of 4-bromo-5-isopropyl-1-(tetrahydro-2H-pyran-2-yl)-1H-indazole (4.0 g, 12.4 mmol), bis(pinacolato)diboron (3.14 g, 12.4 mmol, Spectrochem) and potassium acetate (1.22 g, 12.4 mmol) in 1,4-dioxane (50 mL) was added $PdCl_2$(dppf)-DCM adduct (1.0 g, 1.24 mmol, Chempure) and the mixture was heated at 90° C. for 16 h. Then the reaction mixture was filtered through a pad of celite and washed with EtOAc. The filtrate was concentrated under reduced pressure and the residue was purified on a Redi-Sep pre-packed silica gel column (40 g), eluting with a gradient of 10-15% EtOAc in hexanes to provide 5-isopropyl-1-(tetrahydro-2H-pyran-2-yl)-4-(4,4,5,5-tetramethyl-1,3,2-dioxaborolan-2-yl)-1H-indazole (3.0 g, 66% yield). m/z (ESI): 371.0 $(M+H)^+$.

Steps 1a-1e for the Synthesis of Boronic Ester for Example 1-36

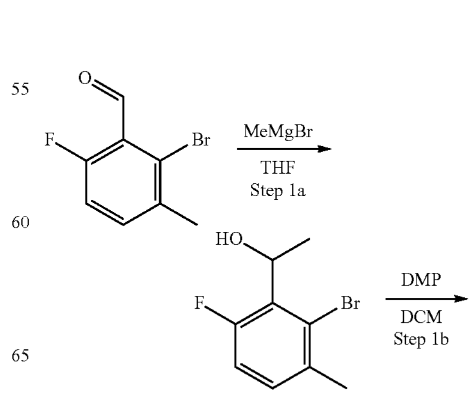

-continued

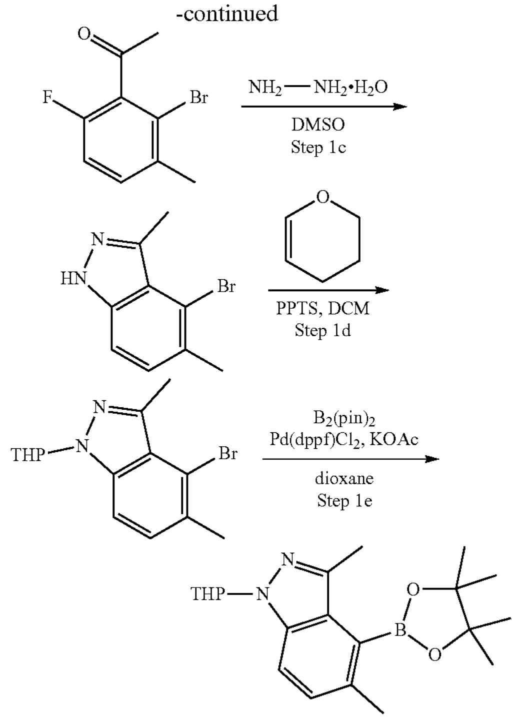

Step 1a: 1-(2-bromo-6-fluoro-3-methylphenyl)ethan-1-ol

To a solution of 2-bromo-6-fluoro-3-methylbenzaldehyde (12.0 g, 55.3 mmol, Combi-Blocks) in THF (150 mL) was dropwise added methyl magnesium bromide (3.0 M solution in $Et_2O$) (36.9 mL, 111 mmol, Symax) at −20° C. and the reaction mixture was stirred at 0° C. for 2 h. Then the reaction mixture was quenched with a satd aqueous solution of $NH_4Cl$ and extracted with EtOAc. The combined organic extracts were washed with brine, dried over $Na_2SO_4$, filtered, and concentrated under reduced pressure. The residue was purified on a Redi-Sep pre-packed silica gel column (120 g), eluting with a gradient of 10-15% EtOAc in hexanes to provide 1-(2-bromo-6-fluoro-3-methylphenyl)ethan-1-ol (12.0 g, 93% yield). $^1H$ NMR (400 MHz, DMSO-$d_6$) δ ppm 7.29 (dd, J=8.4, 5.7 Hz, 1H), 7.11 (dd, J=11.0, 8.4 Hz, 1H), 5.31 (dd, J=20.7, 5.9 Hz, 1H), 2.34 (s, 3H), 1.43 (dd, J=6.6, 1.2 Hz, 3H).

Step 1b: 1-(2-bromo-6-fluoro-3-methylphenyl)ethan-1-one

To solution of 1-(2-bromo-6-fluoro-3-methylphenyl) ethan-1-ol (12.0 g, 51.5 mmol) in DCM (150 mL) was added Dess-Martin periodinane (32.8 g, 77.0 mmol, Chempure) and the reaction mixture was stirred at 0° C. for 1 h. Then the reaction mixture was quenched with a satd aqueous solution of sodium carbonate and extracted with DCM. The combined organic extracts were washed with brine, dried over $Na_2SO_4$, and concentrated under reduced pressure. The residue was purified on a Redi-Sep pre-packed silica gel column (120 g), eluting with a gradient of 5-10% EtOAc in hexanes to provide 1-(2-bromo-6-fluoro-3-methylphenyl) ethan-1-one (10.0 g, 84% yield) as a light-yellow oil. $^1H$ NMR (400 MHz, $CDCl_3$) δ ppm 7.26 (dd, J=7.5, 6.0 Hz, 1H), 7.01 (t, J=8.5 Hz, 1H), 2.59 (s, 3H), 2.41 (s, 3H).

Step 1e: 4-bromo-3,5-dimethyl-1H-indazole

To a solution of 1-(2-bromo-6-fluoro-3-methylphenyl) ethan-1-one (9.0 g, 39.0 mmol) in DMSO (10 mL) was added hydrazine hydrate (9.75 g, 195 mmol, Spectrochem) and the reaction mixture was heated at 110° C. for 16 h. The reaction mixture was quenched with ice-cold water and the precipitated solid was filtered, washed with water and $Et_2O$, and dried to provide 4-bromo-3,5-dimethyl-1H-indazole (4.5 g, 51% yield). $^1H$ NMR (400 MHz, DMSO-$d_6$) δ ppm 12.81 (s, 1H), 7.37 (d, J=8.4 Hz, 1H), 7.26 (d, J=8.4 Hz, 1H), 2.67 (s, 3H), 2.42 (s, 3H). m/z (ESI): 224.9 $(M+H)^+$.

Step 1d: 4-bromo-3,5-dimethyl-1-(tetrahydro-2H-pyran-2-yl)-1H-indazole

A solution of 4-bromo-3,5-dimethyl-1H-indazole (4.5 g, 20.0 mmol), 3,4-dihydropyran (1.83 mL, 20.0 mmol) and PPTS (5.0 g, 20.0 mmol, Spectrochem) in DCM (100 mL) was stirred at rt for 16 h. Then the reaction mixture was diluted with water and extracted with DCM. The combined organic extracts were washed with brine, dried over $Na_2SO_4$, and concentrated under reduced pressure. The residue was purified on a Redi-Sep pre-packed silica gel column (40 g), eluting with a gradient of 5-10% EtOAc in hexanes to provide 4-bromo-3,5-dimethyl-1-(tetrahydro-2H-pyran-2-yl)-1H-indazole (4.0 g, 65% yield). m/z (ESI): 309.8 $(M+H)^+$.

Step 1e: 3,5-dimethyl-1-(tetrahydro-2H-pyran-2-yl)-4-(4,4,5,5-tetramethyl-1,3,2-dioxaborolana-2-yl)-1H-indazole To a degassed solution of 4-bromo-3,5-dimethyl-1-(tetrahydro-2H-pyran-2-yl)-1H-indazole (4.0 g, 12.94 mmol), bis (pinacolato)diboron (3.94 g, 15.5 mmol, Spectrochem) and potassium acetate (1.90 g, 19.40 mmol) in 1,4-dioxane (50 ml) was added $PdCl_2$(dppf)-DCM adduct (1.06 g, 1.29 mmol, Chempure) and the mixture was heated at 90° C. for 16 h. Then the reaction mixture was filtered through a pad of celite and washed with EtOAc. The filtrate was concentrated under reduced pressure and the residue was purified on a Redi-Sep pre-packed silica gel column (40 g), eluting with a gradient of 10-15% EtOAc in hexanes to provide 3,5-dimethyl-1-(tetrahydro-2H-pyran-2-yl)-4-(4,4,5,5-tetramethyl-1,3,2-dioxaborolan-2-yl)-1H-indazole (3.0 g, 65% yield). m/z (ESI): 357.0 $(M+H)^+$.

Alternative Step 2 for Example 1-44

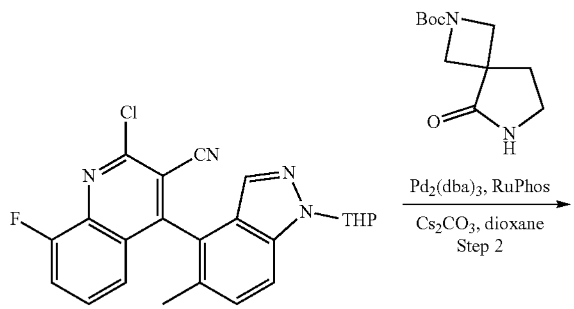

-continued

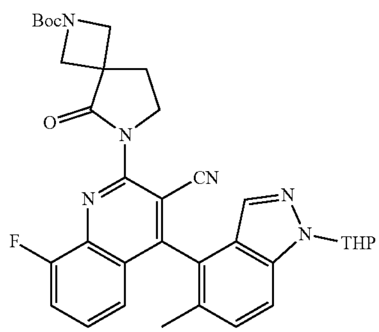

Step 2: tert-butyl 6-(3-Cyano-8-fluoro-4-(5-methyl-1-(tetrahydro-2H-pyran-2-yl)-1H-indazol-4-yl)quinolin-2-yl)-5-oxo-2,6-diazaspiro[3.4]octane-2-carboxylate To a solution of 2-chloro-8-fluoro-4-(5-methy-1H-(tetrahydro-2H-pyran-2-yl)-1H-indazol-4-yl)quinoline-3-carbonitrile (200 mg, 0.475 mmol), tert-butyl 5-oxo-2,6-diazaspiro[3.4]octane-2-carboxylate (129 mg, 0.57 mmol), $Cs_2CO_3$ (464 mg, 1.43 mmol) and 1,4-dioxane (5 mL) was added $Pd_2(dba)_3$ (43.5 mg, 0.048 mmol) and RuPhos (44.4 mg, 0.095 mmol). The system was evacuated and then refilled with $N_2$. The reaction was stirred at 120° C. for 3 h. Upon completion, the reaction mixture was diluted with water (30 mL) and extracted with EtOAc (3×50 mL). The organic extract was washed with brine (3×15 mL), dried over $Na_2SO_4$, and concentrated in vacuo. The crude material was absorbed onto a plug of silica gel and purified by chromatography through a Redi-Sep pre-packed silica gel column (12 g), eluting with a gradient of 0-70% EtOAc in PE, to provide tert-butyl 6-(3-cyano-8-fluoro-4-(5-methyl-1-(tetrahydro-2H-pyran-2-yl)-1H-indazol-4-yl)quinolin-2-yl)-5-oxo-2,6-diazaspiro[3.4]octane-2-carboxylate (60 mg, 21% yield) which was used in the following step as is.

Alternative Step 4 for Example 1-46

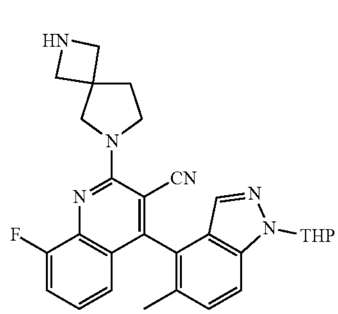

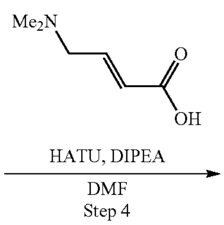

HATU, DIPEA

DMF

Step 4

-continued

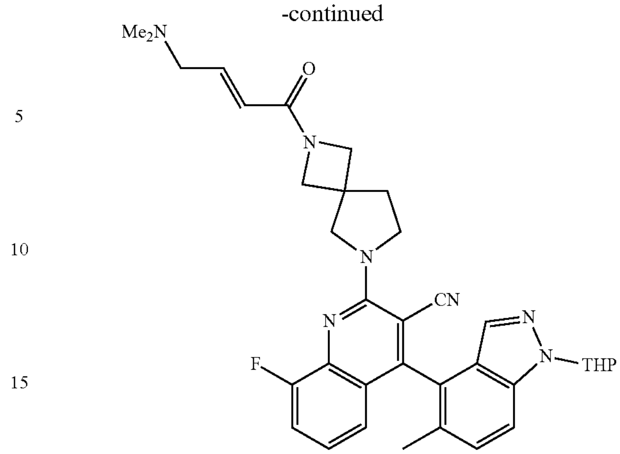

Step 4: (E)-2-(2-(4-(dimethylamino)but-2-enoyl)-2,6-diazaspiro[3.4]octan-6-yl)-8-fluoro-4-(5-methyl-1H-indazol-4-yl)quinoline-3-carbonitrile A solution of 8-fluoro-4-(5-methyl-1H-indazol-4-yl)-2-(2,6-diazaspiro[3.4]octan-6-yl)quinoline-3-carbonitrile (80 mg, 0.194 mmol), (E)-4-(dimethylamino)but-2-enoic acid (35.1 mg, 0.272 mmol), HATU (118 mg, 0.31 mmol) and DIPEA (102 µL, 0.582 mmol) in DMF (2 mL) was stirred at rt for 2 h. Upon completion, the reaction was diluted with water and EtOAc. The mixture was separated and the water phase was extracted with EtOAc twice. The combined organic layers were washed by brine, dried over $MgSO_4$, and concentrated in vacuo. The residue was purified by Prep-HPLC (Phenomenex Gemini $C_{18}$ column, 150×30 mm, 10-100% 0.1% TFA in MeCN/H2O) to give (E)-2-(2-(4-(dimethylamino)but-2-enoyl)-2,6-diazaspiro[3.4]octan-6-yl)-8-fluoro-4-(5-methyl-1H-indazol-4-yl)quinoline-3-carbonitrile (70 mg, 69% yield). m/z (ESI): 524.2 $(M+1H)^+$.

Alternative Step 2 for Examples 1-2 and 1-34

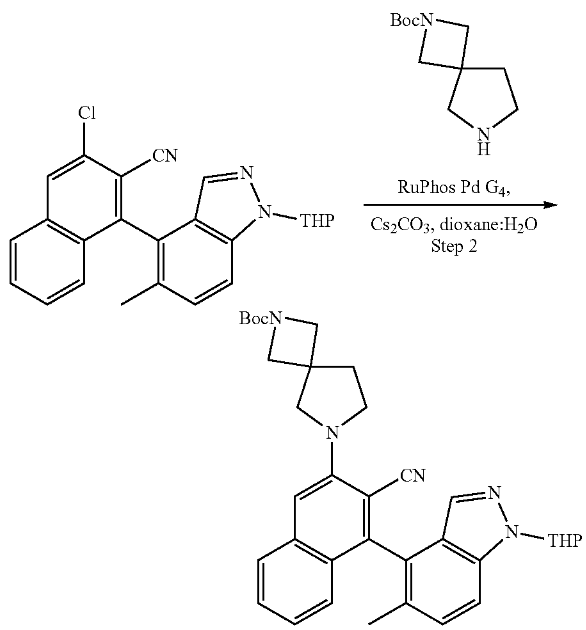

Step 2: tert-butyl 6-(3-cyano-4-(5-methyl-1-(tetrahydro-2H-pyran-2-yl)-1H-indazol-4-yl)naphthalen-2-yl)-2,6-diazaspiro[3.4]octane-2-carboxylate A mixture of 3-chloro-1-(5-methyl-1-(tetrahydro-2H-pyran-2-yl)-1H-indazol-4-yl)-2-naphthonitrile (220 mg, 0.547 mmol), RuPhos Pd G4 (30 mg, 0.05 mmol, Greenchem), $Cs_2CO_3$ (535 mg, 1.642 mmol), and tert-butyl 2,6-diazaspiro[3.4]octane-2-carboxylate (139 mg, 0.657 mmol) in 1,4-dioxane (5 mL) was stirred at 130° C. for 3 h under microwave irradiation. The reaction was extracted with DCM (50 mL×2). The organic phase was washed with brine, dried over $Na_2SO_4$ and concentrated in vacuo. The crude material was purified by silica gel flash chromatography (EtOAc:PE=5:1, v/v) to afford the title compound (202 mg, 63% yield) as a yellow solid. m/z (ESI): 578.3 $(M+H)^+$.

Alternative Step 4 for Example 1-14

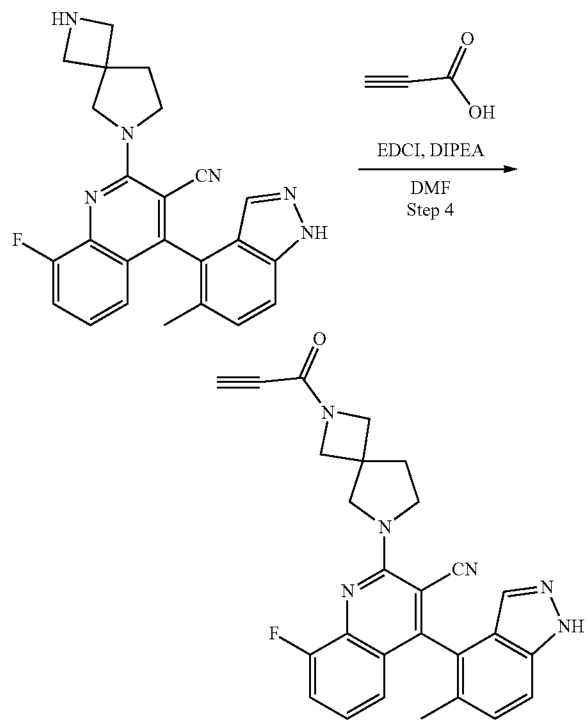

Step 4: 8-fluoro-4-(5-methyl-1H-indazol-4-yl)-2-(2-propioloyl-2,6-diazaspiro[3.4]octan-6-yl)quinoline-3-carbonitrile To a solution of 8-fluoro-4-(5-methyl-1H-indazol-4-yl)-2-(2,6-diazaspiro[3.4]octan-6-yl)quinoline-3-carbonitrile (70 mg, 0.17 mmol) in DMF (2 mL) was added DIPEA (89 μL, 0.51 mmol), 3-(((ethylimino)methylene)amino)-N,N-dimethylpropan-1-amine (81 mg, 0.424 mmol), and propiolic acid (24 mg, 0.339 mmol). The mixture was stirred at room temperature for 2 h. Upon completion, the reaction was diluted with water and EtOAc. The layers were partitioned and the water layer was extracted with EtOAc twice. The combined organic extracts were washed with brine, dried over $MgSO_4$, and concentrated in vacuo. The crude material was purified by Prep-HPLC (Phenomenex Gemini $C_{18}$ column, 150×30 mm, 10-100% 0.1% TFA in MeCN/$H_2O$) to give 8-fluoro-4-(5-methyl-1H-indazol-4-yl)-2-(2-propioloyl-2,6-diazaspiro[3.4]octan-6-yl)quinoline-3-carbonitrile (60.0 mg, 76% yield). m/z (ESI): 465.1 $(M+H)^+$.

Atropisomer Separation Conditions for Examples 1-8 and 1-10

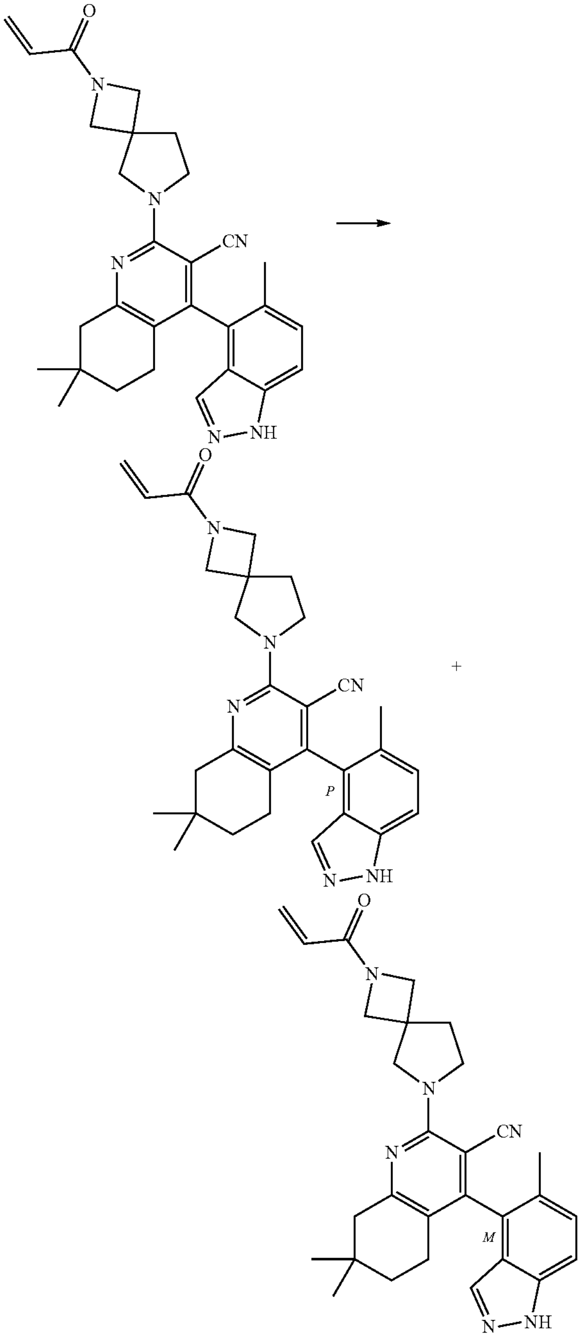

Atropisomer Separation:

The racemic mixture was separated by Chiral SFC-80 (Thar, Waters) in an AD (20×250 mm, 10 μm) (Daicel) column using liquid $CO_2$:MeOH (0.5% $NH_3$) and EtOH (70:30) at 35° C. with a flow rate of 80 g/min to provide the respective P and M isomers of 7,7-dimethyl-4-(5-methyl-1H-indazol-4-yl)-2-(2-(2-propenoyl)-2,6-diazaspiro[3.4]octan-6-yl)-5,6,7,8-tetrahydro-3-quinolinecarbonitrile (110 mg, 0.229 mmol, 39% yield). The stereochemistry of structures was arbitrarily assigned and is not established. 1st eluting atropisomer assigned as the P isomer and 2nd a eluting atropisomer assigned as the M isomer. m/z (ESI): 481.2 $(M+H)^+$.

Alternative Step 2 for Example 1-48

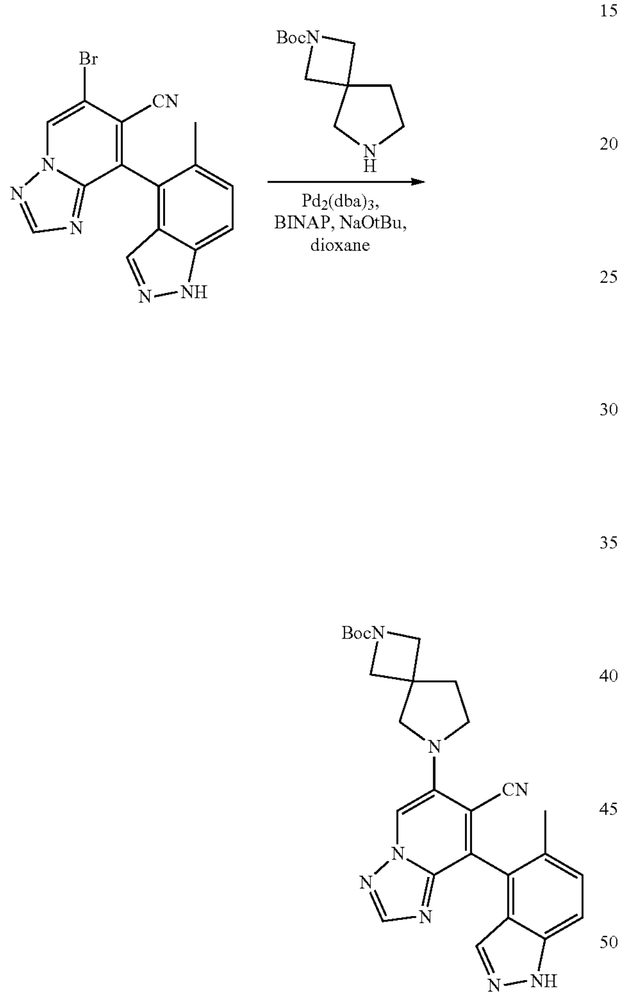

A mixture of tert-butyl 2,6-diazaspiro[3.4]octane-2-carboxylate (19.84 mg, 0.093 mmol), 6-bromo-8-(5-methyl-1H-indazol-4-yl)-[1,2,4]triazolo[1,5-a]pyridine-7-carbonitrile (30 mg, 0.085 mmol), sodium tert-butoxide (16.33 mg, 0.170 mmol), BINAP (5.29 mg, 8.49 μmol), and $Pd_2(dba)_3$ (7.78 mg, 8.49 μmol) in 1,4-dioxane was stirred for 16 h at 90° C. in a RBF under $N_2$. LC-MS suggests complete conversion. The reaction mixture was filtered through a pad of Celite and rinsed with EtOAc, and the filtrate was concentrated in vacuo, purified by HPLC to give the desired product tert-butyl 6-(7-cyano-8-(5-methyl-1H-indazol-4-yl)-[1,2,4]triazolo[1,5-a]pyridin-6-yl)-2,6-diazaspiro[3.4]octane-2-carboxylate (10 mg, 24.3% yield) as a white solid.

Method 2.

Example 2-1: 2-(2-acryloyl-2,6-diazaspiro[3.4]octan-6-yl)-7-methyl-4-(5-methyl-1H-indazol-4-yl)-5,6,7,8-tetrahydroquinoline-3-carbonitrile

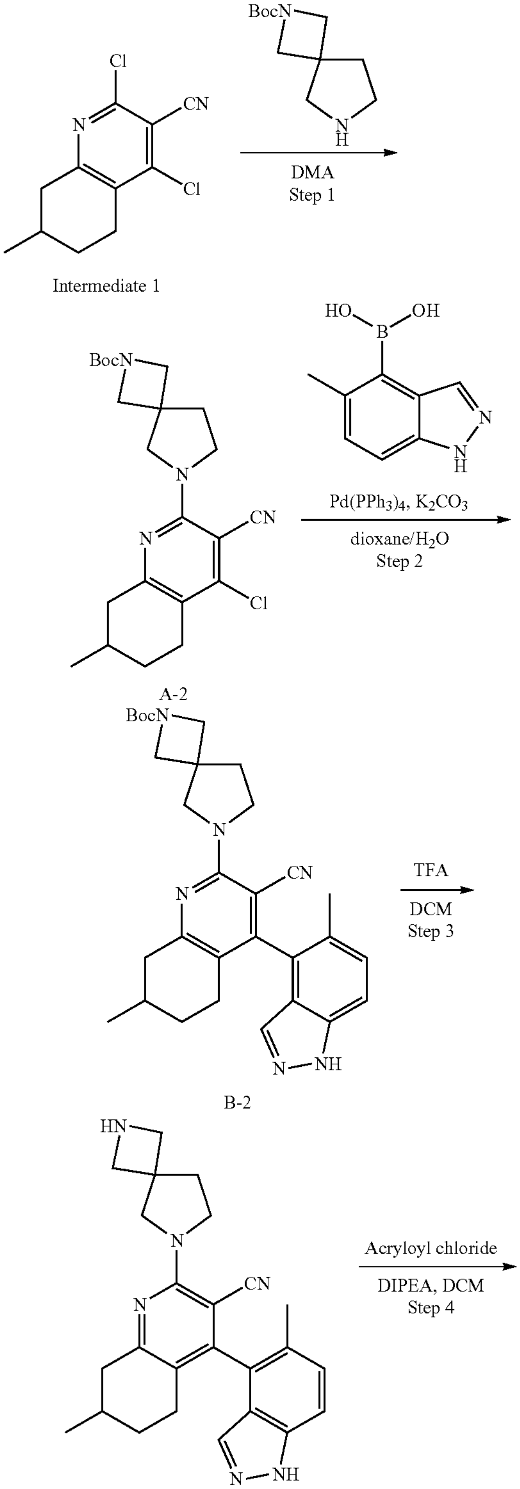

Intermediate 1

A-2

B-2

C-2

-continued

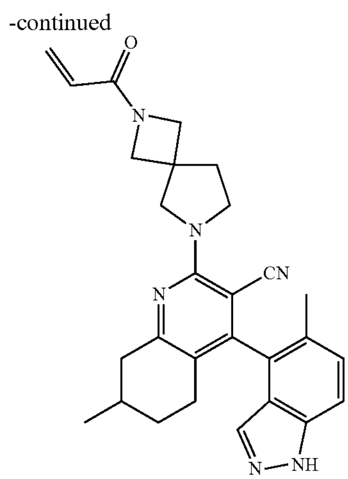

Example 2-1

Step 1: tert-butyl 6-(4-chloro-3-cyano-7-methyl-5,6,7,8-tetrahydroquinolin-2-yl)-2,6-diazaspiro[3.4]octane-2-carboxylate (A-2)

tert-Butyl 2,6-diazaspiro[3.4]octane-2-carboxylate (1.06 g, 4.98 mmol, PharmaBlock) was added to a stirred mixture of 2,4-dichloro-7-methyl-5,6,7,8-tetrahydroquinoline-3-carbonitrile Intermediate 1 (1.0 g, 4.15 mmol) in DMA (10 mL) at 140° C. The reaction mixture was stirred at 140° C. for 2 h. The reaction was then cooled to room temperature, diluted with water (50 mL), and extracted with EtOAc (2×50 mL). The combined organic extracts were washed with brine (2×50 mL), dried over $Na_2SO_4$, filtered, and concentrated in vacuo. The residue was absorbed onto a plug of silica get and purified by column chromatography (silica gel, 20-30% EtOAc in petroleum ether) to give tert-butyl 6-(4-chloro-3-cyano-7n-methyl-5,6,7,8-tetrahydroquinolin-2-yl)-2,6-diazaspiro[3.4]octane-2-carboxylate A-2 (197 mg, 11% yield) as a yellow solid. m/z (ESI): 361.0 $(M+H)^+$.

Step 2: tert-butyl 6-(3-cyano-7-methyl-4-(5-methyl-1H-indazol-4-yl)-5,6,7,8-tetrahydroquinolin-2-yl)-2,6-diazaspiro[3.4]octane-2-carboxylate (B-2)

tert-Butyl 6-(4-chloro-3-cyano-7-methyl-5,6,7,8-tetrahydroquinolin-2-yl)-2,6-diazaspiro[3.4]octane-2-carboxylate A-2 (197 mg, 0.472 mmol), (5-methyl-1II-indazol-4-yl) boronic acid (125 mg, 0.71 mmol), $K_2CO_3$ (163 mg, 1.18 mmol), and $Pd(PPh_3)_4$ (54.6 mg, 0.047 mmol) were mixed in 1,4-dioxane (2 mL) and water (0.5 mL). The reaction mixture was purged with nitrogen for 10 min. The mixture was allowed to stir at 110° C. for 3 h. The reaction mixture was cooled to room temperature, diluted with water (20 mL), and extracted with EtO-Ac (2×20 mL). The combined organic extracts were washed with brine (2×20 mL), dried over $Na_2SO_4$, and concentrated in vacuo. The resulting residue was absorbed onto a plug of silica gel and purified by column chromatography (silica gel, 40-50% EtOAc in PE) to give tert-butyl 6-(3-cyano-7-methyl-4-(5-methyl-1H-indazol-4-yl)-5,6,7,8-tetrahydroquinolin-2-yl)-2,6-diazaspiro[3.4]octane-2-carboxylate B-2 (110 mg, 45% yield) as a yellow solid. m/z (ESI): 513.1 $(M+H)^+$.

Step 3: 7-methyl-4-(5-methyl-1H-indazol-4-yl)-2-(2,6-diazaspiro[3.4]octan-6-yl)-5,6,7,8-tetrahydroquinoline-3-carbonitrile (C-2)

TFA (83 μL, 1.073 mmol) was added to a mixture of tert-butyl 6-(3-cyano-7-methyl-4-(5-methyl-1H-indazol-4-yl)-5,6,7,8-tetrahydroquinolin-2-yl)-2,6-diazaspiro[3.4]octane-2-carboxylate B-2 (110 mg, 0.215 mmol) in DCM (3 mL). The reaction mixture was allowed to stir at room temperature for 1 h. The reaction mixture was filtered, and the filtrate was concentrated in vacuo to give the crude TFA salt of 7-methyl-4-(5-methyl-1H-indazol-4-yl)-2-(2,6-diazaspiro[3.4]octan-6-yl)-5,6,7,8-tetrahydroquinoline-3-carbonitrile C-2 (88 mg, 98% yield) as a yellow solid, which was used directly in the next step. m/z (ESI): 413.0 $(M+H)^+$.

Step 4: 2-(2-acryloyl-2,6-diazaspiro[3.4]octan-6-yl)-7-methyl-4-(5-methyl-1H-indazol-4-yl)-5,6,7,8-tetrahydroquinoline-3-carbonitrile (Example 2-1)

The crude TFA salt of 7-methyl-4-(5-methyl-1H-indazol-4-yl)-2-(2,6-diazaspiro[3.4]octan-6-yl)-5,6,7,8-tetrahydroquinoline-3-carbonitrile C-2 (88 mg, 0.21 mmol), DIPEA (186 μL, 1.07 mmol), and acryloyl chloride (17.3 μL, 0.213 mmol) were mixed in DCM (10 mL) at −60° C. The reaction mixture was allowed to stir at −60° C. for 1 h. The reaction was warmed to room temperature and diluted with water (20 mL). The organic extract was separated, and the aqueous layer was extracted with DCM (2×20 mL). The combined organic extracts were washed with brine (2×20 mL), dried over $Na_2SO_4$, and concentrated in vacuo. The resulting residue was purified by reverse phase preparative chromatography (XBridge Prep $C_{18\ 10}$ μm, 19×250 mm; 40-70% (10 mM $NH_4HCO_3$ in water) in MeCN with a flow rate of 30 mL/min) to give 2-(2-acryloyl-2,6-diazaspiro[3.4]octan-6-yl)-7-methyl-4-(5-methyl-1H-indazol-4-yl)-5,6,7,8-tetrahydroquinoline-3-carbonitrile Example 2-1 (15 mg, 14% yield) as a white solid. m/z (ESI) 467.2 $(M+H)^+$. $^1H$ NMR (400 MHz, DMSO-$d_6$) δ 13.15 (d, J=6.6 Hz, 1H), 7.52 (d, J=8.8 Hz, 2H), 733 (d, J=8.5 Hz, 1H), 6.31 (dd, J=16.9, 10.3 Hz, 1H), 6.09-6.08 (m, 1H), 5.67 (dd, J=10.3, 2.3 Hz, 1H), 4.28-4.26 (m, 1H), 4.17-4.15 (m, 1H), 3.96 (d, J=10.2 Hz, 1H), 3.90-3.83 (m, 3H), 3.72 (t, J=6.7 Hz, 2H), 2.90-2.84 (m, 1H), 2.50-2.38 (m, 1H), 2.19-2.16 (m, 2H), 2.11 (s, 3H), 2.00 (dt, J=30.8, 13.1 Hz, 2H), 1.86-1.84 (m, 1H), 1.65 (d, J=12.3 Hz, 1H), 1.18 (dd, J=15.5, 8.4 Hz, 1H), 1.00 (d, J=6.5 Hz, 3H).

TABLE 3

| Examples 2-2 to 2-111 were prepared following the procedure described in Method 2, Steps 1-4, above as follows: | | | | |
|---|---|---|---|---|
| Ex. # | Chemical Structure | Name | Method changes | Reagent |
| 2-2 | 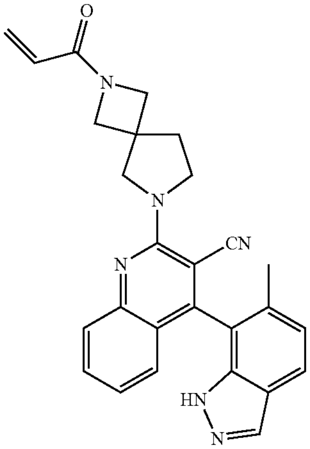 [SMILES: C=CC(=O)N1CC2(CCN(c3nc4ccccc4c(-c4c(C)ccc5cn[nH]c45)c3C#N)C2)C1] | 4-(6-methyl-1H-indazol-7-yl)-2-(2-(2-propenoyl)-2,6-diazaspiro[3.4]octan-6-yl)-3-quinolinecarbonitrile | | Step 1: 2,4-dichloroquinoline-3-carbonitrile (CAS: 69875-54-3, eNovation Chemicals LLC) and Step 2: 6-Methyl-7-(4,4,5,5-tetramethyl-1,3,2-dioxaborolan~2-yl)-1H-indazole (As synthesized for Example 1-25). |
| 2-3 | 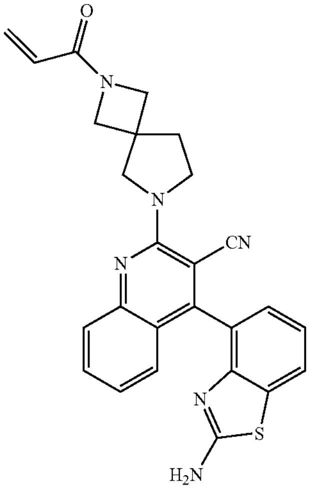 [SMILES: C=CC(=O)N1CC2(CCN(c3nc4ccccc4c(-c4cccc5sc(N)nc45)c3C#N)C2)C1] | 4-(2-amino-1,3-benzothiazol-4-yl)-2-(2-(2-propenoyl)-2,6-diazaspiro[3.4]octan-6-yl)-3-quinolinecarbonitrile | | Step 1: 2,4-dichloroquinoline-3-carbonitrile (CAS: 69875-54-3, eNovation Chemicals LLC) and Step 2: (2-((tert-butoxycarbonyl)amino)benzo[d]thiazol-4-yl)boronic acid (As synthesized for Example 1-23). |
| 2-4 | 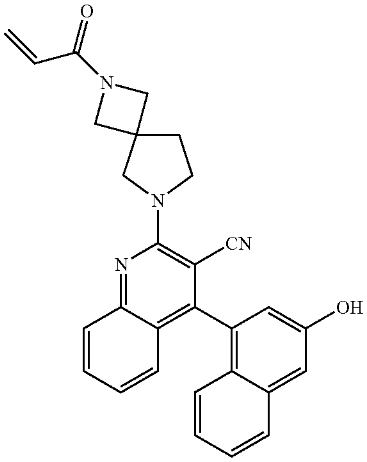 [SMILES: C=CC(=O)N1CC2(CCN(c3nc4ccccc4c(-c4cc(O)cc5ccccc45)c3C#N)C2)C1] | 4-(3-hydroxy-1-naphthalenyl)-2-(2-(2-propenoyl)-2,6-diazaspiro[3.4]octan-6-yl)-3-quinolinecarbonitrile | | Step 1: 2,4-dichloroquinoline-3-carbonitrile (CAS: 69875-54-3, eNovation Chemicals LLC) and Step 2: 2-(3-methoxynaphthalen-1-yl)-4,4,5,5-tetramethyl-1,3,2-dioxaborolane (As synthesized for Example 1-22). |

TABLE 3-continued

Examples 2-2 to 2-111 were prepared following the procedure described in Method 2, Steps 1-4, above as follows:

| Ex. # | Chemical Structure | Name | Method changes | Reagent |
|---|---|---|---|---|
| 2-5 | 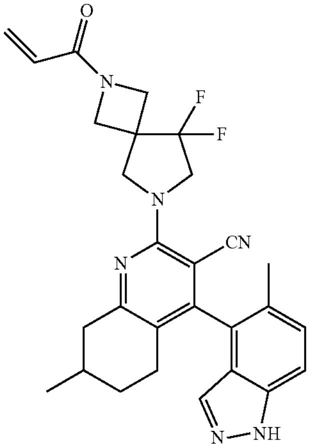 [SMILES: C=CC(=O)N1CC2(C1)CN(c1nc3c(c(-c4c(C)ccc5[nH]ncc45)c1C#N)CCC(C)C3)CC2(F)F] | 2-(8,8-difluoro-2-(2-propenoyl)-2,6-diazaspiro[3.4]octan-6-yl)-7-methyl-4-(5-methyl-1H-indazol-4-yl)-5,6,7,8-tetrahydro-3-quinolinecarbonitrile | | Step 1; tert-butyl 8,8-difluoro-2,6-diazaspiro[3.4]octane-2-carboxylate (CAS: 2137997-74-9, PharmaBlock) and Intermediate 1. |
| 2-6 | 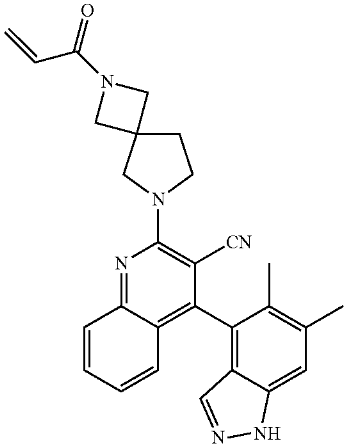 [SMILES: C=CC(=O)N1CC2(CCN(c3nc4ccccc4c(-c4c(C)c(C)cc5[nH]ncc45)c3C#N)C2)C1] | 4-(5,6-dimethyl-1H-indazol-4-yl)-2-(2-(2-propenoyl)-2,6-diazaspiro[3.4]octan-6-yl)-3-quinolinecarbonitrile | See below for synthesis of boronic ester | Step 1: 2,4-dichloroquinoline-3-carbonitrile (CAS: 69875-54-3, eNovation Chemicals LLC) and Step 2: 5,6-dimethyl-1-(tetrahydro-2H-pyran-2-yl)-4-(4,4,5,5-tetramethyl-1,3,2-dioxaborolan-2-yl)-1H-indazole |
| 2-7 | 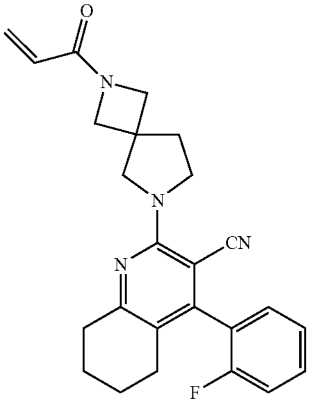 [SMILES: C=CC(=O)N1CC2(CCN(c3nc4c(c(-c5ccccc5F)c3C#N)CCCC4)C2)C1] | 4-(2-fluorophenyl)-2-(2-(2-propenoyl)-2,6-diazaspiro[3.4]octan-6-yl)-5,6,7,8-tetrahydro-3-quinolinecarbonitrile | | Step 1: Intermediate 2 and Step 2: (2-fluorophenyl)boronic acid (CAS: 1993-03-9, Combi-Blocks). |

TABLE 3-continued

Examples 2-2 to 2-111 were prepared following the procedure described in Method 2, Steps 1-4, above as follows:

| Ex. # | Chemical Structure | Name | Method changes | Reagent |
|---|---|---|---|---|
| 2-8 | 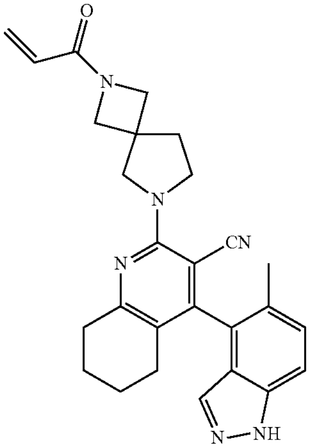 [SMILES: C=CC(=O)N1CC2(CCN(c3nc4c(c(-c5c(C)ccc6[nH]ncc56)c3C#N)CCCC4)C2)C1] | 4-(5-methyl-1H-indazol-4-yl)-2-(2-(2-propenoyl)-2,6-diazaspiro[3.4]octan-6-yl)-5,6,7,8-tetrahydro-3-quinolinecarbonitrile | | Step 1: Intermediate 2. |
| 2-9 | 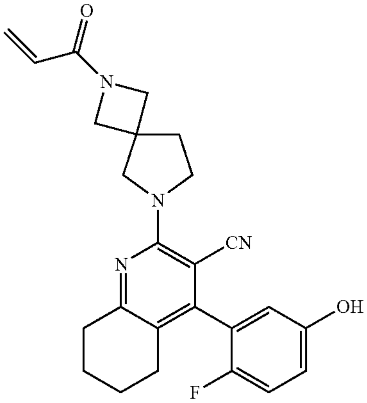 [SMILES: C=CC(=O)N1CC2(CCN(c3nc4c(c(-c5cc(O)ccc5F)c3C#N)CCCC4)C2)C1] | 4-(2-fluoro-5-hydroxyphenyl)-2-(2-(2-propenoyl)-2,6-diazaspiro[3.4]octan-6-yl)-5,6,7,8-tetrahydro-3-quinolinecarbonitrile | | Step 1: Intermediate 2 and Step 2: (2-fluoro-5-hydroxyphenyl) boronic acid (CAS: 1150114-52-5, Combi-Blocks). |
| 2-10 | 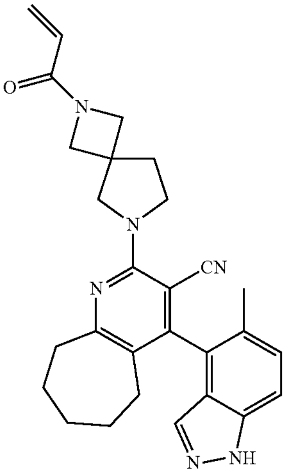 [SMILES: C=CC(=O)N1CC2(CCN(c3nc4c(c(-c5c(C)ccc6[nH]ncc56)c3C#N)CCCCC4)C2)C1] | 4-(5-methyl-1H-indazol-4-yl)-2-(2-(2-propenoyl)-2,6-diazaspiro[3.4]octan-6-yl)-6,7,8,9-tetrahydro-5H-cyclohepta[b]pyridine-3-carbonitrile | Step 1: 3 eq DIPEA and Step 2: $PdCl_2$ (dppf) | Step 1: Intermediate 119 and Step 2: 5-methyl-1-(tetrahydro-2H-pyran-2-yl)-4-(4,4,5,5-tetramethyl-1,3,2-dioxaborolan-2-yl)-1H-indazole (PharmaBlock). |

TABLE 3-continued

Examples 2-2 to 2-111 were prepared following the procedure described in Method 2, Steps 1-4, above as follows:

| Ex. # | Chemical Structure | Name | Method changes | Reagent |
|---|---|---|---|---|
| 2-11 | 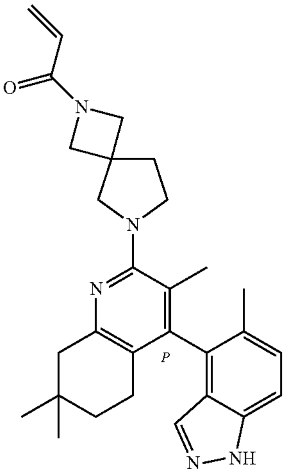 | (P)-1-(6-(3,7,7-trimethyl-4-(5-methyl-1H-indazol-4-yl)-5,6,7,8-tetrahydro-2-quinolinyl)-2,6-diazaspiro[3.4]octan-2-yl)-2-propen-1-one (2nd eluting peak) | See below for Alternative Step 1. Step 2: SPhos Pd G3 and $K_3PO_4$ used. See below for atropisomer separation conditions | Step 1: Intermediate 36. Step 2: 5-methyl-1-(oxan-2-yl)-4-(4,4,5,5-tetramethyl-1,3,2-dioxaborolan-2-yl)-1 H-indazole (PharmaBlock). |
| 2-12 | 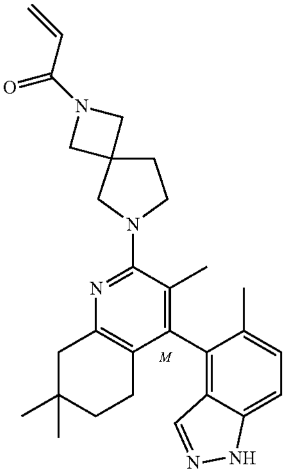 | (M)-1-(6-(3,7,7-trimethyl-4-(5-methyl-1H-indazol-4-yl)-5,6,7,8-tetrahydro-2-quinolinyl)-2,6-diazaspiro[3.4]octan-2-yl)-2-propen-1-one (1st eluting peak) | Alternative Step 1 performed in analogous manner to Example 2-11. Step 2: SPhos Pd G3 and $K_3PO_4$ used. See below for atropisomer separation conditions | Step 1: Intermediate 36. Step 2: 5-methyl-1-(oxan-2-yl)-4-(4,4,5,5-tetramethyl-1,3,2-dioxaborolan-2-yl)-1H-indazole (PharmaBlock). |
| 2-13 | 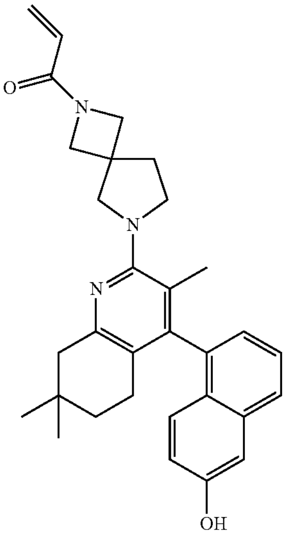 [SMILES: C=CC(=O)N1CC2(CCN(c3nc4c(c(-c5cccc6cc(O)ccc56)c3C)CCC(C)(C)C4)C2)C1] | 1-(6-(4-(6-hydroxy-1-naphthalenyl)-3,7,7-trimethyl-5,6,7,8-tetrahydro-2-quinolinyl)-2,6-diazaspiro[3.4]octan-2-yl)-2-propen-1-one | Alternative Step 1 performed in analogous manner to Example 2-11. | Step 1: Intermediate 36. Step 2: Intermediate 65. |

TABLE 3-continued

| Examples 2-2 to 2-111 were prepared following the procedure described in Method 2, Steps 1-4, above as follows: | | | | |
|---|---|---|---|---|
| Ex. # | Chemical Structure | Name | Method changes | Reagent |
| 2-14 | 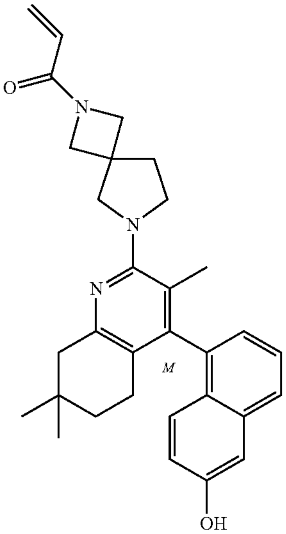 | (M)-1-(6-(4-(6-hydroxy-1-naphthalenyl)-3,7,7-trimethyl-5,6,7,8-tetrahydro-2-quinolinyl)-2,6-diazaspiro[3.4]ctan-2-yl)-2-opropen-1-one (1st eluting peak) | Alternative Step 1 performed in analogous manner to Example 2-11. See below for atropisomer separation conditions | Step 1: Intermediate 36. Step 2: Intermediate 65. |
| 2-15 | 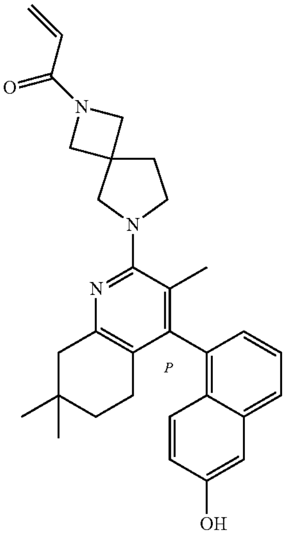 | (P)-1-(6-(4-(6-hydroxy-1-naphthalenyl)-3,7,7-trimethyl-5,6,7,8-tetrahydro-2-quinolinyl)-2,6-diazaspiro[3.4]octan-2-yl)-2-propen-1-one (2nd eluting peak) | Alternative Step 1 performed in analogous manner to Example 2-11. See below for atropisomer separation conditions | Step 1: Intermediate 36. Step 2: Intermediate 65. |

TABLE 3-continued

Examples 2-2 to 2-111 were prepared following the procedure described in Method 2, Steps 1-4, above as follows:

| Ex. # | Chemical Structure | Name | Method changes | Reagent |
|---|---|---|---|---|
| 2-16 | 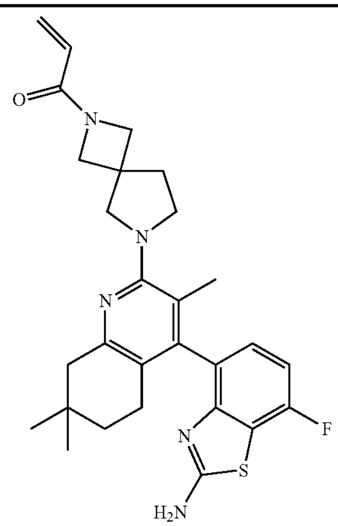 | 4-(2-amino-7-fluoro-1,3-benzothiazol-4-yl)-7,7-dimethyl-2-(2-(2-propenoyl)-2,6-diazaspiro[3,4]octan-6-yl)-7,8-dihydro-5H-pyrano[4,3-b]pyridine-3-carbonitrile | Alternative Step 1 performed in analogous manner to Example 2-11. | Step 1: Intermediate 36. Step 2: (2-((tert-butoxycarbonyl)amino)-7-fluorobenzo[d]thiazol-4-yl)boronic acid (PharmaBlock) |
| 2-17 | 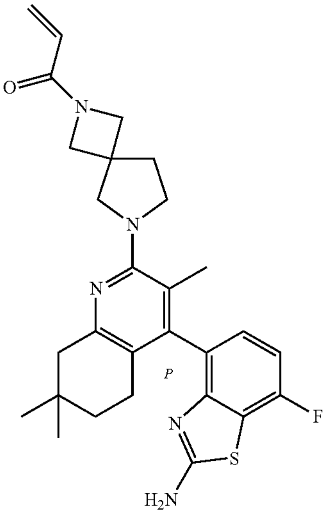 | (P)-4-(2-amino-7-fluoro-1,3-benzothiazol-4-yl)-7,7-dimethyl-2-(2-(2-propenoyl)-2,6-diazaspiro[3.4]octan-6-yl)-7,8-dihydro-5H-pyrano[4,3-b]pyridine-3-carbonitrile (18 eluting peak) | Alternative Step 1 performed in analogous manner to Example 2-11. See below for atropisomer separation conditions. | Step 1: Intermediate 36. Step 2: (2-((tert-butoxycarbonyl)amino)-7-fluorobenzo[d]thiazol-4-yl)boronic acid (PharmaBlock) |
| 2-18 | 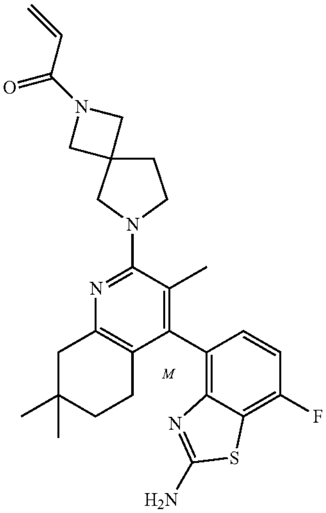 | (M)-4-(2-amino-7-fluoro-1,3-benzothiazol-4-yl)-7,7-dimethyl-2-(2-(2-propenoyl)-2,6-diazaspiro[3.4]octan-6-yl)-7,8-dihydro-5H-pyrano[4,3-b]pyridine-3-carbonitrile ($2^{nd}$ eluting peak) | Alternative Step 1 performed in analogous manner to Example 2-11. See below for atropisomer separation conditions | Step 1: Intermediate 36. Step 2: (2-((tert-butoxycarbonyl)amino)-7-fluorobenzo[d]thiazol-4-yl)boronic acid (PharmaBlock) |

TABLE 3-continued

Examples 2-2 to 2-111 were prepared following the procedure described in Method 2, Steps 1-4, above as follows:

| Ex. # | Chemical Structure | Name | Method changes | Reagent |
|---|---|---|---|---|
| 2-19 | 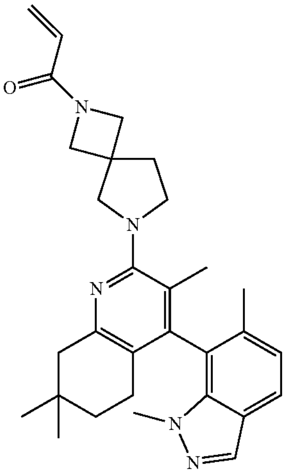 [SMILES: C=CC(=O)N1CC2(CCN(c3nc4c(c(-c5c(C)ccc6cnn(C)c56)c3C)CCC(C)(C)C4)C2)C1] | 1-(6-(4-(1,6-dimethyl-1H-indazol-7-yl)-3,7,7-trimethyl-5,6,7,8-tetrahydro-2-quinolinyl)-2,6-diazaspiro[3,4]octan-2-yl)-2-propen-1-one | Alternative Step 1 performed in analogous manner to Example 2-11. Step 2: SPhos Pd G3; $K_3PO_4$. N-methylation performed after Step 2 using conditions described below. | Step 1: Intermediate 36. Step 2: 6-methyl-7-(4,4,5,5-tetramethyl-1,3,2-dioxaborolan-2-yl)-1H-indazole (PharmaBlock) |
| 2-20 | 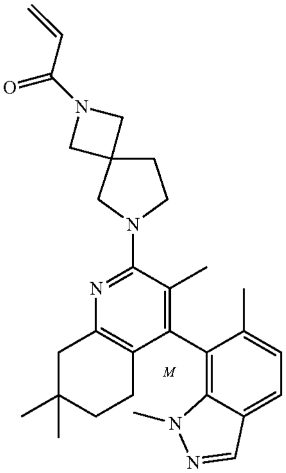 | (M)-1-(6-(4-(1,6-dimethyl-1H-indazol-7-yl)-3,7,7-trimethyl-5,6,7,8-tetrahydro-2-quinolinyl)-2,6-diazaspiro[3.4]octan-2-yl)-2-propen-1-one (1$^{st}$ eluting isomer) | Alternative Step 1 performed in analogous manner to Example 2-11. Step 2: SPhos Pd G3; $K_3PO_4$. N-methylation performed using procedure from Example 2-19 after step 2. See below for atropisomer separation conditions | Step 1: Intermediate 36. Step 2: 6-methyl-7-(4,4,5,5-tetramethyl-1,3,2-dioxaborolan-2-yl)-1H-indazole (PharmaBlock) |
| 2-21 | 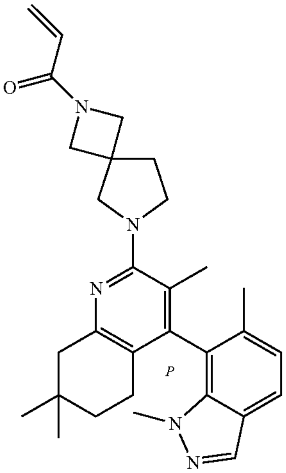 | (P)-1-(6-(4-(1,6-dimethyl-1H-indazol-7-yl)-3,7,7-trimethyl-5,6,7,8-tetrahydro-2-quinolinyl)-2,6-diazaspiro[3.4]octan-2-yl)-2-propen-1-one (2$^{nd}$ eluting isomer) | Alternative Step 1 performed in analogous manner to Example 2-11. Step 2: SPhos Pd G3; $K_3PO_4$. N-methylation performed using procedure from Example 2-19 after step 2. See below for atropisomer separation conditions | Step 1: Intermediate 36. Step 2: 6-methyl-7-(4,4,5,5-tetramethyl-1,3,2-dioxaborolan-2-yl)-1H-indazole (PharmaBlock) |

TABLE 3-continued

Examples 2-2 to 2-111 were prepared following the procedure described in Method 2, Steps 1-4, above as follows:

| Ex. # | Chemical Structure | Name | Method changes | Reagent |
|---|---|---|---|---|
| 2-22 | 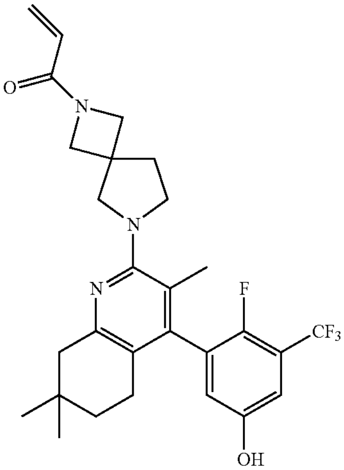 [SMILES: C=CC(=O)N1CC2(CCN(c3nc4c(c(-c5cc(O)cc(C(F)(F)F)c5F)c3C)CCC(C)(C)C4)C2)C1] | 1-(6-(4-(2-fluoro-5-hydroxy-3-(trifluoromethyl) phenyl)-3,7,7-trimethyl-5,6,7,8-tetrahydro-2-quinolinyl)-2,6-diazaspiro[3.4] octan-2-yl)-2-propen-1-one | Alternative Step 1 performed in analogous manner to Example 2-11. | Step 1: Intermediate 36. Step 2: (2-fluoro-5-hydroxy-3-(trifluoromethyl) phenyl)boronic acid (Combi-Blocks) |
| 2-23 | 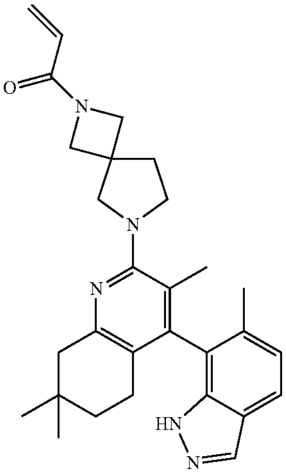 [SMILES: C=CC(=O)N1CC2(CCN(c3nc4c(c(-c5c(C)ccc6cn[nH]c56)c3C)CCC(C)(C)C4)C2)C1] | 1-(6-(3,7,7-trimethyl-4-(6-methyl-1H-indazol-7-yl)-5,6,7,8-tetrahydro-2-quinolinyl)-2,6-diazaspiro[3.4] octan-2-yl)-2-propen-1-one | Alternative Step 1 performed in analogous manner to Example 2-11. Step 2: SPhos Pd G3 and $K_3PO_4$ used. | Step 1: Intermediate 36. Step 2: 6-methyl-7-(4,4,5,5-tetramethyl-1,3,2-dioxaborolan-2-yl)-1H-indazole (PharmaBlock) |
| 2-24 | 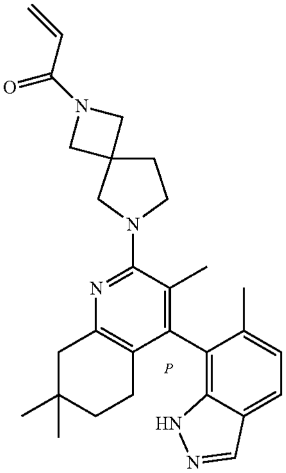 | (P)-1-(6-(3,7,7-trimethyl-4-(6-methyl-1H-indazol-7-yl)-5,6,7,8-tetrahydro-2-quinolinyl)-2,6-diazaspiro[3.4] octan-2-yl)-2-propen-1-one ($2^{nd}$ eluting peak) | Alternative Step 1 performed in analogous manner to Example 2-11. Step 2: SPhos Pd G3 and $K_3PO_4$ used. See below for atropisomer separation conditions | Step 1: Intermediate 36. Step 2: 6-methyl-7-(4,4,5,5-tetramethyl-1,3,2-dioxaborolan-2-yl)-1H-indazole (PharmaBlock) |

TABLE 3-continued

| Ex. # | Chemical Structure | Name | Method changes | Reagent |
|---|---|---|---|---|
| Examples 2-2 to 2-111 were prepared following the procedure described in Method 2, Steps 1-4, above as follows: | | | | |
| 2-25 | 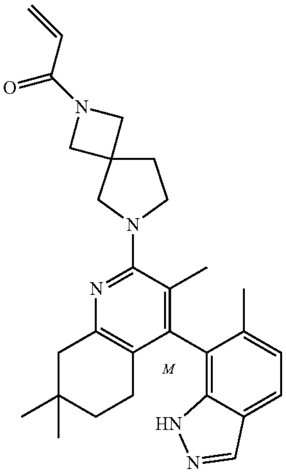 | (M)-1-(6-(3,7,7-trimethyl-4-(6-methyl-1H-indazol-7-yl)-5,6,7,8-tetrahydro-2-quinolinyl)-2,6-diazaspiro[3.4]octan-2-yl)-2-propen-1-one (1st eluting peak) | Alternative Step 1 performed in analogous manner to Example 2-11. Step 2: SPhos Pd G3 and $K_3PO_4$ used. See below for atropisomer separation conditions | Step 1: Intermediate 36. Step 2: 6-methyl-7-(4,4,5,5-tetramethyl-1,3,2-dioxaborolan-2-yl)-1H-indazole (PharmaBlock) |
| 2-26 | 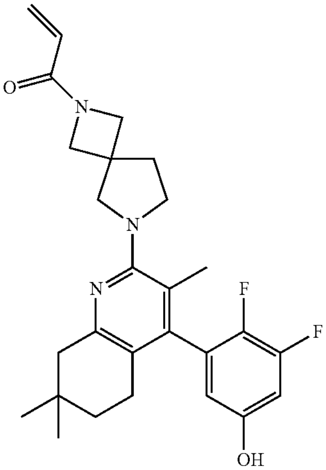 [SMILES: C=CC(=O)N1CC2(CCN(c3nc4c(c(-c5cc(O)cc(F)c5F)c3C)CCC(C)(C)C4)C2)C1] | 1-(6-(4-(2,3-difluoro-5-hydroxyphenyl)-3,7,7-trimethyl-5,6,7,8-tetrahydro-2-quinolinyl)-2,6-diazaspiro[3.4]octan-2-yl)-2-propen-1-one | Alternative Step 1 performed in analogous manner to Example 2-11. Step 2: SPhos Pd G3 and $K_3PO_4$ used. | Step 1: Intermediate 36. Step 2: (5-((tert-butyldimethylsilyl)oxy)-2,3-difluorophenyl)boronic acid (Combi-Blocks) |
| 2-27 | 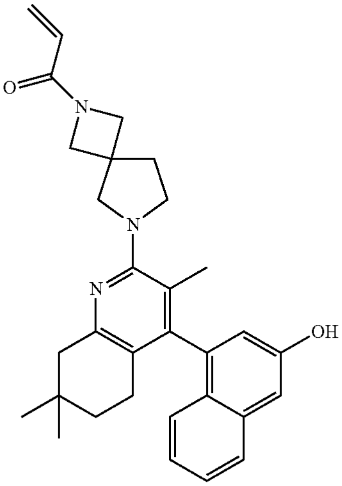 [SMILES: C=CC(=O)N1CC2(CCN(c3nc4c(c(-c5cc(O)cc6ccccc56)c3C)CCC(C)(C)C4)C2)C1] | 1-(6-(4-(3-hydroxy-1-naphthalenyl)-3,7,7-trimethyl-5,6,7,8-tetrahydro-2-quinolinyl)-2,6-diazaspiro[3,4]octan-2-yl)-2-propen-1-one | Alternative Step 1 performed in analogous manner to Example 2-11. Step 2: SPhos Pd G3 and $K_3PO_4$ used. | Step 1: Intermediate 36. Step 2: 3-hydroxynaphthalene-1-boronic acid (eNovation Chemicals LLC) |

TABLE 3-continued

| Examples 2-2 to 2-111 were prepared following the procedure described in Method 2, Steps 1-4, above as follows: | | | | |
|---|---|---|---|---|
| Ex. # | Chemical Structure | Name | Method changes | Reagent |
| 2-28 | 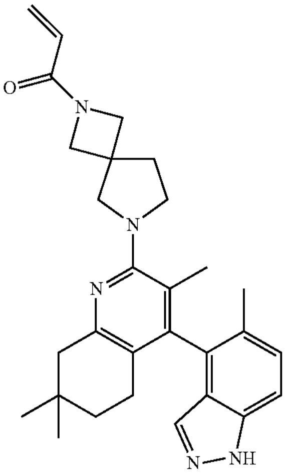 [SMILES: C=CC(=O)N1CC2(CCN(c3nc4c(c(-c5c(C)ccc6[nH]ncc56)c3C)CCC(C)(C)C4)C2)C1] | 1-(6-(3,7,7-trimethyl-4-(5-methyl-1H-indazol-4-yl)-5,6,7,8-tetrahydro-2-quinolinyl)-2,6-diazaspiro[3.4]octan-2-yl)-2-propen-1-one | Alternative Step 1 performed in analogous manner to Example 2-11. Step 2: SPhos Pd G3 and $K_3PO_4$ used. | Step 1: Intermediate 36. Step 2: 5-methyl-1-(oxan-2-yl)-4-(4,4,5,5-tetramethyl-1,3,2-dioxaborolan-2-yl)-1H-indazole (PharmaBlock) |
| 2-29 | 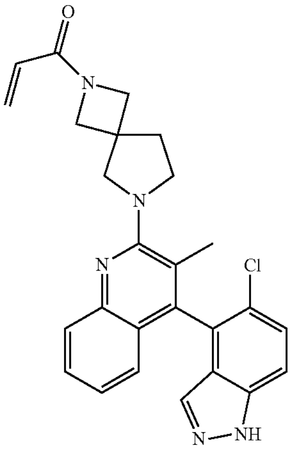 [SMILES: C=CC(=O)N1CC2(CCN(c3nc4ccccc4c(-c4c(Cl)ccc5[nH]ncc45)c3C)C2)C1] | 1-(6-(4-(5-chloro-1H-indazol-4-yl)-3-methyl-2-quinolinyl)-2,6-diazaspiro[3.4]octan-2-yl)-2-propen-1-one | Step 1 used 3 eq of DIEA. Step 2: SPhos Pd G3, $K_3PO_4$ | Step 1: 2,4-dichloro-3-methylquinoline (Combi-Blocks) Step 2: Intermediate 52 |
| 2-30 | 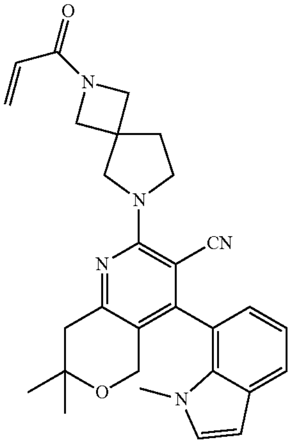 [SMILES: C=CC(=O)N1CC2(CCN(c3nc4c(c(-c5cccc6ccn(C)c56)c3C#N)COC(C)(C)C4)C2)C1] | 7,7-dimethyl-4-(1-methyl-1H-indol-7-yl)-2-(2-(2-propenoyl)-2,6-diazaspiro[3.4]octan-6-yl)-7,8-dihydro-5H-pyrano[4,3-b]pyridine-3-carbonitrile | Step 1: 3 eq DIEA. Step 2: SPhos Pd G3, $K_3PO_4$. Additional N-methylation performed using procedure from Example 2-19 after step 2. | Step 1: Intermediate 20. Step 2: indole-7-boronic acid (Combi-Blocks) |

TABLE 3-continued

| Examples 2-2 to 2-111 were prepared following the procedure described in Method 2, Steps 1-4, above as follows: | | | | |
|---|---|---|---|---|
| Ex. # | Chemical Structure | Name | Method changes | Reagent |
| 2-31 | 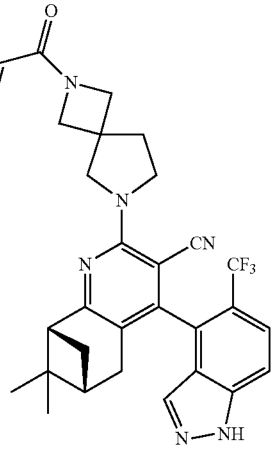 | (1R,9R)-10,10-dimethyl-4-(2-(2-propenoyl)-2,6-diazaspiro[3.4]octan-6-yl)-6-(5-(trifluoromethyl)-1H-indazol-4-yl)-3-azatricyclo[7.1.1.0$^{2,7}$]undeca-2,4,6-triene-5-carbonitrile | Step 1: 3 eq DIEA. Step 2: SPhos Pd G3, $K_3PO_4$. | Step 1: Intermediate 21. Step 2: 1-(tetrahydro-2h-pyran-2-yl)-5-(trifluoromethyl-1H-indazol-4-ylboronic acid (Apollo Scientific) |
| 2-32 | 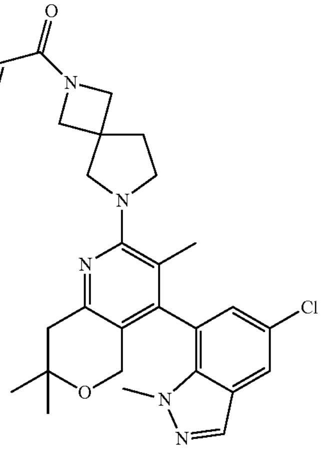 | 1-(6-(4-(5-chloro-1-methyl-1H-indazol-7-yl)-3,7,7-trimethyl-7,8-dihydro-5H-pyrano[4,3-b]pyridin-2-yl)-2,6-diazaspiro[3.4]octan-2-yl)-2-propen-1-one | Step 1:3 eq DIEA. Step 2: SPhos Pd G3, $K_3PO_4$. Additional N-methylation performed using procedure from Example 2-19 after step 2. | Step 1: Intermediate 22. Step 2: 7-bromo-5-chloro-1H-indazole (Combi-Blocks) |
| 2-33 | 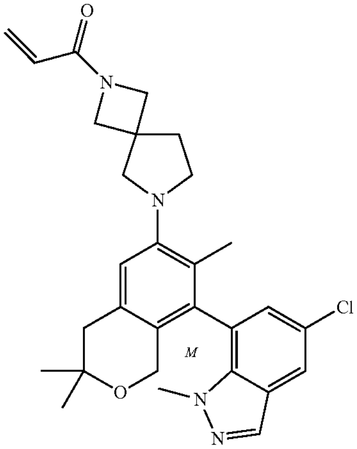 | (M)-1-(6-(4-(5-chloro-1-methyl-1H-indazol-7-yl)-3,7,7-trimethyl-7,8-dihydro-5H-pyrano[4,3-b]pyridin-2-yl)-2,6-diazaspiro[3.4]octan-2-yl)-2-propen-1-one (2$^{nd}$ eluting isomer) | Step 1: 3 eq DIEA. Step 2: SPhos Pd G3, $K_3PO_4$. Additional N-methylation performed using procedure from Example 2-19 after step 2. See below for atropisomer separation conditions | Step 1: Intermediate 22. Step 2: 7-bromo-5-chloro-1H-indazole (Combi-Blocks) |

TABLE 3-continued

| Examples 2-2 to 2-111 were prepared following the procedure described in Method 2, Steps 1-4, above as follows: | | | | |
|---|---|---|---|---|
| Ex. # | Chemical Structure | Name | Method changes | Reagent |
| 2-34 | 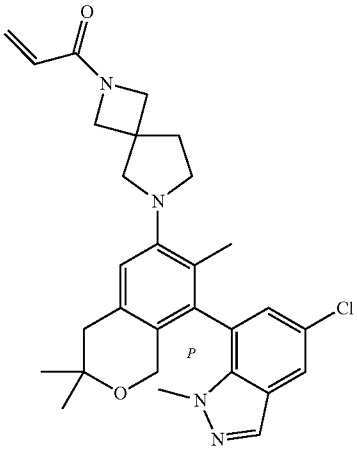 | (P)-1-(6-(4-(5-chloro-1-methyl-1H-indazol-7-yl)-3,7,7-trimethyl-7,8-dihydro-5H-pyrano[4,3-b]pyridin-2-yl)-2,6-diazaspiro[3.4]octan-2-yl)-2-propen-1-one (1st eluting isomer) | Step 1: 3 eq DIEA. Step 2: SPhos Pd G3, $K_3PO_4$. Additional N-methylation performed using procedure from Example 2-19 after step 2. See below for atropisomer separation conditions | Step 1: Intermediate 22. Step 2: 7-bromo-5-chloro-1H-indazole (Combi-Blocks) |
| 2-35 | 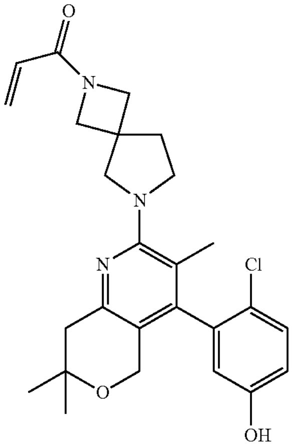 [SMILES: C=CC(=O)N1CC2(CCN(c3nc4c(c(-c5cc(O)ccc5Cl)c3C)COC(C)(C)C4)C2)C1] | 1-(6-(4-(2-chloro-5-hydroxyphenyl)-3,7,7-trimethyl-7,8-dihydro-5H-pyrano[4,3-b]pyridin-2-yl)-2,6-diazaspiro[3.4]octan-2-yl)-2-propen-1-one | Alternative Step 1 performed in analogous manner to Example 2-11. Step 2: SPhos Pd G3 and $K_3PO_4$ used | Step 1: Intermediate 22. Step 2: (2-chloro-5-hydroxyphenyl) boronic acid (Synnovator) |
| 2-36 | 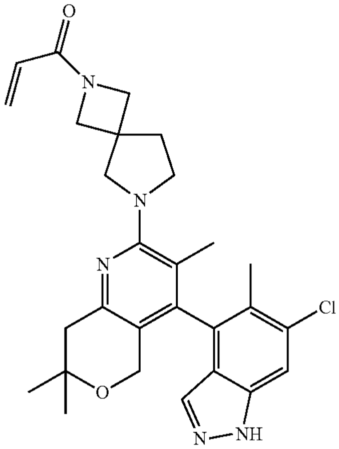 [SMILES: C=CC(=O)N1CC2(CCN(c3nc4c(c(-c5c(C)c(Cl)cc6[nH]ncc56)c3C)COC(C)(C)C4)C2)C1] | 1-(6-(4-(6-chloro-5-methyl-1H-indazol-4-yl)-3,7,7-trimethyl-7,8-dihydro-5H-pyrano[4,3-b]pyridin-2-yl)-2,6-diazaspiro[3.4]octan-2-yl)-2-propen-1-one | Alternative Step 1 performed in analogous manner to Example 2-11. Step 2: SPhos Pd G3 and $K_3PO_4$ used | Step 1: Intermediate 22. Step 2: 6-chloro-5-methyl-1-(tetrahydro-2H-pyran-2-yl)-4-(4,4,5,5-tetramethyl-1,3,2-dioxaborolan-2-yl)-1H-indazole (PharmaBlock) |

TABLE 3-continued

| Examples 2-2 to 2-111 were prepared following the procedure described in Method 2, Steps 1-4, above as follows: | | | | |
|---|---|---|---|---|
| Ex. # | Chemical Structure | Name | Method changes | Reagent |
| 2-37 | 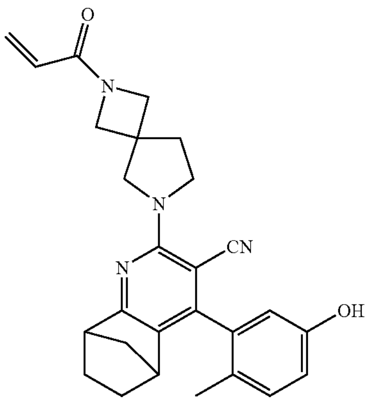 [SMILES: C=CC(=O)N1CC2(CCN(c3nc4c(c(-c5cc(O)ccc5C)c3C#N)C3CCC4C3)C2)C1] | (1R,8S)-6-(5-hydroxy-2-methylphenyl)-4-(2-(2-propenoyl)-2,6-diazaspiro[3.4]octan-6-yl)-3-azatricyclo[6.2.1.0$^{2,7}$]undeca-2,4,6-triene-5-carbonitrile\|(1S,8R)-6-(5-hydroxy-2-methylphenyl)-4-(2-(2-propenoyl)-2,6-diazaspiro[3,4]octan-6-yl)-3-azatricyclo[6.2.1.0$^{2,7}$]undeca-2,4,6-triene-5-carbonitrile | Step 1: See step 2 of intermediate 54. Step 2: SPhos Pd G3 and $K_3PO_4$ used | Step 2: Intermediate 54, step 1. Step 2: (5-hydroxy-2-methylphenyl) boronic acid (Combi-Blocks). |
| 2-38 | 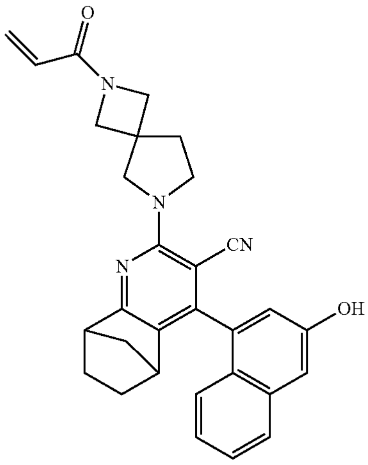 [SMILES: C=CC(=O)N1CC2(CCN(c3nc4c(c(-c5cc(O)cc6ccccc56)c3C#N)C3CCC4C3)C2)C1] | (1R,8S)-6-(3-hydroxy-1-naphthalenyl)-4-(2-(2-propenoyl)-2,6-diazaspiro[3.4]octan-6-yl)-3-azatricyclo[6.2.1.0$^{2,7}$]undeca-2,4,6-triene-5-carbonitrile\|(1S,8R)-6-(3-hydroxy-1-naphthalenyl)-4-(2-(2-propenoyl)-2,6-diazaspiro[3.4]octan-6-yl)-3-azatricyclo[6.2.1.0$^{2,7}$]undeca-2,4,6-triene-5-carbonitrile | Step 1: See step 2 of intermediate 54. Step 2: SPhos Pd G3 and $K_3PO_4$ used | Step 1: Intermediate 54, step 1. Step 2: 3-hydroxynaphthalene-1-boronic acid (eNovation Chemicals LLC). |
| 2-39 | 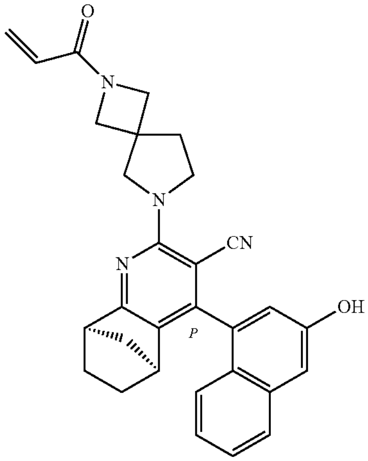 | (P)-(1R,8S)-6-(3-hydroxy-1-naphthalenyl)-4-(2-(2-propenoyl)-2,6-diazaspiro[3,4]octan-6-yl)-3-azatricyclo[6.2.1.0$^{2,7}$]undeca-2,4,6-triene-5-carbonitrile (3$^{rd}$ eluting isomer) | Step 1: See step 2 of intermediate 54. Step 2: SPhos Pd G3 and $K_3PO_4$ used. See below for atropisomer separation conditions | Step 1: Intermediate 54, step 1. Step 2: 3-hydroxynaphthalene-1-boronic acid (eNovation Chemicals LLC). |

TABLE 3-continued

| Ex. # | Chemical Structure | Name | Method changes | Reagent |
|---|---|---|---|---|
| Examples 2-2 to 2-111 were prepared following the procedure described in Method 2, Steps 1-4, above as follows: | | | | |
| 2-40 | 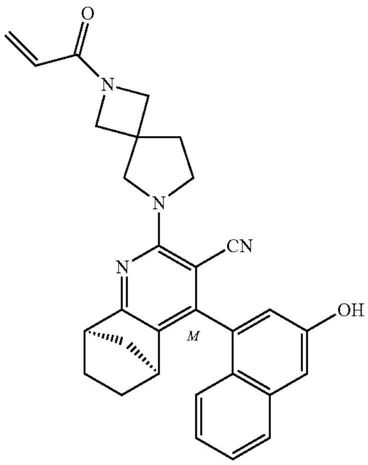 | (M)-(1R,8S)-6-(3-hydroxy-1-naphthalenyl)-4-(2-(2-propenoyl)-2,6-diazaspiro[3.4]octan-6-yl)-3-azatricyclo[6.2.1.0$^{2,7}$]undeca-2,4,6-triene-5-carbonitrile (4$^{th}$ eluting isomer) | Step 1: See step 2 of intermediate 54. Step 2: SPhos Pd G3 and $K_3PO_4$ used. See below for atropisomer separation conditions | Step 1: Intermediate 54, step 1. Step 23-hydroxynaphthalene-1-boronic acid (eNovation Chemicals LLC). |
| 2-41 | 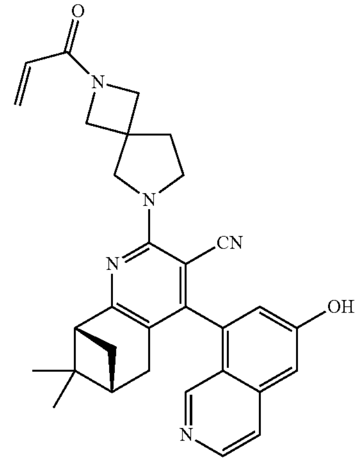 [SMILES: C=CC(=O)N1CC2(CCN(c3nc4c(c(-c5cc(O)cc6ccncc56)c3C#N)C[C@H]3C[C@@H]4C3(C)C)C2)C1] | (1R,9R)-6-(6-hydroxy-8-isoquinolinyl)-10,10-dimethyl-4-(2-(2-propenoyl)-2,6-diazaspiro[3.4]octan-6-yl)-3-azatricyclo[7.1.1.0$^{2,7}$]undeca-2,4,6-triene-5-carbonitrile | Step 1: 2 eq pyridine. Step 2: SPhos Pd G3 and $K_3PO_4$ used. | Step 1: Intermediate 35 and Intermediate 72 |
| 2-42 | 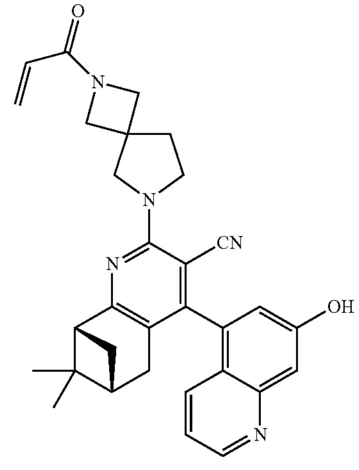 [SMILES: C=CC(=O)N1CC2(CCN(c3nc4c(c(-c5cc(O)cc6ncccc56)c3C#N)C[C@H]3C[C@@H]4C3(C)C)C2)C1] | (1R,9R)-6-(7-hydroxy-5-quinolinyl)-10,10-dimethyl-4-(2-(2-propenoyl)-2,6-diazaspiro[3,4]octan-6-yl)-3-azatricyclo[7.1.1.0$^{2,7}$]undeca-2,4,6-triene-5-carbonitrile | Step 1: 2 eq pyridine. Step 2: SPhos Pd G3 and $K_3PO_4$ used. | Step 1: Intermediate 35 and Intermediate 73 |

TABLE 3-continued

Examples 2-2 to 2-111 were prepared following the procedure described in Method 2, Steps 1-4, above as follows:

| Ex. # | Chemical Structure | Name | Method changes | Reagent |
|---|---|---|---|---|
| 2-43 | 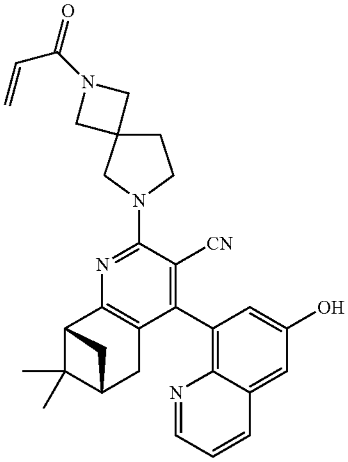 [SMILES: C=CC(=O)N1CC2(CCN(c3nc4c(c(-c5cc(O)cc6cccnc56)c3C#N)C[C@H]3C[C@@H]4C3(C)C)C2)C1] | (1R,9R)-6-(6-hydroxy-8-quinolinyl)-10,10-dimethyl-4-(2-(2-propenoyl)-2,6-diazaspiro[3,4]octan-6-yl)-3-azatricyclo[7.1.1.0$^{2,7}$]undeca-2,4,6-triene-5-carbonitrile | Step 1: 2 eq pyridine. Step 2: SPhos Pd G3 and $K_3PO_4$ used. | Step 1: Intermediate 35 and Intermediate 74 |
| 2-44 | 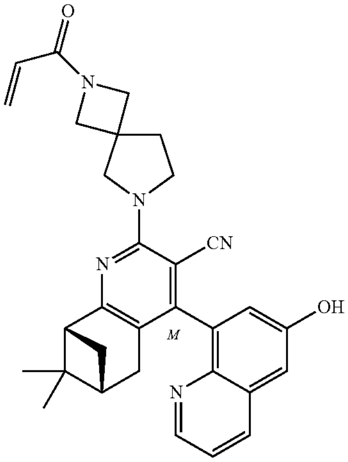 | (M)-(1R,9R)-6-(6-hydroxy-8-quinolinyl)-10,10-dimethyl-4-(2-(2-propenoyl)-2,6-diazaspiro[3.4]octan-6-yl)-3-azatricyclo[7.1.1.0$^{2,7}$]undeca-2,4,6-triene-5-carbonitrile (1$^{st}$ eluting isomer) | Step 1: 2 eq pyridine. Step 2: SPhos Pd G3 and $K_3PO_4$ used. See below for atropisomer separation conditions | Step 1: Intermediate 35 and Intermediate 74 |
| 2-45 | 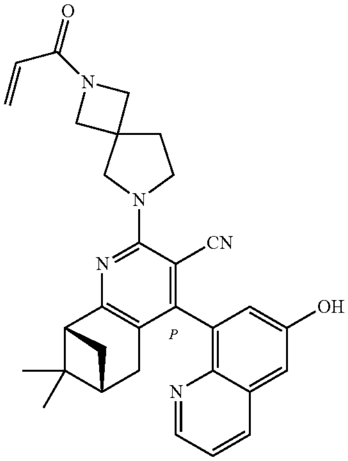 | (P)-(1R,9R)-6-(6-hydroxy-8-quinolinyl)-10,10-dimethyl-4-(2-(2-propenoyl)-2,6-diazaspiro[3.4]octan-6-yl)-3-azatricyclo[7.1.1.0$^{2,7}$]undeca-2,4,6-triene-5-carbonitrile (2$^{nd}$ eluting isomer) | Step 1: 2 eq pyridine. Step 2: SPhos Pd G3 and $K_3PO_4$ used. See below for atropisomer separation conditions | Step 1: Intermediate 35 and Intermediate 74 |

TABLE 3-continued

Examples 2-2 to 2-111 were prepared following the procedure described in Method 2, Steps 1-4, above as follows:

| Ex. # | Chemical Structure | Name | Method changes | Reagent |
| --- | --- | --- | --- | --- |
| 2-46 | 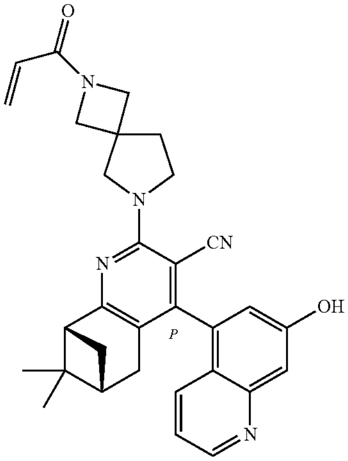 | (P)-(1R,9R)-6-(7-hydroxy-5-quinolinyl)-10,10-dimethyl-4-(2-(2-propenoyl)-2,6-diazaspiro[3.4]octan-6-yl)-3-azatricyclo[7.1.1.0$^{2,7}$]undeca-2,4,6-triene-5-carbonitrile (1$^{st}$ eluting isomer) | Step 1: 2 eq pyridine. Step 2: SPhos Pd G3 and $K_3PO_4$ used. See below for atropisomer separation conditions | Step 1: Intermediate 35 and Intermediate 73 |
| 2-47 | 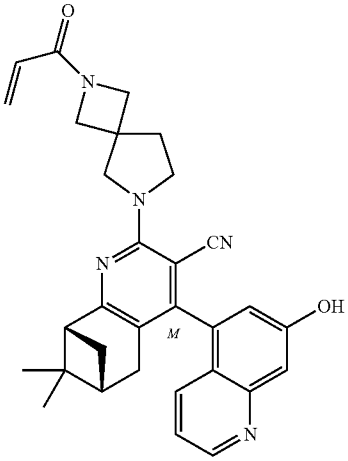 | (M)-(1R,9R)-6-(7-hydroxy-5-quinolinyl)-10,10-dimethyl-4-(2-(2-propenoyl)-2,6-diazaspiro[3.4]octan-6-yl)-3-azatricyclo[7.1.1.0$^{2,7}$]undeca-2,4,6-triene-5-carbonitrile (2$^{nd}$ eluting isomer) | Step 1: 2 eq pyridine. Step 2: SPhos Pd G3 and $K_3PO_4$ used. See below for atropisomer separation conditions | Step 1: Intermediate 35 and Intermediate 73 |
| 2-48 | 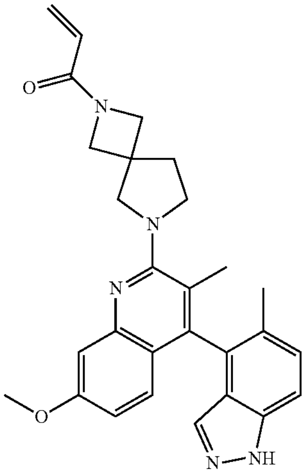 [SMILES: C=CC(=O)N1CC2(CCN(c3nc4cc(OC)ccc4c(-c4c(C)ccc5[nH]ncc45)c3C)C2)C1] | 1-(6-(7-methoxy-3-methyl-4-(5-methyl-1H-indazol-4-yl)-2-quinolinyl)-2,6-diazaspiro[3,4]octan-2-yl)-2-propen-1-one | Step 1: 3 eq. DIPEA. Step 2: $PdCl_2(dppf)$ replaced $Pd(PPh_3)_4$. Step 4: 5 eq. $K_2CO_3$ | Step 1: 2,4-dichloro-7-methoxy-3-methylquinoline (Aurum Pharmatech) |

TABLE 3-continued

Examples 2-2 to 2-111 were prepared following the procedure described in Method 2, Steps 1-4, above as follows:

| Ex. # | Chemical Structure | Name | Method changes | Reagent |
|---|---|---|---|---|
| 2-49 | 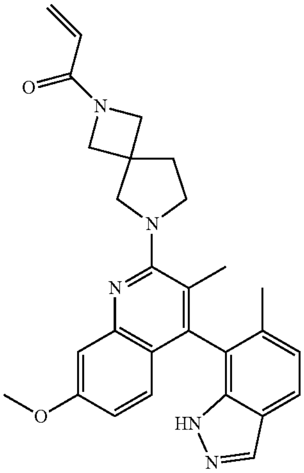 [SMILES: C=CC(=O)N1CC2(CCN(c3nc4cc(OC)ccc4c(-c4c(C)ccc5cn[nH]c45)c3C)C2)C1] | 1-(6-(7-methoxy-3-methyl-4-(6-methyl-1H-indazol-7-yl)-2-quinolinyl)-2,6-diazaspiro[3.4]octan-2-yl)-2-propen-1-one | Step 1: 3 eq. DIPEA. Step 2: RuPhos Pd G4, $K_3PO_4$ replaced $Pd(PPh_3)_4$ and $K_2CO_3$. | Step 1: 2,4-dichloro-7-methoxy-3-methylquinoline (Aurum Pharmatech) Step 2: 6-methyl-7-(4,4,5,5-tetramethyl-1,3,2-dioxaborolan-2-yl)-1H-indazole (PharmaBlock) |
| 2-50 | 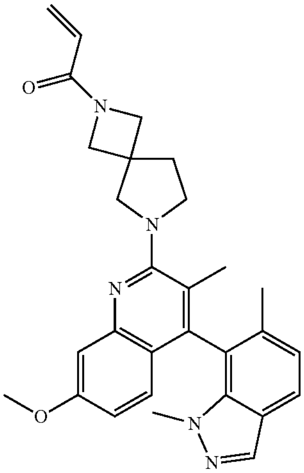 [SMILES: C=CC(=O)N1CC2(CCN(c3nc4cc(OC)ccc4c(-c4c(C)ccc5cnn(C)c45)c3C)C2)C1] | 1-(6-(4-(1,6-dimethyl-1H-indazol-7-yl)-7-methoxy-3-methyl-2-quinolinyl)-2,6-diazaspiro[3,4]octan-2-yl)-2-propen-1-one | Step 1: 3 eq. DIPEA. Step 2: RuPhos Pd G4, $K_3PO_4$ replaced $Pd(PPh_3)_4$ and $K_2CO_3$. Additional N-methylation performed using procedure from Example 2-19 after step 2. | Step 1: 2,4-dichloro-7-methoxy-3-methylquinoline (Aurum Pharmatech) Step 2: 6-methyl-7-(4,4,5,5-tetramethyl-1,3,2-dioxaborolan-2-yl)-1H-indazole (PharmaBlock) |
| 2-51 | 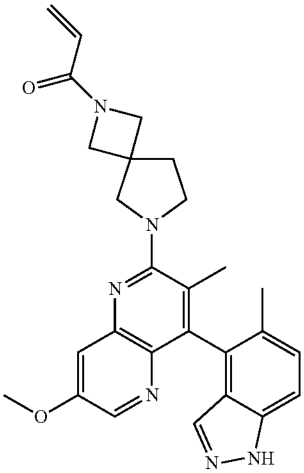 [SMILES: C=CC(=O)N1CC2(CCN(c3nc4cc(OC)cnc4c(-c4c(C)ccc5[nH]ncc45)c3C)C2)C1] | 1-(6-(7-methoxy-3-methyl-4-(5-methyl-1H-indazol-4-yl)-1,5-naphthyridin-2-yl)-2,6-diazaspiro[3.4]octan-2-yl)-2-propen-1-one | Step 1: 3 eq. DIPEA. Step 2: PEPPSI-iPr and $K_3PO_4$ replaced $Pd(PPh_3)_4$ and $K_2CO_3$. | Step 1: Intermediate 75 |

TABLE 3-continued

Examples 2-2 to 2-111 were prepared following the procedure described in Method 2, Steps 1-4, above as follows:

| Ex. # | Chemical Structure | Name | Method changes | Reagent |
|---|---|---|---|---|
| 2-52 | 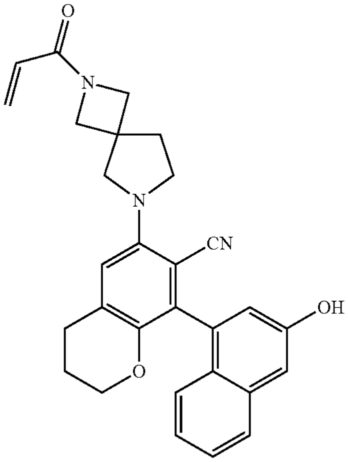 [SMILES: C=CC(=O)N1CC2(CCN(c3cc4c(c(-c5cc(O)cc6ccccc56)c3C#N)OCCC4)C2)C1] | 8-(3-hydroxy-1-naphthalenyl)-6-(2-(2-propenoyl)-2,6-diazaspiro[3.4] octan-6-yl)-3,4-dihydro-2H-chromene-7-carbonitrile | Alternative Step 1 see below. Step 2: SPhos Pd G3, $K_3PO_4$ replaced $Pd(PPh_3)_4$ and $K_2CO_3$. Step 4: DIPEA replaced TEA. | Step 1: Intermediate 79. Step 2: 4-(4,4,5,5-tetramethyl-1,3,2-dioxaborolan-2-yl)-2-naphthol (Combi-Blocks) |
| 2-53 | 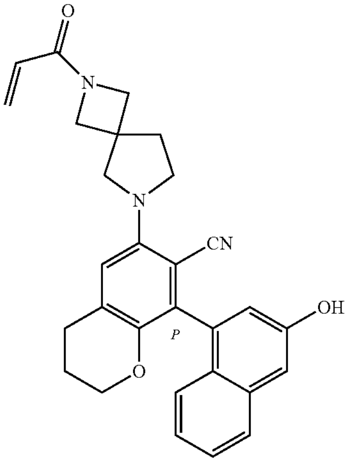 | (P)-8-(3-hydroxy-1-naphthalenyl)-6-(2-(2-propenoyl)-2,6-diazaspiro[3.4] octan-6-yl)-3,4-dihydro-2H-chromene-7-carbonitrile (1st eluting isomer) | Alternative Step 1 performed in analogous manner to Example 2-52. Step 2: SPhos Pd G3, $K_3PO_4$ used. Step 4: DIPEA replaced TEA, See below for atropisomer separation conditions | Step 1: Intermediate 79. Step 2: 4-(4,4,5,5-tetramethyl-1,3,2-dioxaborolan-2-yl)-2-naphthol (Combi-Blocks) |
| 2-54 | 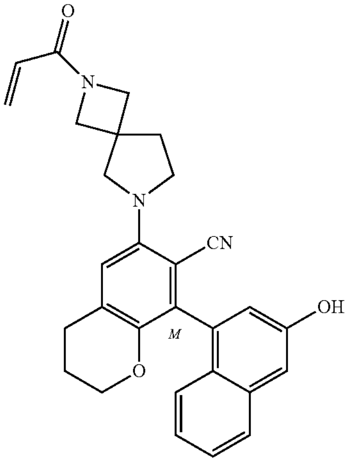 | (M)-8-(3-hydroxy-1-naphthalenyl)-6-(2-(2-propenoyl)-2,6-diazaspiro[3.4] octan-6-yl)-3,4-dihydro-2H-chromene-7-carbonitrile (2nd eluting isomer) | Alternative Step 1 performed in analogous manner to Example 2-52. Step 2: SPhos Pd G3, $K_3PO_4$ used. Step 4: DIPEA replaced TEA. See below for atropisomer separation conditions | Step 1: Intermediate 79. Step 2: 4-(4,4,5,5-tetramethyl-1,3,2-dioxaborolan-2-yl)-2-naphthol (Combi-Blocks) |

TABLE 3-continued

| Examples 2-2 to 2-111 were prepared following the procedure described in Method 2, Steps 1-4, above as follows: | | | | |
|---|---|---|---|---|
| Ex. # | Chemical Structure | Name | Method changes | Reagent |
| 2-55 | 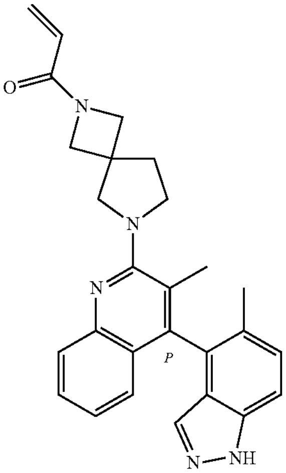 | (P)-1-(6-(3-methyl-4-(5-methyl-1H-indazol-4-yl)-2-quinolinyl)-2,6-diazaspiro[3.4]octan-2-yl)-2-propen-1-one ($1^{st}$ eluting isomer) | Step 1: 3 eq. DIPEA. Step 2: SPhos Pd G3, $K_3PO_4$ used. Step 4: 5 eq. $K_2CO_3$. See below for atropisomer separation conditions | Step 1: 2,4-dichloro-3-methylquinoline (Combi-Blocks) |
| 2-56 | 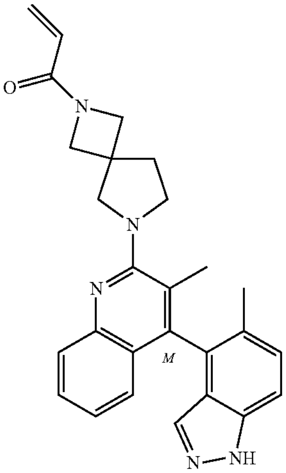 | (M)-1-(6-(3-methyl-4-(5-methyl-1H-indazol-4-yl)-2-quinolinyl)-2,6-diazaspiro[3.4]octan-2-yl)-2-propen-1-one ($2^{nd}$ eluting isomer) | Step 1: 3 eq. DIPEA. Step 2: SPhos Pd G3, $K_3PO_4$ used. Step 4: 5 eq. $K_2CO_3$. See below for atropisomer separation conditions | Step 1: 2,4-dichloro-3-methylquinoline (Combi-Blocks) |
| 2-57 | 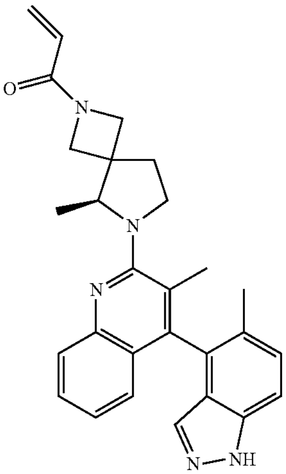 [SMILES: C=CC(=O)N1CC2(CCN(c3nc4ccccc4c(-c4c(C)ccc5[nH]ncc45)c3C)[C@H]2C)C1] | 1-((5S)-5-methyl-6-(3-methyl-4-(5-methyl-1H-indazol-4-yl)-2-quinolinyl)-2,6-diazaspiro[3.4]octan-2-yl)-2-propen-1-one | Step 1: 3 eq. DIPEA. Isomer separation after Step 1, see below for conditions. Peak 1 used. Step 2: $PdCl_2(dppf)$ used. Step 4: 5 eq. $K_2CO_3$ | Step 1: 2,4-dichloro-3-methylquinoline (Combi-Blocks) and tert-butyl 5-methyl-2,6-diazaspiro[3.4]octane-2-carboxylate (Enamine) |

TABLE 3-continued

Examples 2-2 to 2-111 were prepared following the procedure described in Method 2, Steps 1-4, above as follows:

| Ex. # | Chemical Structure | Name | Method changes | Reagent |
|---|---|---|---|---|
| 2-58 | 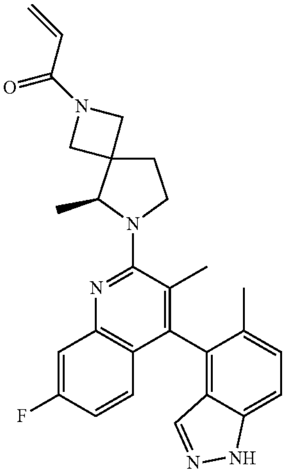 [SMILES: C=CC(=O)N1CC2(CCN(c3nc4cc(F)ccc4c(-c4c(C)ccc5[nH]ncc45)c3C)[C@H]2C)C1] | 1-((5S)-6-(7-fluoro-3-methyl-4-(5-methyl-1H-indazol-4-yl)-2-quinolinyl)-5-methyl-2,6-diazaspiro[3.4]octan-2-yl)-2-propen-1-one | Step 1: 3 eq. DIPEA. Isomer separation after Step 1, see below for conditions. Peak 1 used. Step 2: $PdCl_2$(dppf) used. Step 4: 5 eq. $K_2CO_3$ | Step 1: 2,4-dichloro-7-fluoro-3-methylquinoline (see *J. Med. Chem.* 2012, 55, 17, 7667-7685) and tert-butyl 5-methyl-2,6-diazaspiro[3.4]octane-2-carboxylate (Enamine) |
| 2-59 | 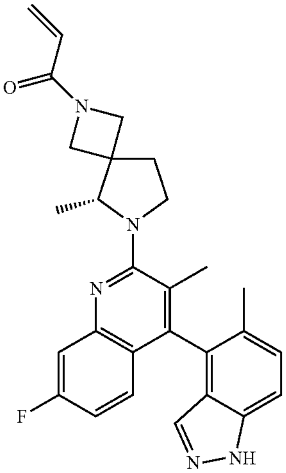 [SMILES: C=CC(=O)N1CC2(CCN(c3nc4cc(F)ccc4c(-c4c(C)ccc5[nH]ncc45)c3C)[C@@H]2C)C1] | 1-((5R)-6-(7-fluoro-3-methyl-4-(5-methyl-1H-indazol-4-yl)-2-quinolinyl)-5-methyl-2,6-diazaspiro[3.4]octan-2-yl)-2-propen-1-one | Step 1: 3 eq. DIPEA. Isomer separation after Step 1, see below for conditions. Peak 2 used. Step 2: $PdCl_2$(dppf) used. Step 4: 5 eq. $K_2CO_3$ | Step 1: 2,4-dichloro-7-fluoro-3-methylquinoline (see *J. Med. Chem.* 2012, 55, 17,7667-7685) and tert-butyl 5-methyl-2,6-diazaspiro[3.4]octane-2-carboxylate (Enamine) |
| 2-60 | 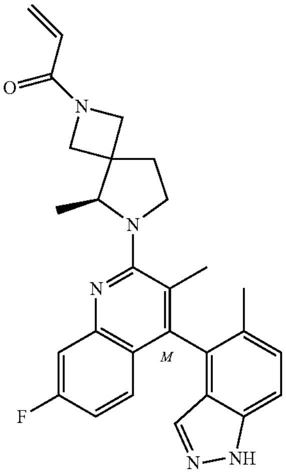 | (M)-1-((5S)-6-(7-fluoro-3-methyl-4-(5-methyl-1H-indazol-4-yl)-2-quinolinyl)-5-methyl-2,6-diazaspiro[3,4]octan-2-yl)-2-propen-1-one (2$^{nd}$ eluting isomer) | Step 1: 3 eq. DIPEA. Isomer separation after Step 1, see below for conditions. Peak 1 used Step 2: $PdCl_2$(dppf) replaced $Pd(PPb_3)_4$. Step 4: 5 eq. $K_2CO_3$. See below for atropisomer separation conditions | Step 1: 2,4-dichloro-7-fluoro-3-methylquinoline (see *J. Med. Chem.* 2012, 55, 17, 7667-7685) and tert-butyl 5-methyl-2,6-diazaspiro[3.4]octane-2-carboxylate (Enamine) |

TABLE 3-continued

Examples 2-2 to 2-111 were prepared following the procedure described in Method 2, Steps 1-4, above as follows:

| Ex. # | Chemical Structure | Name | Method changes | Reagent |
|---|---|---|---|---|
| 2-61 | 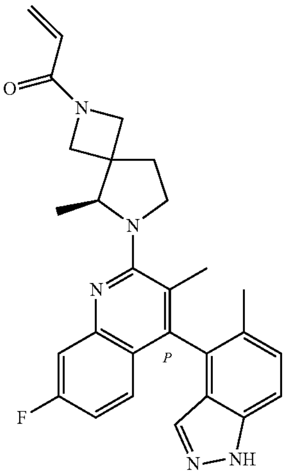 | (P)-1-((5S)-6-(7-fluoro-3-methyl-4-(5-methyl-1H-indazol-4-yl)-2-quinolinyl)-5-methyl-2,6-diazaspiro[3.4]octan-2-yl)-2-propen-1-one (1st eluting isomer) | Step 1: 3 eq. DIPEA. Isomer separation after Step 1 see below for conditions. Peak 1 used Step 2: $PdCl_2$(dppf) used. Step 4: 5 eq. $K_2CO_3$. See below for atropisomer separation conditions | Step 1: 2,4-dichloro-7-fluoro-3-methylquinoline (see *J. Med. Chem.* 2012, 55, 17, 7667-7685) and tert-butyl 5-methyl-2,6-diazaspiro[3.4]octane-2-carboxylate (Enamine) |
| 2-62 | 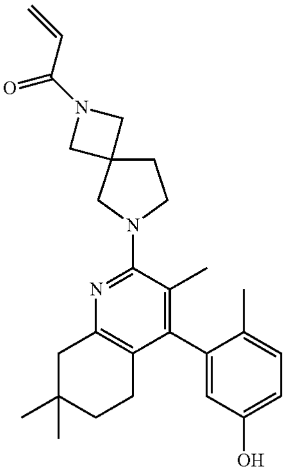 [SMILES: C=CC(=O)N1CC2(CCN(c3nc4c(c(-c5cc(O)ccc5C)c3C)CCC(C)(C)C4)C2)C1] | 1-(6-(4-(5-hydroxy-2-methylphenyl)-3,7,7-trimethyl-5,6,7,8-tetrahydro-2-quinolinyl)-2,6-diazaspiro[3,4]octan-2-yl)-2-propen-1-one | Alternative Step 1 performed in analogous manner to Example 2-11. Step 2: SPhos Pd G3 and $K_3PO_4$ used. | Step 1: Intermediate 36. Step 2: 5-hydroxy-2-methylphenyl-boronic acid (Combi-Blocks) |
| 2-63 | 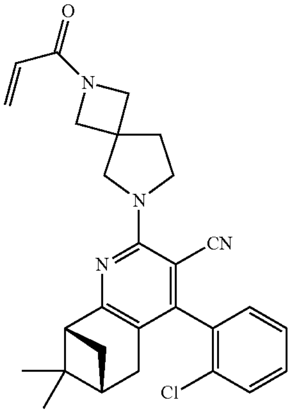 [SMILES: C=CC(=O)N1CC2(CCN(c3nc4c(c(-c5ccccc5Cl)c3C#N)C[C@H]3C[C@@H]4C3(C)C)C2)C1] | (1R,9R)-6-(2-chlorophenyl)-10,10-dimethyl-4-(2-(2-propenoyl)-2,6-diazaspiro[3.4]octan-6-yl)-3-azatricyclo[7.1.1.0$^{2,7}$]undeca-2,4,6-triene-5-carbonitrile | See below for Alternative Step 1. Step 2: SPhos Pd G3 and $K_3PO_4$. | Step 1: Intermediate 82, XPhos Pd G2, $Cs_2CO_3$, toluene. Step 2: 2-chlorophenyl-boronic acid (Matrix Scientific) |

TABLE 3-continued

| Ex. # | Chemical Structure | Name | Method changes | Reagent |
|---|---|---|---|---|
| 2-64 | 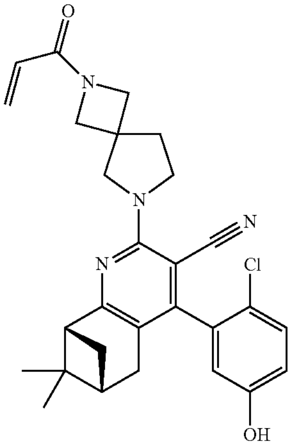 | (1R,9R)-6-(2-chloro-5-hydroxyphenyl)-10,10-dimethyl-4-(2-(2-propenoyl)-2,6-diazaspiro[3.4]octan-6-yl)-3-azatricyclo[7.1.1.0$^{2,7}$]undeca-2,4,6-triene-5-carbonitrile | Alternative Step 1 performed in analogous manner to Example 2-52. Step 2: SPhos Pd G3 and $K_3PO_4$. | Step 1: Intermediate 82, XPhos Pd G2, $Cs_2CO_3$, toluene. Step 2: boronic acid, (2-chloro-5-hydroxyphenyl)- (Synnovator) |
| 2-65 | 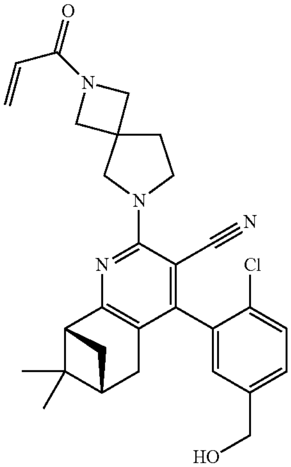 [SMILES: C=CC(=O)N1CC2(CCN(c3nc4c(c(-c5cc(CO)ccc5Cl)c3C#N)C[C@H]3C[C@@H]4C3(C)C)C2)C1] | (1R,9R)-6-(2-chloro-5-(hydroxymethyl)phenyl)-10,10-dimethyl-4-(2-(2-propenoyl)-2,6-diazaspiro[3.4]octan-6-yl)-3-azatricyclo[7.1.1.0$^{2,7}$]undeca-2,4,6-triene-5-carbonitrile | Alternative Step 1 performed in analogous manner to Example 2-52. Step 2: SPhos Pd G3 and $K_3PO_4$. | Step 1: Intermediate 82, XPhos Pd G2, $Cs_2CO_3$, toluene. Step 2: (2-chloro-5-(hydroxymethyl)phenyl)boronic acid (Combi-Blocks) |
| 2-66 | 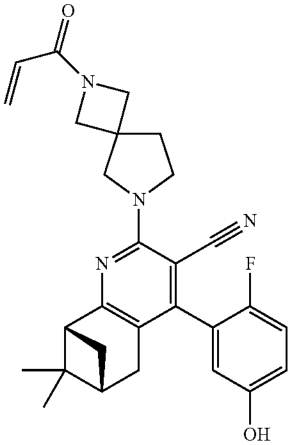 [SMILES: C=CC(=O)N1CC2(CCN(c3nc4c(c(-c5cc(O)ccc5F)c3C#N)C[C@H]3C[C@@H]4C3(C)C)C2)C1] | (1R,9R)-6-(2-fluoro-5-hydroxyphenyl)-10,10-dimethyl-4-(2-(2-propenoyl)-2,6-diazaspiro[3.4]octan-6-yl)-3-azatricyclo[7.1.1.0$^{2,7}$]undeca-2,4,6-triene-5-carbonitrile | Step 1: DIPEA and DMF replaced DMA. Step 2: SPhos Pd G3 and $K_3PO_4$. | Step 1: Intermediate 21. Step 2: 2-fluoro-5-hydroxyphenyl-boronic acid (Combi-Blocks) |

Examples 2-2 to 2-111 were prepared following the procedure described in Method 2, Steps 1-4, above as follows:

TABLE 3-continued

| Ex. # | Chemical Structure | Name | Method changes | Reagent |
|---|---|---|---|---|
| Examples 2-2 to 2-111 were prepared following the procedure described in Method 2, Steps 1-4, above as follows: | | | | |
| 2-67 | 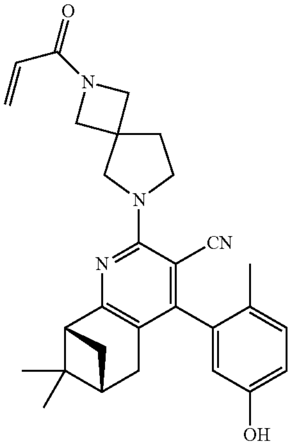 [SMILES: C=CC(=O)N1CC2(CCN(c3nc4c(c(-c5cc(O)ccc5C)c3C#N)C[C@H]3C[C@@H]4C3(C)C)C2)C1] | (1R,9R)-6-(5-hydroxy-2-methylphenyl)-10,10-dimethyl-4-(2-(2-propenoyl)-2,6-diazaspiro[3.4]octan-6-yl)-3-azatricyclo[7.1.1.0$^{2,7}$]undeca-2,4,6-triene-5-carbonitrile | Step 1: DIPEA and DMF replaced DMA. Step 2: SPhos Pd G3 and $K_3PO_4$. | Step 1: Intermediate 21. Step 2: 5-hydroxy-2-methylphenyl-boronic acid (Combi-Blocks) |
| 2-68 | 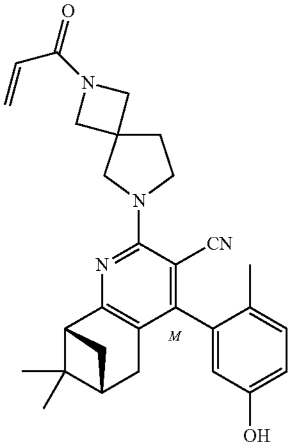 | (M)-(1R,9R)-6-(5-hydroxy-2-methylphenyl)-10,10-dimethyl-4-(2-(2-propenoyl)-2,6-diazaspiro[3,4]octan-6-yl)-3-azatricyclo[7.1.1.0$^{2,7}$]undeca-2,4,6-triene-5-carbonitrile (1$^{st}$ eluting isomer) | Step 1: DIPEA and DMF replaced DMA. Step 2: SPhos Pd G3 and $K_3PO_4$. See below for atropisomer separation conditions | Step 1: Intermediate 21. Step 2: 5-hydroxy-2-methylphenyl-boronic acid (Combi-Blocks) |
| 2-69 | 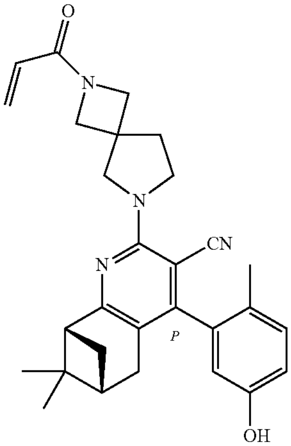 | (P)-(1R,9R)-6-(5-hydroxy-2-methylphenyl)-10,10-dimethyl-4-(2-(2-propenoyl)-2,6-diazaspiro[3.4]octan-6-yl)-3-azatricyclo[7.1.1.0$^{2,7}$]undeca-2,4,6-triene-5-carbonitrile (2$^{nd}$ eluting isomer) | Step 1: DIPEA and DMF replaced DMA. Step 2: SPhos Pd G3 and $K_3PO_4$. See below for atropisomer separation conditions | Step 1: Intermediate 21. Step 2: 5-hydroxy-2-methylphenyl-boronic acid (Combi-Blocks) |

TABLE 3-continued

| Examples 2-2 to 2-111 were prepared following the procedure described in Method 2, Steps 1-4, above as follows: | | | | |
|---|---|---|---|---|
| Ex. # | Chemical Structure | Name | Method changes | Reagent |
| 2-70 | 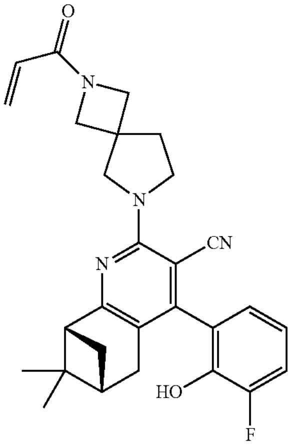 [SMILES: C=CC(=O)N1CC2(CCN(c3nc4c(c(-c5cccc(F)c5O)c3C#N)C[C@H]3C[C@@H]4C3(C)C)C2)C1] | (1R,9R)-6-(3-fluoro-2-hydroxyphenyl)-10,10-dimethyl-4-(2-(2-propenoyl)-2,6-diazaspiro[3.4]octan-6-yl)-3-azatricyclo[7.1.1.0$^{2,7}$]undeca-2,4,6-triene-5-carbonitrile | Step 1; DIPEA and DMF replaced DMA. Step 2: SPhos Pd G3 and $K_3PO_4$. | Step 1: Intermediate 21. Step 2: 3-fluoro-2-hydroxybenzene boronic acid (Combi-Blocks) |
| 2-71 | 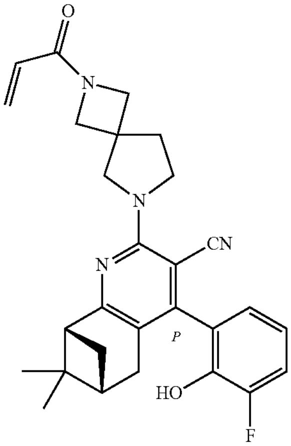 | (P)-(1R,9R)-6-(3-fluoro-2-hydroxyphenyl)-10,10-dimethyl-4-(2-(2-propenoyl)-2,6-diazaspiro[3,4]octan-6-yl)-3-azatricyclo[7.1.1.0$^{2,7}$]undeca-2,4,6-triene-5-carbonitrile (1$^{st}$ eluting isomer) | Step 1: DIPEA and DMF replaced DMA. Step 2: SPhos Pd G3 and $K_3PO_4$. See below for atropisomer separation conditions | Step 1: Intermediate 21. Step 2: 3-fluoro-2-hydroxybenzene boronic acid (Combi-Blocks) |
| 2-72 | 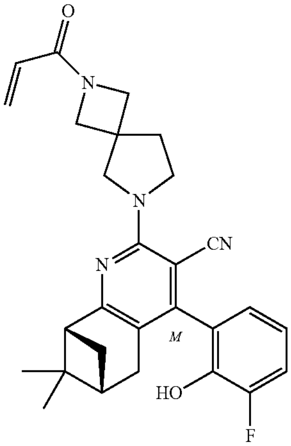 | (M)-(1R,9R)-6-(3-fluoro-2-hydroxyphenyl)-10,10-dimethyl-4-(2-(2-propenoyl)-2,6-diazaspiro[3.4]octan-6-yl)-3-azatricyclo[7.1.1.0$^{2,7}$]undeca-2,4,6-triene-5-carbonitrile (2$^{nd}$ eluting isomer) | Step 1: DIPEA and DMF replaced DMA. Step 2: SPhos Pd G3 and $K_3PO_4$. See below for atropisomer separation conditions | Step 1: Intermediate 21. Step 2: 3-fluoro-2-hydroxybenzene boronic acid (Combi-Blocks) |

TABLE 3-continued

| Examples 2-2 to 2-111 were prepared following the procedure described in Method 2, Steps 1-4, above as follows: | | | | |
|---|---|---|---|---|
| Ex. # | Chemical Structure | Name | Method changes | Reagent |
| 2-73 | 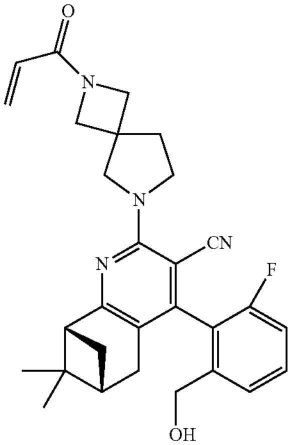 [SMILES: C=CC(=O)N1CC2(CCN(c3nc4c(c(-c5c(F)cccc5CO)c3C#N)C[C@H]3C[C@@H]4C3(C)C)C2)C1] | (1R,9R)-6-(2-fluoro-6-(hydroxymethyl)phenyl)-10,10-dimethyl-4-(2-(2-propenoyl)-2,6-diazaspiro[3.4]octan-6-yl)-3-azatricyclo[7.1.1.0$^{2,7}$]undeca-2,4,6-triene-5-carbonitrile | Step 1: DIPEA and DMF replaced DMA. Step 2: RuPhos, RuPhos Pd G2 and $K_3PO_4$. | Step 1: Intermediate 21. Step 2: (2-fluoro-6-(hydroxymethyl)phenyl)boronic acid (AOB Chem) |
| 2-74 | 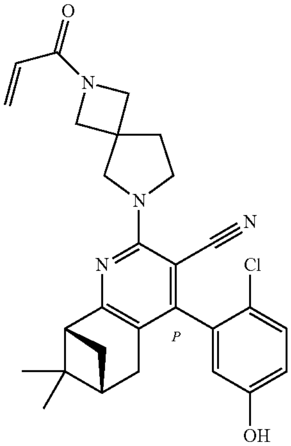 | (P)-(1R,9R)-6-(2-chloro-5-hydroxyphenyl)-10,10-dimethyl-4-(2-(2-propenoyl)-2,6-diazaspiro[3,4]octan-6-yl)-3-azatricyclo[7.1.1.0$^{2,7}$]undeca-2,4,6-triene-5-carbonitrile (1$^{st}$ eluting isomer) | Alternative Step 1 performed in analogous manner to Example 2-52. Step 2: SPhos Pd G3 and $K_3PO_4$. See below for atropisomer separation conditions | Step 1: Intermediate 82, XPhos Pd G2, $Cs_2CO_3$, toluene. Step 2: boronic acid, (2-chloro-5-hydroxyphenyl)-(Synnovator) |
| 2-75 | 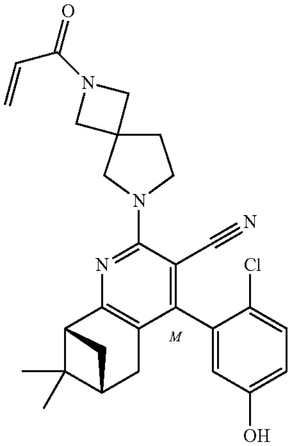 | (M)-(1R,9R)-6-(2-chloro-5-hydroxyphenyl)-10,10-dimethyl-4-(2-(2-propenoyl)-2,6-diazaspiro[3.4]octan-6-yl)-3-azatricyclo[7.1.1.0$^{2,7}$]undeca-2,4,6-triene-5-carbonitrile (2$^{nd}$ eluting isomer) | Alternative Step 1 performed in analogous manner to Example 2-52. Step 2: SPhos Pd G3 and $K_3PO_4$. See below for atropisomer separation conditions | Step 1: Intermediate 82, XPhos Pd G2, $Cs_2CO_3$, toluene. Step 2: boronic acid, (2-chloro-5-hydroxyphenyl)-(Synnovator) |

TABLE 3-continued

Examples 2-2 to 2-111 were prepared following the procedure described in Method 2, Steps 1-4, above as follows:

| Ex. # | Chemical Structure | Name | Method changes | Reagent |
|---|---|---|---|---|
| 2-76 | 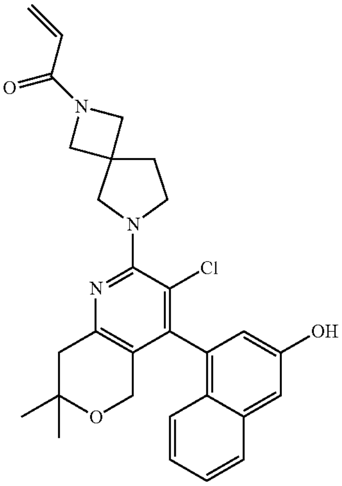 [SMILES: C=CC(=O)N1CC2(CCN(c3nc4c(c(-c5cc(O)cc6ccccc56)c3Cl)COC(C)(C)C4)C2)C1] | 1-(6-(3-chloro-4-(3-hydroxy-1-naphthalenyl)-7,7-dimethyl-7,8-dihydro-5H-pyrano[4,3-b]pyridin-2-yl)-2,6-diazaspiro[3.4]octan-2-yl)-2-propen-1-one | Step 1: DIPEA and DMF replaced DMA. Step 2: SPhos Pd G3 and $K_3PO_4$. | Step 1: Intermediate 24. Step 2: 3-hydroxynaphthalene-1-boronic acid (eNovation Chemicals LLC) |
| 2-77 | 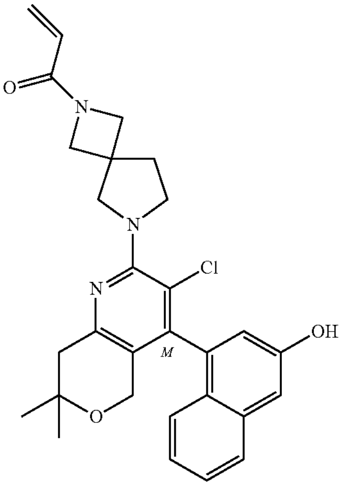 | (M)-1-(6-(3-chloro-4-(3-hydroxy-1-naphthalenyl)-7,7-dimethyl-7,8-dihydro-5H-pyrano[4,3-b]pyridin-2-yl)-2,6-diazaspiro[3.4]octan-2-yl)-2-propen-1-one (1$^{st}$ eluting isomer) | Step 1: DIPEA and DMF replaced DMA. Step 2: SPhos Pd G3 and $K_3PO_4$. See below for atropisomer separation conditions | Step 1: Intermediate 24. Step 2: 3-hydroxynaphthalene-1-boronic acid (eNovation Chemicals LLC) |
| 2-78 | 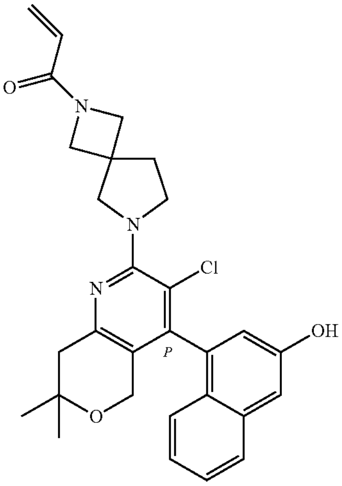 | (P)-1-(6-(3-chloro-4-(3-hydroxy-1-naphthalenyl)-7,7-dimethyl-7,8-dihydro-5H-pyrano[4,3-b]pyridin-2-yl)-2,6-diazaspiro[3,4]octan-2-yl)-2-propen-1-one (2$^{nd}$ eluting isomer) | Step 1: DIPEA and DMF replaced DMA. Step 2: SPhos Pd G3 and $K_3PO_4$. See below for atropisomer separation conditions | Step 1: Intermediate 24. Step 2: 3-hydroxynaphthalene-1-boronic acid (eNovation Chemicals LLC) |

TABLE 3-continued

Examples 2-2 to 2-111 were prepared following the procedure described in Method 2, Steps 1-4, above as follows:

| Ex. # | Chemical Structure | Name | Method changes | Reagent |
|---|---|---|---|---|
| 2-79 | 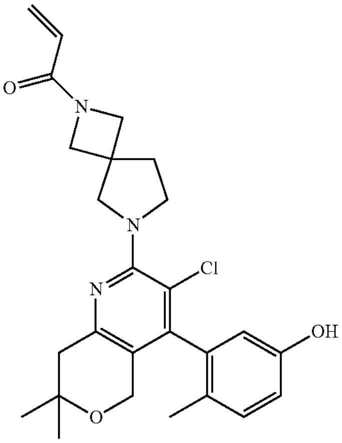 [SMILES: C=CC(=O)N1CC2(CCN(c3nc4c(c(-c5cc(O)ccc5C)c3Cl)COC(C)(C)C4)C2)C1] | 1-(6-(3-chloro-4-(5-hydroxy-2-methylphenyl)-7,7-dimethyl-7,8-dihydro-5H-pyrano[4,3-b]pyridin-2-yl)-2,6-diazaspiro[3.4]octan-2-yl)-2-propen-1-one | Step 1: DIPEA and DMF replaced DMA. Step 2: SPhos Pd G3 and $K_3PO_4$ | Step 1: Intermediate 24. Step 2: 5-hydroxy-2-methylphenyl-boronic acid (Combi-Blocks) |
| 2-80 | 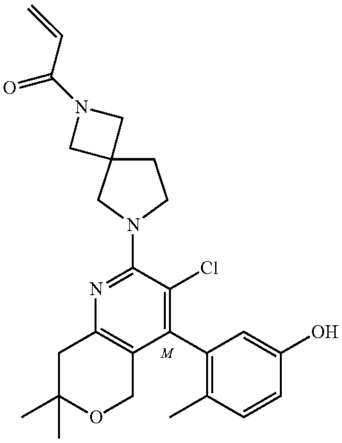 | (M)-1-(6-(3-chloro-4-(5-hydroxy-2-methylphenyl)-7,7-dimethyl-7,8-dihydro-5H-pyrano[4,3-b]pyridin-2-yl)-2,6-diazaspiro[3.4]octan-2-yl)-2-propen-1-one (1$^{st}$ eluting isomer) | Step 1: DIPEA and DMF replaced DMA. Step 2: SPhos Pd G3 and $K_3PO_4$. See below for atropisomer separation conditions | Step 1: Intermediate 24. Step 2: 5-hydroxy-2-methylphenyl-boronic acid (Combi-Blocks) |
| 2-81 | 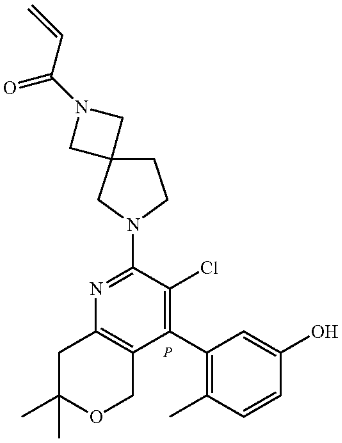 | (P)-1-(6-(3-chloro-4-(5-hydroxy-2-methylphenyl)-7,7-dimethyl-7,8-dihydro-5H-pyrano[4,3-b]pyridin-2-yl)-2,6-diazaspiro[3,4]octan-2-yl)-2-propen-1-one (2$^{nd}$ eluting isomer) | Step 1: DIPEA and DMF replaced DMA. Step 2: SPhos Pd G3 and $K_3PO_4$. See below for atropisomer separation conditions | Step 1: Intermediate 24. Step 2: 5-hydroxy-2-methylphenyl-boronic acid (Combi-Blocks) |

TABLE 3-continued

| Ex. # | Chemical Structure | Name | Method changes | Reagent |
|---|---|---|---|---|
| Examples 2-2 to 2-111 were prepared following the procedure described in Method 2, Steps 1-4, above as follows: | | | | |
| 2-82 | 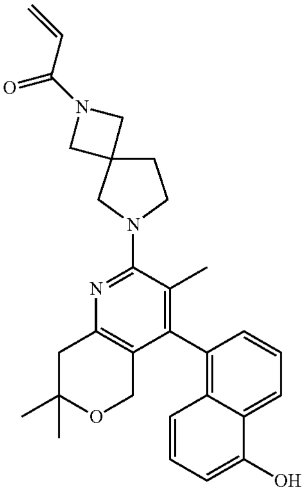 [SMILES: C=CC(=O)N1CC2(CCN(c3nc4c(c(-c5cccc6c(O)cccc56)c3C)COC(C)(C)C4)C2)C1] | 1-(6-(4-(5-hydroxy-1-naphthalenyl)-3,7,7-trimethyl-7,8-dihydro-5H-pyrano[4,3-b]pyridin-2-yl)-2,6-diazaspiro[3,4]octan-2-yl)-2-propen-1-one | Step 1: DIPEA and DMF replaced DMA. Step 2: SPhos Pd G3 and $K_3PO_4$ | Step 1: Intermediate 22. Step 2: Intermediate 83 |
| 2-83 | 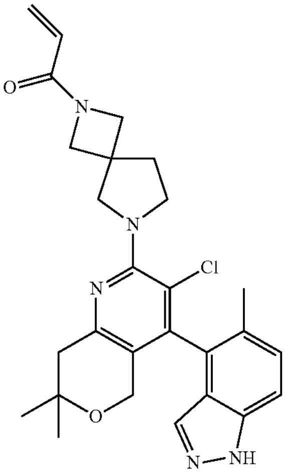 [SMILES: C=CC(=O)N1CC2(CCN(c3nc4c(c(-c5c(C)ccc6[nH]ncc56)c3Cl)COC(C)(C)C4)C2)C1] | 1-(6-(3-chloro-7,7-dimethyl-4-(5-methyl-1H-indazol-4-yl)-7,8-dihydro-5H-pyrano[4,3-b]pyridin-2-yl)-2,6-diazaspiro[3.4]octan-2-yl)-2-propen-1-one | Step 1: DIPEA and DMF replaced DMA. Step 2: SPhos Pd G3 and $K_3PO_4$. | Step 1: Intermediate 24 |
| 2-84 | 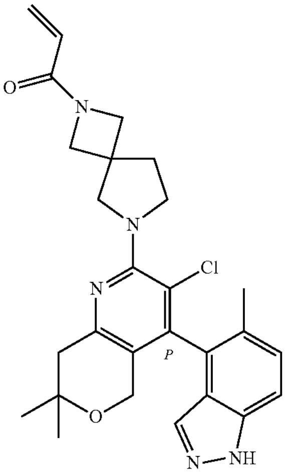 | (P)-1-(6-(3-chloro-7,7-dimethyl-4-(5-methyl-1H-indazol-4-yl)-7,8-dihydro-5H-pyrano[4,3-b]pyridin-2-yl)-2,6-diazaspiro[3.4]octan-2-yl)-2-propen-1-one (2nd eluting isomer) | Step 1: DIPEA and DMF replaced DMA. Step 2: SPhos Pd G3 and $K_3PO_4$. See below for atropisomer separation conditions | Step 1: Intermediate 24 |

TABLE 3-continued

| Examples 2-2 to 2-111 were prepared following the procedure described in Method 2, Steps 1-4, above as follows: | | | | |
|---|---|---|---|---|
| Ex. # | Chemical Structure | Name | Method changes | Reagent |
| 2-85 | 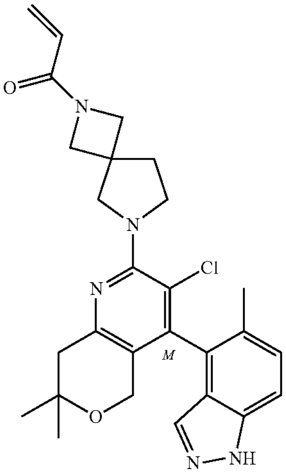 | (M)-1-(6-(3-chloro-7,7-dimethyl-4-(5-methyl-1H-indazol-4-yl)-7,8-dihydro-5H-pyrano[4,3-b]pyridin-2-yl)-2,6-diazaspiro[3.4]octan-2-yl)-2-propen-1-one (1st eluting isomer) | Step 1: DIPEA and DMF replaced DMA. Step 2: SPhos Pd G3 and $K_3PO_4$, See below for atropisomer separation conditions | Step 1: Intermediate 24 |
| 2-86 | 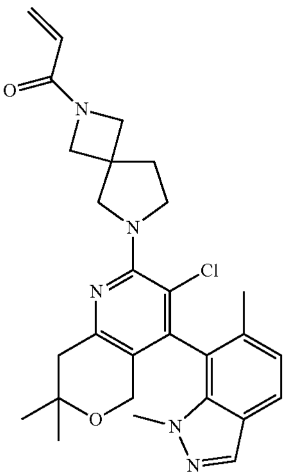 [SMILES: C=CC(=O)N1CC2(CCN(c3nc4c(c(-c5c(C)ccc6cnn(C)c56)c3Cl)COC(C)(C)C4)C2)C1] | 1-(6-(3-chloro-4-(1,6-dimethyl-1H-indazol-7-yl)-7,7-dimethyl-7,8-dihydro-5H-pyrano[4,3-b]pyridin-2-yl)-2,6-diazaspiro[3.4]octan-2-yl)-2-propen-1-one | Step 1: DIPEA and DMF replaced DMA. Step 2: SPhos Pd G3 and $K_3PO_4$. Additional N-methylation performed using procedure from Example 2-19 after step 2 | Step 1: Intermediate 24. Step 2: 6-methyl-7-(4,4,5,5-tetramethyl-1,3,2-dioxaborolan-2-yl)-1H-indazole (PharmaBlock) |
| 2-87 | 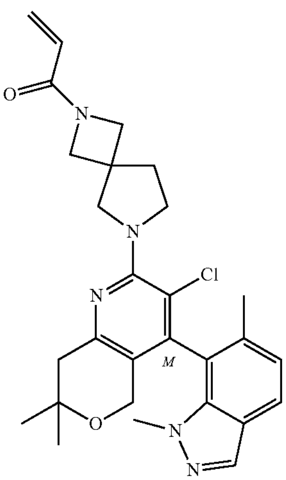 | (M)-1-(6-(3-chloro-4-(1,6-dimethyl-1H-indazol-7-yl)-7,7-dimethyl-7,8-dihydro-5H-pyrano[4,3-b]pyridin-2-yl)-2,6-diazaspiro[3.4]octan-2-yl)-2-propen-1-one (1st eluting isomer) | Step 1: DIPEA and DMF replaced DMA. Step 2: SPhos Pd G3 and $K_3PO_4$ Additional N-methylation performed using procedure from Example 2-19 after step 2. See below for atropisomer separation conditions | Step 1: Intermediate 24. Step 2: 6-methyl-7-(4,4,5,5-tetramethyl-1,3,2-dioxaborolan-2-yl)-1H-indazole (PharmaBlock) |

TABLE 3-continued

Examples 2-2 to 2-111 were prepared following the procedure described in Method 2, Steps 1-4, above as follows:

| Ex. # | Chemical Structure | Name | Method changes | Reagent |
|---|---|---|---|---|
| 2-88 | 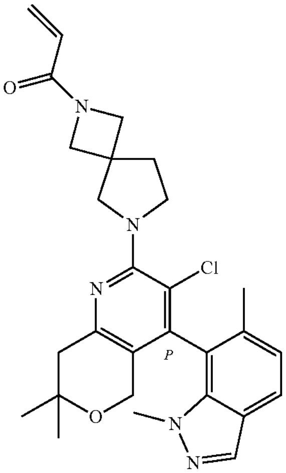 | (P)-1-(6-(3-chloro-4-(1,6-dimethyl-1H-indazol-7-yl)-7,7-dimethyl-7,8-dihydro-5H-pyrano[4,3-b]pyridin-2-yl)-2,6-diazaspiro[3.4]octan-2-yl)-2-propen-1-one (2nd eluting isomer) | Step 1: DIPEA and DMF replaced DMA. Step 2: SPhos Pd G3 and $K_3PO_4$ Additional N-methylation performed using procedure from Example 2-19 after step 2. See below for atropisomer separation conditions | Step 1: Intermediate 24. Step 2: 6-methyl-7-(4,4,5,5-tetramethyl-1,3,2-dioxaborolan-2-yl)-1H-indazole (PharmaBlock) |
| 2-89 | 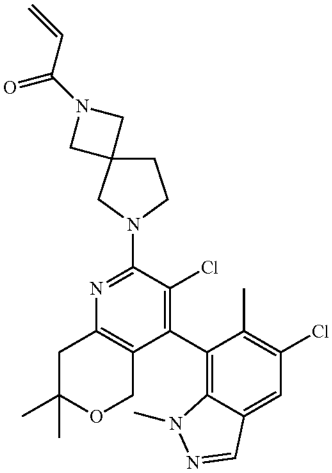 [SMILES: C=CC(=O)N1CC2(CCN(c3nc4c(c(-c5c(C)c(Cl)cc6cnn(C)c56)c3Cl)COC(C)(C)C4)C2)C1] | 1-(6-(3-chloro-4-(1,6-dimethyl-1H-indazol-7-yl)-7,7-dimethyl-7,8-dihydro-5H-pyrano[4,3-b]pyridin-2-yl)-2,6-diazaspiro[3.4]octan-2-yl)-2-propen-1-one | Step 1: DIPEA and DMF replaced DMA. Step 2: SPhos Pd G3 and $K_3PO_4$ Additional N-methylation performed using procedure from Example 2-19 after step 2 | Step 1: Intermediate 24. Step 2: Intermediate 37 |
| 2-90 | 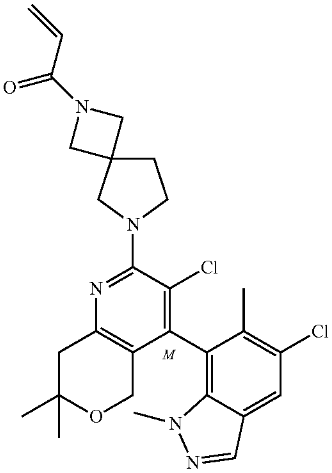 | (M)-1-(6-(3-chloro-4-(5-chloro-1,6-dimethyl-1H-indazol-7-yl)-7,7-dimethyl-7,8-dihydro-5H-pyrano[4,3-b]pyridin-2-yl)-2,6-diazaspiro[3.4]octan-2-yl)-2-propen-1-one (1st eluting isomer) | Step 1: DIPEA and DMF replaced DMA. Step 2: SPhos Pd G3 and $K_3PO_4$. Additional N-methylation performed using procedure from Example 2-19 after step 2. See below for atropisomer separation conditions | Step 1: Intermediate 24. Step 2: Intermediate 37 |

TABLE 3-continued

| Examples 2-2 to 2-111 were prepared following the procedure described in Method 2, Steps 1-4, above as follows: | | | | |
|---|---|---|---|---|
| Ex. # | Chemical Structure | Name | Method changes | Reagent |
| 2-91 | 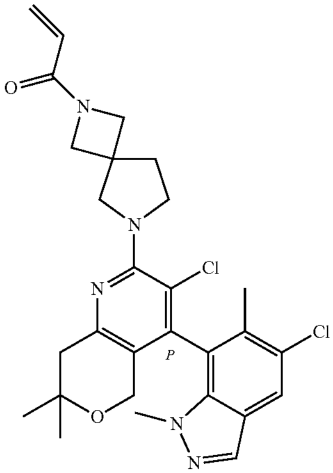 | (P)-1-(6-(3-chloro-4-(5-chloro-1,6-dimethyl-1H-indazol-7-yl)-7,7-dimethyl-7,8-dihydro-5H-pyrano[4,3-b]pyridin-2-yl)-2,6-diazaspiro[3.4]octan-2-yl)-2-propen-1-one (2nd eluting isomer) | Step 1: DIPEA and DMF replaced DMA. Step 2: SPhos Pd G3 and $K_3PO_4$. Additional N-methylation performed using procedure from Example 2-19 after step 2. See below for atropisomer separation conditions | Step 1: Intermediate 24. Step 2: Intermediate 37 |
| 2-92 | 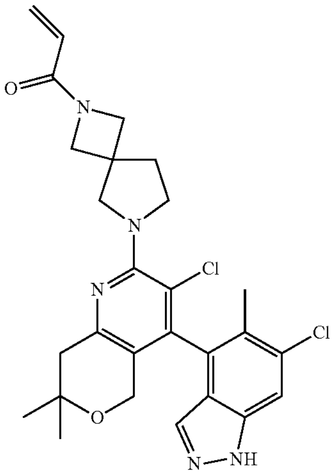 [SMILES: C=CC(=O)N1CC2(CCN(c3nc4c(c(-c5c(C)c(Cl)cc6[nH]ncc56)c3Cl)COC(C)(C)C4)C2)C1] | 1-(6-(3-chloro-4-(6-chloro-5-methyl-1H-indazol-4-yl)-7,7-dimethyl-7,8-dihydro-5H-pyrano[4,3-b]pyridin-2-yl)-2,6-diazaspiro[3.4]octan-2-yl)-2-propen-1-one | Step 1: DIPEA and DMF replaced DMA. Step 2: SPhos Pd G3. | Step 1: Intermediate 24. Step 2: 6-chloro-5-methyl-1-(tetrahydro-2H-pyran-2-yl)-4-(4,4,5,5-tetramethyl-1,3,2-dioxaborolan-2-yl)-1H-indazole (PharmaBlock)) |
| 2-93 | 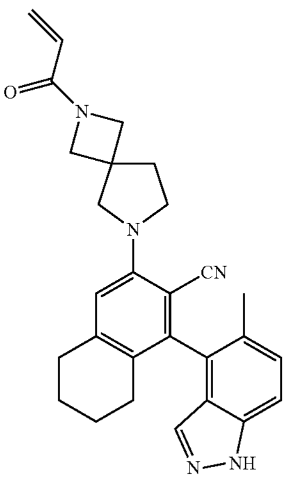 [SMILES: C=CC(=O)N1CC2(CCN(c3cc4c(c(-c5c(C)ccc6[nH]ncc56)c3C#N)CCCC4)C2)C1] | 1-(5-methyl-1H-indazol-4-yl)-3-(2-(2-propenoyl)-2,6-diazaspiro[3.4]octan-6-yl)-5,6,7,8-tetrahydro-2-naphthalene-carbonitrile | Alternative Step 1 see below. Step 2: SPhos Pd G3 | Step 1: Intermediate 81. |

TABLE 3-continued

| Examples 2-2 to 2-111 were prepared following the procedure described in Method 2, Steps 1-4, above as follows: | | | | |
|---|---|---|---|---|
| Ex. # | Chemical Structure | Name | Method changes | Reagent |
| 2-94 | 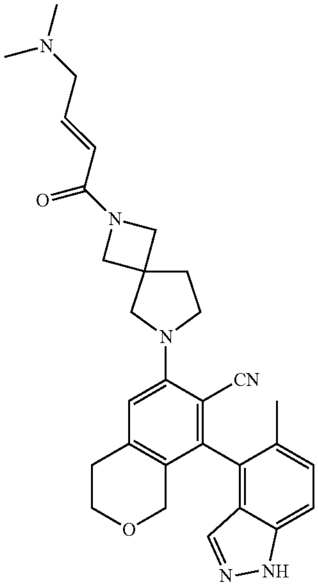 [SMILES: Cc1ccc2[nH]ncc2c1-c1c(C#N)c(N2CCC3(CN(C(=O)/C=C/CN(C)C)C3)C2)cc2c1COCC2] | 6-(2-((2E)-4-(dimethylamino)-2-butenoyl)-2,6-diazaspiro[3.4]octan-6-yl)-8-(5-methyl-1H-indazol-4-yl)-3,4-dihydro-1H-2-benzopyran-7-carbonitrile | Step 1 performed using procedure from Example 2-93. Step 4: Replace with Step 5 from Method 4 | Step 1: Intermediate 78. Step 4: (E)-4-(dimethylamino)but-2-enoic acid hydrochloride (Oakwood Chemical) |
| 2-95 | 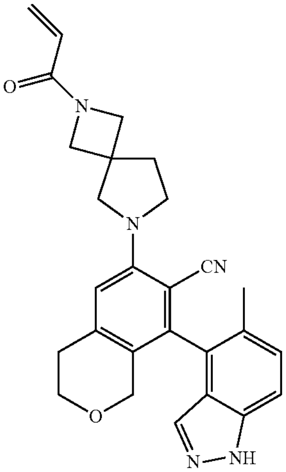 [SMILES: C=CC(=O)N1CC2(CCN(c3cc4c(c(-c5c(C)ccc6[nH]ncc56)c3C#N)COCC4)C2)C1] | 8-(5-methyl-1H-indazol-4-yl)-6-(2-(2-propenoyl)-2,6-diazaspiro[3.4]octan-6-yl)-3,4-dihydro-1H-2-benzopyran-7-carbonitrile | Step 1 performed using procedure from Example 2-93. | Step 1: Intermediate 78. |
| 2-96 | 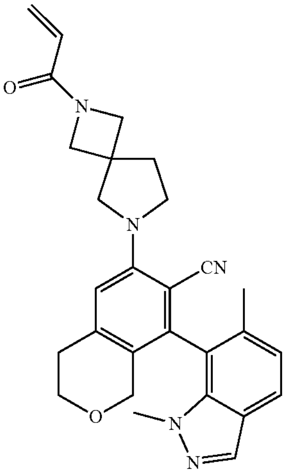 [SMILES: C=CC(=O)N1CC2(CCN(c3cc4c(c(-c5c(C)ccc6cnn(C)c56)c3C#N)COCC4)C2)C1] | 8-(1,6-dimethyl-1H-indazol-7-yl)-6-(2-(2-propenoyl)-2,6-diazaspiro[3,4]octan-6-yl)-3,4-dihydro-1H-2-benzopyran-7-carbonitrile | Step 1 performed using procedure from Example 2-93. Step 2: bis(di-tert-butyl(4-dimethylamino-phenyl)phosphine)dichloro-palladium(II) (0.2 equiv), $K_3PO_4$ (4.0 equiv) replaced $Pd(PPh_3)_4$ and $K_2CO_3$. | Step 1: Intermediate 78. Step 2: 1,6-dimethyl-7-(4,4,5,5-tetramethyl-1,3,2-dioxaborolan-2-yl)-1H-indazole (PharmaBlock) |

TABLE 3-continued

| Examples 2-2 to 2-111 were prepared following the procedure described in Method 2, Steps 1-4, above as follows: | | | | |
|---|---|---|---|---|
| Ex. # | Chemical Structure | Name | Method changes | Reagent |
| 2-97 | 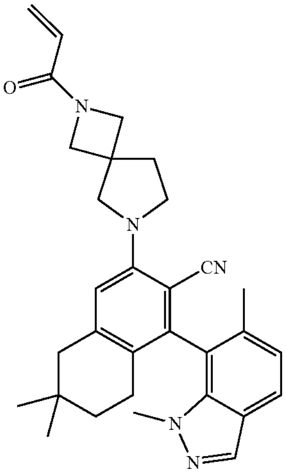 [SMILES: C=CC(=O)N1CC2(CCN(c3cc4c(c(-c5c(C)ccc6cnn(C)c56)c3C#N)CCC(C)(C)C4)C2)C1] | 1-(1,6-dimethyl-1H-indazol-7-yl)-6,6-dimethyl-3-(2-(2-propenoyl)-2,6-diazaspiro[3.4]octan-6-yl)-5,6,7,8-tetrahydro-2-naphthalene-carbonitrile | Step 1 performed using procedure from Example 2-93. Step 2; bis(di-tert-butyl(4-dimethylamino-phenyl) phosphine) dichloro-palladium(II) (0.2 equiv), $K_3PO_4$ (4.0 equiv) replaced $Pd(PPh_3)_4$ and $K_2CO_3$. | Step 1: Intermediate 77. Step 2: 1,6-dimethyl-7-(4,4,5,5-tetramethyl-1,3,2-dioxaborolan-2-yl)-1H-indazole (PharmaBlock) |
| 2-98 | 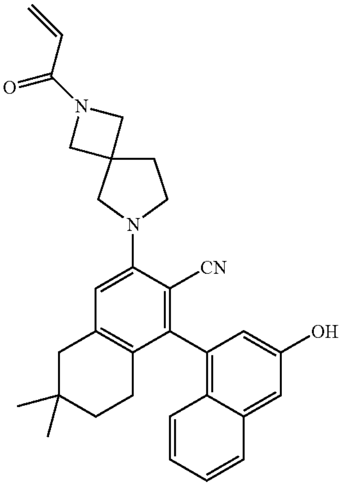 [SMILES: C=CC(=O)N1CC2(CCN(c3cc4c(c(-c5cc(O)cc6ccccc56)c3C#N)CCC(C)(C)C4)C2)C1] | 3'-hydroxy-6,6-dimethyl-3-(2-(2-propenoyl)-2,6-diazaspiro[3,4]octan-6-yl)-5,6,7,8-tetrahydro[1,1'-binaphthalene]-2-carbonitrile | Step 1 performed using procedure from Example 2-93. Step 2: bis(di-tert-butyl(4-dimethylamino-phenyl) phosphine) dichloro-palladium(II) (0.2 equiv), $K_3PO_4$ (4.0 equiv) replaced $Pd(PPh_3)_4$ and $K_2CO_3$. | Step 1: Intermediate 77. Step 2: 3-hydroxynaphthalene-1-boronic acid (eNovation Chemicals) |
| 2-99 | 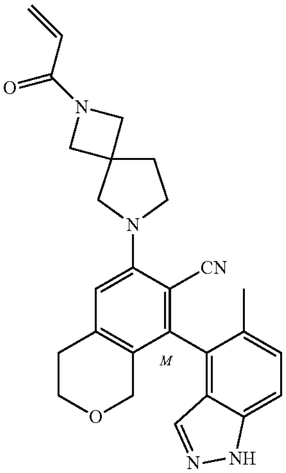 | (M)-8-(5-methyl-1H-indazol-4-yl)-6-(2-(2-propenoyl)-2,6-diazaspiro[3.4]octan-6-yl)-3,4-dihydro-1H-2-benzopyran-7-carbonitrile (1$^{st}$ eluting isomer) | Step 1 performed using procedure from Example 2-93. | Step 1; Intermediate 78. |

TABLE 3-continued

| Examples 2-2 to 2-111 were prepared following the procedure described in Method 2, Steps 1-4, above as follows: | | | | |
|---|---|---|---|---|
| Ex. # | Chemical Structure | Name | Method changes | Reagent |
| 2-100 | 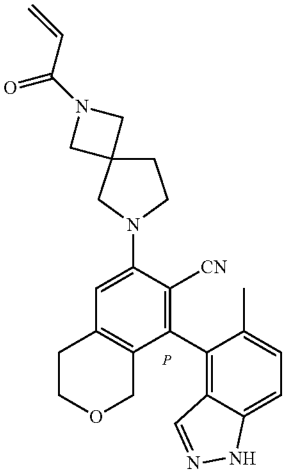 | (P)-8-(5-methyl-1H-indazol-4-yl)-6-(2-(2-propenoyl)-2,6-diazaspiro[3.4]octan-6-yl)-3,4-dihydro-1H-2-benzopyran-7-carbonitrile ($2^{nd}$ eluting isomer) | Step 1 performed using procedure from Example 2-93. | Step 1: Intermediate 78. |
| 2-101 | 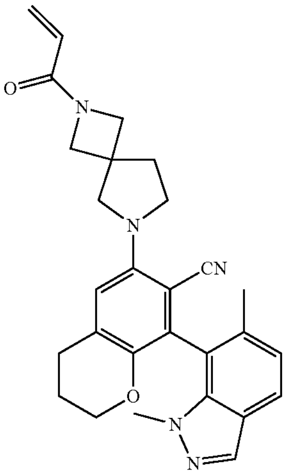 [SMILES: C=CC(=O)N1CC2(CCN(c3cc4c(c(-c5c(C)ccc6cnn(C)c56)c3C#N)OCCC4)C2)C1] | 8-(1,6-dimethyl-1H-indazol-7-yl)-6-(2-(2-propenoyl)-2,6-diazaspiro[3.4]octan-6-yl)-3,4-dihydro-2H-chromene-7-carbonitrile | Step 1 performed using procedure from Example 2-93. Step 2: bis(di-tert-butyl(4-dimethylamino-phenyl) phosphine) dichloro-palladium(II) (0.2 equiv), $K_3PO_4$ (4.0 equiv) replaced $Pd(PPh_3)_4$ and $K_2CO_3$. | Step 1: Intermediate 79. Step 2: 1,6-dimethyl-7-(4,4,5,5-tetramethyl-1,3,2-dioxaborolan-2-yl)-1H-indazole (PharmaBlock) |
| 2-102 | 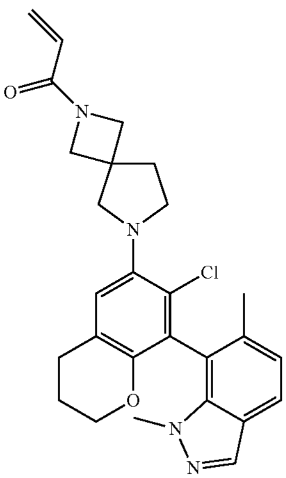 [SMILES: C=CC(=O)N1CC2(CCN(c3cc4c(c(-c5c(C)ccc6cnn(C)c56)c3Cl)OCCC4)C2)C1] | 1-(6-(7-chloro-8-(1,6-dimethyl-1H-indazol-7-yl)-3,4-dihydro-2H-chromen-6-yl)-2,6-diazaspiro[3.4]octan-2-yl)-2-propen-1-one | Step 1 performed using procedure from Example 2-93. Step 2: SPhos Pd G3, $K_3PO_4$. Additional N-methylation performed using procedure from Example 2-19 after step 2. | Step 1: Intermediate 80. Step 2: 6-methyl-7-(4,4,5,5-tetramethyl-1,3,2-dioxaborolan-2-yl)-1H-indazole (Synnovator) |

TABLE 3-continued

Examples 2-2 to 2-111 were prepared following the procedure described in Method 2, Steps 1-4, above as follows:

| Ex. # | Chemical Structure | Name | Method changes | Reagent |
|---|---|---|---|---|
| 2-103 | 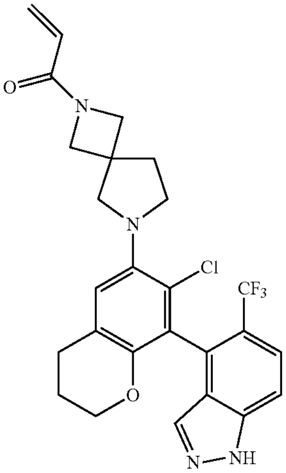 [SMILES: C=CC(=O)N1CC2(CCN(c3cc4c(c(-c5c(C(F)(F)F)ccc6[nH]ncc56)c3Cl)OCCC4)C2)C1] | 1-(6-(7-chloro-8-(5-(trifluoromethyl)-1H-indazol-4-yl)-3,4-dihydro-2H-chromen-6-yl)-2,6-diazaspiro[3.4]octan-2-yl)-2-propen-1-one | Step 1 performed using procedure from Example 2-93. Step 2: SPhos Pd G3, $K_3PO_4$. | Step 1: Intermediate 80. Step 2: 1-(tetrahydro-2H-pyran-2-yl)-5-(trifluoromethyl-1h-indazol-4-ylboronic acid (Apollo Scientific Ltd.) |
| 2-104 | 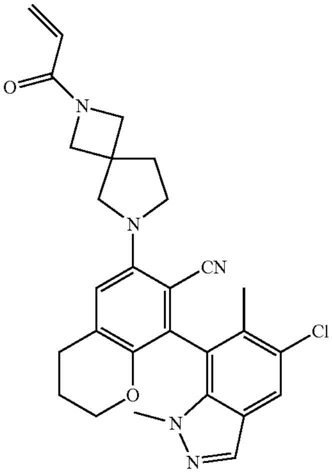 [SMILES: C=CC(=O)N1CC2(CCN(c3cc4c(c(-c5c(C)c(Cl)cc6cnn(C)c56)c3C#N)OCCC4)C2)C1] | 8-(5-chloro-1,6-dimethyl-1H-indazol-7-yl)-6-(2-(2-propenoyl)-2,6-diazaspiro[3.4]octan-6-yl)-3,4-dihydro-2H-chromene-7-carbonitrile | Step 1 performed using procedure from Example 2-94. Step 2: SPhos Pd G3, $K_3PO_4$. Additional N-methylation performed using procedure from Example 2-19 after step 2. | Step 1: Intermediate 79. Step 2: Intermediate 37. |
| 2-105 | 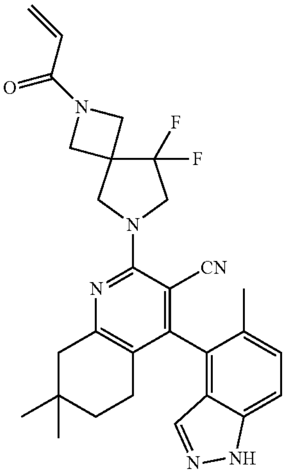 [SMILES: C=CC(=O)N1CC2(C1)CN(c1nc3c(c(-c4c(C)ccc5[nH]ncc45)c1C#N)CCC(C)(C)C3)CC2(F)F] | 2-(8,8-difluoro-2-(2-propenoyl)-2,6-diazaspiro[3.4]octan-6-yl)-7,7-dimethyl-4-(5-methyl-1H-indazol-4-yl)-5,6,7,8-tetrahydro-3-quinolinecarbonitrile | Alternative Step 1 performed in analogous manner to Example 2-93. | Step 1: Intermediate 6 and tert-butyl 8,8-difluoro-2,6-diazaspiro[3,4]octane-2-carboxylate (PharmaBlock). |

TABLE 3-continued

| Examples 2-2 to 2-111 were prepared following the procedure described in Method 2, Steps 1-4, above as follows: | | | | |
|---|---|---|---|---|
| Ex. # | Chemical Structure | Name | Method changes | Reagent |
| 2-106 | 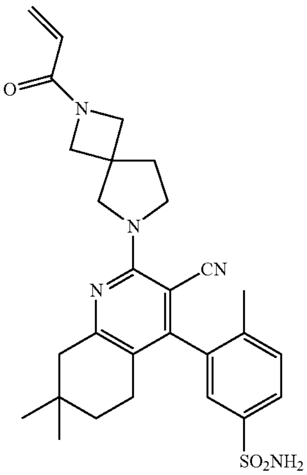 [SMILES: C=CC(=O)N1CC2(CCN(c3nc4c(c(-c5cc(S(N)(=O)=O)ccc5C)c3C#N)CCC(C)(C)C4)C2)C1] | 3-(3-cyano-7,7-dimethyl-2-(2-(2-propenoyl)-2,6-diazaspiro[3.4]octan-6-yl)-5,6,7,8-tetrahydro-4-quinolinyl)-4-methylbenzene-sulfonamide | Step 1 performed using procedure from Example 2-93, with XPhos Pd G4 and $Cs_2CO_3$ in place of XantPhos Pd G3 and $K_2CO_3$ Step 2: SPhos Pd G3, $K_3PO_4$. | Step 1: Intermediate 6. Step 2: 2-methyl-5-sulfamoylphenyl boronic acid pinacol ester (Combi-Blocks) |
| 2-107 | 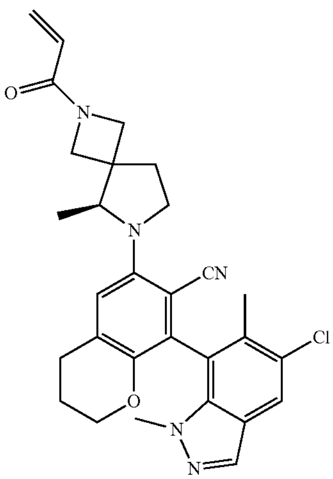 [SMILES: C=CC(=O)N1CC2(CCN(c3cc4c(c(-c5c(C)c(Cl)cc6cnn(C)c56)c3C#N)OCCC4)[C@H]2C)C1] | 8-(5-chloro-1,6-dimethyl-1H-indazol-7-yl)-6-((5S)-5-methyl-2-(2-propenoyl)-2,6-diazaspiro[3.4]octan-6-yl)-3,4-dihydro-2H-chromene-7-carbonitrile | Step 1 performed using procedure from Example 2-93. Step 2: SPhos Pd G3, $K_3PO_4$. Additional N-methylation performed using procedure from Example 2-19 after step 2. Method | Step 1: Intermediate 78 and Amine 3. Step 2: Intermediate 37. |
| 2-108 | 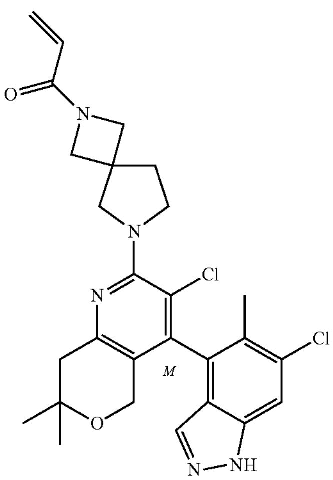 | (M)-1-(6-(3-chloro-4-(6-chloro-5-methyl-1H-indazol-4-yl)-7,7-dimethyl-7,8-dihydro-5H-pyrano[4,3-b]pyridin-2-yl)-2,6-diazaspiro[3.4]octan-2-yl)-2-propen-1-one (1st eluting isomer) | Step 1: DIPEA and DMF replaced DMA. Step 2: SPhos Pd G3. See below for atropisomer separation conditions | Step 1: Intermediate 24. Step 2: 6-chloro-5-methyl-1-(tetrahydro-2H-pyran-2-yl)-4-(4,4,5,5-tetramethyl-1,3,2-dioxaborolan-2-yl)-1H-indazole (PharmaBlock) |

TABLE 3-continued

| Examples 2-2 to 2-111 were prepared following the procedure described in Method 2, Steps 1-4, above as follows: | | | | |
|---|---|---|---|---|
| Ex. # | Chemical Structure | Name | Method changes | Reagent |
| 2-109 | 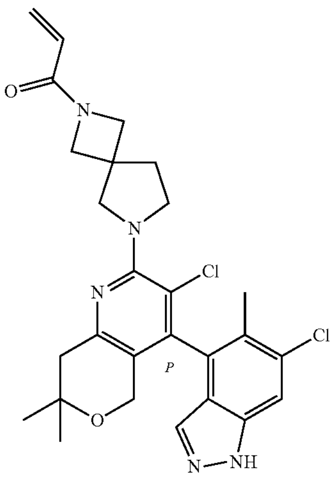 | (P)-1-(6-(3-chloro-4-(6-chloro-5-methyl-1H-indazol-4-yl)-7,7-dimethyl-7,8-dihydro-5H-pyrano[4,3-b]pyridin-2-yl)-2,6-diazaspiro[3.4]octan-2-yl)-2-propen-1-one (2nd eluting isomer) | Step 1: DIPEA and DMF replaced DMA. Step 2: SPhos Pd G3. See below for atropisomer separation conditions | Step 1: Intermediate 24. Step 2: 6-chloro-5-methyl-1-(tetrahydro-2H-pyran-2-yl)-4-(4,4,5,5-tetramethyl-1,3,2-dioxaborolan-2-yl)-1H-indazole (PharmaBlock)) |
| 2-110 | 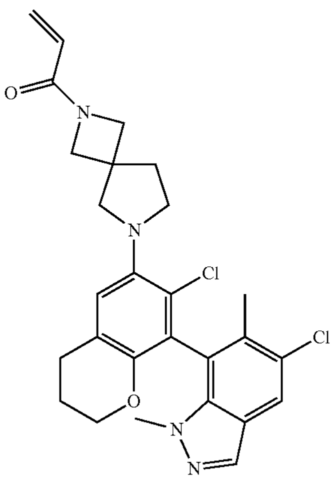 [SMILES: C=CC(=O)N1CC2(CCN(c3cc4c(c(-c5c(C)c(Cl)cc6cnn(C)c56)c3Cl)OCCC4)C2)C1] | 1-(6-(7-chloro-8-(5-chloro-1,6-dimethyl-1H-indazol-7-yl)-3,4-dihydro-2H-chromen-6-yl)-2,6-diazaspiro[3.4]octan-2-yl)-2-propen-1-one | Step 1 performed using procedure from Example 2-94. Additional N-methylation performed using procedure from Example 2-19 after step 2. | Step 1: Intermediate 80. Step 2: Intermediate 37 |
| 2-111 | 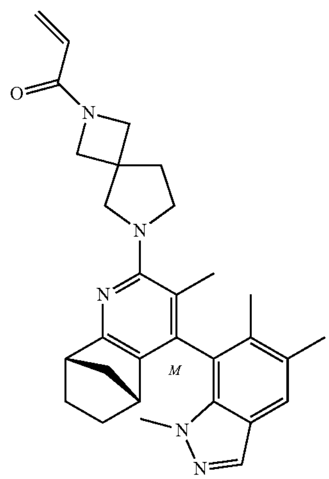 | (M)-1-(6-((1S,8R)-5-methyl-6-(1,5,6-trimethyl-1H-indazol-7-yl)-3-azatricyclo[6.2.1.0$^{2,7}$]undeca-2,4,6-trien-4-yl)-2,6-diazaspiro[3.4]octan-2-yl)-2-propen-1-one (2nd eluting isomer) | See alternate Step 1 from Example 2-11. Enantiomer separation after Step 1. Additional N-methylation performed using procedure from Example 2-19 after step 2. atropisomer separation conditions describe below. | Step 1; Intermediate 117. Step 2: Intermediate 38. |

Synthesis of boronic ester for Example 2-6

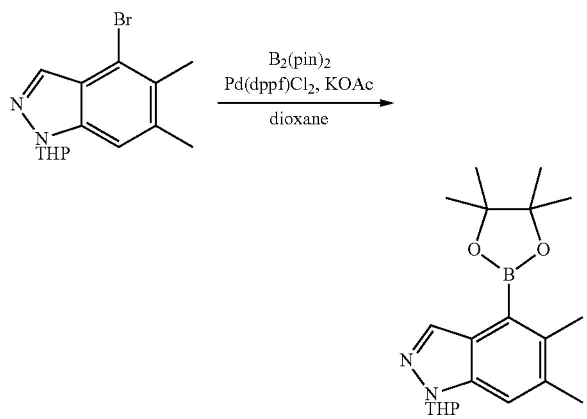

A mixture of 4-bromo-5,6-dimethyl-1-(tetrahydro-2H-pyran-2-yl)-1H-indazole (2.3 g, 7.44 mmol), 4,4,4',4',5,5,5',5'-octamethyl-2,2'-bi(1,3,2-dioxaborolane) (2.27 g, 8.93 mmol), potassium acetate (1.46 g, 14.9 mmol), $PdCl_2$(dppf) (1.09 g, 1.49 mmol) and 1,4-dioxane (40 mL) under $N_2$ was stirred at 100° C. for 12 h. Upon completion, the reaction was quenched with water (50 mL) and the mixture was extracted with DCM (50 mL×3). The combined organic extracts were washed with brine, dried over $Na_2SO_4$, and concentrated. The residue was purified by chromatography (PE:EtOAc=20:1) to afford 5,6-dimethyl-1-(tetrahydro-2H-pyran-2-yl)-4-(4,4,5,5-tetramethyl-1,3,2-dioxaborolan-2-yl)-1H-indazole (1.9 g, 72% yield) as a colorless oil. m/z (ESI): 357.1 $(M+H)^+$.

Alternative Step 1 for Example 2-11

To a 250-mL RBF with a stirring bar was added $K_3PO_4$ (13.04 g, 61.4 mmol, Sigma-Aldrich), CuI, (0.585 g, 3.07 mmol, Sigma-Aldrich), [(2,6-difluorophenyl)carbamoyl] formic acid (2.471 g, 12.29 mmol, Enamine), 2-(tert-butoxycarbonyl)-2,6-diazaspiro[3.4]octane (6.52 g, 30.7 mmol, PharmaBlock) and 2,4-dichloro-3,7,7-trimethyl-5,6,7,8-tetrahydroquinoline (5 g, 20.48 mmol, Intermediate 36). The reaction flask was evacuated and backfilled with nitrogen (3×) before addition of DMSO (102 mL). The reaction mixture was heated to 95° C. Upon completion, the reaction was diluted with aqueous saturated $NH_4Cl$ (100 mL) and EtOAc (200 mL). After extraction, the organic phase was washed with water (2×100 mL), and the combined aqueous phases were extracted with EtOAc (100 mL). The organic phases were washed with brine (100 mL), dried over $Na_2SO_4$, and concentrated in vacuo. The crude material was purified using Biotage Sfar HCD 100 g column with acetone in DCM (0-8%) to provide tert-butyl 6-(4-chloro-3,7,7-trimethyl-5,6,7,8-tetrahydroquinolin-2-yl)-2,6-diazaspiro[3.4]octane-2-carboxylate (6.3 g, 73.2%), was obtained as a light yellow solid. m/z (ESI): $(M+H)^+$=420.2. $^1H$ NMR (400 MHz, $CDCl_3$) δ ppm 3.91-3.98 (m, 2H), 3.82-3.91 (m, 2H), 3.59 (s, 2H), 3.47 (t, J=6.9 Hz, 2H), 2.71 (t, J=6.7 Hz, 2H), 2.54 (s, 2H), 2.30 (s, 3H), 2.11 (t, J=7.0 Hz, 2H), 1.53-1.61 (m, 2H), 1.47 (s, 9H), 1.01 (s, 6H).

Atropisomer Separation for Examples 2-11 and 2-12.

The racemic mixture was separated by preparative SFC using a AZ column (250×21 mm, 5 mm) with a mobile phase of 60% liquid $CO_2$ and 40% MeOH using a flowrate of 70 mL/min to provide the respective P and M isomers of 1-(6-(3,7,7-trimethyl-4-(5-methyl-1H-indazol-4-yl)-5,6,7,8-tetrahydro-2-quinolinyl)-2,6-diazaspiro[3.4]octan-2-yl)-2-propen-1-one. The stereochemistry of structures was arbitrarily assigned and is not established. 1st eluting atropisomer assigned as the M isomer and 2nd eluting atropisomer assigned as the P isomer.

Atropisomer Separation for Examples 2-14 and 2-15.

The racemic mixture was separated by preparative SFC using a Chiralcel OJ column, (250×21 mm), mobile phase of 75% liquid $CO_2$ and 25% MeOH w/0.2% TEA using a flow rate of 80 mL/min to provide the respective P and M isomers of 1-(6-(4-(6-hydroxy-1-naphthalenyl)-3,7,7-trimethyl-5,6,7,8-tetrahydro-2-quinolinyl)-2,6-diazaspiro[3.4]octan-2-yl)-2-propen-1-one. The stereochemistry of structures was arbitrarily assigned and is not established. 1st eluting atropisomer assigned as the M isomer and 2nd eluting atropisomer assigned as the P isomer.

Atropisomer Separation for Examples 2-17 and 2-18.

The racemic mixture was separated by preparative SFC using a Chiralpak IC column (250×21, 5 μm), with a mobile phase of 85% $CO_2$ and 15% MeOH with 0.2% TEA using a flowrate of 120 mL/min to provide the respective P and M isomers of 4-(2-amino-7-fluoro-1,3-benzothiazol-4-yl)-7,7-dimethyl-2-(2(2-propenoyl)-2,6-diazaspiro[3.4]octan-6-yl)-7,8-dihydro-5H-pyrano[4,3-b]pyridine-3-carbonitrile. The stereochemistry of structures was arbitrarily assigned and is not established. 1st eluting atropisomer assigned as the P isomer and 2nd eluting atropisomer assigned as the M isomer.

N-methylation for Example 2-19

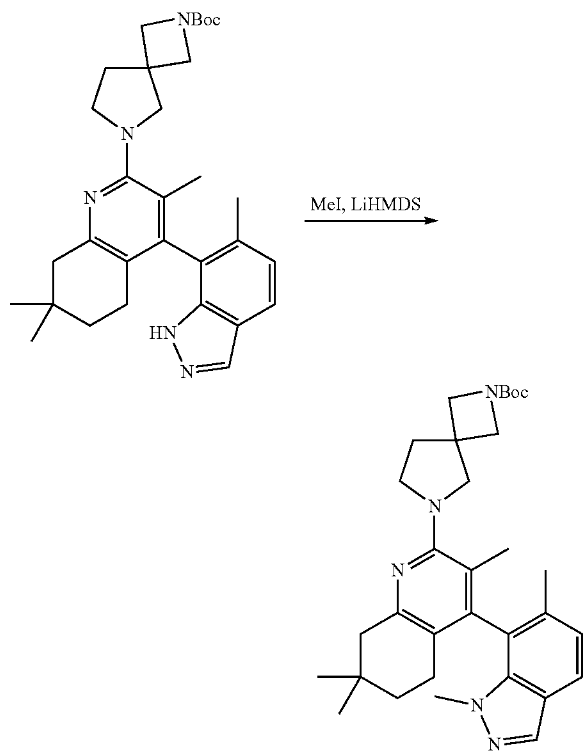

To a 0° C. solution of tert-butyl 6-(3,7,7-trimethyl-4-(6-methyl-1H-indazol-7-yl)-5,6,7,8-tetrahydroquinolin-2-yl)-

2,6-diazaspiro[3.4]octane-2-carboxylate (270 mg, 0.524 mmol) in THE (10,471 mL) was added LiHMDS, 1M in THF (0.524 mL, 0.524 mmol, Sigma-Aldrich) dropwise. After stirring at 0° C. for 30 min, iodomethane (0.098 mL, 1.571 mmol, Sigma-Aldrich) was added at 0° C. The reaction mixture was stirred at 0° C. for 1.5 h. The reaction was quenched by 6 mL of aqueous saturated $NH_4Cl$. The crude material was extracted with EtOAc (3×5 mL), washed with brine, dried over $Na_2SO_4$, and concentrated in vacuo. The crude material was purified using Biotage Sfar HCD 5 g column with acetone in DCM (0-5%) to provide tert-butyl 6-(4-(1,6-dimethyl-1H-indazol-7-yl)-3,7,7-trimethyl-5,6,7,8-tetrahydroquinolin-2-yl)-2,6-diazaspiro[3.4]octane-2-carboxylate (250 mg, 90% yield). ml (ESI): $(M+H)^+$=530.4.

Atropisomer Separation for Examples 2-20 and 2-21.

The racemic mixture was separated by preparative SFC using a (S,S) Whelk-01 column (250×21 mm, 5 μm) with a mobile phase of 75% liquid $CO_2$ and 25% MeOH with 0.2% TEA using a flowrate of 80 mL/min to provide the respective P and M isomers of 1-(6-(4-(1,6-dimethyl-1H-indazol-7-yl)-3,7,7-trimethyl-5,6,7,8-tetrahydro-2-quinolinyl)-2,6-diazaspiro[3.4]octan-2-yl)-2-propen-1-one. The stereochemistry of structures was arbitrarily assigned and is not established. 1$^{st}$ eluting atropisomer assigned as the M isomer and 2$^{nd}$ eluting atropisomer assigned as the P isomer.

Atropisomer Separation for Examples 2-24 and 2-25.

The racemic mixture was separated by preparative SFC using an ID column (250×21 mm, 5 μm) with a mobile phase of 55% liquid $CO_2$ and 45% MeOH with 0.2% TEA using a flowrate of 70 mL/min to provide the respective P and M isomers of 1-(6-(3,7,7-trimethyl-4-(6-methyl-1H-indazol-7-yl)-5,6,7,8-tetrahydro-2-quinolinyl)-2,6-diazaspiro[3.4]octan-2-yl)-2-propen-1-one. The stereochemistry of structures was arbitrarily assigned and is not established. 1$^{st}$ eluting atropisomer assigned as the M isomer and 2$^{nd}$ eluting atropisomer assigned as the P isomer.

Atropisomer Separation for Examples 2-33 and 2-34.

The racemic mixture was separated by preparative SFC using a Chiralpak IG column (250×21 mm, 5 μm) with a mobile phase of 50% liquid $CO_2$ and 50% MeOH using a flowrate of 80 mL/min to provide the respective P and M isomers of 1-(6-(4-(5-chloro-1-methyl-1H-indazol-7-yl)-3,7,7-trimethyl-7,8-dihydro-5H-pyrano[4,3-b]pyridin-2-yl)-2,6-diazaspiro[3.4]octan-2-yl)-2-propen-1-one. The stereochemistry of structures was arbitrarily assigned and is not established. 1$^{st}$ eluting atropisomer assigned as the P isomer and 2$^{nd}$ eluting atropisomer assigned as the M isomer.

Isomer Separation for Examples 2-39 and 2-40.

The racemic mixture was separated by preparative SFC using a Chiralpak AS (21×250 mm, 5 μm) column with a mobile phase of 75% liquid $CO_2$ and 25% MeOH with 0.2% TEA using a flowrate of 80 mL/min to provide the respective P and M isomers of (1R,8S)-6-(3-hydroxy-1-naphthalenyl)-4-(2-(2-propenoyl)-2,6-diazaspiro[3.4]octan-6-yl)-3-azatricyclo[6.2.1.0$^{2,7}$]undeca-2,4,6-triene-5-carbonitrile. The stereochemistry of structures was arbitrarily assigned and is not established. The 1$^{st}$ and 2$^{nd}$ eluting peaks were not resolved completely. The 3rd eluting isomer was assigned as the P,1S,8R isomer and 4th eluting isomer assigned as the M,1S,8R isomer, Atropisomer Separation for Examples 2-44 and 2-45.

The racemic mixture was separated by preparative SFC using a Chiralpak IC (21×150 mm, 5 μm) with a mobile phase of 55% liquid $CO_2$ and 45% MeOH using a flowrate of 80 mL/min to provide the respective P and M isomers of (1R,9R)-6-(6-hydroxy-8-quinolinyl)-10,10-dimethyl-4-(2-(2-propenoyl)-2,6-diazaspiro[3.4]octan-6-yl)-3-azatricyclo[7.1.1.0$^{2,7}$]undeca-2,4,6-triene-5-carbonitrile. The stereochemistry of structures was arbitrarily assigned and is not established. 1$^{st}$ eluting atropisomer assigned as the M isomer and 2$^{nd}$ eluting atropisomer assigned as the P isomer.

Atropisomer Separation for Examples 2-46 and 2-47.

The racemic mixture was separated by preparative SFC using a Chiralcel OX (21×250 mm, 5 μm) with a mobile phase of 55% liquid $CO_2$ and 45% MeOH using a flowrate of 60 mL/min to provide the respective P and M isomers of (1R,9R)-6-(7-hydroxy-5-quinolinyl)-10,10-dimethyl-4-(2-(2-propenoyl)-2,6-diazaspiro[3.4]octan-6-yl)-3-azatricyclo[7.1.1.0$^{2,7}$]undeca-2,4,6-triene-5-carbonitrile. The stereochemistry of structures was arbitrarily assigned and is not established. 1$^{t}$ eluting atropisomer assigned as the P isomer and 2$^{nd}$ eluting atropisomer assigned as the M isomer.

Alternative Step 1 for Example 2-52

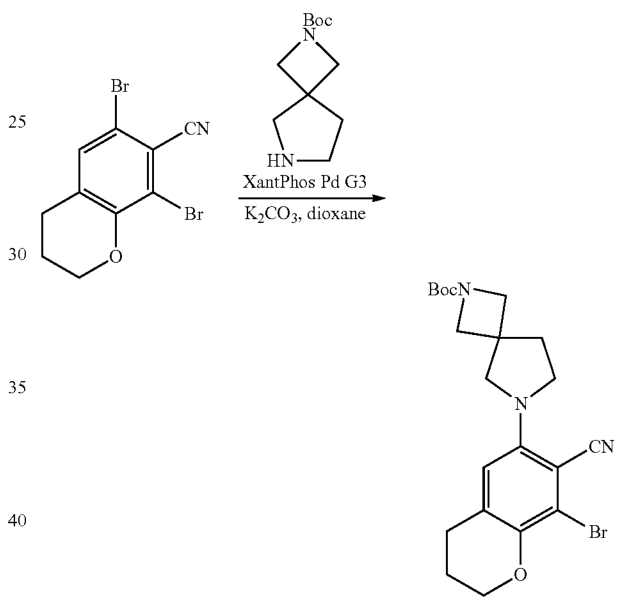

A mixture of 6,8-dibromochromane-7-carbonitrile (306 mg, 0.965 mmol, Intermediate 79), $K_2CO_3$ (267 mg, 1,931 mmol, Sigma-Aldrich), 2-(tert-butoxycarbonyl)-2,6-diazaspiro[3.4]octane (184 mg, 0.869 mmol, PharmaBlock), and Xantphos Pd G3 (92 mg, 0.097 mmol, Sigma-Aldrich) in 1,4-dioxane (6 mL) was stirred at 100° C. overnight. The mixture was concentrated in vacuo and chromatographic purification of the residue (silica gel, 0-100% EtOAc/heptanes) provided tert-butyl 6-(8-bromo-7-cyanochroman-6-yl)-2,6-diazaspiro[3.4]octane-2-carboxylate (110 mg, 25.4% yield) as a yellow solid. ml, (ESI): 448.1 $(M+H)^+$. $^1$H NMR (400 MHz, DMSO-$d_6$) δ ppm 6.63 (s, 1H), 4.14-4.21 (m, 2H), 3.74-3.87 (m, 4H), 3.57 (s, 2H), 3.45 (t, J=6.8 Hz, 2H), 2.79 (t, J=6.4 Hz, 2H), 2.13 (t, J=6.8 Hz, 2H), 1.85-1.94 (m, 2H), 1.39 (s, 9H).

Atropisomer Separation for Examples 2-5 and 2-54.

The racemic mixture was separated by preparative SFC using a Chiralpak AS (21×250, 5 μm) column with a mobile phase of 60% liquid $CO_2$ and 40% MeOH using a flowrate of 80 m/min to provide the respective P and M isomers of 8-(3-hydroxy-1-naphthalenyl)-6-(2-(2-propenoyl)-2,6-diazaspiro[3.4]octan-6-yl)-3,4-dihydro-2H-chromene-7-carbonitrile. The stereochemistry of structures was arbitrarily assigned and is not established. 1st eluting atropisomer assigned as the P isomer and 2nd eluting atropisomer assigned as the M isomer.

Atropisomer Separation for Examples 2-55 and 2-56.

The racemic mixture was separated by preparative SFC using a Chiralpak ID (21×150 mm, 5 am) column with a mobile phase of 55% liquid $CO_2$ and 45% MeOH with 0.2% TEA using a flowrate of 80 mL/min to provide the respective P and M isomers of 1-(6-(3-methyl-4-(5-methyl-1H-indazol-4-yl)-2-quinolinyl)-2,6-diazaspiro[3.4]octan-2-yl)-2-propen-1-one. The stereochemistry of structures was arbitrarily assigned and is not established. 1st eluting atropisomer assigned as the P isomer and 2nd eluting atropisomer assigned as the M isomer.

Isomer Separation for Examples 2-57.

The racemic mixture was separated by preparative SFC suing a Chiral Technologies IG column (250×21 mm, 5 μm) with a mobile phase of 80% liquid $CO_2$ and 20% MeOH with 0.2% TEA using a flowrate of 60 mL/min to provide the respective R and S isomers of 1-((5S)-5-methyl-6-(3-methyl-4-(5-methyl-1H-indazol-4-yl)-2-quinolinyl)-2,6-diazaspiro[3.4]octan-2-yl)-2-propen-1-one. The 1st eluting isomer assigned as the S isomer and 2nd eluting isomer assigned as the R isomer.

Isomer Separation for Examples 2-58 and 2-59.

The racemic mixture was separated by preparative SFC using a Chiral Technologies IG column (250×21 mm, 5 μm) with a mobile phase of 90% liquid $CO_2$ and 10% MeOH with 0.2% TEA using a flowrate of 65 mL/min to provide the respective R and S isomers of 1-(6-(7-fluoro-3-methyl-4-(5-methy-1H-indazol-4-yl)-2-quinolinyl)-5-methyl-2,6-diazaspiro[3.4]octan-2-yl)-2-propen-1-one. The stereochemistry of structures was arbitrarily assigned and is not established. The 1V eluting isomer assigned as the S isomer and 2nd eluting isomer assigned as the R isomer.

Atropisomer Separation for Examples 2-60 and 2-61.

The racemic mixture was separated by preparative SFC using a column 2× Chiralcel OD (250×21 mm, 5 μm) with a mobile phase of mobile phase of 80% liquid $CO_2$ and 20% MeOH with 0.2% TEA using a flowrate of 65 mL/min to provide the respective P and M isomers of 1-((5S)-6-(7-fluoro-3-methyl-4-(5-methyl-1H-indazol-4-yl)-2-quinolinyl)-5-methyl-2,6-diazaspiro[3.4]octan-2-yl)-2-propen-1-one. The stereochemistry of structures was arbitrarily assigned and is not established. 1st eluting atropisomer assigned as the M isomer and 2nd eluting atropisomer assigned as the P isomer.

Atropisomer Separation for Examples 2-68 and 2-69.

The racemic mixture was separated by preparative SFC using a Chiralpak AS column (21×250 mm) with a mobile phase of 75% liquid $CO_2$ and 25% MeOH with 0.2% TEA using a flowrate of 80 mL/min to provide the respective P and M isomers of (1R,9R)-6-(5-hydroxy-2-methylphenyl)-10,10-dimethyl-4-(2-(2-propenoyl)-2,6-diazaspiro[3.4]octan-6-yl)-3-azatricyclo[7.1.1.$0^{2,7}$]undeca-2,4,6-triene-5-carbonitrile. The stereochemistry of structures was arbitrarily assigned and is not established. 1st eluting atropisomer assigned as the M isomer and 2nd eluting atropisomer assigned as the P isomer.

Atropisomer Separation for Examples 2-71 and 2-72.

The racemic mixture was separated by preparative SFC using a (S,S) Whelk O-1 column (21×250 mm) with a mobile phase of 60% liquid $CO_2$ and 40% MeOH using a flowrate of 80 mL/min to provide the respective P and M isomers of (1R,9R)-6-(3-fluoro-2-hydroxyphenyl)-10,10-dimethyl-4-(2-(2-propenoyl)-2,6-diazaspiro[3.4]octan-6-yl)-3-azatricyclo[7.1.1.$0^{2,7}$]undeca-2,4,6-triene-5-carbonitrile. The stereochemistry of structures was arbitrarily assigned and is not established. 1st eluting atropisomer assigned as the P isomer and 2nd eluting atropisomer assigned as the M isomer.

Atropisomer Separation for Examples 2-74 and 2-75.

The racemic mixture was separated by preparative SFC using a Chiralpak IE column (21×250 mm) with a mobile phase of 65% liquid $CO_2$ and 35% MeOH using a flowrate of 80 mL/min to provide the respective P and M isomers of ((1R,9R)-6-(2-chloro-5-hydroxyphenyl)-10,10-dimethyl-4-(2-(2-propenoyl)-2,6-diazaspiro[3.4]octan-6-yl)-3-azatricyclo[7.1.1.$0^{2,7}$]undeca-2,4,6-triene-5-carbonitrile. The stereochemistry of structures was arbitrarily assigned and is not established. 1st eluting atropisomer assigned as the P isomer and 2nd eluting atropisomer assigned as the M isomer.

Atropisomer Separation for Examples 2-77 and 2-78.

The racemic mixture was separated by preparative SFC using a Sepax OD (21×250, 5 μm) column with a mobile phase of 60% liquid $CO_2$ and 40% MeOH with 0.2% TEA using a flowrate of 80 mL/min to provide the respective P and M isomers of 1-(6-(3-chloro-4-(3-hydroxy-1-naphthalenyl)-7,7-dimethyl-7,8-dihydro-5H-pyrano[4,3-b]pyridin-2-yl)-2,6-diazaspiro[3.4]octan-2-yl)-2-propen-1-one. The stereochemistry of structures was arbitrarily assigned and is not established. 1st eluting atropisomer assigned as the M isomer and 2nd eluting atropisomer assigned as the P isomer.

Atropisomer Separation for Examples 2-80 and 2-81.

The racemic mixture was separated by preparative SFC using a Chiralpak AS (21×250, 5 μm) with a mobile phase of 80% liquid $CO_2$ and 20% MeOH with 0.2% TEA using a flowrate of 80 mL/min to provide the respective P and M isomers of 1-(6-(3-chloro-4-(5-hydroxy-2-methylphenyl)-7,7-dimethyl-7,8-dihydro-5H-pyrano[4,3-b]pyridin-2-yl)-2,6-diazaspiro[3.4]octan-2-yl)-2-propen-1-one. The stereochemistry of structures was arbitrarily assigned and is not established. 1st eluting atropisomer assigned as the M isomer and 2nd eluting atropisomer assigned as the P isomer.

Atropisomer Separation for Examples 2-84 and 2-85.

The racemic mixture was separated by preparative SFC using a Chiralcel OD (21×250, 5 μm) column with a mobile phase of 75% liquid $CO_2$ and 25% MeOH with 0.2% TEA using a flowrate of 100 mL/min to provide the respective P and M isomers of 1-(6-(3-chloro-7,7-dimethyl-4-(5-methyl-1H-indazol-4-yl)-7,8-dihydro-5H-pyrano[4,3-b]pyridin-2-yl)-2,6-diazaspiro[3.4]octan-2-yl)-2-propen-1-one. The stereochemistry of structures was arbitrarily assigned and is not established. 1st eluting atropisomer assigned as the P isomer and 2nd eluting atropisomer assigned as the M isomer.

Atropisomer Separation for Examples 2-87 and 2-88.

The racemic mixture was separated by preparative SFC using a Chiralpak ID (21×150, 5 μm) column with a mobile phase of 60% liquid $CO_2$ and 40% MeOH using a flowrate of 80 mL/min to provide the respective P and M isomers of 1-(6-(3-chloro-4-(1,6-dimethyl-1-1H-indazol-7-yl)-7,7-dimethyl-7,8-dihydro-5H-pyrano[4,3-b]pyridin-2-yl)-2,6-diazaspiro[3.4]octan-2-yl)-2-propen-1-one. The stereochemistry of structures was arbitrarily assigned and is not established. 1st eluting atropisomer assigned as the M isomer and 2nd eluting atropisomer assigned as the P isomer.

Atropisomer Separation for Examples 2-90 and 2-91.

The racemic mixture was separated by preparative SFC using a Chiralpak ID column (21×250 mm) with a mobile phase of 60% liquid $CO_2$ and 40% MeOH using a flowrate of 70 mL/min to provide the respective P and M isomers of 1-(6-(3-chloro-4-(5-chloro-1,6-dimethyl-1H-indazol-7-yl)-7,7-dimethyl-7,8-dihydro-5H-pyrano[4,3-b]pyridin-2-yl)-2,6-diazaspiro[3.4]octan-2-yl)-2-propen-1-one. The stereochemistry of structures was arbitrarily assigned and is not established. 1st eluting atropisomer assigned as the M isomer and 2nd eluting atropisomer assigned as the P isomer.

Alternative Step 1 for Example 2-93

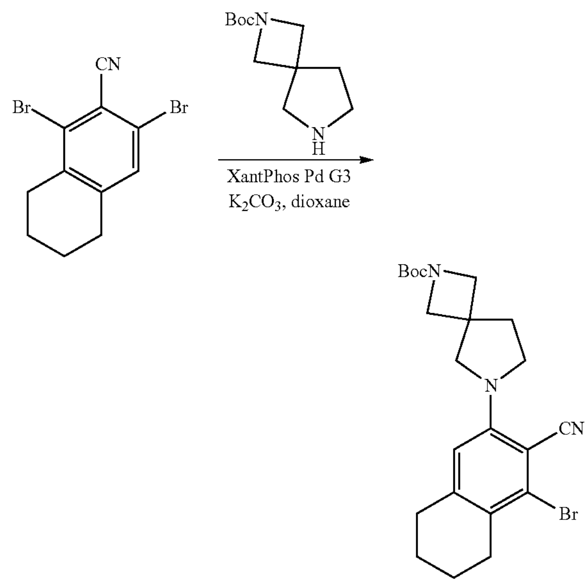

1,3-dibromo-5,6,7,8-tetrahydronaphthalene-2-carbonitrile (156 mg, 0.495 mmol, Intermediate 81), tert-butyl 2,6-diazaspiro[3.4]octane-2-carboxylate (105 mg, 0.495 mmol, PharmaBlock), XantPhos Pd G3 (47.0 mg, 0.050 mmol, Sigma-Aldrich), $K_2CO_3$ (137 mg, 0.990 mmol, Sigma-Aldrich) were mixed in 1,4-dioxane (2 mL) in a sealed vial with pressure relief cap under a nitrogen atmosphere. The reaction mixture was stirred at 100° C. for 10 h. The reaction mixture was quenched with saturated aqueous $NH_4Cl$ (30 mL) and extracted with EtOAc (50 mL). The organic layer was separated, washed with brine (15 mL), dried over $MgSO_4$, filtered, and concentrated in vacuo. Chromatographic purification of the residue (silica gel, 0-40% EtOAc in heptanes) gave tert-butyl 6-(4-bromo-3-cyano-5,6,7,8-tetrahydronaphthalen-2-yl)-2,6-diazaspiro[3.4]octane-2-carboxylate (91 mg, 41.2% yield) as a tan solid. $^1H$ NMR (400 MHz, $CDCl_3$) δ ppm 6.38 (s, 1H), 3.94 (d, J=8.57 Hz, 2H), 3.88 (d, J=8.78 Hz, 2H), 3.71 (s, 2H), 3.62 (t, J=6.69 Hz, 2H), 2.74 (t, J=6.17 Hz, 2H), 2.68 (t, J=6.48 Hz, 2H), 2.18 (t, J=6.79 Hz, 2H), 1.78-1.85 (m, 2H), 1.70-1.78 (m, 2H), 1.47 (s, 9H). m/z (ESI): 446.2 $[M+H]^+$.

Atropisomer Separation for Examples 2-99 and 2-100.

The racemic mixture was separated by preparative SFC using a Lux Cellulose-2 column (21×150 mm) with a mobile phase of 45% liquid $CO_2$ and 55% MeOH with 0.2% TEA using a flowrate of 80 mL/min to provide the respective P and M isomers of 8-(5-methyl-1H-indazol-4-yl)-6-(2-(2-propenoyl)-2,6-diazaspiro[3.4]octan-6-yl)-3,4-dihydro-1H-2-benzopyran-7-carbonitrile. The stereochemistry of structures was arbitrarily assigned and is not established. 1st eluting atropisomer assigned as the M isomer and 2nd eluting atropisomer assigned as the P isomer, Atropisomer Separation for Examples 2-108 and 2-109.

The racemic mixture was separated by preparative SFC using a Chiralcel OD column (21×150 mm) with a mobile phase of 70% liquid $CO_2$ and 30% MeOH with 0.2% TEA using a flowrate of 80 mL/min to provide the respective P and M isomers 1-(6-(3-chloro-4-(6-chloro-5-methyl-1H-indazol-4-yl)-7,7-dimethyl-7,8-dihydro-5H-pyrano[4,3-b]pyridin-2-yl)-2,6-diazaspiro[3.4]octan-2-yl)prop-2-en-1-one. The stereochemistry of structures was arbitrarily assigned and is not established. 1st eluting atropisomer assigned as the M isomer and 2nd eluting atropisomer assigned as the P isomer.

Atropisomer Separation for Examples 2-111.

The racemic mixture was separated by preparative SFC using a Chiralcel OD-H (150×4.6 mm) column with a mobile phase of 85% liquid $CO_2$ and 15% MeOH using a flowrate of 80 mL/min to provide the respective P and M isomer of 1-(6-((1R,8S)-5-methyl-6-(1,5,6-trimethyl-1H-indazol-7-yl)-3-azatricyclo-[6.2.1.0$^{2,7}$]undeca-2,4,6-trien-4-yl)-2,6-diazaspiro[3.4]octan-2-yl)-2-propen-1-one. The stereochemistry of structures was arbitrarily assigned and is not established. 1st eluting atropisomer assigned as the P isomer and 2nd eluting atropisomer assigned as the M isomer.

Individual Examples

Example 3: 1-(6-(3-Methyl-7-(5-methyl-1H-indazol-4-yl)furo[3,2-b]pyridin-5-yl)-2,6-diazaspiro[3.4]octan-2-yl)prop-2-en-1-one

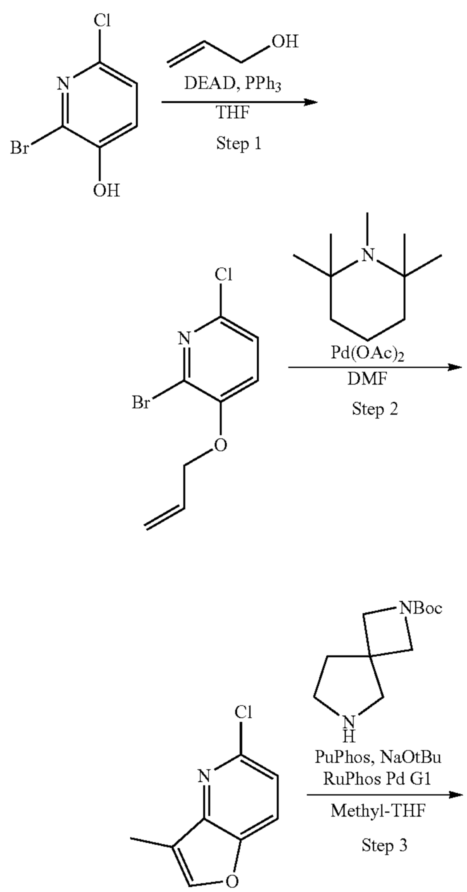

-continued

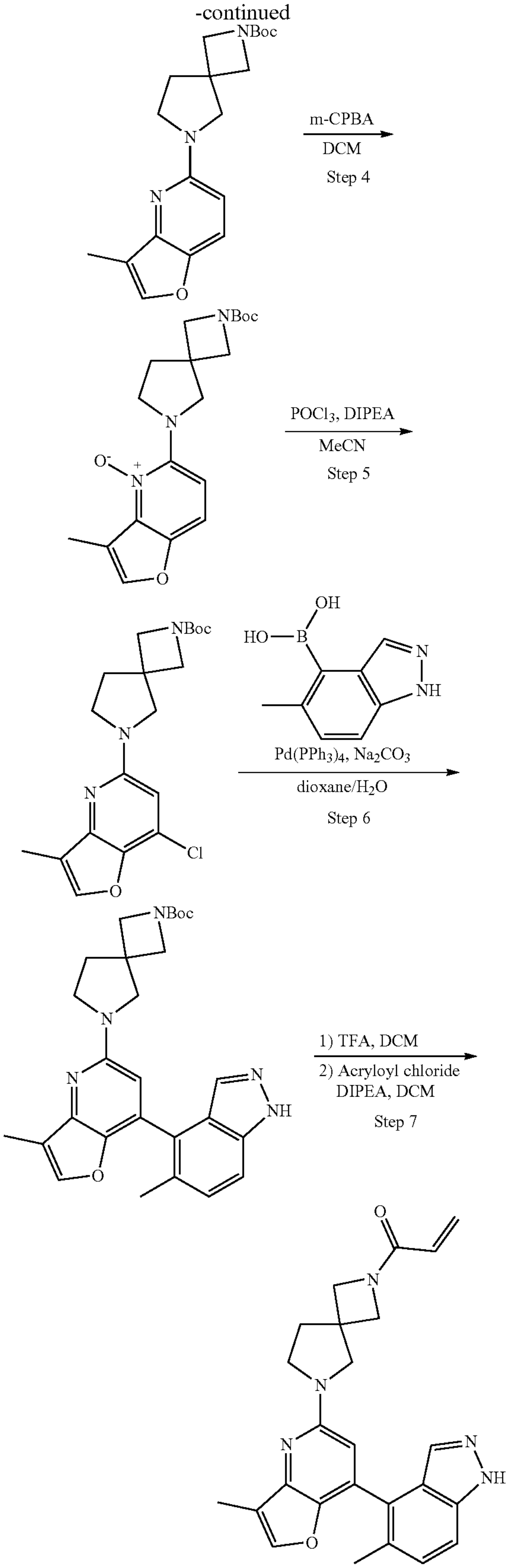

Example 3

Step 1: 3-(allyloxy)-2-bromo-6-chloropyridine

To a solution of triphenylphosphine (2.52 g, 9.60 mmol, Sigma-Aldrich), allyl alcohol (0.56 g, 0.66 mL, 9.60 mmol, Sigma-Aldrich), and 2-bromo-6-chloropyridin-3-ol (2.0 g, 9.60 mmol, Combi-Blocks) in THF (45 mL) under nitrogen at room temperature was added DEAD (40% wt in toluene) (4.18 g, 4.18 mL, 9.60 mmol, Sigma-Aldrich) dropwise. After addition, the mixture was stirred at 50° C. for 5 min. The mixture was diluted with said $NaHCO_3$ (50 mL) and was extracted with EtOAc (2×200 mL). The combined organic extracts were dried over $MgSO_4$ and concentrated in vacuo. Chromatographic purification of the residue (silica gel, 0-100% EtOAc/heptanes) provided 3-(allyloxy)-2-bromo-6-chloropyridine (2.14 g, 90% yield) as a white solid. m/z (ESI): 247.9.

Step 2: 5-chloro-3-methylfuro[3,2-b]pyridine

A mixture of 3-(allyloxy)-2-bromo-6-chloropyridine (1.5 g, 6.04 mmol), palladium (ii) acetate (0.54 g, 2.41 mmol, Sigma-Aldrich), 1,2,2,6,6-pentamethyl-4-piperidinol (4.69 g, 30.2 mmol, Sigma-Aldrich) in DMF (60 mL) was stirred at 110° C. overnight. Then, the mixture was diluted with satd $NaHCO_3$ (30 mL) and extracted with EtOAc (1×100 mL). The organic extract was collected, washed with satd $NaHCO_3$ (2×5 mL), dried over $MgSO_4$ and concentrated in vacuo. Chromatographic purification of the residue (silica gel, 0-100% EtOAc/heptane) provided 5-chloro-3-methylfuro[3,2-b]pyridine (145 mg, 14% yield) as a yellow solid. m/z (ESI): 168.1 $(M+H)^+$.

Step 3: tert-butyl 6-(3-methylfuro[3,2-b]pyridin-5-yl)-2,6-diazaspiro[3.4]octane-2-carboxylate A mixture of 5-chloro-3-methylfuro[3,2-b]pyridine (138 mg, 0.823 mmol), tert-butyl 6-(3-methylfuro[3,2-b]pyridin-5-yl)-2,6-diazaspiro[3.4]octane-2-carboxylate (264 mg, 0.77 mmol), RuPhos (77 mg, 0.165 mmol, Sigma-Aldrich), sodium tert-butoxide (198 mg, 2.059 mmol, Sigma-Aldrich) and RuPhos Pd G1 (135 mg, 0.165 mmol, Strem Chemicals) in 2-methyl-THF (4 mL) was allowed to stir at 80° C. overnight. The mixture was cooled to room temperature, diluted with aqueous saturated $NaHCO_3$ (10 mL), and extracted with EtOAc (2×15 mL). The combined organic extracts were dried over $MgSO_4$ and concentrated in vacuo. Chromatographic purification of the residue (silica gel, 0-100% EtOAc/heptane) provided tert-butyl 6-(3-methylfuro[3,2-b]pyridin-5-yl)-2,6-diazaspiro[3.4]octane-2-carboxylate (264 mg, 93% yield) as a light yellow solid. m/z (ESI): 344.0 $(M+H)^+$.

Step 4: 5-(2-(tert-butoxycarbonyl)-2,6-diazaspiro[3.4]octan-6-yl)-3-methylfuro[3,2-b]pyridine 4-oxide A solution of tert-butyl 6-(3-methylfuro[3,2-b]pyridin-5-yl)-2,6-diazaspiro[3.4]octane-2-carboxylate (264 mg, 0.769 mmol), 3-chloroperoxybenzoic acid (159 mg, 0.92 mmol, Sigma-Aldrich) in DCM (5 mL) was stirred at room temperature overnight. Additional 3-chloroperoxybenzoic acid (159 mg, 0.922 mmol, Sigma-Aldrich) was added and the mixture was stirred at room temperature for 30 min. Then, aqueous saturated sodium thiosulfate (5 mL, 1N) was added and the mixture was stirred at room temperature for 1 h. The mixture was extracted with EtOAc (2×20 in L) and the combined organic extracts were dried over $MgSO_4$ and concentrated in vacuo. Chromatographic purification of the residue (silica gel, 0-100% EtOAc/heptanes) provided 5-(2-(tert-butoxycarbonyl)-2,6-diazaspiro[3.4]octan-6-yl)-3-methylfuro[3,2-b]pyridine 4-oxide (153 mg, 55% yield) as a yellow solid. m/z (ESI): 360.0 $(M+H)^+$.

Step 5: tert-butyl 6-(7-chloro-3-methylfuro[3,2-b]pyridin-5-yl)-2,6-diazaspiro[3.4]octane-2-carboxylate To a solution of 5-(2-(tert-butoxycarbonyl)-2,6-diazaspiro[3.4]octan-6-yl)-3-methylfuro[3,2-b]pyridine 4-oxide (153 mg, 0.43 mmol) and DIPEA (0.164 mL, 0.94 mmol, Sigma-Aldrich) in MeCN (2 mL) was added phosphorus(v)oxychloride (0.080 mL, 0.851 mmol, Sigma-Aldrich). The mixture was stirred at 65° C. under nitrogen for 45 min. The mixture was carefully poured in an ice water (50 mL) and basified to pH=10-12 with NaOH (1N). The mixture was then extracted with EtOAc (2×30 mL) and the combined organic extracts were then dried over $MgSO_4$ and concentrated in vacuo. Chromatographic purification of the residue (silica gel, 0-100% EtOAc/heptane) provided tert-butyl 6-(7-chloro-3-methylfuro[3,2-b]pyridin-5-yl)-2,6-diazaspiro[3.4]octane-2-carboxylate (45 mg, 0.12 mmol, 28% yield) as a yellow solid. m/z (ESI): 378.2 $(M+H)^+$.

Step 6: tert-butyl 6-(3-methyl-7-(5-methyl-1H-indazol-4-yl)furo[3,2-b]pyridin-5-yl)-2,6-diazaspiro[3.4]octane-2-carboxylate A mixture of tert-butyl 6-(7-chloro-3-methylfuro[3,2-b]pyridin-5-yl)-2,6-diazaspiro[3.4]octane-2-carboxylate (45 mg, 0.119 mmol), 5-methyl-1H-indazol-4-yl boronic acid (84 mg, 0.476 mmol, Combi-Blocks), $Pd(PPh_3)_4$ (27.5 mg, 0.024 mmol, Sigma-Aldrich), and $Na_2CO_3$ (50.5 mg, 0.476 mmol, Sigma-Aldrich) in 1,4-dioxane (1 mL) and water (0.25 mL) was stirred at 90° C. overnight. The mixture was subjected to a microwave irradiation at 150° C. for 1 h. The mixture was cooled to room temperature, diluted with aqueous saturated $NaHCO_3$ (5 mL), and extracted with EtOAc (2×10 mL), The combined organic extracts were dried over $MgSO_4$ and concentrated in vacuo. Chromatographic purification of the residue (silica gel, 0-100% EtOAc/heptanes) provided tert-butyl 6-(3-methyl-7-(5-methyl-1H-indazol-4-yl)furo[3,2-b]pyridin-5-yl)-2,6-diazaspiro[3.4]octane-2-carboxylate (14 mg, 25% yield) as a yellow solid. m/z (ESI): 474.2 $(M+H)^+$.

Step 7: 1-(6-(3-methyl-7-(5-methyl-1H-indazol-4-yl)furo[3,2-b]pyridin-5-yl)-2,6-diazaspiro[3.4]octan-2-yl)prop-2-en-1-one (Example 3)

A mixture of tert-butyl 6-(3-methyl-7-(5-methyl-1H-indazol-4-yl)furo[3,2-b]pyridin-5-yl)-2,6-diazaspiro[3.4]octane-2-carboxylate (14 mg, 0.030 mmol) and TFA (0.044 mL, 0.59 mmol, Sigma-Aldrich) in DCM (0.5 mL) was stirred at room temperature for 1 h. Then, the mixture was concentrated and dried in vacuo. The residue was dissolved in DCM (0.5 mL) and DIPEA (0.077 mL, 0.443 mmol, Sigma-Aldrich) was added followed by a solution of acryloyl chloride (2.4 μL, 0.030 mmol, Sigma-Aldrich) in DCM (0.2 mL) at 0° C. The resulting mixture was then stirred at 0° C. for 5 min. Then, the mixture was quenched with satd $NaHCO_3$ (2 mL) and extracted with EtOAc (2×10 mL). The combined organic extracts were dried over $MgSO_4$ and concentrated in vacuo. Chromatographic purification of the residue (silica gel, 0-100% EtOAc:EtOH (3:1)/heptane) provided 1-(6-(3-methyl-7-(5-methyl-1H-indazol-4-yl)furo[3,2-b]pyridin-5-yl)-2,6-diazaspiro[3.4]octan-2-yl)prop-2-en-1-one Example 3 (8.5 mg, 67% yield) as a white solid. m/z (ESI): 428.1 $(M+H)^+$. $^1H$ NMR (400 MHz, Methanol-$d_4$) δ ppm 7.74 (s, 1H), 7.68 (s, 1H), 7.57 (d, J=8.8 Hz, 1H), 7.41 (d, J=8.8 Hz, 1H), 6.51 (d, J=9.0 Hz, 1H), 6.34-6.44 (m, 1H), 6.23-6.31 (m, 1H), 5.75 (dd, J=10.2, 2.1 Hz, 1H), 4.26-4.41 (i, 2H), 4.04-4.15 (m, 2H), 3.75-3.87 (m, 2H), 3.65 (td, J=6.8, 3.0 Hz, 2H), 2.39 (s, 3H), 2.33 (t, J=6.9 Hz, 2H), 2.15 (s, 3H). Indazole NH not observed in Methanol-$d_4$.

Example 4: 2-(2-acryloyl-2,6-diazaspiro[3.4]octan-6-yl)-4-(5-ethyl-1H-indazol-4-yl)quinoline-3-carbonitrile

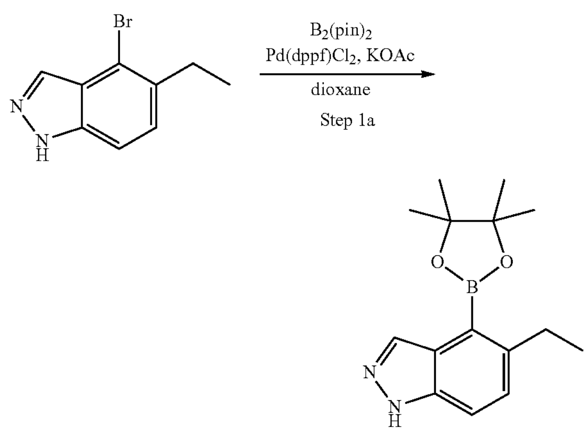

Step 1a: 5-ethyl-4-(4,4,5,5-tetramethyl-1,3,2-dioxaborolan-2-yl)-1H-indazole

A mixture of 4-bromo-5-ethyl-1H-indazole (500 mg, 2.22 mmol, Activate Scientific), bis(pinacolato)diboron (0.85 g, 3.3 mmol, Sigma-Aldrich), KOAc (654 mg, 6.6 mmol, Sigma-Aldrich) and $Pd(dppf)Cl_2$ (163 mg, 0.22 mmol, Combi-Blocks) in 1,4-dioxane (20 mL) was stirred at 100° C. overnight. The mixture was cooled to room temperature, diluted with aqueous saturated $NaHCO_3$ (70 mL) and extracted with EtOAc (2×100 mL). The combined organic extracts were dried over $MgSO_4$ and concentrated in vacuo. Chromatographic purification of the residue (silica gel, 0-100% EtOAc/heptanes) provided 5-ethyl-4-(4,4,5,5-tetramethyl-1,3,2-dioxaborolan-2-yl)-1H-indazole (80 mg, 13% yield) as a yellow solid. m/z (ESI): 273.2 $(M+H)^+$.

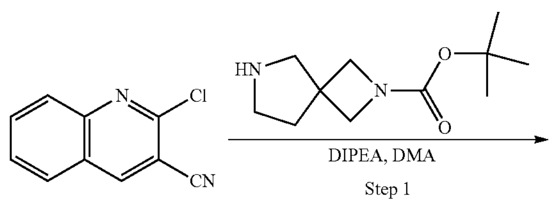

-continued

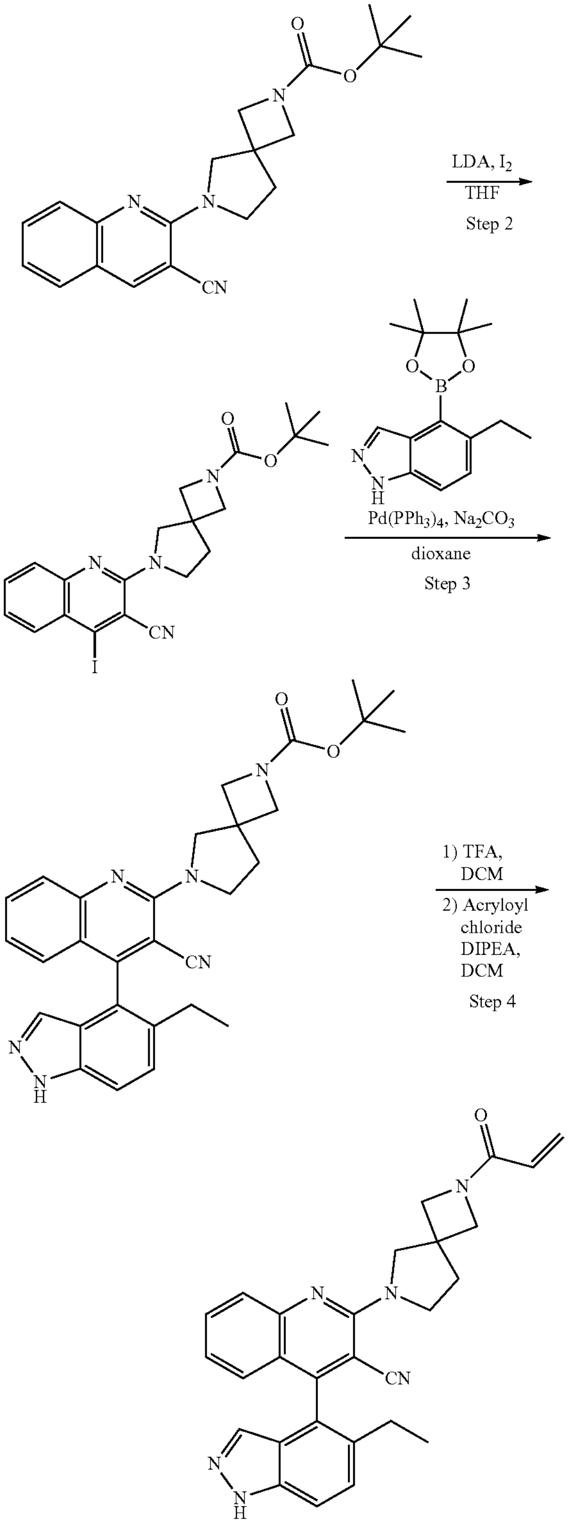

Example 4

Step 1: tert-butyl 6-(3-cyanoquinolin-2-yl)-2,6-diazaspiro[3.4]octane-2-carboxylate A solution of 2-chloroquinoline-3-carbonitrile (3.0 g, 15.91 mmol, Aurum Pharmatech), 2-(tert-butoxycarbonyl)-2,6-diazaspiro[3.4]octane (5.1 g, 23.9 mmol, PharmaBlock) and DIPEA (8.33 mL, 47.7 mmol, Sigma-Aldrich) in DMA (30 mL) was stirred at 120° C. for 40 min. The mixture was cooled to room temperature, diluted with water (100 mL), and extracted with EtOAc (2×150 mL). The combined organic extracts were dried over $MgSO_4$, and concentrated in vacuo. Chromatographic purification of the residue (silica gel, 0-100% EtOAc/heptanes) provided tert-butyl 6-(3-cyanoquinolin-2-yl)-2,6-diazaspiro[3.4]octane-2-carboxylate (5.17 g, 89% yield) as a yellow solid. m/z (ESI): 365.2 $(M+H)^+$. $^1H$ NMR (400 MHz, DMSO-$d_6$) δ ppm 8.77 (s, 1H), 7.77-7.82 (m, 1H), 7.66-7.73 (m, 1H), 7.58 (d, J=8.2 Hz, 1H), 7.27-7.34 (m, 1H), 3.93 (s, 4H), 3.78-3.86 (m, 4H), 2.19 (t, J=6.8 Hz, 2H), 1.40 (s, 9H).

Step 2: tert-butyl 6-(3-cyano-4-iodoquinolin-2-yl)-2,6-diazaspiro[3.4]octane-2-carboxylate To a −78° C. mixture of tert-butyl 6-(3-cyanoquinolin-2-yl)-2,6-diazaspiro[3.4]octane-2-carboxylate (500 mg, 1.37 mmol), iodine (348 mg, 1.372 mmol, Sigma-Aldrich) and THF (9 mL) under $N_2$ was added an LDA solution, 1.0 M in THF/hexanes (1.37 mL, 1.37 mmol, Sigma-Aldrich) dropwise. After addition, the mixture was stirred at the same temperature for 2 h. The mixture was cooled to −78° C. and additional LDA solution, 1.0 M in THF/hexanes (1.37 mL, 1.37 mmol, Sigma-Aldrich) was added dropwise. After addition, the mixture was stirred at −78° C. for 1 h and at room temperature overnight. The mixture was quenched with aqueous saturated $NH_4Cl$ (20 mL) and extracted with EtOAc (2×50 mL). The combined organic extracts were dried over $MgSO_4$ and concentrated in vacuo. Chromatographic purification of the residue (silica gel, 0%-100% EtOAc/heptanes) provided tert-butyl 6-(3-cyano-4-iodoquinolin-2-yl)-2,6-diazaspiro[3.4]octane-2-carboxylate (194 mg, 29% yield) as a yellow solid. m/z (ESI): 491.0 $(M+H)^+$.

Step 3: tert-butyl 6-(3-cyano-4-(5-ethyl-1H-indazol-4-yl)quinolin-2-yl)-2,6-diazaspiro[3.4]octane-2-carboxylate A mixture of tert-butyl 6-(3-cyano-4-iodoquinolin-2-yl)-2,6-diazaspiro[3.4]octane-2-carboxylate (130 mg, 0.265 mmol), 5-ethyl-4-(4,4,5,5-tetramethyl-1,3,2-dioxaborolan-2-yl)-1H-indazole (79 mg, 0.292 mmol), $Na_2CO_3$ (84 mg, 0.795 mmol, Sigma-Aldrich) and $Pd(PPh_3)_4$ (61.3 mg, 0.053 mmol, Strem Chemicals) in 1,4-dioxane (2 mL) and water (0.20 mL) was stirred at 100° C. overnight. The mixture was subjected to a microwave irradiation at 150° C. for 1 h. The mixture was purified by silica gel column chromatography using a gradient of 0-100% EtOAc/heptanes to provide tert-butyl 6-(3-cyano-4-(5-ethyl-1H-indazol-4-yl)quinolin-2-yl)-2,6-diazaspiro[3.4]octane-2-carboxylate (9 mg, 6.7% yield) as a yellow solid. m/z (ESI): 509.3 $(M+H)^+$.

Step 4: 4-(5-ethyl-1H-indazol-4-yl)-2-(2-(2-propenoyl)-2,6-diazaspiro[3.4]octan-6-yl)-3-quinolinecarbonitrile A mixture of tert-butyl 6-(3-cyano-4-(5-ethyl-1H-indazol-4-yl)quinolin-2-yl)-2,6-diazaspiro[3.4]octane-2-carboxylate (9.0 mg, 0.018 mmol) and TFA (0.026 mL, 0.354 mmol, Sigma-Aldrich) in DCM (0.5 mL) was stirred at room temperature for 1 h. The mixture was concentrated in vacuo. The crude was dissolved in DCM (0.5 mL) and DIPEA (31 μL, 0.177 mmol, Sigma-Aldrich) was added. The mixture was cooled to 0° C. under $N_2$ and a solution of acryloyl chloride (1.4 μL, 0.018 mmol, Sigma-Aldrich) in DCM (0.1 mL) was added. The resulting mixture was stirred at 0° C. for 5 min. The mixture was diluted with water (0.5 mL) and concentrated in vacuo. The residue was taken up in DMSO (1 mL) and purified via preparative HPLC (Phenomenex Gemini $C_{18}$ column, 150×30 mm, 10-100% 0.1% TFA in $MeCN/H_2O$) to provide 2-(2-acryloyl-2,6-diazaspiro[3.4]octan-6-yl)-4-(5-ethyl-1H-indazol-4-yl)quinoline-3-carbonitrile (1.0 mg, 12% yield) as a yellow solid, TFA salt. m/z (ESI): 462.8 $(M+H)^+$. $^1H$ NMR (400 MHz, Methanol-$d_4$) δ ppm 7.83 (d J=8.6 Hz, 1H), 7.67-7.75 (m, 2H), 7.56 (d, J=8.8 Hz, 1H), 7.43 (d, J=5.0 Hz, 1H), 7.14-7.21 (m, 1H), 7.05 (d, J=8.2 Hz, 1H), 6.34-6.44 (m, 1H), 6.23-6.31 (m, 1H), 5.75 (dd, J=10.2, 2.1 Hz, 1H), 4.36-4.45 (m, 1H), 4.25-4.36 (m, 1H), 4.13-4.21 (m, 3H), 4.03-4.11 (m, 3H), 2.47 (qd, J=7.6, 4.2 Hz, 2H), 2.36 (t, J=6.9 Hz, 2H), 1.12 (td, J=7.5, 1.3 Hz, 3H). $^{19}F$ NMR (376 MHz, Methanol-$d_4$) δ ppm −77.41 (br d, J=1.7 Hz, 3 F). Indazole NH not observed in Methanol-$d_4$.

Example 5: 1-(6-(7-methyl-4-(5-methyl-1H-indazol-4-yl)-6,7-dihydro-5H-pyrrolo[2,3-d]pyrimidin-2-yl)-2,6-diazaspiro[3.4]octan-2-yl)prop-2-en-1-one

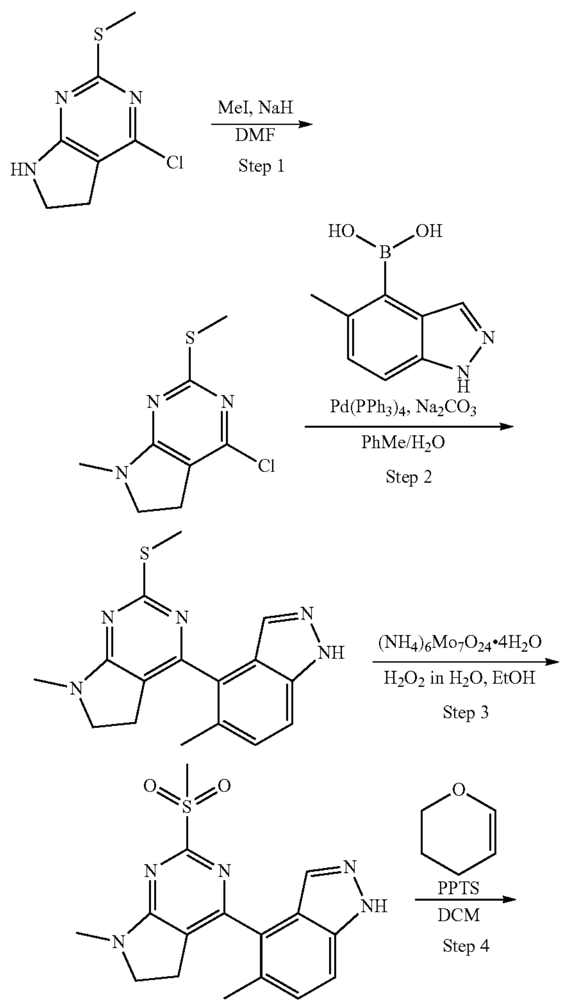

-continued

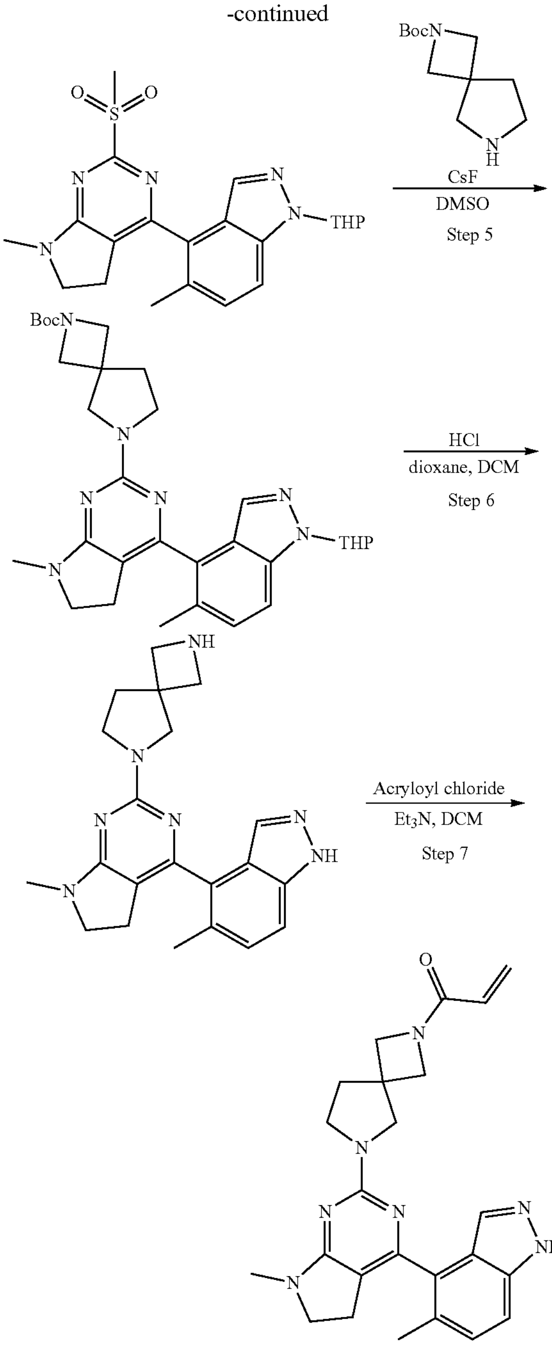

Example 5

Step 1: 4-chloro-7-methyl-2-(methylthio)-6,7-dihydro-5H-pyrrolo[2,3-d]pyrimidine To a solution of 4-chloro-2-(methylthio)-6,7-dihydro-5H-pyrrolo[2,3-d]pyrimidine (obtained as in Example 9, Step 5) (2.5 g, 12.40 mmol) in DMF (25 mL) was added sodium hydride (0.89 g, 18.6 mmol) at 0° C. and stirred for 15 min. Then, methyl iodide (1.55 mL, 24.8 mmol) was added dropwise and the resulting mixture was allowed to stir at room temperature for 1 h. Upon completion, the reaction mixture was quenched with aqueous saturated $NH_4Cl$ and extracted with EtOAc. The organic extracts were washed with brine, dried over $Na_2SO_4$, and concentrated in vacuo to give 4-chloro-7-methyl-2-(methylthio)-6,7-dihydro-5H-pyrrolo[2,3-d]pyrimidine (2.6 g, 97% yield) as a light-yellow solid, which was used in the following step as is. m/z (ESI): 216.0 $(M+H)^+$.

Step 2: 7-methyl-4-(5-methyl-1H-indazol-4-yl)-2-(methylthio)-6,7-dihydro-5H-pyrrolo[2,3-d]pyrimidine To a degassed solution of 4-chloro-7-methyl-2-(methylthio)-6,7-dihydro-5H-pyrrolo[2,3-d]pyrimidine (0.50 g, 2.318 mmol), (5-methyl-1H-indazol-4-yl)boronic acid (0.449 g, 2.55 mmol), and $Na_2CO_3$ (0.614 g, 5.80 mmol) in toluene (10 mL) and water (2.5 mL), was added $Pd(PPh_3)_4$ (0.268 g, 0.232 mmol, Hindustan platinum). The reaction mixture was heated at 90° C. for 20 h. Upon completion, the reaction mixture was cooled to room temperature, diluted with water, and extracted with EtOAc. The combined organic extracts were dried over $Na_2SO_4$, and concentrated in vacuo. The mixture was purified by silica gel chromatography eluting with a gradient of 0-50% EtOAc in hexanes, to provide 7-methyl-4-(5-methyl-1H-indazol-4-yl)-2-(methylthio)-6,7-dihydro-5H-pyrrolo[2,3-d]pyrimidine (0.40 g, 55% yield) as a pale yellow solid. m/z (ESI): 312.1 $(M+H)^+$.

Step 3: 7-methyl-4-(5-methyl-1H-indazol-4-yl)-2-(methylsulfonyl)-6,7-dihydro-5H-pyrrolo[2,3-d]pyrimidine To a solution of 7-methyl-4-(5-methyl-1H-indazol-4-yl)-2-(methylthio)-6,7-dihydro-5H-pyrrolo[2,3-d]pyrimidine (0.40 g, 1.284 mmol) in EtOH (8.0 mL) were added ammonium molybdate tetrahydrate (0.794 g, 0,642 mmol) and $H_2O_2$ (30% in water) (0.197 mal, 6.42 mmol) at 0 C. The reaction mixture was stirred at room temperature for 2 h. An additional 5 equivalents of $H_2O_2$ (30% in water) (0.197 mL, 6.42 mmol) were added and the mixture was allowed to stir at room temperature for 12 h. Upon completion, the reaction was quenched with ice-cold water and extracted with EtOAc. The combined organic extracts were dried over $Na_2SO_4$, and concentrated in vacuo. The residue was purified by silica gel chromatography eluting with a gradient of 0-100% EtOAc in hexanes to provide 7-methyl-4-(5-methyl-1H-indazol-4-yl)-2-(methylsulfonyl)-6,7-dihydro-5H-pyrrolo[2,3-d]pyrimidine (0.30 g, 68% yield) as an off-white solid. m/z (ESI): 344.9 $(M+1H)^+$.

Step 4: 7-methyl-4-(5-methyl-1-(tetrahydro-2H-pyran-2-yl)-1H-indazol-4-yl)-2-(methylsulfonyl)-6,7-dihydro-5H-pyrrolo[2,3-d]pyrimidine To a solution of 7-methyl-4-(5-methyl-1H-indazol-4-yl)-2-(methylsulfonyl)-6,7-dihydro-5H-pyrrolo[2,3-d]pyrimidine (0.15 g, 0.437 mmol) and PPTS (0.022 g, 0.087 mmol) in DCM (1.5 mL) was added 3,4-dihydro-2H-pyran (0.120 mL, 1.310 mmol). The reaction was allowed to stir at concentrated in vacuo for 16 h. Upon completion, the reaction was concentrated and the residue was purified by silica gel chromatography eluting with a gradient of 0-100% EtOAc in hexanes to provide 7-methyl-4-(5-methyl-1-(tetrahydro-2H-pyran-2-yl)-1H-indazol-4-yl)-2-(methylsulfonyl)-6,7-dihydro-5H-pyrrolo[2,3-d]pyrimidine (0.12 g, 64% yield) as a colorless liquid. m/z (ESI): 428.8 $(M+H)^+$.

Step 5: tert-butyl 6-(7-methyl-4-(5-methyl-1-(tetrahydro-2H-pyran-2-yl)-1H-indazol-4-yl)-6,7-dihydro-5H-pyrrolo[2,3-d]pyrimidin-2-yl)-2,6-diazaspiro[3.4]octane-2-carboxylate To a solution of 7-methyl-4-(5-methyl-1-(tetrahydro-2H-pyran-2-yl)-1H-indazol-4-yl)-2-(methylsulfonyl)-6,7-dihydro-5H-pyrrolo[2,3-d]pyrimidine (0.12 g, 0.281 mmol) and tert-butyl 2,6-diazaspiro[3.4]octane-2-carboxylate (0.072 g, 0.337 mmol, J&W Pharma) in DMSO (1.2 mL) was added CsF (0.213 g, 1.40 mmol, Chempure). The reaction mixture was heated to 90° C. for 16 h. Upon completion, the reaction mixture was cooled to room temperature and quenched with ice-cold water and extracted with EtOAc. The combined organic extracts were dried over $Na_2SO_4$ and concentrated in vacuo. The residue was purified by silica gel chromatography eluting with a gradient of 0-100% EtOAc in hexanes to provide tert-butyl 6-(7-methyl-4-(5-methyl-1-(tetrahydro-2H-pyran-2-yl)-1H-indazol-4-yl)-6,7-dihydro-5H-pyrrolo[2,3-d]pyrimidin-2-yl)-2,6-diazaspiro[3.4]octane-2-carboxylate (80 mg, 51% yield) as a colorless liquid. m/z (ESI): 560.8 $(M+H)^+$.

Step 6: 7-methyl-4-(5-methyl-1H-indazol-4-yl)-2-(2,6-diazaspiro[3.4]octan-6-yl)-6,7-dihydro-5H-pyrrolo[2,3-d]pyrimidine hydrochloride To a solution of tert-butyl 6-(7-methyl-4-(5-methyl-1-(tetrahydro-2H-pyran-2-yl)-1H-indazol-4-yl)-6,7-dihydro-5H-pyrrolo[2,3-d]pyrimidin-2-yl)-2,6-diazaspiro[3.4]octane-2-carboxylate (0.08 g, 0.143 mmol) in DCM (2 mL) was added HCl (0.715 mL, 2.86 mmol, 4 M in dioxane) at 0° C. The reaction mixture was stirred at room temperature for 4 h. Upon completion, the mixture was concentrated in vacuo and triturated with $Et_2O$ to afford 7-methyl-4-(5-methyl-1H-indazol-4-yl)-2-(2,6-diazaspiro[3.4]octan-6-yl)-6,7-dihydro-5H-pyrrolo[2,3-d]pyrimidine hydrochloride as an off-white solid, which was used in the following step as is. m/z (ESI): 375.9 $(M+H)^+$.

Step 7: 1-(6-(7-methyl-4-(5-methyl-1H-indazol-4-yl)-6,7-dihydro-5H-pyrrolo[2,3-d]pyrimidin-2-yl)-2,6-diazaspiro[3.4]octan-2-yl)prop-2-en-1-one (Example 5)

To a solution of 7-methyl-4-(5-methyl-1H-indazol-4-yl)-2-(2,6-diazaspiro[3.4]octan-6-yl)-6,7-dihydro-5H-1-pyrrolo[2,3-d]pyrimidine hydrochloride (0.10 g, 0.243 mmol) and TEA (0.102 mL, 0.728 mmol) in DCM (2 mL) was added acryloyl chloride (0.022 mL, 0.267 mmol) at 0° C. The reaction was allowed to stir for 10 min while warming to room temperature. Upon completion, the reaction was concentrated and the residue was purified by preparative HPLC (Phenomenex Gemini $C_{18}$ column, 150×30 mm, 10-100% 0.1% TFA in MeCN/$H_2O$) to afford 1-(6-(7-methyl-4-(5-methyl-1H-indazol-4-yl)-6,7-dihydro-5H-pyrrolo[2,3-d]pyrimidin-2-yl)-2,6-diazaspiro[3.4]octan-2-yl)prop-2-en-1-one Example 5 (0.01 g, 10% yield) as white solid. m/z (ESI): 429.9 $(M+H)^+$. $^1H$ NMR (400 MHz, DMSO-$d_6$) δ ppm 13.00 (s, 1H), 7.69 (s, 1H), 7.45 (d, J=8.4 Hz, 1H), 7.25 (d, J=8.4 Hz, 1H), 6.31-6.33 (m, 1H), 6.10-6.14 (m, 1H), 5.66 (dd, J=10.2, 2.3 Hz, 1H), 4.03-4.37 (m, 2H), 3.87 (t, J=10.8 Hz, 2H), 3.61-3.69 (m, 2H), 3.42-3.49 (m, 4H), 2.92 (s, 3H), 2.54-2.62 (m, 2H), 2.28 (s, 3H), 2.12 (dd, J=8.9, 6.0 Hz, 2H).

Example 6: 1-(6-(3-cyclopropyl-4-(5-methyl-1H-indazol-4-yl)quinolin-2-yl)-2,6-diazaspiro[3.4]octan-2-yl)prop-2-en-1-one

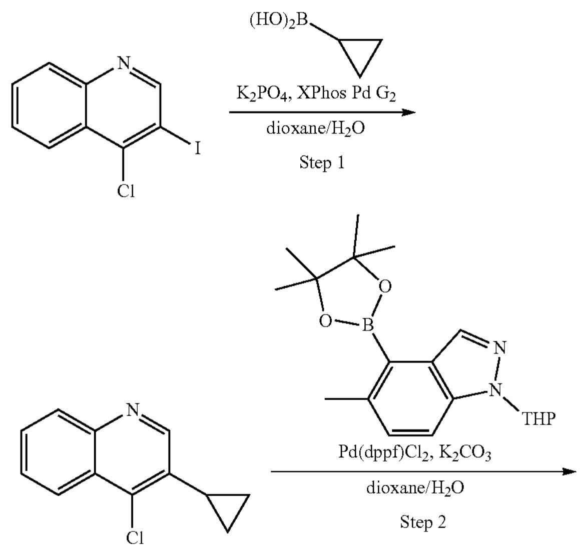

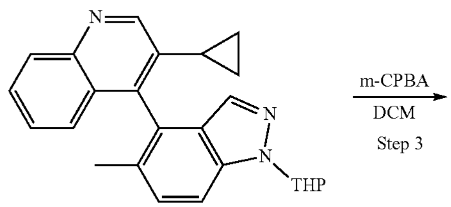

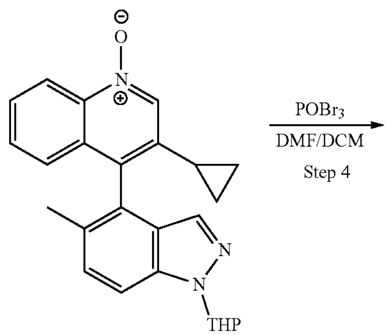

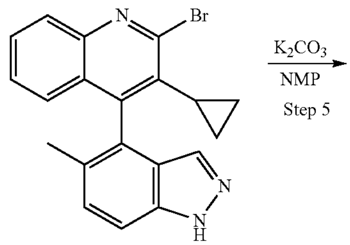

-continued

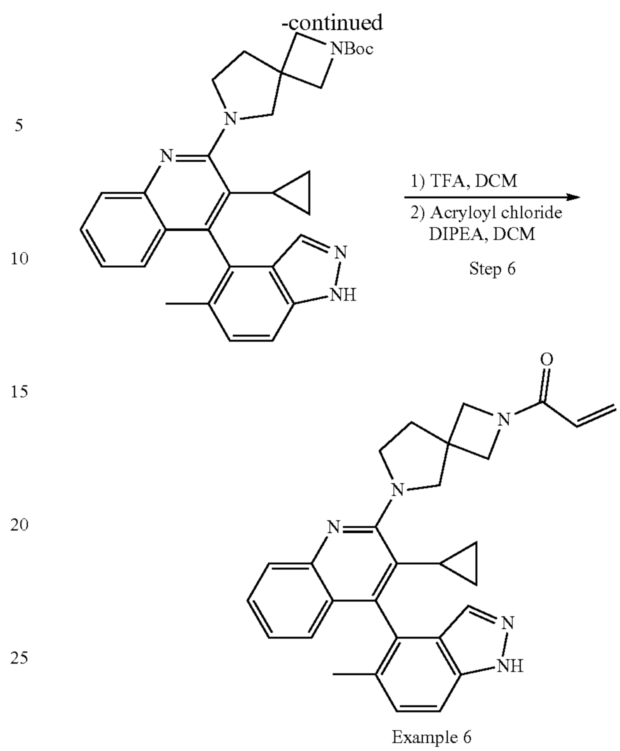

Example 6

Step 1: 4-chloro-3-cyclopropylquinoline

To a solution of 4-chloro-3-iodoquinoline (5.0 g, 17.3 mmol, Accela), cyclopropylboronic acid (2.23 g, 25.9 mmol) and $K_3PO_4$ (9.17 g, 43.2 mmol) in 1,4-dioxane (10 mL) and water (2 mL) was added XPhos Pd G2 (0,679 g, 0.864 mmol, Sigma-Aldrich). The reaction was stirred at 90° C. under $N_2$ for 48 h. The mixture was cooled to room temperature and filtered. The filtrate was concentrated in vacuo. Chromatographic purification of the residue (silica gel, petroleum ether:EtOAc=1:9) provided 4-chloro-3-cyclopropylquinoline (1.66 g, 47% yield) as a yellow solid. m/z (ESI): 204.1 $(M+H)^+$.

Step 2: 3-cyclopropyl-4-(5-methyl-1-(tetrahydro-2H-pyran-2-yl)-1Hindazol-4-yl)quinoline To a solution of 4-chloro-3-cyclopropylquinoline (1.66 g, 8.15 mmol), 5-methyl-1-(tetrahydro-2H-pyran-2-yl)-4-(4,4,5,5-tetramethyl-1,3,2-dioxaborolan-2-yl)-1H-indazole (3.07 g, 8.97 mmol) and $K_2CO_3$ (2.84 g, 20.38 mmol) and 1,4-dioxane (10 mL):water (2 mL) was added $Pd(dppf)Cl_2$ (0.596 g, 0.815 mmol). The resulting mixture was subjected to microwave irradiation at 110° C. for 3 h. The mixture was cooled to room temperature, filtered, and the filtrate concentrated in vacuo. Chromatographic purification of the residue (silica gel, petroleum ether:EtOAc=4:1) provided 3-cyclopropyl-4-(5-methyl-1-(tetrahydro-2H-pyran-2-yl)-1Hindazol-4-yl)quinoline (1.2 g, 38% yield) as a white foam. m/z (ESI): 384.1 $(M+H)^+$.

Step 3: 3-cyclopropyl-4-(5-methyl-1-(tetrahydro-2H-pyran-2-yl)-1H-indazol-4-yl)quinoline 1-oxide To a 0° C. solution of 3-cyclopropyl-4-(5-methyl-1-(tetrahydro-2H-pyran-2-yl)-1H-indazol-4-yl)quinoline (1.2 g, 3.13 mmol) and DCM (30 mL) was added m-CPBA (1.35 g, 7.82 mmol). The reaction was allowed to stir at room temperature. Upon completion, the mixture was quenched with water (20 mL) and extracted with EtOAc (3×20 mL). The combined organics extracts were washed with brine (50 mL), dried over $Na_2SO_4$ and concentrated in vacuo. Chromatographic purification of the residue (silica gel, DCM: MeOH=9:1) provided 3-cyclopropyl-4-(5-methyl-1-(tetrahydro-2H-pyran-2-yl)-1H-indazol-4-yl)quinoline 1-oxide (0.72 g, 58% yield) as a yellow foam, m/z (ESI): 400.2 $(M+H)^+$.

Step 4: 2-bromo-3-cyclopropyl-4-(5-methyl-1H-indazol-4-yl)quinoline

A solution of 3-cyclopropyl-4-(5-methyl-1-(tetrahydro-2H-pyran-2-yl)-1H-indazol-4-yl)quinoline 1-oxide (720 mg, 1.80 mmol) in DCM (6 mL) and DMF (0.1 mL) was added phosphoryl tribromide (620 mg, 2.16 mmol) at 0° C. under $N_2$. The resulting mixture was stirred at room temperature for 1 h. The mixture was quenched with aqueous saturated $NaHCO_3$ (40 mL) and extracted with EtOAc (3×20 mL). The combined organic extracts were washed with brine (50 mL), dried over $Na_2SO_4$, and concentrated in vacuo. Chromatographic purification of the residue (silica gel, DCM:MeOH=9:1) to give 2-bromo-3-cyclopropyl-4-(5-methyl-1H-indazol-4-yl)quinoline (390 mg, 57% yield) as a yellow solid. m/z (ESI): 378.0 $(M+H)^+$.

Step 5: tert-butyl 6-(3-cyclopropyl-4-(5-methyl-1H-indazol-4-yl)quinolin-2-yl)-2,6-diazaspiro[3.4]octane-2-carboxylate A solution of 2-bromo-3-cyclopropyl-4-(5-methyl-1H-indazol-4-yl)quinoline (390 mg, 1.03 mmol), tert-butyl 2,6-diazaspiro[3.4]octane-2-carboxylate (241 mg, 1.13 mmol) and $K_2CO_3$ (285 mg, 2.062 mmol) in NMP (6 mL). The reaction mixture was subjected to microwave irradiation at 130° C. for 2 h. The mixture was filtered and the filtrate concentrated in vacuo. Chromatographic purification of the residue (silica gel, DCM:MeOH, 9:1) afforded tert-butyl 6-(3-cyclopropyl-4-(5-methyl-1H-indazol-4-yl)quinolin-2-yl)-2,6-diazaspiro[3.4]octane-2-carboxylate (450 mg, 86% yield) as a yellow solid. m/z (ESI): 510.2 $(M+H)^+$.

Step 6: 1-(6-(3-cyclopropyl-4-(5-methyl-1H-indazol-4-yl)quinolin-2-yl)-2,6-diazaspiro[3.4]octan-2-yl)prop-2-en-1-one (Example 6)

To a solution of tert-butyl 6-(3-cyclopropyl-4-(5-methyl-1H-indazol-4-yl)quinolin-2-yl)-2,6-diazaspiro[3.4]octane-2-carboxylate (450 mg, 0.883 mmol) in DCM (3 mL) was added TFA (2 mL, 0.883 mmol), The resulting mixture was stirred at room temperature for 1 h. The mixture was concentrated in vacuo. The residue was dissolved in DCM (6 mL) and DIPEA (681 mg, 5.27 mmol) was added followed by acryloyl chloride (88 mg, 0.967 mmol) at −40° C. The resulting mixture was stirred for 20 min at −40° C. The mixture was quenched with water (20 mL) and extracted with DCM (3×20 mL). The organic extracts were dried over $Na_2SO_4$ and concentrated in vacuo. The crude product was purified by HPLC {Instrument Gilson 281 (PIG-009); Column Xtimate Prep $C_{18}$ OBD (21.2×250 mm, 10 um) with a mobile Phase A: Water (10 mM $NH_4HCO_3$); B: MeCN; Gradient 50-60% B with a flow rate of 30 mL/min} to give 1-(6-(3-cyclopropyl-4-(5-methyl-1H-indazol-4-yl)quinolin-2-yl)-2,6-diazaspiro[3.4]octan-2-yl)prop-2-en-1-one Example 6 (130 mg, 32% yield) as a white solid. m/z (ESI): 464.1 $(M+H)^+$. $^1H$ NMR (400 MHz, DMSO-$d_6$) δ ppm 13.20-12.88 (br s, 1H), 765 (d, J=7.9 Hz, 1H), 7.56 (d, J=8.5 Hz, 1H), 7.52-7.44 (m, 2H), 7.39 (d, J=8.6 Hz, 1H), 7.04 (ddd, J=8.4, 7.0, 1.8 Hz, 1H), 6.92-6.85 (m, 1H), 6.39-6.30 (m, 1H), 6.12 (dd, J=17.0, 2.3 Hz, 1H), 5.71-5.64 (n, 1H), 4.29 (d, J=8.5 Hz, 1H), 4.20 (dd, J=16.8, 8.6 Hz, 1H), 4.01 (d, J=10.2 Hz, 1H), 3.96-3.71 (m, 5H), 2.24-2.11 (m, 2H), 2.01 (d, J=10.3 Hz, 3H), 1.77-1.67 (m, 1H), 0.54-0.42 (m, 1H), 0.33-0.07 (m, 3H).

Example 7: 1-methyl-4-(5-methyl-1H-indazol-4-yl)-6-(2-(2-propenoyl)-2,6-diazaspiro[3.4]octan-6-yl)-1H-benzimidazole-5-carbonitrile

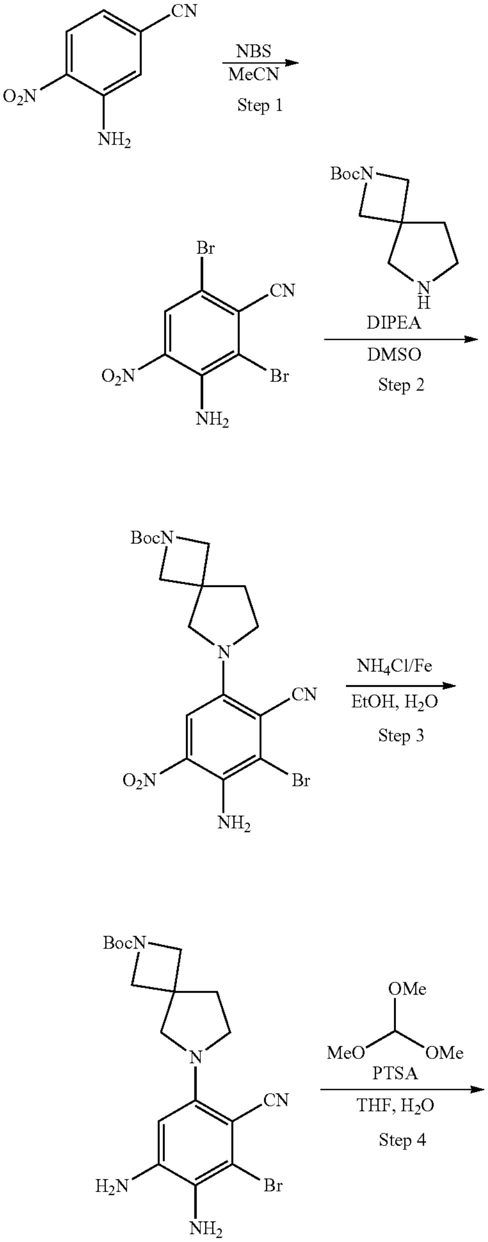

-continued

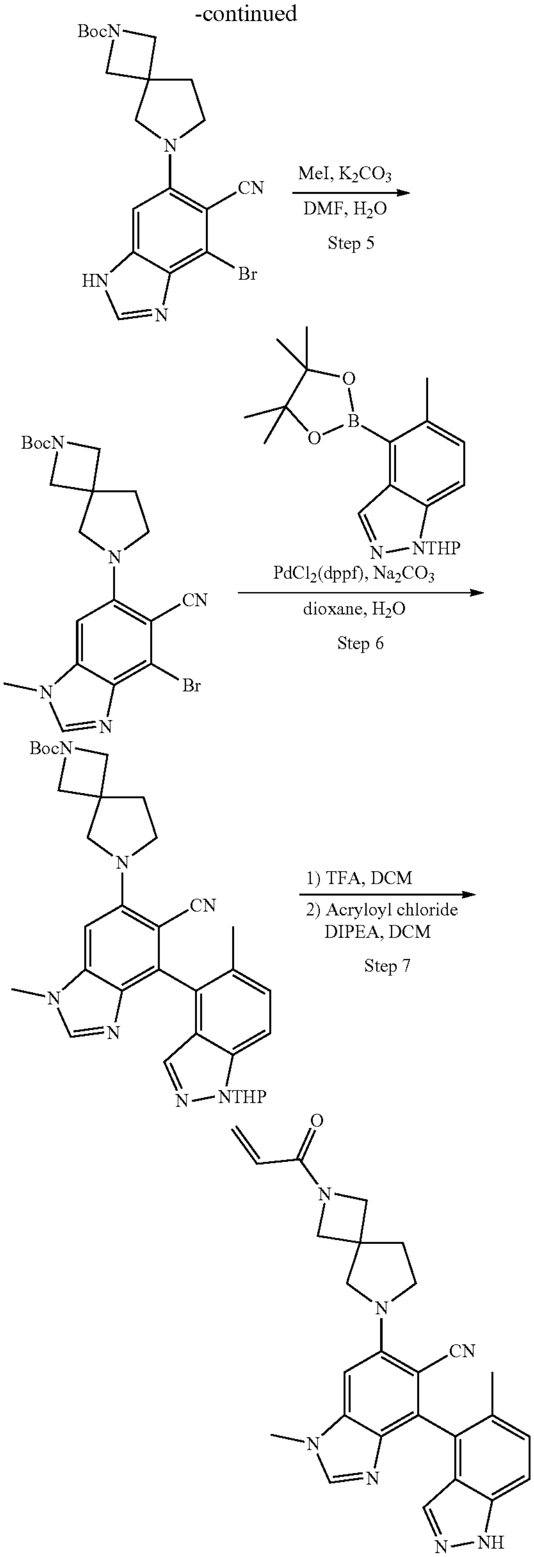

Example 7

Step 1: 3-amino-2,6-dibromo-4-nitrobenzonitrile

A mixture of 3-amino-4-nitrobenzonitrile (500 mg, 3.06 mmol) and NBS (546 mg, 3.06 mmol) in MeCN (10 mL) was stirred at 40° C. for 16 h under $N_2$. The reaction mixture was diluted with water (50 mL) and extracted with EtOAc (100×2 mL). The solution was concentrated in vacuo. The crude material was absorbed onto a plug of silica gel and purified by chromatography through a silica gel column, eluting with a gradient of 0-10% EtOAc in hexanes, to provide 3-amino-2,6-dibromo-4-nitrobenzonitrile (950 mg, 97% yield) as a yellow solid.

Step 2: tert-butyl 6-(4-amino-3-bromo-2-cyano-5-nitrophenyl)-2,6-diazaspiro[3.4]octane-2-carboxylate A mixture of 3-amino-2,6-dibromo-4-nitrobenzonitrile (300 mg, 0.935 mmol) and tert-butyl 2,6-diazaspiro[3.4]octane-2-carboxylate (198 mg, 0,935 mmol) and DIPEA (490 μL, 2.80 mmol) in DMSO (1 mL) was stirred at 120° C. for 2 h. The reaction mixture was diluted with water (10 mL) and extracted with DCM (30 mL). The organic extract was washed with brine (10 mL), dried over $Na_2SO_4$, and concentrated in vacuo. The crude material was absorbed onto a plug of silica gel and purified by chromatography through a Redi-Sep pre-packed silica gel column (12 g), eluting with 20% EtOAc in hexanes, to provide tert-butyl 6-(4-amino-3-bromo-2-cyano-5-nitrophenyl)-2,6-diazaspiro[3.4]octane-2-carboxylate (200 mg, 47% yield) as a yellow solid. m/z (ESI): 474.1 $(M+Na)^+$.

Step 3: tert-butyl 6-(4,5-diamino-3-bromo-2-cyanophenyl)-2,6-diazaspiro[3.4]octane-2-carboxylate A mixture of $NH_4Cl$ (237 mg, 4.42 mmol), iron (247 mg, 4.42 mmol) and tert-butyl 6-(4-amino-3-bromo-2-cyano-5-nitrophenyl)-2,6-diazaspiro[3.4]octane-2-carboxylate (200 mg, 0.442 mmol) in EtOH (10 mL):water (3 mL) was stirred at 60° C. for 2 h. The reaction mixture was diluted with water (10 mL) and extracted with DCM (30 mL). The organic extract was washed with brine (10 mL), dried over $Na_2SO_4$, and concentrated in vacuo. The crude material was absorbed onto a plug of silica gel and purified by chromatography through a Redi-Sep pre-packed silica gel column (12 g), eluting with 20% EtOAc in hexanes, to provide tert-butyl 6-(4,5-diamino-3-bromo-2-cyanophenyl)-2,6-diazaspiro[3.4]octane-2-carboxylate (180 mg, 96% yield) as a yellow solid. m/z (ESI): 422.1 $(M+H)^+$.

Step 4: tert-butyl 6-(7-bromo-6-cyano-1H-benzo[d]indazol-5-yl)-2,6-diazaspiro[3.4]octane-2-carboxylate A mixture of trimethylorthoformate (45.2 mg, 0.426 mmol), PTSA (81 mg, 0.426 mmol) and tert-butyl 6-(4,5-diamino-3-bromo-2-cyanophenyl)-2,6-diazaspiro[3.4]octane-2-carboxylate (180 mg, 0.426 mmol) and THE (10 mL):water (3 mL) was stirred at 60° C. for 2 h. The reaction mixture was diluted with water (10 mL) and extracted with DCM (30 mL). The organic extract was washed with brine (10 mL), dried over $Na_2SO_4$, and concentrated in vacuo. The crude material was absorbed onto a plug of silica get and purified by chromatography through a Redi-Sep pre-packed silica gel column (12 g), eluting with 20% EtOAc in hexanes, to provide tert-butyl 6-(7-bromo-6-cyano-1H-benzo[d]imidazol-5-yl)-2,6-diazaspiro[3.4]octane-2-carboxylate (180 mg, 98% yield) as a yellow solid. m/z (ESI): 432.0 $(M+H)^+$.

Step 5: tert-butyl 6-(7-bromo-6-cyano-1-methyl-1H-benzo[d]indazol-5-yl)-2,6-diazaspiro[3.4]octane-2-carboxylate A mixture of potassium carbonate (57.5 mg 0.416 mmol), methyl iodide (26.0 μL, 0.416 mmol) and tert-butyl 6-(7- bromo-6-cyano-1H-benzo[d]imidazol-5-yl)-2,6-diazaspiro[3.4]octane-2-carboxylate (180 mg, 0.416 mmol) and DMF (10 mL):water (3 mL) was stirred at 20° C. for 2 h. The reaction mixture was diluted with water (10 mL) and extracted with DCM (30 mL). The organic extract was washed with brine (10 mL), dried over $Na_2SO_4$, and concentrated in vacuo. The crude material was absorbed onto a plug of silica gel and purified by chromatography through a Redi-Sep pre-packed silica gel column (12 g), eluting with 20% EtOAc in hexanes, to provide tert-butyl 6-(7-bromo-6-cyano-1-methyl-1H-benzo[d]imidazol-5-yl)-2,6-diazaspiro[3.4]octane-2-carboxylate (180 mg, 97% yield) as a yellow solid. m/z (ESI): 446.0 $(M+H)^+$.

Step 6: tert-butyl 6-(5-cyano-1-methyl-4-(5-methyl-1-(tetrahydro-2H-pyran-2-yl)-1H-indazol-4-yl)-1H-benzo[d]imidazol-6-yl)-2,6-diazaspiro[3.4]octane-2-carboxylate A mixture of $Na_2CO_3$ (71.2 mg, 0.672 mmol), $PdCl_2$(dppf) (16.39 mg, 0.022 mmol), tert-butyl 6-(4-bromo-5-cyano-1-methyl-1H-benzo[d]imidazol-6-yl)-2,6-diazaspiro[3.4]octane-2-carboxylate (100 mg, 0.224 mmol) and 5-methyl-1-(tetrahydro-2H-pyran-2-yl)-4-(4,4,5,5-tetramethyl-1,3,2-dioxaborolan-2-yl)-1H-indazole (77 mg, 0.224 mmol) and 1,4-dioxane (20 mL):water (5 mL) was stirred at 100° C. for 2 h under $N_2$. The reaction mixture was diluted with water (50 mL) and extracted with DCM (50 mL). The organic extract was washed with brine (50×mL), dried over $Na_2SO_4$, and concentrated in vacuo. The crude material was absorbed onto a plug of silica gel and purified by chromatography through a silica gel column, eluting with 20% EtOAc in hexanes, to provide tert-butyl 6-(5-cyano-1-methyl-4-(5-methyl-1-(tetrahydro-2H-pyran-2-yl)-1H-indazol-4-yl)-1H-benzo[d]imidazol-6-yl)-2,6-diazaspiro[3.4]octane-2-carboxylate (120 mg, 92% yield) as a yellow solid.

Step 7: 1-methyl-4-(5-methyl-1H-indazol-4-yl)-6-(2-(2-propenoyl)-2,6-diazaspiro[3.4]octan-6-yl)-1H-benzimidazole-5-carbonitrile A mixture of TFA (47.7 μL, 0.619 mmol) and tert-butyl 6-(5-cyano-1-methyl-4-(5-methyl-1-(tetrahydro-2H-pyran-2-yl)-1H-indazol-4-yl)-1H-benzo[d]imidazol-6-yl)-2,6-diazaspiro[3.4]octane-2-carboxylate (120 mg, 0.206 mmol) and DCM (1 mL) was stirred at 20° C. for 2 h. The solution was concentrated in vacuo to remove as much TFA as possible. The remaining solids were resuspended in DCM (2 mL) and cooled to −40° C. Acryloyl chloride (18.7 mg, 0.21 mmol) and DIPEA (108 μL, 0.62 mmol) were added and the solution was allowed to stir for 2 h. The solution was concentrated in vacuo. The crude material was purified by reverse-phase preparative HPLC using a Phenomenex Luna column, 5 μm, $C_{18}$(2), 100 Å, 150×30 mm, 0.1% $NH_4HCO_3$ in $MeCN/H_2O$, gradient 0-100% over 15 min to provide 6-(2-acryloyl-2,6-diazaspiro[3.4]octan-6-yl)-1-methyl-4-(5-methyl-1H-indazol-4-yl)-1H-benzo[d]imidazole-5-carbonitrile (10.5 mg, 11% yield) as a white solid. $^1H$ NMR (400 MHz, DMSO-$d_6$) δ 13.03 (s, 1H), 8.16 (s, 1H), 7.58 (s, 1H), 748 (d, J=8.5 Hz, 1H), 7.31 (d, J=8.6 Hz, 1H), 6.90 (s, 1H), 6.32 (dd, J=17.3, 10.1 Hz, 1H), 6.11 (dd, J=17.0, 2.3 Hz, 1H), 5.67 (d, J=11.3 Hz, 1H), 4.45-3.85 (m, 8H), 3.78 (s, 3H), 2.31-2.11 (m, 5H). m/z (ESI): 452.1 $(M+H)^+$.

Example 8: 1-(6-(3-Methyl-4-(5-methyl-1H-indazol-4-yl)quinolin-2-yl)-2,6-diazaspiro[3.4]octan-2-yl)prop-2-en-1-one

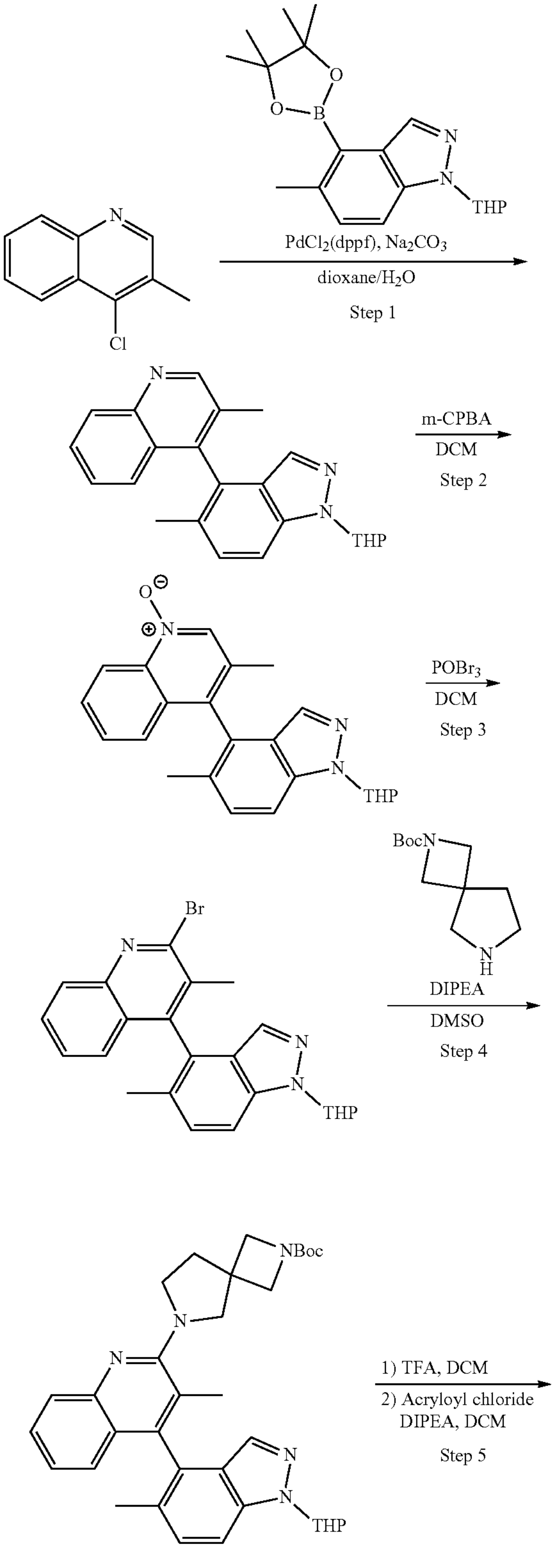

-continued

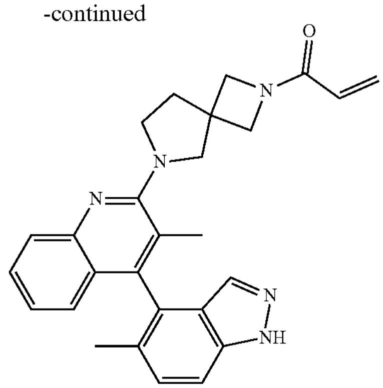

Example 8

Step 1: 3-methyl-4-(5-methyl-1-(tetrahydro-2H-pyran-2-yl)-1H-indazol-4-yl)quinoline A mixture of $Na_2CO_3$ (317 mg, 2.99 mmol), $PdCl_2$(dppf) (72.9 mg, 0.100 mmol), 4-chloro-3-methylquinoline (177 mg, 0.996 mmol, Accela), and 5-methyl-1-(tetrahydro-2H-pyran-2-yl)-4-(4,4,5,5-tetramethyl-1,3,2-dioxaborolan-2-yl)-1H-indazole (341 mg, 0.996 mmol) in 1,4-dioxane (20 mL) and water (5 mL) was stirred at 100° C. for 2 h under $N_2$. The mixture was then cooled to room temperature, diluted with water (50 mL), and extracted with DCM (50 mL), The organic extract was collected, washed with brine (50 mL), dried over $Na_2SO_4$, and concentrated in vacuo. Purification by column chromatography (silica gel, 20-100% EtOAc/heptanes) provided 3-methyl-4-(5-methyl-1-(tetrahydro-2H-pyran-2-yl)-1H-indazol-4-yl)quinoline (300 mg, 84% yield) as a yellow solid. m/z (ESI): 358.0 $(M+H)^+$.

Step 2: 3-methyl-4-(5-methyl-1-(tetrahydro-2H-pyran-2-yl)-1H-indazol-4-yl)quinoline 1-oxide A mixture of m-CPBA (290 mg, 1.679 mmol) and 3-methyl-4-(5-methyl-1-(tetrahydro-2H-pyran-2-yl)-1H-indazol-4-yl)quinoline (300 mg, 0.839 mmol) in DCM (10 mL) was allowed to stir at 0° C. for 2 h. The reaction mixture was then diluted with water (30 mL) and extracted with DCM (30 mL). The organic extract was collected, washed with brine (30 mL), dried over $Na_2SO_4$, and concentrated in vacuo to provide 3-methyl-4-(5-methyl-1-(tetrahydro-2H-pyran-2-yl)-1H-indazol-4-yl)quinoline 1-oxide (300 mg, 96% yield) as a yellow solid. m/z (ESI): 374.2 $(M+H)^+$.

Step 3: 2-bromo-3-methyl-4-(5-methyl-1-(tetrahydro-2H-pyran-2-yl)-1H-indazol-4-yl)quinoline A mixture of phosphorus oxybromide (345 mg, 1.21 mmol) and 3-methyl-4-(5-methyl-1-(tetrahydro-2H-pyran-2-yl)-1H-indazol-4-yl)quinoline 1-oxide (300 mg, 0.80 mmol) in DCM (10 mL) was stirred at 0° C. for 2 h. The reaction mixture was diluted with water (50 mL) and extracted with DCM (30 mL). The organic extracts were washed with brine (10 mL), dried over $Na_2SO_4$, and concentrated in vacuo. Chromatographic purification of the residue (silica gel, 10-100% EtOAc/heptanes) provided 2-bromo-3-methyl-4-(5-methyl-1-(tetrahydro-2H-1-pyran-2-yl)-1H-indazol-4-yl)quinoline (70 mg, 20% yield) as a yellow solid, which was carried to the next step.

Step 4: tert-butyl 6-(3-methyl-4-(5-methyl-1-(tetrahydro-21H-pyran-2-yl)-1H-indazol-4-yl)quinolin-2-yl)-2,6-diazaspiro[3.4]octane-2-carboxylate A mixture of 2-bromo-3-methy-4-(5-methyl-1-(tetrahydro-2H-pyran-2-yl)-H-indazol-4-yl)quinoline (60 mg, 0.138 mmol), tert-butyl 2,6-diazaspiro[3.4]octane-2-carboxylate (29.2 mg, 0.138 mmol) and DIPEA (24 μL, 0.138 mmol) in DMSO (1 mL) was stirred at 120° C. for 2 h. The reaction mixture was diluted with water (10 mL) and extracted with DCM (30 mL). The organic extract was collected, washed with brine (10 mL), dried over $Na_2SO_4$, and concentrated in vacuo. Chromatographic purification of the residue (silica gel, 20-100% EtOAc/heptanes) gave tert-butyl 6-(3-methyl-4-(5-methyl-1-(tetrahydro-2H-pyran-2-yl)-1H-indazol-4-yl)quinolin-2-yl)-2,6-diazaspiro[3.4]octane-2-carboxylate (60 mg, 77% yield) as a yellow solid. m/z (ESI): 568.3 $(M+H)^+$.

Step 5: 1-(6-(3-methyl-4-(5-methy-1H-indazol-4-yl)quinolin-2-yl)-2,6-diazaspiro[3.4]octan-2-yl)prop-2-en-1-one A mixture of TFA (24 μL, 0.317 mmol) and tert-butyl 6-(3-methyl-4-(5-methyl-1-(tetrahydro-2H-pyran-2-yl)-1H-indazol-4-yl)quinolin-2-yl)-2,6-diazaspiro[3.4]octane-2-carboxylate (60 mg, 0.106 mmol) in DCM (1 mL) was allowed to stir at room temperature for 2 h. The solution mixture was concentrated in vacuo. The crude mixture was dissolved in DCM (2 mL) and DIPEA (55 μL, 0.313 mmol) was added followed by acryloyl chloride (9.44 mg, 0.104 mmol) at −40° C. under $N_2$. The resulting mixture was allowed to stir at −40° C. for 2 h. The solution was concentrated in vacuo and the crude material was purified by reverse-phase preparative HPLC using a XBridge Prep $C_{18}$ 5 μm OBD column, 150×30 mm, 0.1% $NH_4HCO_3$ in $CH_3CN/H_2O$, gradient 35-80% over 15 min, flow rate=30 mL/min to provide 1-(6-(3-methyl-4-(5-methyl-1H-indazol-4-yl)quinolin-2-yl)-2,6-diazaspiro[3.4]octan-2-yl)prop-2-en-1-one Example 8 (14.2 mg, 31% yield) as a white solid. $^1H$ NMR (400 MHz, $CDCl_3$) δ ppm 7.86 (s, 1H), 7.52 (d, J=8&5 Hz, 2H), 7.49-7.33 (m, 2H), 7.05 (dd, J=22.1, 15.0 Hz, 1H), 6.91 (d, J=8.2 Hz, 1H), 6.38 (dd, J=17.0, 1.7 Hz, 1H), 6.30-6.12 (m, 1H), 5.70 (dd, J=10.3, 1.6 Hz, 1H), 4.41-4.24 (m, 1H), 4.23-4.05 (m, 3H), 3.97 (s, 2H), 3.80 (s, 2H), 2.25 (t, J=6.7 Hz, 2H), 2.13-1.96 (m, 7H). m/z (ESI): 438.1 $(M+H)^+$.

Example 9: (S)-3-(2-(2-acryloyl-2,6-diazaspiro[3.4]octan-6-yl)-4-(2-fluorophenyl)-5,6-dihydro-7H-pyrrolo[2,3-d]pyrimidin-7-yl)-N,5-dimethylhexanamide

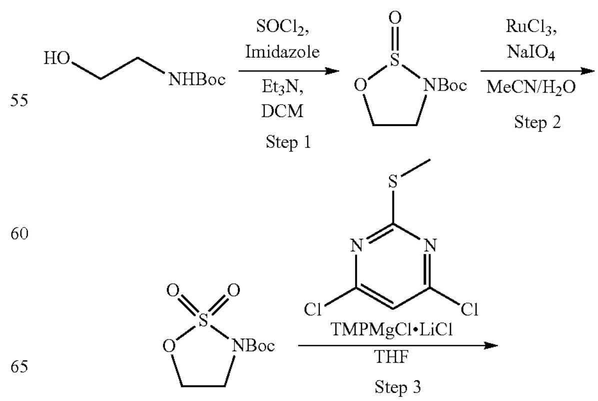

-continued
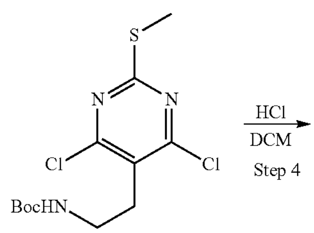
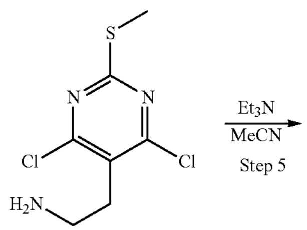
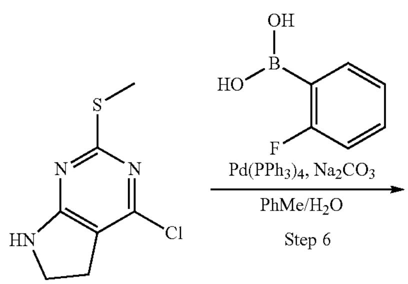
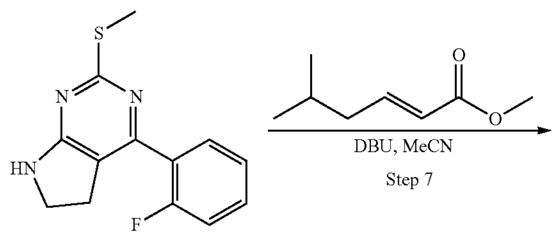
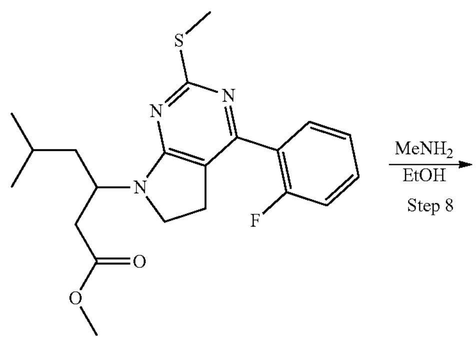
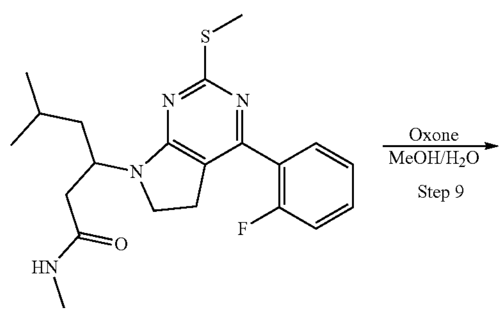
-continued
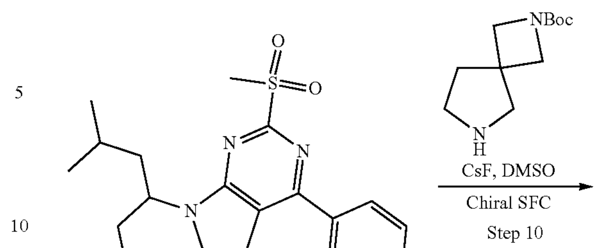
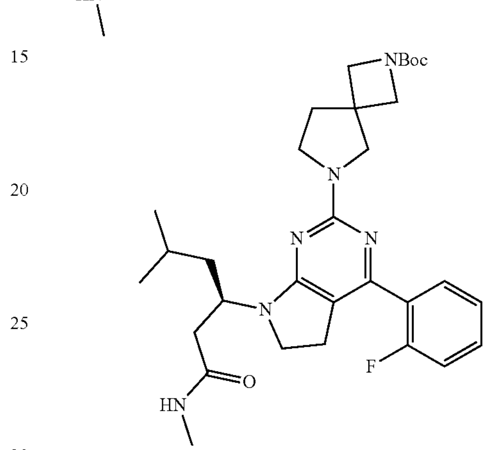
+
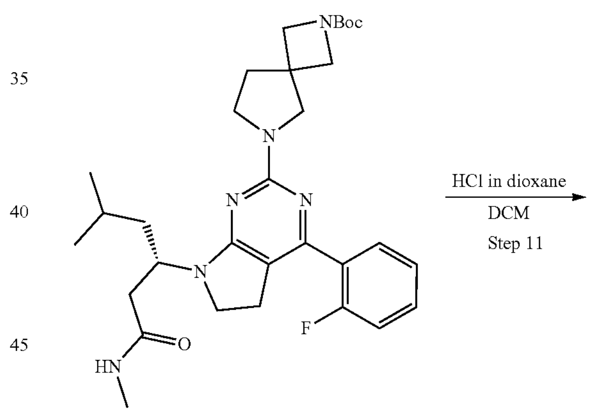
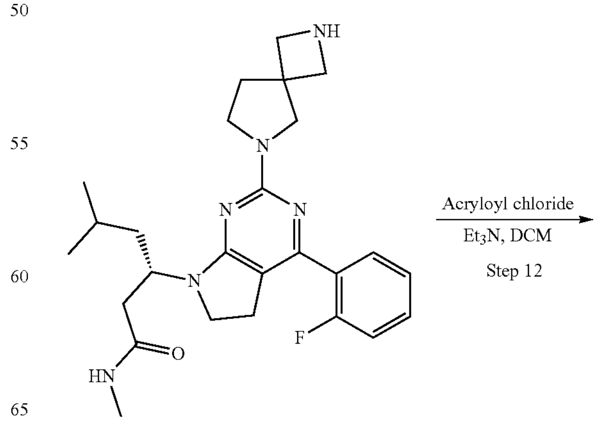

-continued

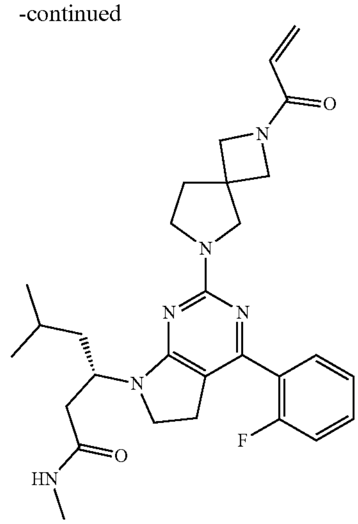

Example 9

Step 1: tert-butyl 1,2,3-oxathiazolidine-3-carboxylate 2-oxide

To a stirred solution of tert-butyl (2-hydroxyethyl) carbamate (10.0 g, 62.0 mmol) in DCM (280 mL) were added imidazole (21.1 g, 310 mmol) and TEA (38.0 mL, 273 mmol) at −60° C. The resulting suspension was stirred for 5 min before thionyl chloride (9.96 mL, 136 mmol) was added dropwise over 30 min at −60° C. The mixture was stirred at the same temperature for 4 h and later at room temperature for 16 h. The reaction mixture was quenched with ice-cold water and extracted with DCM. The organic extracts were washed with brine, dried over $Na_2SO_4$, and concentrated in vacuo to provide tert-butyl 1,2,3-oxathiazolidine-3-carboxylate 2-oxide as a light green viscous oil, which was taken to the next step without further purification.

Step 2: tert-butyl 1,2,3-oxathiazolidine-3-carboxylate 2,2-dioxide

To a solution of tert-butyl 1,2,3-oxathiazolidine-3-carboxylate 2-oxide (14.0 g, 67.6 mmol) in MeCN (140 mL) and water (70 mL) were added $NaIO_4$ (18.1 g, 84.0 mmol, Chempure) portionwise at 0° C., followed by ruthenium(III) chloride hydrate (0.056 g, 0.27 mmol, Chempure). The reaction mixture was allowed to stir at room temperature for 2.5 h. The reaction was quenched with ice-cold water and extracted with $Et_2O$. The organic extracts were washed with brine, dried over $Na_2SO_4$, and concentrated in vacuo. The residue was purified on a Redi-Sep pre-packed silica gel column (120 g), eluting with 15% EtOAc in hexanes to afford tert-butyl 1,2,3-oxathiazolidine-3-carboxylate 2,2-dioxide (6.0 g, 40% yield) as a white solid. $^1H$ NMR (400 MHz, $CDCl_3$) δ ppm 4.63 (t, J=6.4 Hz, 2H), 4.07 (t, J=6.4 Hz, 2H), 1.57 (s, 9H).

Step 3: tert-butyl (2-(4,6-dichloro-2-(methylthio) pyrimidin-5-yl)ethyl)carbamate To a stirred solution of 4,6-dichloro-2-(methylthio)pyrimidine (13.0 g, 66.6 mmol, Combi-Blocks) and THF (250 mL) was added 2,2,6,6-tetramethylpiperidinylmagnesium chloride lithium chloride complex solution (133 mL, 133 mmol, Symax) at room temperature. The reaction was allowed to stir for 30 min. Then, tert-butyl 1,2,3-oxathiazolidine-3-carboxylate 2,2-dioxide (22.0 g, 99.0 mmol) was added portionwise and the reaction was stirred at room temperature for 5 h before it was quenched with 1N citric acid solution and extracted with EtOAc. The organic extracts were washed with brine, dried over $Na_2SO_4$, and concentrated in vacuo to provide tert-butyl (2-(4,6-dichloro-2-(methylthio)pyrimidin-5-yl)ethyl)carbamate as a yellow solid, which was taken to the next step without further purification. m/z (ESI): 282.2 $(M\text{-tbutyl})^+$.

Step 4: 2-(4,6-dichloro-2-(methylthio)pyrimidin-5-yl)ethan-1-amine hydrochloride To a stirred solution of tert-butyl (2-(4,6-dichloro-2-(methylthio)pyrimidin-5-yl)ethyl) carbamate (21.0 g, 62.1 mmol) and DCM (100 mL) was added 4M HCl in dioxane (78 mL, 310 mmol) at 0° C. dropwise and the reaction mixture was allowed to stir for 5 h at room temperature. The reaction was concentrated in vacuo to provide 2-(4,6-dichloro-2-(methylthio)pyrimidin-5-yl)ethan-1-amine hydrochloride (20.0 g) as a yellow solid, which was used in the next step without purification. m/z (ESI): 238.0 $(M+H)^+$.

Step 5: 4-chloro-2-(methylthio)-6,7-dihydro-5H-pyrrolo[2,3-d]pyrimidine

A solution of 2-(4,6-dichloro-2-(methylthio)pyrimidin-5-yl)ethan-1-amine hydrochloride (15.0 g, 54.6 mmol) in MeCN (200 mL) and TEA (38.1 mL, 273 mmol) was stirred at 80° C. for 16 h. Upon completion, the reaction mixture was diluted with water and extracted with EtOAc. The organic extracts were washed with brine, dried over $Na_2SO_4$, and concentrated in vacuo. The residue was purified on a Redi-Sep pre-packed silica gel column, eluting with a gradient of 80-100% EtOAc in hexanes to provide 4-chloro-2-(methylthio)-6,7-dihydro-5H-pyrrolo[2,3-d]pyrimidine (6.2 g, 56% yield) as a light-yellow solid. $^1H$ NMR (400 MHz, DMSO-$d_4$) δ ppm 7.93 (s, 1H), 3.59 (t, J=8.5 Hz, 2H), 2.96 (t, J=8.5, 2H), 2.39 (s, 3H). m/z (ESI): 202.0 $(M+H)^+$.

Step 6: 4-(2-fluorophenyl)-2-(methylthio)-6,7-dihydro-5H-pyrrolo[2,3-d]pyrimidine To a degassed solution of 4-chloro-2-(methylthio)-6,7-dihydro-5H-pyrrolo[2,3-d]pyrimidine (1.5 g, 7.44 mmol), (2-fluorophenyl)boronic acid (1.56 g, 11.2 mmol, Combi-Blocks) and $Na_2CO_3$ (1.97 g, 18.6 mmol) in toluene (30 mL) and water (5 mL) was added $Pd(PPh_3)_4$ (0.86 g, 0.744 mmol, Hindustan platinum). The solution was purged with N for an additional 2 min. The reaction was stirred at 80° C. for 16 h. The reaction was quenched with ice-cold water and extracted with EtOAc. The combined organic extracts were washed with brine, dried over $Na_2SO_4$, and concentrated under reduced pressure. The residue was purified on silica gel eluting with 15-20% EtOAc in hexanes to give 4-(2-fluorophenyl)-2-(methylthio)-6,7-dihydro-5H-pyrrolo[2,3-d]pyrimidine (1.6 g, 82% yield) as a light yellow solid. $^1H$ NMR (400 MHz, DMSO-$d_6$) δ ppm 7.69 (s, 1H), 7.63-7.66 (m, 1H), 7.47-7.54 (m, 1H), 7.26-7.39 (m, 2H), 3.55 (t, J=8.4 Hz, 2H), 2.92 (t, J=8.4 Hz, 2H), 2.41 (s, 3H).

Step 7: methyl 3-(4-(2-fluorophenyl)-2-(methylthio)-5,6-dihydro-7H-pyrrolo[2,3-d]pyrimidin-7-yl)-5-methylhexanoate To a stirred solution of 4-(2-fluorophenyl)-2-(methylthio)-6,7-dihydro-5H-pyrrolo[2,3-d]pyrimidine (1.6 g, 6.12 mmol) in MeCN (25 mL) were added methyl (E)-5-methylhex-2-enoate (1.74 g, 12.3 mmol, synthesized following the procedure described in (*Chem. Commun.* 2015, 51, 8958) and DBU (3.23 mL, 21.4 mmol). The reaction was heated to 95° C. for 16 h. The reaction was diluted with water and extracted with EtOAc. The organic layers were washed with brine, dried over $Na_2SO_4$, and concentrated under reduced pressure. The residue was further purified on silica gel eluting with 10-20% EtOAc in hexanes to give methyl 3-(4-(2-fluorophenyl)-2-(methylthio)-5,6-dihydro-7H-pyrrolo[2,3-d]pyrimidin-7-yl)-5-methylhexanoate (1.70 g, 69% yield) as a light yellow liquid. $^1H$ NMR (400 MHz, DMSO-$d_6$) δ ppm 7.62 (td, J=7.6, 1.7 Hz, 1H), 7.49-7.52 (m, 1H), 7.21-7.45 (m, 2H), 4.55-4.69 (m, 1H), 3.53-3.59 (m, 5H), 2.89-2.94 (m, 2H), 2.58-2.74 (m, 2H), 2.43 (s, 3H), 1.67 (m, 1H), 1.40-1.54 (m, 1H), 1.26-1.34 (m, 1H), 0.91 (dd, J=10.7, 6.5 Hz, 6H). m/z (ESI): 404.1 $(M+H)^+$.

Step 8: 3-(4-(2-fluorophenyl)-2-(methylthio)-5,6-dihydro-71H-pyrrolo[2,3-d]pyrimidin-7-yl)-N,5-dimethylhexanamide A solution of methyl 3-(4-(2-fluorophenyl)-2-(methylthio)-5,6-dihydro-7H-pyrrolo[2,3-d]pyrimidin-7-yl)-5-methylhexanoate (1.70 g, 4.21 mmol) in methanamine (33 wt % in EtOH) (30 mL, 4.21 mmol) was stirred at room temperature for 16 h in a sealed tube. The reaction mixture was concentrated under reduced pressure and purified on silica gel eluting with 80-90% EtOAc in hexanes to give 3-(4-(2-fluorophenyl)-2-(methylthio)-5,6-dihydro-7H-pyrrolo[2,3-d]pyrimidin-7-yl)-N,5-dimethylhexanamide (1.70 g, 99% yield) as an off-white solid. m/z (ESI): 403.2 $(M+H)^+$.

Step 9: 3-(4-(2-fluorophenyl)-2-(methylsulfonyl)-5,6-dihydro-7H-pyrrolo[2,3-d]pyrimidin-7-yl)-N,5-dimethylhexanamide To a solution of 3-(4-(2-fluorophenyl)-2-(methylthio)-5,6-dihydro-7H-pyrrolo[2,3-d]pyrimidin-7-yl)-N,5-dimethylhexamide (1.70 g, 4.22 mmol) in MeOH (70 mL) and water (70 mL) was added oxone monopersulfate (5.19 g, 8.45 mmol, Spectrochem) portion wise at 0'C. The reaction mixture was stirred at rt for 16 h. The reaction was quenched with cold water and extracted with DCM. The combined organic extracts were washed with brine, dried over $Na_2SO_4$, and concentrated under reduced pressure. The residue was purified on silica-gel (230-400 mesh) eluting with 90% EtOAc in hexanes to afford 3-(4-(2-fluorophenyl)-2-(methylsulfonyl)-5,6-dihydro-7H-pyrrolo[2,3-d]pyrimidin-7-yl)-N,5-dimethylhexanamide (1.0 g, 55% yield) as a white solid. m/z (ESI): 435.1 $(M+H)^+$.

Step 10: tert-butyl 6-(4-(2-fluorophenyl)-7-(5-methyl-1-(methylamino)-1-oxohexan-3-yl)-6,7-dihydro-5H-pyrrolo[2,3-d]pyrimidin-2-yl)-2,6-diazaspiro[3.4]octane-2-carboxylate To a solution of 3-(4-(2-fluorophenyl)-2-(methylsulfonyl)-5,6-dihydro-7H-pyrrolo[2,3-d]pyrimidin-7-yl)-N,5-dimethylhexanamide (1.0 g, 2.30 mmol), tert-butyl 2,6-diazaspiro[3.4]octane-2-carboxylate (0.59 g, 2.76 mmol, J&W Pharmalab) and DMSO (15 mL) was added CsF (2.10 g, 13.8 mmol, Loba Chemie). The reaction was heated to 125° C. for 16 h. The reaction was cooled to room temperature, quenched with cold water and extracted with EtOAc. The organic extracts were washed with brine, dried over $Na_2SO_4$, and concentrated under reduced pressure. The residue was purified on silica-gel eluting with 75-90% EtOAc in petroleum ether to afford tert-butyl 6-(4-(2-fluorophenyl)-7-(5-methyl-1-(methylamino)-1-oxohexan-3-yl)-6,7-dihydro-5H-pyrrolo[2,3-d]pyrimidin-2-yl)-2,6-diazaspiro[3.4]octane-2-carboxylate as a yellow solid. m/z (ESI): 566.8 $(M+H)^+$. The racemic mixture was separated by Chiral SFC in Lux-$C_4$ (250×50 mm, 5p) column using Liquid $CO_2$:0.4% diethyl amine in iPrOH (7:3) to provide tert-butyl (S)-6-(4-(2-fluorophenyl)-7-(5-methyl-1-(methylamino)-1-oxohexan-3-yl)-6,7-dihydro-5H-pyrrolo[2,3-d]pyrimidin-2-yl)-2,6-diazaspiro[3.4]octane-2-carboxylate (0.14 g, 28% yield) as Peak 1 and tert-butyl (R)-6-(4-(2-fluorophenyl)-7-(5-methyl-1-(methylamino)-1-oxohexan-3-yl)-6,7-dihydro-5H-pyrrolo[2,3-d]pyrimidin-2-yl)-2,6-diazaspiro[3.4]octane-2-carboxylate (0.16 g, 32% yield) as Peak 2. The stereochemistry of structures was arbitrarily assigned and is not established.

Peak 1: $^1H$ NMR (400 MHz, DMSO-$d_6$) δ ppm 7.81 (d, J=4.9 Hz, 1H), 7.59 (td, J=7.8, 2.0 Hz, 1H), 7.45-7.49 (m, 1H), 7.23-7.31 (m, 2H), 4.54-4.64 (m, 1H), 3.79 (s, 4H), 3.61 (s, 2H), 3.39-3.55 (m, 4H), 2.74 (t, J=8.2 Hz, 2H), 2.52-2.54 (m, 3H), 2.30-2.38 (m, 2H), 2.08 (t, J=6.9 Hz, 2H), 1.60-1.71 (m, 1H), 1.39-1.42 (m, 10H), 1.14-1.22 (m, 1H), 0.94 (d, J=6.5 Hz, 3H), 0.89 (d, J=6.6 Hz, 3H). m/z (ESI): 566.8 $(M+H)^+$.

Peak 2: $^1H$ NMR (400 MHz, DMSO-$d_6$) δ ppm 7.81 (d, J=4.7 Hz, 1H), 7.59 (td, J=7.8, 2.0 Hz, 1H), 7.45-7.49 (m, 1H), 7.23-7.30 (m, 2H), 4.58-4.61 (m, 1H), 3.79-3.82 (m, 4H), 3.61 (s, 2H), 3.46-3.51 (m, 4H), 2.74 (t, J=8.1 Hz, 2H), 2.52-2.54 (m, 3H), 2.35 (d, J=5.8 Hz, 2H), 2.08 (t, J=6.8 Hz, 2H), 1.64 (t, J=12.4 Hz, 1H), 1.39 (s, 10H), 1.19-1.27 (m, 1H), 0.94 (d, J=6.4 Hz, 3H), 0.89 (d, J=6.6 Hz, 3H). m/z (ESI): 566.8 $(M+H)^+$.

Step 11: (S)-3-(4-(2-fluorophenyl)-2-(2,6-diazaspiro[3.4]octan-6-yl)-5,6-dihydro-7Hpyrrolo[2,3-d]pyrimidin-7-yl)-N,5-dimethylhexanamide hydrochloride To a solution of tert-butyl (S)-6-(4-(2-fluorophenyl)-7-(5-methyl-1-(methylamino)-1-oxohexan-3-yl)-6,7-dihydro-5H-pyrrolo[2,3-d]pyrimidin-2-yl)-2,6-diazaspiro[3.4]octane-2-carboxylate (0.16 g, 0.28 mmol) and 1,4-dioxane (2.5 mL) was added 4M HCl in dioxane (2 mL). The reaction was stirred at room temperature for 1.5 h. The mixture was concentrated under reduced pressure and triturated with $Et_2O$ to afford (S)-3-(4-(2-fluorophenyl)-2-(2,6-diazaspiro[3.4]octan-6-yl)-5,6-dihydro-7Hpyrrolo[2,3-d]pyrimidin-7-yl)-N,5-dimethylhexanamide hydrochloride as a yellow solid, which was taken to the next step without further purification. m/z (ESI): 467.0 $(M+H)^+$.

Step 12: (S)-3-(2-(2-acryloyl-2,6-diazaspiro[3.4]octan-6-yl)-4-(2-fluorophenyl)-5,6-dihydro-7H-pyrrolo[2,3-d]pyrimidin-7-yl)-N,5-dimethylhexanamide (Example 9)

To a solution of (S)-3-(4-(2-fluorophenyl)-2-(2,6-diazaspiro[3.4]octan-6-yl)-5,6-dihydro-7H-pyrrolo[2,3-d]pyrimidin-7-yl)-N,5-dimethylhexanamide hydrochloride (0.14 g, 0.278 mmol) in DCM (4 mL) were added TEA (0.19 mL, 1.39 mmol) and acryloyl chloride (0.034 mL, 0.42 mmol) at 0° C. dropwise. The mixture was allowed to stir at room temperature for 1 h. The reaction was quenched with ice-cold water and extracted with DCM. The combined organic extracts were washed with brine, dried over $Na_2SO_4$, concentrated in vacuo, and purified by preparative HPLC using a XBridge Prep $C_{18}$ 5 μm OBD column, 150×30 mm, 0.1% $NH_4HCO_3$ in MeCN/H2O, gradient 35-80% over 15 min, flow rate=30 mL/min to afford (S)-3-(2-(2-acryloyl-2,6-diazaspiro[3.4]octan-6-yl)-4-(2-fluorophenyl)-5,6-dihydro-7H-pyrrolo[2,3-d]pyrimidin-7-yl)-N,5-dimethylhexanamide Example 9 (0.055 g, 38% yield) as a white solid. $^1H$ NMR (400 MHz, DMSO-$d_6$) δ ppm 7.81 (d, J=4.8 Hz, 1H), 7.59 (td, J=7.7, 2.0 Hz, 1H), 7.42-7.48 (m, 1H), 7.20-7.34 (m, 2H), 6.32 (dd, J=17.0, 10.3 Hz, 1H), 6.11 (dd, J=17.0, 2.3 Hz, 1H), 5.67 (dd, J=10.3, 2.3 Hz, 1H), 4.58 (d, J=7.7 Hz, 1H), 4.07-4.27 (m, 2H), 3.89 (d, J=8.0 Hz, 2H), 3.58-3.73 (m, 2H), 3.27-3.55 (m, 7H), 2.75 (t, J=8.2 Hz, 2H), 2.25-2.41 (m, 2H), 2.05-2.20 (m, 2H), 1.58-1.72 (m, 1H), 1.44-1.49 (m, 1H), 1.20-1.26 (m, 1H), 0.88-0.98 (m, 6H). m/z (ESI): 520.8 $(M+H)^+$.

Example 10: (S)-3-(2-(2-acryloyl-2,6-diazaspiro[3.4]octan-6-yl)-4-(2-fluorophenyl)-6,7-dihydro-pyrido[2,3-d]pyrimidin-8(5H)-yl)-N,5-dimethyl-hexanamide

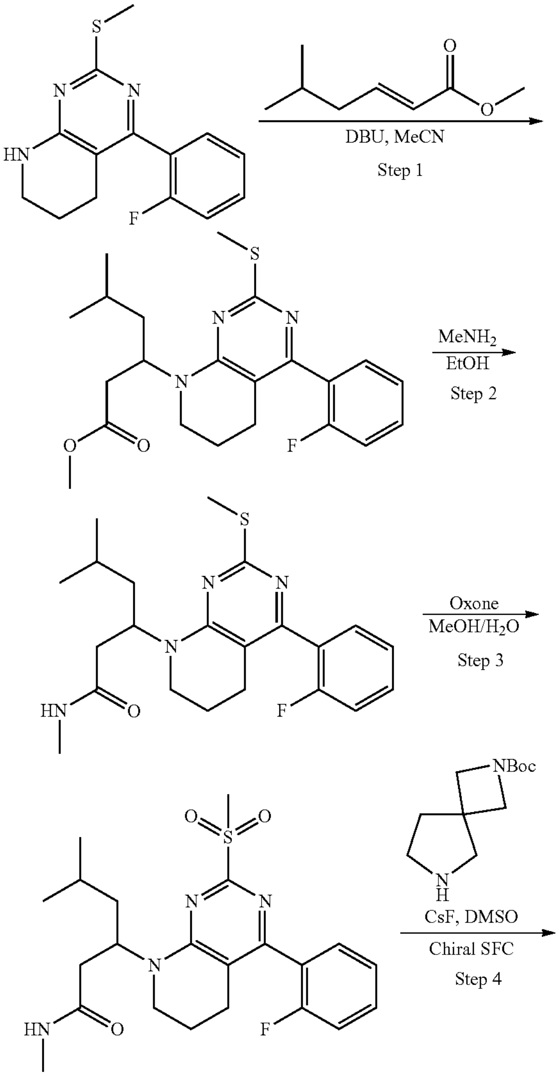

-continued

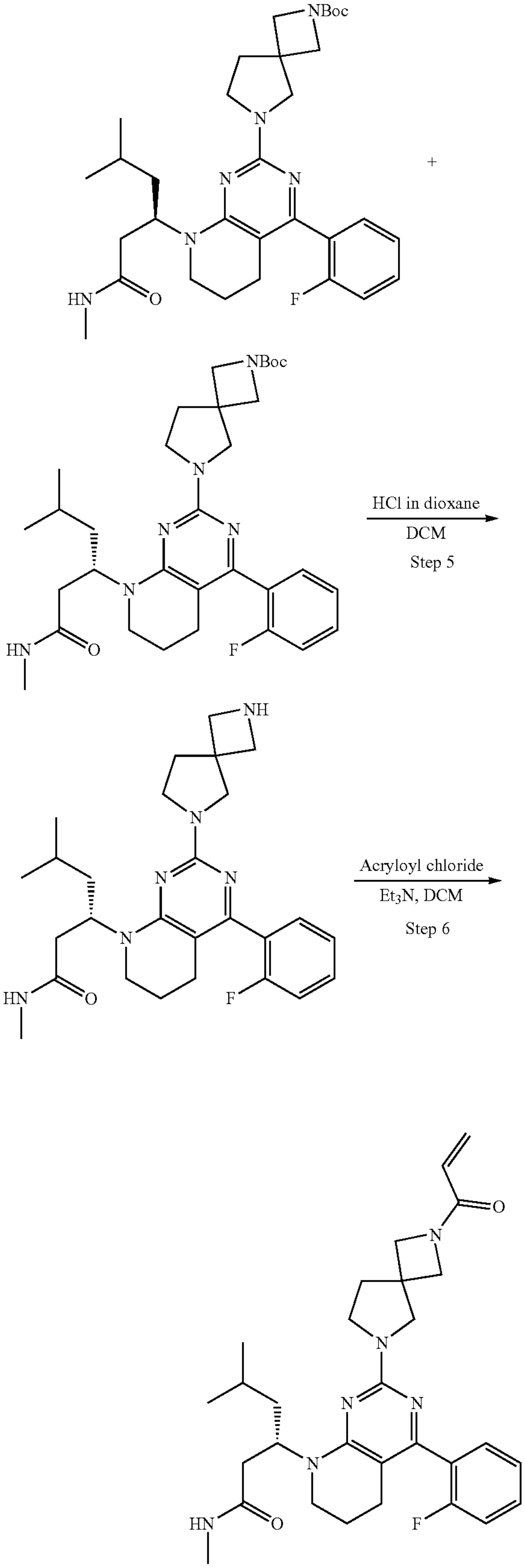

Example 10

Step 1: methyl 3-(4-(2-fluorophenyl)-2-(methylthio)-6,7-dihydropyrido[2,3-d]pyrimidin-8(5H)-yl)-5-methylhexanoate To a stirred solution of 4-(2-fluorophenyl)-2-(methylthio)-5,6,7,8-tetrahydropyrido[2,3-d]pyrimidine (obtained by arylation of Intermediate 15 as in Example 9, step 6) (2.1 g, 7.63 mmol) and MeCN (32 mL) was added methyl (E)-5-methylhex-2-enoate (2.17 g, 15.3 mmol, synthesized following the procedure described in Chem. Commun. 2015, 51, 8958) and DBU (4.0 mL, 26.7 mmol). The reaction mixture was heated at 95° C. for 24 h. The reaction was diluted with water and extracted with EtOAc. The organic layers were washed with brine, dried over $Na_2SO_4$, and concentrated in vacuo to provide methyl 3-(4-(2-fluorophenyl)-2-(methylthio)-6,7-dihydropyrido[2,3-d]pyrimidin-8(5H)-yl)-5-methyl hexanoate (3.5 g, 40% yield) as a light yellow solid, which was taken to the next step without purification. m/z (ESI): 418.2 $(M+H)^+$.

Step 2: 3-(4-(2-fluorophenyl)-2-(methylthio)-6,7-dihydropyrido[2,3-d]pyrimidin-8(5H)-yl)-N,5-dimethylhexanamide A solution of methyl 3-(4-(2-fluorophenyl)-2-(methylthio)-6,7-dihydropyrido[2,3-d]pyrimidin-8(5H)-yl)-5-methylhexanoate (3.5 g, 3.0 mmol) and methanamine 33% in EtOH (20 mL, 3.0 mmol) was stirred in a sealed tube at room temperature for 16 h. The reaction mixture was concentrated and the residue was purified on silica gel eluting with 80-90% EtOAc in petroleum ether to give 3-(4-(2-fluorophenyl)-2-(methylthio)-6,7-dihydropyrido[2,3-d]pyrimidin-8(5H)-yl)-N,5-dimethylhexanamide (0.90 g, 71% yield) as a light yellow liquid. m/z (ESI): 417.1 $(M+H)^+$.

Step 3: 3-(4-(2-fluorophenyl)-2-(methylsulfonyl)-6,7-dihydropyrido[2,3-d]pyrimidin-8(5H)-yl)-N,5-dimethylhexanamide To a solution of 3-(4-(2-fluorophenyl)-2-(methylthio)-6,7-dihydropyrido[2,3-d]pyrimidin-8(5H)-yl)-N,5-dimethylhexanamide (0.90 g, 2.16 mmol) in MeOH (27 mL) and water (27 mL) was added oxone monopersulfate (1.99 g, 6.48 mmol, Avra) at 0° C. The reaction was stirred at room temperature for 16 h. The reaction was diluted with water and extracted with EtOAc. The organic extracts were washed with brine, dried over $Na_2SO_4$, and concentrated under reduced pressure to provide 3-(4-(2-fluorophenyl)-2-(methylsulfonyl)-6,7-dihydropyrido[2,3-d]pyrimidin-8(5H)-yl)-N,5-dimethylhexanamide (0.75 g, 77% yield) as an off-white solid, which was taken to the next step without purification. m/z (ESI): 449.1 $(M+H)^+$.

Step 4: tert-butyl 6-(4-(2-fluorophenyl)-8-(5-methyl-1-(methylamino)-1-oxohexan-3-yl)-5,6,7,8-tetrahydropyrido[2,3-d]pyrimidin-2-yl)-2,6-diazaspiro[3.4]octane-2-carboxylate To a stirred solution of 3-(4-(2-fluorophenyl)-2-(methylsulfonyl)-6,7-dihydropyrido[2,3-d]pyrimidin-8(5H)-yl)-N,5-dimethylhexanamide (0.40 g, 0.892 mmol) and tert-butyl 2,6-diazaspiro[3.4]octane-2-carboxylate (0.28 g, 1.34 mmol, PharmaBlock) in DMSO (8 mL) was added CsF (0.68 g, 4.46 mmol). The resulting mixture was heated at 120° C. for 16 h. The reaction was diluted with water and extracted with EtOAc. The organic extracts were washed with brine, dried over $Na_2SO_4$, and concentrated under reduced pressure. The residue was purified on silica gel eluting with 80-90% EtOAc in hexanes to give tert-butyl 6-(4-(2-fluorophenyl)-8-(5-methyl-1-(methylamino)-1-oxohexan-3-yl)-5,6,7,8-tetrahydropyrido[2,3-d]pyrimidin-2-yl)-2,6-diazaspiro[3.4]octane-2-carboxylate (0.37 g, 71% yield) as a light yellow solid. m/z (ESI): 581.3 $(M+H)^+$. The racemic mixture was separated by Chiral SFC in LUX-$C_4$ (250×50 mm, 5 μm) column using liquid $CO_2$:0.4% diethyl amine in iPrOH (1:1) to provide tert-butyl (S)-6-(4-(2-fluorophenyl)-8-(5-methyl-1-(methylamino)-1-oxohexan-3-yl)-5,6,7,8-tetrahydropyrido[2,3-d]pyrimidin-2-yl)-2,6-diazaspiro[3.4]octane-2-carboxylate (0.10 g, 0.17 mmol, 27% yield) as Peak 1 and tert-butyl (R)-6-(4-(2-fluorophenyl)-8-(5-methyl-1-(methylamino)-1-oxohexan-3-yl)-5,6,7,8-tetrahydropyrido[2,3-d]pyrimidin-2-yl)-2,6-diazaspiro[3.4]octane-2-carboxylate (0.10 g, 27% yield) as Peak 2. The stereochemistry of structures was arbitrarily assigned and is not established.

Step 5: (S)-3-(4-(2-fluorophenyl)-2-(2,6-diazaspiro[3.4]octan-6-yl)-6,7-dihydropyrido [2,3-d]pyrimidin-8(5H)-yl)-N,5-dimethylhexanamide hydrochloride To a solution of tert-butyl (S)-6-(4-(2-fluorophenyl)-8-(5-methyl-1-(methylamino)-1-oxohexan-3-yl)-5,6,7,8-tetrahydropyrido[2,3-d]pyrimidin-2-yl)-2,6-diazaspiro[3.4]octane-2-carboxylate (0.10 g, 0.172 mmol) in DCM (2 mL) was added HCl (4 M in dioxane) (2 mL, 8.0 mmol) at 0° C. The reaction was stirred at room temperature for 3 h. The reaction was concentrated under reduced pressure and triturated with $Et_2O$ to provide (S)-3-(4-(2-fluorophenyl)-2-(2,6-diazaspiro[3.4]octan-6-yl)-6,7-dihydropyrido[2,3-d]pyrimidin-8(5H)-yl)-N,5-dimethylhexanamide hydrochloride (0.085 g, 95% yield) as a light yellow solid, which was taken to the next step without further purification. m/z (ESI): 481.3 $(M+H)^+$.

Step 6: (S)-3-(2-(2-acryloyl-2,6-diazaspiro[3.4]octan-6-yl)-4-(2-fluorophenyl)-6,7-dihydropyrido[2,3-d]pyrimidin-8(5H)-yl)-N,5-dimethylhexanamide (Example 10)

To a solution of (S)-3-(4-(2-fluorophenyl)-2-(2,6-diazaspiro[3.4]octan-6-yl)-6,7-dihydropyrido[2,3-d]pyrimidin-8(5H)-yl)-N,5-dimethylhexanamide hydrochloride (0.08 g, 0.16 mmol) and TEA (0.07 mL, 0.46 mmol) and DCM (2 mL) was added acryloyl chloride (0.014 mL, 0.170 mmol, Symax Ltd.) at 0° C. dropwise. The resulting reaction mixture was stirred at 0° C. for 30 min. The mixture was diluted with water and extracted with EtOAc. The combined organic layers were dried over $Na_2SO_4$, concentrated, and purified by preparative HPLC using a XBridge Prep $C_{18}$ 5 μm OBD column, 150×30 mm, 0.1% $NH_4HCO_3$ in MeCN/$H_2O$, gradient 35-80% over 15 min, flow rate=30 mL/min to obtain (S)-3-(2-(2-acryloyl-2,6-diazaspiro[3.4]octan-6-yl)-4-(2-fluorophenyl)-6,7-dihydropyrido[2,3-d]pyrimidin-8(5H)-yl)-N,5-dimethylhexanamide Example 10 (0.038 g, 46% yield) as an off-white solid. $^1H$ NMR (400 MHz, DMSO-$d_6$) δ ppm 7.77 (d, J=4.9 Hz, 1H), 7.42-7.46 (m, 1H), 7.37 (td, J=7.7, 2.0 Hz, 1H), 7.21-7.31 (m, 2H), 6.32 (dd, J=17.0, 10.3 Hz, 1H), 6.11 (dd, J=17.0, 2.3 Hz, 1H), 5.58-5.71 (m, 2H), 4.10-4.24 (m, 2H), 3.87 (s, 2H), 3.49-3.65 (m, 4H), 3.43 (s, 3H), 3.16-3.19 (m, 2H), 2.24-2.28 (m, 4H), 2.06-2.18 (m, 2H), 1.66-1.69 (m, 2H), 1.52-1.56 (m, 1H), 1.44-1.46 (m, 1H), 1.23-1.25 (m, 1H), 0.91 (dd, J=12.9, 6.5 Hz, 6H). m/z (ESI): 535.3 $(M+H)^+$.
Example 11: (S)-3-(2-(2-acryloyl-2,6-diazaspiro[3.4]octan-6-yl)-4-(2-fluorophenyl)-7H-pyrrolo[2,3-d]pyrimidin-7-yl)-N,5-dimethylhexanamide
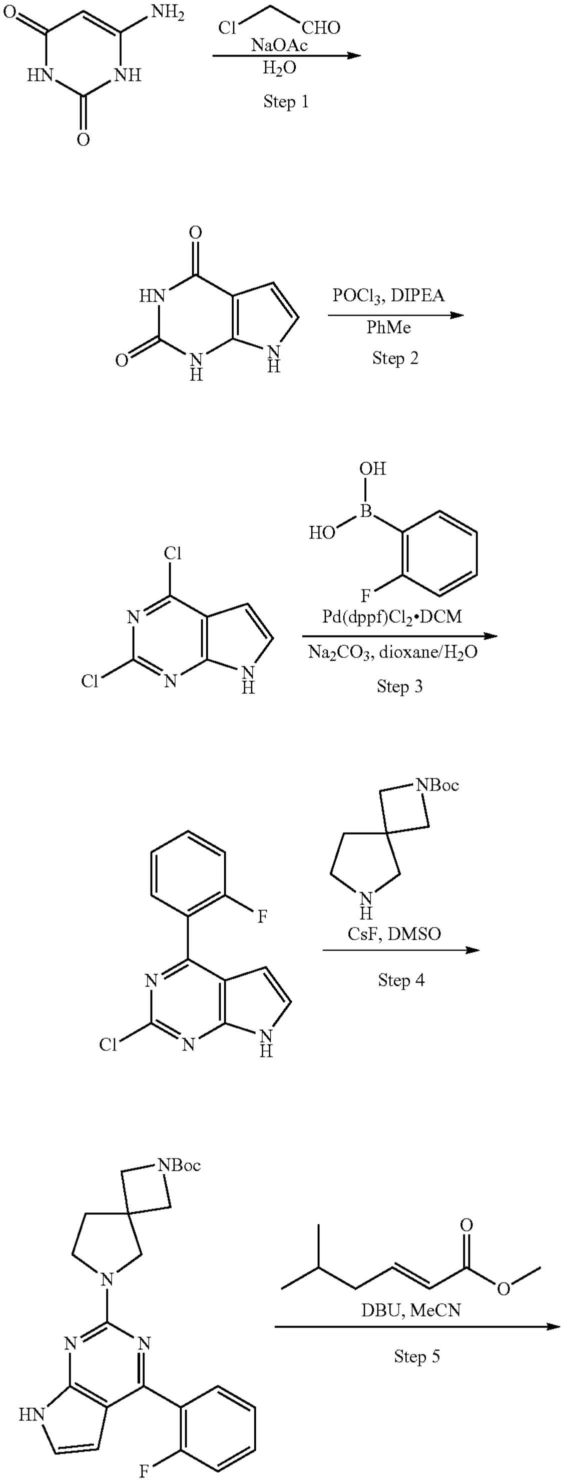
-continued
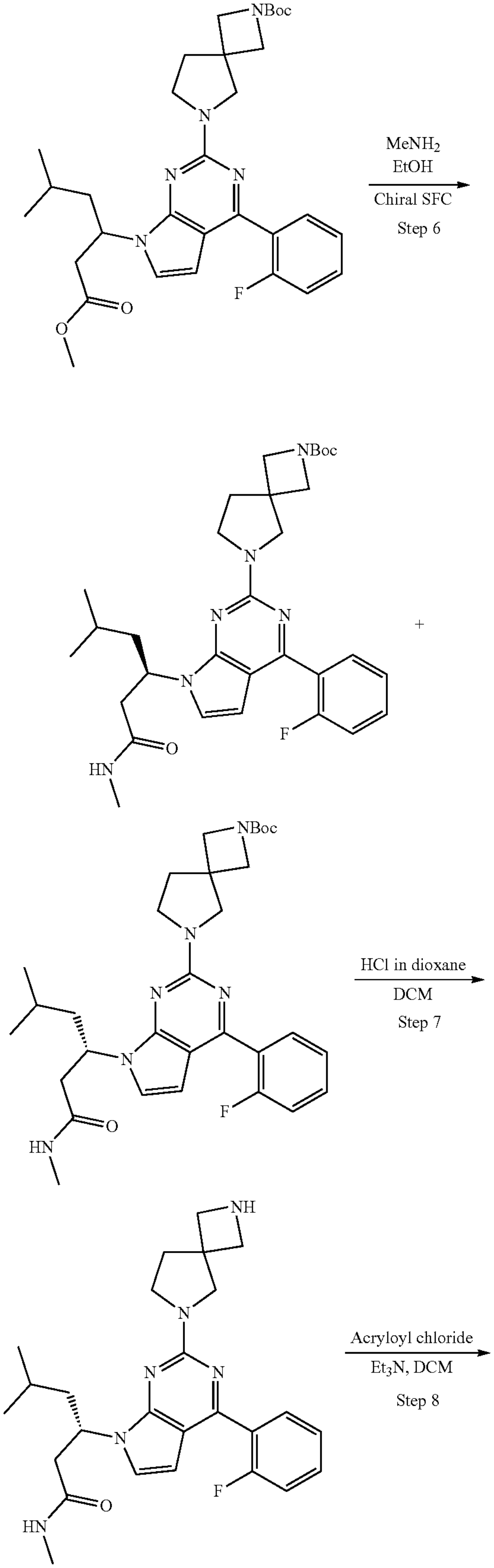

-continued

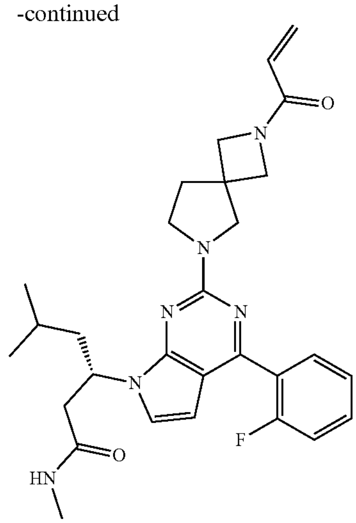

Example 11

Step 1: 1,7-dihydro-2H-pyrrolo[2,3-d]pyrimidine-2,4(3H)-dione

To a solution of 6-aminopyrimidine-2,4(1H,3H)-dione (12.7 g, 100 mmol, Spectrochem), NaOAc (8.2 g, 100 mmol) and water (100 mL) at 80° C. was added 2-chloroacetaldehyde in water (23.5 g, 150 mmol, Spectrochem). The mixture was allowed to stir for 1 h at 80° C. The reaction mixture was cooled to room temperature and the solids were filtered, washed with water, acetone, and dried to obtain 1,7-dihydro-2H-pyrrolo[2,3-d]pyrimidine-2,4(3H)-dione (10.5 g, 70% yield) as a light yellow solid. $^1$H NMR (400 MHz, DMSO-$d_6$) δ ppm 11.44 (s, 1H), 11.09 (s, 1H), 10.47 (s, 1H), 6.57 (t, J=2.8 Hz, 1H), 6.22 (t, J=2.8 Hz, 1H). m/z (ESI): 150.2 (M+H)$^+$.

Step 2: 2,4-dichloro-7H-pyrrolo[2,3-d]pyrimidine

To a solution of 1,7-dihydro-2H-pyrrolo[2,3-d]pyrimidine-2,4(3H)-dione (10.5 g, 69.5 mmol) in toluene (50 mL) was added $POCl_3$ (19.4 mL, 208 mmol). The mixture was heated at 70° C. and DIPEA (24.3 mL, 139 mmol) was added dropwise over a period of 2 h. The reaction temperature was increased to 106° C. and stirred overnight. The reaction mixture was cooled to 0° C. and diluted with water and extracted with EtOAc. The combined organic layers were washed with brine, dried over $Na_2SO_4$, concentrated and purified on a Redi-Sep pre-packed silica gel column, eluting with 0-20% EtOAc in hexanes to provide 2,4-dichloro-7Hpyrrolo[2,3-d]pyrimidine (1.6 g, 12% yield) as a light-yellow solid. $^1$H NMR (400 MHz, DMSO-$d_6$) δ ppm 12.78 (s, 1H), 7.74 (dd, J=3.6, 2.4 Hz, 1H), 6.67 (dd, J=3.6, 1.8 Hz, 1H). m/z (ESI): 188.0 (M+H)$^+$.

Step 3: 2-chloro-4-(2-fluorophenyl)-7H-pyrrolo[2,3-d]pyrimidine

To a degassed solution of 2,4-dichloro-7H-pyrrolo[2,3-d]pyrimidine (1.3 g, 6.91 mmol), (2-fluorophenyl)boronic acid (1.26 g, 9.0 mmol, Combi-Blocks), $Na_2CO_3$ (1.47 g, 13.8 mmol) and 1,4-dioxane (10 mL):water (3 mL) was added Pd(dppf)$Cl_2$·DCM adduct (0.56 g, 0.691 mmol, Hindustan platinum). The reaction was heated at 90° C. for 16 h. The reaction mixture was filtered, concentrated, and purified on a Redi-Sep pre-packed silica gel column, eluting with 30-50% EtOAc in hexanes to provide 2-chloro-4-(2-fluorophenyl)-7H-pyrrolo[2,3-d]pyrimidine (0.41 g, 24% yield) as a yellow solid. $^1$H NMR (400 MHz, DMSO-$d_6$) δ ppm 12.52 (s, 1H), 7.81 (td, J=7.7, 1.8 Hz, 1H), 7.61-7.73 (m, 2H), 7.37-7.51 (m, 2H), 6.55 (t, J=3.7 Hz, 1H). m/z (ESI): 248.0 (M+H)$^+$.

Step 4: tert-butyl 6-(4-(2-fluorophenyl)-7H-pyrrolo[2,3-d]pyrimidin-2-yl)-2,6-diazaspiro[3.4]octane-2-carboxylate A mixture of 2-chloro-4-(2-fluorophenyl)-7H-pyrrolo[2,3-d]pyrimidine (0.80 g, 0.81 mmol), 2-chloro-4-(2-fluorophenyl)-7H-pyrrolo[2,3-d]pyrimidine (0.80 g, 0.81 mmol), CsF (0.61 g, 4.04 mmol) and DMSO (5 mL) was stirred at 90° C. for 16 h. The reaction mixture was diluted with water and extracted with EtOAc. The combined organic layers were washed with brine, dried over $Na_2SO_4$, concentrated, and purified on a Redi-Sep pre-packed silica gel column, eluting with 0-70% EtOAc in hexanes, to provide tert-butyl 6-(4-(2-fluorophenyl)-7H-pyrrolo[2,3-d]pyrimidin-2-yl)-2,6-diazaspiro[3.4]octane-2-carboxylate (0.26 g, 75% yield) as a white solid. $^1$H NMR (400 MHz, DMSO-$d_6$) δ ppm 11.45 (s, 1H), 7.74-7.91 (m, 1H), 7.48-7.70 (m, 1H), 7.28-7.45 (m, 2H), 7.09 (dd, J=3.6, 2.2 Hz, 1H), 6.17-6.22 (m, 1H), 3.76-3.94 (m, 4H), 3.72 (s, 2H), 3.58 (t, J=6.8 Hz, 2H), 2.16 (t, J=6.8 Hz, 2H), 1.39 (s, 9H). m/z (ESI): 324.1 (M−Boc+H)$^+$.

Step 5: tert-butyl 6-(4-(2-fluorophenyl)-7-(1-methoxy-5-methyl-1-oxohexan-3-yl)-7H-pyrrolo[2,3-d]pyrimidin-2-yl)-2,6-diazaspiro[3.4]octane-2-carboxylate To a solution of tert-butyl 6-(4-(2-fluorophenyl)-7H-pyrrolo[2,3-d]pyrimidin-2-yl)-2,6-diazaspiro[3.4]octane-2-carboxylate (0.25 g, 0.59 mmol), methyl (E)-5-methylhex-2-enoate (0.168 g, 1.18 mmol, synthesized following the procedure described in *Chem. Commun.* 2015, 51, 8958) and MeCN (2 mL) was added DBU (0.09 g, 0.59 mmol). The mixture was allowed to stir at 90° C. for 16 h. The reaction mixture was concentrated and purified on a Redi-Sep pre-packed silica gel column, eluting with 0-20% EtOAc in hexanes, to provide tert-butyl 6-(4-(2-fluorophenyl)-7-(1-methoxy-5-methyl-1-oxohexan-3-yl)-7H-pyrrolo[2,3-d]pyrimidin-2-yl)-2,6-diazaspiro[3.4]octane-2-carboxylate (0.19 g, 57% yield) as a white solid. $^1$H NMR (400 MHz, DMSO-$d_6$) δ ppm 7.78 (td, J=7.6, 1.8 Hz, 1H), 7.52-7.61 (m, 1H), 7.33-7.42 (m, 2H), 7.29 (d, J=3.8 Hz, 1H), 6.23 (t, J=3.8 Hz, 1H), 5.05-5.17 (m, 1H), 3.76-3.96 (m, 4H), 3.73 (s, 2H), 3.53-3.66 (m, 2H), 3.50 (s, 3H), 2.88-3.07 (m, 2H), 2.17 (t, J=6.8 Hz, 2H), 1.98-2.11 (m, 1H), 1.51-1.53 (m, 1H), 1.39 (s, 9H), 0.99-1.12 (m, 1H), 0.95 (d, J=6.4 Hz, 3H), 0.79 (d, J=6.6 Hz, 3H). m/z (ESI): 566.3 (M+H)$^+$.

Step 6: tert-butyl 6-(4-(2-fluorophenyl)-7-(5-methyl-1-(methylamino)-1-oxohexan-3-yl)-7H-pyrrolo[2,3-d]pyrimidin-2-yl)-2,6-diazaspiro[3.4]octane-2-carboxylate A mixture of methanamine in EtOH (3 mL, 0.327 mmol) and tert-butyl 6-(4-(2-fluorophenyl)-7-(1-methoxy-5-methyl-1-oxohexan-3-yl)-7H-pyrrolo[2,3-d]pyrimidin-2-yl)-2,6-diazaspiro [3.4]octane-2-carboxylate (0.185 g, 0.327 mmol) was allowed to stir at room temperature for 16 h. The reaction was concentrated and purified on a Redi-Sep pre-packed silica gel column, eluting with 10-50% EtOAc in hexanes, to provide tert-butyl 6-(4-(2-fluorophenyl)-7-(5-methyl-1-(methylamino)-1-oxohexan-3-yl)-7H-pyrrolo[2,3-d]pyrimidin-2-yl)-2,6-diazaspiro[3.4]octane-2-carboxylate (0.185 g, 99% yield) as a white solid. $^1H$ NMR (400 MHz, DMSO-$d_6$) δ ppm 7.69-7.94 (m, 2H), 7.52-7.60 (m, 1H), 7.32-7.42 (m, 2H), 7.17 (d, J=3.8 Hz, 1H), 6.21 (t, J=3.8 Hz, 1H), 4.98-5.17 (m, 1H), 3.78-3.96 (m, 4H), 3.74 (s, 2H), 3.60 (t, J=6.9 Hz, 2H), 2.68 (d, J=7.2 Hz, 3H), 2.17 (t, J=6.9 Hz, 2H), 1.94-2.15 (m, 3H), 1.43-1.58 (m, 1H), 1.39 (s, 9H), 1.00-1.14 (m, 1H), 0.93 (d, J=6.4 Hz, 3H), 0.78 (d, J=6.6 Hz, 3H). m/z (ESI): 565.3 $(M+H)^+$. The racemic mixture was separated by SFC using a ChiralPak AS-H column with a mobile phase of 70% liquid $CO_2$ and 30% iPrOH with 0.2% diethylamine to provide tert-butyl (S)-6-(4-(2-fluorophenyl)-7-(5-methyl-1-(methylamino)-1-oxohexan-3-yl)-7H-pyrrolo[2,3-d]pyrimidin-2-yl)-2,6-diazaspiro[3.4]octane-2-carboxylate (0.075 g, 41% yield) as Peak 1 and tert-butyl (R)-6-(4-(2-fluorophenyl)-7-(5-methyl-1-(methylamino)-1-oxohexan-3-yl)-7H-pyrrolo[2,3-d]pyrimidin-2-yl)-2,6-diazaspiro[3.4]octane-2-carboxylate (0.072 g, 39% yield) as Peak 2. The stereochemistry of structures was arbitrarily assigned and is not established.

Peak 1: $^1H$ NMR (400 MHz, DMSO-$d_6$) δ ppm 7.66-7.89 (m, 2H), 7.47-7.64 (m, 1H), 7.21-7.47 (m, 2H), 7.17 (d, J=3.8 Hz, 1H), 6.21 (t, J=3.8 Hz, 1H), 5.03-5.14 (m, 1H), 3.78-3.96 (m, 4H), 3.74 (s, 2H), 3.60 (t, J=6.9 Hz, 2H), 2.68 (d, J=7.2 Hz, 3H), 2.17 (t, J=6.9 Hz, 2H), 1.93-2.08 (m, 1H), 1.44-1.55 (m, 1H), 1.39 (s, 9H), 1.01-1.12 (m, 3H), 0.93 (d, J=6.4 Hz, 3H), 0.78 (d, J=6.6 Hz, 3H). m/z (ESI): 565.3 $(M+H)^+$.

Peak 2: $^1H$ NMR (400 MHz, DMSO-$d_6$) δ ppm 7.74-7.85 (m, 2H), 7.52-7.60 (m, 1H), 7.27-7.43 (m, 2H), 7.17 (d, J=3.8 Hz, 1H), 6.21 (t, J=3.8 Hz, 1H), 5.03-5.14 (m, 1H), 3.76-3.99 (m, 4H), 3.74 (s, 2H), 3.60 (t, J=6.9 Hz, 2H), 2.68 (d, J=7.2 Hz, 3H), 2.17 (t, J=6.9 Hz, 2H), 1.95-2.07 (m, 1H), 1.49-1.51 (m, 1H), 1.39 (s, 9H), 1.03-1.12 (m, 3H), 0.93 (d, J=6.4 Hz, 3H), 0.78 (d, J=6.6 Hz, 3H). m/z (ESI): 565.3 $(M+H)^+$.

Step 7: (S)-3-(4-(2-fluorophenyl)-2-(2,6-diazaspiro[3.4]octan-6-yl)-7H-pyrrolo[2,3-d]pyrimidin-7-yl)-N,5-dimethylhexanamide hydrochloride To a stirred solution of tert-butyl (S)-6-(4-(2-fluorophenyl)-7-(5-methyl-1-(methylamino)-1-oxohexan-3-yl)-7H-pyrrolo[2,3-d]pyrimidin-2-yl)-2,6-diazaspiro[3.4]octane-2-carboxylate (0.080 g, 0.142 mmol) and DCM (0.5 mL) was added 4M HCl in dioxane (0.35 mL, 1.42 mmol) at 0° C. The resulting reaction mixture was allowed to stir at room temperature for 2 h. The reaction mixture was concentrated under reduced pressure and triturated with $Et_2O$ to provide (S)-3-(4-(2-fluorophenyl)-2-(2,6-diazaspiro[3.4]octan-6-yl)-7H-pyrrolo[2,3-d]pyrimidin-7-yl)-N,5-dimethylhexanamide hydrochloride (0.07 g, 99% yield) as a yellow solid, which was used in the next step without further purification. m/z (ESI): 465.2 $(M+H)^+$.

Step 8: (S)-3-(2-(2-Acryloyl-2,6-diazaspiro[3.4]octan-6-yl)-4-(2-fluorophenyl)-7H-pyrrolo[2,3-d]pyrimidin-7-yl)-N,5-dimethylhexanamide (Example 11)

To a stirred solution of (S)-3-(4-(2-fluorophenyl)-2-(2,6-diazaspiro[3.4]octan-6-yl)-7H-pyrrolo[2,3-d]pyrimidin-7-yl)-N,5-dimethylhexanamide hydrochloride (0.07 g, 0.140 mmol), TEA (0.06 mL, 0.42 mmol) and DCM (2 mL) was added acryloyl chloride (0.013 g, 0.140 mmol, Symax Ltd.) at 0° C. dropwise. The mixture was allowed to stir at 0° C. for 15 min. The reaction mixture was quenched with water and extracted with DCM. The combined organic layers were washed with brine, dried over $Na_2SO_4$, concentrated and purified by preparative HPLC using a XBridge Prep $C_{18}$ 5 μm OBD column, 150×30 mm, 0.1% $NH_4HCO_3$ in MeCN/$H_2O$, gradient 35-80% over 15 min, flow rate=30 mL/min to afford (S)-3-(2-(2-acryloyl-2,6-diazaspiro[3.4]octan-6-yl)-4-(2-fluorophenyl)-7H-pyrrolo[2,3-d]pyrimidin-7-yl)-N,5-dimethylhexanamide Example 11 (0.02 g, 28% yield) as a white solid. $^1H$ NMR (400 MHz, DMSO-$d_6$) δ ppm 7.73-7.85 (m, 2H), 7.51-7.61 (m, 1H), 7.32-7.44 (m, 2H). 7.18 (d, J=3.7 Hz, 1H), 6.33 (dd, J=17.0, 10.3 Hz, 1H), 6.22 (t, J=3.8 Hz, 1H), 6.12 (dd, J=17.0, 2.3 Hz, 1H), 5.68 (dd, J=10.3, 2.3 Hz, 1H), 5.09-5.12 (m, 1H), 4.23-4.32 (m, 1H), 4.19 (d, J=8.7 Hz, 1H), 3.88-4.02 (m, 2H), 3.78-3.81 (m, 2H), 3.54-3.70 (m, 2H), 2.69 (s, 3H), 2.45-2.52 (m, 1H), 2.22 (d, J=7.5 Hz, 2H), 2.01 (t, J=12.7 Hz, 1H), 1.43-1.55 (m, 2H), 1.07-1.10 (m, 1H), 0.93 (d, J=6.4 Hz, 3H), 0.78 (d, J=6.5 Hz, 3H). m/z (ESI): 519.2 $(M+H)^+$.

Method 12

Example 12-1: 1-(6-(4-(2-chloro-5-hydroxy-3-methylphenyl)-3,7,7-trimethyl-7,8-dihydro-5H-pyrano[4,3-b]pyridin-2-yl)-2,6-diazaspiro[3.4]octan-2-yl)prop-2-en-1-one

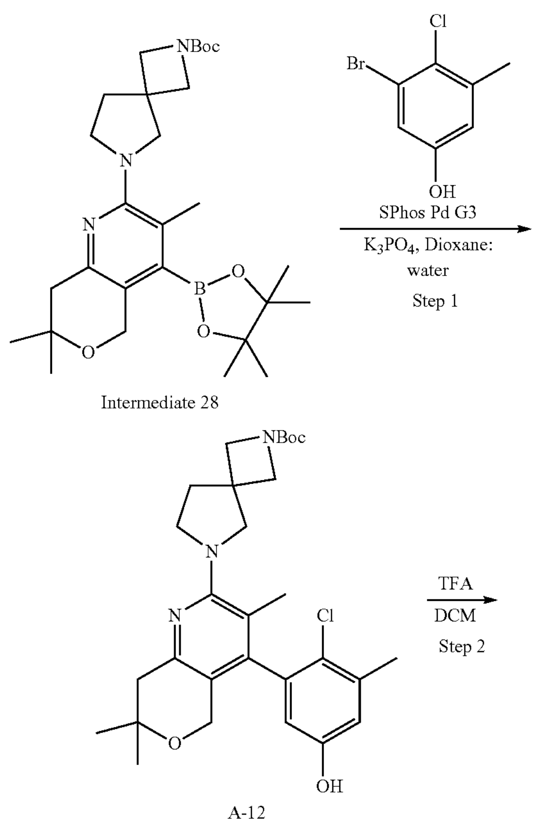

Intermediate 28

A-12

-continued

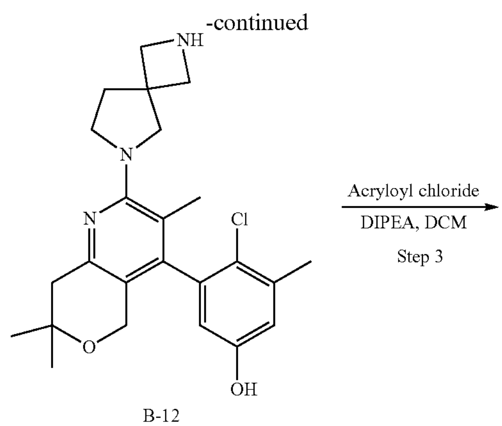

B-12

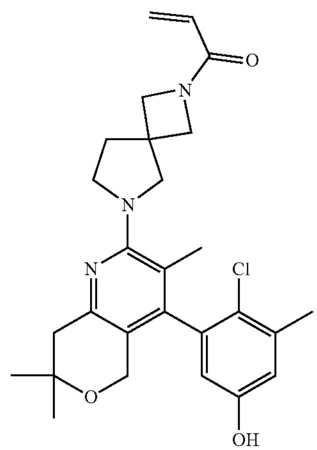

Example 12-1

Step 1: tert-butyl 6-(4-(2-chloro-5-hydroxy-3-methylphenyl)-3,7,7-trimethyl-7,8-dihydro-5H-pyrano[4,3-b]pyridin-2-yl)-2,6-diazaspiro[3.4]octane-2-carboxylate To a solution of tert-butyl 6-(3,7,7-trimethyl-4-(4,4,5,5-tetramethyl-1,3,2-dioxaborolan-2-yl)-7,8-dihydro-5H-pyrano[4,3-b]pyridin-2-yl)-2,6-diazaspiro[3.4]octane-2-carboxylate (306 mg, 0.596 mmol, Intermediate 28), 3-bromo-4-chloro-5-methylphenol (110 mg, 0.497 mmol, Intermediate 56), $K_3PO_4$ (316 mg, 1.490 mmol, Sigma-Aldrich), and SPhos Pd G3 (21.49 mg, 0.025 mmol, Strem) was added 1,4-dioxane (4 mL) and water (0.8 mL). The solution was heated at 60° C. for 24 h. The reaction was allowed to cool to room temperature and adsorbed onto a plug of silica gel and chromatographed through a Redi-Sep® pre-packed silica gel column, eluting with 0-50% EtOAc:EtOH (3:1) in heptanes, to provide tert-butyl 6-(4-(2-chloro-5-hydroxy-3-methylphenyl)-3,7,7-trimethyl-7,8-dihydro-5H-pyrano[4,3-b]pyridin-2-yl)-2,6-diazaspiro[3.4]octane-2-carboxylate A-12 (200 mg, 76% yield), as a light-yellow film. m/z (ESI): 528.2 $(M+H)^+$. The material was carried forward without further purification.

Step 2: 4-chloro-3-methyl-5-(3,7,7-trimethyl-2-(2,6-diazaspiro[3.4]octan-6-yl)-7,8-dihydro-5H-pyrano[4,3-b]pyridin-4-yl)phenol 2,2,2-trifluoroacetate To a solution of tert-butyl 6-(4-(2-chloro-5-hydroxy-3-methylphenyl)-3,7,7-trimethyl-7,8-dihydro-5H-pyrano[4,3-b]pyridin-2-yl)-2,6-diazaspiro[3.4]octane-2-carboxylate (200 mg, 0.189 mmol) and DCM (4 mL) was added TFA (0.5 mL). The solution was stirred at room temperature for 0.5 h. The reaction was concentrated in vacuo to give crude 4-chloro-3-methyl-5-(3,7,7-trimethyl-2-(2,6-diazaspiro[3.4]octan-6-yl)-7,8-dihydro-5H-pyrano[4,3-b]pyridin-4-yl)phenol 2,2,2-trifluoroacetate B-12 (160 mg, quantitative yield), as a brown film. m/z (ESI): 428.2 $(M+H)^+$. The material was carried forward without further purification.

Step 3: 1-(6-(4-(2-chloro-5-hydroxy-3-methylphenyl)-3,7,7-trimethyl-7,8-dihydro-5H-pyrano[4,3-b]pyridin-2-yl)-2,6-diazaspiro[3.4]octan-2-yl)prop-2-en-1-one To a 0° C. solution of 4-chloro-3-methyl-5-(3,7,7-trimethyl-2-(2,6-diazaspiro[3.4]octan-6-yl)-7,8-dihydro-5H-pyrano[4,3-b]pyridin-4-yl)phenol 2,2,2-trifluoroacetate (80 mg, 0.187 mmol) and DCM (4 mL) was added DIEA (0.326 mL, 1.869 mmol, Sigma-Aldrich), followed by acryloyl chloride (0.011 mL, 0.135 mmol, Sigma-Aldrich). After stirring for 5 min, the reaction was diluted with DCM and aqueous saturated $NH_4Cl$. The aqueous layer was extracted with DCM (10 mL). The combined organic layers were concentrated in vacuo and adsorbed onto a plug of silica gel and chromatographed through a Redi-Sep® pre-packed silica gel column, eluting with 0-50% EtOAc:EtOH (3:1) in heptanes, to provide 1-(6-(4-(2-chloro-5-hydroxy-3-methylphenyl)-3,7,7-trimethyl-7,8-dihydro-5H-pyrano[4,3-b]pyridin-2-yl)-2,6-diazaspiro[3.4]octan-2-yl)prop-2-en-1-one Example 12-1 (41 mg, 45.5% yield), as a white solid. m/z (ESI): 482.2 $(M+H)^+$. $^1H$ NMR (400 MHz, $CDCl_3$) δ ppm 6.85-7.13 (m, 1H), 6.80 (d, J=2.5 Hz, 1H), 6.33-6.40 (m, 1H), 6.15-6.28 (m, 1H), 5.95-6.09 (m, 1H), 5.71 (dd, J=10.2, 1.7 Hz, 1H), 4.02-4.27 (m, 6H), 3.57-3.76 (m, 3H), 3.47-3.56 (m, 1H), 2.69-2.81 (m, 2H), 2.39 (s, 3H), 2.16 (br t, J=6.7 Hz, 2H), 1.90 (s, 3H), 1.30 (s, 3H), 1.28 (s, 3H).

TABLE 4

| Examples 12-2 to 12-45 were prepared following the procedure described in Method 12, Steps 1-3, above as follows: | | | | |
|---|---|---|---|---|
| Ex.# | Chemical Structure | Name | Method changes | Reagent |
| 12-2 | 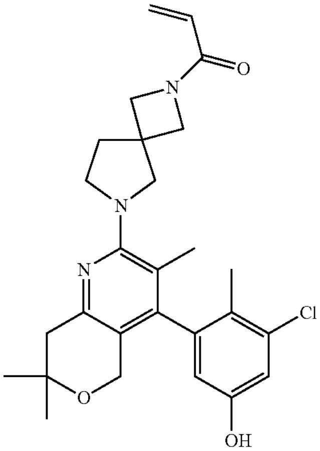 [SMILES: C=CC(=O)N1CC2(CCN(c3nc4c(c(-c5cc(O)cc(Cl)c5C)c3C)COC(C)(C)C4)C2)C1] | 1-(6-(4-(3-chloro-5-hydroxy-2-methylphenyl)-3,7,7-trimethyl-7,8-dihydro-5H-pyrano[4,3-b]pyridin-2-yl)-2,6-diazaspiro[3.4]octan-2-yl)prop-2-en-1-one | | Step 1: Intermediate 57. |
| 12-3 | 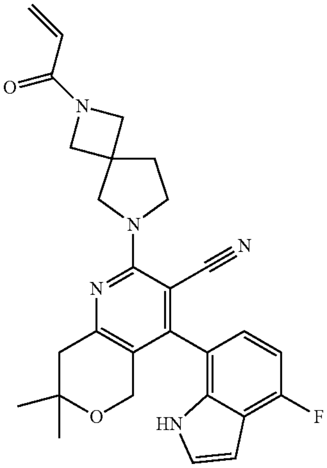 [SMILES: C=CC(=O)N1CC2(CCN(c3nc4c(c(-c5ccc(F)c6cc[nH]c56)c3C#N)COC(C)(C)C4)C2)C1] | 4-(4-fluoro-1H-indol-7-yl)-7,7-dimethyl-2-(2-(2-propenoyl)-2,6-diazaspiro[3.4]octan-6-yl)-7,8-dihydro-5H-pyrano[4,3-b]pyridine-3-carbonitrile | | Step 1: Intermediate 32 and 7-bromo-4-fluoro-1H-indole (AA Blocks), |
| 12-4 | 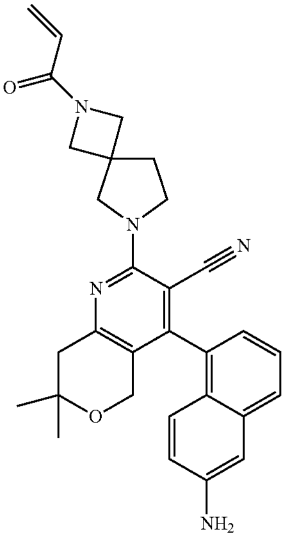 | 4-(6-amino-1-naphthalenyl)-7,7-dimethyl-2-(2-(2-propenoyl)-2,6-diazaspiro[3.4]octan-6-yl)-7,8-dihydro-5H-pyrano[4,3-b]pyridine-3-carbonitrile | | Step 1: Intermediate 32 and 5-bromonaphthalen-2-amine hydrochloride (Chemspace). |

TABLE 4-continued

| Examples 12-2 to 12-45 were prepared following the procedure described in Method 12, Steps 1-3, above as follows: | | | | |
|---|---|---|---|---|
| Ex.# | Chemical Structure | Name | Method changes | Reagent |
| 12-5 | 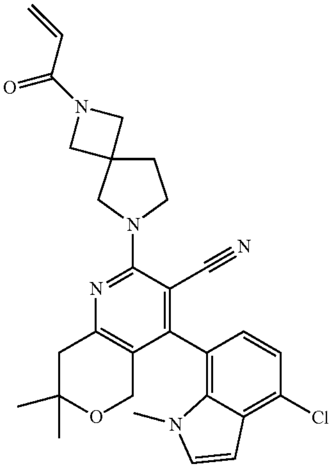 [SMILES: C=CC(=O)N1CC2(CCN(c3nc4c(c(-c5ccc(Cl)c6ccn(C)c56)c3C#N)COC(C)(C)C4)C2)C1] | 4-(4-chloro-1-methyl-1H-indol-7-yl)-7,7-dimethyl-2-(2-(2-propenoyl)-2,6-diazaspiro[3.4]octan-6-yl)-7,8-dihydro-5H-pyrano[4,3-b]pyridine-3-carbonitrile | Additional N-methylation performed using procedure from Example 2-19 after step 1, using LiHMDS and MeI. | Step 1: Intermediate 32 and 7-bromo-4-chloro-1H-indole (Combi-Blocks). |
| 12-6 | 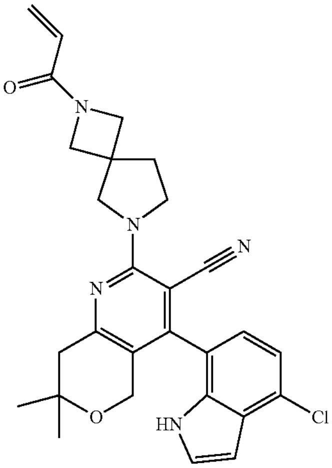 [SMILES: C=CC(=O)N1CC2(CCN(c3nc4c(c(-c5ccc(Cl)c6cc[nH]c56)c3C#N)COC(C)(C)C4)C2)C1] | 4-(4-chloro-1H-indol-7-yl)-7,7-dimethyl-2-(2-(2-propenoyl)-2,6-diazaspiro[3.4]octan-6-yl)-7,8-dihydro-5H-pyrano[4,3-b]pyridine-3-carbonitrile | | Step 1: Intermediate 32 and 7-bromo-4-chloro-1H-indole (Combi-Blocks). |
| 12-7 | 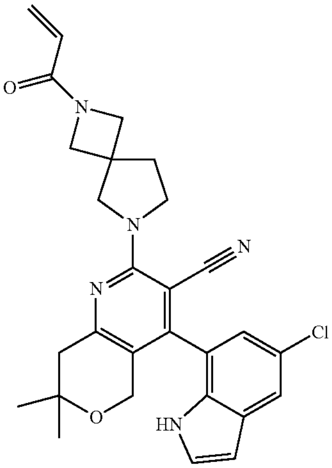 [SMILES: C=CC(=O)N1CC2(CCN(c3nc4c(c(-c5cc(Cl)cc6cc[nH]c56)c3C#N)COC(C)(C)C4)C2)C1] | 4-(5-chloro-1H-indol-7-yl)-7,7-dimethyl-2-(2-(2-propenoyl)-2,6-diazaspiro[3.4]octan-6-yl)-7,8-dihydro-5H-pyrano[4,3-b]pyridine-3-carbonitrile | | Step 1: Intermediate 32 and 7-bromo-5-chloro-1H-indole (Enamine). |

TABLE 4-continued

| Ex.# | Chemical Structure | Name | Method changes | Reagent |
|---|---|---|---|---|
| | Examples 12-2 to 12-45 were prepared following the procedure described in Method 12, Steps 1-3, above as follows: | | | |
| 12-8 | 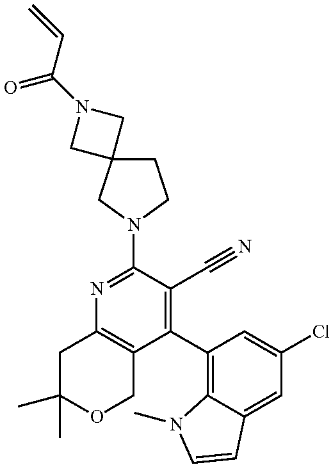 [SMILES: C=CC(=O)N1CC2(CCN(c3nc4c(c(-c5cc(Cl)cc6ccn(C)c56)c3C#N)COC(C)(C)C4)C2)C1] | 4-(5-chloro-1-methyl-1H-indol-7-yl)-7,7-dimethyl-2-(2-(2-propenoyl)-2,6-diazaspiro[3.4]octan-6-yl)-7,8-dihydro-5H-pyrano[4,3-b]pyridine-3-carbonitrile | Additional N-methylation performed using procedure from Example 2-19 after step 1, using LiHMDS and MeI. | Step 1: Intermediate 32 and 7-bromo-5-chloro-1H-indole (Enamine). |
| 12-9 | 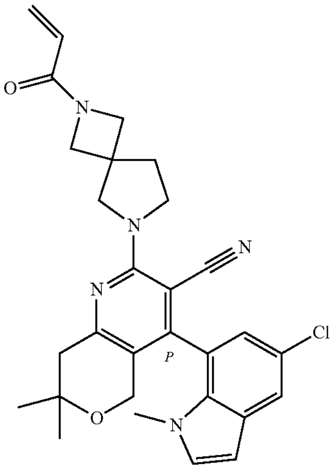 | (P)-4-(5-chloro-1-methyl-1H-indol-7-yl)-7,7-dimethyl-2-(2-(2-propenoyl)-2,6-diazaspiro[3.4]octan-6-yl)-7,8-dihydro-5H-pyrano[4,3-b]pyridine-3-carbonitrile (1$^{st}$ eluting peak) | Additional N-methylation performed using procedure from Example 2-19 after step 1, using LiHMDS and MeI. See atropisomer separation conditions below. | Step 1: Intermediate 32 and 7-bromo-5-chloro-1H-indole (Enamine). |
| 12-10 | 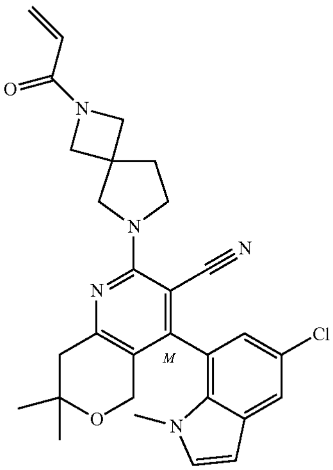 | (M)-4-(5-chloro-1-methyl-1H-indol-7-yl)-7,7-dimethyl-2-(2-(2-propenoyl)-2,6-diazaspiro[3.4]octan-6-yl)-7,8-dihydro-5H-pyrano[4,3-b]pyridine-3-carbonitrile (2$^{nd}$ eluting peak) | Additional N-methylation performed using procedure from Example 2-19 after step 1, using LiHMDS and MeI. See atropisomer separation conditions below. | Step 1: Intermediate 32 and 7-bromo-5-chloro-1H-indole (Enamine). |

TABLE 4-continued

| Examples 12-2 to 12-45 were prepared following the procedure described in Method 12, Steps 1-3, above as follows: | | | | |
|---|---|---|---|---|
| Ex.# | Chemical Structure | Name | Method changes | Reagent |
| 12-11 | 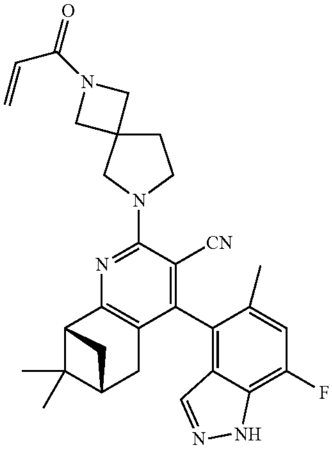 [SMILES: C=CC(=O)N1CC2(CCN(c3nc4c(c(-c5c(C)cc(F)c6[nH]ncc56)c3C#N)C[C@H]3C[C@@H]4C3(C)C)C2)C1] | (1R,9R)-6-(7-fluoro-5-methyl-1H-indazol-4-yl)-10,10-dimethyl-4-(2-(2-propenoyl)-2,6-diazaspiro[3.4]octan-6-yl)-3-azatricyclo[7.1.1.0$^{2,7}$]undeca-2,4,6-triene-5-carbonitrile | Step 1: $Cs_2CO_3$ replaced $K_3PO_4$. | Step 1: Intermediate 33 and Intermediate |
| 12-12 | 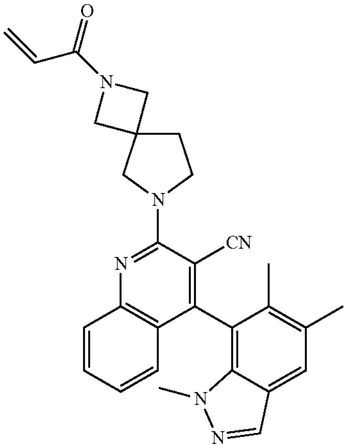 [SMILES: C=CC(=O)N1CC2(CCN(c3nc4ccccc4c(-c4c(C)c(C)cc5cnn(C)c45)c3C#N)C2)C1] | 2-(2-(2-propenoyl)-2,6-diazaspiro[3.4]octan-6-yl)-4-(1,5,6-trimethyl-1H-indazol-7-yl)-3-quinolinecarbonitrile | Additional N-methylation performed using procedure from Example 2-19 after step 1, using NaH and MeI. | Step 1: Intermediate 64 and Intermediate 38, Step 3. |
| 12-13 | 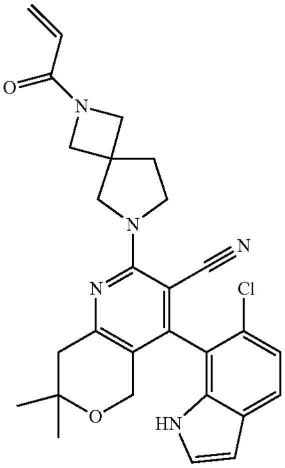 [SMILES: C=CC(=O)N1CC2(CCN(c3nc4c(c(-c5c(Cl)ccc6cc[nH]c56)c3C#N)COC(C)(C)C4)C2)C1] | 4-(6-chloro-1H-indol-7-yl)-7,7-dimethyl-2-(2-(2-propenoyl)-2,6-diazaspiro[3.4]octan-6-yl)-7,8-dihydro-5H-pyrano[4,3-b]pyridine-3-carbonitrile | | Step 1: Intermediate 32, and 7-bromo-6-chloro-1H-indole (Enamine) |

TABLE 4-continued

Examples 12-2 to 12-45 were prepared following the procedure described in Method 12, Steps 1-3, above as follows:

| Ex.# | Chemical Structure | Name | Method changes | Reagent |
|---|---|---|---|---|
| 12-14 | 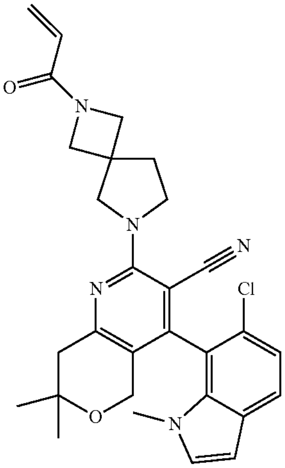 [SMILES: C=CC(=O)N1CC2(CCN(c3nc4c(c(-c5c(Cl)ccc6ccn(C)c56)c3C#N)COC(C)(C)C4)C2)C1] | 4-(6-chloro-1-methyl-1H-indol-7-yl)-7,7-dimethyl-2-(2-(2-propenoyl)-2,6-diazaspiro[3.4]octan-6-yl)-7,8-dihydro-5H-pyrano[4,3-b]pyridine-3-carbonitrile | Additional N-methylation performed using procedure from Example 2-19 after step 1, using NaH and MeI. | Step 1: Intermediate 32 and 7-bromo-6-chloro-1H-indole (Enamine) |
| 12-15 | 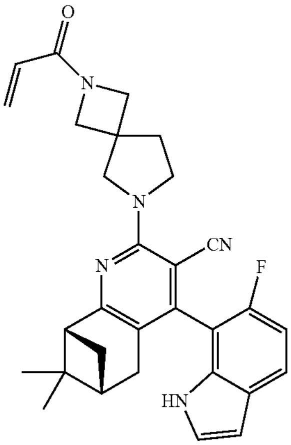 [SMILES: C=CC(=O)N1CC2(CCN(c3nc4c(c(-c5c(F)ccc6cc[nH]c56)c3C#N)C[C@H]3C[C@@H]4C3(C)C)C2)C1] | (1R,9R)-6-(6-fluoro-1H-indol-7-yl)-10,10-dimethyl-4-(2-(2-propenoyl)-2,6-diazaspiro[3.4]octan-6-yl)-3-azatricyclo[7.1.1.0$^{2,7}$]undeca-2,4,6-triene-5-carbonitrile | | Step 1: Intermediate 33 and 7-bromo-6-fluoro-1H-indole (AstaTech, Inc.) |
| 12-16 | 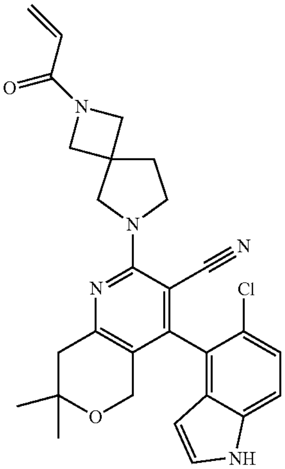 [SMILES: C=CC(=O)N1CC2(CCN(c3nc4c(c(-c5c(Cl)ccc6[nH]ccc56)c3C#N)COC(C)(C)C4)C2)C1] | 4-(5-chloro-1H-indol-4-yl)-7,7-dimethyl-2-(2-(2-propenoyl)-2,6-diazaspiro[3.4]octan-6-yl)-7,8-dihydro-5H-pyrano[4,3-b]pyridine-3-carbonitrile | | Step 1: Intermediate 32 and 4-bromo-5-chloro-1H-indole (AstaTech, Inc) |

TABLE 4-continued

| Examples 12-2 to 12-45 were prepared following the procedure described in Method 12, Steps 1-3, above as follows: | | | | |
|---|---|---|---|---|
| Ex.# | Chemical Structure | Name | Method changes | Reagent |
| 12-17 | 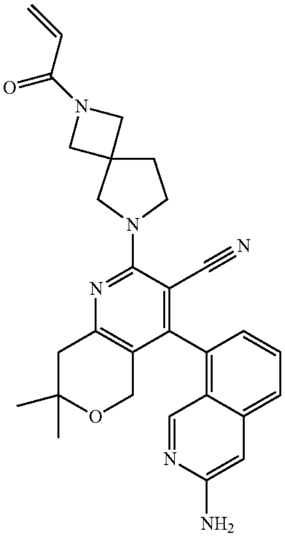 [SMILES: C=CC(=O)N1CC2(CCN(c3nc4c(c(-c5cccc6cc(N)ncc56)c3C#N)COC(C)(C)C4)C2)C1] | 4-(3-amino-8-isoquinolinyl)-7,7-dimethyl-2-(2-(2-propenoyl)-2,6-diazaspiro[3.4]octan-6-yl)-7,8-dihydro-5H-pyrano[4,3-b]pyridine-3-carbonitrile | | Step 1: Intermediate 32 and (8-bromoisoquinolin-3-yl)amine (Combi-Blocks) |
| 12-18 | 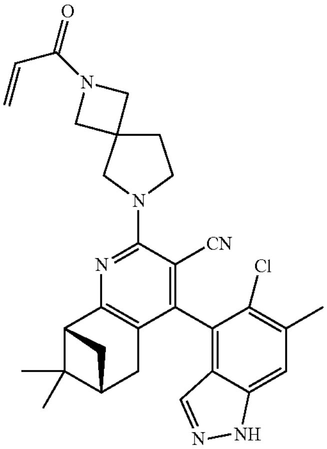 [SMILES: C=CC(=O)N1CC2(CCN(c3nc4c(c(-c5c(Cl)c(C)cc6[nH]ncc56)c3C#N)C[C@H]3C[C@@H]4C3(C)C)C2)C1] | (1R,9R)-6-(5-chloro-6-methyl-1H-indazol-4-yl)-10,10-dimethyl-4-(2-(2-propenoyl)-2,6-diazaspiro[3.4]octan-6-yl)-3-azatricyclo[7.1.1.0$^{2,7}$]undeca-2,4,6-triene-5-carbonitrile | Step 1: RuPhos and RuPhos Pd G3 replaced SPhos Pd G3 | Step 1: Intermediate 33 and 4-bromo-5-chloro-6-methyl-1-(tetrahydro-2H-pyran-2-yl)-1H-indazole (PharmaBlock). |
| 12-19 | 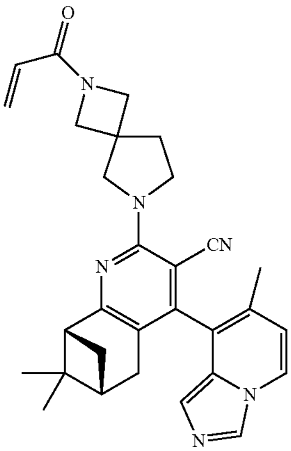 [SMILES: C=CC(=O)N1CC2(CCN(c3nc4c(c(-c5c(C)ccn6cncc56)c3C#N)C[C@H]3C[C@@H]4C3(C)C)C2)C1] | (1R,9R)-10,10-dimethyl-6-(7-methylimidazo[1,5-a]pyridin-8-yl)-4-(2-(2-propenoyl)-2,6-diazaspiro[3.4]octan-6-yl)-3-azatricyclo[7.1.1.0$^{2,7}$]undeca-2,4,6-triene-5-carbonitrile | Step 1: RuPhos and RuPhos Pd G3 replaced SPhos Pd G3 | Step 1: Intermediate 33 and 8-bromo-7-methylimidazo [1,5-a]pyridine (PharmaBlock). |

TABLE 4-continued

| Examples 12-2 to 12-45 were prepared following the procedure described in Method 12, Steps 1-3, above as follows: | | | | |
|---|---|---|---|---|
| Ex.# | Chemical Structure | Name | Method changes | Reagent |
| 12-20 | 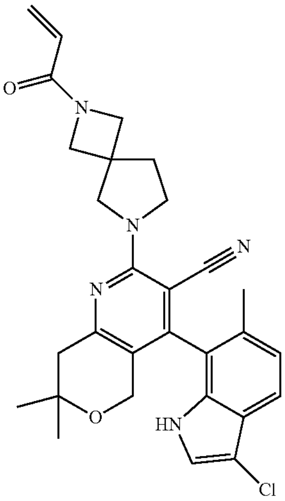 [SMILES: C=CC(=O)N1CC2(CCN(c3nc4c(c(-c5c(C)ccc6c(Cl)c[nH]c56)c3C#N)COC(C)(C)C4)C2)C1] | 4-(3-chloro-6-methyl-1H-indol-7-yl)-7,7-dimethyl-2-(2-(2-propenoyl)-2,6-diazaspiro[3.4]octan-6-yl)-7,8-dihydro-5H-pyrano[4,3-b]pyridine-3-carbonitrile | | Step 1: Intermediate 32 and Intermediate 76 |
| 12-21 | 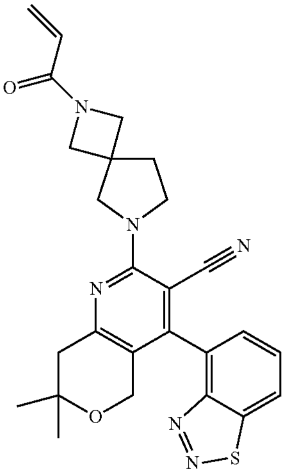 [SMILES: C=CC(=O)N1CC2(CCN(c3nc4c(c(-c5cccc6snnc56)c3C#N)COC(C)(C)C4)C2)C1] | 4-(1,2,3-benzothiadiazol-4-yl)-7,7-dimethyl-2-(2-(2-propenoyl)-2,6-diazaspiro[3.4]octan-6-yl)-7,8-dihydro-5H-pyrano[4,3-b]pyridine-3-carbonitrile | | Step 1: Intermediate 32 and 4-bromo-1,2,3-benzothiadiazole (Enamine) |
| 12-22 | 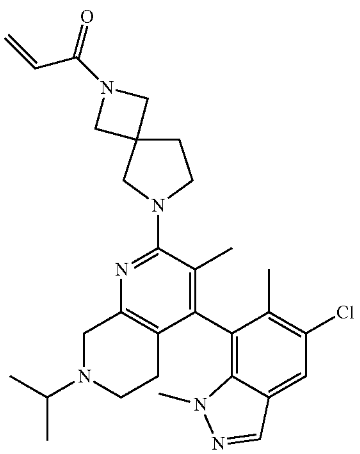 [SMILES: C=CC(=O)N1CC2(CCN(c3nc4c(c(-c5c(C)c(Cl)cc6cnn(C)c56)c3C)CCN(C(C)C)C4)C2)C1] | 1-(6-(4-(5-chloro-1,6-dimethyl-1H-indazol-7-yl)-3-methyl-7-(2-propanyl)-5,6,7,8-tetrahydro-1,7-naphthyridin-2-yl)-2,6-diazaspiro[3.4]octan-2-yl)-2-propen-1-one | Additional N-methylation performed using procedure from Example 2-19 after step 1, using LiHMDS and MeI. | Step 1: Intermediate 51 and Intermediate 37 |

TABLE 4-continued

Examples 12-2 to 12-45 were prepared following the procedure described in Method 12, Steps 1-3, above as follows:

| Ex.# | Chemical Structure | Name | Method changes | Reagent |
|---|---|---|---|---|
| 12-23 | 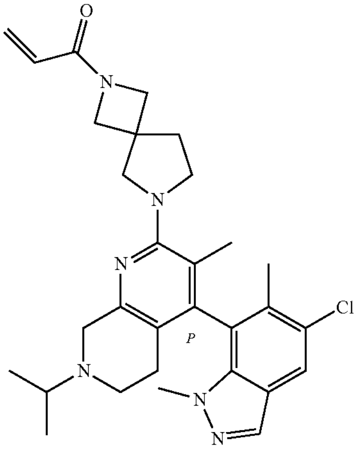 | (P)-1-(6-(4-(5-chloro-1,6-dimethyl-1H-indazol-7-yl)-3-methyl-7-(2-propanyl)-5,6,7,8-tetrahydro-1,7-naphthyridin-2-yl)-2,6-diazaspiro[3.4]octan-2-yl)-2-propen-1-one (1st eluting isomer) | Additional N-methylation performed using procedure from Example 2-19 after step 1, using LiHMDS and MeI. See atropisomer separation conditions below. | Step 1: Intermediate 51 and Intermediate 37 |
| 12-24 | 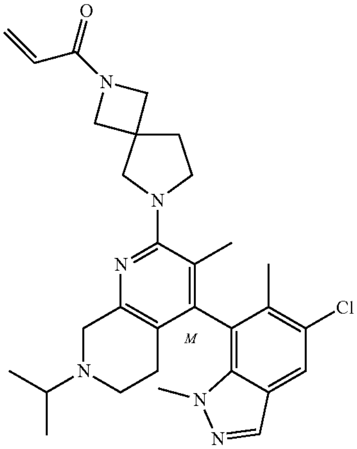 | (M)-1-(6-(4-(5-chloro-1,6-dimethyl-1H-indazol-7-yl)-3-methyl-7-(2-propanyl)-5,6,7,8-tetrahydro-1,7-naphthyridin-2-yl)-2,6-diazaspiro[3.4]octan-2-yl)-2-propen-1-one (2nd eluting isomer) | Additional N-methylation performed using procedure from Example 2-19 after step 1, using LiHMDS and MeI. See atropisomer separation conditions below. | Step 1: Intermediate 51 and Intermediate 37 |
| 12-25 | 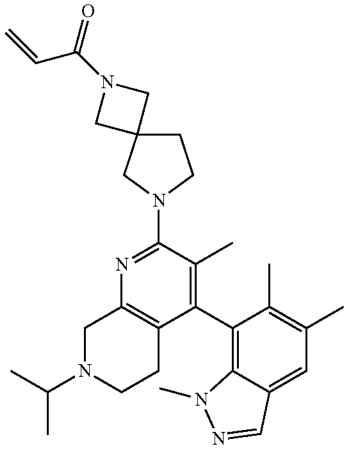 [SMILES: C=CC(=O)N1CC2(CCN(c3nc4c(c(-c5c(C)c(C)cc6cnn(C)c56)c3C)CCN(C(C)C)C4)C2)C1] | 1-(6-(3-methyl-7-(2-propanyl)-4-(1,5,6-trimethyl-1H-indazol-7-yl)-5,6,7,8-tetrahydro-1,7-naphthyridin-2-yl)-2,6-diazaspiro[3.4]octan-2-yl)-2-propen-1-one | Additional N-methylation performed using procedure from Example 2-19 after step 1, using LiHMDS and MeI. | Step 1: Intermediate 51 and Intermediate 38 |

TABLE 4-continued

Examples 12-2 to 12-45 were prepared following the procedure described in Method 12, Steps 1-3, above as follows:

| Ex.# | Chemical Structure | Name | Method changes | Reagent |
|---|---|---|---|---|
| 12-26 | 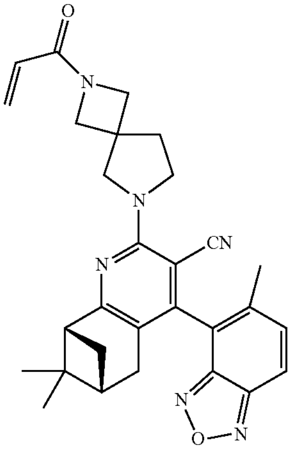 [SMILES: C=CC(=O)N1CC2(CCN(c3nc4c(c(-c5c(C)ccc6nonc56)c3C#N)C[C@H]3C[C@@H]4C3(C)C)C2)C1] | (1R,9R)-10,10-dimethyl-6-(5-methyl-2,1,3-benzoxadiazol-4-yl)-4-(2-(2-propenoyl)-2,6-diazaspiro[3.4]octan-6-yl)-3-azatricyclo[7.1.1.0$^{2,7}$]undeca-2,4,6-triene-5-carbonitrile | | Step 1: Intermediate 33 and 4-bromo-5-methyl-2,1,3-benzoxadiazole (Enamine) |
| 12-27 | 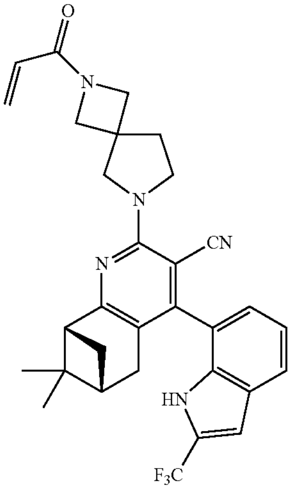 [SMILES: C=CC(=O)N1CC2(CCN(c3nc4c(c(-c5cccc6cc(C(F)(F)F)[nH]c56)c3C#N)C[C@H]3C[C@@H]4C3(C)C)C2)C1] | (1R,9R)-10,10-dimethyl-4-(2-(2-propenoyl)-2,6-diazaspiro[3.4]octan-6-yl)-6-(2-(trifluoromethyl)-1H-indol-7-yl)-3-azatricyclo[7.1.1.0$^{2,7}$]undeca-2,4,6-triene-5-carbonitrile | | Step 1: Intermediate 33 and 7-bromo-2-(trifluoromethyl)indole (Apollo Scientific Ltd.) |
| 12-28 | 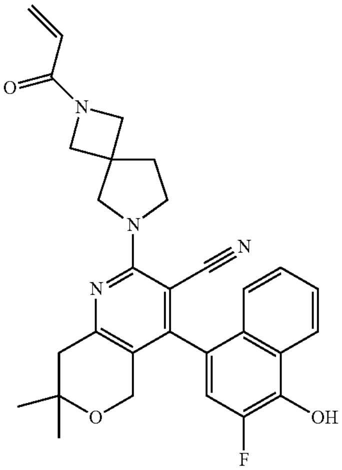 [SMILES: C=CC(=O)N1CC2(CCN(c3nc4c(c(-c5cc(F)c(O)c6ccccc56)c3C#N)COC(C)(C)C4)C2)C1] | 4-(3-fluoro-4-hydroxy-1-naphthalenyl)-7,7-dimethyl-2-(2-(2-propenoyl)-2,6-diazaspiro[3.4]octan-6-yl)-7,8-dihydro-5H-pyrano[4,3-b]pyridine-3-carbonitrile | Step 1: $K_2CO_3$ replaced $K_3PO_4$ | Step 1: Intermediate 32 and Intermediate 84 |

TABLE 4-continued

Examples 12-2 to 12-45 were prepared following the procedure described in Method 12, Steps 1-3, above as follows:

| Ex.# | Chemical Structure | Name | Method changes | Reagent |
|---|---|---|---|---|
| 12-29 | 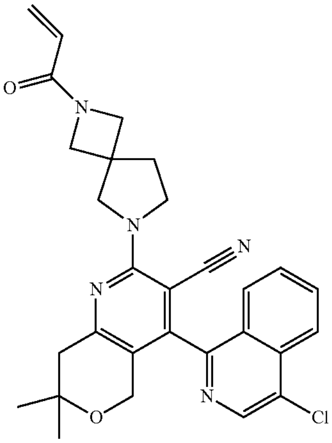 [SMILES: C=CC(=O)N1CC2(CCN(c3nc4c(c(-c5ncc(Cl)c6ccccc56)c3C#N)COC(C)(C)C4)C2)C1] | 4-(4-chloro-8-isoquinolinyl)-7,7-dimethyl-2-(2-(2-propenoyl)-2,6-diazaspiro[3.4]octan-6-yl)-7,8-dihydro-5H-pyrano[4,3-b]pyridine-3-carbonitrile | Step 1: $K_2CO_3$ replaced $K_3PO_4$ | Step 1: Intermediate 32 and 8-bromo-4-chloroisoquinoline (Chemoraga) |
| 12-30 | 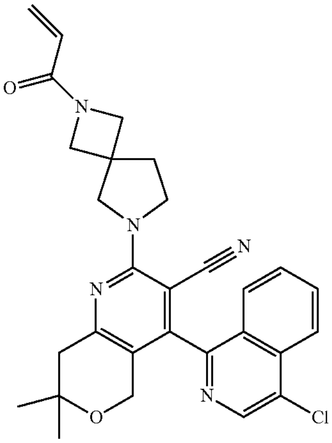 [SMILES: C=CC(=O)N1CC2(CCN(c3nc4c(c(-c5ncc(Cl)c6ccccc56)c3C#N)COC(C)(C)C4)C2)C1] | 4-(4-chloro-1-isoquinolinyl)-7,7-dimethyl-2-(2-(2-propenoyl)-2,6-diazaspiro[3.4]octan-6-yl)-7,8-dihydro-5H-pyrano[4,3-b]pyridine-3-carbonitrile | Step 1: $K_2CO_3$ replaced $K_3PO_4$ | Step 1: Intermediate 32 and 1-bromo-4-chloroisoquinoline (Aurum Pharmatech) |
| 12-31 | 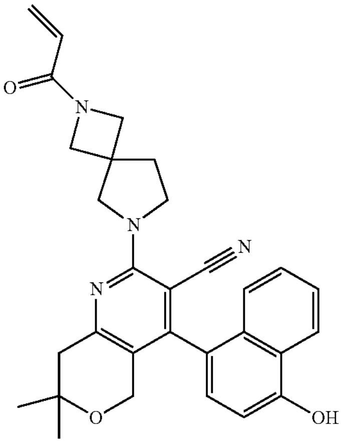 [SMILES: C=CC(=O)N1CC2(CCN(c3nc4c(c(-c5ccc(O)c6ccccc56)c3C#N)COC(C)(C)C4)C2)C1] | 4-(4-hydroxy-1-naphthalenyl)-7,7-dimethyl-2-(2-(2-propenoyl)-2,6-diazaspiro[3.4]octan-6-yl)-7,8-dihydro-5H-pyrano[4,3-b]pyridine-3-carbonitrile | | Step 1: Intermediate 32 and 4-bromo-1-naphthalenol (Combi-Blocks) |

TABLE 4-continued

Examples 12-2 to 12-45 were prepared following the procedure described in Method 12, Steps 1-3, above as follows:

| Ex.# | Chemical Structure | Name | Method changes | Reagent |
|---|---|---|---|---|
| 13-32 | 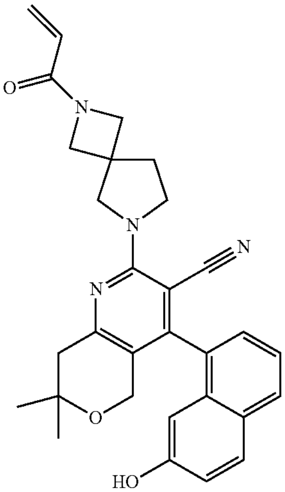 [SMILES: C=CC(=O)N1CC2(CCN(c3nc4c(c(-c5cccc6ccc(O)cc56)c3C#N)COC(C)(C)C4)C2)C1] | 4-(7-hydroxy-1-naphthalenyl)-7,7-dimethyl-2-(2-(2-propenoyl)-2,6-diazaspiro[3.4]octan-6-yl)-7,8-dihydro-5H-pyrano[4,3-b]pyridine-3-carbonitrile | | Step 1: Intermediate 32 and 8-bromonaphthalen-2-ol (Synthonix Inc.) |
| 12-33 | 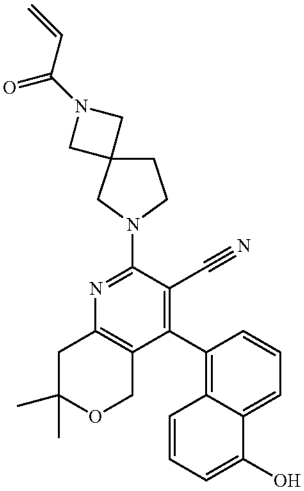 [SMILES: C=CC(=O)N1CC2(CCN(c3nc4c(c(-c5cccc6c(O)cccc56)c3C#N)COC(C)(C)C4)C2)C1] | 4-(5-hydroxy-1-naphthalenyl)-7,7-dimethyl-2-(2-(2-propenoyl)-2,6-diazaspiro[3.4]octan-6-yl)-7,8-dihydro-5H-pyrano[4,3-b]pyridine-3-carbonitrile | | Step 1: Intermediate 32 and 5-bromonaphthalen-1-ol (eNovation) |
| 12-34 | 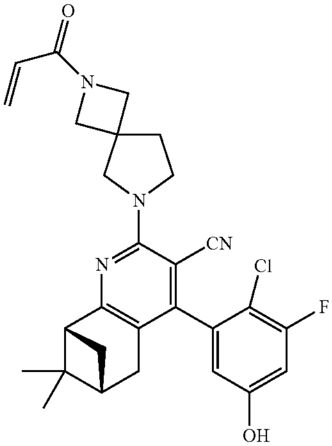 [SMILES: C=CC(=O)N1CC2(CCN(c3nc4c(c(-c5cc(O)cc(F)c5Cl)c3C#N)C[C@H]3C[C@@H]4C3(C)C)C2)C1] | (1R,9R)-6-(2-chloro-3-fluoro-5-hydroxyphenyl)-10,10-dimethyl-4-(2-(2-propenoyl)-2,6-diazaspiro[3.4]octan-6-yl)-3-azatricyclo[7.1.1.0$^{2,7}$]undeca-2,4,6-triene-5-carbonitrile | | Step 1: Intermediate 85 and 3-bromo-4-chloro-5-fluorophenol (Enamine) |

TABLE 4-continued

| Ex.# | Chemical Structure | Name | Method changes | Reagent |
|---|---|---|---|---|
| Examples 12-2 to 12-45 were prepared following the procedure described in Method 12, Steps 1-3, above as follows: | | | | |
| 12-35 | 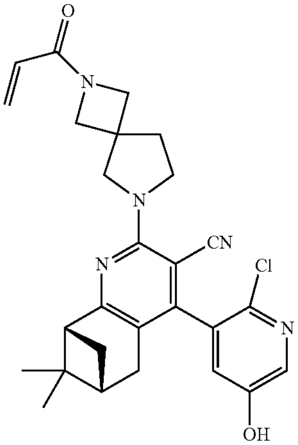 [SMILES: C=CC(=O)N1CC2(CCN(c3nc4c(c(-c5cc(O)cnc5Cl)c3C#N)C[C@H]3C[C@@H]4C3(C)C)C2)C1] | (1R,9R)-6-(2-chloro-5-hydroxy-3-pyridinyl)-10,10-dimethyl-4-(2-(2-propenoyl)-2,6-diazaspiro[3.4]octan-6-yl)-3-azatricyclo[7.1.1.0$^{2,7}$]undeca-2,4,6-triene-5-carbonitrile | | Step 1: Intermediate 33 and 3-bromo-2-chloro-5-hydroxypyridine (Asymchem Laboratories, Inc.) |
| 12-36 | 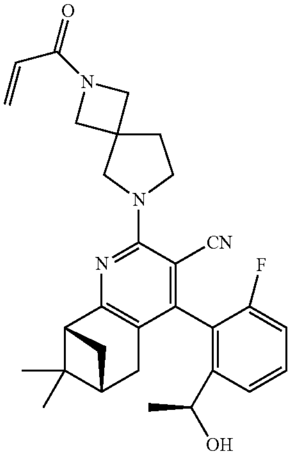 [SMILES: C=CC(=O)N1CC2(CCN(c3nc4c(c(-c5c(F)cccc5[C@H](C)O)c3C#N)C[C@H]3C[C@@H]4C3(C)C)C2)C1] | (1R,9R)-6-(2-fluoro-6-((1S)-1-hydroxyethyl)phenyl)-10,10-dimethyl-4-(2-(2-propenoyl)-2,6-diazaspiro[3.4]octan-6-yl)-3-azatricyclo[7.1.1.0$^{2,7}$]undeca-2,4,6-triene-5-carbonitrile (The stereochemistry of structure was arbitrarily assigned and is not established.) | Step 1: RuPhos and RuPhos Pd G3 replaced SPhos Pd G3. See Grignard addition after Step 1 below. | Step 1: Intermediate 33 and 2-bromo-3-fluorobenz-aldehyde Combi-Blocks) |
| 12-37 | 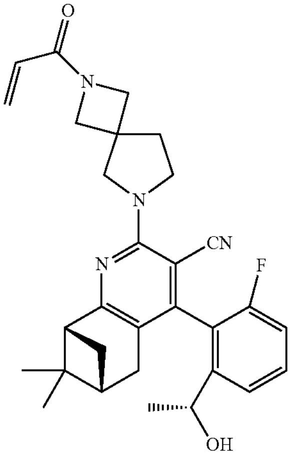 [SMILES: C=CC(=O)N1CC2(CCN(c3nc4c(c(-c5c(F)cccc5[C@@H](C)O)c3C#N)C[C@H]3C[C@@H]4C3(C)C)C2)C1] | (1R,9R)-6-(2-fluoro-6-((1R)-1-hydroxyethyl)phenyl)-10,10-dimethyl-4-(2-(2-propenoyl)-2,6-diazaspiro[3.4]octan-6-yl)-3-azatricyclo[7.1.1.02,7]undeca-2,4,6-triene-5-carbonitrile (The stereochemistry of structure was arbitrarily assigned and is not established.) | Step 1: RuPhos and RuPhos Pd G3 replaced SPhos Pd G3. See Grignard addition after Step 1 below. | Step 1: Intermediate 33 and 2-bromo-3-fluorobenz-aldehyde Combi-Blocks) |

TABLE 4-continued

| Examples 12-2 to 12-45 were prepared following the procedure described in Method 12, Steps 1-3, above as follows: | | | | |
|---|---|---|---|---|
| Ex.# | Chemical Structure | Name | Method changes | Reagent |
| 12-38 | 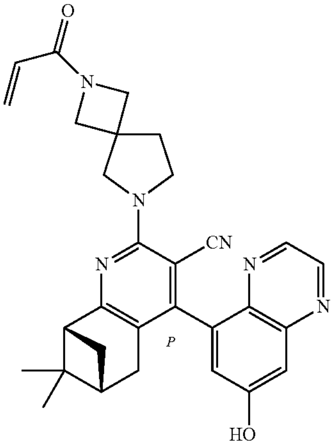 | (P)-(1R,9R)-6-(7-hydroxy-5-quinoxalinyl)-10,10-dimethyl-4-(2-(2-propenoyl)-2,6-diazaspiro[3.4]octan-6-yl)-3-azatricyclo[7.1.1.0$^{2,7}$]undeca-2,4,6-triene-5-carbonitrile | | Step 1: Intermediate 33 and Intermediate 86 |
| 12-39 | 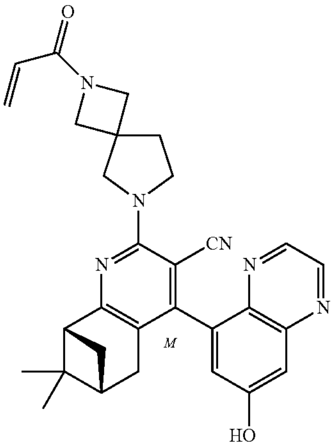 | (M)-(1R,9R)-6-(7-hydroxy-5-quinoxalinyl)-10,10-dimethyl-4-(2-(2-propenoyl)-2,6-diazaspiro[3.4]octan-6-yl)-3-azatricyclo[7.1.1.0$^{2,7}$]undeca-2,4,6-triene-5-carbonitrile | | Step 1: Intermediate 33 and Intermediate 86 |
| 12-40 | 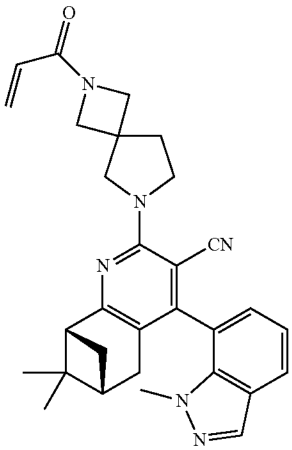 [SMILES: C=CC(=O)N1CC2(CCN(c3nc4c(c(-c5cccc6cnn(C)c56)c3C#N)C[C@H]3C[C@@H]4C3(C)C)C2)C1] | (1R,9R)-10,10-dimethyl-6-(1-methyl-1H-indazol-7-yl)-4-(2-(2-propenoyl)-2,6-diazaspiro[3.4]octan-6-yl)-3-azatricyclo[7.1.1.0$^{2,7}$]undeca-2,4,6-triene-5-carbonitrile | | Step 1: Intermediate 85 and 7-bromo-1-methylindazole (Combi-Blocks) |

TABLE 4-continued

Examples 12-2 to 12-45 were prepared following the procedure described in Method 12, Steps 1-3, above as follows:

| Ex.# | Chemical Structure | Name | Method changes | Reagent |
| --- | --- | --- | --- | --- |
| 12-41 | 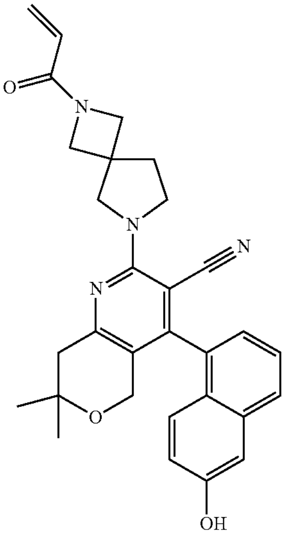 [SMILES: C=CC(=O)N1CC2(CCN(c3nc4c(c(-c5cccc6cc(O)ccc56)c3C#N)COC(C)(C)C4)C2)C1] | 4-(6-hydroxy-1-naphthalenyl)-7,7-dimethyl-2-(2-(2-propenoyl)-2,6-diazaspiro[3.4]octan-6-yl)-7,8-dihydro-5H-pyrano[4,3-b]pyridine-3-carbonitrile | | Step 1: Intermediate 32 and 5-Bromonaphthalen-2-ol (Angewandte Chemie, International Edition (2019), 58(14), 4596-4600) |
| 12-42 | 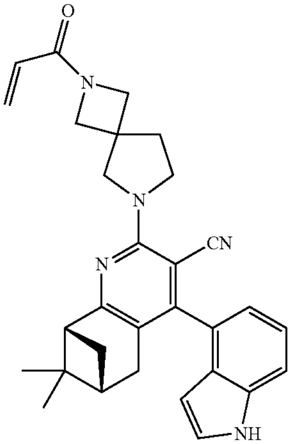 [SMILES: C=CC(=O)N1CC2(CCN(c3nc4c(c(-c5cccc6[nH]ccc56)c3C#N)C[C@H]3C[C@@H]4C3(C)C)C2)C1] | (1R,9R)-6-(1H-indol-4-yl)-10,10-dimethyl-4-(2-(2-propenoyl)-2,6-diazaspiro[3.4]octan-6-yl)-3-azatricyclo[7.1.1.0$^{2,7}$]undeca-2,4,6-triene-5-carbonitrile | | Step 1: Intermediate 85 and 4-bromo-1H-indole (CAS# 52488-36-5) |
| 12-43 | 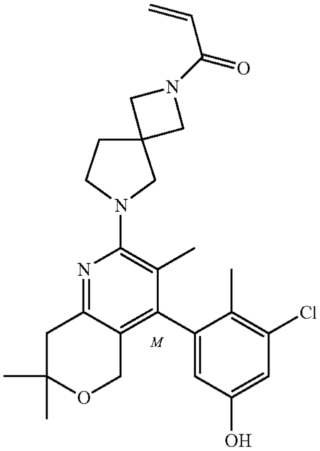 | (M)-1-(6-(4-(3-chloro-5-hydroxy-2-methylphenyl)-3,7,7-trimethyl-7,8-dihydro-5H-pyrano[4,3-b]pyridin-2-yl)-2,6-diazaspiro[3.4]octan-2-yl)prop-2-en-1-one (1$^{st}$ eluting isomer) | See atropisomer separation conditions below. | Step 1: Intermediate 57 |

TABLE 4-continued

| Examples 12-2 to 12-45 were prepared following the procedure described in Method 12, Steps 1-3, above as follows: | | | | |
|---|---|---|---|---|
| Ex.# | Chemical Structure | Name | Method changes | Reagent |
| 12-44 | 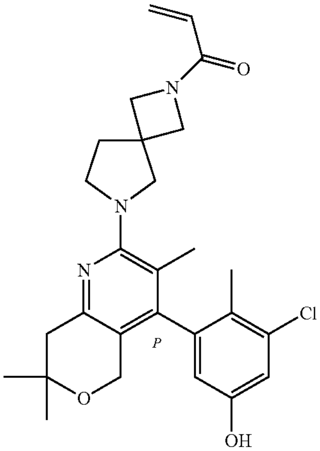 | (P)-1-(6-(4-(3-chloro-5-hydroxy-2-methylphenyl)-3,7,7-trimethyl-7,8-dihydro-5H-pyrano[4,3-b]pyridin-2-yl)-2,6-diazaspiro[3.4]octan-2-yl)prop-2-en-1-one (2nd eluting isomer) | See atropisomer separation conditions below. | Step 1: Intermediate 57 |
| 12-45 | 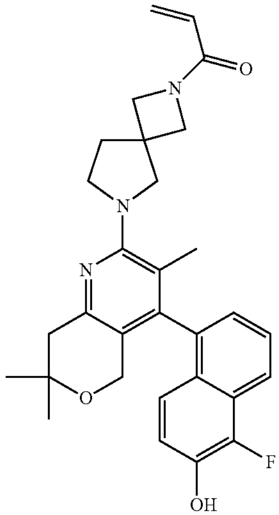 [SMILES: C=CC(=O)N1CC2(CCN(c3nc4c(c(-c5cccc6c(F)c(O)ccc56)c3C)COC(C)(C)C4)C2)C1] | 1-(6-(4-(5-fluoro-6-hydroxy-1-naphthalenyl)-3,7,7-trimethyl-7,8-dihydro-5H-pyrano[4,3-b]pyridin-2-yl)-2,6-diazaspiro[3.4]octan-2-yl)-2-propen-1-one | | Step 1: Intermediate 123 |

Atropisomer Separation for Examples 12-9 and 12-10.

The racemic mixture was separated by preparative SFC using a Chiralcel OJ column (250×21 mm) with a mobile phase of 75% liquid $CO_2$ and 25% MeOH with a flow rate of 80 mL/min to provide the respective P and M isomers of 4-(5-chloro-1-methyl-1H-indol-7-yl)-7,7-dimethyl-2-(2-(2-propenoyl)-2,6-diazaspiro[3.4]octan-6-yl)-7,8-dihydro-5H-pyrano[4,3-b]pyridine-3-carbonitrile. The stereochemistry of structures was arbitrarily assigned and is not established. 1st eluting atropisomer assigned as the P isomer and 2nd eluting atropisomer assigned as the M isomer.

Atropisomer Separation for Examples 12-23 and 12-24.

The racemic mixture was separated by preparative SFC using a Chiralpak IG column (21×250 mm) with a mobile phase of 50% liquid $CO_2$ and 50% MeOH with 0.2% TEA with a flow rate of 60 mL/min to provide the respective P and M isomers of 1-(6-(4-(5-chloro-1,6-dimethyl-1H-indazol-7-yl)-3-methyl-7-(2-propanyl)-5,6,7,8-tetrahydro-1,7-naphthyridin-2-yl)-2,6-diazaspiro[3.4]octan-2-yl)-2-propen-1-one. The stereochemistry of structures was arbitrarily assigned and is not established. 1st eluting atropisomer assigned as the M isomer and 2nd eluting atropisomer assigned as the P isomer.

Grignard Addition in Examples 12-36 and 12-37

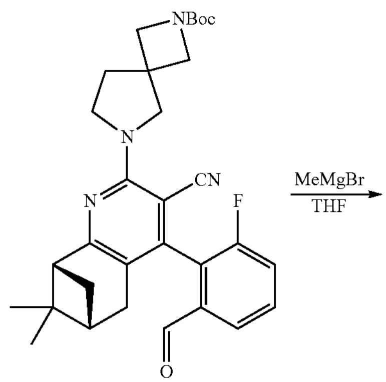

-continued

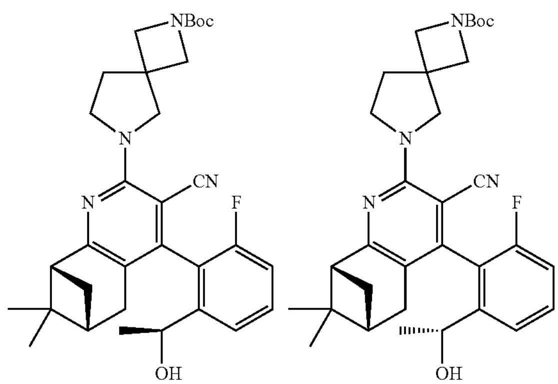

To a −78° C. solution of tert-butyl 6-((6R,8R)-3-cyano-4-(2-fluoro-6-formylphenyl)-7,7-dimethyl-5,6,7,8-tetrahydro-6,8-methanoquinolin-2-yl)-2,6-diazaspiro[3.4]octane-2-carboxylate (110.7 mg, 0.209 mmol) and THF (2 mL) was added methylmagnesium bromide, (0.070 mL, 0.209 mmol, 3.0 M in diethyl ether, Sigma-Aldrich). The reaction mixture was warmed to room temperature and stirred for 15 min. The reaction mixture was quenched with aqueous saturated $NH_4Cl$ and extracted with EtOAc. The organic extracts were washed with brine, dried over $Na_2SO_4$, and concentrated in vacuo. The crude material was absorbed onto a plug of silica gel and purified by chromatography through a Redi-Sep pre-packed silica gel column, eluting with a gradient of 0-30% EtOAc in heptanes, to provide tert-butyl 6-((6R,8R)-3-cyano-4-(2-fluoro-6-(1-hydroxyethyl)phenyl)-7,7-dimethyl-5,6,7,8-tetrahydro-6,8-methanoquinolin-2-yl)-2,6-diazaspiro[3.4]octane-2-carboxylate (76.9 mg, 67.4% yield) as a white solid. m/z (ESI): 547.0 $(M+H)^+$.

Atropisomer Separation for Examples 12-38 and 12-39.

The racemic mixture was separated by preparative HPLC using a Phenomenex Gemini column (C18, 110 Å. Axia, 150×30 mm, 5 μm) with a gradient of 0-100% acetonitrile in water (0.1% TFA) with a flow rate of 45 mL/min to provide the respective P and M isomers of (6R,8R)-2-(2-acryloyl-2,6-diazaspiro[3.4]octan-6-yl)-4-(7-hydroxyquinoxalin-5-yl)-7,7-dimethyl-5,6,7,8-tetrahydro-6,8-methanoquinoline-3-carbonitrile. The stereochemistry of structures was arbitrarily assigned and is not established. 1st eluting atropisomer assigned as the P isomer and 2nd eluting atropisomer assigned as the M isomer.

Atropisomer Separation for Examples 12-43 and 12-44.

The racemic mixture was separated by SFC using a Chiralpak AD column (21×250 mm, 5 μm) with a mobile phase of 70% liquid $CO_2$ and 30% 2-propanol with 0.2% TEA using a flowrate of 80 mL/min to provide the respective P and M isomers of 1-(6-(4-(3-chloro-5-hydroxy-2-methylphenyl)-3,7,7-trimethyl-7,8-dihydro-5H-pyrano[4,3-b]pyridin-2-yl)-2,6-diazaspiro[3.4]octan-2-yl)prop-2-en-1-one. The stereochemistry of structures was arbitrarily assigned and is not established. 1st eluting atropisomer assigned as the P isomer and 2nd eluting atropisomer assigned as the M isomer.

Method 13

Example 13-1 7,7-dimethyl-4-(5-methyl-1H-indazol-4-yl)-2-(2-(($^2H_3$)-2-propenoyl)-2,6-diazaspiro[3.4]octan-6-yl)-5,6,7,8-tetrahydro-3-quinolinecarbonitrile

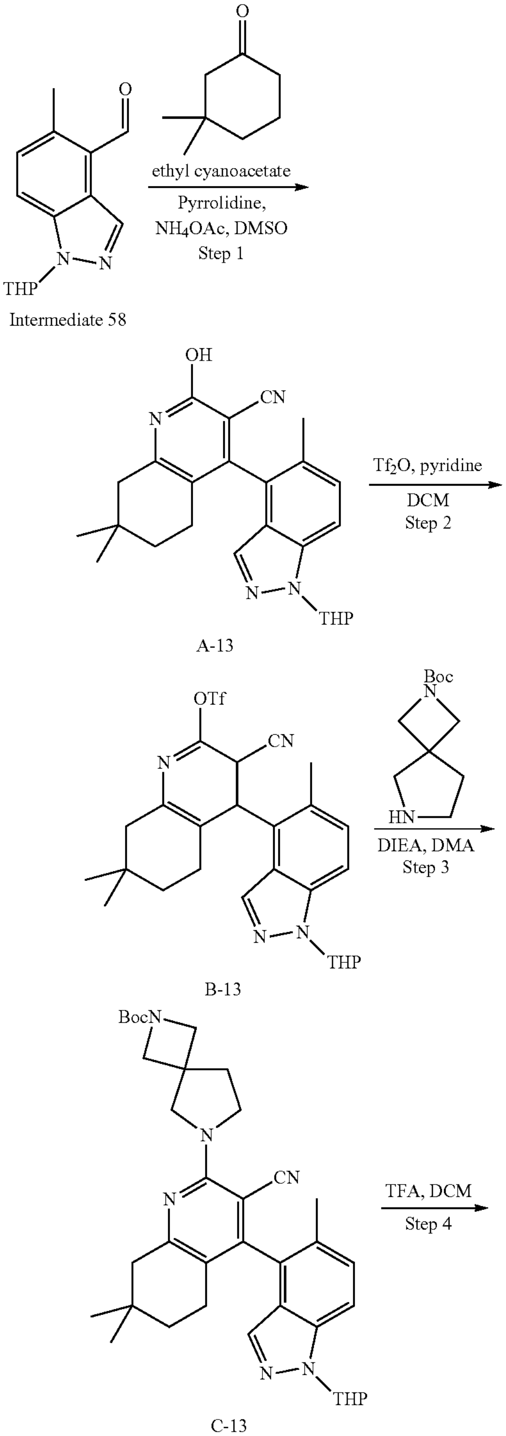

-continued

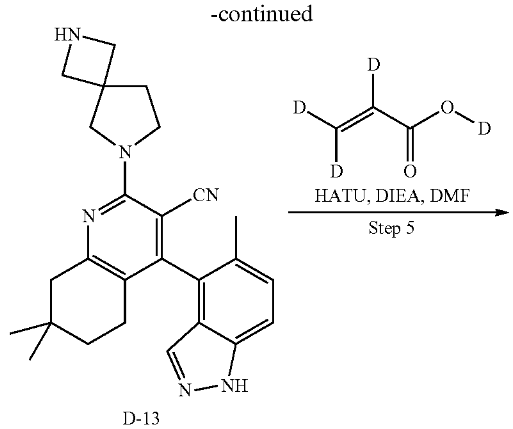

D-13

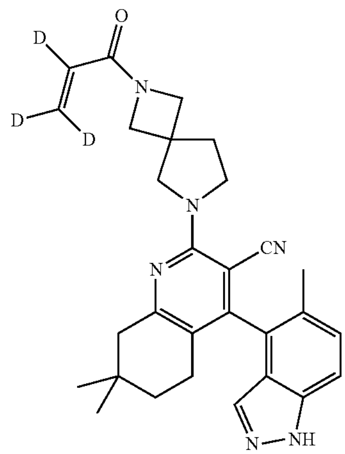

Example 13-1

Step 1: 2-hydroxy-7,7-dimethyl-4-(5-methyl-1-(tetrahydro-2H-pyran-2-yl)-1H-indazol-4-yl)-5,6,7,8-tetrahydroquinoline-3-carbonitrile Pyrrolidine (3.71 μL, 0.044 mmol, Sigma-Aldrich) was added to a solution of 3,3-dimethylcyclohexan-1-one (56 mg, 0.444 mmol, PharmaBlock), 5-methyl-1-(tetrahydro-2H-pyran-2-yl)-1H-indazole-4-carbaldehyde (87 mg, 0.356 mmol, Intermediate 58), ethyl cyanoacetate (0.047 mL, 0.444 mmol, Sigma-Aldrich) and DMSO (0.2 mL). The reaction mixture was stirred at room temperature for 45 min. $NH_4OAc$ (51.3 mg, 0.666 mmol, Sigma-Aldrich Corp) was added, and the reaction mixture was stirred for another 30 min before pyrrolidine (0.045 mL, 0.532 mmol, Sigma-Aldrich) was added. The reaction mixture was stirred at 80° C. for 3 d while open to air. The reaction mixture was partitioned between saturated aqueous $NH_4Cl$ (20 mL) and EtOAc (20 mL). The organic layer was separated, washed with brine (15 mL), dried over $MgSO_4$, and concentrated in vacuo. Chromatographic purification of the residue (silica gel, 0-100% EtOAc in heptane) provided 2-hydroxy-7,7-dimethyl-4-(5-methyl-1-(tetrahydro-2H-pyran-2-yl)-1H-indazol-4-yl)-5,6,7,8-tetrahydroquinoline-3-carbonitrile A-13 (67 mg, 36.2% yield) as a brown solid. $^1H$ NMR (400 MHz, DMSO-$d_6$) δ ppm 12.55 (br s, 1H) 7.73-7.76 (m, 2H) 7.43 (d, J=8.57 Hz, 1H) 5.85-5.91 (m, 1H) 4.04 (q, J=7.11 Hz, 1H) 3.86-3.94 (m, 1H) 3.71-3.82 (m, 1H) 3.25-3.31 (m, 1H) 2.53-2.64 (m, 1H) 2.33-2.46 (m, 2H) 2.19 (s, 3H) 2.01-2.07 (m, 2H) 1.70-1.86 (m, 3H) 1.52-1.66 (m, 2H) 1.30-1.38 (m, 2H) 0.89-0.98 (m, 6H). m/z (ESI): 417.2 $[M+H]^+$.

Step 2: 3-cyano-7,7-dimethyl-4-(5-methyl-1-(tetrahydro-2H-pyran-2-yl)-1H-indazol-4-yl)-5,6,7,8-tetrahydroquinolin-2-yl trifluoromethanesulfonate Trifluoromethanesulfonic anhydride (0.029 mL, 0.029 mmol, 1M in DCM. Sigma-Aldrich) was added to a solution of 7,7-dimethyl-4-(5-methyl-1-(tetrahydro-2H-pyran-2-yl)-1H-indazol-4-yl)-2-oxo-1,2,5,6,7,8-hexahydroquinoline-3-carbonitrile (10 mg, 0.024 mmol), pyridine (5.83 μL, 0.072 mmol, Sigma-Aldrich) and DCM (0.2 mL) at 0° C. The reaction mixture was stirred at 0° C. for 20 min. The reaction mixture was concentrated in vacuo to provide 3-cyano-7,7-dimethyl-4-(5-methyl-1-(tetrahydro-2H-pyran-2-yl)-1H-indazol-4-yl)-5,6,7,8-tetrahydroquinolin-2-yl trifluoromethanesulfonate B-13 as a brown solid which was used in the next step assuming 100% yield.

Step 3: tert-butyl 6-(3-cyano-7,7-dimethyl-4-(5-methyl-1-(tetrahydro-2H-pyran-2-yl)-1H-indazol-4-yl)-5,6,7,8-tetrahydroquinolin-2-yl)-2,6-diazaspiro[3.4]octane-2-carboxylate Tert-butyl 2,6-diazaspiro[3.4]octane-2-carboxylate (10.19 mg, 0.048 mmol, PharmaBlock) was added to a mixture of 3-cyano-7,7-dimethyl-4-(5-methyl-1-(tetrahydro-2H-pyran-2-yl)-1H-indazol-4-yl)-5,6,7,8-tetrahydroquinolin-2-yl trifluoromethanesulfonate (0.013 g, 0.024 mmol). DIPEA (0.021 mL, 0.120 mmol, Sigma-Aldrich) and DMA (0.2 mL). The reaction mixture was heated to 80° C. and stirred for 1.5 h. The reaction mixture was partitioned between saturated aqueous $NH_4Cl$ (10 mL) and EtOAc (15 mL). The organic layers were washed with brine (10 mL), dried over $MgSO_4$, and concentrated in vacuo to provide tert-butyl 6-(3-cyano-7,7-dimethyl-4-(5-methyl-1-(tetrahydro-2H-pyran-2-yl)-1H-indazol-4-yl)-5,6,7,8-tetrahydroquinolin-2-yl)-2,6-diazaspiro[3.4]octane-2-carboxylate C-13 as a brown oil.

Step 4: 7,7-dimethyl-4-(5-methyl-1H-indazol-4-yl)-2-(2,6-diazaspiro[3.4]octan-6-yl)-5,6,7,8-tetrahydroquinoline-3-carbonitrile Trifluoroacetic acid (0.5 mL, 6.71 mmol, Sigma-Aldrich Corp) was added to a mixture of tert-butyl 6-(3-cyano-7,7-dimethyl-4-(5-methyl-1-(tetrahydro-2H-pyran-2-yl)-1H-indazol-4-yl)-5,6,7,8-tetrahydroquinolin-2-yl)-2,6-diazaspiro[3.4]octane-2-carboxylate (11 mg. 0.182 mmol) and DCM (1 mL). The reaction was stirred at room temperature for 2 h. The reaction mixture was concentrated to provide 7,7-dimethyl-4-(5-methyl-1H-indazol-4-yl)-2-(2,6-diazaspiro[3.4]octan-6-yl)-5,6,7,8-tetrahydroquinoline-3-carbonitrile D-13 which was used in the next step assuming 100% yield. m/z (ESI): 427.2 $[M+H]^+$.

Step 5: 7,7-dimethyl-4-(5-methyl-1H-indazol-4-yl)-2-(2-(($^2H_3$)-2-propenoyl)-2,6-diazaspiro[3.4]octan-6-yl)-5,6,7,8-tetrahydro-3-quinolinecarbonitrile A mixture of 7,7-Dimethyl-4-(5-methyl-1H-indazol-4-yl)-2-(2,6-diazaspiro[3.4]octan-6-yl)-5,6,7,8-tetrahydroquinoline-3-carbonitrile (95 mg, 0.223 mmol), acrylic-$d_3$ acid-d (8.47 mg. 0.111 mmol, AAblocks), HATU (85 mg, 0.223 mmol, Combi-Blocks), DIPEA (0.117 mL, 0.668 mmol, Sigma-Aldrich) and DMF (1 mL) was stirred at room temperature for 22 h. The reaction mixture was diluted with EtOAc (50 mL) and washed with saturated aqueous $NaHCO_3$ (30 mL). The organic layer was washed with brine (30 mL), dried over $MgSO_4$ and concentrated in vacuo. Chromatographic purification of the residue (silica gel, 0-10% (2M $NH_3$ in MeOH) in DCM) gave 7,7-dimethyl-4-(5-methyl-1H-indazol-4-yl)-2-(2-(($^2H_3$)-2-propenoyl)-2,6-diazaspiro[3.4]octan-6-yl)-5,6,7,8-tetrahydro-3-quinolinecarbonitrile Example 13-1

(8 mg, 7.43% yield) as a white solid. $^1$H NMR (400 MHz, MeOH-$d_6$) δ ppm 7.47-7.62 (m, 2H), 7.41 (d, J=8.78 Hz, 1H), 4.20-4.43 (m, 2H), 3.94-4.13 (m, 4H), 3.88 (t, J=6.80 Hz, 2H), 2.66 (s, 2H), 2.27 (t, J=6.70 Hz, 2H), 2.20 (s, 3H), 2.07-2.17 (m, 2H), 1.46 (t, J=6.70 Hz, 2H), 1.01 (s, 6H). m/z (ESI): 484.3 [M+H]$^+$.

TABLE 5

Examples 13-2 to 13-157 were prepared following the procedure described in Method 13, steps 1-5, above as follows:

| Ex.# | Chemical Structure | Name | Method changes | Reagent |
|---|---|---|---|---|
| 13-2 | 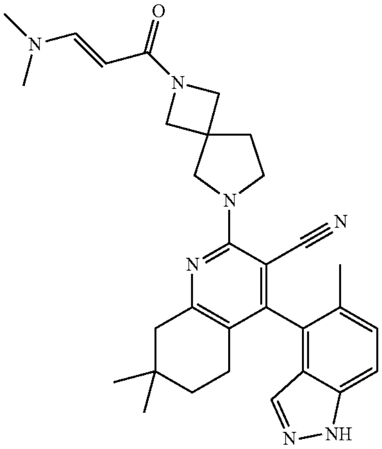 [SMILES: Cc1ccc2[nH]ncc2c1-c1c(C#N)c(N2CCC3(CN(C(=O)/C=C/N(C)C)C3)C2)nc2c1CCC(C)(C)C2] | 2-(2-((2E)-4-(dimethylamino)-2-butenoyl)-2,6-diazaspiro[3.4]octan-6-yl)-7,7-dimethyl-4-(5-methyl-1H-indazol-4-yl)-5,6,7,8-tetrahydro-3-quinolinecarbonitrile | | Step 5: (E)-4-(dimethylamino)but-2-enoic acid hydrochloride (Oakwood Chemical) |
| 13-3 | 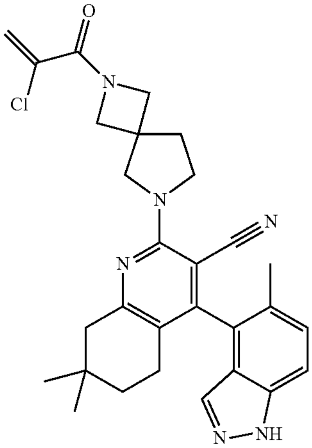 [SMILES: C=C(Cl)C(=O)N1CC2(CCN(c3nc4c(c(-c5c(C)ccc6[nH]ncc56)c3C#N)CCC(C)(C)C4)C2)C1] | 2-(2-(2-chloro-2-propenoyl)-2,6-diazaspiro[3.4]octan-6-yl)-7,7-dimethyl-4-(5-methyl-1H-indazol-4-yl)-5,6,7,8-tetrahydro-3-quinolinecarbonitrile | | Step 5: 2-chloroacrylic acid (Alpha Aesar) |
| 13-4 | 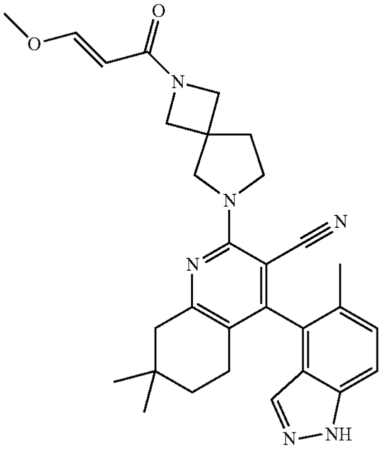 [SMILES: CO/C=C/C(=O)N1CC2(CCN(c3nc4c(c(-c5c(C)ccc6[nH]ncc56)c3C#N)CCC(C)(C)C4)C2)C1] | 2-(2-((2E)-4-methoxy-2-butenoyl)-2,6-diazaspiro[3.4]octan-6-yl)-7,7-dimethyl-4-(5-methyl-1H-indazol-4-yl)-5,6,7,8-tetrahydro-3-quinolinecarbonitrile | | Step 5: (E)-4-methoxybut-2-enoic acid (Enamine) |

TABLE 5-continued

| Examples 13-2 to 13-157 were prepared following the procedure described in Method 13, steps 1-5, above as follows: | | | | |
|---|---|---|---|---|
| Ex.# | Chemical Structure | Name | Method changes | Reagent |
| 13-5 | 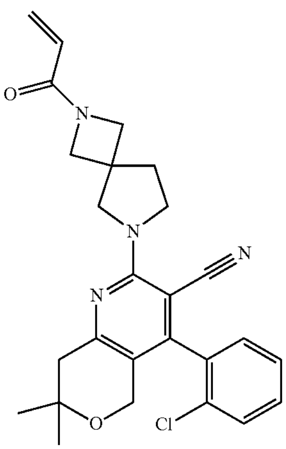 [SMILES: C=CC(=O)N1CC2(CCN(c3nc4c(c(-c5ccccc5Cl)c3C#N)COC(C)(C)C4)C2)C1] | 4-(2-chlorophenyl)-7,7-dimethyl-2-(2-(2-propenoyl)-2,6-diazaspiro[3.4]octan-6-yl)-7,8-dihydro-5H-pyrano[4,3-b]pyridine-3-carbonitrile | Step 5: replaced by Step 4 from Method 2 | Step 1: 2-chlorobenzaldehyde (Sigma-Aldrich) and 2,2-dimethyltetrahydro-4H-pyran-4-one (PharmaBlock) |
| 13-6 | 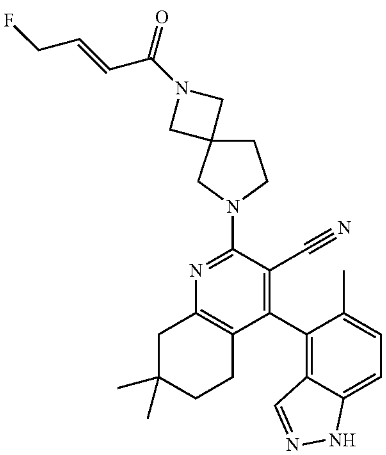 [SMILES: Cc1ccc2[nH]ncc2c1-c1c(C#N)c(N2CCC3(CN(C(=O)/C=C/CF)C3)C2)nc2c1CCC(C)(C)C2] | 2-(2-((2E)-4-fluoro-2-butenoyl)-2,6-diazaspiro[3.4]octan-6-yl)-7,7-dimethyl-4-(5-methyl-1H-indazol-4-yl)-5,6,7,8-tetrahydro-3-quinolinecarbonitrile | | Step 5: (E)-4-fluorobut-2-enoic acid (Enamine) |
| 13-7 | 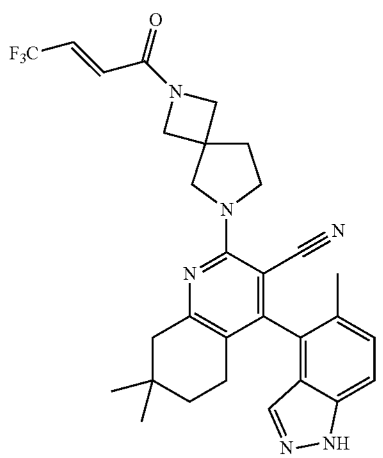 [SMILES: Cc1ccc2[nH]ncc2c1-c1c(C#N)c(N2CCC3(CN(C(=O)/C=C/C(F)(F)F)C3)C2)nc2c1CCC(C)(C)C2] | 7,7-dimethyl-4-(5-methyl-1H-indazol-4-yl)-2-(2-((2E)-4,4,4-trifluoro-2-butenoyl)-2,6-diazaspiro[3.4]octan-6-yl)-5,6,7,8-tetrahydro-3-quinolinecarbonitrile | | Step 5: (E)-4,4,4-trifluorobut-2-enoic acid (Combi-Blocks) |

TABLE 5-continued

| Ex.# | Chemical Structure | Name | Method changes | Reagent |
|---|---|---|---|---|
| | Examples 13-2 to 13-157 were prepared following the procedure described in Method 13, steps 1-5, above as follows: | | | |
| 13-8 | 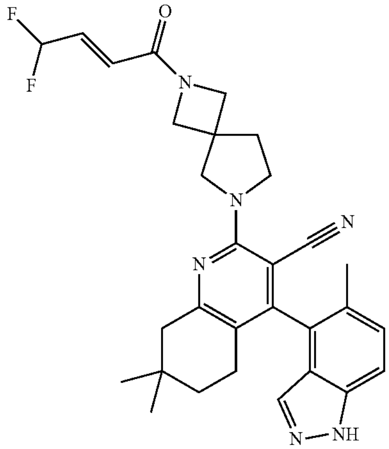 [SMILES: Cc1ccc2[nH]ncc2c1-c1c(C#N)c(N2CCC3(CN(C(=O)/C=C/C(F)F)C3)C2)nc2c1CCC(C)(C)C2] | 2-(2-((2E)-4,4-difluoro-2-butenoyl)-2,6-diazaspiro[3.4]octan-6-yl)-7,7-dimethyl-4-(5-methyl-1H-indazol-4-yl)-5,6,7,8-tetrahydro-3-quinolinecarbonitrile | | Step 5: 4,4-difluroobutenoic acid (SynQuest Laboratories) |
| 13-9 | 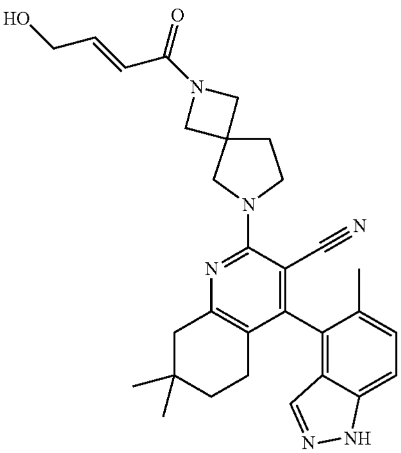 [SMILES: Cc1ccc2[nH]ncc2c1-c1c(C#N)c(N2CCC3(CN(C(=O)/C=C/CO)C3)C2)nc2c1CCC(C)(C)C2] | 2-(2-((2E)-4-hydroxy-2-butenoyl)-2,6-diazaspiro[3.4]octan-6-yl)-7,7-dimethyl-4-(5-methyl-1H-indazol-4-yl)-5,6,7,8-tetrahydro-3-quinolinecarbonitrile | | Step 5: (E)-4-hydroxybut-2-enoic acid (Key Organics) |
| 13-10 | 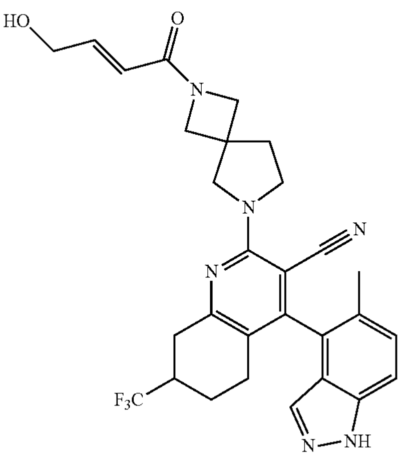 [SMILES: Cc1ccc2[nH]ncc2c1-c1c(C#N)c(N2CCC3(CN(C(=O)/C=C/CO)C3)C2)nc2c1CCC(C(F)(F)F)C2] | (7R)-4-(5-methyl-1H-indazol-4-yl)-2-(2-(2-propenoyl)-2,6-diazaspiro[3.4]octan-6-yl)-7-(trifluoromethyl)-5,6,7,8-tetrahydro-3-quinoline-carbonitrile\|(7S)-4-(5-methyl-1H-indazol-4-yL)-2-(2-(2-propenoyl)-2,6-diazaspiro[3.4]octan-6-yl)-7-(trifluoromethyl)-5,6,7,8-tetrahydro-3-quinolinecarbonitrile | Step 5: replaced by Step 4 from Method 2 | Step 1: 3-(trifluoromethyl)cy-clohexan-1-one (commercially available - Tetrahedron, 2002, 58, 4067-4070). Step 5: (E)-4-hydroxybut-2-enoic acid (Key Organics) |

TABLE 5-continued

Examples 13-2 to 13-157 were prepared following the procedure described in Method 13, steps 1-5, above as follows:

| Ex.# | Chemical Structure | Name | Method changes | Reagent |
|---|---|---|---|---|
| 13-11 | 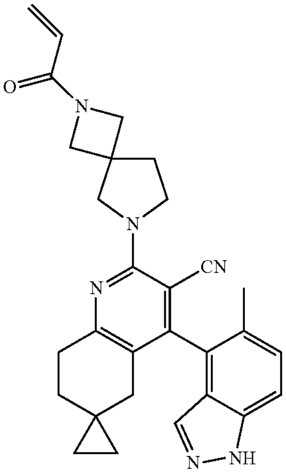 [SMILES: C=CC(=O)N1CC2(CCN(c3nc4c(c(-c5c(C)ccc6[nH]ncc56)c3C#N)CC3(CC4)CC3)C2)C1] | 4'-(5-methyl-1H-indazol-4-yl)-2'-(2-(2-propenoyl)-2,6-diazaspiro[3.4]octan-6-yl)-7',8'-dihydro-5'H-spiro[cyclopropane-1,6'-quinoline]-3'-carbonitrile | Step 5: replaced by Step 4 from Method 2 | Step 1: spiro[2.5]octan-6-one (Enamine) |
| 13-12 | 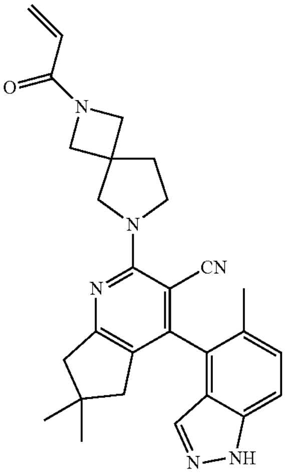 [SMILES: C=CC(=O)N1CC2(CCN(c3nc4c(c(-c5c(C)ccc6[nH]ncc56)c3C#N)CC(C)(C)C4)C2)C1] | 6,6-dimethyl-4-(5-methyl-1H-indazol-4-yl)-2-(2-(2-propenoyl)-2,6-diazaspiro[3.4]octan-6-yl)-6,7-dihydro-5H-cyclopenta[b]pyridine-3-carbonitrile | See below for alternative step 1. Step 5: replaced by Step 4 from Method 2 | Step 1a: Intermediate 58 and step 1b: 3,3-dimethylcyclopentan-1-one (Enamine) |
| 13-13 | 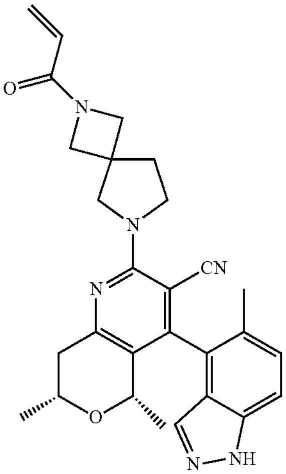 [SMILES: C=CC(=O)N1CC2(CCN(c3nc4c(c(-c5c(C)ccc6[nH]ncc56)c3C#N)[C@H](C)O[C@H](C)C4)C2)C1] | (5R,7S)-5,7-dimethyl-4-(5-methyl-1H-indazol-4-yl)-2-(2-(2-propenoyl)-2,6-diazaspiro[3.4]octan-6-yl)-7,8-dihydro-5H-pyrano[4,3-b]pyridine-3-carbonitrile\|(5S,7R)-5,7-dimethyl-4-(5-methyl-1H-indazol-4-yl)-2-(2-(2-propenoyl)-2,6-diazaspiro[3.4]octan-6-yl)-7,8-dihydro-5H-pyrano[4,3-b]pyridine-3-carbonitrile | Step 1 performed using procedure from Example 13-12. Step 5: replaced by Step 4 from Method 2 | Step 1 using step 1a: Intermediate 58 and step 1b: (2R,6S)-2,6-dimethyltetrahydro-4H-pyran-4-one (Enamine) |

TABLE 5-continued

Examples 13-2 to 13-157 were prepared following the procedure described in Method 13, steps 1-5, above as follows:

| Ex.# | Chemical Structure | Name | Method changes | Reagent |
| --- | --- | --- | --- | --- |
| 13-14 | 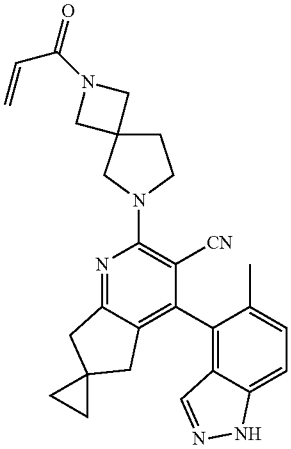 [SMILES: C=CC(=O)N1CC2(CCN(c3nc4c(c(-c5c(C)ccc6[nH]ncc56)c3C#N)CC3(CC3)C4)C2)C1] | 4-(5-methyl-1H-indazol-4-yl)-2-(2-(2-propenoyl)-2,6-diazaspiro[3.4]octan-6-yl)-5,7-dihydrospiro[cyclopenta[b]pyridine-6,1'-cyclopropane]-3-carbonitrile | Step 1 performed using procedure from Example 13-12. Step 5: replaced by Step 4 from Method 2 | Step 1a: Intermediate 58 and step 1b: spiro[2.4]heptan-5-one (PharmaBlock) |
| 13-15 | 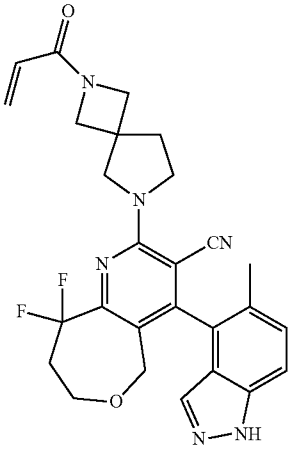 [SMILES: C=CC(=O)N1CC2(CCN(c3nc4c(c(-c5c(C)ccc6[nH]ncc56)c3C#N)COCCC4(F)F)C2)C1] | 9,9-difluoro-4-(5-methyl-1H-indazol-4-yl)-2-(2-(2-propenoyl)-2,6-diazaspiro[3.4]octan-6-yl)-5,7,8,9-tetrahydrooxepino[4,3-b]pyridine-3-carbonitrile | Step 1 performed using procedure from Example 13-12. Step 5: replaced by Step 4 from Method 2 | Step 1a: Intermediate 58 and step 1b: 5,5-difluorooxepan-4-one (PharmaBlock) |
| 13-16 | 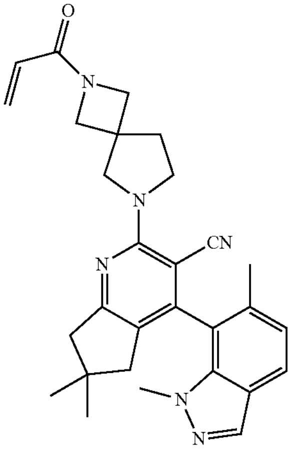 [SMILES: C=CC(=O)N1CC2(CCN(c3nc4c(c(-c5c(C)ccc6cnn(C)c56)c3C#N)CC(C)(C)C4)C2)C1] | 4-(1,6-dimethyl-1H-indazol-7-yl)-6,6-dimethyl-2-(2-(2-propenoyl)-2,6-diazaspiro[3.4]octan-6-yl)-6,7-dihydro-5H-cyclopenta[b]pyridine-3-carbonitrile | Step 1 performed using procedure from Example 13-12. Step 5: replaced by Step 4 from Method 2 | Step 1a: Intermediate 59 and step 1b: 3,3-dimethylcyclopentan-1-one (Enamine) |

TABLE 5-continued

Examples 13-2 to 13-157 were prepared following the procedure described in Method 13, steps 1-5, above as follows:

| Ex.# | Chemical Structure | Name | Method changes | Reagent |
|---|---|---|---|---|
| 13-17 | 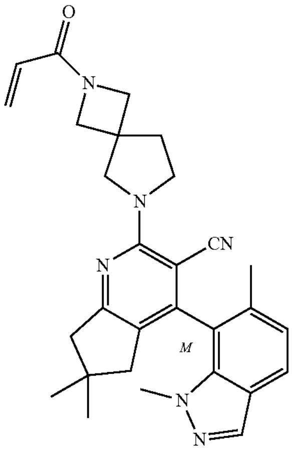 | (M)-4-(1,6-dimethyl-1H-indazol-7-yl)-6,6-dimethyl-2-(2-(2-propenoyl)-2,6-diazaspiro[3.4]octan-6-yl)-6,7-dihydro-5H-cyclopenta[b]pyridine-3-carbonitrile (1st eluting peak). | Step 1 performed using procedure from Example 13-12. Step 5: replaced by Step 4 from Method 2. See atropisomer separation conditions below. | Step 1a: Intermediate 59 and step 1b: 3,3-dimethylcyclopentan-1-one (Enamine) |
| 13-18 | 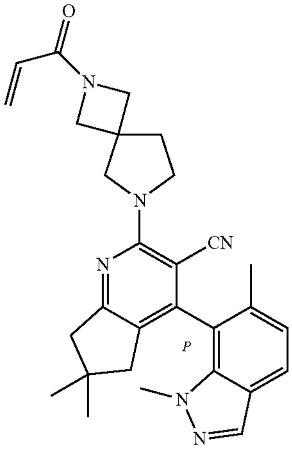 | (P)-4-(1,6-dimethyl-1H-indazol-7-yl)-6,6-dimethyl-2-(2-(2-propenoyl)-2,6-diazaspiro[3.4]octan-6-yl)-6,7-dihydro-5H-cyclopenta[b]pyridine-3-carbonitrile (2nd eluting peak) | Step 1 performed using procedure from Example 13-12. Step 5: replaced by Step 4 from Method 2. See atropisomer separation conditions below. | Step 1a: Intermediate 59 and step 1b: 3,3-dimethylcyclopentan-1-one (Enamine) |
| 13-19 | 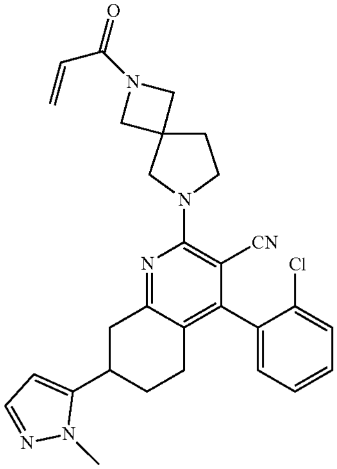 [SMILES: C=CC(=O)N1CC2(CCN(c3nc4c(c(-c5ccccc5Cl)c3C#N)CCC(c3ccnn3C)C4)C2)C1] | (7R)-4-(2-chlorophenyl)-7-(1-methyl-1H-pyrazol-5-yl)-2-(2-(2-propenoyl)-2,6-diazaspiro[3.4]octan-6-yl)-5,6,7,8-tetrahydro-3-quinolinecarbonitrile\|(7S)-4-(2-chlorophenyl)-7-(1-methyl-1H-pyrazol-5-yl)-2-(2-(2-propenoyl)-2,6-diazaspiro[3.4]octan-6-yl)-5,6,7,8-tetrahydro-3-quinolinecarbonitrile | Step 5: replaced by Step 4 from Method 2 | Step 1: 3-(1-methyl-1H-pyrazol-5-yl)cyclohexan-1-one (Enamine) and 2-chlorobenzaldehyde (Sigma-Aldrich) |

TABLE 5-continued

Examples 13-2 to 13-157 were prepared following the procedure described in Method 13, steps 1-5, above as follows:

| Ex.# | Chemical Structure | Name | Method changes | Reagent |
|---|---|---|---|---|
| 13-20 | 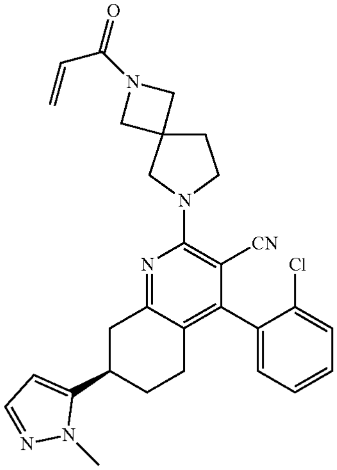 [SMILES: C=CC(=O)N1CC2(CCN(c3nc4c(c(-c5ccccc5Cl)c3C#N)CC[C@@H](c3ccnn3C)C4)C2)C1] | (7R)-4-(2-chlorophenyl)-7-(1-methyl-1H-pyrazol-5-yl)-2-(2-(2-propenoyl)-2,6-diazaspiro[3.4]octan-6-yl)-5,6,7,8-tetrahydro-3-quinolinecarbonitrile. (1st eluting peak) | Step 5: replaced by Step 4 from Method 2. See enantiomer separation conditions below. | Step 1: 3-(1-methyl-1H-pyrazol-5-yl)cyclohexan-1-one (Enamine) and 2-chlorobenzaldehyde (Sigma-Aldrich) |
| 13-21 | 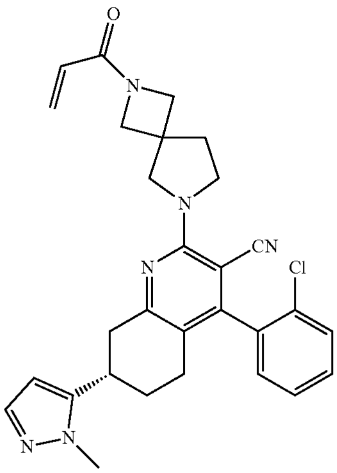 [SMILES: C=CC(=O)N1CC2(CCN(c3nc4c(c(-c5ccccc5Cl)c3C#N)CC[C@H](c3ccnn3C)C4)C2)C1] | (7S)-4-(2-chlorophenyl)-7-(1-methyl-1H-pyrazol-5-yl)-2-(2-(2-propenoyl)-2,6-diazaspiro[3.4]octan-6-yl)-5,6,7,8-tetrahydro-3-quinolinecarbonitrile (2nd eluting peak) | Step 5: replaced by Step 4 from Method 2. See enantiomer separation conditions below. | Step 1: 3-(1-methyl-1H-pyrazol-5-yl)cyclohexan-1-one (Enamine) and 2-chlorobenzaldehyde (Sigma-Aldrich) |
| 13-22 | 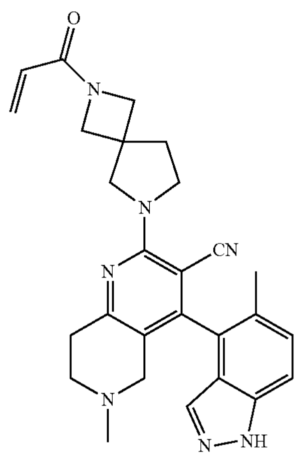 [SMILES: C=CC(=O)N1CC2(CCN(c3nc4c(c(-c5c(C)ccc6[nH]ncc56)c3C#N)CN(C)CC4)C2)C1] | 6-methyl-4-(5-methyl-1H-indazol-4-yl)-2-(2-(2-propenoyl)-2,6-diazaspiro[3.4]octan-6-yl)-5,6,7,8-tetrahydro-1,6-naphthyridine-3-carbonitrile | Step 1 performed using procedure from Example 13-12. Step 5: replaced by Step 4 from Method 2 | Step 1a: Intermediate 58 and step 1b: 1-methyl-4-piperidone (Combi-Blocks) |

TABLE 5-continued

| Examples 13-2 to 13-157 were prepared following the procedure described in Method 13, steps 1-5, above as follows: | | | | |
|---|---|---|---|---|
| Ex.# | Chemical Structure | Name | Method changes | Reagent |
| 13-23 | 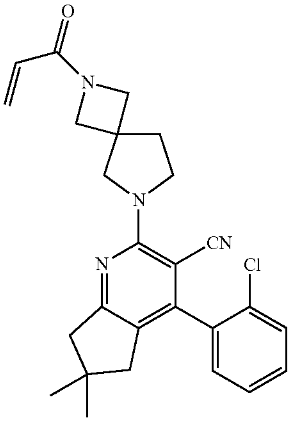 [SMILES: C=CC(=O)N1CC2(CCN(c3nc4c(c(-c5ccccc5Cl)c3C#N)CC(C)(C)C4)C2)C1] | 4-(2-chlorophenyl)-6,6-dimethyl-2-(2-(2-propenoyl)-2,6-diazaspiro[3.4]octan-6-yl)-6,7-dihydro-5H-cyclopenta[b]pyridine-3-carbonitirle | Step 1 performed using procedure from Example 13-12. Step 5: replaced by Step 4 from Method 2 | Step 1a 2-chloro-benzaldehyde (Sigma-Aldrich) and step 1b: 3,3-dimethylcyclopen-tan-1-one (Enamine) |
| 13-24 | 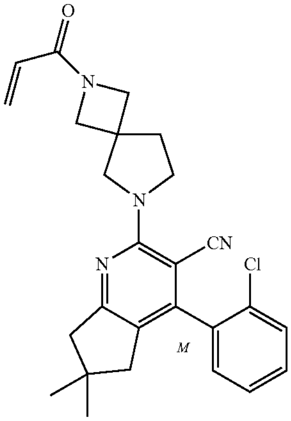 | (M)-4-(2-chlorophenyl)-6,6-dimethyl-2-(2-(2-propenoyl)-2,6-diazaspiro[3.4]octan-6-yl)-6,7-dihydro-5H-cyclopenta[b]pyridine-3-carbonitrile (1$^{st}$ eluting peak) | Step 1 performed using procedure from Example 13-12. Step 5: replaced by Step 4 from Method 2. See atropisomer separation conditions below. | Step 1a 2-chloro-benzaldehyde (Sigma-Aldrich) and step 1b: 3,3-dimethylcyclopen-tan-1-one (Enamine) |
| 13-25 | 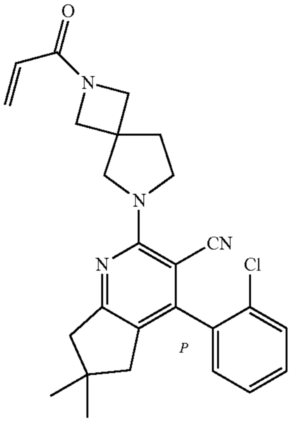 | (P)-4-(2-chlorophenyl)-6,6-dimethyl-2-(2-(2-propenoyl)-2,6-diazaspiro[3.4]octan-6-yl)-6,7-dihydro-5H-cyclopenta[b]pyridine-3-carbonitrile (2$^{nd}$ eluting peak) | Step 1 performed using procedure from Example 13-12. Step 5: replaced by Step 4 from Method 2. See atropisomer separation conditions below. | Step 1a 2-chloro-benzaldehyde (Sigma-Aldrich) and step 1b: 3,3-dimethylcyclopen-tan-1-one (Enamine) |

TABLE 5-continued

Examples 13-2 to 13-157 were prepared following the procedure described in Method 13, steps 1-5, above as follows:

| Ex.# | Chemical Structure | Name | Method changes | Reagent |
|---|---|---|---|---|
| 13-26 | 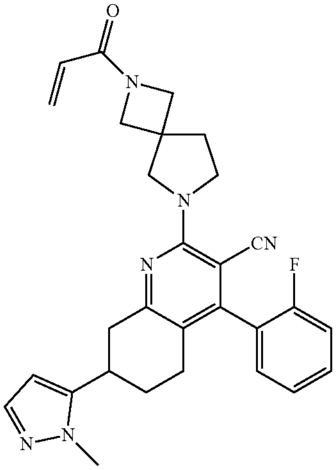 [SMILES: C=CC(=O)N1CC2(CCN(c3nc4c(c(-c5ccccc5F)c3C#N)CCC(c3ccnn3C)C4)C2)C1] | (7R)-4-(2-fluorophenyl)-7-(1-methyl-1H-pyrazol-5-yl)-2-(2-(2-propenoyl)-2,6-diazaspiro[3.4]octan-6-yl)-5,6,7,8-tetrahydro-3-quinolinecarbonitrile\|(7S)-4-(2-fluorophenyl)-7-(1-methyl-1H-pyrazol-5-yl)-2-(2-(2-propenoyl)-2,6-diazaspiro[3.4]octan-6-yl)-5,6,7,8-tetrahydro-3-quinolinecarbonitrile | Step 5: replaced by Step 4 from Method 2 | Step 1: 3-(1-methyl-1H-pyrazol-5-yl)cyclohexan-1-one (Enamine) and 2-fluorobenzaldehdye (Sigma-Aldrich) |
| 13-27 | 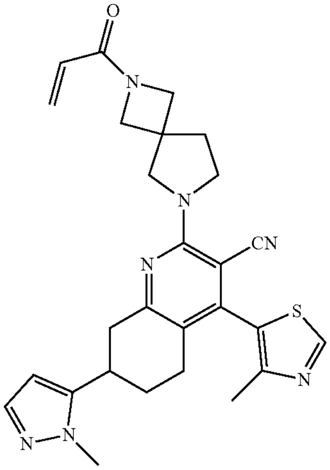 [SMILES: C=CC(=O)N1CC2(CCN(c3nc4c(c(-c5scnc5C)c3C#N)CCC(c3ccnn3C)C4)C2)C1] | (7S)-7-(1-methyl-1H-pyrazol-5-yl)-4-(4-methyl-1,3-thiazol-5-yl)-2-(2-(2-propenoyl)-2,6-diazaspiro[3.4]octan-6-yl)-5,6,7,8-tetrahydro-3-quinolinecarbonitrile\|(7R)-7-(1-methyl-1H-pyrazol-5-yl)-4-(4-methyl-1,3-thiazol-5-yl)-2-(2-(2-propenoyl)-2,6-diazaspiro[3.4]octan-6-yl)-5,6,7,8-tetrahydro-3-quinolinecarbonitrile | Step 5: replaced by Step 4 from Method 2 | Step 1: 4-methyl-1,3-thiazole-5-carbaldehyde (Combi-Blocks) and 3-(1-methyl-1H-pyrazol-5-yl)cyclohexan-1-one (Enamine) |
| 13-28 | 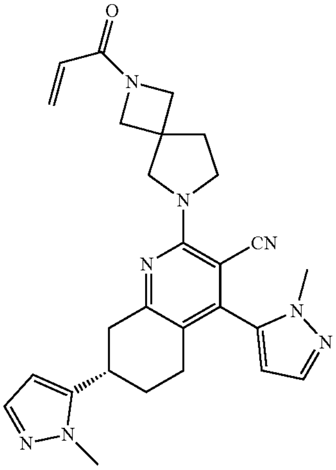 [SMILES: C=CC(=O)N1CC2(CCN(c3nc4c(c(-c5ccnn5C)c3C#N)CC[C@H](c3ccnn3C)C4)C2)C1] | (7S)-4,7-bis(1-methyl-1H-pyrazol-5-yl)-2-(2-(2-propenoyl)-2,6-diazaspiro[3.4]octan-6-yl)-5,6,7,8-tetrahydro-3-quinolinecarbonitrile | Step 5: replaced by Step 4 from Method 2 | Step 1: 1-methyl-1H-pyrazole-5-carbaldehyde (Combi-Blocks) and 3-(1-methyl-1H-pyrazol-5-yl)cyclohexan-1-one (Enamine). The stereochemistry of structures was arbitrarily assigned and is not established |

TABLE 5-continued

| Examples 13-2 to 13-157 were prepared following the procedure described in Method 13, steps 1-5, above as follows: | | | | |
|---|---|---|---|---|
| Ex.# | Chemical Structure | Name | Method changes | Reagent |
| 13-29 | 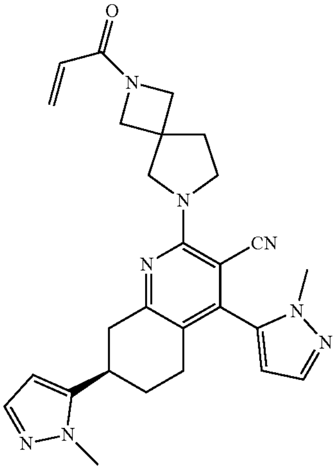 [SMILES: C=CC(=O)N1CC2(CCN(c3nc4c(c(-c5ccnn5C)c3C#N)CC[C@@H](c3ccnn3C)C4)C2)C1] | (7R)-4,7-bis(1-methyl-1H-pyrazol-5-yl)-2-(2-(2-propenoyl)-2,6-diazaspiro[3.4]octan-6-yl)-5,6,7,8-tetrahydro-3-quinolinecarbonitrile | Step 5: replaced by Step 4 from Method 2 | Step 1: 1-methyl-1H-pyrazole-5-carbaldehyde (Combi-Blocks) and 3-(1-methyl-1H-pyrazol-5-yl)cyclohexan-1-one (Enamine). The stereochemistry of structures was arbitrarily assigned and is not established |
| 13-30 | 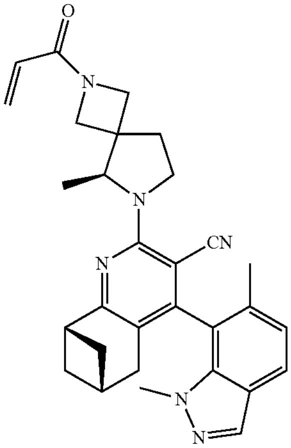 [SMILES: C=CC(=O)N1CC2(CCN(c3nc4c(c(-c5c(C)ccc6cnn(C)c56)c3C#N)C[C@H]3C[C@@H]4C3)[C@H]2C)C1] | (1S,9R)-6-(1,6-dimethyl-1H-indazol-7-yl)-4-((5S)-5-methyl-2-(2-propenoyl)-2,6-diazaspiro[3.4]octan-6-yl)-3-azatricyclo[7.1.1.0$^{2,7}$]undeca-2,4,6-triene-5-carbonitrile | Step 1 performed using procedure from Example 13-12. Step 5: replaced by Step 4 from Method 2 | Step 1a: Intermediate 59 and step 1b: bicyclo[3.1.1]heptan-3-one (PharmaBlock). Step 3: Amine 3. |
| 13-31 | 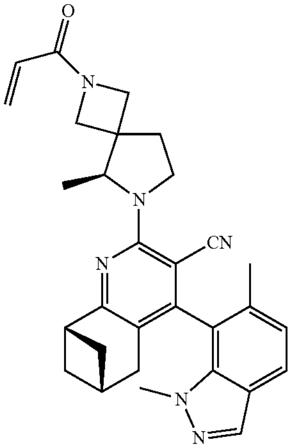 [SMILES: C=CC(=O)N1CC2(CCN(c3nc4c(c(-c5c(C)ccc6cnn(C)c56)c3C#N)C[C@H]3C[C@@H]4C3)[C@H]2C)C1] | (M)-(1S,9R)-6-(1,6-dimethyl-1H-indazol-7-yl)-4-((5S)-5-methyl-2-(2-propenoyl)-2,6-diazaspiro[3.4]octan-6-yl)-3-azatricyclo[7.1.1.0$^{2,7}$]undeca-2,4,6-triene-5-carbonitrile (1$^{st}$ eluting peak) | Step 1 performed using procedure from Example 13-12. Step 5: replaced by Step 4 from Method 2. See atropisomer separation conditions below. | Step 1a: Intermediate 59 and step 1b: bicyclo[3.1.1]heptan-3-one (PharmaBlock). Step 3: Amine 3. |

TABLE 5-continued

| Examples 13-2 to 13-157 were prepared following the procedure described in Method 13, steps 1-5, above as follows: | | | | |
|---|---|---|---|---|
| Ex.# | Chemical Structure | Name | Method changes | Reagent |
| 13-32 | 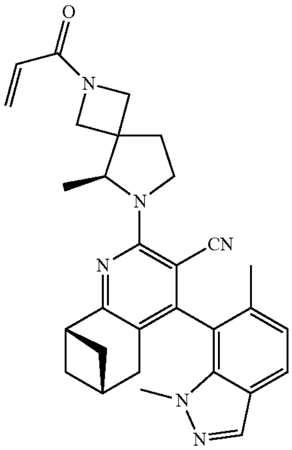 [SMILES: C=CC(=O)N1CC2(CCN(c3nc4c(c(-c5c(C)ccc6cnn(C)c56)c3C#N)C[C@H]3C[C@@H]4C3)[C@H]2C)C1] | (P)-(1S,9R)-6-(1,6-dimethyl-1H-indazol-7-yl)-4-((5S)-5-methyl-2-(2-propenoyl)-2,6-diazaspiro[3.4]octan-6-yl)-3-azatricyclo[7.1.1.0$^{2,7}$]undeca-2,4,6-triene-5-carbonitrile (2$^{nd}$ eluting peak) | See below for alternative step 1. Step 5: replaced by Step 4 from Method 2. See atropisomer separation conditions below. | Step 1a: Intermediate 59 and step 1b: bicyclo[3.1.1]heptan-3-one (PharmaBlock). Step 3: Amine 3. |
| 13-33 | 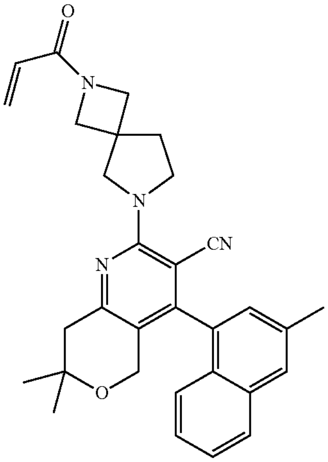 [SMILES: C=CC(=O)N1CC2(CCN(c3nc4c(c(-c5cc(C)cc6ccccc56)c3C#N)COC(C)(C)C4)C2)C1] | 7,7-dimethyl-4-(3-methyl-1-naphthalenyl)-2-(2-(2-propenoyl)-2,6-diazaspiro[3.4]octan-6-yl)-7,8-dihydro-5H-pyrano[4,3-b]pyridine-3-carbonitrile | Step 5: replaced by Step 4 from Method 2 | Step 1: 2,2-dimethyltetrahydro-4H-pyran-4-one (PharmaBlock) and -methyl-1-naphthaldehyde (J&W Pharmalab) |
| 13-34 | 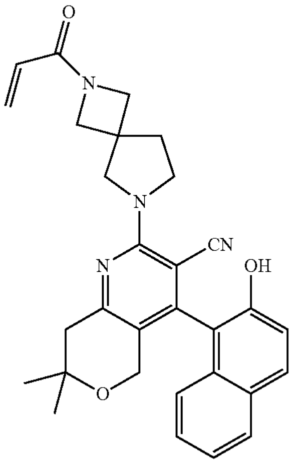 [SMILES: C=CC(=O)N1CC2(CCN(c3nc4c(c(-c5c(O)ccc6ccccc56)c3C#N)COC(C)(C)C4)C2)C1] | 4-(2-hydroxy-1-naphthalenyl)-7,7-dimethyl-2-(2-(2-propenoyl)-2,6-diazaspiro[3.4]octan-6-yl)-7,8-dihydro-5H-pyrano[4,3-b]pyridine-3-carbonitrile | Step 1 performed using procedure from Example 13-12. Step 5: replaced by Step 4 from Method 2 | Step 1a: Intermediate 60 and step 1b: 2,2-dimethyltetrahydro-4H-pyran-4-one (PharmaBlock). |

TABLE 5-continued

| Examples 13-2 to 13-157 were prepared following the procedure described in Method 13, steps 1-5, above as follows: | | | | |
|---|---|---|---|---|
| Ex.# | Chemical Structure | Name | Method changes | Reagent |
| 13-35 | 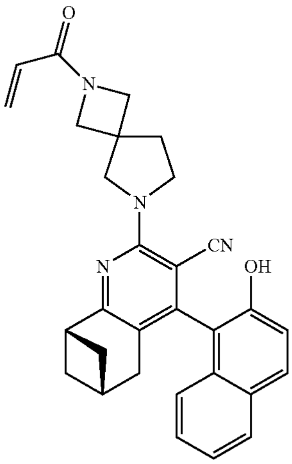 [SMILES: C=CC(=O)N1CC2(CCN(c3nc4c(c(-c5c(O)ccc6ccccc56)c3C#N)C[C@H]3C[C@@H]4C3)C2)C1] | (1S,9S)-6-(2-hydroxy-1-naphthalenyl)-4-(2-(2-propenoyl)-2,6-diazaspiro[3.4]octan-6-yl)-3-azatricyclo[7.1.1.0$^{2,7}$]undeca-2,4,6-triene-5-carbonitrile | Step 1 performed using procedure from Example 13-12. Step 5: replaced by Step 4 from Method 2 | Step 1a: Intermediate 60 and step 1b: bicyclo[3.1.1]heptan-3-one (PharmaBlock). |
| 13-36 | 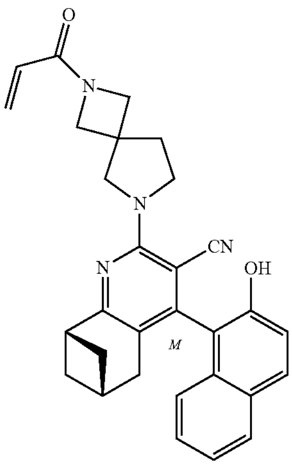 | (M)-(1S,9S)-6-(2-hydroxy-1-naphthalenyl)-4-(2-(2-propenoyl)-2,6-diazaspiro[3.4]octan-6-yl)-3-azatricyclo[7.1.1.0$^{2,7}$]undeca-2,4,6-triene-5-carbonitrile (1$^{st}$ eluting peak) | Step 1 performed using procedure from Example 13-12. Step 5: replaced by Step 4 from Method 2. See atropisomer separation conditions below | Step 1a: Intermediate 60 and step 1b: bicyclo[3.1.1]heptan-3-one (PharmaBlock). |
| 13-37 | 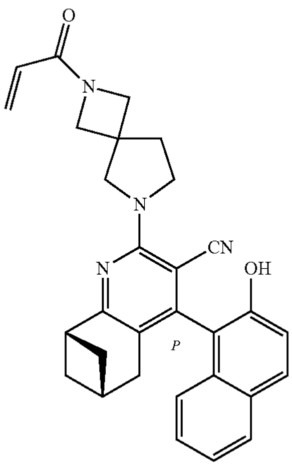 | (P)-(1S,9S)-6-(2-hydroxy-1-naphthalenyl)-4-(2-(2-propenoyl)-2,6-diazaspiro[3.4]octan-6-yl)-3-azatricyclo[7.1.1.0$^{2,7}$]undeca-2,4,6-triene-5-carbonitrile (2$^{nd}$ eluting peak) | Step 1 performed using procedure from Example 13-12. Step 5: replaced by Step 4 from Method 2. See atropisomer separation conditions below | Step 1a: Intermediate 60 and step 1b: bicyclo[3.1.1]heptan-3-one (PharmaBlock). |

TABLE 5-continued

| Examples 13-2 to 13-157 were prepared following the procedure described in Method 13, steps 1-5, above as follows: | | | | |
|---|---|---|---|---|
| Ex.# | Chemical Structure | Name | Method changes | Reagent |
| 13-38 | 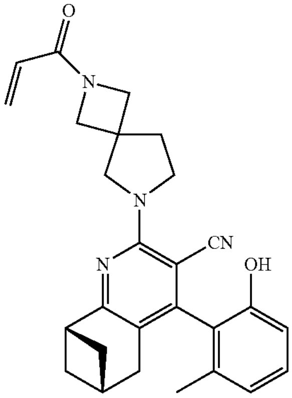 [SMILES: C=CC(=O)N1CC2(CCN(c3nc4c(c(-c5c(C)cccc5O)c3C#N)C[C@H]3C[C@@H]4C3)C2)C1] | (1S,9S)-6-(2-hydroxy-6-methylphenyl)-4-(2-(2-propenoyl)-2,6-diazaspiro[3.4]octan-6-yl)-3-azatricyclo[7.1.1.0$^{2,7}$]undeca-2,4,6-triene-5-carbonitrile | Step 1 performed using procedure from Example 13-12. Step 5: replaced by Step 4 from Method 2 | Step 1a: Intermediate 61 and step 1b: bicyclo[3.1.1]heptan-3-one (PharmaBlock). |
| 13-39 | 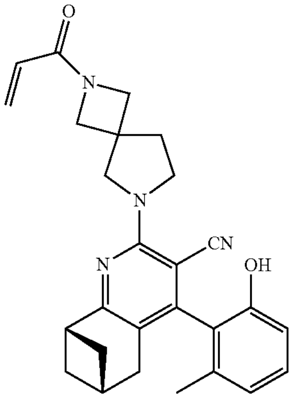 [SMILES: C=CC(=O)N1CC2(CCN(c3nc4c(c(-c5c(C)cccc5O)c3C#N)C[C@H]3C[C@@H]4C3)C2)C1] | (M)-(1S,9S)-6-(2-hydroxy-6-methylphenyl)-4-(2-(2-propenoyl)-2,6-diazaspiro[3.4]octan-6-yl)-3-azatricyclo[7.1.1.0$^{2,7}$]undeca-2,4,6-triene-5-carbonitrile (1$^{st}$ eluting peak) | Step 1 performed using procedure from Example 13-12. Step 5: replaced by Step 4 from Method 2. See atropisomer separation conditions below | Step 1a: Intermediate 61 and step 1b: bicyclo[3.1.1]heptan-3-one (PharmaBlock). |
| 13-40 | 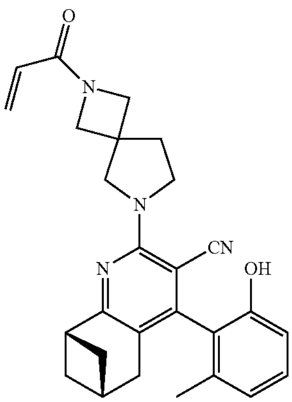 [SMILES: C=CC(=O)N1CC2(CCN(c3nc4c(c(-c5c(C)cccc5O)c3C#N)C[C@H]3C[C@@H]4C3)C2)C1] | (P)-(1S,9S)-6-(2-hydroxy-6-methylphenyl)-4-(2-(2-propenoyl)-2,6-diazaspiro[3.4]octan-6-yl)-3-azatricyclo[7.1.1.0$^{2,7}$]undeca-2,4,6-triene-5-carbonitrile (2$^{nd}$ eluting peak) | Step 1 performed using procedure from Example 13-12. Step 5: replaced by Step 4 from Method 2. See atropisomer separation conditions below | Step 1a: Intermediate 61 and step 1b: bicyclo[3.1.1]heptan-3-one (PharmaBlock). |

TABLE 5-continued

| Ex.# | Chemical Structure | Name | Method changes | Reagent |
|---|---|---|---|---|
| 13-41 | 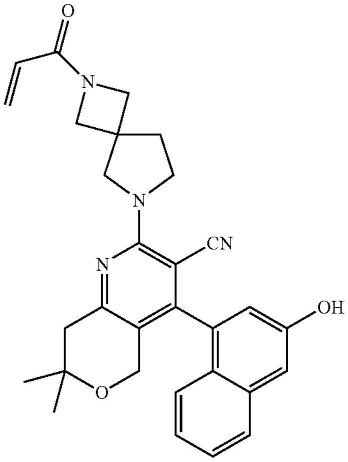 [SMILES: C=CC(=O)N1CC2(CCN(c3nc4c(c(-c5cc(O)cc6ccccc56)c3C#N)COC(C)(C)C4)C2)C1] | 4-(3-hydroxy-1-naphthalenyl)-7,7-dimethyl-2-(2-(2-propenoyl)-2,6-diazaspiro[3.4]octan-6-yl)-7,8-dihydro-5H-pyrano[4,3-b]pyridine-3-carbonitrile | Step 1 performed using procedure from Example 13-12. Step 5: replaced by Step 4 from Method 2 | Step 1a: Intermediate 62 and step 1b: 2,2-dimethyltetrahydro-4H-pyran-4-one (PharmaBlock). |
| 13-42 | 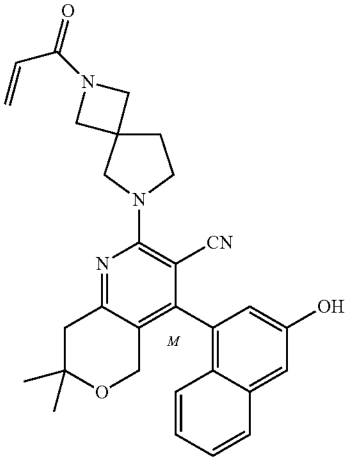 | (M)-4-(3-hydroxy-1-naphthalenyl)-7,7-dimethyl-2-(2-(2-propenoyl)-2,6-diazaspiro[3.4]octan-6-yl)-7,8-dihydro-5H-pyrano[4,3-b]pyridine-3-carbonitrile (1st eluting peak) | Step 1 performed using procedure from Example 13-12. Step 5: replaced by Step 4 from Method 2. See atropisomer separation conditions below. | Step 1a: Intermediate 62 and step 1b: 2,2-dimethyltetrahydro-4H-pyran-4-one (PharmaBlock). |
| 13-43 | 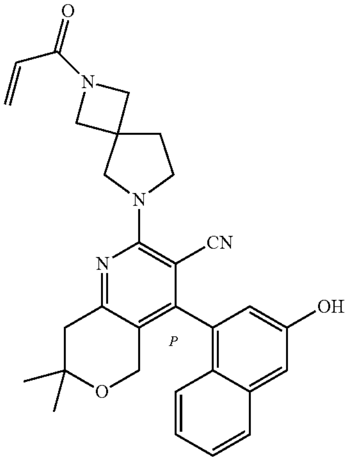 | (P)-4-(3-hydroxy-1-naphthalenyl)-7,7-dimethyl-2-(2-(2-propenoyl)-2,6-diazaspiro[3.4]octan-6-yl)-7,8-dihydro-5H-pyrano[4,3-b]pyridine-3-carbonitrile (2nd eluting peak) | Step 1 performed using procedure from Example 13-12. Step 5: replaced by Step 4 from Method 2. See atropisomer separation conditions below. | Step 1a: Intermediate 62 and step 1b: 2,2-dimethyltetrahydro-4H-pyran-4-one (PharmaBlock). |

Examples 13-2 to 13-157 were prepared following the procedure described in Method 13, steps 1-5, above as follows:

TABLE 5-continued

Examples 13-2 to 13-157 were prepared following the procedure described in Method 13, steps 1-5, above as follows:

| Ex.# | Chemical Structure | Name | Method changes | Reagent |
| --- | --- | --- | --- | --- |
| 13-44 | 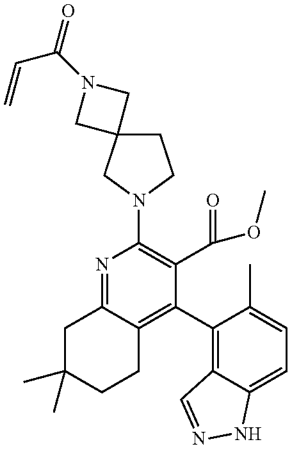 [SMILES: C=CC(=O)N1CC2(CCN(c3nc4c(c(-c5c(C)ccc6[nH]ncc56)c3C(=O)OC)CCC(C)(C)C4)C2)C1] | methyl 7,7-dimethyl-4-(5-methyl-1H-indazol-4-yl)-2-(2-(2-propenoyl)-2,6-diazaspiro[3.4]octan-6-yl)-5,6,7,8-tetrahydro-3-quinolinecarboxylate | Step 1 was omitted. Step 5: replaced by Step 4 from Method 2 with acrylic anhydride used in place of acryloyl chloride | Step 2: Intermediate 67 |
| 13-45 | 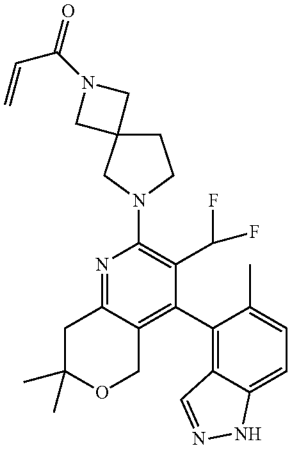 [SMILES: C=CC(=O)N1CC2(CCN(c3nc4c(c(-c5c(C)ccc6[nH]ncc56)c3C(F)F)COC(C)(C)C4)C2)C1] | 1-(6-(3-(difluoromethyl)-7,7-dimethyl-4-(5-methyl-1H-indazol-4-yl)-7,8-dihydro-5H-pyrano[4,3-b]pyridin-2-yl)-2,6-diazaspiro[3.4]octan-2-yl)-2-propen-1-one | Step 1 was omitted. Step 5: replaced by Step 4 from Method 2 with acrylic anhydride used in place of acryloyl chloride. | Step 2: Intermediate 68 |
| 13-46 | 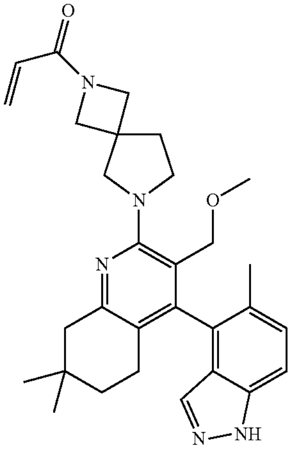 [SMILES: C=CC(=O)N1CC2(CCN(c3nc4c(c(-c5c(C)ccc6[nH]ncc56)c3COC)CCC(C)(C)C4)C2)C1] | 1-(6-(3-(methoxymethyl)-7,7-dimethyl-4-(5-methyl-1H-indazol-4-yl)-5,6,7,8-tetrahydro-2-quinolinyl)-2,6-diazaspiro[3.4]octan-2-yl)-2-propen-1-one | Step 1 was omitted. Step 5: replaced by Step 4 from Method 2 with acrylic anhydride used in place of acryloyl chloride | Step 2: Intermediate 69 |

TABLE 5-continued

| Examples 13-2 to 13-157 were prepared following the procedure described in Method 13, steps 1-5, above as follows: | | | | |
|---|---|---|---|---|
| Ex.# | Chemical Structure | Name | Method changes | Reagent |
| 13-47 | 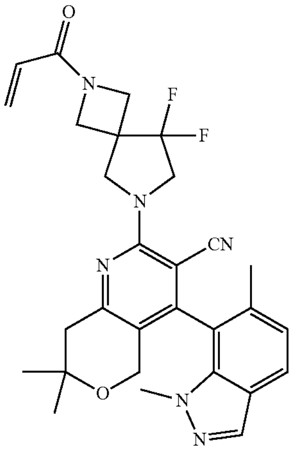 [SMILES: C=CC(=O)N1CC2(C1)CN(c1nc3c(c(-c4c(C)ccc5cnn(C)c45)c1C#N)COC(C)(C)C3)CC2(F)F] | 2-(8,8-difluoro-2-(2-propenoyl)-2,6-diazaspiro[3.4]octan-6-yl)-4-(1,6-dimethyl-1H-indazol-7-yl)-7,7-dimethyl-7,8-dihydro-5H-pyrano[4,3-b]pyridine-3-carbonitrile | Step 1 performed using procedure from Example 13-12. See alternate step 2 below. Step 5: replaced by Step 4 from Method 2 | Step 1a: Intermediate 59 and step 1b: 2,2-dimethyltetrahydro-4H-pyran-4-one (PharmaBlock). step 3: tert-butyl 8,8-difluoro-2,6-diazaspiro[3.4]octane-2-carboxylate (PharmaBlock). |
| 13-48 | 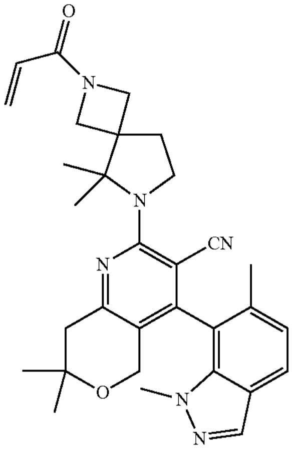 [SMILES: C=CC(=O)N1CC2(CCN(c3nc4c(c(-c5c(C)ccc6cnn(C)c56)c3C#N)COC(C)(C)C4)C2(C)C)C1] | 4-(1,6-dimethyl-1H-indazol-7-yl)-2-(5,5-dimethyl-2-(2-propenoyl)-2,6-diazaspiro[3.4]octan-6-yl)-7,7-dimethyl-7,8-dihydro-5H-pyrano[4,3-b]pyridine-3-carbonitrile | Step 1 performed using procedure from Example 13.12. | Step 1a: Intermediate 59 and step 1b: 2,2-dimethyltetrahydro-4H-pyran-4-one (PharmaBlock). Step 3: tert-butyl 5,5-dimethyl-2,6-diazaspiro[3.4]octane-2-carboxylate (PharmaBlock) |
| 13-49 | 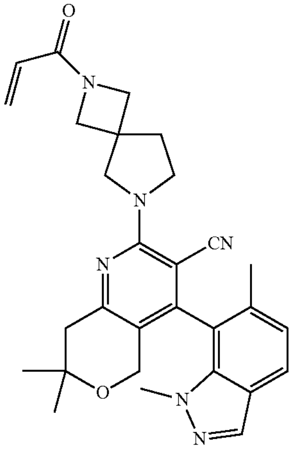 [SMILES: C=CC(=O)N1CC2(CCN(c3nc4c(c(-c5c(C)ccc6cnn(C)c56)c3C#N)COC(C)(C)C4)C2)C1] | 4-(1,6-dimethyl-1H-indazol-7-yl)-7,7-dimethyl-2-(2-(2-propenoyl)-2,6-diazaspiro[3.4]octan-6-yl)-7,8-dihydro-5H-pyrano[4,3-b]pyridine-3-carbonitrile | Step 1 performed using procedure from Example 13-12. and alternative 1b. step 3: DMA replaced with NMP. Step 5: replaced by Step 4 from Method 2 | Step 1a: Intermediate 59 and step 1b: 2,2-dimethyltetrahydro-4H-pyran-4-one (PharmaBlock). |

TABLE 5-continued

Examples 13-2 to 13-157 were prepared following the procedure described in Method 13, steps 1-5, above as follows:

| Ex.# | Chemical Structure | Name | Method changes | Reagent |
|---|---|---|---|---|
| 13-50 | 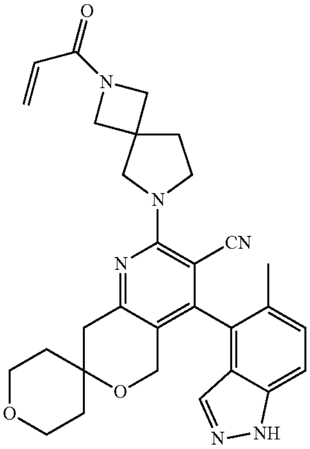 [SMILES: C=CC(=O)N1CC2(CCN(c3nc4c(c(-c5c(C)ccc6[nH]ncc56)c3C#N)COC3(CCOCC3)C4)C2)C1] | 4'-(5-methyl-1H-indazol-4-yl)-2'-(2-(2-propenoyl)-2,6-diazaspiro[3.4]octan-6-yl)-2,3,5,5',6,8'-hexahydrospiro[pyran-4,7'-pyrano[4,3-b]pyridine]-3'-carbonitrile | See below for alternative step 1 and alternative step 1b. step 3: DMA replaced with NMP. Step 5: replaced by Step 4 from Method 2 | Step 1a: Intermediate 58 and step 1b: 1,9-dioxaspiro[5.5]undecan-4-one (Enamine) |
| 13-51 | 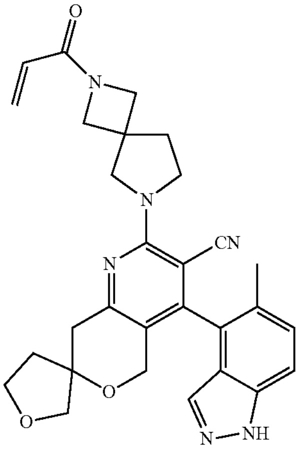 [SMILES: C=CC(=O)N1CC2(CCN(c3nc4c(c(-c5c(C)ccc6[nH]ncc56)c3C#N)COC3(CCOC3)C4)C2)C1] | (3R)-4'-(5-methyl-1H-indazol-4-yl)-2'-(2-(2-propenoyl)-2,6-diazaspiro[3.4]octan-6-yl)-4,5,5',8'-tetrahydrospiro[furan-3,7'-pyrano[4,3-b]pyridine]-3'-carbonitrile\|(3S)-4'-(5-methyl-1H-indazol-4-yl)-2'-(2-(2-propenoyl)-2,6-diazaspiro[3.4]octan-6-yl)-4,5,5',8'-tetrahydrospiro[furan-3,7'-pyrano[4,3-b]pyridine]-3'-carbonitrile | Step 1 performed using procedure from Example 13-12. step 3: DMA replaced with NMP. Step 5: replaced by Step 4 from Method 2 | Step 1a: Intermediate 58 and step 1b: 2,6-dioxaspiro[4.5]decan-9-one (Enamine) |
| 13-52 | 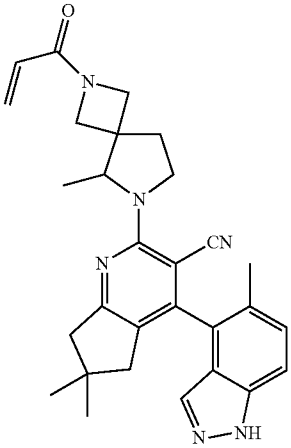 [SMILES: C=CC(=O)N1CC2(CCN(c3nc4c(c(-c5c(C)ccc6[nH]ncc56)c3C#N)CC(C)(C)C4)C2C)C1] | 6,6-dimethyl-4-(5-methyl-1H-indazol-4-yl)-2-((5R)-5-methyl-2-(2-propenoyl)-2,6-diazaspiro[3.4]octan-6-yl)-6,7-dihydro-5H-cyclopenta[b]pyridine-3-carbonitrile\|6,6-dimethyl-4-(5-methyl-1H-indazol-4-yl)-2-((5S)-5-methyl-2-(2-propenoyl)-2,6-diazaspiro[3.4]octan-6-yl)-6,7-dihydro-5H-cyclopenta[b]pyridine-3-carbonitrile | Step 1 performed using procedure from Example 13-12. step 3: DMA replaced with NMP. Step 5: replaced by Step 4 form Method 2 | Step 1a: Intermediate 58 and step 1b: 3,3-dimethylcyclopentan-1-one (Enamine). Step 3: tert-butyl 5-methyl-2,6-diazaspiro[3.4]octane-2-carboxylate (Enamine) |

TABLE 5-continued

| Examples 13-2 to 13-157 were prepared following the procedure described in Method 13, steps 1-5, above as follows: | | | | |
|---|---|---|---|---|
| Ex.# | Chemical Structure | Name | Method changes | Reagent |
| 13-53 | 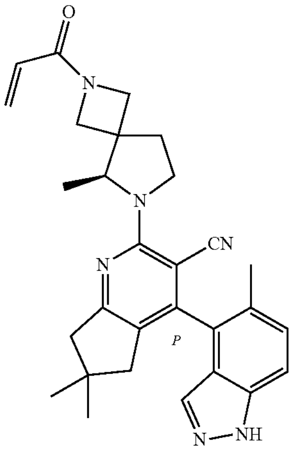 | (P)-6,6-dimethyl-4-(5-methyl-1H-indazol-4-yl)-2-((5S)-5-methyl-2-(2-propenoyl)-2,6-diazaspiro[3.4]octan-6-yl)-6,7-dihydro-5H-cyclopenta[b]pyridine-3-carbonitrile (3rd eluting peak) | Step 1 performed using procedure from Example 13-12. step 3: DMA replaced with NMP. Step 5: replaced by Step 4 from Method 2. See below for stereoisomer separation. | Step 1a: Intermediate 58 and step 1b: 3,3-dimethylcyclopentan-1-one (Enamine). Step 3: tert-butyl 5-methyl-2,6-diazaspiro[4.5]octane-2-carboxylate (Enamine) |
| 13-54 | 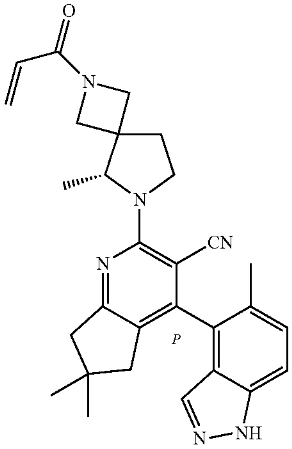 | (P)-6,6-dimethyl-4-(5-methyl-1H-indazol-4-yl)-2-((5R)-5-methyl-2-(2-propenoyl)-2,6-diazaspiro[3.4]octan-6-yl)-6,7-dihydro-5H-cyclopenta[b]pyridine-3-carbonitrile (4th eluting peak) | Step 1 performed using procedure from Example 13-12. step 3: DMA replaced with NMP. Step 5: replaced by Step 4 from Method 2. See below for stereoisomer separation. | Step 1a: Intermediate 58 and step 1b: 3,3-dimethylcyclopentan-1-one (Enamine). Step 3: tert-butyl 5-methyl-2,6-diazaspiro[3.4]octane-2-carboxylate (Enamine) |
| 13-55 | 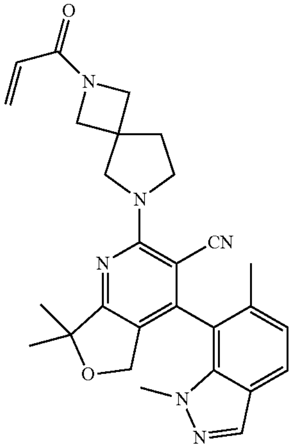 [SMILES: C=CC(=O)N1CC2(CCN(c3nc4c(c(-c5c(C)ccc6cnn(C)c56)c3C#N)COC4(C)C)C2)C1] | 4-(1,6-dimethyl-1H-indazol-7-yl)-7,7-dimethyl-2-(2-(2-propenoyl)-2,6-diazaspiro[3.4]octan-6-yl)-5,7-dihydrofuro[3,4-b]pyridine-3-carbonitrile | Step 1 performed using procedure from Example 13-12. step 3: DMA replaced with NMP. Step 5: replaced by Step 4 from Method 2. | Step 1a: Intermediate 59 and step 1b: 2,2-dimethyldihydrofuran-3(2H)-one (Combi-Blocks). |

TABLE 5-continued

| Examples 13-2 to 13-157 were prepared following the procedure described in Method 13, steps 1-5, above as follows: | | | | |
|---|---|---|---|---|
| Ex.# | Chemical Structure | Name | Method changes | Reagent |
| 13-56 | 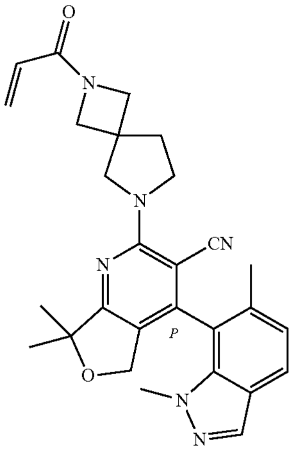 | (P)-4-(1,6-dimethyl-1H-indazol-7-yl)-,7,7-dimethyl-2-(2-(2-propenoyl)-2,6-diazaspiro[3.4]octan-6-yl)-5,7-dihydrofuro[3,4-b]pyridine-3-carbonitrile (1st eluting peak) | Step 1 performed using procedure from Example 13-12. step 3: DMA replaced with NMP. Step 5: replaced by Step 4 from Method 2. See atropisomer separation conditions below | Step 1a: Intermediate 59 and step 1b: 2,2-dimethyldihydro-furan-3(2H)-one (Combi-Blocks). |
| 13-57 | 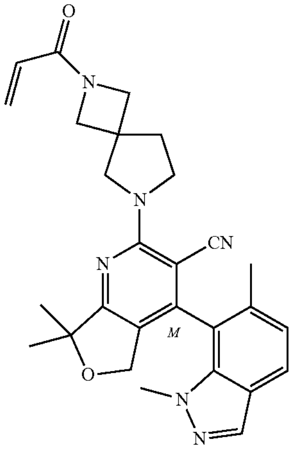 | (M)-4-(1,6-dimethyl-1H-indazol-7-yl)-7,7-dimethyl-2-(2-(2-propenoyl)-2,6-diazaspiro[3.4]octan-6-yl)-5,7-dihydrofuro[3,4-b]pridine-3-carbonitrile (2nd eluting peak) | Step 1 performed using procedure from Example 13-12. step 3: DMA replaced with NMP. Step 5: replaced by Step 4 from Method 2. See atropisomer separation conditions below | Step 1a: Intermediate 59 and step 1b: 2,2-dimethyldihydro-furan-3(2H)-one (Combi-Blocks). |
| 13-58 | 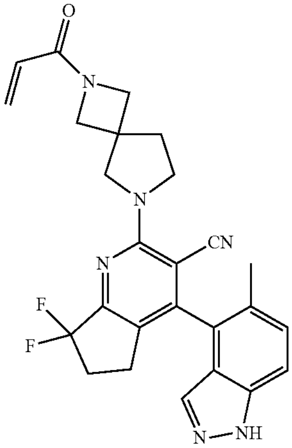 [SMILES: C=CC(=O)N1CC2(CCN(c3nc4c(c(-c5c(C)ccc6[nH]ncc56)c3C#N)CCC4(F)F)C2)C1] | 7,7-difluoro-4-(5-methyl-1H-indazol-4-yl)-2-(2-(2-propenoyl)-2,6-diazaspiro[3.4]octan-6-yl)-6,7-dihydro-5H-cyclopenta[b]pyridine-3-carbonitrile | Step 1 performed using procedure from Example 13-12. step 3: DMA replaced with NMP. Step 5: replaced by Step 4 from Method 2. | Step 1a: Intermediate 58 and step 1b: 2,2-difluorocyclopentan-1-one (Enamine) |

TABLE 5-continued

| Examples 13-2 to 13-157 were prepared following the procedure described in Method 13, steps 1-5, above as follows: | | | | |
|---|---|---|---|---|
| Ex.# | Chemical Structure | Name | Method changes | Reagent |
| 13-59 | 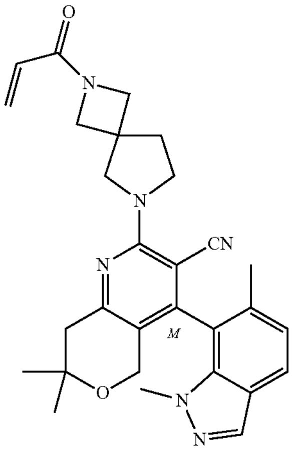 | (M)-4-(1,6-dimethyl-1H-indazol-7-yl)-7,7-dimethyl-2-(2-(2-propenoyl)-2,6-diazaspiro[3.4]octan-6-yl)-7,8-dihydro-5H-pyrano[4,3-b]pyridine-3-carbonitrile | Step 1 performed using procedure from Example 13-49. step 3: DMA replaced with NMP. Step 5: replaced by Step 4 from Method 2. See atropisomer separation conditions below | Step 1a: Intermediate 59 and step 1b: 2,2-dimethyltetrahydro-4H-pyran-4-one (PharmaBlock). |
| 13-60 | 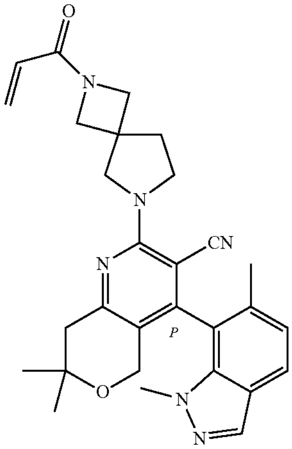 | (P)-4-(1,6-dimethyl-1H-indazol-7-yl)-7,7-dimethyl-2-(2-(2-propenoyl)-2,6-diazaspiro[3.4]octan-6-yl)-7,8-dihydro-5H-pyrano[4,3-b]pyridine-3-carbonitrile | Step 1 performed using procedure from Example 13-49. step 3: DMA replaced with NMP. Step 5: replaced by Step 4 from Method 2. See atropisomer separation conditions below | Step 1a: Intermediate 59 and step 1b: 2,2-dimethyltetrahydro-4H-pyran-4-one (PharmaBlock). |
| 13-61 | 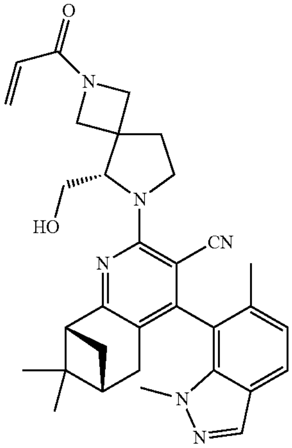 [SMILES: C=CC(=O)N1CC2(CCN(c3nc4c(c(-c5c(C)ccc6cnn(C)c56)c3C#N)C[C@H]3C[C@@H]4C3(C)C)[C@@H]2CO)C1] | (1R,9R)-6-(1,6-dimethyl-1H-indazol-7-yl)-4-((5S)-5-(hydroxymethyl)-2-(2-propenoyl)-2,6-diazaspiro[3.4]octan-6-yl)-10,10-dimethyl-3-azatricyclo[7.1.1.0$^{2,7}$]undeca-2,4,6-triene-5-carbonitrile | Step 1 performed using procedure from Example 13-49. Step 5: replaced by Step 4 from Method 2. | Step 1a: Intermediate 59 and step 1b: (1R)-(+)-nopinone (Sigma-Aldrich). Step 3: Amine 4. |

TABLE 5-continued

| Ex.# | Chemical Structure | Name | Method changes | Reagent |
|---|---|---|---|---|
| Examples 13-2 to 13-157 were prepared following the procedure described in Method 13, steps 1-5, above as follows: | | | | |
| 13-62 | 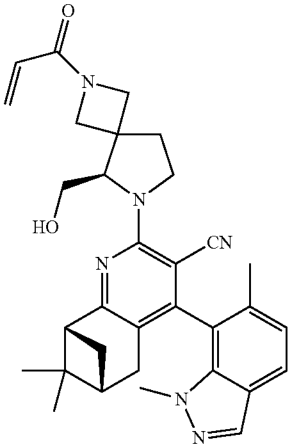 [SMILES: C=CC(=O)N1CC2(CCN(c3nc4c(c(-c5c(C)ccc6cnn(C)c56)c3C#N)C[C@H]3C[C@@H]4C3(C)C)[C@H]2CO)C1] | (1R,9R)-6-(1,6-dimethyl-1H-indazol-7-yl)-4-((5R)-5-(hydroxymethyl)-2-(2-propenoyl)-2,6-diazaspiro[3.4]octan-6-yl)-10,10-dimethyl-3-azatricyclo[7.1.1.0$^{2,7}$]undeca-2,4,6-triene-5-carbonitrile | Step 1 performed using procedure from Example 13-49. Step 5: replaced by Step 4 from Method 2. | Step 1a: Intermediate 59 and step 1b: (1R)-(+)-nopinone (Sigma-Aldrich). Step 3: Amine 4. |
| 13-63 | 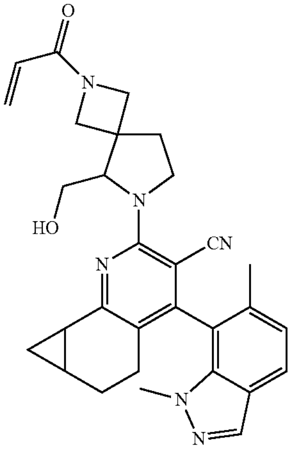 [SMILES: C=CC(=O)N1CC2(CCN(c3nc4c(c(-c5c(C)ccc6cnn(C)c56)c3C#N)CCC3CC43)C2CO)C1] | (6aR,7aR)-4-(1,6-dimethyl-1H-indazol-7-yl)-2-((5R)-5-(hydroxymethyl)-2-(2-propenoyl)-2,6-diazaspiro[3.4]octan-6-yl)-6,6a,7,7a-tetrahydro-5H-cyclopropa[h]quinoline-3-carbonitrile\|(6aR,7aR)-4-(1,6-dimethyl-1H-indazol-7-yl)-2-((5S)-5-(hydroxymethyl)-2-(2-propenoyl)-2,6-diazaspiro[3.4]octan-6-yl)-6,6a,7,7a-tetrahydro-5H-cyclopropa[h]quinoline-3-carbonitrile\|(6aR,7aS)-4-(1,6-dimethyl-1H-indazol-7-yl)-2-((5R)-5-(hydroxymethyl)-2-(2-propenoyl)-2,6-diazaspiro[3.4]octan-6-yl)-6,6a,7,7a-tetrahydro-5H-cyclopropa[h]quinoline-3-carbonitrile\|(6aR,7aS)-4-(1,6-dimethyl-1H-indazol-7-yl)-2-((5S)-5-(hydroxymethyl)-2-(2-propenoyl)-2,6-diazaspiro[3.4]octan-6-yl)-6,6a,7,7a-tetrahydro-5H-cyclopropa[h]quinoline-3-carbonitrile\|(6aS,7aR)-4-(1,6-dimethyl-1H-indazol-7-yl)-2-((5R)-5-(hydroxymethyl)-2-(2-propenoyl)-2,6-diazaspiro[3.4]octan-6-yl)-6,6a,7,7a-tetrahydro-5H-cyclopropa[h]quinoline-3-carbonitrile\|(6aS,7aR)-4-(1,6-dimethyl-1H-indazol-7-yl)-2-((5S)-5-(hydroxymethyl)-2-(2-propenoyl)-2,6-diazaspiro[3.4]octan-6-yl)-6,6a,7,7a-tetrahydro-5H-cyclopropa[h]quinoline-3-carbonitrile\|(6aS,7aS)-4-(1,6-dimethyl-1H-indazol-7-yl)-2-((5R)-5-(hydroxymethyl)-2-(2-propenoyl)-2,6- | Step 1 performed using procedure from Example 13-49. Step 5: replaced by step 4 from Method 2. | Step 1a: Intermediate 59 and step 1b: bicyclo[4.1.0]heptan-2-one (PharmaBlock). Step 3: Amine 4. |

TABLE 5-continued

Examples 13-2 to 13-157 were prepared following the procedure described in Method 13, steps 1-5, above as follows:

| Ex.# | Chemical Structure | Name | Method changes | Reagent |
|---|---|---|---|---|
| | | diazaspiro[3.4]octan-6-yl)-6,6a,7,7a-tetrahydro-5H-cyclopropa[h]quinoline-3-carbonitrile\|(6aS,7aS)-4-(1,6-dimethyl-1H-indazol-7-yl)-2-((5S)-5-(hydroxymethyl)-2-(2-propenoyl)-2,6-diazaspiro[3.4]octan-6-yl)-6,6a,7,7a-tetrahydro-5H-cyclopropa[h]quinoline-3-carbonitrile | | |
| 13-64 | 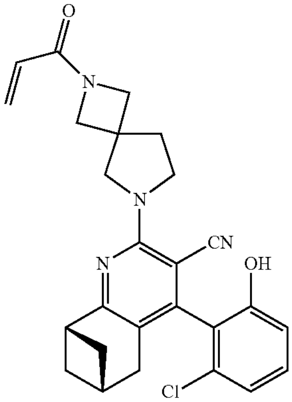 [SMILES: C=CC(=O)N1CC2(CCN(c3nc4c(c(-c5c(O)cccc5Cl)c3C#N)C[C@H]3C[C@@H]4C3)C2)C1] | (1S,9S)-6-(2-chloro-6-hydroxyphenyl)-4-(2-(2-propenoyl)-2,6-diazaspiro[3.4]octan-6-yl)-3-azatricyclo[7.1.1.0$^{2,7}$]undeca-2,4,6-triene-5-carbonitrile | Step 1 performed using procedure from Example 13-12. Step 5: replaced by Step 4 from Method 2. | Step 1a: Intermediate 70 and step 1b: bicyclo[3.1.1]heptan-2-one (Enamine). |
| 13-65 | 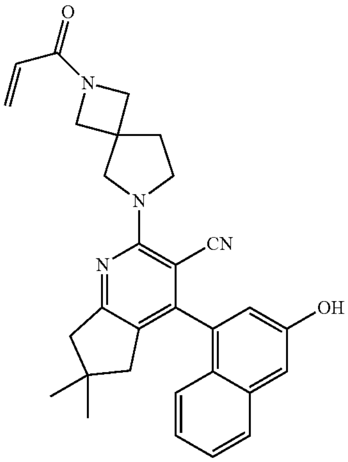 [SMILES: C=CC(=O)N1CC2(CCN(c3nc4c(c(-c5cc(O)cc6ccccc56)c3C#N)CC(C)(C)C4)C2)C1] | 4-(3-hydroxy-1-naphthalenyl)-6,6-dimethyl-2-(2-(2-propenoyl)-2,6-diazaspiro[3.4]octan-6-yl)-6,7-dihydro-5H-cyclopenta[b]pyridine-3-carbonitirle | Step 1 performed using procedure from Example 13-12. Step 5: replaced by Step 4 from Method 2. | Step 1a: Intermediate 62 and step 1b: 3,3-dimethylcyclopentan-1-one (PharmaBlock). |

TABLE 5-continued

Examples 13-2 to 13-157 were prepared following the procedure described in Method 13, steps 1-5, above as follows:

| Ex.# | Chemical Structure | Name | Method changes | Reagent |
|---|---|---|---|---|
| 13-66 | 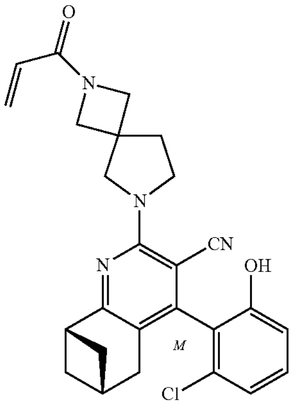 | (M)-(1S,9S)-6-(2-chloro-6-hydroxyphenyl)-4-(2-(2-propenoyl)-2,6-diazaspiro[3.4]octan-6-yl)-3-azatricyclo[7.1.1.0$^{2,7}$]undeca-2,4,6-triene-5-carbonitrile | Step 1 performed using procedure from Example 13-12. Step 5: replaced by Step 4 from Method 2. See atropisomer separation conditions below. | Step 1a: Intermediate 70 and step 1b: bicyclo[3.1.1]heptan-2-one (Enamine) |
| 13-67 | 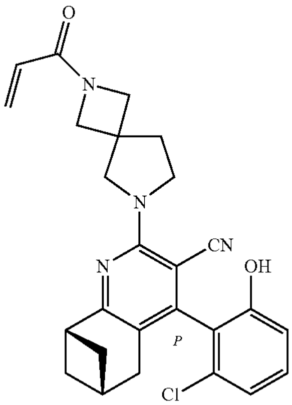 | (P)-(1S,9S)-6-(2-chloro-6-hydroxyphenyl)-4-(2-(2-propenoyl)-2,6-diazaspiro[3.4]octan-6-yl)-3-azatricyclo[7.1.1.0$^{2,7}$]undeca-2,4,6-triene-5-carbonitrile | Step 1 performed using prodcedure from Example 13-12. Step 5: replaced by Step 4 from Method 2. See atropisomer separation conditions below. | Step 1a: Intermediate 70 and step 1b: bicyclo[3.1.1]heptan-2-one (Enamine) |
| 13-68 | 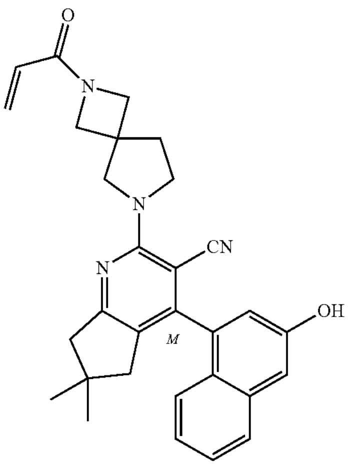 | (M)-4-(3-hydroxy-1 naphthalenyl)-6,6-dimethyl-2-(2-(2-propenoyl)-2,6-diazaspiro[3.4]octan-6-yl)-6,7-dihydro-5H-cyclopenta[b]pyridine-3-carbonitrile | Step 1 performed using procedure from Example 13-12. Step 5: replaced by Step 4 from Method 2. See atropisomer separation conditions below. | Step 1a: Interemdiate 62 and step 1b: 3,3-dimethylcyclopentan-1-one (PharmaBlock). |

TABLE 5-continued

| Ex.# | Chemical Structure | Name | Method changes | Reagent |
|---|---|---|---|---|
| | Examples 13-2 to 13-157 were prepared following the procedure described in Method 13, steps 1-5, above as follows: | | | |
| 13-69 | 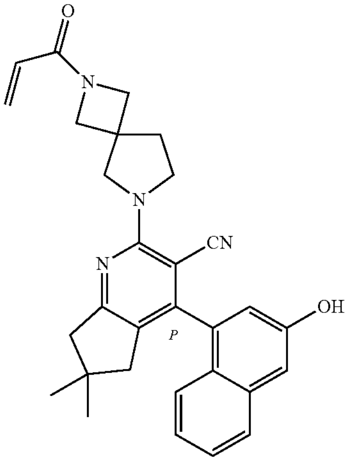 | (P)-4-(3-hydroxy-1-naphthalenyl)-6,6-dimethyl-2-(2-(2-propenoyl)-2,6-diazaspiro[3.4]octan-6-yl)-6,7-dihydro-5H-cyclopenta[b]pyridine-3-carbonitrile | Step 1 performed using procedure from Example 13-12. Step 5: replaced by Step 4 from Method 2. See atropisomer separation conditions below. | Step 1a: Intermediate 62 and step 1b: 3,3-dimethylcyclopentan-1-one (PharmaBlock). |
| 13-70 | 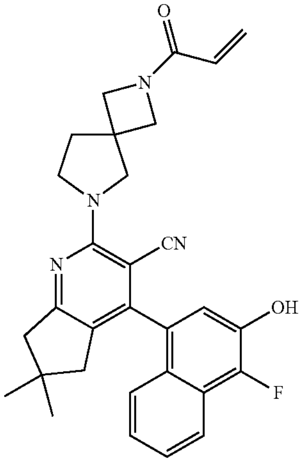 [SMILES: C=CC(=O)N1CC2(CCN(c3nc4c(c(-c5cc(O)c(F)c6ccccc56)c3C#N)CC(C)(C)C4)C2)C1] | 4-(4-fluoro-3-hydroxy-1-naphthalenyl)-6,6-dimethyl-2-(2-(2-propenoyl)-2,6-diazaspiro[3.4]octan-6-yl)-6,7-dihydro-5H-cyclopenta[b]pyridine-3-carbonitrile | Step 1 performed using procedure from Example 13-12. Step 5: replaced by Step 4 from Method 2. | Step 1a: Intermediate 71 and step 1b: 3,3-dimethylcyclopentan-1-one (PharmaBlock). |
| 13-71 | 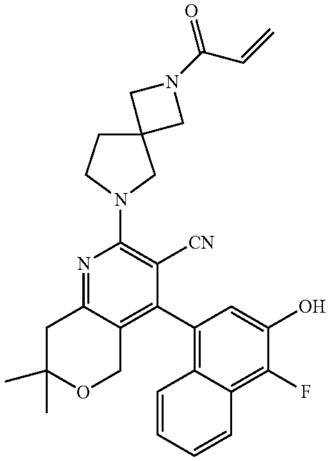 [SMILES: C=CC(=O)N1CC2(CCN(c3nc4c(c(-c5cc(O)c(F)c6ccccc56)c3C#N)COC(C)(C)C4)C2)C1] | 4-(4-fluoro-3-hydroxy-1-naphthalenyl)-7,7-dimethyl-2-(2-(2-propenoyl)-2,6-diazaspiro[3.4]octan-6-yl)-7,8-dihydro-5H-pyrano[4,3-b]pyridine-3-carbonitrile | Step 1 performed using procedure from Example 13-12. Step 5: replaced by Step 4 from Method 2. | Step 1a: Intermediate 71 and step 1b: 2,2-dimethyloxan-4-one (Aurum). |

TABLE 5-continued

| Examples 13-2 to 13-157 were prepared following the procedure described in Method 13, steps 1-5, above as follows: | | | | |
|---|---|---|---|---|
| Ex.# | Chemical Structure | Name | Method changes | Reagent |
| 13-72 | 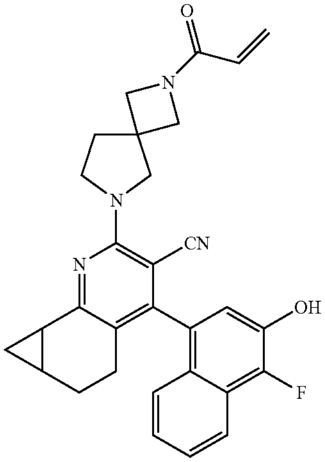 [SMILES: C=CC(=O)N1CC2(CCN(c3nc4c(c(-c5cc(O)c(F)c6ccccc56)c3C#N)CCC3CC43)C2)C1] | (6aR,7aR)-4-(4-fluoro-3-hydroxy-1-naphthalenyl)-2-(2-(2-propenoyl)-2,6-diazaspiro[3.4]octan-6-yl)-6,6a,7,7a-tetrahydro-5H-cyclopropa[h]quinoline-3-carbonitrile\|(6aS,7aS)-4-(4-fluoro-3-hydroxy-1-naphthalenyl)-2-(2-(2-propenoyl)-2,6-diazaspiro[3.4]octan-6-yl)-6,6a,7,7a-tetrahydro-5H-cyclopropa[h]quinoline-3-carbonitrile | Step 1 performed using procedure from Example 13-12. Step 5: replaced by Step 4 from Method 2. | Step 1a: Intermediate 71 and step 1b: bicyclo[4.1.0]heptan-2-one (PharmaBlock) |
| 13-73 | 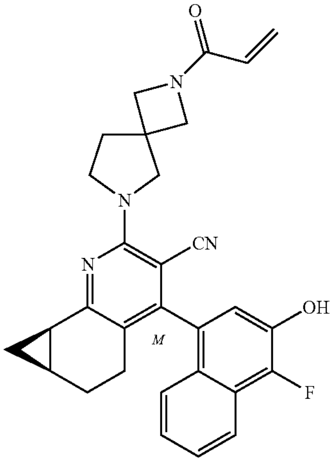 | (M)-(6aS,7aR)-4-(4-fluoro-3-hydroxy-1-naphthalenyl)-2-(2-(2-propenoyl)-2,6-diazaspiro[3.4]octan-6-yl)-6,6a,7,7a-tetrahydro-5H-cyclopropa[h]quinoline-3-carbonitrile (1st eluting peak). | Step 1 performed using procedure from Example 13-12. Step 5: replaced by Step 4 from Method 2. See atropisomer separation conditions below. | Step 1a: Intermediate 71 and step 1b: bicyclo[4.1.0]heptan-2-one (PharmaBlock) |
| 13-74 | 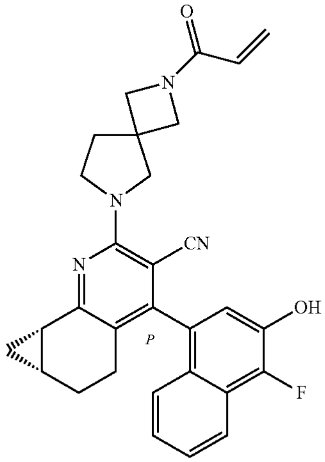 | (P)-(6aR,7aS)-4-(4-fluoro-3-hydroxy-1-naphthalenyl)-2-(2-(2-propenoyl)-2,6-diazaspiro[3.4]octan-6-yl)-6,6a,7,7a-tetrahydro-5H-cyclopropa[h]quinoline-3-carbonitrile (4th eluting peak). | Step 1 performed using procedure from Example 13-12. Step 5: replaced by Step 4 from Method 2. See atropisomer separation conditions below. | Step 1a: Intermediate 71 and step 1b: bicyclo[4.1.0]heptan-2-one (PharmaBlock) |

TABLE 5-continued

Examples 13-2 to 13-157 were prepared following the procedure described in Method 13, steps 1-5, above as follows:

| Ex.# | Chemical Structure | Name | Method changes | Reagent |
|---|---|---|---|---|
| 13-75 | 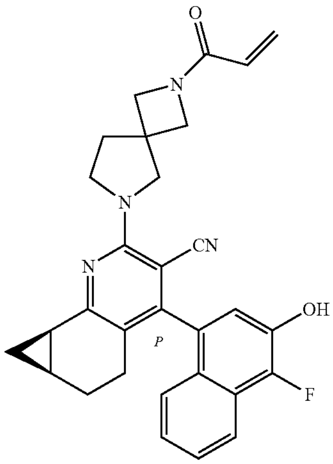 | (P)-(6aS,7aR)-4-(4-fluoro-3-hydroxy-1-naphthalenyl)-2-(2-(2-propenoyl)-2,6-diazaspiro[3.4]octan-6-yl)-6,6a,7,7a-tetrahydro-5H-cyclopropa[h]quinoline-3-carbonitrile (2nd eluting peak). | Step 1 performed using procedure from Example 13-12. Step 5: replaced by Step 4 from Method 2. See atropisomer separation conditions below. | Step 1a: Intermediate 71 and step 1b: bicyclo[4.1.0]heptan-2-one (PharmaBlock) |
| 13-76 | 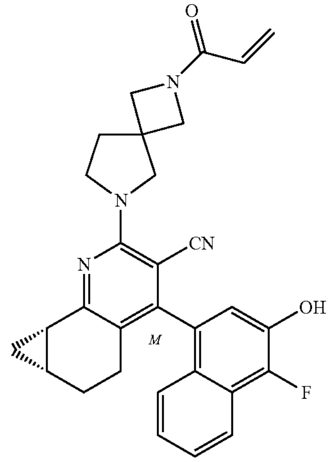 | (M)-(6aR,7aS)-4-(4-fluoro-3-hydroxy-1-naphthalenyl)-2-(2-(2-propenoyl)-2,6-diazaspiro[3.4]octan-6-yl)-6,6a,7,7a-tetrahydro-5H-cyclopropan[h]quinoline-3-carbonitrile (3rd eluting peak). | Step 1 performed using procedure from Example 13-12. Step 5: replaced by Step 4 from Method 2. See atropisomer separation conditions below. | Step 1a: Intermediate 71 and step 1b: bicyclo[4.1.0]heptan-2-one (PharmaBlock) |
| 13-77 | 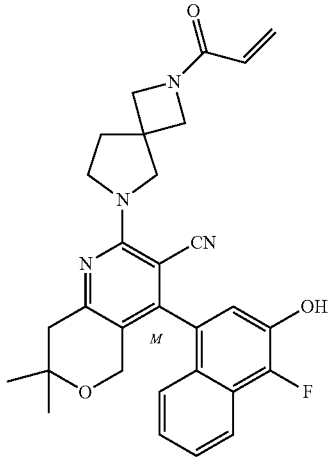 | (M)-4-(4-fluoro-3-hydroxy-1-naphthalenyl)-7,7-dimethyl-2-(2-(2-propenoyl)-2,6-diazaspiro[3.4]octan-6-yl)-7,8-dihydro-5H-pyrano[4,3-b]pyridine-3-carbonitrile (1st eluting peak) | Step 1 performed using procedure from Example 13-12. Step 5: replaced by Step 4 from Method 2. See atropisomer separation conditions below. | Step 1a: Interemdiate 71 and step 1b: 2,2-dimethyloxan-4-one (Aurum). |

TABLE 5-continued

| Examples 13-2 to 13-157 were prepared following the procedure described in Method 13, steps 1-5, above as follows: | | | | |
|---|---|---|---|---|
| Ex.# | Chemical Structure | Name | Method changes | Reagent |
| 13-78 | 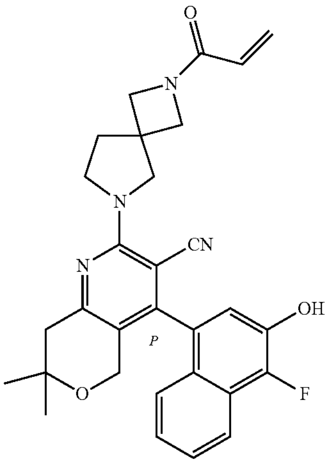 | (P)-4-(4-fluoro-3-hydroxy-1-naphthalenyl)-7,7-dimethyl-2-(2-(2-propenoyl)-2,6-diazaspiro[3.4]octan-6-yl)-7,8-dihydro-5H-pyrano[4,3-b]pyridine-3-carbonitrile (2nd eluting peak) | Step 1 performed using procedure from Example 13-12. Step 5: replaced by Step 4 from Method 2. See atropisomer separation conditions below. | Step 1a: Intermediate 71 and step 1b: 2,2-dimethyloxan-4-one (Aurum). |
| 13-79 | 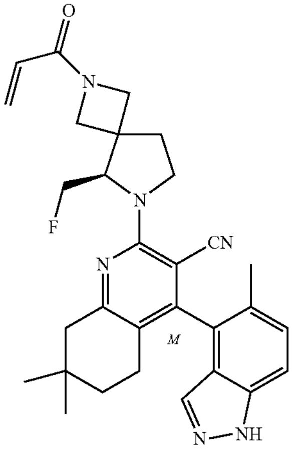 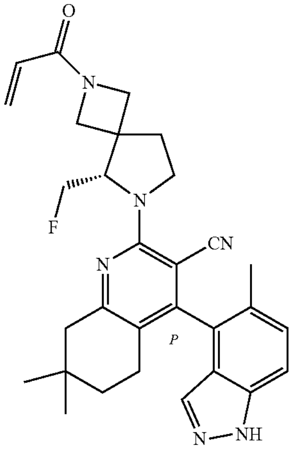 | (M)-2-((5R)-5-(fluoromethyl)-2-(2-propenoyl)-2,6-diazaspiro[3.4]octan-6-yl)-7,7-dimethyl-4-(5-methyl-1H-indaazol-4-yl)-5,6,7,8-tetrahydro-3-quinolinecarbonitrile and (P)-((5S)-5-(fluoromethyl)-2-(2-propenoyl)-2,6-diazaspiro[3.4]octan-6-yl)-7,7-dimethyl-4-(5-methyl-1H-indazol-4-yl)-5,6,7,8-tetrahydro-3-quinolinecarbonitrile | Step 5: replaced by Step 4 from Method 2. | Step 3: tert-butyl 5-(fluoromethyl)-2,6-diazaspiro[3.4]octane-2-carboxylate (LabNetwork) |

TABLE 5-continued

Examples 13-2 to 13-157 were prepared following the procedure described in Method 13, steps 1-5, above as follows:

| Ex.# | Chemical Structure | Name | Method changes | Reagent |
|---|---|---|---|---|
| 13-80 | 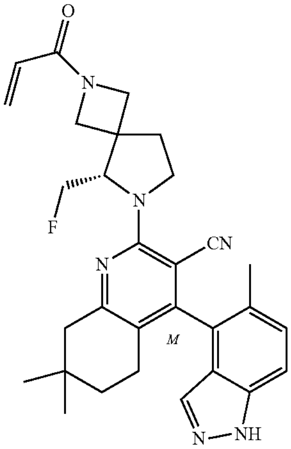 | (M)-2-((5S)-5-(fluoromethyl)-2-(2-propenoyl)-2,6-diazaspiro[3.4]octan-6-yl)-7,7-dimethyl-4-(5-methyl-1H-indazol-4-yl)-5,6,7,8-tetrahydro-3-quinolinecarbonitrile and (P)-2-((5R)-5-(fluoromethyl)-2-(2-propenoyl)-2,6-diazaspiro[3.4]octan-6-yl)-7,7-dimethyl-4-(5-methyl-1H-indazol-4-yl)-5,6,7,8-tetrahydro-3-quinolinecarbonitrile | Step 5: repalced by Step 4 from Method 2. | Step 3: tert-butyl 5-(fluoromethyl)-2,6-diazaspiro[3.4]octane-2-carboxylate (LabNetwork) |
| | 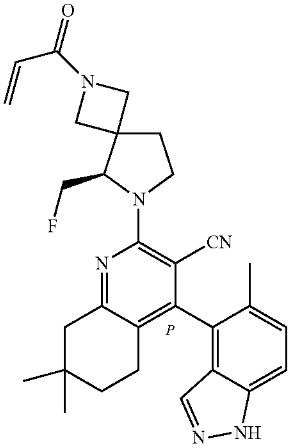 | | | |
| 13-81 | 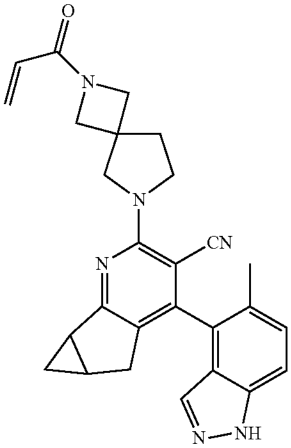 [SMILES: C=CC(=O)N1CC2(CCN(c3nc4c(c(-c5c(C)ccc6[nH]ncc56)c3C#N)CC3CC43)C2)C1] | (5aR,6aR)-4-(5-methyl-1H-indazol-4-yl)-2-(2-(2-propenoyl)-2,6-diazaspiro[3.4]octan-6-yl)-5,5a,6,6a-tetrahydrocyclopropa[4,5]cyclopenta[1,2-b]pyridine-3-carbonitrile\|(5aR,6aS)-4-(5-methyl-1H-indazol-4-yl)-2-(2-(2-propenoyl)-2,6-diazaspiro[3.4]octan-6-yl)-5,5a,6,6a-tetrahydrocyclopropa[4,5]cyclopenta[1,2-b]pyridine-3-carbonitrile\|(5aS,6aR)-4-(5-methyl-1H-indazol-4-yl)-2-(2-(2-propenoyl)-2,6-diazaspiro[3.4]octan-6-yl)-5,5a,6,6a-tetrahydrocyclopropa[4.5]cyclopenta[1,2-b]pyridine-3-carbonitrile\|(5aS,6aS)-4-(5-methyl-1H-indazol-4-yl)-2-(2-(2-propenoyl)-2,6-diazaspiro[3.4]octan-6-yl)-5,5a,6,6a-tetrahydrocyclopropa[4,5]cyclopenta[1,2-b]pyridine-3-carbonitrile | Step 1 performed using procedure from Example 13-12. Step 5: replaced by Step 4 from Method 2. | Step 1a: Intermediate 58 and step 1b: bicyclo[3.1.0]hexan-2-one (PharmaBlock) |

TABLE 5-continued

| Examples 13-2 to 13-157 were prepared following the procedure described in Method 13, steps 1-5, above as follows: | | | | |
|---|---|---|---|---|
| Ex.# | Chemical Structure | Name | Method changes | Reagent |
| 13-82 | 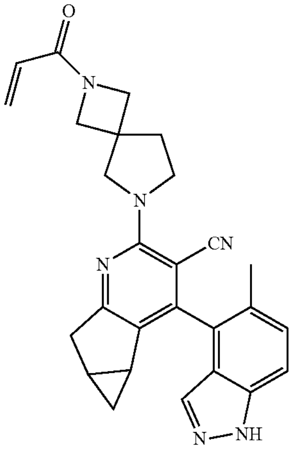 [SMILES: C=CC(=O)N1CC2(CCN(c3nc4c(c(-c5c(C)ccc6[nH]ncc56)c3C#N)C3CC3C4)C2)C1] | (4bR,5aR)-4-(5-methyl-1H-indazol-4-yl)-2-(2-(2-propenoyl)-2,6-diazaspiro[3.4]octan-6-yl)-4b,5,5a,6-tetrahydrocyclopropa[3,4]cyclopenta[1,2-b]pyridine-3-carbonitrile\|(4bR,5aS)-4-(5-methyl-1H-indazol-4-yl)-2-(2-(2-propenoyl)-2,6-diazaspiro[3.4]octan-6-yl)-4b,5,5a,6-tetrahydrocyclopropa[3,4]cyclopenta[1,2-b]pyridine-3-carbonitrile\|(4bS,5aR)-4-(5-methyl-1H-indazol-4-yl)-2-(2-(2-propenoyl)-2,6-diazaspiro[3.4]octan-6-yl)-4b,5,5a,6-tetrahydrocyclopropa[3,4]cyclopenta[1,2-b]pyridine-3-carbonitrile\|(4bS,5aS)-4-(5-methyl-1H-indazol-4-yl)-2-(2-(2-propenoyl)-2,6-diazaspiro[3.4]octan-6-yl)-4b,5,5a,6-tetrahydrocyclopropa[3,4]cyclopenta[1,2-b]pyridine-3-carbonitrile | Step 1 performed using procedure from Example 13-12. Step 5: replaced by Step 4 from Method 2. | Step 1a: Intermediate 58 and step 1b: bicyclo[3.1.0]hexan-3-one (Enamine) |
| 13-83 | 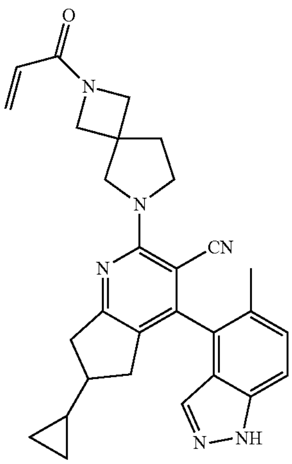 [SMILES: C=CC(=O)N1CC2(CCN(c3nc4c(c(-c5c(C)ccc6[nH]ncc56)c3C#N)CC(C3CC3)C4)C2)C1] | (6R)-6-cyclopropyl-4-(5-methyl-1H-indazol-4-yl)-2-(2-(2-propenoyl)-2,6-diazaspiro[3.4]octan-6-yl)-6,7-dihydro-5H-cyclopenta[b]pyridine-3-carbonitrile\|(6S)-6-cyclopropyl-4-(5-methyl-1H-indazol-4-yl)-2-(2-(2-propenoyl)-2,6-diazaspiro[3.4]octan-6-yl)-6,7-dihydro-5H-cyclopenta[b]pyridine-3-carbonitrile | Step 1 performed using procedure from Example 13-12. Step 5: replaced by Step 4 from Method 2. | Step 1a: Intermediate 58 and step 1b: 3-cyclopropylcyclopentan-1-one (Enamine) |

TABLE 5-continued

| Examples 13-2 to 13-157 were prepared following the procedure described in Method 13, steps 1-5, above as follows: | | | | |
|---|---|---|---|---|
| Ex.# | Chemical Structure | Name | Method changes | Reagent |
| 13-84 | 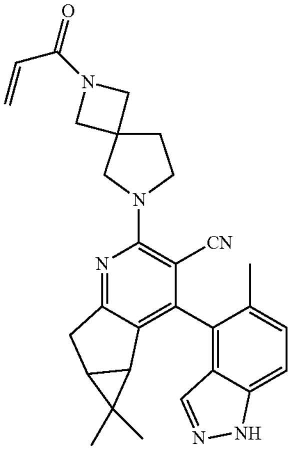 [SMILES: C=CC(=O)N1CC2(CCN(c3nc4c(c(-c5c(C)ccc6[nH]ncc56)c3C#N)C3C(C4)C3(C)C)C2)C1] | (4bR,5aR)-5,5-dimethyl-4-(5-methyl-1H-indazol-4-yl)-2-(2-(2-propenoyl)-2,6-diazaspiro[3.4]octan-6-yl)-4b,5,5a,6-tetrahydrocyclopropan[3,4]cyclopenta[1,2-b]pyridine-3-carbonitrile\|(4bR,5aS)-5,5-dimethyl-4-(5-methyl-1H-indazol-4-yl)-2-(2-(2-propenoyl)-2,6-diazaspiro[3.4]octan-6-yl)-4b,5,5a,6-tetrahydrocyclopropa[3,4]cyclopenta[1,2-b]pyridine-3-carbontrile\|(4bS,5aR)-5,5-dimethyl-4-(5-methyl-1H-indazol-4-yl)-2-(2-(2-propenoyl)-2,6-diazaspiro[3.4]octan-6-yl)-4b,5,5a,6-tetrahydrocyclopropan[3,4]cyclopenta[1,2-b]pyridine-3-carbonitrile\|(4bS,5aS)-5,5-dimethyl-4-(5-methyl-1H-indazol-4-yl)-2-(2-(2-propenoyl)-2,6-diazaspiro[3.4]octan-6-yl)-4b,5,5a,6-tetrahydrocyclopropa[3,4]cyclopenta[1,2-b]pyridine-3-carbonitrile | Step 1 performed using procedure from Example 13-12. Step 5: replaced by Step 4 from Method 2. | Step 1a: Intermediate 58 and step 1b: 6,6-dimethylbicyclo[3.1.0]hexan-3-one (Enamine) |
| 13-85 | 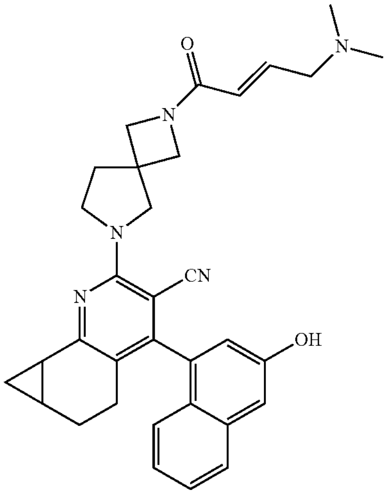 [SMILES: CN(C)C/C=C/C(=O)N1CC2(CCN(c3nc4c(c(-c5cc(O)cc6ccccc56)c3C#N)CCC3CC43)C2)C1] | (6aR,7aS)-2-(2-((2E)-4-(dimethylamino)-2-butenoyl)-2,6-diazaspiro[3.4]octan-6-yl)-4-(3-hydroxy-1-naphthalenyl)-6,6a,7,7a-tetrahydro-5H-cyclopropa[h]quinoline-3-carbontirile\|(6aS,7aR)-2-(2-((2E)-4-(dimethylamino)-2-butenoyl)-2,6-diazaspiro[3.4]octan-6-yl)-4-(3-hydroxy-1-naphthalenyl)-6,6a,7,7a-tetrahydro-5H-cyclopropa[h]quinoline-3-carbonitrile | Step 1 performed using procedure from Example 13-12. | Step 1a: Intermediate 62 and step 1b: bicyclo[4.1.0]heptan-2-one (PharmaBlock). Step 5: (E)-4-(dimethylamino)but-2-enoic acid hydrochloride (Oakwood Products, Inc.) |

TABLE 5-continued

Examples 13-2 to 13-157 were prepared following the procedure described in Method 13, steps 1-5, above as follows:

| Ex.# | Chemical Structure | Name | Method changes | Reagent |
|---|---|---|---|---|
| 13-86 | 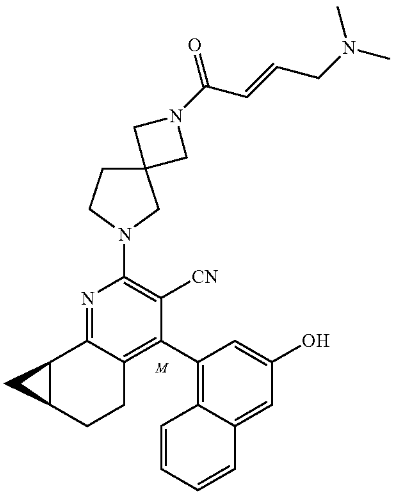 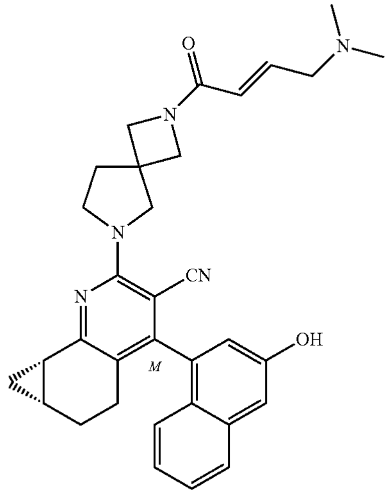 | (M)-(6aR,7aS)-2-(2-((2E)-4-(dimethylamino)-2-butenoyl)-2,6-diazaspiro[3.4]octan-6-yl)-4-(3-hydroxy-1-naphthalenyl)-6,6a,7,7a-tetrahydro-5H-cyclopropa[h]quinoline-3-carbonitrile and (M)-(6aS,7aR)-2-(2-((E)-4-(dimethylamino)but-2-enoyl)-2,6-diazaspiro[3.4]octan-6-yl)-4-(3-hydroxynaphthalen-1-yl)-6,6a,7,7a-tetrahydro-5H-cyclopropan[h]quinoline-3-carbonitrile (1st and 2nd eluting isomer) | Step 1 performed using procedure from Example 13-12. See stereoisomer separation conditions below. | Step 1a: Intermediate 62 and step 1b: bicyclo[4.1.0]heptan-2-one (PharmaBlock). Step 5: (E)-4-(dimethylamino)but-2-enoic acid hydrochloride (Oakwood Products, Inc.) |
| 13-87 | 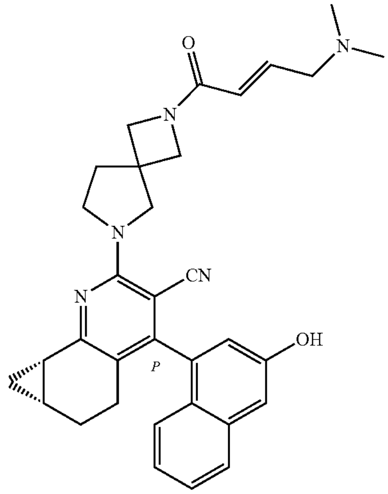 | (P)-(6aR,7aS)-2-(2-((2E)-4-(dimethylamino)-2-butenoyl)-2,6-diazaspiro[3.4]octan-6-yl)-4-(3-hydroxy-1-naphthalenyl)-6,6a,7,7a-tetrahydro-5H-cyclopropa[h]quinoline-3-carbonitrile (3rd eluting isomer) | Step 1 peformed using procedure from Example 13-12. See stereoisomer separation conditions below. | Step 1a: Intermediate 62 and step 1b: bicyclo[4.1.0]heptan-2-one (PharmaBlock). Step 5: (E)-4-(dimethylamino)but-2-enoic acid hydrochloride (Oakwood Products, Inc.) |

TABLE 5-continued

Examples 13-2 to 13-157 were prepared following the procedure described in Method 13, steps 1-5, above as follows:

| Ex.# | Chemical Structure | Name | Method changes | Reagent |
|---|---|---|---|---|
| 13-88 | 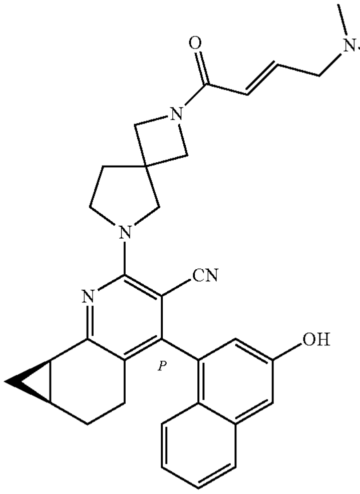 | (P)-(6aS,7aR)-2-(2-((2E)-4-(dimethylamino)-2-butenoyl)-2,6-diazaspiro[3.4]octan-6-yl)-4-(3-hydroxy-1-naphthalenyl)-6,6a,7,7a-tetrahydro-5H-cyclopropa[h]quinoline-3-carbonitrile (4th eluting isomer) | Step 1 performed using procedure from Example 13-12. See stereoisomer separation conditions below. | Step 1a: Intermediate 62 and step 1b: bicyclo[4.1.0]hep-tan-2-one (PharmaBlock). Step 5: (E)-4-(dimethylamino)but-2-enoic acid hydrochloride (Oakwood Products, Inc.) |
| 13-89 | 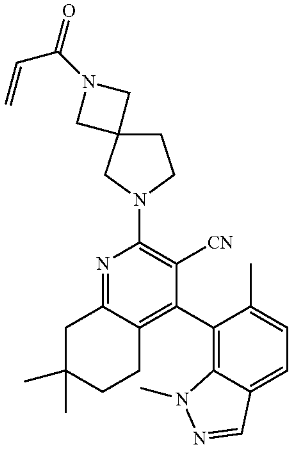 [SMILES: C=CC(=O)N1CC2(CCN(c3nc4c(c(-c5c(C)ccc6cnn(C)c56)c3C#N)CCC(C)(C)C4)C2)C1] | 7,7-dimethyl-2-(2-(2-propenoyl)-2,6-diazaspiro[3.4]octan-6-yl)-4-(1,5,6-trimethyl-1H-indazol-7-yl)-5,6,7,8-tetrahydro-3-quinolinecarbonitrile | Step 1 performed using procedure from Example 13-12. See additional oxidation after step 1 used in Example 33-1, step 4. Step 4: replaced by Step 4 from Method 2. | Step 1a: Intermediate 59 and step 1b: 3,3-dimethylcyclohexa-none (Bide (Pharmatech) |
| 13-90 | 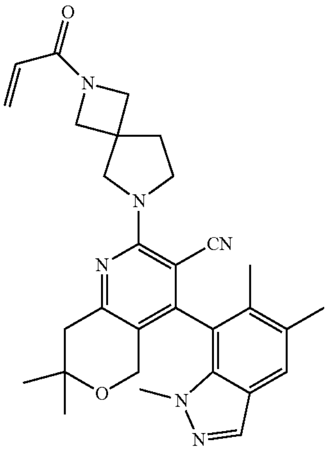 [SMILES: C=CC(=O)N1CC2(CCN(c3nc4c(c(-c5c(C)c(C)cc6cnn(C)c56)c3C#N)COC(C)(C)C4)C2)C1] | 7,7-dimethyl-2-(2-(2-propenoyl)-2,6-diazaspiro[3.4]octan-6-yl)-4-(1,5,6-trimethyl-1H-indazol-7-yl)-7,8-dihydro-5H-pyrano[4,3-b]pyridine-3-carbonitrile | Step 1 performed using procedure from Example 13-12. Step 5: replaced by Step 4 from Method 2. | Step 1a: Intermediate 124 and step 1b: 2,2-dimethyloxan-4-one (PharmaBlock.) |

TABLE 5-continued

Examples 13-2 to 13-157 were prepared following the procedure described in Method 13, steps 1-5, above as follows:

| Ex.# | Chemical Structure | Name | Method changes | Reagent |
|---|---|---|---|---|
| 13-91 | 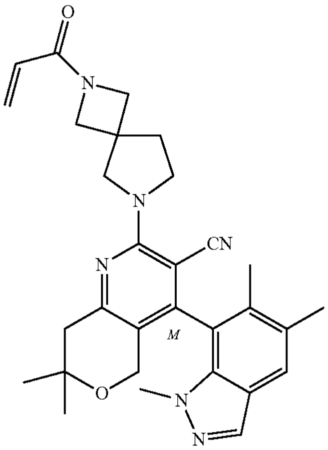 | (M)-7,7-dimethyl-2-(2-(2-propenoyl)-2,6-diazaspiro[3.4]octan-6-yl)-4-(1,5,6-trimethyl-1H-indazol-7-yl)-7,8-dihydro-5H-pyrano[4,3-b]pyridine-3-carbonitrile (1st eluting isomer) | Step 1 performed using procedure from Example 13-12. Step 5: replaced by Step 4 from Method 2. See stereoisomer separation conditions below. | Step 1a: Intermediate 124 and step 1b: 2,2-dimethyloxan-4-one (PharmaBlock.) |
| 13-92 | 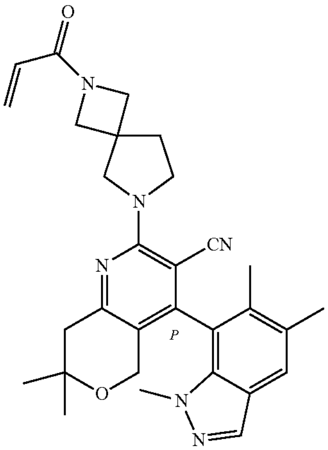 | (P)-7,7-dimethyl-2-(2-(2-propenoyl)-2,6-diazaspiro[3.4]octan-6-yl)-4-(1,5,6-trimethyl-1H-indazol-7-yl)-7,8-dihydro-5H-pyrano[4,3-b]pyridine-3-carbonitrile (2nd eluting isomer) | Step 1 performed using procedure from Example 13-12. Step 5: replaced by Step 4 from Method 2. See stereoisomer separation conditions below. | Step 1a: Intermediate 124 and step 1b: 2,2-dimethyloxan-4-one (PharmaBlock.) |

TABLE 5-continued

Examples 13-2 to 13-157 were prepared following the procedure described in Method 13, steps 1-5, above as follows:

| Ex.# | Chemical Structure | Name | Method changes | Reagent |
|---|---|---|---|---|
| 13-93 | 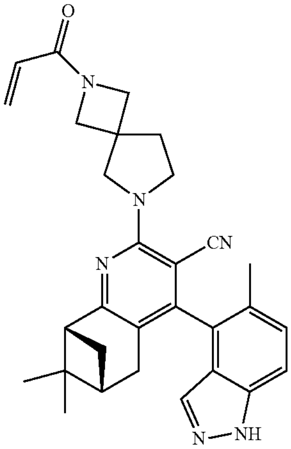 [SMILES: C=CC(=O)N1CC2(CCN(c3nc4c(c(-c5c(C)ccc6[nH]ncc56)c3C#N)C[C@H]3C[C@@H]4C3(C)C)C2)C1] | (6R,8R)-2-(2-acryloyl-2,6-diazaspiro[3.4]octan-6-yl)-7,7-dimethyl-4-(5-methyl-1H-indazol-4-yl)-5,6,7,8-tetrahydro-6,8-methanoquinoline-3-carbonitrile | Step 5: replaced by Step 4 from Method 2. | Step 1: (1R)-(+)-nopinone (Aldrich) |
| 13-94 | 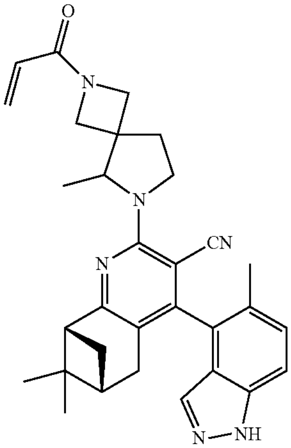 [SMILES: C=CC(=O)N1CC2(CCN(c3nc4c(c(-c5c(C)ccc6[nH]ncc56)c3C#N)C[C@H]3C[C@@H]4C3(C)C)C2C)C1] | (1R,9R)-10,10-dimethyl-6-(5-methyl-1H-indazol-4-yl)-4-((5R)-5-methyl-2-(2-propenoyl)-2,6-diazaspior[3.4]octan-6-yl)-3-azatricyclo[7.1.1.0$^{2,7}$]undeca-2,4,6-triene-5-carbonitrile\|(1R,9R)-10,10-dimethyl-6-(5-methyl-1H-indazol-4-yl)-4-((5S)-5-methyl-2-(2-propenoyl)-2,6-diazaspiro[3.4]octan-6-yl)-3-azatricyclo[7.1.1.0$^{2,7}$]undeca-2,4,6-triene-5-carbonitrile | Step 5: replaced by Step 4 from Method 2. | Step 1: (1R)-(+)-nopinone (Aldrich). Step 3: with tert-butyl 5-methyl-2,6-diazaspiro[3.4]octane-2-carboxylate (Enamine). |
| 13-95 | 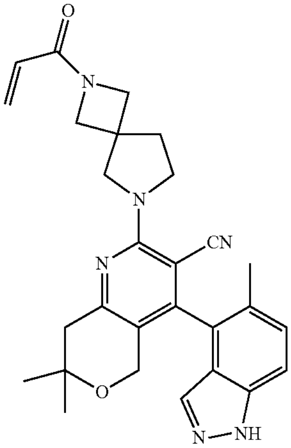 [SMILES: C=CC(=O)N1CC2(CCN(c3nc4c(c(-c5c(C)ccc6[nH]ncc56)c3C#N)COC(C)(C)C4)C2)C1] | 2-(2-acryloyl-2,6-diazaspiro[3.4]octan-6-yl)-7,7-dimethyl-4-(5-methyl-1H-indazol-4-yl)-7,8-dihydro-5H-pyrano[4,3-b]pyridine-3-carbonitrile | Step 5: replaced by Step 4 from Method 2. | Step 1: 2,2-dimethyl-tetrahydro-pyran-4-one (J & W Pharmalab, LLC) |

TABLE 5-continued

| Examples 13-2 to 13-157 were prepared following the procedure described in Method 13, steps 1-5, above as follows: | | | | |
|---|---|---|---|---|
| Ex.# | Chemical Structure | Name | Method changes | Reagent |
| 13-96 | 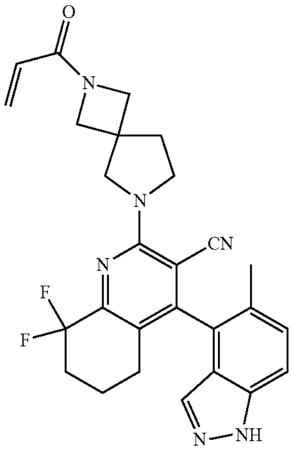 [SMILES: C=CC(=O)N1CC2(CCN(c3nc4c(c(-c5c(C)ccc6[nH]ncc56)c3C#N)CCCC4(F)F)C2)C1] | 2-(2-acryloyl-2,6-diazaspiro[3.4]octan-6-yl)-8,8-difluoro-4-(5-methyl-1H-indazol-4-yl)-5,6,7,8-tetrahydroquinoline-3-carbonitrile | Step 5: replaced by Step 4 from Method 2. | Step 1: 1,1-difluoro-2-oxocyclohexane (Enamine) |
| 13-97 | 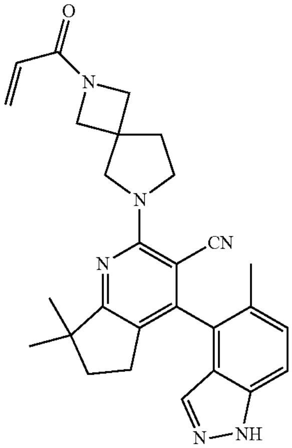 [SMILES: C=CC(=O)N1CC2(CCN(c3nc4c(c(-c5c(C)ccc6[nH]ncc56)c3C#N)CCC4(C)C)C2)C1] | 2-(2-acryloyl-2,6-diazaspiro[3.4]octan-6-yl)-7,7-dimethyl-4-(5-methyl-1H-indazol-4-yl)-6,7-dihydro-5H-cyclopenta[b]pyridine-3-carbonitrile | See below for alternative step 1 for Example 13-97. Step 5: replaced by Step 4 from Method 2. | Step 1a: 2,2-dimethyl-cyclopentan-1-one (Sigma-Aldrich) |
| 13-98 | 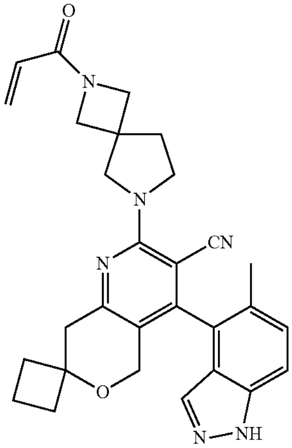 [SMILES: C=CC(=O)N1CC2(CCN(c3nc4c(c(-c5c(C)ccc6[nH]ncc56)c3C#N)COC3(CCC3)C4)C2)C1] | 2'-(2-acryloyl-2,6-diazaspiro[3.4]octan-6-yl)-4'-(5-methyl-1H-indazol-4-yl)-5',8'-dihydrospiro[cyclobutane-1,7'-pyrano[4,3-b]pyridine]-3'-carbonitrile | See below for alternative step 1 for Example 13-97. Step 5: replaced by Step 4 from Method 2. | Step 1a: 5-oxaspiro[3.5]nonan-8-one (PharmaBlock). |

TABLE 5-continued

| Ex.# | Chemical Structure | Name | Method changes | Reagent |
|---|---|---|---|---|
| | Examples 13-2 to 13-157 were prepared following the procedure described in Method 13, steps 1-5, above as follows: | | | |
| 13-99 | 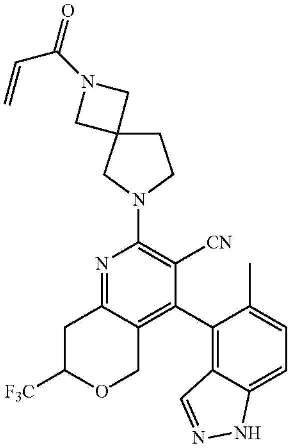 [SMILES: C=CC(=O)N1CC2(CCN(c3nc4c(c(-c5c(C)ccc6[nH]ncc56)c3C#N)COC(C(F)(F)F)C4)C2)C1] | 4-(5-methyl-1H-indazol-4-yl)-2-(2,6-diazaspiro[3.4]octan-6-yl)-7-(trifluoromethyl)-7,8-dihydro-5H-pyrano[4,3-b]pyridine-3-carbonitrile | See below for alternative step 1 for Example 13-97. Step 1b: Used 10 eq. $NH_4OAc$. Step 5: replaced by Step 4 from Method 2. | Step 1a: 2-(trifluoromethyl) tetrahydro-4H-pyran-4-one (Enamine) |
| 13-100 | 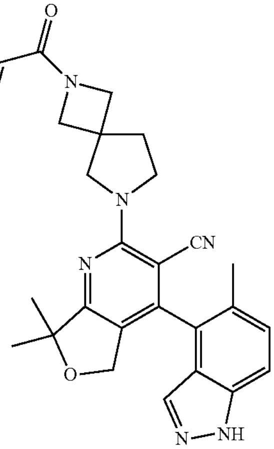 | 2-(2-acryloyl-2,6-diazaspiro[3.4]octan-6-yl)-7,7-dimethyl-4-(5-methyl-1H-indazol-4-yl)-5,7-dihydrofuro[3,4-b]pyridine-3-carbonitrile | See below for alternative step 1 for Example 13-97. Step 5: replaced by Step 4 from Method 2. | Step 1a: 2,2-dimethyldihydro-furan-3(2H)-one (Combi-blocks) |
| 13-101 | 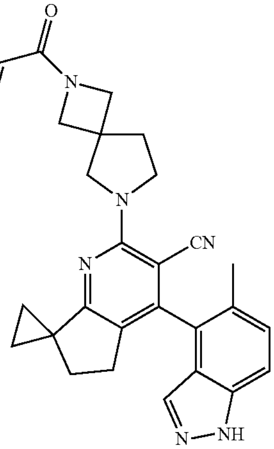 | 2-(2-acryloyl-2,6-diazaspiro[3.4]octan-6-yl)-4-(5-methyl-1H-indazol-4-yl)-5,6-dihydrospiro[cyclopenta[b]pyridine-7,1'-cyclopropane]-3-carbonitrile | See below for alternative step 1 for Example 13-97. Step 5: replaced by Step 4 from method 2. | Step 1a: spiro[2.4]heptan-4-one (Enamine) |

TABLE 5-continued

| Examples 13-2 to 13-157 were prepared following the procedure described in Method 13, steps 1-5, above as follows: | | | | |
|---|---|---|---|---|
| Ex.# | Chemical Structure | Name | Method changes | Reagent |
| 13-102 | 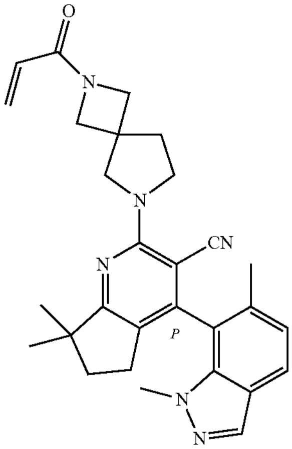 | (P)-2-(2-acryloyl-2,6-diazaspiro[3.4]octan-6-yl)-4-(1,6-dimethyl-1H-indazol-7-yl)-7,7-dimethyl-6,7-dihydro-5H-cyclopenta[b]pyridine-3-carbonitrile (1st eluting isomer) | Step 1 performed using procedure from Example 13-12. Step 5: replaced by Step 4 from Method 2. . See stereoisomer separation conditions below. | Step 1a: Intermediate 59 and 2,2-dimethyl-cyclopentan-1-one (Sigma-Aldrich) |
| 13-103 | 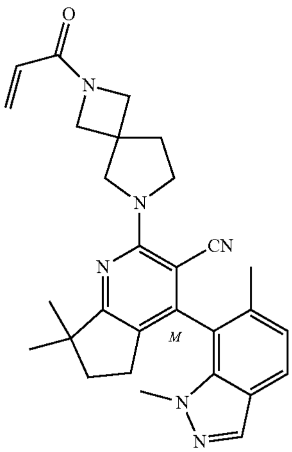 | (M)-2-(2-acryloyl-2,6-diazaspiro[3.4]octan-6-yl)-4-(1,6-dimethyl-1H-indazol-7-yl)-7,7-dimethyl-6,7-dihydro-5H-cyclopenta[b]pyridine-3-carbonitrile (2nd eluting isomer) | Step 1 performed using procedure from Example 13-12. Step 5: replaced by Step 4 from Method 2. . See stereoisomer separation conditions below. | Step 1a: Intermediate 59 and 2,2-dimethyl-cyclopentan-1-one (Sigma-Aldrich) |
| 13-104 | 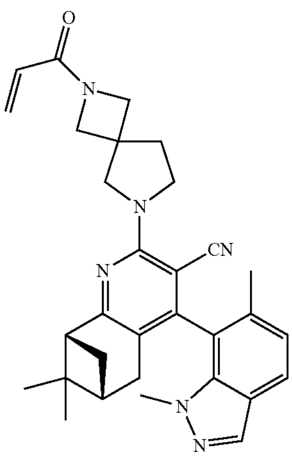 [SMILES: C=CC(=O)N1CC2(CCN(c3nc4c(c(-c5c(C)ccc6cnn(C)c56)c3C#N)C[C@H]3C[C@@H]4C3(C)C)C2)C1] | (1R,9R)-6-(1,6-dimethyl-1H-indazol-7-yl)-10,10-dimethyl-4-(2-(2-propenoyl)-2,6-diazaspiro[3.4]octan-6-yl)-3-azatricyclo[7.1.1.0$^{2,7}$]undeca-2,4,6-triene-5-carbonitrile | Step 1 performed using procedure from Example 13-12. Step 2: DIPEA replaced pyridine. Step 5: replaced by Step 4 from Method 2. | Step 1a: Intermediate 59 and (1R)-(+)-nopinone (Sigma-Aldrich) |

TABLE 5-continued

| Examples 13-2 to 13-157 were prepared following the procedure described in Method 13, steps 1-5, above as follows: | | | | |
|---|---|---|---|---|
| Ex.# | Chemical Structure | Name | Method changes | Reagent |
| 13-105 | 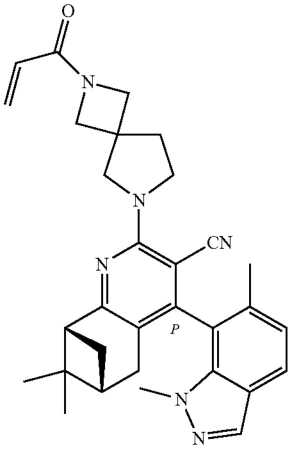 | (P)-(1R,9R)-6-(1,6-dimethyl-1H-indazol-7-yl)-10,10-dimethyl-4-(2-(2-propenoyl)-2,6-diazaspiro[3.4]octan-6-yl)-3-azatricyclo[7.1.1.0$^{2,7}$]undeca-2,4,6-triene-5-carbonitrile (1$^{st}$ eluting isomer) | Step 1 performed using procedure from Example 13-12. Step 2: DIPEA replaced pyridine. Step 5: replaced by Step 4 from Method 2. See stereoisomer separation conditions below. | Step 1a: Intermeidate 59 and step 1b: (1R)-(+)-nopinone (Sigma-Aldrich) |
| 13-106 | 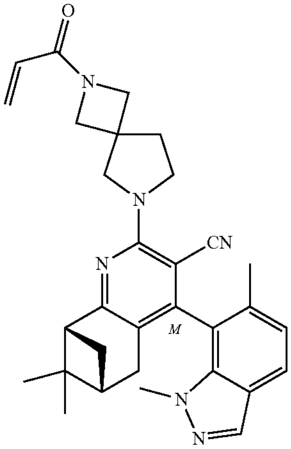 | (M)-(1R,9R)-6-(1,6-dimethyl-1H-indazol-7-yl)-10,10-dimethyl-4-(2-(2-propenoyl)-2,6-diazaspiro[3.4]octan-6-yl)-3-azatricyclo[7.1.1.0$^{2,7}$]undeca-2,4,6-triene-5-carbonitrile (2$^{nd}$ eluting isomer) | Step 1 performed using procedure from Example 13-12. Step 2: DIPEA replaced pyridine. Step 5: replaced by Step 4 from Method 2. See stereoisomer separation conditions below. | Step 1a: Intermeidate 59 and step 1b: (1R)-(+)-nopinone (Sigma-Aldrich) |
| 13-107 | 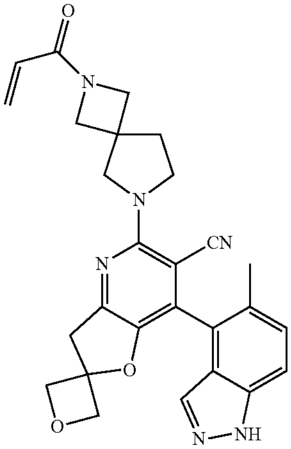 [SMILES: C=CC(=O)N1CC2(CCN(c3nc4c(c(-c5c(C)ccc6[nH]ncc56)c3C#N)OC3(COC3)C4)C2)C1] | 7-(5-methyl-1H-indazol-4-yl)-5-(2-(2-propenoyl)-2,6-diazaspiro[3.4]octan-6-yl)-3H-spiro[furo[3,2-b]pyridin-2,3'-oxetane]-6-carbonitrile | Step 1 performed using procedure from Example 13-12. Step 2: DIPEA replaced pyridine. Step 5: replaced by Step 4 from Method 2. | Step 1a: 2,5-dioxaspiro[3.4]octan-7-one (PharmaBlock) |

TABLE 5-continued

Examples 13-2 to 13-157 were prepared following the procedure described in Method 13, steps 1-5, above as follows:

| Ex.# | Chemical Structure | Name | Method changes | Reagent |
|---|---|---|---|---|
| 13-108 | 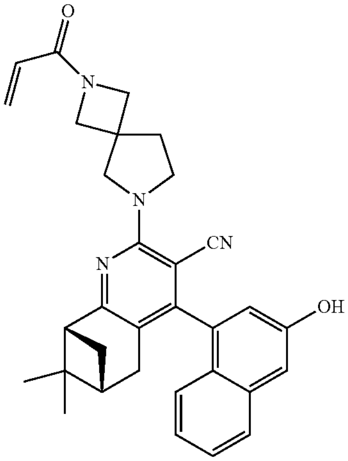 [SMILES: C=CC(=O)N1CC2(CCN(c3nc4c(c(-c5cc(O)cc6ccccc56)c3C#N)C[C@H]3C[C@@H]4C3(C)C)C2)C1] | (1R,9R)-6-(3-hydroxy-1-naphthalenyl)-10,10-dimethyl-4-(2-(2-propenoyl)-2,6-diazaspiro[3.4]octan-6-yl)-3-azatricyclo[7.1.1.0$^{2,7}$]undeca-2,4,6-triene-5-carbonitrile | Step 1 performed using procedure from Example 13-12. Step 2: DIPEA replaced pyridine. Step 5: replaced by Step 4 from Method 2. | Step 1a: Intermediate 62 and step 1b: (1R)-(+)-nopinone (Sigma Aldrich) |
| 13-109 | 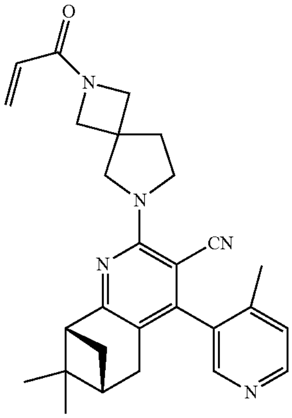 [SMILES: C=CC(=O)N1CC2(CCN(c3nc4c(c(-c5cnccc5C)c3C#N)C[C@H]3C[C@@H]4C3(C)C)C2)C1] | (1R,9R)-10,10-dimethyl-6-(4-methyl-3-pyridinyl)-4-(2-(2-propenoyl)-2,6-diazaspiro[3.4]octan-6-yl)-3-azatricyclo[7.1.1.0$^{2,7}$]undeca-2,4,6-triene-5-carbonitrile | Step 1 performed using procedure from Example 13-12. Step 2: DIPEA replaced pyridine. Step 5: replaced by Step 4 from Method 2. | Step 1a: 4-methylnicotinaldehyde (Combi-Blocks) and step 1b: (1R)-(+)-nopinone (Sigma-Aldrich) |
| 13-110 | 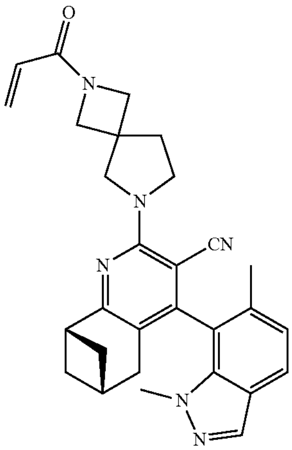 [SMILES: C=CC(=O)N1CC2(CCN(c3nc4c(c(-c5c(C)ccc6cnn(C)c56)c3C#N)C[C@H]3C[C@@H]4C3)C2)C1] | (1S,9S)-6-(1,6-dimethyl-1H-indazol-7-yl)-4-(2-(2-propenoyl)-2,6-diazaspiro[3.4]octan-6-yl)-3-azatricyclo[7.1.1.0$^{2,7}$]undeca-2,4,6-triene-5-carbonitrile | Step 1 performed using procedure from Example 13-12. Step 2: DIPEA replaced pyridine. Step 5: replaced by Step 4 from Method 2. | Step 1a: Intermediate 59 and step 1b: bicyclo[3.1.1]heptan-2-one (Enamine) |

TABLE 5-continued

| Examples 13-2 to 13-157 were prepared following the procedure described in Method 13, steps 1-5, above as follows: | | | | |
|---|---|---|---|---|
| Ex.# | Chemical Structure | Name | Method changes | Reagent |
| 13-111 | 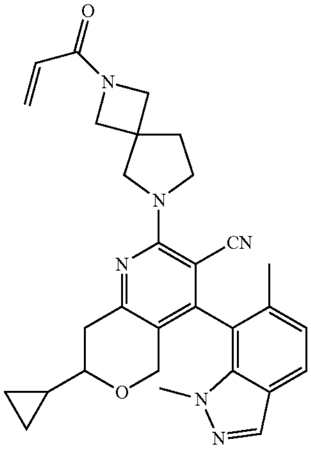 [SMILES: C=CC(=O)N1CC2(CCN(c3nc4c(c(-c5c(C)ccc6cnn(C)c56)c3C#N)COC(C3CC3)C4)C2)C1] | (7R)-7-cyclopropyl-4-(1,6-dimethyl-1H-indazol-7-yl)-2-(2-(2-propenoyl)-2,6-diazaspiro[3.4]octan-6-yl)-7,8-dihydro-5H-pyrano[4,3-b]pyridine-3-carbonitrile\|(7S)-7-cyclopropyl-4-(1,6-dimethyl-1H-indazol-7-yl)-2-(2-(2-propenoyl)-2,6-diazaspiro[3.4]octan-6-yl)-7,8-dihydro-5H-pyrano[4,3-b]pyridine-3-carbonitrile | Step 1 performed using procedure from Example 13-12. Step 2: DIPEA replaced pyridine. Step 5: replaced by Step 4 from Method 2. | Step 1a: Intermediate 59 and step 1b: 2-cyclopropyltetrahydro-4H-pyran-4-one (Abovchem) |
| 13-112 | 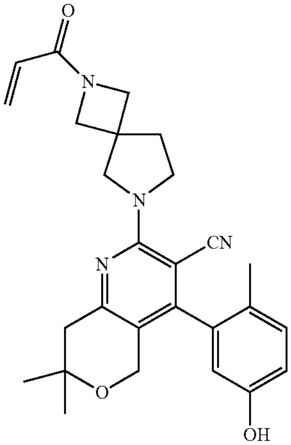 [SMILES: C=CC(=O)N1CC2(CCN(c3nc4c(c(-c5cc(O)ccc5C)c3C#N)COC(C)(C)C4)C2)C1] | 4-(5-hydroxy-2-methylphenyl)-7,7-dimethyl-2-(2-(2-propenoyl)-2,6-diazaspiro[3.4]octan-6-yl)-7,8-dihydro-5H-pyrano[4,3-b]pyridine-3-carbonitrile | Step 1 performed using procedure from Example 13-12. Step 2: DIPEA replaced pyridine. Step 5: replaced by Step 4 from Method 2. | Step 1a: Intermediate 88 and step 1b: 2,2-dimethyltetrahydro-4H-pyran-4-one (PharmaBlock) |
| 13-113 | 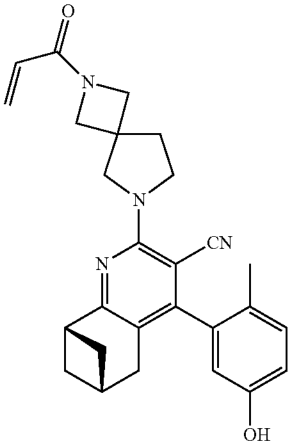 [SMILES: C=CC(=O)N1CC2(CCN(c3nc4c(c(-c5cc(O)ccc5C)c3C#N)C[C@H]3C[C@@H]4C3)C2)C1] | (1S,9S)-6-(5-hydroxy-2-methylphenyl)-4-(2-(2-propenoyl)-2,6-diazaspiro[3.4]octan-6-yl)-3-azatricyclo[7.1.1.0$^{2,7}$]undeca-2,4,6-triene-5-carbonitrile | Step 1 performed using procedure from Example 13-12. Step 2: DIPEA replaced pyridine. Step 5: replaced by Step 4 from Method 2. | Step 1a: Intermediate 88 and step 1b: bicyclo[3.1.1]heptan-2-one (Enamine) |

TABLE 5-continued

| Examples 13-2 to 13-157 were prepared following the procedure described in Method 13, steps 1-5, above as follows: | | | | |
|---|---|---|---|---|
| Ex.# | Chemical Structure | Name | Method changes | Reagent |
| 13-114 | 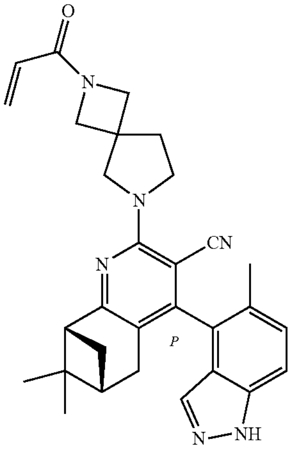 | (P)-(1R,9R)-10,10-dimethyl-6-(5-methyl-1H-indazol-4-yl)-4-(2-(2-propenoyl)-2,6-diazaspiro[3.4]octan-6-yl)-3-azatricyclo[7.1.1.0$^{2,7}$]undeca-2,4,6-triene-5-carbonitrile (1$^{st}$ eluting isomer) | Step 5: replaced by Step 4 from Method 2. See stereoisomer separation conditions below. | Step 1: (1R)-(+)-nopinone (Aldrich) |
| 13-115 | 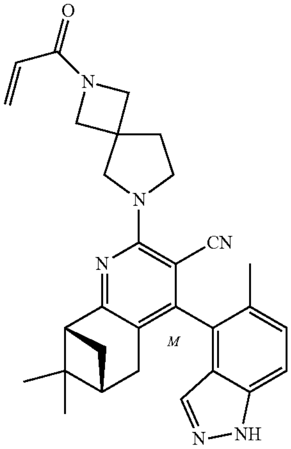 | (M)-(1R,9R)-10,10-dimethyl-6-(5-methyl-1H-indazol-4-yl)-4-(2-(2-propenoyl)-2,6-diazaspiro[3.4]octan-6-yl)-3-azatricyclo[7.1.1.0$^{2,7}$]undeca-2,4,6-triene-5-carbonitrile (2$^{nd}$ eluting isomer) | Step 5: replaced by Step 4 from Method 2. See stereoisomer separation conditions below. | Step 1: (1R)-(+)-nopinone (Aldrich) |
| 13-116 | 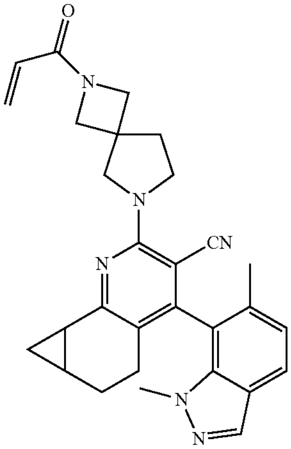 [SMILES: C=CC(=O)N1CC2(CCN(c3nc4c(c(-c5c(C)ccc6cnn(C)c56)c3C#N)CCC3CC43)C2)C1] | (6aR,7aS)-4-(1,6-dimethyl-1H-indazol-7-yl)-2-(2-(2-propenoyl)-2,6-diazaspiro[3.4]octan-6-yl)-6,6a,7,7a-tetrahydro-5H-cyclopropa[h]quinoline-3-carbonitrile\|(6aS,7aR)-4-(1,6-dimethyl-1H-indazol-7-yl)-2-(2-(2-propenoyl)-2,6-diazaspiro[3.4]octan-6-yl)-6,6a,7,7a-tetrahydro-5H-cyclopropa[h]quinoline-3-carbonitrile | Step 1 performed using procedure from Example 13-12. Step 2: DIPEA replaced pyridine. Step 5: replaced by Step 4 from Method 2. | Step 1a: Intermediate 59 and step 1b: bicyclo[4.1.0]heptan-2-one (PharmaBlock). |

TABLE 5-continued

Examples 13-2 to 13-157 were prepared following the procedure described in Method 13, steps 1-5, above as follows:

| Ex.# | Chemical Structure | Name | Method changes | Reagent |
|---|---|---|---|---|
| 13-117 | 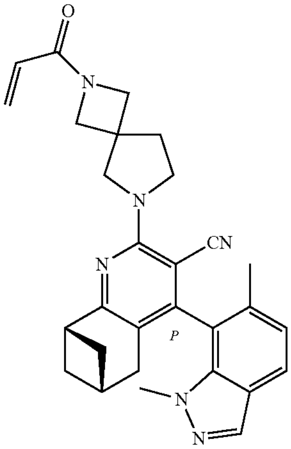 | (P)-(1S,9S)-6-(1,6-dimethyl-1H-indazol-7-yl)-4-(2-(2-propenoyl)-2,6-diazaspiro[3.4]octan-6-yl)-3-azatricyclo[7.1.1.0$^{2,7}$]undeca-2,4,6-triene-5-carbonitrile (1$^{st}$ eluting isomer) | Step 1 performed using procedure from Example 13-12. Step 2: DIPEA replaced pyridine. Step 5: replaced by Step 4 from Method 2. See stereoisomer separation conditions below. | Step 1a: Intermediate 59 and step 1b: bicyclo[3.1.1]heptan-2-one (Enamine) |
| 13-118 | 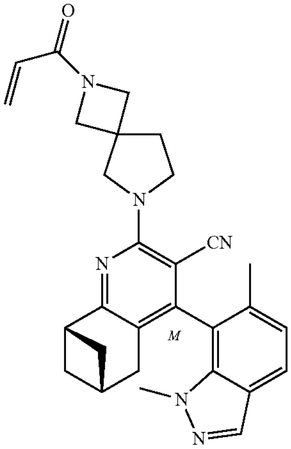 | (M)-(1S,9S)-6-(1,6-dimethyl-1H-indazol-7-yl)-4-(2-(2-propenoyl)-2,6-diazaspiro[3.4]octan-6-yl)-3-azatricyclo[7.1.1.0$^{2,7}$]undeca-2,4,6-triene-5-carbonitrile (2$^{nd}$ eluting isomer) | Step 1 performed using procedure from Example 13-12. Step 2: DIPEA replaced pyridine. Step 5: replaced by Step 4 from Method 2. See stereoisomer separation conditions below. | Step 1a: Intermediate 59 and step 1b: bicyclo[3.1.1]heptan-2-one (Enamine) |
| 13-119 | 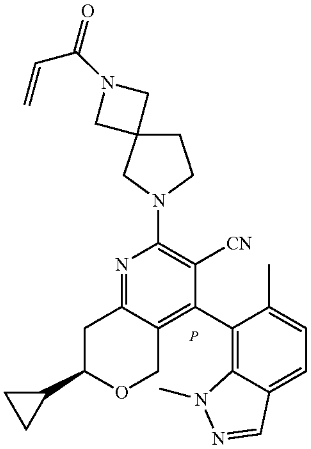 | (P)-(7R)-7-cyclopropyl-4-(1,6-dimethyl-1H-indazol-7-yl)-2-(2-(2-propenoyl)-2,6-diazaspiro[3.4]octan-6-yl)-7,8-dihydro-5H-pyrano[4,3-b]pyridine-3-carbonitrile (1$^{st}$ eluting isomer) | Step 1 performed using procedure from Example 13-12. Step 2: DIPEA replaced pyridine. Step 5: replaced by Step 4 from Method 2. See stereoisomer separation conditions below. | Step 1a: Intermediate 59 and step 1b: 2-cyclopropyltetrahydro-4H-pyran-4-one (Abovchem) |

TABLE 5-continued

| Examples 13-2 to 13-157 were prepared following the procedure described in Method 13, steps 1-5, above as follows: | | | | |
|---|---|---|---|---|
| Ex.# | Chemical Structure | Name | Method changes | Reagent |
| 13-120 | 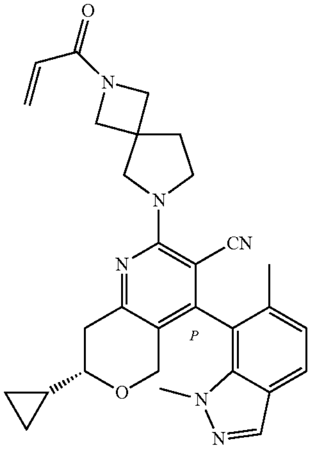 | (P)-(7S)-7-cyclopropyl-4-(1,6-dimethyl-1H-indazol-7-yl)-2-(2-(2-propenoyl)-2,6-diazaspiro[3.4]octan-6-yl)-7,8-dihydro-5H-pyrano[4,3-b]pyridine-3-carbonitrile (2nd eluting isomer) | Step 1 performed using procedure from Example 13-12. Step 2: DIPEA replaced pyridine. Step 5: replaced by Step 4 from Method 2. See stereoisomer separation conditions below. | Step 1a: Intermediate 59 and step 1b: 2-cyclopropyltetrahy-dro-4H-pyran-4-one (Abovchem) |
| 13-121 | 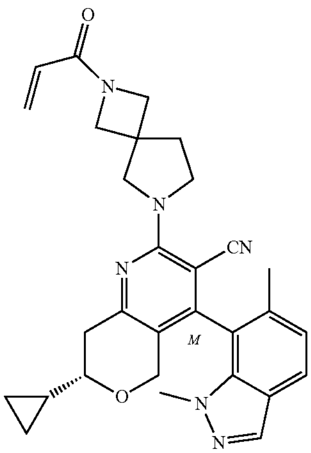 | (M)-7S)-7-cyclopropyl-4-(1,6-dimethyl-1H-indazol-7-yl)-2-(2-(2-propenoyl)-2,6-diazaspiro[3.4]octan-6-yl)-7,8-dihydro-5H-pyrano[4,3-b]pyridine-3-carbonitrile (3rd eluting isomer) | Step 1 performed using procedure from Example 13-12. Step 2: DIPEA replaced pyridine. Step 5: replaced by Step 4 from Method 2. See stereoisomer separation conditions below. | Step 1a: Intermediate 59 and step 1b: 2-cyclopropyltetrahy-dro-4H-pyran-4-one (Abovchem) |
| 13-122 | 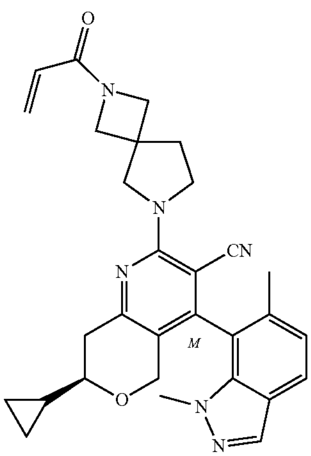 | (M)-(7R)-7-cyclopropyl-4-(1,6-dimethyl-1H-indazol-7-yl)-2-(2-(2-propenoyl)-2,6-diazaspiro[3.4]octan-6-yl)-7,8-dihydro-5H-pyrano[4,3-b]pyridine-3-carbonitrile (4th eluting isomer) | Step 1 performed using procedure from Example 13-12. Step 2: DIPEA replaced pyridine. Step 5: replaced by Step 4 form Method 2. See stereoisomer separation conditions below. | Step 1a: Intermediate: 59 and step 1b: 2-cyclopropyltetrahy-dro-4H-pyran-4-one (Abovchem) |

TABLE 5-continued

| Examples 13-2 to 13-157 were prepared following the procedure described in Method 13, steps 1-5, above as follows: | | | | |
|---|---|---|---|---|
| Ex.# | Chemical Structure | Name | Method changes | Reagent |
| 13-123 | 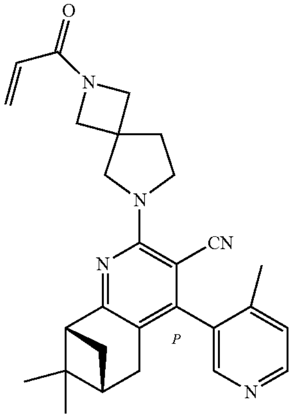 | (P)-(1R,9R)-10,10-dimethyl-6-(4-methyl-3-pyridinyl)-4-(2-(2-propenoyl)-2,6-diazaspiro[3.4]octan-6-yl)-3-azatricyclo[7.1.1.0$^{2,7}$]undeca-2,4,6-triene-5-carbonitrile (1$^{st}$ eluting isomer) | Step 1 performed using procedure from Example 13-12. Step 2: DIPEA replaced pyridine. Step 5: replaced by Step 4 from Method 2. See stereoisomer separation conditions below. | Step 1a: 4-methylnicotinaldehyde (Combi-Blocks) and step 1b: (1R)-(+)-nopinone (Aldrich) |
| 13-124 | 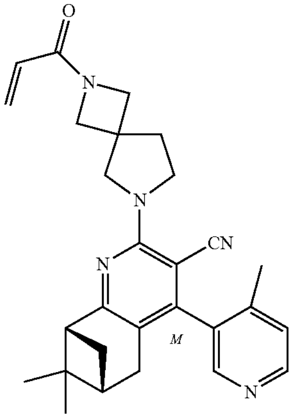 | (M)-(1R,9R)-10,10-dimethyl-6-(4-methyl-3-pyridinyl)-4-(2-(2-propenoyl)-2,6-diazaspiro[3.4]octan-6-yl)-3-azatricyclo[7.1.1.0$^{2,7}$]undeca-2,4,6-triene-5-carbonitrile (2$^{nd}$ eluting isomer) | Step 1 performed using procedure from Example 13-12. Step 2: DIPEA replaced pyridine. Step 5: replaced by Step 4 from Method 2. See stereoisomer separation conditions below. | Step 1a: 4-methylnicotinaldehyde (Combi-Blocks) and step 1b: (1R)-(+)-nopinone (Aldrich) |
| 13-125 | 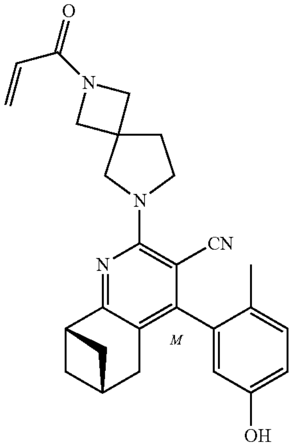 | (M)-(1S,9S)-6-(5-hydroxy-2-methylphenyl)-4-(2-(2-propenoyl)-2,6-diazaspiro[3.4]octan-6-yl)-3-azatricyclo[7.1.1.0$^{2,7}$]undeca-2,4,6-triene-5-carbonitrile (1$^{st}$ eluting isomer) | Step 1 performed using procedure from Example 13-12. Step 2: DIPEA replaced pyridine. Step 5: replaced by Step 4 from Method 2. See stereoisomer separation conditions below. | Step 1a: Intermediate 88 and step 1b: bicyclo[3.1.1]heptan-2-one (Enamine) |

TABLE 5-continued

Examples 13-2 to 13-157 were prepared following the procedure described in Method 13, steps 1-5, above as follows:

| Ex.# | Chemical Structure | Name | Method changes | Reagent |
|---|---|---|---|---|
| 13-126 | 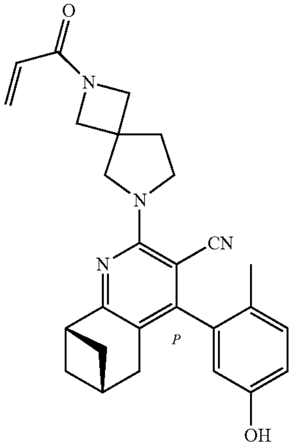 | (P)-(1S,9S)-6-(5-hydroxy-2-methylphenyl)-4-(2-(2-propenoyl)-2,6-diazaspiro[3.4]octan-6-yl)-3-azatricyclo[7.1.1.0$^{2,7}$]undeca-2,4,6-triene-5-carbonitrile (2$^{nd}$ eluting isomer) | Step 1 performed using procedure from Example 13-12. Step 2: DIPEA replaced pyridine. Step 5: replaced by Step 4 from Method 2. See stereoisomer separation conditions below. | Step 1a: Intermediate: 88 and step 1b: bicyclo[3.1.1]heptan-2-one (Enamine) |
| 13-127 | 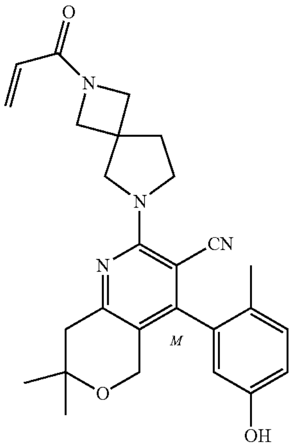 | (M)-4-(5-hydroxy-2-methylphenyl)-7,7-dimethyl-2-(2-(2-propenoyl)-2,6-diazaspiro[3.4]octan-6-yl)-7,8-dihydro-5H-pyrano[4,3-b]pyridine-3-carbonitrile (1$^{st}$ eluting isomer) | Step 1 performed using procedure from Example 13-12. Step 2: DIPEA replaced pyridine. Step 5: replaced by Step 4 from Method 2. See stereoisomer separation conditions below. | Step 1a: Intermediate 88 and step 1b: 2,2-dimethyltetrahydro-4H-pyran-4-one (PharmaBlock) |
| 13-128 | 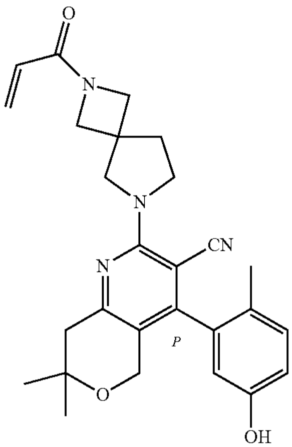 | (P)-4-(5-hydroxy-2-methylphenyl)-7,7-dimethyl-2-(2-(2-propenoyl)-2,6-diazaspiro[3.4]octan-6-yl)-7,8-dihydro-5H-pyrano[4,3-b]pyridine-3-carbonitrile (2$^{nd}$ eluting isomer) | Step 1 performed using procedure from Example 13-12. Step 2: DIPEA replaced pyridine. Step 5: replaced by Step 4 from Method 2. See stereoisomer separation conditions below. | Step 1a: Intermediate 88 and step 1b: 2,2-dimethyltetrahydro-4H-pyran-4-one (PharmaBlock) |

TABLE 5-continued

Examples 13-2 to 13-157 were prepared following the procedure described in Method 13, steps 1-5, above as follows:

| Ex.# | Chemical Structure | Name | Method changes | Reagent |
|---|---|---|---|---|
| 13-129 | 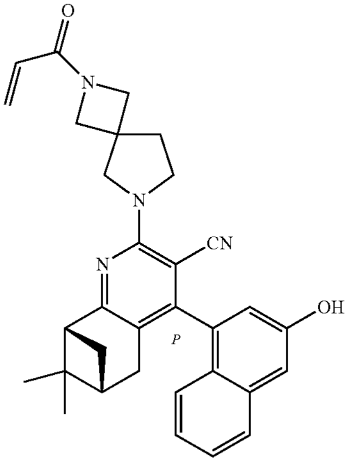 | (P)-(1R,9R)-6-(3-hydroxy-1-naphthalenyl)-10,10-dimethyl-4-(2-(2-propenoyl)-2,6-diazaspiro[3.4]octan-6-yl)-3-azatricyclo[7.1.1.0$^{2,7}$]undeca-2,4,6-triene-5-carbonitrile (1$^{st}$ eluting isomer) | Step 1 performed using procedure from Example 13-12. Step 2: DIPEA replaced pyridine. Step 5: replaced by Step 4 from Method 2. See stereoisomer separation conditions below. | Step 1a: Intermediate 62 and step 1b: (1R)-(+)-nopinone (Aldrich) |
| 13-130 | 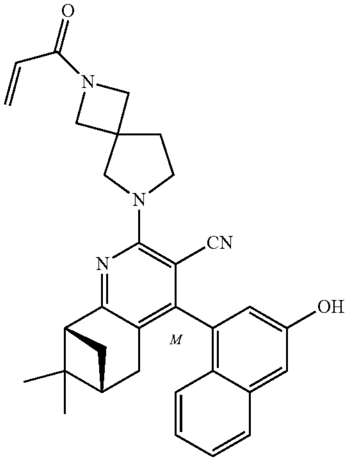 | (M)-(1R,9R)-6-(3-hydroxy-1-naphthalenyl)-10,10-dimethyl-4-(2-(2-propenoyl)-2,6-diazaspiro[3.4]octan-6-yl)-3-azatricyclo[7.1.1.0$^{2,7}$]undeca-2,4,6-triene-5-carbonitrile (2$^{nd}$ eluting isomer) | Step 1 performed using procedure from Example 13-12. Step 2: DIPEA replaced pyridine. Step 5: replaced by Step 4 from Method 2. See stereoisomer separation conditions below. | Step 1a: Intermediate 62 and step 1b: (1R)-(+)-nopinone (Aldrich) |
| 13-131 | 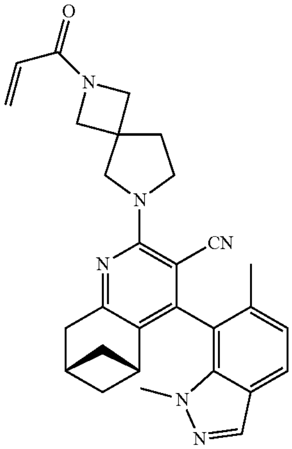 [SMILES: C=CC(=O)N1CC2(CCN(c3nc4c(c(-c5c(C)ccc6cnn(C)c56)c3C#N)[C@H]3C[C@@H](C4)C3)C2)C1] | (1S,9S)-3-(1,6-dimethyl-1H-indazol-7-yl)-5-(2-(2-propenoyl)-2,6-diazaspiro[3.4]octan-6-yl)-6-azatricyclo[7.1.1.0$^{2,7}$]undeca-2,4,6-triene-4-carbonitrile | Step 1 performed using procedure from Example 13-12. Step 2: DIPEA replaced pyridine. Step 5: replaced by Step 4 from Method 2. | Step 1a: Intermediate 59 and step 1b: bicyclo[3.1.1.]heptan-3-one (PharmaBlock) |

TABLE 5-continued

| Examples 13-2 to 13-157 were prepared following the procedure described in Method 13, steps 1-5, above as follows: | | | | |
|---|---|---|---|---|
| Ex.# | Chemical Structure | Name | Method changes | Reagent |
| 13-132 | 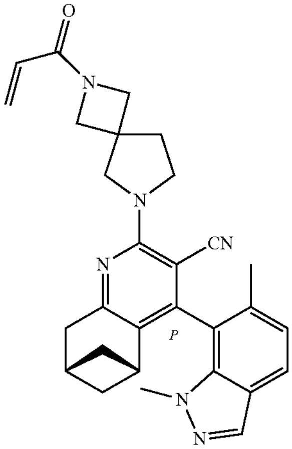 | (P)-(1S,9S)-3-(1,6-dimethyl-1H-indazol-7-yl)-5-(2-(2-propenoyl)-2,6-diazaspiro[3.4]octan-6-yl)-6-azatricyclo[7.1.1.0$^{2,7}$]undeca-2,4,6-triene-4-carbonitrile (1st eluting isomer) | Step 1 performed using procedure from Example 13-12. Step 2: DIPEA replaced pyridine. Step 5: replaced by Step 4 from Method 2. See stereoisomer separation conditions below. | Step 1a: Intermediate 59 and step 1b: bicyclo[3.1.1[hep-tan-3-one (PharmaBlock) |
| 13-133 | 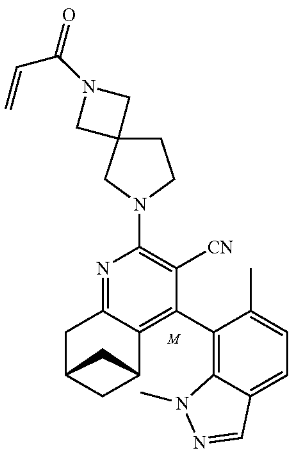 | (M)-(1S,9S)-3-(1,6-dimethyl-1H-indazol-7-yl)-5-(2-(2-propenoyl)-2,6-diazaspiro[3.4]octan-6-yl)-6-azatricyclo[7.1.1.0$^{2,7}$]undeca-2,4,6-triene-4-carbonitrile (2nd eluting isomer) | Step 1 performed using procedure from Example 13-12. Step 2: DIPEA replaced pyridine. Step 5: replaced by Step 4 from Method 2. See stereoisomer separation conditions below. | Step 1a: Intermediate 59 and step 1b: bicyclo[3.1.1[hep-tan-3-one (PharmaBlock) |
| 13-134 | 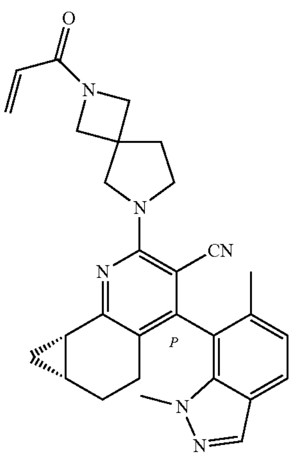 | (P)-(6aR,7aS)-4-(1,6-dimethyl-1H-indazol-7-yl)-2-(2-(2-propenoyl)-2,6-diazaspiro[3.4]octan-6-yl)-6,6a,7,7a-tetrahydro-5H-cyclopropa[h]quinoline-3-carbonitrile (1st eluting isomer) | Step 1 performed using procedure from Example 13-12. Step 2: DIPEA replaced pyridine. Step 5: replaced by Step 4 from Method 2. See stereoisomer separation conditions below. | Step 1a: Intermediate: 59 and step 1b: bicyclo[4.1.0]hep-tan-2-one (PharmaBlock). |

TABLE 5-continued

Examples 13-2 to 13-157 were prepared following the procedure described in Method 13, steps 1-5, above as follows:

| Ex.# | Chemical Structure | Name | Method changes | Reagent |
|---|---|---|---|---|
| 13-135 | 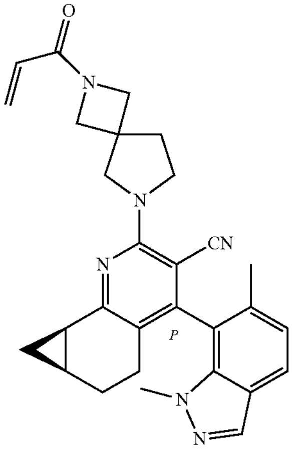 | (P)-(6aS,7aR)-4-(1,6-dimethyl-1H-indazol-7-yl)-2-(2-(2-propenoyl)-2,6-diazaspiro[3.4]octan-6-yl)-6,6a,7,7a-tetrahydro-5H-cyclopropa[h]quinoline-3-carbonitrile (2nd eluting isomer) | Step 1 performed using procedure from Example 13-12. Step 2: DIPEA replaced pyridine. Step 5: replaced by Step 4 from Method 2. See stereoisomer separation conditions below. | Step 1a: Intermediate 59 and step 1b: bicyclo[4.1.0]hep-tan-2-one (PharmaBlock). |
| 13-136 | 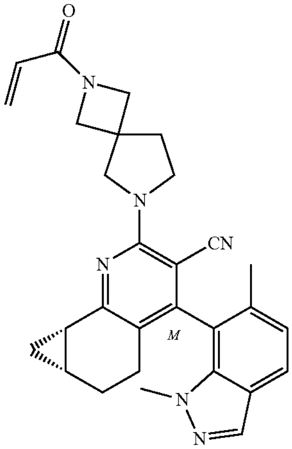 | (M)-(6aR,7aS)-4-(1,6-dimethyl-1H-indazol-7-yl)-2-(2-(2-propenoyl)-2,6-diazaspiro[3.4]octan-6-yl)-6,6a,7,7a-tetrahydro-5H-cyclopropa[h]quinoline-3-carbonitrile (3rd eluting isomer) | Step 1 performed using procedure from Example 13-12. Step 2: DIPEA replaced pyridine. Step 5: replaced by Step 4 from Method 2. See stereoisomer separation conditions below. | Step 1a: Intermediate 59 and step 1b: bicyclo[4.1.0]hep-tan-2-one (PharmaBlock). |
| 13-137 | 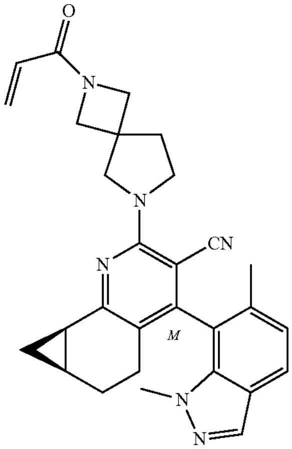 | (M)-(6aS,7aR)-4-(1,6-dimethyl-1H-indazol-7-yl)-2-(2-(2-propenoyl)-2,6-diazaspiro[3.4]octan-6-yl)-6,6a,7,7a-tetrahydro-5H-cyclopropa[h]quinoline-3-carbonitrile (4th eluting isomer) | Step 1 performed using procedure from Example 13-12. Step 2: DIPEA replaced pyridine. Step 5: replaced by Step 4 from Method 2. See stereoisomer separation conditions below. | Step 1a: Intermediate 59 and step 1b: bicyclo[4.1.0]hep-tan-2-one (PharmaBlock). |

TABLE 5-continued

Examples 13-2 to 13-157 were prepared following the procedure described in Method 13, steps 1-5, above as follows:

| Ex.# | Chemical Structure | Name | Method changes | Reagent |
|---|---|---|---|---|
| 13-138 | 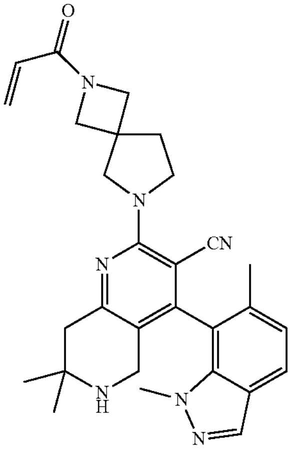 [SMILES: C=CC(=O)N1CC2(CCN(c3nc4c(c(-c5c(C)ccc6cnn(C)c56)c3C#N)CNC(C)(C)C4)C2)C1] | 4-(1,6-dimethyl-1H-indazol-7-yl)-7,7-dimethyl-2-(2-(2-propenoyl)-2,6-diazaspiro[3.4]octan-6-yl)-5,6,7,8-tetrahydro-1,6-naphthyridine-3-carbonitrile | Step 1 performed using procedure from Example 13-12. using 1,2 eq $NH_4OAc$. Step 2: DIPEA replaced pyridine. Step 5: replaced by Step 4 from Method 2. | Step 1a: Intermediate 59 and step 1b: tert-butyl 2,2-dimethyl-4-oxopiperidine-1-carboxylate (AAblocks) |
| 13-139 | 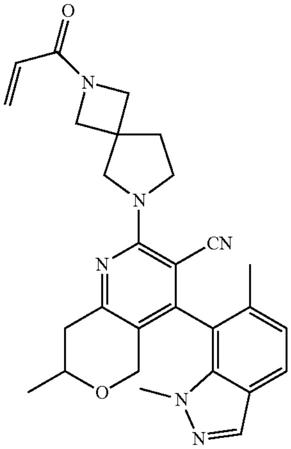 [SMILES: C=CC(=O)N1CC2(CCN(c3nc4c(c(-c5c(C)ccc6cnn(C)c56)c3C#N)COC(C)C4)C2)C1] | (7R)-4-(1,6-dimethyl-1H-indazol-7-yl)-7-methyl-2-(2-(2-propenoyl)-2,6-diazaspiro[3.4]octan-6-yl)-7,8-dihydro-5H-pyrano[4,3-b]pyridine-3-carbonitrile\| (7S)-4-(1,6-dimethyl-1H-indazol-7-yl)-7-methyl-2-(2-(2-propenoyl)-2,6-diazaspiro[3.4]octan-6-yl)-7,8-dihydro-5H-pyrano[4,3-b]pyridine-3-carbonitrile | Step 1 performed using procedure from Example 13-12 using 2 eq $NH_4OAc$. Step 2: DIPEA replaced pyridine. Step 5: replaced by Step 4 from Method 2. | Step 1a: Intermediate 59 and step 1b: 2-methyldihydro-2h-pyran-4(3h)-one (Combi-Blocks) |
| 13-140 | 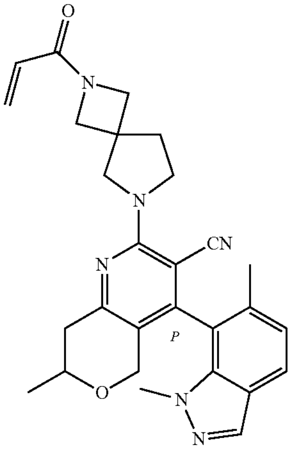 | (7R)-4-(1,6-dimethyl-1H-indazol-7-yl)-7-methyl-2-(2-(2-propenoyl)-2,6-diazaspiro[3.4]octan-6-yl)-7,8-dihydro-5H-pyrano[4,3-b]pyridine-3-carbonitrile\| (7S)-4-(1,6-dimethyl-1H-indazol-7-yl)-7-methyl-2-(2-(2-propenoyl)-2,6-diazaspiro[3.4]octan-6-yl)-7,8-dihydro-5H-pyrano[4,3-b]pyridine-3-carbonitrile (1S$^t$ and 2$^{nd}$ eluting isomers) | Step 1 performed using procedure from Example 13-12 using 2 eq $NH_4OAc$. Step 2: DIPEA replaced pyridine. Step 5: replaced by Step 4 from Method 2. See stereoisomer separation conditions below. | Step 1a: Intermediate 59 and step 1b: 2-methyldihydro-2h-pyran-4(3h)-one (Combi-Blocks) |

TABLE 5-continued

Examples 13-2 to 13-157 were prepared following the procedure described in Method 13, steps 1-5, above as follows:

| Ex.# | Chemical Structure | Name | Method changes | Reagent |
|---|---|---|---|---|
| 13-141 | 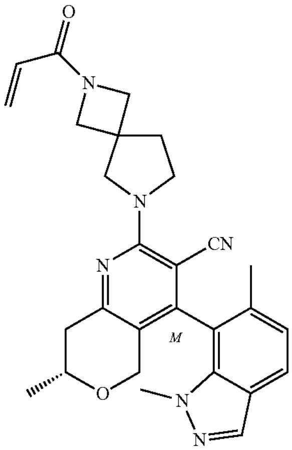 | (M)-(7R)-4-(1,6-dimethyl-1H-indazol-7-yl)-7-methyl-2-(2-(2-propenoyl)-2,6-diazaspiro[3.4]octan-6-yl)-7,8-dihydro-5H-pyrano[4,3-b]pyridine-3-carbonitrile (3rd eluting isomer) | Step 1 performed using procedure from Example 13-12 using 2 eq $NH_4OAc$. Step 2: DIPEA replaced pyridine. Step 5: replaced by Step 4 from Method 2. See stereoisomer separation conditions below. | Step 1a: Intermediate 59 and step 1b: 2-methyldihydro-2h-pyran-4(3h)-one (Combi-Blocks) |
| 13-142 | 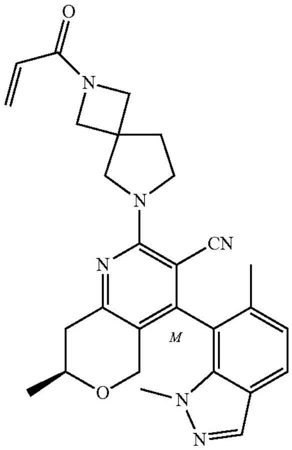 | (M)-(7S)-4-(1,6-dimethyl-1H-indazol-7-yl)-7-methyl-2-(2-(2-propenoyl)-2,6-diazaspiro[3.4]octan-6-yl)-7,8-dihydro-5H-pyrano[4,3-b]pyridine-3-carbonitrile (4th eluting isomer) | Step 1 performed using procedure from Example 13-12 using 2 eq $NH_4OAc$. Step 2: DIPEA replaced pyridine. Step 5: replaced by Step 4 from Method 2. See stereoisomer separation conditions below. | Step 1a: Intermediate 59 and step 1b: 2-methyldihydro-2h-pyran-4(3h)-one (Combi-Blocks) |
| 13-143 | 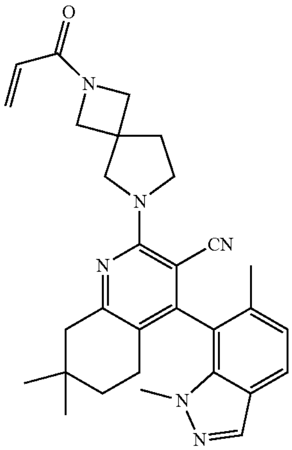 [SMILES: C=CC(=O)N1CC2(CCN(c3nc4c(c(-c5c(C)ccc6cnn(C)c56)c3C#N)CCC(C)(C)C4)C2)C1] | 4-(1,6-dimethyl-1H-indazol-7-yl)-7,7-dimethyl-2-(2-(2-propenoyl)-2,6-diazaspiro[3.4]octan-6-yl)-5,6,7,8-tetrahydro-3-quinolinecarbonitrile | Step 1 performed using procedure from Example 13-12. Step 4 used HCl in place of TFA. Step 5: replaced by Step 4 from Method 2. | Step 1a: Intermediate 59 and step 1b: 3,3-dimethylcyclohexan-1-one (Manchester) |

TABLE 5-continued

Examples 13-2 to 13-157 were prepared following the procedure described in Method 13, steps 1-5, above as follows:

| Ex.# | Chemical Structure | Name | Method changes | Reagent |
|---|---|---|---|---|
| 13-144 | 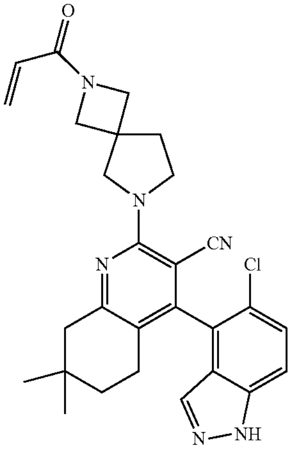 [SMILES: C=CC(=O)N1CC2(CCN(c3nc4c(c(-c5c(Cl)ccc6[nH]ncc56)c3C#N)CCC(C)(C)C4)C2)C1] | 4-(5-chloro-1H-indazol-4-yl)-7,7-dimethyl-2-(2-(2-propenoyl)-2,6-diazaspiro[3.4]octan-6-yl)-5,6,7,8-tetrahydro-3-quinolinecarbonitrile | Step 1 performed using procedure from Exmaple 13-12. Step 4 used HCl in place of TFA. Step 5: replaced by Step 4 from Method 2. | Step 1a: Intermediate 90 and step 1b: 3,3-dimethylcyclo-hexan-1-one (Manchester) |
| 13-145 | 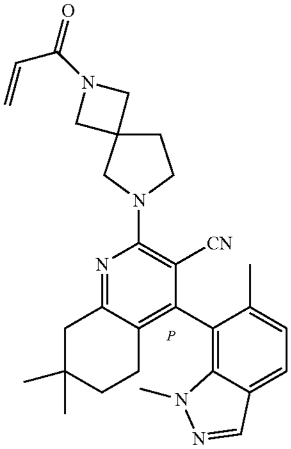 | (P)-4-(1,6-dimethyl-1H-indazol-7-yl)-7,7-dimethyl-2-(2-(2-propenoyl)-2,6-diazaspiro[3.4]octan-6-l)-5,6,7,8-tetrahydro-3-quinolinecarbonitrile (2nd eluting isomer) | Step 1 performed using procedure from Example 13-12. Step 4: HCl replaced TFA. Step 5: replaced by Step 4 from Method 2. See separation conditions below. | Step 1a: Intermediate 59 and step 1b: 3,3-dimethylcyclo-hexan-1-one (Manchester) |
| 13-146 | 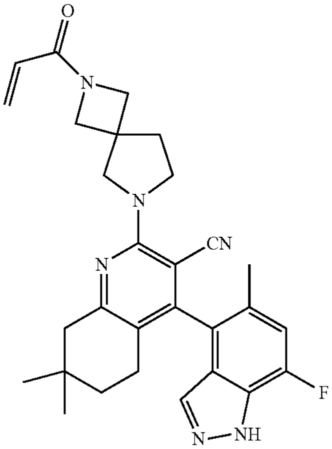 [SMILES: C=CC(=O)N1CC2(CCN(c3nc4c(c(-c5c(C)cc(F)c6[nH]ncc56)c3C#N)CCC(C)(C)C4)C2)C1] | 4-(7-fluoro-5-methyl-1H-indazol-4-yl)-7,7-dimethyl-2-(2-(2-propenoyl)-2,6-diazaspiro[3.4]octan-6-yl)-5,6,7,8-tetrahydro-3-quinolinecarbonitrile | Step 1 performed using procedure from Example 13-12. Step 4: HCl replaced TFA. Step 5: replaced by Step 4 from Method 2. | Step 1a: Intermediate 92 and step 1b: 3,3-dimethylcyclo-hexan-1-one (Manchester) |

TABLE 5-continued

| Examples 13-2 to 13-157 were prepared following the procedure described in Method 13, steps 1-5, above as follows: | | | | |
|---|---|---|---|---|
| Ex.# | Chemical Structure | Name | Method changes | Reagent |
| 13-147 | 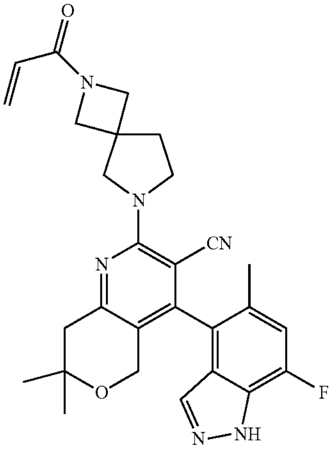 [SMILES: C=CC(=O)N1CC2(CCN(c3nc4c(c(-c5c(C)cc(F)c6[nH]ncc56)c3C#N)COC(C)(C)C4)C2)C1] | 4-(7-fluoro-5-methyl-1H-indazol-4-yl)-7,7-dimethyl-2-(2-(2-propenoyl)-2,6-diazaspiro[3.4]octan-6-yl)-7,8-dihydro-5H-pyrano[4,3-b]pyridine-3-carbonitrile | Step 1 performed using procedure from Example 13-12. Step 4: HCl replaced TFA. Step 5: replaced by Step 4 from Method 2. | Step 1a: Intermediate 92 and step 1b: 2,2-dimethyltetrahydro-4H-pyran-4-one (Combi Blocks) |
| 13-148 | 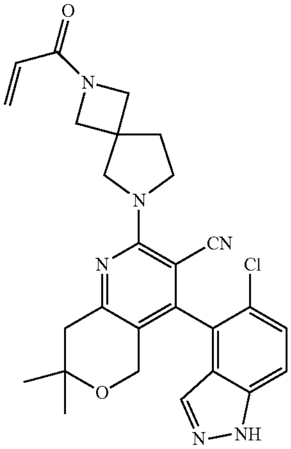 [SMILES: C=CC(=O)N1CC2(CCN(c3nc4c(c(-c5c(Cl)ccc6[nH]ncc56)c3C#N)COC(C)(C)C4)C2)C1] | 4-(5-chloro-1H-indazol-4-yl)-7,7-dimethyl-2-(2-(2-propenoyl)-2,6-diazaspiro[3.4]octan-6-yl)-7,8-dihydro-5H-pyrano[4,3-b]pyridine-3-carbonitrile | Step 1 performed using procedure from Example 13-12. Step 4: HCl replaced TFA. Step 5: replaced by Step 4 from Method 2. | Step 1a: Intermediate 90 and step 1b: 2,2-dimethyltetrahydro-4H-pyran-4-one (Combi Blocks) |
| 13-149 | 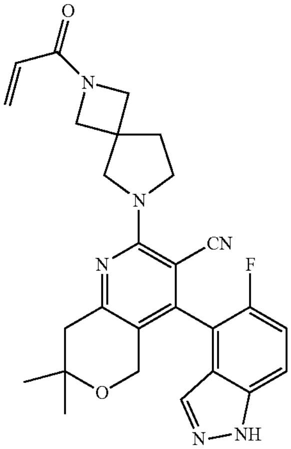 [SMILES: C=CC(=O)N1CC2(CCN(c3nc4c(c(-c5c(F)ccc6[nH]ncc56)c3C#N)COC(C)(C)C4)C2)C1] | 4-(5-fluoro-1H-indazol-4-yl)-7,7-dimethyl-2-(2-(2-propenoyl)-2,6-diazaspiro[3.4]octan-6-yl)-7,8-dihydro-5H-pyrano[4,3-b]pyridine-3-carbonitrile | Step 1 performed using procedure from Example 13-12 Step 4: HCl replaced TFA. Step 5: replaced by Step 4 from Method 2. | Step 1a: Intermediate 91 and step 1b: 2,2-dimethyltetrahydro-4H-pyran-4-one (Combi Blocks) |

TABLE 5-continued

| Ex.# | Chemical Structure | Name | Method changes | Reagent |
|---|---|---|---|---|
| | Examples 13-2 to 13-157 were prepared following the procedure described in Method 13, steps 1-5, above as follows: | | | |
| 13-150 | 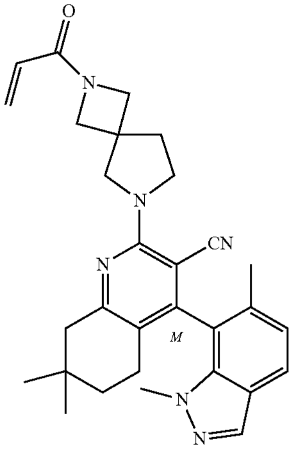 | (M)-4-(1,6-dimethyl-1H-indazol-7-yl)-7,7-dimethyl-2-(2-(2-propenoyl)-2,6-diazaspiro[3.4]octan-6-yl)-5,6,7,8-tetrahydro-3-quinolinecarbonitrile (1st eluting isomer) | Step 1 performed using procedure from Example 13-12. Step 4: HCl replaced TFA. Step 5: replaced by Step 4 from Method 2. See separation conditions below. | Step 1a: Intermediate 59 and step 1b: 3,3-dimethylcyclo-hexan-1-one (Manchester) |
| 13-151 | 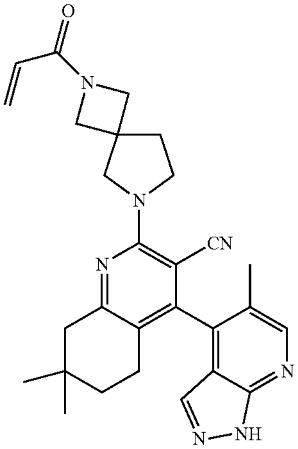 [SMILES: C=CC(=O)N1CC2(CCN(c3nc4c(c(-c5c(C)cnc6[nH]ncc56)c3C#N)CCC(C)(C)C4)C2)C1] | 7,7-dimethyl-4-(5-methyl-1H-pyrazolo[3,4-b]pyridin-4-yl)-2-(2-(2-propenoyl)-2,6-diazaspiro[3.4]octan-6-yl)-5,6,7,8-tetrahydro-3-quinolinecarbonitrile | Step 1 performed using procedure from Example 13-12. Step 4: HCl replaced TFA. Step 5: replaced by Step 4 from Method 2. | Step 1a: Intermediate 93 and step 1b: 3,3-dimethylcyclo-hexan-1-one (Manchester) |
| 13-152 | 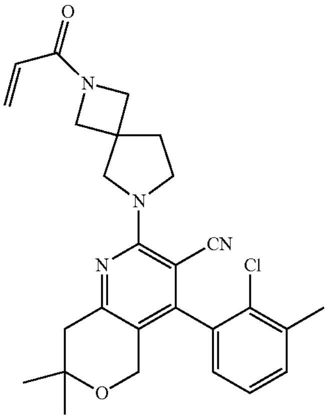 [SMILES: C=CC(=O)N1CC2(CCN(c3nc4c(c(-c5cccc(C)c5Cl)c3C#N)COC(C)(C)C4)C2)C1] | 4-(2-chloro-3-methylphenyl)-7,7-dimethyl-2-(2-(2-propenoyl)-2,6-diazaspiro[3.4]octan-6-yl)-7,8-dihydro-5H-pyrano[4,3-b]pyridine-3-carbonitrile | Step 1 performed using procedure from Example 13-12. Step 4: HCl replaced TFA. Step 5: replaced by Step 4 form Method 2. | Step 1a: 2-Chloro-3-methylbenzalde-hyde (WO 2004/052858) and step 1b: 2,2-dimethyltetrahydro-4H-pyran-4-one (Combi Blocks) |

TABLE 5-continued

Examples 13-2 to 13-157 were prepared following the procedure described in Method 13, steps 1-5, above as follows:

| Ex.# | Chemical Structure | Name | Method changes | Reagent |
|---|---|---|---|---|
| 13-153 | 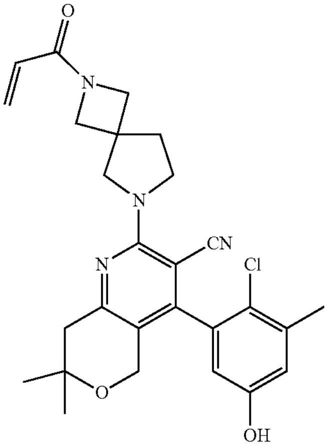 [SMILES: C=CC(=O)N1CC2(CCN(c3nc4c(c(-c5cc(O)cc(C)c5Cl)c3C#N)COC(C)(C)C4)C2)C1] | 4-(2-chloro-5-hydroxy-3-methylphenyl)-7,7-dimethyl-2-(2-(2-propenoyl)-2,6-diazaspiro[3.4]octan-6-yl)-7,8-dihydro-5H-pyrano[4,3-b]pyridine-3-carbonitrile | Step 1 performed using procedure from Example 13-12. Step 4: HCl replaced TFA. Step 5: replaced by Step 4 from Method 2. | Step 1a: Intermediate 94 and step 1b: 2,2-dimethyltetrahydro-4H-pyran-4-one (Combi Blocks) |
| 13-154 | 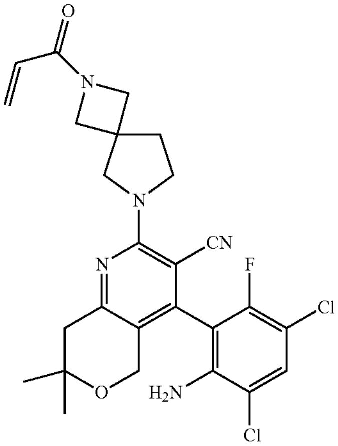 [SMILES: C=CC(=O)N1CC2(CCN(c3nc4c(c(-c5c(N)c(Cl)cc(Cl)c5F)c3C#N)COC(C)(C)C4)C2)C1] | 4-(2-amino-3,5-dichloro-6-fluorophenyl)-7,7-dimethyl-2-(2-(2-propenoyl)-2,6-diazaspiro[3.4]octan-6-yl)-7,8-dihydro-5H-pyrano[4,3-b]pyridine-3-carbonitrile | After Step 3, see addtional reduction and chlorination below. Step 5: replaced by Step 4 from Method 2. | Step 1: 2-fluoro-6-nitrobenzaldehyde (Combi-Blocks) and 2,2-dimethyltetrahydro-4H-pyran-4-one (Combi-Blocks) |
| 13-155 | 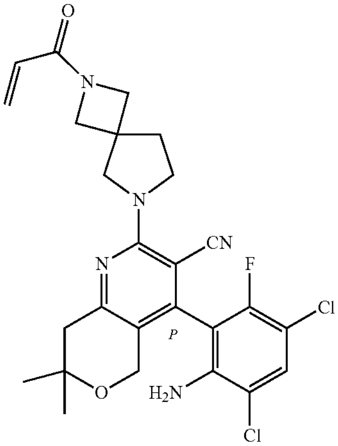 | (P)-4-(2-amino-3,5-dichloro-6-fluorophenyl)-7,7-dimethyl-2-(2-(2-propenoyl)-2,6-diazaspiro[3.4]octan-6-yl)-7,8-dihydro-5H-pyrano[4,3-b]pyridine-3-carbonitrile (2$^{nd}$ eluting isomer) | After Step 3, see additional reduction and chlorination below. Step 5: replaced by Step 4 from Method 2. See separation conditions below. | Step 1: 2-fluoro-6-nitrobenzaldehyde (Combi-Blocks) and 2,2-dimethyltetrahydro-4H-pyran-4-one (Combi-Blocks) |

TABLE 5-continued

Examples 13-2 to 13-157 were prepared following the procedure described in Method 13, steps 1-5, above as follows:

| Ex.# | Chemical Structure | Name | Method changes | Reagent |
| --- | --- | --- | --- | --- |
| 13-156 | 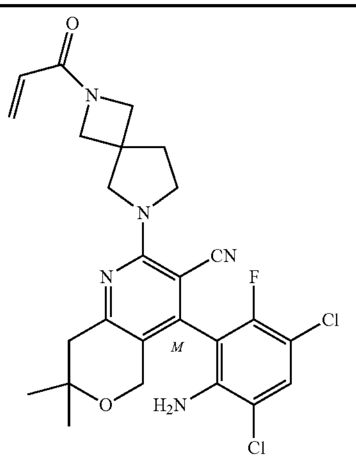 | (M)-4-(2-amino-3,5-dichloro-6-fluorophenyl)-7,7-dimethyl-2-(2-(2-propenoyl)-2,6-diazaspiro[3.4]octan-6-yl)-7,8-dihydro-5H-pyrano[4,3-b]pyridine-3-carbonitrile (1$^{st}$ eluting isomer) | After Step 3, see additional reduction and chlorination below. Step 5: replaced by Step 4 from Method 2. See separation conditions below. | Step 1: 2-fluoro-6-nitrobenzaldehyde (Combi-Blocks) and 2,2-dimethyltetrahydro-4H-pyran-4-one (Combi-Blocks) |
| 13-157 | 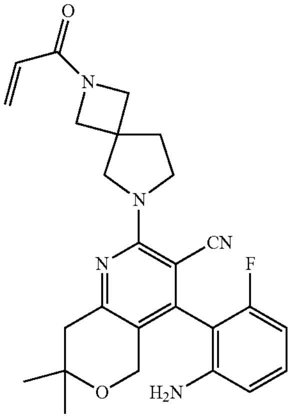 [SMILES: C=CC(=O)N1CC2(CCN(c3nc4c(c(-c5c(N)cccc5F)c3C#N)COC(C)(C)C4)C2)C1] | 4-(2-amino-6-fluorophenyl)-7,7-dimethyl-2-(2-(2-propenoyl)-2,6-diazaspiro[3.4]octan-6-yl)-7,8-dihydro-5H-pyrano[4,3-b]pyridine-3-carbonitrile | After Step 3, see additional reduction below. Step 5: replaced by Step 4 from Method 2. | Step 1: 2-fluoro-6-nitrobenzaldehyde (Combi-Blocks) and 2,2-dimethyltetrahydro-4H-pyran-4-one (Combi-Blocks) |

Alternate Step 1 for Example 13-12.

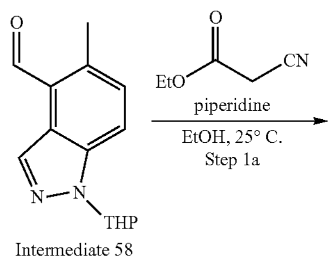

Intermediate 58

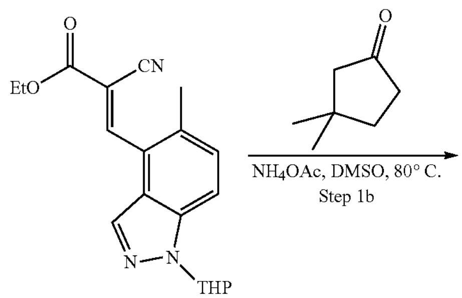

-continued

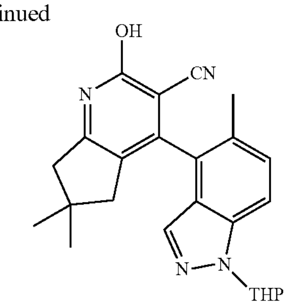

Step 1a: ethyl (E)-2-cyano-3-(5-methyl-1-(tetrahydro-2H-pyran-2-yl)-1H-indazol-4-yl)acrylate To a solution of 5-methyl-1-(tetrahydro-2H-pyran-2-yl)-1H-indazole-4-carbaldehyde (0.1 g, 0.409 mmol, Intermediate 58) in EtOH (4.1 mL, 0.1M) at 25° C. was added piperidine (0.052 g, 0.614 mmol, Spectrum), and ethyl cyanoacetate (0.046 g, 0.409 mmol, Oakwood). The reaction was stirred for 1.5 h and concentrated in vacuo. The crude material was purified by flash chromatography over silica gel eluting with a gradient of 0-100% EtOAc in heptanes to provide ethyl (E)-2-cyano-3-(5-methyl-1-(tetrahydro-2H-pyran-2-yl)-1H-indazol-4-yl)acrylate (111 mg, 80% yield).

Step 1b: 2-hydroxy-6,6-dimethyl-4-(5-methyl-1-(tetrahydro-2H-pyran-2-yl)-1H-indazol-4-yl)-6,7-dihydro-5H-cyclopenta[b]pyridine-3-carbonitrile To a solution of 3,3-dimethylcyclopentan-1-one (87 mg, 0.776 mmol, Enamine) in DSMO (1.382 mL, 0.43 M) at 25° C. was added ethyl (E)-2-cyano-3-(5-methyl-1-(tetrahydro-2H-pyran-2-yl)-1H-indazol-4-yl)acrylate (202.7 mg, 0.597 mmol), and $NH_4OAc$ (460 mg, 5.97 mmol, Sigma-Aldrich). The reaction mixture was heated to 80° C. After 1 h, a needle was used to pierce the septa and allow the reaction to be exposed to air. The reaction mixture was stirred at 80° C. overnight. The reaction was quenched with water and extracted with EtOAc. The organic phases were separated. The organic layer was dried ($Na_2SO_4$, filtered and the volatiles were removed. The crude material was purified by flash chromatography over silica gel eluting with a gradient of 0-100% EtOAc:EtOH (3:1) in heptanes to give 2-hydroxy-6,6-dimethyl-4-(5-methyl-1-(tetrahydro-2H-pyran-2-yl)-1H-indazol-4-yl)-6,7-dihydro-5H-cyclopenta[b]pyridine-3-carbonitrile (42.2 mg, 17% yield).

Atropisomer Separation for Examples 13-17 and 13-18.

The racemic mixture was separated by preparative SFC using a Chiralcel OX (250×21, 5 μm) column with a mobile phase of 60% liquid $CO_2$ and 40% MeOH using a flowrate of 80 mL/min to provide the respective P and M isomers of 4-(1,6-dimethyl-H-indazol-7-yl)-6,6-dimethyl-2-(2-(2-propenoyl)-2,6-diazaspiro[3.4]octan-6-yl)-6,7-dihydro-5H-cyclopenta[b]pyridine-3-carbonitrile. The stereochemistry of structures was arbitrarily assigned and is not established. $1^{st}$ eluting atropisomer assigned as the M isomer and $2^{nd}$ eluting atropisomer assigned as the P isomer.

Enantiomer Separation of Examples 13-20 and 13-21.

The racemic mixture was separated by preparative SFC using a Chiral Technologies OD column (250×21 mm, 5 μm) with a mobile phase of 65% liquid $CO_2$ and 35% MeOH with 0.2% TEA using a flowrate of 80 mL/min to provide the respective R and S isomers of (7)-4-(2-chlorophenyl)-7-(1-methyl-1H-pyrazol-5-yl)-2-(2-(2-propenoyl)-2,6-diazaspiro[3.4]octan-6-yl)-5,6,7,8-tetrahydro-3-quinolinecarbonitrile. The stereochemistry of structures was arbitrarily assigned and is not established. $1^{st}$ eluting enantiomer assigned as the R isomer and $2^{nd}$ eluting enantiomer assigned as the S isomer.

Atropisomer Separation for Examples 13-24 and 13-25.

The racemic mixture was separated by preparative SFC using a Chiral Technologies OJ column (250×21 mm, 5 μm) with a mobile phase of 85% liquid $CO_2$ and 15% MeOH with 0.2% TEA using a flowrate of 90 mL/min to provide the respective P and M isomers of 4-(2-chlorophenyl)-6,6-dimethyl-2-(2-(2-propenoyl)-2,6-diazaspiro[3.4]octan-6-yl)-6,7-dihydro-5H-cyclopenta[b]pyridine-3-carbonitrile. The stereochemistry of structures was arbitrarily assigned and is not established. $1^{st}$ eluting atropisomer assigned as the M isomer and $2^{nd}$ eluting atropisomer assigned as the P isomer.

Atropisomer Separation for Examples 13-31 and 13-32.

The racemic mixture was separated by preparative SFC using a Chiralpak IC (150×21, 5 μm) column with a mobile phase of 40% liquid $CO_2$ and 60% MeOH using a flowrate of 80 mL/min to provide the respective P and M isomers of (1S,9R)-6-(1,6-dimethyl-1H-indazol-7-yl)-4-((5S)-5-methyl-2-(2-propenoyl)-2,6-diazaspiro[3.4]octan-6-yl)-3-azatricyclo[7.1.1.0$^{2,7}$]undeca-2,4,6-triene-5-carbonitrile. The stereochemistry of structures was arbitrarily assigned and is not established. $1^{st}$ eluting atropisomer assigned as the M isomer and $2^{nd}$ eluting atropisomer assigned as the P isomer.

Atropisomer Separation for Examples 13-36 and 13-37.

The racemic mixture was separated by preparative SFC using a Lux Cellulose-2 (250×21 mm, 5 μm) column with a mobile phase of 50% liquid $CO_2$ and 50% MeOH using a flowrate of 60 mL/min to provide the respective P and M isomers of (1S,9S)-6-(2-hydroxy-1-naphthalenyl)-4-(2-(2-propenoyl)-2,6-diazaspiro[3.4]octan-6-yl)-3-azatricyclo[7.1.1.0$^{2,7}$]undeca-2,4,6-triene-5-carbonitrile. The stereochemistry of structures was arbitrarily assigned and is not established. $1^{st}$ eluting atropisomer assigned as the M isomer and $2^{nd}$ eluting atropisomer assigned as the P isomer.

Atropisomer Separation for Examples 13-39 and 13-40.

The racemic mixture was separated by preparative SFC using a Lux Cellulose-2 (250×21 mm, 5 μm) column with a mobile phase of 60% liquid $CO_2$ and 40% MeOH using a flowrate of 75 mL/min to provide the respective P and M isomers of 4-(3-hydroxy-1-naphthalenyl)-7,7-dimethyl-2-(2-(2-propenoyl)-2,6-diazaspiro[3.4]octan-6-yl)-7,8-dihydro-5H-pyrano[4,3-b]pyridine-3-carbonitrile. The stereochemistry of structures was arbitrarily assigned and is not established. $1^{st}$ eluting atropisomer assigned as the M isomer and $2^{nd}$ eluting atropisomer assigned as the P isomer.

Atropisomer Separation for Examples 13-42 and 13-43.

The racemic mixture was separated by preparative SFC using a Chiralpak IC (150×21 mm. 5 μm) column with a mobile phase of 50% liquid $CO_2$ and 50% MeOH using a flowrate of 80 mL/min to provide the respective P and M isomers of (1S,9S)-6-(2-hydroxy-6-methylphenyl)-4-(2-(2-propenoyl)-2,6-diazaspiro[3.4]octan-6-yl)-3-azatricyclo[7.1.1.0$^{2,7}$]undeca-2,4,6-triene-5-carbonitrile. The stereochemistry of structures was arbitrarily assigned and is not established. $1^{st}$ eluting atropisomer assigned as the M isomer and $2^{nd}$ eluting atropisomer assigned as the P isomer.

Alternative Step 2 for Example 13-47

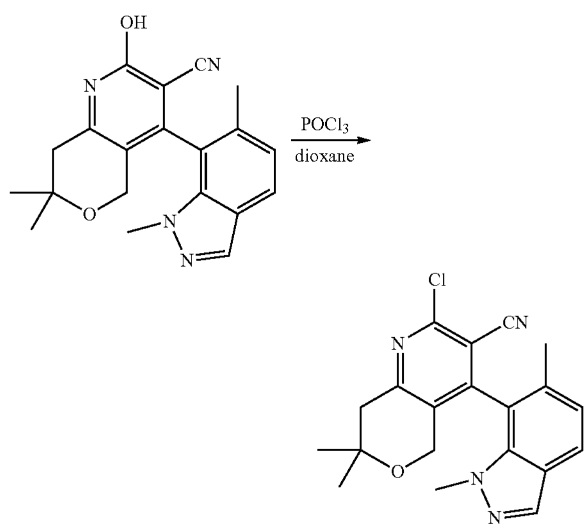

To a 25 mL glass vial was added 4-(1,6-dimethyl-1H-indazol-7-yl)-2-hydroxy-7,7-dimethyl-7,8-dihydro-5H-pyrano[4,3-b]pyridine-3-carbonitrile (100 mg, 0.287 mmol) and $POCl_3$ (0.107 mL, 1.148 mmol) in dioxane. The reaction was heated at 100° C. for 2.5 h. The reaction was concentrated to dryness to give 2-chloro-4-(1,6-dimethyl-1H-indazol-7-yl)-7,7-dimethyl-7,8-dihydro-5H-pyrano[4,3-b]pyridine-3-carbonitrile (105 mg) as a brown oil, which was used in the following step as is assuming quantitative yield. m/z (ESI): 367.1 $(M+H)^+$.

Alternative Step 1b for Example 13-49

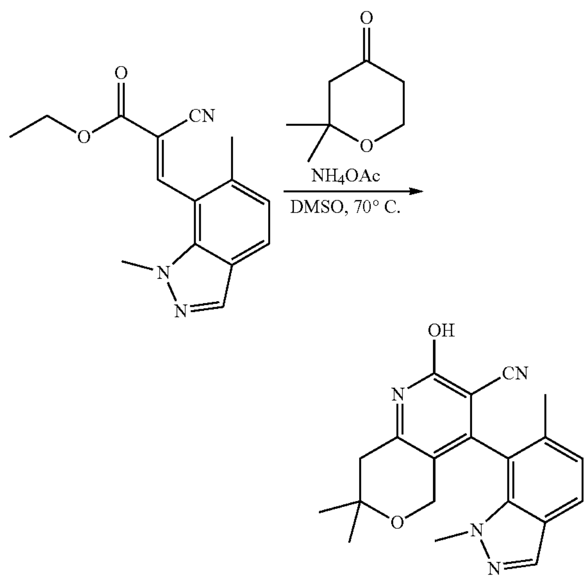

To a solution of 2,2-dimethyltetrahydro-4H-pyran-4-one (395 μL, 2.97 mmol, PharmaBlock) and ethyl (E)-2-cyano-3-(1,6-dimethyl-1H-indazol-7-yl)acrylate (800 mg, 2.97 mmol) in DMSO (10 mL) was added $NH_4OAc$ (2.29 g, 29.7 mmol, Sigma-Aldrich). The reaction was stirred at 70° C. for 1 h, a needle was inserted through the septum to allow air oxidation of the intermediate. After 3 d, the reaction temperature was increased to 80° C., with air bubbling through the reaction mixture. After another 16 h, the reaction was partitioned between water and EtOAc; the organic layer was concentrated. The crude product was purified by column chromatography, eluting with 0-60% (3:1) EtOAc:EtOH in heptanes, to provide 4-(1,6-dimethyl-1H-indazol-7-yl)-2-hydroxy-7,7-dimethyl-7,8-dihydro-5H-pyrano[4,3-b]pyridine-3-carbonitrile (0.79 g, 76% yield) as a tan solid. m/z (ESI): 349.2 $(M+H)^+$.

Alternative Step 1b for Example 13-50

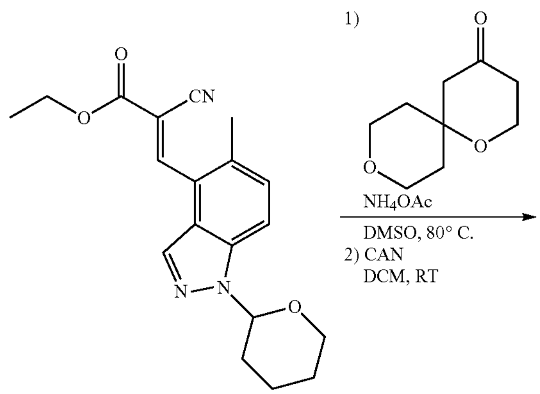

-continued

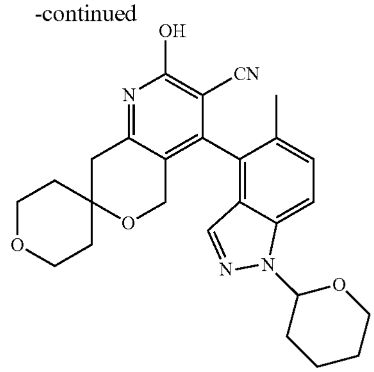

To a solution of 1,9-dioxaspiro[5.5]undecan-4-one (110 mg, 0.648 mmol, Enamine) and ethyl (E)-2-cyano-3-(5-methyl-1-(tetrahydro-2H-pyran-2-yl)-1H-indazol-4-yl)acrylate (200 ng, 0.589 mmol) in DMSO (6 mL) was added $NH_4OAc$ (454 mg, 5.89 mmol, Sigma-Aldrich) and the reaction was stirred at 80° C. for 16 h. The reaction mixture was partitioned between water and EtOAc: the organic layer was concentrated in vacuo. The crude product was purified by column chromatography, eluting with 0-100% (3:1) EtOAc:EtOH in heptanes, to provide the 4'-(5-methyl-1-(tetrahydro-2H-pyran-2-yl)-1H-indazol-4-yl)-2'-oxo-2,2',3,3',4',4a',5,5',6,8'-decahydrospiro[pyran-4,7'-pyrano[4,3-b]pyridine]-3'-carbonitrile (200 mg, 73.4% yield) as an off-white solid.

To a solution of 4'-(5-methyl-1-(tetrahydro-2H-pyran-2-yl)-1H-indazol-4-yl)-2'-oxo-2,2',3,3',4',4a',5,5',6,8'-decahydrospiro[pyran-4,7'-pyrano[4,3-b]pyridine]-3'-carbonitrile (200 mg, 0.432 mmol) in DCM was added ammonium cerium(iv) nitrate (711 mg, 1.297 mmol, Sigma-Aldrich). The reaction was stirred at ambient temperature overnight, and then the reaction temperature was increased to 40° C. After another 20 h, the reaction mixture was diluted with water and extracted with EtOAc; the organic layer was concentrated. The crude product was purified by column chromatography, eluting with 0-100% (3:1) EtOAc:EtOH in heptanes, to provide 2'-hydroxy-4'-(5-methyl-1-(tetrahydro-2H-pyran-2-yl)-1H-indazol-4-yl)-2,3,5,5',6,8'-hexahydrospiro[pyran-4,7'-pyrano[4,3-b]pyridine]-3'-carbonitrile (60 mg, 30.1% yield) as a yellow solid. m/z (ESI): 461.0 $(M+H)^+$.

Stereoisomer Separation for Examples 13-53 and 13-54.

The racemic mixture was separated by preparative SFC using a Chiralpak AD (150×30 mm, 5 μm) column with a mobile phase of 80% liquid $CO_2$ and 20% iPrOH with 0.2% diethylamine using a flowrate of 200 mL/min to provide 4 peaks. Peaks 1 and 2 were of insufficient purity, while peaks 3 and 4 were separated to give the respective P isomers of 2-((S)-2-acryloyl-5-methyl-2,6-diazaspiro[3.4]octan-6-yl)-6,6-dimethyl-4-(5-methyl-1H-indazol-4-yl)-6,7-dihydro-5H-cyclopenta[b]pyridine-3-carbonitrile and 2-((R)-2-acryloyl-5-methyl-2,6-diazaspiro[3.4]octan-6-yl)-6,6-dimethyl-4-(5-methyl-1H-indazol-4-yl)-6,7-dihydro-5H-cyclopenta[b]pyridine-3-carbonitrile. The stereochemistry of structures was arbitrarily assigned and is not established. $3^{rd}$ eluting isomer assigned as the S isomer and $4^{th}$ eluting isomer assigned as the R isomer.

Atropisomer Separation for Examples 13-56 and 13-57.

The racemic mixture was separated by preparative SFC using a Whelk-01 (S,S) (250×21 mm, 5 μm) column with a mobile phase of 70% liquid $CO_2$ and 30% MeOH using a flowrate of 80 mL/min to provide the respective P and M isomers of 4-(1,6-dimethyl-1H-indazol-7-yl)-7,7-dimethyl-2-(2-(2-propenoyl)-2,6-diazaspiro[3.4]octan-6-yl)-5,7-dihydrofuro[3,4-b]pyridine-3-carbonitrile. The stereochemistry of structures was arbitrarily assigned and is not established. 1st eluting atropisomer assigned as the P isomer and 2nd eluting atropisomer assigned as the M isomer.

Atropisomer Separation for Examples 13-59 and 13-60.

The racemic mixture was separated by preparative SFC using a Chiralpak AD (30×150 mm, 5 μm) column with a mobile phase of 80% liquid $CO_2$ and 20% IPA w/0.2% diethyl-amine using a flowrate of 200 mL/min, followed by repurification using Chiralcel OX (21×250 mm, 5 μm) column with a mobile phase of 80% liquid $CO_2$ and 40% MeOH w/0.2% diethylamine using a flowrate of 80 mL/min to provide the respective P and M isomers of 4-(1,6-dimethyl-1H-indazol-7-yl)-7,7-dimethyl-2-(2-(2-propenoyl)-2,6-diazaspiro[3.4]octan-6-yl)-7,8-dihydro-5H-pyrano[4,3-b]pyridine-3-carbonitrile. The stereochemistry of structures was arbitrarily assigned and is not established. 1st eluting atropisomer assigned as the M isomer and 2nd eluting atropisomer assigned as the P isomer.

Atropisomer Separation for Examples 13-66 and 13-67.

The racemic mixture was separated by preparative SFC using a Chiralcel OJ column (21×250 mm) with mobile phase of 85% liquid $CO_2$ and 15% MeOH using a flowrate of 80 mL/min to provide the respective P and M isomers of (1S,9S)-6-(2-chloro-6-hydroxyphenyl)-4-(2-(2-propenoyl)-2,6-diazaspiro[3.4]octan-6-yl)-3-azatricyclo[7.1.1.0$^{2,7}$]undeca-2,4,6-triene-5-carbonitrile. The stereochemistry of structures was arbitrarily assigned and is not established. 1st eluting atropisomer assigned as the M isomer and 2nd eluting atropisomer assigned as the P isomer.

Atropisomer Separation for Examples 13-68 and 13-69.

The racemic mixture was separated by preparative SFC using a Chiralpak IC (21×150 mm, 5 μm) column with a mobile phase of 50% liquid $CO_2$ and 50% MeOH using a flowrate of 80 mL/min to provide the respective P and M isomers of 4-(3-hydroxy-1-naphthalenyl)-6,6-dimethyl-2-(2-(2-propenoyl)-2,6-diazaspiro[3.4]octan-6-yl)-6,7-dihydro-5H-cyclopenta[b]pyridine-3-carbonitrile. The stereochemistry of structures was arbitrarily assigned and is not established. 1st eluting atropisomer assigned as the M isomer and 2nd eluting atropisomer assigned as the P isomer.

Isomer Separation for Examples 13-73, 13-74, 13-75, and 13-76.

The racemic mixture was separated by preparative SFC using a Chiralpak IC (21×150 mm, 5 μm) column with a mobile phase of 45% liquid $CO_2$ and 55% MeOH using a flowrate of 80 mL/min to generate peak 3 and peak 4, along with unresolved peak 1 and peak 2. The Peak 1/Peak 2 mixture was separated by SFC using a Chiralpak IC (21×250 mm, 5 μm) column with a mobile phase of 50% liquid $CO_2$ and 50% iPrOH using a flowrate of 70 mL/min to provide the respective isomers of 2-(2-acryloyl-2,6-diazaspiro[3.4]octan-6-yl)-4-(4-fluoro-3-hydroxynaphthalen-1-yl)-6,6a,7,7a-tetrahydro-5H-cyclopropa[h]quinoline-3-carbonitrile. The stereochemistry of structures was arbitrarily assigned and is not established. 1st eluting isomer assigned as the M,6aS,7aR isomer, 2nd eluting isomer assigned as the P, 6aS,7aR isomer, 3rd eluting isomer assigned as the M, 6aR,7aS isomer, and the 4th eluting isomer as the P, 6aR,7aS isomer.

Atropisomer Separation for Examples 13-77 and 13-78.

The racemic mixture was separated by preparative SFC using a Chiralpak IC column (21×150 mm) with a mobile phase of 55% liquid $CO_2$ and 45% MeOH using a flowrate of 80 mL/min to provide the respective P and M isomers of 4-(4-fluoro-3-hydroxy-1-naphthalenyl)-7,7-dimethyl-2-(2-(2-propenoyl)-2,6-diazaspiro[3.4]octan-6-yl)-7,8-dihydro-5H-pyrano[4,3-b]pyridine-3-carbonitrile. The stereochemistry of structures was arbitrarily assigned and is not established. 1st eluting atropisomer assigned as the M isomer and 2nd eluting atropisomer assigned as the P isomer.

Stereoisomer Separation for Examples 13-86, 13-87 and 13-88.

The racemic mixture was separated by preparative SFC using a Chiralpak IC (21×250 mm, 5 μm) column with a mobile phase of 45% liquid $CO_2$ and 55% MeOH with 0.2% TEA using a flowrate of 80 mL/min to provide 4 peaks. Peaks 1 and 2 were unresolved, while peaks 3 and 4 were separated to give the respective stereoisomers of (6a,7a)-2-(2-((2E)-4-(dimethylamino)-2-butenoyl)-2,6-diazaspiro[3.4]octan-6-yl)-4-(3-hydroxy-1-naphthalenyl)-6,6a,7,7a-tetrahydro-5H-cyclopropa[h]quinoline-3-carbonitrile. The stereochemistry of structures was arbitrarily assigned and is not established. The 1st and 2nd eluting isomers were assigned as a mixture of M isomers of (6aR,7aS)-2-(2-((2E)-4-(dimethylamino)-2-butenoyl)-2,6-diazaspiro[3.4]octan-6-yl)-4-(3-hydroxy-1-naphthalenyl)-6,6a,7.7a-tetrahydro-5H-cyclopropa[h]quinoline-3-carbonitrile and (6aS,7aR)-2-(2-((2E)-4-(dimethylamino)-2-butenoyl)-2,6-diazaspiro[3.4]octan-6-yl)-4-(3-hydroxy-1-naphthalenyl)-6,6a,7,7a-tetrahydro-5H-cyclopropa[h]quinoline-3-carbonitrile while the 3rd eluting isomer assigned as the P isomer of (6aR,7aS)-2-(2-((2E)-4-(dimethylamino)-2-butenoyl)-2,6-diazaspiro[3.4]octan-6-yl)-4-(3-hydroxy-1-naphthalenyl)-6,6a,7,7a-tetrahydro-5H-cyclopropa[h]quinoline-3-carbonitrile and 4th eluting isomer assigned as the P isomer of (6aS,7aR)-2-(2-((2E)-4-(dimethylamino)-2-butenoyl)-2,6-diazaspiro[3.4]octan-6-yl)-4-(3-hydroxy-1-naphthalenyl)-6,6a,7,7a-tetrahydro-5H-cyclopropa[h]quinoline-3-carbonitrile.

Atropisomer Separation for Examples 13-91 and 13-92.

The racemic mixture was separated by preparative SFC using an OX column (250×21 mm, 5 μm) with a mobile phase of 60% liquid $CO_2$ and 40% MeOH using a flowrate of 70 mL/min to provide the respective P and M isomers of 7,7-dimethyl-2-(2-(2-propenoyl)-2,6-diazaspiro[3.4]octan-6-yl)-4-(1,5,6-trimethyl-1H-indazol-7-yl)-7,8-dihydro-5H-pyrano[4,3-b]pyridine-3-carbonitrile. The stereochemistry of structures was arbitrarily assigned and is not established. 1st eluting atropisomer assigned as the M isomer and 2nd eluting atropisomer assigned as the P isomer.

Alternate Step 1 for Example 13-97

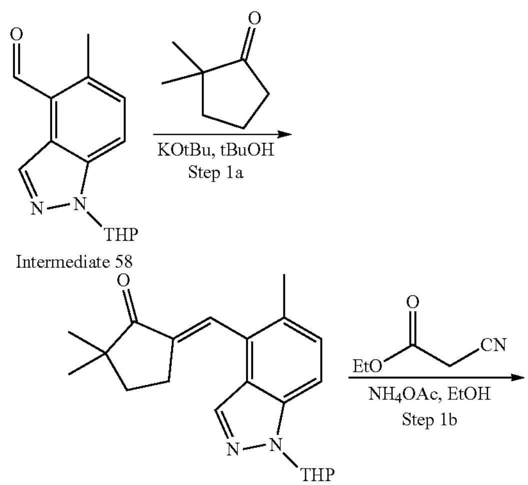

Intermediate 58

-continued

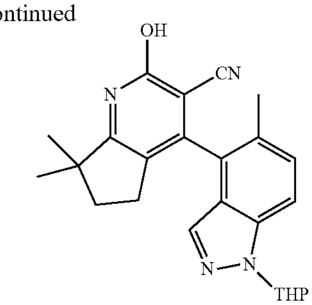

Step 1a: (E)-2,2-dimethyl-5-((5-methyl-1-(tetrahydro-2H-pyran-2-yl)-1H-indazol-4-yl)methylene) cyclopentan-1-one To a glass vial was added 2,2-dimethylcyclopentan-1-one (103 μL, 0.819 mmol, Sigma-Aldrich), 5-methyl-1-(tetrahydro-2H-pyran-2-yl)-1H-indazole-4-carbaldehyde (200 mg, 0.819 mmol, Intermediate 58) and tert-butanol (8187 μL). To the mixture was added KOtBu (110 mg, 0.982 mmol, Sigma-Aldrich) and the reaction was stirred at 80° C. After 15 min, LCMS showed full conversion to the desired product. The reaction was quenched by aqueous saturated $NaHCO_3$ (10 mL), extracted with EtOAc (3×10 mL), dried over $MgSO_4$, filtered, and concentrated to give crude (E)-2,2-dimethyl-5-((5-methyl-1-(tetrahydro-2H-pyran-2-yl)-1H-indazol-4-yl)methylene)cyclopentan-1-one (297 mg, quantitative yield) as yellow solid that was used in the next step with no further purification. m/z (ESI): 339.3 $(M+H)^+$.

Step 1b: 2-hydroxy-7,7-dimethyl-4-(5-methyl-1-(tetrahydro-2H-pyran-2-yl)-1H-indazol-4-yl)-6,7-dihydro-5H-cyclopenta[b]pyridine-3-carbonitrile To a glass vial was added (E)-2,2-dimethyl-5-((5-methyl-1-(tetrahydro-2H-pyran-2-yl)-1H-indazol-4-yl)methylene) cyclopentan-1-one (277 mg, 0.819 mmol), ethyl cyanoacetate (93 mg, 0.819 mmol. Oakwood Products, Inc.) and EtOH (819 μL). $NH_4OAc$ (316 mg, 4.10 mmol, Sigma-Aldrich) was added and the reaction was heated to 80° C. The reaction was concentrated in vacuo, DMSO (1 mL) was added and the reaction was heated to 80° C. overnight open to air (needle on top). The reaction was diluted with aqueous saturated $NaHCO_3$ (10 mL), extracted with EtOAc (3×10 mL), dried over $MgSO_4$, and concentrated in vacuo. The crude material was absorbed onto a plug of silica gel and purified by chromatography through a Redi-Sep pre-packed silica gel column, eluting with a gradient of 0-100% EtOAc in heptanes, to provide 2-hydroxy-7,7-dimethyl-4-(5-methyl-1-(tetrahydro-2H-pyran-2-yl)-1H-indazol-4-yl)-6,7-dihydro-5H-cyclopenta-[b]pyridine-3-carbonitrile (73 mg, 22.14% yield) as a pale brown solid. m/z (ESI): 403.2 $(M+H)^+$.

Atropisomer Separation for Examples 13-102 and 13-103.

The racemic mixture was separated by preparative SFC using a Regis (S,S) Whelk-01 column (250×21 mm, 5 μm) with a mobile phase of 55% liquid $CO_2$ and 45% MeOH with 0.2% TEA using a flowrate of 80 mL/min to provide the respective P and M isomers of 2-(2-acryloyl-2,6-diazaspiro[3.4]octan-6-yl)-4-(1,6-dimethyl-1H-indazol-7-yl)-7,7-dimethyl-6,7-dihydro-5H-cyclopenta[b]pyridine-3-carbonitrile. The stereochemistry of structures was arbitrarily assigned and is not established. 1$^{st}$ eluting atropisomer assigned as the P isomer and 2$^{nd}$ eluting atropisomer assigned as the M isomer.

Atropisomer Separation for Examples 13-105 and 13-106.

The racemic mixture was separated by preparative SFC using a Chiralcel OX column (30×250 mm, 5 μm) with a mobile phase of 65% liquid $CO_2$ and 35% MeOH using a flowrate of 80 mL/min to provide the respective P and M isomers of (6R,8R)-2-(2-acryloyl-2,6-diazaspiro[3.4]octan-6-yl)-4-(1,6-dimethyl-1H-indazol-7-yl)-7,7-dimethyl-5,6,7,8-tetrahydro-6,8-methanoquinoline-3-carbonitrile. The stereochemistry of structures was arbitrarily assigned and is not established. 1$^{st}$ eluting atropisomer assigned as the P isomer and 2$^{nd}$ eluting atropisomer assigned as the M isomer.

Atropisomer Separation for Examples 13-114 and 13-115.

The racemic mixture was separated by preparative SFC using a Chiralcel OX column (21×250 mm) with a mobile phase of 55% liquid $CO_2$ and 45% MeOH using a flowrate of 80 mL/min to provide the respective P and M isomers of (1R,9R)-10,10-dimethyl-6-(5-methyl-1H-indazol-4-yl)-4-(2-(2-propenoyl)-2,6-diazaspiro[3.4]octan-6-yl)-3-azatricyclo[7.1.1.0$^{2,7}$]undeca-2,4,6-triene-5-carbonitrile. The stereochemistry of structures was arbitrarily assigned and is not established. 1$^{st}$ eluting atropisomer assigned as the P isomer and 2$^{nd}$ eluting atropisomer assigned as the M isomer.

Atropisomer Separation for Examples 13-117 and 13-118.

The racemic mixture was separated by preparative SFC using a Chiralcel OX (21×250 mm, 5 μm) with a mobile phase of 60% liquid $CO_2$ and 40% MeOH using a flowrate of 80 mL/min to provide the respective P and M isomers of (1S,9S)-6-(1,6-dimethyl-1H-indazol-7-yl)-4-(2-(2-propenoyl)-2,6-diazaspiro[3.4]octan-6-yl)-3-azatricyclo[7.1.1.0$^{2,7}$]undeca-2,4,6-triene-5-carbonitrile. The stereochemistry of structures was arbitrarily assigned and is not established. 1$^{st}$ eluting atropisomer assigned as the P isomer and 2$^{nd}$ eluting atropisomer assigned as the M isomer.

Isomer Separation for Examples 13-119 to 13-122.

The racemic mixture was separated by preparative SFC using a Chiralcel OX column (21×250 mm, 5 μm) with a mobile phase of 70% liquid $CO_2$ and 30% MeOH using a flowrate of 80 mL/min to provide separated peak 1 and peak 2 along with unresolved peak 3/peak 4. The mixture of peak 3/peak 4 was separated by preparative SFC using a Chiralpak AZ (21×250 mm, 5 pin) column with a mobile phase of 65% liquid $CO_2$ and 35% MeOH using a flowrate of 80 mL/min to provide the separate peak 3 and peak 4. The stereochemistry of structures was arbitrarily assigned and is not established. 1$^{st}$ eluting isomer assigned as the P, 7R isomer, 2$^{nd}$ eluting isomer assigned as the P, 7S isomer, 3$^{rd}$ eluting isomer was assigned as the M, 7S, and the 4, eluting isomer assigned as the M, 7R isomer of 7-cyclopropyl-4-(1,6-dimethyl-1H-indazol-7-yl)-2-(2-(2-propenoyl)-2,6-diazaspiro[3.4]octan-6-yl)-7,8-dihydro-5H-pyrano[4,3-b]pyridine-3-carbonitrile.

Atropisomer Separation for Examples 13-123 and 13-124.

The racemic mixture was separated by preparative SFC using a Lux Cellulose-2 (21×250 mm) column with a mobile phase of 55% liquid $CO_2$ and 45% MeOH using a flowrate of 50 mL/min to provide the respective P and M isomers of (1R,9R)-10,10-dimethyl-6-(4-methyl-3-pyridinyl)-4-(2-(2-propenoyl)-2,6-diazaspiro[3.4]octan-6-yl)-3-azatricyclo[7.1.1.0$^{2,7}$]undeca-2,4,6-triene-5-carbonitrile. The stereochemistry of structures was arbitrarily assigned and is not established. 1$^{st}$ eluting atropisomer assigned as the P isomer and 2$^{nd}$ eluting atropisomer assigned as the M isomer.

Atropisomer Separation for Examples 13-125 and 13-126.

The racemic mixture was separated by preparative SFC using a Chiralcel OJ (21×150 mm) column with a mobile phase of 80/liquid $CO_2$ and 20% MeOH using a flowrate of 80 mL/min to provide the respective P and M isomers of (1S,9S)-6-(5-hydroxy-2-methylphenyl)-4-(2-(2-propenoyl)-2,6-diazaspiro[3.4]octan-6-yl)-3-azatricyclo[7.1.1.0$^{2,7}$]undeca-2,4,6-triene-5-carbonitrile. The stereochemistry of structures was arbitrarily assigned and is not established. 1$^{st}$ eluting atropisomer assigned as the M isomer and 2$^{nd}$ eluting atropisomer assigned as the P isomer.

Atropisomer Separation for Examples 13-127 and 13-128.

The racemic mixture was separated by preparative SFC using a Chiralpak AS (21×250 mm, 5 μm) column with a mobile phase of 70% liquid $CO_2$ and 30% MeOH using a flowrate of 80 mL/min to provide the respective P and M isomers of 4-(5-hydroxy-2-methylphenyl)-7,7-dimethyl-2-(2-(2-propenoyl)-2,6-diazaspiro[3.4]octan-6-yl)-7,8-dihydro-5H-pyrano[4,3-b]pyridine-3-carbonitrile. The stereochemistry of structures was arbitrarily assigned and is not established. 1$^{st}$ eluting atropisomer assigned as the M isomer and 2$^{nd}$ eluting atropisomer assigned as the P isomer.

Atropisomer Separation for Examples 13-129 and 13-130.

The racemic mixture was separated by preparative SFC using a Chiralpak AZ (21×250 mm) column with a mobile phase of 65% liquid $CO_2$ and 35% iPrOH with 0.2% TEA using a flowrate of 70 mL/min to provide the respective P and M isomers of (1R,9R)-6-(3-hydroxy-1-naphthalenyl)-10,10-dimethyl-4-(2-(2-propenoyl)-2,6-diazaspiro[3.4]octan-6-yl)-3-azatricyclo[7.1.1.0$^{2,7}$]undeca-2,4,6-triene-5-carbonitrile. The stereochemistry of structures was arbitrarily assigned and is not established. 1$^{st}$ eluting atropisomer assigned as the P isomer and 2$^{nd}$ eluting atropisomer assigned as the M isomer.

Atropisomer Separation for Examples 13-132 and 13-133.

The racemic mixture was separated by preparative SFC using a Chiralcel OX column (21×250 mm) with a mobile phase of 55% liquid $CO_2$ and 45% MeOH using a flowrate of 70 mL/min to provide the respective P and M isomers of (1S,9S)-3-(1,6-dimethyl-1H-indazol-7-yl)-5-(2-(2-propenoyl)-2,6-diazaspiro[3.4]octan-6-yl)-6-azatricyclo[7.1.1.0$^{2,7}$]undeca-2,4,6-triene-4-carbonitrile. The stereochemistry of structures was arbitrarily assigned and is not established. 1$^{st}$ eluting atropisomer assigned as the P isomer and 2$^{nd}$ eluting atropisomer assigned as the M isomer.

Isomer Separation for Examples 13-134 to 13-137.

The racemic mixture was separated by preparative SFC using a Chiralcel OX column (21×250 mm, 5 μm) with a mobile phase of 80% liquid $CO_2$ and 20% iPrOH using a flowrate of 60 mL/min to provide unresolved peak 1 and peak 2 along with separated peak 3 and peak 4. The mixture of peak 1/peak 2 was separated by preparative SFC using a Chiralpak AZ (21×250 mm, 5 μm) column with a mobile phase of 50% liquid $CO_2$ and 50% iPrOH to provide separated peak 1 and peak 2 The stereochemistry of structures was arbitrarily assigned and is not established. 1$^{st}$ eluting isomer assigned as the P,6aR,7aS isomer, 2$^{nd}$ eluting isomer assigned as the P,6aS7aR isomer, 3$^{rd}$ eluting isomer was assigned as the M,6aR,7aS, and the 4$^{th}$ eluting isomer assigned as the M,6aS,7aR isomer of (6a,7a)-4-(1,6-dimethyl-1H-indazol-7-yl)-2-(2-(2-propenoyl)-2,6-diazaspiro[3.4]octan-6-yl)-6,6a,7,7a-tetrahydro-5H-cyclopropa[h]quinoline-3-carbonitrile.

Isomer Separation for Examples 13-140 to 13-142.

The racemic mixture was separated by preparative SFC using a Chiralcel IC column (21×250 mm, 5 μm) with a mobile phase of 60% liquid $CO_2$ and 40% MeOH using a flowrate of 80 mL/min to provide unresolved peak 1 and peak 2 along with unresolved peak 3 and peak 4. The mixture of peak 3/peak 4 was separated by preparative SFC using a Chiralpak ID (21×250 mm, 5 μm) column with a mobile phase of 50% liquid $CO_2$ and 50% MeOH to provide separated peak 3 and peak 4 The stereochemistry of structures was arbitrarily assigned and is not established. The unresolved 1$^{st}$ and 2$^{nd}$ eluting isomers assigned as the P,7S and P,7R isomer, 3$^{rd}$ eluting isomer was assigned as the M,7R, and the 4$^{th}$ eluting isomer assigned as the M,7S isomer of (7)-2-(2-acryloyl-2,6-diazaspiro[3.4]octan-6-yl)-4-(1,6-dimethyl-1H-indazol-7-yl)-7-methyl-7,8-dihydro-5H-pyrano[4,3-b]pyridine-3-carbonitrile.

Atropisomer Separation for Examples 13-145 and 13-150.

The racemic mixture was separated by preparative SFC using a ChiralPak AD-H column with a mobile phase of 70% liquid $CO_2$ and 30% MeOH to provide the respective P and M isomers of 4-(1,6-dimethyl-1H-indazol-7-yl)-7,7-dimethyl-2-(2-(2-propenoyl)-2,6-diazaspiro[3.4]octan-6-yl)-5,6,7,8-tetrahydro-3-quinolinecarbonitrile. The stereochemistry of structures was arbitrarily assigned and is not established. 1$^{st}$ eluting atropisomer assigned as the M isomer and 2$^{nd}$ eluting atropisomer assigned as the P isomer.

Additional Reduction and Chlorination for Example 13-154

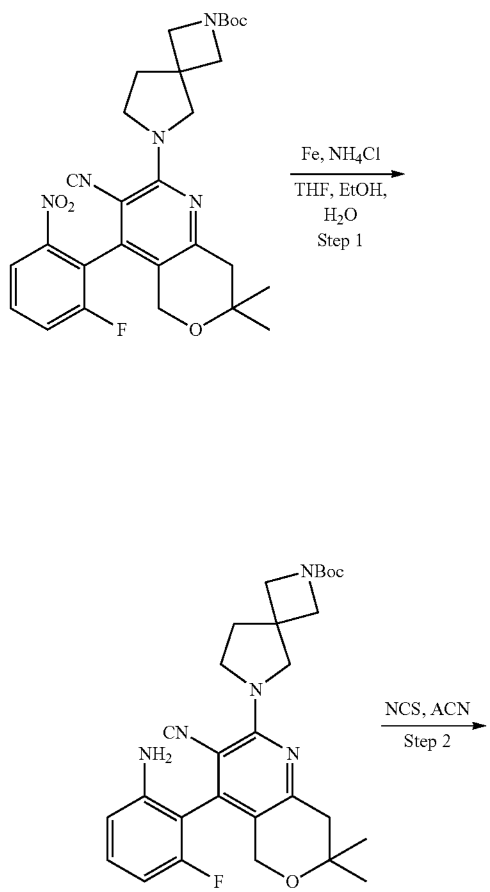

-continued

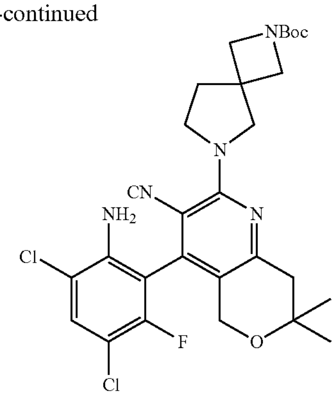

Step 1: tert-butyl 6-(4-(2-amino-6-fluorophenyl)-3-cyano-7,7-dimethyl-7,8-dihydro-5H-pyrano[4,3-b]pyridin-2-yl)-2,6-diazaspiro[3.4]octane-2-carboxylate To a solution of tert-butyl 6-(3-cyano-4-(2-fluoro-6-nitrophenyl)-7,7-dimethyl-7,8-dihydro-5H-pyrano[4,3-b]pyridin-2-yl)-2,6-diazaspiro[3.4]octane-2-carboxylate (100 mg, 0.186 mmol) and THF (1 mL):EtOH (1 mL):water (0.1 mL) was added iron (51.9 mg, 0.930 mmol) and $NH_4Cl$ (49.7 mg, 0.930 mmol). The reaction mixture was heated to 90° C. for 16 h. The reaction was quenched with aqueous saturated $NaHCO_3$, filtered through celite, and extracted with EtOAc (2×20 mL). The organic extract was dried over $Na_2SO_4$ and concentrated in vacuo to give tert-butyl 6-(4-(2-amino-6-fluorophenyl)-3-cyano-7,7-dimethyl-7,8-dihydro-5H-pyrano[4,3-b]pyridin-2-yl)-2,6-diazaspiro[3.4]octane-2-carboxylate as a yellow solid. m/z (ESI): 508.2 $(M+H)^+$.

Step 2: tert-butyl 6-(4-(2-amino-3,5-dichloro-6-fluorophenyl)-3-cyano-7,7-dimethyl-7,8-dihydro-5H-pyrano[4,3-b]pyridin-2-yl)-2,6-diazaspiro[3.4]octane-2-carboxylate To a stirred solution of tert-butyl 6-(4-(2-amino-6-fluorophenyl)-3-cyano-7,7-dimethyl-7,8-dihydro-5H-pyrano[4,3-b]pyridin-2-yl)-2,6-diazaspiro[3.4]octane-2-carboxylate (220 mg, 0.433 mmol) in ACN was added NCS (174 mg, 1.300 mmol). The reaction mixture was stirred at room temperature for 16 h. The reaction mass was quenched with water and extracted with EtOAc (2×20 mL). The organic extracts were dried over $Na_2SO_4$, and concentrated in vacuo to give tert-butyl 6-(4-(2-amino-3,5-dichloro-6-fluorophenyl)-3-cyano-7,7-dimethyl-7,8-dihydro-5H-pyrano[4,3-b]pyridin-2-yl)-2,6-diazaspiro[3.4]octane-2-carboxylate (0.20 g, 80% yield) as an orange oil.

Atropisomer Separation for Examples 13-155 and 13-156.

The racemic mixture was separated by preparative SFC using a Chiralcel OD-H column with a mobile phase of 80% liquid $CO_2$ and 20% MeOH to provide the respective P and M isomers of 4-(2-amino-3,5-dichloro-6-fluorophenyl)-7,7-dimethyl-2-(2-(2-propenoyl)-2,6-diazaspiro[3.4]octan-6-yl)-7,8-dihydro-5H-pyrano[4,3-b]pyridine-3-carbonitrile. The stereochemistry of structures was arbitrarily assigned and is not established. 1$^{st}$ eluting atropisomer assigned as the M isomer and 2$^{nd}$ eluting atropisomer assigned as the P isomer.

Method 14

Example 14-1: 1-(6-((1R,9R)-5-fluoro-6-(3-hydroxy-1-naphthalenyl)-10,10-dimethyl-3-azatricyclo[7.1.1.0$^{2,7}$]undeca-2,4,6-trien-4-yl)-2,6-diazaspiro[3.4]octan-2-yl)-2-propen-1-one

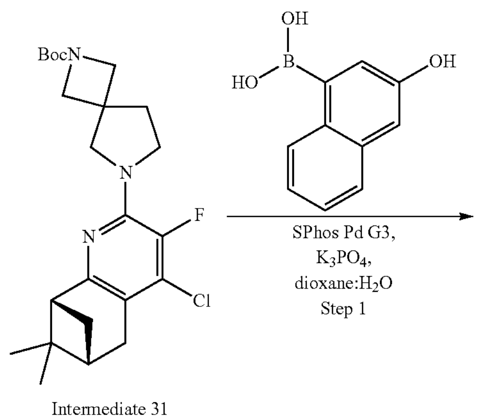

Intermediate 31

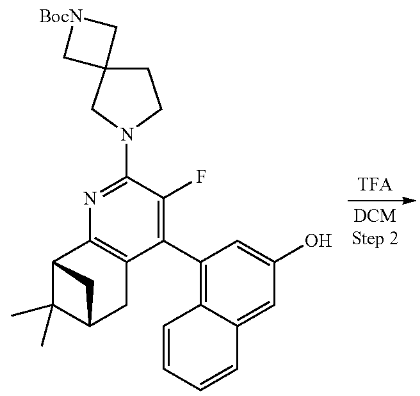

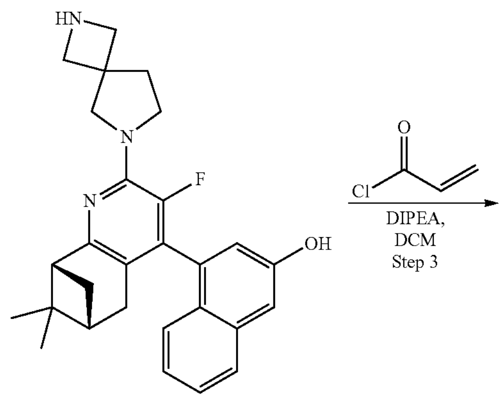

-continued

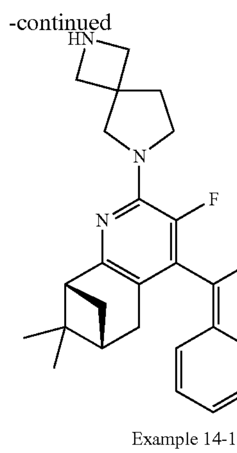

Example 14-1

Step 1: tert-butyl 6-((6R,8R)-3-fluoro-4-(3-hydroxynaphthalen-1-yl)-7,7-dimethyl-5,6,7,8-tetrahydro-6,8-methanoquinolin-2-yl)-2,6-diazaspiro[3.4]octane-2-carboxylate To a 4 mL reaction vial with a stirring bar was added SPhos Pd G3 (38.7 mg, 0.045 mmol, Sigma-Aldrich), $K_3PO_4$ (151 mg, 0.656 mmol, Sigma-Aldrich), 3-hydroxynaphthalene-1-boronic acid (112 mg, 0.596 mmol, eNovation Chemicals), tert-butyl 6-((6R,8R)-4-chloro-3-fluoro-7,7-dimethyl-5,6,7,8-tetrahydro-6,8-methanoquinolin-2-yl)-2,6-diazaspiro[3.4]octane-2-carboxylate (130 mg, 0.298 mmol, Intermediate 31) and 1,4-dioxane (1.8 mL): water (0.18 mL). The reaction mixture was sparged with $N_2$ for 15 min before heating at 95° C. for 1 h. The reaction was quenched by aqueous saturated $NH_4Cl$ (1 mL). The crude material was extracted using EtOAc (3×1 mL), washed with brine, dried over $Na_2SO_4$, and concentrated in vacuo. The crude material was purified using Biotage Sfar HCD 10 g column with acetone in DCM (0-8%) to provide tert-butyl 6-((6R,8R)-3-fluoro-4-(3-hydroxynaphthalen-1-yl)-7,7-dimethyl-5,6,7,8-tetrahydro-6,8-methanoquinolin-2-yl)-2,6-diazaspiro[3.4]octane-2-carboxylate (151 mg, 93% yield). m/z (ESI): 544.2 $(M+H)^+$.

Step 2: 4-((6R,8R)-3-fluoro-7,7-dimethyl-2-(2,6-diazaspiro[3.4]octan-6-yl)-5,6,7,8-tetrahydro-[6,8]methanoquinolin-4-yl)naphthalen-2-ol To a 4-mL reaction vial with a stirring bar was added tert-butyl 6-((6R,8R)-3-fluoro-4-(3-hydroxynaphthalen-1-yl)-7,7-dimethyl-5,6,7,8-tetrahydro-6,8-methanoquinolin-2-yl)-2,6-diazaspiro[3.4]octane-2-carboxylate (145 mg, 0.267 mmol) and TFA (0.4 mL, 5.33 mmol, Sigma-Aldrich) in DCM (2667 μL). The reaction mixture was stirred at room temperature for 3 h and concentrated in vacuo to provide crude 4-((6R,8R)-3-fluoro-7,7-dimethyl-2-(2,6-diazaspiro[3.4]octan-6-yl)-5,6,7,8-tetrahydro-[6,8]methanoquinolin-4-yl)naphthalen-2-ol which was carried forward to the next step as is. m/z (ESI): 444.2 $(M+H)^+$.

Step 3: 1-(6-((6R,8R)-3-fluoro-4-(3-hydroxynaphthalen-1-yl)-7,7-dimethyl-5,6,7,8-tetrahydro-6,8-methanoquinolin-2-yl)-2,6-diazaspiro[3.4]octan-2-yl)prop-2-en-1-one The crude 4-((6R,8R)-3-fluoro-7,7-dimethyl-2-(2,6-diazaspiro[3.4]octan-6-yl)-5,6,7,8-tetrahydro-[6,8]methanoquinolin-4-yl)naphthalen-2-ol was taken up in DCM (1.3 mL) and DIPEA (0.326 mL, 1.867 mmol) and acryloyl chloride (0.2 M in DCM, 1.1 mL, 0.227 mmol) were added and stirred at room temperature for 1 h. The reaction was quenched with aqueous saturated $NaHCO_3$. The reaction was extracted with DCM (3×2 mL), washed with brine, dried over $Na_2SO_4$, and concentrated in vacuo. The crude material was purified using Biotage Sfar HCD 10 g column with EtOAc in heptanes (5-100%) to provide 1-(6-((6R,8R)-3-fluoro-4-(3-hydroxynaphthalen-1-yl)-7,7-dimethyl-5,6,7,8-tetrahydro-6,8-methanoquinolin-2-yl)-2,6-diazaspiro[3.4]octan-2-yl)prop-2-en-1-one (107 mg, 81% yield). m/z (ESI): 498.2 $(M+H)^+$. $^1H$ NMR (400 MHz. $CDCl_3$) δ ppm 7.74-7.79 (m, 1H), 7.38-7.47 (m, 2H), 7.22-7.29 (m, 2H), 6.61-6.91 (m, 1H), 5.48-6.44 (m, 3H), 3.58-4.12 (m, 8H), 2.88-2.97 (m, 1H), 2.59-2.73 (m, 1H), 2.06-2.50 (m, 6H), 1.38 (s, 3H), 0.72-0.81 (m, 3H).

TABLE 6

Examples 14-2 to 14-107 were prepared following the procedure described in Method 14, steps 1-3, above as follows:

| Ex.# | Chemical Structure | Name | Method changes | Reagent |
| --- | --- | --- | --- | --- |
| 14-2 | 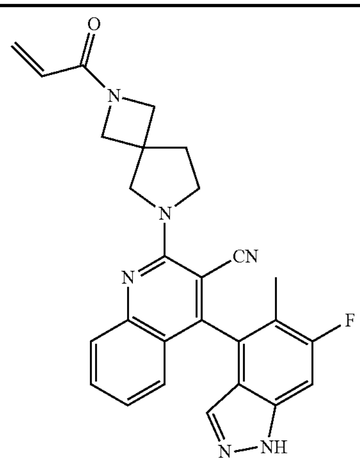 | 4-(6-fluoro-5-methyl-1H-indazol-4-yl)-2-(2-(2-propenoyl)-2,6-diazaspiro[3.4]octan-6-yl)-3-quinolinecarbonitrile | Step 1: RuPhos Pd G3 and $K_2CO_3$ | Step 1: Intermediate 25 and Intermediate 63. |

TABLE 6-continued

Examples 14-2 to 14-107 were prepared following the procedure described in Method 14, steps 1-3, above as follows:

| Ex.# | Chemical Structure | Name | Method changes | Reagent |
|---|---|---|---|---|
| 14-3 | 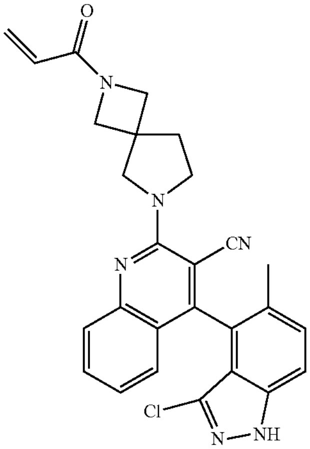 [SMILES: C=CC(=O)N1CC2(CCN(c3nc4ccccc4c(-c4c(C)ccc5[nH]nc(Cl)c45)c3C#N)C2)C1] | 4-(3-chloro-5-methyl-1H-indazol-4-yl)-2-(2-(2-propenoyl)-2,6-diazaspiro[3.4]octan-6-yl)-3-quinolinecarbonitrile | See additional chlorination after step 1 below. | Step 1: Intermediate 25 and 5-methyl-4-(4,4,5,5-tetramethyl-1,3,2-dioxaborolan-2-yl)-1H-indazole |
| 14-4 | 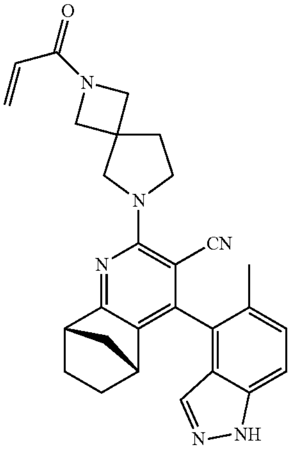 [SMILES: C=CC(=O)N1CC2(CCN(c3nc4c(c(-c5c(C)ccc6[nH]ncc56)c3C#N)[C@@H]3CC[C@H]4C3)C2)C1] | (1S,8R)-6-(5-methyl-1H-indazol-4-yl)-4-(2-(2-propenoyl)-2,6-diazaspiro[3.4]octan-6-yl)-3-azatricyclo[6.2.1.0$^{2,7}$]undeca-2,4,6-triene-5-carbonitrile | | Step 1: Intermediate 54 and 5-methyl-1-(oxan-2-yl)-4-(4,4,5,5-tetramethyl-1,3,2-dioxaborolan-2-yl)-1H-indazole (PharmaBlock) |
| 14-5 | 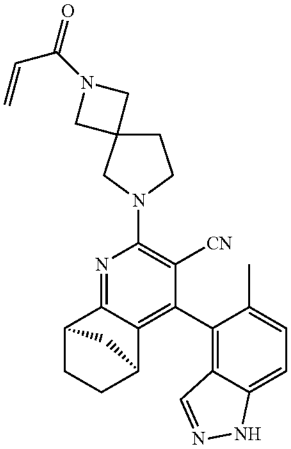 [SMILES: C=CC(=O)N1CC2(CCN(c3nc4c(c(-c5c(C)ccc6[nH]ncc56)c3C#N)[C@H]3CC[C@@H]4C3)C2)C1] | (1R,8S)-6-(5-methyl-1H-indazol-4-yl)-4-(2-(2-propenoyl)-2,6-diazaspiro[3.4]octan-6-yl)-3-azatricyclo[6.2.1.0$^{2,7}$]undeca-2,4,6-triene-5-carbonitrile | | Step 1: Intermediate 55 and 5-methyl-1-(oxan-2-yl)-4-(4,4,5,5-tetramethyl-1,3,2-dioxaborolan-2-yl)-1H-indazole (PharmaBlock) |

TABLE 6-continued

| Examples 14-2 to 14-107 were prepared following the procedure described in Method 14, steps 1-3, above as follows: | | | | |
|---|---|---|---|---|
| Ex.# | Chemical Structure | Name | Method changes | Reagent |
| 14-6 | 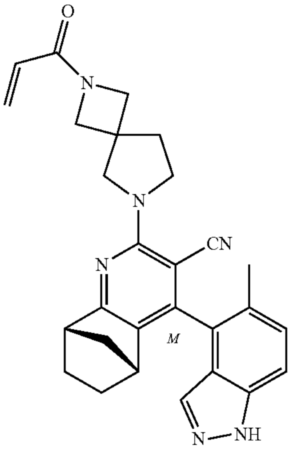 | (M)-(1S,8R)-6-(5-methyl-1H-indazol-4-yl)-4-(2-(2-propenoyl)-2,6-diazaspiro[3.4]octan-6-yl)-3-azatricyclo[6.2.1.0$^{2,7}$]undeca-2,4,6-triene-5-carbonitrile (1$^{st}$ eluting peak) | See below for atropisomer separation conditions. | Step 1: Intermediate 54 and 5-methyl-1-(oxan-2-yl)-4-(4,4,5,5-tetramethyl-1,3,2-dioxaborolan-2-yl)-1H-indazole (PharmaBlock) |
| 14-7 | 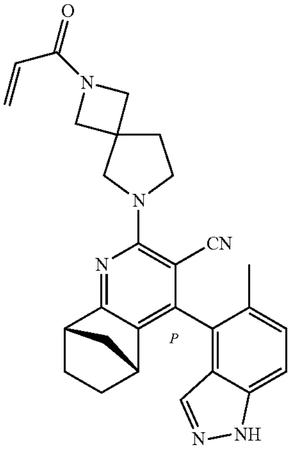 | (P)-(1S,8R)-6-(5-methyl-1H-indazol-4-yl)-4-(2-(2-propenoyl)-2,6-diazaspiro[3.4]octan-6-yl)-3-azatricyclo[6.2.1.0$^{2,7}$]undeca-2,4,6-triene-5-carbonitrile (2$^{nd}$ eluting peak) | See below for atropisomer separation conditions. | Step 1: Intermediate 54 and 5-methyl-1-(oxan-2-yl)-4-(4,4,5,5-tetramethyl-1,3,2-dioxaborolan-2-yl)-1H-indazole (PharmaBlock) |
| 14-8 | 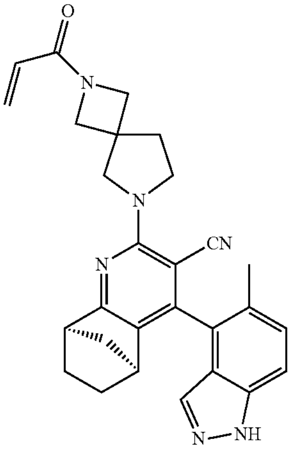 [SMILES: C=CC(=O)N1CC2(CCN(c3nc4c(c(-c5c(C)ccc6[nH]ncc56)c3C#N)[C@H]3CC[C@@H]4C3)C2)C1] | (1R,8S)-6-(5-methyl-1H-indazol-4-yl)-4-(2-(2-propenoyl)-2,6-diazaspiro[3.4]octan-6-yl)-3-azatricyclo[6.2.1.0$^{2,7}$]undeca-2,4,6-triene-5-carbonitrile | See below for atropisomer separation conditions. | Step 1: Intermediate 55 and 5-methyl-1-(oxan-2-yl)-4-(4,4,5,5-tetramethyl-1,3,2-dioxaborolan-2-yl)-1H-indazole (PharmaBlock) |

TABLE 6-continued

Examples 14-2 to 14-107 were prepared following the procedure described in Method 14, steps 1-3, above as follows:

| Ex.# | Chemical Structure | Name | Method changes | Reagent |
|---|---|---|---|---|
| 14-9 | 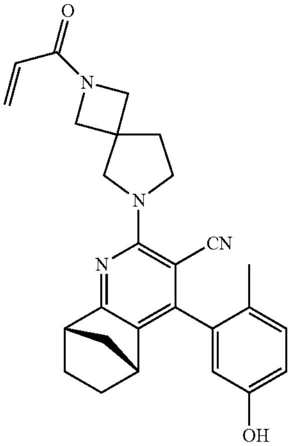 [SMILES: C=CC(=O)N1CC2(CCN(c3nc4c(c(-c5cc(O)ccc5C)c3C#N)[C@@H]3CC[C@H]4C3)C2)C1] | (1R,8S)-6-(5-hydroxy-2-methylphenyl)-4-(2-(2-propenoyl)-2,6-diazaspiro[3.4]octan-6-yl)-3-azatricyclo[6.2.1.0$^{2,7}$]undeca-2,4,6-triene-5-carbonitrile | | Step 1: Intermediate 54 and 5-hydroxy-2-methylphenyl-boronic acid (Aurum Pharmatech) |
| 14-10 | 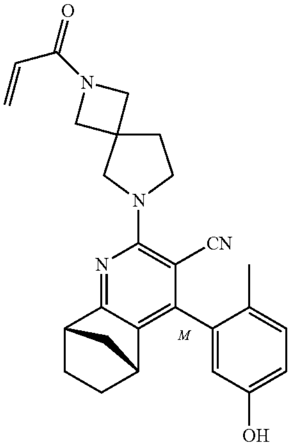 | (M)-(1S,8R)-6-(5-hydroxy-2-methylphenyl)-4-(2-(2-propenoyl)-2,6-diazaspiro[3.4]octan-6-yl)-3-azatricyclo[6.2.1.0$^{2,7}$]undeca-2,4,6-triene-5-carbonitrile (1$^{st}$ eluting peak) | See below for atropisomer separation conditions. | Step 1: Intermediate 54 and 5-hydroxy-2-methylphenyl-boronic acid (Aurum Pharmatech) |
| 14-11 | 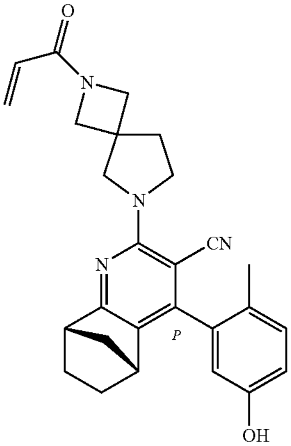 | (P)-(1S,8R)-6-(5-hydroxy-2-methylphenyl)-4-(2-(2-propenoyl)-2,6-diazaspiro[3.4]octan-6-yl)-3-azatricyclo[6.2.1.0$^{2,7}$]undeca-2,4,6-triene-5-carbonitrile (2$^{nd}$ eluting peak) | See below for atropisomer separation conditions. | Step 1: Intermediate 54 and 5-hydroxy-2-methylphenyl-boronic acid (Aurum Pharmatech) |

TABLE 6-continued

Examples 14-2 to 14-107 were prepared following the procedure described in Method 14, steps 1-3, above as follows:

| Ex.# | Chemical Structure | Name | Method changes | Reagent |
|---|---|---|---|---|
| 14-12 | 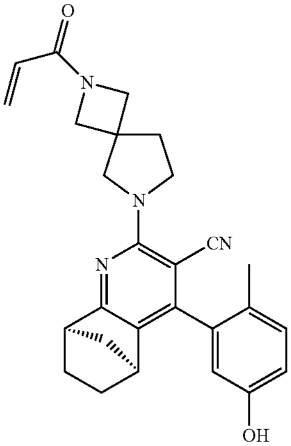 [SMILES: C=CC(=O)N1CC2(CCN(c3nc4c(c(-c5cc(O)ccc5C)c3C#N)[C@H]3CC[C@@H]4C3)C2)C1] | (1R,8S)-6-(5-hydroxy-2-methylphenyl)-4-(2-(2-propenoyl)-2,6-diazaspiro[3.4]octan-6-yl)-3-azatricyclo[6.2.1.0$^{2,7}$]undeca-2,4,6-triene-5-carbonitrile | | Step 1: Intermediate 55 and 5-hydroxy-2-methylphenyl-boronic acid (Aurum Pharmatech) |
| 14-13 | 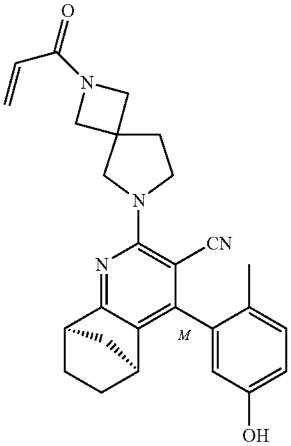 | (M)-(1R,8S)-6-(5-hydroxy-2-methylphenyl)-4-(2-(2-propenoyl)-2,6-diazaspiro[3.4]octan-6-yl)-3-azatricyclo[6.2.1.0$^{2,7}$]undeca-2,4,6-triene-5-carbonitrile (1$^{st}$ eluting peak) | See below for atropisomer separation conditions. | Step 1: Intermediate 55 and 5-hydroxy-2-methylphenyl-boronic acid (Aurum Pharmatech) |
| 14-14 | 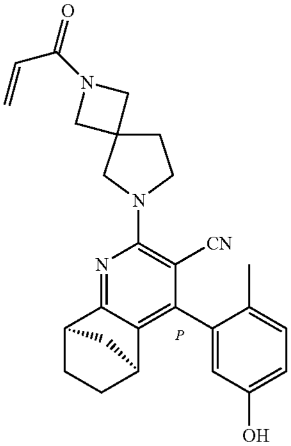 | (P)-(1R,8S)-6-(5-hydroxy-2-methylphenyl)-4-(2-(2-propenoyl)-2,6-diazaspiro[3.4]octan-6-yl)-3-azatricyclo[6.2.1.0$^{2,7}$]undeca-2,4,6-triene-5-carbonitrile (2$^{nd}$ eluting peak) | See below for atropisomer separation conditions. | Step 1: Intermediate 55 and 5-hydroxy-2-methylphenyl-boronic acid (Aurum Pharmatech) |

TABLE 6-continued

Examples 14-2 to 14-107 were prepared following the procedure described in Method 14, steps 1-3, above as follows:

| Ex.# | Chemical Structure | Name | Method changes | Reagent |
| --- | --- | --- | --- | --- |
| 14-15 | 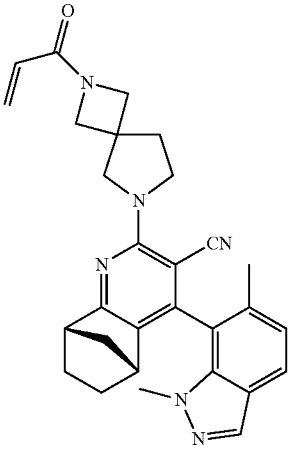 [SMILES: C=CC(=O)N1CC2(CCN(c3nc4c(c(-c5c(C)ccc6cnn(C)c56)c3C#N)[C@@H]3CC[C@H]4C3)C2)C1] | (1S,8R)-6-(1,6-dimethyl-1H-indazol-7-yl)-4-(2-(2-propenoyl)-2,6-diazaspiro[3.4]octan-6-yl)-3-azatricyclo[6.2.1.0$^{2,7}$]undeca-2,4,6-triene-5-carbonitrile | After Step 1, N-methylation was performed using the procedure in Example 2-19 with LiHMDS and MeI. | Step 1: Intermediate 54 and 6-methyl-7-(4,4,5,5-tetramethyl-1,3,2-dioxaborolan-2-yl)-1H-indazole (PharmaBlock) |
| 14-16 | 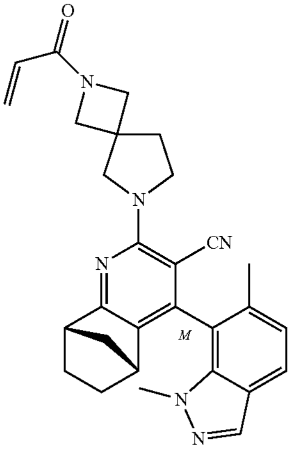 | (M)-(1S,8R)-6-(1,6-dimethyl-1H-indazol-7-yl)-4-(2-(2-propenoyl)-2,6-diazaspiro[3.4]octan-6-yl)-3-azatricyclo[6.2.1.0$^{2,7}$]undeca-2,4,6-triene-5-carbonitrile | After Step 1, N-methylation was performed using the procedure in Example 2-19 with LiHMDS and MeI. | Step 1: Intermediate 54 and 6-methyl-7-(4,4,5,5-tetramethyl-1,3,2-dioxaborolan-2-yl)-1H-indazole (PharmaBlock) |
| 14-17 | 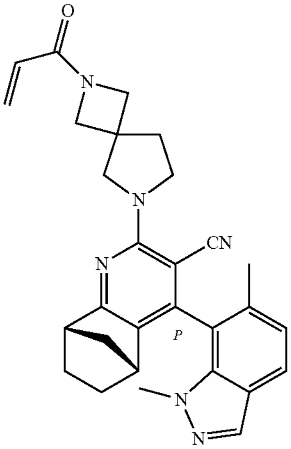 | (P)-(1S,8R)-6-(1,6-dimethyl-1H-indazol-7-yl)-4-(2-(2-propenoyl)-2,6-diazaspiro[3.4]octan-6-yl)-3-azatricyclo[6.2.1.0$^{2,7}$]undeca-2,4,6-triene-5-carbonitrile | After Step 1, N-methylation was performed using the procedure in Example 2-19 with LiHMDS and MeI. | Step 1: Intermediate 54 and 6-methyl-7-(4,4,5,5-tetramethyl-1,3,2-dioxaborolan-2-yl)-1H-indazole (PharmaBlock) |

TABLE 6-continued

| Ex.# | Chemical Structure | Name | Method changes | Reagent |
|---|---|---|---|---|
| Examples 14-2 to 14-107 were prepared following the procedure described in Method 14, steps 1-3, above as follows: | | | | |
| 14-18 | 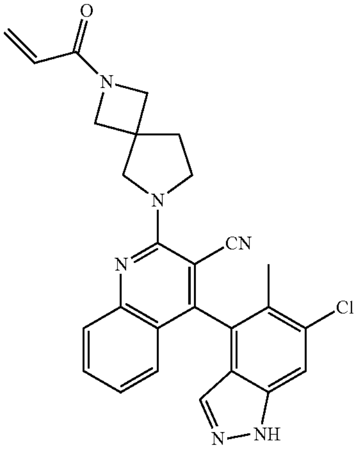 [SMILES: C=CC(=O)N1CC2(CCN(c3nc4ccccc4c(-c4c(C)c(Cl)cc5[nH]ncc45)c3C#N)C2)C1] | 4-(6-chloro-5-methyl-1H-indazol-4-yl)-2-(2-(2-propenoyl)-2,6-diazaspiro[3.4]octan-6-yl)-3-quinolinecarbonitrile | | Step 1: Intermediate 25 and 6-chloro-5-methyl-1-tetrahydropyran-2-yl-4-(4,4,5,5-tetramethyl-1,3,2-dioxaborolan-2-yl)indazole (PharmaBlock). |
| 14-19 | 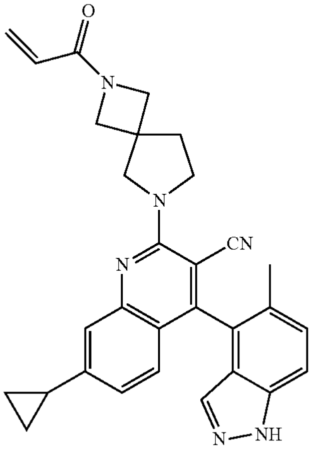 [SMILES: C=CC(=O)N1CC2(CCN(c3nc4cc(C5CC5)ccc4c(-c4c(C)ccc5[nH]ncc45)c3C#N)C2)C1] | 7-cyclopropyl-4-(5-methyl-1H-indazol-4-yl)-2-(2-(2-propenoyl)-2,6-diazaspiro[3.4]octan-6-yl)-3-quinolinecarbonitrile | | Step 1: Intermediate 40 and (5-methyl-1H-indazol-4-yl)boronic acid (Combi-Blocks) |
| 14-20 | 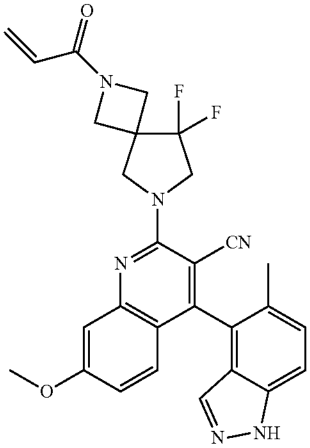 [SMILES: C=CC(=O)N1CC2(C1)CN(c1nc3cc(OC)ccc3c(-c3c(C)ccc4[nH]ncc34)c1C#N)CC2(F)F] | 2-(8,8-difluoro-2-(2-propenoyl)-2,6-diazaspiro[3.4]octan-6-yl)-7-methoxy-4-(5-methyl-1H-indazol-4-yl)-3-quinolinecarbonitrile | | Step 1: Intermediate 41 and (5-methyl-1H-indazol-4-yl)boronic acid (Combi-Blocks) |

TABLE 6-continued

Examples 14-2 to 14-107 were prepared following the procedure described in Method 14, steps 1-3, above as follows:

| Ex.# | Chemical Structure | Name | Method changes | Reagent |
|---|---|---|---|---|
| 14-21 | 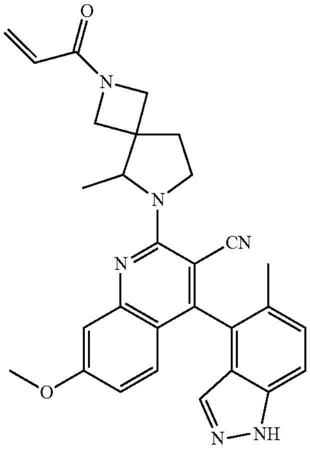 [SMILES: C=CC(=O)N1CC2(CCN(c3nc4cc(OC)ccc4c(-c4c(C)ccc5[nH]ncc45)c3C#N)C2C)C1] | 7-methoxy-4-(5-methyl-1H-indazol-4-yl)-2-((5R)-5-methyl-2-(2-propenoyl)-2,6-diazaspiro[3.4]octan-6-yl)-3-quinolinecarbonitrile\|7-methoxy-4-(5-methyl-1H-indazol-4-yl)-2-((5S)-5-methyl-2-(2-propenoyl)-2,6-diazaspiro[3.4]octan-6-yl)-3-quinolinecarbonitrile | | Step 1: Intermediate 42 and (5-methyl-1H-indazol-4-yl)boronic acid (Combi-Blocks) |
| 14-22 | 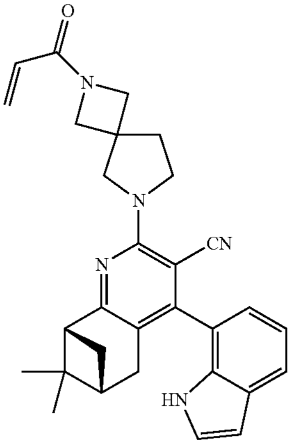 [SMILES: C=CC(=O)N1CC2(CCN(c3nc4c(c(-c5cccc6cc[nH]c56)c3C#N)C[C@H]3C[C@@H]4C3(C)C)C2)C1] | (1R,9R)-6-(1H-indol-7-yl)-10,10-dimethyl-4-(2-(2-propenoyl)-2,6-diazaspiro[3.4]octan-6-yl)-3-azatricyclo[7.1.1.0$^{2,7}$]undeca-2,4,6-triene-5-carbonitrile | | Step 1: Intermediate 35 and indole-7-boronic acid (Combi-Blocks) |
| 14-23 | 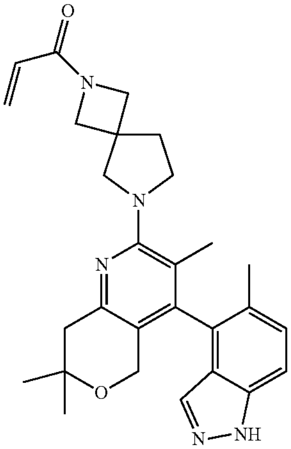 [SMILES: C=CC(=O)N1CC2(CCN(c3nc4c(c(-c5c(C)ccc6[nH]ncc56)c3C)COC(C)(C)C4)C2)C1] | 1-(6-(3,7,7-trimethyl-4-(5-methyl-1H-indazol-4-yl)-7,8-dihydro-5H-pyrano[4,3-b]pyridin-2-yl)-2,6-diazaspiro[3.4]octan-2-yl)-2-propen-1-one | | Step 1: Intermediate 26 and (5-methyl-1H-indazol-4-yl)boronic acid pinacol ester (Combi-Blocks) |

TABLE 6-continued

| Ex.# | Chemical Structure | Name | Method changes | Reagent |
|---|---|---|---|---|
| | Examples 14-2 to 14-107 were prepared following the procedure described in Method 14, steps 1-3, above as follows: | | | |
| 14-24 | 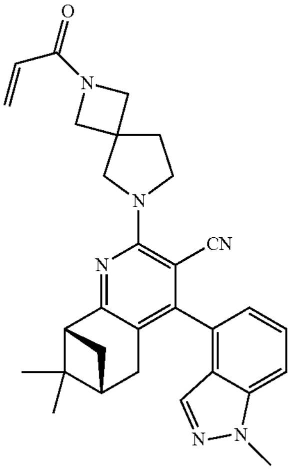 [SMILES: C=CC(=O)N1CC2(CCN(c3nc4c(c(-c5cccc6c5cnn6C)c3C#N)C[C@H]3C[C@@H]4C3(C)C)C2)C1] | (1R,9R)-10,10-dimethyl-6-(1-methyl-1H-indazol-4-yl)-4-(2-(2-propenoyl)-2,6-diazaspiro[3.4]octan-6-yl)-3-azatricyclo[7.1.1.0$^{2,7}$]undeca-2,4,6-triene-5-carbonitrile | | Step 1: Intermediate 35 and 1-methyl-1H-indazole-4-boronic acid pinacol ester (Combi-Blocks) |
| 14-25 | 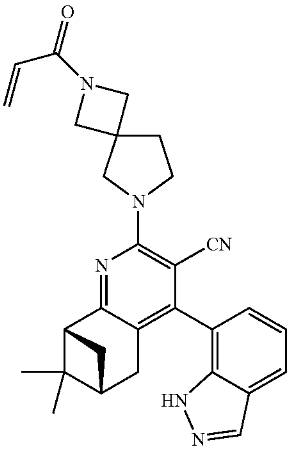 [SMILES: C=CC(=O)N1CC2(CCN(c3nc4c(c(-c5cccc6cn[nH]c56)c3C#N)C[C@H]3C[C@@H]4C3(C)C)C2)C1] | (1R,9R)-6-(1H-indazol-7-yl)-10,10-dimethyl-4-(2-(2-propenoyl)-2,6-diazaspiro[3.4]octan-6-yl)-3-azatricyclo[7.1.1.0$^{2,7}$]undeca-2,4,6-triene-5-carbonitrile | | Step 1: Intermediate 35 and 1H-indazol-7-ylboronic acid (Combi-Blocks) |
| 14-26 | 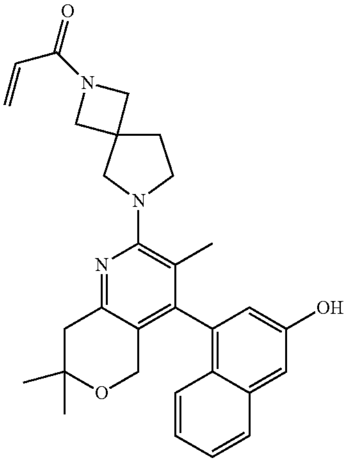 [SMILES: C=CC(=O)N1CC2(CCN(c3nc4c(c(-c5cc(O)cc6ccccc56)c3C)COC(C)(C)C4)C2)C1] | 1-(6-(4-(3-hydroxy-1-naphthalenyl)-3,7,7-trimethyl-7,8-dihydro-5H-pyrano[4,3-b]pyridin-2-yl)-2,6-diazaspiro[3.4]octan-2-yl)-2-propen-1-one | | Step 1: Intermediate 26 and 3-hydroxynaphthalene-1-boronic acid (eNovation Chemicals LLC) |

TABLE 6-continued

| Examples 14-2 to 14-107 were prepared following the procedure described in Method 14, steps 1-3, above as follows: | | | | |
|---|---|---|---|---|
| Ex.# | Chemical Structure | Name | Method changes | Reagent |
| 14-27 | 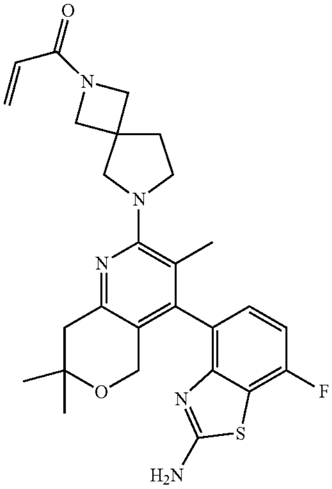 [SMILES: C=CC(=O)N1CC2(CCN(c3nc4c(c(-c5ccc(F)c6sc(N)nc56)c3C)COC(C)(C)C4)C2)C1] | 1-(6-(4-(2-amino-7-fluoro-1,3-benzothiazol-4-yl)-3,7,7-trimethyl-7,8-dihydro-5H-pyrano[4,3-b]pyridin-2-yl)-2,6-diazaspiro[3.4]octan-2-yl)-2-propen-1-one | | Step 1: Intermediate 26 and (2-((tert-butoxycarbonyl) amino)-7-fluorobenzo[d] thiazol-4-yl)boronic acid (PharmaBlock) |
| 14-28 | 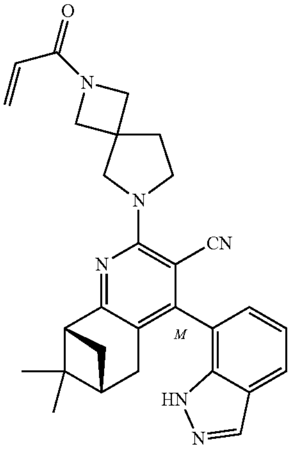 | (M)-(1R,9R)-6-(1H-indazol-7-yl)-10,10-dimethyl-4-(2-(2-propenoyl)-2,6-diazaspiro[3.4]octan-6-yl)-3-azatricyclo[7.1.1.$0^{2,7}$] undeca-2,4,6-triene-5-carbonitrile ($1^{st}$ eluting peak) | See below for atropisomer separation conditions. | Step 1: Intermediate 35 and 1H-indazol-7-ylboronic acid (Combi-Blocks) |
| 14-29 | 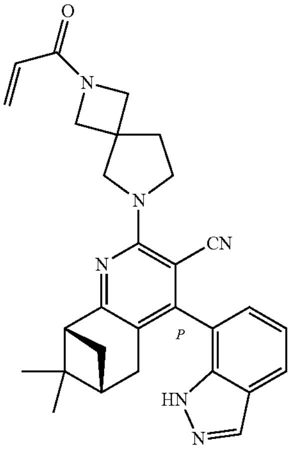 | (P)-(1R,9R)-6-(1H-indazol-7-yl)-10,10-dimethyl-4-(2-(2-propenoyl)-2,6-diazaspiro[3.4]octan-6-yl)-3-azatricyclo[7.1.1.$0^{2,7}$] undeca-2,4,6-triene-5-carbonitrile ($2^{nd}$ eluting peak) | See below for atropisomer separation conditions. | Step 1: Intermediate 35 and 1H-indazol-7-ylboronic acid (Combi-Blocks) |

TABLE 6-continued

| Ex.# | Chemical Structure | Name | Method changes | Reagent |
|---|---|---|---|---|
| Examples 14-2 to 14-107 were prepared following the procedure described in Method 14, steps 1-3, above as follows: | | | | |
| 14-30 | 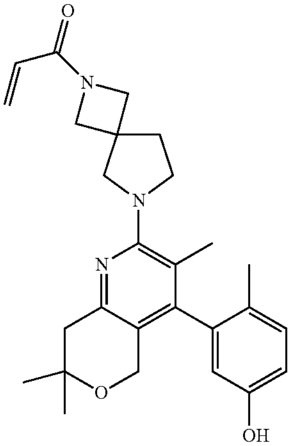 [SMILES: C=CC(=O)N1CC2(CCN(c3nc4c(c(-c5cc(O)ccc5C)c3C)COC(C)(C)C4)C2)C1] | 1-(6-(4-(5-hydroxy-2-methylphenyl)-3,7,7-trimethyl-7,8-dihydro-5H-pyrano[4,3-b]pyridin-2-yl)-2,6-diazaspiro[3.4]octan-2-yl)-2-propen-1-one | | Step 1: Intermediate 26 and (5-hydroxy-2-methylphenyl) boronic acid (Aurum) |
| 14-31 | 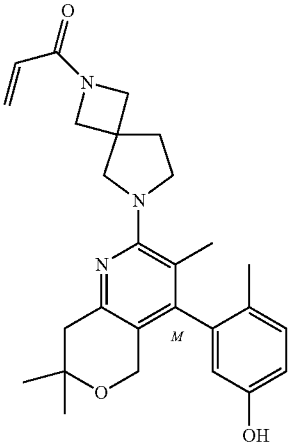 | (M)-1-(6-(4-(5-hydroxy-2-methylphenyl)-3,7,7-trimethyl-7,8-dihydro-5H-pyrano[4,3-b]pyridin-2-yl)-2,6-diazaspiro[3.4]octan-2-yl)-2-propen-1-one (1st eluting peak) | See below for atropisomer separation conditions. | Step 1: Intermediate 26 and (5-hydroxy-2-methylphenyl) boronic acid (Aurum) |
| 14-32 | 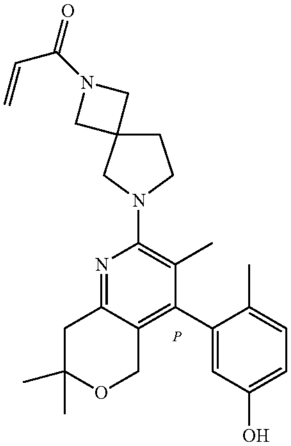 | (P)-1-(6-(4-(5-hydroxy-2-methylphenyl)-3,7,7-trimethyl-7,8-dihydro-5H-pyrano[4,3-b]pyridin-2-yl)-2,6-diazaspiro[3.4]octan-2-yl)-2-propen-1-one (2nd eluting peak) | See below for atropisomer separation conditions. | Step 1: Intermediate 26 and (5-hydroxy-2-methylphenyl) boronic acid (Aurum) |

TABLE 6-continued

Examples 14-2 to 14-107 were prepared following the procedure described in Method 14, steps 1-3, above as follows:

| Ex.# | Chemical Structure | Name | Method changes | Reagent |
|---|---|---|---|---|
| 14-33 | 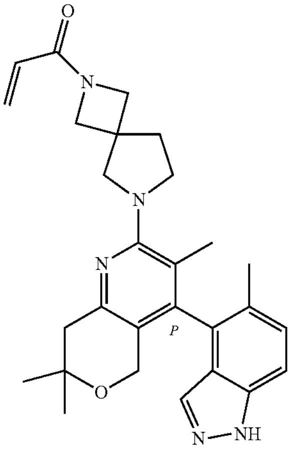 | (P)-1-(6-(3,7,7-trimethyl-4-(5-methyl-1H-indazol-4-yl)-7,8-dihydro-5H-pyrano[4,3-b]pyridin-2-yl)-2,6-diazaspiro[3.4]octan-2-yl)-2-propen-1-one (1st eluting peak) | See below for atropisomer separation conditions. | Step 1: Intermediate 26 and (5-methyl-1H-indazol-4-yl)boronic acid (Combi-Blocks) |
| 14-34 | 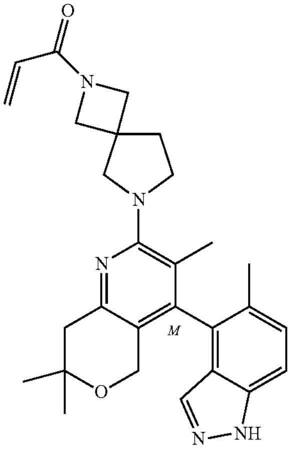 | (M)-1-(6-(3,7,7-trimethyl-4-(5-methyl-1H-indazol-4-yl)-7,8-dihydro-5H-pyrano[4,3-b]pyridin-2-yl)-2,6-diazaspiro[3.4]octan-2-yl)-2-propen-1-one (2nd eluting peak) | See below for atropisomer separation conditions. | Step 1: Intermediate 26 and (5-methyl-1H-indazol-4-yl)boronic acid (Combi-Blocks) |
| 14-35 | 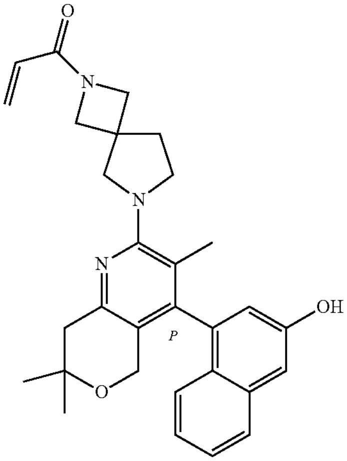 | (P)-1-(6-(4-(3-hydroxy-1-naphthalenyl)-3,7,7-trimethyl-7,8-dihydro-5H-pyrano[4,3-b]pyridin-2-yl)-2,6-diazaspiro[3.4]octan-2-yl)-2-propen-1-one (2nd eluting peak) | See below for atropisomer separation conditions. | Step 1: Intermediate 26 and 3-hydroxy-naphthalene-1-boronic acid (eNovation Chemicals) |

TABLE 6-continued

| Examples 14-2 to 14-107 were prepared following the procedure described in Method 14, steps 1-3, above as follows: | | | | |
|---|---|---|---|---|
| Ex.# | Chemical Structure | Name | Method changes | Reagent |
| 14-36 | 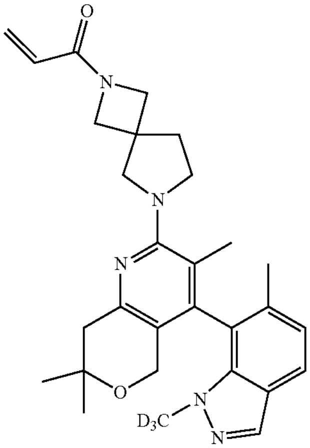 [SMILES: [2H]C([2H])([2H])n1ncc2ccc(C)c(-c3c(C)c(N4CCC5(CN(C(=O)C=C)C5)C4)nc4c3COC(C)(C)C4)c21] | 1-(6-(3,7,7-trimethyl-4-(6-methyl-1-($^2H_3$)methyl-1H-indazol-7-yl)-7,8-dihydro-5H-pyrano[4,3-b]pyridin-2-yl)-2,6-diazaspiro[3.4]octan-2-yl)-2-propen-1-one | After Step 1, N-methylation was performed using the procedure in Example 2-19 with LiHMDS and $CD_3I$ | Step 1: Intermediate 26 and 6-methyl-7-(4,4,5,5-tetramethyl-1,3,2-dioxaborolan-2-yl)-1H-indazole (Synnovator) |
| 14-37 | 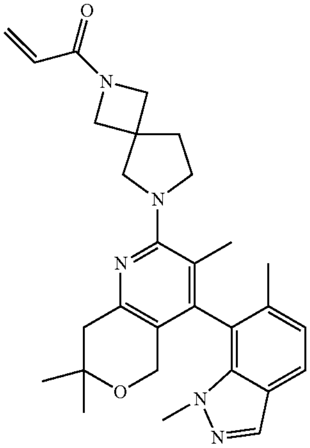 [SMILES: C=CC(=O)N1CC2(CCN(c3nc4c(c(-c5c(C)ccc6cnn(C)c56)c3C)COC(C)(C)C4)C2)C1] | 1-(6-(4-(1,6-dimethyl-1H-indazol-7-yl)-3,7,7-trimethyl-7,8-dihydro-5H-pyrano[4,3-b]pyridin-2-yl)-2,6-diazaspiro[3.4]octan-2-yl)-2-propen-1-one | After Step 1, N-methylation was performed using the procedure in Example 2-19 with LiHMDS and MeI. | Step 1: Intermediate 26 and 6-methyl-7-(4,4,5,5-tetramethyl-1,3,2-dioxaborolan-2-yl)-1H-indazole (Synnovator) |
| 14-38 | 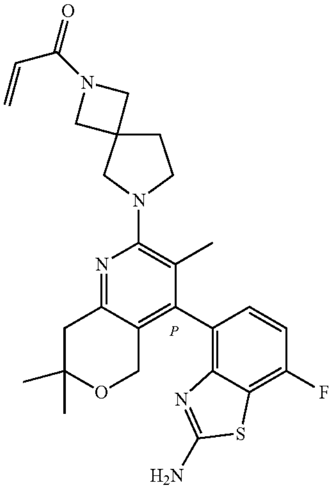 | (P)-1-(6-(4-(2-amino-7-fluoro-1,3-benzothiazol-4-yl)-3,7,7-trimethyl-7,8-dihydro-5H-pyrano[4,3-b]pyridin-2-yl)-2,6-diazaspiro[3.4]octan-2-yl)-2-propen-1-one (1st eluting peak) | See below for atropisomer separation conditions. | Step 1: Intermediate 26 and (2-((tert-butoxycarbonyl)amino)-7-fluorobenzo[d]thiazol-4-yl)boronic acid (PharmaBlock) |

TABLE 6-continued

| Examples 14-2 to 14-107 were prepared following the procedure described in Method 14, steps 1-3, above as follows: | | | | |
|---|---|---|---|---|
| Ex.# | Chemical Structure | Name | Method changes | Reagent |
| 14-39 | 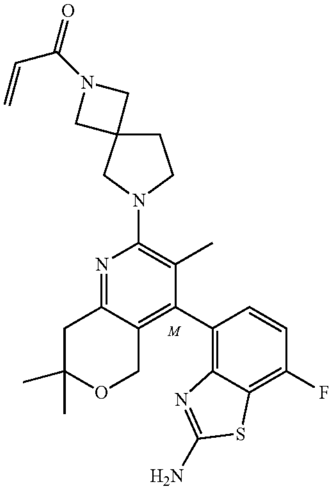 | (M)-1-(6-(4-(2-amino-7-fluoro-1,3-benzothiazol-4-yl)-3,7,7-trimethyl-7,8-dihydro-5H-pyrano[4,3-b]pyridin-2-yl)-2,6-diazaspiro[3.4]octan-2-yl)-2-propen-1-one ($2^{nd}$ eluting peak) | See below for atropisomer separation conditions. | Step 1: Intermediate 26 and (2-((tert-butoxycarbonyl) amino)-7-fluorobenzo[d] thiazol-4-yl)boronic acid (PharmaBlock) |
| 14-40 | 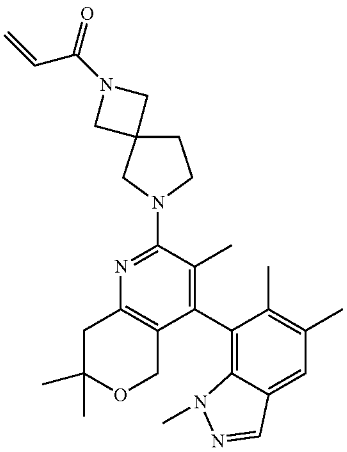 [SMILES: C=CC(=O)N1CC2(CCN(c3nc4c(c(-c5c(C)c(C)cc6cnn(C)c56)c3C)COC(C)(C)C4)C2)C1] | 1-(6-(3,7,7-trimethyl-4-(1,5,6-trimethyl-1H-indazol-7-yl)-7,8-dihydro-5H-pyrano[4,3-b]pyridin-2-yl)-2,6-diazaspiro[3.4]octan-2-yl)-2-propen-1-one | After Step 1, N-methylation was performed using the procedure in Example 2-19 with LiHMDS and MeI. | Step 1: Intermediate 26 and Intermediate 38. |
| 14-41 | 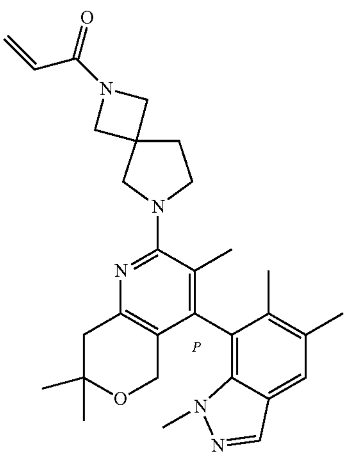 | (P)-1-(6-(3,7,7-trimethyl-4-(1,5,6-trimethyl-1H-indazol-7-yl)-7,8-dihydro-5H-pyrano[4,3-b]pyridin-2-yl)-2,6-diazaspiro[3.4]octan-2-yl)-2-propen-1-one ($2^{nd}$ eluting peak) | After Step 1, N-methylation was performed using the procedure in Example 2-19 with LiHMDS and MeI. See below for atropisomer separation conditions. | Step 1: Intermediate 26 and Intermediate 38. |

TABLE 6-continued

| Examples 14-2 to 14-107 were prepared following the procedure described in Method 14, steps 1-3, above as follows: | | | | |
|---|---|---|---|---|
| Ex.# | Chemical Structure | Name | Method changes | Reagent |
| 14-42 | 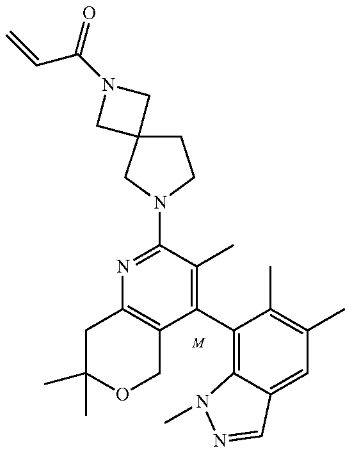 | (M)-1-(6-(3,7,7-trimethyl-4-(1,5,6-trimethyl-1H-indazol-7-yl)-7,8-dihydro-5H-pyrano[4,3-b]pyridin-2-yl)-2,6-diazaspiro[3.4]octan-2-yl)-2-propen-1-one (1$^{st}$ eluting peak) | After Step 1, N-methylation was performed using the procedure in Example 2-19 with LiHMDS and MeI. See below for atropisomer separation conditions. | Step 1: Intermediate 26 and Intermediate 38. |
| 14-43 | 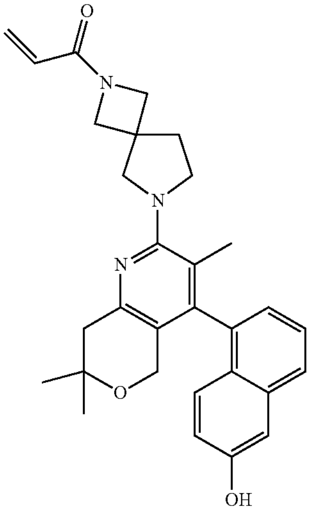 [SMILES: C=CC(=O)N1CC2(CCN(c3nc4c(c(-c5cccc6cc(O)ccc56)c3C)COC(C)(C)C4)C2)C1] | 1-(6-(4-(6-hydroxy-1-naphthalenyl)-3,7,7-trimethyl-7,8-dihydro-5H-pyrano[4,3-b]pyridin-2-yl)-2,6-diazaspiro[3.4]octan-2-yl)-2-propen-1-one | | Step 1: Intermediate 26 and Intermediate 65 |
| 14-44 | 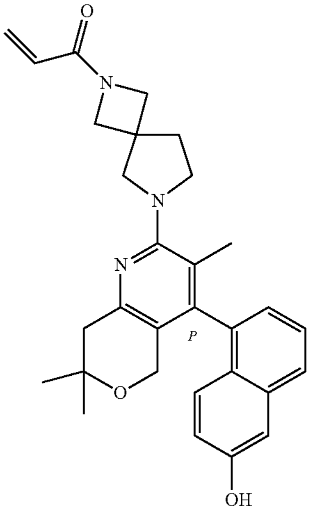 | (P)-1-(6-(4-(6-hydroxy-1-naphthalenyl)-3,7,7-trimethyl-7,8-dihydro-5H-pyrano[4,3-b]pyridin-2-yl)-2,6-diazaspiro[3.4]octan-2-yl)-2-propen-1-one (1$^{st}$ eluting peak) | See below for atropisomer separation conditions. | Step 1: Intermediate 26 and Intermediate 65 |

TABLE 6-continued

Examples 14-2 to 14-107 were prepared following the procedure described in Method 14, steps 1-3, above as follows:

| Ex.# | Chemical Structure | Name | Method changes | Reagent |
| --- | --- | --- | --- | --- |
| 14-45 | 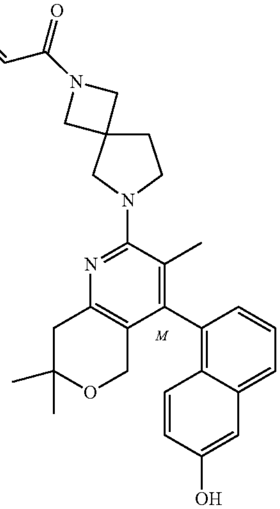 | (M)-1-(6-(4-(6-hydroxy-1-naphthalenyl)-3,7,7-trimethyl-7,8-dihydro-5H-pyrano[4,3-b]pyridin-2-yl)-2,6-diazaspiro[3.4]octan-2-yl)-2-propen-1-one (2nd eluting peak) | See below for atropisomer separation conditions. | Step 1: Intermediate 26 and Intermediate 65 |
| 14-46 | 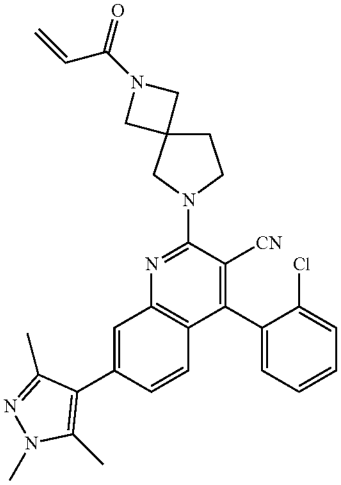 [SMILES: C=CC(=O)N1CC2(CCN(c3nc4cc(-c5c(C)nn(C)c5C)ccc4c(-c4ccccc4Cl)c3C#N)C2)C1] | 4-(2-chlorophenyl)-2-(2-(2-propenoyl)-2,6-diazaspiro[3.4]octan-6-yl)-7-(1,3,5-trimethyl-1H-pyrazol-4-yl)-3-quinolinecarbonitrile | Step 1b: Repeat step 1 procedure | Step 1: Intermediate 43 and 2-chlorophenyl-boronic acid (Matrix Scientific); Step 1b: 1,3,5-trimethyl-4-(4,4,5,5-tetramethyl-1,3,2 dioxaborolan-2-yl)-1H-pyrazole (Boron Molecular) |
| 14-47 | 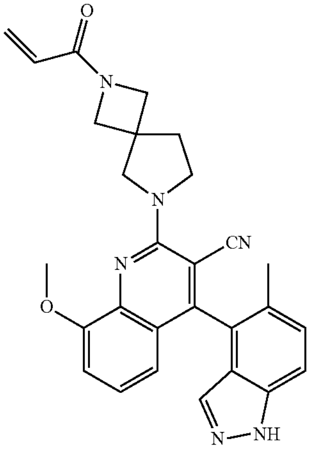 [SMILES: C=CC(=O)N1CC2(CCN(c3nc4c(OC)cccc4c(-c4c(C)ccc5[nH]ncc45)c3C#N)C2)C1] | 8-methoxy-4-(5-methyl-1H-indazol-4-yl)-2-(2-(2-propenoyl)-2,6-diazaspiro[3.4]octan-6-yl)-3-quinolinecarbonitrile | Step 1: Used $PdCl_2$(dppf) and $K_2CO_3$ | Step 1: Intermediate 66 and 5-methyl-1-(oxan-2-yl)-4-(4,4,5,5-tetramethyl-1,3,2-dioxaborolan-2-yl)-1H-indazole (PharmaBlock) |

TABLE 6-continued

Examples 14-2 to 14-107 were prepared following the procedure described in Method 14, steps 1-3, above as follows:

| Ex.# | Chemical Structure | Name | Method changes | Reagent |
|---|---|---|---|---|
| 14-48 | 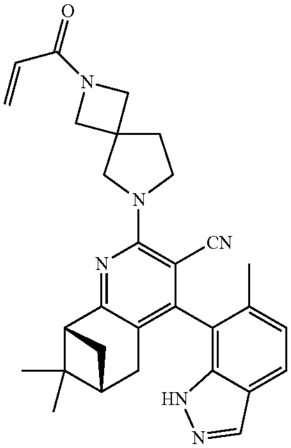 [SMILES: C=CC(=O)N1CC2(CCN(c3nc4c(c(-c5c(C)ccc6cn[nH]c56)c3C#N)C[C@H]3C[C@@H]4C3(C)C)C2)C1] | (1R,9R)-10,10-dimethyl-6-(6-methyl-1H-indazol-7-yl)-4-(2-(2-propenoyl)-2,6-diazaspiro[3.4]octan-6-yl)-3-azatricyclo[7.1.1.0$^{2,7}$]undeca-2,4,6-triene-5-carbonitrile | | Step 1: Intermediate 35 and 6-methyl-7-(4,4,5,5-tetramethyl-1,3,2-dioxaborolan-2-yl)-1H-indazole (Synnovator) |
| 14-49 | 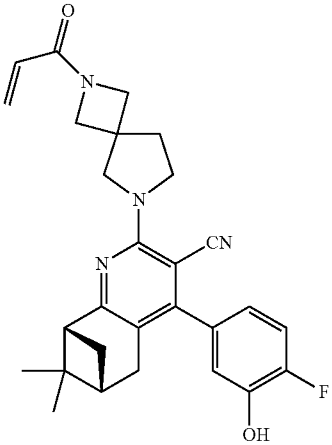 [SMILES: C=CC(=O)N1CC2(CCN(c3nc4c(c(-c5ccc(F)c(O)c5)c3C#N)C[C@H]3C[C@@H]4C3(C)C)C2)C1] | (1R,9R)-6-(4-fluoro-3-hydroxyphenyl)-10,10-dimethyl-4-(2-(2-propenoyl)-2,6-diazaspiro[3.4]octan-6-yl)-3-azatricyclo[7.1.1.0$^{2,7}$]undeca-2,4,6-triene-5-carbonitrile | See alternate step 2 below | Step 1: Intermediate 35 and 2-chloro-4-fluoro-5-methoxyphenyl-boronic acid (Combi-Blocks) |
| 14-50 | 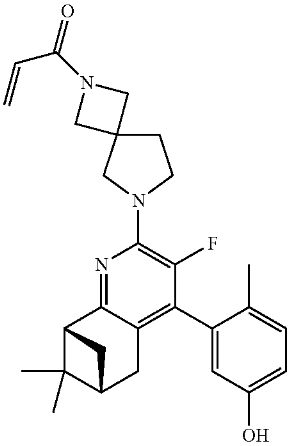 [SMILES: C=CC(=O)N1CC2(CCN(c3nc4c(c(-c5cc(O)ccc5C)c3F)C[C@H]3C[C@@H]4C3(C)C)C2)C1] | 1-(6-((1R,9R)-5-fluoro-6-(5-hydroxy-2-methylphenyl)-10,10-dimethyl-3-azatricyclo[7.1.1.0$^{2,7}$]undeca-2,4,6-trien-4-yl)-2,6-diazaspiro[3.4]octan-2-yl)-2-propen-1-one | | Step 1: Intermediate 31 and 5-hydroxy-2-methylphenyl-boronic acid (Combi-Blocks) |

TABLE 6-continued

Examples 14-2 to 14-107 were prepared following the procedure described in Method 14, steps 1-3, above as follows:

| Ex.# | Chemical Structure | Name | Method changes | Reagent |
|---|---|---|---|---|
| 14-51 | 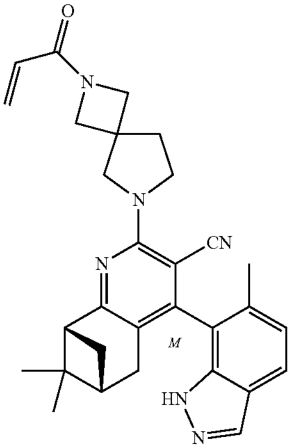 | (M)-(1R,9R)-10,10-dimethyl-6-(6-methyl-1H-indazol-7-yl)-4-(2-(2-propenoyl)-2,6-diazaspiro[3.4]octan-6-yl)-3-azatricyclo[7.1.1.0$^{2,7}$]undeca-2,4,6-triene-5-carbonitrile (1$^{st}$ eluting isomer) | See below for atropisomer separation conditions. | Step 1: Intermediate 35 and 6-methyl-7-(4,4,5,5-tetramethyl-1,3,2-dioxaborolan-2-yl)-1H-indazole (Synnovator) |
| 14-52 | 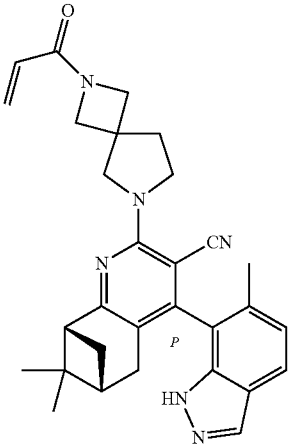 | (P)-(1R,9R)-10,10-dimethyl-6-(6-methyl-1H-indazol-7-yl)-4-(2-(2-propenoyl)-2,6-diazaspiro[3.4]octan-6-yl)-3-azatricyclo[7.1.1.0$^{2,7}$]undeca-2,4,6-triene-5-carbonitrile (2$^{nd}$ eluting isomer) | See below for atropisomer separation conditions. | Step 1: Intermediate 35 and 6-methyl-7-(4,4,5,5-tetramethyl-1,3,2 dioxaborolan-2-yl)-1H-indazole (Synnovator) |
| 14-53 | 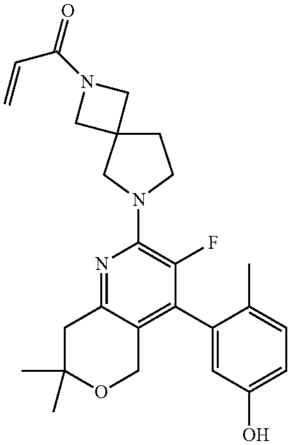 [SMILES: C=CC(=O)N1CC2(CCN(c3nc4c(c(-c5cc(O)ccc5C)c3F)COC(C)(C)C4)C2)C1] | 1-(6-(3-fluoro-4-(5-hydroxy-2-methylphenyl)-7,7-dimethyl-7,8-dihydro-5H-pyrano[4,3-b]pyridin-2-yl)-2,6-diazaspiro[3.4]octan-2-yl)-2-propen-1-one | | Step 1: Intermediate 30 and 5-hydroxy-2-methylphenyl-boronic acid (Combi-Blocks) |

TABLE 6-continued

Examples 14-2 to 14-107 were prepared following the procedure described in Method 14, steps 1-3, above as follows:

| Ex.# | Chemical Structure | Name | Method changes | Reagent |
|---|---|---|---|---|
| 14-54 | 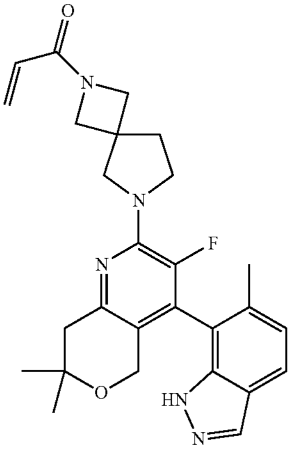 [SMILES: C=CC(=O)N1CC2(CCN(c3nc4c(c(-c5c(C)ccc6cn[nH]c56)c3F)COC(C)(C)C4)C2)C1] | 1-(6-(3-fluoro-7,7-dimethyl-4-(6-methyl-1H-indazol-7-yl)-7,8-dihydro-5H-pyrano[4,3-b]pyridin-2-yl)-2,6-diazaspiro[3.4]octan-2-yl)-2-propen-1-one | | Step 1: Intermediate 30 and 6-methyl-7-(4,4,5,5-tetramethyl-1,3,2-dioxaborolan-2-yl)-1H-indazole (Synnovator) |
| 14-55 | 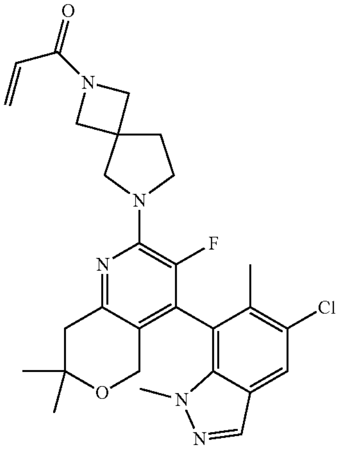 [SMILES: C=CC(=O)N1CC2(CCN(c3nc4c(c(-c5c(C)c(Cl)cc6cnn(C)c56)c3F)COC(C)(C)C4)C2)C1] | 1-(6-(4-(5-chloro-1,6-dimethyl-1H-indazol-7-yl)-3-fluoro-7,7-dimethyl-7,8-dihydro-5H-pyrano[4,3-b]pyridin-2-yl)-2,6-diazaspiro[3.4]octan-2-yl)-2-propen-1-one | After Step 1, N-methylation was performed using the procedure in Example 2-19 with LiHMDS and MeI. | Step 1: Intermediate 30 and Intermediate 37 |
| 14-56 | 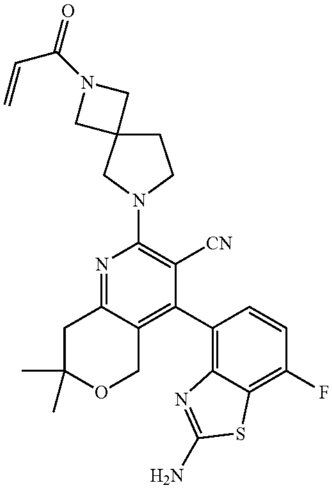 [SMILES: C=CC(=O)N1CC2(CCN(c3nc4c(c(-c5ccc(F)c6sc(N)nc56)c3C#N)COC(C)(C)C4)C2)C1] | 4-(2-amino-7-fluoro-1,3-benzothiazol-4-yl)-7,7-dimethyl-2-(2-(2-propenoyl)-2,6-diazaspiro[3.4]octan-6-yl)-7,8-dihydro-5H-pyrano[4,3-b]pyridine-3-carbonitrile | | Step 1: Intermediate 34 and (2-((tert-butoxycarbonyl)amino)-7-fluorobenzo[d]thiazol-4-yl)boronic acid (PharmaBlock) |

TABLE 6-continued

| Examples 14-2 to 14-107 were prepared following the procedure described in Method 14, steps 1-3, above as follows: | | | | |
|---|---|---|---|---|
| Ex.# | Chemical Structure | Name | Method changes | Reagent |
| 14-57 | 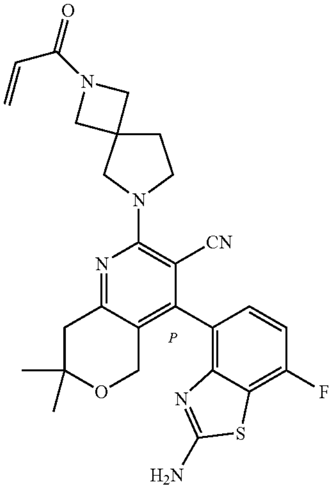 | (P)-4-(2-amino-7-fluoro-1,3-benzothiazol-4-yl)-7,7-dimethyl-2-(2-(2-propenoyl)-2,6-diazaspiro[3.4]octan-6-yl)-7,8-dihydro-5H-pyrano[4,3-b]pyridine-3-carbonitrile (2$^{nd}$ eluting isomer) | See below for atropisomer separation conditions. | Step 1: Intermediate 34 and (2-((tert-butoxycarbonyl) amino)-7-fluorobenzo[d] thiazol-4-yl)boronic acid (PharmaBlock) |
| 14-58 | 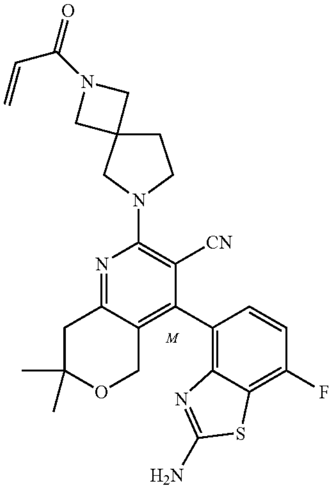 | (M)-4-(2-amino-7-fluoro-1,3-benzothiazol-4-yl)-7,7-dimethyl-2-(2-(2-propenoyl)-2,6-diazaspiro[3.4]octan-6-yl)-7,8-dihydro-5H-pyrano[4,3-b]pyridine-3-carbonitrile (1$^{st}$ eluting isomer) | See below for atropisomer separation conditions. | Step 1: Intermediate 34 and (2-((tert-butoxycarbonyl) amino)-7-fluorobenzo[d] thiazol-4-yl)boronic acid (PharmaBlock) |
| 14-59 | 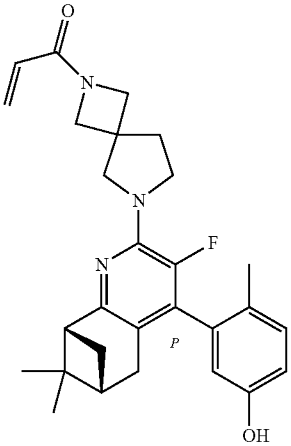 | (P)-1-(6-((1R,9R)-5-fluoro-6-(5-hydroxy-2-methylphenyl)-10,10-dimethyl-3-azatricyclo[7.1.1.0$^{2,7}$] undeca-2,4,6-trien-4-yl)-2,6-diazaspiro[3.4]octan-2-yl)-2-propen-1-one (1$^{st}$ eluting isomer) | See below for atropisomer separation conditions. | Step 1: Intermediate 31 and 5-hydroxy-2-methylphenyl-boronic acid (Combi-Blocks) |

TABLE 6-continued

| Ex.# | Chemical Structure | Name | Method changes | Reagent |
|---|---|---|---|---|
| Examples 14-2 to 14-107 were prepared following the procedure described in Method 14, steps 1-3, above as follows: | | | | |
| 14-60 | 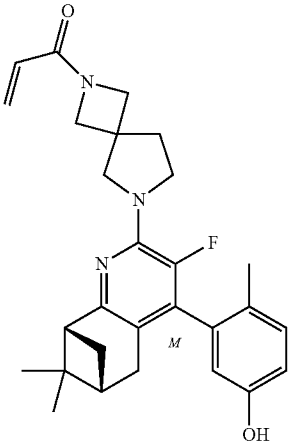 | (M)-1-(6-((1R,9R)-5-fluoro-6-(5-hydroxy-2-methylphenyl)-10,10-dimethyl-3-azatricyclo[7.1.1.0$^{2,7}$]undeca-2,4,6-trien-4-yl)-2,6-diazaspiro[3.4]octan-2-yl)-2-propen-1-one (2$^{nd}$ eluting isomer) | See below for atropisomer separation conditions. | Step 1: Intermediate 31 and 5-hydroxy-2-methylphenyl-boronic acid (Combi-Blocks) |
| 14-61 | 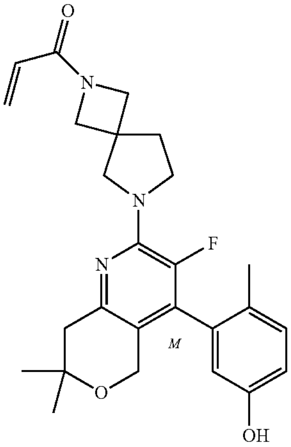 | (M)-1-(6-(3-fluoro-4-(5-hydroxy-2-methylphenyl)-7,7-dimethyl-7,8-dihydro-5H-pyrano[4,3-b]pyridin-2-yl)-2,6-diazaspiro[3.4]octan-2-yl)-2-propen-1-one (2$^{nd}$ eluting isomer) | See below for atropisomer separation conditions. | Step 1: Intermediate 30 and 5-hydroxy-2-methylphenyl-boronic acid (Combi-Blocks) |
| 14-62 | 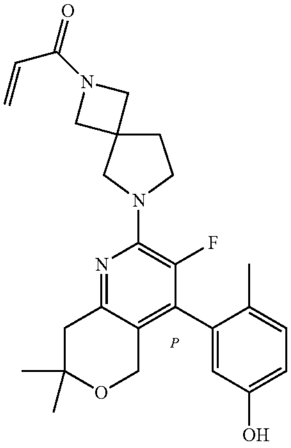 | (P)-1-(6-(3-fluoro-4-(5-hydroxy-2-methylphenyl)-7,7-dimethyl-7,8-dihydro-5H-pyrano[4,3-b]pyridin-2-yl)-2,6-diazaspiro[3.4]octan-2-yl)-2-propen-1-one (1$^{st}$ eluting isomer) | See below for atropisomer separation conditions. | Step 1: Intermediate 30 and 5-hydroxy-2-methylphenyl-boronic acid (Combi-Blocks) |

TABLE 6-continued

| Ex.# | Chemical Structure | Name | Method changes | Reagent |
|---|---|---|---|---|
| Examples 14-2 to 14-107 were prepared following the procedure described in Method 14, steps 1-3, above as follows: | | | | |
| 14-63 | 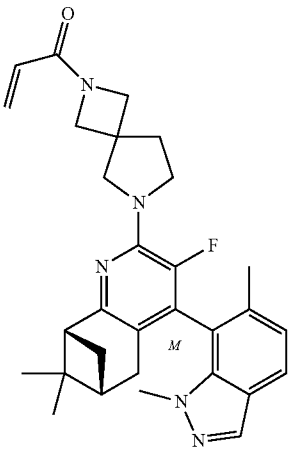 | (M)-1-(6-((1R,9R)-6-(1,6-dimethyl-1H-indazol-7-yl)-5-fluoro-10,10-dimethyl-3-azatricyclo[7.1.1.$0^{2,7}$]undeca-2,4,6-trien-4-yl)-2,6-diazaspiro[3.4]octan-2-yl)-2-propen-1-one (1$^{st}$ eluting isomer) | After Step 1, N-methylation was performed using the procedure in Example 2-19 with LiHMDS and MeI. See below for atropisomer separation conditions. | Step 1: Intermediate 31 and 6-methyl-7-(4,4,5,5-tetramethyl-1,3,2-dioxaborolan-2-yl)-1H-indazole (Synnovator) |
| 14-64 | 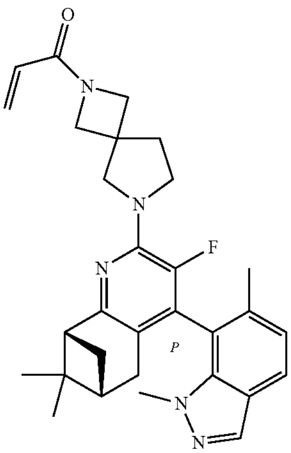 | (P)-1-(6-((1R,9R)-6-(1,6-dimethyl-1H-indazol-7-yl)-5-fluoro-10,10-dimethyl-3-azatricyclo[7.1.1.$0^{2,7}$]undeca-2,4,6-trien-4-yl)-2,6-diazaspiro[3.4]octan-2-yl)-2-propen-1-one (2$^{nd}$ eluting isomer) | After Step 1, N-methylation was performed using the procedure in Example 2-19 with LiHMDS and MeI. See below for atropisomer separation conditions. | Step 1: Intermediate 31 and 6-methyl-7-(4,4,5,5-tetramethyl-1,3,2-dioxaborolan-2-yl)-1H-indazole (Synnovator) |
| 14-65 | 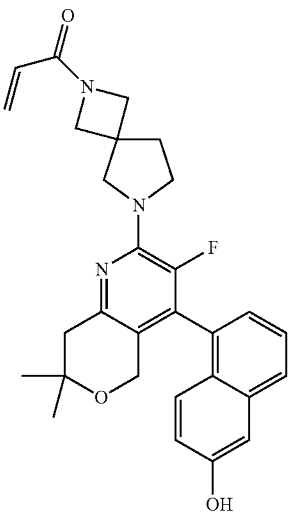 [SMILES: C=CC(=O)N1CC2(CCN(c3nc4c(c(-c5cccc6cc(O)ccc56)c3F)COC(C)(C)C4)C2)C1] | 1-(6-(3-fluoro-4-(6-hydroxy-1-naphthalenyl)-7,7-dimethyl-7,8-dihydro-5H-pyrano[4,3-b]pyridin-2-yl)-2,6-diazaspiro[3.4]octan-2-yl)-2-propen-1-one | | Step 1: Intermediate 30 and Intermediate 65 |

TABLE 6-continued

Examples 14-2 to 14-107 were prepared following the procedure described in Method 14, steps 1-3, above as follows:

| Ex.# | Chemical Structure | Name | Method changes | Reagent |
|---|---|---|---|---|
| 14-66 | 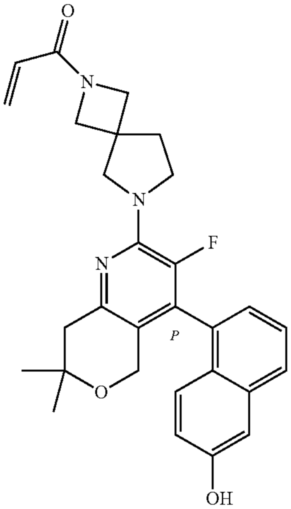 | (P)-1-(6-(3-fluoro-4-(6-hydroxy-1-naphthalenyl)-7,7-dimethyl-7,8-dihydro-5H-pyrano[4,3-b]pyridin-2-yl)-2,6-diazaspiro[3.4]octan-2-yl)-2-propen-1-one (2nd eluting isomer) | See below for atropisomer separation conditions. | Step 1: Intermediate 30 and Intermediate 65 |
| 14-67 | 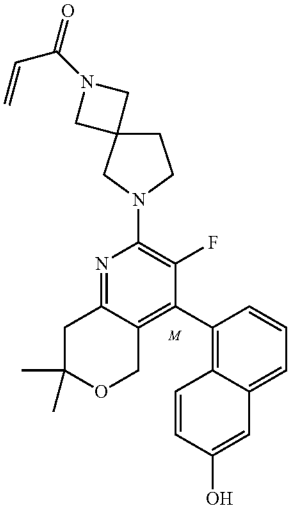 | (M)-1-(6-(3-fluoro-4-(6-hydroxy-1-naphthalenyl)-7,7-dimethyl-7,8-dihydro-5H-pyrano[4,3-b]pyridin-2-yl)-2,6-diazaspiro[3.4]octan-2-yl)-2-propen-1-one (1st eluting isomer) | See below for atropisomer separation conditions. | Step 1: Intermediate 30 and Intermediate 65 |
| 14-68 | 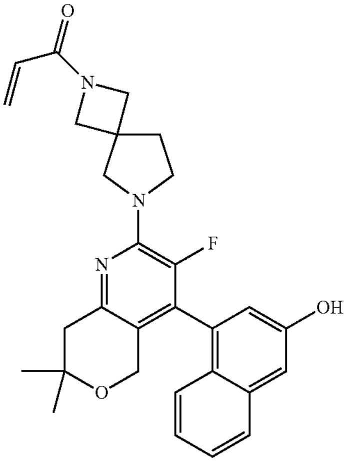 [SMILES: C=CC(=O)N1CC2(CCN(c3nc4c(c(-c5cc(O)cc6ccccc56)c3F)COC(C)(C)C4)C2)C1] | 1-(6-(3-fluoro-4-(3-hydroxy-1-naphthalenyl)-7,7-dimethyl-7,8-dihydro-5H-pyrano[4,3-b]pyridin-2-yl)-2,6-diazaspiro[3.4]octan-2-yl)-2-propen-1-one | | Step 1: Intermediate 30 and 3-hydroxy-naphthalene-1-boronic acid (eNovation Chemicals LLC) |

TABLE 6-continued

| Examples 14-2 to 14-107 were prepared following the procedure described in Method 14, steps 1-3, above as follows: | | | | |
|---|---|---|---|---|
| Ex.# | Chemical Structure | Name | Method changes | Reagent |
| 14-69 | 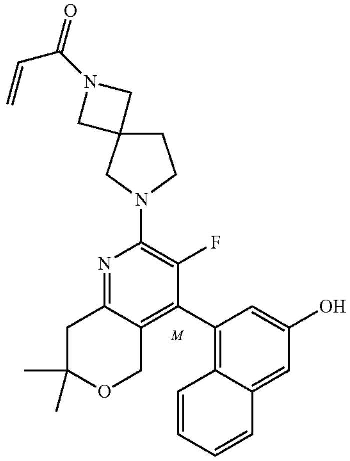 | (M)-1-(6-(3-fluoro-4-(3-hydroxy-1-naphthalenyl)-7,7-dimethyl-7,8-dihydro-5H-pyrano[4,3-b]pyridin-2-yl)-2,6-diazaspiro[3.4]octan-2-yl)-2-propen-1-one ($2^{nd}$ eluting isomer) | See below for atropisomer separation conditions. | Step 1: Intermediate 30 and 3-hydroxy-naphthalene-1-boronic acid (eNovation Chemicals LLC) |
| 14-70 | 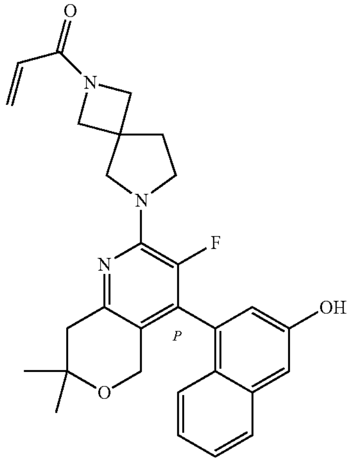 | (P)-1-(6-(3-fluoro-4-(3-hydroxy-1-naphthalenyl)-7,7-dimethyl-7,8-dihydro-5H-pyrano[4,3-b]pyridin-2-yl)-2,6-diazaspiro[3.4]octan-2-yl)-2-propen-1-one ($1^{st}$ eluting isomer) | See below for atropisomer separation conditions. | Step 1: Intermediate 30 and 3-hydroxy-naphthalene-1-boronic acid (eNovation Chemicals LLC) |
| 14-71 | 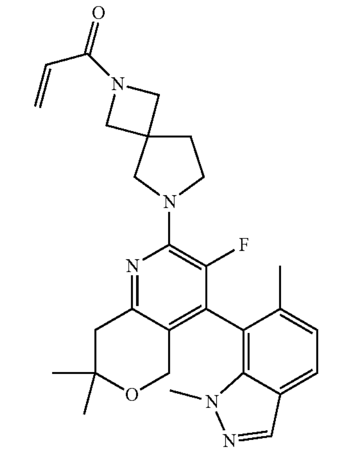 [SMILES: C=CC(=O)N1CC2(CCN(c3nc4c(c(-c5c(C)ccc6cnn(C)c56)c3F)COC(C)(C)C4)C2)C1] | 1-(6-(4-(1,6-dimethyl-1H-indazol-7-yl)-3-fluoro-7,7-dimethyl-7,8-dihydro-5H-pyrano[4,3-b]pyridin-2-yl)-2,6-diazaspiro[3.4]octan-2-yl)-2-propen-1-one | After Step 1, N-methylation was performed using the procedure in Example 2-19 with LiHMDS and MeI. | Step 1: Intermediate 30 and 6-methyl-7-(4,4,5,5-tetramethyl-1,3,2-dioxaborolan-2-yl)-1H-indazole (Synnovator) |

TABLE 6-continued

| Examples 14-2 to 14-107 were prepared following the procedure described in Method 14, steps 1-3, above as follows: | | | | |
|---|---|---|---|---|
| Ex.# | Chemical Structure | Name | Method changes | Reagent |
| 14-72 | 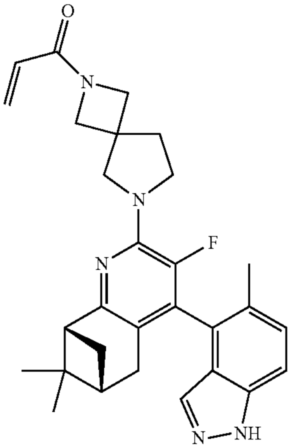 [SMILES: C=CC(=O)N1CC2(CCN(c3nc4c(c(-c5c(C)ccc6[nH]ncc56)c3F)C[C@H]3C[C@@H]4C3(C)C)C2)C1] | 1-(6-((1R,9R)-5-fluoro-10,10-dimethyl-6-(5-methyl-1H-indazol-4-yl)-3-azatricyclo[7.1.1.0$^{2,7}$]undeca-2,4,6-trien-4-yl)-2,6-diazaspiro[3.4]octan-2-yl)-2-propen-1-one | | Step 1: Intermediate 31 and 5-methyl-1-(oxan-2-yl)-4-(4,4,5,5-tetramethyl-1,3,2-dioxaborolan-2-yl)-1H-indazole (PharmaBlock) |
| 14-73 | 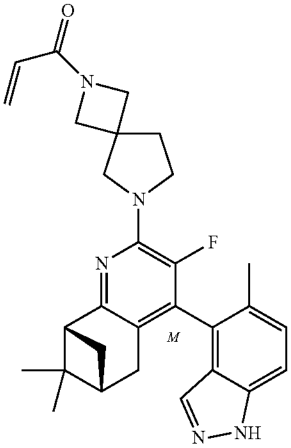 | (M)-1-(6-((1R,9R)-5-fluoro-10,10-dimethyl-6-(5-methyl-1H-indazol-4-yl)-3-azatricyclo[7.1.1.0$^{2,7}$]undeca-2,4,6-trien-4-yl)-2,6-diazaspiro[3.4]octan-2-yl)-2-propen-1-one (1$^{st}$ eluting isomer) | See below for atropisomer separation conditions. | Step 1: Intermediate 31 and 5-methyl-1-(oxan-2-yl)-4-(4,4,5,5-tetramethyl-1,3,2-dioxaborolan-2-yl)-1H-indazole (PharmaBlock) |
| 14-74 | 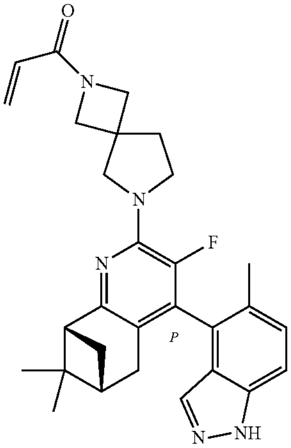 | (P)-1-(6-((1R,9R)-5-fluoro-10,10-dimethyl-6-(5-methyl-1H-indazol-4-yl)-3-azatricyclo[7.1.1.0$^{2,7}$]undeca-2,4,6-trien-4-yl)-2,6-diazaspiro[3.4]octan-2-yl)-2-propen-1-one (2$^{nd}$ eluting isomer) | See below for atropisomer separation conditions. | Step 1: Intermediate 31 and 5-methyl-1-(oxan-2-yl)-4-(4,4,5,5-tetramethyl-1,3,2-dioxaborolan-2-yl)-1H-indazole (PharmaBlock) |

TABLE 6-continued

Examples 14-2 to 14-107 were prepared following the procedure described in Method 14, steps 1-3, above as follows:

| Ex.# | Chemical Structure | Name | Method changes | Reagent |
|---|---|---|---|---|
| 14-75 | 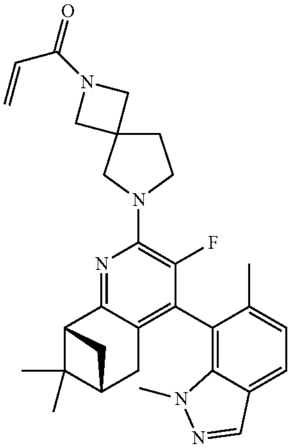 [SMILES: C=CC(=O)N1CC2(CCN(c3nc4c(c(-c5c(C)ccc6cnn(C)c56)c3F)C[C@H]3C[C@@H]4C3(C)C)C2)C1] | 1-(6-((1R,9R)-6-(1,6-dimethyl-1H-indazol-7-yl)-5-fluoro-10,10-dimethyl-3-azatricyclo[7.1.1.0$^{2,7}$]undeca-2,4,6-trien-4-yl)-2,6-diazaspiro[3.4]octan-2-yl)-2-propen-1-one (2$^{nd}$ eluting isomer) | After Step 1, N-methylation was performed using the procedure in Example 2-19 with LiHMDS and MeI. | Step 1: Intermediate 31 and 6-methyl-7-(4,4,5,5-tetramethyl-1,3,2-dioxaborolan-2-yl)-1H-indazole (Synnovator) |
| 14-76 | 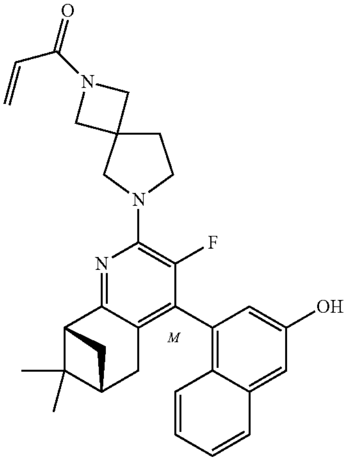 | (M)-1-(6-((1R,9R)-5-fluoro-6-(3-hydroxy-1-naphthalenyl)-10,10-dimethyl-3-azatricyclo[7.1.1.0$^{2,7}$]undeca-2,4,6-trien-4-yl)-2,6-diazaspiro[3.4]octan-2-yl)-2-propen-1-one (1$^{st}$ eluting isomer) | See below for atropisomer separation conditions. | Step 1: Intermediate 31 and 3-hydroxy-naphthalene-1-boronic acid (eNovation Chemicals LLC) |
| 14-77 | 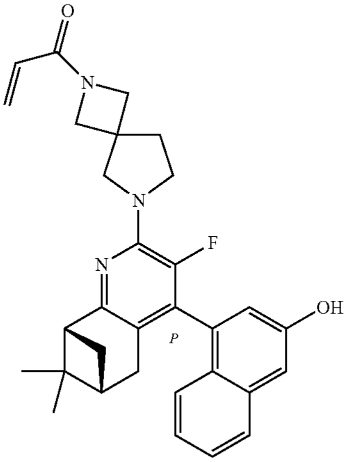 | (P)-1-(6-((1R,9R)-5-fluoro-6-(3-hydroxy-1-naphthalenyl)-10,10-dimethyl-3-azatricyclo[7.1.1.0$^{2,7}$]undeca-2,4,6-trien-4-yl)-2,6-diazaspiro[3.4]octan-2-yl)-2-propen-1-one (2$^{nd}$ eluting isomer) | See below for atropisomer separation conditions. | Step 1: Intermediate 31 and 3-hydroxy-naphthalene-1-boronic acid (eNovation Chemicals LLC) |

TABLE 6-continued

Examples 14-2 to 14-107 were prepared following the procedure described in Method 14, steps 1-3, above as follows:

| Ex.# | Chemical Structure | Name | Method changes | Reagent |
|---|---|---|---|---|
| 14-78 | 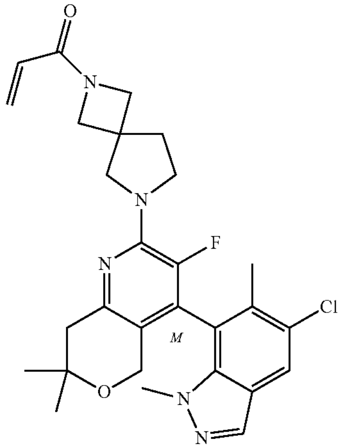 | (M)-1-(6-(4-(5-chloro-1,6-dimethyl-1H-indazol-7-yl)-3-fluoro-7,7-dimethyl-7,8-dihydro-5H-pyrano[4,3-b]pyridin-2-yl)-2,6-diazaspiro[3.4]octan-2-yl)-2-propen-1-one (1st eluting isomer) | After Step 1, N-methylation was performed using the procedure in Example 2-19 with LiHMDS and MeI. See below for atropisomer separation conditions. | Step 1: Intermediate 30 and Intermediate 37 |
| 14-79 | 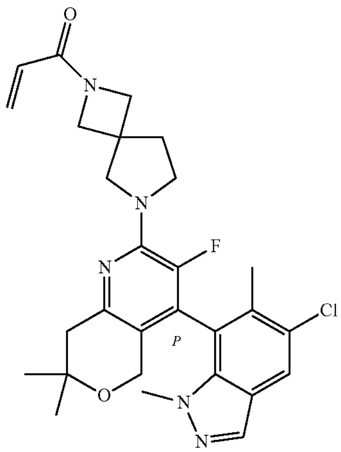 | (P)-1-(6-(4-(5-chloro-1,6-dimethyl-1H-indazol-7-yl)-3-fluoro-7,7-dimethyl-7,8-dihydro-5H-pyrano[4,3-b]pyridin-2-yl)-2,6-diazaspiro[3.4]octan-2-yl)-2-propen-1-one (2nd eluting isomer) | After Step 1, N-methylation was performed using the procedure in Example 2-19 with LiHMDS and MeI. See below for atropisomer separation conditions. | Step 1: Intermediate 30 and Intermediate 37 |
| 14-80 | 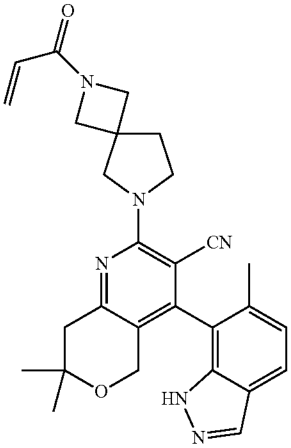 [SMILES: C=CC(=O)N1CC2(CCN(c3nc4c(c(-c5c(C)ccc6cn[nH]c56)c3C#N)COC(C)(C)C4)C2)C1] | 7,7-dimethyl-4-(6-methyl-1H-indazol-7-yl)-2-(2-(2-propenoyl)-2,6-diazaspiro[3.4]octan-6-yl)-7,8-dihydro-5H-pyrano[4,3-b]pyridine-3-carbonitrile | | Step 1: Intermediate 34 and 6-methyl-7-(4,4,5,5-tetramethyl-1,3,2-dioxaborolan-2-yl)-1H-indazole (Synnovator) |

TABLE 6-continued

| Examples 14-2 to 14-107 were prepared following the procedure described in Method 14, steps 1-3, above as follows: | | | | |
|---|---|---|---|---|
| Ex.# | Chemical Structure | Name | Method changes | Reagent |
| 14-81 | 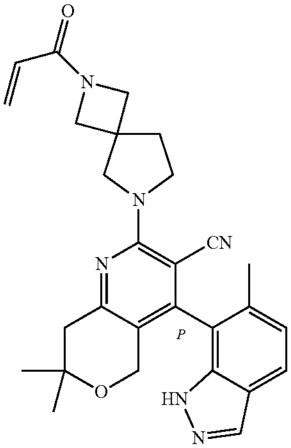 | (P)-7,7-dimethyl-4-(6-methyl-1H-indazol-7-yl)-2-(2-(2-propenoyl)-2,6-diazaspiro[3.4]octan-6-yl)-7,8-dihydro-5H-pyrano[4,3-b]pyridine-3-carbonitrile (2$^{nd}$ eluting isomer) | See below for atropisomer separation conditions. | Step 1: Intermediate 34 and 6-methyl-7-(4,4,5,5-tetramethyl-1,3,2-dioxaborolan-2-yl)-1H-indazole (Synnovator) |
| 14-82 | 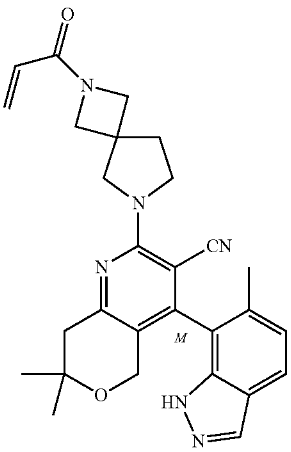 | (M)-7,7-dimethyl-4-(6-methyl-1H-indazol-7-yl)-2-(2-(2-propenoyl)-2,6-diazaspiro[3.4]octan-6-yl)-7,8-dihydro-5H-pyrano[4,3-b]pyridine-3-carbonitrile (1$^{st}$ eluting isomer) | See below for atropisomer separation conditions. | Step 1: Intermediate 34 and 6-methyl-7-(4,4,5,5-tetramethyl-1,3,2-dioxaborolan-2-yl)-1H-indazole (Synnovator) |
| 14-83 | 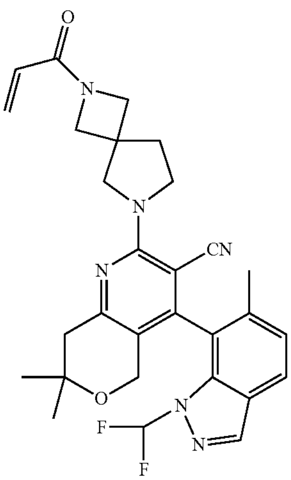 [SMILES: C=CC(=O)N1CC2(CCN(c3nc4c(c(-c5c(C)ccc6cnn(C(F)F)c56)c3C#N)COC(C)(C)C4)C2)C1] | 4-(1-(difluoromethyl)-6-methyl-1H-indazol-7-yl)-7,7-dimethyl-2-(2-(2-propenoyl)-2,6-diazaspiro[3.4]octan-6-yl)-7,8-dihydro-5H-pyrano[4,3-b]pyridine-3-carbonitrile | After Step 1, N-methylation was performed using the procedure in Example 2-19 with LiHMDS and 10 wt % difluoroiodomethane in THF (Synquest Laboratories) | Step 1: Intermediate 34 and 6-methyl-7-(4,4,5,5-tetramethyl-1,3,2-dioxaborolan-2-yl)-1H-indazole (Synnovator) |

TABLE 6-continued

| Examples 14-2 to 14-107 were prepared following the procedure described in Method 14, steps 1-3, above as follows: | | | | |
|---|---|---|---|---|
| Ex.# | Chemical Structure | Name | Method changes | Reagent |
| 14-84 | 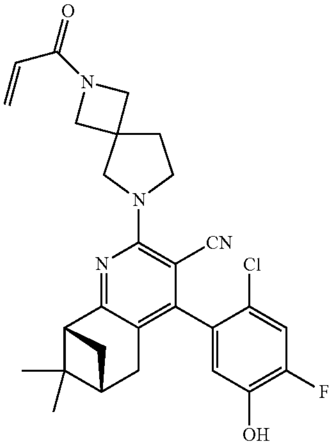 [SMILES: C=CC(=O)N1CC2(CCN(c3nc4c(c(-c5cc(O)c(F)cc5Cl)c3C#N)C[C@H]3C[C@@H]4C3(C)C)C2)C1] | (1R,9R)-6-(2-chloro-4-fluoro-5-hydroxyphenyl)-10,10-dimethyl-4-(2-(2-propenoyl)-2,6-diazaspiro[3.4]octan-6-yl)-3-azatricyclo[7.1.1.0$^{2,7}$]undeca-2,4,6-triene-5-carbonitrile | See alternative Step 2. | Step 1: Intermediate 35 and 2-chloro-4-fluoro-5-methoxyphenyl-boronic acid (Combi-Blocks) |
| 14-85 | 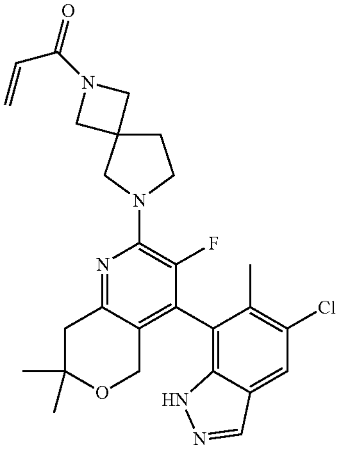 [SMILES: C=CC(=O)N1CC2(CCN(c3nc4c(c(-c5c(C)c(Cl)cc6cn[nH]c56)c3F)COC(C)(C)C4)C2)C1] | 1-(6-(4-(5-chloro-1,6-dimethyl-1H-indazol-7-yl)-3-fluoro-7,7-dimethyl-7,8-dihydro-5H-pyrano[4,3-b]pyridin-2-yl)-2,6-diazaspiro[3.4]octan-2-yl)-2-propen-1-one | | Step 1: Intermediate 30 and Intermediate 37 |
| 14-86 | 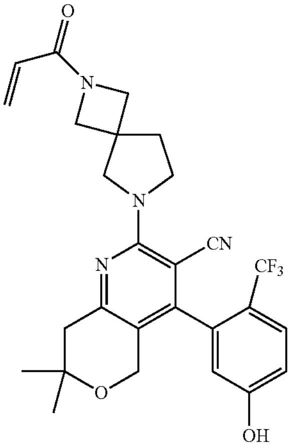 [SMILES: C=CC(=O)N1CC2(CCN(c3nc4c(c(-c5cc(O)ccc5C(F)(F)F)c3C#N)COC(C)(C)C4)C2)C1] | 4-(5-hydroxy-2-(trifluoromethyl)phenyl)-7,7-dimethyl-2-(2-(2-propenoyl)-2,6-diazaspiro[3.4]octan-6-yl)-7,8-dihydro-5H-pyrano[4,3-b]pyridine-3-carbonitrile | Step 1: $K_2CO_3$ replaced $K_3PO_4$ | Step 1: Intermediate 34 and Intermediate 87 |

TABLE 6-continued

| Examples 14-2 to 14-107 were prepared following the procedure described in Method 14, steps 1-3, above as follows: | | | | |
|---|---|---|---|---|
| Ex.# | Chemical Structure | Name | Method changes | Reagent |
| 14-87 | 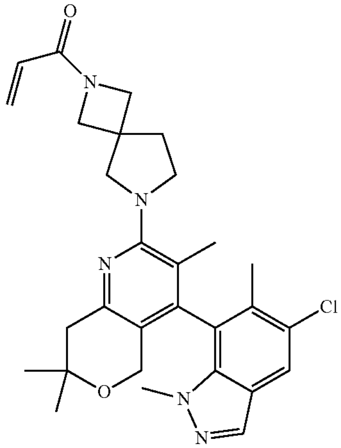 [SMILES: C=CC(=O)N1CC2(CCN(c3nc4c(c(-c5c(C)c(Cl)cc6cnn(C)c56)c3C)COC(C)(C)C4)C2)C1] | 1-(6-(4-(5-chloro-1,6-dimethyl-1H-indazol-7-yl)-3,7,7-trimethyl-7,8-dihydro-5H-pyrano[4,3-b]pyridin-2-yl)-2,6-diazaspiro[3.4]octan-2-yl)-2-propen-1-one | After Step 1, N-methylation was performed using the procedure in Example 2-19 with LiHMDS and MeI. | Step 1: Intermediate 26 and Intermediate 37 |
| 14-88 | 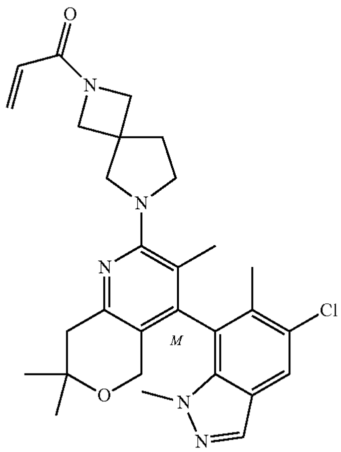 | (M)-1-(6-(4-(5-chloro-1,6-dimethyl-1H-indazol-7-yl)-3,7,7-trimethyl-7,8-dihydro-5H-pyrano[4,3-b]pyridin-2-yl)-2,6-diazaspiro[3.4]octan-2-yl)-2-propen-1-one (1st eluting isomer) | After Step 1, N-methylation was performed using the procedure in Example 2-19 with LiHMDS and MeI. See below for atropisomer separation conditions. | Step 1: Intermediate 26 and Intermediate 37 |
| 14-89 | 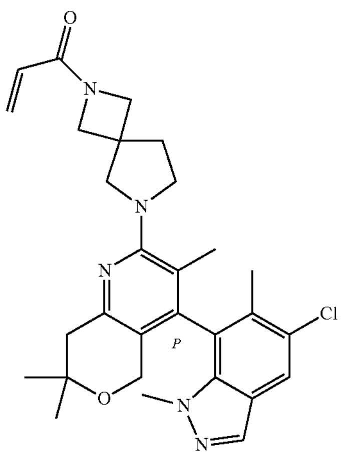 | (P)-1-(6-(4-(5-chloro-1,6-dimethyl-1H-indazol-7-yl)-3,7,7-trimethyl-7,8-dihydro-5H-pyrano[4,3-b]pyridin-2-yl)-2,6-diazaspiro[3.4]octan-2-yl)-2-propen-1-one (2nd eluting isomer) | After Step 1, N-methylation was performed using the procedure in Example 2-19 with LiHMDS and MeI. See below for atropisomer separation conditions. | Step 1: Intermediate 26 and Intermediate 37 |

TABLE 6-continued

Examples 14-2 to 14-107 were prepared following the procedure described in Method 14, steps 1-3, above as follows:

| Ex.# | Chemical Structure | Name | Method changes | Reagent |
| --- | --- | --- | --- | --- |
| 14-90 | 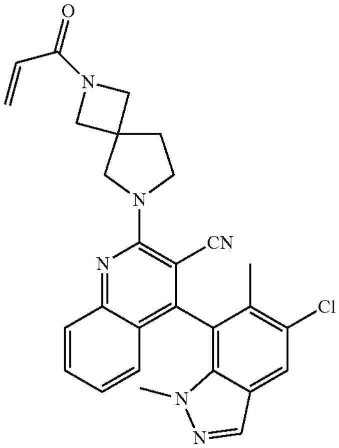 [SMILES: C=CC(=O)N1CC2(CCN(c3nc4ccccc4c(-c4c(C)c(Cl)cc5cnn(C)c45)c3C#N)C2)C1] | 4-(5-chloro-1,6-dimethyl-1H-indazol-7-yl)-2-(2-(2-propenoyl)-2,6-diazaspiro[3.4]octan-6-yl)-3-quinolinecarbonitrile | Step 1: cataCXium A-Pd-G2 replaced SPhos Pd G3. After Step 1, N-methylation was performed using the procedure in Example 2-19 with LiHMDS and MeI. | Step 1: Intermediate 25 and Intermediate 37 |
| 14-91 | 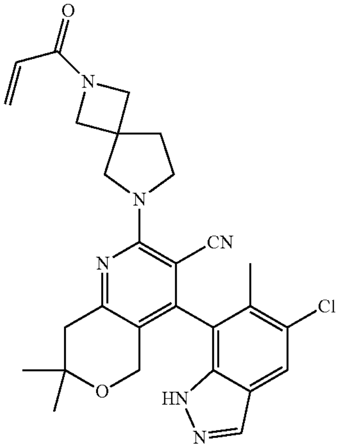 [SMILES: C=CC(=O)N1CC2(CCN(c3nc4c(c(-c5c(C)c(Cl)cc6cn[nH]c56)c3C#N)COC(C)(C)C4)C2)C1] | 4-(5-chloro-6-methyl-1H-indazol-7-yl)-7,7-dimethyl-2-(2-(2-propenoyl)-2,6-diazaspiro[3.4]octan-6-yl)-7,8-dihydro-5H-pyrano[4,3-b]pyridine-3-carbonitrile | Step 1: Pd-PEPPSI-Ipent replaced SPhos Pd G3. | Step 1: Intermediate 34 and Intermediate 37 |
| 14-92 | 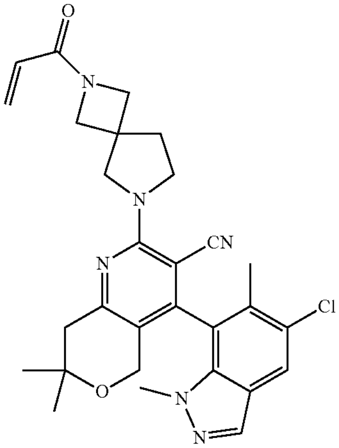 [SMILES: C=CC(=O)N1CC2(CCN(c3nc4c(c(-c5c(C)c(Cl)cc6cnn(C)c56)c3C#N)COC(C)(C)C4)C2)C1] | 4-(5-chloro-1,6-dimethyl-1H-indazol-7-yl)-7,7-dimethyl-2-(2-(2-propenoyl)-2,6-diazaspiro[3.4]octan-6-yl)-7,8-dihydro-5H-pyrano[4,3-b]pyridine-3-carbonitrile | Step 1: Pd-PEPPSI-Ipent replaced SPhos Pd G3. After Step 1, N-methylation was performed using the procedure in Example 2-19 with LiHMDS and MeI. | Step 1: Intermediate 34 and Intermediate 37 |

TABLE 6-continued

Examples 14-2 to 14-107 were prepared following the procedure described in Method 14, steps 1-3, above as follows:

| Ex.# | Chemical Structure | Name | Method changes | Reagent |
|---|---|---|---|---|
| 14-93 | 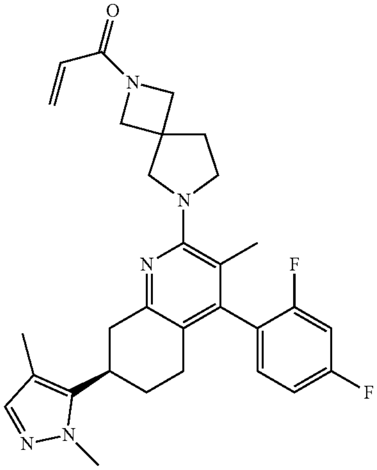 [SMILES: C=CC(=O)N1CC2(CCN(c3nc4c(c(-c5ccc(F)cc5F)c3C)CC[C@@H](c3c(C)cnn3C)C4)C2)C1] | 1-(6-((7R)-4-(2,4-difluorophenyl)-7-(1,4-dimethyl-1H-pyrazol-5-yl)-3-methyl-5,6,7,8-tetrahydro-2-quinolinyl)-2,6-diazaspiro[3.4]octan-2-yl)-2-propen-1-one | Step 1: XPhos Pd G3 replaced SPhos Pd G3. | Step 1: Intermediate 110-1 and (2,4-difluorophenyl) boronic acid (Combi-Blocks) |
| 14-94 | 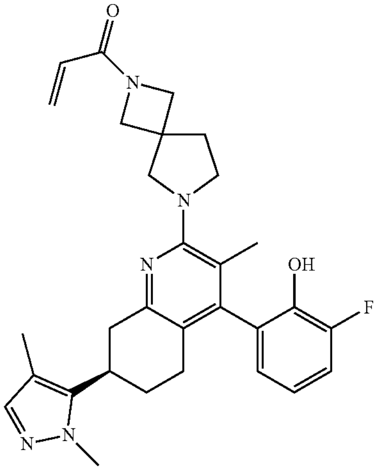 [SMILES: C=CC(=O)N1CC2(CCN(c3nc4c(c(-c5cccc(F)c5O)c3C)CC[C@@H](c3c(C)cnn3C)C4)C2)C1] | 1-(6-((7R)-7-(1,4-dimethyl-1H-pyrazol-5-yl)-4-(3-fluoro-2-hydroxyphenyl)-3-methyl-5,6,7,8-tetrahydro-2-quinolinyl)-2,6-diazaspiro[3.4]octan-2-yl)-2-propen-1-one | Step 1: XPhos Pd G3 replaced SPhos Pd G3. Step 2: $BBr_3$ was used in place of TFA to deprotect Boc and methoxy. | Step 1: Intermediate 110-1 and (3-fluoro-2-methoxyphenyl) boronic acid (Combi-Blocks) |
| 14-95 | 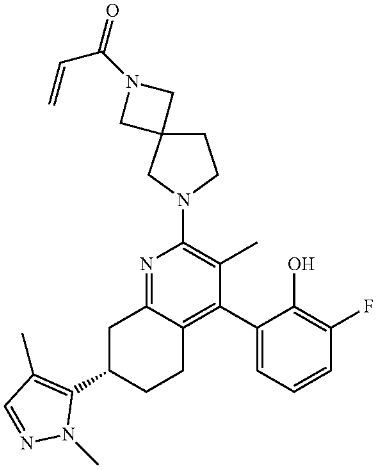 [SMILES: C=CC(=O)N1CC2(CCN(c3nc4c(c(-c5cccc(F)c5O)c3C)CC[C@H](c3c(C)cnn3C)C4)C2)C1] | 1-(6-((7S)-7-(1,4-dimethyl-1H-pyrazol-5-yl)-4-(3-fluoro-2-hydroxyphenyl)-3-methyl-5,6,7,8-tetrahydro-2-quinolinyl)-2,6-diazaspiro[3,4]octan-2-yl)-2-propen-1-one | Step 1: XPhos Pd G3 replaced SPhos Pd G3. Step 2: $BBr_3$ was used in place of TFA to deprotect Boc and methoxy. | Step 1: Intermediate 110-2 and (3-fluoro-2-methoxyphenyl) boronic acid (Combi-Blocks) |

TABLE 6-continued

| Examples 14-2 to 14-107 were prepared following the procedure described in Method 14, steps 1-3, above as follows: | | | | |
|---|---|---|---|---|
| Ex.# | Chemical Structure | Name | Method changes | Reagent |
| 14-96 | 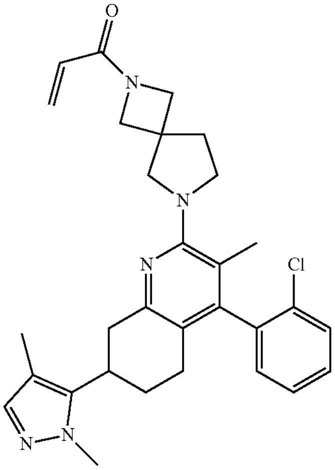 [SMILES: C=CC(=O)N1CC2(CCN(c3nc4c(c(-c5ccccc5Cl)c3C)CCC(c3c(C)cnn3C)C4)C2)C1] | 1-(6-((7R)-4-(2-chlorophenyl)-7-(1,4-dimethyl-1H-pyrazol-5-yl)-3-methyl-5,6,7,8-tetrahydro-2-quinolinyl)-2,6-diazaspiro[3.4]octan-2-yl)-2-propen-1-one\|1-(6-((7S)-4-(2-chlorophenyl)-7-(1,4-dimethyl-1H-pyrazol-5-yl)-3-methyl-5,6,7,8-tetrahydro-2-quinolinyl)-2,6-diazaspiro[3.4]octan-2-yl)-2-propen-1-one | Step 1: XPhos Pd G3 replaced SPhos Pd G3. | Step 1: Intermediate 110 and 2-(2-Chlorophenyl)-4,4,5,5-tetramethyl-1,3,2-dioxaborolane (Oakwood Chemical) |
| 14-97 | 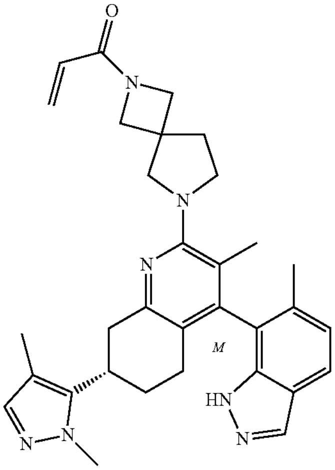 | (M)-1-(6-((7S)-7-(1,4-dimethyl-1H-pyrazol-5-yl)-3-methyl-4-(6-methyl-1H-indazol-7-yl)-5,6,7,8-tetrahydro-2-quinolinyl)-2,6-diazaspiro[3.4]octan-2-yl)-2-propen-1-one | Step 1: XPhos Pd G3 replaced SPhos Pd G3. See atropisomer separation conditions below after step 1. | Step 1: Intermediate 110-2 and 6-methyl-7-(4,4,5,5-tetramethyl-1,3,2-dioxaborolan-2-yl)-1H-indazole (Synnovator) Step 2: Peak 1 of separation was used. |
| 14-98 | 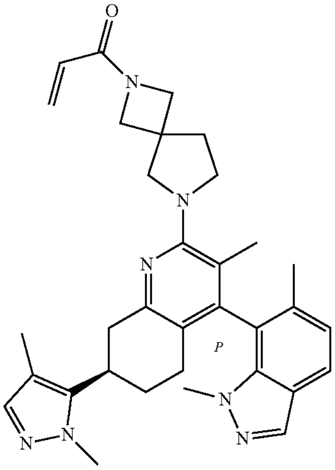 | (P)-1-(6-((7R)-7-(1,4-dimethyl-1H-pyrazol-5-yl)-3-methyl-4-(6-methyl-1H-indazol-7-yl)-5,6,7,8-tetrahydro-2-quinolinyl)-2,6-diazaspiro[3.4]octan-2-yl)-2-propen-1-one | Step 1: XPhos Pd G3 replaced SPhos Pd G3. See atropisomer separation conditions below after step 1. After Step 1, N-methylation was performed using the procedure in Example 2-19 with LiHMDS and MeI. | Step 1: Intermediate 110-1 and 6-methyl-7-(4,4,5,5-tetramethyl-1,3,2-dioxaborolan-2-yl)-1H-indazole (Synnovator). N-Methylation was performed with peak 2 of separation. |

TABLE 6-continued

Examples 14-2 to 14-107 were prepared following the procedure described in Method 14, steps 1-3, above as follows:

| Ex.# | Chemical Structure | Name | Method changes | Reagent |
|---|---|---|---|---|
| 14-99 | 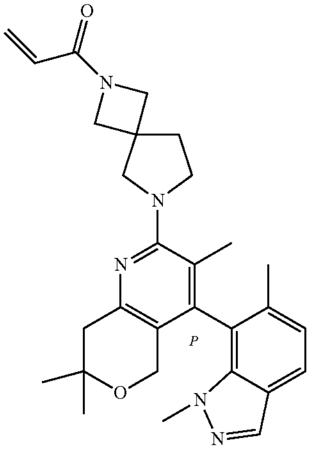 | (P)-1-(6-(4-(1,6-dimethyl-1H-indazol-7-yl)-3,7,7-trimethyl-7,8-dihydro-5H-pyrano[4,3-b]pyridin-2-yl)-2,6-diazaspiro[3.4]octan-2-yl)-2-propen-1-one (2nd eluting isomer) | After Step 1, N-methylation was performed using the procedure in Example 2-19 with LiHMDS and MeI. See below for atropisomer separation after N-methylation. | Step 1: Intermediate 26 and 6-methyl-7-(4,4,5,5-tetramethyl-1,3,2-dioxaborolan-2-yl)-1H-indazole (Synnovator) |
| 14-100 | 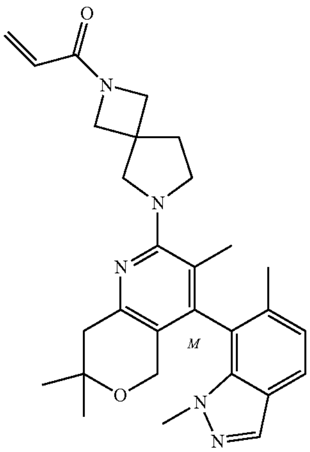 | (M)-1-(6-(4-(1,6-dimethyl-1H-indazol-7-yl)-3,7,7-trimethyl-7,8-dihydro-5H-pyrano[4,3-b]pyridin-2-yl)-2,6-diazaspiro[3.4]octan-2-yl)-2-propen-1-one (1st eluting isomer) | After Step 1, N-methylation was performed using the procedure in Example 2-19 with LiHMDS and MeI. See below for atropisomer separation after N-methylation. | Step 1: Intermediate 26 and 6-methyl-7-(4,4,5,5-tetramethyl-1,3,2-dioxaborolan-2-yl)-1H-indazole (Synnovator) |
| 14-101 | 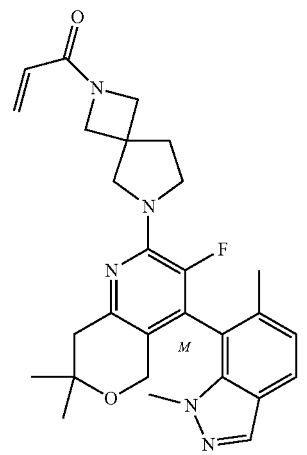 | (M)-1-(6-(4-(1,6-dimethyl-1H-indazol-7-yl)-3-fluoro-7,7-dimethyl-7,8-dihydro-5H-pyrano[4,3-b]pyridin-2-yl)-2,6-diazaspiro[3.4]octan-2-yl)-2-propen-1-one (1st eluting isomer) | After Step 1, N-methylation was performed using the procedure in Example 2-19 with LiHMDS and MeI. See below for atropisomer separation after N-methylation | Step 1: Intermediate 30 and 6-methyl-7-(4,4,5,5-tetramethyl-1,3,2-dioxaborolan-2-yl)-1H-indazole (Synnovator) |

TABLE 6-continued

| Examples 14-2 to 14-107 were prepared following the procedure described in Method 14, steps 1-3, above as follows: | | | | |
|---|---|---|---|---|
| Ex.# | Chemical Structure | Name | Method changes | Reagent |
| 14-102 | 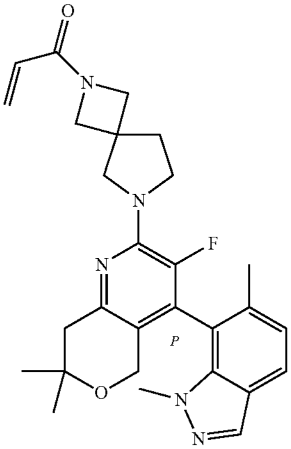 | (P)-1-(6-(4-(1,6-dimethyl-1H-indazol-7-yl)-3-fluoro-7,7-dimethyl-7,8-dihydro-5H-pyrano[4,3-b]pyridin-2-yl)-2,6-diazaspiro[3.4]octan-2-yl)-2-propen-1-one ($2^{nd}$ eluting isomer) | After Step 1, N-methylation was performed using the procedure in Example 2-19 with LiHMDS and MeI. See below for atropisomer separation after N-methylation | Step 1: Intermediate 30 and 6-methyl-7-(4,4,5,5-tetramethyl-1,3,2-dioxaborolan-2-yl)-1H-indazole (Synnovator) |
| 14-103 | 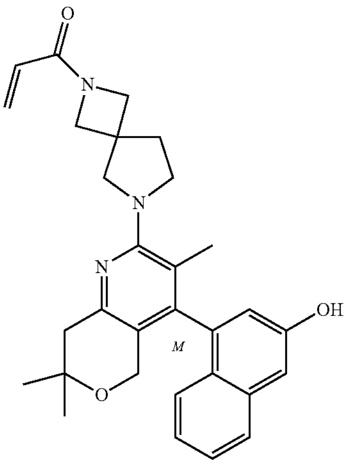 | (M)-1-(6-(4-(3-hydroxy-1-naphthalenyl)-3,7,7-trimethyl-7,8-dihydro-5H-pyrano[4,3-b]pyridin-2-yl)-2,6-diazaspiro[3.4]octan-2-yl)-2-propen-1-one ($2^{nd}$ eluting peak) | See below for atropisomer separation conditions. | Step 1: Intermediate 26 and 3-hydroxy-naphthalene-1-boronic acid (eNovation Chemicals) |
| 14-104 | 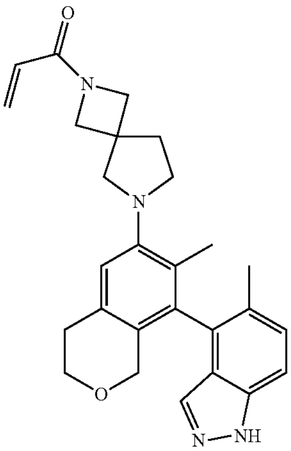 [SMILES: C=CC(=O)N1CC2(CCN(c3cc4c(c(-c5c(C)ccc6[nH]ncc56)c3C)COCC4)C2)C1] | 1-(6-(7-methyl-8-(5-methyl-1H-indazol-4-yl)-3,4-dihydro-1H-2-benzopyran-6-yl)-2,6-diazaspiro[3.4]octan-2-yl)-2-propen-1-one | | Step 1: Intermediate 115 and [5-methyl-1-(oxan-2-yl)-1h-indazol-4-yl]boronic acid (Ambeed) |

TABLE 6-continued

Examples 14-2 to 14-107 were prepared following the procedure described in Method 14, steps 1-3, above as follows:

| Ex.# | Chemical Structure | Name | Method changes | Reagent |
|---|---|---|---|---|
| 14-105 | 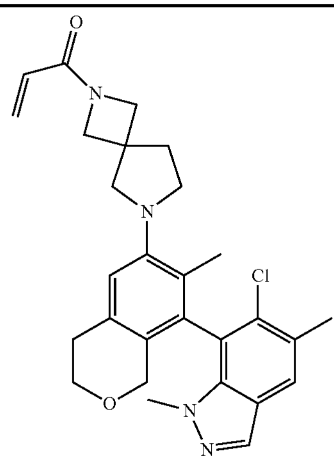 | 1-(6-(4-(6-chloro-1,5-dimethyl-1H-indazol-7-yl)-3,7,7-trimethyl-7,8-dihydro-5H-pyrano[4,3-b]pyridin-2-yl)-2,6-diazaspiro[3.4]octan-2-yl)-2-propen-1-one | After Step 1, N-methylation was performed using the procedure in Example 2-19 with LiHMDS and MeI. | Step 1: Intermediate 115 and Intermediate 116 |
| 14-106 | 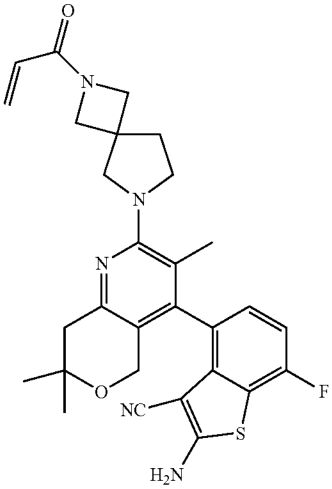 [SMILES: C=CC(=O)N1CC2(CCN(c3nc4c(c(-c5ccc(F)c6sc(N)c(C#N)c56)c3C)COC(C)(C)C4)C2)C1] | 2-amino-7-fluoro-4-(3,7,7-trimethyl-2-(2-(2-propenoyl)-2,6-diazaspiro[3.4]octan-6-yl)-7,8-dihydro-5H-pyrano[4,3-b]pyridin-4-yl)-1-benzothiophene-3-carbonitrile | Step 1: $Pd_2(dba)_3$ and (R)-MOP replaced SPhos Pd G3 and water was omitted. | Step 1: Intermediate 26 and tert-butyl (3-cyano-4-(5,5-dimethyl-1,3,2-dioxaborinan-2-yl)-7-fluorobenzo[b] thiophen-2-yl)carbamate (PharmaBlock) |
| 14-107 | 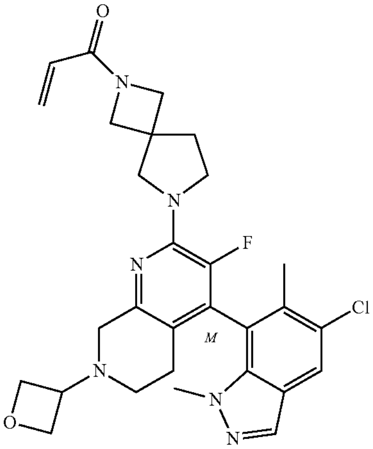 | (M)-1-(6-(4-(5-chloro-1,6-dimethyl-1H-indazol-7-yl)-3-fluoro-7-(3-oxetanyl)-5,6,7,8-tetrahydro-1,7-naphthyridin-2-yl)-2,6-diazaspiro[3.4]octan-2-yl)-2-propen-1-one ($2^{nd}$ eluting isomer) | After Step 1, N-methylation was performed using the procedure in Example 2-19 with LiHMDS and MeI. | Step 1: Intermediate 126 and Intermediate 37 |

Additional Chlorination Step for Example 14-3.

A mixture of tert-butyl 6-(3-cyano-4-(5-methyl-1H-indazol-4-yl)quinolin-2-yl)-2,6-diazaspiro[3.4]octane-2-carboxylate (130 mg, 0.263 mmol) and NCS (28.1 mg, 0.210 mmol) in acetonitrile (5 mL) was stirred at 65° C. for 48 h. The reaction mixture was concentrated and the residue was purified by Prep HPLC to afford tert-butyl 6-(4-(3-chloro-5-methyl-1H-indazol-4-yl)-3-cyanoquinolin-2-yl)-2,6-diazaspiro[3.4]octane-2-carboxylate (23 mg, 15.50% yield) as a yellow solid. m/z (ESI): 529.0 $(M+H)^+$.

Atropisomer separation for Examples 14-6 and 14-7. The racemic mixture was separated by preparative SFC using a OD column (250×21 mm, 5 μm) with a mobile phase of 65% liquid $CO_2$ and 35% MeOH with 0.2% TEA using a flowrate of 70 mL/min to provide the respective P and M isomers of (1S,8R)-6-(5-methyl-1H-indazol-4-yl)-4-(2-(2-propenoyl)-2,6-diazaspiro[3.4]octan-6-yl)-3-azatricyclo[6.2.1.$0^{2,7}$]undeca-2,4,6-triene-5-carbonitrile. The stereochemistry of structures was arbitrarily assigned and is not established. $1^{st}$ eluting atropisomer assigned as the M isomer and $2^{nd}$ eluting atropisomer assigned as the P isomer.

Atropisomer Separation for Examples 14-8.

The racemic mixture was separated by preparative SFC using a Chiralcel OD (150×21 mm, 5 μm) mobile phase of 70% liquid $CO_2$ and 30% MeOH with 0.2% TEA using a flowrate of 100 mL/min to provide the respective P and M isomers of (1R,8S)-6-(5-methyl-1H-indazol-4-yl)-4-(2-(2-propenoyl)-2,6-diazaspiro[3.4]octan-6-yl)-3 azatricyclo [6.2.1.$0^{2,7}$]undeca-2,4,6-triene-5-carbonitrile. The stereochemistry of structures was arbitrarily assigned and is not established. $1^{st}$ eluting atropisomer assigned as the M isomer and $2^{nd}$ eluting atropisomer assigned as the P isomer.

Atropisomer Separation for Examples 14-10 and 14-11.

The racemic mixture was separated by preparative SFC using a Chiralpak AS column (150×21 mm, 5 μm) with a mobile phase of 65% liquid $CO_2$ and 35% MeOH with 0.2% TEA using a flowrate of 80 mL/min to provide the respective P and M isomers of (1S,8R)-6-(5-hydroxy-2-methylphenyl)-4-(2-(2-propenoyl)-2,6-diazaspiro[3.4]octan-6-yl)-3-azatricyclo[6.2.1.$0^{2,7}$]undeca-2,4,6-triene-5-carbonitrile. The stereochemistry of structures was arbitrarily assigned and is not established. $1^{st}$ eluting atropisomer assigned as the M isomer and $2^{nd}$ eluting atropisomer assigned as the P isomer.

Atropisomer Separation for Examples 14-13 and 14-14.

The racemic mixture was separated by preparative SFC using a Chiral Technologies OJ column (250×21 mm, 5 μm) with a mobile phase of 80% liquid $CO_2$ and 20% MeOH with 0.2% TEA using a flowrate of 80 mL/min to provide the respective P and M isomers of (1R,8S)-6-(5-hydroxy-2-methylphenyl)-4-(2-(2-propenoyl)-2,6-diazaspiro[3.4]octan-6-yl)-3-azatricyclo[6.2.1.$0^{2,7}$]undeca-2,4,6-triene-5-carbonitrile. The stereochemistry of structures was arbitrarily assigned and is not established. $1^{st}$ eluting atropisomer assigned as the M isomer and $2^{nd}$ eluting atropisomer assigned as the P isomer.

Atropisomer Separation for Examples 14-16 and 14-17.

The racemic mixture was separated by preparative SFC using a OJ column (250×21 mm, 5 μm) with a mobile phase of 90% liquid $CO_2$ and 10% MeOH with 0.2% TEA using a flowrate of 100 mL/min to provide the respective P and M isomers of (1S,8R)-6-(1,6-dimethyl-1H-indazol-7-yl)-4-(2-(2-propenoyl)-2,6-diazaspiro[3.4]octan-6-yl)-3-azatricyclo [6.2.1.$0^{2,7}$]undeca-2,4,6-triene-5-carbonitrile. The stereochemistry of structures was arbitrarily assigned and is not established. $1^{st}$ eluting atropisomer assigned as the M isomer and $2^{nd}$ eluting atropisomer assigned as the P isomer.

Atropisomer Separation for Examples 14-28 and 14-29.

The racemic mixture was separated by preparative SFC using a Regis (S,S) Whelk-01 column (250×21 mm, 5 μm) with a mobile phase of 50% liquid $CO_2$ and 50% MeOH with 0.2% TEA using a flowrate of 70 mL/min to provide the respective P and M isomers of (1R,9R)-6-(1H-indazol-7-yl)-10,10-dimethyl-4-(2-(2-propenoyl)-2,6-diazaspiro[3.4]octan-6-yl)-3-azatricyclo[7.1.1.$0^{2,7}$]undeca-2,4,6-triene-5-carbonitrile. The stereochemistry of structures was arbitrarily assigned and is not established. $1^{st}$ eluting atropisomer assigned as the M isomer and $2^{nd}$ eluting atropisomer assigned as the P isomer.

Atropisomer Separation for Examples 14-31 and 14-32.

The racemic mixture was separated by preparative SFC using a Chiralpak IC column (250×21 mm, 5 μm) with a mobile phase of 60% liquid $CO_2$ and 40% MeOH with 0.2% TEA using a flowrate of 80 mL/min to provide the respective P and M isomers of 1-(6-(4-(5-hydroxy-2-methylphenyl)-3,7,7-trimethyl-7,8-dihydro-5H-pyrano[4,3-b]pyridin-2-yl)-2,6-diazaspiro[3.4]octan-2-yl)-2-propen-1-one. The stereochemistry of structures was arbitrarily assigned and is not established. $1^{st}$ eluting atropisomer assigned as the M isomer and $2^{nd}$ eluting atropisomer assigned as the P isomer.

Atropisomer Separation for Examples 14-33 and 14-34.

The racemic mixture was separated by preparative SFC using a IG column (250×21 mm, 5 μm) with a mobile phase of 50% liquid $CO_2$ and 50% MeOH with 0.2% TEA using a flowrate of 70 mL/min to provide the respective P and M isomers of 1-(6-(3,7,7-trimethyl-4-(5-methyl-1H-indazol-4-yl)-7,8-dihydro-5H-pyrano[4,3-b]pyridin-2-yl)-2,6-diazaspiro[3.4]octan-2-yl)-2-propen-1-one. The stereochemistry of structures was arbitrarily assigned and is not established. $1^{st}$ eluting atropisomer assigned as the P isomer and $2^{nd}$ eluting atropisomer assigned as the M isomer.

Atropisomer Separation for Examples 14-35 and 14-103.

The racemic mixture was separated by preparative SFC using a OD column (250×21 mm, 5 μm) with a mobile phase of 50% liquid $CO_2$ and 50% MeOH with 0.2% TEA using a flowrate of 60 mL/min to provide the respective P and M isomers of 1-(6-(4-(3-hydroxy-1-naphthalenyl)-3,7,7-trimethyl-7,8-dihydro-5H-pyrano[4,3-b]pyridin-2-yl)-2,6-diazaspiro[3.4]octan-2-yl)-2-propen-1-one. The stereochemistry of structures was arbitrarily assigned and is not established. $1^{st}$ eluting atropisomer assigned as the P isomer and $2^{nd}$ eluting atropisomer assigned as the M isomer.

Atropisomer Separation for Examples 14-38 and 14-39.

The racemic mixture was separated by preparative SFC using a Chiralcel OD (250×21 mm, 5 μm) with a mobile phase of 85% liquid $CO_2$ and 15% MeOH with 0.2% TEA using a flowrate of 80 mL/min to provide the respective P and M isomers of 1-(6-(4-(2-amino-7-fluoro-1,3-benzothiazol-4-yl)-3,7,7-trimethyl-7,8-dihydro-5H-pyrano[4,3-b] pyridin-2-yl)-2,6-diazaspiro[3.4]octan-2-yl)-2-propen-1-one. The stereochemistry of structures was arbitrarily assigned and is not established. $1^{st}$ eluting atropisomer assigned as the P isomer and $2^{nd}$ eluting atropisomer assigned as the M isomer.

Atropisomer Separation for Examples 14-41 and 14-42.

The racemic mixture was separated by preparative SFC using a (S,S) Whelk-01 (250×21 mm, 5 μm) with a mobile phase of 75% liquid $CO_2$ and 25% MeOH with 0.2% TEA using a flowrate of 100 mL/min to provide the respective P and M isomers of 1-(6-(3,7,7-trimethyl-4-(1,5,6-trimethyl-1H-indazol-7-yl)-7,8-dihydro-5H-pyrano[4,3-b]pyridin-2-yl)-2,6-diazaspiro[3.4]octan-2-yl)-2-propen-1-one. The stereochemistry of structures was arbitrarily assigned and is not established. $1^{st}$ eluting atropisomer assigned as the M isomer and $2^{nd}$ eluting atropisomer assigned as the P isomer.

Atropisomer Separation for Examples 14-44 and 14-45.

The racemic mixture was separated by preparative SFC using a Chiralpak AD column (250×21 mm, 5 μm) with a mobile phase of 80% liquid $CO_2$ and 20% MeOH with 0.2% TEA using a flowrate of 80 mL/min to provide the respective P and M isomers of 1-(6-(4-(6-hydroxy-1-naphthalenyl)-3,7,7-trimethyl-7,8-dihydro-5H-pyrano[4,3-b]pyridin-2-yl)-2,6-diazaspiro[3.4]octan-2-yl)-2-propen-1-one. The stereochemistry of structures was arbitrarily assigned and is not established. 1st eluting atropisomer assigned as the P isomer and 2nd eluting atropisomer assigned as the M isomer.

Alternate Step 2 for Example 14-49 and 14-84

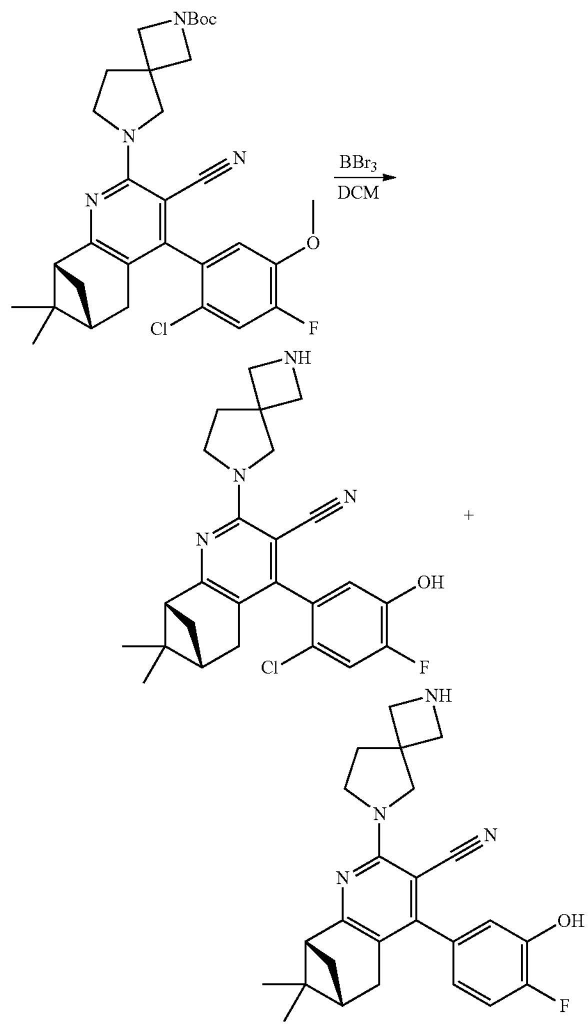

To a 0° C. solution of tert-butyl 6-((6R,8R)-4-(2-chloro-4-fluoro-5-methoxyphenyl)-3-cyano-7,7-dimethyl-5,6,7,8-tetrahydro-6,8-methanoquinolin-2-yl)-2,6-diazaspiro[3.4]octane-2-carboxylate (64.1 mg, 0.113 mmol) and DCM (1130 μL) was added boron tribromide (339 μL, 0.339 mmol, Sigma-Aldrich). The reaction mixture was stirred at room temperature for 22 h. The reaction was quenched with MeOH and concentrated in vacuo to give (6R,8R)-4-(2-chloro-4-fluoro-5-hydroxyphenyl)-7,7-dimethyl-2-(2,6-diazaspiro[3.4]octan-6-yl)-5,6,7,8-tetrahydro-6,8-methanoquinoline-3-carbonitrile and (6R,8R)-4-(4-fluoro-3-hydroxyphenyl)-7,7-dimethyl-2-(2,6-diazaspiro[3.4]octan-6-yl)-5,6,7,8-tetrahydro-6,8-methanoquinoline-3-carbonitrile, which were carried together as a mixture until acrylamide formation where they were separated by slice gel chromatography.

Atropisomer Separation for Examples 14-51 and 14-52.

The racemic mixture was separated by preparative SFC using a Chiralcel OD column (21×250 mm) mobile phase of 80% liquid $CO_2$ and 20% MeOH with 0.2% TEA using a flowrate of 80 mL/min to provide the respective P and M isomers of (1R,9R)-10,10-dimethyl-6-(6-methyl-H-indazol-7-yl)-4-(2-(2-propenoyl)-2,6-diazaspiro[3.4]octan-6-yl)-3-azatricyclo[7.1.1.$0^{2,7}$]undeca-2,4,6-triene-5-carbonitrile. The stereochemistry of structures was arbitrarily assigned and is not established. 1st eluting atropisomer assigned as the M isomer and 2nd eluting atropisomer assigned as the P isomer.

Atropisomer Separation for Examples 14-57 and 14-58.

The racemic mixture was separated by preparative SFC using a Chiralcel OX (21×250 mm, 5 μm) column with a mobile phase of 55% liquid $CO_2$ and 45% MeOH using a flowrate of 90 mL/min to provide the respective P and M isomers of 4-(2-amino-7-fluoro-1,3-benzothiazol-4-yl)-7,7-dimethyl-2-(2-(2-propenoyl)-2,6-diazaspiro[3.4]octan-6-yl)-7,8-dihydro-5H-pyrano[4,3-b]pyridine-3-carbonitrile. The stereochemistry of structures was arbitrarily assigned and is not established. 1st eluting atropisomer assigned as the M isomer and 2nd eluting atropisomer assigned as the P isomer.

Atropisomer Separation for Examples 14-59 and 14-60.

The racemic mixture was separated by preparative SFC using a Chiral Technologies IG column (250×21 mm, 5 μm) with a mobile phase of 50% liquid $CO_2$ and 50% MeOH with 0.2% TEA using a flowrate of 70 mL/min to provide the respective P and M isomers of 1-(6-((1R,9R)-5-fluoro-6-(5-hydroxy-2-methylphenyl)-10,10-dimethyl-3-azatricyclo[7.1.1.$0^{2,7}$]undeca-2,4,6-trien-4-yl)-2,6-diazaspiro[3.4]octan-2-yl)-2-propen-1-one. The stereochemistry of structures was arbitrarily assigned and is not established. 1st eluting atropisomer assigned as the P isomer and 2nd eluting atropisomer assigned as the M isomer.

Atropisomer Separation for Examples 14-61 and 14-62.

The racemic mixture was separated by preparative SFC using a Chiralpak AS (21×150 mm, 5 μm) column with a mobile phase of 75% liquid $CO_2$ and 25% MeOH using a flowrate of 80 mL/min to provide the respective P and M isomers of 1-(6-(3-fluoro-4-(5-hydroxy-2-methylphenyl)-7,7-dimethyl-7,8-dihydro-5H-pyrano[4,3-b]pyridin-2-yl)-2,6-diazaspiro[3.4]octan-2-yl)-2-propen-1-one. The stereochemistry of structures was arbitrarily assigned and is not established. 1st eluting atropisomer assigned as the P isomer and 2nd eluting atropisomer assigned as the M isomer.

Atropisomer Separation for Examples 14-63 and 14-64.

The racemic mixture was separated by preparative SFC using a Chiralpak IG column (21×150 mm, 5 μm) with a mobile phase of 50% liquid $CO_2$ and 25% MeOH using a flowrate of 80 mL/min to provide the respective P and M of 1-(6-((1R,9R)-6-(1,6-dimethyl-1H-indazol-7-yl)-5-fluoro-10,10-dimethyl-3-azatricyclo[7.1.1.$0^{2,7}$]undeca-2,4,6-trien-4-yl)-2,6-diazaspiro[3.4]octan-2-yl)-2-propen-1-one. The stereochemistry of structures was arbitrarily assigned and is not established. 1st eluting atropisomer assigned as the M isomer and 2nd eluting atropisomer assigned as the P isomer.

Atropisomer Separation for Examples 14-66 and 14-67.

The racemic mixture was separated by preparative SFC using a Chiralpak AS column (21×150 mm, 5 μm) with a mobile phase of 65% liquid $CO_2$ and 35% MeOH using a flowrate of 80 mL/min to provide the respective P and M isomers of 1-(6-(3-fluoro-4-(6-hydroxy-1-naphthalenyl)-7,7-dimethyl-7,8-dihydro-5H-pyrano[4,3-b]pyridin-2-yl)-2,6-diazaspiro[3.4]octan-2-yl)-2-propen-1-one. The stereochemistry of structures was arbitrarily assigned and is not established. 1st eluting atropisomer assigned as the M isomer and 2nd eluting atropisomer assigned as the P isomer.

Atropisomer Separation for Examples 14-69 and 14-70.

The racemic mixture was separated by preparative SFC using a Chiralpak AS column (21×150 mm, 5 μm) with a mobile phase of 65% liquid $CO_2$ and 35% MeOH with 0.2% TEA using a flowrate of 80 mL/min to provide the respective P and M isomers of 1-(6-(3-fluoro-4-(3-hydroxy-1-naphthalenyl)-7,7-dimethyl-7,8-dihydro-5H-pyrano[4,3-b]pyridin-2-yl)-2,6-diazaspiro[3.4]octan-2-yl)-2-propen-1-one. The stereochemistry of structures was arbitrarily assigned and is not established. $1^{st}$ eluting atropisomer assigned as the P isomer and $2^{nd}$ eluting atropisomer assigned as the M isomer.

Atropisomer Separation for Examples 14-73 and 14-74.

The racemic mixture was separated by preparative SFC using a Chiralcel OD-H column (21×150 mm) with a mobile phase of 50% liquid $CO_2$ and 50% MeOH with 0.2% TEA using a flowrate of 80 mL/min to provide the respective P and M isomers of 1-(6-((1R,9R)-5-fluoro-10,10-dimethyl-6-(5-methyl-1H-indazol-4-yl)-3-azatricyclo[7.1.1.$0^{2,7}$]undeca-2,4,6-trien-4-yl)-2,6-diazaspiro[3.4]octan-2-yl)-2-propen-1-one. The stereochemistry of structures was arbitrarily assigned and is not established. $1^{st}$ eluting atropisomer assigned as the M isomer and $2^{nd}$ eluting atropisomer assigned as the P isomer.

Atropisomer Separation for Examples 14-76 and 14-77.

The racemic mixture was separated by preparative SFC using a Chiralcel OD column (21×250 mm) with a mobile phase of 50% liquid $CO_2$ and 50% MeOH with 0.2% TEA using a flowrate of 80 mL/min to provide the respective P and M isomers of 1-(6-((1R,9R)-5-fluoro-6-(3-hydroxy-1-naphthalenyl)-10,10-dimethyl-3-azatricyclo[7.1.1.$0^{2,7}$]undeca-2,4,6-trien-4-yl)-2,6-diazaspiro[3.4]octan-2-yl)-2-propen-1-one. The stereochemistry of structures was arbitrarily assigned and is not established. $1^{st}$ eluting atropisomer assigned as the M isomer and $2^{nd}$ eluting atropisomer assigned as the P isomer.

Atropisomer Separation for Examples 14-78 and 14-79.

The racemic mixture was separated by preparative SFC using a Chiralpak AZ column (21×150 mm, 5 μm) with a mobile phase of 55% liquid $CO_2$ and 45% MeOH using a flowrate of 80 mL/min to provide the respective P and M isomers of 1-(6-(4-(5-chloro-1,6-dimethyl-1H-indazol-7-yl)-3-fluoro-7,7-dimethyl-7,8-dihydro-5H-pyrano[4,3-b]pyridin-2-yl)-2,6-diazaspiro[3.4]octan-2-yl)-2-propen-1-one. The stereochemistry of structures was arbitrarily assigned and is not established. $1^{st}$ eluting atropisomer assigned as the M isomer and $2^{nd}$ eluting atropisomer assigned as the P isomer.

Atropisomer Separation for Examples 14-81 and 14-82.

The racemic mixture was separated by preparative SFC using a Chiral Technologies IC column (250×21 mm, 5 μm) with a mobile phase of 50% liquid $CO_2$ and 50% MeOH with 0.2% TEA using a flowrate of 60 mL/min to provide the respective P and M isomers of 7,7-dimethyl-4-(6-methyl-1H-indazol-7-yl)-2-(2-(2-propenoyl)-2,6-diazaspiro[3.4]octan-6-yl)-7,8-dihydro-5H-pyrano[4,3-b]pyridine-3-carbonitrile. The stereochemistry of structures was arbitrarily assigned and is not established. $1^{st}$ eluting atropisomer assigned as the M isomer and $2^{nd}$ eluting atropisomer assigned as the P isomer.

Atropisomer Separation for Examples 14-88 and 14-89.

The racemic mixture was separated by preparative SFC using a Chiralpak IC column (21×250 mm, 5 μm) with a mobile phase of 70% liquid $CO_2$ and 30% (1:1) MeOH:ACN using a flowrate of 100 mL/min to provide the respective P and M isomers of 1-(6-(4-(5-chloro-1,6-dimethyl-1H-indazol-7-yl)-3,7,7-trimethyl-7,8-dihydro-5H-pyrano[4,3-b]pyridin-2-yl)-2,6-diazaspiro[3.4]octan-2-yl)-2-propen-1-one. The stereochemistry of structures was arbitrarily assigned and is not established. $1^{st}$ eluting atropisomer assigned as the M isomer and $2^{nd}$ eluting atropisomer assigned as the P isomer.

Atropisomer Separation for Examples 14-97

The product of Step 1 was purified by silica gel chromatography using 0-100% EtOAc in petroleum ether to provide the P and M isomers of tert-butyl 6-((7S)-7-(1,4-dimethyl-1H-pyrazol-5-yl)-3-methyl-4-(6-methyl-1H-indazol-7-yl)-5,6,7,8-tetrahydroquinolin-2-yl)-2,6-diazaspiro[3.4]octane-2-carboxylate. The stereochemistry of structures was arbitrarily assigned and is not established. $1^{st}$ eluting atropisomer assigned as the M isomer and $2^{nd}$ eluting atropisomer assigned as the P isomer.

Atropisomer Separation for Examples 14-98.

The product of Step 1 was purified by silica gel chromatography using 0-100% EtOAc in petroleum ether to provide the P and M isomers of tert-butyl 6-((7R)-7-(1,4-dimethyl-1H-pyrazol-5-yl)-3-methyl-4-(6-methyl-1H-indazol-7-yl)-5,6,7,8-tetrahydroquinolin-2-yl)-2,6-diazaspiro[3.4]octane-2-carboxylate. The stereochemistry of structures was arbitrarily assigned and is not established. $1^{st}$ eluting atropisomer assigned as the M isomer and $2^{nd}$ eluting atropisomer assigned as the P isomer.

Atropisomer Separation for Examples 14-99 and 14-100.

The racemic mixture was separated by preparative SFC using (S,S) Whelk O-1 column (250×21 mm, 5 μm) with a mobile phase of 80% liquid $CO_2$ and 20% MeOH using a flowrate of 80 mL/min to provide the respective P and M isomers of tert-butyl 6-(4-(1,6-dimethyl-1H-indazol-7-yl)-3,7,7-trimethyl-7,8-dihydro-5H-pyrano[4,3-b]pyridin-2-yl)-2,6-diazaspiro[3.4]octane-2-carboxylate. The stereochemistry of structures was arbitrarily assigned and is not established. $1^{st}$ eluting atropisomer assigned as the M isomer and $2^{nd}$ eluting atropisomer assigned as the P isomer.

Atropisomer Separation for Examples 14-101 and 14-102.

The racemic mixture was separated by preparative SFC using Chiralcel OD (21×250 mm, 5 μm) column with a mobile phase of 65% liquid $CO_2$ and 35% MeOH using a flowrate of 80 mL/min to provide the respective P and M isomers of 1-(6-(4-(1,6-dimethyl-1H-indazol-7-yl)-3-fluoro-7,7-dimethyl-7,8-dihydro-5H-pyrano[4,3-b]pyridin-2-yl)-2,6-diazaspiro[3.4]octan-2-yl)prop-2-en-1-one. The stereochemistry of structures was arbitrarily assigned and is not established. $1^{st}$ eluting atropisomer assigned as the M isomer and $2^{nd}$ eluting atropisomer assigned as the P isomer.

Atropisomer Separation for Examples 14-107.

The racemic mixture was separated by preparative SFC using Chiralcel OJ-H (21×250 mm, 5 μm) column with a mobile phase of 80% liquid $CO_2$ and 20% MeOH:ACN using a flowrate of 100 mL/min to provide the respective P and M isomers of 1-(6-(4-(5-chloro-1,6-dimethyl-1H-indazol-7-yl)-3-fluoro-7-(3-oxetanyl)-5,6,7,8-tetrahydro-1,7-naphthyridin-2-yl)-2,6-diazaspiro[3.4]octan-2-yl)-2-propen-1-one. The stereochemistry of structures was arbitrarily assigned and is not established. $1^{st}$ eluting atropisomer assigned as the P isomer and $2^{nd}$ eluting atropisomer assigned as the M isomer.

Method 15

Example 15-1: 4-(5-methyl-1H-indazol-4-yl)-7-(1-methyl-1H-pyrazol-5-yl)-2-(2-(2-propenoyl)-2,6-diazaspiro[3.4]octan-6-yl)-3-quinolinecarbonitrile

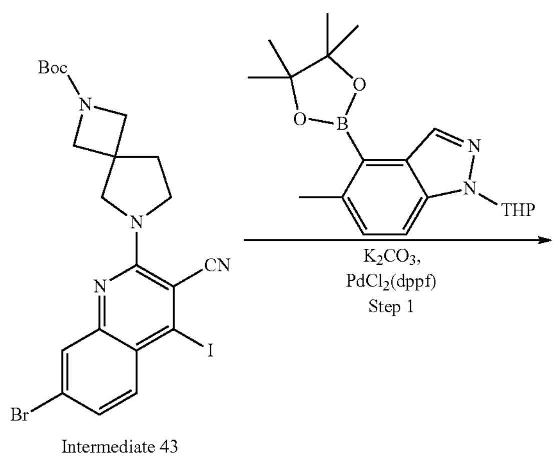

Intermediate 43

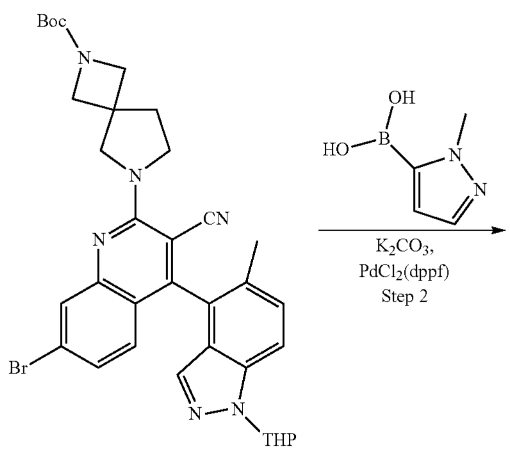

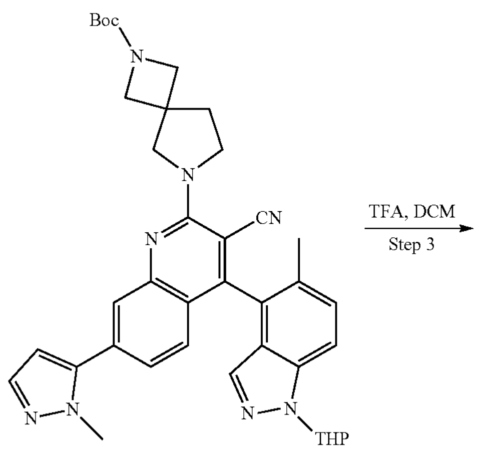

-continued

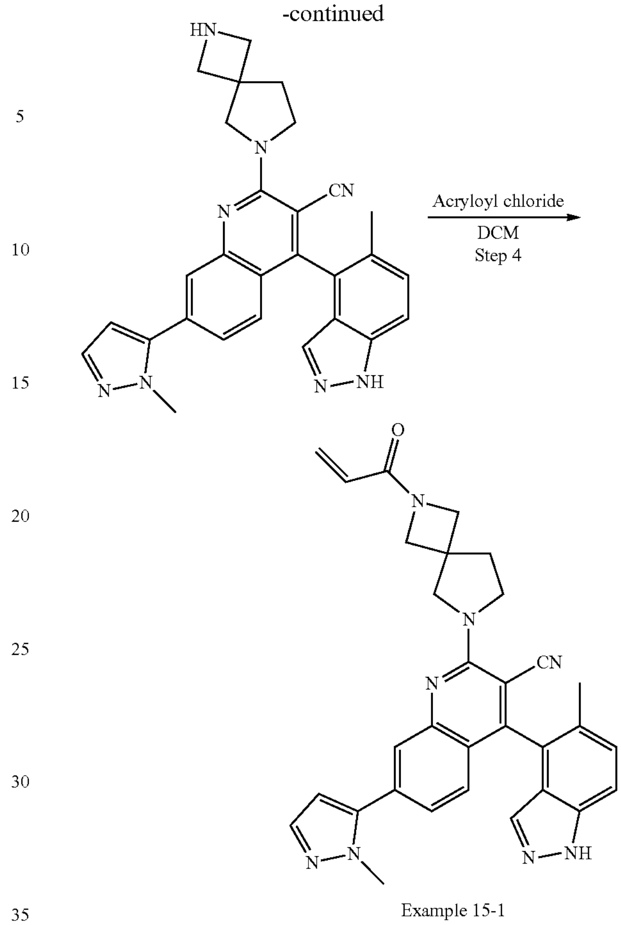

Example 15-1

Step 1: tert-butyl 6-(7-bromo-3-cyano-4-(5-methyl-1-(tetrahydro-2H-pyran-2-yl)-1H-indazol-4-yl)quinolin-2-yl)-2,6-diazaspiro[3.4]octane-2-carboxylate A mixture of tert-butyl 6-(7-bromo-3-cyano-4-iodoquinolin-2-yl)-2,6-diazaspiro[3.4]octane-2-carboxylate (0.852 g, 1.497 mmol, Intermediate 43), 5-methyl-1-(tetrahydro-2H-pyran-2-yl)-4-(4,4,5,5-tetramethyl-1,3,2-dioxaborolan-2-yl)-1H-indazole (0.282 g, 0.823 mmol, PharmaBlock), $PdCl_2(dppf)$ DCM adduct (0.244 g, 0.299 mmol, Sigma-Aldrich) and $K_2CO_3$ (0.621 g, 4.49 mmol, Sigma-Aldrich) was purged with $N_2$ followed by the addition of 1,4-dioxane/water (10:0.6 mL) and the resulting mixture was heated at 100° C. for 20 h. The mixture was brought to room temperature, diluted with aqueous saturated $NaHCO_3$ and extracted with EtOAc. The combined organics were dried over $Na_2SO_4$, filtered, concentrated and chromatographed on silica gel using 0-30% (3:1) EtOAc:EtOH in heptanes to afford tert-butyl 6-(7-bromo-3-cyano-4-(5-methyl-1-(tetrahydro-2H-pyran-2-yl)-1H-indazol-4-yl)quinolin-2-yl)-2,6-diazaspiro[3.4]octane-2-carboxylate as a light yellow solid that was used without further purification. m/z (ESI): 656.7 $(M+H)^+$.

Step 2: tert-butyl 6-(3-cyano-4-(5-methyl-1-(tetrahydro-2H-pyran-2-yl)-1H-indazol-4-yl)-7-(1-methyl-1H-pyrazol-5-yl)quinolin-2-yl)-2,6-diazaspiro[3.4]octane-2-carboxylate A mixture of tert-butyl 6-(7-bromo-3-cyano-4-(5-methyl-1-(tetrahydro-2H-pyran-2-yl)-1H-indazol-4-yl)quinolin-2- yl)-2,6-diazaspiro[3.4]octane-2-carboxylate (0.300 g, 0.456 mmol), (1-methyl-1H-pyrazol-5-yl)boronic acid (0.115 g, 0.912 mmol, Combi-Blocks), $PdCl_2$(dppf) DCM adduct (1:1) (0.075 g, 0.091 mmol, Sigma-Aldrich) and $K_2CO_3$ (0.252 g, 1.825 mmol, Sigma-Aldrich) was purged with $N_2$ followed by the addition of 1,4-dioxane:water (5:0.5 mL) and the resulting mixture was heated at 90° C. overnight. The reaction was brought to room temperature, diluted with aqueous saturated $NaHCO_3$ and extracted with EtOAc. The combined organics were dried over $Na_2SO_4$, filtered, concentrated and chromatographed on silica gel using 0-30% (3:1) EtOAc:EtOH in heptanes to afford tert-butyl 6-(3-cyano-4-(5-methyl-1-(tetrahydro-2H-pyran-2-yl)-1H-indazol-4-yl)-7-(1-methyl-1H-pyrazol-5-yl)quinolin-2-yl)-2,6-diazaspiro[3.4]octane-2-carboxylate (0.081 g, 27.0% yield) as a yellow solid. m/z (ESI): 658.8 $(M+H)^+$.

Step 3: 4-(5-methyl-1H-indazol-4-yl)-7-(1-methyl-1H-pyrazol-5-yl)-2-(2,6-diazaspiro[3.4]octan-6-yl)quinoline-3-carbonitrile To a solution of tert-butyl 6-(3-cyano-4-(5-methyl-1-(tetrahydro-2H-pyran-2-yl)-1H-indazol-4-yl)-7-(1-methyl-1H-pyrazol-5-yl)quinolin-2-yl)-2,6-diazaspiro[3.4]octane-2-carboxylate (0.081 g, 0.123 mmol) in DCM (2 mL) was added TFA (6.0 mL, 78 mmol, Sigma-Aldrich) and the reaction was stirred at room temperature for 30 min. The reaction was basified with aqueous 10% $Na_2CO_3$ and extracted with DCM. The combined organics were dried over $Na_2SO_4$, and concentrated to afford 4-(5-methyl-1H-indazol-4-yl)-7-(1-methyl-1H-pyrazol-5-yl)-2-(2,6-diazaspiro[3.4]octan-6-yl)quinoline-3-carbonitrile as a yellow film which was carried forward to the next step as is. m/z (ESI): 474.8 $(M+H)^+$.

Step 4: 2-(2-acryloyl-2,6-diazaspiro[3.4]octan-6-yl)-4-(5-methyl-1H-indazol-4-yl)-7-(1-methyl-1H-pyrazol-5-yl)quinoline-3-carbonitrile To a solution of 4-(5-methyl-1H-indazol-4-yl)-7-(1-methyl-1H-pyrazol-5-yl)-2-(2,6-diazaspiro[3.4]octan-6-yl)quinoline-3-carbonitrile in DCM (10 mL) was added acryloyl chloride (0.553 mL, 0.111 mmol, Sigma-Aldrich) and stirred at room temperature for 10 min. The reaction was concentrated and chromatographed on silica gel using 0-10% MeOH in DCM to afford 2-(2-acryloyl-2,6-diazaspiro[3.4]octan-6-yl)-4-(5-methyl-1H-indazol-4-yl)-7-(1-methyl-1H-pyrazol-5-yl)quinoline-3-carbonitrile (0.008 g, 12.3% yield) as a yellow solid. $^1H$ NMR (400 MHz, DMSO-$d_6$) δ ppm 13.12-13.42 (m, 1H), 7.80 (d, J=1.5 Hz, 1H), 7.68 (d, J=8.6 Hz, 1H), 7.57 (d, J=1.9 Hz, 1H), 7.52 (d, J=1.9 Hz, 1H), 7.47 (d, J=8.6 Hz, 1H), 7.32 (dd, J=8.5, 1.8 Hz, 1H), 6.98 (d, J=8.8 Hz, 1H), 6.58 (d, J=1.9 Hz, 1H), 6.27-6.39 (m, 1H), 6.12 (dd, J=17.0, 2.2 Hz, 1H), 5.63-5.73 (m, 1H), 4.33 (d, J=8.8 Hz, 1H), 4.22 (dd, J=8.6, 3.1 Hz, 1H), 4.00-4.10 (m, 4H), 3.90-3.98 (m, 7H), 2.16-2.21 (m, 2H), 2.12 (d, J=2.5 Hz, 3H). m/z (ESI): 528.8 $(M+H)^+$.

TABLE 7

Examples 15-2 to 15-7 were prepared following the procedure described in Method 15, steps 1-4, above as follows:

| Ex.# | Chemical Structure | Name | Method changes | Reagent |
|---|---|---|---|---|
| 15-2 | 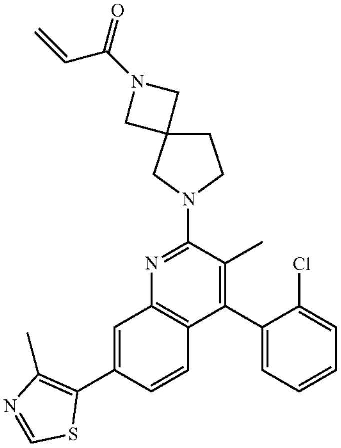 [SMILES: C=CC(=O)N1CC2(CCN(c3nc4cc(-c5scnc5C)ccc4c(-c4ccccc4Cl)c3C)C2)C1] | 1-(6-(4-(2-chlorophenyl)-3-methyl-7-(4-methyl-1,3-thiazol-5-yl)-2-quinolinyl)-2,6-diazaspiro[3.4]octan-2-yl)-2-propen-1-one | The order of Step 1 and Step 2 was reversed. Step 1 used SPhos Pd G3 and $K_3PO_4$. | Step 1: Intermediate 47 and 4-methyl-5-(4,4,5,5-tetramethyl-1,3,2-dioxaborolan-2-yl)thiazole (Combi-Blocks). Step 2: 2-chloro-phenylboronic acid (Matrix Scientific) |

TABLE 7-continued

Examples 15-2 to 15-7 were prepared following the procedure described in Method 15, steps 1-4, above as follows:

| Ex.# | Chemical Structure | Name | Method changes | Reagent |
|---|---|---|---|---|
| 15.3 | 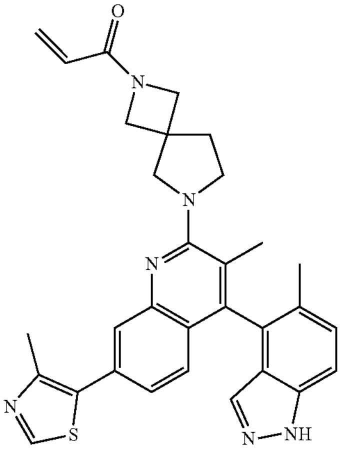 [SMILES: C=CC(=O)N1CC2(CCN(c3nc4cc(-c5scnc5C)ccc4c(-c4c(C)ccc5[nH]ncc45)c3C)C2)C1] | 1-(6-(3-methyl-4-(5-methyl-1H-indazol-4-yl)-7-(4-methyl-1,3-thiazol-5-yl)-2-quinolinyl)-2,6-diazaspiro[3.4]octan-2-yl)-2-propen-1-one | The order of Step 1 and Step 2 was reversed. Step 1 used Pd tetrakis and $Na_2CO_3$. | Step 1: Intermediate 47 and 4-methyl-5-(4,4,5,5-tetramethyl-1,3,2-dioxaborolan-2-yl)thiazole (Combi-Blocks). Step 2: 5-methyl-1H-indazol-4-yl boronic acid (Combi-Blocks) |
| 15-4 | 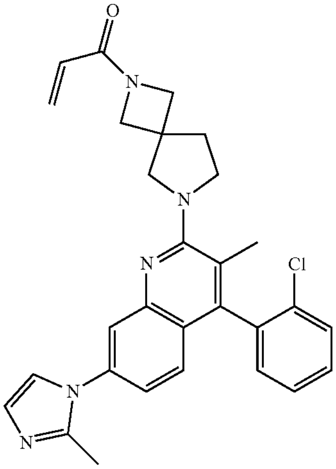 [SMILES: C=CC(=O)N1CC2(CCN(c3nc4cc(-n5ccnc5C)ccc4c(-c4ccccc4Cl)c3C)C2)C1] | 1-(6-(4-(2-chlorophenyl)-3-methyl-7-(2-methyl-1H-imidazol-1-yl)-2-quinolinyl)-2,6-diazaspiro[3.4]octan-2-yl)-2-propen-1-one | The order of Step 1 and Step 2 was reversed. See alternate Step 1 below. Step 2: SPhos Pd G3 and $K_3PO_4$ used. | Step 2: 2-chloro-phenylboronic acid (Matrix Scientific) |
| 15-5 | 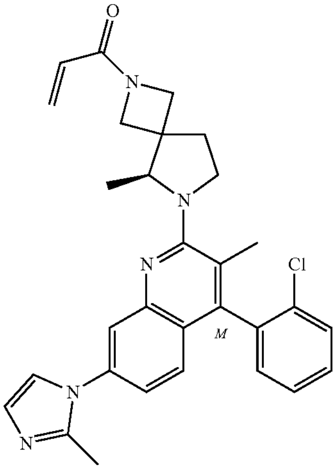 | (M)-1-((5S)-6-(4-(2-chlorophenyl)-3-methyl-7-(2-methyl-1H-imidazol-1-yl)-2-quinolinyl)-5-methyl-2,6-diazaspiro[3.4]octan-2-yl)-2-propen-1-one (1$^{st}$ eluting peak) | The order of Step 1 and Step 2 was reversed. Step 1 performed using procedure in Exampe 15-4, Step 1. Step 2: SPhos Pd G3 and $K_3PO_4$ used. Atropisomer separation conditions below. | Alternate Step 1: Intermediate 49 and Amine 3. Step 2: 2-chloro-phenylboronic acid (Matrix Scientific) |

TABLE 7-continued

Examples 15-2 to 15-7 were prepared following the procedure described in Method 15, steps 1-4, above as follows:

| Ex.# | Chemical Structure | Name | Method changes | Reagent |
| --- | --- | --- | --- | --- |
| 15-6 | 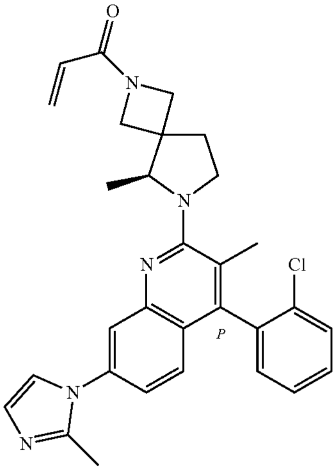 | (P)-1-((5S)-6-(4-(2-chlorophenyl)-3-methyl-7-(2-methyl-1H-imidazol-1-yl)-2-quinolinyl)-5-methyl-2,6-diazaspiro[3.4]octan-2-yl)-2-propen-1-one ($2^{nd}$ eluting peak) | The order of Step 1 and Step 2 was reversed. Step 1 performed using procedure in Exampe 15-4, Step 1. Step 2: SPhos Pd G3 and $K_3PO_4$ used. Atropisomer separation conditions below. | Alternate Step 1: Intermediate 49 and Amine 3. Step 2: 2-chloro-phenylboronic acid (Matrix Scientific) |
| 15-7 | 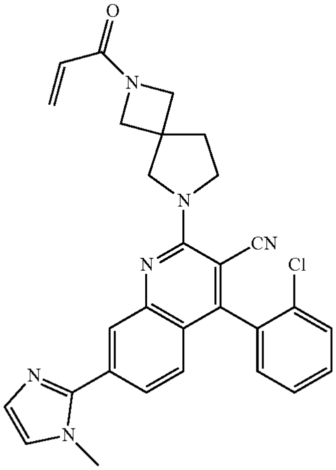 [SMILES: C=CC(=O)N1CC2(CCN(c3nc4cc(-c5nccn5C)ccc4c(-c4ccccc4Cl)c3C#N)C2)C1] | 4-(2-chlorophenyl)-7-(1-methyl-1H-imidazol-2-yl)-2-(2-(2-propenoyl)-2,6-diazaspiro[3.4]octan-6-yl)-3-quinolinecarbonitrile | Step 2: Pd tetrakis used. | Step 1: 2-chloro-phenylboronic acid (Matrix Scientific). Step 2: 1-methyl-2-(tributylstannyl)-1H-imidazole (Synthonix). |

Alternate Step 1 for Example 15-4

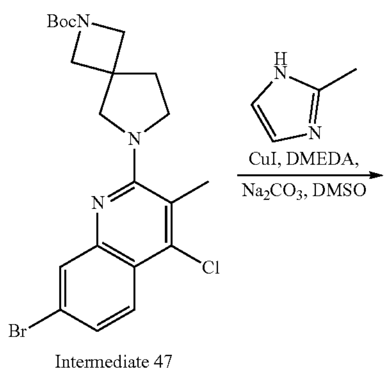

Intermediate 47

-continued

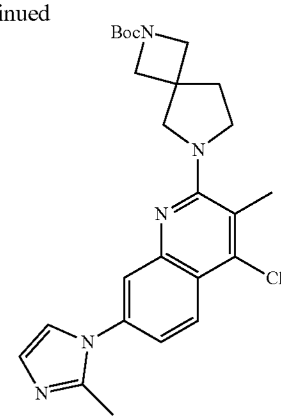

A mixture of tert-butyl 6-(7-bromo-4-chloro-3-methylquinolin-2-yl)-2,6-diazaspiro[3.4]octane-2-carboxylate (0.203 g, 0.435 mmol, Intermediate 47), 2-methyl-1H-imidazole (0.071 g, 0.870 mmol, Combi-Blocks), CuI (0.166 g, 0.870 mmol, Sigma-Aldrich), and $Na_2CO_3$ (0.184 g, 1.739 mmol, Sigma-Aldrich) was purged with $N_2$, followed by the addition of N,N'-dimethylethylenediamine (0.140 mL, 1.305 mmol, Sigma-Aldrich) and degassed DMSO (5 mL). The resulting mixture was heated at 120° C. for 2 h. The reaction was washed with water, washed with aqueous saturated $NH_4Cl$, dried over $Na_2SO_4$, concentrated in vacuo and chromatographed on silica gel using 0-30% (3:1EtOAc/EtOH) in heptanes to afford tert-butyl 6-(4-chloro-3-methyl-7-(2-methyl-1H-imidazol-1-yl)quinolin-2-yl)-2,6-diazaspiro-[3.4]octane-2-carboxylate (0.120 g, 59.0% yield) as a white solid. m/z (ESI): 468.2 $(M+H)^+$.

Atropisomer Separation for Examples 15-4 and 15-5.

The racemic mixture was separated by SFC using a Chiralpak AZ column (250×21 mm, 5 μm) with a mobile phase of 60% liquid $CO_2$ and 40% iPrOH with 0.2% TEA using a flowrate of 80 mL/min to generate a mixture of peak 1 and peak 2 along with separated peak 3 and peak 4. The mixture of peak 1 and peak 2 was separated by SFC using a Chiralcel OD column (500×21 mm, 5 μm) with a mobile phase of 75% liquid $CO_2$ and 25% MeOH with 0.2% TEA using a flowrate of 50 mL/min to provide the respective P and M isomers of 1-((5S)-6-(4-(2-chlorophenyl)-3-methyl-7-(2-methyl-1H-imidazol-1-yl)-2-quinolinyl)-5-methyl-2,6-diazaspiro[3.4]octan-2-yl)-2-propen-1-one. The stereochemistry of structures was arbitrarily assigned and is not established. 1st eluting atropisomer assigned as the M isomer and 2nd eluting atropisomer assigned as the P isomer.

Method 16

Example 16-1: 1-(6-(4-(2-chlorophenyl)-3-methyl-7-(1-methyl-1H-pyrazol-5-yl)quinolin-2-yl)-2,6-diazaspiro[3.4]octan-2-yl)prop-2-en-1-one

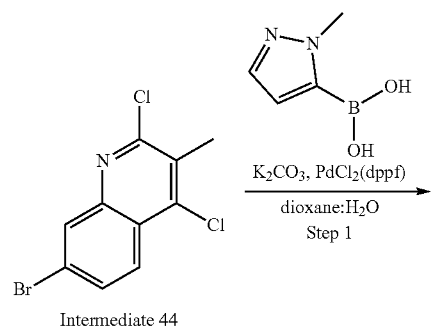

Intermediate 44

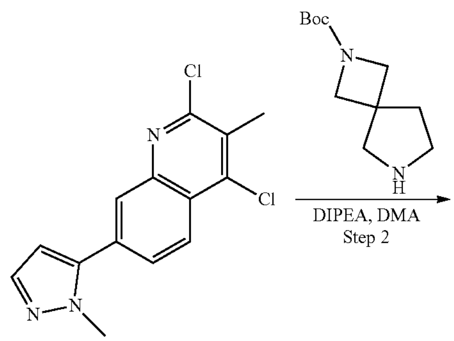

-continued

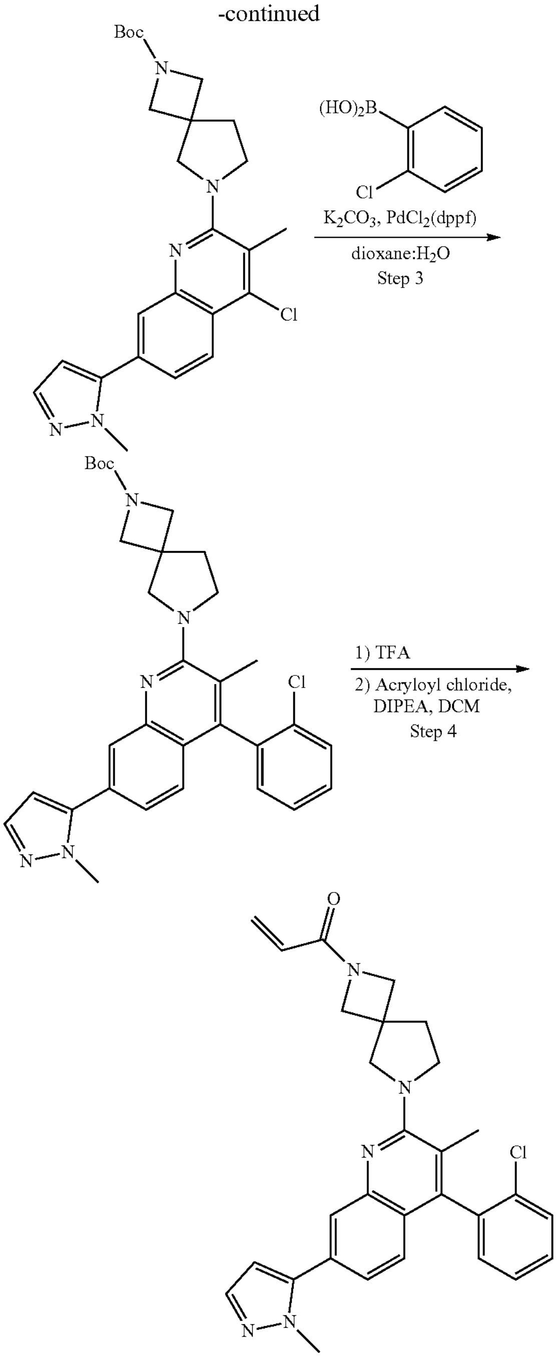

Example 16-1

Step 1: 2,4-dichloro-3-methyl-7-(1-methyl-1H-pyrazol-5-yl)quinoline

A mixture of 7-bromo-2,4-dichloro-3-methylquinoline (0.300 g, 1.031 mmol, Intermediate 44), (1-methyl-1H-pyrazol-5-yl)boronic acid (0.260 g, 2.062 mmol, Combi-Blocks), $PdCl_2$(dppf) DCM adduct (0.168 g, 0.206 mmol. Sigma-Aldrich), and $K_2CO_3$ (0.570 g, 4.12 mmol, Sigma-Aldrich) was purged with $N_2$ followed by the addition of 1,4-dioxane:water (5:0.5 mL) and the resulting mixture was heated at 95° C. for 3 h. The reaction was cooled to room temperature, diluted with aqueous saturated $NaHCO_3$ and extracted with EtOAc. The combined organics were dried over $Na_2SO_4$, concentrated, and chromatographed on silica gel using 0-30% (3:1) EtOAc:EtOH in heptanes to afford 2,4-dichloro-3-methyl-7-(1-methyl-1H-pyrazol-5-yl)quinoline as a yellow solid. m/z (ESI): 292.0 $(M+H)^+$.

Step 2: tert-butyl 6-(4-chloro-3-methyl-7-(1-methyl-1H-pyrazol-5-yl)quinolin-2-yl)-2,6-diazaspiro[3.4]octane-2-carboxylate A mixture of 2,4-dichloro-3-methyl-7-(1-methyl-1H-pyrazol-5-yl)quinoline (86 mg, 0.294 mmol), DIPEA (0.257 mL, 1.472 mmol, Sigma-Aldrich), and tert-butyl 2,6-diazaspiro[3.4]octane-2-carboxylate (62.5 mg, 0.294 mmol, PharmaBlock) in DMA (5 mL) was stirred at 100° C. for 4 h. The mixture was brought to room temperature, diluted with aqueous saturated $NaHCO_3$ and extracted with EtOAc. The combined organics were chromatographed on silica gel using 0-20% (3:1) EtOAc:EtOH in heptanes to afford tert-butyl 6-(4-chloro-3-methyl-7-(1-methyl-1H-pyrazol-5-yl)quinolin-2-yl)-2,6-diazaspiro-[3.4]octane-2-carboxylate (0.104 g, 75% yield) as a yellow oil. m/z (ESI): 468.2 $(M+H)^+$.

Step 3: tert-butyl 6-(4-chloro-3-methyl-7-(1-methyl-1H-pyrazol-5-yl)quinolin-2-yl)-2,6-diazaspiro[3.4]octane-2-carboxylate A mixture of tert-butyl 6-(4-chloro-3-methyl-7-(1-methyl-1H-pyrazol-5-yl)quinolin-2-yl)-2,6-diazaspiro[3.4]octane-2-carboxylate (0.104 g, 0.222 mmol), 2-chlorophenylboronic acid (0.174 g, 1.111 mmol, Matrix Scientific), $PdCl_2$(dppf) DCM adduct (0.036 g, 0.044 mmol, Sigma-Aldrich) and $K_2CO_3$ (0.307 g, 2.222 mmol, Sigma-Aldrich) was purged with $N_2$ followed by the addition of 1,4-dioxane:water (6:0.6 mL) and the resulting mixture was heated at 100° C. for 3 h. The mixture was cooled to room temperature, diluted with aqueous saturated $NaHCO_3$ and extracted with EtOAc. The combined organics were dried over $Na_2SO_4$, concentrated, and chromatographed on silica gel using 0-30% (3:1) EtOAc:EtOH in heptanes to afford tert-butyl 6-(4-(2-chlorophenyl)-3-methyl-7-(1-methyl-1H-pyrazol-5-yl)quinolin-2-yl)-2,6-diazaspiro[3.4]octane-2-carboxylate (0.087 g, 72.0% yield) as a yellow solid. m/z (ESI): 544.2 $(M+H)^+$.

Step 4: 1-(6-(4-(2-chlorophenyl)-3-methyl-7-(1-methyl-1H-pyrazol-5-yl)quinolin-2-yl)-2,6-diazaspiro[3.4]octan-2-yl)prop-2-en-1-one To a solution of tert-butyl 6-(4-(2-chlorophenyl)-3-methyl-7-(1-methyl-1H-pyrazol-5-yl)quinolin-2-yl)-2,6-diazaspiro[3.4]octane-2-carboxylate (0.087 g, 0.160 mmol) in DCM (1 mL) was added TFA (3.0 mL, 38.9 mmol, Sigma-Aldrich) and the resulting mixture was stirred at room temperature for 30 min. The reaction was basified with 10% $Na_2CO_3$ and extracted with DCM. The combined organics were concentrated to afford 4-(2-chlorophenyl)-3-methyl-7-(1-methyl-1H-pyrazol-5-yl)-2-(2,6-diazaspiro[3.4]octan-6-yl)quinoline as a pale yellow solid to be used as is. m/z (ESI): 444.2 $(M+H)^+$.

To a solution of 4-(2-chlorophenyl)-3-methyl-7-(1-methyl-1H-pyrazol-5-yl)-2-(2,6-diazaspiro[3.4]octan-6-yl)quinoline in DCM (5 mL) was added DIPEA (2.0 mL, 11.45 mmol, Sigma-Aldrich) followed by the addition of acryloyl chloride (0.799 mL, 0.160 mmol, Sigma-Aldrich) and stirred at room temperature for 10 min. The reaction was concentrated and chromatographed on silica gel using 0-30% (3:1) EtOAc:EtOH in heptanes, then 5% MeOH in DCM to afford 1-(6-(4-(2-chlorophenyl)-3-methyl-7-(1-methyl-1H-pyrazol-5-yl)quinolin-2-yl)-2,6-diazaspiro[3.4]octan-2-yl)prop-2-en-1-one (0.057 g, 71.6% yield) as a light yellow solid. $^1H$ NMR (400 MHz, DMSO-$d_6$) δ ppm 7.70-7.77 (m, 2H), 7.53-7.62 (m, 2H), 7.50 (d, J=1.9 Hz, 1H), 7.36 (dd, J=6.7, 2.2 Hz, 1H), 7.31 (dd, J=8.4, 1.8 Hz, 1H), 6.94 (d, J=8.5 Hz, 1H), 6.49 (d, J=1.9 Hz, 1H), 6.28-6.40 (m, 1H), 6.12 (dd, J=17.0, 2.1 Hz, 1H), 5.68 (dd, J=10.4, 2.1 Hz, 1H), 4.16-4.31 (m, 2H), 3.85-4.02 (m, 8H), 3.74 (br t, J=6.5 Hz, 2H), 2.18 (br t, J=5.6 Hz, 1H), 2.12 (s, 3H). m/z (ESI): 498.2 $(M+H)^+$.

TABLE 8

Examples 16-2 to 16-14 were prepared following the procedure described in Method 16, Steps 1-5, above as follows:

| Ex.# | Chemical Structure | Name | Method changes | Reagent |
|---|---|---|---|---|
| 16-2 | 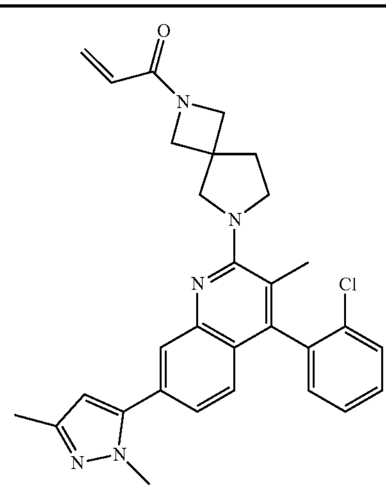 | 1-(6-(4-(2-chlorophenyl)-7-(1,3-dimethyl-1H-pyrazol-5-yl)-3-methyl-2-quinolinyl)-2,6-diazaspiro[3.4]octan-2-yl)-2-propen-1-one | | Step 1: 1,3-dimethyl-5-(4,4,5,5-tetramethyl-1,3,2-dioxaborolan-2-yl)-1H-pyrazole (Combi-Blocks) |

TABLE 8-continued

| Examples 16-2 to 16-14 were prepared following the procedure described in Method 16, Steps 1-5, above as follows: | | | | |
|---|---|---|---|---|
| Ex.# | Chemical Structure | Name | Method changes | Reagent |
| 16-3 | 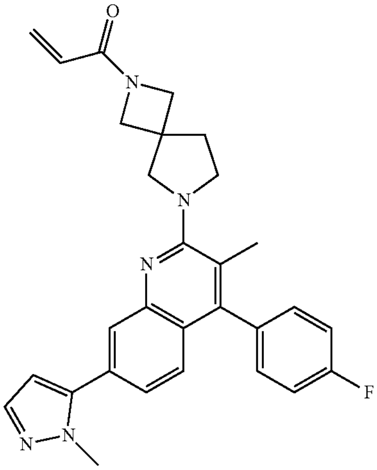 [SMILES: C=CC(=O)N1CC2(CCN(c3nc4cc(-c5ccnn5C)ccc4c(-c4ccc(F)cc4)c3C)C2)C1] | 1-(6-(4-(4-fluorophenyl)-3-methyl-7-(1-methyl-1H-pyrazol-5-yl)-2-quinolinyl)-2,6-diazaspiro[3.4]octan-2-yl)-2-propen-1-one | | Step 3: (4-fluorophenyl) boranediol (Frontier Scientific Services, Inc.) |
| 16-4 | 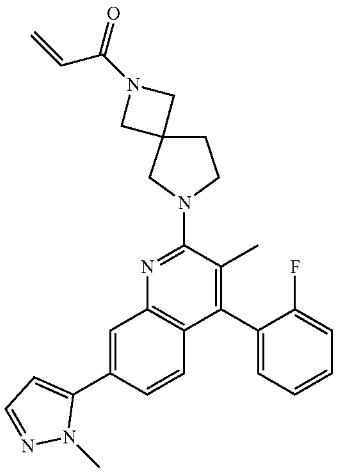 [SMILES: C=CC(=O)N1CC2(CCN(c3nc4cc(-c5ccnn5C)ccc4c(-c4ccccc4F)c3C)C2)C1] | 1-(6-(4-(2-fluorophenyl)-3-methyl-7-(1-methyl-1H-pyrazol-5-yl)-2-quinolinyl)-2,6-diazaspiro[3,4]octan-2-yl)-2-propen-1-one | | Step 3: (2-fluorophenyl) boranediol (Combi-Blocks) |
| 16-5 | 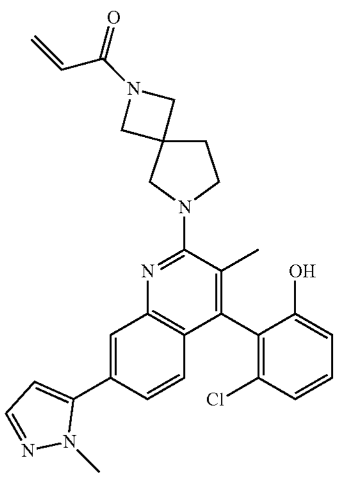 [SMILES: C=CC(=O)N1CC2(CCN(c3nc4cc(-c5ccnn5C)ccc4c(-c4c(O)cccc4Cl)c3C)C2)C1] | 1-(6-(4-(2-chloro-6-hydroxyphenyl)-3-methyl-7-(1-methyl-1H-pyrazol-5-yl)-2-quinolinyl)-2,6-diazaspiro[3.4]octan-2-yl)-2-propen-1-one | Step 3: $PdCl_2$(dppf) replaced with RuPhos and RuPhos Pd G2 | Step 3: (2-chloro-6-hydroxy-phenyl) boronic acid (Combi-Blocks) |

TABLE 8-continued

Examples 16-2 to 16-14 were prepared following the procedure described in Method 16, Steps 1-5, above as follows:

| Ex.# | Chemical Structure | Name | Method changes | Reagent |
|---|---|---|---|---|
| 16-6 | 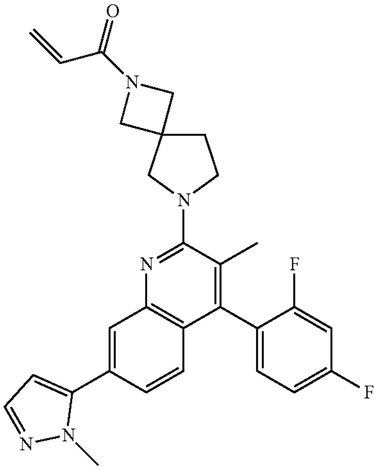 [SMILES: C=CC(=O)N1CC2(CCN(c3nc4cc(-c5ccnn5C)ccc4c(-c4ccc(F)cc4F)c3C)C2)C1] | 1-(6-(4-(2,4-difluorophenyl)-3-methyl-7-(1-methyl-1H-pyrazol-5-yl)-2-quinolinyl)-2,6-diazaspiro[3.4]octan-2-yl)-2-propen-1-one | Step 1 and step 2 were reversed. Step 3: SPhos Pd G3 and $K_3PO_4$ replaced $PdCl_2$(dppf) and $K_2CO_3$ | Step 3: (2,4-difluoro-phenyl) boranediol (Combi-Blocks) |
| 16-7 | 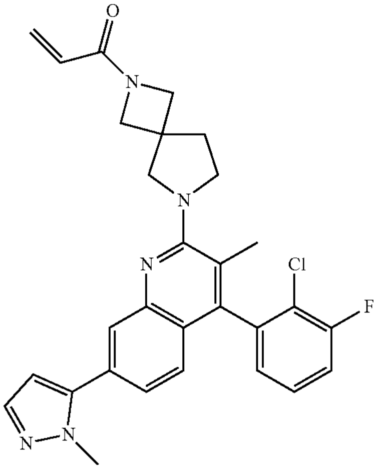 [SMILES: C=CC(=O)N1CC2(CCN(c3nc4cc(-c5ccnn5C)ccc4c(-c4cccc(F)c4Cl)c3C)C2)C1] | 1-(6-(4-(2-chloro-3-fluorophenyl)-3-methyl-7-(1-methyl-1H-pyrazol-5-yl)-2-quinolinyl)-2,6-diazaspiro[3.4]octan-2-yl)-2-propen-1-one | Step 1 and step 2 were reversed. Step 3: SPhos Pd G3 and $K_3PO_4$ replaced $PdCl_2$(dppf) and $K_2CO_3$ | Step 3: 1-borono-2-chloro-3-fluorobenzene (Combi-Blocks) |
| 16-8 | 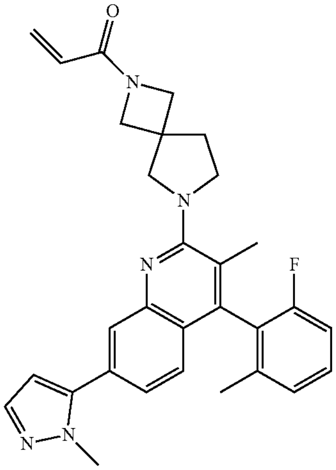 [SMILES: C=CC(=O)N1CC2(CCN(c3nc4cc(-c5ccnn5C)ccc4c(-c4c(C)cccc4F)c3C)C2)C1] | 1-(6-(4-(2-fluoro-6-methylphenyl)-3-methyl-7-(1-methyl-1H-pyrazol-5-yl)-2-quinolinyl)-2,6-diazaspiro[3.4]octan-2-yl)-2-propen-1-one | Step 1 and step 2 were reversed. Step 3: RuPhos, RuPhos Pd G2 and $K_3PO_4$ replaced $PdCl_2$(dppf) and $K_2CO_3$ | Step 3: 2-fluoro-6-methylphenyl boronic acid (Combi-Blocks) |

TABLE 8-continued

| Examples 16-2 to 16-14 were prepared following the procedure described in Method 16, Steps 1-5, above as follows: | | | | |
|---|---|---|---|---|
| Ex.# | Chemical Structure | Name | Method changes | Reagent |
| 16-9 | 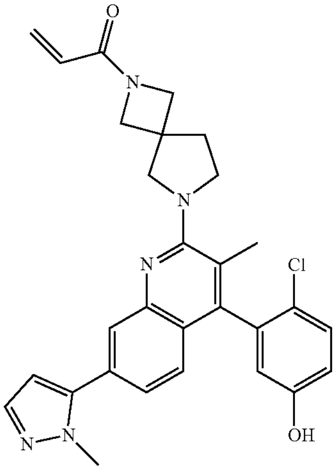 [SMILES: C=CC(=O)N1CC2(CCN(c3nc4cc(-c5ccnn5C)ccc4c(-c4cc(O)ccc4Cl)c3C)C2)C1] | 1-(6-(4-(2-chloro-5-hydroxyphenyl)-3-methyl-7-(1-methyl-1H-pyrazol-5-yl)-2-quinolinyl)-2,6-diazaspiro[3.4]octan-2-yl)-2-propen-1-one | Step 1 and step 2 were reversed. Step 3: SPhos Pd G3 and $K_3PO_4$ replaced $PdCl_2$(dppf) and $K_2CO_3$ | Step 3: (2-chloro-5-hydroxy-phenyl) boronic acid (Synnovator) |
| 16-10 | 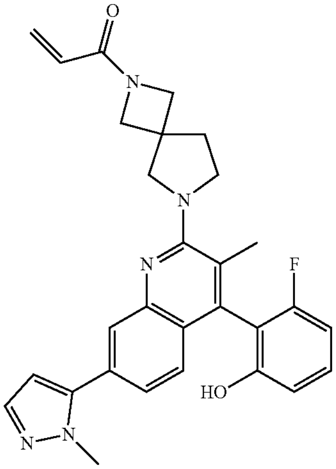 [SMILES: C=CC(=O)N1CC2(CCN(c3nc4cc(-c5ccnn5C)ccc4c(-c4c(O)cccc4F)c3C)C2)C1] | 1-(6-(4-(2-fluoro-6-hydroxyphenyl)-3-methyl-7-(1-methyl-1H-pyrazol-5-yl)-2-quinolinyl)-2,6-diazaspiro[3,4]octan-2-yl)-2-propen-1-one | Step 1 and step 2 were reversed. Step 3: RuPhos, RuPhos Pd G2 and $K_3PO_4$ replaced $PdCl_2$(dppf) and $K_2CO_3$ | Step 3: (2-fluoro-6-hydroxy-phenyl) boronic acid (Ark Pharm) |
| 16-11 | 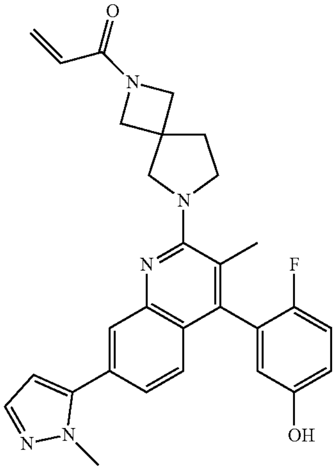 [SMILES: C=CC(=O)N1CC2(CCN(c3nc4cc(-c5ccnn5C)ccc4c(-c4cc(O)ccc4F)c3C)C2)C1] | 1-(6-(4-(2-fluoro-5-hydroxyphenyl)-3-methyl-7-(1-methyl-1H-pyrazol-5-yl)-2-quinolinyl)-2,6-diazaspiro[3,4]octan-2-yl)-2-propen-1-one | Step 1 and step 2 were reversed. Step 3: SPhos Pd G3 and $K_3PO_4$ replaced $PdCl_2$(dppf) and $K_2CO_3$ | Step 3: (2-fluoro-5-hydroxy-phenyl-boronic acid (Combi-Blocks) |

TABLE 8-continued

Examples 16-2 to 16-14 were prepared following the procedure described in Method 16, Steps 1-5, above as follows:

| Ex.# | Chemical Structure | Name | Method changes | Reagent |
|---|---|---|---|---|
| 16-12 | 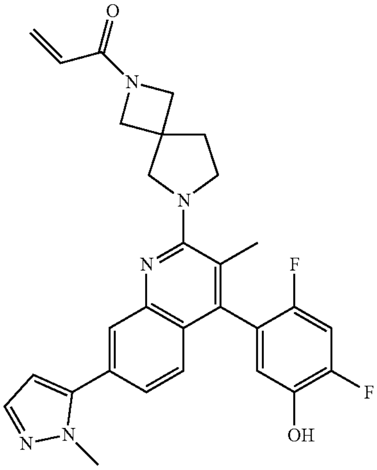 [SMILES: C=CC(=O)N1CC2(CCN(c3nc4cc(-c5ccnn5C)ccc4c(-c4cc(O)c(F)cc4F)c3C)C2)C1] | 1-(6-(4-(2,4-difluoro-5-hydroxyphenyl)-3-methyl-7-(1-methyl-1H-pyrazol-5-yl)-2-quinolinyl)-2,6-diazaspiro[3.4]octan-2-yl)-2-propen-1-one | Step 1 and step 2 were reversed. Step 3: SPhos Pd G3 and $K_3PO_4$ replaced $PdCl_2$(dppf) and $K_2CO_3$ | Step 3: (2,4-difluoro-5-hydroxy-phenyl) boronic acid (Combi-Blocks) |
| 16-13 | 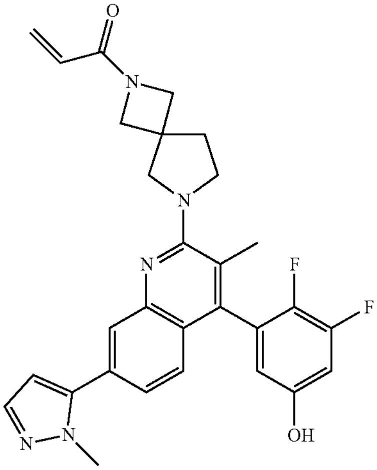 [SMILES: C=CC(=O)N1CC2(CCN(c3nc4cc(-c5ccnn5C)ccc4c(-c4cc(O)cc(F)c4F)c3C)C2)C1] | 1-(6-(4-(2,3-difluoro-5-hydroxyphenyl)-3-methyl-7-(1-methyl-1H-pyrazol-5-yl)-2-quinolinyl)-2,6-diazaspiro[3.4]octan-2-yl)-2-propen-1-one | Step 1 and step 2 were reversed. Step 3: SPhos Pd G3 and $K_3PO_4$ replaced $PdCl_2$(dppf) and $K_2CO_3$. See alternate step 4 exemplified in Example 14-49 (methoxy and Boc deprotection) | Step 3: (2,3-difluoro-5-methoxyy-phenyl) boronic acid (Combi-Blocks) |
| 16-14 | 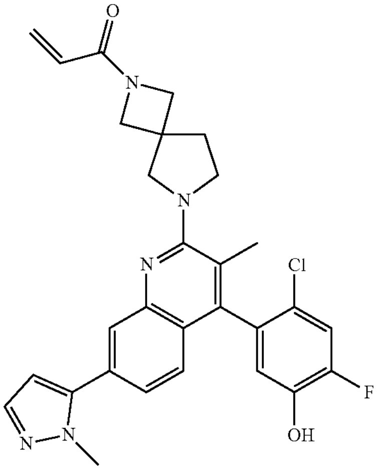 [SMILES: C=CC(=O)N1CC2(CCN(c3nc4cc(-c5ccnn5C)ccc4c(-c4cc(O)c(F)cc4Cl)c3C)C2)C1] | 1-(6-(4-(2-chloro-4-fluoro-5-hydroxyphenyl)-3-methyl-7-(1-methyl-1H-pyrazol-5-yl)-2-quinolinyl)-2,6-diazaspiro[3.4]octan-2-yl)-2-propen-1-one | Step 1 and step 2 were reversed. Step 3: SPhos Pd G3 and $K_3PO_4$ replaced $PdCl_2$(dppf) and $K_2CO_3$. See alternate step 4 exemplified in Example 14-49 (methoxy and Boc deprotection) | Step 3: 2-chloro-4-fluoro-5-methoxy-phenyl-boronic acid (Combi-Blocks) |

Method 17

Example 17-1: 2-(2-acryloyl-5-methyl-2,6-diazaspiro[3.4]octan-6-yl)-4-(2-chlorophenyl)-7-(1-methyl-1H-pyrazol-5-yl)quinoline-3-carbonitrile

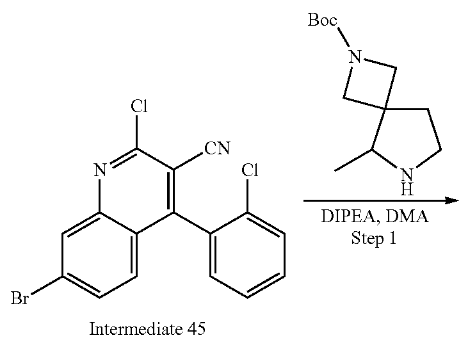

Intermediate 45

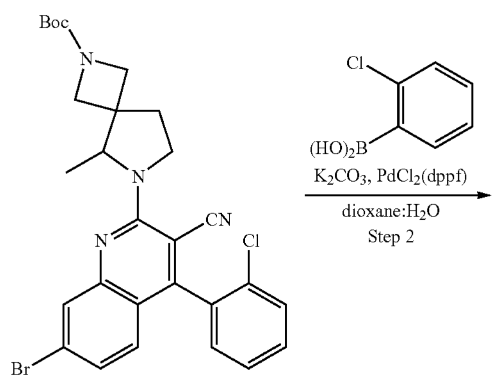

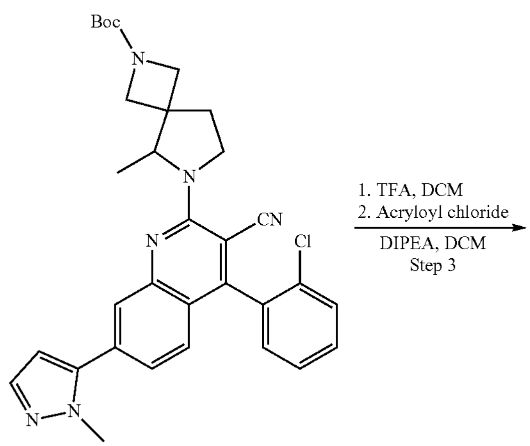

-continued

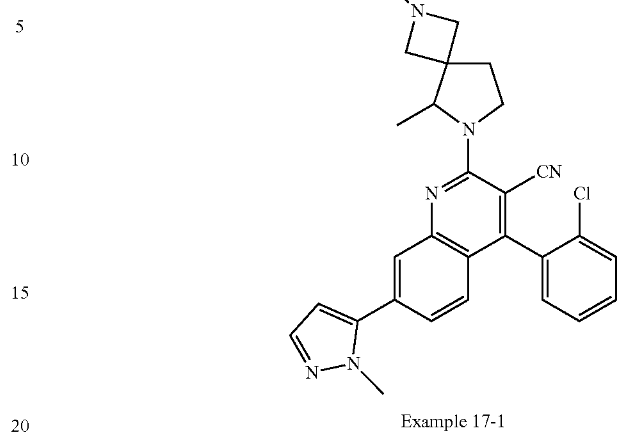

Example 17-1

Step 1: tert-butyl 6-(7-bromo-4-(2-chlorophenyl)-3-cyanoquinolin-2-yl)-5-methyl-2,6-diazaspiro[3.4]octane-2-carboxylate A mixture of 7-bromo-2-chloro-4-(2-chlorophenyl)quinoline-3-carbonitrile (0.500 g, 1.323 mmol, Intermediate 45), DIPEA (1.155 mL, 6.61 mmol, Sigma-Aldrich), and tert-butyl 5-methyl-2,6-diazaspiro[3.4]octane-2-carboxylate (0.359 g, 1.587 mmol, Enamine) in DMA (8 mL) was stirred at 95° C. for 2 h. The mixture was cooled to room temperature, diluted with aqueous saturated $NaHCO_3$ and extracted with EtOAc. The combined organics were chromatographed on silica gel using 0-10% (3:1) EtOAc:EtOH in heptanes to afford tert-butyl 6-(7-bromo-4-(2-chlorophenyl)-3-cyanoquinolin-2-yl)-5-methyl-2,6-diazaspiro[3.4]octane-2-carboxylate (0.750 g, 100% yield) as a bright yellow oil. m/z (ESI): 566.8 $(M+H)^+$.

Step 2: tert-butyl 6-(4-(2-chlorophenyl)-3-cyano-7-(1-methyl-1H-pyrazol-5-yl)quinolin-2-yl)-5-methyl-2,6-diazaspiro[3.4]octane-2-carboxylate A mixture of tert-butyl 6-(7-bromo-4-(2-chlorophenyl)-3-cyanoquinolin-2-yl)-5-methyl-2,6-diazaspiro[3.4]octane-2-carboxylate (498 mg, 0.88 mmol), (1-methyl-1H-pyrazol-5-yl)boronic acid (0.222 g, 1.761 mmol, Combi-Blocks), $PdCl_2$(dppf) DCM adduct (0.144 g, 0.176 mmol, Sigma-Aldrich) and $K_2CO_3$ (0.365 g, 2.64 mmol, Sigma-Aldrich) was purged with $N_2$ followed by the addition of 1,4-dioxane/water (5:0.5 mL) and the resulting mixture was heated at 95° C. for 1 h. The reaction was cooled to room temperature, diluted with aqueous saturated $NaHCO_3$ and extracted with EtOAc. The combined organics were dried over $Na_2SO_4$, concentrated and chromatographed on silica gel using 0-20% (3:1) EtOAc:EtOH in heptanes to afford tert-butyl 6-(4-(2-chlorophenyl)-3-cyano-7-(1-methyl-1H-pyrazol-5-yl)quinolin-2-yl)-5-methyl-2,6-diazaspiro[3.4]octane-2-carboxylate (0.358 g, 71.4% yield) as a bright yellow solid. m/z (ESI): 568.9 $(M+H)^+$.

Step 3: 2-(2-acryloyl-5-methyl-2,6-diazaspiro[3.4]octan-6-yl)-4-(2-chlorophenyl)-7-(1-methyl-1H-pyrazol-5-yl)quinoline-3-carbonitrile To a solution of tert-butyl 6-(4-(2-chlorophenyl)-3-cyano-7-(1-methyl-1H-pyrazol-5-yl)quinolin-2-yl)-5-methyl-2,6- diazaspiro[3.4]octane-2-carboxylate (0.358 g, 0.629 mmol) in DCM (5 mL) was added TFA (6.0 mL, 78 mmol, Sigma-Aldrich) and the mixture was stirred at room temperature for 30 min. The reaction was concentrated to afford 4-(2-chlorophenyl)-7-(1-methyl-1H-pyrazol-5-yl)-2-(5-methyl-2,6-diazaspiro[3.4]octan-6-yl)quinoline-3-carbonitrile as a yellow oil to be used as is. m/z (ESI): 469.2 $(M+H)^+$.

To a solution of 4-(2-chlorophenyl)-7-(1-methyl-1H-pyrazol-5-yl)-2-(5-methyl-2,6-diazaspiro[3.4]octan-6-yl) quinoline-3-carbonitrile, DIPEA (2.197 mL, 12.58 mmol, Sigma-Aldrich) and DCM (10 mL) was added acryloyl chloride (3.15 mL, 0.629 mmol, Sigma-Aldrich). The reaction was stirred at room temperature for 10 min then concentrated and chromatographed on silica gel using 0-50% (3:1) EtOAc:EtOH in heptanes to afford 2-(2-acryloyl-5-methyl-2,6-diazaspiro[3.4]octan-6-yl)-4-(2-chlorophenyl)-7-(1-methyl-1H-pyrazol-5-yl)quinoline-3-carbonitrile (0.232 g, 70.5% yield for two steps) as a yellow solid. $^1H$ NMR (400 MHz, DMSO-$d_6$) δ ppm 7.77 (br s, 2H), 7.55-7.69 (m, 3H), 7.53 (d, J=1.9 Hz, 1H), 7.42 (br d, J=8.3 Hz, 1H), 7.07-7.15 (m, 1H), 6.59 (s, 1H), 6.24-6.43 (m, 1H), 6.07-6.17 (m, 1H), 5.63-5.73 (m, 1H), 4.72 (br s, 1H), 4.31-4.47 (m, 1H), 4.01-4.20 (m, 3H), 3.94 (s, 3H), 3.75-3.91 (m, 2H), 3.45 (br dd, J=7.0, 5.0 Hz, 1H), 1.33 (br d, J=7.0 Hz, 3H), 2.21-2.25 (m, 2H). m/z (ESI): 522.9 $(M+H)^+$.

TABLE 9

Examples 17-2 to 17-10 were prepared following the procedure described in Method 17, Steps 1-3, above as follows:

| Ex.# | Chemical Structure | Name | Method changes | Reagent |
| --- | --- | --- | --- | --- |
| 17-2 | 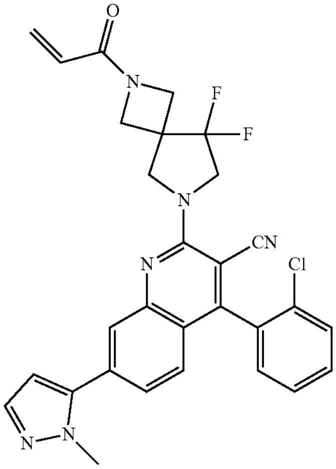 [SMILES: C=CC(=O)N1CC2(C1)CN(c1nc3cc(-c4ccnn4C)ccc3c(-c3ccccc3Cl)c1C#N)CC2(F)F] | 4-(2-chlorophenyl)-2-(8,8-difluoro-2-(2-propenoyl)-2,6-diazaspiro[3.4]octan-6-yl)-7-(1-methyl-1H-pyrazol-5-yl)-3-quinolinecarbonitrile | | Step 1: tert-butyl 8,8-difluoro-2,6-diazaspiro[3.4]octane-2-carboxylate (PharmaBlock). |
| 17-3 | 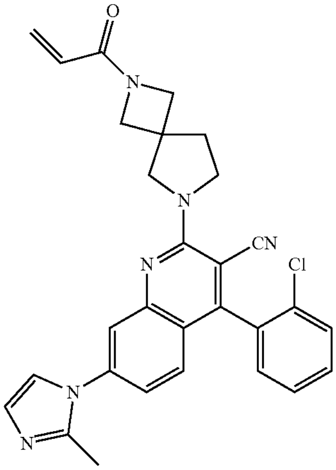 [SMILES: C=CC(=O)N1CC2(CCN(c3nc4cc(-n5ccnc5C)ccc4c(-c4ccccc4Cl)c3C#N)C2)C1] | 4-(2-chlorophenyl)-7-(2-methyl-1H-imidazol-1-yl)-2-(2-(2-propenoyl)-2,6-diazaspiro[3.4]octan-6-yl)-3-quinolinecarbonitrile | See alternate step 2 below. | Step 1: tert-butyl 2,6-diazaspiro[3.4]octane-2-carboxylate (PharmaBlock). |

TABLE 9-continued

| Ex.# | Chemical Structure | Name | Method changes | Reagent |
|---|---|---|---|---|
| Examples 17-2 to 17-10 were prepared following the procedure described in Method 17, Steps 1-3, above as follows: | | | | |
| 17-4 | 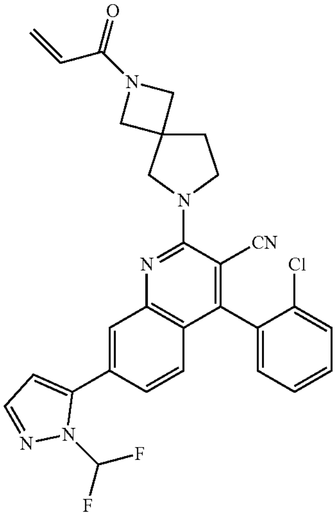 [SMILES: C=CC(=O)N1CC2(CCN(c3nc4cc(-c5ccnn5C(F)F)ccc4c(-c4ccccc4Cl)c3C#N)C2)C1] | 4-(2-chlorophenyl)-7-(1-(difluoromethyl)-1H-pyrazol-5-yl)-2-(2-(2-propenoyl)-2,6-diazaspiro[3.4]octan-6-yl)-3-quinolinecarbonitrile | | Step 1: tert-butyl 2,6-diazaspiro[3.4]octane-2-carboxylate (PharmaBlock). Step 2: Intermediate 46 |
| 17-5 | 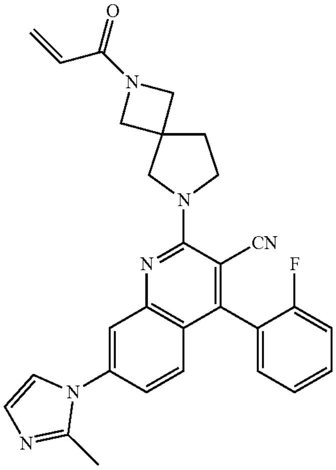 [SMILES: C=CC(=O)N1CC2(CCN(c3nc4cc(-n5ccnc5C)ccc4c(-c4ccccc4F)c3C#N)C2)C1] | 4-(2-fluorophenyl)-7-(2-methyl-1H-imidazol-1-yl)-2-(2-(2-propenoyl)-2,6-diazaspiro[3.4]octan-6-yl)-3-quinolinecarbonitrile | Step 2 performed using the procedure from Example 17-3. | Step 1: Intermediate 48, tert-butyl 2,6-diazaspiro[3.4]octane-2-carboxylate (PharmaBlock) |
| 17-6 | 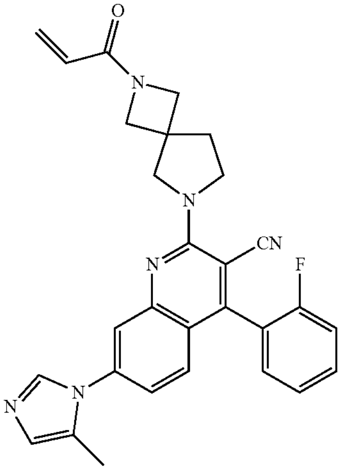 [SMILES: C=CC(=O)N1CC2(CCN(c3nc4cc(-n5cncc5C)ccc4c(-c4ccccc4F)c3C#N)C2)C1] | 4-(2-fluorophenyl)-7-(5-methyl-1H-imidazol-1-yl)-2-(2-(2-propenoyl)-2,6-diazaspiro[3.4]octan-6-yl)-3-quinolinecarbonitrile | Step 2 performed using the procedure from Example 17-3. | Step 1: Intermediate 48, tert-butyl 2,6-diazaspiro[3.4]octane-2-carboxylate (PharmaBlock). Step 2: 4-methylimidazole (Acros Organics). |

TABLE 9-continued

Examples 17-2 to 17-10 were prepared following the procedure described in Method 17, Steps 1-3, above as follows:

| Ex.# | Chemical Structure | Name | Method changes | Reagent |
|---|---|---|---|---|
| 17-7 | 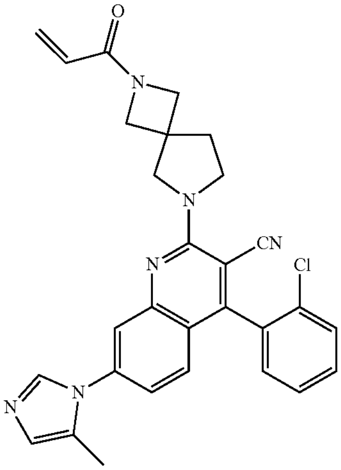 [SMILES: C=CC(=O)N1CC2(CCN(c3nc4cc(-n5cncc5C)ccc4c(-c4ccccc4Cl)c3C#N)C2)C1] | 4-(2-chlorophenyl)-7-(5-methyl-1H-imidazol-1-yl)-2-(2-(2-propenoyl)-2,6-diazaspiro[3.4]octan-6-yl)-3-quinolinecarbonitrile | Step 2 performed using the procedure from Example 17-3. | Step 1: tert-butyl 2,6-diazaspiro[3.4]octane-2-carboxylate (PharmaBlock). Step 2: 4-methylimidazole (Acros Organics). |
| 17-8 | 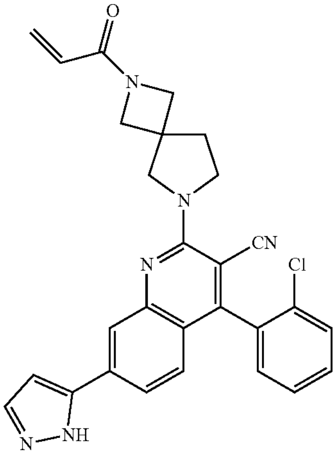 [SMILES: C=CC(=O)N1CC2(CCN(c3nc4cc(-c5ccn[nH]5)ccc4c(-c4ccccc4Cl)c3C#N)C2)C1] | 4-(2-chlorophenyl)-2-(2-(2-propenoyl)-2,6-diazaspiro[3.4]octan-6-yl)-7-(1H-pyrazol-3-yl)-3-quinolinecarbonitrile | The order of Step 2 and Step 3 were reversed. Step 2: SPhos Pd G3 and $K_3PO_4$ were used. | Step 1: Intermediate 45, tert-butyl 2,6-diazaspiro[3.4]octane-2-carboxylate (PharmaBlock). Step 2: Pyrazol-3-ylboronic acid (Combi-Blocks) |
| 17-9 | 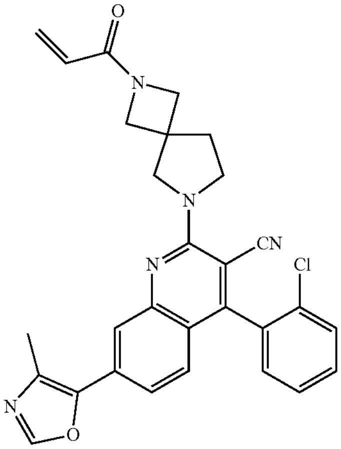 [SMILES: C=CC(=O)N1CC2(CCN(c3nc4cc(-c5ocnc5C)ccc4c(-c4ccccc4Cl)c3C#N)C2)C1] | 4-(2-chlorophenyl)-7-(4-methyl-1,3-oxazol-5-yl)-2-(2-(2-propenoyl)-2,6-diazaspiro[3.4]octan-6-yl)-3-quinolinecarbonitrile | Step 2; SPhos Pd G3 and $K_3PO_4$ were used. | Step 1: tert-butyl 2,6-diazaspiro[3.4]octane-2-carboxylate (PharmaBlock), Step 2: 4-methyl-5-(4,4,5,5-tetramethyl-1,3,2-dioxaborolan-2-yl)oxazole (J&W Pharmalab). |

TABLE 9-continued

Examples 17-2 to 17-10 were prepared following the procedure described in Method 17, Steps 1-3, above as follows:

| Ex.# | Chemical Structure | Name | Method changes | Reagent |
|---|---|---|---|---|
| 17-10 | 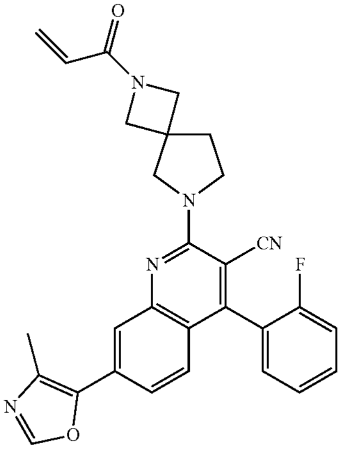 [SMILES: C=CC(=O)N1CC2(CCN(c3nc4cc(-c5ocnc5C)ccc4c(-c4ccccc4F)c3C#N)C2)C1] | 4-(2-fluorophenyl)-7-(4-methyl-1,3-oxazol-5-yl)-2-(2-(2-propenoyl)-2,6-diazaspiro[3.4]octan-6-yl)-3-quinolinecarbonitrile | Step 2; SPhos Pd G3 and $K_3PO_4$ were used. | Step 1: Intermediate 48, tert-butyl 2,6-diazaspiro[3.4]octane-2-carboxylate (PharmaBlock), Step 2: 2: 4-methyl-5-(4,4,5,5-tetramethyl-1,3,2-dioxaborolan-2-yl)oxazole (J&W Pharmalab). |

Alternate Step 2 for Example 17-3

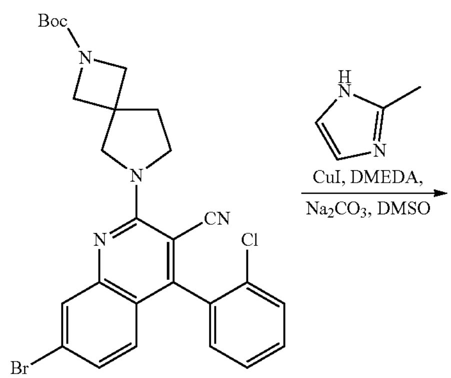

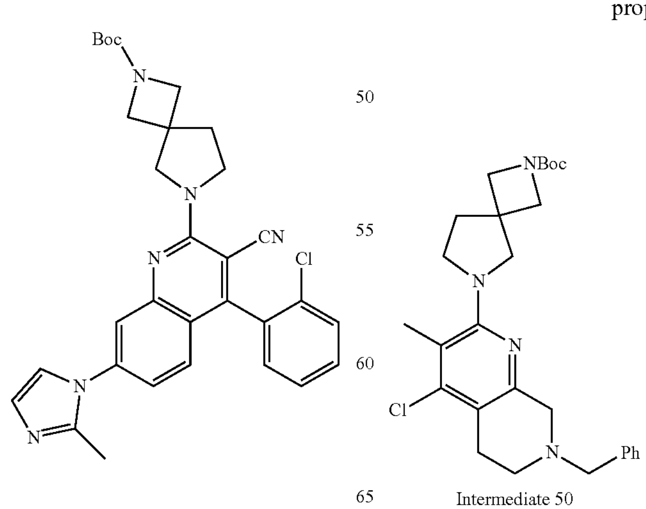

A mixture of tert-butyl 6-(7-bromo-4-(2-chlorophenyl)-3-cyanoquinolin-2-yl)-2,6-diazaspiro[3.4]octane-2-carboxylate (0.135 g, 0.244 mmol), 2-methyl-1H-imidazole (0.040 g 0.487 mmol, Combi-Blocks), CuI (0.093 g, 0.487 mmol, Sigma-Aldrich), $Na_2CO_3$ (0.103 g, 0.975 mmol, Sigma-Aldrich) was purged with $N_2$, followed by the addition of N,N'-dimethylethylenediamine (0.079 mL, 0.731 mmol, Sigma-Aldrich) and degassed DMSO (5 mL). The reaction was heated at 120° C. for 2 h. The reaction was washed with water, aqueous saturated $NH_4Cl$, dried over $Na_2SO_4$, concentrated and chromatographed on silica gel using 0-30% (3:1) EtOAc:EtOH in heptanes to afford tert-butyl 6-(4-(2-chlorophenyl)-3-cyano-7-(2-methyl-1H-imidazol-1-yl)quinolin-2-yl)-2,6-diazaspiro[3.4]octane-2-carboxylate (0.0391 g, 28.9% yield) as a bright yellow solid. m/z (ESI): 555.2 $(M+H)^+$.

Method 18

Example 18-1: 1-(6-(4-(6-Hydroxy-1-naphthalenyl)-3-methyl-7-(2-propanyl)-5,6,7,8-tetrahydro-1,7-naphthyridin-2-yl)-2,6-diazaspiro[3.4]octan-2-yl)-2-propen-1-one

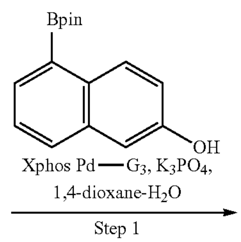

Intermediate 50

-continued

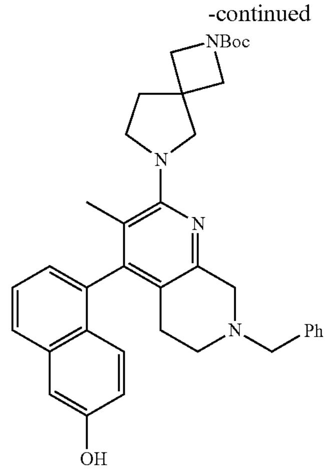

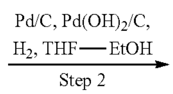

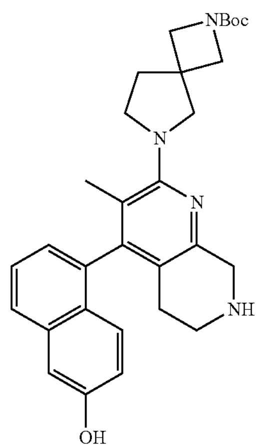

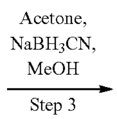

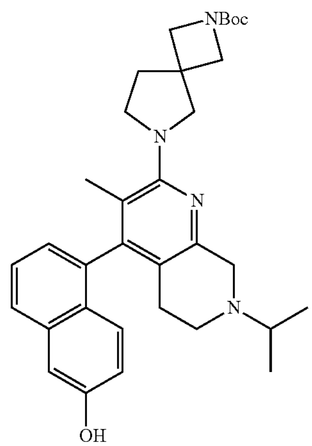

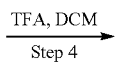

-continued

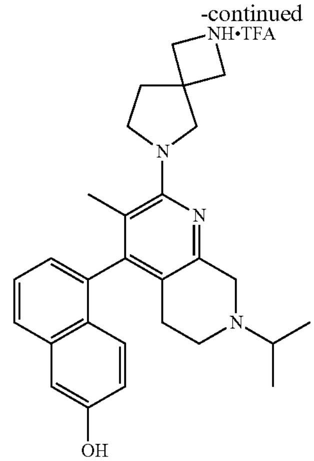

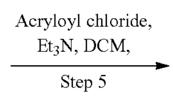

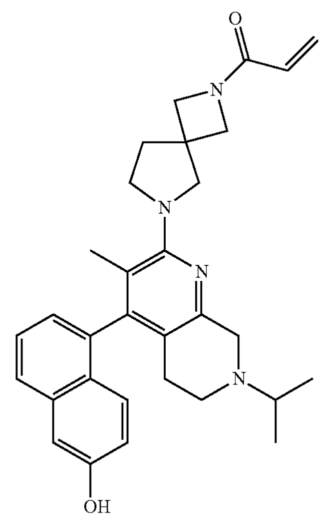

Example 18-1

Step 1: tert-Butyl 6-(7-benzyl-4-(6-hydroxynaphthalen-1-yl)-3-methyl-5,6,7,8-tetrahydro-1,7-naphthyridin-2-yl)-2,6-diazaspiro[3.4]octane-2-carboxylate To a degassed mixture of tert-butyl 6-(7-benzyl-4-chloro-3-methyl-5,6,7,8-tetrahydro-1,7-naphthyridin-2-yl)-2,6-diazaspiro[3.4]octane-2-carboxylate (100 mg, 0.207 mmol, Intermediate 50). 5-(4,4,5,5-tetramethyl-1,3,2-dioxaborolan-2-yl)naphthalen-2-ol (67.1 mg, 0.248 mmol, Intermediate 65), $K_1PO_4$ (132 mg, 0.621 mmol) and 1,4-dioxane (2 mL):water (0.2 mL) was added XPhos Pd G3 (17.52 mg, 0.021 mmol, Strem) and the reaction mixture was heated at 95° C. for 16 h. The reaction mixture was cooled to room temperature and filtered through a celite pad and washed with EtOAc. The filtrate was concentrated under reduced pressure. The residue was purified on a Redi-Sep pre-packed silica gel column (12 g) eluting with a gradient of 70-75% EtOAc in petroleum ether to provide tert-butyl 6-(7-benzyl-4-(6-hydroxynaphthalen-1-yl)-3-methyl-5,6,7,8-tetrahydro-1,7-naphthyridin-2-yl)-2,6-diazaspiro[3.4]octane-2-carboxylate (120 mg, 98% yield) as a pale yellow gummy solid. m/z (ESI): 591.0 $(M+H)^+$.

Step 2: tert-Butyl 6-(4-(6-hydroxynaphthalen-1-yl)-3-methyl-5,6,7,8-tetrahydro-1,7-naphthyridin-2-yl)-2,6-diazaspiro[3.4]octane-2-carboxylate A mixture of tert-butyl 6-(7-benzyl-4-(6-hydroxynaphthalen-1-yl)-3-methyl-5,6,7,8-tetrahydro-1,7-naphthyridin-2- yl)-2,6-diazaspiro[3.4]octane-2-carboxylate (120 mg, 0.203 mmol), $Pd(OH)_2$ (28.5 mg, 0.203 mmol, 10% on Carbon, Hindustan Platinum) and Pd (100 mg, 0.940 mmol, 10% on Carbon, Hindustan Platinum) in EtOH (2 mL) and THE (2 mL) was stirred under a hydrogen atmosphere at 1 atm pressure for 16 h. The reaction mixture was filtered through a celite bed and washed with 10% MeOH in DCM. The filtrate was concentrated under reduced pressure to provide tert-butyl 6-(4-(6-hydroxynaphthalen-1-yl)-3-methyl-5,6,7,8-tetrahydro-1,7-naphthyridin-2-yl)-2,6-diazaspiro[3.4]octane-2-carboxylate (100 mg, 98% yield) as a gummy solid which was used in the next step without purification. m/z (ESI): 501.3 $(M+H)^+$.

Step 3: tert-Butyl 6-(4-(6-hydroxynaphthalen-1-yl)-7-isopropyl-3-methyl-5,6,7,8-tetrahydro-1,7-naphthyridin-2-yl)-2,6-diazaspiro[3.4]octane-2-carboxylate To a solution of tert-butyl 6-(4-(6-hydroxynaphthalen-1-yl)-3-methyl-5,6,7,8-tetrahydro-1,7-naphthyridin-2-yl)-2,6-diazaspiro[3.4]octane-2-carboxylate (100 mg, 0.200 mmol) and acetone (17.40 mg, 0.300 mmol) in MeOH (1 mL) was added a drop of acetic acid. The reaction mixture was stirred at room temperature for 16 h before $NaCNBH_3$ (37.7 mg, 0.599 mmol) was added. The reaction mixture was stirred at room temperature for 16 h, then quenched with ice-cold water and extracted with DCM. The organic extracts were washed with brine, dried over $Na_2SO_4$, and concentrated under reduced pressure. The residue was purified on a Redi-Sep pre-packed silica gel column eluting with a gradient of 2-5% MeOH in $CHCl_3$ to provide tert-butyl 6-(4-(6-hydroxynaphthalen-1-yl)-7-isopropyl-3-methyl-5,6,7,8-tetrahydro-1,7-naphthyridin-2-yl)-2,6-diazaspiro[3.4]octane-2-carboxylate (0.06 g, 55.3% yield) as a light-yellow solid. m/z (ESI): 543.0 $(M+H)^+$.

Step 4: 2,2,2-trifluoro-1-(6-(4-(6-hydroxynaphthalen-1-yl)-7-isopropyl-3-methyl-5,6,7,8-tetrahydro-1,7-naphthyridin-2-yl)-2,6-diazaspiro[3.4]octan-2-yl)ethan-1-one To a solution of tert-butyl 6-(4-(6-hydroxynaphthalen-1-yl)-7-isopropyl-3-methyl-5,6,7,8-tetrahydro-1,7-naphthyridin-2-yl)-2,6-diazaspiro[3.4]octane-2-carboxylate (0.06 g, 0.111 mmol) in DCM (1 mL) was added TFA (0.043 mL, 0.553 mmol) at 0° C. and the reaction mixture was stirred at room temperature for 2 h. The reaction mixture was concentrated under reduced pressure and triturated with diethyl ether to provide 2,2,2-trifluoro-1-(6-(4-(6-hydroxynaphthalen-1-yl)-7-isopropyl-3-methyl-5,6,7,8-tetrahydro-1,7-naphthyridin-2-yl)-2,6-diazaspiro[3.4]octan-2-yl)ethan-1-one (0.046 g, 94% yield) as a colorless gummy mass which was taken on to the next step without further purification. m/z (ESI): 443.0 $(M+H)^+$.

Step 5: 1-(6-(4-(6-hydroxynaphthalen-1-yl)-7-isopropyl-3-methyl-5,6,7,8-tetrahydro-1,7-naphthyridin-2-yl)-2,6-diazaspiro[3.4]octan-2-yl)prop-2-en-1-one To a solution of 2,2,2-trifluoro-1-(6-(4-(6-hydroxynaphthalen-1-yl)-7-isopropyl-3-methyl-5,6,7,8-tetrahydro-1,7-naphthyridin-2-yl)-2,6-diazaspiro[3.4]octan-2-yl)ethan-1-one (0.045 g, 0.102 mmol) and TEA (0.043 mL, 0.305 mmol) in DCM (1 mL) was added acryloyl chloride (9.20 mg, 0.102 mmol, Symax Ltd.) at −78° C. dropwise and stirred for 15 min. The reaction mixture was diluted with water and extracted with DCM. The combined organic layers were dried over anhydrous $Na_2SO_4$, concentrated and purified by preparative HPLC to provide 1-(6-(4-(6-hydroxynaphthalen-1-yl)-7-isopropyl-3-methyl-5,6,7,8-tetrahydro-1,7-naphthyridin-2-yl)-2,6-diazaspiro[3.4]octan-2-yl)prop-2-en-1-one (0.010 g, 19.80% yield) as a light yellow solid. $^1H$ NMR (400 MHz, DMSO-$d_6$) δ ppm 9.79 (s, 1H), 7.72 (d, J=8.3 Hz, 1H), 7.47 (dd, J=8.3, 6.9 Hz, 1H), 7.19 (d, J=2.4 Hz, 1H), 7.10 (dd, J=9.1, 5.4 Hz, 1H), 7.05-6.94 (m, 2H), 6.33 (dd, J=16.9, 10.3 Hz, 1H), 6.11 (dd, J=16.9, 2.3 Hz, 1H), 5.67 (dt, J=10.3, 1.8 Hz, 1H), 4.28-4.14 (m, 2H), 3.98-3.85 (m, 2H), 3.68-3.37 (m, 6H), 2.85-2.74 (m, 1H), 2.48-2.40 (m, 2H), 2.22-2.05 (m, 3H), 1.88-1.77 (m, 1H), 1.74 (s, 3H), 1.02 (d, J=6.5 Hz, 6H). m/z (ESI): 497.0 $(M+H)^+$.

TABLE 10

Examples 18-2 to 18-22 were prepared following the procedure described in Method 18, Steps 1-5, above as follows:

| Ex.# | Chemical Structure | Name | Method changes | Reagent |
|---|---|---|---|---|
| 18-2 | 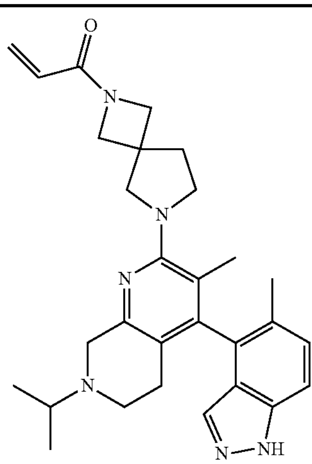 | 1-(6-(3-methyl-4-(5-methyl-1H-indazol-4-yl)-7-(2-propanyl)-5,6,7,8-tetrahydro-1,7-naphthyridin-2-yl)-2,6-diazaspiro[3.4]octan-2-yl)-2-propen-1-one | | Step 1: 5-methyl-1-(tetrahydro-2H-pyran-2-yl)-4-(4,4,5,5-tetramethyl-1,3,2-dioxaborolan-2-yl)-1H-indazole (Synnovator) |

TABLE 10-continued

| Examples 18-2 to 18-22 were prepared following the procedure described in Method 18, Steps 1-5, above as follows: | | | | |
|---|---|---|---|---|
| Ex.# | Chemical Structure | Name | Method changes | Reagent |
| 18-3 | 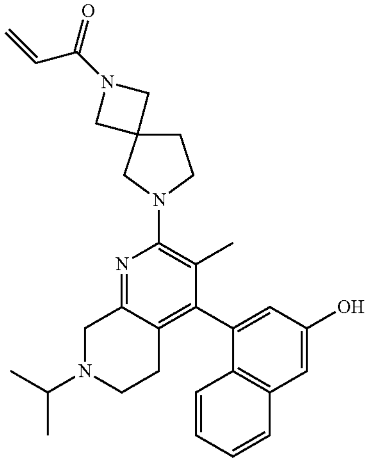 [SMILES: C=CC(=O)N1CC2(CCN(c3nc4c(c(-c5cc(O)cc6ccccc56)c3C)CCN(C(C)C)C4)C2)C1] | 1-(6-(4-(3-hydroxy-1-naphthalenyl)-3-methyl-7-(2-propanyl)-5,6,7,8-tetrahydro-1,7-naphthyridin-2-yl)-2,6-diazaspiro[3.4]octan-2-yl)-2-propen-1-one | | Step 1: 4-(4,4,5,5-tetramethyl-1,3,2-dioxaborolan-2-yl)naphthalen-2-ol (eNovation Chemicals) |
| 18-4 | 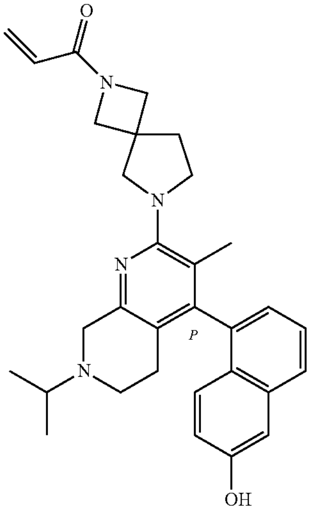 | (P)-1-(6-(4-(6-hydroxy-1-naphthalenyl)-3-methyl-7-(2-propanyl)-5,6,7,8-tetrahydro-1,7-naphthyridin-2-yl)-2,6-diazaspiro[3.4]octan-2-yl)-2-propane-1-one | atropisomer separation of product from Example 18-1, Step 3. See separation conditions below. | Step 4: Peak 2 of atropisomer separation used as starting material. |
| 18-5 | 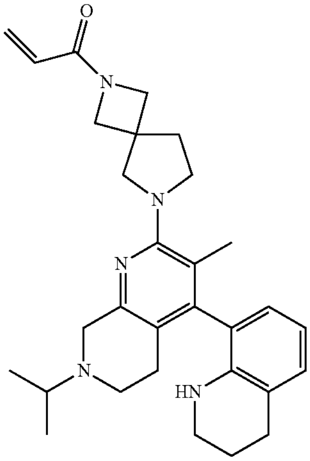 [SMILES: C=CC(=O)N1CC2(CCN(c3nc4c(c(-c5cccc6c5NCCC6)c3C)CCN(C(C)C)C4)C2)C1] | 1-(6-(3-methyl-7-(2-propanyl)-4-(1,2,3,4-tetrahydro-8-quinolinyl)-5,6,7,8-tetrahydro-1,7-naphthyridin-2-yl)-2,6-diazaspiro[3.4]octan-2-yl)-2-propen-1-one | | Step 1: 8-(4,4,5,5-tetramethyl-1,3,2-dioxaborolan-2-yl)quinoline |

TABLE 10-continued

Examples 18-2 to 18-22 were prepared following the procedure described in Method 18, Steps 1-5, above as follows:

| Ex.# | Chemical Structure | Name | Method changes | Reagent |
| --- | --- | --- | --- | --- |
| 18-6 | 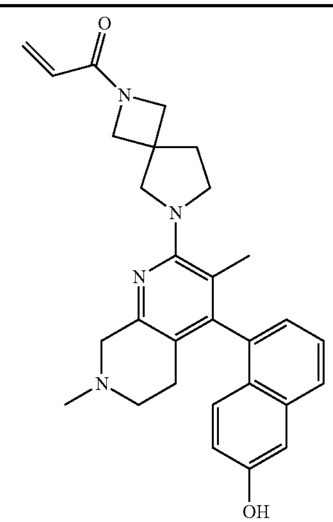 | 1-(6-(4-(6-hydroxy-1-naphthalenyl)-3,7-dimethyl-5,6,7,8-tetrahydro-1,7-naphthyridin-2-yl)-2,6-diazaspiro[3.4]octan-2-yl)-2-propen-1-one | Step 4: $BBr_3$ was used for deprotection of Boc and methoxy in place of TFA. | Step 1: 2-(6-methoxynaphthalen-1-yl)-4,4,5,5-tetramethyl-1,3,2-dioxaborolane (Arbor) Step 3: paraformaldehyde |
| 18-7 | 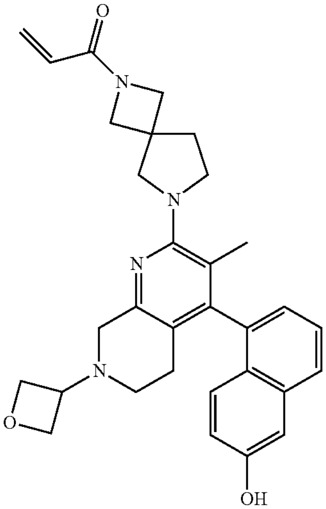 [SMILES: C=CC(=O)N1CC2(CCN(c3nc4c(c(-c5cccc6cc(O)ccc56)c3C)CCN(C3COC3)C4)C2)C1] | 1-(6-(4-(6-hydroxy-1-naphthalenyl)-3-methyl-7-(3-oxetanyl)-5,6,7,8-tetrahydro-1,7-naphthyridin-2-yl)-2,6-diazaspiro[3.4]octan-2-yl)-2-propen-1-one | | Step 3: oxetan-3-one (Combi-Blocks) |
| 18-8 | 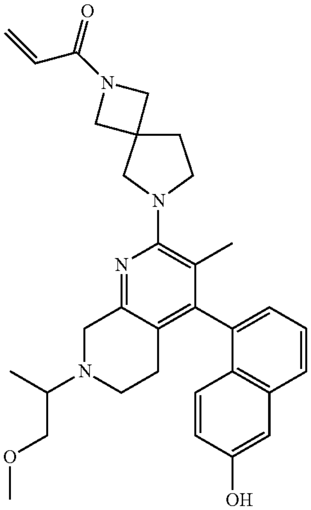 [SMILES: C=CC(=O)N1CC2(CCN(c3nc4c(c(-c5cccc6cc(O)ccc56)c3C)CCN(C(C)COC)C4)C2)C1] | 1-(6-(4-(6-hydroxy-1-naphthalenyl)-7-((2R)-1-methoxy-2-propanyl)-3-methyl-5,6,7,8-tetrahydro-1,7-naphthyridin-2-yl)-2,6-diazaspiro[3.4]octan-2-yl)-2-propen-1-one\|1-(6-(4-(6-hydroxy-1-naphthalenyl)-7-((2S)-1-methoxy-2-propanyl)-3-methyl-5,6,7,8-tetrahydro-1,7-naphthyridin-2-yl)-2,6-diazaspiro[3.4]octan-2-yl)-2-propen-1-one | | Step 3: 1-methoxypropan-2-one (CAS#5878-19-3) |

TABLE 10-continued

Examples 18-2 to 18-22 were prepared following the procedure described in Method 18, Steps 1-5, above as follows:

| Ex.# | Chemical Structure | Name | Method changes | Reagent |
|---|---|---|---|---|
| 18-9 | 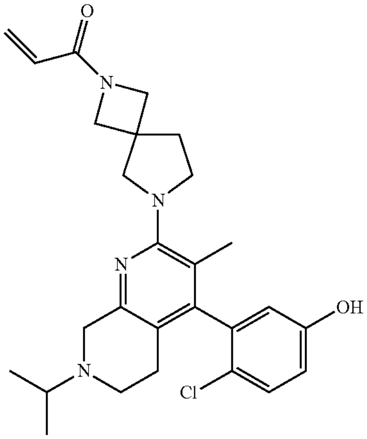 [SMILES: C=CC(=O)N1CC2(CCN(c3nc4c(c(-c5cc(O)ccc5Cl)c3C)CCN(C(C)C)C4)C2)C1] | 1-(6-(4-(2-chloro-5-hydroxyphenyl)-3-methyl-7-(2-propanyl)-5,6,7,8-tetrahydro-1,7-naphthyridin-2-yl)-2,6-diazaspiro[3.4]octan-2-yl)-2-propen-1-one | | Step 1: (2-chloro-5-hydroxyphenyl)boronic acid (Combi-Blocks) |
| 18-10 | 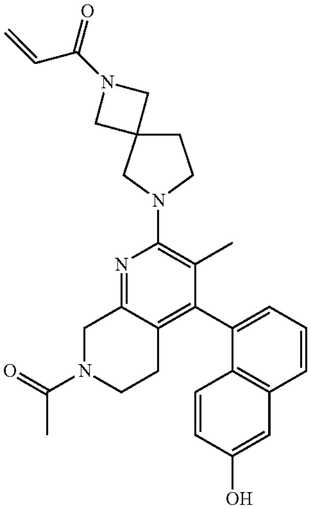 [SMILES: C=CC(=O)N1CC2(CCN(c3nc4c(c(-c5cccc6cc(O)ccc56)c3C)CCN(C(C)=O)C4)C2)C1] | 1-(6-(7-acetyl-4-(6-hydroxy-1-naphthalenyl)-3-methyl-5,6,7,8-tetrahydro-1,7-naphthyridin-2-yl)-2,6-diazaspiro[3.4]octan-2-yl)-2-propen-1-one | See alternate Step 3 below. Step 4: $BBr_3$ was used for deprotection of Boc and methoxy in place of TFA. | Step 1: 2-(6-methoxynaphthalen-1-yl)-4,4,5,5-tetramethyl-1,3,2-dioxaborolane (Arbor) |
| 18-11 | 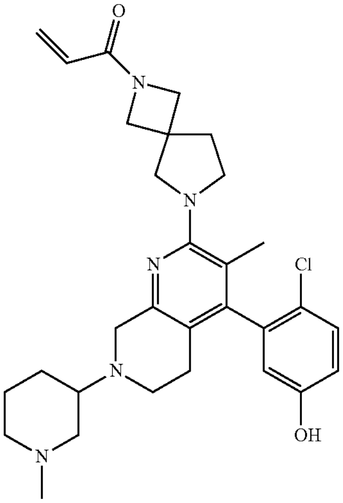 [SMILES: C=CC(=O)N1CC2(CCN(c3nc4c(c(-c5cc(O)ccc5Cl)c3C)CCN(C3CCCN(C)C3)C4)C2)C1] | 1-(6-(4-(2-chloro-5-hydroxyphenyl)-3-methyl-7-((3R)-1-methyl-3-piperidinyl)-5,6,7,8-tetrahydro-1,7-naphthyridin-2-yl)-2,6-diazaspiro[3.4]octan-2-yl)-2-propen-1-one\|1-(6-(4-(2-chloro-5-hydroxyphenyl)-3-methyl-7-((3S)-1-methyl-3-piperidinyl)-5,6,7,8-tetrahydro-1,7-naphthyridin-2-yl)-2,6-diazaspiro[3.4]octan-2-yl)-2-propen-1-one | | Step 1: (2-chloro-5-hydroxyphenyl)boronic acid (Combi-Blocks). Step 3: 1-methylpiperidin-3-one |

TABLE 10-continued

| Examples 18-2 to 18-22 were prepared following the procedure described in Method 18, Steps 1-5, above as follows: | | | | |
|---|---|---|---|---|
| Ex.# | Chemical Structure | Name | Method changes | Reagent |
| 18-12 | 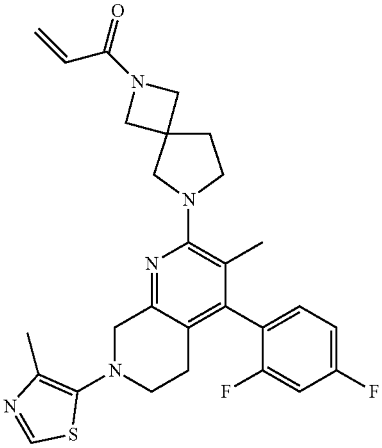 [SMILES: C=CC(=O)N1CC2(CCN(c3nc4c(c(-c5ccc(F)cc5F)c3C)CCN(c3scnc3C)C4)C2)C1] | 1-(6-(4-(2,4-difluorophenyl)-3-methyl-7-(4-methyl-1,3-thiazol-5-yl)-5,6,7,8-tetrahydro-1,7-naphthyridin-2-yl)-2,6-diazaspiro[3.4]octan-2-yl)-2-propane-1-one | See alternate Step 3 below. | Step 1: (2,4-difluorophenyl)boronic acid (CAS#144025-03-6) |
| 18-13 | 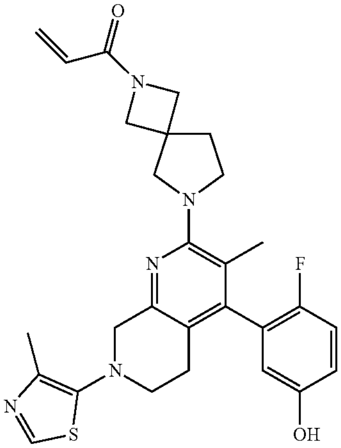 [SMILES: C=CC(=O)N1CC2(CCN(c3nc4c(c(-c5cc(O)ccc5F)c3C)CCN(c3scnc3C)C4)C2)C1] | 1-(6-(4-(2-fluoro-5-hydroxyphenyl)-3-methyl-7-(4-methyl-1,3-thiazol-5-yl)-5,6,7,8-tetrahydro-1,7-naphthyridin-2-yl)-2,6-diazaspiro[3.4]octan-2-yl)-2-propen-1-one | See alternate Step 3 below. Step 4: $BBr_3$ was used for deprotection of Boc and methoxy in place of TFA. | Step 1: (2-fluoro-5-methoxyphenyl)boronic acid (Combi-Blocks) |
| 18-14 | 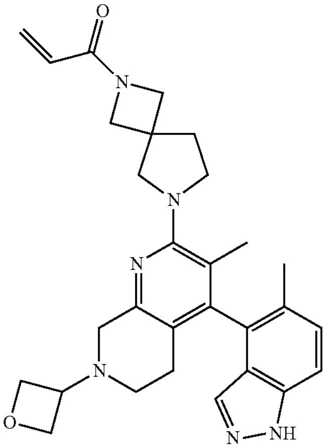 [SMILES: C=CC(=O)N1CC2(CCN(c3nc4c(c(-c5c(C)ccc6[nH]ncc56)c3C)CCN(C3COC3)C4)C2)C1] | 1-(6-(3-methyl-4-(5-methyl-1H-indazol-4-yl)-7-(3-oxetanyl)-5,6,7,8-tetrahydro-1,7-naphthyridin-2-yl)-2,6-diazaspiro[3.4]octan-2-yl)-2-propen-1-one | | Step 1: 5-methyl-1-(tetrahydro-2H-pyran-2-yl)-4-(4,4,5,5-tetramethyl-1,3,2-dioxaborolan-2-yl)-1H-indazole (Synnovator). Step 3: Oxetan-3-one (Combi-Blocks) |

TABLE 10-continued

Examples 18-2 to 18-22 were prepared following the procedure described in Method 18, Steps 1-5, above as follows:

| Ex.# | Chemical Structure | Name | Method changes | Reagent |
|---|---|---|---|---|
| 18-15 | 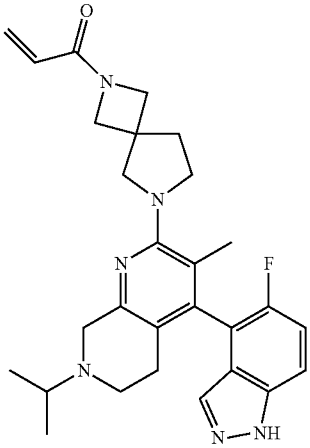 [SMILES: C=CC(=O)N1CC2(CCN(c3nc4c(c(-c5c(F)ccc6[nH]ncc56)c3C)CCN(C(C)C)C4)C2)C1] | 1-(6-(4-(5-fluoro-1H-indazol-4-yl)-3-methyl-7-(2-propanyl)-5,6,7,8-tetrahydro-1,7-naphthyridin-2-yl)-2,6-diazaspiro[3.4]octan-2-yl)-2-propen-1-one | | Step 1: 5-fluoro-4-(4,4,5,5-tetramethyl-1,3,2-dioxaborolan-2-yl)-1H-indazole (synthesized analogously to Intermediate 52 using Intermediate 91 Step 1 |
| 18-16 | 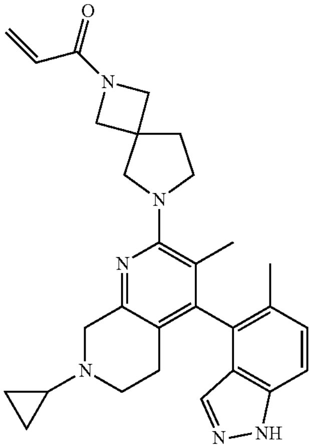 [SMILES: C=CC(=O)N1CC2(CCN(c3nc4c(c(-c5c(C)ccc6[nH]ncc56)c3C)CCN(C3CC3)C4)C2)C1] | 1-(6-(7-cyclopropyl-3-methyl-4-(5-methyl-1H-indazol-4-yl)-5,6,7,8-tetrahydro-1,7-naphthyridin-2-yl)-2,6-diazaspiro[3.4]octan-2-yl)-2-propen-1-one | | Step 1: 5-methyl-1-(tetrahydro-2H-pyran-2-yl)-4-(4,4,5,5-tetramethyl-1,3,2-dioxaborolan-2-yl)-1H-indazole (Synnovator). Step 3: (1-ethoxycyclopropoxy) trimethylsilane (Sigma-Aldrich) |
| 18-17 | 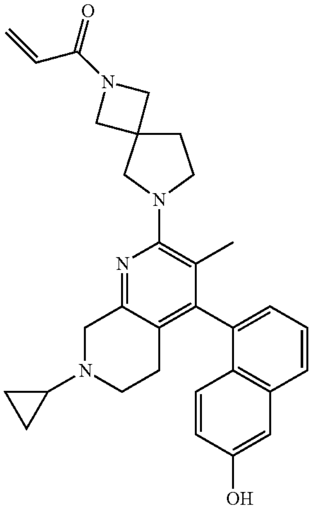 [SMILES: C=CC(=O)N1CC2(CCN(c3nc4c(c(-c5cccc6cc(O)ccc56)c3C)CCN(C3CC3)C4)C2)C1] | 1-(6-(7-cyclopropropyl-4-(6-hydroxy-1-naphthalenyl)-3-methyl-5,6,7,8-tetrahydro-1,7-naphthyridin-2-yl)-2,6-diazaspiro[3.4]octan-2-yl)-2-propen-1-one | | Step 3: (1-ethoxycyclopropoxy) trimethylsilane (Sigma-Aldrich) |

TABLE 10-continued

| Examples 18-2 to 18-22 were prepared following the procedure described in Method 18, Steps 1-5, above as follows: | | | | |
|---|---|---|---|---|
| Ex.# | Chemical Structure | Name | Method changes | Reagent |
| 18-18 | 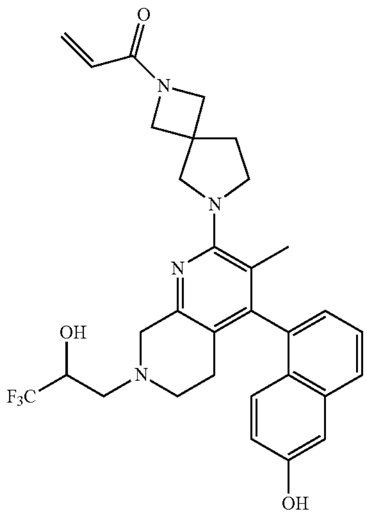 [SMILES: C=CC(=O)N1CC2(CCN(c3nc4c(c(-c5cccc6cc(O)ccc56)c3C)CCN(CC(O)C(F)(F)F)C4)C2)C1] | 1-(6-(4-(6-hydroxy-1-naphthalenyl)-3-methyl-7-((2R)-3,3,3-trifluoro-2-hydroxypropyl)-5,6,7,8-tetrahydro-1,7-naphthyridin-2-yl)-2,6-diazaspiro[3.4]octan-2-yl)-2-propen-1one\|1-(6-(4-(6-hydroxy-1-naphthalenyl)-3-methyl-7-((2S)-3,3,3-trifluoro-2-hydroxypropyl)-5,6,7,8-tetrahydro-1,7-naphthyridin-2-yl)-2,6-diazaspiro[3.4]octan-2-yl)-2-propen-1-one | See alternate step 3 below | |
| 18-19 | 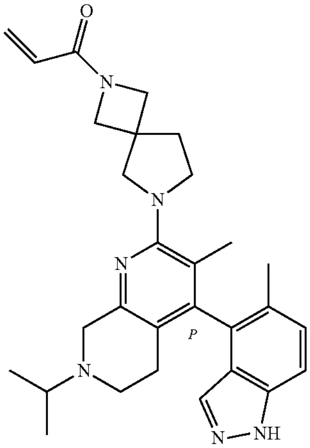 | (P)-1-(6-(3-methyl-4-(5-methyl-1H-indazol-4-yl)-7-(2-propanyl)-5,6,7,8-tetrahydro-1,7-naphthyridin-2-yl)-2,6-diazaspiro[3.4]octan-2-yl)-2-propane-1-one | atropisomer separation of product from Example 18-2, Step 4. See separation conditions below. | Step 1: 5-methyl-1-(tetrahydro-2H-pyran-2-yl)-4-(4,4,5,5-tetramethyl-1,3,2-dioxaborolan-2-yl)-1H-indazole (Synnovator). Step 4: Peak 2 of atropisomer separation used as starting material. |
| 18-20 | 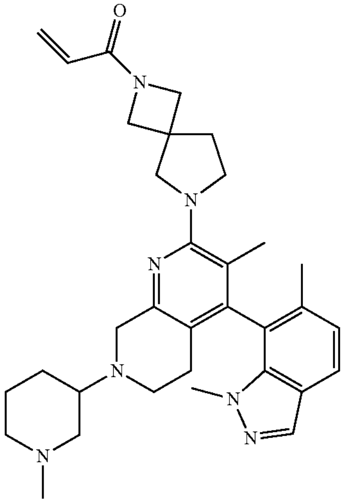 [SMILES: C=CC(=O)N1CC2(CCN(c3nc4c(c(-c5c(C)ccc6cnn(C)c56)c3C)CCN(C3CCCN(C)C3)C4)C2)C1] | 1-(6-(4-(1,6-dimethyl-1H-indazol-7-yl)-3-methyl-7-((3R)-1-methyl-3-piperidinyl)-5,6,7,8-tetrahydro-1,7-naphthyridin-2-yl)-2,6-diazaspiro[3.4]octan-2-yl)-2-propen-1-one\|1-(6-(4-(1,6-dimethyl-1H-indazol-7-yl)-3-methyl-7-((3S)-1-methyl-3-piperidinyl)-5,6,7,8-tetrahydro-1,7-naphthyridin-2-yl)-2,6-diazaspiro[3.4]octan-2-yl)-2-propen-1-one | After Step 1, N-methylation was carried out in an analogous fashion to the N-methylation in Example 2-19 using LiHMDS and MeI. | Step 1: 6-methyl-7-(4,4,5,5-tetramethyl-1,3,2-dioxaborolan-2-yl)-1H-indazole (PharmaBlock). Step 3: 1-methylpiperidin-3-one |

TABLE 10-continued

| Examples 18-2 to 18-22 were prepared following the procedure described in Method 18, Steps 1-5, above as follows: | | | | |
|---|---|---|---|---|
| Ex.# | Chemical Structure | Name | Method changes | Reagent |
| 18-21 | 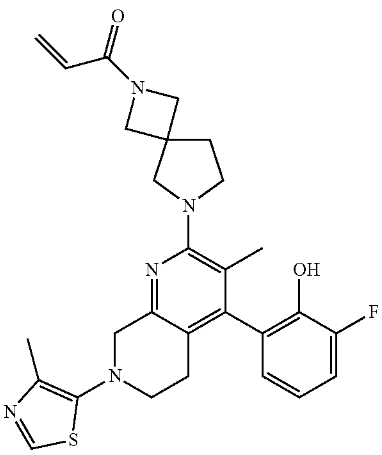 [SMILES: C=CC(=O)N1CC2(CCN(c3nc4c(c(-c5cccc(F)c5O)c3C)CCN(c3scnc3C)C4)C2)C1] | 1-(6-(4-(3-fluoro-2-hydroxyphenyl)-3-methyl-7-(4-methyl-1,3-thiazol-5-yl)-5,6,7,8-tetrahydro-1,7-naphthyridin-2-yl)-2,6-diazaspiro[3.4]octan-2-yl)-2-propen-1-one | See alternate Step 3 below. Step 4: $BBr_3$ was used for deprotection of Boc and methoxy in place of TFA. | Step 1: (3-fluoro-2-methoxy-phenyl)boronic acid (Combi-Blocks) |
| 18-22 | 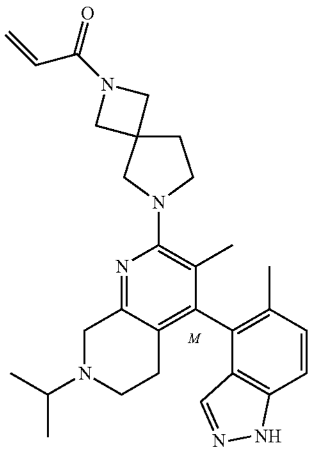 | (M)-1-(6-(3-methyl-4-(5-methyl-1H-indazol-4-yl)-7-(2-propanyl)-5,6,7,8-tetrahydro-1,7-naphthyridin-2-yl)-2,6-diazaspiro[3.4]octan-2-yl)-2-propen-1-one | atropisomer separation of product from Example 18-2, Step 4. See separation conditions below. | Step 1: 5-methyl-1-(tetrahydro-2H-pyran-2-yl)-4-(4,4,5,5-tetramethyl-1,3,2-dioxaborolan-2-yl)-1H-indazole (Synnovator). Step 4: Peak 1 of atropisomer separation used as starting material. |

Atropisomer Separation for Examples 18-1, step 3.

The racemic mixture was separated by SFC using a ChiralPak OD-H column with a mobile phase of 80% liquid $CO_2$ and 20% MeOH with 0.2% diethyl amine to provide the respective P and M isomers of tert-butyl 6-(4-(6-hydroxynaphthalen-1-yl)-7-isopropyl-3-methyl-5,6,7,8-tetrahydro-1,7-naphthyridin-2-yl)-2,6-diazaspiro[3.4]octane-2-carboxylate. The stereochemistry of structures was arbitrarily assigned and is not established. 1$^{st}$ eluting atropisomer assigned as the M isomer and 2$^{nd}$ eluting atropisomer assigned as the P isomer.

Alternate Step 3 for Example 18-12

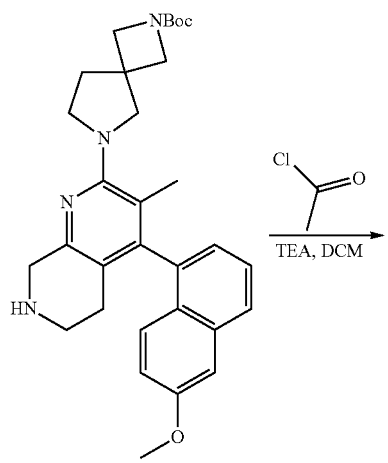

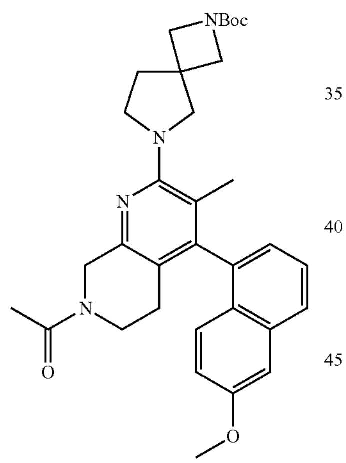

To a 0° C. solution of tert-butyl 6-(4-(6-methoxynaphthalen-1-yl)-3-methyl-5,6,7,8-tetrahydro-1,7-naphthyridin-2-yl)-2,6-diazaspiro[3.4]octane-2-carboxylate (0.2 g, 0.389 mmol), TEA (0.271 mL, 1.943 mmol) and DCM (5 mL) was added acetyl chloride (0.041 mL, 0.583 mmol). The reaction was stirred for 30 min. The reaction mixture was diluted with water (25 mL) and extracted with DCM (2×25 mL). The organic extracts were dried over $Na_2SO_4$, and concentrated in vacuo. The material was absorbed onto a plug of silica gel and purified by chromatography through a Redi-Sep pre-packed silica gel column, eluting with a gradient of 0-3% MeOH in DCM, to provide tert-butyl 6-(7-acetyl-4-(6-methoxynaphthalen-1-yl)-3-methyl-5,6,7,8-tetrahydro-1,7-naphthyridin-2-yl)-2,6-diazaspiro[3.4]octane-2-carboxylate (0.17 g, 79% yield) as light-yellow solid. m/z (ESI): 557.0 $(M+H)^+$.

Alternate Step 3 for Example 18-12

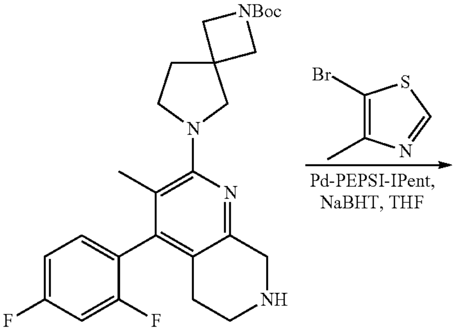

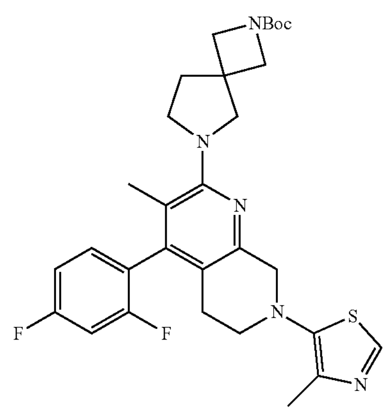

To a degassed solution of tert-butyl 6-(4-(2,4-difluorophenyl)-3-methyl-5,6,7,8-tetrahydro-1,7-naphthyridin-2-yl)-2,6-diazaspiro[3.4]octane-2-carboxylate (300 mg, 0.638 mmol), sodium 2,6-di-tert-butyl-4-methylphenolate (309 mg, 1.275 mmol, Essen Scientific), 5-bromo-4-methylthiazole (170 mg, 0.956 mmol, Combi-Blocks) and THF (6 mL) was added Pd-PEPPSI-Ipent catalyst (50.5 mg, 0.064 mmol, Sigma-Aldrich). The reaction was stirred at room temperature for 16 h. The reaction mixture was diluted with water and extracted with EtOAc. The organic extracts were washed with brine, dried over $Na_2SO_4$, and concentrated under reduced pressure. The residue was purified on a Redi-Sep pre-packed silica gel column eluting with 40-50% EtOAc in hexanes to provide tert-butyl 6-(4-(2,4-difluorophenyl)-3-methyl-7-(4-methylthiazol-5-yl)-5,6,7,8-tetrahydro-1,7-naphthyridin-2-yl)-2,6-diazaspiro[3.4]octane-2-carboxylate (0.105 g, 29% yield)) as a light-yellow solid. m/z (ESI): 567.9 $(M+H)^+$.

Alternate Step 3 for Example 18-12

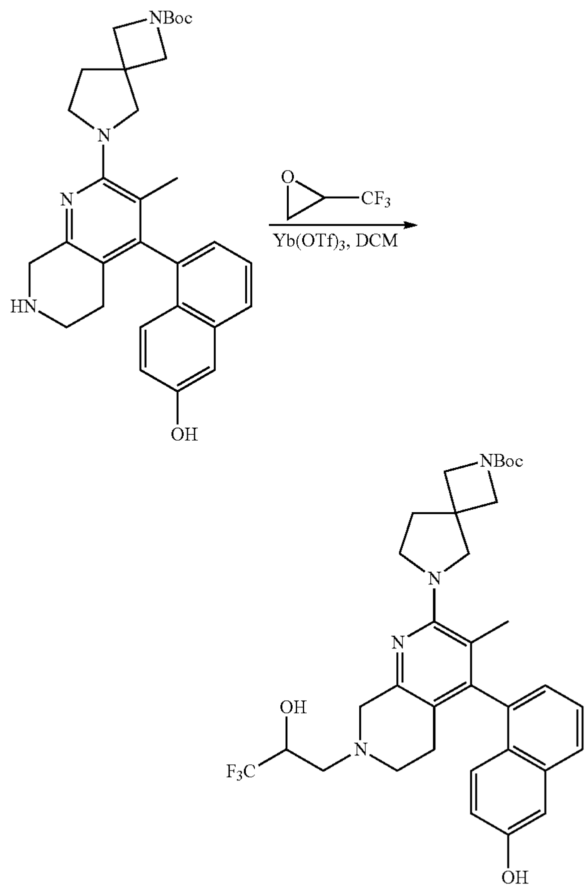

Tert-butyl 6-(4-(6-hydroxynaphthalen-1-yl)-3-methyl-5,6,7,8-tetrahydro-1,7-naphthyridin-2-yl)-2,6-diazaspiro[3.4]octane-2-carboxylate (150 mg, 0.300 mmol), 2-(trifluoromethyl)oxirane (336 mg, 3.00 mmol, Sigma-Aldrich), ytterbium(III) trifluoromethanesulfonate (18.58 mg, 0.030 mmol) and DCM (5 mL) were stirred at room temperature for 16 h. The reaction was concentrated in vacuo and absorbed onto a plug of silica gel and purified by chromatography through a Redi-Sep pre-packed silica gel column, eluting with a gradient of 40-50% EtOAc in hexane, to provide tert-butyl 6-(4-(6-hydroxynaphthalen-1-yl)-3-methyl-7-(3,3,3-trifluoro-2-hydroxypropyl)-5,6,7,8-tetrahydro-1,7-naphthyridin-2-yl)-2,6-diazaspiro[3.4]octane-2-carboxylate (100 mg, 54.5% yield) as a liquid. m/z (ESI): 612.2 $(M)^+$.

Atropisomer Separation for Examples 18-19 and 18-22, step 4.

The racemic mixture was separated by SFC using a ChiralPak IG column with a mobile phase of 90% liquid $CO_2$ and 10% MeOH to provide the respective P and M isomers of 7-isopropyl-3-methyl-4-(5-methyl-1H-indazol-4-yl)-2-(2,6-diazaspiro[3.4]octan-6-yl)-5,6,7,8-tetrahydro-1,7-naphthyridine. The stereochemistry of structures was arbitrarily assigned and is not established. 1st eluting atropisomer assigned as the M isomer and 2nd eluting atropisomer assigned as the P isomer.

Method 19

Example 19-1: 4-(2,3-Dimethylphenyl)-7-(4-methyl-1,3-thiazol-5-yl)-2-(2-(2-propenoyl)-2,6-diazaspiro[3.4]octan-6-yl)-1,5-naphthyridine-3-carbonitrile

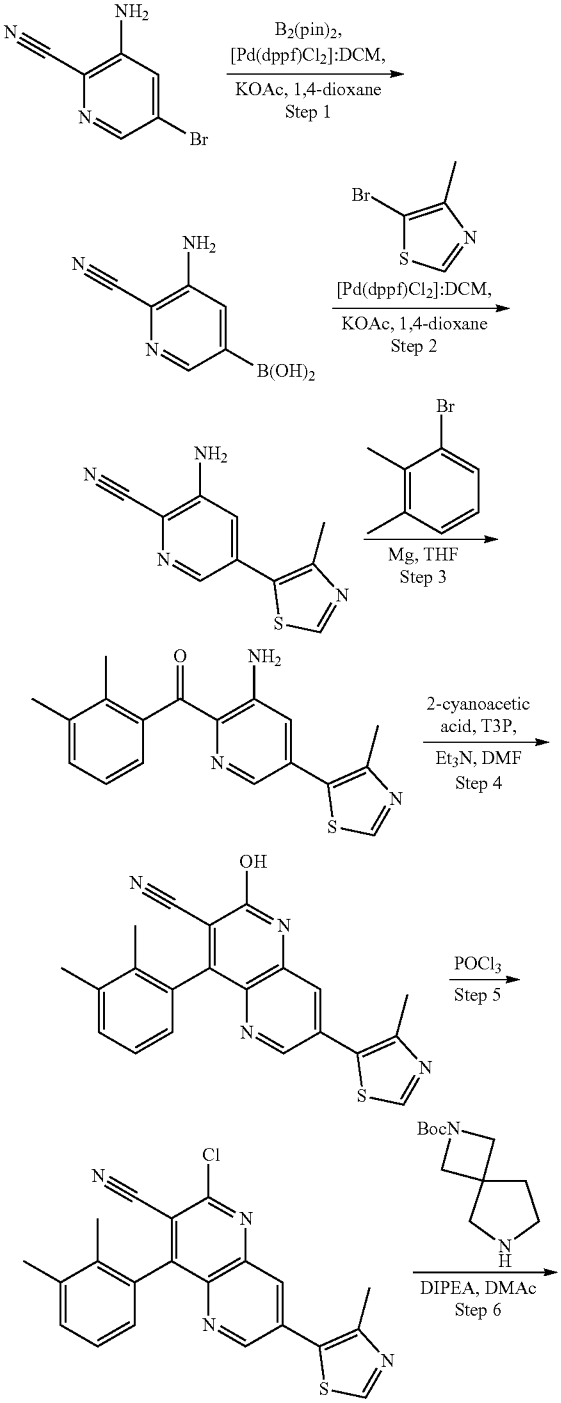

-continued

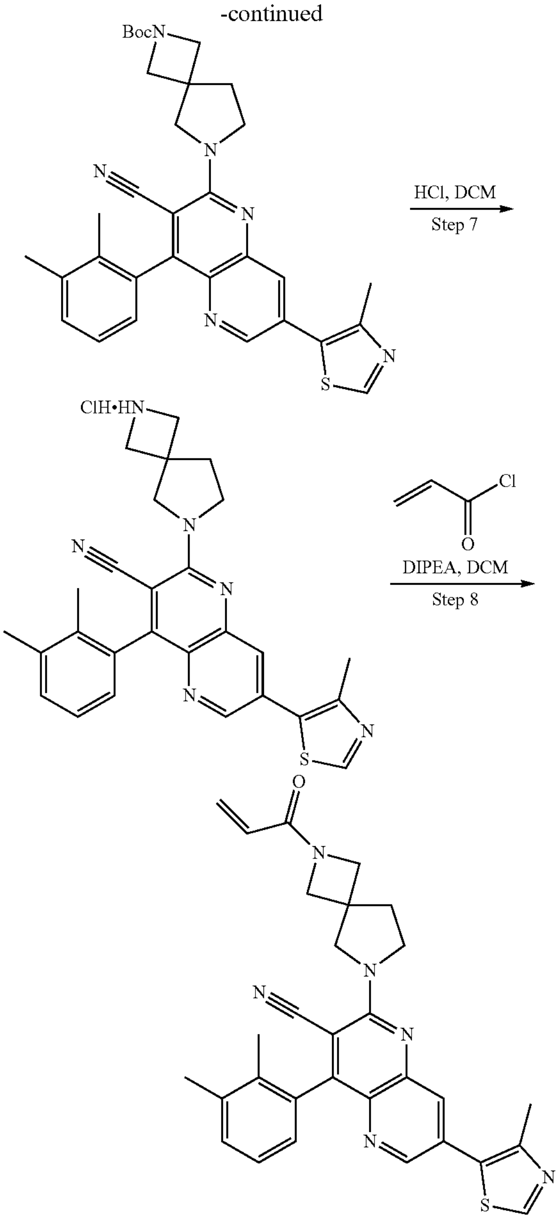

Step 1: (5-Amino-6-cyanopyridin-3-yl)boronic acid

To a degassed solution of 3-amino-5-bromopicolinonitrile (1 g, 5.05 mmol, Combi blocks), bis(pinacolato)diboron (1.539 g, 6.06 mmol, Chempure) and KOAc (1.487 g, 15.15 mmol) in 1,4-dioxane (15 mL) was added $PdCl_2$(dppf)-DCM adduct (0.206 g, 0.252 mmol, Chempure) and the reaction mixture was stirred at 100° C. for 2.5 h before it was filtered through a celite pad and washed with EtOAc (50 mL). The filtrate was concentrated under reduced pressure to afford (5-amino-6-cyanopyridin-3-yl)boronic acid (1.5 g) as a pale brown color liquid which was used in the next step without purification. m/z (ESI): 164.1 $(M+H)^+$.

Step 2:
3-Amino-5-(4-methylthiazol-5-yl)picolinonitrile

To a degassed solution of (5-amino-6-cyanopyridin-3-yl) boronic acid (4.5 g, 27.6 mmol), 5-bromo-4-methylthiazole (5.90 g, 33.1 mmol, Avra) and $K_2CO_3$ (11.45 g, 83 mmol) in 1,4-dioxane (20 mL) and water (2 mL) was added $PdCl_2$(dppf)-DCM adduct (1.128 g, 1.381 mmol, Chempure) and the reaction mixture was stirred at 100° C. for 16 h. The reaction mixture was cooled to room temperature and filtered through a celite pad and washed with EtOAc (50 mL). The filtrated was concentrated under reduced pressure. The residue was purified on a Redi-Sep pre-packed silica gel column eluting with a gradient of 0-30% EtOAc in hexanes to provide 3-amino-5-(4-methylthiazol-5-yl)picolinonitrile (1.1 g, 18.42% yield) as a yellow solid. $^1H$ NMR (400 MHz, DMSO-$d_6$) δ ppm 9.12 (s, 1H), 8.02 (d, J=1.9 Hz, 1H), 7.35 (d, J=1.9 Hz, 1H), 6.48 (s, 2H), 1.07 (s, 3H). m/z (ESI): 217.2 $(M+H)^+$.

Step 3: (3-Amino-5-(4-methylthiazol-5-yl)pyridin-2-yl)(2,3-dimethylphenyl)methanone To a suspension of magnesium (0.865 g, 35.6 mmol) and iodine (one crystal) in dry THF (20 mL) was drop wise added a solution of 1-bromo-2,3-dimethylbenzene (6.59 g, 35.6 mmol, Combi Blocks) in THF (20 mL). The reaction mixture was stirred at 25° C. for 20 min. To this reaction mixture was added dropwise a solution of 3-amino-5-(4-methylthiazol-5-yl)picolinonitrile (1.1 g, 5.09 mmol) in THF (20 mL) at 0° C. The resulting mixture was stirred at room temperature for 16 h before it was diluted with ice-cold water and extracted with EtOAc (2×50 mL). The organic extracts were washed with brine, dried over $Na_2SO_4$, filtered and concentrated under reduced pressure. The residue was purified on a Redi-Sep pre-packed silica gel column eluting with a gradient of 50-60% EtOAc in petroleum ether to provide (3-amino-5-(4-methylthiazol-5-yl)pyridin-2-yl)(2,3-dimethylphenyl)methanone (1.2 g, 72.9% yield) as a light yellow gummy solid. m/z (ESI): 323.0 $(M+H)^+$.

Step 4: 4-(2,3-Dimethylphenyl)-2-hydroxy-7-(4-methylthiazol-5-yl)-1,5-naphthyridine-3-carbonitrile To a solution of (3-amino-5-(4-methylthiazol-5-yl)pyridin-2-yl)(2,3-dimethylphenyl)-methanone (0.5 g, 1.546 mmol), 2-cyanoacetic acid (0.197 g, 2.319 mmol, Spectrochem) and TEA (0.539 mL, 3.87 mmol) in DMF (10 mL) was added T3P (2.163 g, 3.40 mmol, 50% in EtOAc, Spectrochem) at 0° C. The reaction mixture was stirred at room temperature for 16 h and then at 70° C. for 4 h. The reaction mixture was diluted with ice-cold water and extracted with EtOAc. The organic extracts were washed with brine, dried over $Na_2SO_4$, filtered and concentrated under reduced pressure. The residue was purified on a Redi-Sep pre-packed silica gel column (12 g) eluting with 90% EtOAc in petroleum ether to provide 4-(2,3-dimethylphenyl)-2-hydroxy-7-(4-methylthiazol-5-yl)-1,5-naphthyridine-3-carbonitrile (0.2 g, 34.7% yield) as a brown gummy solid. m/z (ESI): 372.8 $(M+H)^+$.

Step 5: 2-Chloro-4-(2,3-dimethylphenyl)-7-(4-methylthiazol-5-yl)-1,5-naphthyridine-3-carbonitrile A solution of 4-(2,3-dimethylphenyl)-2-hydroxy-7-(4-methylthiazol-5-yl)-1,5-naphthyridine-3-carbonitrile (0.2 g, 0.537 mmol) in $POCl_3$ (1.2 mL, 12.87 mmol) was heated at 120° C. for 16 h. The reaction mixture was concentrated under reduced pressure and the residue was diluted with ice-cold water and extracted with DCM. The organic extracts were washed with 10% aqueous $NaHCO_3$ and brine, dried over $Na_2SO_4$, and concentrated under reduced pressure. The residue was purified on a Redi-Sep pre-packed silica gel column eluting with a gradient of 30-40/o EtOAc in petroleum ether to provide 2-chloro-4-(2,3-dimethylphenyl)-7-(4-methylthiazol-5-yl)-1,5-naphthyridine-3-carbonitrile (0.13 g, 61.9% yield) as a light brown solid. $^1$H NMR (400 MHz, DMSO-$d_6$) δ ppm 9.10-9.12 (m, 2H), 8.66 (d, J=2.3 Hz, 1H), 7.37 (d, J=7.8 Hz, 1H), 7.28 (t, J=7.6 Hz, 1H), 7.20 (dd, J=7.8, 1.6 Hz, 1H), 2.60 (s, 3H), 2.36 (s, 3H), 1.92 (s, 3H). m/z (ESI): 390.8 $(M+H)^+$.

Step 6: tert-Butyl 6-(3-cyano-4-(2,3-dimethylphenyl)-7-(4-methylthiazol-5-yl)-1,5-naphthyridin-2-yl)-2,6-diazaspiro[3.4]octane-2-carboxylate A solution of 2-chloro-4-(2,3-dimethylphenyl)-7-(4-methylthiazol-5-yl)-1,5-naphthyridine-3-carbonitrile (0.13 g, 0.333 mmol), tert-butyl 2,6-diazaspiro[3.4]octane-2-carboxylate (0.085 g, 0.399 mmol, Combi-Blocks) and DIPEA (0.184 mL, 0.998 mmol) in DMA (2 mL) was heated at 16 h at 120° C. The reaction mixture was diluted with ice-cold water and extracted with EtOAc. The combined organic extracts were washed with brine, separated, dried over $Na_2SO_4$, and concentrated under reduced pressure. The residue was purified on a Redi-Sep pre-packed silica gel column eluting with 40-50% EtOAc in petroleum ether to provide tert-butyl 6-(3-cyano-4-(2,3-dimethylphenyl)-7-(4-methylthiazol-5-yl)-1,5-naphthyridin-2-yl)-2,6-diazaspiro[3.4]octane-2-carboxylate (0.18 g, 96% yield) as light yellow gummy liquid. m/z (ESI): 566.7 $(M+H)^+$.

Step 7: 4-(2,3-Dimethylphenyl)-7-(4-methylthiazol-5-yl)-2-(2,6-diazaspiro[3.4]octan-6-yl)-1,5-naphthyridine-3-carbonitrile hydrochloride To a solution of tert-butyl 6-(3-cyano-4-(2,3-dimethylphenyl)-7-(4-methylthiazol-5-yl)-1,5-naphthyridin-2-yl)-2,6-diazaspiro[3.4]octane-2-carboxylate (0.18 g, 0.318 mmol) in DCM (2 mL) was added 4M HCl in dioxane (0.5 mL, 2.00 mmol) at 0° C. and the reaction mixture was stirred at room temperature for 1 h. The reaction mixture was concentrated under reduced pressure and triturated with diethyl ether to provide 4-(2,3-dimethylphenyl)-7-(4-methylthiazol-5-yl)-2-(2,6-diazaspiro[3.4]octan-6-yl)-1,5-naphthyridine-3-carbonitrile hydrochloride (0.15 g, 94% yield) as a light yellow solid. m/z (ESI): 466.8 $(M+H)^+$.

Step 8: 4-(2,3-Dimethylphenyl)-7-(4-methyl-1,3-thiazol-5-yl)-2-(2-(2-propenoyl)-2,6-diazaspiro[3.4]octan-6-yl)-1,5-naphthyridine-3-carbonitrile To a solution of 4-(2,3-dimethylphenyl)-7-(4-methylthiazol-5-yl)-2-(2,6-diazaspiro[3.4]octan-6-yl)-1,5-naphthyridine-3-carbonitrile hydrochloride (0.15 g, 0.298 mmol) and $Et_3N$ (0.125 mL, 0.895 mmol) in DCM (2 mL) was added acryloyl chloride (0.019 mL, 0.239 mmol, Symax Ltd.) dropwise at −78° C. and the reaction stirred for 15 min. The reaction mixture was diluted with water and extracted with DCM. The combined organic extracts were dried over $Na_2SO_4$, concentrated and purified by preparative HPLC to provide 2-(2-acryloyl-2,6-diazaspiro[3.4]octan-6-yl)-4-(2,3-dimethylphenyl)-7-(4-methylthiazol-5-yl)-1,5-naphthyridine-3-carbonitrile (0.060 g, 38.6% yield) as an off-white solid. $^1$H NMR (400 MHz, DMSO-$d_6$) δ ppm 9.16 (s, 1H), 8.72 (d, J=2.3 Hz, 1H), 8.04 (d, J=2.2 Hz, 1H), 7.31 (d, J=7.5 Hz, 1H), 7.23 (t, J=7.6 Hz, 1H), 7.10 (d, J=7.5 Hz, 1H), 6.32 (m, 1H), 6.12 (dd, J=17.0, 2.3 Hz, 1H), 5.68 (dd, J=10.3, 2.3 Hz, 1H), 4.31 (dd, J=8.7, 6.5 Hz, 1H), 4.21 (dd, J=8.8, 3.8 Hz, 1H), 4.11-3.98 (m, 3H), 3.98-3.82 (m, 3H), 2.56 (s, 3H), 2.34 (s, 3H), 2.25 (m, 2H), 1.90 (d, J=2.7 Hz, 3H). m/z (ESI): 520.8 $(M+H)^+$.

TABLE 11

Examples 19-2 to 19-15 were prepared following the procedure described in Method 19, Steps 1-8, above as follows:

| Ex.# | Chemical Structure | Name | Method changes | Reagent |
| --- | --- | --- | --- | --- |
| 19-2 | 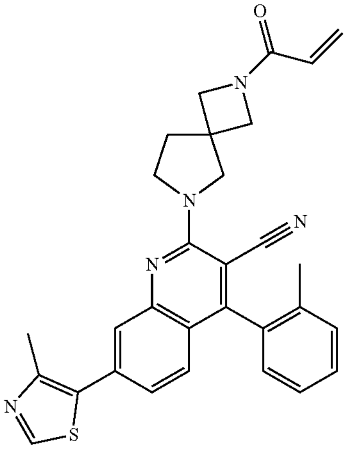 [SMILES: C=CC(=O)N1CC2(CCN(c3nc4cc(-c5scnc5C)ccc4c(-c4ccccc4C)c3C#N)C2)C1] | 4-(2-methylphenyl)-7-(4-methyl-1,3-thiazol-5-yl)-2-(2-(2-propenoyl)-2,6-diazaspiro[3.4]octan-6-yl)-3-quinolinecarbonitrile | See below for alternate Step 1 and Step 2 replacing steps 1-3 | |

TABLE 11-continued

| Examples 19-2 to 19-15 were prepared following the procedure described in Method 19, Steps 1-8, above as follows: | | | | |
|---|---|---|---|---|
| Ex.# | Chemical Structure | Name | Method changes | Reagent |
| 19-3 | 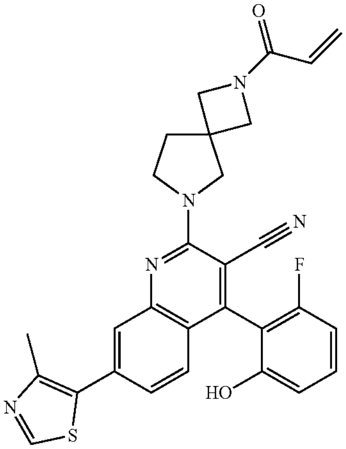 [SMILES: C=CC(=O)N1CC2(CCN(c3nc4cc(-c5scnc5C)ccc4c(-c4c(O)cccc4F)c3C#N)C2)C1] | 4-(2-fluoro-6-hydroxyphenyl)-7-(4-methyl-1,3-thiazol-5-yl)-2-(2-(2-propenoyl)-2,6-diazaspiro[3.4]octan-6-yl)-3-quinolinecarbonitrile | See below for alternate Step 1 and Step 2 Example 19-2 replacing Steps 1-3. Step 5 was performed using the procedure from Example 19-5, Step 5 | Step 2: (2-fluoro-6-hydroxyphenyl) boronic acid (Arbor Chemicals) |
| 19-4 | 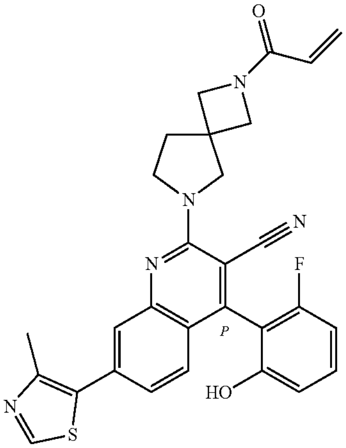 | (P)-4-(2-fluoro-6-hydroxyphenyl)-7-(4-methyl-1,3-thiazol-5-yl)-2-(2-(2-propenoyl)-2,6-diazaspiro[3.4]octan-6-yl)-3-quinolinecarbonitrile (2nd eluting isomer) | See below for alternate Step 1 and Step 2 Example 19-2 replacing Steps 1-3, Step 5 was performed using the procedure from Example 19-5, Step 5 See atropisomer separation conditions below. | Step 2: (2-fluoro-6-hydroxyphenyl) boronic acid (Arbor Chemicals) |
| 19-5 | 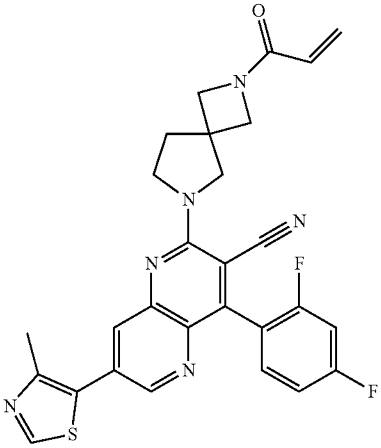 | 4-(2,4-difluorophenyl)-7-(4-methyl-1,3-thiazol-5-yl)-2-(2-(2-propenoyl)-2,6-diazaspiro[3.4]octan-6-yl)-1,5-naphthyridine-3-carbonitrile | See alternate step 5 below | Step 3: 1-bromo-2,4-difluorobenzene (Avra Chemicals). |

TABLE 11-continued

| Examples 19-2 to 19-15 were prepared following the procedure described in Method 19, Steps 1-8, above as follows: | | | | |
|---|---|---|---|---|
| Ex.# | Chemical Structure | Name | Method changes | Reagent |
| 19-6 | 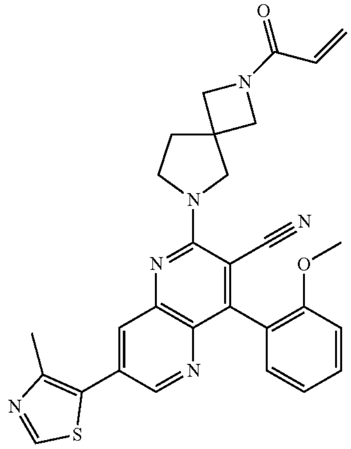 | 4-(2-methoxyphenyl)-7-(4-methyl-1,3-thiazol-5-yl)-2-(2-(2-propenoyl)-2,6-diazaspiro[3.4]octan-6-yl)-1,5-naphthyridine-3-carbonitrile | Alternate Step 5 performed in an analogous manner to Example 19-5 | Step 3: 1-bromo-2-methoxybenzene (Combi-Blocks). |
| 19-7 | 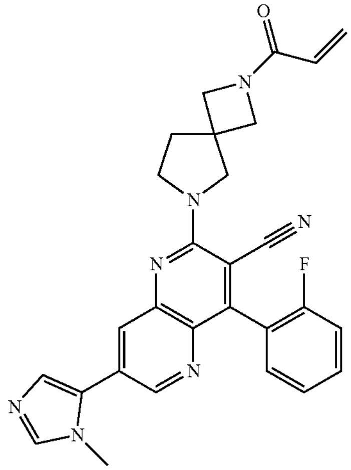 [SMILES: C=CC(=O)N1CC2(CCN(c3nc4cc(-c5cncn5C)cnc4c(-c4ccccc4F)c3C#N)C2)C1] | 4-(2-fluorophenyl)-7-(1-methyl-1H-imidazol-5-yl)-2-(2-(2-propenoyl)-2,6-diazaspiro[3.4]octan-6-yl)-1,5-naphthyridine-3-carbonitrile | Alternate Step 5 performed in an analogous manner to Example 19-5 | Step 2: 5-bromo-1-methyl-1H-imidazole (J&W Pharma). Step 3: 1-bromo-2-fluorobenzene (Combi-Blocks). |
| 19-8 | 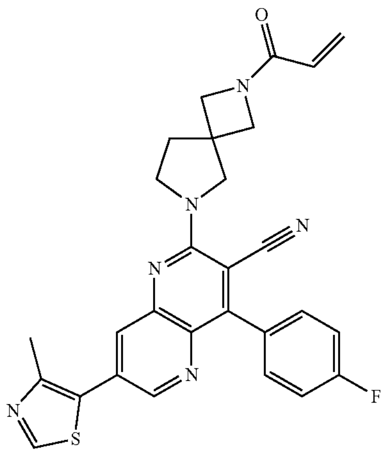 [SMILES: C=CC(=O)N1CC2(CCN(c3nc4cc(-c5scnc5C)cnc4c(-c4ccc(F)cc4)c3C#N)C2)C1] | 4-(4-fluorophenyl)-7-(4-methyl-1,3-thiazol-5-yl)-2-(2-(2-propenoyl)-2,6-diazaspiro[3.4]octan-6-yl)-1,5-naphthyridine-3-carbonitrile | Alternate Step 5 performed in an analogous manner to Example 19-5 | Step 3: 1-bromo-4-fluorobenzene (Spectrochem). |

TABLE 11-continued

Examples 19-2 to 19-15 were prepared following the procedure described in Method 19, Steps 1-8, above as follows:

| Ex.# | Chemical Structure | Name | Method changes | Reagent |
|---|---|---|---|---|
| 19-9 | 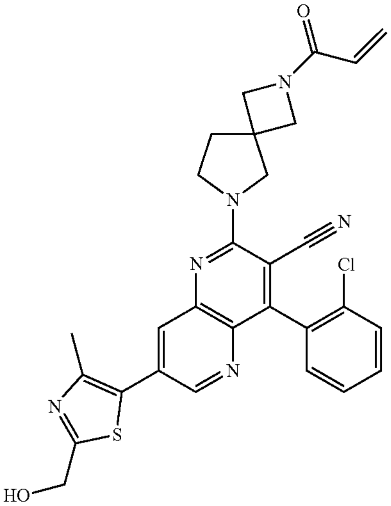 [SMILES: C=CC(=O)N1CC2(CCN(c3nc4cc(-c5sc(CO)nc5C)cnc4c(-c4ccccc4Cl)c3C#N)C2)C1] | 4-(2-chlorophenyl)-7-(2-(hydroxymethyl)-4-methyl-1,3-thiazol-5-yl)-2-(2-(2-propenoyl)-2,6-diazaspiro[3.4]octan-6-yl)-1,5-naphthyridine-3-carbonitrile | See additional protection step below performed after Step 2. Alternate Step 5 performed in an analogous manner to Example 19-5 | Step 2: (5-bromo-4-methylthiazol-2-yl)methanol (Ambeed). Step 3: 1-bromo-2-chlorobenzene (Combi Blocks) |
| 19-10 | 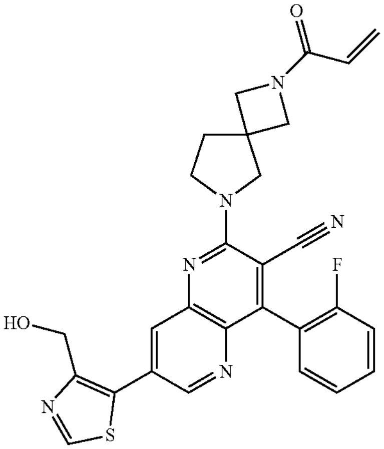 [SMILES: C=CC(=O)N1CC2(CCN(c3nc4cc(-c5scnc5CO)cnc4c(-c4ccccc4F)c3C#N)C2)C1] | 4-(2-fluorophenyl)-7-(4-(hydroxymethyl)-1,3-thiazol-5-yl)-2-(2-(2-propenoyl)-2,6-diazaspiro[3.4]octan-6-yl)-1,5-naphthyridine-3-carbonitrile | Alternate Step 5 performed in an analogous manner to Example 19-5. Step 7: $BBr_3$ was used for deprotection of Boc and methoxy in place of HCl. | Step 2: Intermediate 89. Step 3: 1-bromo-2-fluorobenzene (Combi Blocks) |
| 19-11 | 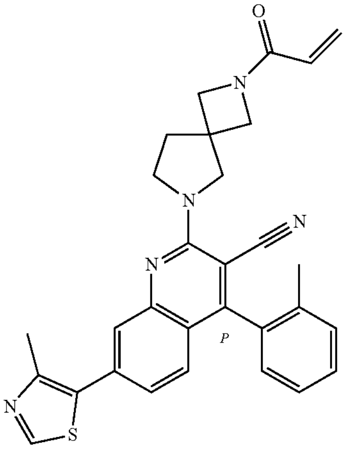 | (P)-4-(2-methylphenyl)-7-(4-methyl-1,3-thiazol-5-yl)-2-(2-(2-propenoyl)-2,6-diazaspiro[3.4]octan-6-yl)-3-quinolinecarbonitrile (2$^{nd}$ eluting isomer) | See alternate Step 1 and Step 2 from Example 19-2. See atropisomer separation conditions below. | |

TABLE 11-continued

| Examples 19-2 to 19-15 were prepared following the procedure described in Method 19, Steps 1-8, above as follows: | | | | |
|---|---|---|---|---|
| Ex.# | Chemical Structure | Name | Method changes | Reagent |
| 19-12 | 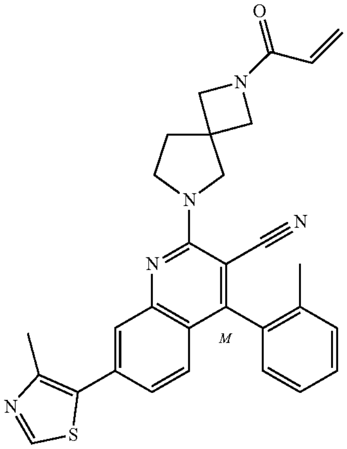 | (M)-4-(2-methylphenyl)-7-(4-methyl-1,3-thiazol-5-yl)-2-(2-(2-propenoyl)-2,6-diazaspiro[3.4]octan-6-yl)-3-quinolinecarbonitrile (1st eluting isomer) | See alternate Step 1 and Step 2 from Example 19-2. See atropisomer separation conditions below. | |
| 19-13 | 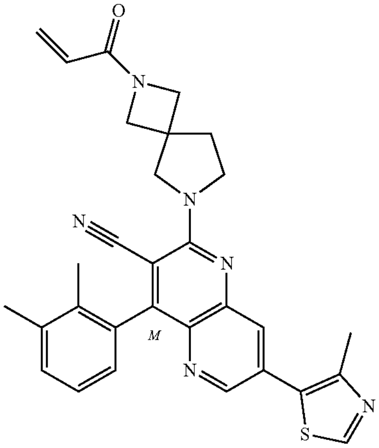 | (M)-4-(2,3-dimethylphenyl)-7-(4-methyl-1,3-thiazol-5-yl)-2-(2-(2-propenoyl)-2,6-diazaspiro[3.4]octan-6-yl)-1,5-naphthyridine-3-carbonitrile (1st eluting isomer) | See atropisomer separation conditions below. | |
| 19-14 | 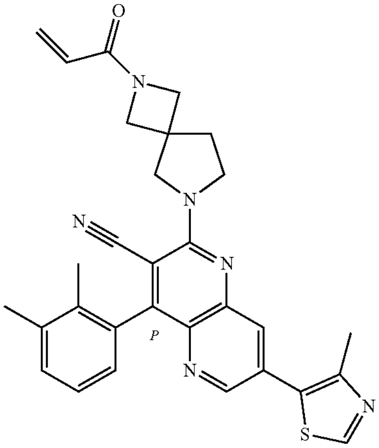 | (P)-4-(2,3-dimethylphenyl)-7-(4-methyl-1,3-thiazol-5-yl)-2-(2-(2-propenoyl)-2,6-diazaspiro[3.4]octan-6-yl)-1,5-naphthyridine-3-carbonitrile (2nd eluting isomer) | See atropisomer separation conditions below. | |

TABLE 11-continued

Examples 19-2 to 19-15 were prepared following the procedure described in Method 19, Steps 1-8, above as follows:

| Ex.# | Chemical Structure | Name | Method changes | Reagent |
| --- | --- | --- | --- | --- |
| 19-15 | 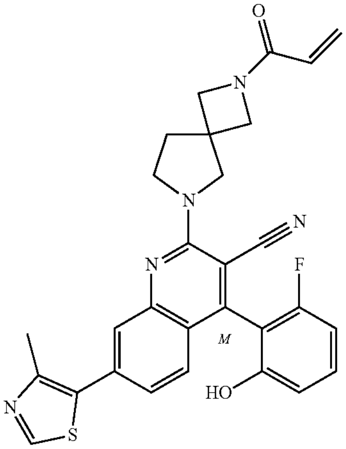 | (M)-4-(2-fluoro-6-hydroxyphenyl)-7-(4-methyl-1,3-thiazol-5-yl)-2-(2-(2-propenoyl)-2,6-diazaspiro[3.4]octan-6-yl)-3-quinolinecarbonitrile ($1^{st}$ eluting isomer) | See below for alternate Step 1 and Step 2 Example 19-2 replacing Steps 1-3. Step 5 was performed using the procedure from Example 19-5, Step 5 See atropisomer separation conditions below. | Alternate Step 2: (2-fluoro-6-hydroxyphenyl) boronic acid (Arbor Chemicals) |

Alternate Step 1 and Step 2 for Example 19-2

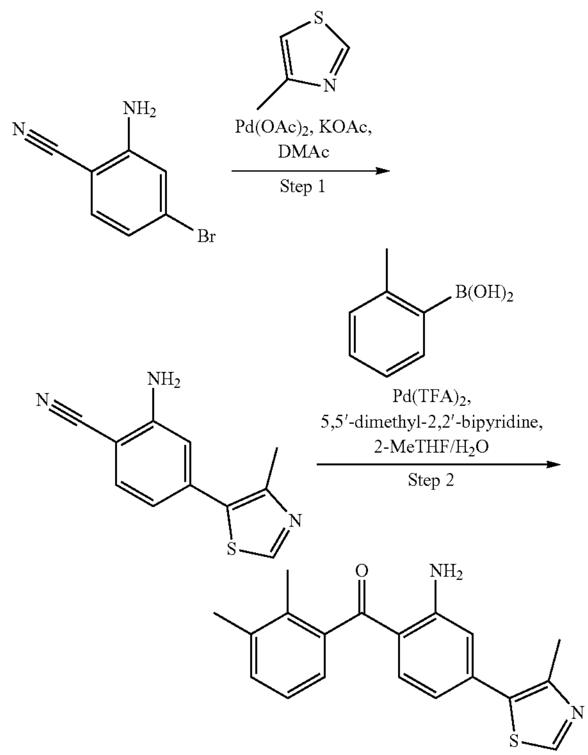

Step 1: 2-Amino-4-(4-methylthiazol-5-yl)benzonitrile

To a degassed mixture of 2-amino-4-bromobenzonitrile (15 g, 76 mmol, Combi-Blocks) and 4-methylthiazole (15.10 g, 152 mmol, Oakwood), KOAc (14.94 g, 152 mmol) in DMA (150 mL) was added Pd(OAc)$_2$ (0.684 g, 3.05 mmol, Hindustan Platinum) and the reaction was heated at 135° C. for 16 h. The reaction mixture was cooled to room temperature, filtered through a celite pad, and washed with EtOAc (50 mL). The filtrate was concentrated under reduced pressure. The residue was purified on a Redi-Sep pre-packed silica gel column, eluting with a gradient of 0-60% EtOAc in petroleum ether to provide 2-amino-4-(4-methylthiazol-5-yl)benzonitrile (13.5 g, 82% yield) as a yellow solid. $^1$H NMR (400 MHz, DMSO-d$_6$) δ 9.03 (s, 1H), 7.47 (d, J=8.2 Hz, 1H), 6.93 (d, J=1.7 Hz, 1H), 6.71 (dd, J=8.1, 1.7 Hz, 1H), 6.23 (s, 2H), 2.47 (s, 3H). m/z (ESI): 216.0 (M+H)$^+$.

Step 2: (2-Amino-4-(4-methylthiazol-5-yl)phenyl)(o-tolyl)methanone

To a degassed mixture of 2-amino-4-(4-methylthiazol-5-yl)benzonitrile (0.5 g, 2.323 mmol), o-tolylboronic acid (0.632 g, 4.65 mmol, Combi-Blocks), methanesulfonic acid (1.51 mL, 23.23 mmol, Spectrochem), 5,5'-dimethyl-2,2'-bipyridine (0.032 g, 0.174 mmol, Combi-Blocks) and 2-MeTHF (10 mL) and water (2.5 mL) was added palladium (II) trifluoroacetate (0.039 g, 0.116 mmol, Combi-Blocks) and the reaction was heated to 80° C. for 24 h. The reaction mixture was cooled to room temperature, filtered through a celite pad, and washed with EtOAc (50 mL). The filtrated was concentrated under reduced pressure. The residue was purified on a Redi-Sep pre-packed silica gel column eluting with a gradient of 0-10% EtOAc in hexanes to provide (2-amino-4-(4-methylthiazol-5-yl)phenyl)(o-tolyl)methanone (0.4 g, 55.8% yield) as a yellow solid. m/z (ESI): 308.9 (M+H)$^+$.

Atropisomer Separation for Examples 19-4 and 19-15.

The racemic mixture was separated by SFC using a Chiralcel OJ-H column with a mobile phase of 60% liquid $CO_2$ and 40% MeOH to provide the respective P and M isomers of 4-(2-fluoro-6-hydroxyphenyl)-7-(4-methyl-1,3-thiazol-5-yl)-2-(2-(2-propenoyl)-2,6-diazaspiro[3.4]octan-6-yl)-3-quinolinecarbonitrile. The stereochemistry of structures was arbitrarily assigned and is not established. $1^{st}$ eluting atropisomer assigned as the M isomer and $2^{nd}$ eluting atropisomer assigned as the P isomer.

Alternate Step 5 for Example 19-5

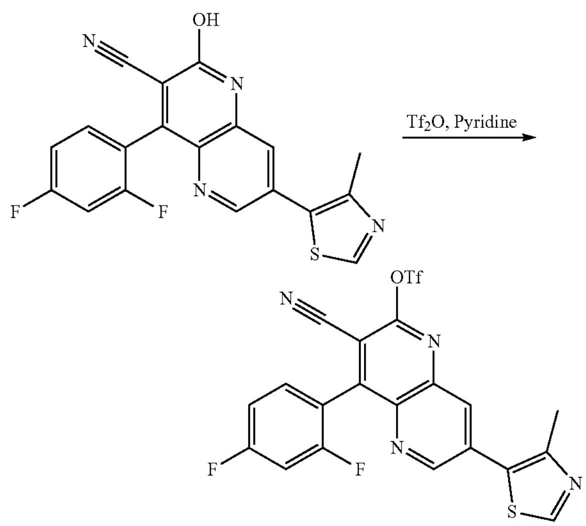

To a solution of 4-(2,4-difluorophenyl)-2-hydroxy-7-(4-methylthiazol-5-yl)-1,5-naphthyridine-3-carbonitrile (0.13 g, 0.342 mmol) and pyridine (0.081 g, 1.025 mmol) in DCM (2.6 mL) was added $Tf_2O$ (0.115 mL, 0.684 mmol) at 0° C. and the reaction was stirred for 1 h. The reaction mixture was concentrated under reduced pressure and co-evaporated with toluene to provide 3-cyano-4-(2,4-difluorophenyl)-7-(4-methylthiazol-5-yl)-1,5-naphthyridin-2-yl trifluoromethanesulfonate which was taken to the next step without further purification. m/z (ESI): 512.8 $(M+H)^+$.

Additional protection step for Example 19-9

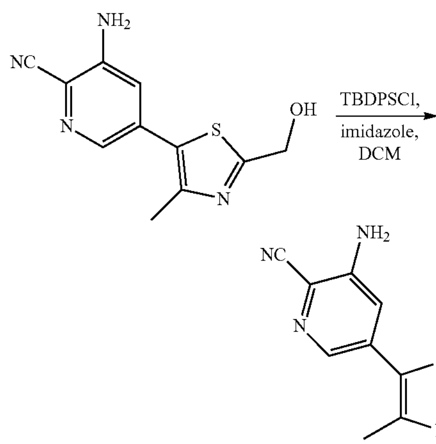

To a suspension of 3-amino-5-(2-(hydroxymethyl)-4-methylthiazol-5-yl)picolinonitrile (0.45 g, 1.827 mmol) in DCM (15 mL) was added imidazole (0.373 g, 5.48 mmol), followed by TBDPS-Cl (0.563 mL, 2.193 mmol) dropwise at 0° C. The reaction mixture was stirred at ambient temperature for 16 h. The reaction was quenched with water and extracted with EtOAc (2×40 mL). The combined extracts were washed with water (25 mL) and brine solution (25 mL), dried over $Na_2SO_4$ and concentrated under reduced pressure. The crude product was purified through Biotage® Isolera using 40% EtOAc in petroleum ether to afford 3-amino-5-(2-(((tert-butyldiphenylsilyl)oxy)methyl)-4-methylthiazol-5-yl)picolinonitrile (0.4 g, 0.825 mmol, 45.2% yield) as a pale yellow gum. $^1H$ NMR (400 MHz, DMSO-$d_6$) δ ppm 8.03 (d, J=2.0 Hz, 1H), 7.71-7.65 (m, 4H), 7.55-7.44 (m, 6H), 7.35 (d, J=2.0 Hz, 1H), 6.46 (s, 2H), 4.97 (s, 2H), 2.42 (s, 3H), 1.08 (s, 9H).

Atropisomer Separation for Examples 19-11 and 19-12.

The racemic mixture was separated by SFC using a Chiralcel OJ-H column with a mobile phase of 60% liquid $CO_2$ and 40% MeOH to provide the respective P and M isomers of 4-(2-methylphenyl)-7-(4-methyl-1,3-thiazol-5-yl)-2-(2-(2-propenoyl)-2,6-diazaspiro[3.4]octan-6-yl)-3-quinolinecarbonitrile. The stereochemistry of structures was arbitrarily assigned and is not established. 1st eluting atropisomer assigned as the M isomer and 2nd eluting atropisomer assigned as the P isomer.

Atropisomer Separation for Examples 19-13 and 19-14.

The racemic mixture was separated by SFC using a Chiralcel OJ-H column with a mobile phase of 60% liquid $CO_2$ and 40% MeOH to provide the respective P and M isomers of 4-(2,3-dimethylphenyl)-7-(4-methyl-1,3-thiazol-5-yl)-2-(2-(2-propenoyl)-2,6-diazaspiro[3.4]octan-6-yl)-1,5-naphthyridine-3-carbonitrile. The stereochemistry of structures was arbitrarily assigned and is not established. 1st eluting atropisomer assigned as the M isomer and 2nd eluting atropisomer assigned as the P isomer.

Method 20

Example 20-1: 4-(2-chlorophenyl)-7-(4-methyl-1,3-thiazol-5-yl)-2-(2-(2-propenoyl)-2,6-diazaspiro[3.4]octan-6-yl)-3-quinolinecarbonitrile

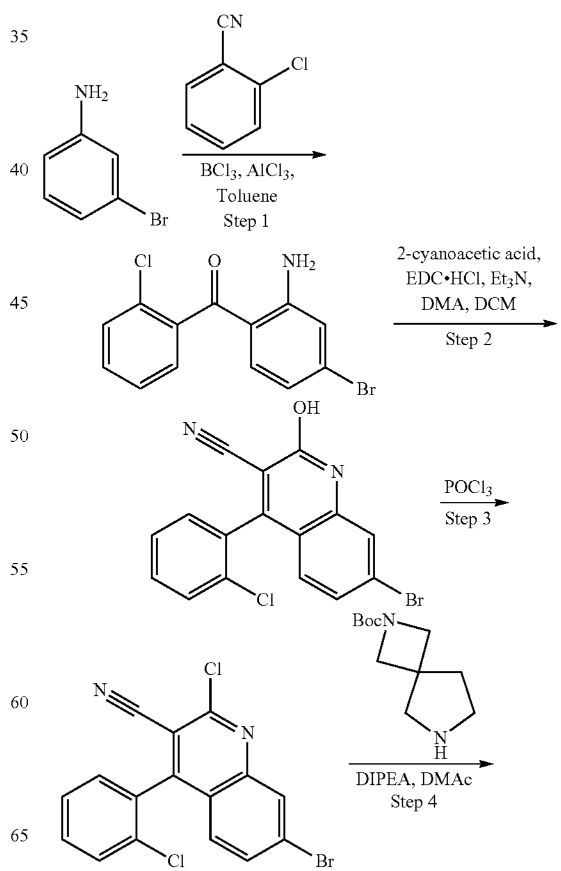

-continued

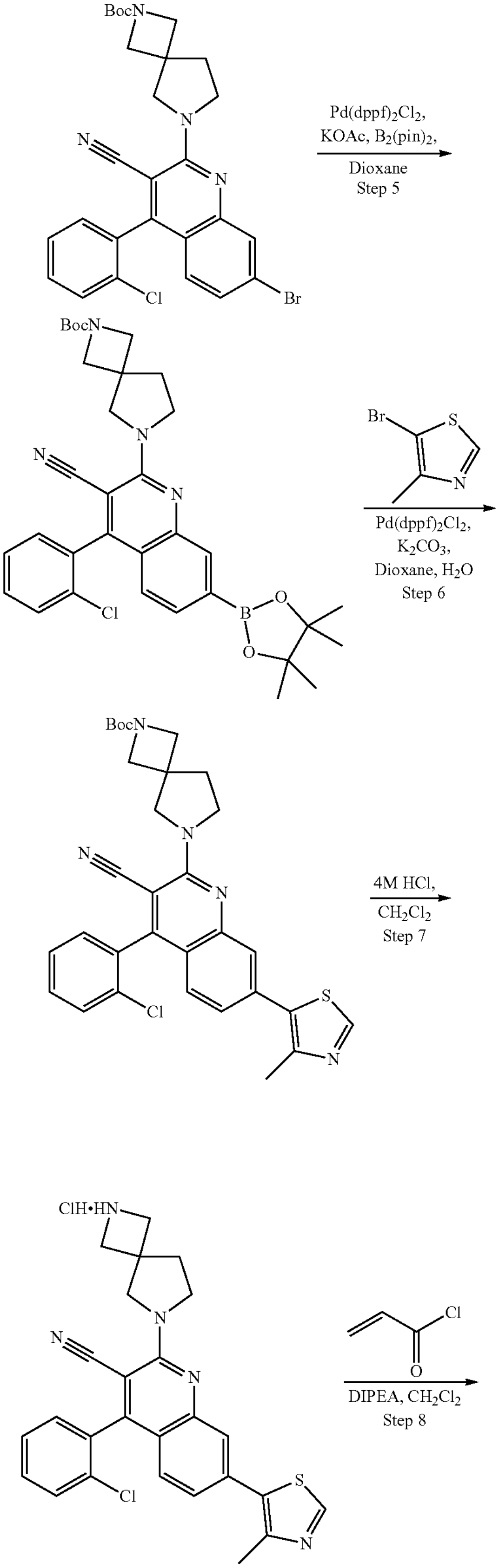

-continued

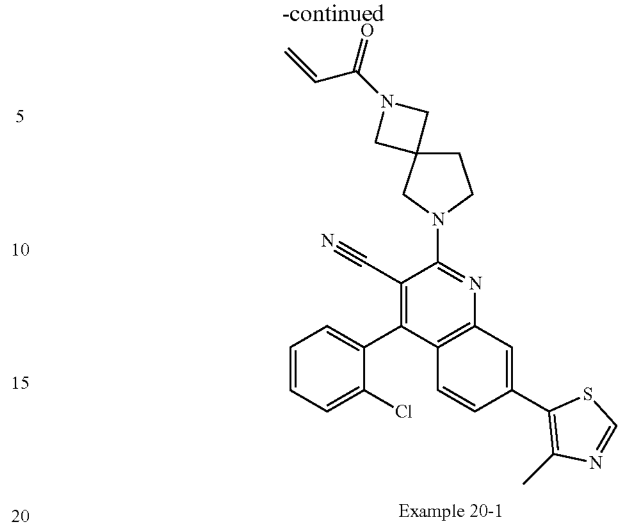

Example 20-1

Step 1: (2-Amino-4-bromophenyl)(2-chlorophenyl)methanone

To a solution of 2-chlorobenzonitrile (4 g, 29.1 mmol, Avra) and 3-bromoaniline (5 g, 29.1 mmol, Oakwood) in toluene (120 mL) was added $BCl_3$ (29.1 mL, 29.1 mmol, 1M in heptane, Symax) dropwise at 0° C. and stirred at room temperature for 1 h. The reaction mixture was further cooled to 0° C. and was added $AlCl_3$ (3.88 g, 29.1 mmol, Spectrochem) portion-wise. The reaction mixture was slowly allowed to warm to room temperature and heated to 120° C. for 5 h and then stirred at room temperature for 16 h. The reaction mixture was cooled to 0° C. and quenched with 1.5N HCl (80 mL). The resulting mixture was heated at 120° C. for 2 h. The reaction mixture was cooled to 0° C. and basified with 10% NaOH solution to pH 8-9 and extracted with EtOAc. The organic extracts were washed with brine, dried over $Na_2SO_4$, and concentrated under reduced pressure. The residue was purified on a Redi-Sep pre-packed silica gel column eluting with 0-5% EtOAc in hexanes to provide (2-amino-4-bromophenyl)(2-chlorophenyl)methanone (0.85 g, 1.971 mmol, 6.78% yield) as a pale yellow liquid. m/z (ESI): 310.9 $(M+H)^+$.

Step 2: 7-Bromo-4-(2-chlorophenyl)-2-hydroxyquinoline-3-carbonitrile

To a solution of (2-amino-4-bromophenyl)(2-chlorophenyl)methanone (0.4 g, 1.288 mmol), 2-cyanoacetic acid (0.164 g, 1.932 mmol, Spectrochem) and N,N-dimethylaniline (0.312 g, 2.58 mmol) in DCM (12 mL) was added EDC HCl (0.494 g, 2.58 mmol, Chempure) at 0° C. The reaction mixture was stirred at room temperature for 10 h. Then TEA (0.359 mL, 2.58 mmol) was added to the reaction mixture and stirring was continued for additional 2 h. The reaction mixture was diluted with ice-cold water and extracted with EtOAc. The organic extracts were washed with brine, dried over $Na_2SO_4$, and concentrated under reduced pressure. The residue was purified on a Redi-Sep pre-packed silica gel column eluting with 30% EtOAc in hexanes to provide 7-bromo-4-(2-chlorophenyl)-2-hydroxyquinoline-3-carbonitrile (0.4 g, 86% yield) as an off-white solid. $^1H$ NMR (400 MHz, DMSO-$d_6$) δ ppm 12.79 (s, 1H), 7.76 (dd, J=7.8, 1.4

Hz, 1H), 7.53-7.71 (m, 4H), 7.41 (dd, J=8.8, 2.0 Hz, 1H), 6.91 (d, J=8.7 Hz, 1H). m/z (ESI): 360.6 $(M+H)^+$.

Step 3: 7-Bromo-2-chloro-4-(2-chlorophenyl)quinoline-3-carbonitrile

A solution of 7-bromo-4-(2-chlorophenyl)-2-hydroxyquinoline-3-carbonitrile (0.4 g, 1.112 mmol) in $POCl_3$ (4.037 mL, 43.3 mmol) was heated at 110° C. for 5 h. The reaction mixture was concentrated under reduced pressure and the residue was diluted with ice-cold water and extracted with DCM. The organic extracts were washed with 10% aqueous $NaHCO_3$ solution and brine, dried over $Na_2SO_4$, and concentrated under reduced pressure. The residue was purified on a Redi-Sep pre-packed silica gel column eluting with a gradient of 0-20% EtOAc in hexanes to provide 7-bromo-2-chloro-4-(2-chlorophenyl)quinoline-3-carbonitrile (0.3 g, 71.3% yield) as off-white solid. m/z (ESI): 379.0 $(M+H)^+$.

Step 4: tert-butyl 6-(7-bromo-4-(2-chlorophenyl)-3-cyanoquinolin-2-yl)-2,6-diazaspiro[3.4]octane-2-carboxylate A solution of 7-bromo-2-chloro-4-(2-chlorophenyl)quinoline-3-carbonitrile (0.4 g, 1.058 mmol), tert-butyl 2,6-diazaspiro[3.4]octane-2-carboxylate (0.225 g, 1.058 mmol, Combi-Blocks) and DIPEA (0.370 mL, 2.116 mmol) in DMA (4 mL) was stirred at 100° C. for 16 h. The reaction mixture was diluted with ice-cold water and extracted with EtOAc. The combined organic extracts were washed with brine, dried over $Na_2SO_4$, and concentrated under reduced pressure. The residue was purified on a Redi-Sep pre-packed silica gel column, eluting with 0-20% EtOAc in petroleum ether to provide tert-butyl 6-(7-bromo-4-(2-chlorophenyl)-3-cyanoquinolin-2-yl)-2,6-diazaspiro[3.4]octane-2-carboxylate (0.43 g, 73.4% yield) as an off-white solid. m/z (ESI): 554.1 $(M+H)^+$.

Step 5: tert-butyl 6-(4-(2-chlorophenyl)-3-cyano-7-(4,4,5,5-tetramethyl-1,3,2-dioxaborolan-2-yl)quinolin-2-yl)-2,6-diazaspiro[3.4]octane-2-carboxylate To a degassed mixture of tert-butyl 6-(7-bromo-4-(2-chlorophenyl)-3-cyanoquinolin-2-yl)-2,6-diazaspiro[3.4]octane-2-carboxylate (0.23 g, 0.415 mmol), KOAc (0.122 g, 1.246 mmol) and bis(pinacolato)diboron (0.127 g, 0.498 mmol, Chempure) in 1,4-dioxane (2.3 mL) was added $PdCl_2$(dppf)-DCM adduct (0.017 g, 0.021 mmol, Chempure). The reaction mixture was heated at 100° C. for 1 h before it was cooled to room temperature, filtered through celite pad and washed with EtOAc. The filtrated was concentrated under reduced pressure to afford tert-butyl 6-(4-(2-chlorophenyl)-3-cyano-7-(4,4,5,5-tetramethyl-1,3,2-dioxaborolan-2-yl)quinolin-2-yl)-2,6-diazaspiro[3.4]octane-2-carboxylate (0.5 g) which was directly taken to the next step without further purification. m/z (ESI): 601.8 $(M+H)^+$.

Step 6: tert-butyl 6-(4-(2-chlorophenyl)-3-cyano-7-(4-methylthiazol-5-yl)quinolin-2-yl)-2,6-diazaspiro[3.4]octane-2-carboxylate To a degassed mixture tert-butyl 6-(4-(2-chlorophenyl)-3-cyano-7-(4,4,5,5-tetramethyl-1,3,2-dioxaborolan-2-yl)quinolin-2-yl)-2,6-diazaspiro[3.4]octane-2-carboxylate (0.25 g, 0.416 mmol), 5-bromo-4-methylthiazole (0.089 g, 0.499 mmol, Combi-Blocks) and $K_2CO_3$ (0.172 g, 1.248 mmol) in 1,4-dioxane (2.5 mL) and water (0.25 mL) was added $PdCl_2$(dppf)-DCM adduct (0.034 g, 0.042 mmol, Chempure), and the reaction mixture was stirred at 90° C. for 16 h. The reaction mixture was cooled to room temperature, filtered through a celite pad, and washed with EtOAc. The filtrated was concentrated under reduced pressure. The residue was purified on a Redi-Sep pre-packed silica gel column (24 g) eluting with a gradient of 0-30% EtOAc in hexanes to provide tert-butyl 6-(4-(2-chlorophenyl)-3-cyano-7-(4-methylthiazol-5-yl)quinolin-2-yl)-2,6-diazaspiro[3.4]octane-2-carboxylate (0.2 g, 84% yield) as a yellow solid. m/z (ESI): 572.7 $(M+H)^+$.

Step 7: 4-(2-chlorophenyl)-7-(4-methylthiazol-5-yl)-2-(2,6-diazaspiro[3.4]octan-6-yl)quinoline-3-carbonitrile hydrochloride To a solution of tert-butyl 6-(4-(2-chlorophenyl)-3-cyano-7-(4-methylthiazol-5-yl)quinolin-2-yl)-2,6-diazaspiro[3.4]octane-2-carboxylate (0.2 g, 0.350 mmol) in DCM (2 mL) was added 4M HCl in dioxane (0.437 mL, 1.748 mmol) at 0° C., and the reaction mixture was stirred at room temperature for 1 h. The reaction mixture was concentrated under reduced pressure and triturated with diethyl ether to provide 4-(2-chlorophenyl)-7-(4-methylthiazol-5-yl)-2-(2,6-diazaspiro[3.4]octan-6-yl)quinoline-3-carbonitrile hydrochloride (0.25 g, 94% yield) as a yellow solid. m/z (ESI): 471.8 $(M+H)^+$.

Step 8: 4-(2-chlorophenyl)-7-(4-methyl-1,3-thiazol-5-yl)-2-(2-(2-propenoyl)-2,6-diazaspiro[3.4]octan-6-yl)-3-quinolinecarbonitrile To a solution of 4-(2-chlorophenyl)-7-(4-methylthiazol-5-yl)-2-(2,6-diazaspiro[3.4]octan-6-yl)quinoline-3-carbonitrile hydrochloride (0.18 g, 0.354 mmol) and TEA (0.247 mL, 1.770 mmol) in DCM (2.3 mL) was added acryloyl chloride (0.029 mL, 0.354, Symax Ltd.) dropwise at −78° C. dropwise and the reaction mixture stirred for 15 min. The reaction mixture was diluted with water and extracted with DCM. The combined organic extracts were dried over anhydrous $Na_2SO_4$, concentrated and purified by preparative HPLC to provide 4-(2-chlorophenyl)-7-(4-methyl-1,3-thiazol-5-yl)-2-(2-(2-propenoyl)-2,6-diazaspiro[3.4]octan-6-yl)-3-quinolinecarbonitrile (0.06 g, 32.2% yield) as a yellow solid. $^1$H NMR (400 MHz, DMSO-$d_6$) δ ppm 9.11 (s, 1H), 7.84-7.50 (m, 5H), 7.39 (dd, J=8.6, 1.9 Hz, 1H), 7.11 (d, J=8.6 Hz, 1H), 6.33 (m, 1H), 6.12 (dd, J=17.0, 2.3 Hz, 1H), 5.69 (dd, J=10.3, 2.3 Hz, 1H), 4.32 (dd, J=8.6, 5.5 Hz, 1H), 4.21 (dd, J=8.7, 4.9 Hz, 1H), 4.13-3.81 (m, 6H), 2.56 (s, 3H), 2.26 (m, 2H). m/z (ESI): 525.6 $(M+H)^+$.

TABLE 12

Examples 20-2 to 20-22 were prepared following the procedure described in Method 20, Steps 1-8, above as follows:

| Ex. # | Chemical Structure | Name | Method changes | Reagent |
|---|---|---|---|---|
| 20-2 | 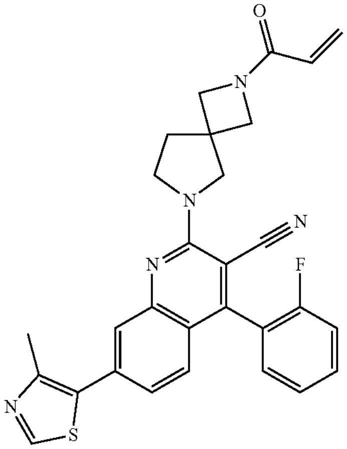 [SMILES: C=CC(=O)N1CC2(CCN(c3nc4cc(-c5scnc5C)ccc4c(-c4ccccc4F)c3C#N)C2)C1] | 4-(2-fluorophenyl)-7-(4-methyl-1,3-thiazol-5-yl)-2-(2-(2-propenoyl)-2,6-diazaspiro[3.4]octan-6-yl)-3-quinolinecarbonitrile | | Step 1: 2-fluorobenzonitrile (Spectrochem). |
| 20-3 | 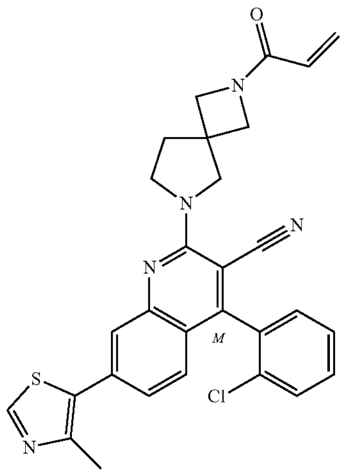 | (M)-4-(2-chlorophenyl)-7-(4-methyl-1,3-thiazol-5-yl)-2-(2-(2-propenoyl)-2,6-diazaspiro[3.4]octan-6-yl)-3-quinolinecarbonitrile (1$^{st}$ eluting isomer) | See atropisomer separation conditions below | |
| 20-4 | 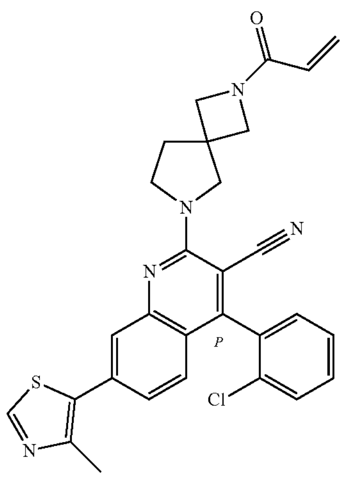 | (P)-4-(2-chlorophenyl)-7-(4-methyl-1,3-thiazol-5-yl)-2-(2-(2-propenoyl)-2,6-diazaspiro[3.4]octan-6-yl)-3-quinolinecarbonitrile (2$^{nd}$ eluting isomer) | See atropisomer separation conditions below | |

TABLE 12-continued

| Examples 20-2 to 20-22 were prepared following the procedure described in Method 20, Steps 1-8, above as follows: | | | | |
|---|---|---|---|---|
| Ex. # | Chemical Structure | Name | Method changes | Reagent |
| 20-5 | 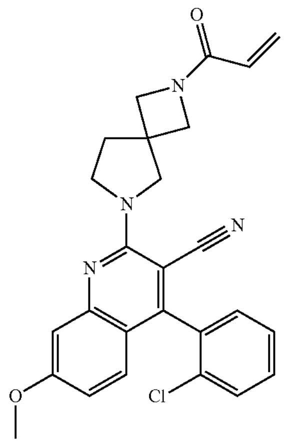 [SMILES: C=CC(=O)N1CC2(CCN(c3nc4cc(OC)ccc4c(-c4ccccc4Cl)c3C#N)C2)C1] | 4-(2-chlorophenyl)-7-methoxy-2-(2-(2-propenoyl)-2,6-diazaspiro[3.4]octan-6-yl)-3-quinolinecarbonitrile | See alternate step 6 below | |
| 20-6 | 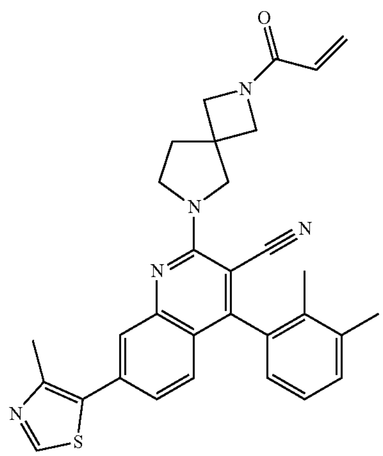 [SMILES: C=CC(=O)N1CC2(CCN(c3nc4cc(-c5scnc5C)ccc4c(-c4cccc(C)c4C)c3C#N)C2)C1] | 4-(2,3-dimethylphenyl)-7-(4-methyl-1,3-thiazol-5-yl)-2-(2-(2-propenoyl)-2,6-diazaspiro[3.4]octan-6-yl)-3-quinolinecarbonitrile | See alternate step 1 below | |
| 20-7 | 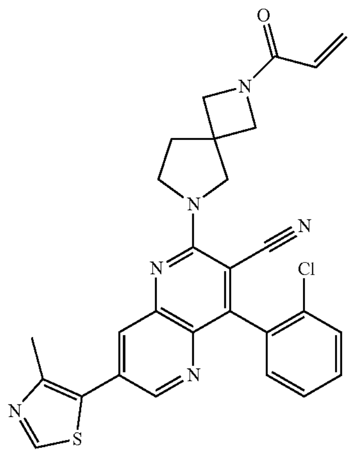 [SMILES: C=CC(=O)N1CC2(CCN(c3nc4cc(-c5scnc5C)cnc4c(-c4ccccc4Cl)c3C#N)C2)C1] | 4-(2-chlorophenyl)-7-(4-methyl-1,3-thiazol-5-yl)-2-(2-(2-propenoyl)-2,6-diazaspiro[3.4]octan-6-yl)-1,5-naphthyridine-3-carbonitrile | See alternate step 1 and step 3 below | |

TABLE 12-continued

| Ex. # | Chemical Structure | Name | Method changes | Reagent |
|---|---|---|---|---|
| Examples 20-2 to 20-22 were prepared following the procedure described in Method 20, Steps 1-8, above as follows: | | | | |
| 20-8 | 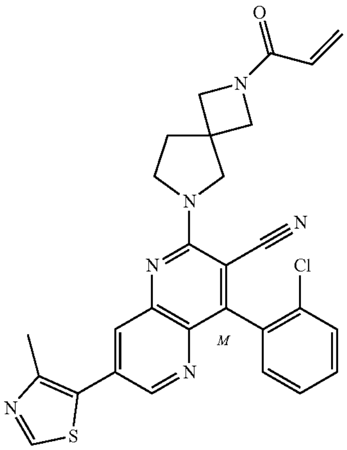 | (M)-4-(2-chlorophenyl)-7-(4-methyl-1,3-thiazol-5-yl)-2-(2-(2-propenoyl)-2,6-diazaspiro[3.4]octan-6-yl)-1,5-naphthyridine-3-carbonitrile (1st eluting isomer) | See alternate step 1 and step 3 below. See atropisomer separation conditions below. | |
| 20-9 | 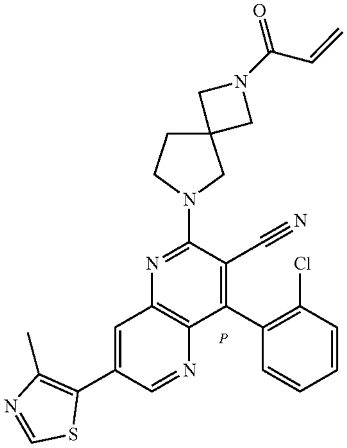 | (P)-4-(2-chlorophenyl)-7-(4-methyl-1,3-thiazol-5-yl)-2-(2-(2-propenoyl)-2,6-diazaspiro[3.4]octan-6-yl)-1,5-naphthyridine-3-carbonitrile (2nd eluting isomer) | See alternate step 1 and step 3 below. See atropisomer separation conditions below. | |
| 20-10 | 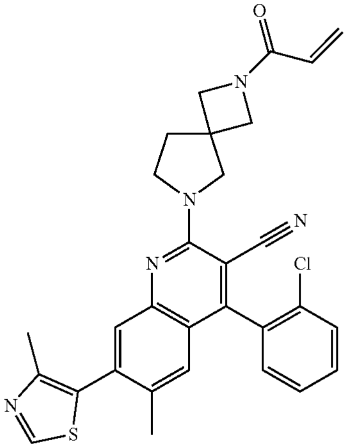 [SMILES: C=CC(=O)N1CC2(CCN(c3nc4cc(-c5scnc5C)c(C)cc4c(-c4ccccc4Cl)c3C#N)C2)C1] | 2-(2-acryloyl-2,6-diazaspiro[3.4]octan-6-yl)-4-(2-chlorophenyl)-6-methyl-7-(4-methylthiazol-5-yl)quinoline-3-carbonitrile | | Step 1: 3-bromo-4-methylaniline (Combi-Blocks). |

TABLE 12-continued

Examples 20-2 to 20-22 were prepared following the procedure described in Method 20, Steps 1-8, above as follows:

| Ex. # | Chemical Structure | Name | Method changes | Reagent |
|---|---|---|---|---|
| 20-11 | 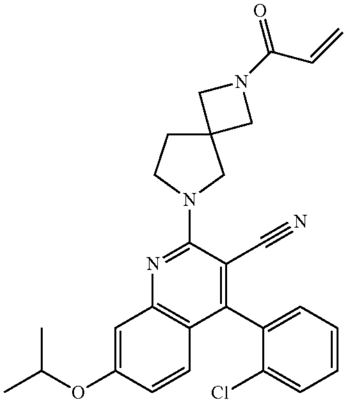 [SMILES: C=CC(=O)N1CC2(CCN(c3nc4cc(OC(C)C)ccc4c(-c4ccccc4Cl)c3C#N)C2)C1] | 4-(2-chlorophenyl)-7-(2-propanyloxy)-2-(2-(2-propenoyl)-2,6-diazaspiro[3.4]octan-6-yl)-3-quinolinecarbonitrile | Alternate Step 6 performed in an analogous manner to Example 20-5 | Step 6: 2-bromopropane (Avra) |
| 20-12 | 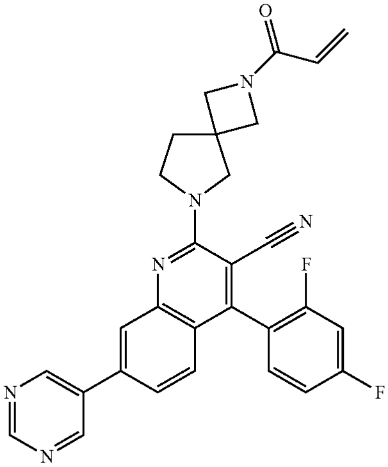 [SMILES: C=CC(=O)N1CC2(CCN(c3nc4cc(-c5cncnc5)ccc4c(-c4ccc(F)cc4F)c3C#N)C2)C1] | 4-(2,4-difluorophenyl)-2-(2-(2-propenoyl)-2,6-diazaspiro[3.4]octan-6-yl)-7-(5-pyrimidinyl)-3-quinolinecarbonitrile | See alternate Step 1 below for Example 20-6 and Step 3 was replaced with the alternate Step 5 for Example 19-5 | Step 1: (2,4-difluorophenyl) boronic acid (Combi-Blocks). Step 6: 5-bromopyrimidine (Combi-Blocks). |
| 20-13 | 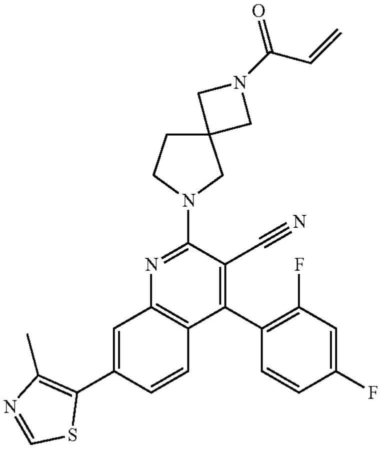 [SMILES: C=CC(=O)N1CC2(CCN(c3nc4cc(-c5scnc5C)ccc4c(-c4ccc(F)cc4F)c3C#N)C2)C1] | 4-(2,4-difluorophenyl)-7-(4-methyl-1,3-thiazol-5-yl)-2-(2-(2-propenoyl)-2,6-diazaspiro[3.4]octan-6-yl)-3-quinolinecarbonitrile | See alternate Step 1 below for Example 20-6 and Step 3 was replaced with the alternate Step 5 for Example 19-5 | Step 1: (2,4-difluorophenyl) boronic acid (Combi-Blocks), |

TABLE 12-continued

| Examples 20-2 to 20-22 were prepared following the procedure described in Method 20, Steps 1-8, above as follows: | | | | |
|---|---|---|---|---|
| Ex. # | Chemical Structure | Name | Method changes | Reagent |
| 20-14 | 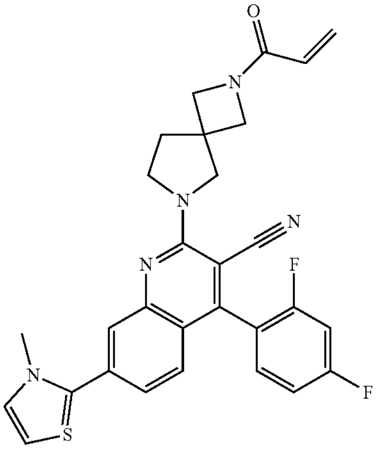 | 4-(2,4-difluorophenyl)-7-(1-methyl-1H-imidazol-2-yl)-2-(2-(2-propenoyl)-2,6-diazaspiro[3.4]octan-6-yl)-3-quinolinecarbonitrile | See alternate step 1 below for Example 20-6 and Step 3 was replaced with the alternate Step 5 for Example 19-5 | Step 1: (2,4-difluorophenyl) boronic acid (Combi-Blocks). Step 6: 2-bromo-1-methyl-1H-imidazole (Combi-Blocks). |
| 20-15 | 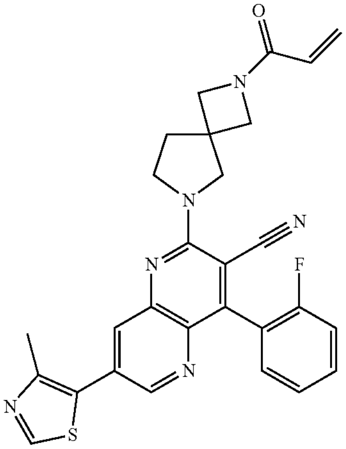 [SMILES: C=CC(=O)N1CC2(CCN(c3nc4cc(-c5scnc5C)cnc4c(-c4ccccc4F)c3C#N)C2)C1] | 4-(2-fluorophenyl)-7-(4-methyl-1,3-thiazol-5-yl)-2-(2-(2-propenoyl)-2,6-diazaspiro[3.4]octan-6-yl)-1,5-naphthyridine-3-carbonitrile | See alternate step 1 below for Example 20-7 and Atep 3 was replaced with the Iternate Step 5 for Example 19-5 | Step 1: 1-bromo-2-fluorobenzene (Combi-Blocks). |
| 20-16 | 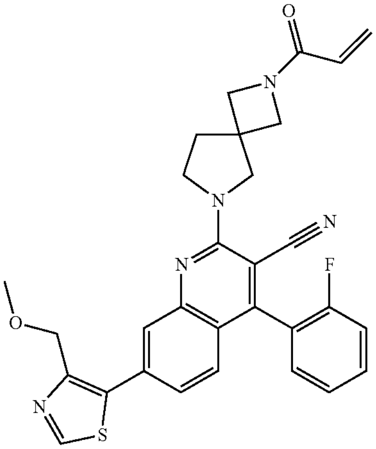 [SMILES: C=CC(=O)N1CC2(CCN(c3nc4cc(-c5scnc5COC)ccc4c(-c4ccccc4F)c3C#N)C2)C1] | 4-(2-fluorophenyl)-7-(4-(methoxymethyl)-1,3-thiazol-5-yl)-2-(2-(2-propenoyl)-2,6-diazaspiro[3.4]octan-6-yl)-3-quinolinecarbonitrile | Step 3 was replaced with the alternate Step 5 for Example 19-5 | Step 1:2-fluorobenzontrile (Combi-Blocks). Step 6: Intermediate 89 |

TABLE 12-continued

| Ex. # | Chemical Structure | Name | Method changes | Reagent |
|---|---|---|---|---|
| | Examples 20-2 to 20-22 were prepared following the procedure described in Method 20, Steps 1-8, above as follows: | | | |
| 20-17 | 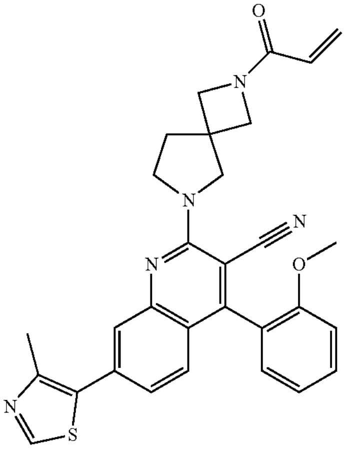 [SMILES: C=CC(=O)N1CC2(CCN(c3nc4cc(-c5scnc5C)ccc4c(-c4ccccc4OC)c3C#N)C2)C1] | 4-(2-methoxyphenyl)-7-(4-methyl-1,3-thiazol-5-yl)-2-(2-(2-propenoyl)-2,6-diazaspiro[3.4]octan-6-yl)-3-quinolinecarbonitrile | Step 3 was replaced with the alternate Step 5 for Example 19-5 | Step 1: 2-methoxybenzonitrile (Combi-Blocks). |
| 20-18 | 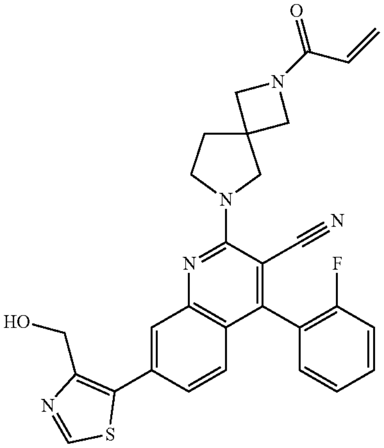 [SMILES: C=CC(=O)N1CC2(CCN(c3nc4cc(-c5scnc5CO)ccc4c(-c4ccccc4F)c3C#N)C2)C1] | 4-(2-fluorophenyl)-7-(4-(hydroxymethyl)-1,3-thiazol-5-yl)-2-(2-(2-propenoyl)-2,6-diazaspiro[3.4]octan-6-yl)-3-quinolinecarbonitrile | Step 3 was replaced with the Alternate Step 5 for Example 19-5. See alternate Step 7 and 8 below. | Step 1: 2-fluorobenzontrile (Combi-Blocks). Step 6: Intermediate 89 |
| 20-19 | 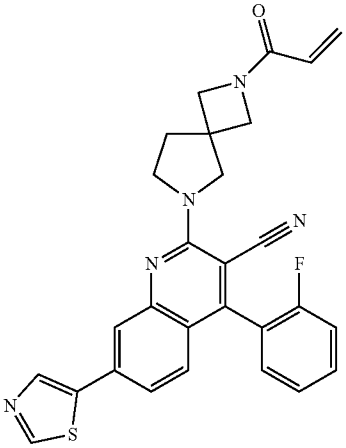 [SMILES: C=CC(=O)N1CC2(CCN(c3nc4cc(-c5cncs5)ccc4c(-c4ccccc4F)c3C#N)C2)C1] | 4-(2-fluorophenyl)-2-(2-(2-propenoyl)-2,6-diazaspiro[3.4]octan-6-yl)-7-(1,3-thiazol-5-yl)-3-quinolinecarbonitrile | Step 3 was replaced with the Alternate Step 5 for Example 19-5 | Step 1: 2-fluorobenzontrile (Combi-Blocks). Step 6: 5-bromothiazole (Enamine). |

TABLE 12-continued

Examples 20-2 to 20-22 were prepared following the procedure described in Method 20, Steps 1-8, above as follows:

| Ex. # | Chemical Structure | Name | Method changes | Reagent |
|---|---|---|---|---|
| 20-20 | 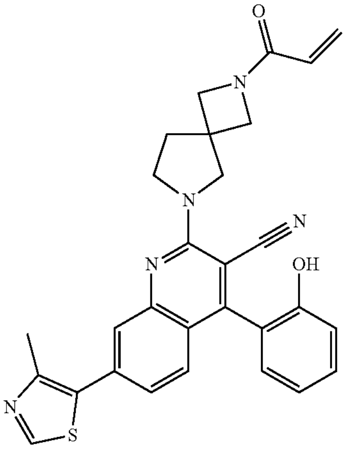 [SMILES: C=CC(=O)N1CC2(CCN(c3nc4cc(-c5scnc5C)ccc4c(-c4ccccc4O)c3C#N)C2)C1] | 4-(2-hydroxyphenyl)-7-(4-methyl-1,3-thiazol-5-yl)-2-(2-(2-propenoyl)-2,6-diazaspiro[3.4]octan-6-yl)-3-quinolinecarbonitrile | Step 3 was replaced with the Alternate Step 5 for Example 19-5. Step 7 and 8 replaced with alternate steps 7 and 8 in Example 20-18 | Step 1: 2-methoxybenzonitrile (Combi-Blocks). |
| 20-21 | 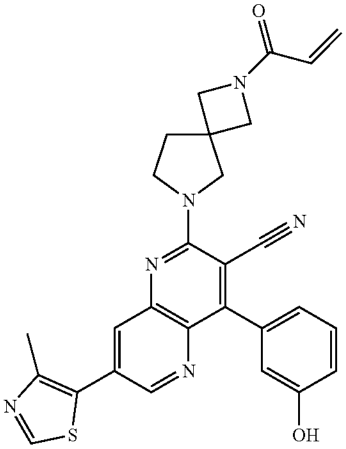 [SMILES: C=CC(=O)N1CC2(CCN(c3nc4cc(-c5scnc5C)cnc4c(-c4cccc(O)c4)c3C#N)C2)C1] | 4-(3-hydroxyphenyl)-7-(4-methyl-1,3-thiazol-5-yl)-2-(2-(2-propenoyl)-2,6-diazaspiro[3.4]octan-6-yl)-1,5-naphthyridine-3-carbonitrile | See alternate step 1 below for Example 20-7 and step 3 was replaced with the Alternate Step 5 for Example 19-5. Step 7 and 8 replaced with alternate steps 7 and 8 in Example 20-18 | Step 1: 1-bromo-3-methoxybenzene (Avra) |
| 20-22 | 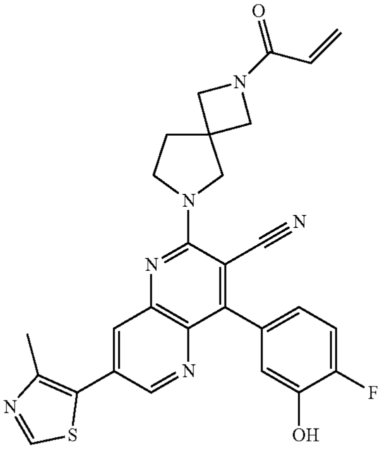 [SMILES: C=CC(=O)N1CC2(CCN(c3nc4cc(-c5scnc5C)cnc4c(-c4ccc(F)c(O)c4)c3C#N)C2)C1] | 4-(4-fluoro-3-hydroxyphenyl)-7-(4-methyl-1,3-thiazol-5-yl)-2-(2-(2-propenoyl)-2,6-diazaspiro[3.4]octan-6-yl)-1,5-naphthyridine-3-carbonitrile | See alternate step 1 below for Example 20-7 and step 3 was replaced with the Alternate Step 5 for Example 19-5. Step 7 and 8 replaced with alternate steps 7 and 8 in Example 20-18 | Step 1: 4-bromo-1-fluoro-2-methoxybenzene (BLD Pharmatech) |

Atropisomer Separation for Examples 20-3 and 20-4.

The racemic mixture was separated by SFC using a Chiralcel OJ-H column with a mobile phase of 60% liquid $CO_2$ and 40% MeOH to provide the respective P and M isomers of 4-(2-chlorophenyl)-7-(4-methyl-1,3-thiazol-5-yl)-2-(2-(2-propenoyl)-2,6-diazaspiro[3.4]octan-6-yl)-3-quinolinecarbonitrile. The stereochemistry of structures was arbitrarily assigned and is not established. $1^{st}$ eluting atropisomer assigned as the M isomer and $2^{nd}$ eluting atropisomer assigned as the P isomer.

Alternate Step 6 for Example 20-5

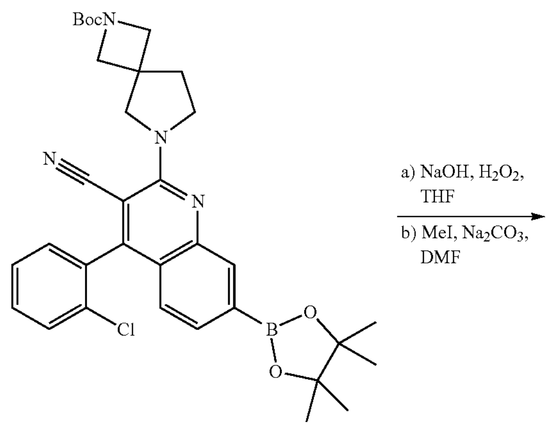

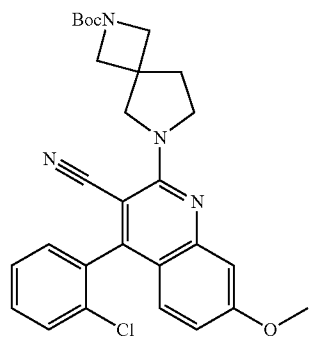

To a suspension of tert-butyl 6-(4-(2-chlorophenyl)-3-cyano-7-(4,4,5,5-tetramethyl-1,3,2-dioxaborolan-2-yl)quinolin-2-yl)-2,6-diazaspiro[3.4]octane-2-carboxylate (0.22 g, 0.366 mmol, Example 20-1, step 5) and NaOH (0.015 g, 0.366 mmol) in THF (4 mL) was added $H_2O_2$ (0.034 mL, 0.366 mmol) at 0° C. The reaction mixture was stirred at room temperature for 2 h before it was diluted with ice-cold water and extracted with EtOAc. The organic extracts were washed with brine, dried over $Na_2SO_4$, and concentrated under reduced pressure. The residue was purified on a Redi-Sep pre-packed silica gel column eluting with a gradient of 0-30% EtOAc in hexanes to provide tert-butyl 6-(4-(2-chlorophenyl)-3-cyano-7-hydroxyquinolin-2-yl)-2,6-diazaspiro[3.4]octane-2-carboxylate (0.18 g, 100% yield) as a yellow liquid. m/z (ESI): 490.8 $(M+H)^+$.

To a mixture of tert-butyl 6-(4-(2-chlorophenyl)-3-cyano-7-hydroxyquinolin-2-yl)-2,6-diazaspiro[3.4]octane-2-carboxylate (0.18 g, 0.367 mmol) and $Na_2CO_3$ (0.078 g, 0.733 mmol) in DMF (1.8 mL) was added iodomethane (0.027 mL, 0.440 mmol, Symax) dropwise at 0° C. and stirred at room temperature for 16 h in a sealed tube. The reaction mixture was diluted with water and extracted with EtOAc. The organic extracts were washed with brine, dried over $Na_2SO_4$, filtered and concentrated under reduced pressure to provide tert-butyl 6-(4-(2-chlorophenyl)-3-cyano-7-methoxyquinolin-2-yl)-2,6-diazaspiro[3.4]octane-2-carboxylate (0.18 g 97% yield). m/z (ESI): 505.2 $(M+H)^+$.

Alternate Step 1 for Example 20-6

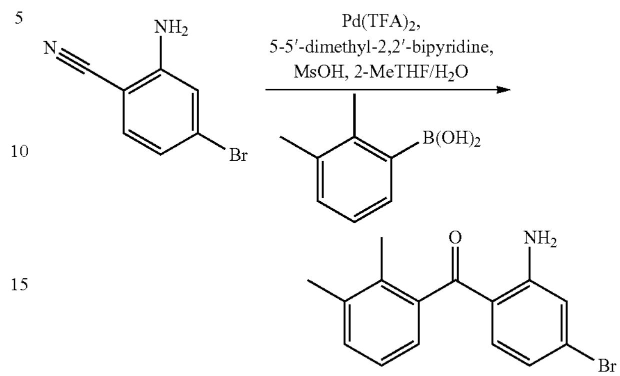

To a degassed solution of 2-amino-4-bromobenzonitrile (1 g, 5.08 mmol, Combi-Blocks), (2,3-dimethylphenyl)boronic acid (1.522 g, 10.15 mmol, Combi-Blocks), methanesulfonic acid (3.30 mL, 50.8 mmol, Spectrochem), 5,5'-dimethyl-2,2'-bipyridine (0.070 g, 0.381 mmol, Combi Blocks) in 2-MeTHF (10 mL) and water (2.5 mL) was added palladium (II) trifluoroacetate (0.084 g, 0.254 mmol, Combi-Blocks) and the reaction mixture heated at 80° C. for 40 h. The reaction mixture was cooled to room temperature, filtered through a celite pad and washed with EtOAc (50 mL). The filtrate was concentrated under reduced pressure. The residue was purified on a Redi-Sep pre-packed silica gel column eluting with a gradient of 0-10% EtOAc in hexanes to provide (2-amino-4-bromophenyl)(2,3-dimethylphenyl) methanone (0.520 g, 33.7% yield) as an off-white solid. m/z (ESI): 303.8 $(M+H)^+$.

Alternate Step 1 for Example 20-7

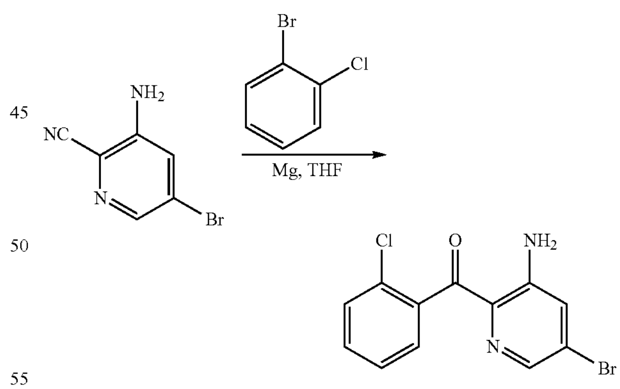

To a suspension of magnesium (1.841 g, 76 mmol) and iodine (one crystal) in dry THF (18 mL) was added dropwise a solution of 1-bromo-2-chlorobenzene (14.5 g, 76 mmol, Avra Chemicals) in THE (29 mL). The reaction mixture was stirred at 25° C. for 20 min. To this reaction mixture was added dropwise a solution of 3-amino-5-bromopicolinonitrile (3.0 g, 15.15 mmol, Combi-Blocks) in THE (13 mL) at 0° C. The resulting mixture was stirred at room temperature for 16 h before it was diluted with ice-cold water and extracted with EtOAc (2×50 mL). The organic extracts were washed with brine, dried over $Na_2SO_4$, and concentrated under reduced pressure. The residue was purified on a Redi-Sep pre-packed silica gel column eluting with a gradient of 0-30% EtOAc in hexanes to provide (3-amino-5-bromopyridin-2-yl)(2-chlorophenyl)methanone (4 g, 46.6% yield) as a yellow solid. m/z (ESI): 310.9 $(M+H)^+$.

Alternate Step 3 for Example 20-7

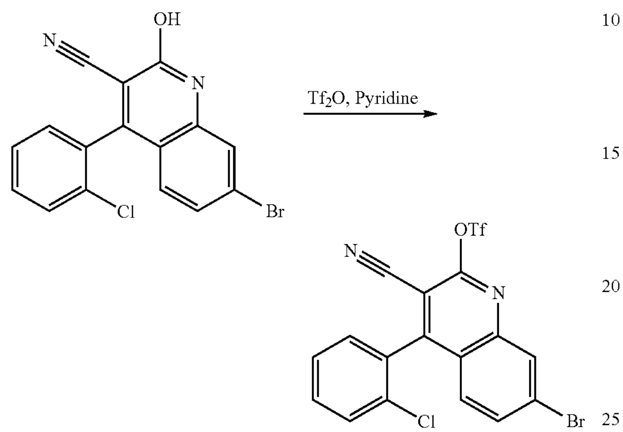

To a solution of 7-bromo-4-(2-chlorophenyl)-2-hydroxyquinoline-3-carbonitrile (0.65 g, 1.803 mmol), pyridine (0.428 g, 5.41 mmol) and DCM (6.5 mL) was added $Tf_2O$ (0.61 mL, 3.61 mmol) at 0° C. and the reaction stirred for 1 h. The reaction mixture was concentrated under reduced pressure and co-evaporated with toluene to provide 7-bromo-4-(2-chlorophenyl)-3-cyanoquinolin-2-yl trifluoromethanesulfonate which was taken to the next step without further purification. m/z (ESI): 493.3 $(M+H)^+$.

Atropisomer Separation for Examples 20-8 and 20-9.

The racemic mixture was separated by SFC using a Chiralcel OJ-H column with a mobile phase of 60% liquid $CO_2$ and 40% MeOH to provide the respective P and M isomers of 4-(2-chlorophenyl)-7-(4-methyl-1,3-thiazol-5-yl)-2-(2-(2-propenoyl)-2,6-diazaspiro[3.4]octan-6-yl)-1,5-naphthyridine-3-carbonitrile. The stereochemistry of structures was arbitrarily assigned and is not established. 1st eluting atropisomer assigned as the M isomer and 2nd eluting atropisomer assigned as the P isomer.

Alternate Step 7 and Step 8 for Example 20-18

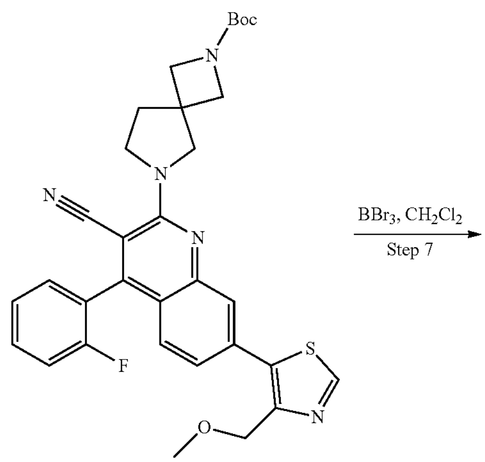

-continued

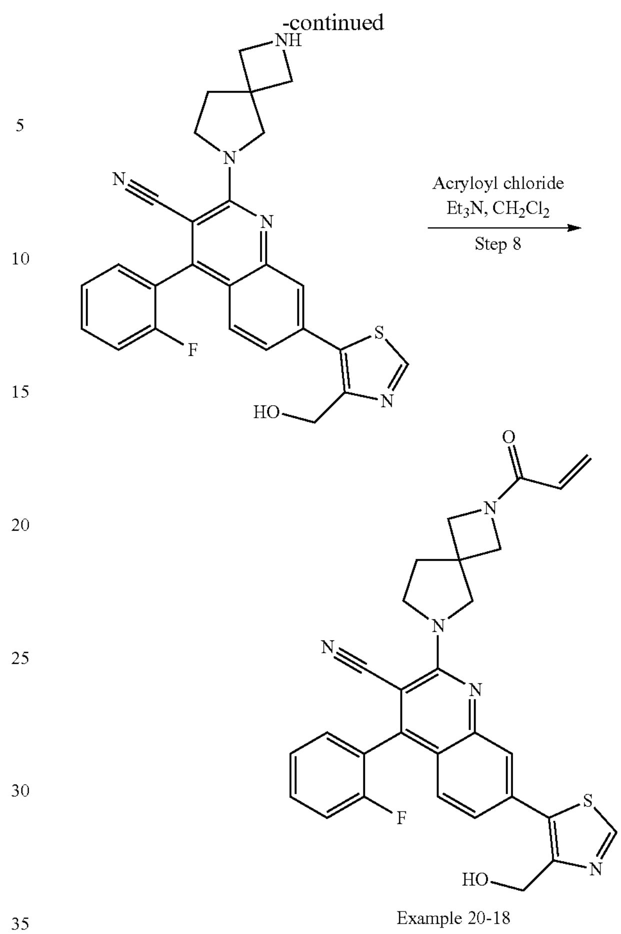

Example 20-18

Step 7: 4-(2-fluorophenyl)-7-(4-(hydroxymethyl)thiazol-5-yl)-2-(2,6-diazaspiro[3.4]octan-6-yl)quinoline-3-carbonitrile To a solution of tert-butyl 6-(3-cyano-4-(2-fluorophenyl)-7-(4-(methoxymethyl)thiazol-5-yl)quinolin-2-yl)-2,6-diazaspiro[3.4]octane-2-carboxylate (0.150 g, 0.256 mmol, Example 20-16, Step 6) in DCM (5 mL) was added $BBr_3$ (2.56 mL, 2.56 mmol, 1M in DCM, Chempure) at −78° C. The reaction mixture was warmed up to room temperature and stirred for 16 h before it was quenched with an aqueous solution of $NaHCO_3$ and extracted with 10% MeOH in DCM. The organic extracts were washed with brine, dried over $Na_2SO_4$, filtered and concentrated under reduced pressure to provide 4-(2-fluorophenyl)-7-(4-(hydroxymethyl)thiazol-5-yl)-2-(2,6-diazaspiro[3.4]octan-6-yl)quinoline-3-carbonitrile (0.1 g) which was taken to next step without purification. m/z (ESI): 471.9 $(M+H)^+$.

Step 8: 4-(2-fluorophenyl)-7-(4-(hydroxymethyl)-1,3-thiazol-5-yl)-2-(2-(2-propenoyl)-2,6-diazaspiro[3.4]octan-6-yl)-3-quinolinecarbonitrile To a solution of 4-(2-fluorophenyl)-7-(4-(hydroxymethyl)thiazol-5-yl)-2-(2,6-diazaspiro[3.4]octan-6-yl)quinoline-3-carbonitrile (0.100 g, 0.212 mmol) in DCM (5 mL) were added TEA (0.148 mL, 1.060 mmol) and acryloyl chloride (0.014 mL, 0.170 mmol) at −78° C. The reaction mixture was stirred for 10 min at the same temperature before it was diluted with water and extracted with DCM. The organic extracts were washed with brine, dried over $Na_2SO_4$, and concentrated under reduced pressure. The residue was purified by reverse phase HPLC to provide 4-(2-fluorophenyl)-7-(4-(hydroxymethyl)-1,3-thiazol-5-yl)-2-(2-(2-propenoyl)-2,6-diazaspiro[3.4]octan-6-yl)-3-quinolinecarbonitrile (0.02 g, 18% yield) as an off-white solid. m/z (ESI): 525.9 $(M+H)^+$. $^1H$ NMR (400 MHz, DMSO-d6) δ ppm 9.15 (s, 1H), 7.92 (d, J=1.8 Hz, 1H), 7.71 (m, 1H), 7.63-7.42 (m, 4H), 7.25 (dd, J=8.6, 1.3 Hz, 1H), 6.32 (m, 1H), 6.12 (dd, J=17.0, 2.3 Hz, 1H), 5.68 (dd, J=10.3, 2.3 Hz, 1H), 5.49 (t, J=5.4 Hz, 1H), 4.61 (d, J=5.4 Hz, 2H), 4.32 (m, 1H), 4.21 (dd, J=8.7, 3.0 Hz, 1H), 4.13-3.98 (m, 3H), 3.92 (m, 3H), 2.26 (m, 2H).

Method 21

Example 21-1: 4-(2-fluorophenyl)-7-(4-methyl-1,3-thiazol-5-yl)-2-(2-(2-propenoyl)-2,6-diazaspiro[3.4]octan-6-yl)-5,6,7,8-tetrahydro-1,7-naphthyridine-3-carbonitrile

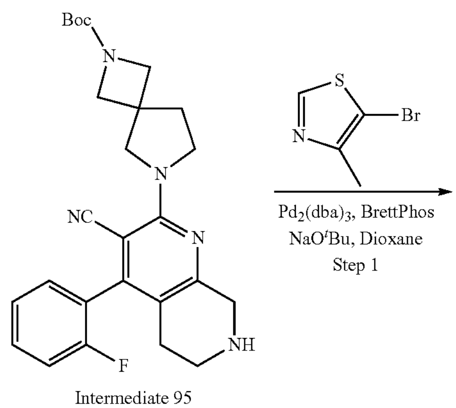

Intermediate 95

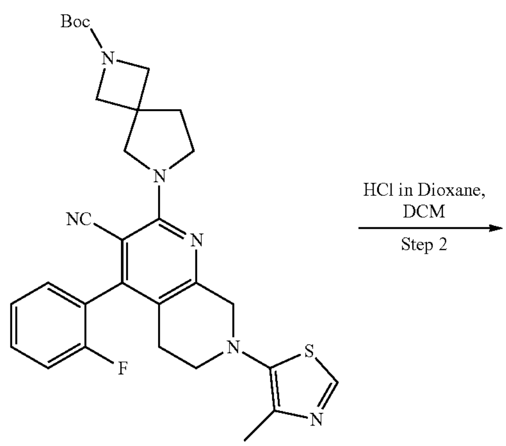

-continued

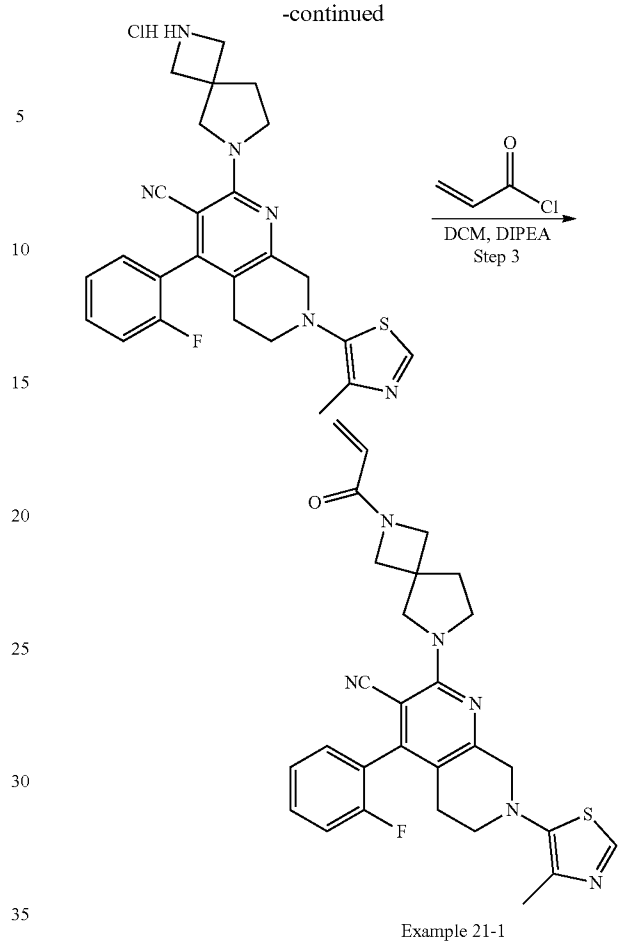

Example 21-1

Step 1: tert-Butyl 6-(3-cyano-4-(2-fluorophenyl)-7-(4-methylthiazol-5-yl)-5,6,7,8-tetrahydro-1,7-naphthyridin-2-yl)-2,6-diazaspiro[3.4]octane-2-carboxylate To a degassed solution of tert-butyl 6-(3-cyano-4-(2-fluorophenyl)-5,6,7,8-tetrahydro-1,7-naphthyridin-2-yl)-2,6-diazaspiro[3.4]octane-2-carboxylate (0.15 g, 0.324 mmol, Intermediate 95). 5-bromo-4-methylthiazole (0.069 g, 0.388 mmol, Avra), NaO$^t$Bu (0.093 g, 0.971 mmol, Chempure) and 1,4-dioxane (3 mL) was added $Pd_2(dba)_3$ (0.015 g, 0.016 mmol, Hindustan Platinum) and BrettPhos (8.68 mg, 0.016 mmol, Combi-Blocks) and the reaction mixture was heated at 80° C. for 16 h. The reaction mixture was diluted with water and extracted with EtOAc. The organic extracts were washed with brine, dried over $Na_2SO_4$, and concentrated under reduced pressure. The residue was purified on a Redi-Sep pre-packed silica gel column eluting with 35% EtOAc in hexanes to provide tert-butyl 6-(3-cyano-4-(2-fluorophenyl)-7-(4-methylthiazol-5-yl)-5,6,7,8-tetrahydro-1,7-naphthyridin-2-yl)-2,6-diazaspiro[3.4]octane-2-carboxylate (0.13 g, 71.7% yield) as yellow solid. m/z (ESI): 561.8 $(M+H)^+$.

Step 2: 4-(2-fluorophenyl)-7-(4-methylthiazol-5-yl)-2-(2,6-diazaspiro[3.4]octan-6-yl)-5,6,7,8-tetrahydro-1,7-naphthyridine-3-carbonitrile hydrochloride To a solution of tert-butyl 6-(3-cyano-4-(2-fluorophenyl)-7-(4-methylthiazol-5-yl)-5,6,7,8-tetrahydro-1,7-naphthyridin-2-yl)-2,6-diazaspiro[3.4]octane-2-carboxylate (0.13 g, 0.232 mmol) in DCM (2 mL) was added 4M HCl in dioxane (0.580 mL, 2.319 mmol) at 0° C. and the reaction mixture was stirred at room temperature for 1 h. The reaction mixture was concentrated under reduced pressure and triturated with diethyl ether to provide 4-(2-fluorophenyl)-7-(4-methylthiazol-5-yl)-2-(2,6-diazaspiro[3.4]octan-6-yl)-5,6,7,8-tetrahydro-1,7-naphthyridine-3-carbonitrile hydrochloride (0.115 g) as brown solid which was taken on without further purification. m/z (ESI): 461.8 $(M+H)^+$.

Step 3: 4-(2-fluorophenyl)-7-(4-methyl-1,3-thiazol-5-yl)-2-(2-(2-propenoyl)-2,6-diazaspiro[3.4]octan-6-yl)-5,6,7,8-tetrahydro-1,7-naphthyridine-3-carbonitrile To a solution of 4-(2-fluorophenyl)-7-(4-methylthiazol-5-yl)-2-(2,6-diazaspiro[3.4]octan-6-yl)-5,6,7,8-tetrahydro-1,7-naphthyridine-3-carbonitrile hydrochloride (0.115 g, 0.231 mmol) and DIPEA (0.427 mL, 2.314 mmol) in DCM (5 mL) was added acryloyl chloride (0.021 g, 0.231 mmol, Symax Ltd.) dropwise at −78° and the reaction stirred for 15 min. The reaction mixture was diluted with water and extracted with DCM. The combined organic extracts were dried over anhydrous $Na_2SO_4$, concentrated and purified by preparative HPLC to provide 4-(2-fluorophenyl)-7-(4-methyl-1,3-thiazol-5-yl)-2-(2-(2-propenoyl)-2,6-diazaspiro[3.4]octan-6-yl)-5,6,7,8-tetrahydro-1,7-naphthyridine-3-carbonitrile (0.05 g, 42.0% yield) as a light yellow solid. $^1H$ NMR (400 MHz. DMSO-$d_6$) δ ppm 8.71 (s, 1H), 7.66-7.52 (m, 1H), 7.50-7.33 (m, 3H), 6.31 (m, 1H), 6.11 (dd, J=17.0, 2.3 Hz, 1H), 5.67 (dd, J=10.3, 2.3 Hz, 1H), 4.26 (dd, J=8.7, 5.3 Hz, 1H), 4.17 (dd, J=8.6, 2.8 Hz, 1H), 4.01 (s, 2H), 3.99-3.79 (m, 4H), 3.75 (t, J=6.8 Hz, 2H), 3.07 (t, J=5.8 Hz, 2H), 2.46-2.31 (m, 2H), 2.27 (s, 3H), 2.19 (dd, J=7.4, 4.6 Hz, 2H). m/z (ESI): 515.2 $(M+H)^+$.

TABLE 13

Examples 21-2 to 21-39 were prepared following the procedure described in Method 21, Steps 1-3, above as follows:

| Ex. # | Chemical Structure | Name | Method changes | Reagent |
|---|---|---|---|---|
| 21-2 | 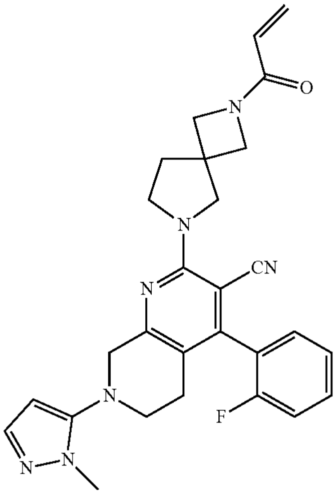 [SMILES: C=CC(=O)N1CC2(CCN(c3nc4c(c(-c5ccccc5F)c3C#N)CCN(c3ccnn3C)C4)C2)C1] | 4-(2-fluorophenyl)-7-(1-methyl-1H-pyrazol-5-yl)-2-(2-(2-propenoyl)-2,6-diazaspiro[3.4]octan-6-yl)-5,6,7,8-tetrahydro-1,7-naphthyridine-3-carbonitrile | | Step 1: 5-bromo-1-methyl-1H-pyrazole (Combi-Blocks) |
| 21-3 | 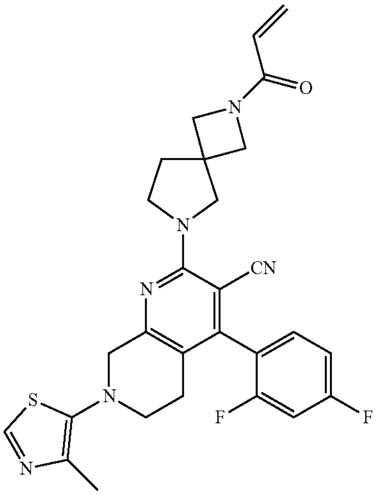 [SMILES: C=CC(=O)N1CC2(CCN(c3nc4c(c(-c5ccc(F)cc5F)c3C#N)CCN(c3scnc3C)C4)C2)C1] | 4-(2,4-difluorophenyl)-7-(4-methyl-1,3-thiazol-5-yl)~2-(2-(2-propenoyl)-2,6-diazaspiro[3.4]octan-6-yl)-5,6,7,8-tetrahydro-1,7-naphthyridine-3~carbonitrile | | Step 1: Intermediate 97 |

TABLE 13-continued

| Ex. # | Chemical Structure | Name | Method changes | Reagent |
|---|---|---|---|---|
| | Examples 21-2 to 21-39 were prepared following the procedure described in Method 21, Steps 1-3, above as follows: | | | |
| 21-4 | 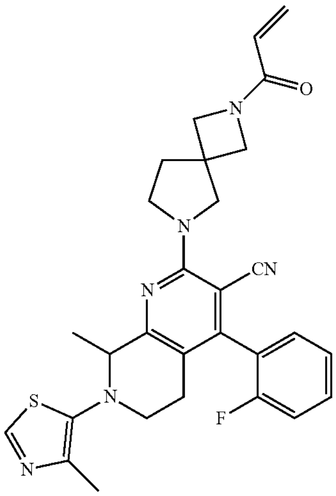 [SMILES: C=CC(=O)N1CC2(CCN(c3nc4c(c(-c5ccccc5F)c3C#N)CCN(c3scnc3C)C4C)C2)C1] | (8R)-4-(2-fluorophenyl)-8-methyl-7-(4-methyl-1,3-thiazol-5-yl)-2-(2-(2-propenoyl)-2,6-diazaspiro[3.4]octan-6-yl)-5,6,7,8-tetrahydro-1,7-naphthyridine-3-carbonitrile (8S)-4-(2-fluorophenyl)-8-methyl-7-(4-methyl-1,3-thiazol-5-yl)-2-(2-(2-propenoyl)-2,6-diazaspiro[3.4]octan-6-yl)-5,6,7,8-tetrahydro-1,7-naphthyridine-3-carbonitrile | | Step 1: Intermediate 96 |
| 21-5 | 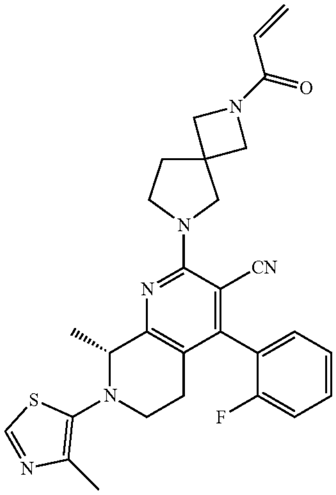 [SMILES: C=CC(=O)N1CC2(CCN(c3nc4c(c(-c5ccccc5F)c3C#N)CCN(c3scnc3C)[C@@H]4C)C2)C1] | (8R)-4-(2-fluorophenyl)-8-methyl-7-(4-methyl-1,3-thiazol-5-yl)-2-(2-(2-propenoyl)-2,6-diazaspiro[3.4]octan-6-yl)-5,6,7,8-tetrahydro-1,7-naphthyridine-3-carbonitrile | Stereoisomer separation after Step 1, see conditions below | Step 1: Intermediate 96 |
| 21-6 | 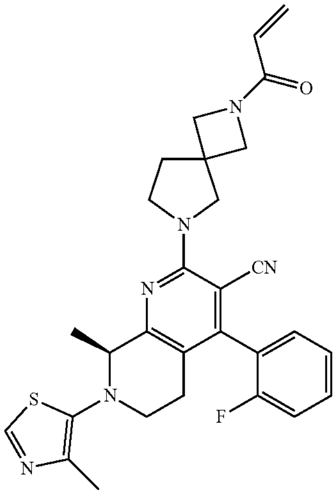 [SMILES: C=CC(=O)N1CC2(CCN(c3nc4c(c(-c5ccccc5F)c3C#N)CCN(c3scnc3C)[C@H]4C)C2)C1] | (8S)-4-(2-fluorophenyl)-8-methyl-7-(4-methyl-1,3-thiazol-5-yl)-2-(2-(2-propenoyl)-2,6-diazaspiro[3.4]octan-6-yl)-5,6,7,8-tetrahydro-1,7-naphthyridine-3-carbonitrile | Stereoisomer separation after Step 1, see conditions below | Step 1: Intermediate 96 |

TABLE 13-continued

Examples 21-2 to 21-39 were prepared following the procedure described in Method 21, Steps 1-3, above as follows:

| Ex. # | Chemical Structure | Name | Method changes | Reagent |
|---|---|---|---|---|
| 21-7 | 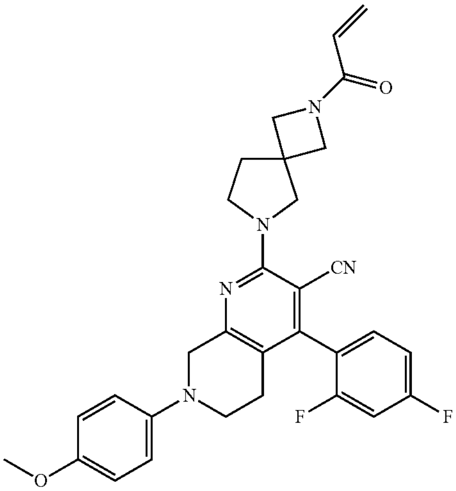 [SMILES: C=CC(=O)N1CC2(CCN(c3nc4c(c(-c5ccc(F)cc5F)c3C#N)CCN(c3ccc(OC)cc3)C4)C2)C1] | 4-(2,4-difluorophenyl)-7-(4-methoxyphenyl)-2-(2-(2-propenoyl)-2,6-diazaspiro[3.4]octan-6-yl)-5,6,7,8-tetrahydro-1,7-naphthyridine-3-carbonitrile | | Step 1: Intermediate 97 and 4-bromoanisole (Combi-Blocks) |
| 21-8 | 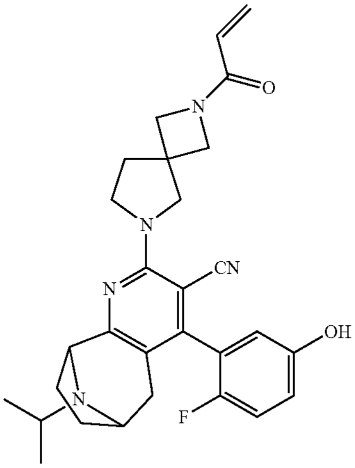 [SMILES: C=CC(=O)N1CC2(CCN(c3nc4c(c(-c5cc(O)ccc5F)c3C#N)CC3CCC4N3C(C)C)C2)C1] | (1R,9R)-6-(2-fluoro-5-hydroxyphenyl)-12-(2-propanyl)-4-(2-(2-propenoyl)-2,6-diazaspiro[3.4]octan-6-yl)-3,12-diazatricyclo[7.2.1.0$^{2,7}$]dodeca-2,4,6-triene-5-carbonitrile (1R,9S)-6-(2-fluoro-5-hydroxyphenyl)-12-(2-propanyl)-4-(2-(2-propenoyl)-2,6-diazaspiro[3.4]octan-6-yl)-3,12-diazatricyclo[7.2.1.0$^{2,7}$]dodeca-2,4,6-triene-5-carbonitrile (1S,9R)-6-(2-fluoro-5-hydroxyphenyl)-12-(2-propanyl)-4-(2-(2-propenoyl)-2,6-diazaspiro[3.4]octan-6-yl)-3,12-diazatricyclo[7.2.1.0$^{2,7}$]dodeca-2,4,6-triene-5-carbonitrile (1S,9S)-6-(2-fluoro-5-hydroxyphenyl)-12-(2-propanyl)-4-(2-(2-propenoyl)-2,6-diazaspiro[3.4]octan-6-yl)-3,12-diazatricyclo[7.2.1.0$^{2,7}$]dodeca-2,4,6-triene-5-carbonitrile | See Alternate Step 1 below. Step 2: $BBr_3$ was used for deprotection of Boc and methoxy in place of TFA. | |

TABLE 13-continued

Examples 21-2 to 21-39 were prepared following the procedure described in Method 21, Steps 1-3, above as follows:

| Ex. # | Chemical Structure | Name | Method changes | Reagent |
|---|---|---|---|---|
| 21-9 | 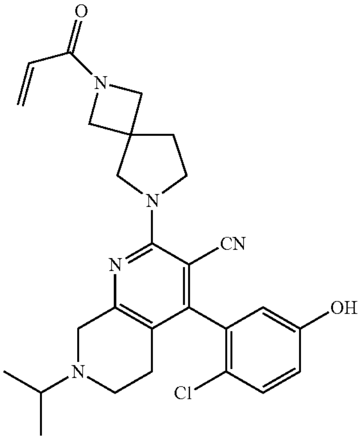 [SMILES: C=CC(=O)N1CC2(CCN(c3nc4c(c(-c5cc(O)ccc5Cl)c3C#N)CCN(C(C)C)C4)C2)C1] | 4-(2-chloro-5-hydroxyphenyl)-7-(2-propanyl)-2-(2-(2-propenoyl)-2,6-diazaspiro[3.4]octan-6-yl)-5,6,7,8-tetrahydro-1,7-naphthyridine-3-carbonitrile | See Alternate Step 1 from Example 21-8. Step 2: $BBr_3$ was used for deprotection of Boc and methoxy in place of TFA. | Step 1: Intermediate 102 |
| 21-10 | 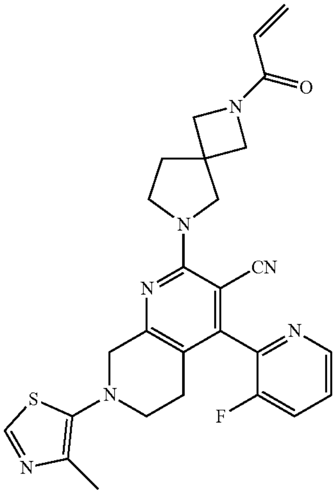 [SMILES: C=CC(=O)N1CC2(CCN(c3nc4c(c(-c5ncccc5F)c3C#N)CCN(c3scnc3C)C4)C2)C1] | 4-(3-fluoro-2-pyridinyl)-7-(4-methyl-1,3-thiazol-5-yl)-2-(2-(2-propenoyl)-2,6-diazaspiro[3.4]octan-6-yl)-5,6,7,8-tetrahydro-1,7-naphthyridine-3-carbonitrile | | Step 1: Intermediate 99 |
| 21-11 | 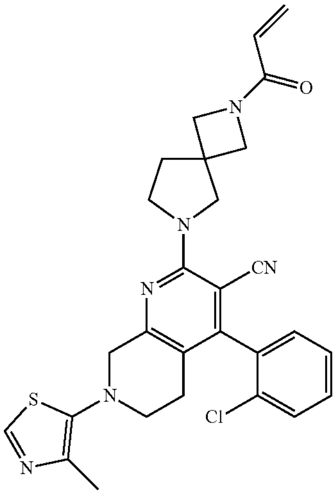 [SMILES: C=CC(=O)N1CC2(CCN(c3nc4c(c(-c5ccccc5Cl)c3C#N)CCN(c3scnc3C)C4)C2)C1] | 4-(2-chlorophenyl)-7-4-methyl-1,3-thiazol-5-yl)-2-(2-(2-propenoyl)-2,6-diazaspiro[3.4]octan-6-yl)-5,6,7,8-tetrahydro-1,7-naphthyridine-3-carbonitrile | | Step 1: Intermediate 100 |

TABLE 13-continued

| Examples 21-2 to 21-39 were prepared following the procedure described in Method 21, Steps 1-3, above as follows: | | | | |
|---|---|---|---|---|
| Ex. # | Chemical Structure | Name | Method changes | Reagent |
| 21-12 | 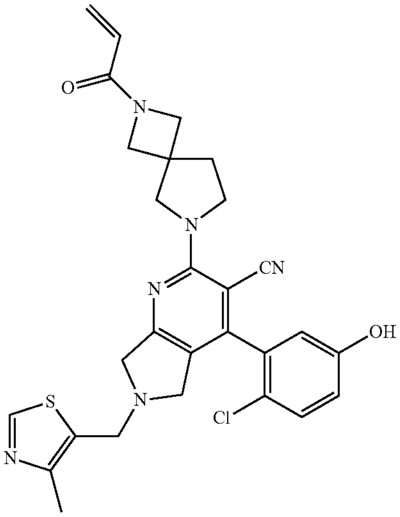 [SMILES: C=CC(=O)N1CC2(CCN(c3nc4c(c(-c5cc(O)ccc5Cl)c3C#N)CN(Cc3scnc3C)C4)C2)C1] | 4-(2-chloro-5-hydroxyphenyl)-6-((4-methyl-1,3-thiazol-5-yl)methyl)-2-(2-(2-propenoyl)-2,6-diazaspiro[3.4]octan-6-yl)-6,7-dihydro-5H-pyrrolo[3,4-b]pyridine-3-carbonitrile | See Alternate Step 1 below. Step 2: $BBr_3$ was used for deprotection of Boc and methoxy in place of TFA. | |
| 21-13 | 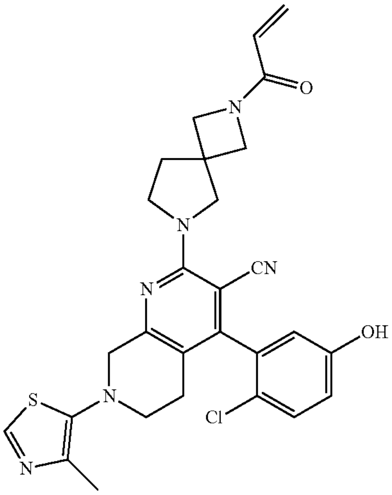 [SMILES: C=CC(=O)N1CC2(CCN(c3nc4c(c(-c5cc(O)ccc5Cl)c3C#N)CCN(c3scnc3C)C4)C2)C1] | 4-(2-chloro-5-hydroxyphenyl)-7-(4-methyl-1,3-thiazol-5-yl)-2-(2-(2-propenoyl)-2,6-diazaspiro[3.4]octan-6-yl)-5,6,7,8-tetrahydro-1,7-naphthyridine-3-carbonitrile | Step 2: $BBr_3$ was used for deprotection of Boc and methoxy in place of TFA. | Step 1: Intermediate 102 |
| 21-14 | 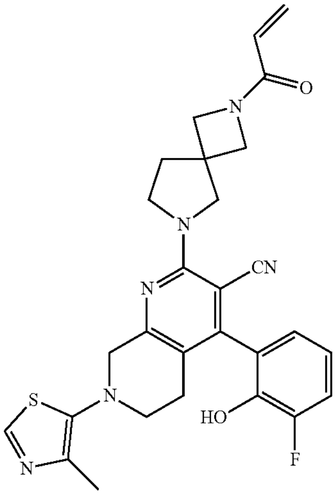 [SMILES: C=CC(=O)N1CC2(CCN(c3nc4c(c(-c5cccc(F)c5O)c3C#N)CCN(c3scnc3C)C4)C2)C1] | 4-(3-fluoro-2-hydroxyphenyl)-7-(4-methyl-1,3-thiazol-5-yl)-2-(2-(2-propenoyl)-2,6-diazaspiro[3.4]octan-6-yl)-5,6,7,8-tetrahydro-1,7-naphthyridine-3-carbonitrile | Step 2: $BBr_3$ was used for deprotection of Boc and methoxy in place of TFA. | Step 1: Intermediate 103 |

TABLE 13-continued

| Examples 21-2 to 21-39 were prepared following the procedure described in Method 21, Steps 1-3, above as follows: | | | | |
|---|---|---|---|---|
| Ex. # | Chemical Structure | Name | Method changes | Reagent |
| 21-15 | 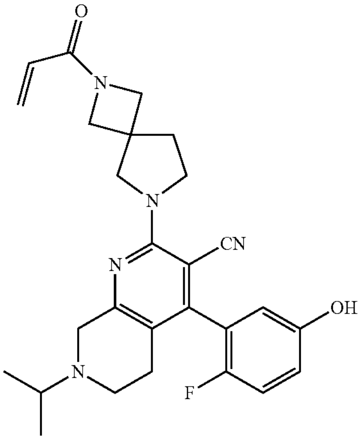 [SMILES: C=CC(=O)N1CC2(CCN(c3nc4c(c(-c5cc(O)ccc5F)c3C#N)CCN(C(C)C)C4)C2)C1] | 4-(2-fluoro-5-hydroxyphenyl)-7-(2-propanyl)-2-(2-(2-propenoyl)-2,6-diazaspiro[3.4]octan-6-yl)-5,6,7,8-tetrahydro-1,7-naphthyridine-3-carbonitrile | See Alternate Step 1 from Example 21-8. Step 2: $BBr_3$ was used for deprotection of Boc and methoxy in place of TFA. | Step 1: Intermediate 106 |
| 21-16 | 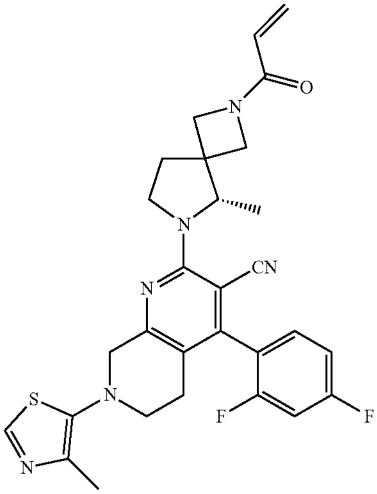 [SMILES: C=CC(=O)N1CC2(CCN(c3nc4c(c(-c5ccc(F)cc5F)c3C#N)CCN(c3scnc3C)C4)[C@H]2C)C1] | 4-(2,4-difluorophenyl)-2-((5S)-5-methyl-2-(2-propenoyl)-2,6-diazaspiro[3.4]octan-6-yl)-7-(4-methyl-1,3-thiazol-5-yl)-5,6,7,8-tetrahydro-1,7-naphthyridine-3-carbonitrile | | Step 1: Intermediate 104 |
| 21-17 | 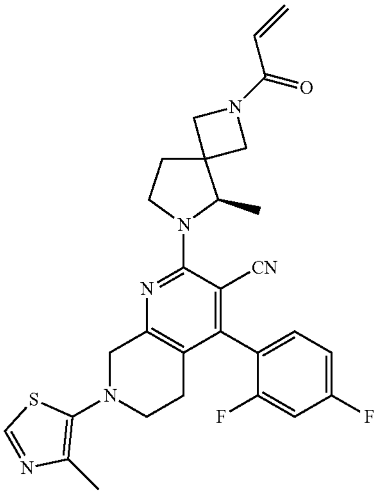 [SMILES: C=CC(=O)N1CC2(CCN(c3nc4c(c(-c5ccc(F)cc5F)c3C#N)CCN(c3scnc3C)C4)[C@@H]2C)C1] | 4-(2,4-difluorophenyl)-2-((5R)-5-methyl-2-(2-propenoyl)-2,6-diazaspiro[3.4]octan-6-yl)-7-(4-methyl-1,3-thiazol-5-yl)-5,6,7,8-tetrahydro-1,7-naphthyridine-3-carbonitrile | | Step 1: Intermediate 105 |

TABLE 13-continued

| Ex. # | Chemical Structure | Name | Method changes | Reagent |
|---|---|---|---|---|
| | Examples 21-2 to 21-39 were prepared following the procedure described in Method 21, Steps 1-3, above as follows: | | | |
| 21-18 | 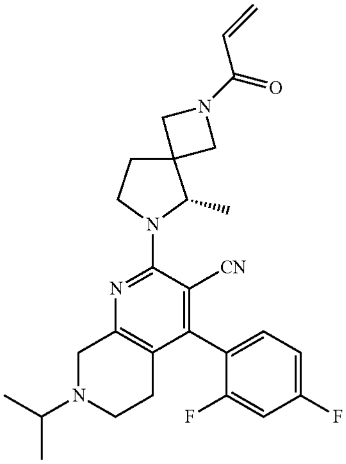 [SMILES: C=CC(=O)N1CC2(CCN(c3nc4c(c(-c5ccc(F)cc5F)c3C#N)CCN(C(C)C)C4)[C@H]2C)C1] | 4-(2,4-difluorophenyl)-2-((5S)-5-methyl-2-(2-propenoyl)-2,6-diazaspiro[3.4]octan-6-yl)-7-(2-propanyl)-5,6,7,8-tetrahydro-1,7-naphthyridine-3-carbonitrile | See Alternate Step 1 from Example 21-8. | Step 1: Intermediate 104 |
| 21-19 | 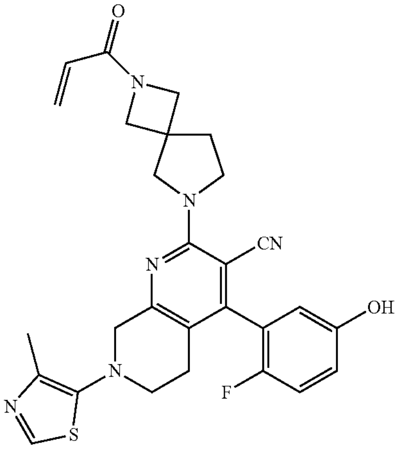 [SMILES: C=CC(=O)N1CC2(CCN(c3nc4c(c(-c5cc(O)ccc5F)c3C#N)CCN(c3scnc3C)C4)C2)C1] | 4-(2-fluoro-5-hydroxyphenyl)-7-(4-methyl-1,3-thiazol-5-yl)-2-(2-(2-propenoyl)-2.6-diazaspiro[3.4]octan-6-yl)-5,6,7,8-tetrahydro-1,7-naphthyridine-3-carbonitrile | Step 2: $BBr_3$ was used for deprotection of Boc and methoxy in place of TFA. | Step 1: Intermediate 106 |
| 21-20 | 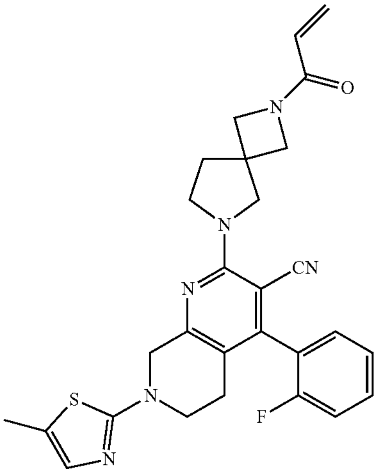 [SMILES: C=CC(=O)N1CC2(CCN(c3nc4c(c(-c5ccccc5F)c3C#N)CCN(c3ncc(C)s3)C4)C2)C1] | 4-(2-fluorophenyl)-7-(5-methyl-1,3-thiazol-2-yl)-2-(2-(2-propenoyl)-2.6-diazaspiro[3.4]octan-6-yl)-5,6,7,8-tetrahydro-1,7-naphthyridine-3-carbonitrile | | Step 1: 2-bromo-5-methylthiazole (Combi-Blocks) |

TABLE 13-continued

| Examples 21-2 to 21-39 were prepared following the procedure described in Method 21, Steps 1-3, above as follows: | | | | |
|---|---|---|---|---|
| Ex. # | Chemical Structure | Name | Method changes | Reagent |
| 21-21 | 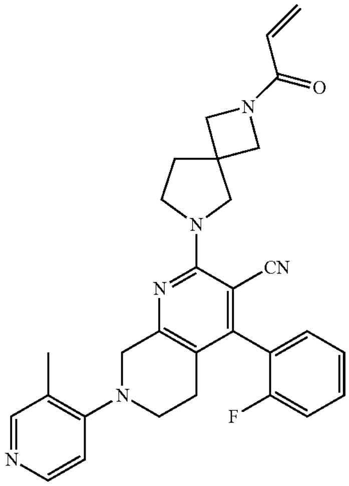 [SMILES: C=CC(=O)N1CC2(CCN(c3nc4c(c(-c5ccccc5F)c3C#N)CCN(c3ccncc3C)C4)C2)C1] | 4-(2-fluorophenyl)-7-(3-methyl-4-pyridinyl)-2-(2-(2-propenoyl)-2,6-diazaspiro[3.4]octan-6-yl)-5,6,7,8-tetrahydro-1,7-naphthyridine-3-carbonitrile | | Step 1: 4-bromo-3-methylpyridine hydrochloride (Combi-Blocks) |
| 21-22 | 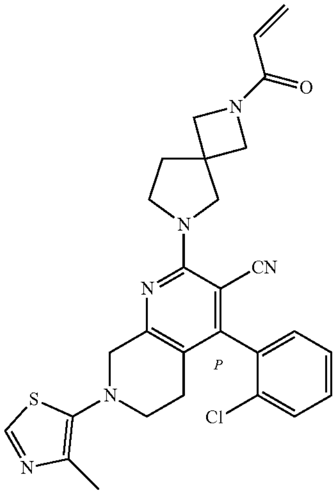 | (P)-4-(2-chlorophenyl)-7-(4-methyl-1,3-thiazol-5-yl)-2-(2-(2-propenoyl)-2,6-diazaspiro[3.4]octan-6-yl)-5,6,7,8-tetrahydro-1,7-naphthyridine-3-carbonitrile (1st eluting isomer) | See atropisomer separation conditions below. | Step 1: Intermediate 100 |
| 21-23 | 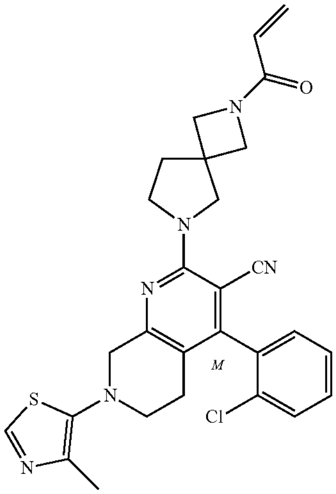 | (M)-4-(2-chlorophenyl)-7-(4-methyl-1,3-thiazol-5-yl)-2-(2-(2-propenoyl)-2,6-diazaspiro[3.4]octan-6-yl)-5,6,7,8-tetrahydro-1,7-naphthyridine-3-carbonitrile (2nd eluting isomer) | See atropisomer separation conditions below. | Step 1: Intermediate 100 |

TABLE 13-continued

Examples 21-2 to 21-39 were prepared following the procedure described in Method 21, Steps 1-3, above as follows:

| Ex. # | Chemical Structure | Name | Method changes | Reagent |
|---|---|---|---|---|
| 21-24 | 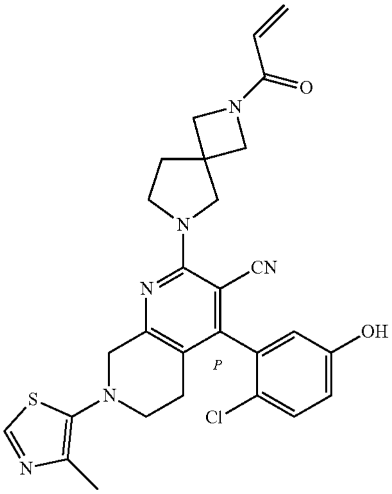 | (P)-4-(2-chloro-5-hydroxyphenyl)-7-(4-methyl-1,3-thiazol-5-yl)-2-(2-(2-propenoyl)-2,6-diazaspiro[3.4]octan-6-yl)-5,6,7,8-tetrahydro-1,7-naphthyridine-3-carbonitrile (1st eluting isomer) | Step 2: $BBr_3$ was used for deprotection of Boc and methoxy in place of TFA. See atropisomer separation conditions below. | Step 1: Intermediate 102 |
| 21-25 | 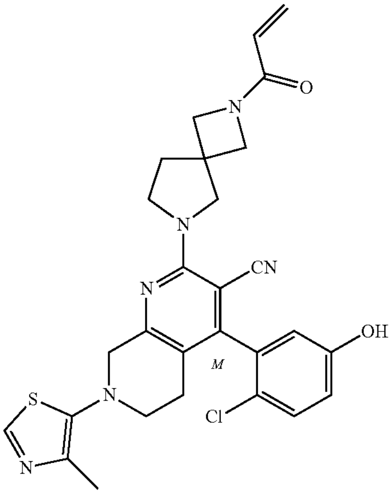 | (M)-4-(2-chloro-5-hydroxyphenyl)-7-(4-methyl-1,3-thiazol-5-yl)-2-(2-(2-propenoyl)-2,6-diazaspiro[3.4]octan-6-yl)-5,6,7,8-tetrahydro-1,7-naphthyridine-3-carbonitrile (2nd eluting isomer) | Step 2: $BBr_3$ was used for deprotection of Boc and methoxy in place of TFA. See atropisomer separation conditions below. | Step 1: Intermediate 102 |
| 21-26 | 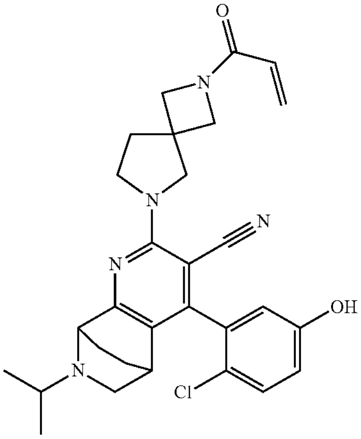 [SMILES: C=CC(=O)N1CC2(CCN(c3nc4c(c(-c5cc(O)ccc5Cl)c3C#N)C3CCC4N(C(C)C)C3)C2)C1] | (1R,8R)-6-(2-chloro-5-hydroxyphenyl)-10-(2-propanyl)-4-(2-(2-propenoyl)-2,6-diazaspiro[3.4]octan-6-yl)-3,10-diazatricyclo[6.2.2.0$^{2,7}$]dodeca-2,4,6-triene-5-carbonitrile (1R,8S)-6-(2-chloro-5-hydroxyphenyl)-10-(2-propanyl)-4-(2-(2-propenoyl)-2,6-diazaspiro[3.4]octan-6-yl)-3,10-diazatricyclo[6.2.2.0$^{2,7}$]dodeca-2,4,6-triene-5-carbonitrile (1S,8R)-6-(2-chloro-5-hydroxyphenyl)-10-(2-propanyl)-4-(2-(2-propenoyl)-2,6-diazaspiro[3.4]octan-6-yl)-3,10-diazatricyclo[6.2.2.0$^{2,7}$]dodeca-2,4,6-triene-5- | See Alternate Step 1 from Example 21-8. Step 2: $BBr_3$ was used for deprotection of Boc and methoxy in place of TFA. | Step 1: Intermediate 107 |

TABLE 13-continued

| Ex. # | Chemical Structure | Name | Method changes | Reagent |
|---|---|---|---|---|
| Examples 21-2 to 21-39 were prepared following the procedure described in Method 21, Steps 1-3, above as follows: | | | | |
| | | carbonitrile (1S,8S)-6-(2-chloro-5-hydroxyphenyl)-10-(2-propanyl)-4-(2-(2-propenoyl)-2,6-diazaspiro[3.4]octan-6-yl)-3,10-diazatricyclo[6.2.2.0$^{2,7}$]dodeca-2,4,6-triene-5-carbonitrile | | |
| 21-27 | 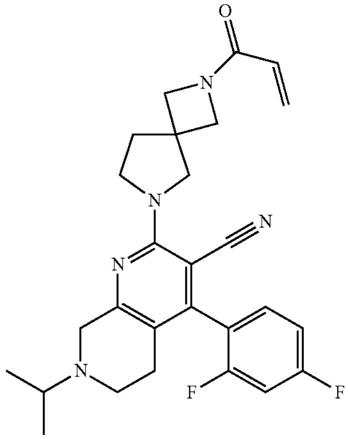 [SMILES: C=CC(=O)N1CC2(CCN(c3nc4c(c(-c5ccc(F)cc5F)c3C#N)CCN(C(C)C)C4)C2)C1] | 4-(2,4-difluorophenyl)-7-(2-propanyl)-2-(2-(2-propenoyl)-2,6-diazaspiro[3.4]octan-6-yl)-5,6,7,8-tetrahydro-1,7-naphthyridine-3-carbonitrile | See Alternate Step 1 from Example 21-8. | Step 1: Intermediate 97 |
| 21-28 | 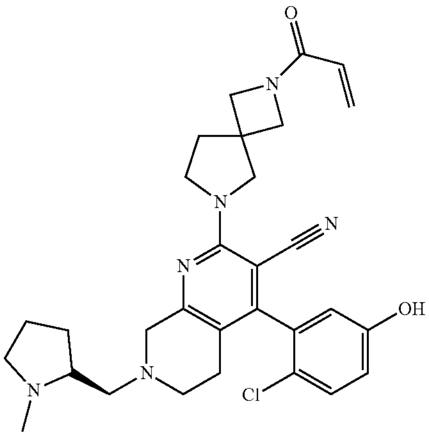 | 4-(2-chloro-5-hydroxyphenyl)-7-(((2S)-1-methyl-2-pyrrolidinyl)methyl)-2-(2-(2-propenoyl)-2,6-diazaspiro[3.4]octan-6-yl)-5,6,7,8-tetrahydro-1,7-naphthyridine-3-carbonitrile | See Alternate Step 1 from Example 21-8. Step 2: $BBr_3$ was used for deprotection of Boc and methoxy in place of TFA. | Step 1: Intermediate 102 and Intermediate 108 |

TABLE 13-continued

| Ex. # | Chemical Structure | Name | Method changes | Reagent |
|---|---|---|---|---|
| Examples 21-2 to 21-39 were prepared following the procedure described in Method 21, Steps 1-3, above as follows: | | | | |
| 21-29 | 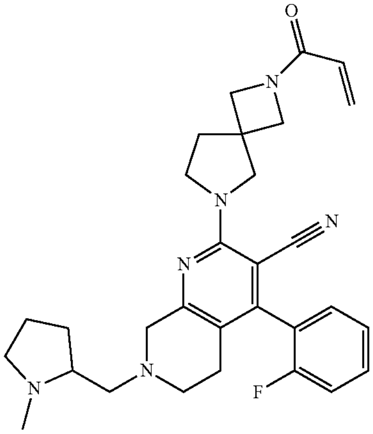 [SMILES: C=CC(=O)N1CC2(CCN(c3nc4c(c(-c5ccccc5F)c3C#N)CCN(CC3CCCN3C)C4)C2)C1] | 4-(2-fluorophenyl)-7-(((2R)-1-methyl-2-pyrrolidinyl)methyl)-2-(2-(2-propenoyl)-2,6-diazaspiro[3.4]octan-6-yl)-5,6,7,8-tetrahydro-1,7-naphthyridine-3-carbonitrile 4-(2-fluorophenyl)-7-(((2S)-1-methyl-2-pyrrolidinyl)methyl)-2-(2-(2-propenoyl)-2,6-diazaspiro[3.4]octan-6-yl)-5,6,7,8-tetrahydro-1,7-naphthyridine-3-carbonitrile | See Alternate Step 1 from Example 21-8. Step 2: $BBr_3$ was used for deprotection of Boc and methoxy in place of TFA. | Step 1: Intermediate 95 and (1-methylpyrrolidin-2-yl)methyl methanesulfonate (WO 2017/181177) |
| 21-30 | 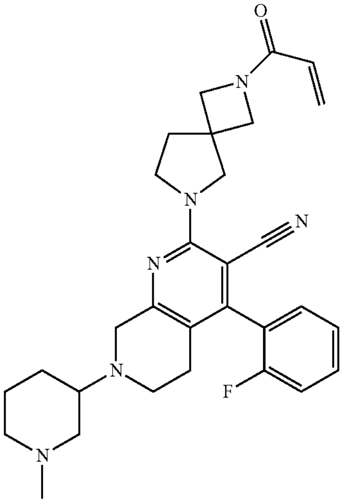 [SMILES: C=CC(=O)N1CC2(CCN(c3nc4c(c(-c5ccccc5F)c3C#N)CCN(C3CCCN(C)C3)C4)C2)C1] | 4-(2-fluorophenyl)-7-((3R)-1-methyl-3-piperidinyl)-2-(2-(2-propenoyl)-2,6-diazaspiro[3.4]octan-6-yl)-5,6,7,8-tetrahydro-1,7-naphthyridine-3-carbonitrile 4-(2-fluorophenyl)-7-((3S)-1-methyl-3-piperidinyl)-2-(2-(2-propenoyl)-2,6-diazaspiro[3.4]octan-6-yl)-5,6,7,8-tetrahydro-1,7-naphthyridine-3-carbonitrile | See alternate Step 1 below. | |
| 21-31 | 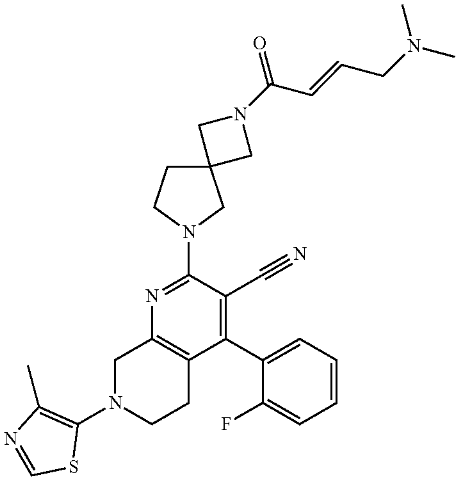 [SMILES: Cc1ncsc1N1CCc2c(nc(N3CCC4(CN(C(=O)/C=C/CN(C)C)C4)C3)c(C#N)c2-c2ccccc2F)C1] | 2-(2-((2E)-4-(dimethylamino)-2-butenoyl)-2,6-diazaspiro[3.4]octan-6-yl)-4-(2-fluorophenyl)-7-(4-methyl-1,3-thiazol-5-yl)-5,6,7,8-tetrahydro-1,7-naphthyridine-3-carbonitrile | Step 3 replaced by Method 13, Step 5 | Step 5: (E)-4-(dimethylamino) but-2-enoic acid (Enamine) |

TABLE 13-continued

Examples 21-2 to 21-39 were prepared following the procedure described in Method 21, Steps 1-3, above as follows:

| Ex. # | Chemical Structure | Name | Method changes | Reagent |
|---|---|---|---|---|
| 21-32 | 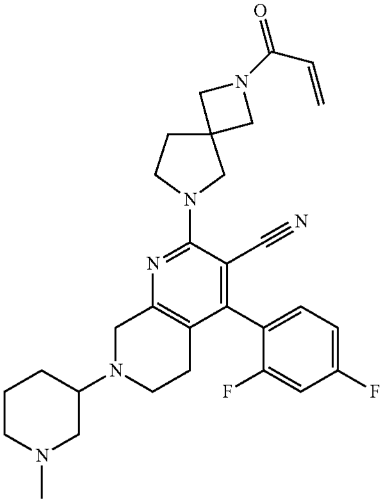 [SMILES: C=CC(=O)N1CC2(CCN(c3nc4c(c(-c5ccc(F)cc5F)c3C#N)CCN(C3CCCN(C)C3)C4)C2)C1] | 4-(2,4-difluorophenyl)-7-((3R)-1-methyl-3-piperidinyl)-2-(2-(2-propenoyl)-2,6-diazaspiro[3.4]octan-6-yl)-5,6,7,8-tetrahydro-1,7-naphthyridine-3-carbonitrile\|4-(2,4-difluorophenyl)-7-((3S)-1-methyl-3-piperidinyl)-2-(2-(2-propenoyl)-2,6-diazaspiro[3.4]octan-6-yl)-5,6,7,8-tetrahydro-1,7-naphthyridine-3-carbonitrile | See alternate Step 1 from Example 21-30. | Step 1: Intermediate 97 |
| 21-33 | 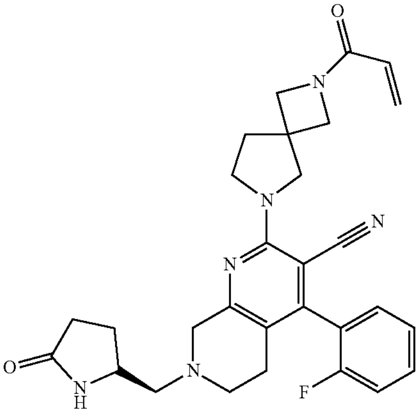 | 4-(2-fluorophenyl)-7-(((2S)-5-oxo-2-pyrrolidinyl)methyl)-2-(2-(2-propenoyl)-2,6-diazaspiro[3.4]octan-6-yl)-5,6,7,8-tetrahydro-1,7-naphthyridine-3-carbonitrile | See Alternate Step 1 from Example 21-8. | Step 1: Intermediate 97 and (S)-(5-oxopyrrolidin-2-yl)methyl methanesulfonate (WO 2014/093337) |
| 21-34 | 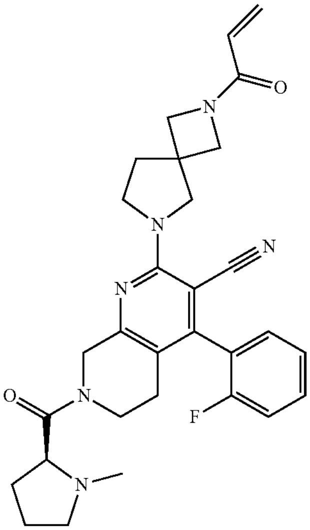 [SMILES: C=CC(=O)N1CC2(CCN(c3nc4c(c(-c5ccccc5F)c3C#N)CCN(C(=O)[C@@H]3CCCN3C)C4)C2)C1] | 4-(2-fluorophenyl)-7-(1-methyl-L-prolyl)-2-(2-(2-propenoyl)-2,6-diazaspiro[3.4]octan-6-yl)-5,6,7,8-tetrahydro-1,7-naphthyridine-3-carbonitrile | See alternate Step 1 below | |

TABLE 13-continued

Examples 21-2 to 21-39 were prepared following the procedure described in Method 21, Steps 1-3, above as follows:

| Ex. # | Chemical Structure | Name | Method changes | Reagent |
|---|---|---|---|---|
| 21-35 | 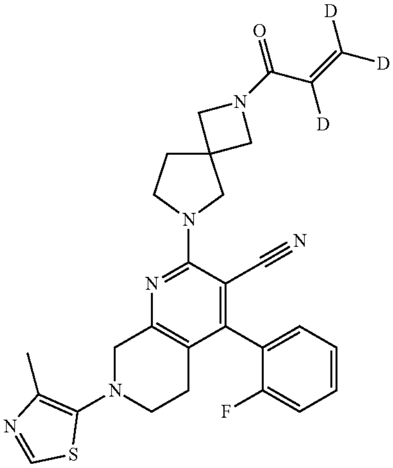 [SMILES: [2H]C([2H])=C([2H])C(=O)N1CC2(CCN(c3nc4c(c(-c5ccccc5F)c3C#N)CCN(c3scnc3C)C4)C2)C1] | 4-(3-fluoro-2-pyridinyl)-7-(4-methyl-1,3-thiazol-5-yl)-2-(2-(($^2H_3$)-2-propenoyl)-2,6-diazaspiro[3.4]octan-6-yl)-5,6,7,8-tetrahydro-1,7-naphthyridine-3-carbonitrile | Step 3 replaced by Method 13, Step 5 | |
| 21-36 | 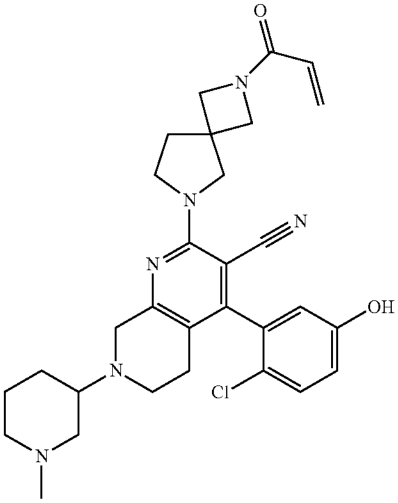 [SMILES: C=CC(=O)N1CC2(CCN(c3nc4c(c(-c5cc(O)ccc5Cl)c3C#N)CCN(C3CCCN(C)C3)C4)C2)C1] | 4-(2-chloro-5-hydroxyphenyl)-7-((3R)-1-methyl-3-piperidinyl)-2-(2-(2-propenoyl)-2,6-diazaspiro[3.4]octan-6-yl)-5,6,7,8-tetrahydro-1,7-naphthyridine-3-carbonitrile 4-(2-chloro-5-hydroxyphenyl)-7-((3S)-1-methyl-3-piperidinyl)-2-(2-(2-propenoyl)-2,6-diazaspiro[3.4]octan-6-yl)-5,6,7,8-tetrahydro-1,7-naphthyridine-3-carbonitrile | See alternate Step 1 from Example 21-30. Step 2: $BBr_3$ was used for deprotection of Boc and methoxy in place of TFA. | Step 1: Intermediate 102 |
| 21-37 | 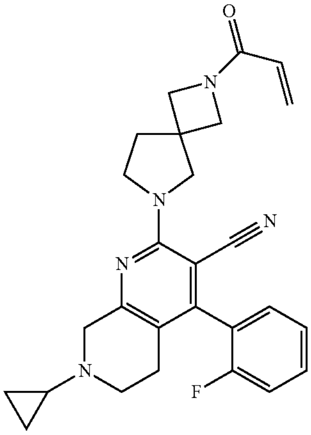 [SMILES: C=CC(=O)N1CC2(CCN(c3nc4c(c(-c5ccccc5F)c3C#N)CCN(C3CC3)C4)C2)C1] | 7-cyclopropyl-4-(2-fluorophenyl)-2-(2-(2-propenoyl)-2,6-diazaspiro[3.4]octan-6-yl)-5,6,7,8-tetrahydro-1,7-naphthyridine-3-carbonitrile | See alternate Step 1 from Example 21-30. | Step 1: (1-ethoxycycloprop-oxy)trimethylsilane (Combi-Blocks) |

TABLE 13-continued

| Ex. # | Chemical Structure | Name | Method changes | Reagent |
|---|---|---|---|---|
| | Examples 21-2 to 21-39 were prepared following the procedure described in Method 21, Steps 1-3, above as follows: | | | |
| 21-38 | 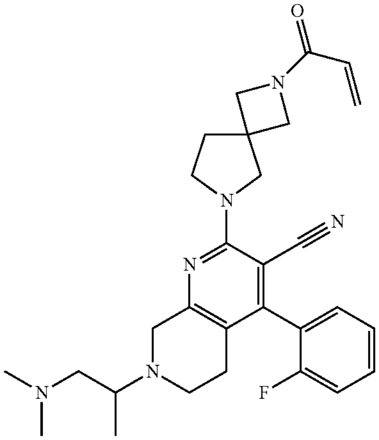 [SMILES: C=CC(=O)N1CC2(CCN(c3nc4c(c(-c5ccccc5F)c3C#N)CCN(C(C)CN(C)C)C4)C2)C1] | 7-((2R)-1-(dimethylamino)-2-propanyl)-4-(2-fluorophenyl)-2-(2-(2-propenoyl)-2,6-diazaspiro[3.4]octan-6-yl)-5,6,7,8-tetrahydro-1,7-naphthyridine-3-carbonitrile 7-((2S)-1-(dimethylamino)-2-propanyl)-4-(2-fluorophenyl)-2-(2-(2-propenoyl)-2,6-diazaspiro[3.4]octan-6-yl)-5,6,7,8-tetrahydro-1,7-naphthyridine-3-carbonitrile | See alternate Step 1 from Example 21-30. | Step 1: 1-(dimethylamino) propan-2-one (Combi Blocks) |
| 21-39 | 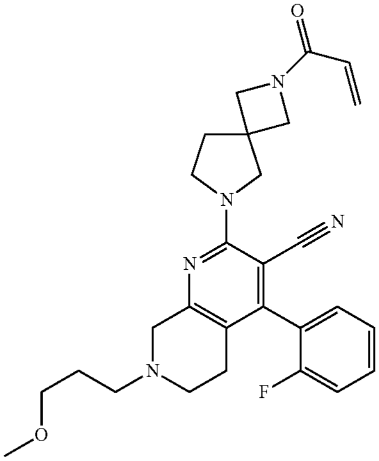 [SMILES: C=CC(=O)N1CC2(CCN(c3nc4c(c(-c5ccccc5F)c3C#N)CCN(CCCOC)C4)C2)C1] | 4-(2-fluorophenyl)-7-(3-methoxypropyl)-2-(2-(2-propenoyl)-2,6-diazaspiro[3.4]octan-6-yl)-5,6,7,8-tetrahydro-1,7-naphthyridine-3-carbonitrile | See alternate Step 1 from Example 21-8. | Step 1: Intermediate 95 and 1-bromo-3-methoxypropane (BLD Pharma) |

Stereoisomer Separation for Examples 21-5 and 21-6.

The racemic mixture was separated by SFC using a ChiralPak OD-H (150×4.6 mm) column with a mobile phase of 80% liquid $CO_2$ and 20% MeOH to provide the respective 8R and 8S isomers of 4-(2-fluorophenyl)-8-methyl-7-(4-methyl-1,3-thiazol-5-yl)-2-(2-(2-propenoyl)-2,6-diazaspiro[3.4]octan-6-yl)-5,6,7,8-tetrahydro-1,7-naphthyridine-3-carbonitrile. The stereochemistry of structures was arbitrarily assigned and is not established. 1st eluting isomer assigned as the 8R isomer and 2nd eluting isomer assigned as the 8S isomer.

Alternate Step 1 for Example 21-8

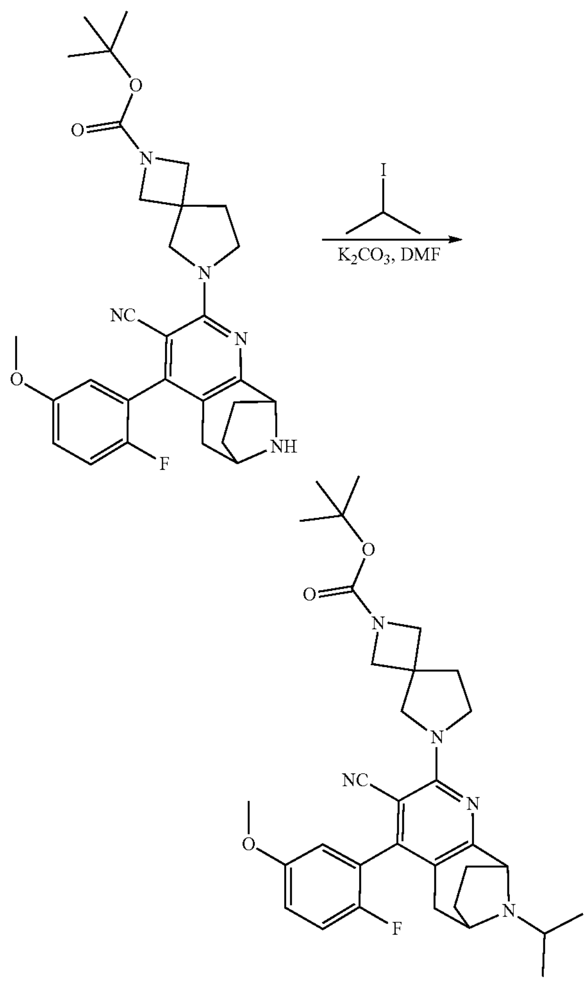

To a RBF was added tert-butyl 6-(3-cyano-4-(2-fluoro-5-methoxyphenyl)-6,7,8,9-tetrahydro-5H-6,9-epiminocyclohepta[b]pyridin-2-yl)-2,6-diazaspiro[3.4]octane-2-carboxylate (0.21 g, 0.404 mmol, Intermediate 98) and $K_2CO_3$ (0.112 g, 0.808 mmol) in DMF (2 mL). 2-Iodopropane (0.103 g, 0.606 mmol) was added and the reaction mixture was stirred at 70° C. for 16 h. The reaction mixture was diluted with water (50 mL) and extracted with EtOAc (3×50 mL). The organic extracts were dried over $Na_2SO_4$, and concentrated in vacuo. The crude material was absorbed onto a plug of silica gel and purified by chromatography through a Redi-Sep pre-packed silica gel column, eluting with a gradient of 5-10% MeOH in DCM, to provide tert-butyl 6-(3-cyano-4-(2-fluoro-5-methoxyphenyl)-10-isopropyl-6,7,8,9-tetrahydro-5H-6,9-epiminocyclohepta[b]pyridin-2-yl)-2,6-diazaspiro[3.4]octane-2-carboxylate (0.19 g, 84% yield) as a yellow solid. m/z (ESI): 562.0 $(M+H)^+$.

Alternate Step 1 for Example 21-12

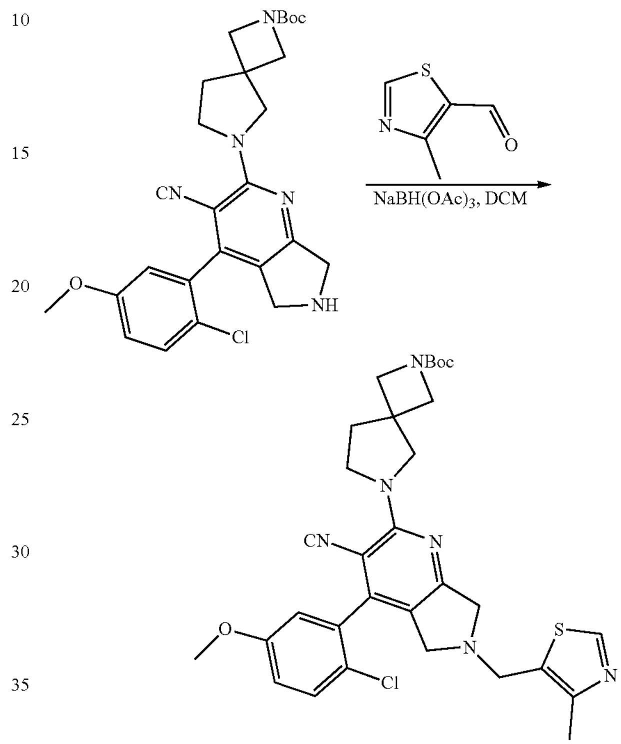

To a solution of tert-butyl 6-(4-(2-chloro-5-methoxyphenyl)-3-cyano-6,7-dihydro-5H-pyrrolo[3,4-b]pyridin-2-yl)-2,6-diazaspiro[3.4]octane-2-carboxylate (125 mg, 0.252 mmol) in DCM (5 mL) and 1 drop of HOAc was added 4-methylthiazole-5-carbaldehyde (48.1 mg, 0.378 mmol, Intermediate 120, Step 1) at 0° C. The reaction was stirred at room temperature. After 1 h, $NaBH(OAc)_3$ (107 mg, 0.504 mmol) was added to the reaction. The reaction was stirred at room temperature overnight. The reaction was diluted with cold water and extracted with DCM. The organic extracts were dried over $Na_2SO_4$, and concentrated in vacuo. The crude compound was purified by column chromatography using MeOH in DCM to give tert-butyl 6-(4-(2-chloro-5-methoxyphenyl)-3-cyano-6-((4-methylthiazol-5-yl)methyl)-6,7-dihydro-5H-pyrrolo[3,4-b]pyridin-2-yl)-2,6-diazaspiro[3.4]octane-2-carboxylate (0.065 g, 42.5% yield) as a brown semi-solid.

Atropisomer Separation for Examples 21-22 and 21-23.

The racemic mixture was separated by SFC using a ChiralPak OD-H column with a mobile phase of 80% liquid $CO_2$ and 20% MeOH to provide the respective P and M isomers of 4-(2-chlorophenyl)-7-(4-methyl-1,3-thiazol-5-yl)-2-(2-(2-propenoyl)-2,6-diazaspiro[3.4]octan-6-yl)-5,6,7,8-tetrahydro-1,7-naphthyridine-3-carbonitrile. The stereochemistry of structures was arbitrarily assigned and is not established. 1st eluting atropisomer assigned as the P isomer and 2nd eluting atropisomer assigned as the M isomer.

Atropisomer Separation for Examples 21-24 and 21-25.

The racemic mixture was separated by SFC using a ChiralPak OD-H column with a mobile phase of 60% liquid $CO_2$ and 40% MeOH to provide the respective P and M isomers of 4-(2-chloro-5-hydroxyphenyl)-7-(4-methyl-1,3-thiazol-5-yl)-2-(2-(2-propenoyl)-2,6-diazaspiro[3.4]octan-6-yl)-5,6,7,8-tetrahydro-1,7-naphthyridine-3-carbonitrile. The stereochemistry of structures was arbitrarily assigned and is not established. 1st eluting atropisomer assigned as the P isomer and 2nd eluting atropisomer assigned as the M isomer.

Alternate Step 1 for Example 21-30

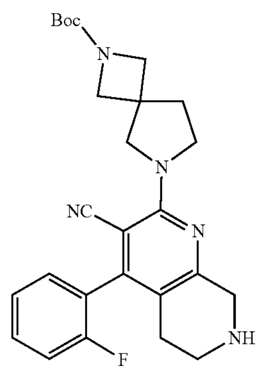

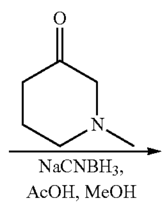

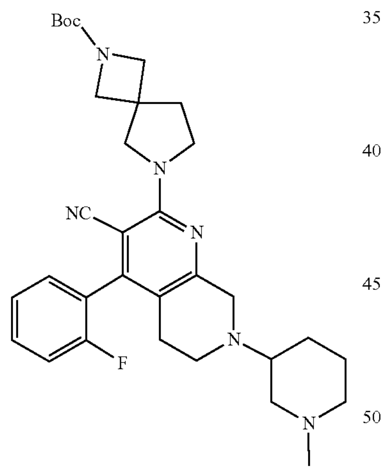

To a solution of tert-butyl 6-(3-cyano-4-(2-fluorophenyl)-5,6,7,8-tetrahydro-1,7-naphthyridin-2-yl)-2,6-diazaspiro[3.4]octane-2-carboxylate (0.2 g, 0.431 mmol, Intermediate 95) and 1-methylpiperidin-3-one hydrochloride (0.258 g, 1.726 mmol, Enamine) in MeOH (5 mL) was added a drop of HOAc. The reaction mixture was stirred at room temperature for 16 h before $NaCNBH_3$ (0.136 g, 2.157 mmol) was added. The reaction mixture was stirred at room temperature for 30 h before it was quenched with ice-cold water and extracted with DCM. The organic extracts were washed with brine, dried over $Na_2SO_4$, filtered and concentrated under reduced pressure. The residue was purified on a Redi-Sep pre-packed silica gel column eluting with a gradient of 2-5% MeOH in $CHCl_3$ to provide tert-butyl 6-(3-cyano-4-(2-fluorophenyl)-7-(1-methylpiperidin-3-yl)-5,6,7,8-tetrahydro-1,7-naphthyridin-2-yl)-2,6-diazaspiro[3.4]octane-2-carboxylate (0.11 g, 45.5% yield) as a yellow solid. $^1H$ NMR (400 MHz, DMSO-$d_6$) δ ppm 7.60-7.52 (m, 1H), 7.43-7.33 (m, 3H), 3.94-3.74 (m, 6H), 3.69 (m, 4H), 2.89 (d, J=10.7 Hz, 1H), 2.78-2.63 (m, 4H), 2.37 (d, J=7.1 Hz, 1H), 2.30-2.10 (m, 5H), 1.81 (d, J=11.9 Hz, 3H), 1.76-1.59 (m, 2H), 1.39 (s, 9H), 1.29-1.14 (m, 2H). m/z (ESI): 561.0 $(M+H)^+$.

Alternate Step 1 for Example 21-34

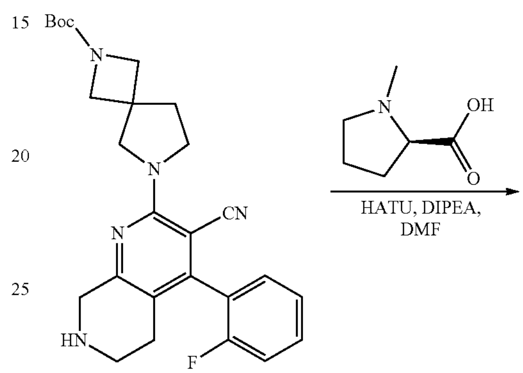

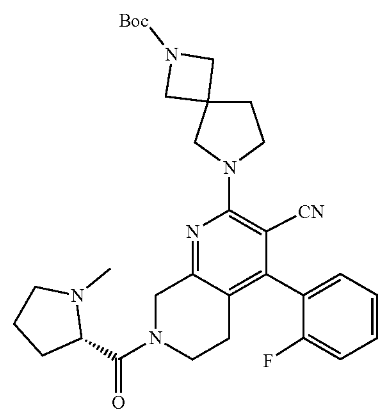

A solution of tert-butyl 6-(3-cyano-4-(2-fluorophenyl)-5,6,7,8-tetrahydro-1,7-naphthyridin-2-yl)-2,6-diazaspiro[3.4]octane-2-carboxylate (250 mg, 0.539 mmol, Intermediate 95), methyl-L-proline (58.0 mg, 0.449 mmol, Combi-Blocks), HATU (205 mg, 0.539 mmol, Avra) and DIPEA (196 μL, 1.124 mmol) in DMF (5 mL) was stirred at room temperature for 16 h. The reaction mixture was diluted with ice-cold water and extracted with EtOAc. The combined organic extracts were washed with brine, separated, dried over $Na_2SO_4$, filtered, and concentrated under reduced pressure. The residue was triturated with pentane-diethyl ether to provide tert-butyl 6-(3-cyano-4-(2-fluorophenyl)-7-(methyl-L-prolyl)-5,6,7,8-tetrahydro-1,7-naphthyridin-2-yl)-2,6-diazaspiro[3.4]octane-2-carboxylate as (0.400 g, quantitative yield) as an off-white solid which was used in next step without further purification. m/z (ESI): 575.2 $(M+H)^+$.

Method 22
Example 22-1 and Example 22-2: 1-(6-((7R)-4-(2,3-dimethylphenyl)-7-(4-methyl-1,3-thiazol-5-yl)-5,6,7,8-tetrahydro-2-quinazolinyl)-2,6-diazaspiro[3.4]octan-2-yl)-2-propen-1-one and 1-(6-((7S)-4-(2,3-dimethylphenyl)-7-(4-methyl-1,3-thiazol-5-yl)-5,6,7,8-tetrahydro-2-quinazolinyl)-2,6-diazaspiro[3.4]octan-2-yl)-2-propen-1-one
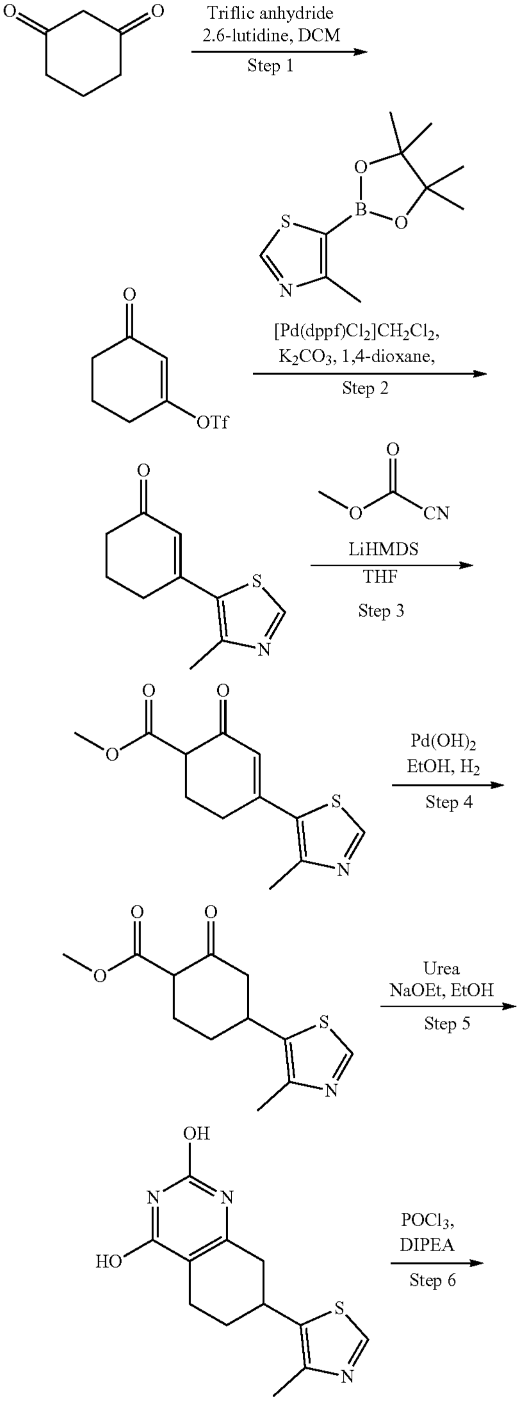
-continued
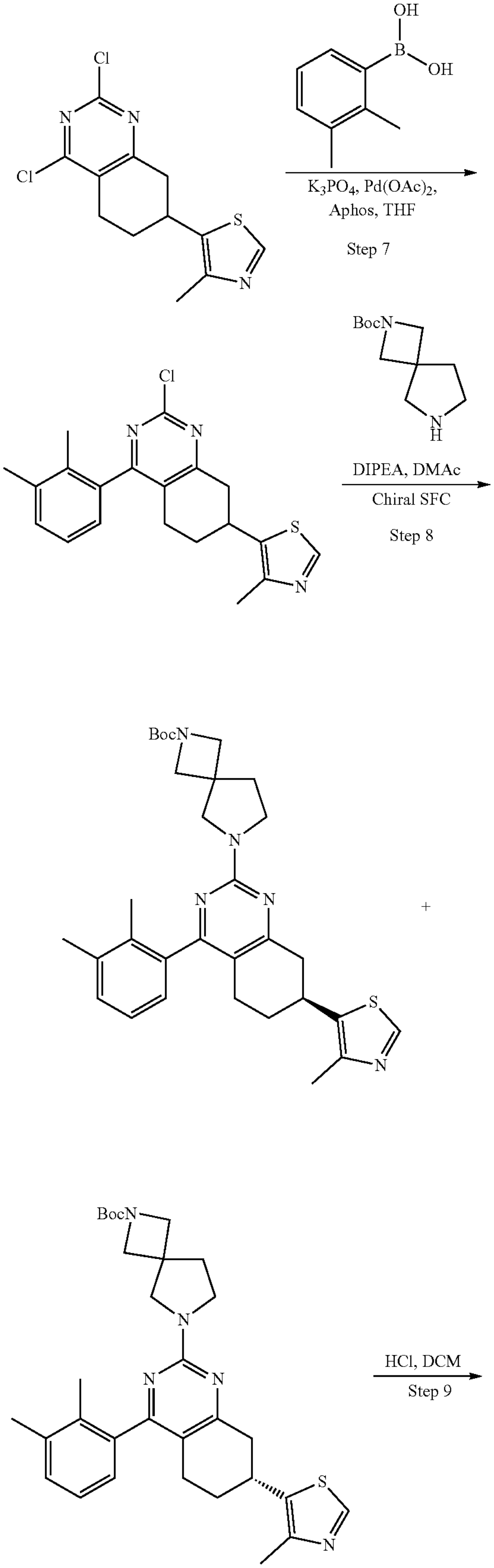

-continued

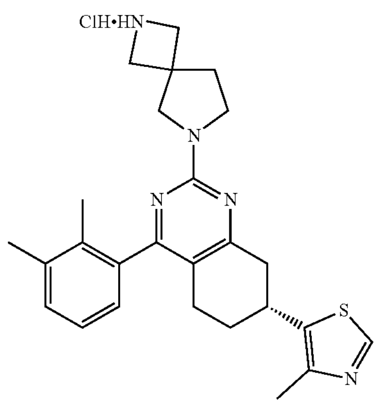

+

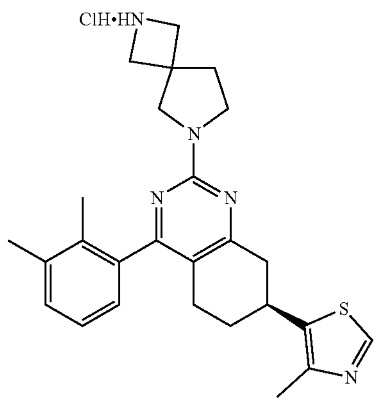

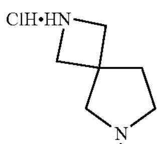

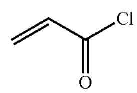

DIPEA, DCM

Step 10

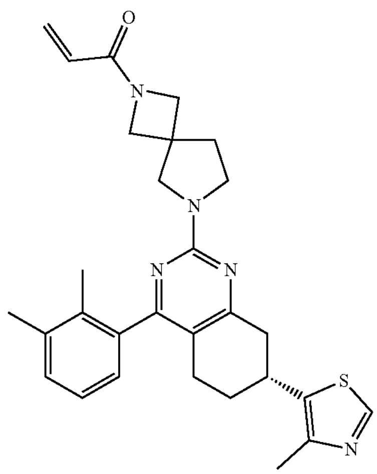

+

Example 22-1

-continued

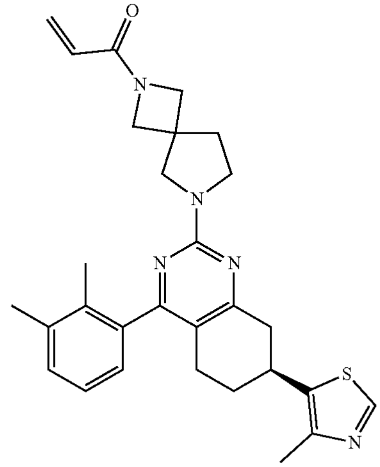

Example 22-2

Step 1: 3-oxocyclohex-1-en-1-yl trifluoromethanesulfonate

To a solution of cyclohexane-1,3-dione (15 g, 134 mmol, Avra), and 2,6-dimethylpyridine (28.7 g, 268 mmol) in DCM (550 mL) was added $Tf_2O$ (33.9 mL, 201 mmol, Spectrochem) dropwise at 0° C. The reaction mixture was slowly warmed to room temperature and stirred for 1 h before it was quenched with water and extracted with DCM (2×200 mL). The organic extracts were washed with 1.5 N HCl solution, water, and brine, dried over $Na_2SO_4$, and concentrated under reduced pressure. The residue was purified on a Redi-Sep pre-packed silica gel column eluting with 20-30% EtOAc in petroleum ether to provide 3-oxocyclohex-1-en-1-yl trifluoromethanesulfonate (30 g, 92% yield) as a pale-yellow oil. $^1H$ NMR (400 MHz, $CDCl_3$) δ ppm 6.08 (s, 1H), 2.72-2.68 (m, 2H), 2.52-2.44 (m, 2H), 2.21-2.10 (in, 2H). m/z (ESI): 244.9 $(M+H)^+$.

Step 2: 3-(4-methylthiazol-5-yl)cyclohex-2-en-1-one

To a degassed mixture of 3-oxocyclohex-1-en-1-yl trifluoromethanesulfonate (20 g, 82 mmol), 4-methyl-5-(4,4,5,5-tetramethyl-1,3,2-dioxaborolan-2-yl)thiazole (27.7 g, 123 mmol, J&W Pharmalab), and $K_2CO_3$ (34.0 g, 246 mmol, Spectrochem) in 1,4-dioxane (80 mL) and water (10 mL) was added $PdCl_2$(dppf)-DCM adduct (6.69 g, 8.19 mmol, Hindustan Platinum). The reaction mixture was stirred at 100° C. for 16 h. The reaction mixture was quenched with water (100 mL) and extracted with EtOAc. The combined organic extracts were washed with brine, dried over $Na_2SO_4$, and concentrated under reduced pressure. The residue was purified on a Redi-Sep pre-packed silica gel column eluting with 30-40% EtOAc in petroleum ether to provide 3-(4-methylthiazol-5-yl)cyclohex-2-en-1-one (15.83 g, 100% yield) as a light yellow oil. m/z (ESI): 194.1 $(M+H)^+$.

Step 3: methyl 4-(4-methylthiazol-5-yl)-2-oxocyclohex-3-ene-1-carboxylate

To a solution of 3-(4-methylthiazol-5-yl)cyclohex-2-en-1-one (8 g 41.4 mmol) in THF (70 mL) was added LiHMDS (62.1 mL, 62.1 mmol, 1M in THF, Sigma-Aldrich) dropwise at −78° C. The resulting reaction mixture was stirred for 30 min before a solution of methyl carbonocyanidate (4.58 g, 53.8 mmol, Sigma-Aldrich) in THF (10 mL) was added dropwise to the reaction at the same temperature. The reaction mixture was stirred at −30° C. for 1.5 h. The reaction mixture was quenched with a $NH_4Cl$ solution (100 mL) and extracted with EtOAc. The combined organic extracts were washed with brine, dried over $Na_2SO_4$, and concentrated under reduced pressure. The residue was purified on a Redi-Sep pre-packed silica gel column eluting with 35-45% EtOAc in petroleum ether to provide methyl 4-(4-methylthiazol-5-yl)-2-oxocyclohex-3-ene-1-carboxylate (6.0 g, 57.7% yield) as a light yellow oil. m/z (ESI): 252.1 $(M+H)^+$.

Step 4: methyl 2-oxo-4-(thiazol-2-yl)cyclohexane-1-carboxylate

A mixture of methyl 2-oxo-4-(thiazol-2-yl)cyclohex-3-ene-1-carboxylate (4.5 g, 18.97 mmol) and $Pd(OH)_2$ (0.45 g, 0.641 mmol, 20% on Carbon, Sigma-Aldrich) in EtOH (20 mL) was stirred under a $H_2$ atmosphere at 5 $kg/cm^3$ pressure for 16 h. The reaction mixture was filtered through a celite bed and washed with EtOAc (100 mL). The filtrate was concentrated under reduced pressure. The residue was purified on a Redi-Sep pre-packed silica gel column eluting with a gradient of 20-40% EtOAc in petroleum ether to provide methyl 2-oxo-4-(thiazol-2-yl)cyclohexane-1-carboxylate (1.9 g. 41.9% yield) as a light yellow solid. m/z (ESI): 254.1 $(M+H)^+$.

Step 5: 7-(4-methylthiazol-5-yl)-5,6,7,8-tetrahydroquinazoline-2,4(1H,3H)-dione

A solution of methyl 4-(4-methylthiazol-5-yl)-2-oxocyclohexane-1-carboxylate (1.5 g, 5.92 mmol), urea (0.427 g, 7.11 mmol, Avra) and NaOEt (2.88 g, 8.88 mmol, 21 wt % in EtOH, Symax) in EtOH (30 mL) was stirred at 80° C. for 16 h. The reaction mass was cooled to 0° C. and the precipitated solids were filtered and dried to provide 7-(4-methylthiazol-5-yl)-5,6,7,8-tetrahydroquinazoline-2,4(1H,3H)-dione (1.2 g, 77% yield) as a brown solid which was taken to the next step without further purification. m/z (ESI): 264.1 $(M+H)^+$.

Step 6: 5-(2,4-dichloro-5,6,7,8-tetrahydroquinazolin-7-yl)-4-methythiazole

A solution of 7-(4-methylthiazol-5-yl)-5,6,7,8-tetrahydroquinazoline-2,4(1H,3H)-dione (1.2 g, 4.56 mmol) and DIPEA (1.59 mL, 9.11 mmol, Spectrochem) in $POCl_3$ (15 mL, 161 mmol, Spectrochem) was heated at 80° C. for 16 h. The reaction mixture was concentrated under reduced pressure and the residue was diluted with ice-cold water and extracted with DCM. The organic extracts were washed with 10% aqueous $NaHCO_3$ solution and brine, dried over $Na_2SO_4$, and concentrated under reduced pressure. The residue was purified on a Redi-Sep pre-packed silica gel column eluting with a gradient of 30-40% EtOAc in petroleum ether to provide 5-(2,4-dichloro-5,6,7,8-tetrahydroquinazolin-7-yl)-4-methylthiazole (0.4 g, 29.2% yield) as a light yellow solid. m/z (ESI): 299.9 $(M+H)^+$.

Step 7: 5-(2-chloro-4-(2,3-dimethylphenyl)-5,6,7,8-tetrahydroquinazolin-7-yl)-4-methylthiazole To a degassed solution of 5-(2,4-dichloro-5,6,7,8-tetrahydroquinazolin-7-yl)-4-methylthiazole (0.2 g, 0.666 mmol), (2,3-dimethylphenyl)boronic acid (0.100 g, 0.666 mmol, Combi-Blocks), and $K_3PO_4$ (0.348 g, 1.999 mmol, Strem Chemicals) in THF (2 mL) was added $Pd(OAc)_2$ (0.015 g, 0.067 mmol, Hindustan Platinum) and APhos (0.018 g, 0.067 mmol, Sigma Sigma-Aldrich). The reaction mixture was stirred at 60° C. for 16 h. The reaction mixture was diluted with ice-cold water and extracted with EtOAc. The combined organic extracts were washed with brine, dried over $Na_2SO_4$, and concentrated under reduced pressure. The residue was purified on a Redi-Sep pre-packed silica gel column eluting with 35-45% EtOAc in petroleum ether to provide 5-(2-chloro-4-(2,3-dimethylphenyl)-5,6,7,8-tetrahydroquinazolin-7-yl)-4-methylthiazole (0.24 g) as a light yellow solid. m/z (ESI): 369.9 $(M+H)^+$.

Step 8: tert-butyl (R)-6-(4-(2,3-dimethylphenyl)-7-(4-methylthiazol-5-yl)-5,6,7,8-tetrahydroquinazolin-2-yl)-2,6-diazaspiro[3.4]octane-2-carboxylate and tert-butyl (S)-6-(4-(2,3-dimethylphenyl)-7-(4-methylthiazol-5-yl)-5,6,7,8-tetrahydroquinazolin-2-yl)-2,6-diazaspiro[3.4]octane-2-carboxylate A solution of 5-(2-chloro-4-(2,3-dimethylphenyl)-5,6,7,8-tetrahydroquinazolin-7-yl)-4-methylthiazole (0.36 g, 0.973 mmol), tert-butyl 2,6-diazaspiro[3.4]octane-2-carboxylate (0.248 g, 1.168 mmol, Combi-Blocks) and DIPEA (0.539 mL, 2.92 mmol) in DMA (2 mL) was heated at 110° C. for 16 h. The reaction mixture was diluted with ice-cold water and extracted with EtOAc. The combined organic extracts were washed with brine, dried over $Na_2SO_4$, and concentrated under reduced pressure. The residue was purified on a Redi-Sep pre-packed silica gel column eluting with 40-50% EtOAc in petroleum ether to provide tert-butyl 6-(4-(2,3-dimethylphenyl)-7-(4-methylthiazol-5-yl)-5,6,7,8-tetrahydroquinazolin-2-yl)-2,6-diazaspiro[3.4]octane-2-carboxylate (0.30 g, 56.5% yield) as a brown solid. m/z (ESI): 545.8 $(M+H)^+$.

The racemic mixture (0.30 g, 0.55 mmol) was separated with a ChiralPak IC (250×20 mm) column using a mobile phase of 75% liquid $CO_2$ and 25% EtOH to provide tert-butyl (R)-6-(4-(2,3-dimethylphenyl)-7-(4-methylthiazol-5-yl)-5,6,7,8-tetrahydroquinazolin-2-yl)-2,6-diazaspiro[3.4]octane-2-carboxylate as Peak 1 (0.10 g, 0.18 mmol) and tert-butyl (S)-6-(4-(2,3-dimethylphenyl)-7-(4-methylthiazol-5-yl)-5,6,7,8-tetrahydroquinazolin-2-yl)-2,6-diazaspiro[3.4]octane-2-carboxylate as Peak 2 (0.10 g, 0.18 mmol). The stereochemistry was arbitrary assigned and is not established.

Step 9: (R)-5-(4-(2,3-dimethylphenyl)-2-(2,6-diazaspiro[3.4]octan-6-yl)-5,6,7,8-tetrahydroquinazolin-7-yl)-4-methylthiazole hydrochloride and (S)-5-(4-(2,3-dimethylphenyl)-2-(2,6-diazaspiro[3.4]octan-6-yl)-5,6,7,8-tetrahydroquinazolin-7-yl)-4-methylthiazole hydrochloride To a solution of tert-butyl (R)-6-(4-(2,3-dimethylphenyl)-7-(4-methylthiazol-5-yl)-5,6,7,8-tetrahydroquinazolin-2-yl)-2,6-diazaspiro[3.4]octane-2-carboxylate (0.1 g, 0.183 mmol) in DCM (2 mL) was added 4M HCl in dioxane (0.458 mL, 1.832 mmol, Symax) at 0° C. and the reaction mixture was stirred at room temperature for 1 h. The reaction mixture was concentrated under reduced pressure and triturated with diethyl ether to provide (R)-5-(4-(2,3-dimethylphenyl)-2-(2,6-diazaspiro[3.4]octan-6-yl)-5,6,7,8-tetrahydroquinazolin-7-yl)-4-methylthiazole hydrochloride (0.085 g, 96% yield) as a light yellow gummy solid, which was used in next step without further purification. m/z (ESI): 446.3 $(M+H)^+$.

Following a similar procedure, tert-butyl (S)-6-(4-(2,3-dimethylphenyl)-7-(4-methylthiazol-5-yl)-5,6,7,8-tetrahydroquinazolin-2-yl)-2,6-diazaspiro[3.4]octane-2-carboxylate (0.1 g, 0.183 mmol) provided (S)-5-(4-(2,3-dimethylphenyl)-2-(2,6-diazaspiro[3.4]octan-6-yl)-5,6,7,8-tetrahydroquinazolin-7-yl)-4-methylthiazole hydrochloride (0.085 g, quantitative yield) as light yellow gummy solid, which was used in next step without further purification. m/z (ESI): 446.3 $(M+H)^+$.

Step 10: 1-(6-((7R)-4-(2,3-dimethylphenyl)-7-(4-methyl-1,3-thiazol-5-yl)-5,6,7,8-tetrahydro-2-quinazolinyl)-2,6-diazaspiro[3.4]octan-2-yl)-2-propen-1-one and 1-(6-((7S)-4-(2,3-dimethylphenyl)-7-(4-methyl-1,3-thiazol-5-yl)-5,6,7,8-tetrahydro-2-quinazolinyl)-2,6-diazaspiro[3.4]octan-2-yl)-2-propen-1-one To a solution of (R)-5-(4-(2,3-dimethylphenyl)-2-(2,6-diazaspiro[3.4]octan-6-yl)-5,6,7,8-tetrahydroquinazolin-7-yl)-4-methylthiazole hydrochloride (0.09 g, 0.187 mmol) and TEA (0.075 mL, 0.560 mmol) in DCM (2 mL) was added acryloyl chloride (0.017 g, 0.187 mmol, Symax Ltd.) at dropwise −78° C. and the reaction stirred for 15 min. The reaction mixture was diluted with water and extracted with DCM. The combined organic extracts were dried over $Na_2SO_4$, concentrated, and purified by preparative HPLC to provide 1-(6-((7R)-4-(2,3-dimethylphenyl)-7-(4-methyl-1,3-thiazol-5-yl)-5,6,7,8-tetrahydro-2-quinazolinyl)-2,6-diazaspiro[3.4]octan-2-yl)-2-propen-1-one (0.015 g, 16.08% yield, Example 22-1) as an off-white solid. $^1H$ NMR (400 MHz, DMSO-$d_6$) δ ppm 8.84 (s, 1H), 7.23-7.11 (m, 2H), 6.99-6.89 (m, 1H), 6.30 (dd, J=17.0, 10.3 Hz, 1H), 6.09 (dd, J=17.0, 2.3 Hz, 1H), 5.66 (dd, J=10.3, 2.4 Hz, 1H), 4.20 (d, J=8.3 Hz, 1H), 4.14 (d, J=8.5 Hz, 1H), 3.88 (m, 2H), 3.63 (d, J=9.5 Hz, 2H), 3.47-3.30 (m, 3H), 3.03-2.72 (m, 2H), 2.50 (s, 3H), 2.36 (s, 3H), 2.28 (s, 3H), 2.14 (td, J=6.8, 2.9 Hz, 2H), 1.97 (m, 2H), 1.80-1.70 (m, 2H). m/z (ESI): 500.3 $(M+H)^+$.

Following similar procedure, (S)-5-(4-(2,3-dimethylphenyl)-2-(2,6-diazaspiro[3.4]octan-6-yl)-5,6,7,8-tetrahydroquinazolin-7-yl)-4-methylthiazole hydrochloride (0.09 g, 0.187 mmol) provided 1-(6-((7S)-4-(2,3-dimethylphenyl)-7-(4-methyl-1,3-thiazol-5-yl)-5,6,7,8-tetrahydro-2-quinazolinyl)-2,6-diazaspiro[3.4]octan-2-yl)-2-propen-1-one (0.018 g, 19.30% yield. Example 22-2) as an off-white solid. $^1H$ NMR (400 MHz, DMSO-$d_6$) δ ppm 8.84 (s, 1H), 7.23-7.12 (m, 2H), 6.97-6.89 (m, 1H), 6.30 (dd, J=17.0, 10.3 Hz, 1H), 6.09 (dd, J=17.0, 2.3 Hz, 1H), 5.66 (dd, J=10.3, 2.3 Hz, 1H), 4.20 (d, J=8.6 Hz, 1H), 4.14 (d, J=8.6 Hz, 1H), 3.89-3.86 (m, 2H), 3.63 (d, J=10.4 Hz, 2H), 3.48-3.45 (m, 2H), 3.03 (dd, J=17.8, 5.1 Hz, 1H), 2.78-2.69 (m, 2H), 2.55 (s, 3H), 2.36 (s, 3H), 2.28 (s, 3H), 2.14 (td, J=6.7, 2.6 Hz, 2H), 1.97 (d, J=7.4 Hz, 2H), 1.80-1.70 (m, 2H). m/z (ESI): 500.3 $(M+H)^+$.

TABLE 14

Examples 22-3 to 22-4 were prepared following the procedure described in Method 22, Steps 1-9, above as follows:

| Ex.# | Chemical Structure | Name | Method changes | Reagent |
|---|---|---|---|---|
| 22-3 | 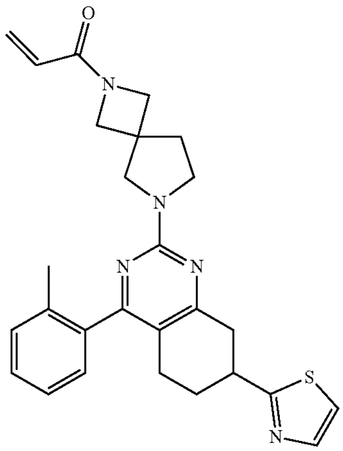 [SMILES: C=CC(=O)N1CC2(CCN(c3nc4c(c(-c5ccccc5C)n3)CCC(c3nccs3)C4)C2)C1] | 1-(6-((7R)-4-(2,3-dimethylphenyl)-7-(1,3-thiazol-2-yl)-5,6,7,8-tetrahydro-2-quinazolinyl)-2,6-diazaspiro[3.4]octan-2-yl)-2-propen-1-one\|1-(6-((7S)-4-(2,3-dimethylphenyl)-7-(1,3-thiazol-2-yl)-5,6,7,8-tetrahydro-2-quinazolinyl)-2,6-diazaspiro[3.4]octan-2-yl)-2-propen-1-one | Omit Steps 1 & 2 and chiral SFC after Step 8 | Step 3: 3-(thiazol-2-yl)cyclohex-2-en-1-one (WO 2007/092364) |

TABLE 14-continued

Examples 22-3 to 22-4 were prepared following the procedure described in Method 22, Steps 1-9, above as follows:

| Ex.# | Chemical Structure | Name | Method changes | Reagent |
|---|---|---|---|---|
| 22-4 | 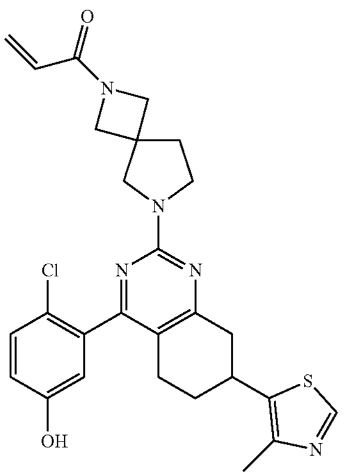 [SMILES: C=CC(=O)N1CC2(CCN(c3nc4c(c(-c5cc(O)ccc5Cl)n3)CCC(c3scnc3C)C4)C2)C1] | 1-(6-((7R)-4-(2-chloro-5-hydroxyphenyl)-7-(4-methyl-1,3-thiazol-5-yl)-5,6,7,8-tetrahydro-2-quinazolinyl)-2,6-diazaspiro[3.4]octan-2-yl)-2-propen-1-one\| 1-(6-((7S)-4-(2-chloro-5-hydroxyphenyl)-7-(4-methyl-1,3-thiazol-5-yl)-5,6,7,8-tetrahydro-2-quinazolinyl)-2,6-diazaspiro[3.4]octan-2-yl)-2-propen-1-one | Omit chiral SFC after Step 8 | Step 7: 4-chloro-3-(4,4,5,5-tetramethyl-1,3,2-dioxaborolan-2-yl)phenol (WO 2009/109743) |

Method 23

Example 23-1: 4-(3-Methyl-2-pyridinyl)-7-(4-methyl-1,3-thiazol-5-yl)-2-(2-(2-propenoyl)-2,6-diazaspiro[3.4]octan-6-yl)-5,6-dihydro-3-quinolinecarbonitrile

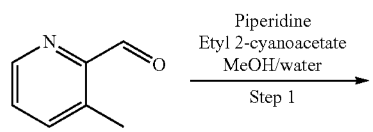

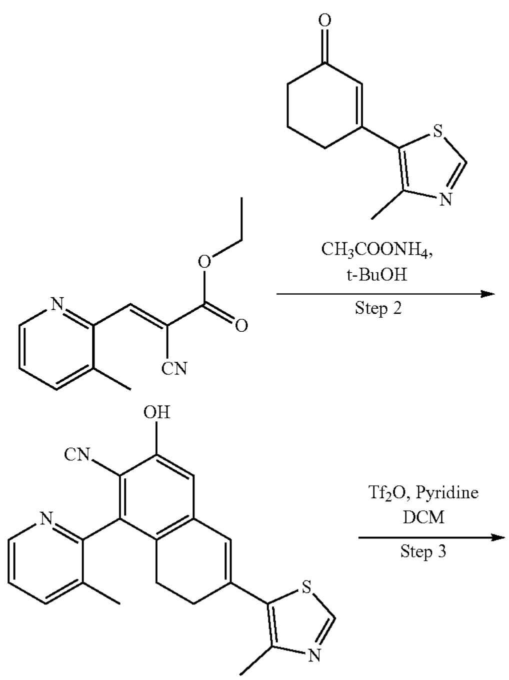

-continued

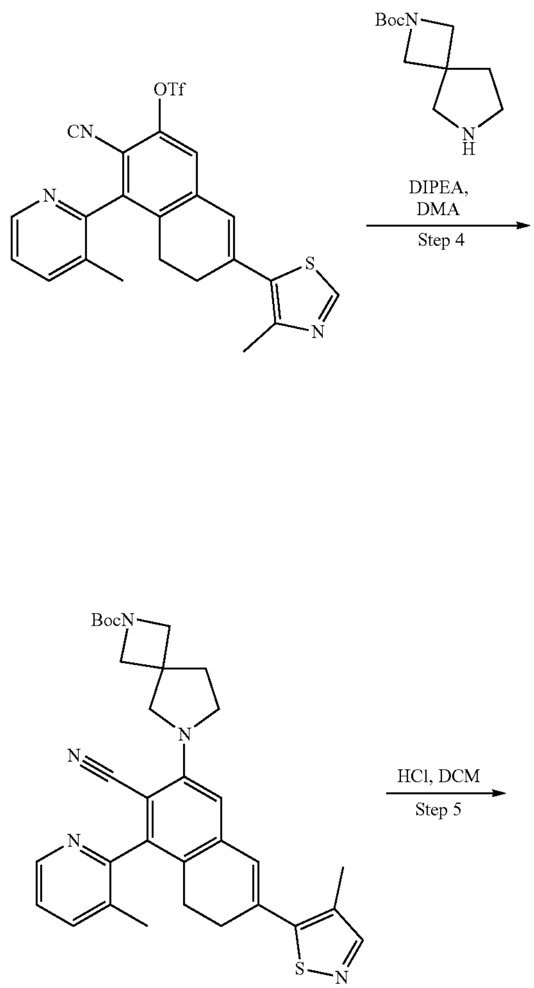

-continued

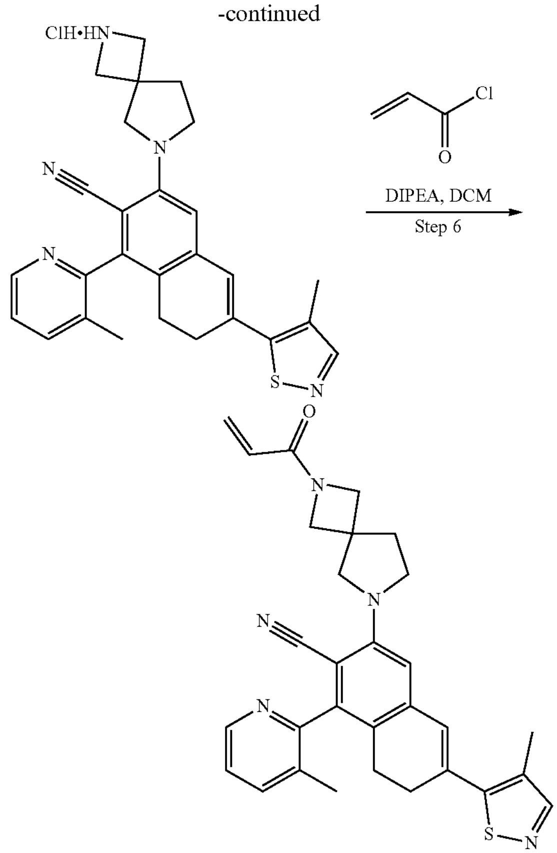

Example 23-1

Step 1: ethyl (E)-2-cyano-3-(3-methylpyridin-2-yl) acrylate

To a solution of ethyl 2-cyanoacetate (2.55 g, 22.52 mmol) and piperidine (0.405 mL, 4.09 mmol, Avra) in MeOH (40 mL) and water (10 mL) was added 3-methylpicolin-aldehyde (2.48 g, 20.47 mmol, WO 2006/004200) at room temperature. The resulting reaction mixture was stirred at room temperature for 2 h before it was diluted with water and extracted with EtOAc. The organic extracts were washed with brine, dried over $Na_2SO_4$, filtered and concentrated under reduced pressure. The residue was purified on a Redi-Sep pre-packed silica gel column eluting with 50-60% EtOAc in petroleum ether to provide ethyl (E)-2-cyano-3-(3-methylpyridin-2-yl)acrylate (3.5 g, 79% yield) as a yellow solid. $^1$H NMR (400 MHz, DMSO-$d_6$) δ ppm 8.60 (dd, J=4.6, 1.7 Hz, 1H), 8.48 (s, 1H), 7.82-7.80 (m, 1H), 7.50 (dd, J=7.8, 4.6 Hz, 1H), 4.35 (q, J=7.1 Hz, 2H), 2.48 (s, 3H), 1.33 (t, J=7.1 Hz, 3H).

Step 2: 2-hydroxy-4-(3-methylpyridin-2-yl)-7-(4-methylthiazol-5-yl)-5,6-dihydroquinoline-3-carbonitrile To a solution of 3-(4-methylthiazol-5-yl)cyclohex-2-en-1-one (0.5 g, 2.59 mmol, Example 22-1, step 2) and ethyl (E)-2-cyano-3-(3-methylpyridin-2-yl)acrylate (0.799 g, 2.59 mmol) in tert-butanol (2.5 mL) was added $NH_4OAc$ (1.99 g, 25.9 mmol, Avra Synthesis). The reaction mixture was stirred at 80° C. for 16 h. The reaction mixture was diluted with water and extracted with EtOAc. The organic extracts were washed with brine, dried over $Na_2SO_4$, and concentrated to provide 2-hydroxy-4-(3-methylpyridin-2-yl)-7-(4-methylthiazol-5-yl)-5,6-dihydroquinoline-3-carbonitrile (0.8 g crude) as a yellow gummy solid which was taken to the next step without further purification. m/z (ESI): 361.1 $(M+H)^+$.

Step 3: 3-cyano-4-(3-methylpyridin-2-yl)-7-(4-methylthiazol-5-yl)-5,6-dihydroquinolin-2-yl trifluoromethanesulfonate To a solution of 2-hydroxy-4-(3-methylpyridin-2-yl)-7-(4-methylthiazol-5-yl)-5,6-dihydroquinoline-3-carbonitrile (0.8 g, 0.999 mmol) in DCM (10 mL) were added pyridine (0.237 g, 3.00 mmol) and $Tf_2O$ (253 μL, 1.498 mmol, Spectrochem) at 0° C. The reaction mixture was stirred at 0° C. for 30 min. before it was concentrated under reduced pressure and co-evaporated with toluene to provide the 3-cyano-4-(3-methylpyridin-2-yl)-7-(4-methylthiazol-5-yl)-5,6-dihydroquinolin-2-yl trifluoromethanesulfonate (0.9 g crude) as a yellow solid. The crude material was taken to the next step without further purification. m/z (ESI): 493.0 $(M+H)^+$.

Step 4: tert-butyl 6-(3-cyano-4-(3-methylpyridin-2-yl)-7-(4-methylthiazol-5-yl)-5,6-dihydroquinolin-2-yl)-2,6-diazaspiro[3.4]octane-2-carboxylate To a solution of 3-cyano-4-(3-methylpyridin-2-yl)-7-(4-methylthiazol-5-yl)-5,6-dihydroquinolin-2-yl trifluoromethanesulfonate (0.9 g, 1.827 mmol), tert-butyl 2,6-diazaspiro[3.4]octane-2-carboxylate (388 mg, 1.827 mmol, PharmaBlocks) and DMA (10 mL) in a sealed tube was added DIPEA (0.95 mL, 5.48 mmol). The resulting reaction mixture was heated at 80° C. for 16 h. The reaction mass was diluted with water and extracted with EtOAc. The organic extracts were washed with brine, dried over $Na_2SO_4$, and concentrated under reduced pressure. The residue was purified on a Redi-Sep pre-packed silica gel column eluting with 15-20% EtOAc in petroleum ether to provide tert-butyl 6-(3-cyano-4-(3-methylpyridin-2-yl)-7-(4-methylthiazol-5-yl)-5,6-dihydroquinolin-2-yl)-2,6-diazaspiro-[3.4]octane-2-carboxylate (450 mg, 44.4% yield) as a yellow solid. $^1$H NMR (400 MHz, DMSO-$d_6$) δ ppm 9.02 (s, 1H), 8.54-8.52 (m, 1H), 7.83 (dd, J=8.1, 1.6 Hz, 1H), 7.42 (dd, J=7.8, 4.8 Hz, 1H), 6.68 (d, J=1.5 Hz, 1H), 3.86-3.74 (m, 8H), 2.65 (t, J=8.1 Hz, 2H), 2.56 (s, 3H), 2.51-2.39 (m, 2H), 2.42-2.23 (m, 2H), 2.15 (s, 3H), 1.39 (s, 9H). m/z (ESI): 555.2 $(M+H)^+$.

Step 5: 4-(3-methylpyridin-2-yl)-7-(4-methylthiazol-5-yl)-2-(2,6-diazaspiro[3.4]octan-6-yl)-5,6-dihydroquinoline-3-carbonitrile hydrochloride To a solution of tert-butyl 6-(3-cyano-4-(3-methylpyridin-2-yl)-7-(4-methylthiazol-5-yl)-5,6-dihydroquinolin-2-yl)-2,6-diazaspiro[3.4]octane-2-carboxylate (0.45 g, 0.811 mmol) in DCM (5 mL) was added 4M HCl in dioxane (406 μL, 1.622 mmol, Symax) and the reaction stirred at room temperature for 3 h. The reaction mixture was concentrated under reduced pressure and triturated with diethyl ether to obtain 4-(3-methylpyridin-2-yl)-7-(4-methylthiazol-5-yl)-2-(2,6-diazaspiro[3.4]octan-6-yl)-5,6-dihydroquinoline-3-carbonitrile hydrochloride (0.39 g, 0.794 mmol, 98% yield) as a pale yellow gummy solid which was used in the next step without further purification. m/z (ESI): 454.0 $(M+H)^+$.

Step 6: 4-(3-methyl-2-pyridinyl)-7-(4-methyl-1,3-thiazol-5-yl)-2-(2-(2-propenoyl)-2,6-diazaspiro[3.4]octan-6-yl)-5,6-dihydro-3-quinolinecarbonitrile To a solution of 4-(3-methylpyridin-2-yl)-7-(4-methylthiazol-5-yl)-2-(2,6-diazaspiro[3.4]octan-6-yl)-5,6-dihydroquinoline-3-carbonitrile hydrochloride (0.39 g, 0.794 mmol) and $Et_3N$ (332 μL, 2.383 mmol) in DCM (5 mL) was added acryloyl chloride (0.072 g, 0.794 mmol, Symax) at dropwise 0° C. and the reaction stirred for 10 min. The reaction mixture was diluted with water and extracted with DCM. The combined organic layers were washed with brine, dried over $Na_2SO_4$, concentrated, and purified by reverse phase preparative HPLC to provide 2-(2-acryloyl-2,6-diazaspiro[3.4]octan-6-yl)-4-(3-methylpyridin-2-yl)-7-(4-methylthiazol-5-yl)-5,6-dihydroquinoline-3-carbonitrile (0.095 g, 23.52% yield) as a yellow solid. $^1H$ NMR (400 MHz, DMSO-$d_6$) δ ppm 9.02 (s, 1H), 8.54 (dd, J=4.9, 1.6 Hz, 1H), 7.88-7.78 (m, 1H), 7.42 (dd, J=7.8, 4.8 Hz, 1H), 6.67 (d, J=1.5 Hz, 1H), 6.30 (dd, J=16.9, 10.4 Hz, 1H), 6.10 (dd, J=17.0, 2.3 Hz, 1H), 5.67 (dd, J=10.3, 2.3 Hz, 1H), 4.27 (dd, J=8.7, 3.5 Hz, 1H), 4.16 (dd, J=8.7, 4.0 Hz, 1H), 4.00-3.83 (m, 4H), 3.75 (t, J=6.5 Hz, 2H), 2.66-2.62 (m, 2H), 2.56 (s, 3H), 2.40-2.17 (m, 4H), 2.14 (s, 3H). m/z (ESI): 509.0 $(M+H)^+$.

TABLE 15

Examples 23-2 to 23-61 were prepared following the procedure described in Method 23, Steps 1-6, above as follows:

| Ex.# | Chemical Structure | Name | Method changes | Reagent |
| --- | --- | --- | --- | --- |
| 23-2 | 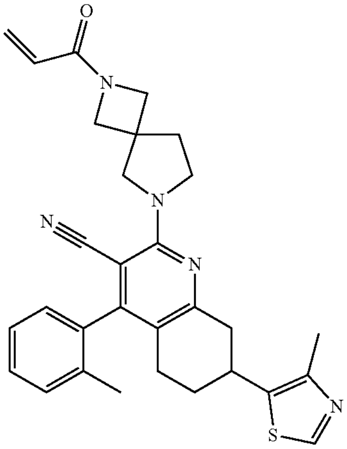 [SMILES: C=CC(=O)N1CC2(CCN(c3nc4c(c(-c5ccccc5C)c3C#N)CCC(c3scnc3C)C4)C2)C1] | (7R)-4-(2-methylphenyl)-7-(4-methyl-1,3-thiazol-5-yl)-2-(2-(2-propenoyl)-2,6-diazaspiro[3.4]octan-6-yl)-5,6,7,8-tetrahydro-3-quinolinecarbonitrile (7S)-4-(2-methylphenyl)-7-(4-methyl-1,3-thiazol-5-yl)-2-(2-(2-propenoyl)-2,6-diazaspiro[3.4]octan-6-yl)-5,6,7,8-tetrahydro-3-quinolinecarbonitrile | See additional hydrogenation below to obtain starting material for Step 2 | Step 1: 2-methylbenzaldehyde (Combi-Blocks). Step 2: 3-(4-methylthiazol-5-yl)cyclohexan-1-one |
| 23-3 | 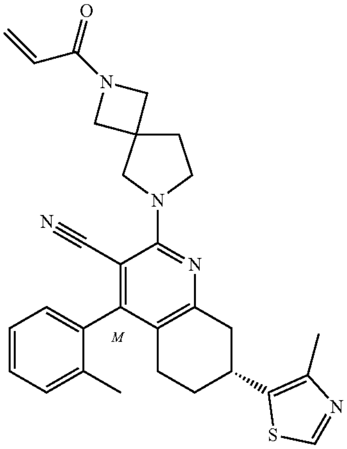 | (M)-(7R)-4-(2-methylphenyl)-7-(4-methyl-1,3-thiazol-5-yl)-2-(2-(2-propenoyl)-2,6-diazaspiro[3.4]octan-6-yl)-5,6,7,8-tetrahydro-3-quinolinecarbonitrile ($4^{th}$ eluting isomer) | See additional hydrogenation step from Example 23-2. See isomer separation conditions below | Step 1: 2-methylbenzaldehyde (Combi-Blocks). Step 2: 3-(4-methylthiazol-5-yl)cyclohexan-1-one |

TABLE 15-continued

| Examples 23-2 to 23-61 were prepared following the procedure described in Method 23, Steps 1-6, above as follows: | | | | |
|---|---|---|---|---|
| Ex.# | Chemical Structure | Name | Method changes | Reagent |
| 23-4 | 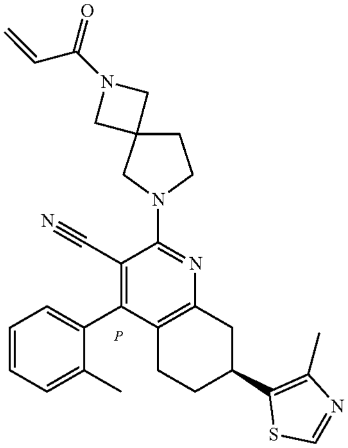 | (P)-(7S)-4-(2-methylphenyl)-7-(4-methyl-1,3-thiazol-5-yl)-2-(2-(2-propenoyl)-2,6-diazaspiro[3.4]octan-6-yl)-5,6,7,8-tetrahydro-3-quinolinecarbonitrile (3rd eluting isomer) | See additional hydrogenation step from Example 23-2. See isomer separation conditions below | Step 1: 2-methylbenzaldehyde (Combi-Blocks). Step 2: 3-(4-methylthiazol-5-yl)cyclohexan-1-one |
| 23-5 | 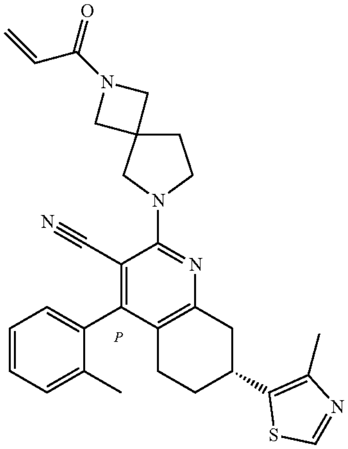 | (P)-(7R)-4-(2-methylphenyl)-7-(4-methyl-1,3-thiazol-5-yl)-2-(2-(2-propenoyl)-2,6-diazaspiro[3.4]octan-6-yl)-5,6,7,8-tetrahydro-3-quinolinecarbonitrile (1st eluting isomer) | See additional hydrogenation step from Example 23-2. See isomer separation conditions below | Step 1: 2-methylbenzaldehyde (Combi-Blocks). Step 2: 3-(4-methylthiazol-5-yl)cyclohexan-1-one |
| 23-6 | 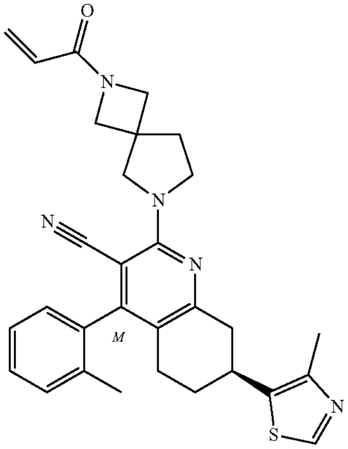 | (M)-(7S)-4-(2-methylphenyl)-7-(4-methyl-1,3-thiazol-5-yl)-2-(2-(2-propenoyl)-2,6-diazaspiro[3.4]octan-6-yl)-5,6,7,8-tetrahydro-3-quinolinecarbonitrile (2nd eluting isomer) | See additional hydrogenation step from Example 23-2. See isomer separation conditions below | Step 1: 2-methylbenzaldehyde (Combi-Blocks). Step 2: 3-(4-methylthiazol-5-yl)cyclohexan-1-one |

TABLE 15-continued

Examples 23-2 to 23-61 were prepared following the procedure described in Method 23, Steps 1-6, above as follows:

| Ex.# | Chemical Structure | Name | Method changes | Reagent |
|---|---|---|---|---|
| 23-7 | 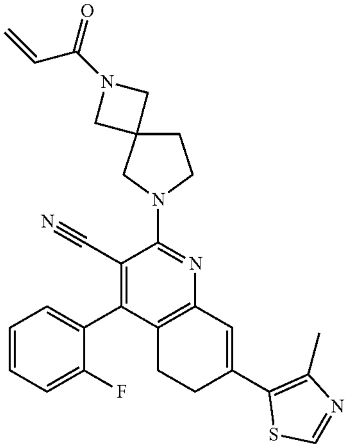 [SMILES: C=CC(=O)N1CC2(CCN(c3nc4c(c(-c5ccccc5F)c3C#N)CCC(c3scnc3C)=C4)C2)C1] | 4-(2-fluorophenyl)-7-(4-methyl-1,3-thiazol-5-yl)-2-(2-(2-propenoyl)-2,6-diazaspiro[3.4]octan-6-yl)-5,6-dihydro-3-quinolinecarbonitrile | | Step 1: 2-fluorobenzaldehyde (Combi-Blocks) |
| 23-8 | 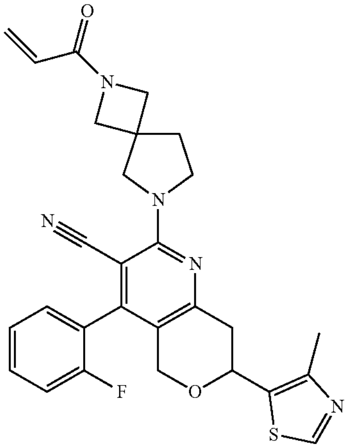 [SMILES: C=CC(=O)N1CC2(CCN(c3nc4c(c(-c5ccccc5F)c3C#N)COC(c3scnc3C)C4)C2)C1] | (7R)-4-(2-fluorophenyl)-7-(4-methyl-1,3-thiazol-5-yl)-2-(2-(2-propenoyl)-2,6-diazaspiro[3.4]octan-6-yl)-7,8-dihydro-5H-pyrano[4,3-b]pyridine-3-carbonitrile(7S)-4-(2-fluorophenyl)-7-(4-methyl-1,3-thiazol-5-yl)-2-(2-(2-propenoyl)-2,6-diazaspiro[3.4]octan-6-yl)-7,8-dihydro-5H-pyrano[4,3-b]pyridine-3-carbonitrile | | Step 1: 2-fluorobenzaldehyde (Combi-Blocks). Step 2: Intermediate 120 |
| 23-9 | 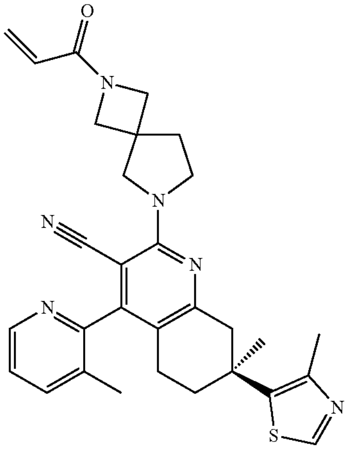 [SMILES: C=CC(=O)N1CC2(CCN(c3nc4c(c(-c5ncccc5C)c3C#N)CC[C@](C)(c3scnc3C)C4)C2)C1] | (7S)-7-methyl-4-(3-methyl-2-pyridinyl)-7-(4-methyl-1,3-thiazol-5-yl)-2-(2-(2-propenoyl)-2,6-diazaspiro[3.4]octan-6-yl)-5,6,7,8-tetrahydro-3-quinolinecarbonitrile | | Step 2: Intermediate 121 |

TABLE 15-continued

| Ex.# | Chemical Structure | Name | Method changes | Reagent |
|---|---|---|---|---|
| Examples 23-2 to 23-61 were prepared following the procedure described in Method 23, Steps 1-6, above as follows: | | | | |
| 23-10 | 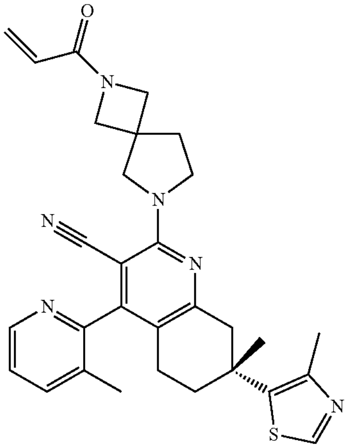 [SMILES: C=CC(=O)N1CC2(CCN(c3nc4c(c(-c5ncccc5C)c3C#N)CC[C@@](C)(c3scnc3C)C4)C2)C1] | (7R)-7-methyl-4-(3-methyl-2-pyridinyl)-7-(4-methyl-1,3-thiazol-5-yl)-2-(2-(2-propenoyl)-2,6-diazaspiro[3.4]octan-6-yl)-5,6,7,8-tetrahydro-3-quinolinecarbonitrile | | Step 2: Intermediate 121 |
| 23-11 | 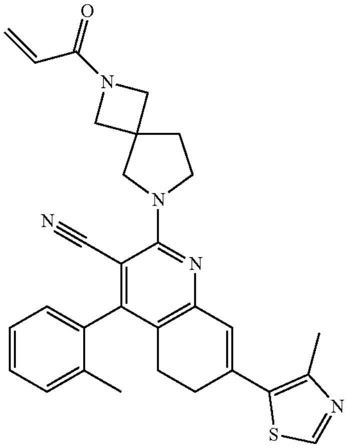 [SMILES: C=CC(=O)N1CC2(CCN(c3nc4c(c(-c5ccccc5C)c3C#N)CCC(c3scnc3C)=C4)C2)C1] | 4-(2-methylphenyl)-7-(4-methyl-1,3-thiazol-5-yl)-2-(2-(2-propenoyl)-2,6-diazaspiro[3.4]octan-6-yl)-5,6-dihydro-3-quinolinecarbonitrile | | Step 1: 2-methylbenzaldehyde (Combi-Blocks) |
| 23-12 | 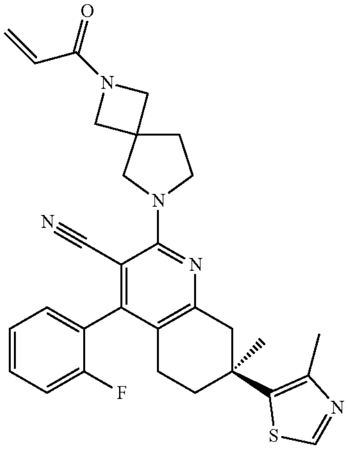 [SMILES: C=CC(=O)N1CC2(CCN(c3nc4c(c(-c5ccccc5F)c3C#N)CC[C@](C)(c3scnc3C)C4)C2)C1] | (7S)-4-(2-fluorophenyl)-7-methyl-7-(4-methyl-1,3-thiazol-5-yl)-2-(2-(2-propenoyl)-2,6-diazaspiro[3.4]octan-6-yl)-5,6,7,8-tetrahydro-3-quinolinecarbonitrile | | Step 1: 2-fluorobenzaldehyde (Combi-Blocks). Step 2: Intermediate 121 |

TABLE 15-continued

| Examples 23-2 to 23-61 were prepared following the procedure described in Method 23, Steps 1-6, above as follows: | | | | |
|---|---|---|---|---|
| Ex.# | Chemical Structure | Name | Method changes | Reagent |
| 23-13 | 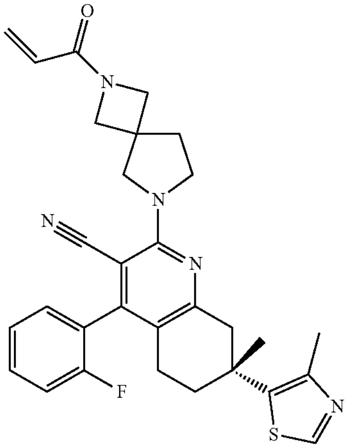 [SMILES: C=CC(=O)N1CC2(CCN(c3nc4c(c(-c5ccccc5F)c3C#N)CC[C@@](C)(c3scnc3C)C4)C2)C1] | (7R)-4-(2-fluorophenyl)-7-methyl-7-(4-methyl-1,3-thiazol-5-yl)-2-(2-(2-propenoyl)-2,6-diazaspiro[3.4]octan-6-yl)-5,6,7,8-tetrahydro-3-quinolinecarbonitrile | | Step 1: 2-fluorobenzaldehyde (Combi-Blocks). Step 2: Intermediate 121 |
| 23-14 | 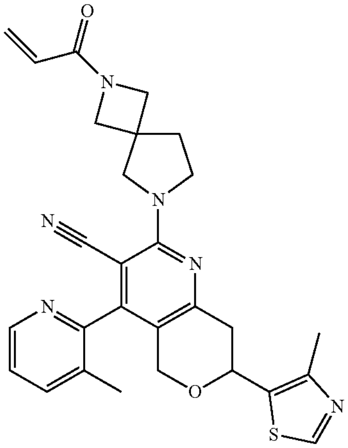 [SMILES: C=CC(=O)N1CC2(CCN(c3nc4c(c(-c5ncccc5C)c3C#N)COC(c3scnc3C)C4)C2)C1] | (7R)-4-(3-methyl-2-pyridinyl)-7-(4-methyl-1,3-thiazol-5-yl)-2-(2-(2-propenoyl)-2,6-diazaspiro[3.4]octan-6-yl)-7,8-dihydro-5H-pyrano[4,3-b]pyridine-3-carbonitrile (7S)-4-(3-methyl-2-pyridinyl)-7-(4-methyl-1,3-thiazol-5-yl)-2-(2-(2-propenoyl)-2,6-diazaspiro[3.4]octan-6-yl)-7,8-dihydro-5H-pyrano[4,3-b]pyridine-3-carbonitrile | | Step 2: Intermediate 120 |
| 23-15 | 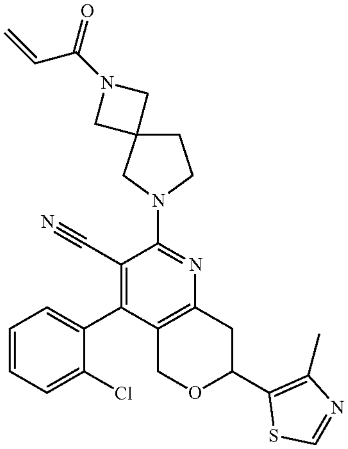 [SMILES: C=CC(=O)N1CC2(CCN(c3nc4c(c(-c5ccccc5Cl)c3C#N)COC(c3scnc3C)C4)C2)C1] | (7R)-4-(2-chlorophenyl)-7-(4-methyl-1,3-thiazol-5-yl)-2-(2-(2-propenoyl)-2,6-diazaspiro[3.4]octan-6-yl)-7,8-dihydro-5H-pyrano[4,3-b]pyridine-3-carbonitrile (7S)-4-(2-chlorophenyl)-7-(4-methyl-1,3-thiazol-5-yl)-2-(2-(2-propenoyl)-2,6-diazaspiro[3.4]octan-6-yl)-7,8-dihydro-5H-pyrano[4,3-b]pyridine-3-carbonitrile | | Step 1: 2-chlorobenzaldehyde (Sigma-Aldrich). Step 2: Intermediate 120 |

TABLE 15-continued

| Examples 23-2 to 23-61 were prepared following the procedure described in Method 23, Steps 1-6, above as follows: | | | | |
|---|---|---|---|---|
| Ex.# | Chemical Structure | Name | Method changes | Reagent |
| 23-16 | 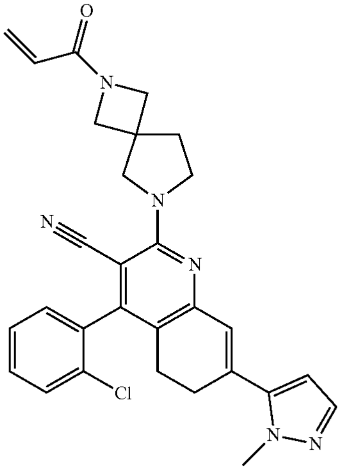 [SMILES: C=CC(=O)N1CC2(CCN(c3nc4c(c(-c5ccccc5Cl)c3C#N)CCC(c3ccnn3C)=C4)C2)C1] | 4-(2-chlorophenyl)-7-(1-methyl-1H-pyrazol-5-yl)-2-(2-(2-propenoyl)-2,6-diazaspiro[3.4]octan-6-yl)-3-quinolinecarbonitrile | | Step 1: 2-chlorobenzaldehyde (Sigma-Aldrich). Step 2: (1-methyl-1H-pyrazol-5-yl)boronic acid (Combi-Blocks) |
| 23-17 | 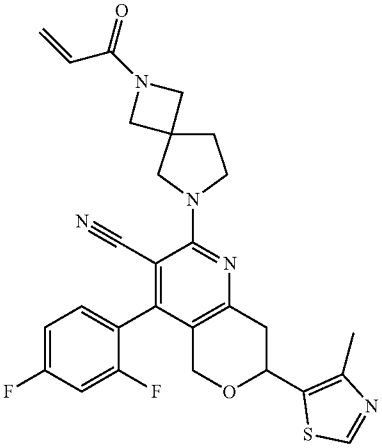 [SMILES: C=CC(=O)N1CC2(CCN(c3nc4c(c(-c5ccc(F)cc5F)c3C#N)COC(c3scnc3C)C4)C2)C1] | (7R)-4-(2,4-difluorophenyl)-7-(4-methyl-1,3-thiazol-5-yl)-2-(2-(2-propenoyl)-2,6-diazaspiro[3.4]octan-6-yl)-7,8-dihydro-5H-pyrano[4,3-b]pyridine-3-carbonitrile (7S)-4-(2,4-difluorophenyl)-7-(4-methyl-1,3-thiazol-5-yl)-2-(2-(2-propenoyl)-2,6-diazaspiro[3.4]octan-6-yl)-7,8-dihydro-5H-pyrano[4,3-b]pyridine-3-carbonitrile | | Step 1: 2,4-difluorobenzaldehyde (Combi-Blocks). Step 2: Intermediate 120 |
| 23-18 | 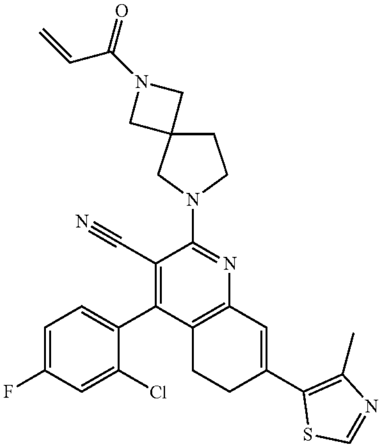 [SMILES: C=CC(=O)N1CC2(CCN(c3nc4c(c(-c5ccc(F)cc5Cl)c3C#N)CCC(c3scnc3C)=C4)C2)C1] | 4-(2-chloro-4-fluorophenyl)-7-(4-methyl-1,3-thiazol-5-yl)-2-(2-(2-propenoyl)-2,6-diazaspiro[3.4]octan-6-yl)-5,6-dihydro-3-quinolinecarbonitrile | | Step 1: 2-chloro-4-fluoro-benzaldehyde (Eur. J. Org. Chem. (2012), 2012(2), 260-263) |

TABLE 15-continued

| Examples 23-2 to 23-61 were prepared following the procedure described in Method 23, Steps 1-6, above as follows: | | | | |
|---|---|---|---|---|
| Ex.# | Chemical Structure | Name | Method changes | Reagent |
| 23-19 | 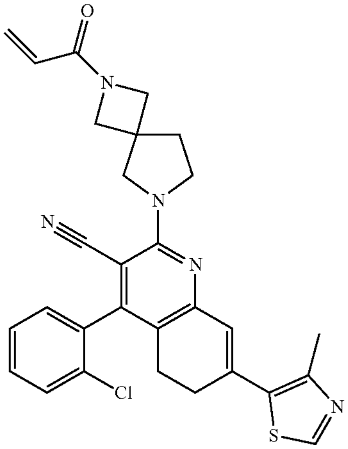 | 4-(2-chlorophenyl)-7-(4-methyl-1,3-thiazol-5-yl)-2-(2-(2-propenoyl)-2,6-diazaspiro[3.4]octan-6-yl)-5,6-dihydro-3-quinolinecarbonitrile | | Step 1: 2-chloro-benzaldehyde (Sigma-Aldrich) |
| 23-20 | 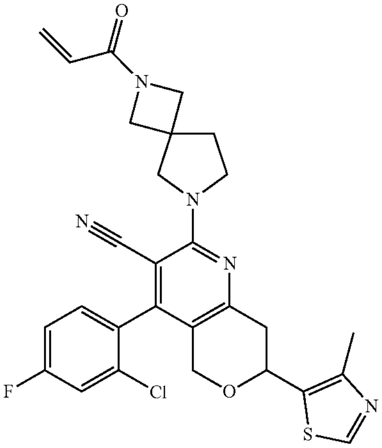 | (7R)-4-(2-chloro-4-fluorophenyl)-7-(4-methyl-1,3-thiazol-5-yl)-2-(2-(2-propenoyl)-2,6-diazaspiro[3.4]octan-6-yl)-7,8-dihydro-5H-pyrano[4,3-b]pyridine-3-carbonitrile (7S)-4-(2-chloro-4-fluorophenyl)-7-(4-methyl-1,3-thiazol-5-yl)-2-(2-(2-propenoyl)-2,6-diazaspiro[3.4]octan-6-yl)-7,8-dihydro-5H-pyrano[4,3-b]pyridine-3-carbonitrile | | Step 1: 2-chloro-4-fluoro-benzaldehyde (Eur. J. Org. Chem. (2012), 2012(2), 260-263). Step 2: Intermediate 120 |
| 23-21 | 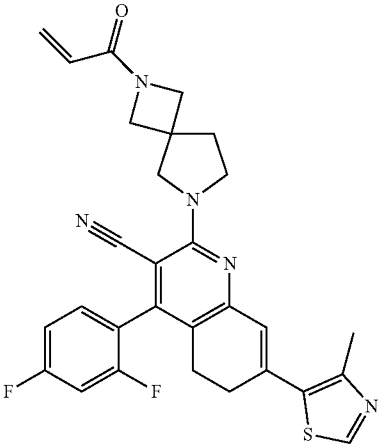 [SMILES: C=CC(=O)N1CC2(CCN(c3nc4c(c(-c5ccc(F)cc5F)c3C#N)CCC(c3scnc3C)=C4)C2)C1] | 4-(2,4-difluorophenyl)-7-(4-methyl-1,3-thiazol-5-yl)-2-(2-(2-propenoyl)-2,6-diazaspiro[3.4]octan-6-yl)-5,6-dihydro-3-quinolinecarbonitrile | | Step 1: 2,4-difluorobenzaldehyde (Combi-Blocks). |

TABLE 15-continued

| Ex.# | Chemical Structure | Name | Method changes | Reagent |
|---|---|---|---|---|
| Examples 23-2 to 23-61 were prepared following the procedure described in Method 23, Steps 1-6, above as follows: | | | | |
| 23-22 | 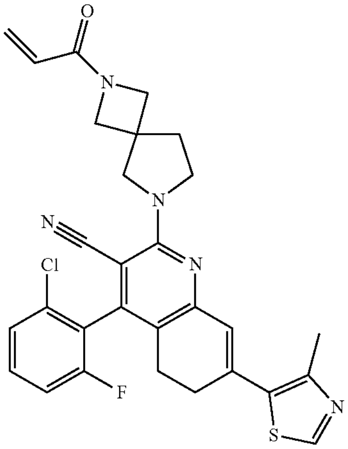 [SMILES: C=CC(=O)N1CC2(CCN(c3nc4c(c(-c5c(F)cccc5Cl)c3C#N)CCC(c3scnc3C)=C4)C2)C1] | 4-(2-chloro-6-fluorophenyl)-7-(4-methyl-1,3-thiazol-5-yl)-2-(2-(2-propenoyl)-2,6-diazaspiro[3.4]octan-6-yl)-5,6-dihydro-3-quinolinecarbonitrile | | Step 1: 2-chloro-6-fluoro-benzaldehyde (Syn. Comm. (2008), 38(15), 2638-2645) |
| 23-23 | 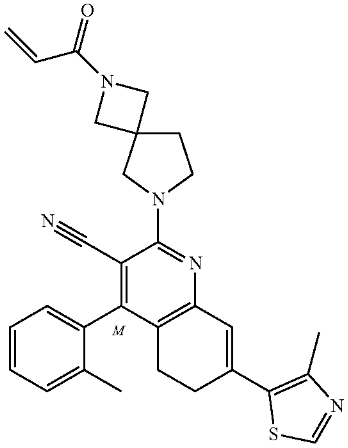 | (M)-4-(2-methylphenyl)-7-(4-methyl-1,3-thiazol-5-yl)-2-(2-(2-propenoyl)-2,6-diazaspiro[3.4]octan-6-yl)-5,6-dihydro-3-quinolinecarbonitrile (1$^{st}$ eluting isomer) | See atropisomer separation conditions below | Step 1: 2-methylbenzaldehyde (Combi-Blocks). |
| 23-24 | 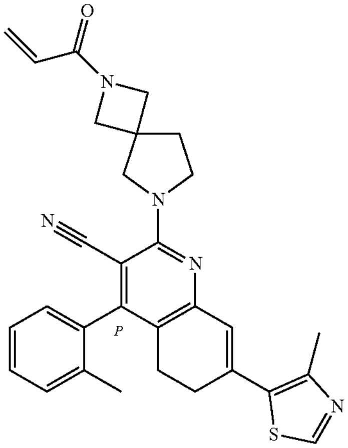 | (P)-4-(2-methylphenyl)-7-(4-methyl-1,3-thiazol-5-yl)-2-(2-(2-propenoyl)-2,6-diazaspiro[3.4]octan-6-yl)-5,6-dihydro-3-quinolinecarbonitrile (2$^{nd}$ eluting isomer) | See atropisomer separation conditions below | Step 1: 2-methylbenzaldehyde (Combi-Blocks). |

TABLE 15-continued

| Examples 23-2 to 23-61 were prepared following the procedure described in Method 23, Steps 1-6, above as follows: | | | | |
|---|---|---|---|---|
| Ex.# | Chemical Structure | Name | Method changes | Reagent |
| 23-25 | 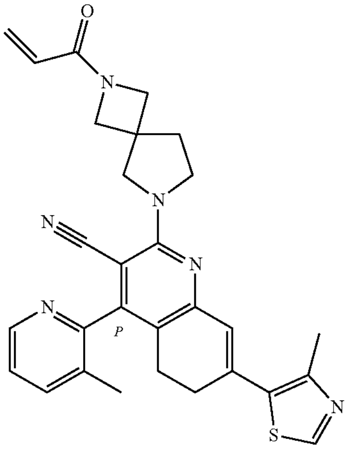 | (P)-4-(3-methyl-2-pyridinyl)-7-(4-methyl-1,3-thiazol-5-yl)-2-(2-(2-propenoyl)-2,6-diazaspiro[3.4]octan-6-yl)-5,6-dihydro-3-quinolinecarbonitrile (1st eluting isomer) | See atropisomer separation conditions below | |
| 23-26 | 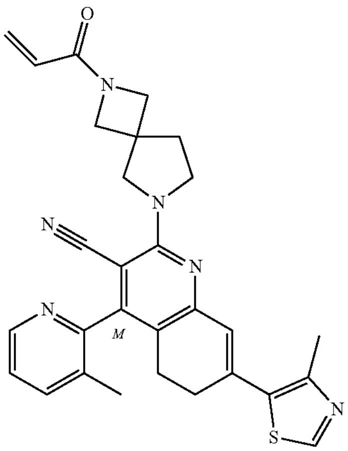 | (M)-4-(3-methyl-2-pyridinyl)-7-(4-methyl-1,3-thiazol-5-yl)-2-(2-(2-propenoyl)-2,6-diazaspiro[3.4]octan-6-yl)-5,6-dihydro-3-quinolinecarbonitrile (2nd eluting isomer) | See atropisomer separation conditions below | |
| 23-27 | 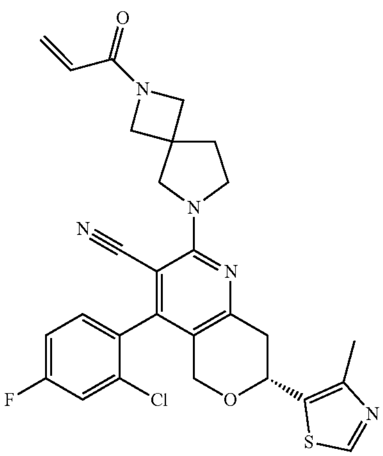 [SMILES: C=CC(=O)N1CC2(CCN(c3nc4c(c(-c5ccc(F)cc5Cl)c3C#N)CO[C@@H](c3scnc3C)C4)C2)C1] | (7R)-4-(2-chloro-4-fluorophenyl)-7-(4-methyl-1,3-thiazol-5-yl)-2-(2-(2-propenoyl)-2,6-diazaspiro[3.4]octan-6-yl)-7,8-dihydro-5H-pyrano[4,3-b]pyridine-3-carbonitrile (1st eluting isomer) | See isomer separation conditions below | Step 1: 2-chloro-4-fluoro-benzaldehyde (Eur. J. Org. Chem. (2012), 2012(2), 260-263). Step 2: Intermediate 120 |

TABLE 15-continued

| Examples 23-2 to 23-61 were prepared following the procedure described in Method 23, Steps 1-6, above as follows: | | | | |
|---|---|---|---|---|
| Ex.# | Chemical Structure | Name | Method changes | Reagent |
| 23-28 | 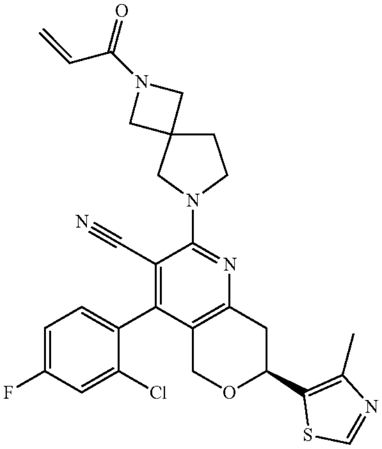 [SMILES: C=CC(=O)N1CC2(CCN(c3nc4c(c(-c5ccc(F)cc5Cl)c3C#N)CO[C@H](c3scnc3C)C4)C2)C1] | (7S)-4-(2-chloro-4-fluorophenyl)-7-(4-methyl-1,3-thiazol-5-yl)-2-(2-(2-propenoyl)-2,6-diazaspiro[3.4]octan-6-yl)-7,8-dihydro-5H-pyrano[4,3-b]pyridine-3-carbonitrile (2$^{nd}$ eluting isomer) | See isomer separation conditions below | Step 1: 2-chloro-4-fluoro-benzaldehyde (Eur. J. Org. Chem. (2012), 2012(2), 260-263). Step 2: Intermediate 120 |
| 23-29 | 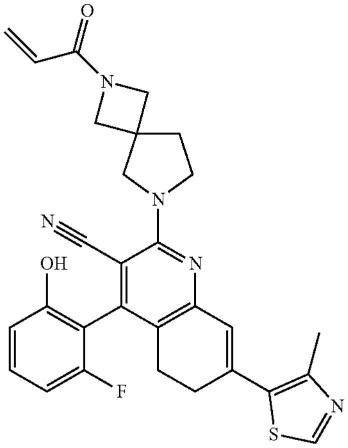 [SMILES: C=CC(=O)N1CC2(CCN(c3nc4c(c(-c5c(O)cccc5F)c3C#N)CCC(c3scnc3C)=C4)C2)C1] | 4-(2-fluoro-6-hydroxyphenyl)-7-(4-methyl-1,3-thiazol-5-yl)-2-(2-(2-propenoyl)-2,6-diazaspiro[3.4]octan-6-yl)-5,6-dihydro-3-quinolinecarbonitrile | | Step 1: 2-fluoro-6-hydroxy-benzaldehyde (WO 2009/125606) |
| 23-30 | 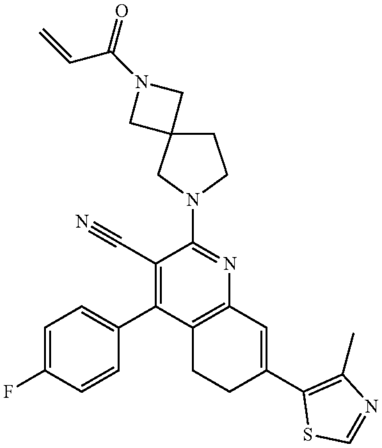 [SMILES: C=CC(=O)N1CC2(CCN(c3nc4c(c(-c5ccc(F)cc5)c3C#N)CCC(c3scnc3C)=C4)C2)C1] | 4-(4-fluorophenyl)-7-(4-methyl-1,3-thiazol-5-yl)-2-(2-(2-propenoyl)-2,6-diazaspiro[3.4]octan-6-yl)-5,6-dihydro-3-quinolinecarbonitrile | | Step 1: 4-fluoro-benzaldehyde (Combi-Blocks) |

TABLE 15-continued

Examples 23-2 to 23-61 were prepared following the procedure described in Method 23, Steps 1-6, above as follows:

| Ex.# | Chemical Structure | Name | Method changes | Reagent |
|---|---|---|---|---|
| 23-31 | 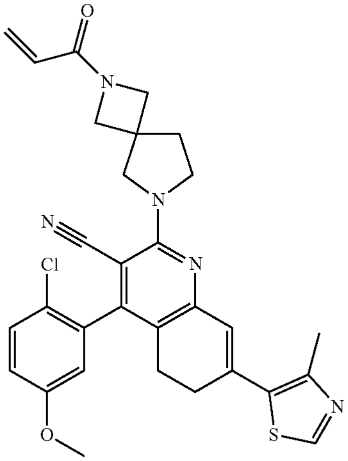 | 4-(2-chloro-5-methoxyphenyl)-7-(4-methyl-1,3-thiazol-5-yl)-2-(2-(2-propenoyl)-2,6-diazaspiro[3.4]octan-6-yl)-5,6-dihydro-3-quinolinecarbonitrile | | Step 1: 2-chloro-5-methoxy-benzaldehyde (Org. Lett. (2019), 21(10), 3692-3695) |
| 23-32 | 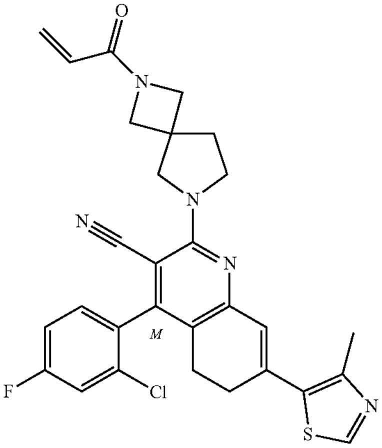 | (M)-4-(2-chloro-4-fluorophenyl)-7-(4-methyl-1,3-thiazol-5-yl)-2-(2-(2-propenoyl)-2,6-diazaspiro[3.4]octan-6-yl)-5,6-dihydro-3-quinolinecarbonitrile (2nd eluting isomer) | See atropisomer separation conditions below | Step 1: 2-chloro-4-fluoro-benzaldehyde (Eur. J. Org. Chem. (2012), 2012(2), 260-263) |
| 23-33 | 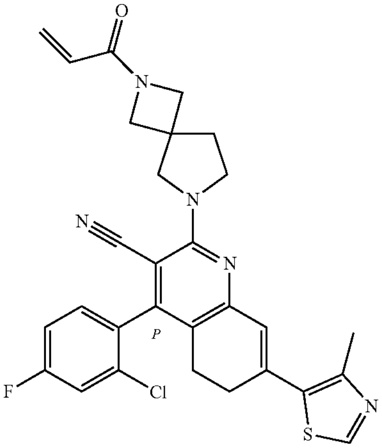 | (P)-4-(2-chloro-4-fluorophenyl)-7-(4-methyl-1,3-thiazol-5-yl)-2-(2-(2-propenoyl)-2,6-diazaspiro[3.4]octan-6-yl)-5,6-dihydro-3-quinolinecarbonitrile (1st eluting isomer) | See atropisomer separation conditions below | Step 1: 2-chloro-4-fluoro-benzaldehyde (Eur. J. Org. Chem. (2012), 2012(2), 260-263) |

TABLE 15-continued

| Examples 23-2 to 23-61 were prepared following the procedure described in Method 23, Steps 1-6, above as follows: | | | | |
|---|---|---|---|---|
| Ex.# | Chemical Structure | Name | Method changes | Reagent |
| 23-34 | 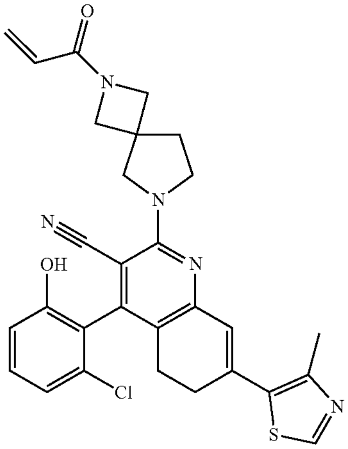 [SMILES: C=CC(=O)N1CC2(CCN(c3nc4c(c(-c5c(O)cccc5Cl)c3C#N)CCC(c3scnc3C)=C4)C2)C1] | 4-(2-chloro-6-hydroxyphenyl)-7-(4-methyl-1,3-thiazol-5-yl)-2-(2-(2-propenoyl)-2,6-diazaspiro[3.4]octan-6-yl)-5,6-dihydro-3-quinolinecarbonitrile | | Step 1: 2-chloro-6-hydroxybenzaldehyde (WO 2009/062308) |
| 23-35 | 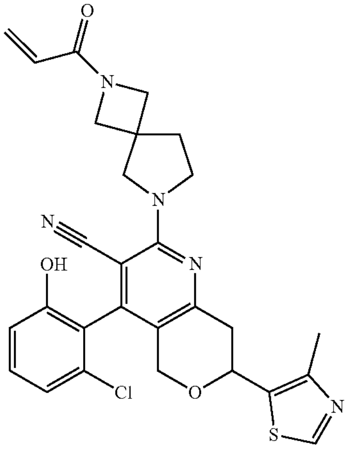 [SMILES: C=CC(=O)N1CC2(CCN(c3nc4c(c(-c5c(O)cccc5Cl)c3C#N)COC(c3scnc3C)C4)C2)C1] | (7R)-4-(2-chloro-6-hydroxyphenyl)-7-(4-methyl-1,3-thiazol-5-yl)-2-(2-(2-propenoyl)-2,6-diazaspiro[3.4]octan-6-yl)-7,8-dihydro-5H-pyrano[4,3-b]pyridine-3-carbonitrile (7S)-4-(2-chloro-6-hydroxyphenyl)-7-(4-methyl-1,3-thiazol-5-yl)-2-(2-(2-propenoyl)-2,6-diazaspiro[3.4]octan-6-yl)-7,8-dihydro-5H-pyrano[4,3-b]pyridine-3-carbonitrile | | Step 1: 2-chloro-6-hydroxybenzaldehyde (WO 2009/062308). Step 2: Intermediate 120 |
| 23-36 | 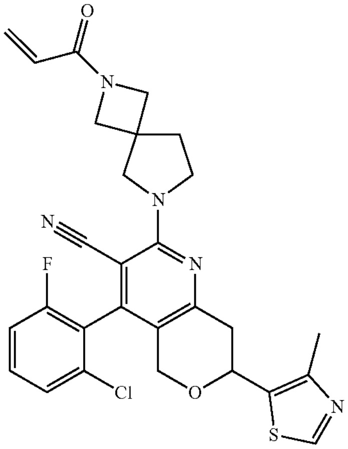 [SMILES: C=CC(=O)N1CC2(CCN(c3nc4c(c(-c5c(F)cccc5Cl)c3C#N)COC(c3scnc3C)C4)C2)C1] | (7R)-4-(2-chloro-6-fluorophenyl)-7-(4-methyl-1,3-thiazol-5-yl)-2-(2-(2-propenoyl)-2,6-diazaspiro[3.4]octan-6-yl)-7,8-dihydro-5H-pyrano[4,3-b]pyridine-3-carbonitrile (7S)-4-(2-chloro-6-fluorophenyl)-7-(4-methyl-1,3-thiazol-5-yl)-2-(2-(2-propenoyl)-2,6-diazaspiro[3.4]octan-6-yl)-7,8-dihydro-5H-pyrano[4,3-b]pyridine-3-carbonitrile | | Step 1: 2-chloro-6-fluorobenzaldehyde (Syn. Comm. (2008), 38(15), 2638-2645). Step 2: Intermediate 120 |

TABLE 15-continued

Examples 23-2 to 23-61 were prepared following the procedure described in Method 23, Steps 1-6, above as follows:

| Ex.# | Chemical Structure | Name | Method changes | Reagent |
|---|---|---|---|---|
| 23-37 | 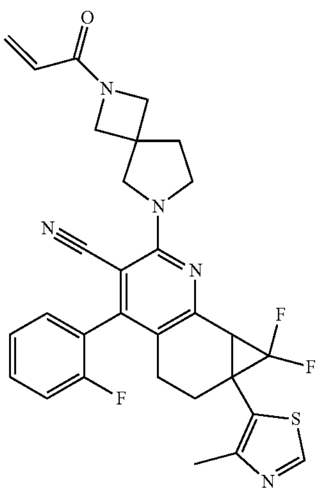 [SMILES: C=CC(=O)N1CC2(CCN(c3nc4c(c(-c5ccccc5F)c3C#N)CCC3(c5scnc5C)C4C3(F)F)C2)C1] | (6aR,7aR)-7,7-difluoro-4-(2-fluorophenyl)-6a-(4-methyl-1,3-thiazol-5-yl)-2-(2-(2-propenoyl)-2,6-diazaspiro[3.4]octan-6-yl)-6,6a,7,7a-tetrahydro-5H-cyclopropa[h]quinoline-3-carbonitrile\|(6aR,7aS)-7,7-difluoro-4-(2-fluorophenyl)-6a-(4-methyl-1,3-thiazol-5-yl)-2-(2-(2-propenoyl)-2,6-diazaspiro[3.4]octan-6-yl)-6,6a,7,7a-tetrahydro-5H-cyclopropa[h]quinoline-3-carbonitrile (6aS,7aR)-7,7-difluoro-4-(2-fluorophenyl)-6a-(4-methyl-1,3-thiazol-5-yl)-2-(2-(2-propenoyl)-2,6-diazaspiro[3.4]octan-6-yl)-6,6a,7,7a-tetrahydro-5H-cyclopropa[h]quinoline-3-carbonitrile (6aS,7aS)-7,7-difluoro-4-(2-fluorophenyl)-6a-(4-methyl-1,3-thiazol-5-yl)-2-(2-(2-propenoyl)-2,6-diazaspiro[3.4]octan-6-yl)-6,6a,7,7a-tetrahydro-5H-cyclopropa[h]quinoline-3-carbonitrile | | Step 1: 2-fluoro-benzaldehyde (Combi-Blocks). Step 2: Intermediate 122. |
| 23-38 | 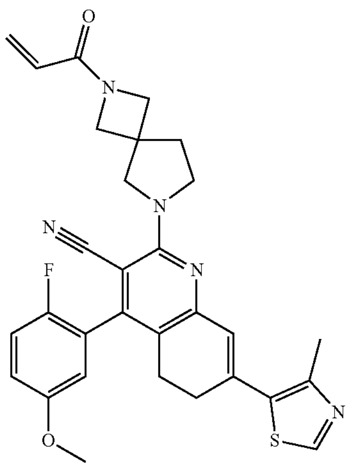 [SMILES: C=CC(=O)N1CC2(CCN(c3nc4c(c(-c5cc(OC)ccc5F)c3C#N)CCC(c3scnc3C)=C4)C2)C1] | 4-(2-fluoro-5-methoxyphenyl)-7-(4-methyl-1,3-thiazol-5-yl)-2-(2-(2-propenoyl)-2,6-diazaspiro[3.4]octan-6-yl)-5,6-dihydro-3-quinolinecarbonitrile | | Step 1: 2-fluoro-5-methoxy-benzaldehyde (WO 2017/027310) |
| 23-39 | 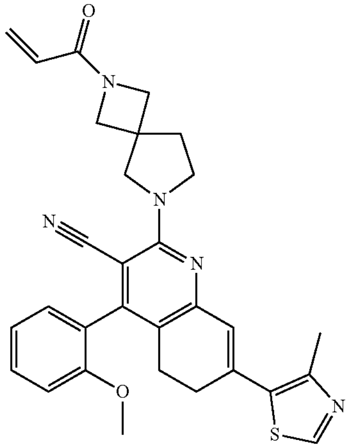 [SMILES: C=CC(=O)N1CC2(CCN(c3nc4c(c(-c5ccccc5OC)c3C#N)CCC(c3scnc3C)=C4)C2)C1] | 4-(2-methoxyphenyl)-7-(4-methyl-1,3-thiazol-5-yl)-2-(2-(2-propenoyl)-2,6-diazaspiro[3.4]octan-6-yl)-5,6-dihydro-3-quinolinecarbonitrile | | Step 1: 2-methoxy-benzaldehyde (Combi-Blocks) |

TABLE 15-continued

Examples 23-2 to 23-61 were prepared following the procedure described in Method 23, Steps 1-6, above as follows:

| Ex.# | Chemical Structure | Name | Method changes | Reagent |
|---|---|---|---|---|
| 23-40 | 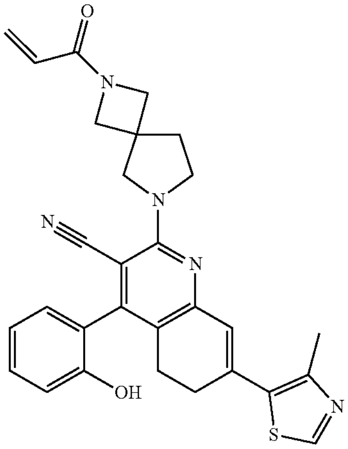 [SMILES: C=CC(=O)N1CC2(CCN(c3nc4c(c(-c5ccccc5O)c3C#N)CCC(c3scnc3C)=C4)C2)C1] | 4-(2-hydroxyphenyl)-7-(4-methyl-1,3-thiazol-5-yl)-2-(2-(2-propenoyl)-2,6-diazaspiro[3.4]octan-6-yl)-5,6-dihydro-3-quinolinecarbonitrile | Step 5: $BBr_3$ was used for deprotection of Boc and methoxy in place of TFA. | Step 1: 2-methoxy-benzaldehyde (Combi-Blocks) |
| 23-41 | 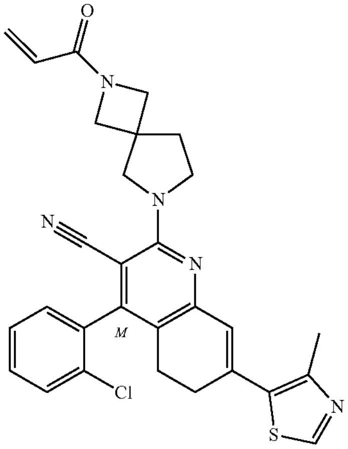 | (M)-4-(2-chlorophenyl)-7-(4-methyl-1,3-thiazol-5-yl)-2-(2-(2-propenoyl)-2,6-diazaspiro[3.4]octan-6-yl)-5,6-dihydro-3-quinolinecarbonitrile (1$^{st}$ eluting isomer) | See atropisomer separation conditions below | Step 1: 2-chloro-benzaldehyde (Combi-Blocks). |
| 23-42 | 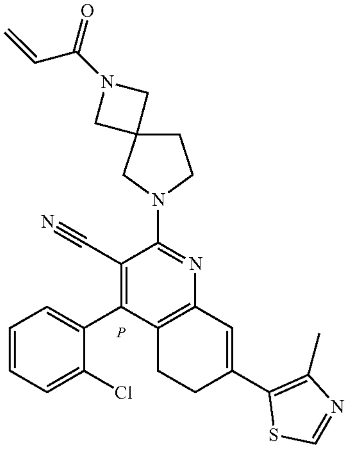 | (P)-4-(2-chlorophenyl)-7-(4-methyl-1,3-thiazol-5-yl)-2-(2-(2-propenoyl)-2,6-diazaspiro[3.4]octan-6-yl)-5,6-dihydro-3-quinolinecarbonitrile (2$^{nd}$ eluting isomer) | See atropisomer separation conditions below | Step 1: 2-chlorobenzaldehyde (Combi-Blocks). |

TABLE 15-continued

| Ex.# | Chemical Structure | Name | Method changes | Reagent |
|---|---|---|---|---|
| Examples 23-2 to 23-61 were prepared following the procedure described in Method 23, Steps 1-6, above as follows: | | | | |
| 23-43 | 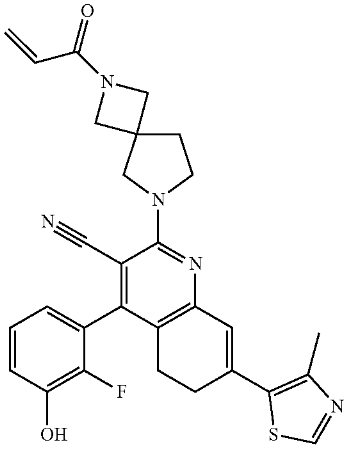 [SMILES: C=CC(=O)N1CC2(CCN(c3nc4c(c(-c5cccc(O)c5F)c3C#N)CCC(c3scnc3C)=C4)C2)C1] | 4-(2-fluoro-3-hydroxyphenyl)-7-(4-methyl-1,3-thiazol-5-yl)-2-(2-(2-propenoyl)-2,6-diazaspiro[3.4]octan-6-yl)-5,6-dihydro-3-quinolinecarbonitrile | Step 5: $BBr_3$ was used for deprotection of Boc and methoxy in place of TFA | Step 1: 2-fluoro-3-methoxy-benzaldehyde (WO 2004/043931) |
| 23-44 | 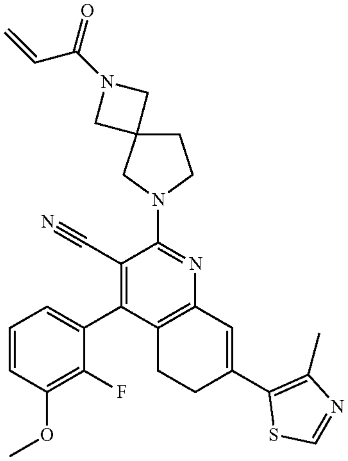 [SMILES: C=CC(=O)N1CC2(CCN(c3nc4c(c(-c5cccc(OC)c5F)c3C#N)CCC(c3scnc3C)=C4)C2)C1] | 4-(2-fluoro-3-methoxyphenyl)-7-(4-methyl-1,3-thiazol-5-yl)-2-(2-(2-propenoyl)-2,6-diazaspiro[3.4]octan-6-yl)-5,6-dihydro-3-quinolinecarbonitrile | | Step 1: 2-fluoro-3-methoxy-benzaldehyde (WO 2004/043931) |
| 23-45 | 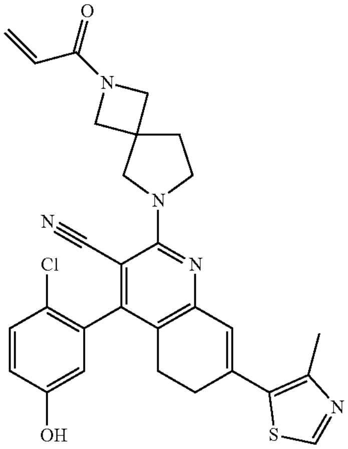 [SMILES: C=CC(=O)N1CC2(CCN(c3nc4c(c(-c5cc(O)ccc5Cl)c3C#N)CCC(c3scnc3C)=C4)C2)C1] | 4-(2-chloro-5-hydroxyphenyl)-7-(4-methyl-1,3-thiazol-5-yl)-2-(2-(2-propenoyl)-2,6-diazaspiro[3.4]octan-6-yl)-5,6-dihydro-3-quinolinecarbonitrile | Step 5: $BBr_3$ was used for deprotection of Boc and methoxy in place of TFA | Step 1: 2-chloro-5-methoxy Benzaldehyde (Org. Lett. (2019), 21(10), 3692-3695) |

TABLE 15-continued

| Examples 23-2 to 23-61 were prepared following the procedure described in Method 23, Steps 1-6, above as follows: | | | | |
|---|---|---|---|---|
| Ex.# | Chemical Structure | Name | Method changes | Reagent |
| 23-46 | 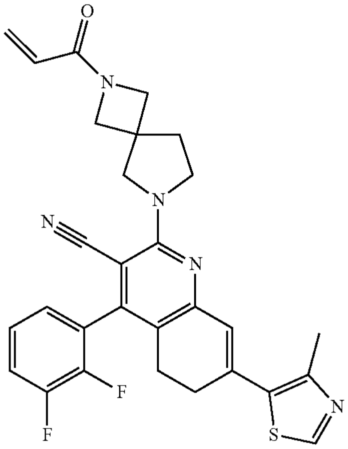 [SMILES: C=CC(=O)N1CC2(CCN(c3nc4c(c(-c5cccc(F)c5F)c3C#N)CCC(c3scnc3C)=C4)C2)C1] | 4-(2,3-difluorophenyl)-7-(4-methyl-1,3-thiazol-5-yl)-2-(2-(2-propenoyl)-2,6-diazaspiro[3.4]octan-6-yl)-5,6-dihydro-3-quinolinecarbonitrile | | Step 1: 2,3-difluorobenzaldehyde (Combi-Blocks) |
| 23-47 | 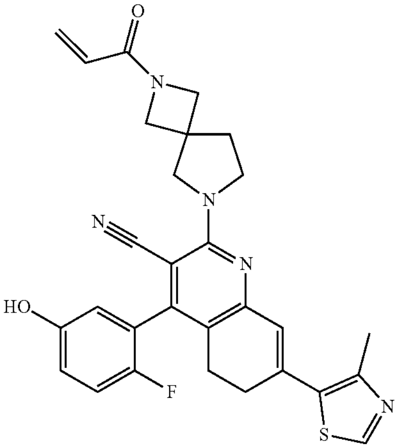 [SMILES: C=CC(=O)N1CC2(CCN(c3nc4c(c(-c5cc(O)ccc5F)c3C#N)CCC(c3scnc3C)=C4)C2)C1] | 4-(2-fluoro-5-hydroxyphenyl)-7-(4-methyl-1,3-thiazol-5-yl)-2-(2-(2-propenoyl)-2,6-diazaspiro[3.4]octan-6-yl)-5,6-dihydro-3-quinolinecarbonitrile | Step 5: $BBr_3$ was used for deprotection of Boc and methoxy in place of TFA | Step 1: 2-fluoro-5-methoxy-benzaldehyde (WO 2017/027310) |
| 23-48 | 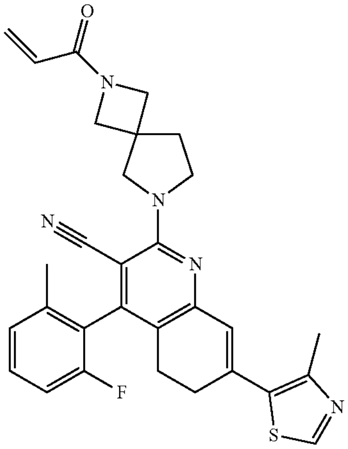 [SMILES: C=CC(=O)N1CC2(CCN(c3nc4c(c(-c5c(C)cccc5F)c3C#N)CCC(c3scnc3C)=C4)C2)C1] | 4-(2-fluoro-6-methylphenyl)-7-(4-methyl-1,3-thiazol-5-yl)-2-(2-(2-propenoyl)-2,6-diazaspiro[3.4]octan-6-yl)-5,6-dihydro-3-quinolinecarbonitrile | | Step 1: 2-fluoro-6-methyl-benzaldehyde (JACS, (2018), 140(8), 2789-2792) |

TABLE 15-continued

| Examples 23-2 to 23-61 were prepared following the procedure described in Method 23, Steps 1-6, above as follows: | | | | |
|---|---|---|---|---|
| Ex.# | Chemical Structure | Name | Method changes | Reagent |
| 23-49 | 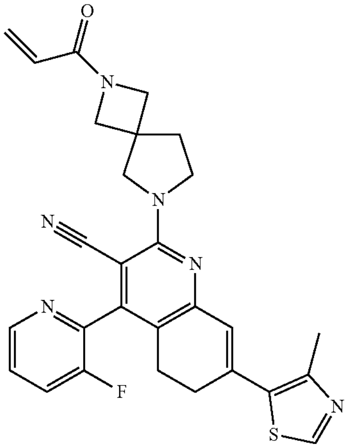 [SMILES: C=CC(=O)N1CC2(CCN(c3nc4c(c(-c5ncccc5F)c3C#N)CCC(c3scnc3C)=C4)C2)C1] | 4-(3-fluoro-2-pyridinyl)-7-(4-methyl-1,3-thiazol-5-yl)-2-(2-(2-propenoyl)-2,6-diazaspiro[3.4]octan-6-yl)-5,6-dihydro-3-quinolinecarbonitrile | | Step 1: 3-fluoropicolinaldehyde (WO 2007/146719). |
| 23-50 | 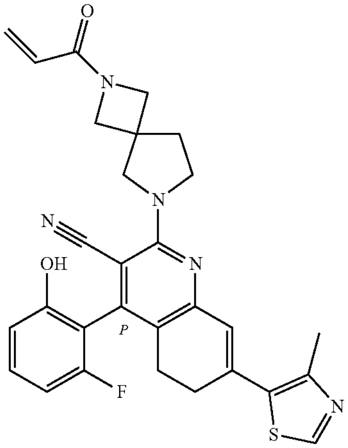 | (P)-4-(2-fluoro-6-hydroxyphenyl)-7-(4-methyl-1,3-thiazol-5-yl)-2-(2-(2-propenoyl)-2,6-diazaspiro[3.4]octan-6-yl)-5,6-dihydro-3-quinolinecarbonitrile (2$^{nd}$ eluting isomer) | See atropisomer separation conditions below | Step 1: 2-fluoro-6-hydroxy-benzaldehyde (WO 2009/125606) |
| 23-51 | 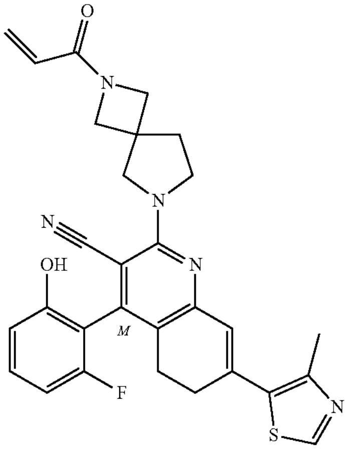 | (M)-4-(2-fluoro-6-hydroxyphenyl)-7-(4-methyl-1,3-thiazol-5-yl)-2-(2-(2-propenoyl)-2,6-diazaspiro[3.4]octan-6-yl)-5,6-dihydro-3-quinolinecarbonitrile (1$^{st}$ eluting isomer) | See atropisomer separation conditions below | Step 1: 2-fluoro-6-hydroxy-benzaldehyde (WO 2009/125606) |

TABLE 15-continued

| Examples 23-2 to 23-61 were prepared following the procedure described in Method 23, Steps 1-6, above as follows: | | | | |
|---|---|---|---|---|
| Ex.# | Chemical Structure | Name | Method changes | Reagent |
| 23-52 | 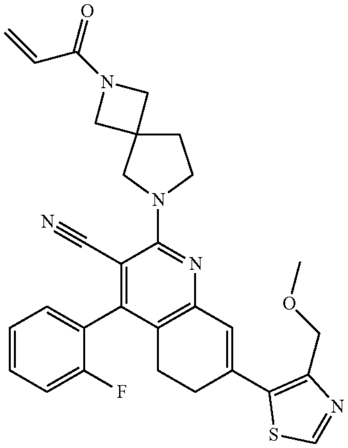 [SMILES: C=CC(=O)N1CC2(CCN(c3nc4c(c(-c5ccccc5F)c3C#N)CCC(c3scnc3COC)=C4)C2)C1] | 4-(2-fluorophenyl)-7-(4-(methoxymethyl)-1,3-thiazol-5-yl)-2-(2-(2-propenoyl)-2,6-diazaspiro[3.4]octan-6-yl)-5,6-dihydro-3-quinolinecarbonitrile | | Step 1: 2-fluoro-benzaldehyde (Combi-Blocks), Step 2: Intermediate 125 |
| 23-53 | 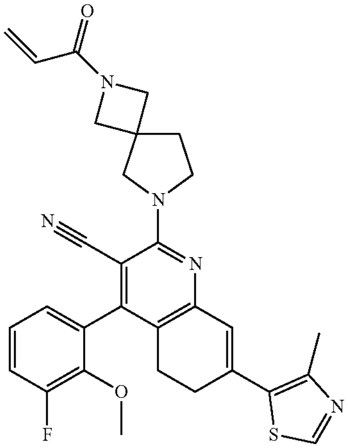 [SMILES: C=CC(=O)N1CC2(CCN(c3nc4c(c(-c5cccc(F)c5OC)c3C#N)CCC(c3scnc3C)=C4)C2)C1] | 4-(3-fluoro-2-methoxyphenyl)-7-(4-methyl-1,3-thiazol-5-yl)-2-(2-(2-propenoyl)-2,6-diazaspiro[3.4]octan-6-yl)-5,6-dihydro-3-quinolinecarbonitrile | | Step 1: 3-fluoro-2-methoxy-benzaldehyde (WO 2004/043931) |
| 23-54 | 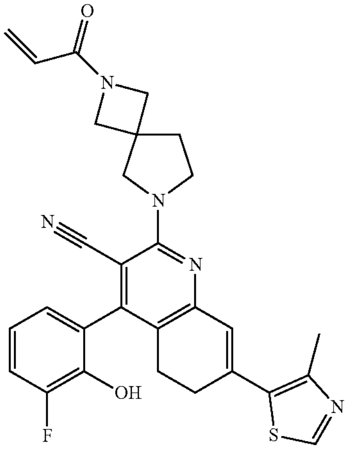 [SMILES: C=CC(=O)N1CC2(CCN(c3nc4c(c(-c5cccc(F)c5O)c3C#N)CCC(c3scnc3C)=C4)C2)C1] | 4-(3-fluoro-2-hydroxyphenyl)-7-(4-methyl-1,3-thiazol-5-yl)-2-(2-(2-propenoyl)-2,6-diazaspiro[3.4]octan-6-yl)-5,6-dihydro-3-quinolinecarbonitrile | Step 5: $BBr_3$ was used for deprotection of Boc and methoxy in place of TFA | Step 1: 3-fluoro-2-methoxy-benzaldehyde (WO 2004/043931) |

TABLE 15-continued

Examples 23-2 to 23-61 were prepared following the procedure described in Method 23, Steps 1-6, above as follows:

| Ex.# | Chemical Structure | Name | Method changes | Reagent |
|---|---|---|---|---|
| 23-55 | 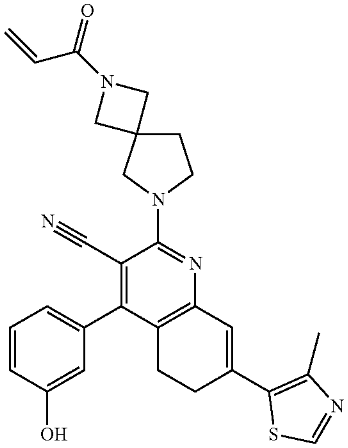 [SMILES: C=CC(=O)N1CC2(CCN(c3nc4c(c(-c5cccc(O)c5)c3C#N)CCC(c3scnc3C)=C4)C2)C1] | 4-(3-hydroxyphenyl)-7-(4-methyl-1,3-thiazol-5-yl)-2-(2-(2-propenoyl)-2,6-diazaspiro[3.4]octan-6-yl)-5,6-dihydro-3-quinolinecarbonitrile | Step 5: $BBr_3$ was used for deprotection of Boc and methoxy in place of TFA | Step 1: 3-methoxy-benzaldehyde (Combi-Blocks) |
| 23-56 | 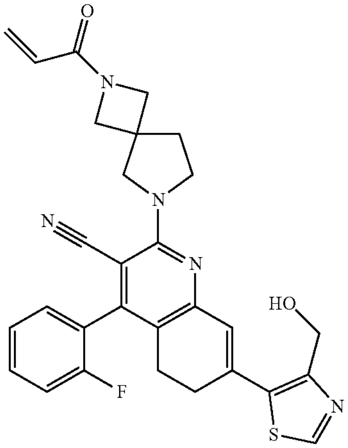 [SMILES: C=CC(=O)N1CC2(CCN(c3nc4c(c(-c5ccccc5F)c3C#N)CCC(c3scnc3CO)=C4)C2)C1] | 4-(2-fluorophenyl)-7-(4-(hydroxymethyl)-1,3-thiazol-5-yl)-2-(2-(2-propenoyl)-2,6-diazaspiro[3.4]octan-6-yl)-5,6-dihydro-3-quinolinecarbonitrile | Step 5: $BBr_3$ was used for deprotection of Boc and methoxy in place of TFA | Step 1: 2-fluorobenzaldehyde (Combi-Blocks). Step 2: Intermediate 125 |
| 23-57 | 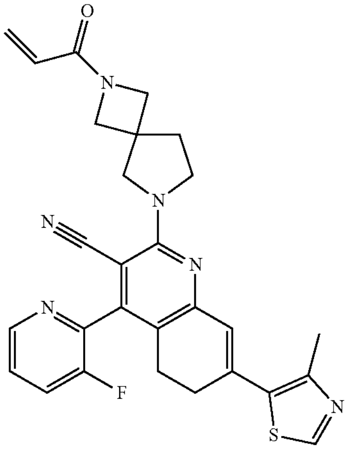 | (7R)-4-(3-fluoro-2-pyridinyl)-7-(4-methyl-1,3-thiazol-5-yl)-2-(2-(2-propenoyl)-2,6-diazaspiro[3.4]octan-6-yl)-5,6,7,8-tetrahydro-3-quinolinecarbonitrile (7S)-4-(3-fluoro-2-pyridinyl)-7-(4-methyl-1,3-thiazol-5-yl)-2-(2-(2-propenoyl)-2,6-diazaspiro[3.4]octan-6-yl)-5,6,7,8-tetrahydro-3-quinolinecarbonitrile | See additional hydrogenation step from Example 23-2. | Step 1: 3-fluoropicolinaldehyde (WO 2007/146719), Step 2: 3-(4-methylthiazol-5-yl)cyclohexan-1-one |

TABLE 15-continued

Examples 23-2 to 23-61 were prepared following the procedure described in Method 23, Steps 1-6, above as follows:

| Ex.# | Chemical Structure | Name | Method changes | Reagent |
|---|---|---|---|---|
| 23-58 | 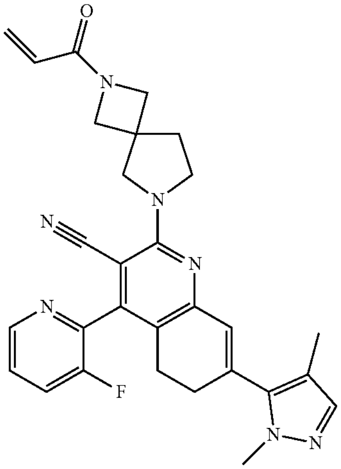 [SMILES: C=CC(=O)N1CC2(CCN(c3nc4c(c(-c5ncccc5F)c3C#N)CCC(c3c(C)cnn3C)=C4)C2)C1] | 7-(1,4-dimethyl-1H-pyrazol-5-yl)-4-(3-fluoro-2-pyridinyl)-2-(2-(2-propenoyl)-2,6-diazaspiro[3.4]octan-6-yl)-5,6-dihydro-3-quinolinecarbonitrile | | Step 1: 3-fluoropicolinaldehyde (WO 2007/146719). Step 2: Intermediate 109, step 2 |
| 23-59 | 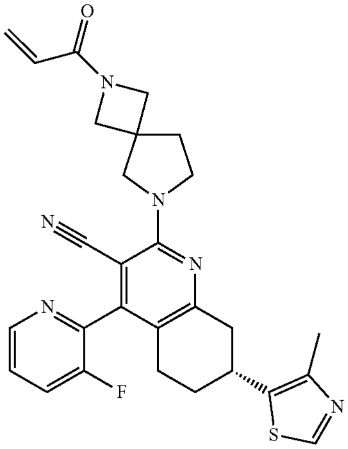 [SMILES: C=CC(=O)N1CC2(CCN(c3nc4c(c(-c5ncccc5F)c3C#N)CC[C@@H](c3scnc3C)C4)C2)C1] | (7R)-4-(3-fluoro-2-pyridinyl)-7-(4-methyl-1,3-thiazol-5-yl)-2-(2-(2-propenoyl)-2,6-diazaspiro[3.4]octan-6-yl)-5,6,7,8-tetrahydro-3-quinolinecarbonitrile (1$^{st}$ eluting isomer) | See additional hydrogenation step from Example 23-2. See Isomer separation conditions below. | Step 1: 3-fluoropicolinaldehyde (WO 2007/146719). Step 2: 3-(4-methylthiazol-5-yl)cyclohexan-1-one |
| 23-60 | 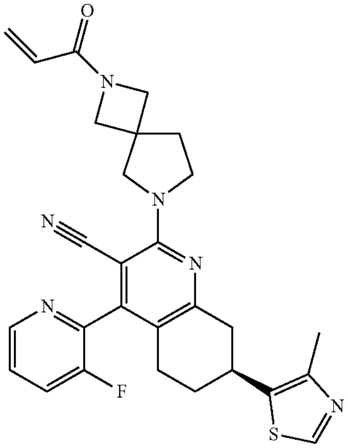 [SMILES: C=CC(=O)N1CC2(CCN(c3nc4c(c(-c5ncccc5F)c3C#N)CC[C@H](c3scnc3C)C4)C2)C1] | (7S)-4-(3-fluoro-2-pyridinyl)-7-(4-methyl-1,3-thiazol-5-yl)-2-(2-(2-propenoyl)-2,6-diazaspiro[3.4]octan-6-yl)-5,6,7,8-tetrahydro-3-quinolinecarbonitrile (2$^{nd}$ eluting isomer) | See additional hydrogenation step from Example 23-2. See Isomer separation conditions below. | Step 1: 3-fluoropicolinaldehyde (WO 2007/146719). Step 2: 3-(4-methylthiazol-5-yl)cyclohexan-1-one |

TABLE 15-continued

| Examples 23-2 to 23-61 were prepared following the procedure described in Method 23, Steps 1-6, above as follows: | | | | |
|---|---|---|---|---|
| Ex.# | Chemical Structure | Name | Method changes | Reagent |
| 23-61 | 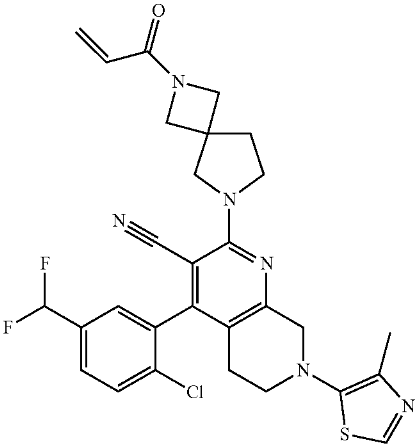 [SMILES: C=CC(=O)N1CC2(CCN(c3nc4c(c(-c5cc(C(F)F)ccc5Cl)c3C#N)CCN(c3scnc3C)C4)C2)C1] | 4-(2-chloro-5-(difluoromethyl)phenyl)-7-(4-methyl-1,3-thiazol-5-yl)-2-(2-(2-propenoyl)-2,6-diazaspiro[3.4]octan-6-yl)-5,6,7,8-tetrahydro-1,7-naphthyridine-3-carbonitrile | | Step 1: 2-Chloro-5-(difluoro-methyl)benzaldehyde (CAS#1785512-75-5) Step 2: 1-(4-methylthiazol-5-yl)piperidin-3-one (Example 35-1, step 1) |

Hydrogenation of Intermediate for Example 23-2.

To a solution of 3-(4-methylthiazol-5-yl)cyclohex-2-en-1-one (3.5 g, 18.11 mmol, Example 22-1, Step 1) in EtOAc (50 mL) and MeOH (8 mL) was added $Pd(OH)_2$ (1.1 g, 1.567 mmol, 20% on carbon). The reaction mixture was stirred at 25° C. for 20 h with 5 kg/$cm^2$ of $H_2$ pressure in a tiny autoclave. Once completed, the reaction was filtered and the filtrate concentrated under reduced pressure to afford 3-(4-methylthiazol-5-yl)cyclohexan-1-one (3.5 g, 17.92 mmol, 99% yield) as a gum. m/z (ESI)=196.2 $(M+H)^+$ Isomer Separation for Examples 23-3 to 23-6.

The racemic mixture was separated by SFC using a Chiralpak Lux $C_3$ column with a mobile phase of 80% liquid $CO_2$ and 20% MeOH:ACN to provide the respective isomers of (7)-4-(2-methylphenyl)-7-(4-methyl-1,3-thiazol-5-yl)-2-(2-(2-propenoyl)-2,6-diazaspiro[3.4]octan-6-yl)-5,6,7,8-tetrahydro-3-quinolinecarbonitrile. The stereochemistry was arbitrarily assigned and is not established. $1^{st}$ eluting isomer assigned as the P,7R isomer, $2^{nd}$ eluting isomer assigned as the M,7S isomer, $3^{rd}$ eluting isomer assigned as the P,7S isomer, and $4^{th}$ eluting isomer assigned as the M,7R isomer of (7)-4-(2-methylphenyl)-7-(4-methyl-1,3-thiazol-5-yl)-2-(2-(2-propenoyl)-2,6-diazaspiro[3.4]octan-6-yl)-5,6,7,8-tetrahydro-3-quinolinecarbonitrile.

Atropisomer Separation for Examples 23-23 to 23-24.

The racemic mixture was separated by SFC using a Chiralcel OJ-H column with a mobile phase of 75% liquid $CO_2$ and 25% MeOH:ACN to provide the respective P and M isomers of 4-(2-methylphenyl)-7-(4-methyl-1,3-thiazol-5-yl)-2-(2-(2-propenoyl)-2,6-diazaspiro[3.4]octan-6-yl)-5,6-dihydro-3-quinolinecarbonitrile. The stereochemistry was arbitrarily assigned and is not established. $1^{st}$ eluting isomer assigned as the M isomer and $2^{nd}$ eluting isomer assigned as the P isomer.

Atropisomer Separation for Examples 23-25 to 23-26.

The racemic mixture was separated by SFC using a ChiralPak AD-H column with a mobile phase of 50% liquid $CO_2$ and 50% MeOH:ACN to provide the respective P and M isomers of 4-(3-methyl-2-pyridinyl)-7-(4-methyl-1,3-thiazol-5-yl)-2-(2-(2-propenoyl)-2,6-diazaspiro[3.4]octan-6-yl)-5,6-dihydro-3-quinolinecarbonitrile. The stereochemistry was arbitrarily assigned and is not established. $1^{st}$ eluting isomer assigned as the P isomer and $2^{nd}$ eluting isomer assigned as the M isomer.

Isomer Separation for Examples 23-27 to 23-28.

The racemic mixture was separated by SFC using a Chiralcel OJ-H column with a mobile phase of 70% liquid $CO_2$ and 30% MeOH to provide the respective R and S isomers of (7)-4-(2-chloro-4-fluorophenyl)-7-(4-methyl-1,3-thiazol-5-yl)-2-(2-(2-propenoyl)-2,6-diazaspiro[3.4]octan-6-yl)-7,8-dihydro-5H-pyrano[4,3-b]pyridine-3-carbonitrile. The stereochemistry was arbitrarily assigned and is not established. $1^{st}$ eluting isomer assigned as the R isomer and $2^{nd}$ eluting isomer assigned as the S isomer.

Atropisomer Separation for Examples 23-32 to 23-33.

The racemic mixture was separated by SFC using a Lux-C4 column with a mobile phase of 50% liquid $CO_2$ and 50% iPrOH:ACN to provide the respective P and M isomers of 4-(2-chloro-4-fluorphenyl)-7-(4-methyl-1,3-thiazol-5-yl)-2-(2-(2-propenoyl)-2,6-diazaspiro[3.4]octan-6-yl)-5,6-dihydro-3-quinolinecarbonitrile. The stereochemistry was arbitrarily assigned and is not established. $1^{st}$ eluting isomer assigned as the P isomer and $2^{nd}$ eluting isomer assigned as the M isomer.

Atropisomer Separation for Examples 23-41 to 23-42.

The racemic mixture was separated by SFC using a Chiralpak IG column with a mobile phase of 60% liquid $CO_2$ and 40% DCM:MeOH to provide the respective P and M isomers of 4-(2-chlorophenyl)-7-(4-methyl-1,3-thiazol-5-yl)-2-(2-(2-propenoyl)-2,6-diazaspiro[3.4]octan-6-yl)-5,6-dihydro-3-quinolinecarbonitrile. The stereochemistry was arbitrarily assigned and is not established. $1^{st}$ eluting isomer assigned as the M isomer and $2^{nd}$ eluting isomer assigned as the P isomer.

Atropisomer Separation for Examples 23-41 to 23-42.

The racemic mixture was separated by SFC using a Chiralcel OJ-H column with a mobile phase of 70% liquid $CO_2$ and 30% MeOH to provide the respective P and M isomers of 4-(2-fluoro-6-hydroxyphenyl)-7-(4-methyl-1,3-thiazol-5-yl)-2-(2-(2-propenoyl)-2,6-diazaspiro[3.4]octan-6-yl)-5,6-dihydro-3-quinolinecarbonitrile. The stereochemistry was arbitrarily assigned and is not established. $1^{st}$ eluting isomer assigned as the M isomer and 2nd eluting isomer assigned as the P isomer.

Atropisomer Separation for Examples 23-50 to 23-51.

The racemic mixture was separated by SFC using a Chiralcel OJ-H column with a mobile phase of 70% liquid $CO_2$ and 30% MeOH to provide the respective P and M isomers of 4-(2-fluoro-6-hydroxyphenyl)-7-(4-methyl-1,3-thiazol-5-yl)-2-(2-(2-propenoyl)-2,6-diazaspiro[3.4]octan-6-yl)-5,6-dihydro-3-quinolinecarbonitrile. The stereochemistry was arbitrarily assigned and is not established. 1st eluting isomer assigned as the M isomer and 2nd eluting isomer assigned as the P isomer.

Isomer Separation for Examples 23-59 to 23-60.

The racemic mixture was separated by SFC using a OJ column (250×21 mm, 5 μm) with a mobile phase of 65% liquid $CO_2$ and 35% MeOH with 0.2% TEA to provide the respective R and S isomers of (7)-4-(3-fluoro-2-pyridinyl)-7-(4-methyl-1,3-thiazol-5-yl)-2-(2-(2-propenoyl)-2,6-diazaspiro[3.4]octan-6-yl)-5,6,7,8-tetrahydro-3-quinolinecarbonitrile. The stereochemistry was arbitrarily assigned and is not established. 1st eluting isomer assigned as the R isomer and 2nd eluting isomer assigned as the S isomer.

Example 24-1: (6R)-4-(5-methyl-1H-indazol-4-yl)-6-(2-propanyl)-2-(2-(2-propenoyl)-2,6-diazaspiro[3.4]octan-6-yl)-6,7-dihydro-5H-cyclopenta[b]pyridine-3-carbonitrile and (6S) 4-(5-methyl-1H-indazol-4-yl)-6-(2-propanyl)-2-(2-(2-propenoyl)-2,6-diazaspiro[3.4]octan-6-yl)-6,7-dihydro-5H-cyclopenta[b]pyridine-3-carbonitrile

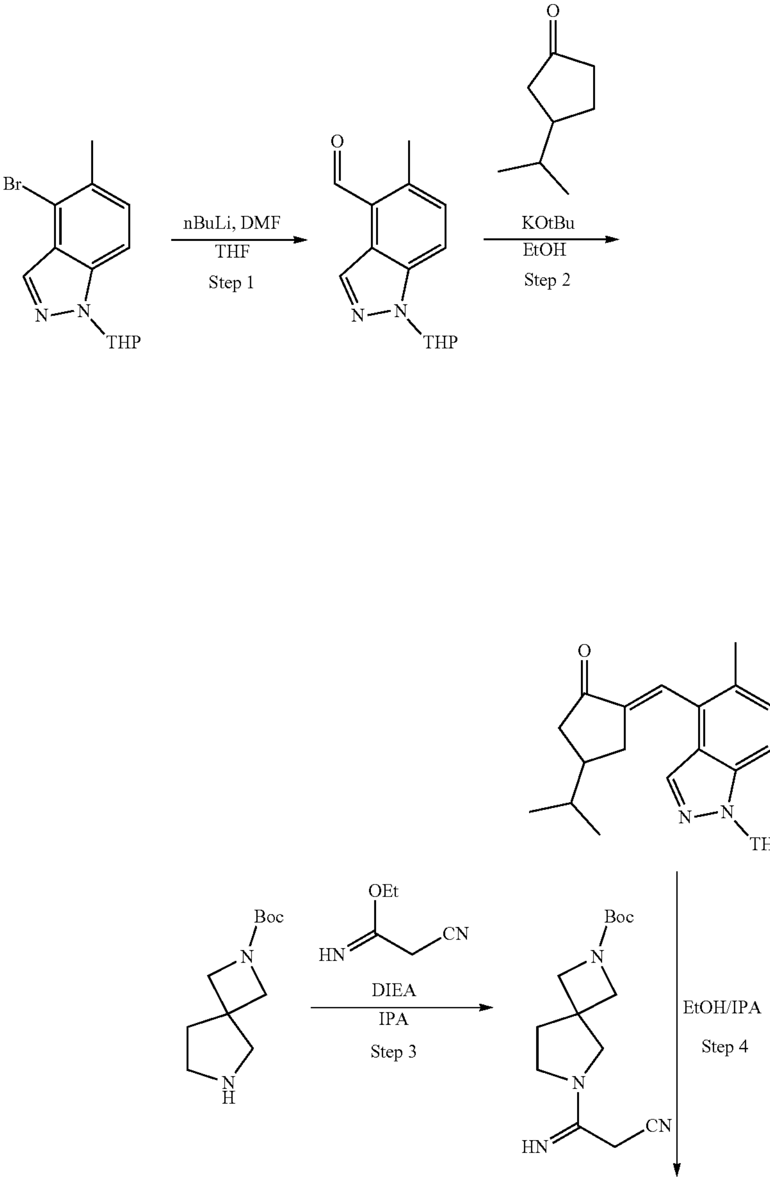

-continued

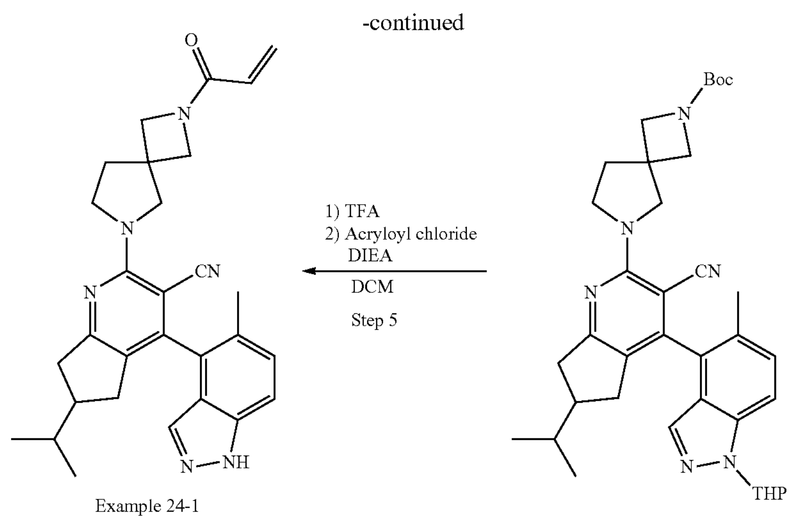

Example 24-1

Step 1: 5-methyl-1-(tetrahydro-2H-pyran-2-yl)-1H-indazole-4-carbaldehyde

To a solution of 4-bromo-5-methyl-1-(tetrahydro-2H-pyran-2-yl)-1H-indazole (4 g, 13.5 mmol, Combi-Blocks) and THF (45 mL) at −78° C. was added n-butyllithium (11.9 mL, 30 mmol, 2.5M in hexanes, Sigma-Aldrich). After 30 min, DMF (4.2 mL, 54.2 mmol, Sigma-Aldrich) was added, and the reaction mixture was allowed to warm to ambient temperature. After 2 h, the reaction was quenched with saturated aqueous $NaHCO_3$ (25 mL), extracted with EtOAc (3×30 mL). The combined organics were dried over $MgSO_4$, and concentrated to provide the crude material as a thick orange oil that was used in the next step without further purification. m/z (ESI): 245.2 $(M+H)^+$.

Step 2: (E)-4-isopropyl-2-((5-methyl-1-(tetrahydro-2H-pyran-2-yl)-1H-indazol-4-yl)methylene)cyclopentan-1-one To a solution of 5-methyl-1-(tetrahydro-2H-pyran-2-yl)-1H-indazole-4-carbaldehyde (200 mg, 0.819 mmol) and 3-isopropylcyclopentan-1-one (103 mg, 0.82 mmol, Aurum) in EtOH (2.7 mL) was added KOtBu (96 mg, 0.86 mmol, Sigma-Aldrich). The reaction was stirred at ambient temperature. After 1 h, the reaction mixture was partitioned between EtOAc and half-saturated aqueous $NaHCO_3$. The organic layer was concentrated in vacuo and purified by column chromatography, eluting with 0-100% EtOAc in heptanes, to provide (E)-4-isopropyl-2-((5-methyl-1-(tetrahydro-2H-pyran-2-yl)-1H-indazol-4-yl)methylene)cyclopentan-1-one (128 mg, 0.363 mmol, 44.4% yield) as a light-yellow oil. m/z (ESI): 353.3 $(M+H)^+$.

Step 3: tert-butyl 6-(2-cyano-1-iminoethyl)-2,6-diazaspiro[3.4]octane-2-carboxylate A suspension of tert-butyl 2,6-diazaspiro[3.4]octane-2-carboxylate (139 mg, 0.654 mmol, Aurum), ethyl 2-cyanoacetimidate (110 mg, 0.785 mmol, Enamine), and DIEA (57.1 μL, 0.327 mmol, Sigma-Aldrich) in isopropanol (1.3 mL) was irradiated in a microwave vial at 100° C. After 60 min, the reaction mixture was concentrated to provide crude tert-butyl 6-(2-cyano-1-iminoethyl)-2,6-diazaspiro[3.4]octane-2-carboxylate (0.26 g, 0.93 mmol) as a yellow oil. The isolated product was used in the next reaction without further purification. m/z (ESI): 279.2 $(M+H)^+$.

Step 4: tert-butyl 6-(3-cyano-6-isopropyl-4-(5-methyl-1-(tetrahydro-2H-pyran-2-yl)-1H-indazol-4-yl)-6,7-dihydro-5H-cyclopenta[b]pyridin-2-yl)-2,6-diazaspiro[3.4]octane-2-carboxylate A solution of (E)-4-isopropyl-2-((5-methyl-1-(tetrahydro-2H-pyran-2-yl)-1H-indazol-4-yl)methylene)cyclopentan-1-one (64 mg, 0.182 mmol) and tert-butyl 6-(2-cyano-1-iminoethyl)-2,6-diazaspiro[3.4]octane-2-carboxylate (76 mg, 0.272 mmol) in 1:1 EtOH/iPrOH (800 μL) was stirred at 90° C. overnight, and then at 100° C. for 24 h. The reaction mixture was partitioned between water and EtOAc. The organic layer was concentrated in vacuo and purified by column chromatography, eluting with 0-100% EtOAc in heptanes, to provide tert-butyl 6-(3-cyano-6-isopropyl-4-(5-methyl-1-(tetrahydro-2H-pyran-2-yl)-1H-indazol-4-yl)-6,7-dihydro-5H-cyclopenta[b]pyridin-2-yl)-2,6-diazaspiro[3.4]octane-2-carboxylate (30 mg, 27% yield). m/z (ESI): 611.4 $(M+H)^+$.

Step 5: tert-butyl 6-(3-cyano-6-isopropyl-4-(5-methyl-1-(tetrahydro-2H-pyran-2-yl)-1H-indazol-4-yl)-6,7-dihydro-5H-cyclopenta[b]pyridin-2-yl)-2,6-diazaspiro[3.4]octane-2-carboxylate To a solution of tert-butyl 6-(3-cyano-6-isopropyl-4-(5-methyl-1-(tetrahydro-2H-pyran-2-yl)-1H-indazol-4-yl)-6,7-dihydro-5H-cyclopenta[b]pyridin-2-yl)-2,6-diazaspiro[3.4]octane-2-carboxylate (75 mg, 0.123 mmol) in DCM (1.2 mL) was added TFA (142 μL, 1.842 mmol, Sigma-Aldrich). The reaction was stirred at ambient temperature. After 90 min, the reaction mixture was concentrated, and the residue was redissolved in DCM (1.2 mL). To the reaction was added DIEA (385 μL, 2.210 mmol, Sigma-Aldrich) and acryloyl chloride (10.97 μL, 0.135 mmol, Sigma-Aldrich), and the reaction was stirred at ambient temperature. After 30 min, the reaction was diluted with DCM, washed with water, and concentrated. The crude product was purified by column chromatography, eluting with 0-100% (3:1 EtOAc:EtOH) in heptanes, to provide 2-(2-acryloyl-2,6-diazaspiro[3.4]octan-6-yl)-6-isopropyl-4-(5-methyl-1H-indazol-4-yl)-6,7-dihydro-5H-cyclopenta[b]pyridine-3-carbonitrile (23 mg, 39.0% yield) as an off-white solid. $^1$H NMR (400 MHz, $CDCl_3$) δ ppm 7.61 (br d, J=7.52 Hz, 1H), 7.49 (d, J=8.57 Hz, 1H), 7.38 (d, J=8.57 Hz, 1H), 6.33-6.45 (m, 1H), 6.16-6.29 (m, 1H), 5.68-5.76 (m, 1H), 4.23-4.33 (m, 1H), 3.86-4.22 (m, 8H), 3.00-3.15 (m, 1H), 2.68-2.84 (m, 1H), 2.36-2.52 (m, 1H), 2.07-2.33 (m, 8H), 0.94 (d, J=6.48 Hz, 3H), 0.79-0.86 (m, 3H). m/z (ESI): 481.2 $(M+H)^+$.

Example 25-1: N-(4-(3-cyano-6,6-dimethyl-2-(2-(2-propenoyl)-2,6-diazaspiro[3.4]octan-6-yl)-6,7-dihydro-5H-cyclopenta[b]pyridin-4-yl)-2-naphthalenyl)methanesulfonamide

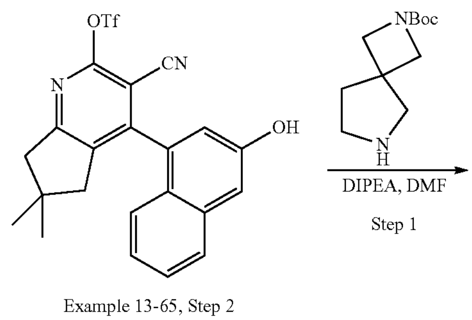

Example 13-65, Step 2

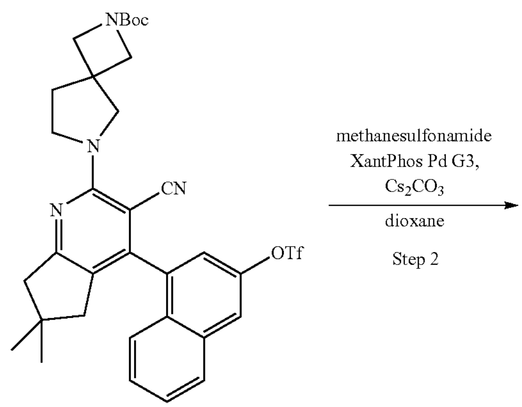

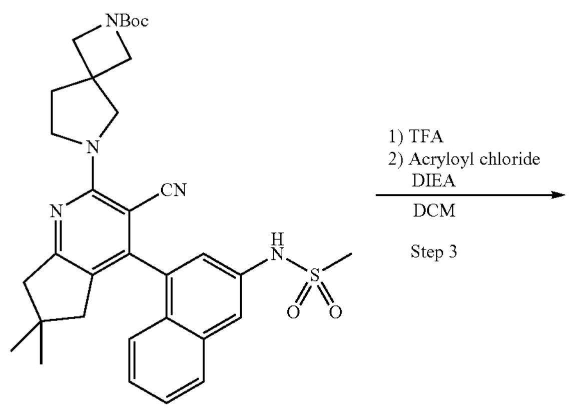

-continued

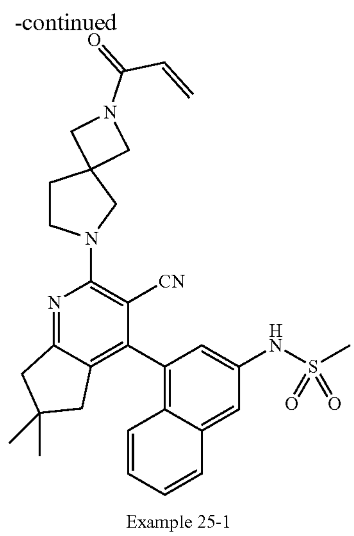

Example 25-1

Step 1: tert-butyl 6-(3-cyano-6,6-dimethyl-4-(3-(((trifluoromethyl)sulfonyl)oxy)-naphthalen-1-yl)-6,7-dihydro-5H-cyclopenta[b]pyridin-2-yl)-2,6-diazaspiro[3.4]octane-2-carboxylate To a solution of 4-(3-cyano-6,6-dimethyl-2-(((trifluoromethyl)sulfonyl)oxy)-6,7-dihydro-5H-cyclopenta[b]pyridin-4-yl)naphthalen-2-yl trifluoromethanesulfonate (0.274 g, 0.461 mmol, Example 13-65, Step 2) and DIEA (0.40 mL, 2.3 mmol, Sigma-Aldrich) in DMF (1.5 mL) was added tert-butyl 2,6-diazaspiro[3.4]octane-2-carboxylate (0.196 g, 0.922 mmol, Aurum). The reaction was stirred at 60° C. After 30 min, the reaction mixture was partitioned between water and EtOAc. The organic layer was concentrated in vacuo and purified by column chromatography, eluting with 0-100% EtOAc in heptane, to provide tert-butyl 6-(3-cyano-6,6-dimethyl-4-(3-(((trifluoromethyl)sulfonyl)oxy)naphthalen-1-yl)-6,7-dihydro-5H-cyclopenta[b]pyridin-2-yl)-2,6-diazaspiro[3.4]octane-2-carboxylate (107 mg, 35.4% yield) as a yellow oil. m/z (ESI): 601.2 $(M-tBu)^+$.

Step 2: tert-butyl 6-(3-cyano-6,6-dimethyl-4-(3-(methylsulfonamido)naphthalen-1-yl)-6,7-dihydro-5H-cyclopenta[b]pyridin-2-yl)-2,6-diazaspiro[3.4]octane-2-carboxylate To a suspension of tert-butyl 6-(3-cyano-6,6-dimethyl-4-(3-(((trifluoromethyl)sulfonyl)oxy)-naphthalen-1-yl)-6,7-dihydro-5H-cyclopenta[b]pyridin-2-yl)-2,6-diazaspiro[3.4]octane-2-carboxylate (107 mg, 0.163 mmol) and methanesulfonamide (23.25 mg, 0.244 mmol, Sigma-Aldrich) in 1,4-dioxane (1.6 mL) was added $Cs_2CO_3$ (106 mg, 0.326 mmol, Sigma-Aldrich) followed by XantPhos Pd G3 (33.7 mg, 0.033 mmol, Strem Chemicals). The reaction was sparged with argon and stirred at 90° C. After 16 h, the reaction mixture was partitioned between water and EtOAc. The organic layer was concentrated in vacuo and purified by column chromatography, eluting with 0-100% (3:1, EtOAc:EtOH) in heptanes, to provide tert-butyl 6-(3-cyano-6,6-dimethyl-4-(3-(methylsulfonamido)-naphthalen-1-yl)-6,7-dihydro-5H-cyclopenta[b]pyridin-2-yl)-2,6-diazaspiro[3.4]octane-2-carboxylate (70 mg, 71.4% yield) as an off-white solid. m/z (ESI): 624.2 $(M+Na)^+$.

Step 3: N-(4-(3-cyano-6,6-dimethyl-2-(2-(2-propenoyl)-2,6-diazaspiro[3.4]octan-6-yl)-6,7-dihydro-5H-cyclopenta[b]pyridin-4-yl)-2-naphthalenyl)methanesulfonamide To a solution of tert-butyl 6-(3-cyano-6,6-dimethyl-4-(3-(methylsulfonamido)naphthalen-1-yl)-6,7-dihydro-5H-cyclopenta[b]pyridin-2-yl)-2,6-diazaspiro[3.4]octane-2-carboxylate (70 mg, 0.116 mmol) and DCM (400 μL) was added TFA (134 μL, 1.745 mmol, Sigma-Aldrich). The reaction was stirred at ambient temperature. After 1 h, the reaction temperature was increased to 40° C. After a further 1 h, the reaction mixture was concentrated and the residue was redissolved in DCM (400 μL). To the reaction was added DIEA (365 μL, 2.094 mmol, Sigma-Aldrich) and acryloyl chloride (10.40 μL, 0.128 mmol, Sigma-Aldrich) and the reaction was stirred at ambient temperature. After 30 min, the reaction mixture was diluted with DCM, washed with saturated aqueous $NaHCO_3$, and concentrated in vacuo. The crude product was purified by column chromatography, eluting with 0-100% (3:1, EtOAc:EtOH) in heptanes, to provide N-(4-(3-cyano-6,6-dimethyl-2-(2-(2-propenoyl)-2,6-diazaspiro[3.4]octan-6-yl)-6,7-dihydro-5H-cyclopenta[b]pyridin-4-yl)-2-naphthalenyl)methanesulfonamide (22 mg, 34.0% yield) as a white solid. $^1H$ NMR (400 MHz, DMSO-$d_6$) δ ppm 10.14 (br d, J=3.76 Hz, 1H), 7.95 (d, J=8.57 Hz, 1H), 7.76 (d, J=1.88 Hz, 1H), 7.51-7.59 (m, 1H), 7.34-7.46 (m, 2H), 7.30 (d, J=2.09 Hz, 1H), 6.32 (dd, J=17.04, 10.35 Hz, 1H), 6.11 (dd, J=16.93, 2.30 Hz, 1H), 5.62-5.71 (m, 1H), 4.24-4.33 (m, 1H), 4.14-4.21 (m, 1H), 3.83-4.01 (m, 4H), 3.78 (s, 2H), 3.09 (s, 2H), 2.76 (s, 2H), 2.14-2.24 (m, 3H), 2.02-2.11 (m, 1H), 1.05 (d, J=2.93 Hz, 6H). m/z (ESI): 556.2 $(M+H)^+$.

Example 26-1: (P)-1-(6-(3-ethenyl-4-(5-methyl-1H-indazol-4-yl)-2-quinolinyl)-2,6-diazaspiro[3.4]octan-2-yl)-2-propen-1-one

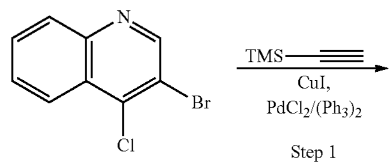

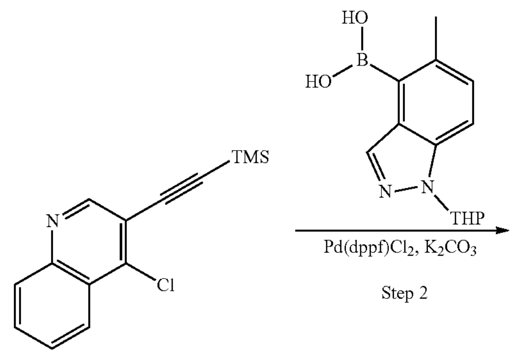

-continued

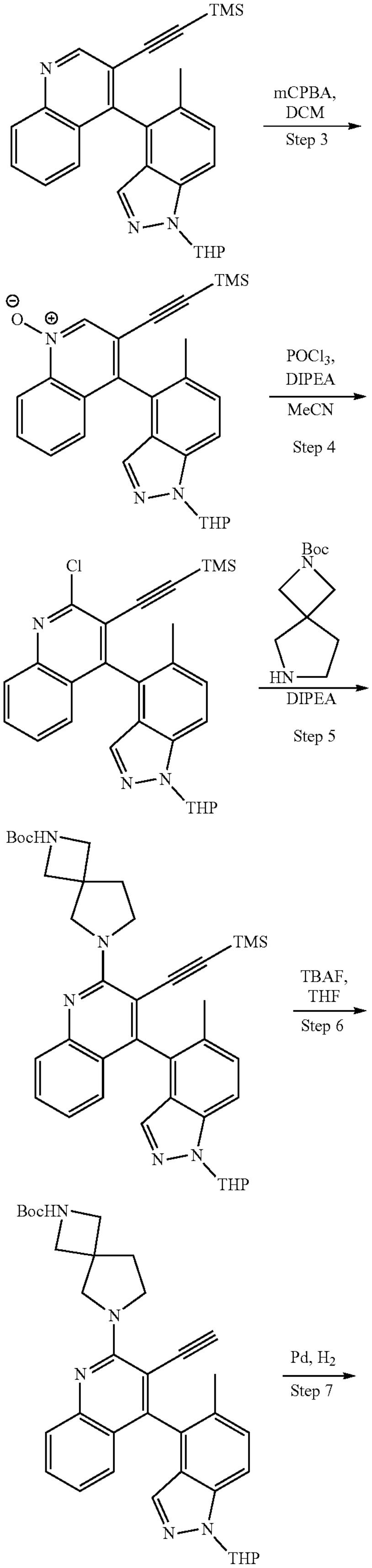

-continued

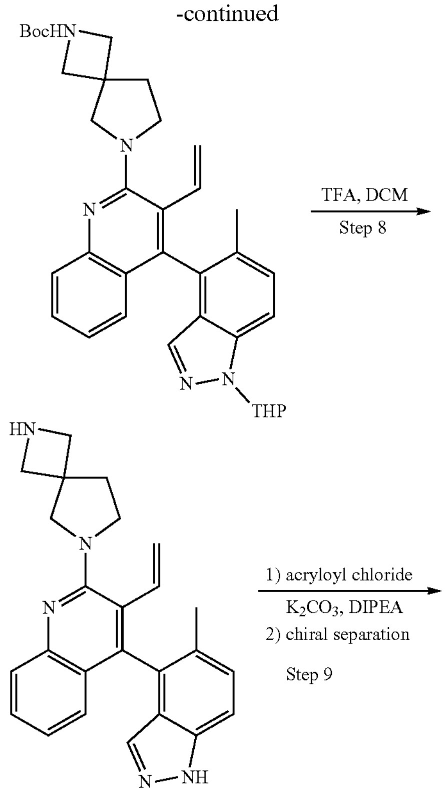

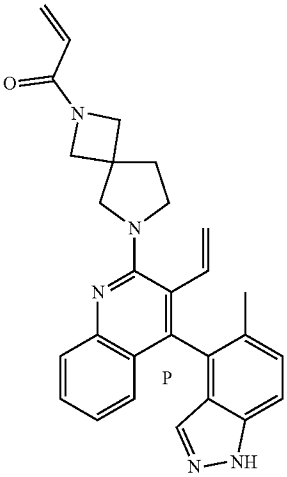

Example 26-1

Step 1: 4-chloro-3-((trimethylsilyl)ethynyl)quinoline

To a mixture of 3-bromo-4-chloroquinoline (2.0 g, 8.25 mmol, Enamine), trans-$PdCl_2(PPh_3)_2$ (0.579 g, 0.825 mmol, Strem Chemicals), CuI (0.314 g, 1.649 mmol, Sigma-Aldrich), and (trimethylsilyl)acetylene (1.761 mL, 12.37 mmol, Matrix Scientific) in THE (28 mL) at 0° C. was added TEA (6.95 mL, 49.5 mmol, Sigma-Aldrich). The resulting mixture was stirred at room temperature overnight. The mixture was diluted with aqueous saturated $NaHCO_3$ (40 mL) and extracted with EtOAc (2×100 mL). The combined organic extracts were dried over $MgSO_4$ and concentrated in vacuo. Chromatographic purification of the residue (silica gel, 0-100% EtOAc/heptanes) provided 4-chloro-3((trimethylsilyl)-ethynyl)quinoline (1.79 g, 84% yield) as a light brown oil. $^1$H NMR (400 MHz, MeOH-$d_4$) δ ppm 8.83 (s, 1H), 8.32 (dd, J=8.5, 1.4 Hz, 1H), 8.08 (d, J=8.8 Hz, 1H), 7.87 (ddd, J=8.4, 7.1, 1.5 Hz, 1H), 7.76-7.81 (m, 1H), 0.33 (s, 9H). m/z (ESI): 260.1 $(M+H)^+$.

Step 2: 4-(5-methyl-1-(tetrahydro-2H-pyran-2-yl)-1H-indazol-4-yl)-3-((trimethylsilyl)ethynyl)quinoline A mixture of 4-chloro-3-((trimethylsilyl)ethynyl)quinoline (790 mg, 3.04 mmol), $PdCl_2$(dppf) DCM adduct (222 mg, 0.304 mmol, Strem Chemicals), (5-methyl-1-(tetrahydro-2H-pyran-2-yl)-1H-indazol-4-yl)boronic acid (1186 mg, 4.56 mmol, Synnovator), $K_2CO_3$ (840 mg, 6.08 mmol, Sigma-Aldrich) and 1,4-dioxane (12 mL):water (2.400 mL) was subjected to microwave irradiation at 130° C. for 2 h. The mixture was diluted with aqueous saturated $NaHCO_3$ (50 mL), extracted with EtOAc (2×100 mL). The combined organic extracts were dried over $MgSO_4$ and concentrated in vacuo. Chromatographic purification of the residue (silica gel, 0-100% EtOAc/heptanes) provided 4-(5-methyl-1-(tetrahydro-2H-pyran-2-yl)-1H-indazol-4-yl)-3-((trimethylsilyl)ethynyl)-quinoline (0.788 g) as a yellow solid. $^1$H NMR (400 MHz, MeOH-$d_4$) δ ppm 8.97 (d, J=1.3 Hz, 1H), 8.15 (d, J=9.0 Hz, 1H), 7.71-7.87 (m, 2H), 7.46-7.60 (m, 2H), 7.23-7.42 (m, 2H), 5.86 (ddd, J=9.7, 5.0, 2.8 Hz, 1H), 3.98-4.07 (m, 1H), 3.75-3.92 (m, 1H), 2.41-2.61 (m, 1H), 2.10 (d, J=1.3 Hz, 4H), 2.04-2.22 (m, 1H), 1.80-1.93 (m, 1H), 1.62-1.76 (m, 2H), −0.11 (d, J=9.6 Hz, 9H). m/z (ESI): 440.2 $(M+H)^+$.

Step 3: 4-(5-methyl-1-(tetrahydro-2H-pyran-2-yl)-1H-indazol-4-yl)-3-((trimethylsilyl)ethynyl)quinoline 1-oxide To a 0° C. solution of 4-(5-methyl-1-(tetrahydro-2H-pyran-2-yl)-1H-indazol-4-yl)-3-((trimethylsilyl)ethynyl) quinoline (1.77 g, 4.03 mmol) and DCM (27 mL) was added 3-chloroperoxybenzoic acid (1.042 g, 6.04 mmol, Sigma-Aldrich). The mixture was stirred at room temperature overnight. The reaction was quenched with sodium thiosulfate (1N, 7 mL) and aqueous saturated $NaHCO_3$ (7 mL). The mixture was extracted with DCM (2×50 mL). The combined organic extracts were dried over $MgSO_4$ and concentrated in vacuo to provide 4-(5-methyl-1-(tetrahydro-2H-pyran-2-yl)-1H-indazol-4-yl)-3-((trimethylsilyl)ethynyl)quinoline 1-oxide as a yellow solid, which was used in the next step without purification. m/z (ESI): 456.2 $(M+H)^+$.

Step 4: 2-chloro-4-(5-methyl-1-(tetrahydro-2H-pyran-2-yl)-1H-indazol-4-yl)-3-((trimethylsilyl)ethynyl)quinoline To a solution of 4-(5-methyl-1-(tetrahydro-2H-pyran-2-yl)-1H-indazol-4-yl)-3-((trimethylsilyl)ethynyl)quinoline 1-oxide (1.817 g, 3.99 mmol), DIPEA (3.48 mL, 19.94 mmol, Sigma-Aldrich) and acetonitrile (30 mL) was added $POCl_3$ (1.858 mL, 19.94 mmol, Sigma-Aldrich) dropwise. The reaction was stirred at 80° C. for 1.5 h. The mixture was cooled to room temperature and poured into a solution of ice and aqueous saturated $Na_2CO_3$ (10 mL). The mixture was stirred at room temperature for 1 h, extracted with EtOAc (2×100 mL). The combined organic extracts were dried over $MgSO_4$ and concentrated in vacuo. Chromatographic purification of the residue (silica gel, 0-100% EtOAc/heptanes) provided 2-chloro-4-(5-methyl-1-(tetrahydro-2H-pyran-2-yl)-1H-indazol-4-yl)-3-((trimethylsilyl)ethynyl)quinoline (669 mg, 35.4% yield) as a yellow solid. m/z (ESI): 474.2 $(M+H)^+$. $^1$H NMR (400 MHz, MeOH-$d_4$) δ ppm 8.05 (d, J=9.2 Hz, 1H), 7.75-7.87 (m, 2H), 7.44-7.57 (m, 2H), 7.31-7.36 (m, 1H), 7.22-7.31 (m, 1H), 5.86 (ddd, J=9.8, 5.3, 2.7 Hz, 1H), 3.97-4.11 (m, 1H), 3.78-3.90 (m, 1H), 2.41-2.58 (m, 1H), 2.10 (d, J=1.5 Hz, 4H), 2.03 (br dd, J=13.6, 2.9 Hz, 1H), 1.61-1.91 (m, 3H), −0.13 (d, J=9.4 Hz, 9H).

Step 5: tert-butyl 6-(4-(5-methyl-1-(tetrahydro-2H-pyran-2-yl)-1H-indazol-4-yl)-3-((trimethylsilyl)ethynyl)quinolin-2-yl)-2,6-diazaspiro[3.4]octane-2-carboxylate A mixture of 2-chloro-4-(5-methyl-1-(tetrahydro-2H-pyran-2-yl)-1H-indazol-4-yl)-3-((trimethylsilyl)ethynyl) quinoline (328 mg, 0.692 mmol), tert-butyl 2,6-diazaspiro [3.4]octane-2-carboxylate (220 mg, 1.038 mmol, PharmaBlock), and DIPEA (0.266 mL, 1.522 mmol, Sigma-Aldrich) in DMA (4 mL) was subjected to a microwave irradiation at 110° C. for 90 min. The mixture was diluted with aqueous saturated $NaHCO_3$ (30 mL) and extracted with EtOAc (2×40 mL). The combined organic extracts were dried over $MgSO_4$ and concentrated in vacuo to provide tert-butyl 6-(4-(5-methyl-1-(tetrahydro-2H-pyran-2-yl)-1H-indazol-4-yl)-3-((trimethylsilyl)ethynyl)-quinolin-2-yl)-2,6-diazaspiro[3.4]octane-2-carboxylate as a yellow solid which was used in the next step without purification. m/z (ESI): 650.2 $(M+H)^+$.

Step 6: tert-butyl 6-(3-ethynyl-4-(5-methyl-1-(tetrahydro-2H-pyran-2-yl)-1H-indazol-4-yl)quinolin-2-yl)-2,6-diazaspiro[3.4]octane-2-carboxylate To a 0° C. solution of tert-butyl 6-(4-(5-methyl-1-(tetrahydro-2H-pyran-2-yl)-1H-indazol-4-yl)-3-((trimethylsilyl) ethynyl)quinolin-2-yl)-2,6-diazaspiro[3.4]octane-2-carboxylate (450 mg, 0.692 mmol) and THF (3 mL) under $N_2$ was added TBAF (1M in THF. 0.900 mL, 0.900 mmol, Sigma-Aldrich) dropwise. The mixture was stirred at 0° C. for 15 min, then diluted with aqueous saturated $NH_4Cl$ (40 mL) and extracted with EtOAc (1×50 mL). The organic layer was washed with aqueous saturated $NH_4Cl$ (2×40 mL), dried over $MgSO_4$, and concentrated in vacuo to provide tert-butyl 6-(3-ethynyl-4-(5-methyl-1-(tetrahydro-2H-pyran-2-yl)-1H-indazol-4-yl)quinolin-2-yl)-2,6-diazaspiro [3.4]octane-2-carboxylate as a yellow solid, which was used in the next step without purification. m/z (ESI): 578.2 $(M+H)^+$.

Step 7: tert-butyl 6-(4-(5-methyl-1-(tetrahydro-2H-pyran-2-yl)-1H-indazol-4-yl)-3-vinylquinolin-2-yl)-2,6-diazaspiro[3.4]octane-2-carboxylate To a solution of tert-butyl 6-(3-ethynyl-4-(5-methyl-1-(tetrahydro-2H-pyran-2-yl)-1H-indazol-4-yl)quinolin-2-yl)-2,6-diazaspiro[3.4]octane-2-carboxylate (400 mg, 0.692 mmol) and EtOH (4 mL) was added a solution of Pd/C (10 wt % wet, 73.7 mg, 0.692 mmol, Sigma-Aldrich) in EtOAc (0.5 mL). The resulting mixture was stirred at room temperature under $H_2$ (40 psi) for 30 min. The mixture was filtered through celite and the celite washed with EtOAc (3×5 mL). The filtrate was concentrated in vacuo to provide tert-butyl 6-(4-(5-methyl-1-(tetrahydro-2H-pyran-2-yl)-1H-indazol-4-yl)-3-vinylquinolin-2-yl)-2,6-diazaspiro[3.4]octane-2-carboxylate as a yellow solid, which was used in the next step without purification. m/z (ESI): 580.2 $(M+H)^+$.

Step 8: 4-(5-methyl-1H-indazol-4-yl)-2-(2,6-diazaspiro[3.4]octan-6-yl)-3-vinylquinoline To a solution of tert-butyl 6-(4-(5-methyl-1-(tetrahydro-2H-pyran-2-yl)-1H-indazol-4-yl)-3-vinylquinolin-2-yl)-2,6-diazaspiro[3.4]octane-2-carboxylate (401 mg, 0.692 mmol) and DCM (4 mL) was added TFA (1.031 mL, 13.83 mmol, Sigma-Aldrich). The resulting mixture was stirred at room temperature for 1 h. The mixture was concentrated in vacuo to provide 4-(5-methyl-1H-indazol-4-yl)-2-(2,6-diazaspiro [3.4]octan-6-yl)-3-vinylquinoline as a yellow solid (TFA salt) which was used in the next step without purification. m/z (ESI): 396.3 $(M+H)^+$.

Step 9: (P)-1-(6-(3-ethenyl-4-(5-methyl-1H-indazol-4-yl)-2-quinolinyl)-2,6-diazaspiro[3.4]octan-2-yl)-2-propen-1-one To a 0° C. solution of 4-(5-methyl-1H-indazol-4-yl)-2-(2,6-diazaspiro[3.4]octan-6-yl)-3-vinylquinoline (274 mg, 0.693 mmol) and DCM (5 mL) under $N_2$ was added $K_2CO_3$ (479 mg. 3.46 mmol, Sigma-Aldrich) and DIPEA (1.210 mL, 6.93 mmol, Sigma-Aldrich). The resulting mixture was stirred at 0° C. for 5 min, before a solution of acryloyl chloride (0.056 mL, 0.693 mmol, Sigma-Aldrich) in DCM (0.2 mL) was added. The resulting mixture was stirred at 0° C. for 5 min, then quenched with aqueous saturated $NaHCO_3$ (15 mL) and extracted with EtOAc (1×50 mL). The organic layer was dried over $MgSO_4$ and concentrated in vacuo to provide 1-(6-(4-(5-methyl-1H-indazol-4-yl)-3-vinylquinolin-2-yl)-2,6-diazaspiro[3.4]octan-2-yl)prop-2-en-1-one (311 mg) as a yellow solid. The solids were purified by Prep SFC using two Whelk-O—R,R columns (250×21 mm, Sum) with a mobile phase of 65% liquid $CO_2$ and 35% MeOH with 0.2% TEA using a flowrate of 60 mL/min to provide (P)-1-(6-(4-(5-methyl-1H-indazol-4-yl)-3-vinylquinolin-2-yl)-2,6-diazaspiro[3.4]octan-2-yl)prop-2-en-1-one (1$^{st}$ eluting isomer). m/z (ESI): 450.2 $(M+H)^+$. $^1$H NMR (400 MHz, DMSO-$d_6$) δ ppm 13.08 (br d, J=1.9 Hz, 1H), 7.69 (d, J=8.2 Hz, 1H), 7.49-7.57 (m, 2H), 7.30-7.39 (m, 2H), 7.04 (t, J=6.9 Hz, 1H), 6.76 (d, J=8.4 Hz, 1H), 6.40-6.52 (m, 1H), 6.27-6.38 (m, 1H), 6.11 (dd, J=17.0, 2.2 Hz, 1H), 5.63-5.71 (m, 1H), 5.04-5.14 (m, 1H), 4.91 (d, J=18.2 Hz, 1H), 4.21-4.31 (m, 1H), 4.17 (t, J=8.6 Hz, 1H), 3.85-4.01 (m, 2H), 3.72-3.83 (m, 2H), 3.54-3.71 (m, 2H), 2.16 (br t, J=6.5 Hz, 2H), 1.95 (d, J=9.4 Hz, 3H). The stereochemistry was assigned arbitrarily and is not established.

Example 26-2: (M)-1-(6-(3-ethenyl-4-(5-methyl-1H-indazol-4-yl)-2-quinolinyl)-2,6-diazaspiro[3.4]octan-2-yl)-2-propen-1-one This example was the second eluting isomer in the separation described in Example 26-1, Step 9. m/z (ESI): 450.3 $(M+H)^+$. $^1$H NMR (400 MHz, DMSO-$d_6$) δ ppm 13.07 (br s, 1H), 7.68 (d, J=8.3 Hz, 1H), 7.45-7.58 (m, 2H), 7.31-7.41 (m, 2H), 7.03 (t, J=7.0 Hz, 1H), 6.76 (d, J=7.5 Hz, 1H), 6.44 (dd, J=17.9, 11.5 Hz, 1H), 6.23-6.36 (m, 1H), 5.97-6.15 (m, 1H), 5.66 (dd, J=10.2, 2.3 Hz, 1H), 5.04-5.17 (m, 1H), 4.81-4.98 (m, 1H), 4.08-4.30 (m, 2H), 3.53-3.99 (m, 6H), 2.15 (br t, J=6.2 Hz, 2H), 1.94 (d, J=9.5 Hz, 3H).

Example 27-1: 1-(6-(3-fluoro-7-methoxy-4-(5-methyl-1H-indazol-4-yl)-2-quinolinyl)-2,6-diazaspiro[3.4]octan-2-yl)-2-propen-1-one

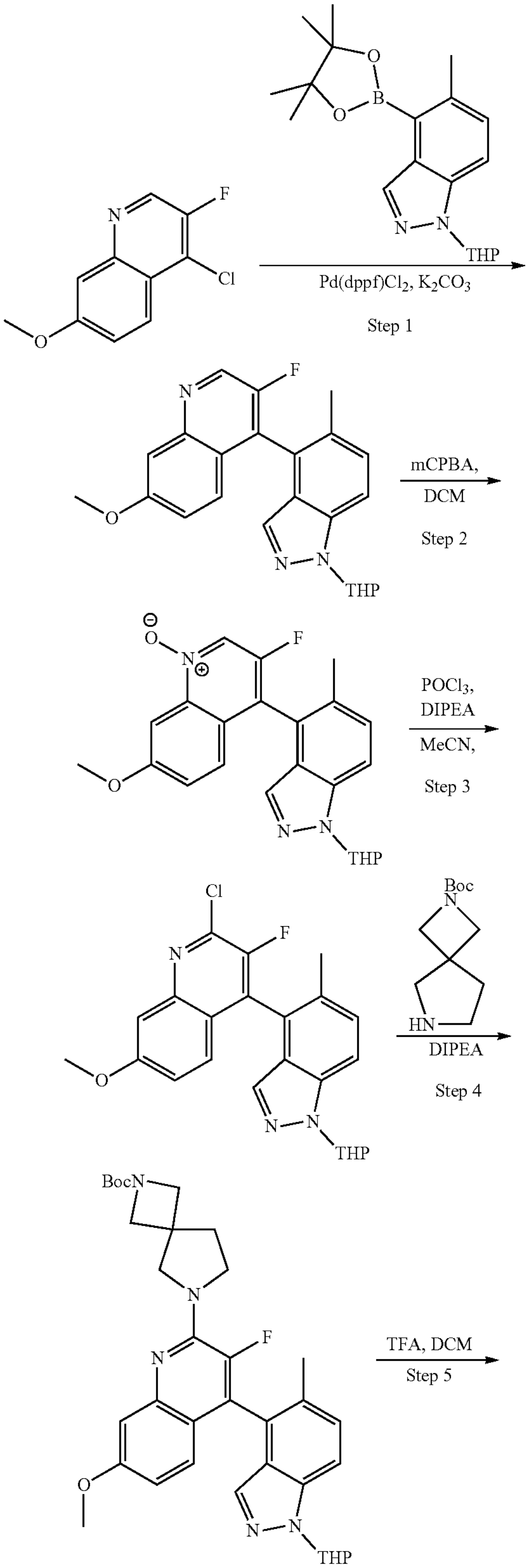

-continued

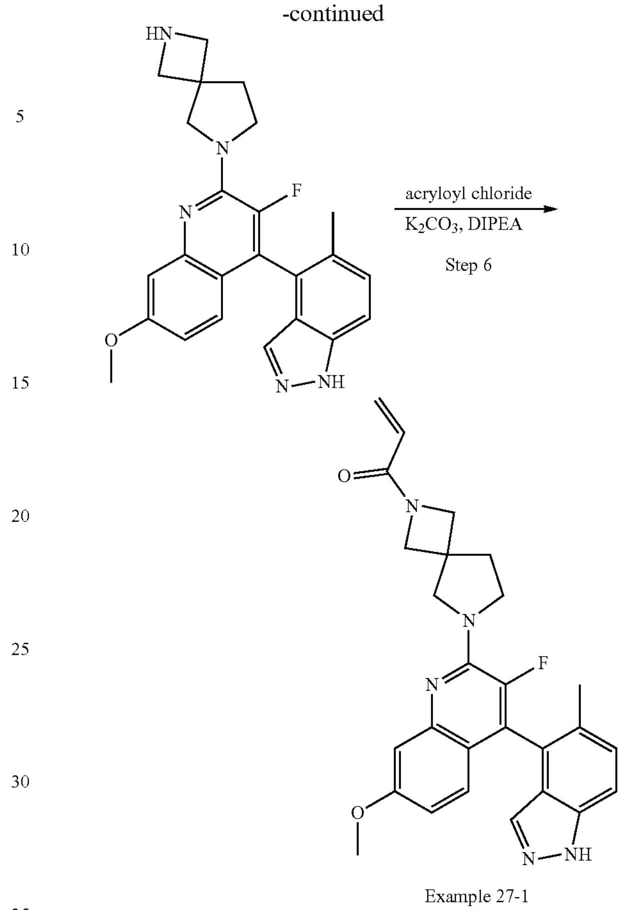

Example 27-1

Step 1: 3-fluoro-7-methoxy-4-(5-methyl-1-(tetrahydro-2H-pyran-2-yl)-1H-indazol-4-yl)quinoline A mixture of 5-methyl-1(5-methyl-(tetrahydro-2H-pyran-2-yl)-4-(4,4,5,5-tetramethyl-1,3,2-dioxaborolan-2-yl)-1H-indazole (1617 mg, 4.73 mmol, Enovation Chemicals), $PdCl_2$(dppf) DCM adduct (346 mg, 0.473 mmol, Strem Chemicals), $K_2CO_3$ (1306 mg, 9.45 mmol, Sigma-Aldrich), and 4-chloro-3-fluoro-7-methoxyquinoline (500 mg, 2.363 mmol, CAS: 852062-11-4) in 1,4-dioxane (10 mL) and water (2.0 mL) was subjected to microwave irradiation at 130° C. for 10 h. The mixture was cooled to room temperature and concentrated in vacuo. Chromatographic purification of the residue (silica gel, 0-100% EtOAc/heptanes) provided 3-fluoro-7-methoxy-4-(5-methyl-1-(tetrahydro-2H-pyran-2-yl)-1H-indazol-4-yl)quinoline (783 mg) as a white solid. m/z (ESI): 392.3 $(M+H)^+$. $^1H$ NMR (400 MHz, DMSO-$d_6$) δ ppm 9.04 (d, J=2.7 Hz, 1H), 7.85 (d, J=8.8 Hz, 1H), 7.57 (d, J=2.5 Hz, 1H), 7.52 (d, J=8.6 Hz, 1H), 7.43 (s, 1H), 7.18-7.24 (m, 1H), 7.05-7.14 (m, 1H), 5.85-5.95 (m, 1H), 3.94 (s, 3H), 3.91 (br s, 1H), 3.72-3.85 (m, 1H), 2.28-2.40 (m, 1H), 2.08 (s, 3H), 1.94-2.05 (m, 2H), 1.69-1.84 (m, 1H), 1.59 (br d, J=3.8 Hz, 2H).

Step 2: 3-fluoro-7-methoxy-4-(5-methyl-1-(tetrahydro-2H-pyran-2-yl)-1H-indazol-4-yl)quinoline 1-oxide A mixture of 3-fluoro-7-methoxy-4-(5-methyl-1-(tetrahydro-2H-pyran-2-yl)-1H-indazol-4-yl)quinoline (783 mg, 2.00 mmol) and 3-chloroperoxybenzoic acid (518 mg, 3.00 mmol, Sigma-Aldrich) in DCM (15 mL) was stirred at room temperature for 3 h. The mixture was quenched with sodium thiosulfate (1N, 7 mL) and saturated $NaHCO_3$ (7 mL). The mixture was extracted with DCM (2×50 mL). The combined organic extracts were dried over $MgSO_4$, concentrated, and dried in vacuo to provide 3-fluoro-7-methoxy-4-(5-methyl-1-(tetrahydro-2H-pyran-2-yl)-1H-indazol-4-yl)quinoline 1-oxide as a yellow solid which was used in the next step without purification. m/z (ESI): 408.2 $(M+H)^+$.

Step 3: 2-chloro-3-fluoro-7-methoxy-4-(5-methyl-1-(tetrahydro-2H-pyran-2-yl)-1H-indazol-4-yl)quinoline To a solution of 3-fluoro-7-methoxy-4-(5-methyl-1-tetrahydro-2H-pyran-2-yl)-1H-indazol-4-yl)quinoline 1-oxide (815 mg, 2.000 mmol) in acetonitrile (20 mL) was added DIPEA (1.747 mL, 10.00 mmol, Sigma-Aldrich) followed by $POCl_3$ (0.932 mL, 10.00 mmol, Sigma-Aldrich). The resulting mixture was stirred at 75° C. for 5 h. The mixture was cooled to room temperature and poured into a mixture of ice and aqueous saturated $NaHCO_3$ (40 mL). The resulting mixture was stirred at room temperature for 1 h and extracted with EtOAc (2×100 mL). The combined organic extracts were dried over $MgSO_4$ and concentrated in vacuo. Chromatographic purification of the residue (silica gel, 0-100% EtOAc/heptanes) provided 2-chloro-3-fluoro-7-methoxy-4-(5-methyl-1-(tetrahydro-2H-pyran-2-yl)-1H-indazol-4-yl)quinoline (170 mg) as yellow solid. m/z (ESI): 426.1 $(M+H)^+$.

Step 4: tert-butyl 6-(3-fluoro-7-methoxy-4-(5-methyl-1-(tetrahydro-2H-pyran-2-yl)-1H-indazol-4-yl)quinolin-2-yl)-2,6-diazaspiro[3.4]octane-2-carboxylate A mixture of 2-chloro-3-fluoro-7-methoxy-4-(5-methyl-1-(tetrahydro-2H-pyran-2-yl)-1H-indazol-4-yl)quinoline (170 mg, 0.399 mmol), tert-butyl 2,6-diazaspiro[3.4]octane-2-carboxylate (127 mg, 0.599 mmol, PharmaBlock), and DIPEA (0.279 mL, 1.597 mmol, Sigma-Aldrich) in DMA (2 mL) was subjected to microwave irradiation at 130° C. for 2 h. The mixture was cooled to room temperature and diluted with aqueous saturated $NaHCO_3$ (30 mL). The mixture was extracted with EtOAc (2×50 mL). The combined organic extracts were dried over $MgSO_4$ and concentrated in vacuo. Chromatographic purification of the residue (silica gel, 0-100% EtOAc/heptanes) provided tert-butyl 6-(3-fluoro-7-methoxy-4-(5-methyl-1-(tetrahydro-2H-pyran-2-yl)-1H-indazol-4-yl)quinolin-2-yl)-2,6-diazaspiro[3.4]-octane-2-carboxylate (227 mg, 95% yield) as a light yellow solid. m/z (ESI): 602.30 $(M+H)^+$.

Step 5: 3-fluoro-7-methoxy-4-(5-methyl-1H-indazol-4-yl)-2-(2,6-diazaspiro[3.4]octan-6-yl)quinoline A mixture of tert-butyl 6-(3-fluoro-7-methoxy-4-(5-methyl-1-(tetrahydro-2H-pyran-2-yl)-1H-indazol-4-yl)quinolin-2-yl)-2,6-diazaspiro[3.4]octane-2-carboxylate (227 mg, 0.377 mmol) and TFA (0.562 mL, 7.54 mmol, Sigma-Aldrich) in DCM (2 mL) was stirred at room temperature for 2 h. The mixture was concentrated and dried in vacuo provided 3-fluoro-7-methoxy-4-(5-methyl-1H-indazol-4-yl)-2-(2,6-diazaspiro[3.4]octan-6-yl)quinoline (TFA salt, yellow solid) which was used in the next step without purification. m/z (ESI): 418.3 $(M+H)^+$.

Step 6: 1-(6-(3-fluoro-7-methoxy-4-(5-methyl-1H-indazol-4-yl)-2-quinolinyl)-2,6-diazaspiro[3.4]octan-2-yl)-2-propen-1-one To a 0° C. solution of 3-fluoro-7-methoxy-4-(5-methyl-1H-indazol-4-yl)-2-(2,6-diazaspiro[3.4]octan-6-yl)quinoline (157 mg, 0.376 mmol) in DCM (3 mL) under $N_2$ was added $K_2CO_3$ (260 mg, 1.880 mmol, Sigma-Aldrich), DIPEA (0.657 mL, 3.76 mmol, Sigma-Aldrich), followed by a solution of acryloyl chloride (0.031 mL, 0.376 mmol, Sigma-Aldrich) in DCM (0.2 mL). The resulting mixture was stirred at 0° C. for 5 min, then quenched with aqueous saturated $NaHCO_3$ (20 mL). The mixture was extracted with EtOAc (2×50 mL) and combined organic extracts were dried over $MgSO_4$ and concentrated in vacuo. The residue was taken up in DMSO (1 mL) and purified via preparative HPLC (Phenomenex Gemini C18 column, 150×30 mm, 10 μm, 110 A, 10-100% 0.1% TFA in $MeCN/H_2O$). The desired fractions were diluted with aqueous saturated $NaHCO_3$ (20 mL) and extracted with EtOAc (2×50 mL). The combined organic extracts were washed with aqueous saturated $NaHCO_3$ (1×20 mL), dried over $MgSO_4$, concentrated, and dried in vacuo provided 1-(6-(3-fluoro-7-methoxy-4-(5-methyl-1H-indazol-4-yl)quinolin-2-yl)-2,6-diazaspiro[3.4]octan-2-yl)prop-2-en-1-one (64 mg) as a white solid. m/z (ESI): 472.3 $(M+H)^+$. $^1H$ NMR (400 MHz, DMSO-$d_6$) δ ppm 13.15 (s, 1H), 7.60 (d, J=8.8 Hz, 1H), 7.45 (s, 1H), 7.41 (d, J=8.6 Hz, 1H), 7.07-7.12 (m, 1H), 6.75 (s, 2H), 6.26-6.37 (m, 1H), 6.11 (dd, J=17.1, 2.3 Hz, 1H), 5.63-5.71 (m, 1H), 4.29 (d, J=8.8 Hz, 1H), 4.19 (br d, J=8.4 Hz, 1H), 3.97-4.02 (m, 1H), 3.87-3.97 (m, 3H), 3.85 (s, 3H), 3.75-3.82 (m, 2H), 2.15-2.23 (m, 2H), 2.09 (d, J=1.3 Hz, 3H).

Example 27-2: 1-(6-(3-chloro-4-(5-methyl-1H-indazol-4-yl)-2-quinolinyl)-2,6-diazaspiro[3.4]octan-2-yl)-2-propen-1-one This compound was synthesized in an analogous manner to Example 27-1 using 4-bromo-3-chloroquinoline (Aurum Pharmatech) as the starting material to give 1-(6-(3-chloro-4-(5-methyl-1H-indazol-4-yl)-2-quinolinyl)-2,6-diazaspiro[3.4]octan-2-yl)-2-propen-1-one. m/z (ESI): 458.1 (M+H)+, 1H NMR (400 MHz, DMSO-d6) δ ppm 13.15 (s, 1H), 7.73 (d, J=7.9 Hz, 1H), 7.53-7.63 (m, 2H), 7.36-7.43 (m, 2H), 7.11 (t, J=7.4 Hz, 1H), 6.78 (d, J=8.4 Hz, 1H), 6.28-6.38 (m, 1H), 6.11 (dd, J=16.9, 2.3 Hz, 1H), 5.64-5.72 (m, 1H), 4.30 (dd, J=8.3, 2.0 Hz, 1H), 4.19 (dd, J=8.7, 5.3 Hz, 1H), 3.96-4.03 (m, 3H), 3.81-3.94 (m, 3H), 2.19 (br t, J=5.7 Hz, 2H), 2.00 (d, J=6.1 Hz, 3H).

Example 28-1: 1-(6-(3-chloro-4-(2-fluorophenyl)-7-(4-methylthiazol-5-yl)-1,5-naphthyridin-2-yl)-2,6-diazaspiro[3.4]octan-2-yl)prop-2-en-1-one

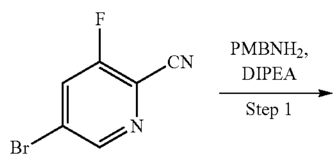

-continued
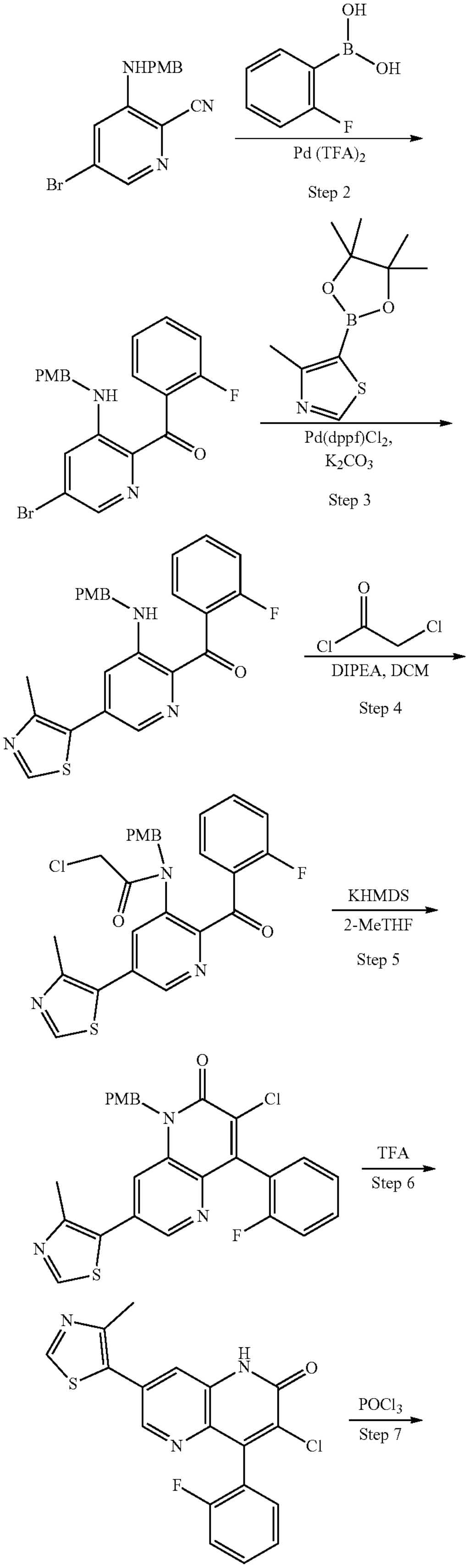
-continued
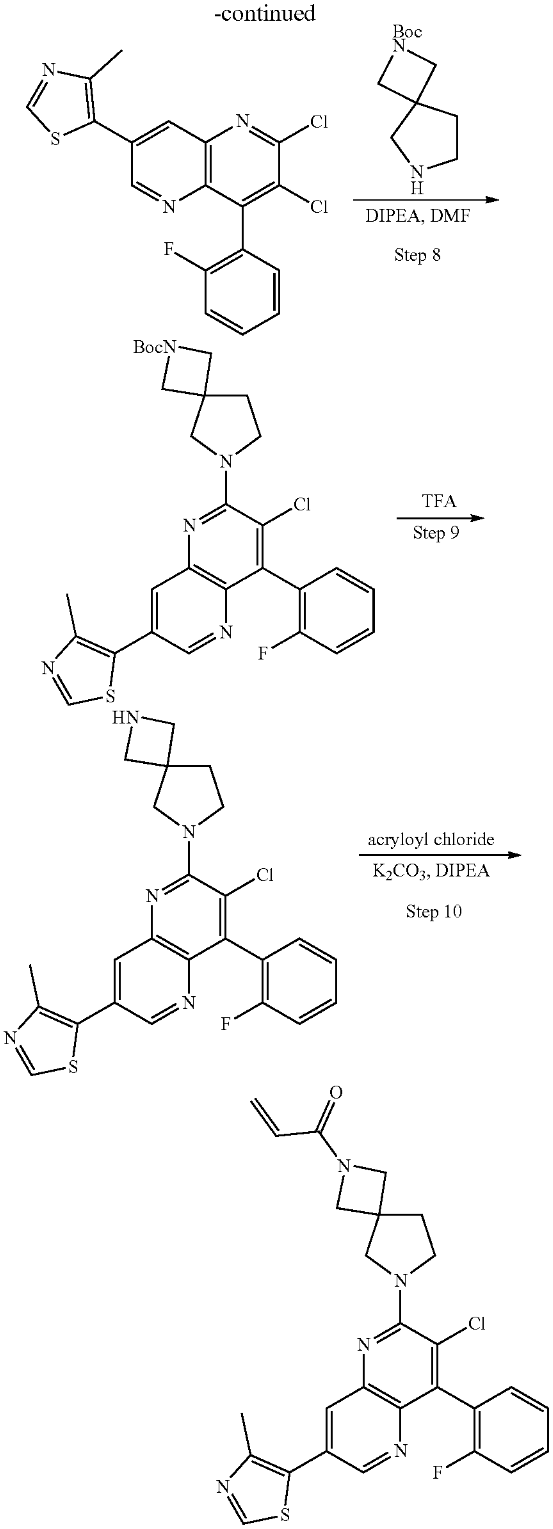
Step 1: 5-bromo-3-((4-methoxybenzyl)amino)picolinonitrile
A mixture of 4-methoxybenzylamine (3.94 mL, 29.9 mmol, Sigma-Aldrich), DIPEA (8.69 mL, 49.8 mmol, Sigma-Aldrich), and 5-bromo-3-fluoropicolinonitrile (5 g, 24.88 mmol, Combi-blocks) in acetonitrile (100 mL) was stirred at 85° C. for 1 h. The mixture was cooled to room temperature, diluted with aqueous saturated $NaHCO_3$ (200 mL), and extracted with EtOAc (2×200 mL). The combined organic extracts were dried over $MgSO_4$ and concentrated in vacuo. Chromatographic purification of the residue (silica gel, 0-100% EtOAc in heptanes) provided 5-bromo-3-((4-methoxybenzyl)amino)picolinonitrile (4.45 g, 56.2% yield) as a yellow solid. m/z (ESI): 318.0, 320.1 $(M+H)^+$. $^1H$ NMR (400 MHz, DMSO-d) δ ppm 7.94 (d, J=1.9 Hz, 1H), 7.38 (d, J=1.9 Hz, 1H), 7.29 (d, J=8.8 Hz, 2H), 6.91 (d, J=8.6 Hz, 2H), 4.40 (d, J=6.1 Hz, 2H), 3.73 (s, 3H).

Step 2: (5-bromo-3-((4-methoxybenzyl)amino)pyridin-2-yl)(2-fluorophenyl)methanone A mixture of 5-bromo-3-((4-methoxybenzyl)amino)picolinonitrile (4.45, 14 mmol), 5,5'-dimethyl-2,2'-bipyridine (387 mg, 2.098 mmol, Combi-blocks), 2-fluorophenylboronic acid (3.91 g, 28 mmol, Combi-Blocks), bis(2,2,2-trifluoroacetoxy)palladium (465 mg, 1.399 mmol, Oakwood Chemicals), methanesulfonic acid (9.08 mL, 0.140 mmol. Oakwood Chemicals) and 2-MeTHF (40 mL):water (20 mL) was stirred at 85° C. under $N_2$ overnight. The mixture was diluted with aqueous saturated $NaHCO_3$ (80 mL) and extracted with EtOAc (2×100 mL). The combined organic extracts were dried over $MgSO_4$ and concentrated in vacuo. Chromatographic purification of the residue (silica gel, 0-100% EtOAc/heptanes) provided (5-bromo-3-((4-methoxybenzyl)amino)pyridin-2-yl)(2-fluorophenyl)methanone (414 mg, 7.1% yield) as a yellow solid. m/z (ESI): 415.0, 417.1 $(M+H)^+$.

Step 3: (2-fluorophenyl)(3-((4-methoxybenzyl)amino)-5-(4-methylthiazol-5-yl)pyridin-2-yl)methanone A mixture of (5-bromo-3-((4-methoxybenzyl)amino)pyridin-2-yl)(2-fluorophenyl)methanone (414 mg, 0.997 mmol), $PdCl_2$(dppf) DCM adduct (1:1) (163 mg, 0.199 mmol, Oakwood Products), $K_2CO_3$ (413 mg, 2.99 mmol, Sigma-Aldrich), 4-methyl-5-(4,4,5,5-tetramethyl-1,3,2-dioxaborolan-2-yl)thiazole (449 mg, 1.994 mmol, JW Pharma) and 1,4-dioxane (6 mL):water (0.6 mL) was stirred at 95° C. for 2 h. The mixture was cooled to room temperature and was concentrated in vacuo. Chromatographic purification of the residue (silica gel, 0-100% EtOAc/heptanes) provided (2-fluorophenyl)(3-((4-methoxybenzyl)amino)-5-(4-methylthiazol-5-yl)pyridin-2-yl)methanone (432 mg) as a yellow solid. m/z (ESI): 434.1 $(M+H)^+$.

Step 4: 2-chloro-N-(2-(2-fluorobenzoyl)-5-(4-methylthiazol-5-yl)pyridin-3-yl)-N-(4-methoxybenzyl)acetamide To a solution of (2-fluorophenyl)(3-((4-methoxybenzyl)amino)-5-(4-methylthiazol-5-yl)pyridin-2-yl)methanone (432 mg), DIPEA (0.696 mL, 3.99 mmol, Sigma-Aldrich) and DCM (7 mL) at 0° C. under $N_2$ was added a solution of chloroacetyl chloride (0.167 mL, 2.093 mmol, Sigma-Aldrich) in DCM (0.2 mL). The resulting mixture was stirred at room temperature overnight. Chromatographic purification of the mixture (silica gel, 0-100% EtOAc/heptanes) provided 2-chloro-N-(2-(2-fluorobenzoyl)-5-(4-methylthiazol-5-yl)pyridin-3-yl)-N-(4-methoxybenzyl)acetamide (108 mg, 21.25% yield) as a yellow solid. m/z (ESI): 510.1 $(M+H)^+$.

Step 5: 3-chloro-4-(2-fluorophenyl)-1-(4-methoxybenzyl)-7-(4-methylthiazol-5-yl)-1,5-naphthyridin-2(1H)-one To a mixture of 2-chloro-N-(2-(2-fluorobenzoyl)-5-(4-methylthiazol-5-yl)pyridin-3-yl)-N-(4-methoxybenzyl)acetamide (108 mg, 0.212 mmol) and 2-MeTHF (5 mL) at 0° C. under $N_2$ was added KHMDS, 1M in THF (0.212 mL, 0.212 mmol, Sigma-Aldrich) dropwise. The reaction was stirred at 0° C. for 1 h and quenched with aqueous saturated $NaHCO_3$ (2 mL). The mixture was concentrated in vacuo and chromatographic purification of the residue (silica gel, 0-100% EtOAc:EtOH (3:1)/heptane) provided 3-chloro-4-(2-fluorophenyl)-1-(4-methoxybenzyl)-7-(4-methylthiazol-5-yl)-1,5-naphthyridin-2(1H)-one as a yellow solid. m/z (ESI): 492.1 $(M+H)^+$.

Step 6: 3-chloro-4-(2-fluorophenyl)-7-(4-methylthiazol-5-yl)-1,5-naphthyridin-2(1H)-one A mixture of 3-chloro-4-(2-fluorophenyl)-1-(4-methoxybenzyl)-7-(4-methylthiazol-5-yl)-1,5-naphthyridin-2(1H)-one (104 mg, 0.211 mmol) and TFA (788 μL, 10.57 mmol, Sigma-Aldrich) was subjected to microwave irradiation at 120° C. for 1 h. The mixture was concentrated in vacuo to provide 3-chloro-4-(2-fluorophenyl)-7-(4-methylthiazol-5-yl)-1,5-naphthyridin-2(1H)-one as a yellow solid, which was used in the next step without purification. m/z (ESI): 372.1 $(M+H)^+$.

Step 7: 5-(6,7-dichloro-8-(2-fluorophenyl)-1,5-naphthyridin-3-yl)-4-methylthiazole To a solution of 3-chloro-4-(2-fluorophenyl)-7-(4-methylthiazol-5-yl)-1,5-naphthyridin-2(1H)-one (79 mg, 0.212 mmol) and acetonitrile (1 mL) was added $POCl_3$ (0.198 mL, 2.125 mmol, Sigma-Aldrich). The resulting mixture was stirred at 85° C. overnight. The mixture was cooled to room temperature and poured into a mixture of ice water and $Na_2CO_3$ (30 mL). The mixture was diluted with EtOAc (50 mL) and stirred at room temperature for 1 h. The organic layer was partitioned and the aqueous layer was extracted with EtOAc (30 mL). The combined organic extracts were dried over $MgSO_4$ and concentrated in vacuo to provide 5-(6,7-dichloro-8-(2-fluorophenyl)-1,5-naphthyridin-3-yl)-4-methylthiazole as a yellow solid, which was used in the next step without purification. m/z (ESI): 390.0, 392.1 $(M+H)^+$.

Step 8: tert-butyl 6-(3-chloro-4-(2-fluorophenyl)-7-(4-methylthiazol-5-yl)-1,5-naphthyridin-2-yl)-2,6-diazaspiro[3.4]octane-2-carboxylate A mixture of 5-(6,7-dichloro-8-(2-fluorophenyl)-1,5-naphthyridin-3-yl)-4-methylthiazole (83 mg, 0.213 mmol), 2-(tert-butoxycarbonyl)-2,6-diazaspiro[3.4]octane (45.2 mg, 0.213 mmol, PharmaBlock), DIPEA (0.111 mL, 0.638 mmol, Sigma-Aldrich) and DMF (1.6 mL) was stirred at 100° C. overnight. The mixture was concentrated in vacuo and chromatographic purification of the residue (silica gel, 0-100% EtOAc/heptanes) provided tert-butyl 6-(3-chloro-4-(2-fluorophenyl)-7-(4-methylthiazol-5-yl)-1,5-naphthyridin-2-yl)-2,6-diazaspiro[3.4]octane-2-carboxylate (23 mg, 19.17% yield) as a yellow solid. m/z (ESI): 566.2, 568.1 $(M+H)^+$.

Step 9: 5-(7-chloro-8-(2-fluorophenyl)-6-(2,6-diazaspiro[3.4]octan-6-yl)-1,5-naphthyridin-3-yl)-4-methylthiazole (TFA Salt)

A solution of tert-butyl 6-(3-chloro-4-(2-fluorophenyl)-7-(4-methylthiazol-5-yl)-1,5-naphthyridin-2-yl)-2,6-diazaspiro[3.4]octane-2-carboxylate (23 mg, 0.041 mmol), TFA (0.030 mL, 0.406 mmol, Sigma-Aldrich) and DCM (1 mL) was stirred at room temperature for 2 h. The mixture was concentrated in vacuo to provide 5-(7-chloro-8-(2-fluorophenyl)-6-(2,6-diazaspiro[3.4]octan-6-yl)-1,5-naphthyridin-3-yl)-4-methylthiazole (TFA salt) which was used in the next step without purification. m/z (ESI): 466.1, 468.1 $(M+H)^+$.

Step 10: 1-(6-(3-chloro-4-(2-fluorophenyl)-7-(4-methylthiazol-5-yl)-1,5-naphthyridin-2-yl)-2,6-diazaspiro[3.4]octan-2-yl)prop-2-en-1-one To a solution of 5-(7-chloro-8-(2-fluorophenyl)-6-(2,6-diazaspiro[3.4]octan-6-yl)-1,5-naphthyridin-3-yl)-4-methylthiazole, TFA salt (18.93 mg, 0.041 mmol) and DCM (1 mL) was added $K_2CO_3$ (28.1 mg, 0.203 mmol, Sigma-Aldrich) and DIPEA (0.035 mL, 0.203 mmol, Sigma-Aldrich) followed by a solution of acryloyl chloride (3.31 µL, 0.041 mmol, Sigma-Aldrich) in DCM (0.1 mL). The resulting mixture was stirred at room temperature for 15 min, before quenching with aqueous saturated $NaHCO_3$ (2 mL). The mixture was extracted with EtOAc (2×30 mL). The combined organic extracts were dried over $MgSO_4$ and concentrated in vacuo. The residue was taken up in DMSO (1 mL) and purified via preparative HPLC (Phenomenex Gemini C18 column, 150×30 mm, 10 µm, 110 A. 10-100% 0.1% TFA in $MeCN/H_2O$). The desired fractions were diluted with aqueous saturated $Na_2CO_3$ (20 mL) and extracted with EtOAc (2×50 mL). The combined organic extracts were dried over $MgSO_4$ and concentrated in vacuo to provide 1-(6-(3-chloro-4-(2-fluorophenyl)-7-(4-methylthiazol-5-yl)-1,5-naphthyridin-2-yl)-2,6-diazaspiro[3.4]octan-2-yl)prop-2-en-1-one (15 mg, 71.0% yield) as a light yellow solid. m/z (ESI): 520.0, 522.2 $(M+H)^+$. $^1H$ NMR (400 MHz, DMSO-$d_6$) δ ppm 9.13 (s, 1H), 8.68 (s, 1H), 8.09 (s, 1H), 7.51-7.60 (m, 1H), 7.33-7.45 (m, 3H), 6.32 (br dd, J=16.9, 10.2 Hz, 1H), 6.07-6.16 (m, 1H), 5.67 (br d, J=10.0 Hz, 1H), 4.24-4.34 (m, 1H), 4.19 (br d, J=5.0 Hz, 1H), 3.96-4.08 (m, 3H), 3.85-3.95 (m, 3H), 2.54 (s, 3H), 2.20 (br s, 2H).

Example 29-1: 1-(6-(3-(difluoromethyl)-4-(1,6-dimethyl-1H-indazol-7-yl)-7,7-dimethyl-7,8-dihydro-5H-pyrano[4,3-b]pyridin-2-yl)-2,6-diazaspiro[3.4]octan-2-yl)-2-propen-1-one

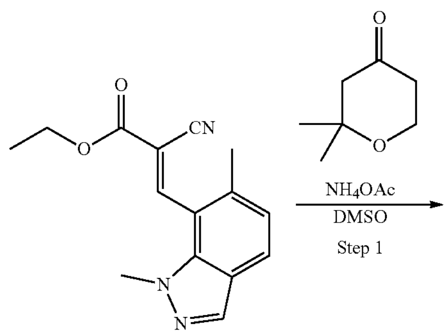

-continued

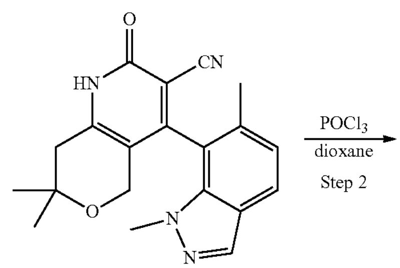

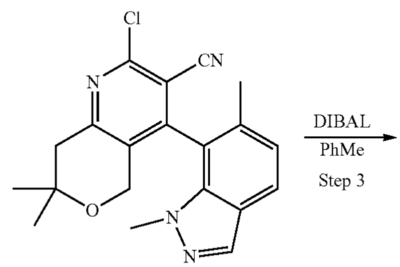

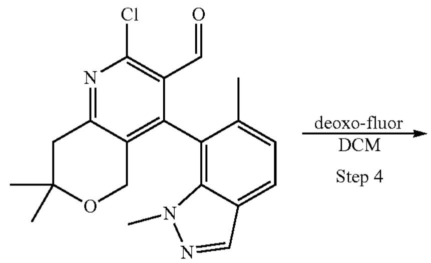

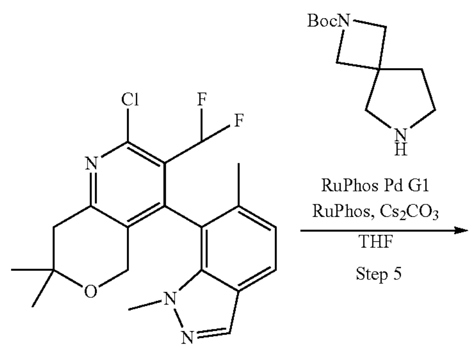

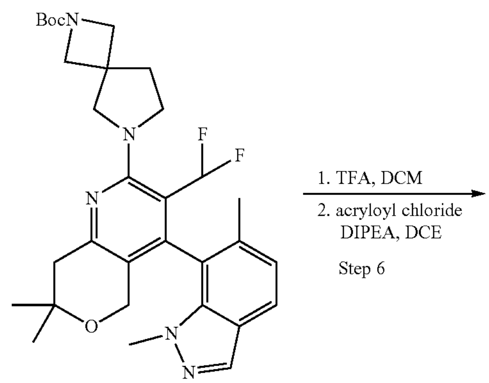

-continued

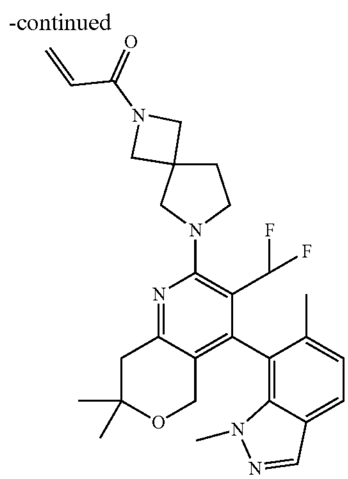

Example 29-1

Step 1: 4-(1,6-dimethyl-1H-indazol-7-yl)-7,7-dimethyl-2-oxo-1,5,7,8-tetrahydro-2H-pyrano[4,3-b]pyridine-3-carbonitrile Ethyl (E)-2-cyano-3-(1,6-dimethyl-1H-indazol-7-yl)acrylate (2.94 g, 10.92 mmol), 2,2-dimethyltetrahydro-4H-pyran-4-one (1.82 g, 14.2 mmol, PharmaBlock), and $NH_4OAc$ (8.42 g, 109 mmol) were mixed in DMSO (15 mL). The reaction was stirred at 80° C. open to air for 6 d. Upon completion, the reaction was partitioned between aqueous saturated $NH_4Cl$ and EtOAc. The organic layer was separated, washed with brine, dried over $MgSO_4$, and concentrated. Chromatographic purification of the residue (silica gel, 0-100% EtOAc in heptanes) provided 4-(1,6-dimethyl-1H-indazol-7-yl)-7,7-dimethyl-2-oxo-1,5,7,8-tetrahydro-2H-pyrano[4,3-b]pyridine-3-carbonitrile (2.90 g, 76% yield) as a tan solid. m/z (ESI): 349.3 $(M+H)^+$.

Step 2: 2-chloro-4-(1,6-dimethyl-1H-indazol-7-yl)-7,7-dimethyl-7,8-dihydro-5H-pyrano[4,3-b]pyridine-3-carbonitrile To a vial was added 4-(1,6-dimethyl-1H-indazol-7-yl)-2-hydroxy-7,7-dimethyl-7,8-dihydro-5H-pyrano[4,3-b]pyridine-3-carbonitrile (500 mg, 1.44 mmol), dioxane (7 mL), and $POCl_3$ (880 mg, 0.535 mL, 5.74 mmol). The mixture was capped and allowed to stir at 100° C. for 2 h. The reaction was poured into a separation funnel containing 100 mL of aqueous saturated $NaHCO_3$. The aqueous solution was extracted with EtOAc, dried over $MgSO_4$, and concentrated to give 2-chloro-4-(1,6-dimethyl-1H-indazol-7-yl)-7,7-dimethyl-7,8-dihydro-5H-pyrano[4,3-b]pyridine-3-carbonitrile (424 mg, 81% yield) as a brown solid. m/z (ESI): 367.2 $(M+H)^+$.

Step 3: 2-chloro-4-(1,6-dimethyl-1H-indazol-7-yl)-7,7-dimethyl-7,8-dihydro-5H-pyrano[4,3-b]pyridine-3-carbaldehyde A solution of 2-chloro-4-(1,6-dimethyl-1H-indazol-7-yl)-7,7-dimethyl-7,8-dihydro-5H-pyrano[4,3-b]pyridine-3-carbonitrile (200 mg, 0.545 mmol) in toluene (5 mL) was cooled to −78° C. and DIBAL (1M in toluene, 0.650 mL, 0.650 mmol) was added. The mixture was allowed to warm to room temperature and stirred for 18 h. Upon completion, the mixture was quenched with saturated Rochelle's salt and extracted with EtOAc. Organics were dried over $MgSO_4$ and concentrated to give 2-chloro-4-(1,6-dimethyl-1H-indazol-7-yl)-7,7-dimethyl-7,8-dihydro-5H-pyrano[4,3-b]pyridine-3-carbaldehyde (201 mg) as a light yellow solid, which was used in the following reaction as is assuming quantitative yield. m/z (ESI): 370.2 $(M+H)^+$.

Step 4: 2-chloro-3-(difluoromethyl)-4-(1,6-dimethyl-1H-indazol-7-yl)-7,7-dimethyl-7,8-dihydro-5H-pyrano[4,3-b]pyridine Deoxo-fluor (240 mg, 1.09 mmol) was added to a 0° C. solution of 2-chloro-4-(1,6-dimethyl-1H-indazol-7-yl)-7,7-dimethyl-7,8-dihydro-5H-pyrano[4,3-b]pyridine-3-carbaldehyde (201 mg, 0.543 mmol) and DCM (5 mL). The reaction was warmed to room temperature and stirred for 16 h. The reaction was quenched with aqueous saturated $NaHCO_3$, extracted with EtOAc, dried over $MgSO_4$, and concentrated to give 2-chloro-3-(difluoromethyl)-4-(1,6-dimethyl-1H-indazol-7-yl)-7,7-dimethyl-7,8-dihydro-5H-pyrano[4,3-b]pyridine (213 mg) as an orange oil, which was used in the following step as is assuming quantitative yield. m/z (ESI): 392.2 $(M+H)^+$.

Step 5: tert-butyl 6-(3-(difluoromethyl)-4-(1,6-dimethyl-1H-indazol-7-yl)-7,7-dimethyl-7,8-dihydro-5H-pyrano[4,3-b]pyridin-2-yl)-2,6-diazaspiro[3.4]octane-2-carboxylate To a 25-mL vial was added 2-chloro-3-(difluoromethyl)-4-(1,6-dimethyl-1H-indazol-7-yl)-7,7-dimethyl-7,8-dihydro-5H-pyrano[4,3-b]pyridine (213 mg, 0.543 mmol), $Cs_2CO_3$ (354 mg, 1.09 mmol), RuPhos Pd G1 (89 mg, 0.109 mmol), RuPhos (50.7 mg, 0.109 mmol), and tert-butyl 2,6-diazaspiro[3.4]octane-2-carboxylate (231 mg, 1.09 mmol). The vial was purged with $N_2$ and THF (3 mL) was added. The reaction was heated to 90° C. for 3 h. The reaction was cooled to room temperature and chromatographed with 0-100% (3:1, EtOAc:EtOH) in heptanes to give tert-butyl 6-(3-(difluoromethyl)-4-(1,6-dimethyl-1H-indazol-7-yl)-7,7-dimethyl-7,8-dihydro-5H-pyrano[4,3-b]pyridin-2-yl)-2,6-diazaspiro[3.4]octane-2-carboxylate (195 mg, 63% yield) as an orange solid. m/z (ESI): 567.9 $(M+H)^+$.

Step 6: 1-(6-(3-(difluoromethyl)-(1,6-dimethyl-1H-indazol-7-yl)-7,7-dimethyl-7,8-dihydro-5H-pyrano[4,3-b]pyridin-2-yl)-2,6-diazaspiro[3.4]octan-2-yl)-2-propen-1-one A mixture of tert-butyl 6-(3-(difluoromethyl)-4-(1,6-dimethyl-1H-indazol-7-yl)-7,7-dimethyl-7,8-dihydro-5H-pyrano[4,3-b]pyridin-2-yl)-2,6-diazaspiro[3.4]octane-2-carboxylate (195 mg, 0.344 mmol) and TFA (0.265 mL, 3.44 mmol) in DCM (3.5 mL) was stirred at 40° C. for 1 h. Upon completion, the mixture was concentrated to dryness, redissolved in DCE (3.5 mL), and DIPEA (0.30 mL, 1.72 mmol) was added. The mixture was cooled to 0° C. and acryloyl chloride (0.028 mL, 0.344 mmol) was added. Upon completion, the reaction was concentrated and purified via reverse phase chromatography to give 1-(6-(3-(difluoromethyl)-4-(1,6-dimethyl-1H-indazol-7-yl)-7,7-dimethyl-7,8-dihydro-5H-pyrano[4,3-b]pyridin-2-yl)-2,6-diazaspiro[3.4]octan-2-yl)prop-2-en-1-one (38 mg, 21% yield) as a yellow solid. m/z (ESI): 522.2 $(M+H)^+$. $^1H$ NMR (400 MHz, $CDCl_3$) δ ppm 8.03 (s, 1H), 7.73 (d, J=8.4 Hz, 1H), 7.14 (d, J=8.4 Hz, 1H), 6.15-6.58 (m, 3H), 5.76-5.82 (m, 1H), 4.32 (br d, J=7.7 Hz, 1H), 3.92-4.02 (m, 4H), 3.86 (br t, J=6.7 Hz, 2H), 3.59 (s, 3H), 2.89 (s, 2H), 2.28 (t, J=7.1 Hz, 2H), 2.16 (s, 3H), 1.30 (d, J=4.4 Hz, 6H).

Example 30-1: 2-(2-((2E)-4-(difluoromethoxy)-2-butenoyl)-2,6-diazaspiro[3.4]octan-6-yl)-7,7-dimethyl-4-(5-methyl-1H-indazol-4-yl)-5,6,7,8-tetrahydro-3-quinolinecarbonitrile

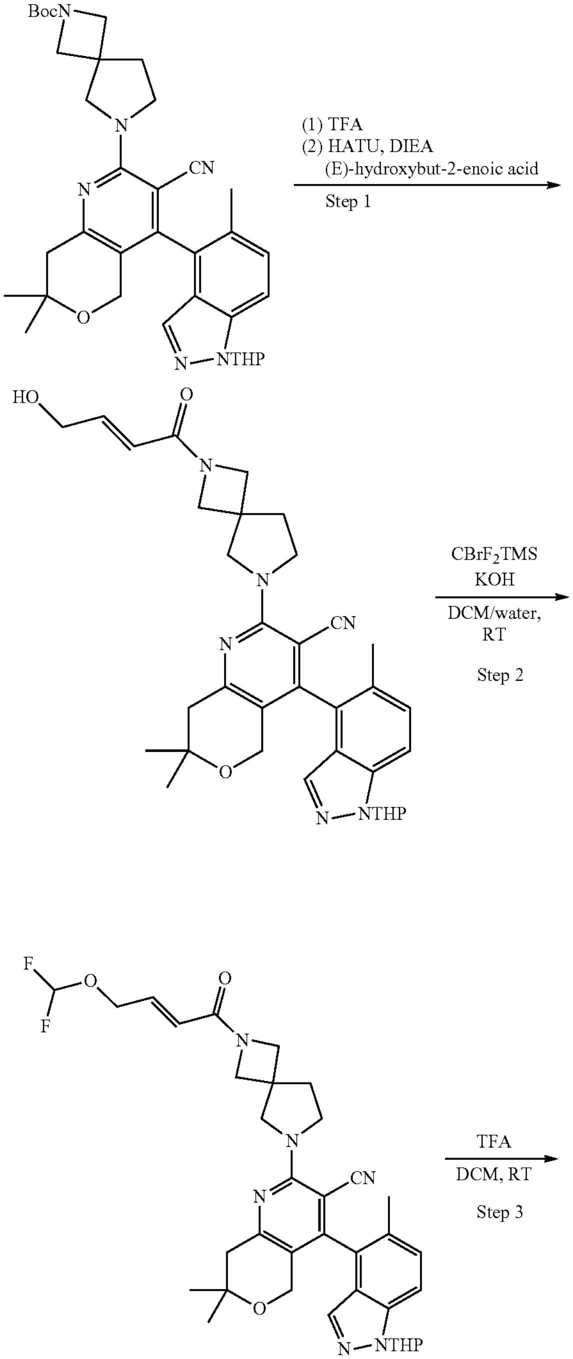

-continued

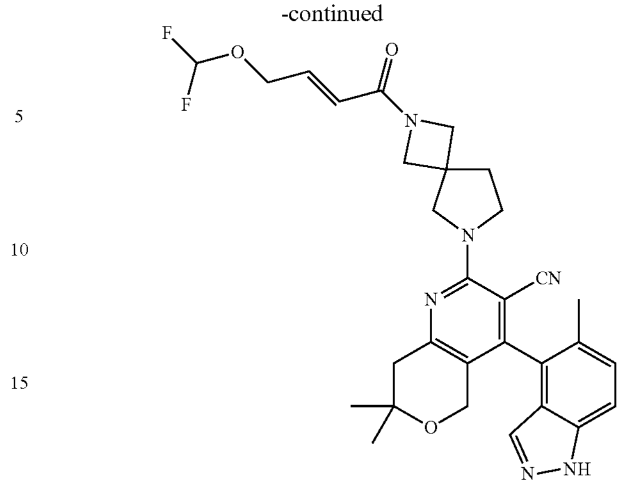

Step 1: (E)-2-(2-(4-hydroxybut-2-enoyl)-2,6-diazaspiro[3.4]octan-6-yl)-7,7-dimethyl-4-(5-methyl-1-(tetrahydro-2H-pyran-2-yl)-1H-indazol-4-yl)-5,6,7,8-tetrahydroquinoline-3-carbonitrile Trifluoroacetic acid (3.06 g, 2 mL, 26.8 mmol) was added to a stirred mixture of tert-butyl 6-(3-cyano-7,7-dimethyl-4-(5-methyl-1-(tetrahydro-2H-pyran-2-yl)-1H-indazol-4-yl)-5,6,7,8-tetrahydroquinolin-2-yl)-2,6-diazaspiro[3.4]octane-2-carboxylate (1.20 g, 1.965 mmol, Example 13, Step 3) in DCM (20 mL) at 0° C. The reaction mixture was stirred at 0° C. for 9 h and concentrated in vacuo to give crude 7,7-dimethyl-4-(5-methyl-1-(tetrahydro-2H-pyran-2-yl)-1H-indazol-4-yl)-2-(2,6-diazaspiro[3.4]octan-6-yl)-5,6,7,8-tetrahydroquinoline-3-carbonitrile that was used as is.

The crude 7,7-dimethyl-4-(5-methyl-1-(tetrahydro-2H-pyran-2-yl)-1H-indazol-4-yl)-2-(2,6-diazaspiro[3.4]octan-6-yl)-5,6,7,8-tetrahydroquinoline-3-carbonitrile, (E)-4-hydroxybut-2-enoic acid (0.360 g, 3.52 mmol, Key Organics Ltd), HATU (1.489 g, 3.92 mmol), and DIPEA (1.710 mL, 9.79 mmol) were mixed in DMF (8 mL). The reaction mixture was stirred at room temperature for 20 h. The reaction mixture was diluted with EtOAc (100 mL) and washed with saturated aqueous $NH_4Cl$ (75 mL). The organic layer was separated, washed with brine (50 mL), dried over $MgSO_4$, and concentrated in vacuo. Chromatographic purification of the residue (silica gel, 0-75% (3:1) EtOAc:EtOH in heptanes) provided (E)-2-(2-(4-hydroxybut-2-enoyl)-2,6-diazaspiro[3.4]octan-6-yl)-7,7-dimethyl-4-(5-methyl-1-(tetrahydro-2H-pyran-2-yl)-1H-indazol-4-yl)-5,6,7,8-tetrahydroquinoline-3-carbonitrile (330 mg, 28.3% yield) as a white solid. $^1$H NMR (400 MHz, DMSO-$d_6$) δ ppm 7.73 (d, J=8.57 Hz, 1H), 7.58 (s, 1H), 7.43 (d, J=8.36 Hz, 1H), 6.74 (dt, J=15.26, 3.87 Hz, 1H), 6.09-6.15 (m, 1H), 5.85-5.91 (m, 1H), 5.02 (t, J=5.33 Hz, 1H), 4.24 (br d, J=8.36 Hz, 1H), 4.09-4.16 (m, 3H), 3.81-3.97 (m, 5H), 3.67-3.81 (m, 3H), 2.59 (s, 2H), 2.36-2.48 (m, 1H), 2.15-2.22 (m, 2H), 2.13 (s, 3H), 1.91-2.08 (m, 4H), 1.70-1.83 (m, 1H), 1.55-1.63 (m, 2H), 1.38 (q, J=6.62 Hz, 2H), 0.94 (s, 6H). m/z (ESI): 595.3 $[M+H]^+$.

Step 2: (E)-2-(2-(4-(difluoromethoxy)but-2-enoyl)-2,6-diazaspiro[3.4]octan-6-yl)-7,7-dimethyl-4-(5-methyl-1-(tetrahydro-2H-pyran-2-yl)-1H-indazol-4-yl)-5,6,7,8-tetrahydroquinoline-3-carbonitrile Trimethyl(bromodifluoromethyl)silane (102 mg, 0.504 mmol, Combi-Blocks) was added to a stirred mixture of (E)-2-(2-(4-hydroxybut-2-enoyl)-2,6-diazaspiro[3.4]octan-6-yl)-7,7-dimethyl-4-(5-methyl-1-(tetrahydro-2H-pyran-2-yl)-1H-indazol-4-yl)-5,6,7,8-tetrahydroquinoline-3-carbonitrile (100 mg, 0.168 mmol) and KOH (75 mg, 1.345 mmol) in DCM (1 mL) and water (0.3 mL). The reaction mixture was stirred at room temperature for 18 h. Additional trimethyl(bromodifluoromethyl)silane (102 mg, 0.504 mmol, Combi-Blocks) was added, and the reaction mixture was stirred for another 3 h. The reaction mixture was diluted with DCM (15 mL) and water (10 mL). The organic layer was separated, dried over $MgSO_4$, and concentrated in vacuo. Chromatographic purification of the residue (silica gel, 0-50% (3:1) EtOAc:EtOH in heptanes) provided (E)-2-(2-(4-(difluoromethoxy)but-2-enoyl)-2,6-diazaspiro[3.4]octan-6-yl)-7,7-dimethyl-4-(5-methyl-1-(tetrahydro-2H-pyran-2-yl)-1H-indazol-4-yl)-5,6,7,8-tetrahydroquinoline-3-carbonitrile (18 mg, 16.60% yield) as an off-white solid. m/z (ESI): 645.3 $[M+H]^+$.

Step 3: 2-(2-((2E)-4-(difluoromethoxy)-2-butenoyl)-2,6-diazaspiro[3.4]octan-6-yl)-7,7-dimethyl-4-(5-methyl-1H-indazol-4-yl)-5,6,7,8-tetrahydro-3-quinolinecarbonitrile Trifluoroacetic acid (0.1 mL, 1.342 mmol) was added to a stirred mixture of (E)-2-(2-(4-(difluoromethoxy)but-2-enoyl)-2,6-diazaspiro[3.4]octan-6-yl)-7,7-dimethyl-4-(5-methyl-1-(tetrahydro-2H-pyran-2-yl)-1H-indazol-4-yl)-5,6,7,8-tetrahydroquinoline-3-carbonitrile (18 mg, 0.028 mmol) in DCM (0.4 mL) at room temperature for 2 h. The reaction mixture was concentrated in vacuo. Chromatographic purification of the residue (silica gel, 0-70% (3:1) EtOAc:EtOH in heptanes) provided (E)-2-(2-(4-(difluoromethoxy)but-2-enoyl)-2,6-diazaspiro[3.4]octan-6-yl)-7,7-dimethyl-4-(5-methyl-1H-indazol-4-yl)-5,6,7,8-tetrahydroquinoline-3-carbonitrile (10 mg, 63.9% yield) as a white solid. $^1$H NMR (500 MHz, DMSO-$d_6$) δ ppm 13.15 (s, 1H), 7.50-7.56 (m, 2H), 7.35 (d, J=8.69 Hz, 1H), 6.66 (dt, J=15.41, 4.69 Hz, 1H), 6.74 (t, J=75.40 Hz, 1H), 6.20 (dd, J=15.44, 0.91 Hz, 1H), 4.57 (dd, J=4.67, 1.69 Hz, 2H), 4.27 (d, J=8.43 Hz, 1H), 4.16 (br d, J=7.91 Hz, 1H), 3.97 (br d, J=10.10 Hz, 1H), 3.81-3.92 (m, 3H), 3.74 (br t, J=6.94 Hz, 2H), 2.59 (s, 2H), 2.14-2.23 (m, 2H), 2.12 (d, J=1.56 Hz, 3H), 1.92-2.04 (m, 2H), 1.38 (br t, J=6.88 Hz, 2H), 0.92-0.97 (m, 6H). m/z (ESI): 561.3 $[M+H]^+$.

Example 31-1: 1-(6-(7-chloro-8-(5-methyl-1H-indazol-4-yl)-3,4-dihydro-2H-chromen-6-yl)-2,6-diazaspiro[3.4]octan-2-yl)-2-propen-1-one

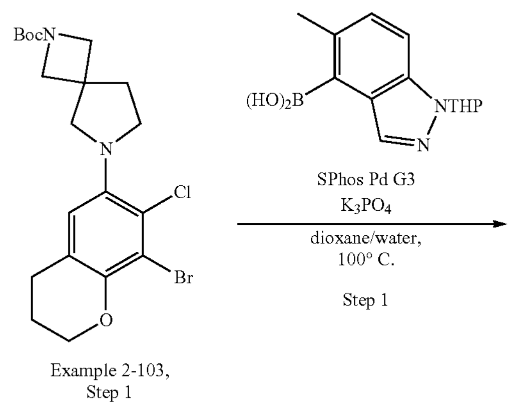

Example 2-103, Step 1

-continued

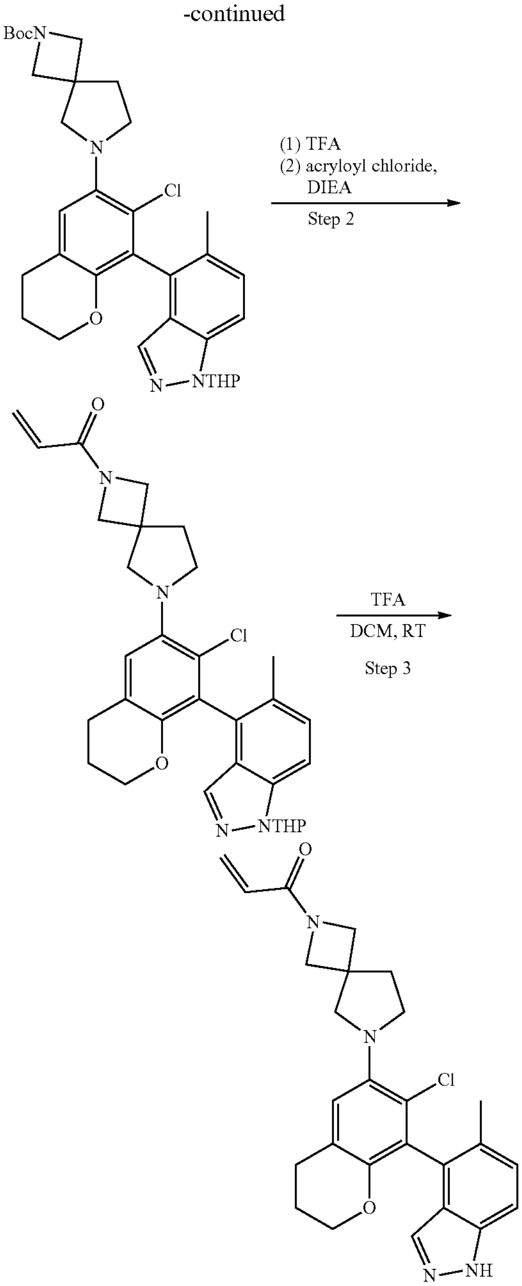

Example 31-1

Step 1: tert-butyl 6-(7-chloro-8-(5-methyl-1-(tetrahydro-2H-pyran-2-yl)-1H-indazol-4-yl)chroman-6-yl)-2,6-diazaspiro[3.4]octane-2-carboxylate tert-Butyl 6-(8-bromo-7-chlorochroman-6-yl)-2,6-diazaspiro[3.4]octane-2-carboxylate (121 mg, 0.264 mmol, Example 2-103, Step 1). [5-methyl-1-(oxan-2-yl)-1H-indazol-4-yl]boronic acid (206 mg, 0.793 mmol, Ambeed), SPhos Pd G3 (22.87 mg, 0.026 mmol), and $K_3PO_4$ (281 mg, 1.322 mmol) were mixed in 1,4-dioxane (1 mL) and water (0.1 mL) in a sealed vial under a $N_2$ atmosphere. The reaction mixture was stirred at 100° C. for 1 h. The reaction mixture was partitioned between EtOAc (40 mL) and water (30 mL). The organic layer was separated, washed with brine (20 mL), dried over $MgSO_4$, and concentrated in vacuo. Chromatographic purification of the residue (silica gel, 0-25% (3:1) EtOAc:EtOH in heptanes) provided tert-butyl 6-(7-chloro-8-(5-methyl-1-(tetrahydro-2H-pyran-2-yl)-1H-indazol-4-yl)chroman-6-yl)-2,6-diazaspiro[3.4]octane-2-carboxylate (125 mg, 0.211 mmol, 80% yield) as an off-white solid. m/z (ESI): 593.2 $[M+H]^+$.

Step 2: 1-(6-(7-chloro-8-(5-methyl-1-(tetrahydro-2H-pyran-2-yl)-1H-indazol-4-yl)chroman-6-yl)-2,6-diazaspiro[3.4]octan-2-yl)prop-2-en-1-one Trifluoroacetic acid (383 mg, 0.25 mL, 3.35 mmol) was added to a stirred mixture of tert-butyl 6-(7-chloro-8-(5-methyl-1-(tetrahydro-2H-pyran-2-yl)-1H-indazol-4-yl)chroman-6-yl)-2,6-diazaspiro[3.4]octane-2-carboxylate (125 mg, 0.211 mmol) in DCM (1 mL) at 0° C. The reaction mixture was stirred at 0° C. for 6 h. The reaction mixture was concentrated in vacuo to give crude 4-(7-chloro-6-(2,6-diazaspiro[3.4]octan-6-yl)chroman-8-yl)-5-methyl-1-(tetrahydro-2H-pyran-2-yl)-1H-indazole that was used as is.

Acryloyl chloride (10.32 μL, 0.127 mmol, Sigma-Aldrich) was added to a stirred mixture of DIPEA (0.092 mL, 0.527 mmol, Sigma-Aldrich) and the crude 4-(7-chloro-6-(2,6-diazaspiro[3.4]octan-6-yl)chroman-8-yl)-5-methyl-1-(tetrahydro-2H-pyran-2-yl)-1H-indazole (52 mg, 0.105 mmol) in DCM (1 mL) at 0° C. The reaction mixture was stirred at 0° C. for 15 min. The reaction mixture was diluted with DCM (20 mL) and washed with saturated aqueous $NH_4Cl$ (15 mL). The organic layer was separated, washed with brine (10 mL), dried over $MgSO_4$, and concentrated in vacuo to give crude 1-(6-(7-chloro-8-(5-methyl-1-(tetrahydro-2H-pyran-2-yl)-1H-indazol-4-yl)chroman-6-yl)-2,6-diazaspiro[3.4]octan-2-yl)prop-2-en-1-one that was used as is. m/z (ESI): 547.3 $[M+H]^+$.

Step 3: 1-(6-(7-chloro-8-(5-methyl-1H-indazol-4-yl)-3,4-dihydro-2H-chromen-6-yl)-2,6-diazaspiro[3.4]octan-2-yl)-2-propen-1-one Trifluoroacetic acid (0.5 mL, 6.71 mmol) was added to a stirred mixture of crude 1-(6-(7-chloro-8-(5-methyl-1-(tetrahydro-2H-pyran-2-yl)-1H-indazol-4-yl)chroman-6-yl)-2,6-diazaspiro[3.4]octan-2-yl)prop-2-en-1-one (58 mg, 0.106 mmol) in DCM (0.5 mL) at room temperature. The reaction mixture was stirred at room temperature for 3.5 h. The reaction mixture was concentrated in vacuo. Chromatographic purification of the residue (silica gel, 0-100% (3:1) EtOAc:EtOH in heptanes) provided 1-(6-(7-chloro-8-(5-methyl-1H-indazol-4-yl)chroman-6-yl)-2,6-diazaspiro[3.4]octan-2-yl)prop-2-en-1-one (38 mg, 77% yield) as an off-white solid. $^1$H NMR (400 MHz, DMSO-$d_6$) δ ppm 12.87 (s, 1H), 7.37-7.43 (m, 2H), 7.26 (d, J=8.36 Hz, 1H), 6.89 (s, 1H), 6.31 (dd, J=17.04, 10.35 Hz, 1H), 6.10 (dd, J=17.04, 2.19 Hz, 1H), 5.66 (dd, J=10.24, 2.30 Hz, 1H), 4.20-4.26 (m, 1H), 4.15-4.20 (m, 1H), 3.86-3.97 (m, 4H), 3.37-3.44 (m, 2H), 3.28 (s, 2H), 2.81 (t, J=6.58 Hz, 2H), 2.15 (br t, J=7.00 Hz, 2H), 2.07 (s, 3H), 1.83-1.90 (m, 2H). m/z (ESI): 463.2 $[M+H]^+$.

Example 32-1: (2E)-1-(6-(7-chloro-8-(5-methyl-1H-indazol-4-yl)-3,4-dihydro-2H-chromen-6-yl)-2,6-diazaspiro[3.4]octan-2-yl)-4-(dimethylamino)-2-buten-1-one

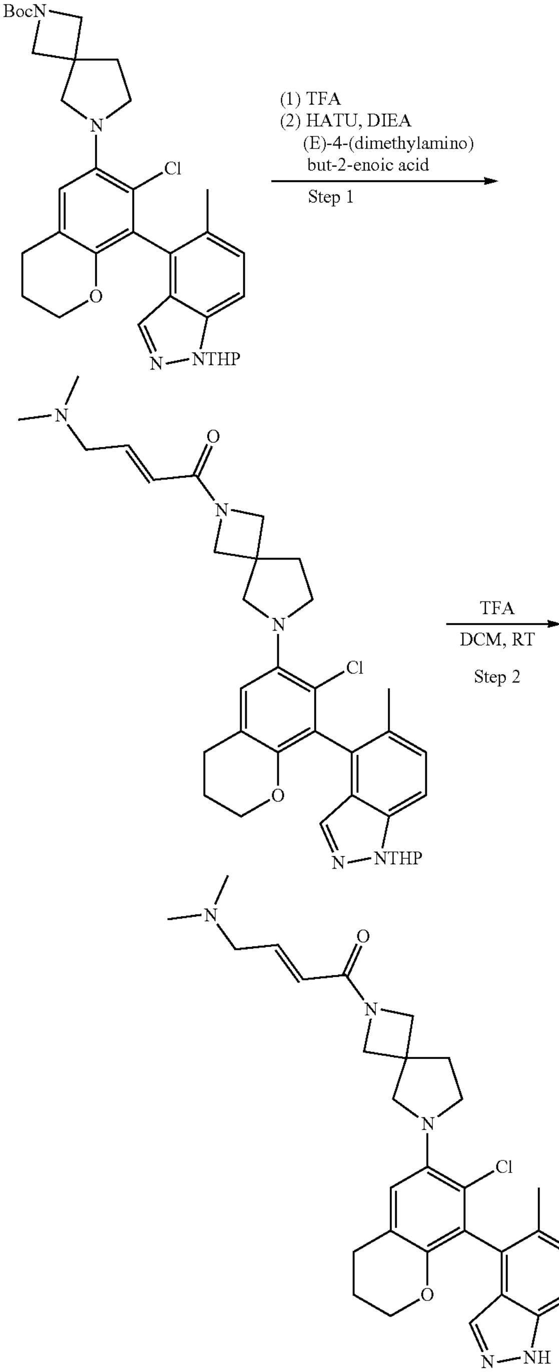

Example 32-1

(E)-1-(6-(7-chloro-8-(5-methyl-1H-indazol-4-yl)chroman-6-yl)-2,6-diazaspiro[3.4]octan-2-yl)-4-(dimethylamino)but-2-en-1-one synthesized in an analogous manner to Example 31-1 replacing the second part of step 2 for Method 13 step 5 and using (E)-4-(dimethylamino)but-2-enoic acid hydrochloride (Oakwood Chemical) in this step.

$^1$H NMR (400 MHz, MeOH-$d_4$) δ ppm 7.41-7.45 (m, 2H), 7.32 (d, J=8.57 Hz, 1H), 6.95 (s, 1H), 6.80 (dt, J=15.36, 6.64 Hz, 1H), 6.19 (dt, J=15.36, 1.41 Hz, 1H), 4.32 (d, J=8.99 Hz, 1H), 4.25 (d, J=8.78 Hz, 1H), 4.09 (d, J=10.45 Hz, 1H), 4.02 (d, J=10.66 Hz, 1H), 3.94-3.99 (m, 2H), 3.43-3.48 (m, 2H), 3.27-3.43 (m, 2H), 3.15 (dd, J=6.58, 1.36 Hz, 2H), 2.86 (t, J=6.48 Hz, 2H), 2.28 (s, 6H), 2.24 (t, J=7.11 Hz, 2H), 2.14 (s, 3H), 1.92-2.00 (m, 2H). m/z (ESI): 520.3 $[M+H]^+$.

Example 33-1: 4-(4-bromo-3-oxo-2,3-dihydro-1-isoquinolinyl)-7,7-dimethyl-2-(2-(2-propenoyl)-2,6-diazaspiro[3.4]octan-6-yl)-5,6,7,8-tetrahydro-3-quinolinecarbonitrile and Example 33-2: 7,7-dimethyl-4-(3-oxo-2,3-dihydro-1-isoquinolinyl)-2-(2-(2-propenoyl)-2,6-diazaspiro[3.4]octan-6-yl)-5,6,7,8-tetrahydro-3-quinolinecarbonitrile

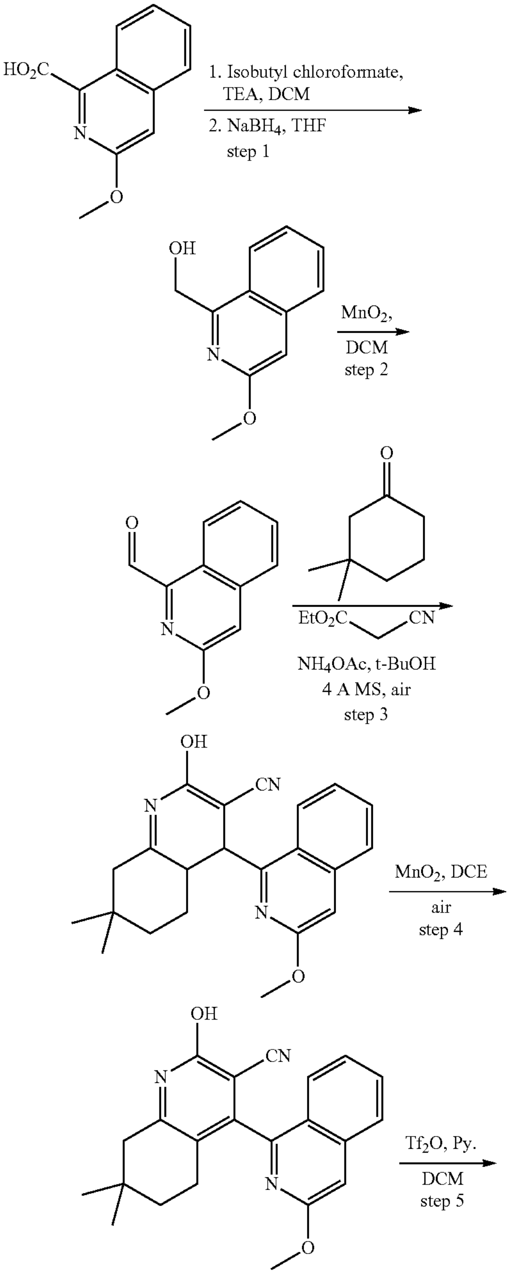

-continued

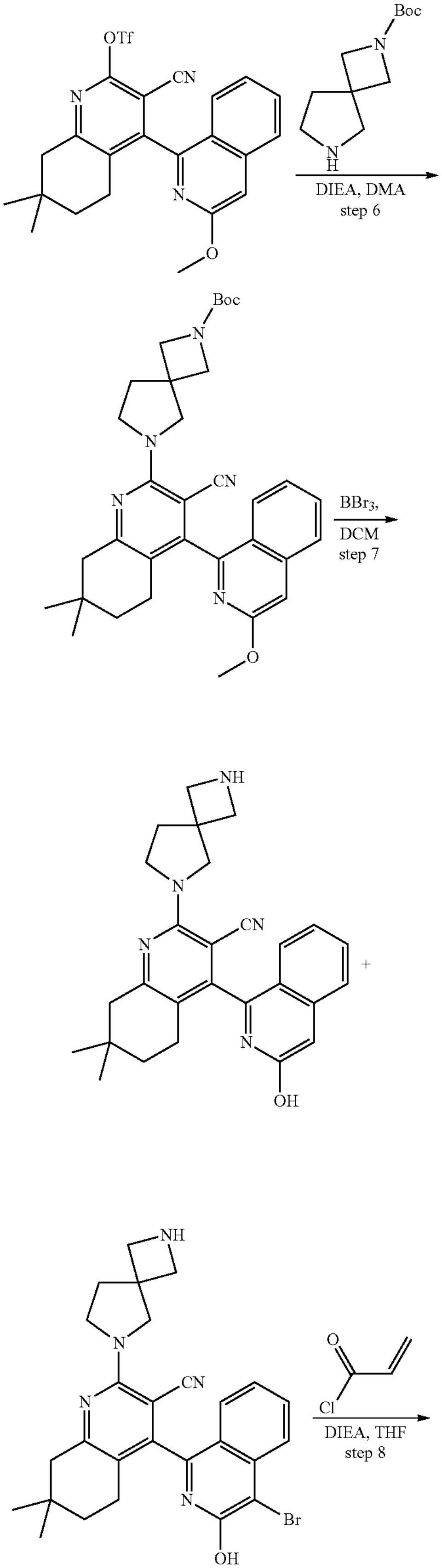

-continued

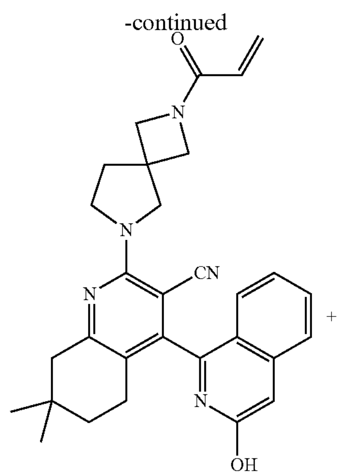

Example 33-2

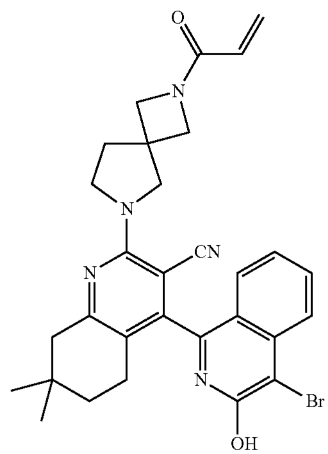

Example 33-1

Step 1: (3-methoxy-1-isoquinolyl)methanol

To a solution of 3-methoxyisoquinoline-1-carboxylic acid (3 g, 14.76 mmol, Shanghai Haohong Pharmaceutical Co., Ltd) and TEA (2.26 mL, 16.24 mmol) in THF (30 mL) was added isobutyl carbonochloridate (2.13 mL, 16.24 mmol) at −10° C. The mixture was stirred at −10° C. for 0.5 h. Then, $NaBH_4$ (1.68 g, 44.29 mmol) in THF (0.5 mL) was added to the mixture at −10° C. and stirred at 15° C. for 0.5 h. The reaction mixture was quenched by addition of $H_2O$ (15 mL) at 0° C. and extracted with EtOAc (3×20 mL). The combined organic extracts were washed with brine (50 mL), dried over $Na_2SO_4$, and concentrated under reduced pressure to provide (3-methoxy-1-isoquinolyl)methanol (3 g, crude) as a yellow solid. m/z (ESI): 190.1 $[M+H]^+$.

Step 2: 3-methoxyisoquinoline-1-carbaldehyde

To a solution of (3-methoxy-1-isoquinolyl)methanol (1 g, 5.29 mmol) in DCM (10 mL) was added $MnO_2$ (1.38 g, 15.86 mmol). The mixture was stirred at 40° C. for 8 h. The reaction mixture was filtered and the filtrate concentrated under reduced pressure. The residue was purified by column chromatography ($SiO_2$, 0-100% petroleum ether/EtOAc) to provide 3-methoxyisoquinoline-1-carbaldehyde (595 mg, 59.37% yield) as a white solid. $^1H$ NMR (400 MHz, $CDCl_3$) δ ppm 10.34 (s, 1H), 9.21 (d, J=8.80 Hz, 1H), 7.78 (d, J=8.40 Hz, 1H), 7.62-7.66 (m, 1H), 7.52-7.56 (m, 1H), 7.31 (s, 1H), 4.14 (s, 3H).

Step 3: 2-hydroxy-4-(3-methoxy-1-isoquinolyl)-7,7-dimethyl-4a,5,6,8-tetrahydro-4H-quinoline-3-carbonitrile To a solution of 3,3-dimethylcyclohexanone (640.44 mg, 5.07 mmol, Bide Pharmatech) in t-BuOH (20 mL) was added $NH_4OAc$ (3.13 g, 40.60 mmol) and 4 Å MS (100 mg) at 15° C. The mixture was stirred at 15° C. for 0.5 h. 3-methoxyisoquinoline-1-carbaldehyde (950 mg, 5.07 mmol) and ethyl 2-cyanoacetate (0.541 mL, 5.07 mmol) were added to the mixture at 15° C. The mixture was stirred at 60° C. for 2 h. The reaction mixture was filtered and concentrated under reduced pressure to provide 2-hydroxy-4-(3-methoxy-1-isoquinolyl)-7,7-dimethyl-4a,5,6,8-tetrahydro-4H-quinoline-3-carbonitrile (1.8 g, crude) as an orange solid. m/z (ESI): 362.2 $[M+H]^+$.

Step 4: 2-hydroxy-4-(3-methoxy-1-isoquinolyl)-7,7-dimethyl-6,8-dihydro-5H-quinoline-3-carbonitrile A mixture of 2-hydroxy-4-(3-methoxy-1-isoquinolyl)-7,7-dimethyl-4a,5,6,8-tetrahydro-4H-quinoline-3-carbonitrile (1.8 g, 4.98 mmol) and $MnO_2$ (4.33 g, 49.80 mmol) in DCE (20 mL) was degassed and purged with $N_2$ (3×), and the mixture was stirred at 60° C. for 8 h open to the air. The reaction mixture was filtered and concentrated under reduced pressure. The residue was purified by column chromatography ($SiO_2$, petroleum ether/EtOAc=1/0 to 0/1) to provide 2-hydroxy-4-(3-methoxy-1-isoquinolyl)-7,7-dimethyl-6,8-dihydro-5H-quinoline-3-carbonitrile (670 mg, 37.43% yield) as an orange solid. m/z (ESI): 360.2 $[M+H]^+$.

Step 5: [3-cyano-4-(3-methoxy-1-isoquinolyl)-7,7-dimethyl-6,8-dihydro-5H-quinolin-2-yl] trifluoromethanesulfonate To a solution of 2-hydroxy-4-(3-methoxy-1-isoquinolyl)-7,7-dimethyl-6,8-dihydro-5H-quinoline-3-carbonitrile (490 mg, 1.36 mmol) in DCM (10 mL) was added pyridine (330.11 uL, 4.09 mmol) and $Tf_2O$ (449.87 uL, 2.73 mmol) at 0° C. The mixture was stirred at 0° C. for 1 h. The reaction mixture was quenched by addition of $H_2O$ (5 mL) at 15° C. and extracted with DCM (3×5 mL). The combined organic extracts were washed with brine (5 mL), dried over $Na_2SO_4$, filtered and the filtrate was concentrated under reduced pressure to provide [3-cyano-4-(3-methoxy-1-isoquinolyl)-7,7-dimethyl-6,8-dihydro-5H-quinolin-2-yl]trifluoromethanesulfonate (670 mg, crude) as a yellow solid. m/z (ESI): 492.0 $[M+H]^+$.

Step 6: tert-butyl 7-[3-cyano-4-(3-methoxy-1-isoquinolyl)-7,7-dimethyl-6,8-dihydro-5H-quinolin-2-yl]-2,7-diazaspiro[3.4]octane-2-carboxylate To a solution of [3-cyano-4-(3-methoxy-1-isoquinolyl)-7,7-dimethyl-6,8-dihydro-5H-quinolin-2-yl] trifluoromethanesulfonate (670 mg, 1.36 mmol) and DIEA (1.19 mL, 6.82 mmol) in DMA (10 mL) was added tert-butyl 2,7-diazaspiro[3.4]octane-2-carboxylate (578.79 mg, 2.73 mmol, Labnetwork). The mixture was stirred at 80° C. for 1 h. The reaction mixture was quenched by addition of $H_2O$ (20 mL) at 15° C. and extracted with EtOAc (3×10 mL). The combined organic layers were washed with brine (10 mL), dried over $Na_2SO_4$, and concentrated under reduced pressure. The residue was purified by column chromatography ($SiO_2$, petroleum ether/EtOAc=1/0 to 0/1) to provide tert-butyl 7-[3-cyano-4-(3-methoxy-1-isoquinolyl)-7,7-dimethyl-6,8-dihydro-5H-quinolin-2-yl]-2,7-diazaspiro[3.4]octane-2-carboxylate (160 mg, 21.20% yield) as a yellow solid. m/z (ESI): 554.4 $[M+H]^+$. $^1H$ NMR (400 MHz, $CDCl_3$) δ ppm 7.78 (d, J=8.40 Hz, 1H), 7.58 (t, J=7.20 Hz, 1H), 7.42 (d, J=8.40 Hz, 1H), 7.31 (t, J=7.20 Hz, 1H), 7.09 (s, 1H), 4.05 (s, 3H), 3.94-3.96 (m, 4H), 3.88-3.90 (m, 4H), 2.68 (s, 2H), 2.26-2.32 (m, 1H), 2.16-2.19 (m, 2H), 2.00-2.02 (m, 1H), 1.46 (s, 9H), 1.38-1.42 (m, 2H), 1.00 (d, J=10.40 Hz, 6H).

Step 7: 2-(2,6-diazaspiro[3.4]octan-6-yl)-4-(3-hydroxy-1-isoquinolyl)-7,7-dimethyl-6,8-dihydro-5H-quinoline-3-carbonitrile and 4-(4-bromo-3-hydroxy-isoquinolin-1-yl)-7,7-dimethyl-2-(2,6-diazaspiro[3.4]octan-6-yl)-5,6,7,8-tetrahydroquinoline-3-carbonitrile To a solution of tert-butyl 7-[3-cyano-4-(3-methoxy-1-isoquinolyl)-7,7-dimethyl-6,8-dihydro-5H-quinolin-2-yl]-2,7-diazaspiro[3.4]octane-2-carboxylate (70 mg, 126.42 μmol) in DCM (1 mL) was added $BBr_3$ (0.121 mL, 1.26 mmol). The mixture was stirred at 40° C. for 7 h. The reaction mixture was added to water (5 mL) at 15° C. and extracted with EtOAc (3×3 mL). The combined organic layers were dried over $Na_2SO_4$, filtered and concentrated under reduced pressure to provide a mixture of 2-(2,6-diazaspiro[3.4]octan-6-yl)-4-(3-hydroxy-1-isoquinolyl)-7,7-dimethyl-6,8-dihydro-5H-quinoline-3-carbonitrile and 4-(4-bromo-3-hydroxyisoquinolin-1-yl)-7,7-dimethyl-2-(2,6-diazaspiro[3.4]octan-6-yl)-5,6,7,8-tetrahydroquinoline-3-carbonitrile (55 mg) as a yellow solid.

Step 8: 4-(4-bromo-3-oxo-2,3-dihydro-1-isoquinolinyl)-7,7-dimethyl-2-(2-(2-propenoyl)-2,6-diazaspiro[3.4]octan-6-yl)-5,6,7,8-tetrahydro-3-quinolinecarbonitrile and 7,7-dimethyl-4-(3-oxo-2,3-dihydro-1-isoquinolinyl)-2-(2-(2-propenoyl)-2,6-diazaspiro[3.4]octan-6-yl)-5,6,7,8-tetrahydro-3-quinolinecarbonitrile To a solution of 2-(2,6-diazaspiro[3.4]octan-6-yl)-4-(3-hydroxy-1-isoquinolyl)-7,7-dimethyl-6,8-dihydro-5H-quinoline-3-carbonitrile and 4-(4-bromo-3-hydroxyisoquinolin-1-yl)-7,7-dimethyl-2-(2,6-diazaspiro[3.4]octan-6-yl)-5,6,7,8-tetrahydroquinoline-3-carbonitrile (55 mg) in THF (2 mL) was added DIPEA (0.130 mL, 0.750 mmol) and acryloyl chloride (10 μL, 0.125 mmol). The mixture was stirred at 0° C. for 1 h. The reaction mixture was concentrated under reduced pressure and the residue was purified by prep-HPLC with a Xbridge BEH C18 column (100×30 mm, 10 μm) with a mobile phase of water (10 mM $NH_4HCO_3$)-ACN] with a gradient of 45-75% over 8 min to provide 4-(3-hydroxy-1-isoquinolyl)-7,7-dimethyl-2-(2-prop-2-enoyl-2,7-diazaspiro[3.4]octan-7-yl)-6,8-dihydro-5H-quinoline-3-carbonitrile (30 mg, crude) as a yellow solid and 4-(4-bromo-3-oxo-2,3-dihydro-1-isoquinolinyl)-7,7-dimethyl-2-(2-(2-propenoyl)-2,6-diazaspiro[3.4]octan-6-yl)-5,6,7,8-tetrahydro-3-quinolinecarbonitrile (6 mg, Example 33-1) as a yellow solid. m/z (ESI): 574.0 $[M+H]^+$. $^1H$ NMR (400 MHz, $CDCl_3$) δ ppm 8.16 (d, J=8.80 Hz, 1H), 7.74 (t, J=8.00 Hz, 1H), 7.36-7.45 (m, 2H) 6.35 (s, 1H) 6.16-6.23 (m, 1H) 5.70 (d, J=10.00 Hz, 1H), 4.22-4.25 (m, 1H), 4.05-4.15 (m, 2H), 3.98-4.00 (m, 1H), 3.93-3.96 (m, 2H), 3.90-3.92 (m, 1H), 2.67 (s, 2H), 2.22-2.35 (m, 2H), 1.42-1.44 (m, 3H), 1.00 (d, J=14.40 Hz, 6H), 4-(3-Hydroxy-1-isoquinolyl)-7,7-dimethyl-2-(2-prop-2-enoyl-2,7-diazaspiro[3.4]octan-7-yl)-6,8-dihydro-5H-quinoline-3-carbonitrile was further purified by prep-HPLC (column: Waters Xbridge BEH C18 (100×30 mm, 10 μm) with a mobile phase of water (10 mM $NH_4HCO_3$)-ACN] with a gradient of 40-65% over 8 min to provide 7,7-dimethyl-4-(3-oxo-2,3-dihydro-1-isoquinolinyl)-2-(2-(2-propenoyl)-2,6-diazaspiro[3.4]octan-6-yl)-5,6,7,8-tetrahydro-3-quinolinecarbonitrile (5 mg, Example 33-2) as a white solid. m/z (ESI): 494.1 $[M+H]^+$. $^1H$ NMR (400 MHz, DMSO-$d_6$) δ ppm 7.84 (d, J=7.60 Hz, 1H), 7.62 (t, J=6.40 Hz, 1H), 7.31-7.36 (m, 2H), 7.05 (s, 1H), 6.27-6.31 (m, 1H), 6.08-6.13 (m, 1H), 5.65-5.69 (m, 1H), 4.25 (t, J=8.00 Hz, 1H), 4.17 (d, J=8.00 Hz, 1H), 3.90-3.96 (m, 1H), 3.84-3.88 (m, 3H), 3.72-3.74 (m, 2H), 3.29 (s, 2H), 2.60 (s, 2H), 2.17-2.19 (m, 2H), 1.37 (t, J=7.20 Hz, 2H), 0.93 (s, 6H).

Example 34-1: 4-(2-fluorophenyl)-7-(1-methyl-1H-imidazol-2-yl)-2-(2-(2-propenoyl)-2,6-diazaspiro[3.4]octan-6-yl)-5,6,7,8-tetrahydro-1,7-naphthyridine-3-carbonitrile

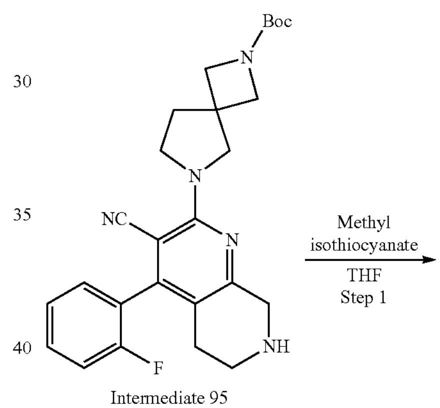

Intermediate 95

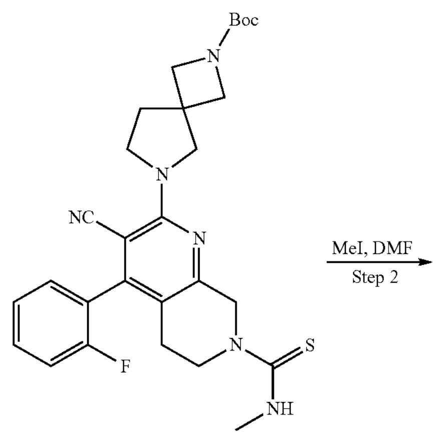

-continued

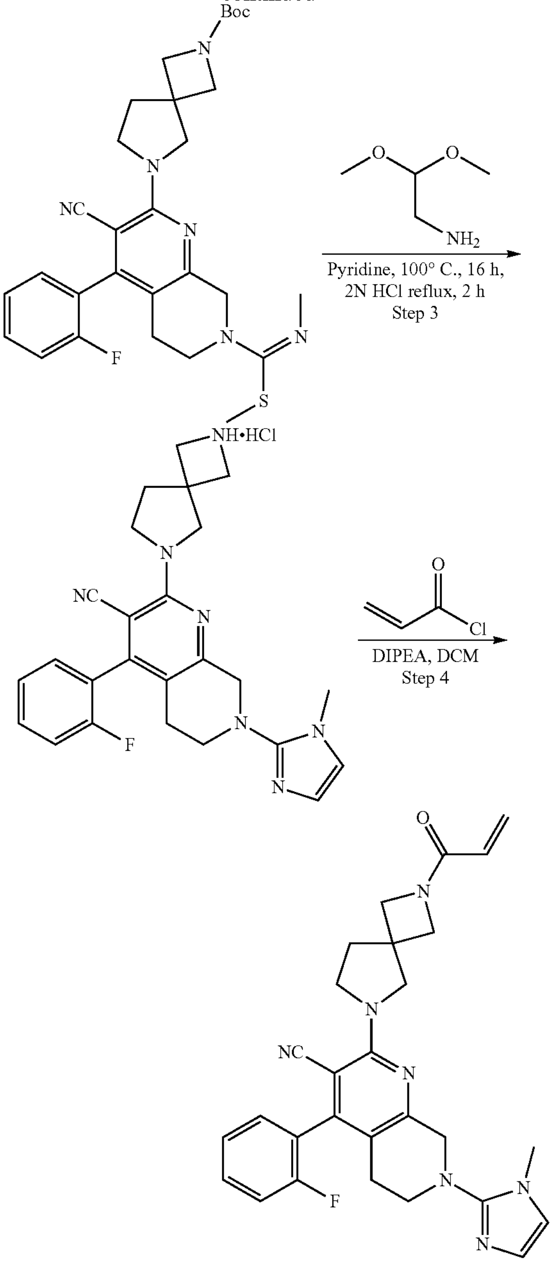

Example 34-1

Step 1: tert-butyl 6-(3-cyano-4-(2-fluorophenyl)-7-(methylcarbamothioyl)-5,6,7,8-tetrahydro-1,7-naphthyridin-2-yl)-2,6-diazaspiro[3.4]octane-2-carboxylate A solution of tert-butyl 6-(3-cyano-4-(2-fluorophenyl)-5,6,7,8-tetrahydro-1,7-naphthyridin-2-yl)-2,6-diazaspiro[3.4]octane-2-carboxylate (0.1 g, 0.216 mmol) and methyl isothiocyanate (0.016 g, 0.216 mmol) in THF (1 mL) was stirred at room temperature for 20 h. The reaction mixture was concentrated under reduced pressure to provide tert-butyl 6-(3-cyano-4-(2-fluorophenyl)-7-(methylcarbamothioyl)-5,6,7,8-tetrahydro-1,7-naphthyridin-2-yl)-2,6-diazaspiro[3.4]octane-2-carboxylate (0.09 g) as a pale yellow oil which was used in next step without further purification. m/z (ESI): 537.0 $(M+H)^+$.

Step 2: tert-butyl 6-(3-cyano-4-(2-fluorophenyl)-7-(1-methylpiperidin-3-yl)-5,6,7,8-tetrahydro-1,7-naphthyridin-2-yl)-2,6-diazaspiro[3.4]octane-2-carboxylate A solution of tert-butyl 6-(3-cyano-4-(2-fluorophenyl)-7-(methylcarbamothioyl)-5,6,7,8-tetrahydro-1,7-naphthyridin-2-yl)-2,6-diazaspiro[3.4]octane-2-carboxylate (0.09 g, 0.17 mmol), methyl iodide (0.031 mL, 0.503 mmol, Spectrochem) in DMF (1.5 mL) was stirred at room temperature for 16 h. The reaction mixture was concentrated under reduced pressure to provide tert-butyl (Z)-6-(3-cyano-4-(2-fluorophenyl)-7-((methylimino)(methylthio)methyl)-5,6,7,8-tetrahydro-1,7-naphthyridin-2-yl)-2,6-diazaspiro[3.4]octane-2-carboxylate (0.1 g) as a pale yellow liquid which was taken to the next step without further purification. m/z (ESI): 551.2 $(M+H)^+$.

Step 3: 4-(2-fluorophenyl)-7-(1-methyl-1H-imidazol-2-yl)-2-(2,6-diazaspiro[3.4]octan-6-yl)-5,6,7,8-tetrahydro-1,7-naphthyridine-3-carbonitrile hydrochloride A solution of tert-butyl (Z)-6-(3-cyano-4-(2-fluorophenyl)-7-((methylimino)(methylthio)methyl)-5,6,7,8-tetrahydro-1,7-naphthyridin-2-yl)-2,6-diazaspiro[3.4]octane-2-carboxylate (0.09 g, 0.16 mmol) and 2,2-dimethoxyethan-1-amine (0.019 g, 0.180 mmol, Avra) in pyridine (1 mL) was heated at 100° C. for 16 h. The reaction mixture was concentrated under reduced pressure. The residue was dissolved in 4M HCl in dioxane (1.6 mL, 6.4 mmol) and heated to reflux for 2 h. The reaction mixture was concentrated under reduced pressure to provide 4-(2-fluorophenyl)-7-(1-methyl-1H-imidazol-2-yl)-2-(2,6-diazaspiro[3.4]octan-6-yl)-5,6,7,8-tetrahydro-1,7-naphthyridine-3-carbonitrile hydrochloride (0.085 g) as a pale orange liquid which was taken to the next step without purification. m/z (ESI): 444.2 $(M+H)^+$.

Step 4: 4-(2-fluorophenyl)-7-(1-methyl-1H-imidazol-2-yl)-2-(2-(2-propenoyl)-2,6-diazaspiro[3.4]octan-6-yl)-5,6,7,8-tetrahydro-1,7-naphthyridine-3-carbonitrile To a solution of 4-(2-fluorophenyl)-7-(1-methyl-1H-imidazol-2-yl)-2-(2,6-diazaspiro[3.4]octan-6-yl)-5,6,7,8-tetrahydro-1,7-naphthyridine-3-carbonitrile hydrochloride (0.075 g, 0.156 mmol) and DIPEA (0.289 mL, 1.563 mmol) in DCM (5 mL) was added acryloyl chloride (0.014 g, 0.156 mmol, Symax Ltd.) at −78° C. dropwise and stirred for 15 min. The reaction mixture was diluted with water and extracted with DCM. The combined organic extracts were dried over $Na_2SO_4$, concentrated and purified by preparative HPLC to provide 4-(2-fluorophenyl)-7-(1-methyl-1H-imidazol-2-yl)-2-(2-(2-propenoyl)-2,6-diazaspiro[3.4]octan-6-yl)-5,6,7,8-tetrahydro-1,7-naphthyridine-3-carbonitrile (0.018 g, 23.15% yield) as a light yellow solid. $^1H$ NMR (400 MHz, DMSO-$d_6$) δ ppm 7.58 (m, 1H), 7.35-7.46 (m, 3H), 6.90 (d, J=1.4 Hz, 1H), 6.61 (d, J=1.4 Hz, 1H), 6.31 (dd, J=17.0, 10.3 Hz, 1H), 6.11 (dd, J=17.0, 2.3 Hz, 1H), 5.68 (dd, J=10.3, 2.3 Hz, 1H), 4.27 (dd, J=8.7, 5.0 Hz, 1H), 4.18 (d, J=5.5 Hz, 3H), 3.82-4.00 (m, 4H), 3.75 (t, J=6.8 Hz, 2H), 3.46 (s, 3H), 3.17 (t, J=6.0 Hz, 2H), 2.38 (m, 2H), 2.20 (m, 2H). m/z (ESI): 498.9 $(M+H)^+$.

Example 35-1: 4-(2-fluoro-3-hydroxyphenyl)-7-(4-methyl-1,3-thiazol-5-yl)-2-(2-(2-propenoyl)-2,6-diazaspiro[3.4]octan-6-yl)-5,6,7,8-tetrahydro-1,7-naphthyridine-3-carbonitrile

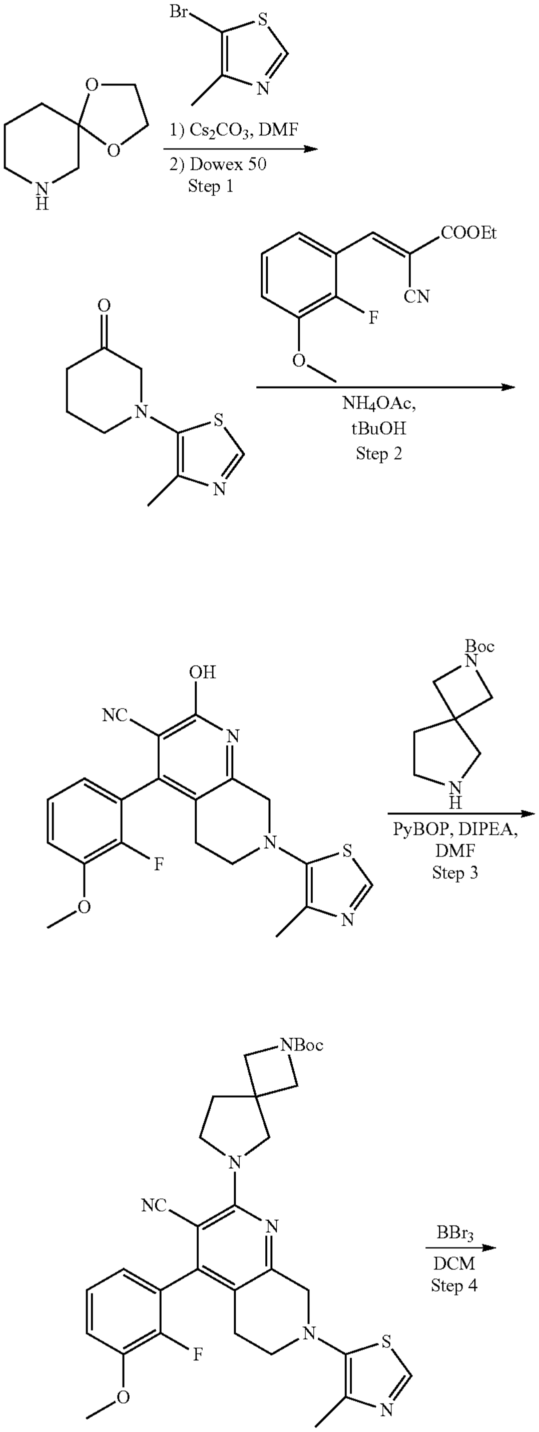

-continued

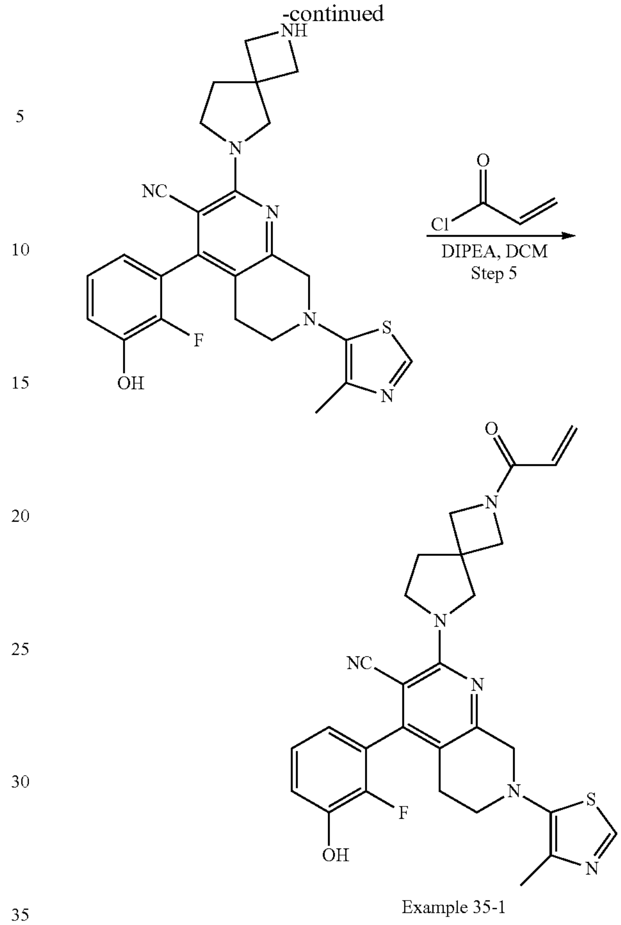

Example 35-1

Step 1: 1-(4-methylthiazol-5-yl)piperidin-3-one

5-Bromo-4-methylthiazole (1.368 g, 7.68 mmol), 1,4-dioxa-7-azaspiro[4.5]decane (1 g, 6.98 mmol), $Cs_2CO_3$ (4.55 g, 13.97 mmol) and DMF (20 mL) and stirred at 80° C. until LCMS indicated completion. The reaction was cooled, diluted with water, and extracted with EtOAc (3×10 mL). The combined organic layers were washed with water, dried over $Na_2SO_4$, and concentrated in vacuo. The residue was purified by silica gel chromatography to provide 7-(4-methylthiazol-5-yl)-1,4-dioxa-7-azaspiro[4.5]decane. m/z (APCI): 241.1 $(M+H^+)$. 7-(4-Methylthiazol-5-yl)-1,4-dioxa-7-azaspiro[4.5]decane (0.1 g, 0.416 mmol) was taken up in acetone (10 mL) with Dowex W50X8 (0.1 g, 0.416 mmol) and stirred at 60° C. until TLC indicated completion. The reaction mixture was filtered, concentrated, and the residue purified by silica gel chromatography to provide 1-(4-methylthiazol-5-yl)piperidin-3-one which was carried forward without further purification.

Step 2: 4-(2-fluoro-3-methoxyphenyl)-2-hydroxy-7-(4-methylthiazol-5-yl)-5,6,7,8-tetrahydro-1,7-naphthyridine-3-carbonitrile Ethyl (E)-2-cyano-3(2-fluoro-3-methoxyphenyl)acrylate (914 mg, 3.67 mmol), 1-(4-methylthiazol-5-yl)piperidin-3-one (600 mg, 3.06 mmol) and $NH_4OAc$ (2356 mg, 30.6 mmol) are dissolved in tert-butanol (5 mL) and heated at 100° C. until TLC indicated consumption of starting material. The solvent was evaporated and the residue purified by column chromatography to provide 4-(2-fluoro-3-methoxyphenyl)-2-hydroxy-7-(4-methylthiazol-5-yl)-5,6,7,8-tetrahydro-1,7-naphthyridine-3-carbonitrile (220 mg). m/z (APCI): 397.0 (M+H$^+$)

Step 3: tert-butyl 6-(3-cyano-4-(2-fluoro-3-methoxyphenyl)-7-(4-methylthiazol-5-yl)-5,6,7,8-tetrahydro-1,7-naphthyridin-2-yl)-2,6-diazaspiro[3.4]octane-2-carboxylate To a mixture of 4-(2-Fluoro-3-methoxyphenyl)-2-hydroxy-7-(4-methylthiazol-5-yl)-5,6,7,8-tetrahydro-1,7-naphthyridine-3-carbonitrile (220 mg, 0.555 mmol), tert-butyl 2,6-diazaspiro[3.4]octane-2-carboxylate (130 mg, 0.610 mmol), PyBOP (347 mg, 0.666 mmol) and DMF (2 mL) was added DIPEA (291 μL, 1.665 mmol). The reaction mixture was stirred until LCMS indicated completion. The reaction was quenched with water and extracted with EtOAc. The combined organic extracts were dried over $Na_2SO_4$ and concentrated in vacuo. The residue was purified by column chromatography to provide tert-butyl 6-(3-cyano-4-(2-fluoro-3-methoxyphenyl)-7-(4-methylthiazol-5-yl)-5,6,7,8-tetrahydro-1,7-naphthyridin-2-yl)-2,6-diazaspiro[3.4]octane-2-carboxylate. m/z (APCI): 590.8 (M+H$^+$)

Step 4: 4-(2-fluoro-3-hydroxyphenyl)-7-(4-methylthiazol-5-yl)-2-(2,6-diazaspiro[3.4]octan-6-yl)-5,6,7,8-tetrahydro-1,7-naphthyridine-3-carbonitrile To a solution of tert-butyl 6-(3-cyano-4-(2-fluoro-3-methoxyphenyl)-7-(4-methylthiazol-5-yl)-5,6,7,8-tetrahydro-1,7-naphthyridin-2-yl)-2,6-diazaspiro[3.4]octane-2-carboxylate (138 mg, 0.234 mmol) and DCM (5 mL) at −78° C. was added $BBr_3$ (1168 μL, 1.168 mmol) dropwise and the reaction mixture allowed to warm to room temperature and stirred until LCMS indicated completion. The reaction mixture was cooled in an ice bath and MeOH (5 mL) was carefully added. The reaction was concentrated in vacuo to give 4-(2-fluoro-3-hydroxyphenyl)-7-(4-methylthiazol-5-yl)-2-(2,6-diazaspiro[3.4]octan-6-yl)-5,6,7,8-tetrahydro-1,7-naphthyridine-3-carbonitrile. m/z (APCI): 476.8 (M+H$^+$)

Step 5: 4-(2-fluoro-3-hydroxyphenyl)-7-(4-methyl-1,3-thiazol-5-yl)-2-(2-(2-propenoyl)-2,6-diazaspiro[3.4]octan-6-yl)-5,6,7,8-tetrahydro-1,7-naphthyridine-3-carbonitrile 4-(2-Fluoro-3-hydroxyphenyl)-7-(4-methylthiazol-5-yl)-2-(2,6-diazaspiro[3.4]octan-6-yl)-5,6,7,8-tetrahydro-1,7-naphthyridine-3-carbonitrile (110 mg, 0.231 mmol) and DIPEA (0.4 mL, 2.308 mmol) was taken up in DCM (5 mL) and cooled to −78° C. Acryloyl chloride (19 μL, 0.231 mmol) was added and the reaction mixture warmed to 0° C. and stirred until LCMS indicated completion. The reaction was quenched with water (1 mL) and concentrated. The residue was purified by preparative HPLC to provide 4-(2-fluoro-3-hydroxyphenyl)-7-(4-methyl-1,3-thiazol-5-yl)-2-(2-(2-propenoyl)-2,6-diazaspiro[3.4]octan-6-yl)-5,6,7,8-tetrahydro-1,7-naphthyridine-3-carbonitrile (19 mg, 15% yield). m/z (APCI): 530.7 (M+H$^+$). $^1$H NMR (400 MHz, DMSO-d$_6$) δ ppm 10.17 (s, 1H), 8.71 (s, 1H), 7.24-7.01 (m, 2H), 6.74 (ddd, J=7.8, 6.0, 1.8 Hz, 1H), 6.31 (ddd, J=17.0, 10.3, 1.9 Hz, 1H), 6.11 (dd, J=17.0, 2.3 Hz, 1H), 5.68 (dd, J=10.3, 2.3 Hz, 1H), 4.21 (ddd, J=35.5, 8.7, 4.6 Hz, 2H), 4.06-3.79 (m, 5H), 3.74 (t, J=6.8 Hz, 2H), 3.07 (t, J=6.2 Hz, 2H), 2.45-2.34 (m, 2H), 2.27 (s, 3H), 2.20 (tt, J=7.0, 3.5 Hz, 2H).

Example 36-1: 1-(6-(4-(1,6-dimethyl-1H-indazol-7-yl)-3-methyl-7-(3-methyl-3-oxetanyl)-5,6,7,8-tetrahydro-1,7-naphthyridin-2-yl)-2,6-diazaspiro[3.4]octan-2-yl)-2-propen-1-one

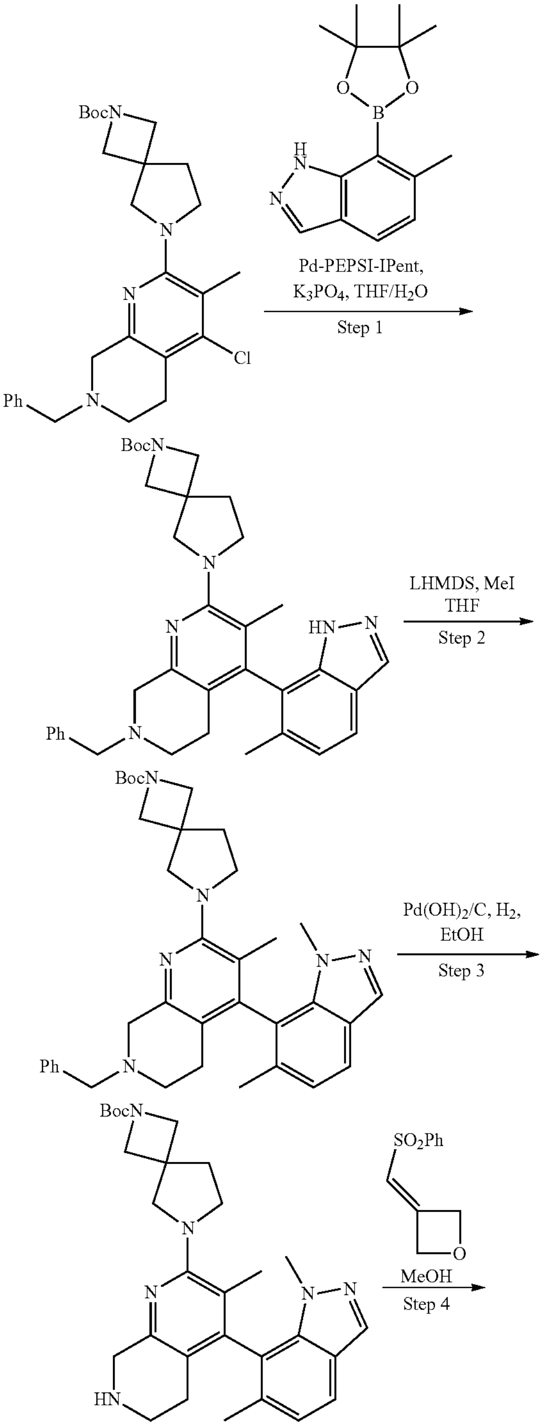

-continued

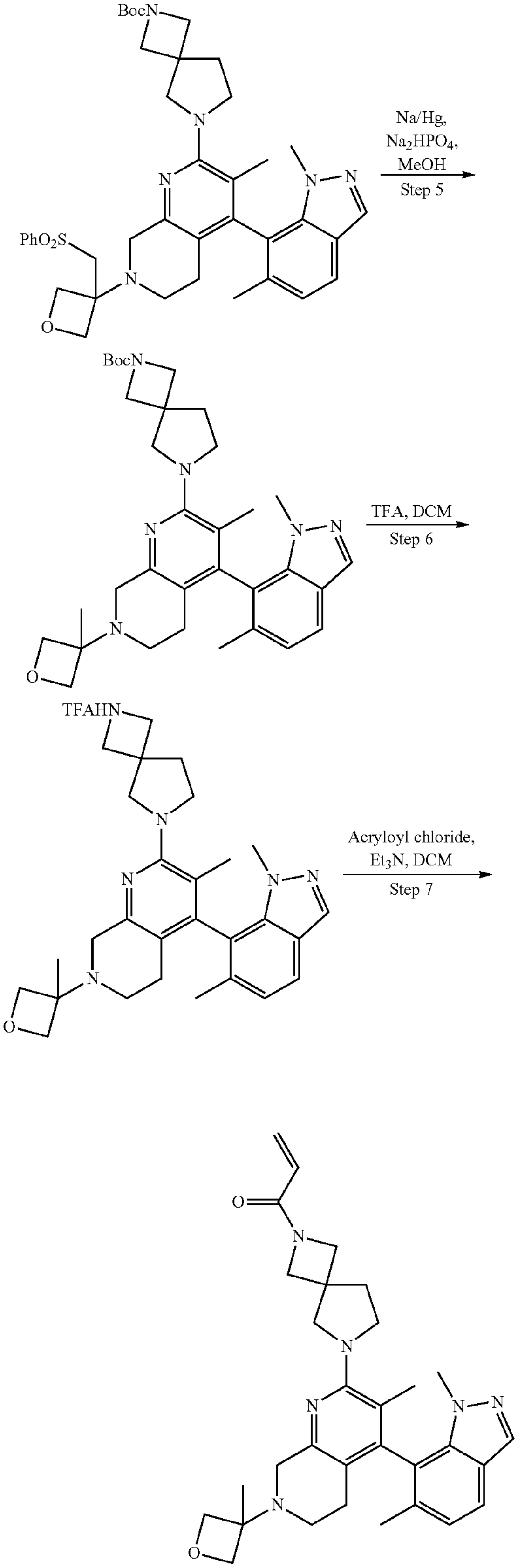

Step 1: tert-butyl 6-(7-benzyl-3-methyl-4-(6-methyl-1H-indazol-7-yl)-5,6,7,8-tetrahydro-1,7-naphthyridin-2-yl)-2,6-diazaspiro[3.4]octane-2-carboxylate To a degassed solution of tert-butyl 6-(7-ben yl-4-chloro-3-methyl-5,6,7,8-tetrahydro-1,7-naphthyridin-2-yl)-2,6-diazaspiro[3.4]octane-2-carboxylate (2 g, 4.14 mmol, Intermediate 50), 6-methyl-7-(4,4,5,5-tetramethyl-1,3,2-dioxaborolan-2-yl)-1H-indazole (1.389 g, 5.38 mmol), $K_3PO_4$ (2.64 g, 12.42 mmol) in THF (20 mL) and water (4 mL) was added Pd-PEPPSI-IPent (350 mg, 0.414 mmol, Strem) and the reaction mixture was heated at 80° C. for 16 h. The reaction mixture was cooled to room temperature and filtered through celite pad and washed with EtOAc. The filtrated was concentrated under reduced pressure. The residue was purified on a Redi-Sep pre-packed silica gel column eluting with 60% EtOAc in petroleum ether to provide tert-butyl 6-(7-benzyl-3-methyl-4-(6-methyl-1H-indazol-7-yl)-5,6,7,8-tetrahydro-1,7-naphthyridin-2-yl)-2,6-diazaspiro[3.4]octane-2-carboxylate (2.3 g, 96% yield) as an off-white solid. m/z (ESI): 579.0 $(M+H)^+$.

Step 2: tert-butyl 6-(7-benzyl-4-(1,6-dimethyl-1H-indazol-7-yl)-3-methyl-5,6,7,8-tetrahydro-1,7-naphthyridin-2-yl)-2,6-diazaspiro[3.4]octane-2-carboxylate To a solution of tert-butyl 6-(7-benzyl-3-methyl-4-(6-methyl-1H-indazol-7-yl)-5,6,7,8-tetrahydro-1,7-naphthyridin-2-yl)-2,6-diazaspiro[3.4]octane-2-carboxylate (2.3 g, 3.97 mmol) in THF (1 mL) was added LiHMDS (4.77 mL, 4.77 mmol, 1M in THF) at 0° C. and stirred for 30 min. Then iodomethane (0.745 mL, 11.92 mmol) was added to the reaction and stirring was continued for 2 h. The reaction mixture was quenched with ice-cold water and extracted with EtOAc. The organic extracts were washed with brine, dried over $Na_2SO_4$, and concentrated under reduced pressure. The residue was purified on a Redi-Sep pre-packed silica gel column eluting with 0-5% MeOH in $CHCl_3$ to provide tert-butyl 6-(7-benzyl-4-(1,6-dimethyl-1H-indazol-7-yl)-3-methyl-5,6,7,8-tetrahydro-1,7-naphthyridin-2-yl)-2,6-diazaspiro-[3.4]octane-2-carboxylate (1.8 g, 76% yield) as pale yellow oil. m/z (ESI): 593.0 $(M+H)^+$.

Step 3: tert-butyl 6-(4-(1,6-dimethyl-1H-indazol-7-yl)-3-methyl-5,6,7,8-tetrahydro-1,7-naphthyridin-2-yl)-2,6-diazaspiro[3.4]octane-2-carboxylate A solution of tert-butyl 6-(7-benzyl-4-(1,6-dimethyl-1H-indazol-7-yl)-3-methyl-5,6,7,8-tetrahydro-1,7-naphthyridin-2-yl)-2,6-diazaspiro[3.4]octane-2-carboxylate (1.8 g, 3.04 mmol), $Pd(OH)_2$ (426 mg, 0.607 mmol, 10% on Carbon, Hindustan Platinum) in EtOH (18 mL) was stirred under $H_2$ at 1 atm pressure for 16 h. The reaction mixture was filtered through a celite bed and washed with 10% MeOH in DCM. The filtrate was concentrated under reduced pressure to provide tert-butyl 6-(4-(1,6-dimethyl-1H-indazol-7-yl)-3-methyl-5,6,7,8-tetrahydro-1,7-naphthyridin-2-yl)-2,6-diazaspiro[3.4]octane-2-carboxylate (1.1 g, 2.188 mmol, 72% yield) obtained as a light brown oil which was used in next step without purification. m/z (ESI): 503.0 $(M+H)^+$.

Step 4: tert-butyl 6-(4-(1,6-dimethyl-1H-indazol-7-yl)-3-methyl-7-(3-((phenylsulfonyl)methyl)oxetan-3-yl)-5,6,7,8-tetrahydro-1,7-naphthyridin-2-yl)-2,6-diazaspiro[3.4]octane-2-carboxylate A solution of tert-butyl 6-(4-(1,6-dimethyl-1H-indazol-7-yl)-3-methyl-5,6,7,8-tetrahydro-1,7-naphthyridin-2-yl)-2,6- diazaspiro[3.4]octane-2-carboxylate (0.13 g, 0.259 mmol) and 3-((phenylsulfonyl)methylene)oxetane (0.072 g, 0.344 mmol, Combi Blocks) in MeOH (2.0 mL) was stirred at 50° C. for 12 h. The reaction mixture was diluted with ice-cold water and extracted with DCM. The organic extracts were washed with brine, dried over $Na_2SO_4$, and concentrated under reduced pressure. The residue was purified on a Redi-Sep pre-packed silica gel column eluting with 0-5% MeOH in $CHCl_3$ to provide tert-butyl 6-(4-(1,6-dimethyl-1H-indazol-7-yl)-3-methyl-7-(3-((phenylsulfonyl)methyl) oxetan-3-yl)-5,6,7,8-tetrahydro-1,7-naphthyridin-2-yl)-2,6-diazaspiro[3.4]octane-2-carboxylate (0.095 g, 51.5% yield) as a pale yellow semi-solid. m/z (ESI): 713.3 $(M+H)^+$.

Step 5: tert-butyl 6-(4-(1,6-dimethyl-1H-indazol-7-yl)-3-methyl-7-(3-methyloxetan-3-yl)-5,6,7,8-tetrahydro-1,7-naphthyridin-2-yl)-2,6-diazaspiro[3.4]octane-2-carboxylate A solution of tert-butyl 6-(4-(1,6-dimethyl-1H-indazol-7-yl)-3-methyl-7-(3-((phenylsulfonyl)methyl)oxetan-3-yl)-5,6,7,8-tetrahydro-1,7-naphthyridin-2-yl)-2,6-diazaspiro[3.4]octane-2-carboxylate (0.09 g, 0.126 mmol), $Na_2HPO_4$ (0.179 g, 1.262 mmol) and Na/Hg alloy (0.141 g, 0.631 mmol, Chempure) in MeOH (2.0 mL) was stirred at room temperature for 12 h. The reaction mixture was filtered through a celite bed and washed with DCM. The filtrate was washed with water and brine, dried over $Na_2SO_4$, and concentrated under reduced pressure to provide tert-butyl 6-(4-(1,6-dimethyl-1H-indazol-7-yl)-3-methyl-7-(3-methyloxetan-3-yl)-5,6,7,8-tetrahydro-1,7-naphthyridin-2-yl)-2,6-diazaspiro[3.4]octane-2-carboxylate (0.06 g, 83% yield) as pale yellow solid which was taken to the next step without further purification. m/z (ESI): 573.1 $(M+H)^+$.

Step 6: 1-(6-(4-(1,6-dimethyl-1H-indazol-7-yl)-3-methyl-7-(3-methyloxetan-3-yl)-5,6,7,8-tetrahydro-1,7-naphthyridin-2-yl)-214,6-diazaspiro[3.4]octan-2-yl)-2,2,2-trifluoroethan-1-one To a solution of tert-butyl 6-(4-(1,6-dimethyl-1H-indazol-7-yl)-3-methyl-7-(3-methyloxetan-3-yl)-5,6,7,8-tetrahydro-1,7-naphthyridin-2-yl)-2,6-diazaspiro[3.4]octane-2-carboxylate (0.06 g, 0.105 mmol) in DCM (2 mL) was added TFA (0.040 mL, 0.524 mmol) at 0° C. and the reaction was stirred at room temperature for 2 h. The reaction was concentrated under reduced pressure and triturated with diethyl ether to provide 1-(6-(4-(1,6-dimethyl-1H-indazol-7-yl)-3-methyl-7-(3-methyloxetan-3-yl)-5,6,7,8-tetrahydro-1,7-naphthyridin-2-yl)-214,6-diazaspiro[3.4]octan-2-yl)-2,2,2-trifluoroethan-1-one (0.058 g, 97% yield) as colorless gummy mass which was taken to next step without further purification. m/z (ESI): 473.1 $(M+H)^+$.

Step 7: 1-(6-(4-(1,6-dimethyl-1H-indazol-7-yl)-3-methyl-7-(3-methyl-3-oxetanyl)-5,6,7,8-tetrahydro-1,7-naphthyridin-2-yl)-2,6-diazaspiro[3.4]octan-2-yl)-2-propen-1-one To a solution of 1-(6-(4-(1,6-dimethyl-1H-indazol-7-yl)-3-methyl-7-(3-methyloxetan-3-yl)-5,6,7,8-tetrahydro-1,7-naphthyridin-2-yl)-214,6-diazaspiro[3.4]octan-2-yl)-2,2,2-trifluoroethan-1-one (0.05 g, 0.088 mmol) and TEA (0.037 mL, 0.263 mmol) in DCM (2 mL) was added acryloyl chloride (8.74 mg, 0.097 mmol, Symax Ltd.) at −78° C. dropwise and stirred for 15 min. The reaction mixture was diluted with water and extracted with DCM. The combined extracts were dried over $Na_2SO_4$, concentrated and purified by preparative HPLC to provide 1-(6-(4-(1,6-dimethyl-1H-indazol-7-yl)-3-methyl-7-(3-methyl-3-oxetanyl)-5,6,7,8-tetrahydro-1,7-naphthyridin-2-yl)-2,6-diazaspiro[3.4]octan-2-yl)-2-propen-1-one (0.005 g, 11% yield) as an off-white solid. $^1H$ NMR (400 MHz, DMSO-$d_6$) δ ppm 8.02 (s, 1H), 7.68 (d, J=8.1 Hz, 1H), 7.14 (d, J=8.3, Hz, 1H), 6.33 (dd, J=17.0, 10.3 Hz, 1H), 6.11 (dd, J=17.0, 2.3 Hz, 1H), 5.67 (dd, J=10.3, 2.3 Hz, 1H), 4.50-4.42 (m, 2H), 4.27-4.15 (m, 4H), 3.97-3.85 (m, 2H), 3.70-3.35 (m, 9H), 2.44-2.35 (m, 2H), 2.20-1.90 (m, 7H), 1.82 (s, 3H), 1.34 (s, 3H). m/z (ESI): 527.3 $(M+H)^+$.

Example 36-2: (M)-1-(6-(4-(1,6-dimethyl-H-indazol-7-yl)-3-methyl-7-(3-methyl-3-oxetanyl)-5,6,7,8-tetrahydro-1,7-naphthyridin-2-yl)-2,6-diazaspiro[3.4]octan-2-yl)-2-propen-1-one and Example 36-3: (P)-1-(6-(4-(1,6-dimethyl-1H-indazol-7-yl)-3-methyl-7-(3-methyl-3-oxetanyl)-5,6,7,8-tetrahydro-1,7-naphthyridin-2-yl)-2,6-diazaspiro[3.4]octan-2-yl)-2-propen-1-one The racemic mixture from Example 36-1, Step 3 was separated by SFC using a Chiralcel OD-H column with a mobile phase of 70% liquid $CO_2$ and 30% MeOH to provide the respective isomers P and M isomers of tert-butyl 6-(4-(1,6-dimethyl-1H-indazol-7-yl)-3-methyl-5,6,7,8-tetrahydro-1,7-naphthyridin-2-yl)-2,6-diazaspiro[3.4]octane-2-carboxylate. The stereochemistry of structures was arbitrarily assigned and is not established. 1$^{st}$ eluting isomer assigned as the M isomer and 2$^{nd}$ eluting isomer assigned as the P isomer. The separated material was carried forward through the rest of the synthesis described in Example 36-1.

Example 37-1: 4-(2-amino-3-methoxy-6-methylphenyl)-7,7-dimethyl-2-(2-(2-propenoyl)-2,6-diazaspiro[3.4]octan-6-yl)-7,8-dihydro-5H-pyrano[4,3-b]pyridine-3-carbonitrile

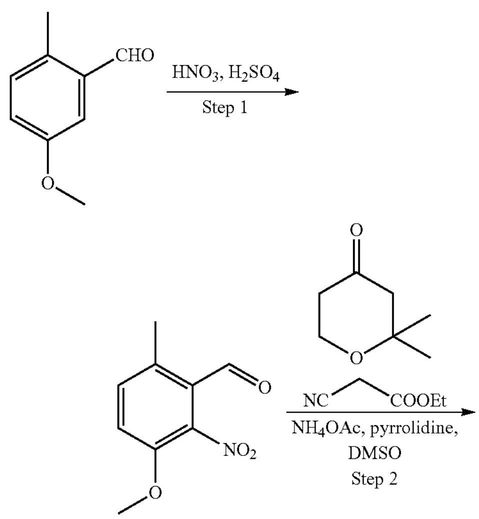

-continued

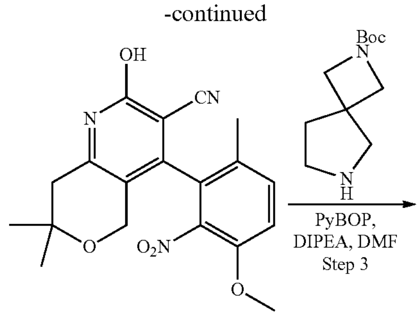

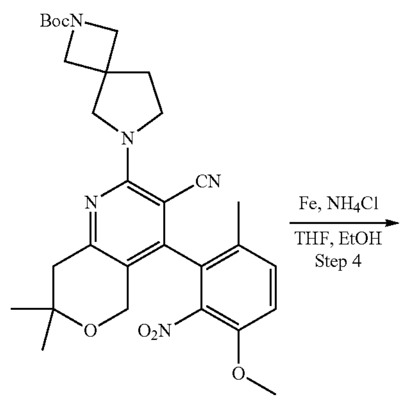

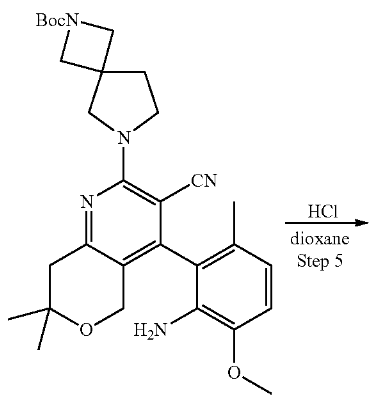

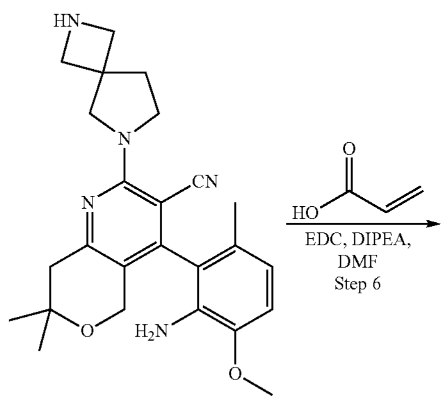

-continued

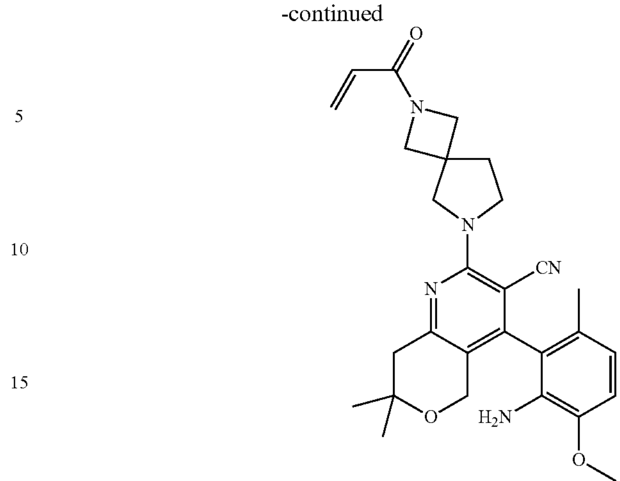

Example 37-1

Step 1: 3-methoxy-6-methyl-2-nitrobenzaldehyde 5-methoxy-2-methylbenzaldehyde (5 g, 33.3 mmol, Combi-Blocks) was added to a mixture of nitric acid (22.89 mL, 333 mmol) and sulfuric acid (9.05 mL, 166 mmol) at 0° C. When TLC indicated the starting material was consumed, the mixture was poured into 50 mL of ice water and extracted with DCM (3×20 mL). The combined organic extracts were washed with aqueous saturated $NaHCO_3$ and dried over $Na_2SO_4$ before concentrating to give crude 3-methoxy-6-methyl-2-nitrobenzaldehyde (3.5 g, 53.9%). m/z (APCI): 196.0 $(M+H)^+$.

Step 2: 2-hydroxy-4-(3-methoxy-6-methyl-2-nitrophenyl)-7,7-dimethyl-7,8-dihydro-5H-pyrano[4,3-b]pyridine-3-carbonitrile To a mixture of 3-methoxy-6-methyl-2-nitrobenzaldehyde (500 mg, 2.56 mmol),2,2-dimethyltetrahydro-4H-pyran-4-one (657 mg, 5.12 mmol, Combi-Blocks), ethyl 2-cyano-acetate (435 mg, 3.84 mmol) and $NH_4OAc$ (987 mg, 12.81 mmol) in DMSO (5 mL) was slowly added pyrrolidine (231 μL, 2.82 mmol). After 1 h at room temperature, the reaction was heated to 80° C. until TLC indicated completion. The reaction was diluted with water and extracted with EtOAc (3×10 mL). The combined organic extracts were dried over $Na_2SO_4$ and concentrated. The residue was purified by silica gel chromatography to provide 2-hydroxy-4-(3-methoxy-6-methyl-2-nitrophenyl)-7,7-dimethyl-7,8-dihydro-5H-pyrano[4,3-b]pyridine-3-carbonitrile (700 mg, 74% yield). m/z (APCI): 370.3 $(M+H^+)$ Step 3: tert-butyl 6-(3-cyano-4-(3-methoxy-6-methyl-2-nitrophenyl)-7,7-dimethyl-7,8-dihydro-5H-pyrano[4,3-b]pyridin-2-yl)-26-diazaspiro[3.4]octane-2-carboxylate To a mixture of 2-hydroxy-4-(3-methoxy-6-methyl-2-nitrophenyl)-7,7-dimethyl-7,8-dihydro-5H-pyrano[4,3-b]pyridine-3-carbonitrile (1.5 g, 4.06 mmol), PyBOP (2.54 g, 4.87 mmol), and tert-butyl 2,6-diazaspiro[3.4]octane-2-carboxylate (0.948 g, 4.47 mmol) in DMF (15 mL) was added DIPEA (2.128 mL, 12.18 mmol). The reaction stirred at room temperature until LCMS indicated completion. The reaction mixture was diluted with water and extracted with EtOAc (3×10 mL). The combined organic layer was washed with water, dried over $Na_2SO_4$ and concentrated in vacuo. The residue was purified by silica gel chromatography to provide tert-butyl 6-(3-cyano-4-(3-methoxy-6-methyl-2-nitrophenyl)-7,7-dimethyl-7,8-dihydro-5H-pyrano[4,3-b]pyridin-2-yl)-2,6-diazaspiro[3.4]octane-2-carboxylate (1.2 g, 52% yield). m/z (APCI): 563.8 (M−H+).

Step 4: tert-butyl 6-(4-(2-amino-3-methoxy-6-methylphenyl)-3-cyano-7,7-dimethyl-7,8-dihydro-5H-pyrano[4,3-b]pyridin-2-yl)-2,6-diazaspiro[3.4]octane-2-carboxylate To a solution of tert-butyl 6-(3-cyano-4-(3-methoxy-6-methyl-2-nitrophenyl)-7,7-dimethyl-7,8-dihydro-5H-pyrano[4,3-b]pyridin-2-yl)-2,6-diazaspiro[3.4]octane-2-carboxylate (1.2 g, 2.129 mmol) and THF (10 mL):EtOH (10 mL) was added $NH_4Cl$ (0.569 g, 10.64 mmol) dissolved in water (10 mL), followed by iron (0.594 g, 10.64 mmol). The reaction mixture was stirred at 90° C. until LCMS indicated completion. The reaction was diluted with water and the aqueous layer was extracted with EtOAc (3×10 mL). The combined organic extracts were dried over $Na_2SO_4$ and concentrated to give tert-butyl 6-(4-(2-amino-3-methoxy-6-methylphenyl)-3-cyano-7,7-dimethyl-7,8-dihydro-5H-pyrano[4,3-b]pyridin-2-yl)-2,6-diazaspiro[3.4]octane-2-carboxylate (650 mg, 57% yield). m/z (APCI): 534.2 ($M+H^+$)

Step 5: 4-(2-amino-3-methoxy-6-methylphenyl)-7,7-dimethyl-2-(2,6-diazaspiro[3.4]octan-6-yl)-7,8-dihydro-5H-pyrano[4,3-b]pyridine-3-carbonitrile To a 0° C. solution of tert-butyl 6-(4-(2-amino-3-methoxy-6-methylphenyl)-3-cyano-7,7-dimethyl-7,8-dihydro-5H-pyrano[4,3-b]pyridin-2-yl)-2,6-diazaspiro[3.4]octane-2-carboxylate (200 mg, 0.375 mmol) and 1,4-dioxane (5 mL) was added HCl in 1,4-dioxane (0.937 mL, 3.75 mmol) and the reaction mixture brought to room temperature until LCMS indicated completion. The reaction mixture was concentrated in vacuo to give 4-(2-amino-3-methoxy-6-methylphenyl)-7,7-dimethyl-2-(2,6-diazaspiro[3.4]octan-6-yl)-7,8-dihydro-5H-pyrano[4,3-b]pyridine-3-carbonitrile (160 mg, 98% yield). m/z (APCI): 434.5 ($M+H^+$)

Step 6: 4-(2-amino-3-methoxy-6-methylphenyl)-7,7-dimethyl-2-(2-(2-propenoyl)-2,6-diazaspiro[3.4]octan-6-yl)-7,8-dihydro-5H-pyrano[4,3-b]pyridine-3-carbonitrile To a stirred solution of 4-(2-amino-3-methoxy-6-methylphenyl)-7,7-dimethyl-2-(2,6-diazaspiro[3.4]octan-6-yl)-7,8-dihydro-5H-pyrano[4,3-b]pyridine-3-carbonitrile (160 mg, 0.369 mmol), EDC (106 mg, 0.554 mmol), and DMF (5 mL) was added DIPEA (0.645 mL, 3.69 mmol) and acrylic acid (25 μL, 0.369 mmol) in portions until LCMS indicated completion The reaction mixture was diluted with water and extracted with EtOAc (3×10 mL). The combined organic layers were washed with water and concentrated in vacuo. The residue was purified by preparative HPLC to provide 4-(2-amino-3-methoxy-6-methylphenyl)-7,7-dimethyl-2-(2-(2-propenoyl)-2,6-diazaspiro[3.4]octan-6-yl)-7,8-dihydro-5H-pyrano[4,3-b]pyridine-3-carbonitrile (29 mg, 16% yield). m/z (APCI): 488.0 $(M+H)^+$. $^1H$ NMR (400 MHz, DMSO-$d_6$) δ ppm 6.78 (d, J=8.2 Hz, 1H), 6.54 (dd, J=8.1, 0.9 Hz, 1H), 6.32 (dd, J=17.0, 10.2 Hz, 1H), 6.11 (dd, J=17.0, 2.3 Hz, 1H), 5.68 (dd, J=10.3, 2.3 Hz, 1H), 4.26 (d, J=6.3 Hz, 3H), 4.22-4.08 (m, 2H), 4.03-3.94 (m, 2H), 3.94-3.83 (m, 3H), 3.79 (s, 3H), 3.78-3.69 (m, 2H), 2.69 (s, 2H), 2.19 (q, J=6.0 Hz, 2H), 1.84 (s, 3H), 1.21 (d, J=12.0 Hz, 6H).

Example 38-1: 4-(3-amino-1-naphthalenyl)-7,7-dimethyl-2-(2-(2-propenoyl)-2,6-diazaspiro[3.4]octan-6-yl)-7,8-dihydro-5H-pyrano[4,3-b]pyridine-3-carbonitrile

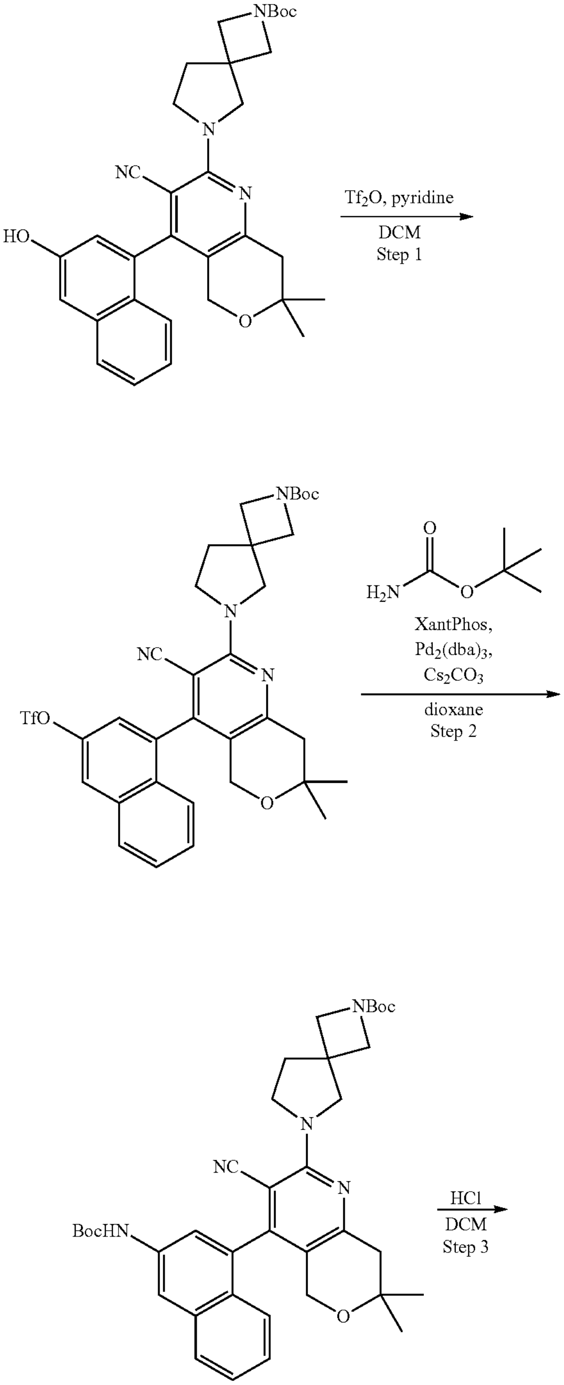

-continued

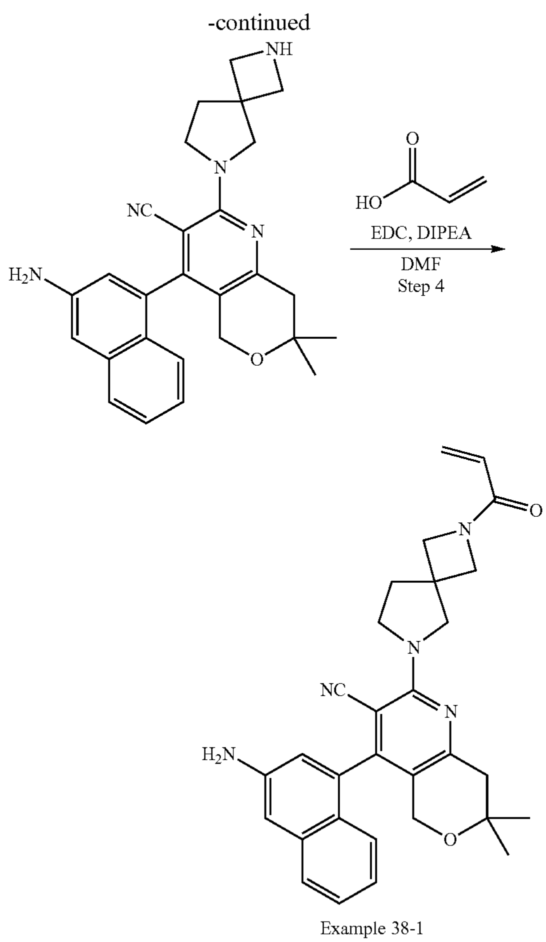

Example 38-1

Step 1: tert-butyl 6-(3-cyano-7,7-dimethyl-4-(3-(((trifluoromethyl)sulfonyl)oxy)-naphthalen-1-yl)-7,8-dihydro-5H-pyrano[4,3-b]pyridin-2-yl)-2,6-diazaspiro[3.4]octane-2-carboxylate To a solution of tert-butyl 6-(3-cyano-4-(3-hydroxynaphthalen-1-yl)-7,7-dimethyl-7,8-dihydro-5H-pyrano[4,3-b]pyridin-2-yl)-2,6-diazaspiro[3.4]octane-2-carboxylate (0.29 g, 0.536 mmol, Example 13-41, Step 3) and DCM (3 mL) was added pyridine (0.130 mL, 1.609 mmol) and triflic anhydride (0.109 mL, 0.644 mmol) at 0° C. The reaction mixture was stirred for 30 min at 0° C. The reaction mixture was diluted with ice cold water and extracted with DCM (2×50 mL), the organic extracts were washed with brine (100 mL) and dried over $Na_2SO_4$. The solution was filtered and concentrated under reduced pressure. The crude was purified on silica gel eluting with 40-50% EtOAc in petroleum ether to give tert-butyl 6-(3-cyano-7,7-dimethyl-4-(3-(((trifluoromethyl)sulfonyl)oxy)naphthalen-1-yl)-7,8-dihydro-5H-pyrano[4,3-b]pyridin-2-yl)-2,6-diazaspiro[3.4]octane-2-carboxylate (0.3 g, 83% yield) as a light yellow gummy liquid. m/z (ESI): 672.8 $(M+H)^+$. $^1H$ NMR (400 MHz. DMSO-$d_6$) δ ppm 8.34 (d, J=2.6 Hz, 1H), 8.22 (d, J=8.1 Hz, 1H), 7.71-7.75 (m, 2H), 7.64-7.68 (m, 1H), 7.48 (d, J=8.6 Hz, 1H), 4.15 (d, J=15.3 Hz, 1H), 3.87 (d, J=12.5 Hz, 5H), 3.84-3.69 (m, 5H), 2.75 (d, J=3.1 Hz, 2H), 2.16 (t, J=6.9 Hz, 2H), 1.39 (s, 9H), 1.21 (d, J=10.0 Hz, 6H).

Step 2: tert-butyl 6-(4-(3-((tert-butoxycarbonyl)amino)naphthalen-1-yl)-3-cyano-7,7-dimethyl-7,8-dihydro-5H-pyrano[4,3-b]pyridin-2-yl)-2,6-diazaspiro[3.4]octane-2-carboxylate To a stirred solution of tert-butyl 6-(3-cyano-7,7-dimethyl-4-(3-(((trifluoromethyl)sulfonyl)-oxy)naphthalen-1-yl)-7,8-dihydro-5H-pyrano[4,3-b]pyridin-2-yl)-2,6-diazaspiro[3.4]octane-2-carboxylate (0.75 g, 1.115 mmol) in 1,4-dioxane (14 mL) was added tert-butyl carbamate (0.196 g, 1.672 mmol) followed by $Cs_2CO_3$ (0.726 g, 2.230 mmol). The reaction mass was purged with $N_2$ for 2 min. XantPhos (0.065 g, 0.111 mmol) and $Pd_2(dba)_3$ (0.102 g, 0.111 mmol) were added and the reaction was again purged for 2 min with $N_2$ and heated to 80° C. for 16 h. The reaction was carried out in a sealed tube. The reaction was diluted with ice cold water and extracted with DCM (2×75 mL), the organic extracts were washed with brine (100 mL), dried over $Na_2SO_4$, and concentrated under reduced pressure. The crude was purified on silica gel eluting with 20-30% EtOAc in petroleum ether to give tert-butyl 6-(4-(3-((tert-butoxycarbonyl)amino)-naphthalen-1-yl)-3-cyano-7,7-dimethyl-7,8-dihydro-5H-pyrano[4,3-b]pyridin-2-yl)-2,6-diazaspiro[3.4]octane-2-carboxylate (0.45 g, 63.1% yield) as a light yellow gummy liquid. m/z (ESI): 639.9 $(M+H)^+$. $^1H$ NMR (400 MHz, DMSO-$d_6$) δ ppm 9.72 (s, 1H), 8.20 (s, 1H), 7.89 (d, J=8.2 Hz, 1H), 7.49-7.53 (m, 1H), 7.41 (d, J=2.1 Hz, 1H), 7.34-7.38 (m, 1H), 7.26-7.22 (m, 1H), 4.18-4.08 (m, 1H), 3.88-3.71 (m, 8H), 3.17 (d, J=5.3 Hz, 1H), 2.75 (s, 2H), 2.20-2.11 (m, 2H), 1.52 (s, 9H), 1.39 (s, 9H), 1.20 (d, J=7.2 Hz, 6H).

Step 3: 4-(3-aminonaphthalen-1-yl)-7,7-dimethyl-2-(2,6-diazaspiro[3.4]octan-6-yl)-7,8-dihydro-5H-pyrano[4,3-b]pyridine-3-carbonitrile hydrochloride To a solution of tert-butyl 6-(4-(3-((tert-butoxycarbonyl)amino)naphthalen-1-yl)-3-cyano-7,7-dimethyl-7,8-dihydro-5H-pyrano[4,3-b]pyridin-2-yl)-2,6-diazaspiro[3.4]octane-2-carboxylate (0.38 g, 0.594 mmol) in DCM (3 mL) was added HCl (4M in dioxane, 3 mL, 12.00 mmol) at 0° C. The reaction was stirred at room temperature for 1 h. After 1 h, starting material was consumed. The reaction was concentrated in vacuo, co-evaporated with toluene (2×), followed by trituration with diethyl ether to provide 4-(3-aminonaphthalen-1-yl)-7,7-dimethyl-2-(2,6-diazaspiro[3.4]octan-6-yl)-7,8-dihydro-5H-pyrano[4,3-b]pyridine-3-carbonitrile hydrochloride (0.25 g, 82% yield) as a yellow solid.

Step 4: 2-(2-acryloyl-2,6-diazaspiro[3.4]octan-6-yl)-4-(3-aminonaphthalen-1-yl)-7,7-dimethyl-7,8-dihydro-5H-pyrano[4,3-b]pyridine-3-carbonitrile To a stirred solution of 4-(3-((12-chloraneyl)amino)naphthalen-1-yl)-7,7-dimethyl-2-(2,6-diazaspiro[3.4]octan-6-yl)-7,8-dihydro-5H-pyrano[4,3-b]pyridine-3-carbonitrile HCl (0.25 g, 0.489 mmol) in DMF (1 mL) was added DIPEA (0.427 mL, 2.444 mmol), EDC (0.141 g, 0.733 mmol) and acrylic acid (0.035 g, 0.489 mmol) at 0° C. The reaction was stirred at room temperature for 4 h. The reaction was diluted with ice cold water and extracted with EtOAc (2×50 mL). The organic extracts were washed with brine (50 mL), dried over $Na_2SO_4$, and concentrated under reduced pressure. The crude was purified by prep HPLC to provide 2-(2-acryloyl-2,6-diazaspiro[3.4]octan-6-yl)-4-(3-aminonaphthalen-1-yl)-7,7-dimethyl-7,8-dihydro-5H-pyrano[4,3-b]pyridine-3-carbonitrile (0.015 g, 6.22% yield) as an off white solid. m/z (ESI): 494.0 $(M+H)^+$. $^1H$ NMR (400 MHz. DMSO-$d_6$) δ ppm 7.61 (d, J=8.3 Hz, 1H), 7.30-7.34 (m, 1H), 7.07 (d, J=6.4 Hz, 2H), 6.93 (d, J=2.2 Hz, 1H), 6.81 (d, J=2.2 Hz, 1H), 6.30-6.35 (m, 1H), 6.11 (dd, J=17.0, 2.4 Hz, 1H), 5.68 (dd, J=10.2, 2.3 Hz, 1H), 5.56 (s, 2H), 4.28 (dd, J=8.6, 5.2 Hz, 1H), 4.20-4.11 (m, 2H), 4.02-3.86 (m, 5H), 3.76 (t, J=6.8 Hz, 2H), 2.74 (d, J=2.9 Hz, 2H), 2.17-2.22 (m, 2H), 1.20 (d, J=4.2 Hz, 6H).

Synthesis of Intermediates

Intermediate 1: 2,4-dihydroxy-7-methyl-5,6,7,8-tetrahydroquinoline-3-carbonitrile

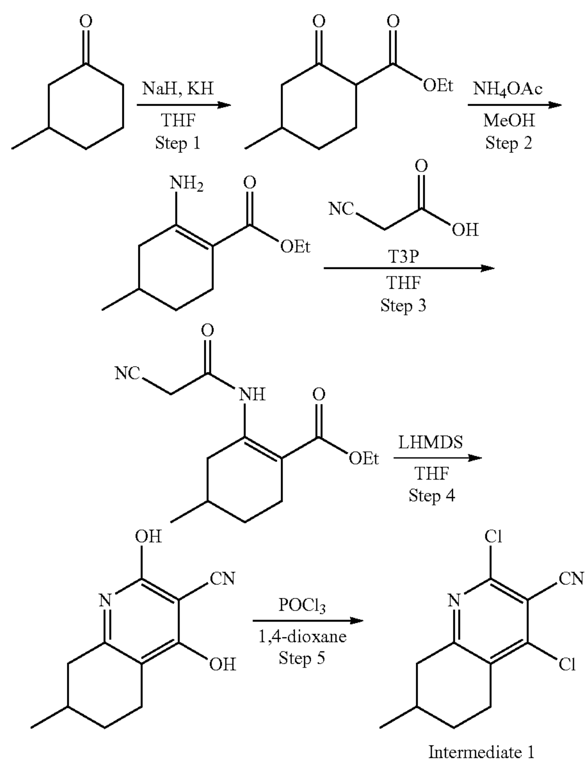

Intermediate 1

Step 1: 2-oxocyclohexanes-1-carboxylate

To a stirred suspension of NaH (75 wt %, 8.91 g, 279 mmol) in THF (55 mL) under a $N_2$ atmosphere was added diethyl carbonate (26.30 g, 22.3 mmol). The mixture was brought to reflux before one third of a prepared solution of 3-methylcyclohexan-1-one (10.0 g, 8.92 mmol, Adamas) in THF (20 mL) was added dropwise followed by a catalytic amount of KH (35 wt %, 600 mg, 5.24 mmol). The remaining solution of 3-methylcyclohexan-1-one in THF was added dropwise, and the mixture was refluxed for 30 min. The reaction mixture was cooled in an ice bath and quenched with 3 M aqueous AcOH (35 mL). The mixture was diluted with satd aqueous NaCl (120 mL) and extracted with MTBE (3×150 mL). The combined organic extracts were dried over $MgSO_4$, filtered, and concentrated in vacuo. Chromatographic purification of the residue (silica gel, 5% MTBE in cyclohexane) gave ethyl 2-oxocyclohexanes-1-carboxylate as a colorless oil (8.6 g, 52.1 mmol, 58% yield). m/z (ESI): 185.2 $(M+H)^+$.

Step 2: Ethyl 2-amino-4-methylcyclohex-1-ene-1-carboxylate

Ammonium acetate (10.87 g, 141 mmol) and ethyl 2-oxo-cyclohexanes-1-carboxylate (9.6 g, 56.4 mmol) were mixed in MeOH (100 mL). The reaction mixture was stirred at room temperature for 4 h. The reaction mixture was diluted with water (100 mL) and extracted with EtOAc (2×100 mL). The combined organic extracts were washed with satd aqueous NaCl (2×100 mL), dried over $Na_2SO_4$, filtered, and concentrated in vacuo. The solution was filtered and concentrated in vacuo to give the crude material. The resulting residue was absorbed onto a plug of silica gel and purified by column chromatography (silica gel, 50-60% EtOAc in PE) to give ethyl 2-amino-4-methylcyclohex-1-ene-1-carboxylate (8.25 g, 38.7 mmol, 69% yield) as a white solid. m/z (ESI): 184.1 $(M+H)^+$.

Step 3: ethyl 2-(2-cyanoacetamido)-4-methylcyclohex-1-ene-1-carboxylate

Ethyl 2-amino-4-methylcyclohex-1-ene-1-carboxylate (8.4 g, 45.8 mmol), 2-cyanoacetic acid (5.85 g, 68.8 mmol), and 2,4,6-tripropyl-1,3,5,2,4,6-trioxatriphosphinane 2,4,6-trioxide (14.59 g, 45.8 mmol) were mixed in THF (100 mL). The reaction mixture was stirred at 60° C. for 6 h. The reaction mixture was cooled to room temperature, diluted with water (100 mL), and extracted with EtOAc (2×100 mL). The combined organic extracts were washed with satd aqueous NaCl (2×100 mL), dried over $Na_2SO_4$, filtered, and concentrated in vacuo. The resulting residue was absorbed onto a plug of silica gel and purified by column chromatography (silica gel, 20-30% EtOAc in PE) to give ethyl 2-(2-cyanoacetamido)-4-methylcyclohex-1-ene-1-carboxylate (7.7 g, 30.8 mmol, 67% yield) as a yellow oil. m/z (ESI): 251.1 $(M+H)^+$.

Alternative Step 3 (for intermediates 4, 5, and 6): methyl 2-(2-cyanoacetamido)-3-fluorobenzoate To a 0° C. solution of methyl 2-amino-3-fluorobenzoate (2.0 g, 11.82 mmol), DIPEA (6.20 mL, 35.5 mmol) and THF (6 mL) was added 2-cyanoacetyl chloride (1.59 g, 15.37 mmol) dropwise. Upon completion, the reaction solution was diluted with water and EtOAc. The aqueous layer was extracted with EtOAc. The combined organic phases were washed with brine, dried over $MgSO_4$, and concentrated. The residue was purified by chromatography (PE/EtOAc, 99/1 to 3/2) to give methyl 2-(2-cyanoacetamido)-3-fluorobenzoate (800 mg, 29% yield).

Step 4: 2,4-dihydroxy-7-methyl-5,6,7,8-tetrahydroquinoline-3-carbonitrile

Ethyl 2-(2-cyanoacetamido)-4-methylcyclohex-1-ene-1-carboxylate (7.7 g, 30.8 mmol) and LHMDS (36.9 mL, 36.9 mmol, 1M in THF) were mixed in THF (80 mL). The reaction mixture was stirred at −60° C. for 4 h. The reaction mixture was warmed to room temperature, diluted with water (100 mL), and extracted with EtOAc (2×100 mL). The combined organic extracts were washed with brine (2×100 mL), dried over $Na_2SO_4$, and concentrated in vacuo. The residue was absorbed onto a plug of silica gel and purified by chromatography (silica gel, 50-60% EtOAc in PE) to give 2,4-dihydroxy-7-methyl-5,6,7,8-tetrahydroquinoline-3-carbonitrile (5.8 g, 92% yield) as a yellow solid. m/z (ESI): 205.1 $(M+H)^+$.

Step 5: 2,4-dihydroxy-7-methyl-5,6,7,8-tetrahydro-quinoline-3-carbonitrile 2,4-Dihydroxy-7-methyl-5,6,7,8-tetrahydroquinoline-3-carbonitrile (5.8 g, 28.4 mmol) and $POCl_3$ (13.23 mL, 142 mmol) were mixed in 1,4-dioxane (50 mL). The reaction mixture was stirred at 100° C. for 16 h. The reaction mixture was cooled and poured into ice water. The resulting aqueous mixture was extracted with EtOAc (2×200 mL). The combined organic extracts were washed with satd aqueous NaCl (2×100 mL), dried over $Na_2SO_4$, filtered, and concentrated in vacuo. The resulting residue was absorbed onto a plug of silica gel and purified by column chromatography (silica gel, 50-60% EtOAc in PE) to give 2,4-dichloro-7-methyl-5,6,7,8-tetrahydroquinoline-3-carbonitrile (4.75 g, 19.7 mmol, 69% yield) as a yellow solid. m/z (ESI): 241.1 $(M+H)^+$.

TABLE 16

Intermediates 2-8 were prepared following the procedure described for Intermediate 1, Steps 1-5, above as follows:

| Int.# | Chemical Structure | Name | LC/MS ($ESI^+$) m/z | Conditions | Reagent |
|---|---|---|---|---|---|
| 2 | 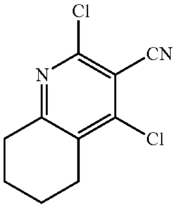 [SMILES: N#Cc1c(Cl)nc2c(c1Cl)CCCC2] | 2,4-dichloro-5,6,7,8-tetrahydroquinoline-3-carbonitrile | 227.0 | Omit Step 1 | Step 2: ethyl 2-oxocyclohexanes-1-carboxylate (CAS: 1655-07-8). |
| 3 | 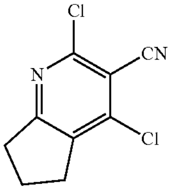 [SMILES: N#Cc1c(Cl)nc2c(c1Cl)CCC2] | 2,4-dichloro-6,7-dihydro-5H-cyclopenta[b]pyridine-3-carbonitrile | 213.1 | Omit Step 1 | Step 2: ethyl 2-oxocyclopentane-1-carboxylate (CAS: 611-10-9). |
| 4 | 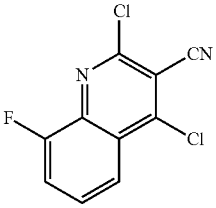 [SMILES: N#Cc1c(Cl)nc2c(F)cccc2c1Cl] | 2,4-dichloro-8-fluoroquinoline-3-carbonitrile | 240.9 | Omit Steps 1 and 2. Use Alternative Step 3 | Step 3: methyl 2-amino-3-fluorobenzoate (CAS:144851-82-1) and 2-cyanoacetyl chloride (CAS: 16130-58-8). |
| 5 | 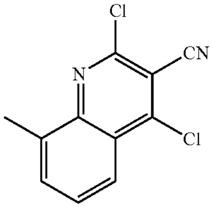 | 2,4-dichloro-8-methylquinoline-3-carbonitrile | 237.0 | Omit Steps 1 and 2. Use Alternative Step 3 | Step 3: methyl 2-amino-3-methylbenzoate (CAS: 22223-49-0) and 2-cyanoacetyl chloride (CAS: 16130-58-8). |
| 6 | 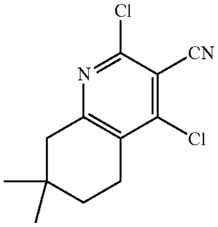 [SMILES: CC1(C)CCc2c(nc(Cl)c(C#N)c2Cl)C1] | 2,4-dichloro-7,7-dimethyl-5,6,7,8-tetrahydroquinoline-3-carbonitrile | 255.1 | | Step 1: 3,3-dimethylcyclohexan-1-one (CAS: 2979-19-3, PharmaBlock). |

TABLE 16-continued

| Intermediates 2-8 were prepared following the procedure described for Intermediate 1, Steps 1-5, above as follows: | | | | | |
|---|---|---|---|---|---|
| Int.# | Chemical Structure | Name | LC/MS ($ESI^+$) m/z | Conditions | Reagent |
| 7 | 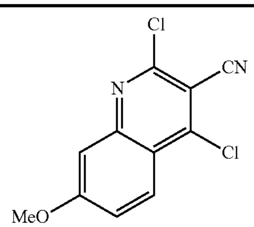 | 2,4-dichloro-7-methoxyquinoline-3-carbonitrile | 253.0 | Omit Steps 1 and 2. | Step 3: methyl 2-amino-4-methoxybenzoate (CAS: 50413-30-4, Combi-Blocks). |

Intermediate 8: 6-bromo-8-iodo-2-phenylimidazo[1,2-a]pyridine-7-carbonitrile

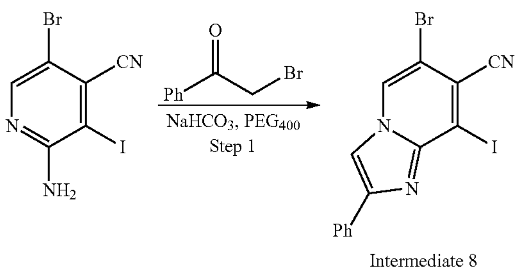 [SMILES: N#Cc1c(Br)cnc(N)c1I ; O=C(CBr)c1ccccc1 ; N#Cc1c(Br)cn2cc(-c3ccccc3)nc2c1I]

Intermediate 8

Step 1: 6-bromo-8-iodo-2-phenylimidazo[1,2-a]pyridine-7-carbonitrile

A glass microwave reaction vessel was charged with 2-amino-5-bromo-3-iodoisonicotinonitrile (0.30 g, 0.926 mmol) and 2-bromo-1-phenylethan-1-one (0.369 g, 1.852 mmol, Adamas) and $NaHCO_3$ (0.156 g, 1.852 mmol, Acros) in PEG400 (3 mL). The reaction mixture was stirred and heated in an initiator microwave reactor at 120° C. for 2 h. The reaction mixture was diluted with water (200 mL) and extracted with EtOAc (2×200 mL). The organic extracts were washed with water (1×100 mL), dried over $Na_2SO_4$, and concentrated in vacuo. The crude material was absorbed onto a plug of silica gel and purified by chromatography through a Redi-Sep pre-packed silica gel column, eluting with a gradient of 50-80% EtOAc in hexanes, to provide 6-bromo-8-iodo-2-phenylimidazo[1,2-a]pyridine-7-carbonitrile (55 mg, 14% yield) as a tan solid. m/z ESI: 422 $(M+H)^+$.

Intermediate 9: 2,4-dichloro-8-methyl-5,6,7,8-tetrahydroquinazoline

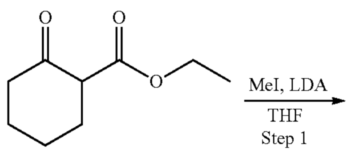

-continued

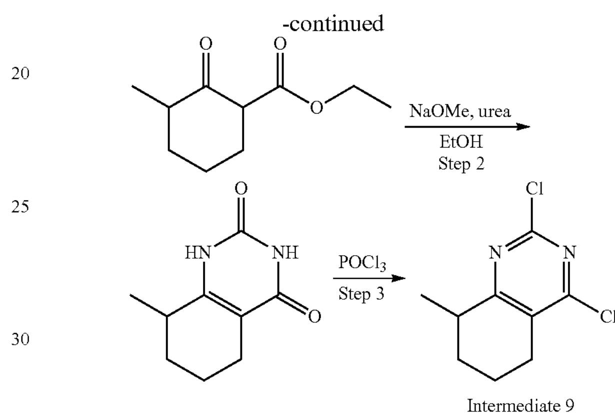

Intermediate 9

Step 1: ethyl 3-methyl-2-oxocyclohexanes-1-carboxylate

To a mixture of ethyl 2-oxocyclohexanes-1-carboxylate (20.0 g, 117 mmol, ADAMAS) in THE (300 mL) was stirred at 0° C., a solution of LDA (117 mL, 2.0 M in THF) was added dropwise. The mixture was allowed to stir for 0.5 h. Methyl iodide (16.7 g, 117.6 mmol) was added and the resulting mixture was stirred for 1 h. An aqueous saturated solution of $NH_4Cl$ was added and the mixture was extracted with EtOAc (200 mL×3). The combined organic extracts were washed with brine, dried over $Na_2SO_4$, and concentrated to afford crude ethyl 3-methyl-2-oxocyclohexanes-1-carboxylate (21.0 g, 97% yield) as a yellow oil, which was used in the next step without further purification.

Step 2: 8-methyl-5,6,7,8-tetrahydroquinazoline-2,4(1H,3H)-dione

To a RBF was added ethyl 3-methyl-2-oxocyclohexanes-1-carboxylate (21.0 g, 114 mmol) and urea (10.26 g, 171 mmol), sodium methoxide (6.32 g, 171 mmol) and EtOH (150 mL). The reaction mixture was stirred at 80° C. for 16 h. The solution was concentrated in vacuo to give the crude product. The residue was suspend in DCM (100 mL) and the mixture was filtered and the solids washed with DCM (50 mL×3) and dried to afford 8-methyl-5,6,7,8-tetrahydroquinazoline-2,4(1H,3H)-dione (10.0 g, 48% yield) as a brown solid. m/z (ESI): 181.0 $(M+H)^+$.

Step 3: 2,4-dichloro-8-methyl-5,6,7,8-tetrahydroquinazoline

A mixture of 8-methyl-5,6,7,8-tetrahydroquinazoline-2,4(1H,3H)-dione (7.8 g, 43.3 mmol) and $POCl_3$ (80 mL) was heated to 100° C. and allowed to stir for 16 h. The mixture was cooled to room temperature and the residue was adjusted pH=8-9 with a saturated solution of $NaHCO_3$ at 0° C. The mixture was extracted with DCM (100 mL×3). The combined organic layers were washed with brine, dried over $Na_2SO_4$, and concentrated in vacuo. The residue was purified by silica gel chromatography (PE:EtOAc=20:1) to afford 2,4-dichloro-8-methyl-5,6,7,8-tetrahydroquinazoline (3.0 g, 32% yield) as a yellow solid. m/z (ESI): 217.1 $(M+H)^+$. $^1H$ NMR: (400 MHz. $CDCl_3$) δ ppm 2.98-2.93 (m, 1H), 2.73 (t, J=6.0 Hz, 2H), 2.03-1.91 (m, 2H), 1.82-1.77 (m, 1H), 1.66-1.59 (m, 1H), 1.37 (d, J=7.2 Hz, 3H).

Step 1: methyl 4,4-dimethyl-2-oxocyclohexanes-1-carboxylate

To a solution of 3,3-dimethylcyclohexan-1-one (25.0 g, 198 mmol, Combi-Blocks) and dimethyl carbonate (44.6 g, 495 mmol) in THF (250 mL) at 0° C. was added NaH (19.81 g, 495 mmol) portionwise and allowed to warm room temperature. The reaction was then heated to reflux for 16 h. The reaction was poured into ice-cold aqueous saturated $NH_4Cl$ and extracted with EtOAc. The combined organic extracts were washed with brine, separated, dried over $Na_2SO_4$, and concentrated under reduced pressure to obtain

TABLE 17

Intermediates 10-12 were prepared following the procedure described for Intermediate 9, Steps 1-3, above as follows:

| Int.# | Chemical Structure | Name | LC/MS $(ESI^+)$ m/z | Conditions | Reagent |
|---|---|---|---|---|---|
| 10 | 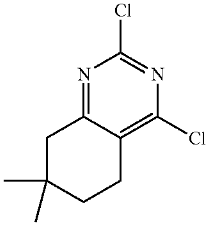 | 2,4-Dichloro-7,7-dimethyl-5,6,7,8-tetrahydroquinazoline | 232.9 | See below for alternate Step 1 for intermediate 10 | Step 1: 3,3-dimethylcyclohexan-1-one (Combi-Blocks) |
| 11 | 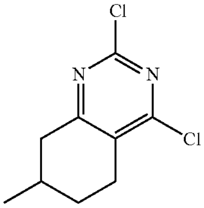 | 2,4-dichloro-7-methyl-5,6,7,8-tetrahydroquinazoline | 217.1 | Omit Step 1 | Step 2: Ethyl 4-methyl-2-oxocyclohexanes-1-carboxylate (CAS: 13537-82-1, Chemto, China). |
| 12 | 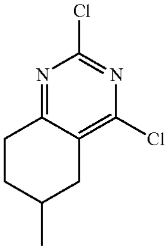 | 2,4-Dichloro-6-methyl-5,6,7,8-tetrahydroquinazoline | 216.9 | See below for alternate Step 1 for intermediate 12 | Step 1: 4-methylcyclohexan-1-one (CAS 589-92-4, Combi-Blocks). |

Alternative Step 1 (for Intermediate 10 and Intermediate 12): methyl 4,4-dimethyl-2-oxocyclohexanes-1-carboxylate

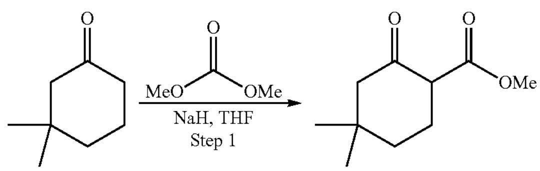

methyl 4,4-dimethyl-2-oxocyclohexanes-1-carboxylate (36.5 g, 100% yield) as a pale yellow liquid, which was used in next step without purification. m/z (ESI): 185.1 $(M+H)^+$.

Intermediate 13: 2,4-dichloro-8-methyl-7,8-dihydro-6H-pyrimido[5,4-b][1,4]oxazine

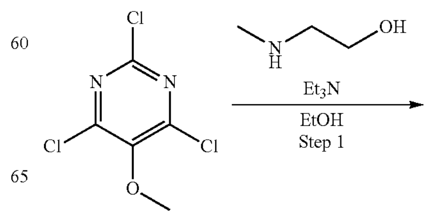

-continued

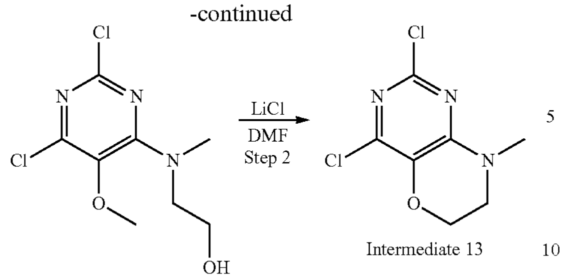

Intermediate 13

-continued

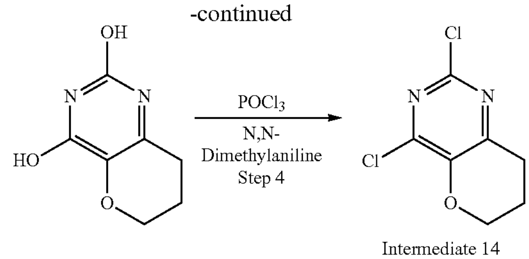

Intermediate 14

Step 1: 2-((2,6-dichloro-5-methoxypyrimidin-4-yl)(methyl)amino)ethan-1-ol

To a solution of 2,4,6-trichloro-5-methoxypyrimidine (4.5 g, 21.08 mmol, Sozhou Sibian) in EtOH (75 mL) were added $Et_3N$ (7.35 mL, 52.7 mmol) and 2-(methylamino)ethan-1-ol (1.900 g, 25.3 mmol, Sigma-Aldrich) and the reaction mixture was stirred at room temperature for 16 h. The reaction mixture was quenched with ice-cold water and extracted with EtOAc. The organic extracts were washed with brine, separated, dried over $Na_2SO_4$, and concentrated in vacuo. The residue was purified on a Redi-Sep pre-packed silica gel column (100 g), eluting with 25-35% EtOAc in hexanes to provide 2-((2,6-dichloro-5-methoxypyrimidin-4-yl)(methyl)amino)ethan-1-ol (5.2 g, 98% yield) as a clear viscous oil. $^1H$ NMR (400 MHz, DMSO-$d_6$) δ ppm 4.82 (t, J=5.4 Hz, 1H), 3.72 (t, J=5.7 Hz, 2H), 3.69 (s, 3H), 3.60 (q, J=5.6 Hz, 2H), 3.22 (s, 3H). m/z (ESI): 252.0 $(M+H)^+$.

Step 2: 2,4-dichloro-8-methyl-7,8-dihydro-6H-pyrimido[5,4-b][1,4]oxazine

A solution of 2-((2,6-dichloro-5-methoxypyrimidin-4-yl)(methyl)amino)ethan-1-ol (3.0 g, 11.90 mmol) and LiCl (1.412 g, 33.32 mmol, Avra) in DMF (28 mL) was irradiated in a microwave at 160° C. for 5 h. The reaction mixture was poured on crushed ice. The precipitated solid was filtered, washed with water, and dried to afford 2,4-dichloro-8-methyl-7,8-dihydro-6H-pyrimido[5,4-b][1,4]oxazine as a pale yellow solid (1.48 g, 56% yield). $^1H$ NMR (400 MHz, DMSO-$d_6$) δ ppm 4.29 (dd, J=5.1, 4.1 Hz, 2H), 3.57-3.64 (m, 2H), 3.10 (s, 3H). m/z (ESI): 219.9 $(M+H)^+$.

Intermediate 14: 2,4-dichloro-7,8-dihydro-6H-pyrano[3,2-d]pyrimidine

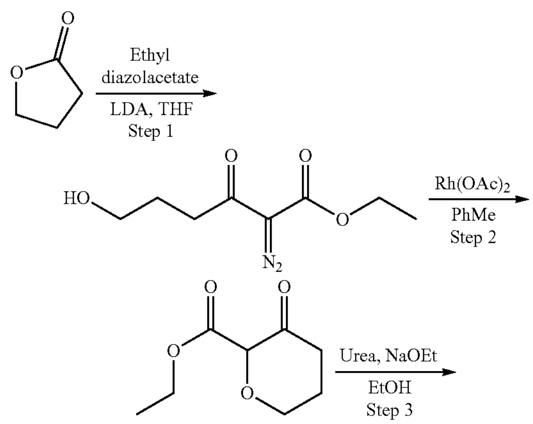

Step 1: ethyl 2-diazo-6-hydroxy-3-oxohexanoate

To a solution of ethyl 2-diazoacetate (6.75 mL, 63.9 mmol, TCI), dihydrofuran-2(3H)-one (4.42 mL, 58.1 mmol, Chempure) and THF (75 mL) at −78° C. was added a freshly prepared solution of LDA (65.8 mL, 99 mmol, 1.5M in THF) dropwise. The solution was stirred at −78° C. for 30 min, before AcOH (21.94 mL, 383 mmol) was added dropwise to the reaction mixture at −78° C. The reaction mixture was diluted with ice-cold water and extracted with EtOAc. The organic extracts were washed with brine, dried over $Na_2SO_4$, and concentrated under reduced pressure. The residue was purified on a Redi-Sep pre-packed silica gel column eluting with a gradient of 20-30% EtOAc in PE to provide ethyl 2-diazo-6-hydroxy-3-oxohexanoate (2.0 g, 17% yield) as a brown liquid. $^1H$ NMR (400 MHz, $CDCl_3$) δ ppm 4.14-4.53 (m, 2H), 3.70 (t, J=6.1 Hz, 2H), 3.00 (t, J=7.0 Hz, 2H), 1.94 (m, 2H), 1.27-1.45 (m, 3H).

Step 2: ethyl 3-oxotetrahydro-2H-pyran-2-carboxylate

To a suspension of rhodium(II) acetate dimer (0.088 g, 0.200 mmol) in toluene (30 mL) was added a solution of ethyl 2-diazo-6-hydroxy-3-oxohexanoate (2.0 g, 9.99 mmol) in toluene (30 mL) over 90 min at 90° C. The mixture was then stirred at 90° C. for 30 min. before it was concentrated under reduced pressure and the residue was purified on a Redi-Sep pre-packed silica gel column (40 g), eluting with a gradient of 10% EtOAc in PE to provide ethyl 3-oxotetrahydro-2H-pyran-2-carboxylate (700 mg, 41% yield) as a pale yellow liquid. $^1H$ NMR (400 MHz, $CDCl_3$) δ ppm 4.18-4.48 (m, 2H), 3.78-4.04 (m, 2H), 2.40 (t, J=6.7 Hz, 2H), 1.87-2.01 (m, 2H), 1.13-1.51 (m, 3H).

Step 3: 7,8-dihydro-6H-pyrano[3,2-d]pyrimidine-2,4-diol

To a solution of ethyl 3-oxotetrahydro-2H-pyran-2-carboxylate (5.0 g, 29.0 mmol) in EtOH (50 mL) were added urea (1.74 g, 29.0 mmol, Avra) and sodium ethoxide (14.52 mL, 43.6 mmol, 21% solution in EtOH, Symax) and the reaction mixture was heated at 80° C. for 16 h. Then the reaction mixture was concentrated under reduced pressure and the residue was purified by reverse-phase column chromatography eluting with a gradient of 0-10% MeCN in $H_2O$ to provide 7,8-dihydro-1H-pyrano[3,2-d]pyrimidine-2,4(3H,6H)-dione (4.7 g, 96% yield) as a light brown solid. $^1H$ NMR (400 MHz, $D_2O$) δ ppm 3.81-3.50 (m, 2H), 2.20-2.24 (m, 2H), 1.65-1.71 (m, 2H). m/z (ESI): 169.1 $(M+H)^+$.

Step 4: 2,4-dichloro-7,8-dihydro-6H-pyrano[3,2-d]pyrimidine

A solution of 7,8-dihydro-1H-pyrano[3,2-d]pyrimidine-2,4(3H,6H)-dione (500 mg, 2.97 mmol) and N,N-dimethylaniline (360 mg, 2.97 mmol) in $POCl_3$ (10 mL, 107 mmol) was heated at 80° C. for 16 h. Then the reaction mixture was concentrated under reduced pressure and the residue was purified on a Redi-Sep pre-packed silica gel column, eluting with a gradient of 25-30% EtOAc in PE to provide 2,4-dichloro-7,8-dihydro-6H-pyrano[3,2-d]pyrimidine (150 mg, 25% yield) as pale yellow liquid. m/z (ESI): 206.9 $(M+H)^+$.

Intermediate 15: 4-chloro-2-(methylthio)-5,6,7,8-tetrahydropyrido[2,3-d]pyrimidine

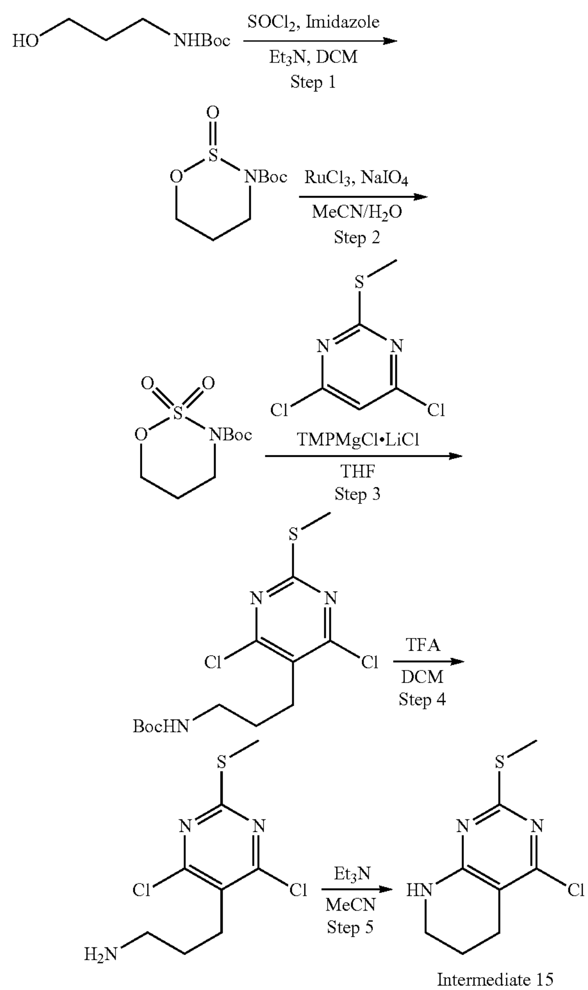

Step 1: tert-butyl 1,2,3-oxathiazinane-3-carboxylate 2-oxide

To a stirred solution of tert-butyl (3-hydroxypropyl)carbamate (15.0 g, 86 mmol, Combi-Blocks) in DCM (400 mL) was added imidazole (29.1 g, 428 mmol) and $Et_3N$ (52.5 mL, 377 mmol) at −60° C. The resulting suspension was stirred for 5 min before thionyl chloride (13.7 mL, 188 mmol) was added dropwise over a period of 30 min at −60° C. The reaction mixture was stirred at same temperature for 4 h and later at room temperature for 16 h. The reaction mixture was quenched with ice-cold water and extracted with DCM. The organic extracts were washed with brine, separated, dried over $Na_2SO_4$, and concentrated in vacuo to give tert-butyl 1,2,3-oxathiazinane-3-carboxylate 2-oxide (18.5 g, 98% yield) as a light-yellow liquid, which was taken to the next step without purification.

Step 2: tert-butyl 1,2,3-oxathiazinane-3-carboxylate 2,2-dioxide

To a stirred suspension of tert-butyl 1,2,3-oxathiazinane-3-carboxylate 2-oxide (18.5 g, 84 mmol) in MeCN (185 mL) and water (92.5 mL) was added ruthenium (III) chloride hydrate (0.094 g, 0.418 mmol, Chempure) followed by $NaIO_4$ (22.35 g, 105 mmol, Chempure) portionwise at −10° C. over a period of 5 min. The reaction mixture was slowly allowed to warm to room temperature and stirred for 3 h. The reaction mixture was quenched with ice-cold water and extracted with $Et_2O$. The organic extracts were washed with brine solution, separated, dried over $Na_2SO_4$, and concentrated under reduced pressure. The residue was purified on silica gel eluting with 15-20% EtOAc in hexanes to give tert-butyl 1,2,3-oxathiazinane-3-carboxylate 2,2-dioxide (14.5 g, 73% yield) as an off-white solid. $^1H$ NMR (400 MHz, $CDCl_3$) δ ppm 4.69 (t, J=6.0 Hz, 2H), 3.99-4.07 (m, 2H), 2.11 (m, 2H), 1.55 (s, 9H).

Step 3: tert-butyl (3-(4,6-dichloro-2-(methylthio)pyrimidin-5-yl)propyl)carbamate To a stirred solution of 4,6-dichloro-2-(methylthio)pyrimidine (8.0 g, 41.0 mmol) in THF (150 mL) was added 2,2,6,6-tetramethylpiperidinylmagnesium chloride lithium chloride complex solution (82 mL, 82 mmol, Symax Ltd.) at room temperature and stirred for 30 min. Then tert-butyl 1,2,3-oxathiazinane-3-carboxylate 2,2-dioxide (14.4 g, 60.7 mmol) was added portion wise. The reaction was stirred for 5 h before it was quenched with a 1N citric acid solution and extracted with EtOAc. The organic extracts were washed with brine, separated, dried over $Na_2SO_4$, and concentrated under reduced pressure to provide tert-butyl (3-(4,6-dichloro-2-(methylthio)pyrimidin-5-yl)propyl)carbamate (18.0 g, 90% yield) as a yellow solid, which was taken to the next step without purification. m/z (ESI): 296.0 $(M\text{-tbutyl})^+$.

Step 4: 3-(4,6-dichloro-2-(methylthio)pyrimidin-5-yl)propan-1-amine

To a solution of tert-butyl (3-(4,6-dichloro-2-(methylthio)pyrimidin-5-yl)propyl)carbamate (18.0 g, 37.0 mmol) in DCM (80 mL) was added TFA (80 mL, 1038 mmol) at 0° C. drop wise. The resulting reaction was stirred for 3 h at rt before it was concentrated under reduced pressure and triturated with toluene to provide the 3-(4,6-dichloro-2-(methylthio)pyrimidin-5-yl)propan-1-amine (9.2 g, 98% yield) as a brown viscous liquid, which was directly taken for next step without purification.

Step 5: 4-chloro-2-(methylthio)-5,6,7,8-tetrahydropyrido[2,3-d]pyrimidine

To a solution of 3-(4,6-dichloro-2-(methylthio)pyrimidin-5-yl)propan-1-amine (9.2 g, 36.5 mmol) in MeCN (460 mL) was added $Et_3N$ (25.4 mL, 182 mmol) drop wise at 0° C. The resulting mixture was stirred for 16 h at 80° C. The reaction was diluted with water and extracted with EtOAc. The organic extracts were washed with brine, separated, dried over $Na_2SO_4$, filtered, and concentrated under reduced pressure. The residue was purified on silica gel eluting with 15-20% EtOAc in petroleum ether to give 4-chloro-2-

(methylthio)-5,6,7,8-tetrahydropyrido[2,3-d]pyrimidine (5.0 g, 64% yield) as a light yellow solid. $^1$H NMR (400 MHz, DMSO-$d_6$) δ ppm 7.89 (s, 1H), 3.20-3.28 (m, 2H), 2.57 (t, J=6.3 Hz, 2H), 2.38 (s, 3H), 1.73-1.83 (m, 2H). m/z (ESI): 216.1 $(M+H)^+$.

Intermediate 16: 2,4-dichloro-7-methylpyrido[3,2-d]pyrimidine

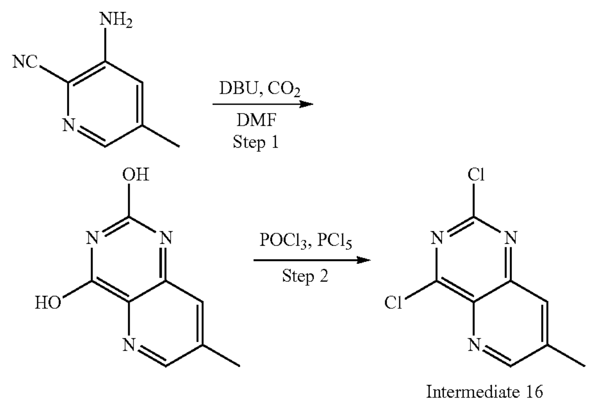

Intermediate 16

Step 1: 7-methylpyrido[3,2-d]pyrimidine-2,4-diol

To a degassed solution of 3-amino-5-methylpicolinonitrile (10.0 g, 75.0 mmol, Arbor) in DMF (100 mL) was added DBU (11.32 mL, 75 mmol, Spectrochem) at room temperature. The reaction mixture was stirred under a $CO_2$ atmosphere at 105° C. for 5 h and at room temperature for 12 h. The reaction was cooled to 0° C. and acidified with 1.5 N HCl. The precipitated solids were filtered, washed with EtOAc, and dried under vacuum to give 7-methylpyrido[3,2-d]pyrimidine-2,4-diol (7.6 g, 57% yield) as an off-white solid, which was taken to the next step without purification. $^1$H NMR (400 MHz, DMSO-$d_6$) δ ppm 11.40 (s, 1H), 11.17 (s, 1H), 8.30 (s, 1H), 7.33 (s, 1H), 2.37 (s, 3H). m/z (ESI): 178.0 $(M+H)^+$.

Step 2: 2,4-dichloro-7-methylpyrido[3,2-d]pyrimidine

To a solution of 7-methylpyrido[3,2-d]pyrimidine-2,4-diol (4.0 g, 22.58 mmol) in $POCl_3$ (40.0 mL, 429 mmol) was added $PCI_5$ (18.81 g, 90 mmol) and the reaction mixture was stirred at 135° C. for 15 h. The reaction was concentrated in vacuo and the residue was diluted with DCM. Then ice-cold water was added to the resulting solution and extracted with DCM. The combined organic extracts were washed with brine, dried over $Na_2SO_4$, and concentrated in vacuo. The residue was purified on a Redi-Sep pre-packed silica gel column (120 g) eluting with a gradient of 30-50% EtOAc in hexanes to provide 2,4-dichloro-7-methylpyrido[3,2-d]pyrimidine (1.7 g, 35% yield) as an off-white solid. $^1$H NMR (400 MHz, DMSO-$d_6$) δ ppm 9.07 (d, J=1.6 Hz, 1H), 8.27 (d, J=1.6 Hz, 1H), 2.61 (s, 3H). m/z (ESI): 215.9 $(M+H)^+$.

Intermediate 17: 6-bromo-8-iodoimidazo[1,2-a]pyridine-7-carbonitrile

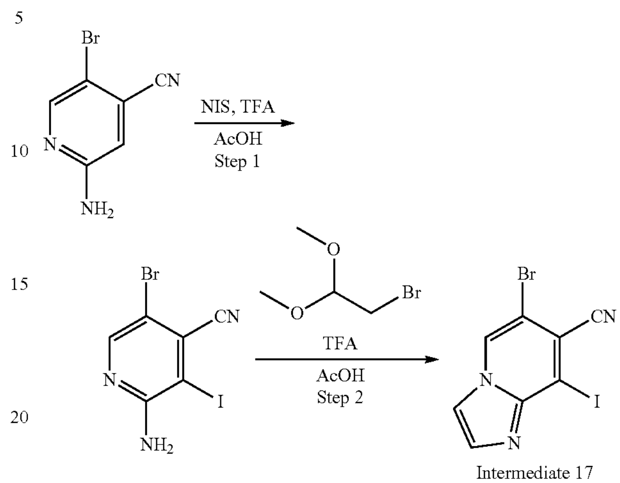

Intermediate 17

Step 1: 2-amino-5-bromo-3-iodoisonicotinonitrile

To the mixture of 2-amino-5-bromoisonicotinonitrile (1.0 g, 6.54 mmol) dissolved in AcOH (10 mL) was added TFA (1 mL, 13.02 mmol) and NIS (1.47 g, 7.189 mmol). The mixture was allowed to stir at 60° C. for 2 h. Upon completion, the mixture was cooled to 0° C. and filtered to provide 2-amino-5-bromo-3-iodoisonicotinonitrile (1.1 g, 3.94 mmol, 60% yield) as a green solid. $^1$H NMR (400 MHz, DMSO-$d_6$) δ ppm: δ 8.25 (s, 1H), 6.89 (s, 2H). m/z (ESI): 324.0 $(M+H)^+$.

Step 2: 6-bromo-8-iodoimidazo[1,2-a]pyridine-7-carbonitrile

To a solution of 2-amino-5-bromo-3-iodoisonicotinonitrile (1.1 g, 3.94 mmol) in AcOH (10 mL) and TFA (1 mL) was added 2-bromo-1,1-dimethoxyethane (1.33 g, 7.88 mmol). The mixture was stirred at 60° C. for 16 h. Upon completion, the mixture was cooled to 0° C. and filtered to give 6-bromo-8-iodoimidazo[1,2-a]pyridine-7-carbonitrile (800 mg, 58% yield) as a green solid, which was used in the next step as is. $^1$H NMR (400 MHz, DMSO-$d_6$) δ ppm: δ 9.19 (s, 1H), 8.29 (s, 1H), 7.97 (m, 1H). m/z (ESI): 348.0 $(M+H)^+$.

Intermediate 18: 1-bromo-3-chloro-2-naphthonitrile

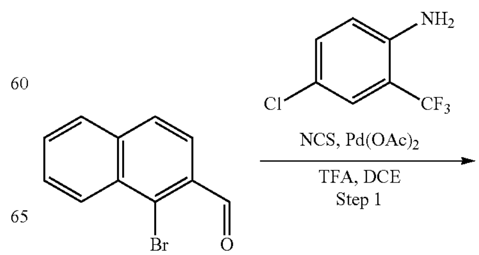

-continued

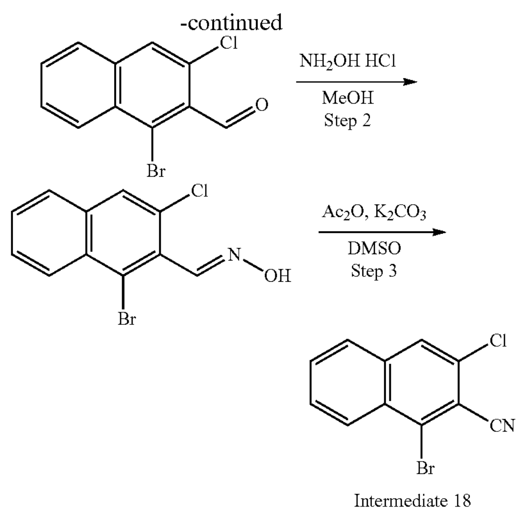

Intermediate 18

Step 1: 1-bromo-3-chloro-2-naphthaldehyde

A solution of NCS (1.36 g, 10.21 mmol, ADAMAS), $Pd(OAc)_2$ (0.478 g, 2.127 mmol, Aopudishi), 1-bromo-2-naphthaldehyde (2.0 g, 8.51 mmol, ADAMAS), and 4-chloro-2-(trifluoromethyl)aniline (0.832 g, 4.25 mmol, ADAMAS) in TFA (2 mL) and DCE (10 mL) was stirred at 60° C. for 24 h. Upon completion, the reaction was diluted with DCM and water. The aqueous phase was extracted with DCM (50 mL×2). The organic phase was washed with brine, dried over $Na_2SO_4$ and concentrated in vacuum to give crude product, which was purified by silica gel flash chromatography (EtOAc:PE=1:10, v/v) to afford the title compound (1.80 g, 78% yield) as a yellow solid.

Step 2: (E)-1-bromo-3-chloro-2-naphthaldehyde oxime

A mixture of hydroxylamine hydrochloride (0.696 g, 10.02 mmol), sodium acetate (0.882 g, 13.36 mmol) and 1-bromo-3-chloro-2-naphthaldehyde (1.8 g, 6.68 mmol) in water (6.0 mL) and MeOH (20 mL). The mixture was stirred for 1 h at room temperature, then diluted with water. The solution was extracted with DCM (3×). The combined organic extracts were dried over $Na_2SO_4$ and concentrated in vacuo to provide the title compound (1.50 g, 79% yield) as a yellow solid. m/z (ESI): 285.9 $(M+H)^+$.

Step 3: 1-bromo-3-chloro-2-naphthonitrile

To a solution of (E)-1-bromo-3-chloro-2-naphthaldehyde oxime (1.5 g, 5.27 mmol) and DMSO (20 mL) was added $K_2CO_3$ (1.457 g, 10.54 mmol) and $Ac_2O$ (1.076 g, 10.54 mmol). The resulting mixture was stirred at 50° C. for 0.5 h, the reaction was diluted with water. The solution was extracted with DCM (3×). The combined organic extracts were dried over $Na_2SO_4$ and concentrated in vacuo. The crude material was purified by silica gel flash chromatography (EtOAc:petroluem ether=1:5, v/v) to afford (902 mg, 64% yield) as a white solid. $^1H$ NMR (400 MHz, $CDCl_3$) δ ppm 8.30-8.27 (m, 1H), 7.95 (s, 1H), 6.82-7.80 (m, 1H), 7.73-7.70 (m, 2H).

Intermediate 19: 6-bromo-8-iodo-3-methylimidazo[1,2-a]pyridine-7-carbonitrile

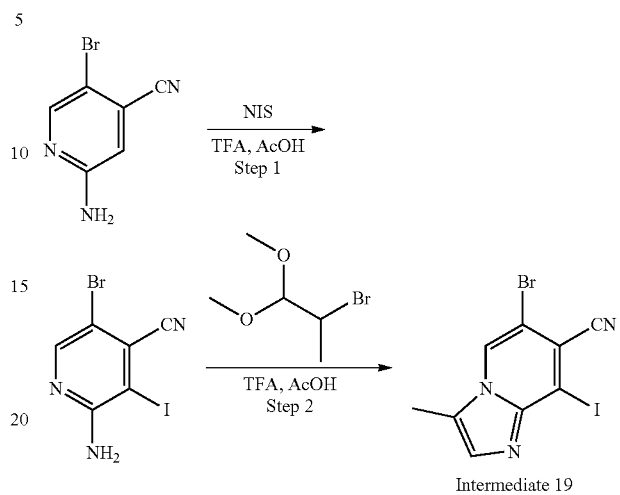

Intermediate 19

Step 1: 2-amino-5-bromo-3-iodoisonicotinonitrile

To a 50-mL round-bottomed flask was added 2-amino-5-bromoisonicotinonitrile (2.0 g, 10.1 mmol) and TFA (2.30 g, 20.2 mmol) in AcOH (20 mL). To the mixture was added NIS (2.50 g, 11.1 mmol). The reaction was stirred at 60° C. for 2.5 h. The reaction mixture was cooled to 0° C. and the precipitate filtered off. After filtration, the solid was diluted with water (50 mL) and extracted with DCM (1×100 mL). The organic extract was concentrated to afford 2-amino-5-bromo-3-iodoisonicotinonitrile (1.9 g, 5.87 mmol, 58% yield) as a tan solid. m/z: 325.8 $(M+H)^+$.

Step 2: 6-bromo-8-iodo-3-methylimidazo[1,2-a]pyridine-7-carbonitrile

A glass microwave reaction vessel was charged with 2-amino-5-bromo-3-iodoisonicotinonitrile (1.0 g, 3.09 mmol), TFA (0.605 g, 6.17 mmol) and AcOH (10 mL). To the mixture was added 2-bromo-1,1-dimethoxypropane (1.13 g, 6.17 mmol) and the reaction mixture was stirred at 80° C. for 6 h. The mixture was cooled to 0° C. and the solid formed was filtered to afford 6-bromo-8-iodo-3-methylimidazo[1,2-a]pyridine-7-carbonitrile (980 mg, 2.71 mmol, 88% yield) as a tan solid. m/z: 361.9 $(M+H)^+$.

Intermediate 20: 4-chloro-3-cyano-7,7-dimethyl-7,8-dihydro-5H-pyrano[4,3-b]pyridin-2-yl trifluoromethanesulfonate

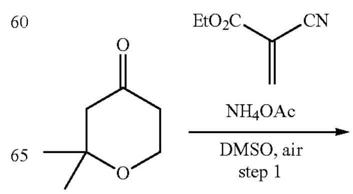

-continued

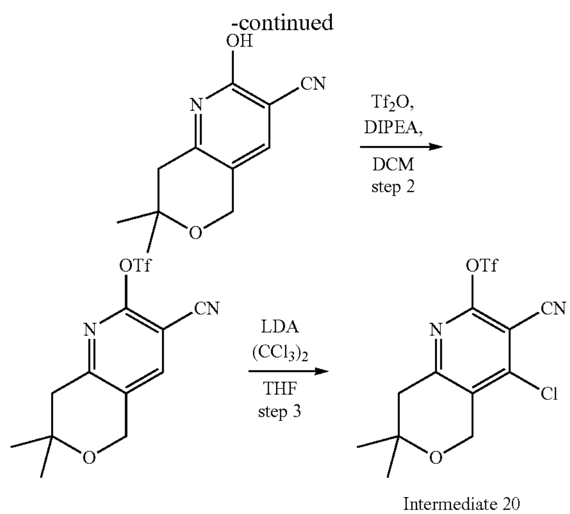

Intermediate 20

Step 1: 2-hydroxy-7,7-dimethyl-7,8-dihydro-5H-pyrano[4,3-b]pyridine-3-carbonitrile To a RBF was added ethyl 2-cyanoacrylate (4.88 g, 39.0 mmol, Combi-Blocks), 2,2-dimethyloxan-4-one (5.19 mL, 39.0 mmol, PharmaBlock) and ammonium acetate (15.04 g, 195 mmol, Sigma-Aldrich) in DMSO (39.0 mL). The reaction was heated to 80° C. open to air over the weekend. After 3 d, the reaction was diluted with aqueous saturated $NH_4Cl$ (30 mL), water (10 mL) and extracted with EtOAc (3×30 mL). The organic extracts were concentrated in vacuo and redissolved in EtOAc (about 20 mL). The desired product precipitated out as an off-white solid and was collected by vacuum filtration. The mother liquor was concentrated and the procedure repeated until no more solid crushed out. 2-hydroxy-7,7-dimethyl-7,8-dihydro-5H-pyrano[4,3-b]pyridine-3-carbonitrile (4.2 g, 52.7% yield) was obtained as an off-white solid. m/z (ESI): 205.3 $(M+H)^+$.

Step 2: 3-cyano-7,7-dimethyl-7,8-dihydro-5H-pyrano[4,3-b]pyridin-2-yl trifluoromethanesulfonate To a 0° C. solution of 2-hydroxy-7,7-dimethyl-7,8-dihydro-5H-pyrano[4,3-b]pyridine-3-carbonitrile (4.2 g, 20.57 mmol), DIPEA (10.78 mL, 61.7 mmol, Sigma-Aldrich) and DCM (68.6 mL) was added trifluoromethanesulfonic anhydride (1M in DCM, 24.68 mL, 24.68 mmol, Sigma-Aldrich). After 5 min, the ice-bath was removed and the reaction was left stirring at room temperature. After 15 min, LCMS showed full conversion to the desired triflate. The reaction was concentrated to give the crude 3-cyano-7,7-dimethyl-7,8-dihydro-5H-pyrano[4,3-b]pyridin-2-yl trifluoromethanesulfonate as dark solid, that was used in the next step with no further purification. m/z (ESI): 337.0 $(M+H)^+$.

Step 3: 4-chloro-3-cyano-7,7-dimethyl-7,8-dihydro-5H-pyrano[4,3-b]pyridin-2-yl trifluoromethanesulfonate To a −78° C. solution of 3-cyano-7,7-dimethyl-7,8-dihydro-5H-pyrano[4,3-b]pyridin-2-yl trifluoromethanesulfonate (207 mg, 0.616 mmol), hexachloroethane (146 mg, 0.616 mmol, Combi-Blocks), and THF (5 mL) was added LDA (1M in THF/hexanes, 0.923 mL, 0.923 mmol, Sigma-Aldrich) in a dropwise fashion. After 5 min, additional LDA (0.5 mL) was added. The reaction was quenched with aqueous saturated $NH_4Cl$ and partitioned between EtOAc and water. The aqueous layer was extracted with EtOAc (3×10 mL). The combined organic extracts were washed with brine and concentrated in vacuo to give crude 4-chloro-3-cyano-7,7-dimethyl-7,8-dihydro-5H-pyrano[4,3-b]pyridin-2-yl trifluoromethanesulfonate (265 mg, quantitative yield) as a brown solid. m/z (ESI): 371.1 $(M+H)^+$. The material was carried forward as is.

Intermediate 21: (6R,8R)-4-chloro-3-cyano-7,7-dimethyl-5,6,7,8-tetrahydro-6,8-methanoquinolin-2-yl trifluoromethanesulfonate

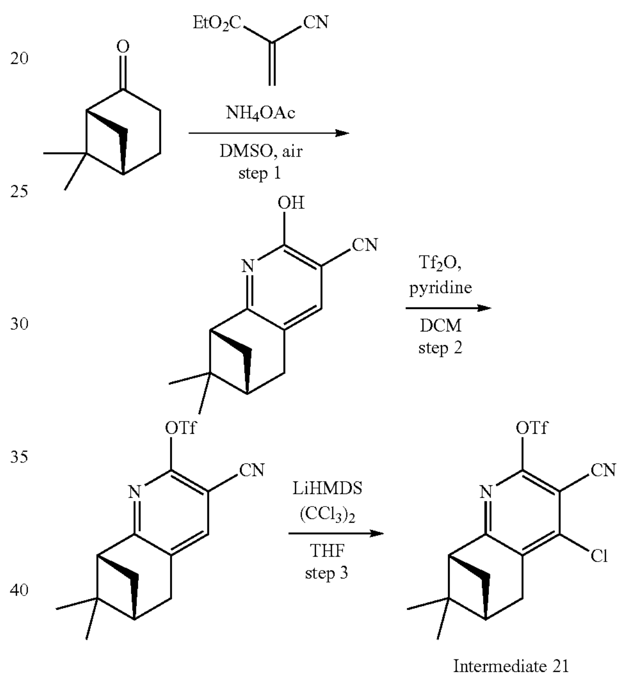

Intermediate 21

This intermediate can be synthesized in an analogous manner to intermediate 20, using (1R)-(+)-nopinone (Sigma-Aldrich).

Intermediate 22: 2,4-dichloro-3,7,7-trimethyl-5,8-dihydropyrano[4,3-b]pyridine

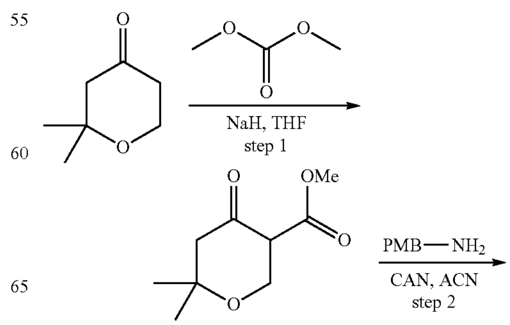

-continued

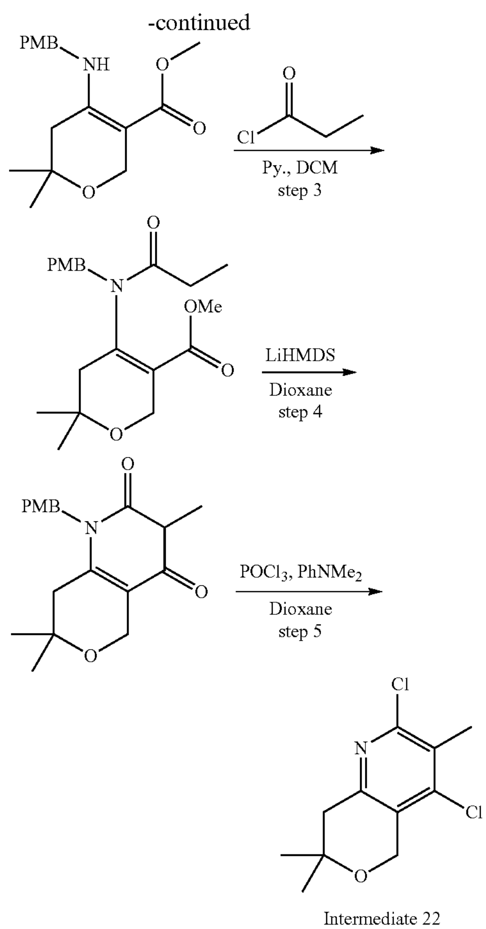

Intermediate 22

Step 1: methyl 4-hydroxy-6,6-dimethyl-2,5-dihydropyran-3-carboxylate

To a solution of NaH (36.00 g, 900.09 mmol, 60% wt %) in THF (1 L) was added 2,2-dimethyltetrahydropyran-4-one (100 g, 780.22 mmol, Bide Pharmatech) at 15° C. The mixture was stirred at 15° C. for 0.5 h and dimethyl carbonate (164.21 mL, 1.95 mol) was added dropwise. The mixture was stirred at 70° C. for 0.5 h. TLC indicated the starting material was consumed completely and a new spot formed. The reaction mixture was quenched by $H_2O$ (2 L) at 15° C., and HCl (2M) was added until pH=4. The mixture was extracted with EtOAc (1 L×4). The combined organic extracts were dried over $Na_2SO_4$, filtered and concentrated under reduced pressure to give methyl 4-hydroxy-6,6-dimethyl-2,5-dihydropyran-3-carboxylate (103 g, crude) as yellow oil which was used without further purification.

Step 2: methyl 4-[(4-methoxyphenyl)methylamino]-6,6-dimethyl-2,5-dihydropyran-3-carboxylate To a solution of methyl 4-hydroxy-6,6-dimethyl-2,5-dihydropyran-3-carboxylate (103 g, 553.16 mmol) and (4-methoxyphenyl)methanamine (93.06 mL, 719.10 mmol) in ACN (1 L) was added CAN (15.16 g, 27.66 mmol) at 0° C. The mixture was stirred at 70° C. for 6 h. The reaction mixture was concentrated under reduced pressure to give a residue, which was purified by column chromatography ($SiO_2$, Petroleum ether/EtOAc=20:1 to 15:1) to provide methyl 4-[(4-methoxyphenyl)methylamino]-6,6-dimethyl-2,5-dihydropyran-3-carboxylate (100 g, 59.2% yield) as a yellow solid. $^1H$ NMR (400 MHz, $CDCl_3$) δ ppm 9.00 (s, 1H), 7.17 (d, J=8.80 Hz, 2H), 6.88 (d, J=8.40 Hz, 2H), 4.32-4.35 (m, 4H), 3.80 (s, 3H), 3.68 (s, 3H), 2.22 (s, 2H), 1.23 (s, 6H).

Step 3: methyl 4-[(4-methoxyphenyl)methyl-propanoyl-amino]-6,6-dimethyl-2,5-dihydropyran-3-carboxylate To a solution of methyl 4-[(4-methoxyphenyl)methylamino]-6,6-dimethyl-2,5-dihydropyran-3-carboxylate (50 g, 163.74 mmol) in DCM (1 L) was added pyridine (13.22 mL, 163.74 mmol) in DCM (50 mL) and propionyl chloride (15.15 mL, 163.74 mmol) in DCM (50 mL) at 0° C. The mixture was stirred at 15° C. for 12 h. The reaction mixture was diluted with $H_2O$ (1 L) and extracted with DCM (3×1 L). The combined organic layers were dried over $Na_2SO_4$, and concentrated under reduced pressure to give a residue which was purified by column chromatography ($SiO_2$, 5-100% EtOAc in Petroleum ether) to provide methyl 4-[(4-methoxyphenyl)methyl-propanoyl-amino]-6,6-dimethyl-2,5-dihydropyran-3-carboxylate (50 g, 66.7% yield) as a yellow oil. m/z (ESI): 362.2 $[M+H]^+$.

Step 4: 1-[(4-methoxyphenyl)methyl]-3,7,7-trimethyl-5,8-dihydropyrano[4,3-b]pyridine-2,4-dione To a solution of methyl 4-[(4-methoxyphenyl)methyl-propanoyl-amino]-6,6-dimethyl-2,5-dihydropyran-3-carboxylate (59 g, 163.24 mmol) in dioxane (600 mL) at 0° C. was added LiHMDS (1 M, 326.48 mL). The mixture was stirred at 0° C. for 1 h. The reaction mixture was quenched by $H_2O$ (1 L) and extracted with EtOAc (1 L). The aqueous phase was treated with HCl (2M) until pH=4. The mixture was extracted with EtOAc (4×500 mL). The combined organic layers were concentrated under reduced pressure to give a residue which was washed with petroleum ether/EtOAc=10:1 (100 mL) to provide 1-[(4-methoxyphenyl)methyl]-3,7,7-trimethyl-5,8-dihydropyrano[4,3-b]pyridine-2,4-dione (16 g, 14.88% yield) as a white solid. m/z (ESI): 330.1 $[M+H]^+$. $^1H$ NMR (400 MHz, $CDCl_3$) δ ppm 7.01 (d, J=8.80 Hz, 2H), 6.82 (d, J=8.40 Hz, 2H), 5.23 (s, 2H), 4.58 (s, 2H), 3.77 (s, 3H), 2.46 (s, 2H), 2.06 (s, 3H), 1.21 (s, 6 Hs).

Step 5: 2,4-dichloro-3,7,7-trimethyl-5,8-dihydropyrano[4,3-b]pyridine

To a solution of $POCl_3$ (28.21 mL, 303.59 mmol) in dioxane (100 mL) was added N,N-dimethylaniline (11.54 mL, 91.08 mmol) and 1-[(4-methoxyphenyl)methyl]-3,7,7-trimethyl-5,8-dihydropyrano[4,3-b]pyridine-2,4-dione (10 g, 30.36 mmol). The mixture was stirred at 80° C. for 16 h. The reaction mixture was concentrated under reduced pressure. The residue was diluted with $H_2O$ (300 mL) and extracted with EtOAc (3×200 mL). The combined organic layers were dried over $Na_2SO_4$, filtered and concentrated under reduced pressure. The residue was purified by column chromatography ($SiO_2$, Petroleum ether/EtOAc=1:0 to 50:1) to provide 2,4-dichloro-3,7,7-trimethyl-5,8-dihydropyrano[4,3-b]pyridine (4 g, 15.76 mmol, 51.92% yield) was obtained as a white solid. m/z (ESI): 246.0 $[M+H]^+$. $^1H$ NMR (400 MHz, $CDCl_3$) δ ppm 4.72 (s, 2H), 2.81 (s, 2H), 2.46 (s, 3H), 1.31 (s, 6H).

Intermediate 23: (1R,9R)-4,6-dichloro-5,10,10-trimethyl-3-azatricyclo[7.1.1.0$^{2,7}$]undeca-2,4,6-triene

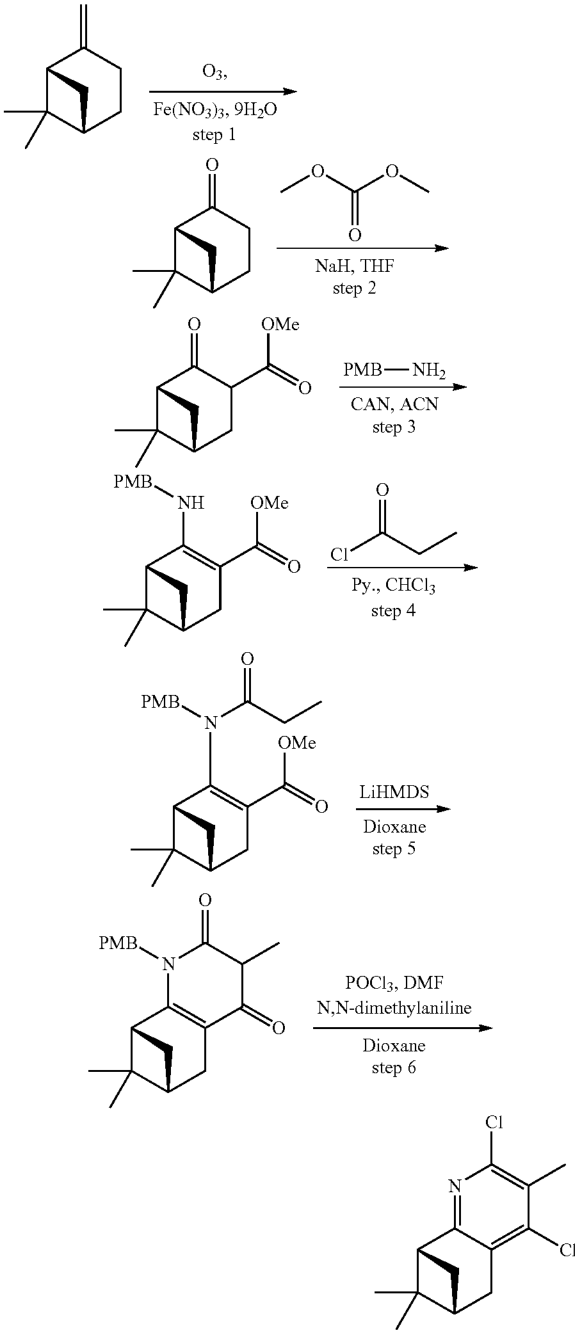

Intermediate 23

Step 1: (1R,5S)-6,6-dimethylnorpinan-2-one

Ozone was bubbled into a solution of (1S,5S)-6,6-dimethyl-2-methylene-norpinane (100 g, 734.03 mmol, Energy Chemical) in MeOH (1010 mL) at −40° C. for 6 h. After excess 03 was purged by $N_2$, $Fe(NO_3)_3\cdot 9H_2O$ (296.55 g, 734.03 mmol) was added to the mixture at 15° C., and stirred for 0.5 h. The reaction mixture was concentrated under reduced pressure to remove MeOH, and then diluted with $H_2O$ (2 L) and extracted with EtOAc (3×1 L). The combined organic layers were dried over $Na_2SO_4$, filtered and concentrated under reduced pressure. The residue was purified by column chromatography ($SiO_2$, Petroleum ether/EtOAc=1/0 to 95/1) to provide (1R,5S)-6,6-dimethylnorpinan-2-one (140 g, crude) as a yellow oil. $^1H$ NMR (400 MHz, $CDCl_3$) δ ppm 2.48-2.53 (m, 3H), 2.33-2.35 (m, 1H), 2.21-2.22 (m, 1H), 1.95-2.13 (m, 1H), 1.80-1.90 (m, 1H), 1.56 (d, J=10.00 Hz, 1H), 1.31 (s, 3H), 0.83 (s, 3H).

Step 2: methyl (1R,5R)-6,6-dimethyl-2-oxo-norpinane-3-carboxylate

To a mixture of (1R,5S)-6,6-dimethylnorpinan-2-one (50 g, 361.78 mmol) and dimethyl carbonate (76.14 mL, 904.45 mmol) in THF (1 L) was added NaH (21.70 g, 542.67 mmol, 60 wt %) in portions at 0° C. under $N_2$. The mixture was stirred at 40° C. for 6 h. The reaction mixture was quenched with $H_2O$ (300 mL) at 0° C., and extracted with EtOAc (3×150 mL). The combined organic layers were dried over $Na_2SO_4$, filtered, and concentrated under reduced pressure. The residue was purified by column chromatography ($SiO_2$, petroleum ether/EtOAc=1/0 to 95/1) to provide methyl (1R,5R)-6,6-dimethyl-2-oxo-norpinane-3-carboxylate (90 g, crude) as a yellow oil. m/z (ESI): 197.2 $[M+H]^+$.

Step 3: methyl (1R,5R)-2-[(4-methoxyphenyl)methylamino]-6,6-dimethyl-bicyclo[3.1.1]hept-2-ene-3-carboxylate To a mixture of methyl (1R,5R)-6,6-dimethyl-2-oxo-norpinane-3-carboxylate (44 g, 224.21 mmol) and (4-methoxyphenyl)methanamine (37.72 mL, 291.48 mmol) in ACN (500 mL) was added CAN (5.59 mL, 11.21 mmol) at 0° C. under $N_2$. The mixture was stirred at 70° C. for 12 h. The reaction mixture was diluted with $H_2O$ (200 mL) and extracted with EtOAc (3×100 mL). The combined organic layers were dried over anhydrous $Na_2SO_4$, filtered, and concentrated under reduced pressure. The residue was purified by column chromatography ($SiO_2$. Petroleum ether/EtOAc=1/0 to 20/1) to provide methyl (1R,5R)-2-[(4-methoxyphenyl)methylamino]-6,6-dimethyl-bicyclo[3.1.1]hept-2-ene-3-carboxylate (25 g, crude) was obtained as yellow oil. m/z (ESI): 316.2 $[M+H]^+$.

Step 4: methyl (1R,5R)-2-[(4-methoxyphenyl) methyl-propanoyl-amino]-6, 6-dimethyl-bicyclo [3.1.1] hept-2-ene-3-carboxylate To a 0° C. solution of methyl (1R,5R)-2-[(4-methoxyphenyl) methylamino]-6, 6-dimethyl-bicyclo [3.1.1] hept-2-ene-3-carboxylate (20 g, 63.41 mmol), pyridine (15.35 mL, 190.23 mmol), and $CHCl_3$ (300 mL) was added propanoyl chloride (10.56 mL, 114.14 mmol). The mixture was stirred at 60° C. for 12 h. The reaction mixture was diluted with water (100 mL) and extracted with $CHCl_3$ (3×50 mL). The combined organic layers were dried over anhydrous $Na_2SO_4$, and concentrated under reduced pressure. The residue was purified by column chromatography ($SiO_2$, Petroleum ether/EtOAc=1/10 to 51) to provide methyl (1R, 5R)-2-[(4-methoxyphenyl) methyl-propanoyl-amino]-6, 6-dimethyl-bicyclo [3.1.1] hept-2-ene-3-carboxylate (40 g, 64.5% yield) as a yellow oil. m/z (ESI): 372.3 $[M+H]^+$.

Step 5: (1R,9R)-3-[(4-methoxyphenyl)methyl]-5,10,10-trimethyl-3-azatricyclo[7.1.1.0$^{2,7}$]undec-2(7)-ene-4,6-dione Methyl (1R,5R)-2-[(4-methoxyphenyl)methyl-propanoyl-amino]-6,6-dimethyl-bicyclo [3.1.1]hept-2-ene-3-carboxylate (20 g, 53.84 mmol) was dissolved in dioxane (200 mL), LiHMDS (1M in THF, 118.45 mL) was added in one portion at 0° C. under $N_2$. The mixture was stirred at 100° C. for 6 h. The reaction mixture was quenched by addition of $H_2O$ (200 mL) at 0° C. and basified with aqueous $NaHCO_3$ to pH=7-8. The reaction mixture was extracted with EtOAc (3×100 mL). The combined organic layers were dried over $Na_2SO_4$, filtered, and concentrated under reduced pressure. The residue was purified by column chromatography ($SiO_2$. 0-100% petroleum ether in EtOAc) to provide (1R,9R)-3-[(4-methoxyphenyl)methyl]-5,10,10-trimethyl-3-azatricyclo[7.1.1.0$^{2,7}$]undec-2(7)-ene-4,6-dione (56 g, crude) as a yellow solid. m/z (ESI): 340.3 $[M+H]^+$. $^1H$ NMR (400 MHz, DMSO-$d_6$) S ppm 9.31 (s, 1H), 7.00 (d, J=8.40 Hz, 2H), 6.84 (d, J=8.80 Hz, 2H), 4.99-5.36 (m, 2H), 3.70 (s, 3H), 2.98-3.00 (m, 1H), 2.59-2.63 (m, 1H), 2.43-2.46 (m, 2H), 2.15-2.25 (m, 1H), 1.93 (s, 3H), 1.17 (s, 3H), 1.11 (d, J=8.80 Hz, 1H), 0.36 (s, 3H).

Step 6: (1R,9R)-4,6-dichloro-5,10,10-trimethyl-3-azatricyclo[7.1.1.0$^{2,7}$]undeca-2,4,6-triene (1R,9R)-3-[(4-methoxyphenyl)methyl]-5,10,10-trimethyl-3-azatricyclo[7.1.1.0$^{2,7}$]undec-2(7)-ene-4,6-dione (10 g, 29.46 mmol) was dissolved in dioxane (100 mL) and $POCl_3$ (21.90 mL, 235.69 mmol) at 25° C. under $N_2$. Then N,N-dimethylaniline (22.41 mL, 176.77 mmol) was added in one portion, the mixture was stirred at 100° C. for 12 h. The reaction mixture was quenched with water (200 mL) and basified with aqueous $NaHCO_3$ to pH=7-8, then extracted with EtOAc (3×100 mL). The combined organic layers were dried over anhydrous $Na_2SO_4$, filtered and concentrated under reduced pressure. The residue was purified by column chromatography ($SiO_2$, petroleum ether/EtOAc=1/0 to 5/1) to provide (1R,9R)-4,6-dichloro-5,10,10-trimethyl-3-azatricyclo[7.1.1.0$^{2,7}$]undeca-2,4,6-triene (50 g) as a yellow oil. m/z (ESI): 255.9 $[M+H]^+$. $^1H$ NMR (400 MHz, $CDCl_3$) δ ppm 2.90-2.93 (m, 1H), 2.81 (d, J=10.40 Hz, 2H), 2.64-2.68 (m, 1H), 2.40 (s, 3H), 2.33 (s, 1H), 1.36 (s, 3H), 1.20 (m, 1H), 0.62 (s, 3H).

Intermediate 24: 4-bromo-3-chloro-2-fluoro-7,7-dimethyl-5,8-dihydropyrano[4,3-b]pyridine

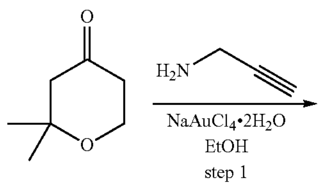

-continued

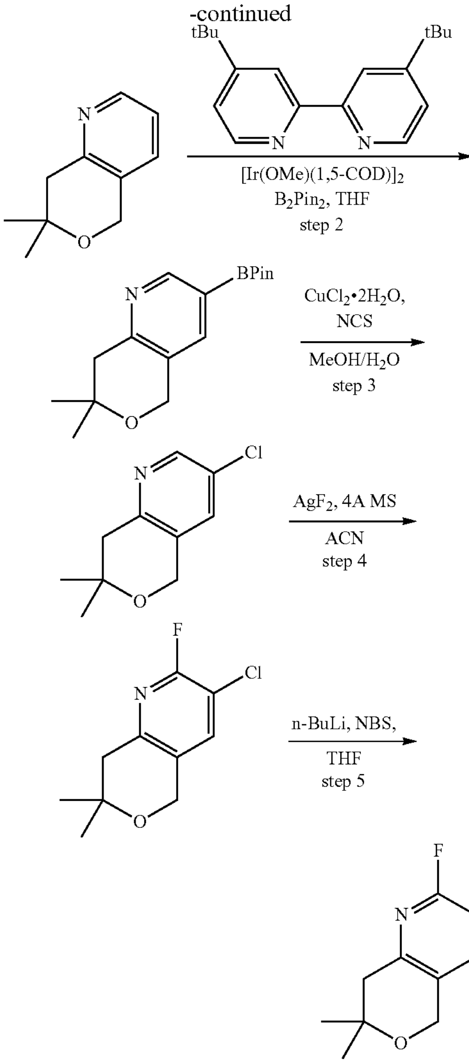

Intermediate 24

Step 1: 7,7-dimethyl-5,8-dihydropyrano[4,3-b]pyridine

To a solution of 2,2-dimethyltetrahydropyran-4-one (150 g, 1.17 mol, Bide Pharmatech) and prop-2-yn-1-amine (149.91 mL, 2.34 mol, Titan (Adamas)) in EtOH (2 L) was added $NaAuCl_4 \cdot 2H_2O$ (11.64 g, 29.26 mmol, Bide Pharmatech). The mixture was stirred at 90° C. for 12 h. The mixture was filtered and the filtrate was concentrated under reduced pressure. The residue was purified by column chromatography ($SiO_2$, 0-100% Petroleum ether in EtOAc) to provide 7,7-dimethyl-5,8-dihydropyrano[4,3-b]pyridine (200 g) as a brown oil. $^1H$ NMR (400 MHz, $CDCl_3$) δ ppm 8.44 (d, J=4.40 Hz, 1H), 7.33 (d, J=8.00 Hz, 1H), 7.12 (t, J=4.40 Hz, 1H), 4.80 (s, 2H), 2.89 (s, 2H), 1.33 (s, 6H).

Step 2: 7,7-dimethyl-3-(4,4,5,5-tetramethyl-1,3,2-dioxaborolan-2-yl)-5,8-dihydropyrano[4,3-b]pyridine To a solution of 7,7-dimethyl-5,8-dihydropyrano[4,3-b]pyridine (61.5 g, 376.80 mmol) and 4,4,5,5-tetramethyl-2-(4,4,5,5-tetramethyl-1,3,2-dioxaborolan-2-yl)-1,3,2-dioxaborolane (76.55 g, 301.44 mmol) in THF (750 mL) was added 4-tert-butyl-2-(4-tert-butyl-2-pyridyl)pyridine (8.09 g, 30.14 mmol) and $[Ir(1,5\text{-COD})(OMe)]_2$ (9.99 g, 15.07 mmol, Cynthia Tech). The mixture was stirred at 70° C. for 5 h. The mixture was filtered and concentrated under reduced pressure to provide 7,7-dimethyl-3-(4,4,5,5-tetramethyl-1,3,2-dioxaborolan-2-yl)-5,8-dihydropyrano[4,3-b]pyridine (70 g, crude) as a brown oil. m/z (ESI): 290.1 $[M+H]^+$.

Step 3: 3-chloro-7,7-dimethyl-5,8-dihydropyrano[4,3-b]pyridine

To a solution of 7,7-dimethyl-3-(4,4,5,5-tetramethyl-1,3,2-dioxaborolan-2-yl)-5,8-dihydropyrano[4,3-b]pyridine (120 g, 414.97 mmol) and MeOH (1 L):$H_2O$ (1 L) was added $CuCl_2 \cdot 2H_2O$ (212.24 g, 1.24 mol) at 25° C. and stirred for 1 h. Then NCS (55.41 g, 414.97 mmol) was added to the mixture. The mixture was stirred at 90° C. for 3 h. The reaction mixture was concentrated under reduced pressure to remove MeOH. The residue was diluted with EtOAc (2 L) and extracted with EtOAc (2×1 L). The combined organic layers were dried over $Na_2SO_4$, filtered and concentrated under reduced pressure. The residue was purified by column chromatography ($SiO_2$, petroleum ether/EtOAc=100/1 to 10/1) to provide 3-chloro-7,7-dimethyl-5,8-dihydropyrano[4,3-b]pyridine (24 g, 121.42 mmol, 29.26% yield) as a colorless oil.

Step 4: 3-chloro-2-fluoro-7,7-dimethyl-5,8-dihydropyrano[4,3-b]pyridine

To a solution of 3-chloro-7,7-dimethyl-5,8-dihydropyrano[4,3-b]pyridine (6 g, 30.36 mmol) in ACN (180 mL) was added $AgF_2$ (17.71 g, 121.42 mmol) and 4 Å MS. The mixture was stirred at 85° C. for 12 h. The mixture was filtered and the filtrate was concentrated under reduced pressure. The residue was purified by column chromatography ($SiO_2$, petroleum ether/EtOAc=100/1 to 5/1) to provide 3-chloro-2-fluoro-7,7-dimethyl-5,8-dihydropyrano[4,3-b]pyridine (15 g, crude) as a yellow oil.

Step 5: 4-bromo-3-chloro-2-fluoro-7,7-dimethyl-5,8-dihydropyrano[4,3-b]pyridine

To a solution of 3-chloro-2-fluoro-7,7-dimethyl-5,8-dihydropyrano[4,3-b]pyridine (7.7 g, 35.71 mmol) in THF (80 mL) was added dropwise n-BuLi (2.5 M, 28.56 mL) at −78° C. and stirred for 1 h, then NBS (12.71 g, 71.41 mmol) in THF (80 mL) was added dropwise at −78° C. The mixture was stirred at −78° C. for 2 h. The reaction mixture was quenched by addition of aqueous $NH_4Cl$ (500 mL) at −78° C. and extracted with EtOAc (2×100 mL). The combined organic layers were washed with brine (2×100 mL), dried over $Na_2SO_4$, filtered and concentrated under reduced pressure. The residue was purified by column chromatography ($SiO_2$, Petroleum ether/EtOAc=100/1 to 10/1) to provide 4-bromo-3-chloro-2-fluoro-7,7-dimethyl-5,8-dihydropyrano[4,3-b]pyridine (3.1 g, 10.52 mmol, 29.48% yield) as a light yellow solid. $^1H$ NMR (400 MHz, $CDCl_3$) δ 4.69 (dd, J=2.0, 1.1 Hz, 2H), 2.86-2.71 (m, 2H), 1.33 (s, 6H). m/z (ESI): 293.8 $(M+H)^+$.

Intermediate 25: tert-butyl 7-(3-cyano-4-iodo-2-quinolyl)-2,7-diazaspiro[3.4]octane-2-carboxylate

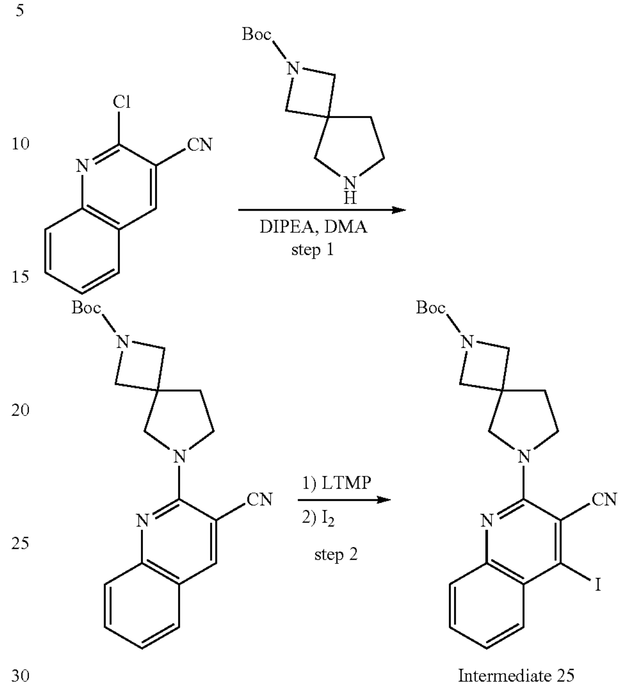

Intermediate 25

Step 1: tert-butyl 7-(3-cyano-2-quinolyl)-2,7-diazaspiro[3.4]octane-2-carboxylate To a solution of 2-chloroquinoline-3-carbonitrile (5 g, 26.51 mmol, Bide Pharmatech) and tert-butyl 2,7-diazaspiro[3.4]octane-2-carboxylate (5.63 g, 26.51 mmol, LabNetwork) in DMA (100 mL) was added DIPEA (13.85 mL, 79.53 mmol). The mixture was stirred at 120° C. for 40 min. The reaction mixture was quenched by addition $H_2O$ (100 mL) and extracted with EtOAc (2×100 mL). The combined organic layers were washed with $H_2O$ (200 mL), dried over $Na_2SO_4$, filtered and concentrated under reduced pressure. The residue was washed with petroleum ether/EtOAc=10/1 (50 mL) to provide tert-butyl 7-(3-cyano-2-quinolyl)-2,7-diazaspiro[3.4]octane-2-carboxylate (9 g, crude) as a yellow solid.

Step 2: tert-butyl 7-(3-cyano-4-iodo-2-quinolyl)-2,7-diazaspiro[3.4]octane-2-carboxylate To a solution of TMP (8.39 mL, 49.39 mmol) in THF (37 mL) was added n-BuLi (2.5 M, 19.76 mL) at −60° C. The mixture was added to a solution of tert-butyl 7-(3-cyano-2-quinolyl)-2,7-diazaspiro[3.4]octane-2-carboxylate (9 g, 24.70 mmol) in THF (90 mL) at −60° C. The mixture was stirred at −60° C. for 0.5 h. Then $I_2$ (12.54 g, 49.39 mmol) in THF (90 mL) was added to the mixture at −60° C. The mixture was stirred at 15° C. for 1.5 h. The reaction mixture was quenched by addition $H_2O$ (200 mL) at 15° C. and extracted with EtOAc (3×100 mL). The combined organic layers were dried over $Na_2SO_4$, filtered and concentrated under reduced pressure. The residue was purified by column chromatography ($SiO_2$, petroleum ether/EtOAc=20/1 to 3/1)

to provide tert-butyl 7-(3-cyano-4-iodo-2-quinolyl)-2,7-diazaspiro[3.4]octane-2-carboxylate (8 g, 16.32 mmol, 66.1% yield) as a yellow solid.

Intermediate 26: tert-butyl 7-(4-chloro-3,7,7-trimethyl-5,8-dihydropyrano[4,3-b]pyridin-2-yl)-2,7-diazaspiro[3.4]octane-2-carboxylate

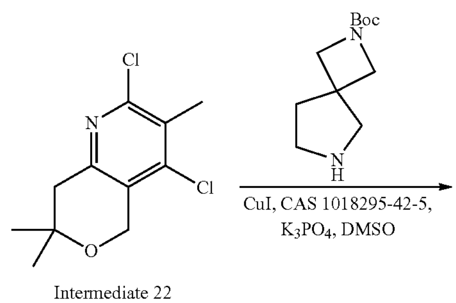

Intermediate 22

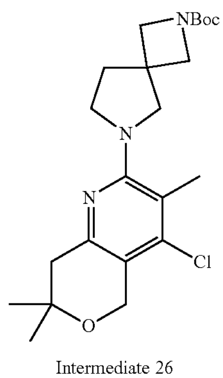

Intermediate 26

A mixture of 2,4-dichloro-3,7,7-trimethyl-5,8-dihydropyrano[4,3-b]pyridine (26 g, 105.63 mmol), tert-butyl 2,7-diazaspiro[3.4]octane-2-carboxylate (56.06 g, 264.09 mmol, LabNetwork), $K_3PO_4$ (112.11 g, 528.17 mmol), CuI (4.02 g, 21.13 mmol) and 2,6-difluoroanilino(oxo)acetic acid (10.62 g, 52.82 mmol, LabNetwork) in DMSO (300 mL) was degassed and purged with $N_2$ (3×). The mixture was stirred at 100° C. for 12 h under a $N_2$ atmosphere. The reaction mixture was quenched by aqueous saturated $NH_4Cl$ (500 mL) and diluted with $H_2O$ (500 mL), extracted with EtOAc (3×400 mL). The combined organic layers were washed with brine (300 mL), dried over $Na_2SO_4$, filtered, and concentrated under reduced pressure. The residue was purified by column chromatography ($SiO_2$, Petroleum ether/EtOAc=30:1 to 5:1) to provide tert-butyl 7-(4-chloro-3,7,7-trimethyl-5,8-dihydropyrano[4,3-b]pyridin-2-yl)-2,7-diazaspiro[3.4]octane-2-carboxylate (20 g, 46.53 mmol, 44.04% yield, 98.16% purity) as a white solid. m/z (ESI): 422.1 $[M+H]^+$.

Intermediate 27: tert-butyl 7-[(1R,9R)-6-chloro-5,10,10-trimethyl-3-azatricyclo[7.1.1.0$^1$]undeca-2,4,6-trien-4-yl]-2,7-diazaspiro[3.4]octane-2-carboxylate

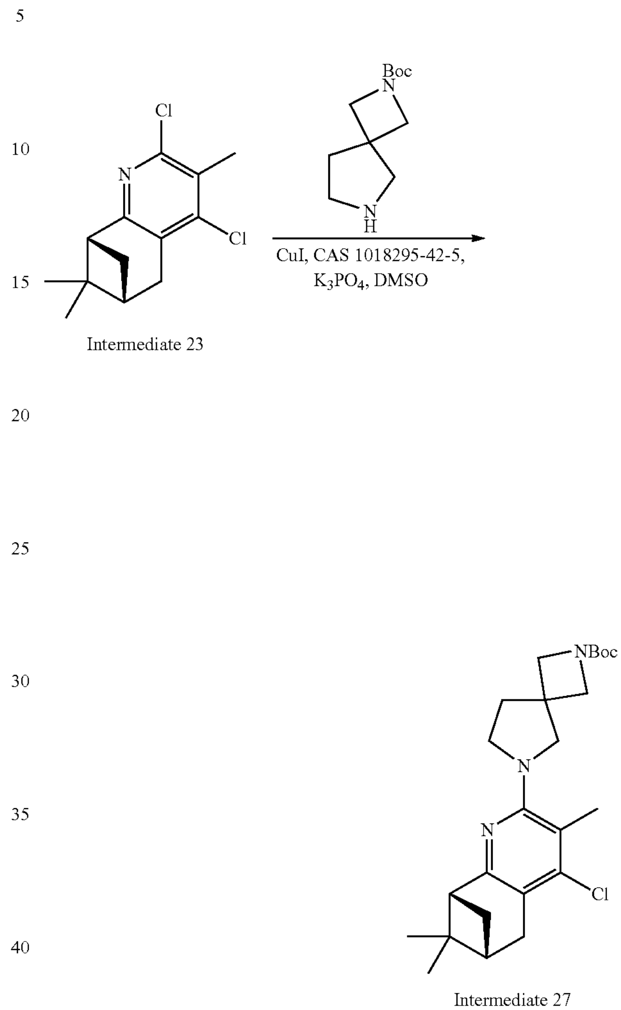

Intermediate 23

Intermediate 27

To a mixture of (1R,9R)-4,6-dichloro-5,10,10-trimethyl-3-azatricyclo[7.1.1.0$^{2,7}$]undeca-2,4,6-triene (25 g, 97.59 mmol), tert-butyl 2,7-diazaspiro[3.4]octane-2-carboxylate (51.79 g, 243.98 mmol, Labnetwork), $K_3PO_4$ (103.58 g, 487.96 mmol), CuI (3.72 g, 19.52 mmol) and 2-(2,6-difluoroanilino)-2-oxo-acetic acid (9.81 g, 48.80 mmol, LabNetwork) in DMSO (500 mL) at 15° C. under $N_2$. The mixture was stirred at 100° C. for 12 h. The reaction mixture was filtered and the filtrate was diluted with $H_2O$ (200 mL) and extracted with EtOAc (3×80 mL). The combined organic layers were dried over $Na_2SO_4$, filtered, and concentrated under reduced pressure. The residue was purified by column chromatography ($SiO_2$, Petroleum ether/EtOAc=1/0 to 5/1) to provide tert-butyl 7-[(1R,9R)-6-chloro-5,10,10-trimethyl-3-azatricyclo[7.1.1.0$^{2,7}$]undeca-2,4,6-trien-4-yl]-2,7-diazaspiro[3.4]octane-2-carboxylate (12.5 g, 28.36 mmol, 14.53% yield) as a white oil. m/z (ESI): 432.2 $[M+H]^+$. $^1H$ NMR (400 MHz, $CDCl_3$) δ ppm 3.91-3.94 (m, 2H), 3.85-3.87 (m, 2H), 3.57-3.60 (m, 2H), 3.35-3.45 (m, 2H), 2.78-2.81 (m, 3H), 2.57-2.62 (m, 1H), 2.29-2.32 (m, 1H), 2.28 (s, 3H), 2.08-2.10 (m, 2H), 1.45 (s, 9H), 1.40 (s, 3H), 1.24-1.27 (m, 2H), 0.67 (s, 3H).

Intermediate 28: tert-butyl 7-[3,7,7-trimethyl-4-(4,4,5,5-tetramethyl-1,3,2-dioxaborolan-2-yl)-5,8-dihydropyrano[4,3-b]pyridin-2-yl]-2,7-diazaspiro[3.4]octane-2-carboxylate

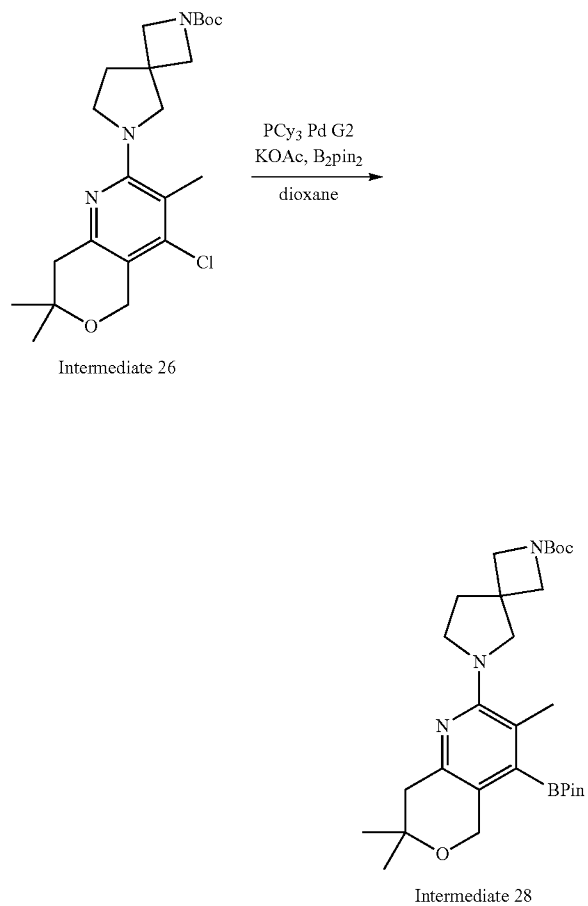

Intermediate 26

Intermediate 28

A mixture of tert-butyl 7-(4-chloro-3,7,7-trimethyl-5,8-dihydropyrano[4,3-b]pyridin-2-yl)-2,7-diazaspiro[3.4]octane-2-carboxylate (5 g, 11.85 mmol), 4,4,5,5-tetramethyl-2-(4,4,5,5-tetramethyl-1,3,2-dioxaborolan-2-yl)-1,3,2-dioxaborolane (15.05 g, 59.25 mmol), $PCy_3$ Pd G2 (699.73 mg, 1.18 mmol, Jiangsu Aikon Biopharmaceutical R&D), KOAc (3.49 g, 35.55 mmol) in dioxane (100 mL) was degassed and purged with $N_2$ (3×). The mixture was stirred at 95° C. for 12 h. The reaction mixture was diluted with $H_2O$ (200 mL) and extracted with EtOAc (3×200 mL). The combined organic layers were dried over $Na_2SO_4$, filtered and concentrated under reduced pressure. The residue was purified by column chromatography ($SiO_2$, petroleum ether/EtOAc=30:1 to 10:1). The crude product was re-purified by reversed-phase HPLC (0.1% $NH_3 \cdot H_2O$, MeOH) to provide tert-butyl 7-[3,7,7-trimethyl-4-(4,4,5,5-tetramethyl-1,3,2-dioxaborolan-2-yl)-5,8-dihydropyrano[4,3-b]pyridin-2-yl]-2,7-diazaspiro[3.4]octane-2-carboxylate (5.1 g, 9.941 mmol, 83% yield) as a yellow solid. m/z (ESI): 514.2 $[M+H]^+$. $^1H$ NMR (400 MHz, $CDCl_3$) δ ppm 4.76 (s, 2H), 3.91 (d, J=8.40 Hz, 2H), 3.85 (d, J=8.40 Hz, 2H), 3.57 (s, 2H), 3.43-3.47 (m, 2H), 2.69 (s, 2H), 2.28 (s, 3H), 2.07-2.11 (m, 2H), 1.46 (s, 9H), 1.38 (s, 12H), 1.29 (s, 6H).

Intermediate 29: tert-butyl 7-[(1R,9R)-5,10,10-trimethyl-6-(4,4,5,5-tetramethyl-1,3,2-dioxaborolan-2-yl)-3-azatricyclo[7.1.1.0$^{2,7}$]undeca-2,4,6-trien-4-yl]-2,7-diazaspiro[3.4]octane-2-carboxylate

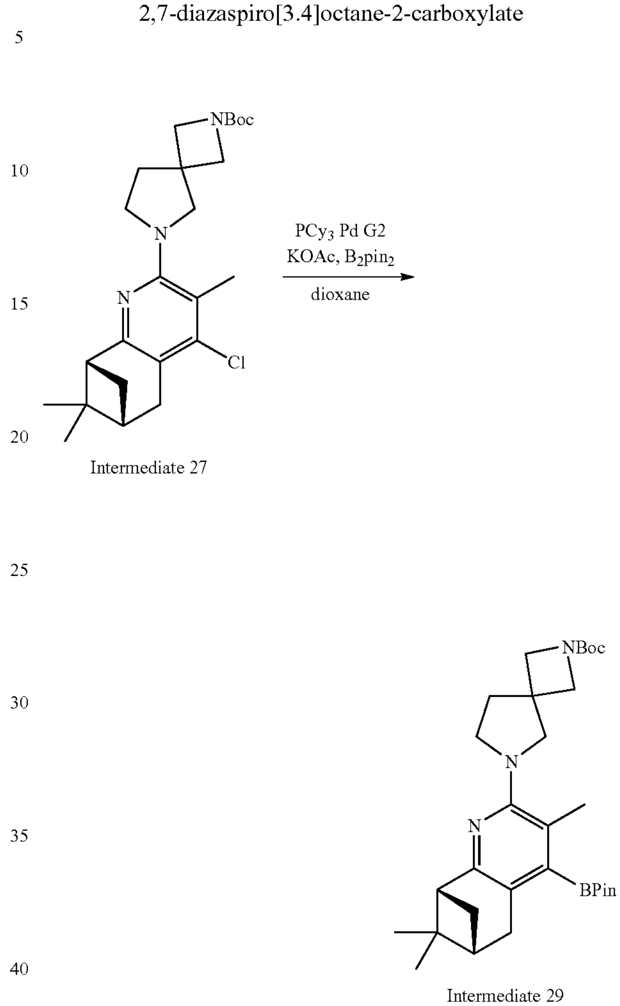

Intermediate 27

Intermediate 29

To a mixture of tert-butyl 7-[(1R,9R)-6-chloro-5,10,10-trimethyl-3-azatricyclo[7.1.1.0$^{2,7}$]undeca-2,4,6-trien-4-yl]-2,7-diazaspiro[3.4]octane-2-carboxylate (1.5 g, 3.47 mmol) and 4,4,5,5-tetramethyl-2-(4,4,5,5-tetramethyl-1,3,2-dioxaborolan-2-yl)-1,3,2-dioxaborolane (4.41 g, 17.36 mmol) in dioxane (20 mL) was added PCy3 Pd G2 (254.07 mg, 0.347 mmol, Jiangsu Aikon Biopharmaceutical R&D) and KOAc (1.02 g, 10.42 mmol) in one portion at 20° C. under $N_2$. The mixture was stirred at 110° C. for 10 h. The reaction mixture was diluted with $H_2O$ (20 mL) and extracted with EtOAc (3×10 mL). The combined organic layers were dried over $Na_2SO_4$, filtered, and concentrated under reduced pressure. The residue was purified by column chromatography ($SiO_2$, Petroleum ether/EtOAc=1/0 to 10/1) to provide tert-butyl 7-[(1R,9R)-5,10,10-trimethyl-6-(4,4,5,5-tetramethyl-1,3,2-dioxaborolan-2-yl)-3-azatricyclo[7.1.1.0$^{2,7}$]undeca-2,4,6-trien-4-yl]-2,7-diazaspiro[3.4]octane-2-carboxylate (310 mg, 0.592 mmol, 15.50% yield) as a yellow solid. m/z (ESI): 524.2 $[M+H]^+$. $^1H$ NMR (400 MHz, $CDCl_3$) δ ppm 3.91-3.94 (m, 2H), 3.84-3.86 (m, 2H), 3.58-3.61 (m, 2H), 3.41-3.42 (m, 2H), 2.76-2.87 (m, 3H), 2.61 (s, 1H), 2.26 (m, 4H), 2.06-2.10 (m, 2H), 1.45 (9H, s), 1.40 (s, 12H), 1.38 (s, 3H), 1.26-1.29 (m, 1H), 0.68 (s, 3H).

Intermediate 30: tert-butyl 7-(4-chloro-3-fluoro-7,7-dimethyl-5,8-dihydropyrano[4,3-b]pyridin-2-yl)-2,7-diazaspiro[3.4]octane-2-carboxylate

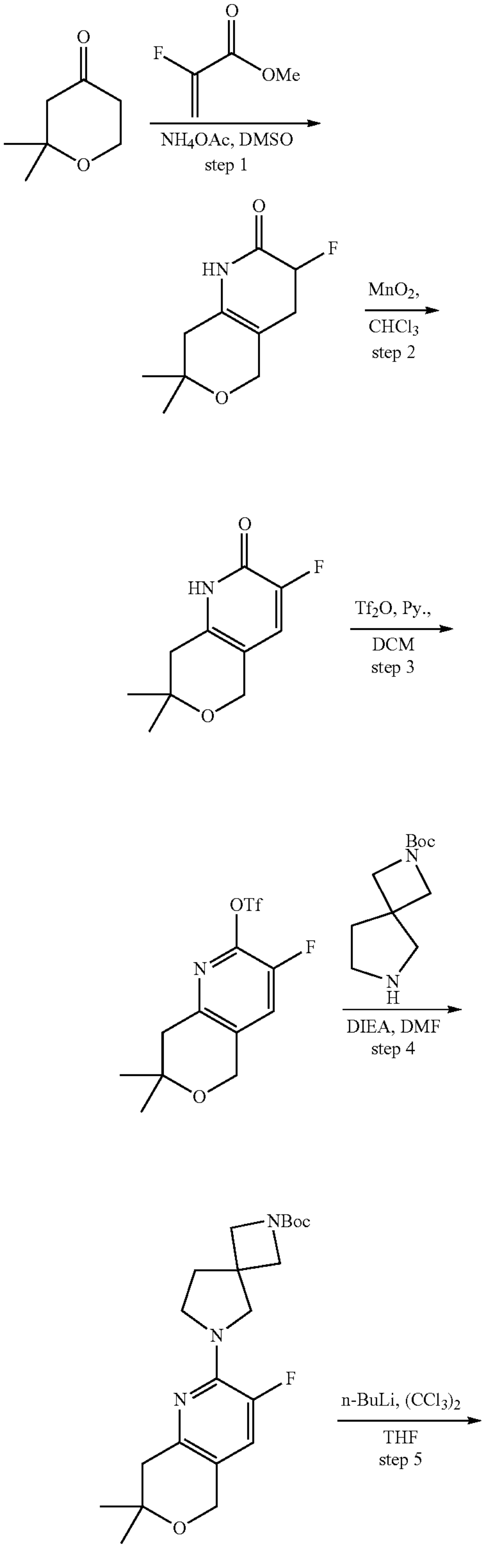

-continued

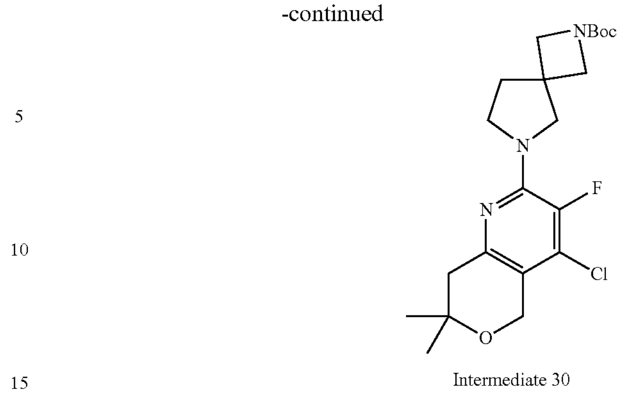

Intermediate 30

Step 1: 3-fluoro-7,7-dimethyl-3,4,5,8-tetrahydro-1H-pyrano[4,3-b]pyridin-2-one

To a solution of 2,2-dimethyltetrahydropyran-4-one (20 g, 156.04 mmol, Bide Pharmatech) and methyl 2-fluoroprop-2-enoate (81.21 g, 780.22 mmol, Qinba Chemie) in DMSO (200 mL) was added $NH_4OAc$ (24.06 g, 312.09 mmol). The mixture was stirred at 80° C. for 12 h. The reaction was diluted with brine (300 mL), extracted with EtOAc (3×300 mL), dried over $Na_2SO_4$, filtered and concentrated under reduced pressure. The residue was purified by column chromatography ($SiO_2$, petroleum ether/EtOAc=1:0 to 1:1) to provide 3-fluoro-7,7-dimethyl-3,4,5,8-tetrahydro-1H-pyrano[4,3-b]pyridin-2-one (25 g, crude) as a yellow solid.

Step 2: 3-fluoro-7,7-dimethyl-5,8-dihydro-1H-pyrano[4,3-b]pyridin-2-one

To a solution of 3-fluoro-7,7-dimethyl-3,4,5,8-tetrahydro-1H-pyrano[4,3-b]pyridin-2-one (30 g, 150.59 mmol) in $CHCl_3$ (300 mL) was added $MnO_2$ (261.83 g, 3.01 mol). The mixture was stirred at 70° C. for 24 h. The reaction mixture was filtered and concentrated under reduced pressure. The residue was purified by column chromatography ($SiO_2$, petroleum ether/EtOAc=30:1 to 0:1) to provide 3-fluoro-7,7-dimethyl-5,8-dihydro-1H-pyrano[4,3-b]pyridin-2-one (3 g, crude) as a yellow solid. m/z (ESI): 198.1 $[M+H]^+$.

Step 3: (3-fluoro-7,7-dimethyl-5,8-dihydropyrano[4,3-b]pyridin-2-yl) trifluoromethanesulfonate To a solution of 3-fluoro-7,7-dimethyl-5,8-dihydro-1H-pyrano[4,3-b]pyridin-2-one (20 g, 101.42 mmol) in DCM (200 mL) was added pyridine (24.56 mL, 304.25 mmol) and $Tf_2O$ (25.10 mL, 152.13 mmol) at 0° C. The mixture was stirred at 20° C. for 12 h. The reaction mixture was diluted with $H_2O$ (500 mL) and extracted with DCM (3×500 mL). The combined organic layers were dried over $Na_2SO_4$, filtered, and concentrated under reduced pressure. The residue was purified by column chromatography ($SiO_2$, petroleum ether/EtOAc=30:1 to 5:1) to provide (3-fluoro-7,7-dimethyl-5,8-dihydropyrano[4,3-b]pyridin-2-yl) trifluoromethanesulfonate (26 g, 78.96 mmol, 65.0% yield) as a yellow oil. m/z (ESI): 330.0 $[M+H]^+$. $^1H$ NMR (400 MHz, $CDCl_3$) δ ppm 7.33 (d, J=8.40 Hz, 1H), 4.80 (s, 2H), 2.82 (s, 2H), 1.33 (s, 6H).

Step 4: tert-butyl-7-(3-fluoro-7,7-dimethyl-5,8-dihydropyrano[4,3-b]pyridin-2-yl)-2,7-diazaspiro[3.4]octane-2-carboxylate To a solution of (3-fluoro-7,7-dimethyl-5,8-dihydropyrano[4,3-b]pyridin-2-yl) trifluoromethanesulfonate (13 g, 39.48 mmol) in DMF (100 mL) was added DIPEA (20.63 mL, 118.44 mmol) and tert-butyl 2,7-diazaspiro[3.4]octane-2-carboxylate (8.38 g, 39.48 mmol, Labnetwork) at 20° C. The mixture was stirred at 60° C. for 6 h. The reaction mixture was diluted by $H_2O$ (300 mL) and extracted with EtOAc (3×300 mL). The combined organic layers were dried over $Na_2SO_4$, filtered, and concentrated under reduced pressure. The residue was purified by column chromatography ($SiO_2$, petroleum ether/EtOAc=30:1 to 1:1) to provide tert-butyl-7-(3-fluoro-7,7-dimethyl-5,8-dihydropyrano[4,3-b]pyridin-2-yl)-2,7-diazaspiro[3.4]octane-2-carboxylate (12 g, 29.43 mmol, 77% yield, 96% purity) as a white solid. m/z (ESI): 392.3 $[M+H]^+$. $^1H$ NMR (400 MHz, $CDCl_3$) δ ppm 6.84 (d, J=12.80 Hz, 1H), 4.64 (s, 2H), 3.92-3.94 (m, 2H), 3.85-3.87 (m, 2H), 3.76 (s, 2H), 3.67-3.68 (m, 2H), 2.64 (s, 2H), 2.12 (t, J=6.80 Hz, 2H), 1.45 (s, 9H), 1.30 (s, 6H).

Step 5: tert-butyl 7-(4-chloro-3-fluoro-7,7-dimethyl-5,8-dihydropyrano[4,3-b]pyridin-2-yl)-2,7-diazaspiro[3.4]octane-2-carboxylate To a solution of n-BuLi (2.5 M, 30.65 mL) in THF (80 mL) was added tert-butyl-7-(3-fluoro-7,7-dimethyl-5,8-dihydropyrano[4,3-b]pyridin-2-yl)-2,7-diazaspiro[3.4]octane-2-carboxylate (12 g, 30.65 mmol) in THF (30 mL) at −78° C. The mixture was stirred at −78° C. for 1 h, and then 1,1,1,2,2,2-hexachloroethane (10.42 mL, 91.96 mmol) in THF (30 mL) was added dropwise at −78° C. The mixture was stirred at −78° C. for 1 h. The reaction mixture was quenched by $H_2O$ (500 mL) and extracted with EtOAc (3×300 mL). The combined organic layers were dried over $Na_2SO_4$, filtered and concentrated under reduced pressure. The residue was purified by column chromatography ($SiO_2$, petroleum ether/EtOAc=1:0 to 20:1) to provide tert-butyl 7-(4-chloro-3-fluoro-7,7-dimethyl-5,8-dihydropyrano[4,3-b]pyridin-2-yl)-2,7-diazaspiro[3.4]octane-2-carboxylate (7.65 g, 17.60 mmol, 57.42% yield) as a yellow solid. m/z (ESI): 426.1 $[M+H]^+$. $^1H$ NMR (400 MHz, $CDCl_3$) δ ppm 4.65 (s, 2H), 3.92-3.94 (m, 2H), 3.85-3.87 (m, 2H), 3.76 (s, 2H) 3.68-3.69 (m, 2H), 2.62 (s, 2H), 2.14 (t, J=6.80 Hz, 2H), 1.47 (s, 9H), 1.29 (s, 6H).

Intermediate 31: tert-butyl 7-[(1R,9R)-6-chloro-5-fluoro-10,10-dimethyl-3-azatricyclo[7.1.1.0$^{2,7}$]undeca-2,4,6-trien-4-yl]-2,7-diazaspiro[3.4]octane-2-carboxylate

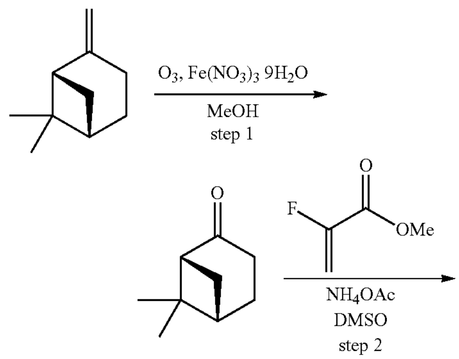

-continued

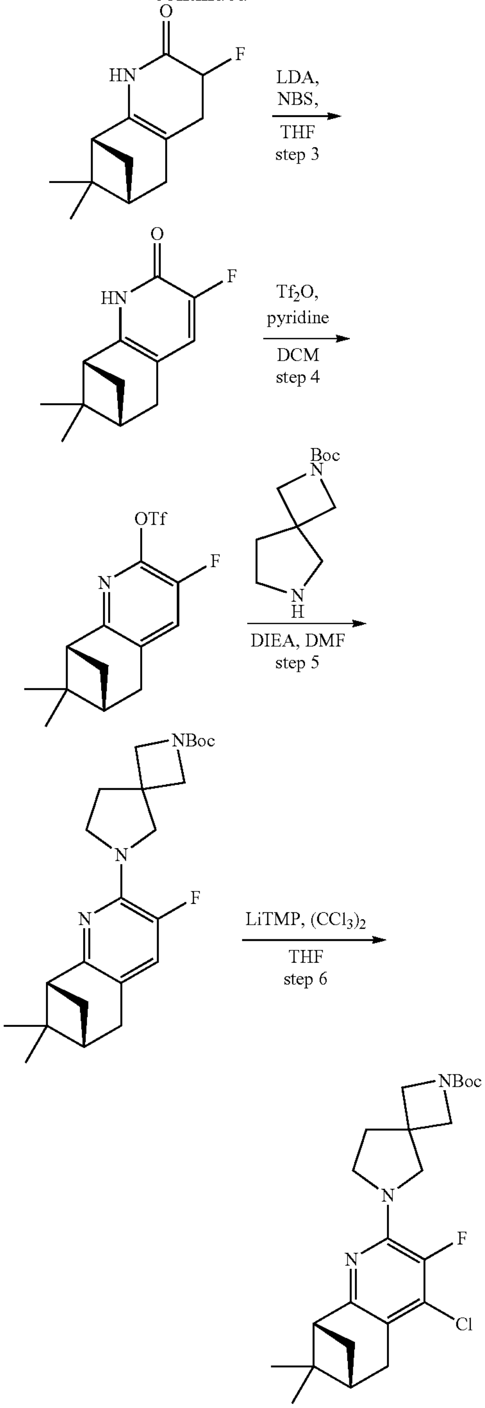

Intermediate 31

Step 1: (1R,5S)-6,6-dimethylnorpinan-2-one

See Intermediate 23 Step 1

Step 2: (1R,9R)-5-fluoro-10,10-dimethyl-3-azatricyclo[7.1.1.0$^{2,7}$]undec-2(7)-en-4-one To a mixture of (1R,5S)-6, 6-dimethylnorpinan-2-one (79 g, 571.61 mmol) and methyl 2-fluoroprop-2-enoate (178.48 g, 1.71 mol, Qinba Chemie) in DMSO (1 L) was added $NH_4OAc$ (66.10 g, 857.58 mmol) in one portion at 25° C. under $N_2$. The mixture was stirred at 80° C. for 12 h. The reaction mixture was diluted with $H_2O$ (500 mL) and extracted with EtOAc (3×200 mL). The combined organic layers were dried over $Na_2SO_4$, filtered, and concentrated under reduced pressure. The residue was purified by column chromatography ($SiO_2$, petroleum ether/EtOAc=1/0 to 90/1) to provide (1R,9R)-5-fluoro-10,10-dimethyl-3-azatricyclo [7.1.1.$0^{2,7}$]undec-2(7)-en-4-one (28 g, 133.81 mmol, 11.70% yield) as a yellow solid.

Step 3: (1R,9R)-5-fluoro-10,10-dimethyl-3-azatricyclo[7.1.1.$0^{2,7}$]undeca-2(7),5-dien-4-one (1R,9R)-5-fluoro-10,10-dimethyl-3-azatricyclo[7.1.1.$0^{2,7}$]undec-2(7)-en-4-one (14 g, 66.90 mmol) was dissolved in THF (500 mL), then LDA (2M, 26.76 mL) was added in one portion at −78° C. and stirred for 30 min under $N_2$. NBS (14.29 g, 80.28 mmol) was added and stirred at 25° C. for 1 h. The reaction mixture was quenched by $H_2O$ (100 mL) at 0° C., and extracted with EtOAc (3×50 mL). The combined organic layers were dried over $Na_2SO_4$, filtered, and concentrated under reduced pressure. The crude product was recrystallized from petroleum ether/EtOAc=8/1 to provide (1R,9R)-5-fluoro-10,10-dimethyl-3-azatricyclo[7.1.1.$0^{2,7}$] undeca-2(7),5-dien-4-one (24 g, 115.81 mmol, 86.55% yield) as a yellow solid. m/z (ESI): 208.2 $[M+H]^+$. $^1H$ NMR (400 MHz. $CDCl_3$) δ ppm 7.14 (d, J=10.00 Hz, 1H), 2.88-2.91 (m, 1H), 2.65-2.71 (m 3H), 2.28-2.29 (m, 1H), 1.73 (s, 1H), 1.40 (s, 3H), 0.75 (s, 3H).

Step 4: [(1R,9R)-5-fluoro-10,10-dimethyl-3-azatricyclo[7.1.1.0-]undeca-2,4,6-trien-4-yl]trifluoromethanesulfonate (1R,9R)-5-fluoro-10,10-dimethyl-3-azatricyclo [7.1.1.0&]undeca-2(7),5-dien-4-one (12 g, 57.90 mmol) was dissolved in DCM (440 mL), pyridine (9.35 mL, 115.81 mmol) was added at 0° C. under $N_2$. $Tf_2O$ (10.51 mL, 63.69 mmol) was added and the mixture was stirred at 0° C. for 0.25 h. The reaction mixture was diluted with $H_2O$ (300 mL) and extracted with DCM (3×120 mL). The combined organic layers were dried over $Na_2SO_4$, filtered, and concentrated under reduced pressure to provide [(1R,9R)-5-fluoro-10,10-dimethyl-3-azatricyclo[7.1.1.$0^{2,7}$]undeca-2,4,6-trien-4-yl] trifluoromethanesulfonate (39 g, crude) as a yellow oil.

Step 5: tert-butyl-7-[(1R,9R)-5-fluoro-10,10-dimethyl-3-azatricyclo[7.1.1.$0^{2,7}$]undeca-2,4,6-trien-4-yl]-2,7-diazaspiro[3.4]octane-2-carboxylate To a mixture of [(1R,9R)-5-fluoro-10,10-dimethyl-3-azatricyclo[7.1.1.$0^{2,7}$]undeca-2,4,6-trien-4-yl] trifluoromethanesulfonate (15 g, 44.21 mmol) and tert-butyl 2,7-diazaspiro[3.4]octane-2-carboxylate (11.26 g, 53.05 mmol, Labnetwork) in DMF (150 mL) was added DIEA (19.25 mL, 110.52 mmol) at 25° C. under $N_2$. The mixture was stirred at 80° C. for 6 h. The reaction mixture was diluted with $H_2O$ (200 mL) and extracted with EtOAc (3×100 mL). The combined organic layers were dried over $Na_2SO_4$, filtered, and concentrated under reduced pressure. The residue was purified by column chromatography ($SiO_2$, petroleum ether/EtOAc=1/0 to 5/1) to provide tert-butyl-7-[(1R,9R)-5-fluoro-10,10-dimethyl-3-azatricyclo[7.1.1.$0^{2,7}$]undeca-2,4,6-trien-4-yl]-2,7-diazaspiro[3.4]octane-2-carboxylate (15.8 g, 36.20 mmol, 81.89% yield) as a yellow oil. m/z (ESI): 402.3 $(M+H)^+$.

Step 6: tert-butyl 7-[(1R,9R)-6-chloro-5-fluoro-10,10-dimethyl-3-azatricyclo[7.1.1.$0^{2,7}$]undeca-2,4,6-trien-4-yl]-2,7-diazaspiro[3.4]octane-2-carboxylate 2,2,6,6-tetramethylpiperidine (23.38 mL, 137.73 mmol) and n-BuLi (2.5 M, 47.22 mL) were dissolved in THF (100 mL) at −78° C. under $N_2$. The mixture was stirred at −40° C. for 1 h. tert-butyl-7-[(1R,9R)-5-fluoro-10,10-dimethyl-3-azatricyclo[7.1.1.$0^{2,7}$]undeca-2,4,6-trien-4-yl]-2,7-diazaspiro[3.4]octane-2-carboxylate (15.8 g, 39.35 mmol) in THF (10 mL) was added at −78° C. and stirred for 0.5 h. Then 1,1,1,2,2,2-hexachloroethane (46.58 g, 196.75 mmol, 22.29 mL) in THF (30 mL) was added at −78° C. The mixture was stirred at −78° C. for 1.5 h. The reaction mixture was quenched by $H_2O$ (300 mL) at 0° C. and extracted with EtOAc (3×150 mL). The combined organic layers were dried over $Na_2SO_4$, filtered, and concentrated under reduced pressure. The residue was purified by column chromatography ($SiO_2$, petroleum ether/EtOAc=1/0 to 5/1) to provide tert-butyl 7-[(1R,9R)-6-chloro-5-fluoro-10,10-dimethyl-3-azatricyclo[7.1.1.$0^{2,7}$]undeca-2,4,6-trien-4-yl]-2,7-diazaspiro[3.4]octane-2-carboxylate (17.8 g, 0.034 mol, 85% yield) as a white solid. m/z (ESI): 436.1 $(M+H)^+$.

Intermediate 32: [2-(2-tert-butoxycarbonyl-2,7-diazaspiro[3.4]octan-7-yl)-3-cyano-7,7-dimethyl-5,8-dihydropyrano[43-b]pyridin-4-yl]boronic acid

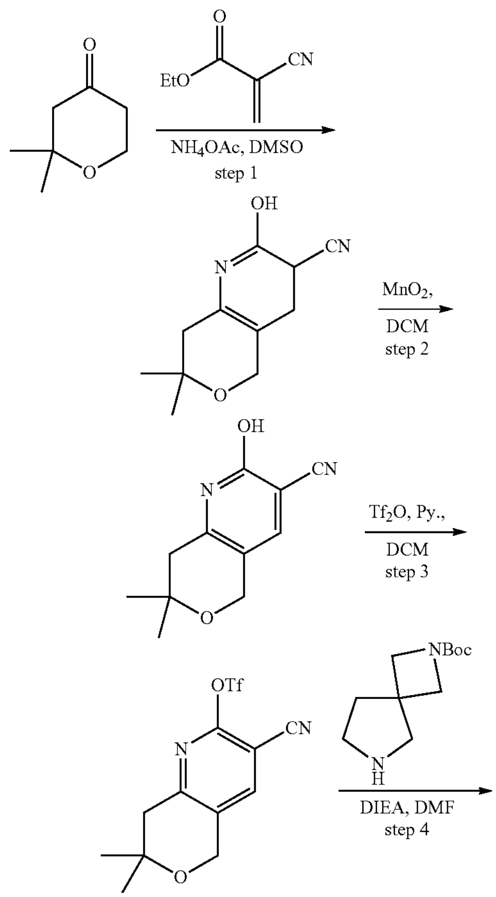

-continued

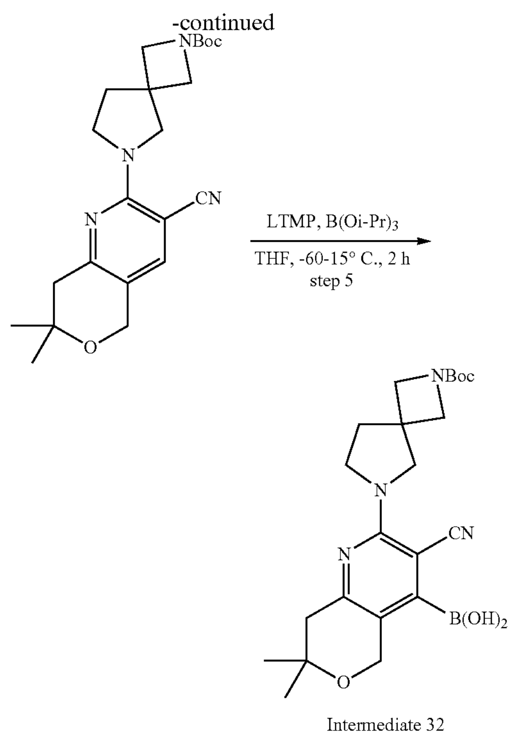

Intermediate 32

Step 1: 2-hydroxy-7,7-dimethyl-3,4,5,8-tetrahydro-pyrano[4,3-b]pyridine-3-carbonitrile To a solution of 2,2-dimethyltetrahydropyran-4-one (100 g, 780.22 mmol, Bide Pharmatech) in DMSO (1 L) was added $NH_4OAc$ (300.71 g, 3.90 mol) and ethyl 2-cyano-prop-2-enoate (97.63 g, 780.22 mmol, Beijing FeiLongrui Trading) at 15° C. The mixture was stirred at 80° C. for 12 h. The reaction mixture was poured slowly into $H_2O$ (3 L) and extracted with EtOAc (4×2 L). The combined organic layers were washed with brine (2×4 L), dried over $Na_2SO_4$, filtered and concentrated under reduced pressure to provide crude 2-hydroxy-7,7-dimethyl-3,4,5,8-tetrahydropyrano[4,3-b]pyridine-3-carbonitrile (126 g) as a yellow oil that was used in the next step without further purification. m/z (ESI): 207.1 $(M+H)^+$.

Step 2: 2-hydroxy-7,7-dimethyl-5,8-dihydropyrano[4,3-b]pyridine-3-carbonitrile

To a mixture of 2-hydroxy-7,7-dimethyl-3,4,5,8-tetrahydropyrano[4,3-b]pyridine-3-carbonitrile (126 g, 610.94 mmol) in DCM (1 L) was added $MnO_2$ (265.56 g, 3.05 mol). The mixture was stirred at 40° C. for 5 h. The mixture was filtered and concentrated to dryness. The crude product was triturated with EtOAc (100 mL) at 15° C. for 30 min to provide 2-hydroxy-7,7-dimethyl-5,8-dihydropyrano[4,3-b]pyridine-3-carbonitrile (50 g, 244.83 mmol, 40.07% yield) as a yellow solid.

Step 3: (3-cyano-7,7-dimethyl-5,8-dihydropyrano[4,3-b]pyridin-2-yl) trifluoromethanesulfonate To a solution of 2-hydroxy-7,7-dimethyl-5,8-dihydropyrano[4,3-b]pyridine-3-carbonitrile (50 g, 244.83 mmol) in DCM (500 mL) was added pyridine (59.28 mL, 734.49 mmol) and $Tf_2O$ (60.59 mL, 367.24 mmol) in DCM (125 mL) at 0° C. The mixture was stirred at 15° C. for 0.5 h. The reaction mixture was quenched with aqueous saturated $NaHCO_3$ (1 L) at 15° C., extracted with DCM (3×500 mL). The combined organic layers were dried over $Na_2SO_4$, filtered and concentrated under reduced pressure. The residue was purified by column chromatography ($SiO_2$, petroleum ether/EtOAc=20/1 to 3/1) to provide (3-cyano-7,7-dimethyl-5,8-dihydropyrano[4,3-b]pyridin-2-yl) trifluoromethanesulfonate (78 g, 231.95 mmol, 94.74% yield) as a white solid.

Step 4: tert-butyl 7-(3-cyano-7,7-dimethyl-5,8-dihydropyrano[4,3-b]pyridin-2-yl)-2,7-diazaspiro[3.4]octane-2-carboxylate To a solution of (3-cyano-7,7-dimethyl-5,8-dihydropyrano[4,3-b]pyridin-2-yl) trifluoromethanesulfonate (57 g, 169.50 mmol) in DMF (600 mL) was added DIEA (88.57 mL, 508.49 mmol) and tert-butyl 2,7-diazaspiro[3.4]octane-2-carboxylate (35.98 g, 169.50 mmol, Labnetwork). The mixture was stirred at 80° C. for 0.5 h. TLC indicated the reaction was complete. The reaction mixture was quenched with brine (2 L) and extracted with EtOAc (3×1 L). The combined organic layers were washed with brine (2×1.5 L), dried over $Na_2SO_4$, filtered and concentrated under reduced pressure. The crude product was triturated with (petroleum ether/EtOAc=10/1, 500 mL) at 15° C. to provide tert-butyl 7-(3-cyano-7,7-dimethyl-5,8-dihydropyrano[4,3-b]pyridin-2-yl)-2,7-diazaspiro[3.4]octane-2-carboxylate (57 g, 143.04 mmol, 84.39% yield) as a yellow solid.

Step 5: [2-(2-tert-butoxycarbonyl-2,7-diazaspiro[3.4]octan-7-yl)-3-cyano-7,7-dimethyl-5,8-dihydropyrano[4,3-b]pyridin-4-yl]boronic acid To a solution of TMP (25.56 mL, 150.57 mmol) in THF (50 mL) was added n-BuLi (2.5 M, 60.23 mL) at −60° C., and stirred for 30 min. The mixture was added dropwise to a solution of tert-butyl 7-(3-cyano-7,7-dimethyl-5,8-dihydropyrano[4,3-b]pyridin-2-yl)-2,7-diazaspiro[3.4]octane-2-carboxylate (30 g, 75.28 mmol) in THF (400 mL) at −60° C. The mixture was stirred at −60° C. for 30 min. Triisopropyl borate (69.23 mL, 301.13 mmol) was added dropwise at −40° C. and the mixture stirred at 15° C. for 1 h. The reaction mixture was poured slowly into aqueous $NH_4Cl$ (2 L) and extracted with EtOAc (3×1 L). The combined organic phase was dried over $Na_2SO_4$, filtered, and concentrated to dryness. The crude product was recrystallized (petroleum ether/EtOAc=20/1, 1 L) to provide [2-(2-tert-butoxycarbonyl-2,7-diazaspiro[3.4]octan-7-yl)-3-cyano-7,7-dimethyl-5,8-dihydropyrano[4,3-b]pyridin-4-yl]boronic acid (106.7 g, 207.46 mmol, 61.17% yield) as a yellow solid. m/z (ESI): 443.1 $(M+H)^+$. $^1H$ NMR (400 MHz, Methanol-$d_6$) δ ppm 4.59-4.71 (in, 2H), 3.79-3.96 (m, 8H), 2.71 (s, 2H), 2.21 (t, J=6.80 Hz, 2H), 1.47 (s, 9H), 1.28 (s, 6H).

Intermediate 33: [(1R,9R)-4-(2-tert-butoxycarbonyl-2,7-diazaspiro[3.4]octan-7-yl)-5-cyano-10,10-dimethyl-3-azatricyclo[7.1.1.0$^{2,7}$]undeca-2,4,6-trien-6-yl]boronic acid

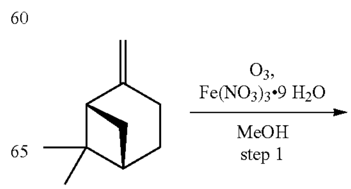

-continued

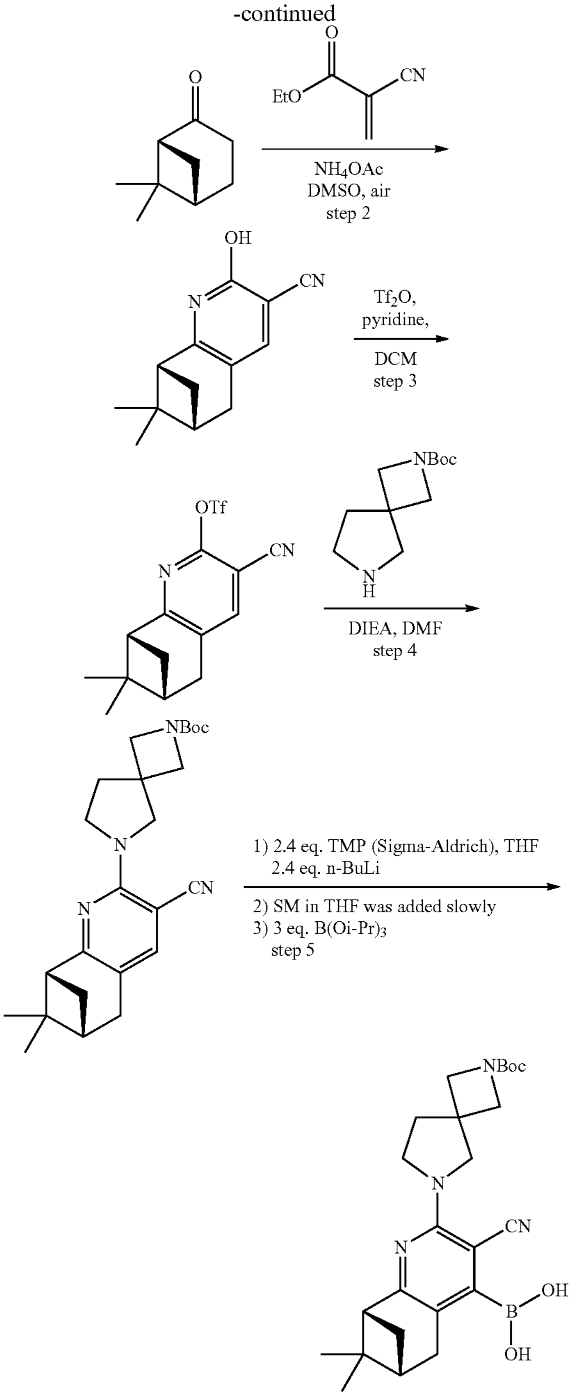

Intermediate 33

Step 1: (1R,5S)-6,6-dimethylnorpinan-2-one

See Intermediate 23 Step 1.

Step 2: (1R,9R)-4-hydroxy-10,10-dimethyl-3-azatricyclo[7.1.1.0;]undeca-2(7),3,5-triene-5-carbonitrile To a solution of (1R,5S)-6,6-dimethylnorpinan-2-one (50 g, 361.78 mmol) and $NH_4OAc$ (83.66 g, 1.09 mol) in DMSO (500 mL) was added ethyl 2-cyanoprop-2-enoate (90.53 g, 723.56 mmol, Beijing FeiLongrui Trading). The mixture was stirred at 80° C. for 36 h. The reaction mixture was diluted with $H_2O$ (2 L) and extracted with EtOAc (3×1 L). The combined organic layers were washed with brine (4×500 mL), dried over $Na_2SO_4$, and concentrated under reduced pressure. The residue was purified by column chromatography ($SiO_2$, petroleum ether/EtOAc=100/1 to 0/1) to provide (1R,9R)-4-hydroxy-10,10-dimethyl-3-azatricyclo[7.1.1.$0^{2,7}$]undeca-2(7),3,5-triene-5-carbonitrile (15 g, 70.01 mmol, 9.68% yield) as a white solid.

Step 3: [(1R,9R)-5-cyano-10,10-dimethyl-3-azatricyclo[7.1.1.$0^{2,7}$]undeca-2(7),3,5-trien-4-yl] trifluoromethanesulfonate To a solution of (1R,9R)-4-hydroxy-10,10-dimethyl-3-azatricyclo[7.1.1.$0^{2,7}$]undeca-2(7),3,5-triene-5-carbonitrile (15.2 g, 70.94 mmol) and pyridine (17.18 mL, 212.82 mmol) in DCM (150 mL) was added $Tf_2O$ (17.56 mL, 106.41 mmol) in DCM (20 mL) at 0° C. The mixture was stirred at 15° C. for 15 min. The reaction mixture was diluted with aqueous $NaHCO_3$ (200 mL) and extracted with EtOAc (3×100 mL). The combined organic layers were washed with brine (2×100 mL), dried over $Na_2SO_4$, and concentrated under reduced pressure to provide [(1R,9R)-5-cyano-10,10-dimethyl-3-azatricyclo[7.1.1.$0^{2,7}$]undeca-2(7),3,5-trien-4-yl]trifluoromethanesulfonate (75 g, crude) as a yellow solid.

Step 4: tert-butyl 7-[(1R,9R)-5-cyano-10,10-dimethyl-3-azatricyclo[7.1.1.04]undeca-2,4,6-trien-4-yl]-2,7-diazaspiro[3.4]octane-2-carboxylate To a solution of [(1R,9R)-5-cyano-10,10-dimethyl-3-azatricyclo[7.1.1.$0^{2,7}$]undeca-2(7),3,5-trien-4-yl] trifluoromethanesulfonate (25 g, 72.19 mmol) and tert-butyl 2,7-diazaspiro-[3.4]octane-2-carboxylate (16.86 g, 79.41 mmol, Labnetwork) in DMF (250 mL) was added DIPEA (37.72 mL, 216.56 mmol). The mixture was stirred at 50° C. for 1 h. The reaction mixture was diluted with $H_2O$ (500 mL) and extracted with EtOAc (3×100 mL). The combined organic layers were washed with brine (2×100 mL), dried over $Na_2SO_4$, and concentrated under reduced pressure. The residue was purified by column chromatography ($SiO_2$, petroleum ether/EtOAc=100/1 to 3/1) to provide tert-butyl 7-[(1R,9R)-5-cyano-10,10-dimethyl-3-azatricyclo[7.1.1.$0^{2,7}$]undeca-2,4,6-trien-4-yl]-2,7-diazaspiro[3.4]octane-2-carboxylate (25.7 g, 62.99 mmol, 87.26% yield) as a white solid.

Step 5: [(1R,9R)-4-(2-tert-butoxycarbonyl-2,7-diazaspiro[3.4]octan-7-yl)-5-cyano-10,10-dimethyl-3-azatricyclo[7.1.1.$0^{2,7}$]undeca-2,4,6-trien-6-yl]boronic acid To a solution of 2,2,6,6-tetramethylpiperidine (6.98 mL, 41.12 mmol) in THF (100 mL) was added dropwise n-BuLi (2.5M, 16.45 mL) at −40° C. The mixture was stirred at −40° C. for 30 min. Tert-butyl 7-[(1R,9R)-5-cyano-10,10-dimethyl-3-azatricyclo[7.1.1.$0^{2,7}$]undeca-2,4,6-trien-4-yl]-2,7-diazaspiro[3.4]octane-2-carboxylate (7 g, 17.13 mmol) in THF (300 mL) was added dropwise to the mixture at −78° C. and stirred for 1 h. Then triisopropyl borate (14.18 mL, 61.68 mmol) was added dropwise to the mixture at −78° C. The resulting mixture was stirred at −78° C. for 2 h. The reaction mixture was quenched by addition of $H_2O$ (300 mL) at 0° C. and extracted with EtOAc (3×100 mL). The combined organic layers were washed with brine (2×150 mL), dried over $Na_2SO_4$, and concentrated under reduced pressure to provide [(1R,9R)-4-(2-tert-butoxycarbonyl-2,7-diazaspiro[3.4]octan-7-yl)-5-cyano-10,10-dimethyl-3-aza-tricyclo[7.1.1.$0^{2,7}$]undeca-2,4,6-trien-6-yl]boronic acid (5.5 g, 10.94 mmol, 63.86% yield) as a white solid. m/z (ESI): 453.3 $(M+H)^+$. $^1H$ NMR (400 MHz, Methanol-$d_6$) δ ppm 3.79-3.94 (m, 8H), 2.72-2.78 (m, 3H), 2.31 (s, 1H), 2.19 (t, J=6.80 Hz, 2H), 1.77-1.82 (m, 1H), 1.45 (s, 9H), 1.41 (s, 3H), 1.23 (d, J=9.60 Hz, 1H), 0.69 (s, 3H).

Intermediate 34: tert-butyl 7-(4-chloro-3-cyano-7,7-dimethyl-5,8-dihydropyrano[4,3-b]pyridin-2-yl)-2,7-diazaspiro[3.4]octane-2-carboxylate

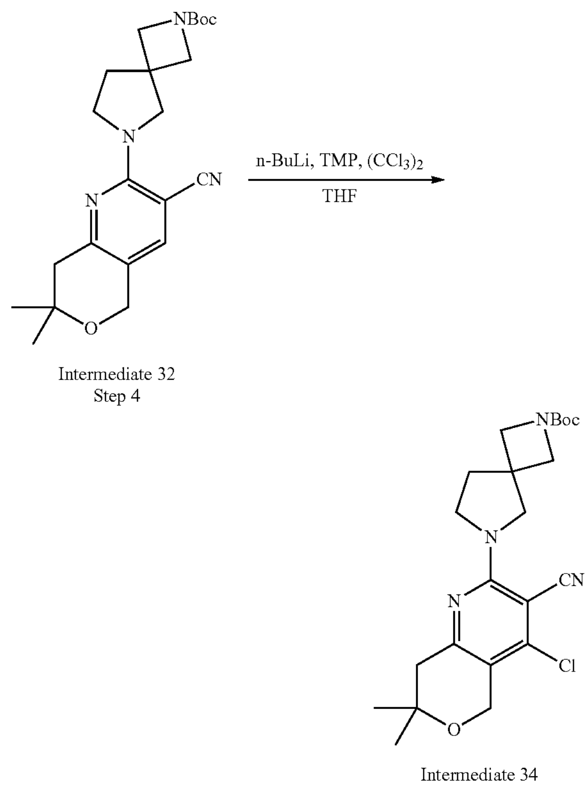

Intermediate 32 Step 4

Intermediate 34

To a solution of 2,2,6,6-tetramethylpiperidine (3.20 mL, 18.82 mmol) in THF (10 mL) was added dropwise n-BuLi (2.5M, 7.53 mL) at −60° C. The mixture was added dropwise to a solution of tert-butyl 7-(3-cyano-7,7-dimethyl-5,8-dihydropyrano[4,3-b]pyridin-2-yl)-2,7-diazaspiro[3.4]octane-2-carboxylate (5 g, 12.55 mmol, Intermediate 32, Step 4) in THF (50 mL) at −60° C. and the reaction mixture was stirred at −60° C. for 10 min. Hexachloroethane (4.26 mL, 37.64 mmol) in THF (10 mL) was added to the mixture at −60° C. The reaction mixture was stirred at −60° C. for 20 min. The reaction mixture was poured slowly into aqueous $NH_4Cl$ (500 mL) and extracted with EtOAc (3×250 mL). The combined organic layers were washed with brine (2×500 mL), dried over $Na_2SO_4$, and concentrated under reduced pressure. The residue was purified by column chromatography ($SiO_2$, petroleum ether/EtOAc=20/1 to 3/1) to provide tert-butyl 7-(4-chloro-3-cyano-7,7-dimethyl-5,8-dihydropyrano[4,3-b]pyridin-2-yl)-2,7-diazaspiro[3.4]octane-2-carboxylate (16.5 g, 37.73 mmol, 75.18% yield) as a yellow solid. m/z (ESI): 377.0 $(M-tBu)^+$. $^1H$ NMR (400 MHz, $CDCl_3$) δ ppm 4.59 (s, 2H), 3.75-3.87 (m, 8H) 2.61 (s, 2H), 2.10 (t, J=6.80 Hz, 2H), 1.38 (s, 9H), 1.22 (s, 6H).

Intermediate 35: tert-butyl 7-[(1R,9R)-6-chloro-5-cyano-10,10-dimethyl-3-azatricyclo[7.1.1.$0^{2,7}$]undeca-2,4,6-trien-4-yl]-2,7-diazaspiro[3.4]octane-2-carboxylate

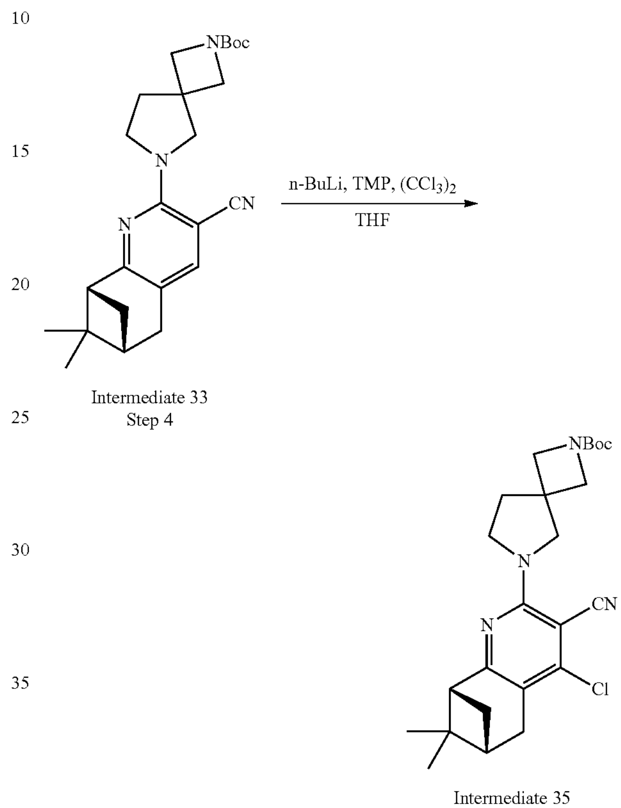

Intermediate 33 Step 4

Intermediate 35

To a solution of 2,2,6,6-tetramethylpiperidine (8.98 mL, 52.87 mmol) in THF (100 mL) was added dropwise n-BuLi (2.5 M, 21.15 mL) at −40° C. The mixture was stirred at −40° C. for 30 min, then a solution of tert-butyl 7-[(1R,9R)-5-cyano-10,10-dimethyl-3-azatricyclo-[7.1.1.$0^{2,7}$]undeca-2,4,6-trien-4-yl]-2,7-diazaspiro[3.4]octane-2-carboxylate (9 g, 22.03 mmol, Intermediate 33, Step 4) in THF (30 mL) was added dropwise to the mixture at −78° C. and stirred for 60 min. Then a solution of 1,1,1,2,2,2-hexachloroethane (26.08 g, 110.15 mmol, 12.48 mL) in THF (30 mL) was added to the mixture at −78° C. The resulting mixture was stirred at −78° C. for 2 h. The reaction mixture was quenched by addition of $H_2O$ (800 mL) at 0° C., and extracted with EtOAc (3×200 mL). The combined organic layers were washed with brine (2×150 mL), dried over $Na_2SO_4$, and concentrated under reduced pressure. The residue was purified by column chromatography ($SiO_2$, petroleum ether/EtOAc=100/1 to 3/1) to provide tert-butyl 7-[(1R,9R)-6-chloro-5-cyano-10,10-dimethyl-3-azatricyclo[7.1.1.$0^{17}$] undeca-2,4,6-trien-4-yl]-2,7-diazaspiro-[3.4]octane-2-carboxylate (12.82 g) as a brown solid. m/z (ESI): 387.1 $(M-tBu)^+$. $^1H$ NMR (400 MHz, Methanol-$d_4$) δ ppm 3.80-3.94 (m, 8H), 2.73-2.81 (m, 4H), 2.35-2.37 (m, 1H), 2.20 (t, J=6.80 Hz, 2H), 1.45 (s, 9H), 1.41 (s, 3H), 1.23 (d, J=6.00 Hz, 1H), 0.68 (s, 3H).

Intermediate 36: 2,4-dichloro-3,7,7-trimethyl-6,8-dihydro-5H-quinoline

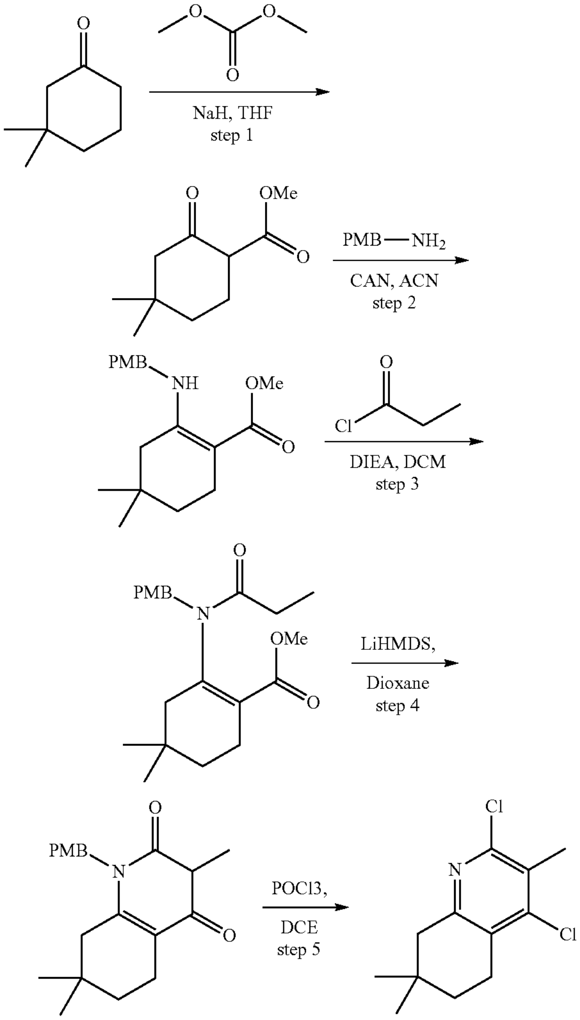

Intermediate 36

This intermediate was synthesized in an analagous manner to Intermediate 22 using 3,3-dimethylcyclohexanone. m/z (ESI): 244.0 $(M+H)^+$. $^1$H NMR (400 MHz, DMSO) δ ppm 2.66 (t, J=6.40 Hz, 2H) 2.54 (s, 2H), 2.35 (s, 3H), 1.55 (t, J=6.40 Hz, 2H), 0.93 (s, 6H).

Intermediate 37: 5-chloro-6-methyl-7-(4,4,5,5-tetramethyl-1,3,2-dioxaborolan-2-yl)-1H-indazole

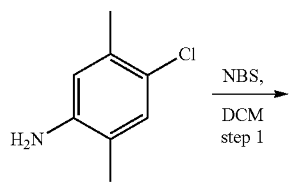

-continued

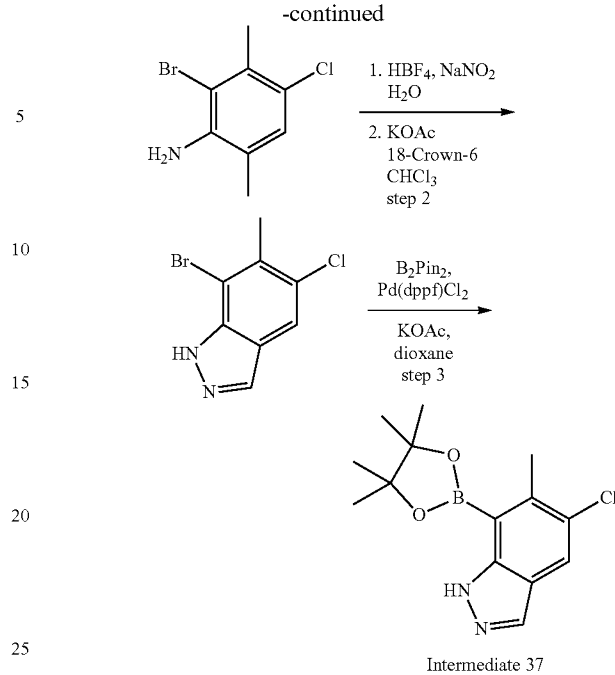

Intermediate 37

Step 1: 2-bromo-4-chloro-3,6-dimethyl-aniline

To a solution of 4-chloro-2,5-dimethyl-aniline (40 g, 257.03 mmol, Orgunion) in DCM (400 mL) was added NBS (50.32 g, 282.73 mmol) in portions at 0° C. The mixture was warmed to 25° C. and stirred for 3 h. The mixture was diluted with $H_2O$ (500 mL) and extracted with EtOAc (2×150 mL). The combined organic layers were washed with brine (2×150 mL), dried over $Na_2SO_4$, filtered and concentrated under reduced pressure. The residue was purified by column chromatography ($SiO_2$, petroleum ether/EtOAc=100/1 to 3/1) to provide 2-bromo-4-chloro-3,6-dimethyl-aniline (49 g. 81.29% yield) as a pink solid. $^1$H NMR (400 MHz, $CDCl_3$) δ ppm 7.04 (s, 1H), 4.13 (br s, 2H), 2.48 (s, 3H), 2.19 (s, 3H).

Step 2: 7-bromo-5-chloro-6-methyl-1H-indazole

To a RBF charged with 2-bromo-4-chloro-3,6-dimethyl-aniline (49 g, 208.94 mmol) was added $HBF_4$ (487.96 mL, 3.13 mol, 40 wt %) in one portion at 0° C. under $N_2$, then $NaNO_2$ (28.83 g, 417.87 mmol) in $H_2O$ (50 mL) was added dropwise to the solution. The solution was stirred at 0° C. for 1 h, then stirred at 25° C. for 0.5 h. The resulting precipitate was filtered, washed with $(i\text{-}Pr)_2O$ (300 mL) and concentrated in vacuo. The crude diazonium salt was added to a solution of KOAc (41.01 g. 417.87 mmol) and 1,4,7,10,13,16-hexaoxacyclooctadecane (2.76 g, 10.45 mmol) in $CHCl_3$ (600 mL). The mixture was stirred at 35° C. for 0.5 h. The mixture was filtered and concentrated under reduced pressure. The residue was purified by column chromatography ($SiO_2$, petroleum ether/EtOAc=100/1 to 3/1) to provide 7-bromo-5-chloro-6-methyl-1H-indazole (34 g, 64.96% yield) as a brown solid. $^1$H NMR (400 MHz, DMSO-$d_6$) δ ppm 8.16 (s, 1H), 7.92 (s, 1H), 2.56 (s, 3H).

Step 3: 5-chloro-6-methyl-7-(4,4,5,5-tetramethyl-1,3,2-dioxaborolan-2-yl)-1H-indazole To a solution of 7-bromo-5-chloro-6-methyl-1H-indazole (6.8 g, 23.67 mmol) and 4,4,5,5-tetramethyl-2-(4,4,5,5-tetramethyl-1,3,2-dioxaborolan-2-yl)-1,3,2-dioxaborolane (48.08 g, 189.33 mmol) in dioxane (230 mL) was added $PdCl_2$(dppf) (1.73 g, 2.37 mmol) and KOAc (6.97 g, 71.00 mmol). The mixture was stirred at 100° C. for 12 h. The reaction mixture was diluted with $H_2O$ (100 mL) and extracted with EtOAc (2×50 mL). The combined organic layers were washed with brine (2×50 mL), dried over $Na_2SO_4$, filtered and concentrated under reduced pressure. The residue was purified by column chromatography ($SiO_2$, petroleum ether/EtOAc=100/1 to 3/1) to provide 5-chloro-6-methyl-7-(4,4,5,5-tetramethyl-1,3,2-dioxaborolan-2-yl)-1H-indazole (3.4 g, 28.05% yield) as a white solid. m/z (ESI): 293.2 $(M+H)^+$. $^1H$ NMR (400 MHz, DMSO-$d_6$) δ ppm 12.40 (br s, 1H), 8.04 (s, 1H), 7.99 (s, 1H), 2.64 (s, 3H), 1.38 (s, 12H).

Intermediate 38: 5,6-dimethyl-7-(4,4,5,5-tetramethyl-1,3,2-dioxaborolan-2-yl)-1H-indazole

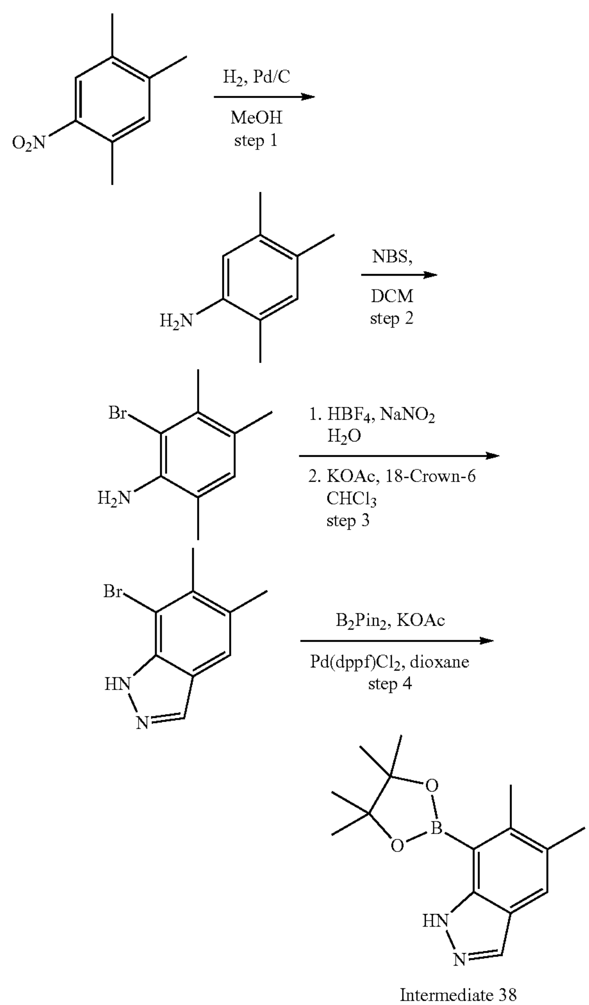

Intermediate 38

Step 1: 2,4,5-trimethylaniline

To a solution of 1,2,4-trimethyl-5-nitro-benzene (80 g, 484.29 mmol, TCAS Chem) in MeOH (1 L) was added Pd/C (30 g, 10 wt %). The suspension was degassed under vacuum and purged with $H_2$ (30 psi) several times. The mixture was stirred under $H_2$ (30 psi) at 30° C. for 12 h. The mixture was filtered and the filtrate was concentrated under reduced pressure. The residue was washed by Petroleum ether (300 mL) to provide 2,4,5-trimethylaniline (63 g, crude) as a red solid that was carried forward without further purification. $^1H$ NMR (400 MHz, $CDCl_3$) δ ppm 6.84 (s, 1H), 6.53 (s, 1H), 2.18 (s, 3H), 2.16 (s, 3H), 2.14 (s, 3H).

Steps 2-4: These steps were carried out in an analogous manner to Intermediate 37, Steps 1-3 to provide 5,6-dimethyl-7-(4,4,5,5-tetramethyl-1,3,2-dioxaborolan-2-yl)-1H-indazole (10 g, 36.01 mmol, 54.44% yield) as a white solid. m/z (ESI): 273.1 $(M+H)^+$. $^1H$ NMR (400 MHz, $CDCl_3$) δ ppm 7.95 (s, 1H), 7.63 (s, 1H), 2.65 (s, 3H), 2.39 (s, 3H), 1.44 (s, 3H).

Intermediate 39: 4,6-dichloro-1-methyl-1H-pyrrolo[2,3-b]pyridine-5-carbonitrile

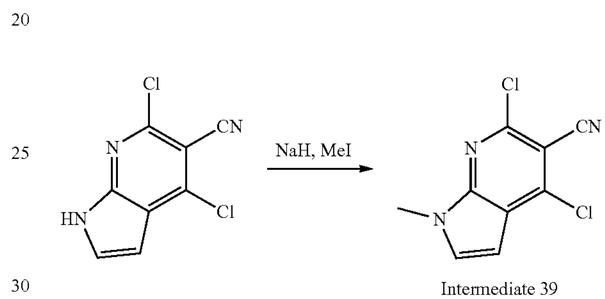

Intermediate 39

To a solution of 4,6-dichloro-1H-pyrrolo[2,3-b]pyridine-5-carbonitrile (300 mg, 1.415 mmol, CAS: 2393885-54-4, WO 2019/232319) in DMF (1 mL) at room temperature was added NaH (34.0 mg, 1.415 mmol). The mixture was stirred at room temperature for 30 min, then iodomethane (241 mg, 1.698 mmol) was added. The mixture was stirred at 90° C. for 2 h, then carefully quenched with water until no bubbles were observed. The mixture was extracted with EtOAc (2×100 mL). The combined organic extracts were then dried over $MgSO_4$ and concentrated in vacuo. Chromatographic purification of the residue (silica gel, 0%-100% EtOAc/heptanes) provided 4,6-dichloro-1-methyl-1H-pyrrolo[2,3-b]pyridine-5-carbonitrile (220 mg, 0.973 mmol, 68.8% yield).

Intermediate 40: tert-butyl 6-(3-cyano-7-cyclopropyl-4-iodoquinolin-2-yl)-2,6-diazaspiro[3.4]octane-2-carboxylate

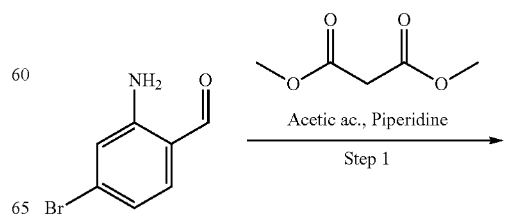

-continued

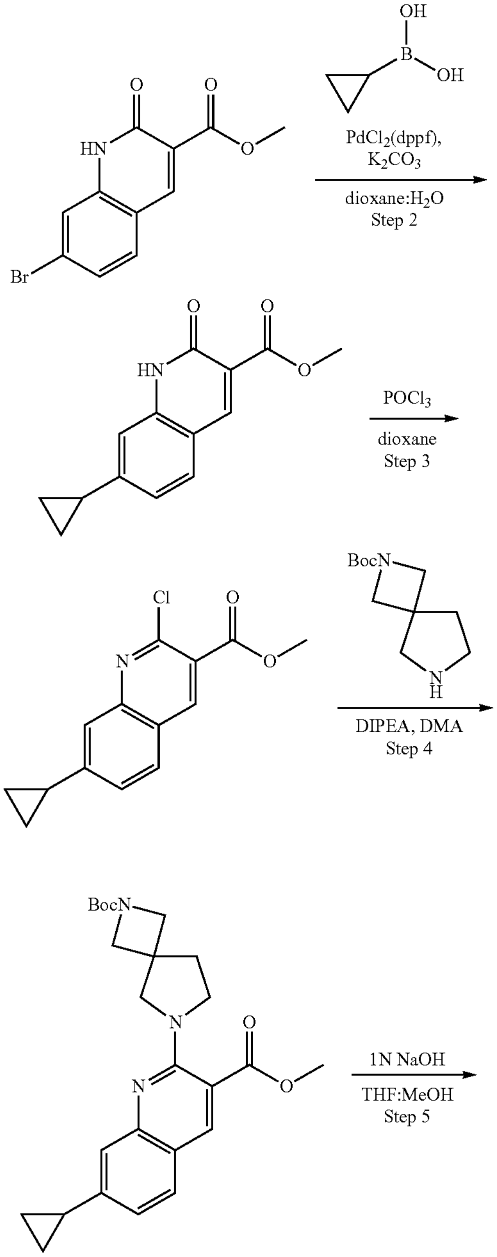

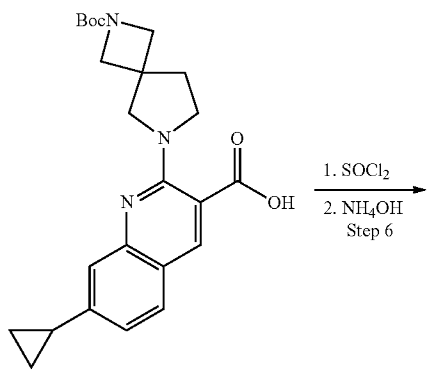

-continued

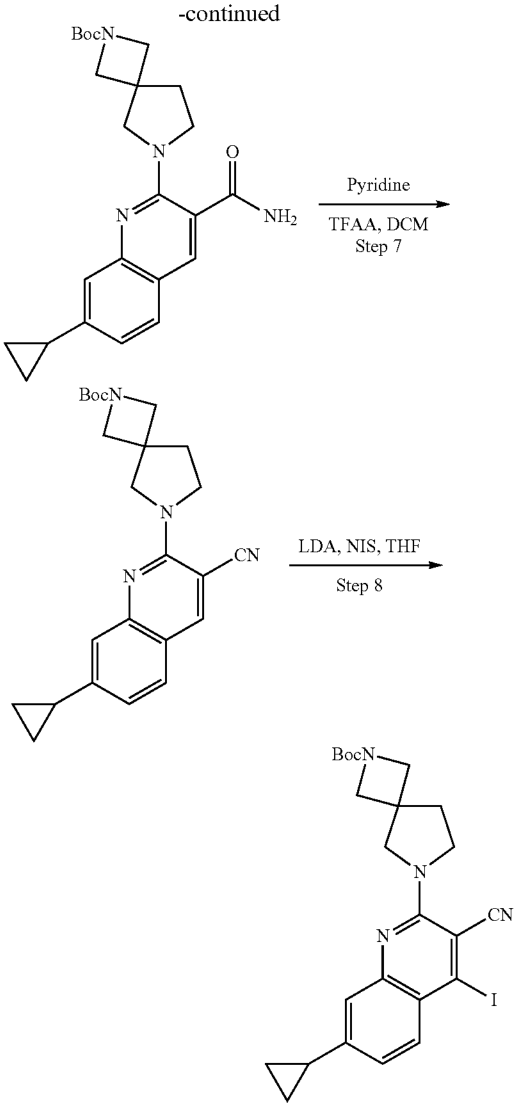

Intermediate 40

Step 1: Methyl 7-bromo-2-oxo-1,2-dihydroquinoline-3-carboxylate

A mixture of 2-amino-4-bromobenzaldehyde (2.80 g, 14.00 mmol, Ark Pharm), 1,3-dimethyl propanedioate (4.46 mL, 39.2 mmol, TC America), piperidine (4.16 mL, 42.0 mmol, Spectrum Chemical) and acetic acid (0.088 mL, 1.540 mmol, Sigma-Aldrich) in MeOH (40 mL) was heated at 60° C. After stirring overnight, the reaction was allowed to cool to room temperature. The white precipitate was filtered, washed with MeOH and dried under high vacuum to afford methyl 7-bromo-2-oxo-1,2-dihydroquinoline-3-carboxylate (3.50 g, 12.41 mmol, 89% yield) as a pale-yellow solid. m/z (ESI): 303.8 $(M+Na)^+$

Step 2: methyl 7-cyclopropyl-2-oxo-1,2-dihydroquinoline-3-carboxylate

A mixture of methyl 7-bromo-2-oxo-1,2-dihydroquinoline-3-carboxylate (0.530 g, 1.879 mmol), cyclopropylboronic acid (0.484 g, 5.64 mmol. Combi-Blocks), $PdCl_2$ (dppf)-DCM (1:1) (0.153 g, 0.188 mmol, Sigma-Aldrich) and $K_2CO_3$ (1.039 g, 7.52 mmol, Sigma-Aldrich) was purged with $N_2$ followed by the addition of 1,4-dioxane: water (10:1 mL) and the resulting mixture was heated at 90° C. for 3 h. The mixture was cooled to room temperature, diluted with aqueous saturated $NaHCO_3$ and extracted with EtOAc. The combined organics were dried over $Na_2SO_4$, filtered, concentrated and chromatographed on silica gel using 0-30% (3:1, EtOAc:EtOH) in heptanes to afford methyl 7-cyclopropyl-2-oxo-1,2-dihydroquinoline-3-carboxylate (0.170 g, 0.699 mmol, 37.2% yield) as a light yellow solid. m/z (ESI): 244.2 $(M+H)^+$ Step 3: methyl 7-bromo-2-chloroquinoline-3-carboxylate To a solution of methyl 7-bromo-2-oxo-1,2-dihydroquinoline-3-carboxylate (0.500 g, 1.772 mmol) in 1,4-dioxane (4 mL) was added $POCl_3$ (3.30 mL, 35.4 mmol, Sigma-Aldrich). The reaction was stirred at 100° C. for 40 min. The reaction was allowed to cool to room temperature, carefully poured into cold aqueous saturated $NaHCO_3$ to basify the reaction. The mixture was extracted with EtOAc and the combined organics were dried over $Na_2SO_4$, filtered and concentrated to afford methyl 7-bromo-2-chloroquinoline-3-carboxylate (0.523 g, 1.740 mmol, 98% yield) as a light yellow solid. m/z (ESI): 262.0, 264.1 $(M+H)^+$.

Step 4: methyl 2-(2-(tert-butoxycarbonyl)-2,6-diazaspiro[3.4]octan-6-yl)-7-cyclopropylquinoline-3-carboxylate A mixture of methyl 2-chloro-7-cyclopropylquinoline-3-carboxylate (0.183 g, 0.699 mmol), 2-(tert-butoxycarbonyl)-2,6-diazaspiro[3.4]octane (0.223 g, 1.049 mmol, Combi-Blocks) and DIPEA (0.366 mL, 2.098 mmol, Sigma-Aldrich) in DMA (5 mL) was heated at 120° C. for 1 h. The reaction was brought to room temperature, washed with aqueous saturated $NH_4Cl$, water, brine and dried over $Na_2SO_4$, and concentrated in vacuo. The material was chromatographed on silica gel using 0-30% (3:1, EtOAc:EtOH) in heptanes to afford methyl 2-(2-(tert-butoxycarbonyl)-2,6-diazaspiro[3.4]octan-6-yl)-7-cyclopropylquinoline-3-carboxylate (0.246 g, 0.562 mmol, 80% yield) as a light yellow foam. m/z (ESI): 438.1 $(M+H)^+$.

Step 5: 2-(2-(tert-butoxycarbonyl)-2,6-diazaspiro[3.4]octan-6-yl)-7-cyclopropylquinoline-3-carboxylic acid To a solution of methyl 2-(2-(tert-butoxycarbonyl)-2,6-diazaspiro[3.4]octan-6-yl)-7-cyclopropylquinoline-3-carboxylate (0.720 g, 1.646 mmol) in THF/MeOH (8 mL, 1:1) was added NaOH (15 mL, 15.00 mmol, Fisher Chemical) and the resulting mixture was heated at 90° C. for 4 h. The reaction was brought to room temperature and acidified to a pH=6 with 1M HCl (4 mL). The resulting mixture was extracted with DCM and the combined organics were dried over $Na_2SO_4$, filtered and concentrated to afford 2-(2-(tert-butoxycarbonyl)-2,6-diazaspiro[3.4]octan-6-yl)-7-cyclopropylquinoline-3-carboxylic acid (0.700 g, 1.653 mmol, 100% yield) as a light yellow foam. m/z (ESI): 423.8 $(M+H)^+$.

Step 6: tert-butyl 6-(3-carbamoyl-7-cyclopropylquinolin-2-yl)-2,6-diazaspiro[3.4]octane-2-carboxylate A mixture of 2-(2-(tert-butoxycarbonyl)-2,6-diazaspiro[3.4]octan-6-yl)-7-cyclopropylquinoline-3-carboxylic acid (0.700 g, 1.653 mmol) in DCE (15 mL) was brought to 0° C., then $SOCl_2$ (0.180 mL, 2.468 mmol, Sigma-Aldrich) was added and the mixture was heated at 80° C. for 1 h. The excess of $SOCl_2$ was removed in vacuo, and the resulting residue was dissolved in THF (15 mL) and brought to 0° C., then $NH_4OH$ (0.915 mL, 6.58 mmol, J. T. Baker, 30 wt %) was added dropwise. The mixture was stirred at 0° C. and after 15 min, the reaction was concentrated to afford tert-butyl 6-(3-carbamoyl-7-cyclopropylquinolin-2-yl)-2,6-diazaspiro[3.4]octane-2-carboxylate to be used as is. The residue was azeotropically dried with toluene. m/z (ESI): 422.8 $(M+H)^+$.

Step 7: tert-butyl 6-(3-cyano-7-cyclopropylquinolin-2-yl)-2,6-diazaspiro[3.4]octane-2-carboxylate To a solution of tert-butyl 6-(3-carbamoyl-7-cyclopropylquinolin-2-yl)-2,6-diazaspiro-[3.4]octane-2-carboxylate (0.695 g, 1.645 mmol) and pyridine (0.266 mL, 3.29 mmol. Sigma-Aldrich) in DCM (3 mL) was cooled to 0° C. Then TFAA (0.465 mL, 3.29 mmol, Sigma-Aldrich) was added dropwise. After the addition, the ice-bath was removed and the reaction stirred for 10 min. The mixture was quenched with water and extracted with DCM. The combined organics were concentrated and chromatographed on silica gel using 0-40% EtOAc in heptanes to afford tert-butyl 6-(3-cyano-7-cyclopropylquinolin-2-yl)-2,6-diazaspiro-[3.4]octane-2-carboxylate. m/z (ESI): 426.8 $(M+Na)^+$.

Step 8: Tert-butyl 6-(3-cyano-7-cyclopropyl-4-iodoquinolin-2-yl)-2,6-diazaspiro[3.4]octane-2-carboxylate A solution of tert-butyl 6-(3-cyano-7-cyclopropylquinolin-2-yl)-2,6-diazaspiro[3.4]octane-2-carboxylate (0.28 g, 0.692 mmol) in THF (5 mL) was brought to −78° C. followed by the drop-wise addition of LDA (1.038 mL, 1.038 mmol. Sigma-Aldrich). The mixture was stirred at −78° C. for 1 h, then a solution of iodine (0.211 g, 0.831 mmol, Sigma-Aldrich) in THF (2 mL) was added drop-wise. After stirring for 1 h, additional LDA and iodine (0.211 g, 0.831 mmol, Sigma-Aldrich) were added at −78° C. and stirred for 1 h. The reaction was quenched with water and extracted with EtOAc. The combined organics were chromatographed on silica gel using 0-10% EtOAc in heptanes to afford tert-butyl 6-(3-cyano-7-cyclopropyl-4-iodoquinolin-2-yl)-2,6-diazaspiro[3.4]octane-2-carboxylate (0.101 g, 0.190 mmol, 27.5% yield) as a bright yellow foam, m/z (ESI): 530.8 $(M+H)^+$.

Intermediate 41: tert-butyl 6-(3-cyano-4-iodo-7-methoxyquinolin-2-yl)-8,8-difluoro-2,6-diazaspiro[3.4]octane-2-carboxylate

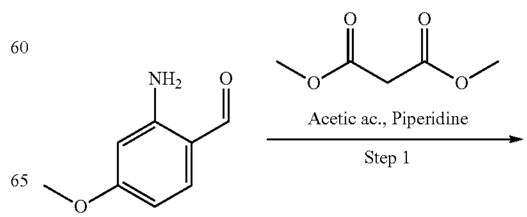

-continued

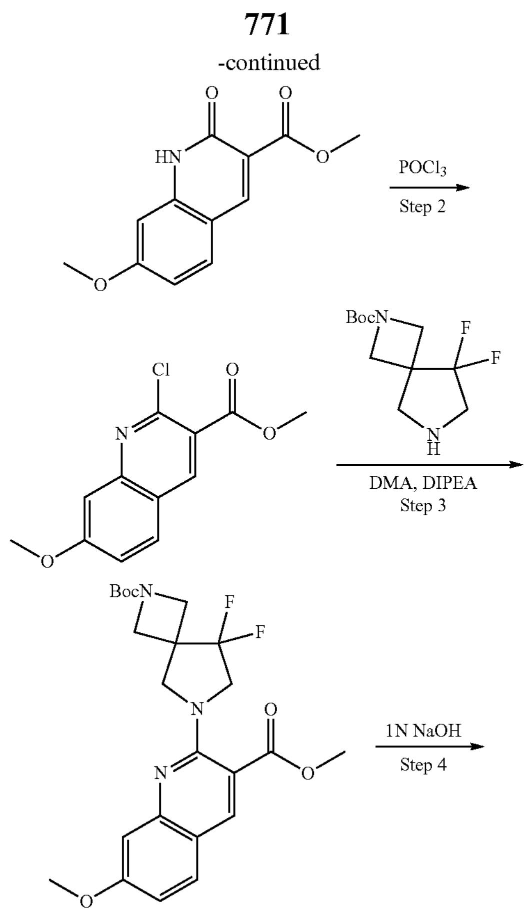

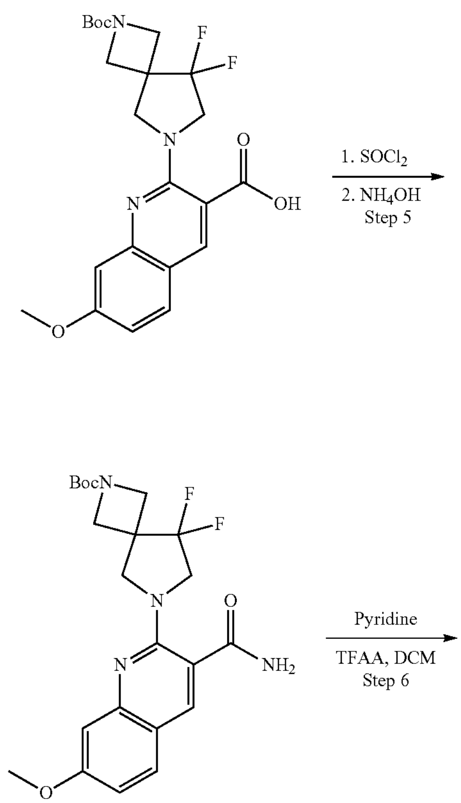

-continued

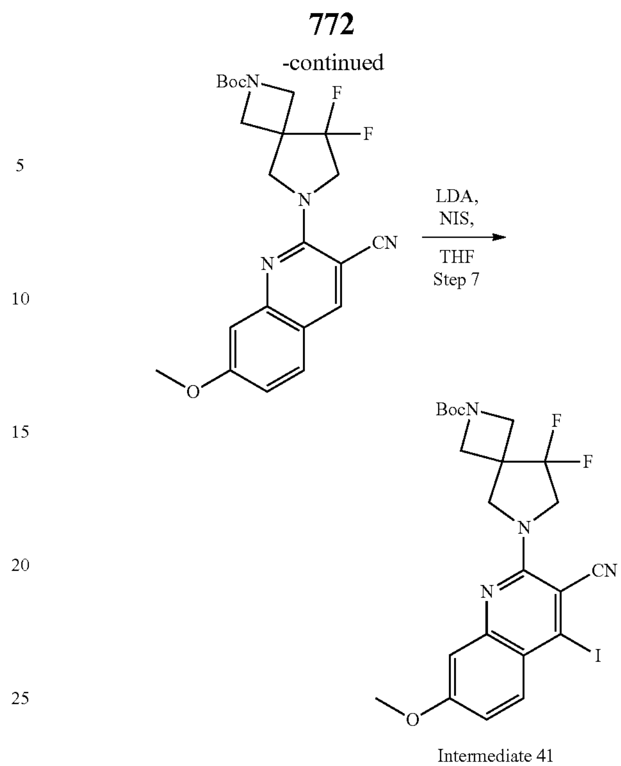

Intermediate 41

Intermediate 41 was synthesized in an analogous manner to Intermediate 40 omitting the Suzuki-Miyaura coupling step. 2-amino-4-methoxybenzaldehyde (AChemblock) was used in Step 1 and tert-butyl 8,8-difluoro-2,6-diazaspiro[3.4]octane-2-carboxylate (PharmaBlock) was used in Step 3.

Intermediate 42: tert-butyl 6-(3-cyano-4-iodo-7-methoxyquinolin-2-yl)-5-methyl-2,6-diazaspiro[3.4]octane-2-carboxylate

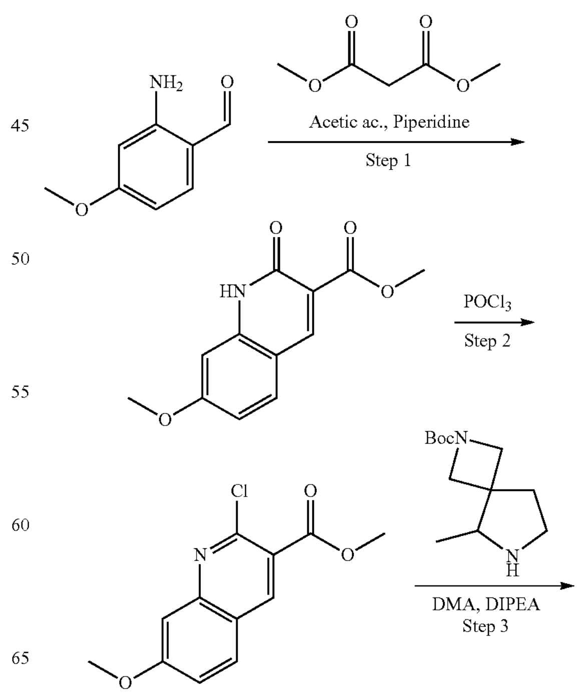

-continued
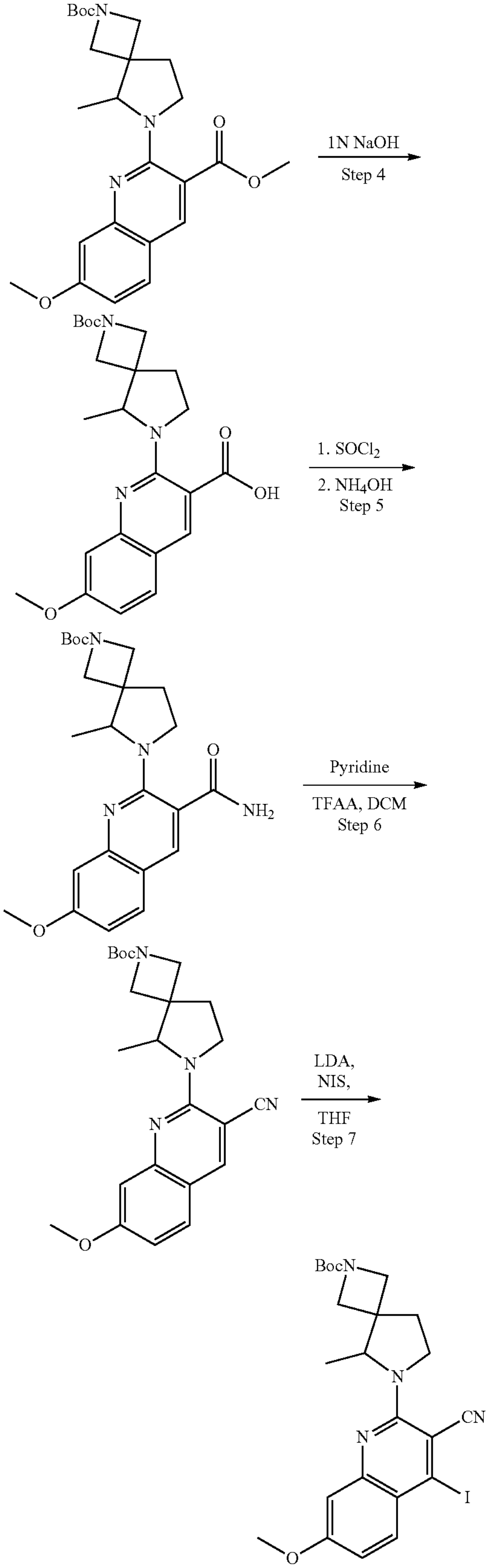
Intermediate 42
Intermediate 42 was synthesized in an analogous manner to Intermediate 41 but using tert-butyl 5-methyl-2,6-diazaspiro[3.4]octane-2-carboxylate (Enamine) in Step 3.
Intermediate 43: tert-butyl 6-(7-bromo-3-cyano-4-iodoquinolin-2-yl)-2,6-diazaspiro[3.4]octane-2-carboxylate
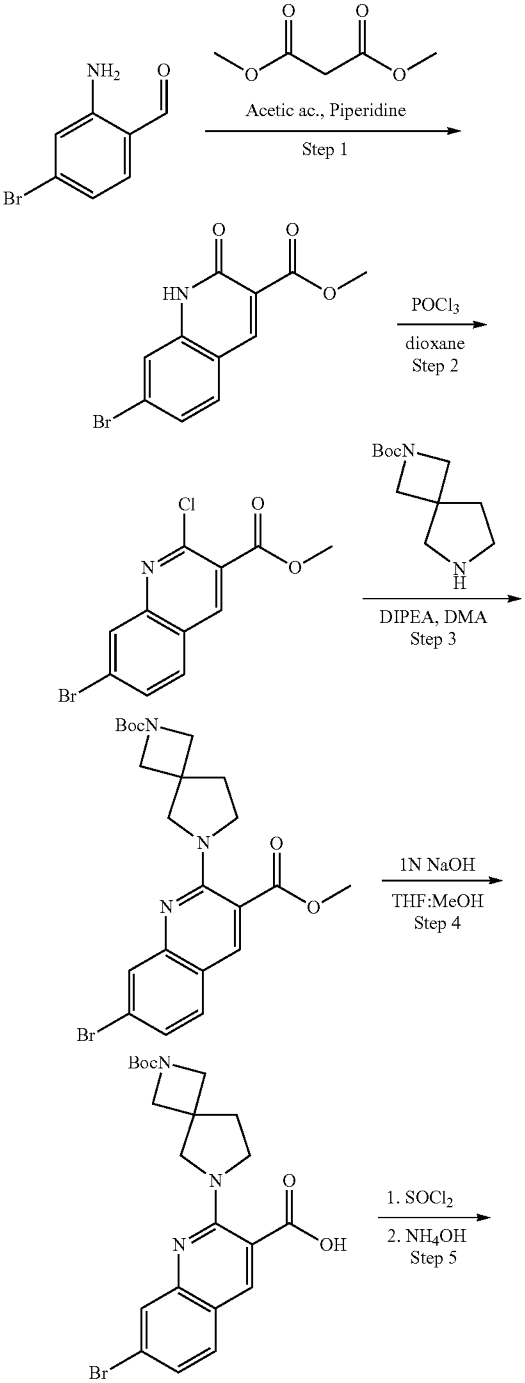

-continued

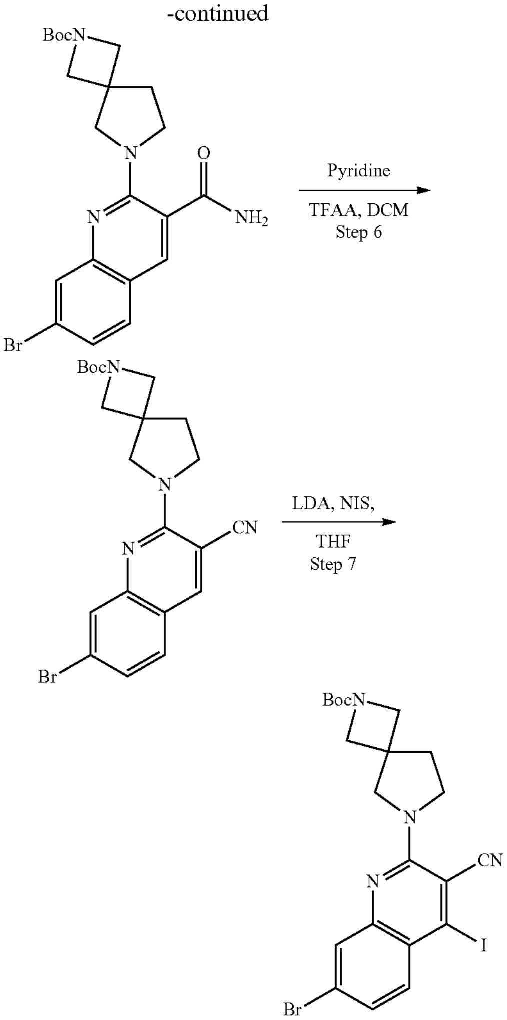

Intermediate 43

Intermediate 43 was synthesized in an analogous manner to Intermediate 40 omitting the Suzuki-Miyaura coupling step.

Intermediate 44: 7-bromo-2,4-dichloro-3-methylquinoline

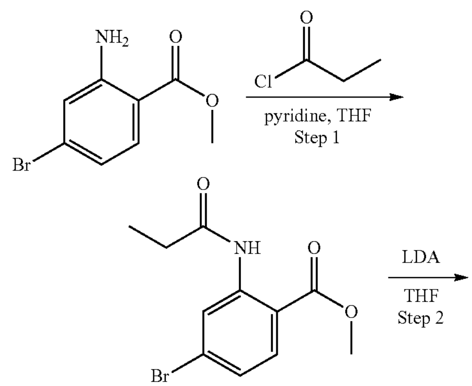

-continued

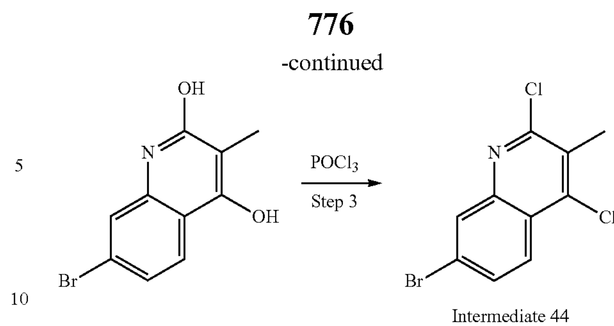

Intermediate 44

Step 1: methyl 4-bromo-2-propionamidobenzoate

To a solution of methyl 2-amino-4-bromobenzoate (1.18 g, 5.13 mmol, Combi-Blocks) in THF (30 mL) was added pyridine (0.830 mL, 10.26 mmol, Sigma-Aldrich) followed by the addition of propionyl chloride (0.896 mL, 10.26 mmol, Sigma-Aldrich). After stirring at room temperature for 15 min, the reaction was diluted with EtOAc, washed with aqueous saturated $NH_4Cl$, and water. The combined organics were dried over $Na_2SO_4$, and concentrated to afford methyl 4-bromo-2-propionamidobenzoate (1.40 g, 4.89 mmol, 95% yield) as a light yellow solid to be used as is. m/z (ESI): 285.9 $(M+H)^+$.

Step 2: methyl 4-bromo-2-propionamidobenzoate

To a solution of methyl 4-bromo-2-propionamidobenzoate (1.40 g, 4.89 mmol) in THF (15 mL) at room temperature was added LDA (9.79 mL, 9.79 mmol, Sigma-Aldrich) and the mixture was heated at 80° C. for 7 h. The reaction was brought to room temperature and quenched with MeOH. To the quenched solution was added some silica gel and the mixture was concentrated in vacuo and chromatographed on silica gel (12 g) using 0-20% (3:1) EtOAc:EtOH in heptanes and then 10% MeOH in DCM to afford 7-bromo-3-methylquinoline-2,4-diol (0.983 g, 3.87 mmol, 79% yield) as a yellow foam. Azeotropically dried with toluene. m/z (ESI): 253.8 $(M+H)^+$.

Step 3: 7-bromo-2,4-dichloro-3-methylquinoline

To a solution of 7-bromo-3-methylquinoline-2,4-diol (0.983 g, 3.87 mmol) in 1,4-dioxane (15 mL) was added $POCl_3$ (5.41 mL, 58.0 mmol, Sigma-Aldrich). The reaction was stirred at 100° C. for 30 min. The reaction was cooled to room temperature, carefully poured into cold aqueous saturated $NaHCO_3$, then solid $K_2CO_3$ was added in portions to basify the reaction. The mixture was extracted with EtOAc and the combined organics were dried over $Na_2SO$, concentrated, and chromatographed on silica gel using 0-20% (3:1) EtOAc:EtOH in heptanes to afford 7-bromo-2,4-dichloro-3-methylquinoline (0.361 g, 1.241 mmol, 32.1% yield) as a light yellow solid. m/z (ESI): 289.8 $(M+H)^+$.

Intermediate 45: 7-bromo-2-chloro-4-(2-chlorophenyl)quinoline-3-carbonitrile

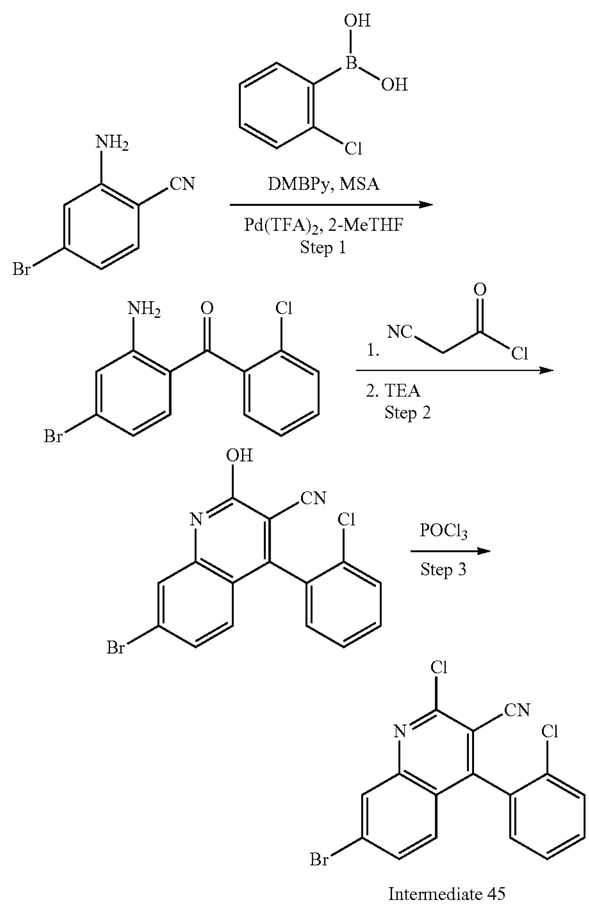

Intermediate 45

Step 1: (2-amino-4-bromophenyl)(2-chlorophenyl)methanone

A mixture of 2-amino-4-bromobenzonitrile (3.0 g, 15.23 mmol, Combi-Blocks), 2-chloro-phenylboronic acid (4.76 g, 30.5 mmol, Combi-Blocks), 5,5'-dimethyl-2,2'-bipyridine (0.421 g, 2.284 mmol, Combi-Blocks), bis(2,2,2-trifluoroacetoxy)palladium (0.506 g, 1.523 mmol, Sigma-Aldrich) and methanesulfonic acid (9.89 mL, 152 mmol, Sigma-Aldrich) was purged with $N_2$ followed by the addition of 2-MeTHF (40 mL) and water (20 mL) and the resulting mixture was heated at 80° C. for 40 h. The reaction was diluted with EtOAc, washed with aqueous saturated $NaHCO_3$, brine, dried over $Na_2SO_4$, filtered, concentrated, and chromatographed on silica gel using 0-20% EtOAc in heptanes to afford (2-amino-4-bromophenyl)(2-chlorophenyl)methanone as a yellow solid. m/z (ESI): 309.9 $(M+H)^+$.

Step 2: 7-bromo-4-(2-chlorophenyl)-2-hydroxyquinoline-3-carbonitrile

To a solution of (2-amino-4-bromophenyl)(2-chlorophenyl)methanone (2.6 g, 8.37 mmol) and pyridine (1.354 mL, 16.74 mmol, Sigma-Aldrich) in THF (40 mL) was added 2-cyanoacetyl chloride 20% solution in DCM (8.66 g, 16.74 mmol, Aurum) and the resulting mixture was stirred at room temperature for 15 min. The reaction was diluted with aqueous saturated $NH_4Cl$ and extracted with EtOAc. The combined organics were dried over $Na_2SO_4$, and concentrated to afford N-(5-bromo-2-(2-chlorobenzoyl)phenyl)-2-cyanoacetamide as a brown oil to be used as is. m/z (ESI): 376.8 $(M+H)^+$.

N-(5-bromo-2-(2-chlorobenzoyl)phenyl)-2-cyanoacetamide was dissolved in DCM (50 mL) and TEA (3.50 mL, 25.1 mmol, Sigma-Aldrich) was added and the resulting mixture was heated at 45° C. for 1.5 h. The mixture was cooled to room temperature, diluted with DCM, washed with aqueous saturated $NH_4Cl$, brine, dried over $Na_2SO_4$, and concentrated in vacuo to afford 7-bromo-4-(2-chlorophenyl)-2-hydroxyquinoline-3-carbonitrile as a brown solid to be used as is. m/z (ESI): 358.8 $(M+H)^+$.

Step 3: 7-bromo-2-chloro-4-(2-chlorophenyl)quinoline-3-carbonitrile

To a solution of 7-bromo-4-(2-chlorophenyl)-2-hydroxyquinoline-3-carbonitrile (3.01 g, 8.37 mmol) in 1,4-dioxane (30 mL) was added $POCl_3$ (10 mL, 107 mmol, Sigma-Aldrich). The reaction was stirred at 100° C. for 1 h. The reaction was cooled to room temperature and carefully poured into cold aqueous saturated $NaHCO_3$, then solid $K_2CO_3$ was added in portions to basify the reaction. The mixture was extracted with EtOAc and the combined organics were dried over $Na_2SO_4$, concentrated and chromatographed on silica gel using 0-20% (3:1) EtOAc:EtOH in heptanes to afford 7-bromo-2-chloro-4-(2-chlorophenyl)quinoline-3-carbonitrile (2.10 g, 5.55 mmol, 66.4% yield) as a brown solid. m/z (ESI): 377.0 $(M+H)^+$.

Intermediate 46: 1-(difluoromethyl)-5-(4,4,5,5-tetramethyl-1,3,2-dioxaborolan-2-yl)-1H-pyrazole

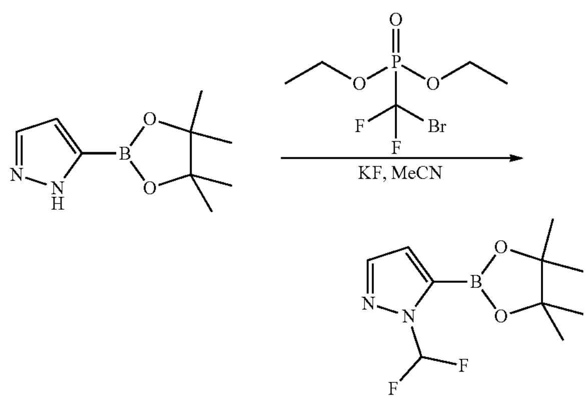

A mixture of 5-(4,4,5,5-tetramethyl-1,3,2-dioxaborolan-2-yl)-1H-pyrazole (1.0 g, 5.15 mmol, Activate Scientific), (bromodifluoromethyl)phosphonic acid diethyl ester (1.514 g, 1.514 mL, 5.67 mmol, Combi-Blocks) and KF (0.599 g, 10.31 mmol. Sigma-Aldrich) was purged with $N_2$, followed by the addition of MeCN (10 mL) and the mixture was stirred at room temperature for 2 h. The reaction was concentrated to afford 1-(difluoromethyl)-5-(4,4,5,5-tetramethyl-1,3,2-dioxaborolan-2-yl)-1H-pyrazole as a light yellow solid to be used as. m/z (ESI): 245.2 $(M+H)^+$.

Intermediate 47: tert-butyl 6-(7-bromo-4-chloro-3-methylquinolin-2-yl)-2,6-diazaspiro[3.4]octane-2-carboxylate

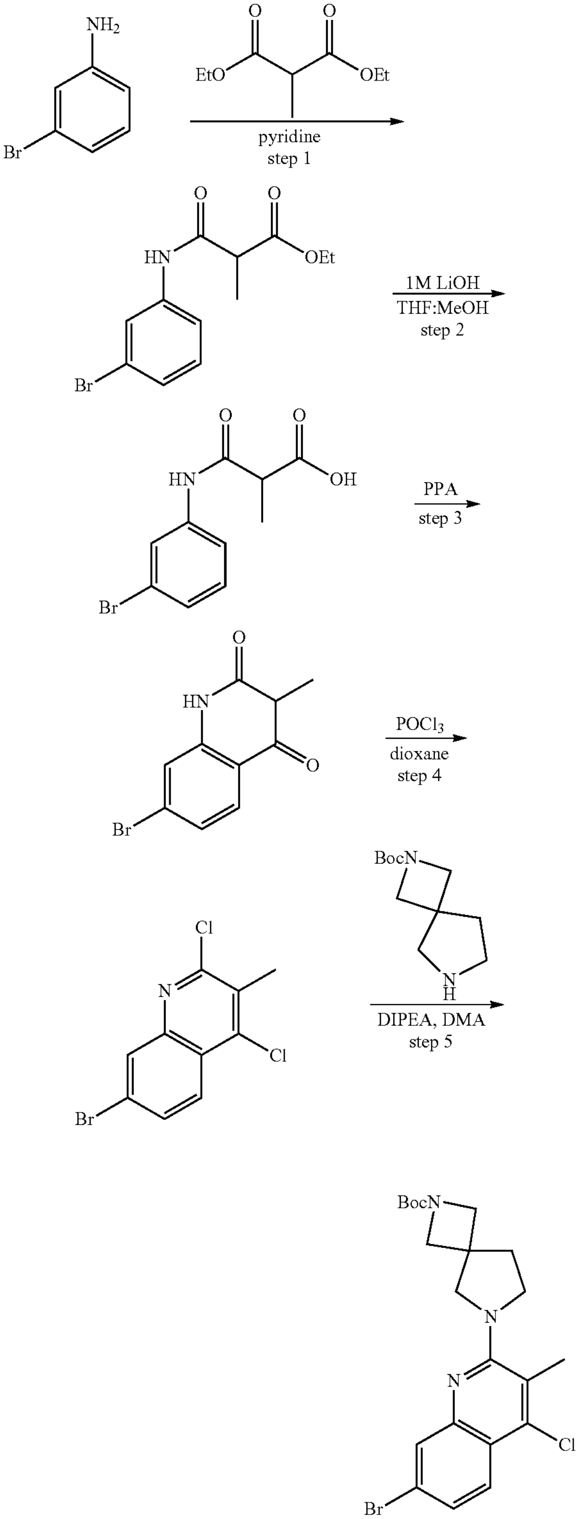

Intermediate 47

Step 1: ethyl 3-((3-bromophenyl)amino)-2-methyl-3-oxopropanoate

To a solution of 3-bromoaniline (1.603 mL, 14.53 mmol, Sigma-Aldrich) and pyridine (4 mL) was added diethyl 2-methylmalonate (3.72 mL, 21.80 mmol, Sigma-Aldrich). The reaction was stirred at 130° C. After 16 h, the reaction was treated with additional diethyl-2-methylmalonate (1.5 mL) and stirred at 130° C. for 24 h. The residue was partitioned between EtOAc and water. The aqueous layer was back extracted with EtOAc (2×25 mL). The combined EtOAc layers were concentrated in vacuo and adsorbed onto a plug of silica gel and chromatographed through a Redi-Sep) pre-packed silica gel column, eluting with 0-50% EtOAc in heptanes, to provide ethyl 3-((3-bromophenyl) amino)-2-methyl-3-oxopropanoate (3.74 g, 12.46 mmol, 86% yield) as a light reddish oil. m/z (ESI): 300.1, 302.1 $(M+H)^+$.

Step 2: 3-((3-bromophenyl)amino)-2-methyl-3-oxopropanoic acid

To a solution of ethyl 3-((3-bromophenyl)amino)-2-methyl-3-oxopropanoate (3.74 g, 9.47 mmol) and THF (30 mL):MeOH (6 mL) was added 1M LiOH (12 mL). The reaction was stirred at room temperature. After 16 h, the reaction was partitioned between water and EtOAc and neutralized with 2N HCl. The aqueous layer was extracted with EtOAc (2×20 mL). The combined organics were concentrated in vacuo to provide crude 3-((3-bromophenyl) amino)-2-methyl-3-oxopropanoic acid (3.45 g, 12.68 mmol, 134% yield) as a light pink solid. The material was carried forward as is. m/z (ESI): 272.1, 274.0 $(M+H)^+$.

Step 3: 7-bromo-3-methylquinoline-2,4-diol

To a RBF containing 3-((3-bromophenyl)amino)-2-methyl-3-oxopropanoic acid (3.45 g, 9.51 mmol) was added polyphoshoric acid (38.0 g, 9.51 mmol, Sigma-Aldrich). The reaction was stirred at 130° C. After 3 h, the reaction was cooled to room temperature and cautiously diluted with aqueous 2.5N NaOH. A sticky/gummy solid came out of solution. The reaction was partitioned between EtOAc and water. The aqueous layer was extracted with EtOAc (2×30 mL). The combined organic layers were washed with water, brine, dried over $MgSO_4$, and concentrated in vacuo to provide a crude mixture of the regioisomer products as a light pink solid. The material was carried forward as is. m/z (ESI): 254.0, 256.0 $(M+H)^+$.

Step 4: 7-bromo-2,4-dichloro-3-methylquinoline

To a RBF containing a mixture of 7-bromo-3-methylquinoline-2,4-diol and 5-bromo-3-methylquinoline-2,4-diol (2.270 g, 8.93 mmol) in 1,4-dioxane (20 mL) was added $POCl_3$ (8.35 mL, 89 mmol, Sigma-Aldrich). The reaction was stirred at 80° C. After 3 h, the reaction was cooled to room temperature and concentrated in vacuo. The residue was partitioned between EtOAc and aqueous saturated $NaHCO_3$. The aqueous layer was extracted with EtOAc (2×25 mL). The combined organic layers were washed with brine, dried over $MgSO_4$, and concentrated in vacuo to give a crude mixture of 7-bromo-2,4-dichloro-3-methylquinoline and 5-bromo-2,4-dichloro-3-methylquinoline (2.20 g, 7.56 mmol, 85% yield) as a light brown solid. The material was carried forward as is. m/z (ESI): 289.9, 292.0 $(M+H)^+$.

Step 5: tert-butyl 6-(7-bromo-4-chloro-3-methylquinolin-2-yl)-2,6-diazaspiro[3.4]octane-2-carboxylate To a solution of 7-bromo-2,4-dichloro-3-methylquinoline (2.20 g, 6.80 mmol) and 5-bromo-2,4-dichloro-3-methylquinoline (2.200 g, 6.80 mmol) in DMA (20 mL) was added DIPEA (2.97 mL, 17.01 mmol, Sigma-Aldrich) and 2-(tert-butoxycarbonyl)-2,6-diazaspiro[3.4]octane (1.445 g, 6.80 mmol, PharmaBlock). The reaction was stirred at 80° C. After 16 h, the reaction was allowed to cool to room temperature and partitioned between EtOAc and water. The aqueous layer was extracted with EtOAc (2×25 mL). The combined organic layers were washed with water, brine, dried over $MgSO_4$, and concentrated in vacuo. The crude mixture was adsorbed onto a plug of silica gel and chromatographed through a Redi-Sep® pre-packed silica gel column eluting with 0-20% EtOAc in heptanes, to provide tert-butyl 6-(7-bromo-4-chloro-3-methylquinolin-2-yl)-2,6-diazaspiro[3.4]octane-2-carboxylate (623 mg, 1.335 mmol, 19.61% yield) as a light yellow foam and tert-butyl 6-(5-bromo-4-chloro-3-methylquinolin-2-yl)-2,6-diazaspiro[3.4]octane-2-carboxylate (654 mg, 1.401 mmol, 20.59% yield) as a tan solid. $^1H$ NMR (400 MHz, DMSO-$d_6$) δ ppm 7.87 (d, J=8.8 H7, 1H), 7.78 (d, J=1.9 Hz, 1H), 7.47 (dd, J=8.8, 1.9 Hz, 1H), 3.75-3.90 (m, 6H), 3.60-3.70 (m, 2H), 2.48-2.49 (m, 3H), 2.10 (t, J=6.8 Hz, 2H), 1.39 (s, 9H). m/z (ESI): 466.0, 468.0 $(M+H)^+$.

Intermediate 48: 7-bromo-2-chloro-4-(2-fluorophenyl)quinoline-3-carbonitrile

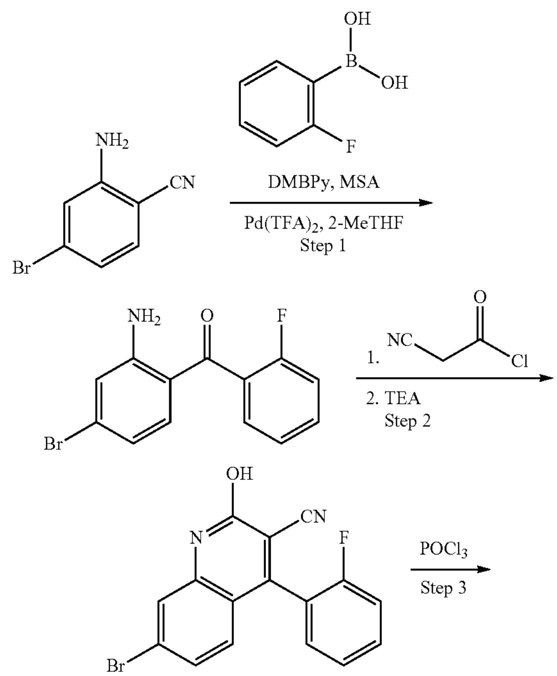

-continued

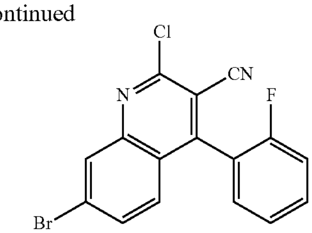

Intermediate 48

Intermediate 48 was synthesized in an analogous manner to Intermediate 45 but using (2-fluorophenyl)boronic acid (Combi-Blocks) in Step 1.

Intermediate 49: tert-butyl 6-(7-bromo-4-chloro-3-methylquinolin-2-yl)-5-methyl-2,6-diazaspiro[3.4]octane-2-carboxylate Intermediate 49 was synthesized in an analogous manner to Intermediate 47 but using tert-butyl 5-methyl-2,6-diazaspiro[3.4]octane-2-carboxylate (Enamine) in Step 5.

Intermediate 50: tert-butyl 6-(7-benzyl-4-chloro-3-methyl-5,6,7,8-tetrahydro-1,7-naphthyridin-2-yl)-2,6-diazaspiro[3.4]octane-2-carboxylate

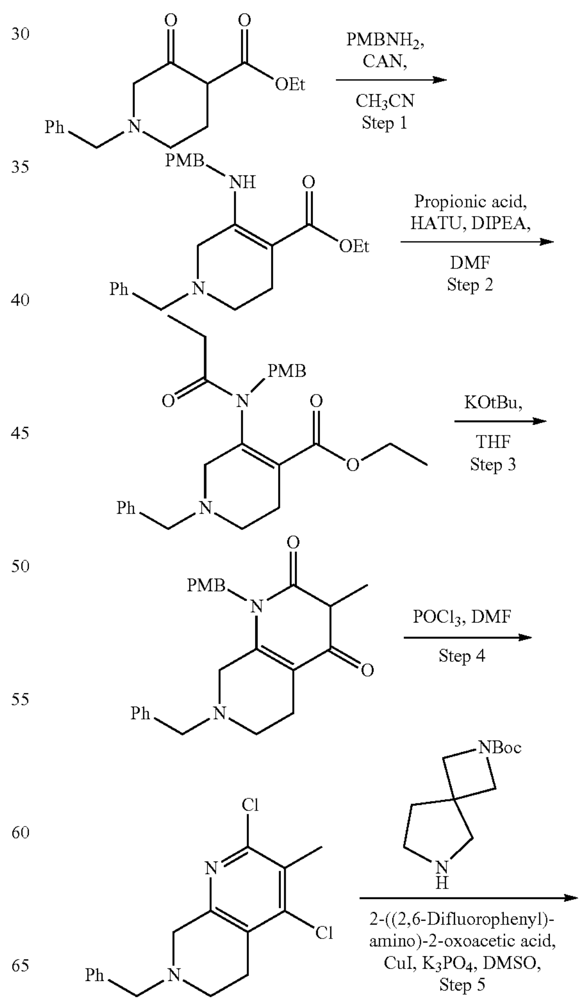

-continued

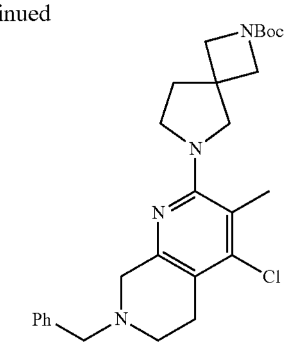

Step 1: Ethyl 1-benzyl-5-((4-methoxybenzyl)amino)-1,2,3,6-tetrahydropyridine-4-carboxylate To a solution of ethyl 1-benzyl-3-oxopiperidine-4-carboxylate (1 kg, 3.827 mol, Sozhou Sibian Chemical) in MeCN (10 L) was added (4-methoxyphenyl)methanamine (682.0 g, 4.975 mol, Chempure) followed by ceric ammonium nitrate (105.0 g, 191.0 mmol, Avra) at 0° C. and stirred at room temperature for 16 h. The reaction was quenched with water (5 L) and extracted with EtOAc (2×5 L). The organic layer was washed with brine (3 L), dried over $Na_2SO_4$, and concentrated under reduced pressure. The residue was purified by column chromatography over silica gel using 40% EtOAc in hexanes as the eluent to provide ethyl 1-benzyl-5-((4-methoxybenzyl)amino)-1,2,3,6-tetrahydropyridine-4-carboxylate (1.20 kg, 82% yield) as a tan solid. $^1$H NMR (400 MHz, DMSO-$d_6$) δ 8.89 (t, J=6.0 Hz, 1H), 7.37-7.21 (m, 5H), 7.17-7.08 (m, 2H), 6.95-6.81 (m, 2H), 4.21 (d, J=6.0 Hz, 2H), 4.02 (q, J=7.1 Hz, 2H), 3.74 (s, 3H), 3.55 (s, 2H), 3.22 (s, 2H), 2.43 (t, J=5.8 Hz, 2H), 2.24 (t, J=5.7 Hz, 2H), 1.17 (t, J=7.1 Hz, 3H). m/z (ESI): 380.9 $(M+H)^+$.

Step 2: Ethyl 1-benzyl-5-(N-(4-methoxybenzyl)propionamido)-1,2,3,6-tetrahydropyridine-4-carboxylate To a solution of ethyl 1-benzyl-5-((4-methoxybenzyl)amino)-1,2,3,6-tetrahydropyridine-4-carboxylate (850.0 g, 2.234 mol) in DMF (8.5 L) was added propionic acid (331.0 g, 4.468 mol) followed by DIPEA (1.155 kg, 8.936 mol) and HATU (1.274 kg, 3.351 mol) at room temperature and the reaction was stirred at 60° C. for 16 h. The reaction was quenched with ice water (7 L) and extracted with EtOAc (2×10 L). The organic layer was washed with brine (7 L), dried over $Na_2SO_4$, and concentrated under reduced pressure. The residue was purified by column chromatography over silica gel using 20% EtOAc in hexanes as the eluent to provide ethyl 1-benzyl-5-(N-(4-methoxybenzyl)propionamido)-1,2,3,6-tetrahydropyridine-4-carboxylate (780.0 g, 80% yield) as a wine red oil. m/z (ESI): 437.2 $(M+H)^+$.

Step 3: 7-Benzyl-1-(4-methoxybenzyl)-3-methyl-5,6,7,8-tetrahydro-1,7-naphthyridine-2,4(1H,3H)-dione To a solution of ethyl 1-benzyl-5-(N-(4-methoxybenzyl)propionamido)-1,2,3,6-tetrahydropyridine-4-carboxylate (340.0 g, 779.0 mmol) in THF (3400 mL) was added KOtBu (1M in THF, 2.336 L, 2.336 mol) at room temperature and the reaction was stirred at 65° C. for 1 h. The reaction was cooled to room temperature and the suspension was filtered. The filter cake was washed with EtOAc (200 mL), dried under vacuum to provide 7-Benzyl-1-(4-methoxybenzyl)-3-methyl-5,6,7,8-tetrahydro-1,7-naphthyridine-2,4(1H,3H)-dione (255.0 g, 83% yield) as an off-white solid. $^1$H NMR (400 MHz, DMSO-$d_6$) δ 7.46-7.06 (m, 5H), 6.91 (d, J=8.4 Hz, 2H), 6.72 (dd, J=6.8, 1.6 Hz, 2H), 4.86 (s, 1H), 3.70 (s, 3H), 3.49 (s, 2H), 3.16 (s, 2H), 2.43-2.50 (m, 2H), 2.20-2.28 (m, 2H), 1.68 (s, 3H). (Note: One $CH_2$ group obscured by NMR solvent). m/z (ESI): 391.0 $(M+H)^+$.

Step 4: 7-Benzyl-2,4-dichloro-3-methyl-5,6,7,8-tetrahydro-1,7-naphthyridine

A solution of 7-benzyl-1-(4-methoxybenzyl)-3-methyl-5,6,7,8-tetrahydro-1,7-naphthyridine-2,4(1H,3H)-dione (100.0 g, 256 mmol) in $POCl_3$ (500 mL, 5.378 mol) was added DMF (9.91 mL, 128 mmol) at −10° C. and stirred at 80° C. for 16 h. The reaction was concentrated under reduced pressure and the residue was quenched with cold 10% aqueous $NaHCO_3$ (pH 6-7) and extracted with DCM (500 mL×3). The organic layers were dried over $Na_2SO_4$, and concentrated under reduced pressure. The residue was purified by column chromatography over silica gel using 20% EtOAc in hexanes as an eluent to provide 7-benzyl-2,4-dichloro-3-methyl-5,6,7,8-tetrahydro-1,7-naphthyridine (29.0 g, 37% yield over two steps) as a pale yellow solid. $^1$H NMR (400 MHz, DMSO-$d_6$) δ 7.70-6.96 (m, 5H), 3.70 (s, 2H), 3.53 (s, 2H), 2.60-2.75 (br s, 4H), 2.40 (s, 3H). m/z (ESI): 307.0 $(M+H)^+$.

Step 5: tert-Butyl 6-(7-benzyl-4-chloro-3-methyl-5,6,7,8-tetrahydro-1,7-naphthyridin-2-yl)-2,6-diazaspiro[3.4]octane-2-carboxylate A mixture of 7-benzyl-2,4-dichloro-3-methyl-5,6,7,8-tetrahydro-1,7-naphthyridine (6.0 g, 19.53 mmol), tert-butyl 2,6-diazaspiro[3.4]octane-2-carboxylate (10.37 g, 48.8 mmol, J&W Pharma) and $K_3PO_4$ (20.73 g, 98.0 mmol) in DMSO (150 mL) was degassed and purged with nitrogen for 5 min. To this mixture was added CuI (0.744 g, 3.91 mmol) followed by 2-((2,6-difluorophenyl)amino)-2-oxoacetic acid (1.571 g, 7.81 mmol) and the reaction was stirred at 100° C. for 16 h. The reaction mixture was quenched with cold saturated aqueous $NH_4Cl$ solution (150 mL) and extracted with EtOAc (2×150 mL). The organic layers were washed with brine solution (200 mL), dried ($Na_2SO_4$), filtered and concentrated under reduced pressure. The crude residue was purified by column chromatography over silica gel using 15% EtOAc in hexanes as the eluent to provide tert-butyl 6-(7-benzyl-4-chloro-3-methyl-5,6,7,8-tetrahydro-1,7-naphthyridin-2-yl)-2,6-diazaspiro[3.4]octane-2-carboxylate (4.1 g, 42% yield) as a yellow oil. $^1$H NMR (400 MHz, DMSO-$d_6$) δ 7.38-7.27 (m, 5H), 3.83-3.69 (m, 4H), 3.65 (s, 2H), 3.49 (s, 2H), 3.41-3.34 (m, 4H), 2.74-2.66 (m, 4H), 2.24 (s, 3H), 2.01 (t, J=6.8 Hz, 2H), 1.37 (s, 9H). m/z (ESI): 483.1 $(M+H)^+$.

Intermediate 51: tert-butyl 6-(4-chloro-7-isopropyl-3-methyl-5,6,7,8-tetrahydro-1,7-naphthyridin-2-yl)-2,6-diazaspiro[3.4]octane-2-carboxylate

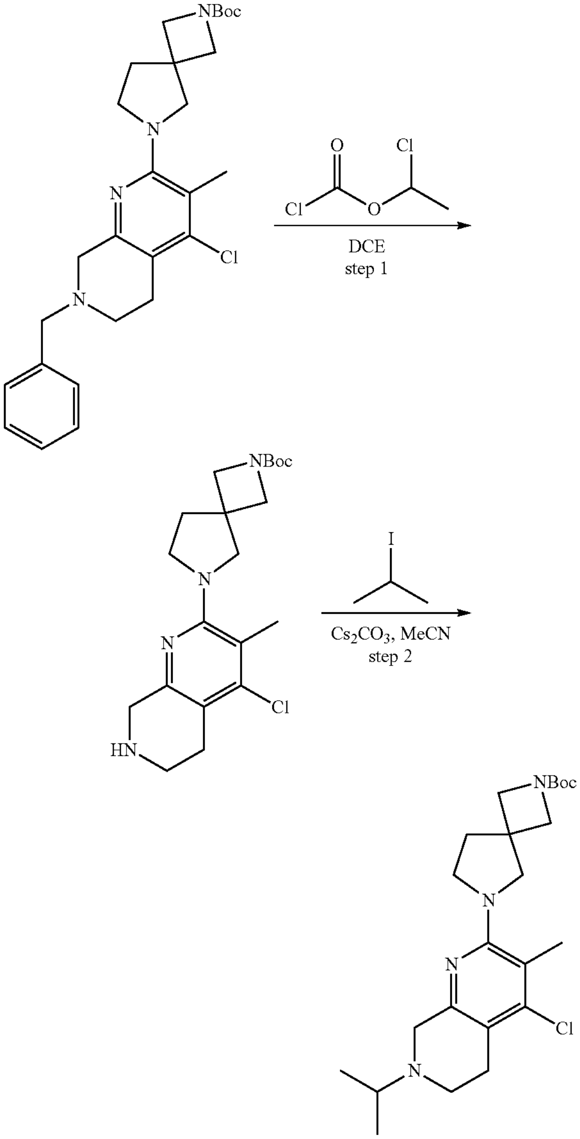

Step 1: tert-butyl 6-(4-chloro-3-methyl-5,6,7,8-tetrahydro-1,7-naphthyridin-2-yl)-2,6-diazaspiro[3.4]octane-2-carboxylate To a solution of tert-butyl 6-(7-benzyl-4-chloro-3-methyl-5,6,7,8-tetrahydro-1,7-naphthyridin-2-yl)-2,6-diazaspiro[3.4]octane-2-carboxylate (1.0 g, 2.070 mmol, Intermediate 50) in DCE (15 mL) at 0° C. was added dropwise 1-chloroethyl chloroformate (0.339 mL, 3.11 mmol, Sigma-Aldrich). After stirring at 0° C. for 3 min, the reaction was heated to reflux for 2 h. The reaction was concentrated and taken up in MeOH (15 mL) and the mixture was heated to reflux for 30 min. The reaction was concentrated, diluted in DCM and washed with aqueous saturated $NaHCO_3$. The organic phase was dried over $Na_2SO_4$, filtered and concentrated to afford crude tert-butyl 6-(4-chloro-3-methyl-5,6,7,8-tetrahydro-1,7-naphthyridin-2-yl)-2,6-diazaspiro[3.4]octane-2-carboxylate as a yellow oil. m/z (ESI): 393.2 $(M+H)^+$.

Step 2: tert-butyl 6-(4-chloro-7-isopropyl-3-methyl-5,6,7,8-tetrahydro-1,7-naphthyridin-2-yl)-2,6-diazaspiro[3.4]octane-2-carboxylate To a mixture of tert-butyl 6-(4-chloro-3-methyl-5,6,7,8-tetrahydro-1,7-naphthyridin-2-yl)-2,6-diazaspiro[3.4]octane-2-carboxylate (1.0 g, 2.54 mmol) in MeCN (15 mL) was added $Cs_2CO_3$ (2.073 g, 6.36 mmol, Sigma-Aldrich) followed by 2-iodopropane (0.865 mL, 5.09 mmol, Combi-Blocks). The mixture was heated at 80° C. overnight. The mixture was cooled to room temperature, diluted with water, and extracted with EtOAc. The combined organics were chromatographed on silica gel using 0-40% (3:1, EtOAc:EtOH) in heptanes to afford tert-butyl 6-(4-chloro-7-isopropyl-3-methyl-5,6,7,8-tetrahydro-1,7-naphthyridin-2-yl)-2,6-diazaspiro[3.4]octane-2-carboxylate. m/z (ESI): 435.2 $(M+H)^+$.

Intermediate 52: 5-chloro-1-(tetrahydro-2H-pyran-2-yl)-4-(4,4,5,5-tetramethyl-1,3,2-dioxaborolan-2-yl)-1H-indazole

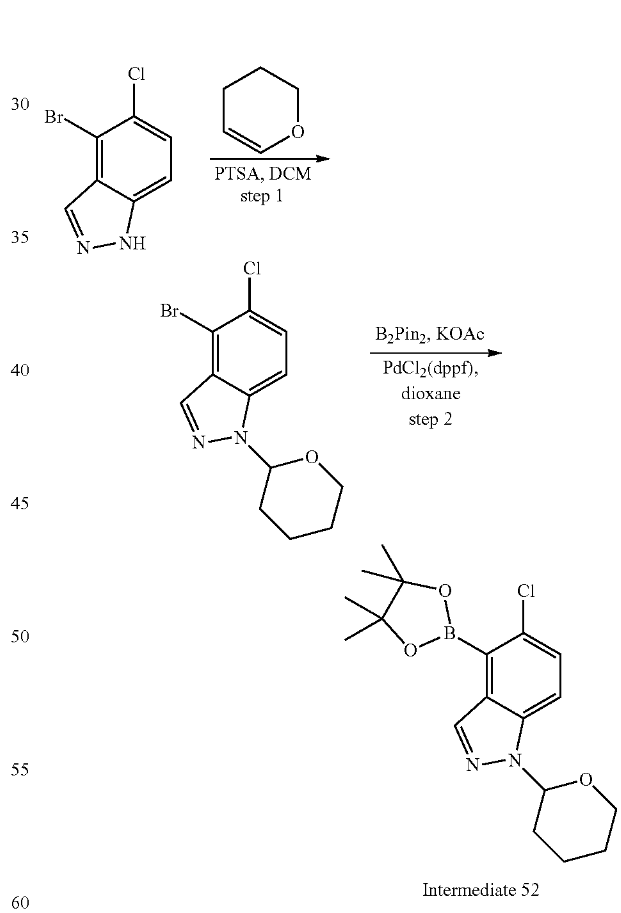

Intermediate 52

Step 1: 4-bromo-5-chloro-1-(tetrahydro-2H-pyran-2-yl)-1H-indazole

To a solution of 4-bromo-5-chloro-1H-indazole (2 g, 8.64 mmol, PharmaBlock) and DCM (30 mL) was added 3,4- dihydro-2H-pyran (2.370 mL, 25.9 mmol, Sigma-Aldrich) and para-toluenesulfonic acid, monohydrate (0.164 g, 0.864 mmol, Sigma-Aldrich). The solution was stirred at room temperature. After stirring over the weekend, the reaction was washed with aqueous saturated $NaHCO_3$ and concentrated in vacuo to provide crude 4-bromo-5-chloro-1-(tetrahydro-2H-pyran-2-yl)-1H-indazole (3.4 g, 10.77 mmol, 125% yield) as a brown solid. m/z (ESI): 315.0 $(M+H)^+$. The material was carried forward as is.

Step 2: 5-chloro-1-(tetrahydro-2H-pyran-2-yl)-4-(4,4,5,5-tetramethyl-1,3,2-dioxaborolan-2-yl)-1H-indazole To a solution of 4-bromo-5-chloro-1-(tetrahydro-2H-pyran-2-yl)-1H-indazole (2.73 g, 8.65 mmol) and 1,4-dioxane (40 mL) was added potassium acetate (2.55 g, 26.0 mmol, Sigma-Aldrich), bis(pinacolato)diboron (2.64 g, 10.38 mmol, Strem, Inc.), and $PdCl_2$(dppf) (0.353 g, 0.433 mmol, Oakwood Products, Inc.). The solution was purged with $N_2$ and stirred at 80° C. A power outage after 2 h occurred and after stirring a further 14 h at room temperature, LC-MS suggests <20% conversion. The reaction was reheated to 80° C. After 36 h, the reaction was allowed to cool to room temperature and adsorbed onto a plug of silica gel and chromatographed through a Redi-Sep® pre-packed silica gel column, eluting with 0-100° % EtOAc in heptanes, to provide 5-chloro-1-(tetrahydro-2H-pyran-2-yl)-4-(4,4,5,5-tetramethyl-1,3,2-dioxaborolan-2-yl)-1H-indazole (703 mg, 1.938 mmol, 22.41% yield) as an off-white solid. m/z (ESI): 363.1 $(M+H)^+$.

Intermediate 53: 6-bromo-8-iodo-[1,2,4]triazolo[1,5-a]pyridine-7-carbonitrile

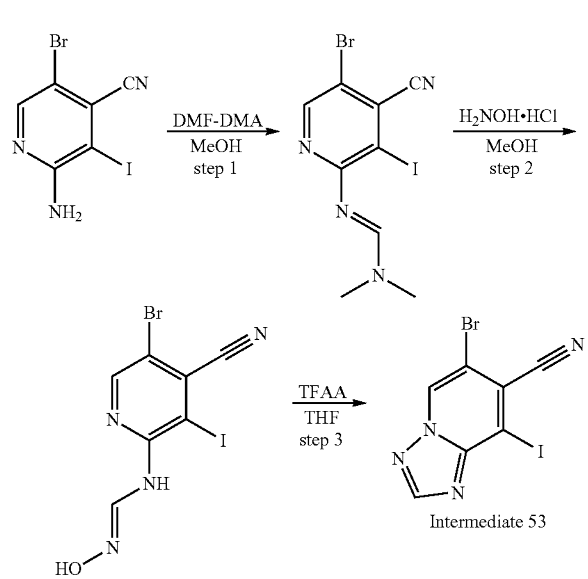

Intermediate 53

Step 1: (E)-N'-(5-bromo-4-cyano-3-iodopyridin-2-yl)-N,N-dimethylformimidamide

A mixture of 2-amino-5-bromo-3-iodoisonicotinonitrile (200 mg, 0.617 mmol, domestic) and DMF-DMA (99 µL, 0.741 mmol) in MeOH (10 mL) was stirred for 16 h at 75° C. under $N_2$. The reaction mixture was concentrated in vacuo, the crude product was used for the next step. m/z (ESI): 379.8 $(M+H)^+$.

Step 2: (E)-N-(5-bromo-4-cyano-3-iodopyridin-2-yl)-N'-hydroxyformimidamide

A mixture of (E)-N'-(5-bromo-4-cyano-3-iodopyridin-2-yl)-N,N-dimethylformimidamide (100 mg, 0.264 mmol) and hydroxylamine hydrochloride (25.7 mg, 0.369 mmol) in MeOH (5 mL) was stirred for 16 h at 25° C. in a RBF under $N_2$. The reaction mixture was filtered through a pad of Celite with EtOAc/H2O, and the combined organics were concentrated in vacuo. The crude product was used for the next step. m/z (ESI): 367.0 $(M+H)^+$.

Step 3: 6-bromo-8-iodo-[1,2,4]triazolo[1,5-a]pyridine-7-carbonitrile

A mixture of (E)-N-(5-bromo-4-cyano-3-iodopyridin-2-yl)-N'-hydroxyformimidamide (50 mg, 0.136 mmol) and TFAA (19.25 µL, 0.136 mmol) in THF (5 mL) was stirred for 16 h at 25° C. in a RBF under $N_2$. The reaction mixture was filtered through a pad of Celite with EtOAc/$H_2O$ to provide crude 6-bromo-8-iodo-[1,2,4]triazolo[1,5-a]pyridine-7-carbonitrile that was carried forward as is. m/z (ESI): 348.9 $(M+H)^+$.

Intermediate 54: tert-butyl 6-((5R,8S)-4-chloro-3-cyano-5,6,7,8-tetrahydro-5,8-methanoquinolin-2-yl)-2,6-diazaspiro[3.4]octane-2-carboxylate

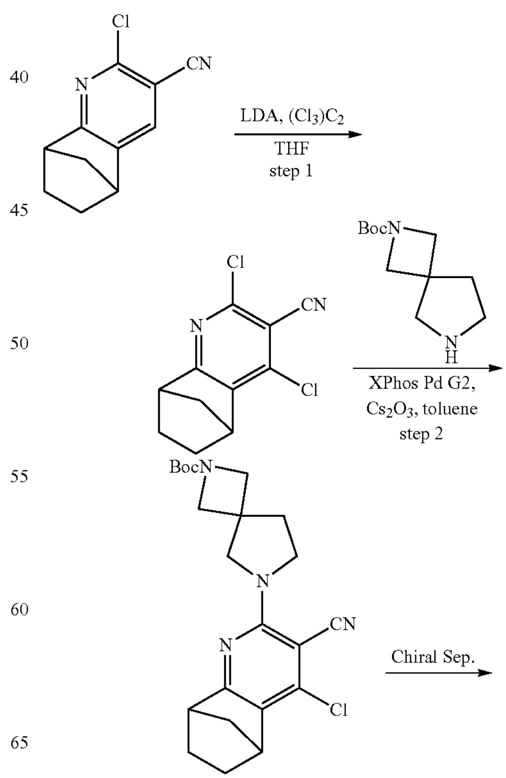

-continued

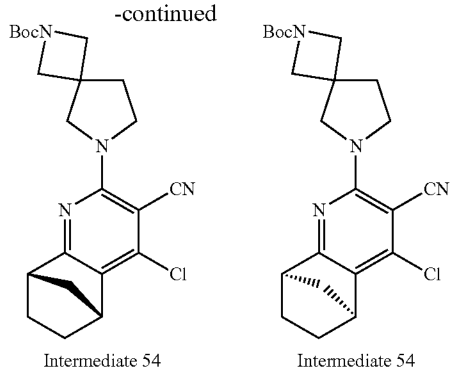

Intermediate 54

Intermediate 54

Step 1: 2,4-dichloro-5,6,7,8-tetrahydro-5,8-methanoquinoline-3-carbonitrile

To a −78° C. solution of LDA, 1M in THF/hexanes (22.98 mL, 22.98 mmol, Sigma-Aldrich) and THE (70 mL) in a 3 necked flask equipped with a thermometer was added a solution of 4-chloro-3-azatricyclo[6.2.1.0,$^{2,7}$]undeca-2(7),3,5-triene-5-carbonitrile (4.5 g, 20.89 mmol, Enamine) in THE (20 mL) at a fast drip (temp did not exceed −55° C.). The solution was immediately treated with a solution of hexachloroethane (5.99 g, 25.07 mmol, Combi-Blocks) in THF (10 mL) at a fast stream (~1 min, temp raised to −50° C.). After stirring in the cooling bath for 10 min, the reaction was quenched with aqueous sat'd $NH_4Cl$. The reaction was partitioned between EtOAc and water. The aqueous layer was extracted with EtOAc (3×50 mL). The combined organic layers were washed with brine and concentrated in vacuo. The material was adsorbed onto a plug of silica gel and chromatographed through a Redi-Sep® pre-packed silica gel column, eluting with 0-100% EtOAc in heptanes, to provide 2,4-dichloro-5,6,7,8-tetrahydro-5,8-methanoquinoline-3-carbonitrile (1.83 g, 7.65 mmol, 36.6% yield) as a light-yellow solid. m/z (ESI): 239.0 $(M+H)^+$.

Step 2: tert-butyl 6-(4-chloro-3-cyano-5,6,7,8-tetrahydro-5,8-methanoquinolin-2-yl)-2,6-diazaspiro[3.4]octane-2-carboxylate To a RBF charged with 2,4-dichloro-5,6,7,8-tetrahydro-5,8-methanoquinoline-3-carbonitrile (1.83 g, 7.65 mmol), $Cs_2CO_3$ (7.48 g, 22.96 mmol, Sigma-Aldrich), 2-(tert-butoxycarbonyl)-2,6-diazaspiro[3.4]octane (1.625 g, 7.65 mmol, PharmaBlock), and XPhos Pd G2 (0.602 g, 0.765 mmol, Sigma-Aldrich). The flask was evacuated and backfilled with $N_2$ (3×). Toluene (80 mL) was added and the reaction mixture stirred at 100° C. After 20 h, the reaction was allowed to cool to room temperature. The reaction was partitioned between EtOAc and water. The aqueous layer was extracted with EtOAc (3×25 mL). The combined organic layers were washed with brine and concentrated in vacuo. The crude material was adsorbed onto a plug of silica gel and chromatographed through a Redi-Sep® pre-packed silica gel column eluting with 0-100% EtOAc in heptanes, to provide tert-butyl 6-(4-chloro-3-cyano-5,6,7,8-tetrahydro-5,8-methanoquinolin-2-yl)-2,6-diazaspiro[3.4]octane-2-carboxylate (2.06 g, 4.96 mmol, 64.9% yield) as a light-yellow solid. m/z (ESI): 437.2 $(M+Na)^+$.

Chiral Separation conditions: The sample was purified by SFC using a Chiralcel OJ column, 21×150 mm, mobile phase of 80% CO2 and 20% MeOH using a flow rate of 80 mL/min to provide the 5R,8S and 5S,8R isomers of tert-butyl 6-(4-chloro-3-cyano-5,6,7,8-tetrahydro-5,8-methanoquinolin-2-yl)-2,6-diazaspiro[3.4]octane-2-carboxylate The stereochemistry was arbitrarily assigned and is not established. The 1$^{st}$ eluting isomer was assigned 5R,8S.

Intermediate 55: tert-butyl 6-((5S,8R)-4-chloro-3-cyano-5,6,7,8-tetrahydro-5,8-methanoquinolin-2-yl)-2,6-diazaspiro[3.4]octane-2 carboxylate The second eluting peak in the separation conditions described in intermediate 54 provided intermediate 55. The stereochemistry of structures was arbitrarily assigned and is not established.

Intermediate 56: 3-bromo-4-chloro-5-methylphenol

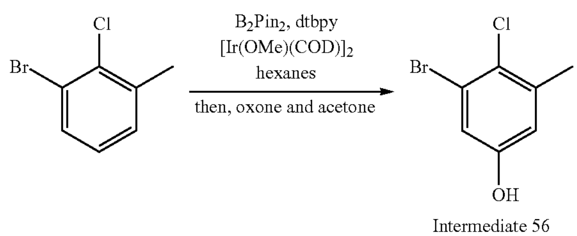

Intermediate 56

To a RBF with 4,4'-di-tert-butyl-2,2'-dipyridyl (19.59 mg, 0.073 mmol, Sigma-Aldrich), di-mu-methoxybis(1,5-cyclootadiene)diiridium(I) (24.19 mg, 0.037 mmol, Strem Chemicals, Inc.), and bis(pinacolato)diboron (371 mg, 1.460 mmol, Combi-Blocks). The flask was evacuated and backfilled with $N_2$ (3×), then 3-bromo-2-chlorotoluene (0.318 mL, 2.433 mmol, Combi-Blocks) and hexanes were added (note: dried over molecular sieves). The reaction was stirred at room temperature. After 16 h, the reaction was concentrated in vacuo and taken up in acetone (5 mL) and treated dropwise with a solution of OXONE®, monopersulfate compound (1795 mg, 2.92 mmol, Sigma-Aldrich) in water (5 mL). After 10 min, the reaction was quenched with sat'd $NaHSO_3$. The reaction was diluted with water and extracted with DCM (3×20 mL). The combined organic layers were concentrated in vacuo and adsorbed onto a plug of silica gel and chromatographed through a Redi-Sep® pre-packed silica gel column (Gold, 12 g), eluting with 0-30% EtOAc in heptanes, to provide 3-bromo-4-chloro-5-methylphenol (110 mg, 0.497 mmol, 20.41% yield) as a tan solid. $^1H$ NMR (400 MHz, DMSO-$d_6$) δ ppm 9.91 (br s, 1H), 6.98 (d, J=2.9 Hz, 1H), 6.78 (dd, J=2.8, 0.7 Hz, 1H), 2.32 (s, 3H).

Intermediate 57: 3-bromo-5-chloro-4-methylphenol

Intermediate 57 was synthesized in an analogous manner to Intermediate 56 using 2-bromo-6-chlorotoluene (Combi-Blocks). $^1H$ NMR (400 MHz, DMSO-$d_6$) δ ppm 10.03 (s, 1H), 7.01 (d, J=2.1 Hz, 1H), 6.87 (d, J=2.5 Hz, 1H), 2.33 (s, 3H).

Intermediate 58: 5-methyl-1-(tetrahydro-2H-pyran-2-yl)-1H-indazole-4-carbaldehyde

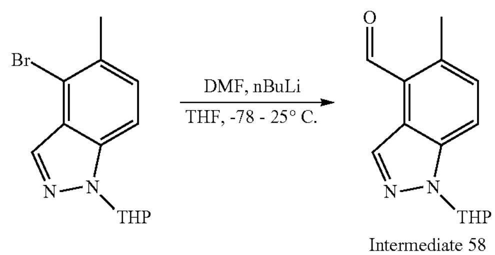

Intermediate 58

To a RBF was added 4-bromo-5-methyl-1-(tetrahydro-2H-pyran-2-yl)-1H-indazole (2.0 g, 6.78 mmol, PharmaBlock) in THF (23 mL, 0.3 M). The reaction was cooled to −78° C. Next, n-BuLi (14.91 mmol, Sigma-Aldrich) was added. The reaction mixture was stirred at −78° C. for 30 min. Next, DMF (1.98 g, 27.1 mmol, Sigma-Aldrich) was added. The reaction mixture was warmed to room temperature. After 2 h, the reaction was quenched with aqueous saturated sodium bicarbonate and extracted with EtOAc. The organic layers were dried ($Na_2SO_4$), filtered and the volatiles were removed. The crude material was purified by flash chromatography over silica gel eluting with a gradient of 0-100% EtOAc in heptanes to give 5-methyl-1-(tetrahydro-2H-pyran-2-yl)-1H-indazole-4-carbaldehyde.

Intermediate 59: 1,6-dimethyl-1H-indazole-7-carbaldehyde

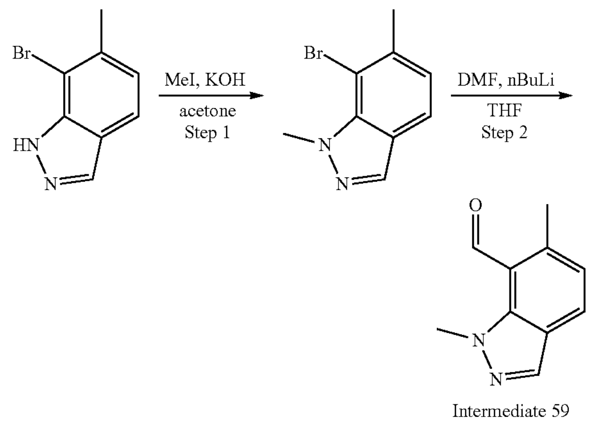

Intermediate 59

Step 1: 7-bromo-1,6-dimethyl-1H-indazole

To a RBF was added 7-bromo-6-methyl-1H-indazole (1 g, 4.74 mmol, PharmaBlock) and acetone (10 mL). The reaction was cooled to 0° C. Next, KOH (0.797 g, 14.21 mmol, Sigma-Aldrich) was added. The reaction mixture was stirred at 0° C. for 60 min. Next, iodomethane (0.444 mL, 7.11 mmol, Sigma-Aldrich) was added. The reaction mixture was warmed to room temperature and the reaction was quenched with aqueous saturated $NaHCO_3$ and extracted with EtOAc. The combined organic layers were dried ($Na_2SO_4$) and the volatiles were removed. The crude material was purified by flash chromatography over silica gel eluting with a gradient of 0-100% EtOAc in heptanes to give 7-bromo-1,6-dimethyl-1H-indazole (0.67 g, 2.98 mmol, 62.8% yield). $^1H$ NMR (400 MHz, DMSO-$d_6$) δ ppm 8.05 (s, 1H), 7.66 (d, J=7.94 Hz, 1H), 7.11 (d, J=8.15 Hz, 1H), 4.35 (s, 3H), 2.49 (s, 3H).

Step 2: 1,6-dimethyl-1H-indazole-7-carbaldehyde

To a RBF was added 7-bromo-1,6-dimethyl-1H-indazole (3.43 g, 15.24 mmol) and THF (76.0 mL). The reaction was cooled to −78° C. Next, n-BuLi (2.5 M in hexanes, 13.41 mL, 33.5 mmol, Sigma-Aldrich) was added. The reaction mixture was stirred at −78° C. for 30 min. Next, DMF (4.74 mL, 61.0 mmol, Sigma-Aldrich) was added. The reaction mixture was warmed to room temperature. After 2 h, the reaction was quenched with aqueous saturated sodium bicarbonate and extracted with EtOAc. The combined organic layers were dried ($Na_2SO_4$), filtered and the volatiles were removed. The crude material was purified by flash chromatography over silica gel eluting with a gradient of 0-100% EtOAc in heptanes to give 1,6-dimethyl-1H-indazole-7-carbaldehyde that was used as is.

Intermediate 60: 2-((2-(trimethylsilyl)ethoxy)methoxy)-1-naphthaldehyde

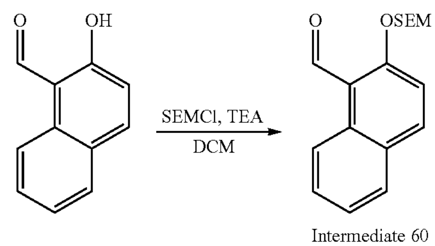

Intermediate 60

To a solution of 2-hydroxy-1-naphthaldehyde (1.0 g, 5.81 mmol, Combi-Blocks) and TEA (3.89 mL, 27.9 mmol, Sigma Sigma-Aldrich) in DCM (19.36 mL) was added 2-(trimethylsilyl)-ethoxymethyl chloride (4.53 mL, 25.6 mmol, Sigma-Aldrich). The reaction was stirred at 25° C. overnight. The reaction was quenched with aqueous saturated $NaHCO_3$ and extracted with EtOAc. The organic layer was dried over $Na_2SO_4$, and the volatiles were removed to provide 2-((2-(trimethylsilyl)ethoxy)methoxy)-1-naphthaldehyde. The crude material was moved forward without any purification.

Intermediate 61: 2-methyl-6-((2-(trimethylsilyl)ethoxy)methoxy)benzaldehyde

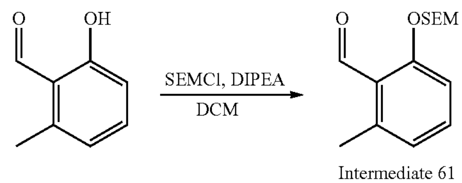

Intermediate 61

To a solution of 2-hydroxy-6-methylbenzaldehyde (1.0 g, 7.34 mmol, Synthonix) and DIPEA (6.16 mL, 35.3 mmol, Sigma-Aldrich) in DCM (24.48 mL) was added 2-(trimethylsilyl)-ethoxymethyl chloride (5.73 mL, 32.3 mmol, Sigma-Aldrich). The reaction was stirred at 25° C. overnight. The reaction was quenched with aqueous saturated $NaHCO_3$ and extracted with EtOAc. The organic layer was dried ($Na_2SO_4$), filtered and the volatiles were removed to provide 2-methyl-6-((2-(trimethylsilyl)ethoxy)methoxy) benzaldehyde. The crude material was moved forward without any purification.

Intermediate 62: 3-((tetrahydro-2H-pyran-2-yl)oxy)-1-naphthaldehyde

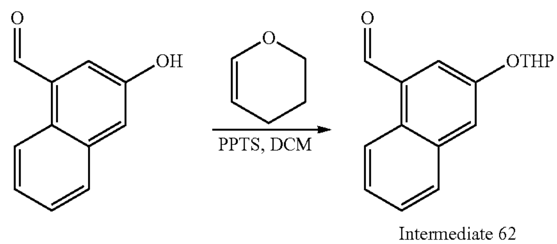

Intermediate 62

To a solution of 3-hydroxy-1-naphthaldehyde (1.0 g, 5.81 mmol, Enamine) in DCM (21.51 mL) was added 3,4-dihydro-2h-pyran (0.733 g, 8.71 mmol, Sigma-Aldrich) and pyridinium p-toluenesulfonate (0.073 g, 0.290 mmol, Sigma-Aldrich). The reaction mixture was stirred at room temperature overnight. The reaction was quenched with aqueous saturated $NaHCO_3$ and extracted with EtOAc. The organic phases were separated. The organic layer was dried ($Na_2SO_4$), filtered and the volatiles were removed. The crude material was absorbed onto a plug of silica gel and purified by chromatography eluting with a gradient of 0-100% EtOAc in heptanes, to provide 3-((tetrahydro-2H-pyran-2-yl)oxy)-1-naphthaldehyde (1.686 g 113% yield) as an off-white solid.

Intermediate 63: 4-bromo-6-fluoro-5-methyl-1-tetrahydropyran-2-yl-indazole

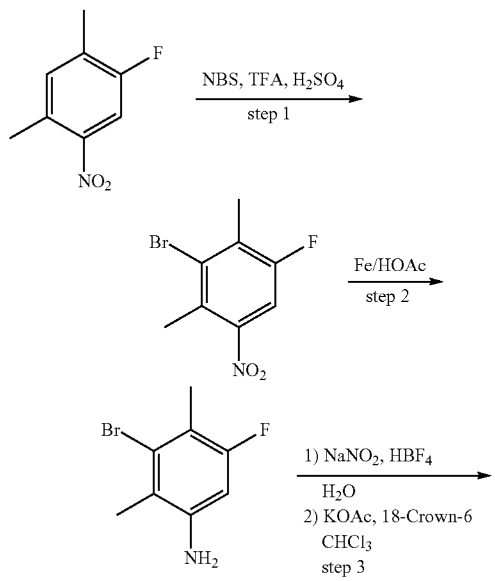

-continued

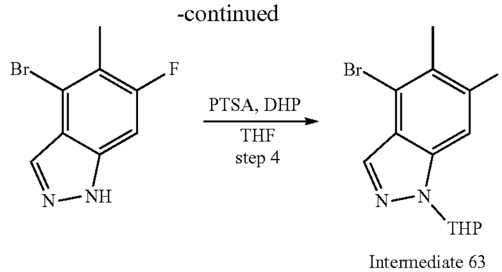

Intermediate 63

Step 1: 3-bromo-1-fluoro-2,4-dimethyl-5-nitro-benzene

To a mixture of 1-fluoro-2,4-dimethyl-5-nitro-benzene (2.5 g, 14.78 mmol, Scochem) in TFA (15 mL) was added NBS (4.21 g, 23.65 mmol) and $H_2SO_4$ (2.84 mL, 53.21 mmol) at 15° C. under $N_2$. The mixture was stirred at 15° C. for 12 h, then heated to 50° C. and stirred for 4 h. The reaction mixture was partitioned between EtOAc (500 mL) and $H_2O$ (500 mL). The organic phase was separated and concentrated under reduced pressure to provide crude 3-bromo-1-fluoro-2,4-dimethyl-5-nitro-benzene (3.5 g, 95.5% yield) as a colorless oil. m/z (ESI): 248.0 $(M+H)^+$. $^1H$ NMR (400 MHz, $CDCl_3$) δ ppm 7.53 (d, J=8.40 Hz, 1H), 2.58 (s, 3H), 2.45 (s, 3H).

Step 2: 3-bromo-5-fluoro-2,4-dimethyl-aniline

To a mixture of 3-bromo-1-fluoro-2,4-dimethyl-5-nitro-benzene (3.5 g, 14.11 mmol) in EtOH (30 mL) and HOAc (30 mL) was added Fe (3.94 g, 70.55 mmol) in portions at 25° C. under $N_2$. The mixture was stirred at 60° C. for 5 h. LC-MS indicate desired product was detected. The reaction was partitioned between EtOAc (500 mL) and $H_2O$ (500 mL). The organic phase was separated and concentrated under reduced pressure. The residue was purified by column chromatography ($SiO_2$, 1-20% EtOAc in petroleum ether) to provide 3-bromo-5-fluoro-2,4-dimethyl-aniline (2 g, 65.0% yield) as a brown solid. m/z (ESI): 218.0 $(M+H)^+$. $^1H$ NMR (400 MHz, $CDCl_3$) δ ppm 6.39 (d, J=10.80 Hz, 1H), 3.70 (br s, 2H), 2.26 (s, 6H).

Step 3: 4-bromo-6-fluoro-5-methyl-1H-indazole 3-bromo-5-fluoro-2,4-dimethyl-aniline (1.6 g, 7.34 mmol) was added $HBF_4$ (17.14 mL, 110.06 mmol, 40 wt %) in one portion at 0° C. under $N_2$, then $NaNO_2$ (1.52 g, 22.01 mmol) in $H_2O$ (2 mL) was added dropwise to the solution at 0° C. and stirred 1 h. The solution was warmed to 15° C. and stirred for 1.5 h. The resulting precipitate was filtered, washed with $(i-Pr)_2O$ (100 mL) and concentrated under vacuum to provide the crude diazonium salt. Then the diazonium salt in $CHCl_3$ (20 mL) was added KOAc (1.44 g, 14.67 mmol) and 18-Crwon-6 (96.97 mg, 0.366 mmol). The mixture was stirred at 35° C. for 0.5 h. The mixture was filtered and the filtrate was concentrated to dryness. The residue was purified by prep-TLC ($SiO_2$, 25% EtOAc in petroleum ether) to provide 4-bromo-6-fluoro-5-methyl-1H-indazole (620 mg, 36.9% yield) as a yellow solid.

Step 4: 4-bromo-6-fluoro-5-methyl-1-tetrahydropyran-2-yl-indazole

To a solution of 4-bromo-6-fluoro-5-methyl-1H-indazole (400 mg, 1.75 mmol) in THF (8 mL) was added 3,4-dihydro- 2H-pyran (0.798 mL, 8.73 mmol) and PTSA (30.07 mg, 0.174 mmol). The mixture was stirred at 50° C. for 12 h. The mixture was concentrated to dryness. The residue was purified by column chromatography ($SiO_2$, 5-20% EtOAc in petroleum ether) to provide 4-bromo-6-fluoro-5-methyl-1-tetrahydropyran-2-yl-indazole (0.5 g, 74.1% yield) as a white solid. m/z (ESI): 313.1 $(M+H)^+$.

Intermediate 64: tert-butyl 7-[3-cyano-4-(4,4,5,5-tetramethyl-1,3,2-dioxaborolan-2-yl)-2-quinolyl]-2,7-diazaspiro[3.4]octane-2-carboxylate

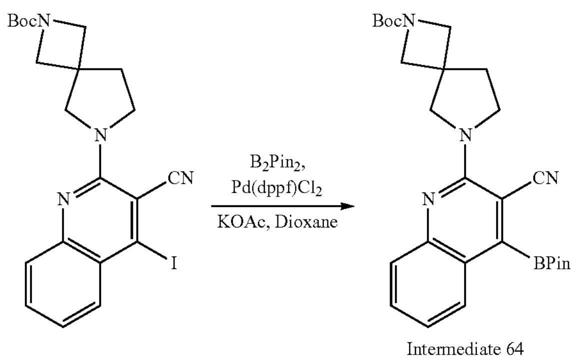

Intermediate 64

To a solution of tert-butyl 7-(3-cyano-4-iodo-2-quinolyl)-2,7-diazaspiro[3.4]octane-2-carboxylate (2 g, 4.08 mmol, Intermediate 25) in dioxane (40 mL) was added $Pin_2B_2$ (8.29 g, 32.63 mmol), KOAc (1.20 g, 12.24 mmol) and Pd(dppf)$Cl_2$ (298.45 mg, 0.407 mmol) under $N_2$. The mixture was stirred at 120° C. for 24 h. The mixture was filtered and concentrated to dryness. The residue was purified by column chromatography ($SiO_2$, Petroleum ether/EtOAc=20/1 to 3/1) to provide tert-butyl 7-[3-cyano-4-(4,4,5,5-tetramethyl-1,3,2-dioxaborolan-2-yl)-2-quinolyl]-2,7-diazaspiro[3.4]octane-2-carboxylate (1 g, 50% yield) as a yellow oil.

Intermediate 65: 5-(4,4,5,5-tetramethyl-1,3,2-dioxaborolan-2-yl)naphthalen-2-ol

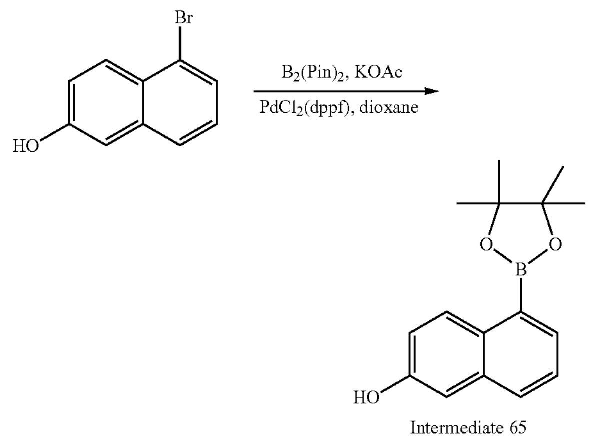 [SMILES: Oc1ccc2c(Br)cccc2c1 ; CC1(C)OB(c2cccc3cc(O)ccc23)OC1(C)C]

Intermediate 65

To a solution of 5-bromonaphthalen-2-ol (3.7 g, 16.59 mmol, Spectrochem) in 1,4-dioxane (100 mL) was added 4,4,4',4',5,5,5',5'-octamethyl-2,2'-bi(1,3,2-dioxaborolane) (6.32 g, 24.88 mmol), KOAc (4.07 g, 41.5 mmol) and $PdCl_2$(dppf)-DCM adduct (1.355 g, 1.659 mmol). The solution was purged with $N_2$ for 5 min and stirred at 100° C. for 16 h. The reaction was quenched with water and diluted with EtOAc. The aqueous layer was extracted with EtOAc and the combined the organic layers were dried over $Na_2SO_4$. The crude reaction mixture was purified by silica gel column chromatography (25% EtOAc in petroleum ether) to afford 5-(4,4,5,5-tetramethyl-1,3,2-dioxaborolan-2-yl)naphthalen-2-ol (4 g, 89% yield) as an off white solid. m/z (ESI): 271.0 $(M+H)^+$.

Intermediate 66: tert-butyl 6-(4-chloro-3-cyano-8-methoxyquinolin-2-yl)-2,6-diazaspiro[3.4]octane-2-carboxylate

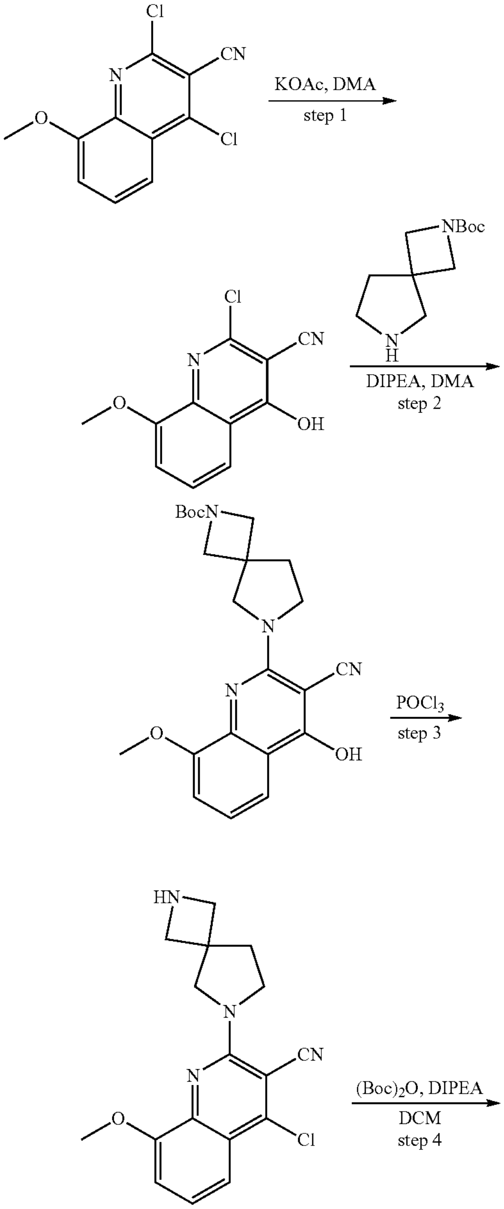

-continued

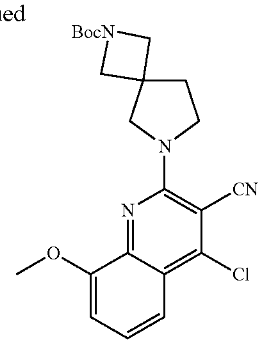

Intermediate 66

2,4-dichloro-8-methoxyquinoline-3-carbonitrile was synthesized using the method described in Intermediate 1 using methyl 2-amino-3-methoxybenzoate (CAS #5121-34-6, commercially available)

Step 1: 2-chloro-4-hydroxy-8-methoxyquinoline-3-carbonitrile

To a solution of 2,4-dichloro-8-methoxyquinoline-3-carbonitrile (700 mg, 2.71 mmol) in N, N-dimethylacetamide (10 mL) was added potassium acetate (1330 mg, 13.55 mmol) and the reaction was stirred at 80° C. stirred for 5 h. The pH was adjusted to neutral, and filtered and rinsed with water to obtain a residue. Drying under vacuum provided crude 2-chloro-4-hydroxy-8-methoxyquinoline-3-carbonitrile (590 mg, 92% yield). m/z (ESI): 235.2 $(M+H)^+$ Step 2: tert-butyl 6-(3-cyano-4-hydroxy-8-methoxyquinolin-2-yl)-2,6-diazaspiro[3.4]octane-2-carboxylate To a solution of 2-chloro-4-hydroxy-8-methoxyquinoline-3-carbonitrile (590 mg, 2.489 mmol) in N, N-dimethylacetamide (8 mL) was added DIPEA (1304 μL, 7.47 mmol) and tert-butyl 2,6-diazaspiro[3.4]octane-2-carboxylate (528 mg, 2.489 mmol). The mixture was stirred for 3 h at 120° C. The pH was adjusted to neutral, filtered, and rinsed with water to obtain a residue. Drying under vacuum provided crude tert-butyl 6-(3-cyano-4-hydroxy-8-methoxyquinolin-2-yl)-2,6-diazaspiro[3.4]octane-2-carboxylate (745 mg, 1.761 mmol, 70.7% yield). m/z (ESI): 411.2 $(M+H)^+$.

Step 3: 4-chloro-8-methoxy-2-(2,6-diazaspiro[3.4]octan-6-yl)quinoline-3-carbonitrile To a mixture of tert-butyl 6-(3-cyano-4-hydroxy-8-methoxyquinolin-2-yl)-2,6-diazaspiro-[3.4]octane-2-carboxylate (330 mg, 0.780 mmol) in 1,4-dioxane (3 mL) was added $POCl_3$ (4.5 mL, 48.3 mmol). The mixture was stirred for 5 h at 90° C. The reaction was cooled and saturated sodium bicarbonate solution was added to the solution. The reaction was poured into EtOAc and water. The aqueous layer was extracted with EtOAc and the combined organic layers were concentrated in vacuo. The crude product was purified by flash chromatography to give 4-chloro-8-methoxy-2-(2,6-diazaspiro[3.4]octan-6-yl)quinoline-3-carbonitrile (250 mg, 88% yield). m/z (ESI): 329.1 $(M+H)^+$.

Step 4: tert-butyl 6-(4-chloro-3-cyano-8-methoxyquinolin-2-yl)-2,6-diazaspiro[3.4]octane-2-carboxylate To a solution of 4-chloro-8-methoxy-2-(2,6-diazaspiro[3.4]octan-6-yl)quinoline-3-carbonitrile (400 mg, 1.217 mmol) in DCM (2 mL) was added DIPEA (637 μL, 3.65 mmol) and di-tert-butyl dicarbonate (266 mg, 1.217 mmol). The mixture was stirred for 2 h at room temperature. The mixture was concentrated in vacuo and purified by flash chromatography to give tert-butyl 6-(4-chloro-3-cyano-8-methoxyquinolin-2-yl)-2,6-diazaspiro[3.4]octane-2-carboxylate (250 mg, 47.9% yield). m/z (ESI): 429.1 $(M+H)^+$.

Intermediate 67: methyl 2-hydroxy-7,7-dimethyl-4-(5-methyl-1-(tetrahydro-2H-pyran-2-yl)-[1]H-indazol-4-yl)-5,6,7,8-tetrahydroquinoline-3-carboxylate

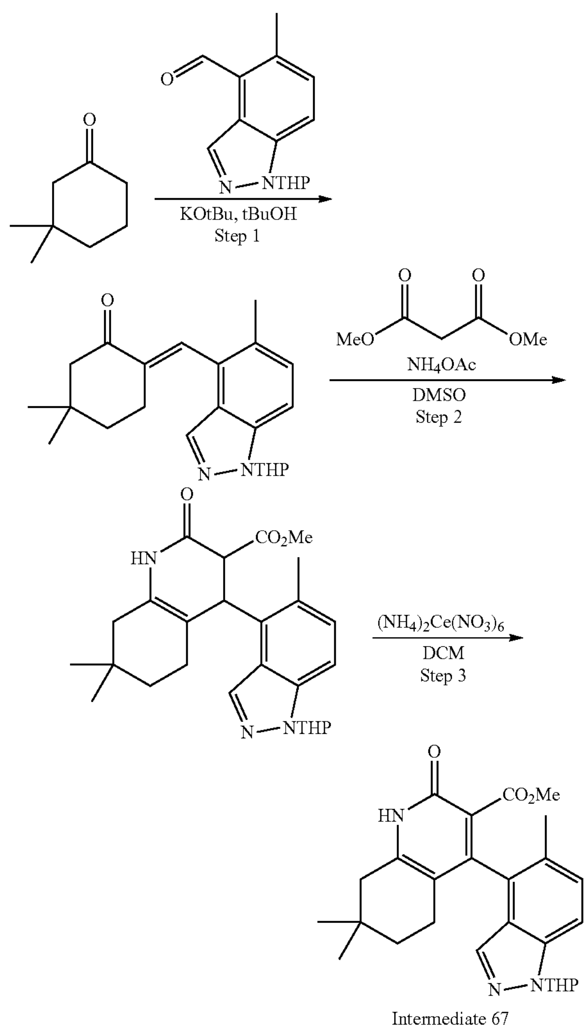

Intermediate 67

Step 1: (E)-5,5-dimethyl-2-((5-methyl-1-(tetrahydro-2H-pyran-2-yl)-1H-indazol-4-yl)methylene)cyclohexan-1-one A solution of 3,3-dimethylcyclohexan-1-one (0.500 g, 3.96 mmol, PharmaBlock Sciences, Inc.), 5-methyl-1-(tetrahydro-2H-pyran-2-yl)-1H-indazole-4-carbaldehyde (0.993 g, 4.06 mmol, Intermediate 58), and potassium t-butoxide (0.534 g, 4.75 mmol) in tert-butanol was stirred for 15 min at room temperature. The reaction was diluted with water and extracted with EtOAc (3×). Organics layers were dried and concentrated to give (E)-5,5-dimethyl-2-((5- methyl-1-(tetrahydro-2H-pyran-2-yl)-1H-indazol-4-yl) methylene)cyclohexan-1-one (1.39 g) as a light yellow oil, which was used in the following step as is assuming quantitative yield. m/z (ESI): 353.3

Step 2: methyl 7,7-dimethyl-4-(5-methyl-1-(tetrahydro-2H-pyran-2-yl)-1H-indazol-4-yl)-2-oxo-1,2,3,4,5,6,7,8-octahydroquinoline-3-carboxylate A solution of (E)-5,5-dimethyl-2-((5-methyl-1-(tetrahydro-2H-pyran-2-yl)-1H-indazol-4-yl)methylene)cyclohexan-1-one (1.39 g, 3.94 mmol), dimethyl malonate (1.563 g, 1.359 mL, 11.83 mmol), and $NH_4OAc$ (1.824 g, 23.66 mmol) in DMSO (19.7 mL) was stirred at 80° C. for 48 h. The reaction was diluted with water and extracted with EtOAc (3×). The combined organic layers were concentrated and further purified by column chromatography to give methyl 7,7-dimethyl-4-(5-methyl-1-(tetrahydro-2H-pyran-2-yl)-1H-indazol-4-yl)-2-oxo-1,2,3,4,5,6,7,8-octahydroquinoline-3-carboxylate (0.450 g, 25% yield) as a light yellow oil. m/z (ESI): 452.3 $(M+H)^+$.

Step 3: methyl 2-hydroxy-7,7-dimethyl-4-(5-methyl-1-(tetrahydro-2H-pyran-2-yl)-1H-indazol-4-yl)-5,67,8-tetrahydroquinoline-3-carboxylate A suspension of methyl 2-hydroxy-7,7-dimethyl-4-(5-methyl-1-(tetrahydro-2H-pyran-2-yl)-1H-indazol-4-yl)-4,4a,5,6,7,8-hexahydroquinoline-3-carboxylate (840 mg, 1.860 mmol) and ammonium cerium(iv) nitrate (3.06 g, 5.58 mmol, 3.0 equiv) in DCM (19 mL) was stirred at room temperature for 18 h. The reaction was diluted with water and extracted with EtOAc. The organic layers were dried, concentrated and chromatographed with 0-100% (3:1 EtOAc:EtOH) in heptane to give methyl 2-hydroxy-7,7-dimethyl-4-(5-methyl-1-(tetrahydro-2H-pyran-2-yl)-1H-indazol-4-yl)-5,6,7,8-tetrahydroquinoline-3-carboxylate (491 mg, 59% yield) as a yellow solid. m/z (ESI): 450.4 $(M+H)^+$.

Intermediate 68: 3-(difluoromethyl)-7,7-dimethyl-4-(5-methyl-1-(tetrahydro-2H-pyran-2-yl)-1H-indazol-4-yl)-7,8-dihydro-5H-pyrano[4,3-b]pyridin-2-ol

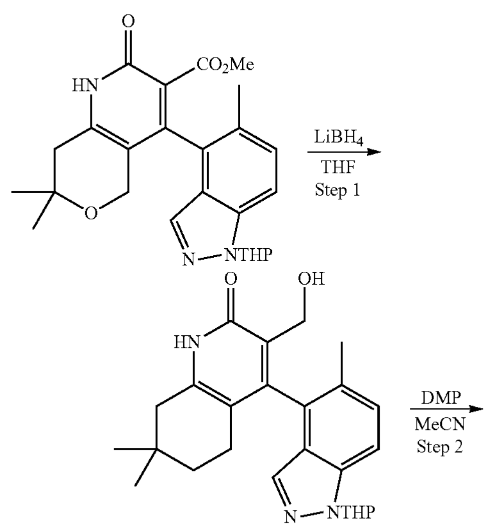

-continued

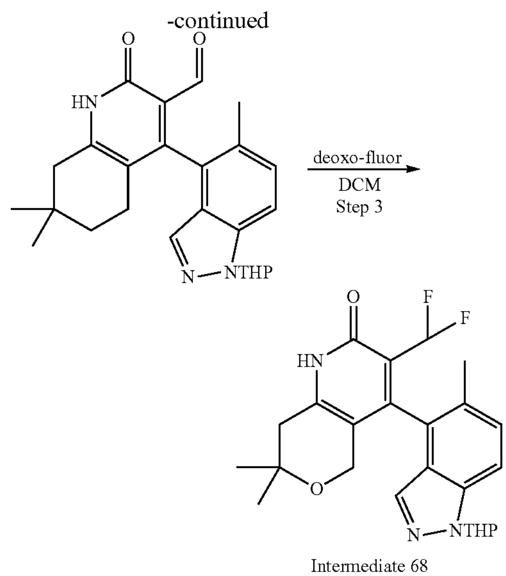

Intermediate 68 methyl 2-hydroxy-7,7-dimethyl-4-(5-methyl-1-(tetrahydro-2H-pyran-2-yl)-1H-indazol-4-yl)-5,6,7,8-tetrahydroquinoline-3-carboxylate was synthesized using the method described in Intermediate 67 using 2,2-dimethyltetrahydro-4H-pyran-4-one (PharmaBlock).

Step 1: 3-(hydroxymethyl)-7,7-dimethyl-4-(5-methyl-1-(tetrahydro-2H-pyran-2-yl)-1H-indazol-4-yl)-7,8-dihydro-5H-pyrano[4,3-b]pyridin-2-ol $LiBH_4$ (1M in THF) (0.89 mL, 1.77 mmol) was added to a 0° C. solution of methyl 2-hydroxy-7,7-dimethyl-4-(5-methyl-1-(tetrahydro-2H-pyran-2-yl)-1H-indazol-4-yl)-5,6,7,8-tetrahydroquinoline-3-carboxylate (100 mg, 0.22 mmol) in THF. The reaction was warmed to 50° C. and stirred for 2 h. The reaction was quenched with aqueous saturated $NH_4Cl$, extracted with EtOAc, dried, and concentrated to give 3-(hydroxymethyl)-7,7-dimethyl-4-(5-methyl-1-(tetrahydro-2H-pyran-2-yl)-1H-indazol-4-yl)-7,8-dihydro-5H-pyrano[4,3-b]pyridin-2-ol (188 mg) as a yellow solid, which was used in the following step as is assuming quantitative yield. m/z (ESI): 424.3 $(M+H)^+$.

Step 2: 2-hydroxy-7,7-dimethyl-4-(5-methyl-1-(tetrahydro-2H-pyran-2-yl)-1H-indazol-4-yl)-7,8-dihydro-5H-pyrano[4,3-b]pyridine-3-carbaldehyde 3-(hydroxymethyl)-7,7-dimethyl-4-(5-methyl-1-(tetrahydro-2H-pyran-2-yl)-1H-indazol-4-yl)-7,8-dihydro-5H-pyrano[4,3-b]pyridin-2-ol (188 mg, 0.44 mmol) and DMP (207 mg, 0.487 mmol) were dissolved in MeCN (9 mL). The mixture was stirred at room temperature for 4 h. Upon completion, the reaction was concentrated and chromatographed with 0-100% (3:1) EtOAc:EtOH in heptanes to give 2-hydroxy-7,7-dimethyl-4-(5-methyl-1-(tetrahydro-2H-pyran-2-yl)-1H-indazol-4-yl)-7,8-dihydro-5H-pyrano[4,3-b]pyridine-3-carbaldehyde (116 mg, 62% yield) as a yellow solid. m/z (ESI): 422.3 $(M+H)^+$.

Step 3: 3-(difluoromethyl)-7,7-dimethyl-4-(5-methyl-1-(tetrahydro-2H-pyran-2-yl)-1H-indazol-4-yl)-7,8-dihydro-5H-pyrano[4,3-b]pyridin-2-ol Deoxo-fluor (122 mg, 0.100 mL, 0.550 mmol, 2.0 equiv) was added to a 0° C. solution of 2-hydroxy-7,7-dimethyl- 4-(5-methyl-1-(tetrahydro-2H-pyran-2-yl)-1H-indazol-4-yl)-7,8-dihydro-5H-pyrano[4,3-b]pyridine-3-carbaldehyde (116 mg, 0.275 mmol) in DCM (5 mL). The reaction is allowed to stir for 2 h at room temperature. The reaction was concentrated and chromatographed with 0-100% (3:1) EtOAc:EtOH in heptanes to give 3-(difluoromethyl)-7,7-dimethyl-4-(5-methyl-1-(tetrahydro-2H-pyran-2-yl)-1H-indazol-4-yl)-7,8-dihydro-5H-pyrano[4,3-b]pyridin-2-ol (14 mg, 12% yield) as a yellow oil. m/z (ESI): 444.4 $(M+H)^+$.

Intermediate 69: 3-(methoxymethyl)-7,7-dimethyl-4-(5-methyl-1-(tetrahydro-2H-pyran-2-yl)-1H-indazol-4-yl)-5,6,7,8-tetrahydroquinolin-2(1H)-one

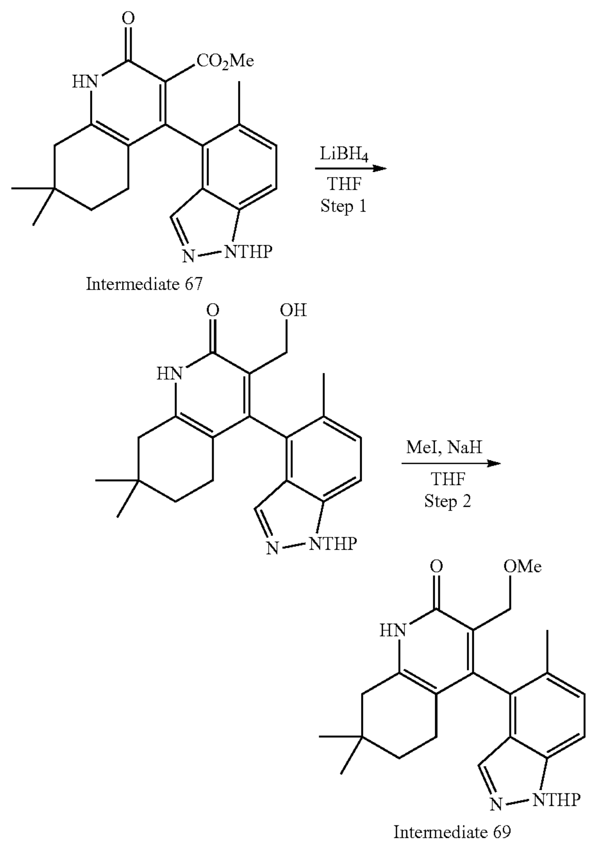

Intermediate 67

Intermediate 69

Step 1: 3-(hydroxymethyl)-7,7-dimethyl-4-(5-methyl-1-(tetrahydro-2H-pyran-2-yl)-1H-indazol-4-yl)-5,6,7,8-tetrahydroquinolin-2(1H)-one methyl 7,7-dimethyl-4-(5-methyl-1-(tetrahydro-2H-pyran-2-yl)-1H-indazol-4-yl)-2-oxo-1,2,5,6,7,8-hexahydroquinoline-3-carboxylate (980 mg, 2.18 mmol, Intermediate 67) was dissolved in THF (10 mL). The mixture was cooled to 0° C. and $LiBH_4$ (1M in THF, 5.40 mL, 5.40 mmol) was added. The mixture was heated to 50° C. for 18 h. Upon completion, the reaction was quenched with aqueous saturated $NH_4Cl$, extracted with EtOAc, dried, and concentrated. The resulting solid was further purified by chromatography to obtain 3-(hydroxymethyl)-7,7-dimethyl-4-(5-methyl-1-(tetrahydro-2H-pyran-2-yl)-1H-indazol-4-yl)-5,6,7,8-tetrahydroquinolin-2(1H)-one (430 mg, 47% yield) as a pale yellow solid. m/z (ESI): 422.3 $(M+H)^+$.

Step 2: 3-(methoxymethyl)-7,7-dimethyl-4-(5-methyl-1-(tetrahydro-2H-pyran-2-yl)-1H-indazol-4-yl)-5,6,7,8-tetrahydroquinolin-2(1H)-one 3-(hydroxymethyl)-7,7-dimethyl-4-(5-methyl-1-(tetrahydro-2H-pyran-2-yl)-1H-indazol-4-yl)-5,6,7,8-tetrahydroquinolin-2(1H)-one (300 mg, 0.712 mmol) was dissolved in THF (10 mL). The mixture was cooled to 0° C. and sodium hydride (85 mg, 3.56 mmol, 5.0 mmol) was added. The reaction was allowed to stir for 1 h and iodomethane (202 mg, 1.42 mmol, 2.0 equiv) was added. The mixture was allowed to stir for 1 h. The reaction was quenched with water and extracted with EtOAc. The organic layers were concentrated and further purified by column chromatography with 95:5 DCM:MeOH to obtain 3-(methoxymethyl)-7,7-dimethyl-4-(5-methyl-1-(tetrahydro-2H-pyran-2-yl)-1H-indazol-4-yl)-5,6,7,8-tetrahydroquinolin-2(1H)-one (100 mg, 32% yield) as a pale yellow solid. m/z (ESI): 436.2 $(M+H)^+$.

Intermediate 70: 2-chloro-6-((2-(trimethylsilyl)ethoxy)methoxy)benzaldehyde

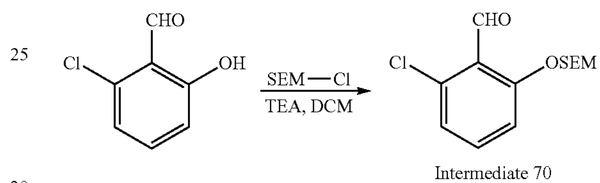

Intermediate 70

To a solution of 2-chloro-6-hydroxybenzaldehyde (0.5 g, 3.19 mmol, Combi-Blocks) and TEA (0.534 mL, 3.83 mmol, Sigma-Aldrich) in DCM (10 mL) was added 2-(trimethylsilyl)ethoxymethyl chloride (0.62 mL, 3.5 mmol, Sigma-Aldrich). The reaction was stirred at ambient temperature. After 1 h, another portion of TEA (0.388 g, 0.534 mL, 3.83 mmol, Sigma-Aldrich) and 2-(trimethylsilyl)ethoxymethyl chloride (0.623 mL, 3.51 mmol, Sigma-Aldrich) were added, and the reaction was continued. After 16 h, another portion of TEA (1.1 mL) and SEM·Cl (1.25 mL) were added, and the reaction was continued. After another 4 h, the reaction mixture was washed with saturated aqueous $NaHCO_3$ and concentrated to provide 2-chloro-6-((2-(trimethylsilyl)ethoxy)methoxy)-benzaldehyde (1.48 g. 162% yield) as a yellow oil. m/z (ESI): 309.0 $(M+Na)^+$.

Intermediate 71: 4-fluoro-3-((2-(trimethylsilyl)ethoxy)methoxy)-1-naphthaldehyde

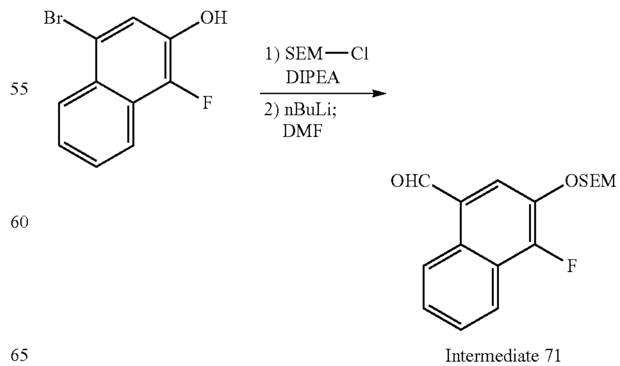

Intermediate 71

To a solution of 4-bromo-1-fluoronaphthalen-2-ol (2 g, 8.30 mmol, Combi-Blocks) and DIPEA (2.90 mL, 16.59 mmol) in DCM (28 mL) was added 2-(trimethylsilyl) ethoxymethyl chloride (2.07 g, 2.21 mL, 12.4 mmol, Combi-Blocks). The reaction was stirred at ambient temperature. After 16 h, the reaction mixture was washed with saturated aqueous $NaHCO_3$ and concentrated. The crude product was purified by column chromatography, eluting with 0-100% EtOAc in heptanes, to provide the intermediate (2-(((4-bromo-1-fluoronaphthalen-2-yl)oxy)methoxy)ethyl)trimethylsilane (3.26 g, 8.78 mmol, 106% yield) as a yellow oil. To a −78° C. solution of (2-(((4-bromo-1-fluoronaphthalen-2-yl)oxy)methoxy)ethyl)-trimethylsilane (3.0 g, 8.08 mmol) in THF (32.3 mL) was added a 2.5-M solution of n-butyllithium in hexanes (4.80 mL, 9.70 mmol, Sigma-Aldrich) dropwise. The reaction was stirred at −78° C. for 5 min, and then DMF (2.5 mL, 32 mmol, Sigma-Aldrich) was added. The reaction mixture was allowed to warm to ambient temperature. After 30 min, the reaction was quenched with saturated aqueous $NH_4Cl$ and extracted with EtOAc; the organic layer was concentrated. The crude product was purified by column chromatography, eluting with 0-100% EtOAc in heptanes, to provide 4-fluoro-3-((2-(trimethylsilyl)ethoxy)methoxy)-1-naphthaldehyde (2.82 g, 109% yield) as a yellow oil. m/z (ESI): 321.2 $(M+H)^+$.

Intermediate 72: 8-(4,4,5,5-tetramethyl-1,3,2-dioxaborolan-2-yl)isoquinolin-6-ol

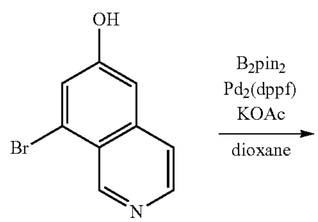

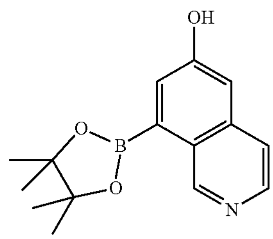

Intermediate 72

To a suspension of 8-bromoisoquinolin-6-ol hydrobromide (275 mg, 0.902 mmol, Enamine), bis(pinacolato)diboron (458 mg, 1.80 mmol, Sigma-Aldrich), and KOAc (265 mg, 2.71 mmol, Sigma-Aldrich) in 1,4-dioxane (6.0 mL) was added $PdCl_2(dppf)$ (147 mg, 0.180 mmol, Strem). The vial was sparged with argon, capped, and stirred at 90° C. overnight. After 16 h, the reaction mixture was filtered through Celite, washed with EtOAc, and concentrated in vacuo to provide crude 8-(4,4,5,5-tetramethyl-1,3,2-dioxaborolan-2-yl)isoquinolin-6-ol which was used without further purification.

Intermediate 73: 5-(4,4,5,5-tetramethyl-1,3,2-dioxaborolan-2-yl)quinolin-7-ol

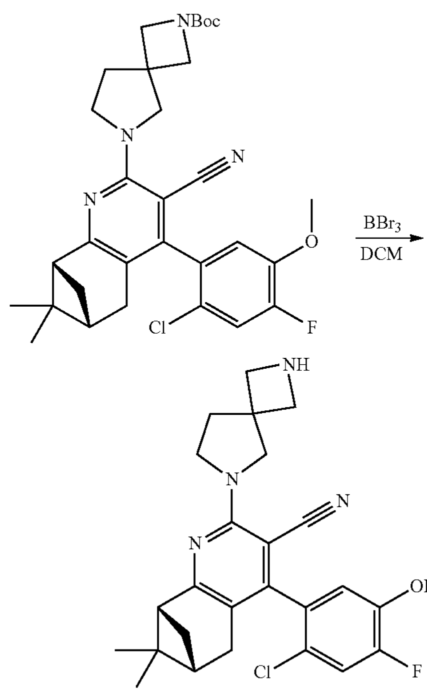

+

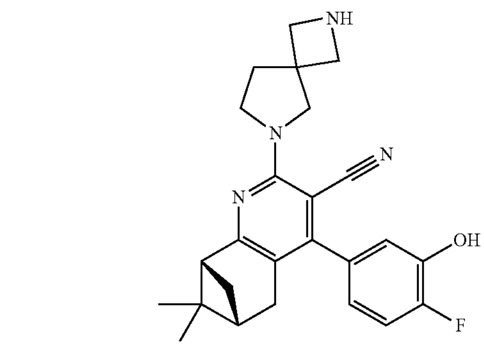

Synthesized in an analogous manner to intermediate 72 using 5-bromoquinolin-7-ol hydrobromide (Enamine).

Intermediate 74: 8-(4,4,5,5-tetramethyl-1,3,2-dioxaborolan-2-yl)quinolin-6-ol

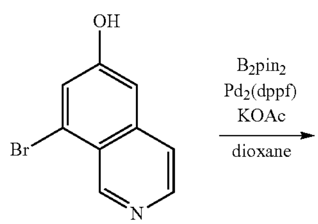

-continued

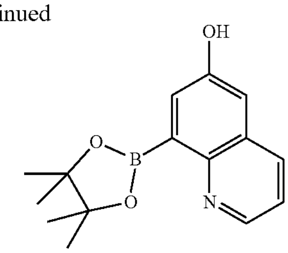

Intermediate 74

Synthesized in an analogous manner to intermediate 72 using 8-bromoquinolin-6-olhydrobromide (J&W Pharmalab).

Intermediate 75: 2,4-dichloro-7-methoxy-3-methyl-1,5-naphthyridine

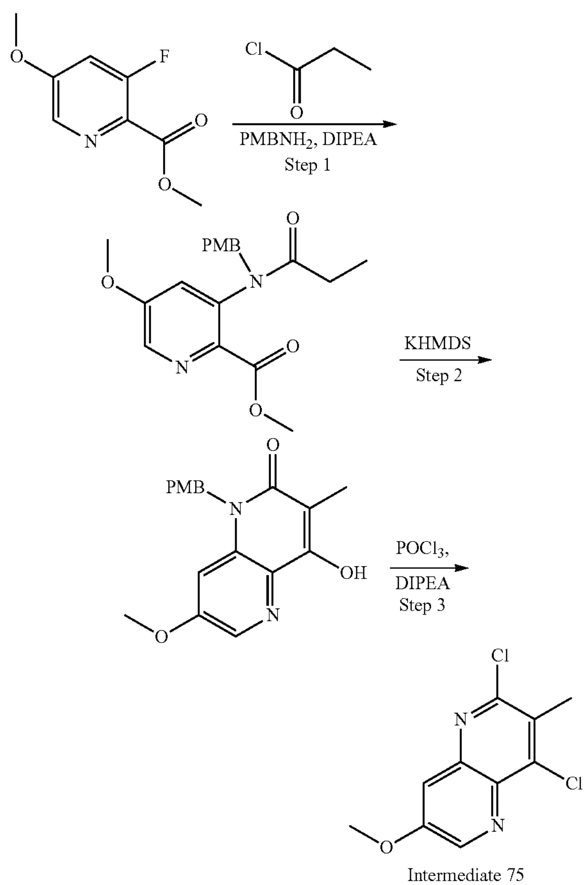

Intermediate 75

Step 1: methyl 5-methoxy-3-(N-(4-methoxybenzyl) propionamido)picolinate

A mixture of (4-methoxyphenyl)methanamine (1.785 mL, 13.66 mmol, Sigma-Aldrich), methyl 3-fluoro-5-methoxypicolinate (2.53 g, 13.66 mmol, Combi-blocks), and DIPEA (7.16 mL, 41.0 mmol, Sigma-Aldrich) in acetonitrile (30 mL) was stirred at 70° C. under $N_2$ overnight. Additional (4-methoxyphenyl)methanamine (0.89 mL, 0.5 eq), DIPEA (1.5 eq, 3.58 mL), and DMA (5 mL) were added stirring continued at 85° C. overnight. Then, DIPEA (7.16 mL, 41.0 mmol, Sigma-Aldrich) was added followed by propionyl chloride (5.75 mL, 68.3 mmol, Sigma-Aldrich). The resulting mixture was stirred at room temperature overnight. The mixture was diluted with aqueous saturated $NaHCO_3$ (100 mL) and extracted with EtOAc (1×200 mL). The organic extracts were dried over $MgSO_4$ and concentrated in vacuo. Chromatographic purification of the residue (silica gel, 0-100% EtOAc/heptanes) provided methyl 5-methoxy-3-(N-(4-methoxybenzyl)-propionamido)picolinate (3.92 g, 80% yield) as a light yellow solid. m/z (ESI): 359.3 $(M+H)^+$.

Step 2: 4-hydroxy-7-methoxy-1-(4-methoxybenzyl)-3-methyl-1,5-naphthyridin-2(1H)-one To a solution of methyl 5-methoxy-3-(N-(4-methoxybenzyl)propionamido)picolinate (3.5 g, 9.77 mmol) in THE (45 mL) at −78° C. under $N_2$ was added KHMDS, 1M in THE (19.53 mL, 19.53 mmol, Sigma-Aldrich). The resulting mixture was then stirred at −78° C. under $N_2$ for 5 min. The mixture was then quenched with water (15 mL). The mixture was concentrated and dried in vacuo. Chromatographic purification of the residue (silica gel, 0-100% EtOAc/heptanes) provided 4-hydroxy-7-methoxy-1-(4-methoxybenzyl)-3-methyl-1,5-naphthyridin-2(1H)-one (2.49 g) as a white solid. m/z (ESI): 327.2 $(M+H)^+$.

Step 3: 2,4-dichloro-7-methoxy-3-methyl-1,5-naphthyridine

A solution of 4-hydroxy-7-methoxy-1-(4-methoxybenzyl)-3-methyl-1,5-naphthyridin-2(1H)-one (1.0 g, 3.06 mmol) in acetonitrile (20 mL) was added DIPEA (2.68 mL, 15.32 mmol, Sigma-Aldrich) followed by $POCl_3$ (1.428 mL, 15.32 mmol, Sigma-Aldrich) dropwise. After addition, the mixture was stirred at 75° C. overnight under $N_2$. Then, $POCl_3$ (2.8 mL) was added and the mixture was stirred at reflux under $N_2$ overnight. The mixture was carefully poured into an ice water (200 mL) containing saturated $K_2CO_3$ and was diluted with EtOAc (200 mL). The mixture was stirred at room temperature for 30 min. The organic layer was dried over $MgSO_4$ and concentrated in vacuo. Chromatographic purification of the residue (silica gel, 0-100% EtOAc/heptanes) provided 2,4-dichloro-7-methoxy-3-methyl-1,5-naphthyridine (156 mg) as a yellow solid. m/z (ESI): 243.1 $(M+H)^+$. $^1H$ NMR (400 MHz, DMSO-$d_6$) δ ppm 8.84 (d, J=2.7 Hz, 1H), 7.83 (d, J=2.7 Hz, 1H), 4.00 (s, 3H), 2.63 (s, 3H).

Intermediate 76: 7-bromo-3-chloro-6-methyl-1H-indole

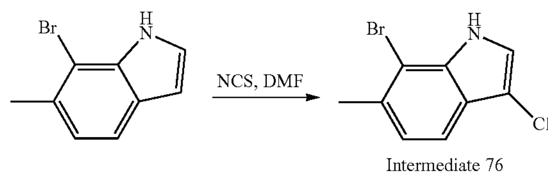

Intermediate 76

A mixture of 7-bromo-6-methyl-1H-indole (1.5 g, 7.14 mmol, Enamine) in DMF (40 mL) was added N-chlorosuccinimide (1.144 g, 8.57 mmol, Sigma-Aldrich). The resulting mixture was then stirred at room temperature overnight. The mixture was then concentrated in vacuo. Chromatographic purification of the residue (silica gel, 0-100% EtOAc:EtOH (3:1)/heptanes) provided 7-bromo-3-chloro-6-methyl-1H-indole (1.67 g, 96% yield) as a brown solid. m/z (ESI): 244.0, 246.1 $(M+H)^+$.

Intermediate 77: 6,8-dibromoisochromane-7-carbonitrile

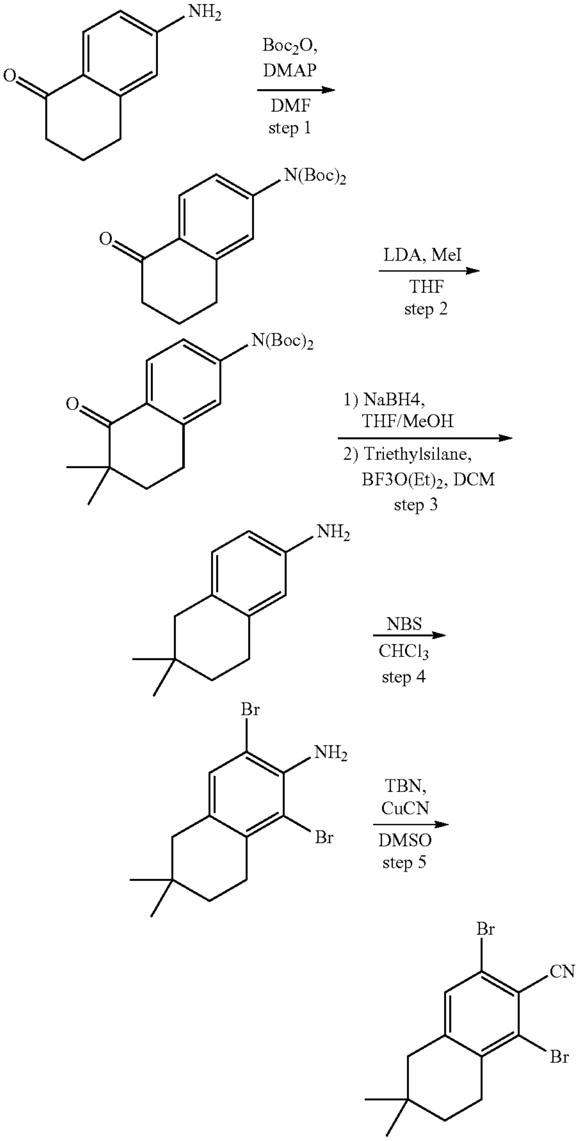

Intermediate 77

Step 1: tert-butyl (tert-butoxycarbonyl)(5-oxo-5,6,7,8-tetrahydronaphthalen-2-yl)carbamate To a stirred solution of 6-amino-3,4-dihydronaphthalen-1(2H)-one (70 g, 434 mmol, Combi-Blocks) in DMF (700 mL) was added di-tert-butyl dicarbonate (302 mL, 1303 mmol) followed by DMAP (63.7 g, 521 mmol) at room temperature and stirred for 16 h. The reaction mixture was quenched with aqueous saturated $NH_4Cl$ solution (3 L). The reaction mixture was diluted with EtOAc (1 L) and extracted with EtOAc (2×1 L). The combined organic layers were washed with brine (1×2 L) and dried over $Na_2SO_4$. The solution was filtered and concentrated in vacuo to give the crude material as a tan oil. The crude residue was purified by column chromatography over silica gel using with 20% EtOAc in hexanes as the eluent to give tert-butyl (tert-butoxycarbonyl)(5-oxo-5,6,7,8-tetrahydronaphthalen-2-yl) carbamate (65 g, 41.4% yield) as a light-yellow solid. m/z (ESI): 262.0 $[M+H-Boc]^+$. $^1$H NMR (400 MHz, $CDCl_3$) δ ppm 8.06 (1H, d, J=8.2 Hz) 7.05-7.18 (2H, m) 2.99 (2H, t, J=6.1 Hz) 2.58-2.73 (2H, m) 2.17 (3H, p, J=6.3 Hz) 1.47 (18H, s).

Step 2: tert-butyl (tert-butoxycarbonyl)(6,6-dimethyl-5-oxo-5,6,7,8-tetrahydronaphthalen-2-yl)carbamate To a stirred solution of tert-butyl (tert-butoxycarbonyl) (5-oxo-5,6,7,8-tetrahydronaphthalen-2-yl)carbamate (35 g, 97 mmol) in THF (350 mL) was added LiHMDS (968 mL, 968 mmol) at 0° C. and the reaction mixture stirred at 0° C. for 30 min, then iodomethane (60.5 mL, 968 mmol) was added dropwise at 0° C. The reaction mixture was stirred at room temperature for 16 h. The reaction mixture was cooled to 0° C. and diluted with aqueous saturated $NH_4Cl$ (1×500 mL) and extracted with EtOAc (2×1 L), the organic layers were washed with brine (1×1 L) The combined organic layers were dried over $Na_2SO_4$. The solution was filtered and concentrated in vacuo to give the crude material as a tan oil. The crude residue was purified by column chromatography over silica gel using with 20% EtOAc in hexanes as the eluent to give tert-butyl (tert-butoxycarbonyl)(6,6-dimethyl-5-oxo-5,6,7,8-tetrahydronaphthalen-2-yl)carbamate as yellow oil. m/z (ESI): 290.0 $[M+H-Boc]^+$. $^1$H NMR (400 MHz, DMSO-$d_6$) δ ppm 7.88 (1H, d, J=8.2 Hz) 7.06-7.25 (2H, m) 2.97 (2H, t, J=6.3 Hz) 1.92 (2H, dt, J=20.6, 6.3 Hz) 1.42 (18H, s) 1.12 (6H, d, J=3.7 Hz).

Step 3: 6,6-dimethyl-5,6,7,8-tetrahydronaphthalen-2-amine

To a stirred solution of tert-butyl (tert-butoxycarbonyl)(6,6-dimethyl-5-oxo-5,6,7,8-tetrahydronaphthalen-2-yl)carbamate (80 g, 205 mmol) in THF (400 mL), MeOH (400 mL) mixture, $NaBH_4$ (23.31 g, 616 mmol) was added portionwise at 0° C. The reaction mixture was stirred at room temperature for 30 min. The reaction mixture was diluted with water (200 mL) and extracted with EtOAc (2×300 mL). The organic layers were mixed and washed with brine (1×1 L). The organic layer was dried over $Na_2SO_4$. The solution was filtered and concentrated in vacuo to give (80 g) as a yellow oil. The crude as such as taken for next step without any purification.

To a stirred solution of intermediate (80 g) in DCM (500 mL), triethylsilane (47.8 g, 411 mmol) and boron trifluoride etherate (52.1 mL, 411 mmol) were added at −78° C. and stirred at same temperature for 1 h., The reaction mixture was stirred at room temperature for 16 h. The reaction mixture was quenched with aqueous saturated $NaHCO_3$ (200 mL) and extracted with DCM (2×500 mL). The combined organic layers were washed with brine (500 mL) and dried over $Na_2SO_4$, filtered and concentrated under reduced pressure. The crude residue was purified by column chromatography over silica gel using 20% EtOAc in hexane, to provide 6,6-dimethyl-5,6,7,8-tetrahydronaphthalen-2-amine (18 g, 50.0% yield in two steps) as a tan oil. m/z (ESI): 176.3 $[M+H]^+$. $^1$H NMR (400 MHz, DMSO-$d_6$) δ ppm 6.66 (1H, d, J=8.0 Hz) 6.22-6.45 (2H, m) 4.68 (2H, s) 2.59 (2H, t, J=6.8 Hz) 2.31 (2H, s) 1.44 (2H, t, J=6.8 Hz) 0.91 (6H, s).

Step 4: 1,3-dibromo-6,6-dimethyl-5,6,7,8-tetrahydronaphthalen-2-amine

To a stirred solution of 6,6-dimethyl-5,6,7,8-tetrahydronaphthalen-2-amine (18 g, 103 mmol) in chloroform (300 mL) were added NBS (40.2 g, 226 mmol) portion wise at −10° C. and stirred at same temperature for 30 min. The reaction mixture was quenched with water (200 mL) and extracted with DCM (2×300 mL). The combined organic layers were washed with brine (300 mL) and dried over $Na_2SO_4$, and concentrated under reduced pressure. The crude residue was purified by column chromatography over silica gel using 2% EtOAc in hexane, to provide 1,3-dibromo-6,6-dimethyl-5,6,7,8-tetrahydronaphthalen-2-amine (25 g, 73.1% yield), as tan oil. m/z (ESI): 334.0 $[M+H]^+$. $^1H$ NMR (400 MHz, DMSO-$d_6$) δ ppm 7.17 (1H, s) 5.08 (2H, s) 2.57 (2H, t, J=6.8 Hz) 2.40 (2H, s) 1.52 (2H, t, J=6.8 Hz) 0.91 (6H, s).

Step 5: 1,3-dibromo-6,6-dimethyl-5,6,7,8-tetrahydronaphthalene-2-carbonitrile

To a stirred solution of 1,3-dibromo-6,6-dimethyl-5,6,7,8-tetrahydronaphthalen-2-amine (1.0 g, 3.00 mmol) in DMSO (10.00 mL) was added copper (I) cyanide (350 mg, 3.90 mmol) and tert-butyl nitrite (1.161 mL, 9.01 mmol) at 50° C. and stirred for 2 h. The reaction was quenched with aqueous saturated $NaHCO_3$ (50 mL) and extracted with EtOAc (2×100 mL). The combined organic layers were dried over $Na_2SO_4$ and concentrated under vacuum. The crude residue was purified by column chromatography over silica gel using with 3% EtOAc in hexanes to provide 1,3-dibromo-6,6-dimethyl-5,6,7,8-tetrahydronaphthalene-2-carbonitrile (300 mg, 29% yield) as a pale brown solid. $^1H$ NMR (400 MHz, DMSO-$d_6$) δ ppm 7.68 (s, 1H), 2.64 (d, J=10.8 Hz, 4H), 1.59 (t, J=6.8 Hz, 2H), 0.92 (d, J=5.9 Hz, 6H).

TABLE 18

Intermediates 78 to 81 were prepared following the procedure described in Intermediate 77, Steps 1-5, above as follows

| Ex.# | Chemical Structure | Name | Method changes | Reagent |
|---|---|---|---|---|
| 78 | 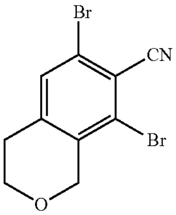 [SMILES: N#Cc1c(Br)cc2c(c1Br)COCC2] | 6,8-dibromoisochromane-7-carbonitrile | Omit steps 1-3. Step 4: AcOH as solvent. Step 5: Alternative procedure below | Step 4: isochroman-7-amine (Enamine) |
| 79 | 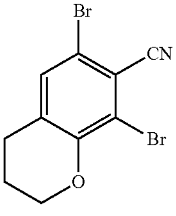 [SMILES: N#Cc1c(Br)cc2c(c1Br)OCCC2] | 6,8-dibromochromane-7-carbonitrile | Omit steps 1-3. Step 4: AcOH as solvent. | Step 4: chroman-7-amine hydrochloride (Angel Pharmatech) |
| 80 | 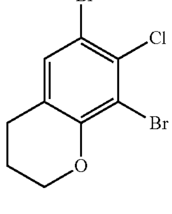 | 6,8-dibromo-7-chlorochromane | Omit steps 1-3. Step 4: AcOH as solvent. Step 5: $CuCl_2$ used | Step 4: chroman-7-amine hydrochloride (Angel Pharmatech Ltd.) |
| 81 | 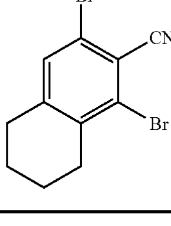 | 1,3-dibromo-5,6,7,8-tetrahydronaphthalene-2-carbonitrile | Omit steps 1-3. Step 4: AcOH as solvent. | Step 4: 5,6,7,8-tetrahydronaphthalen-2-amine (Sigma Sigma-Aldrich) |

Alternative Step 5 for Intermediate 78

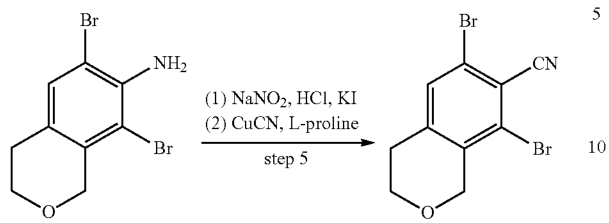

Sodium nitrite (94 ng, 1.360 mmol) was added to a stirred mixture of 6,8-dibromoisochroman-7-amine (348 mg, 1.134 mmol) in water (10 mL) and 12 N hydrochloric acid (5 mL, 60.0 mmol) at 0° C. The mixture was stirred at 0° C. for 15 min before potassium iodide (565 mg, 3.40 mmol) was added. The reaction mixture was stirred at 0° C. for another 2 h. The reaction mixture was diluted with water (75 mL) and extracted with EtOAc (100 mL). The organic layer was separated, washed with brine (50 mL), dried over $MgSO_4$, filtered, and concentrated. Chromatographic purification of the residue (silica gel, 0-20% EtOAc in heptane) gave 6,8-dibromo-7-iodoisochromane (228 mg, 48.1% yield) as a light pink solid.

The above isolated 6,8-dibromo-7-iodoisochromane (228 mg, 0.546 mmol), copper (i) cyanide (98 mg, 1.091 mmol), and L-proline (62.8 mg, 0.546 mmol) were mixed in N, N-dimethylformamide (2 mL). The reaction mixture was heated to 80° C. and stirred for 19 h. The reaction mixture was diluted with EtOAc (50 mL) and washed with saturated $NaHCO_3$ (30 mL). The organic layer was separated, washed with brine (30 mL), dried over $MgSO_4$, filtered, and concentrated in vacuo. Chromatographic purification of the residue (silica gel, 0-20% EtOAc in heptane) gave 6,8-dibromoisochromane-7-carbonitrile (121 mg, 70.0% yield) as a white solid. $^1$H NMR (400 MHz, $CDCl_3$) δ ppm 7.47 (1H, s) 4.67 (2H, s) 3.95 (2H, t, J=5.64 Hz) 2.91 (2H. td, J=5.64, 1.05 Hz). MS (ESI, +ve) m/z: 316.0 $[M+H]^+$.

Intermediate 82: (6R,8R)-2,4-dichloro-7,7-dimethyl-5,6,7,8-tetrahydro-6,8-methanoquinoline-3-carbonitrile

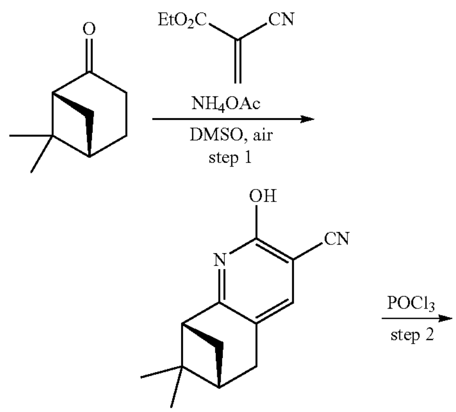

-continued

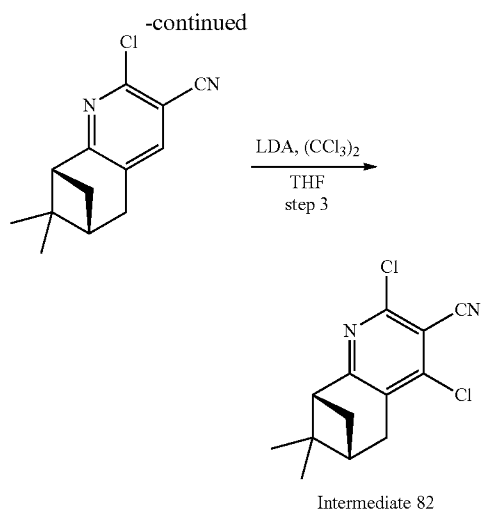

Intermediate 82

Synthesized in an Analogous Manner to Intermediate 21 Using an Alternate Step 2:

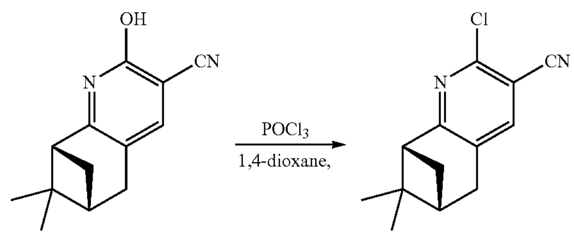

To a suspension of (6R,8R)-2-hydroxy-7,7-dimethyl-5,6,7,8-tetrahydro-6,8-methanoquinoline-3-carbonitrile (0.582 g, 2.72 mmol) in 1,4-dioxane (13 mL) was added $POCl_3$ (4.16 g, 2.53 mL, 27.2 mmol, Sigma-Aldrich). The reaction mixture stirred at 95° C. for 3 h. The reaction mixture was poured into a cold solution of aqueous saturated $NaHCO_3$ and solid $K_2CO_3$ was added to the stirring reaction mixture until bubbling ceased and a basic pH was measured. The reaction mixture was extracted with EtOAc and the organic extracts were washed with brine, dried over $Na_2SO_4$, and concentrated in vacuo. The crude material was absorbed onto a plug of silica gel and purified by chromatography through a Redi-Sep pre-packed silica gel column, eluting with a gradient of 0-20% EtOAc:EtOH (3:1) in heptanes, to provide (6R,8R)-2-chloro-7,7-dimethyl-5,6,7,8-tetrahydro-6,8-methanoquinoline-3-carbonitrile (0.367 g, 58.1% yield) as a light-yellow solid. m/z (ESI): 233.1 $(M+H)^+$.

Intermediate 83: 5-(4,4,5,5-tetramethyl-1,3,2-dioxaborolan-2-yl)naphthalen-1-ol

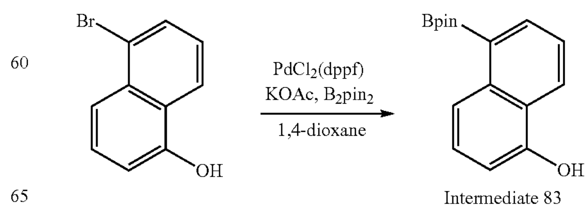

Intermediate 83

To a 40 mL red capped vial was added $PdCl_2$(dppf) DCM adduct (0.183 g, 0.224 mmol, Strem Chemicals, Inc.), KOAc (0.440 g, 4.48 mmol, Sigma-Aldrich), bis(pinacalato) diboron (1.138 g, 4.48 mmol, Combi-Blocks), and 5-bromonaphthalen-1-ol (0.5 g, 2.241 mmol, eNovation). The reaction vessel was evacuated and backfilled with $N_2$, and 1,4-dioxane (4.48 mL) was added. The reaction mixture was heated to 100° C. and stirred for 1 h. The reaction mixture was filtered through a plug of silica and concentrated in vacuo. The crude material was absorbed onto a plug of silica gel and purified by chromatography through a Redi-Sep pre-packed silica gel column, eluting with a gradient of 0-30% EtOAc in heptanes, to provide 5-(4,4,5,5-tetramethyl-1,3,2-dioxaborolan-2-yl)naphthalen-1-ol (0.814 g, quantitative yield) as a gray solid. The material contained some unremovable impurities and was used without further purification. m/z (ESI): 271.2 $(M+H)^+$.

Intermediate 84: 4-bromo-2-fluoronaphthalen-1-ol

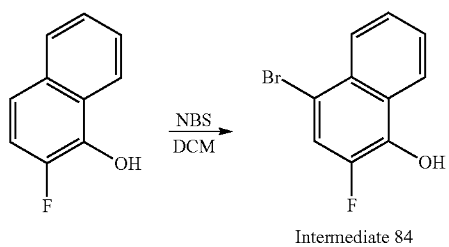

Intermediate 84

To a −50° C. solution of 2-fluoronaphthalen-1-ol (200 mg, 1.233 mmol, Enamine) in DCM (3.2 mL) was added NBS (209 mg, 1.172 mmol, Sigma-Aldrich) and the reaction mixture was stirred for 15 min. The reaction was quenched with water and extracted with DCM. The organic extracts were dried through a plug of $Na_2SO_4$ and concentrated in vacuo. The crude material was absorbed onto a plug of silica gel and purified by chromatography through a Redi-Sep pre-packed silica gel column, eluting with a gradient of 0-5% EtOAc in heptanes, to provide 4-bromo-2-fluoronaphthalen-1-ol (0.2328 g, 78% yield) as a light-yellow solid. $^1H$ NMR (400 MHz, $CDCl_3$) δ ppm 8.21-8.30 (m, 1H), 8.12-8.18 (m, 1H), 7.62-7.67 (in, 1H), 7.54-7.61 (m, 2H), 5.53 (d, J=4.4 Hz, 1H).

Intermediate 85: tert-butyl 6-((6R,8R)-3-cyano-7,7-dimethyl-4-(4,4,5,5-tetramethyl-1,3,2-dioxaborolan-2-yl)-5,6,7,8-tetrahydro-6,8-methanoquinolin-2-yl)-2,6-diazaspiro[3.4]octane-2-carboxylate

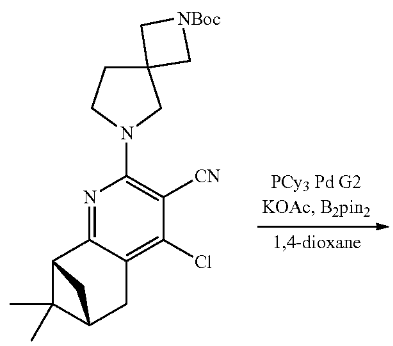

-continued

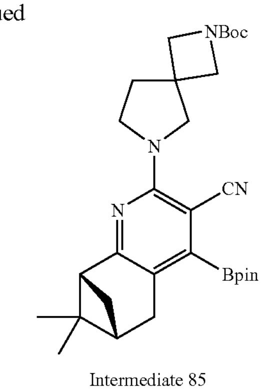

Intermediate 85

To a red capped vial was added $PCy_3$ Pd G2 (0.245 g, 0.415 mmol, Sigma-Aldrich), KOAc (0.815 g, 8.31 mmol, Sigma-Aldrich), bis(pinacalato)diboron (2.110 g, 8.31 mmol, Combi-Blocks), and tert-butyl 6-((6R,8R)-4-chloro-3-cyano-7,7-dimethyl-5,6,7,8-tetrahydro-6,8-methanoquinolin-2-yl)-2,6-diazaspiro[3.4]octane-2-carboxylate (1.84 g, 4.15 mmol, Intermediate 35). The reaction vessel was evacuated and backfilled with $N_2$, and 1,4-dioxane (20 mL) was added. The reaction was heated to 95° C. and stirred for 3 h. The reaction mixture was filtered over celite, eluted with EtOAc, concentrated in vacuo, and chromatographed on silica gel, eluting with a gradient of 0-20% EtOAc in heptanes, to provide tert-butyl 6-((6R,8R)-3-cyano-7,7-dimethyl-4-(4,4,5,5-tetramethyl-1,3,2-dioxaborolan-2-yl)-5,6,7,8-tetrahydro-6,8-methanoquinolin-2-yl)-2,6-diazaspiro[3.4]octane-2-carboxylate (1.5 g, 67.6% yield) as a tan solid. The final isolated material is a 1:1 mixture of desired product and protodeborylated product. m/z (ESI): 535.4 $(M+H)^+$.

Intermediate 86: 8-bromoquinoxalin-6-ol

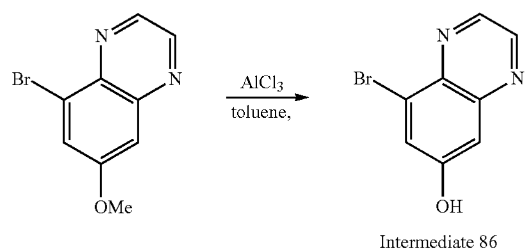

Intermediate 86

To a suspension of 5-bromo-7-methoxyquinoxaline (200 mg, 0.837 mmol, Aurum Pharmatech) in toluene (4 mL) was added aluminum chloride (390 mg, 2.93 mmol, Sigma-Aldrich) and the reaction mixture was heated to 100° C. and stirred for 2 h. To the reaction mixture was slowly added water followed by 1M aq. NaOH. The reaction mixture was extracted with EtOAc and the organic extracts were washed with brine, dried over $Na_2SO_4$, filtered and concentrated in vacuo. The crude material was absorbed onto a plug of silica gel and purified by chromatography through a Redi-Sep pre-packed silica gel column (12 g), eluting with a gradient of 0-40% EtOAc:EtOH (3:1) in heptanes, to provide 8-bromoquinoxalin-6-ol (56 mg, 29.7% yield) as an orange solid. The sample was carried forward as is. m/z (ESI): 225.0 $(M+H)^+$.

Intermediate 87: 3-(4,4,5,5-tetramethyl-1,3,2-dioxaborolan-2-yl)-4-(trifluoromethyl)phenol

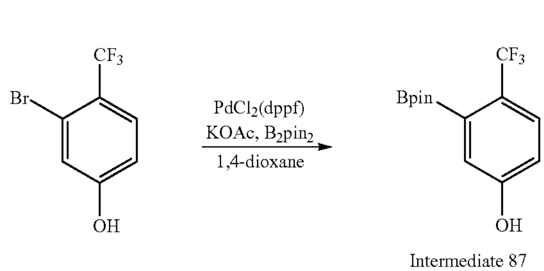

Intermediate 87

To a 20 mL red capped vial was added $PdCl_2$(dppf) DCM adduct (169 mg, 0.207 mmol, Strem Chemicals, Inc.), KOAc (407 mg, 4.15 mmol, Sigma-Aldrich), bis(pinacalato) diboron (1054 mg, 4.15 mmol, Combi-Blocks), and 3-bromo-4-trifluoromethylphenol (500 mg, 2.075 mmol, AstaTech, Inc). The reaction vessel was evacuated and backfilled with $N_2$, and 1,4-dioxane (5 mL) was added. The reaction mixture was heated to 100° C. and stirred for 3 h. The reaction mixture was filtered through a plug of silica and concentrated in vacuo. The crude material was absorbed onto a plug of silica gel and purified by chromatography through a Redi-Sep pre-packed silica gel column (24 g), eluting with a gradient of 0-30% EtOAc in heptanes, to provide 3-(4,4,5,5-tetramethyl-1,3,2-dioxaborolan-2-yl)-4-(trifluoromethyl)phenol (1.02 g, quantitative yield) as a yellow semi-solid. The material was used without further purification. $^1$H NMR (400 MHz, $CDCl_3$) δ ppm 7.53-7.57 (m, 1H), 7.12-7.17 (m, 1H), 6.88-6.95 (m, 1H), 1.32-1.40 (m, 12H).

Intermediate 88: 2-methyl-5-((tetrahydro-2H-pyran-2-yl)oxy)benzaldehyde

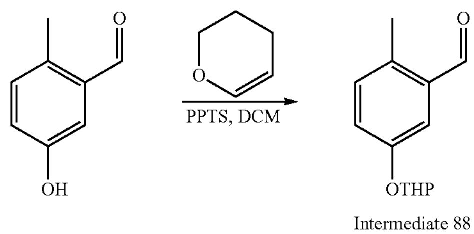

Intermediate 88

To a RBF was added pyridinium p-toluenesulfonate (0.046 g, 0.185 mmol, Sigma-Aldrich), 3,4-dihydro-2h-pyran (0.467 g, 0.507 mL, 5.55 mmol, Sigma-Aldrich), 5-hydroxy-2-methylbenzaldehyde (0.5034 g, 3.70 mmol, CAS #23942-00-9) and DCM (18 mL). The reaction mixture was stirred at room temperature overnight. The reaction mixture was diluted with water (20 mL) and extracted with DCM (3×20 mL). The organic extract was washed with brine (10 mL) and dried over $MgSO_4$. The solution was filtered and concentrated in vacuo to give the crude 2-methyl-5-((tetrahydro-2H-pyran-2-yl)oxy)benzaldehyde as a light-yellow oil that was used in the next step with no further purification. m/z (ESI): 221.2 $(M+H)^+$.

Intermediate 89: 5-bromo 4-(methoxymethyl)thiazole

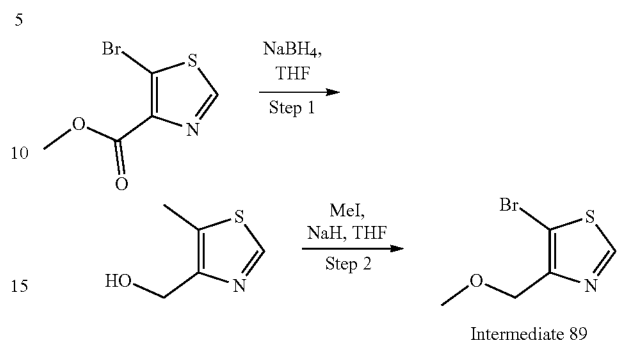

Intermediate 89

Step 1: (5-bromothiazol-4-yl)methanol

To a solution of methyl 5-bromothiazole-4-carboxylate (2.0 g. 9.01 mmol, Combi-Blocks) in THF (20 mL) was added $NaBH_4$ (0.852 g, 22.52 mmol) portion wise at 0° C. The reaction mixture was stirred at room temperature for 16 h, then diluted with aqueous saturated $NH_4Cl$ solution and extracted with EtOAc. The organic extracts were washed with brine, dried over $Na_2SO_4$, and concentrated under reduced pressure. The residue was purified on a Redi-Sep pre-packed silica gel column eluting with a gradient of 50-60% EtOAc in hexanes to provide 5-bromothiazol-4-yl) methanol (0.500 g, 28.6% yield) as a light-yellow solid.

Step 2: 5-bromo-4-(methoxymethyl)thiazole

To a solution of (5-bromothiazol-4-yl)methanol (0.500 g, 2.58 mmol) in THF (10 mL) was added sodium hydride (0.309 g, 7.73 mmol, 60 wt %, Spectrochem) at 0° C. and the mixture was stirred for 30 min before methyl iodide (0.806 mL, 12.88 mmol, Spectrochem) was added dropwise to the reaction mixture and stirring was continued for 16 h at room temperature. The reaction mixture was diluted with aqueous saturated $NH_4Cl$ solution and extracted with EtOAc. The organic extracts were washed with brine, dried over $Na_2SO_4$, filtered and concentrated under reduced pressure. The residue was purified on a Redi-Sep pre-packed silica gel column (40 g) eluting with a gradient of 40-50% EtOAc in petroleum ether to provide 5-bromo-4-(methoxymethyl)thiazole (0.300 g, 56.0% yield) as a light yellow solid. $^1$H NMR (400 MHz, $CDCl_3$) δ ppm 8.80 (s, 1H), 4.60 (s, 2H), 3.46 (s, 3H). m/z (ESI): 209.9 $(M+H)^+$.

Intermediate 90: 5-Chloro-1-(tetrahydro-2H-pyran-2-yl)-1H-indazole-4-carbaldehyde

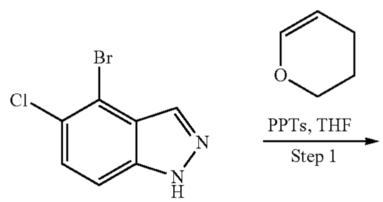

-continued

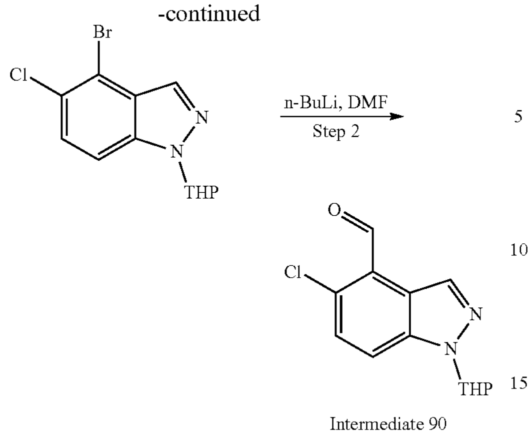

Intermediate 90

Step 1: 4-bromo-5-chloro-1-(tetrahydro-2H-pyran-2-yl)-1H-indazole

A solution of 4-bromo-5-chloro-1H-indazole (5.0 g, 21.60 mmol, Combi-blocks), 3,4-dihydro-2H-pyran (5.45 g, 64.8 mmol, Avra) and PPTS (1.086 g, 4.32 mmol, Avra) in THF (20 mL) was stirred at room temperature for 12 h. The reaction mixture was diluted with ice-cold water and extracted with EtOAc. The combined organic extracts were washed with brine, separated, dried over $Na_2SO_4$, filtered, and concentrated under reduced pressure. The residue was purified on a Redi-Sep pre-packed silica gel column eluting with 10-15% EtOAc in hexanes to provide 4-bromo-5-chloro-1-(tetrahydro-2H-pyran-2-yl)-1H-indazole (4.5 g, 66.0% yield) as a white solid. $^1H$ NMR (400 MHz, $CDCl_3$) δ ppm 8.17 (d, J=1.0 Hz, 1H), 7.61 (dd, J=9.1, 1.0 Hz, 1H), 7.30 (d, J=9.0 Hz, 1H), 5.67-5.69 (m, 1H), 4.16-4.17 (m, 1H), 3.80-3.82 (m, 1H), 1.99-2.31 (m, 2H), 1.63-1.91 (m, 4H). m/z (ESI): 314.8 $(M+H)^+$.

Step 2: 5-chloro-1-(tetrahydro-2H-pyran-2-yl)-1H-indazole-4-carbaldehyde

To a solution of 4-bromo-5-chloro-1-(tetrahydro-2H-pyran-2-yl)-1H-indazole (0.6 g, 1.901 mmol) in THF (10 mL) at −78° C. was added n-butyllithium (1.673 mL, 4.18 mmol, Sainor Ltd) dropwise. The reaction mixture was allowed to stir for 30 min before DMF (0.556 g, 7.60 mmol, Sigma Sigma-Aldrich) was added and stirring was continued for 1 h. The reaction mixture was diluted with ice-cold water and extracted with EtOAc. The combined organic extracts were washed with brine, separated, dried over $Na_2SO_4$, filtered, and concentrated under reduced pressure. The residue was purified on a Redi-Sep pre-packed silica gel column eluting with 10-15% EtOAc in hexanes to provide 5-chloro-1-(tetrahydro-2H-pyran-2-yl)-1H-indazole-4-carbaldehyde (0.480 g).

Intermediate 91: 5-Fluoro-1-(tetrahydro-2H-pyran-2-yl)-1H-indazole-4-carbaldehyde

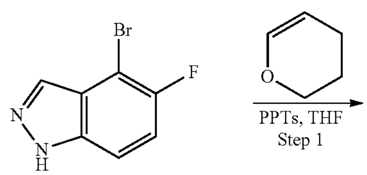

-continued

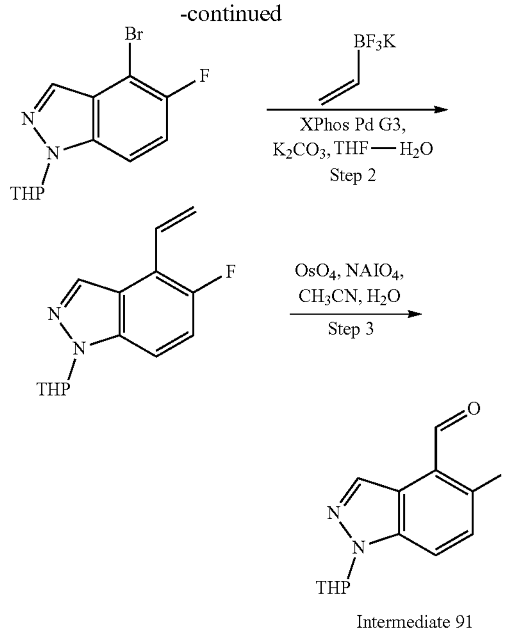

Intermediate 91

Step 1: 4-bromo-5-fluoro-1-(tetrahydro-2H-pyran-2-yl)-1H-indazole

A solution of 4-bromo-5-fluoro-1H-indazole (5 g, 23.25 mmol, Combi-Blocks), 3,4-dihydro-2H-pyran (5.87 g, 69.8 mmol, Avra), PPTS (1.169 g, 4.65 mmol, Avra) and THF (50 mL) was stirred at room temperature for 12 h. The reaction mixture was diluted with ice-cold water and extracted with EtOAc. The combined organic extracts were washed with brine, separated, dried over $Na_2SO_4$, filtered, and concentrated under reduced pressure. The residue was purified on a Redi-Sep pre-packed silica gel column eluting with 10-15% EtOAc in hexanes to provide 4-bromo-5-fluoro-1-(tetrahydro-2H-pyran-2-yl)-1H-indazole (6 g, 86% yield) as off-white solid. m/z (ESI): 301.0 $(M+H)^+$.

Step 2: 5-fluoro-1-(tetrahydro-2H-pyran-2-yl)-4-vinyl-1H-indazole

To a degassed solution of 4-bromo-5-fluoro-1-(tetrahydro-2H-pyran-2-yl)-1H-indazole (3 g. 10.03 mmol), potassium trifluoro(vinyl)borate (2.69 g, 20.06 mmol, Combi-Blocks), $K_2CO_3$ (4.16 g, 30.1 mmol) in THF (50 mL) and water (5 mL) was added XPhos Pd G3 (0.849 g, 1.003 mmol, Stream) and the reaction mixture was heated at 95° C. for 16 h. The reaction mixture was cooled to room temperature and filtered through a celite pad and washed with EtOAc. The filtrate was concentrated under reduced pressure. The residue was purified on a Redi-Sep pre-packed silica gel column eluting with a gradient of 0-50% EtOAc in hexanes to provide 5-fluoro-1-(tetrahydro-2H-pyran-2-yl)-4-vinyl-1H-indazole (1.5 g, 60.7% yield) as an off-white solid. m/z (ESI): 247.2 $(M+H)^+$.

Step 3: 5-fluoro-1-(tetrahydro-2H-pyran-2-yl)-1H-indazole-4-carbaldehyde

To a solution of 5-fluoro-1-(tetrahydro-2H-pyran-2-yl)-4-vinyl-1H-indazole (1.5 g, 6.09 mmol) and $NaIO_4$ (3.91 g, 18.27 mmol, Spectrochem) in acetonitrile (15 mL) and water (15 mL) was added $OsO_4$ (0.383 mL, 1.219 mmol, 4% solution in water, Chempure) at 0° C. and the reaction mixture was stirred at room temperature for 1 h. Then the reaction mixture was quenched with ice-cold water and extracted with EtOAc. The organic extracts were washed with brine, dried over $Na_2SO_4$, filtered and concentrated under reduced pressure. The residue was purified on a Redi-Sep pre-packed silica gel column eluting with a gradient of 0-50% EtOAc in petroleum ether to provide 5-fluoro-1-(tetrahydro-2H-pyran-2-yl)-1H-indazole-4-carbaldehyde (0.4 g, 26.5% yield) as an off-white solid. m/z (ESI): 249.1 $(M+H)^+$.

Intermediate 92: 7-Fluoro-5-methyl-1-(tetrahydro-2H-pyran-2-yl)-1H-indazole-4-carbaldehyde

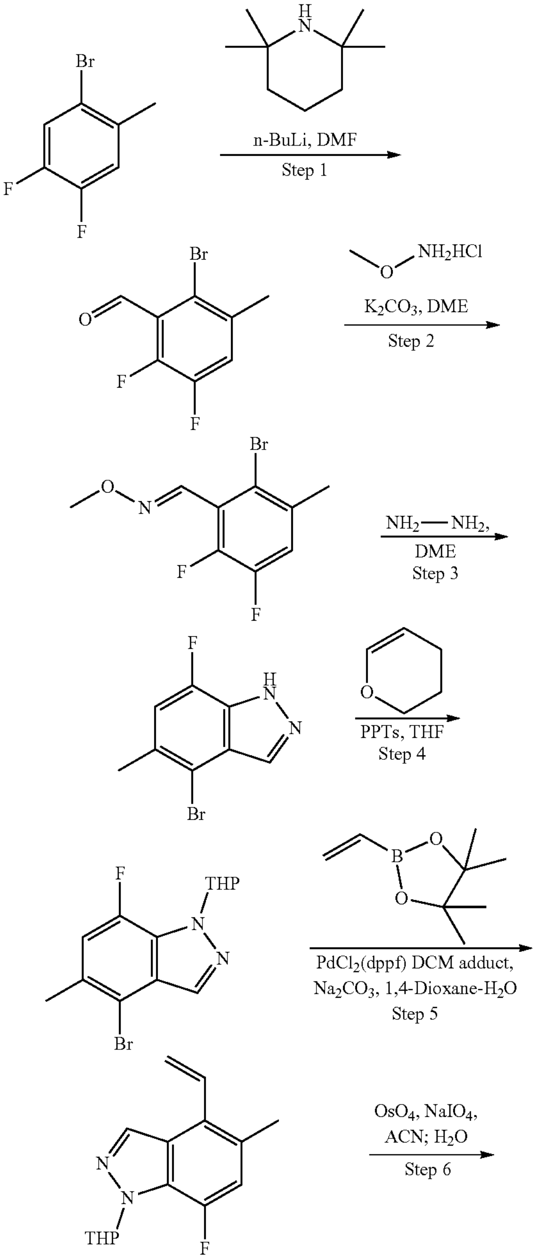

-continued

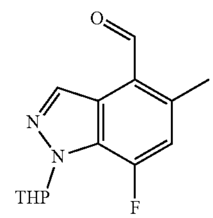

Intermediate 92

Step 1: 2-Bromo-5,6-difluoro-3-methylbenzaldehyde

To a solution of 2,2,6,6-tetramethylpiperidine (4.91 g, 34.8 mmol, Chempure) in THF (50 mL) at −78° C. was added n-butyllithium (12.75 mL, 31.9 mmol) dropwise and allowed to stir for 20 min. Then a solution of 1-bromo-4,5-difluoro-2-methylbenzene (6 g, 29.0 mmol, Combi-blocks) in THF (50 mL) was added at −78° C. and the resulting mixture was stirred for 2 h before DMF (3.18 g, 43.5 mmol) was added and stirring was continued for 30 min at −78° C. The reaction mixture was quenched with aqueous saturated $NH_4Cl$ and extracted with EtOAc. The organic extracts were washed with water, brine, dried over $Na_2SO_4$, filtered and concentrated under reduced pressure. The residue was purified on a Redi-Sep pre-packed silica gel column (12 g) eluting with a gradient of 20% EtOAc in petroleum ether to provide 2-bromo-5,6-difluoro-3-methylbenzaldehyde (6.1 g, 90% yield) as a pale yellow solid. $^1H$ NMR (400 MHz, $CDCl_3$) δ ppm 10.37 (s, 1H), 7.32 (s, 1H), 2.45 (s, 3H).

Step 2: (E)-2-bromo-5,6-difluoro-3-methylbenzaldehyde O-methyl oxime

A solution of 2-bromo-5,6-difluoro-3-methylbenzaldehyde (6.0 g, 25.5 mmol), $K_2CO_3$ (4.59 g, 33.2 mmol) and O-methylhydroxylamine hydrochloride (2.56 g, 30.6 mmol, Chempure) in 1,2-dimethoxyethane (20 mL) was stirred at room temperature for 15 h. The reaction mixture was diluted with ice-cold water and extracted with EtOAc. The combined organic extracts were washed with brine, dried over $Na_2SO_4$, filtered and concentrated under reduced pressure to provide (E)-2-bromo-5,6-difluoro-3-methylbenzaldehyde O-methyl oxime (6.5 g, 96% yield) as a pale yellow oil which was taken to the next step without purification. $^1H$ NMR (400 MHz, $CDCl_3$) δ ppm 8.29 (s, 1H), 7.19-7.08 (m, 1H), 4.06 (s, 3H), 2.41 (s, 3H).

Step 3: 4-Bromo-7-fluoro-5-methyl-1H-indazole

A solution of (E)-2-bromo-5,6-difluoro-3-methylbenzaldehyde O-methyl oxime (6.5 g, 24.61 mmol) and hydrazine hydrate (7.73 mL, 246 mmol, Spectrochem) in 1,2-dimethoxyethane (20 mL) was stirred at 90° C. for 15 h. The reaction mixture was diluted with ice-cold water and the precipitated solids were filtered off and washed with cold water to provide 4-bromo-7-fluoro-5-methyl-1H-indazole (5.05 g, 90% yield) as a pale yellow solid. $^1H$ NMR (400 MHz, DMSO-$d_6$) δ ppm 13.78 (s, 1H), 8.07 (d, J=3.2 Hz, 1H), 7.25 (d, J=11.8 Hz, 1H), 2.41 (s, 3H). m/z (ESI): 229.0 $(M+H)^+$.

Step 4: 4-Bromo-7-fluoro-5-methyl-1-(tetrahydro-2H-pyran-2-yl)-1H-indazole

A solution of 4-bromo-7-fluoro-5-methyl-1H-indazole (5.0 g, 21.83), 3,4-dihydro-2H-pyran (5.51 g, 65.5 mmol, Avra) and PPTS (1.097 g, 4.37 mmol, Avra) in THF (20 mL) was stirred at room temperature for 12 h. Then the reaction mixture was diluted with ice-cold water and extracted with EtOAc. The combined organic extracts were washed with brine, separated, dried over $Na_2SO_4$, filtered, and concentrated under reduced pressure. The residue was purified on a Redi-Sep pre-packed silica gel column (12 g) eluting with 10-15% EtOAc in hexanes to provide 4-bromo-7-fluoro-5-methyl-1-(tetrahydro-2H-pyran-2-yl)-1H-indazole (4.0 g, 58.5% yield) as white solid. $^1H$ NMR (400 MHz, $CDCl_3$) δ ppm 8.19 (s, 1H), 6.87 (d, J=11.6 Hz, 1H), 5.71-5.72 (m, 1H), 4.09-4.22 (m, 1H), 4.05 (s, 1H), 3.76-3.95 (m, 1H), 2.46 (s, 3H), 2.02-2.24 (m, 2H), 1.60-1.89 (m, 4H). m/z (ESI): 230.9 $(M+H-THP)^+$.

Step 5: 7-fluoro-5-methyl-1-(tetrahydro-2H-pyran-2-yl)-4-vinyl-1H-indazole

To a degassed solution of 4-bromo-7-fluoro-5-methyl-1-(tetrahydro-2H-pyran-2-yl)-1H-indazole (1.2 g, 3.83 mmol), 4,4,5,5-tetramethyl-2-vinyl-1,3,2-dioxaborolane (1.180 g, 7.66 mmol, Oakwood) and $Na_2CO_3$ (1.218 g, 11.50 mmol) in 1,4-dioxane (12 mL) and water (6 mL) was added $PdCl_2$(dppf)-DCMadduct (0.313 g, 0.383 mmol, Chempure Ltd) and the reaction mixture was heated in a sealed tube at 90° C. for 16 h. The reaction mixture was filtered through a celite pad and washed with EtOAc. The filtrate was washed with water, brine, dried over $Na_2SO_4$, and concentrated under reduced pressure. The residue was purified on a Redi-Sep pre-packed silica gel column (24 g) eluting with 10-15% EtOAc in hexanes to provide 7-fluoro-5-methyl-1-(tetrahydro-2H-pyran-2-yl)-4-vinyl-1H-indazole (0.6 g) as a pale yellow syrup. $^1H$ NMR (400 MHz, DMSO-$d_6$) δ ppm 8.72 (d, J=3.0 Hz, 1H), 6.97 (d, J=12.5 Hz, 1H), 5.81-5.75 (m, 2H), 5.57-5.50 (m, 1H), 4.06-3.98 (m, 1H), 3.78-3.68 (m, 1H), 2.37 (s, 3H), 2.32-2.21 (m, 1H), 2.10-1.95 (m, 2H), 1.82-1.68 (m, 1H), 1.62 (m, 2H), 1.55-1.43 (m, 1H). m/z (ESI): 261.2 $(M+H)^+$.

Step 6: 7-fluoro-5-methyl-1-(tetrahydro-2H-pyran-2-yl)-1H-indazole-4-carbaldehyde To a solution of 7-fluoro-5-methyl-1-(tetrahydro-2H-pyran-2-yl)-4-vinyl-1H-indazole (1.2 g, 4.61 mmol) in acetonitrile (7 mL) and water (7.0 mL) was added $NaIO_4$ (2.96 g, 13.83 mmol, Spectrochem Pvt. Ltd) and $OsO_4$ (1 mL, 0.127 mmol, 4% in $H_2O$, Chempure) at 0° C. The reaction mixture was stirred at room temperature for 30 min. The reaction mixture was quenched with ice-cold water and extracted with EtOAc. The organic extracts were washed with brine, dried over $Na_2SO_4$, filtered and concentrated under reduced pressure. The residue was purified on a Redi-Sep pre-packed silica gel column (12 g) eluting with a gradient of 10% EtOAc in petroleum ether to provide 7-fluoro-5-methyl-1-(tetrahydro-2H-pyran-2-yl)-1H-indazole-4-carbaldehyde (0.4 g, 33.1% yield) as a white solid. $^1H$ NMR (400 MHz, DMSO-$d_6$) δ ppm 10.48 (s, 1H), 8.91 (d, J=2.9 Hz, 1H), 7.15 (d, J=12.3 Hz, 1H), 5.86 (dd, J=9.5, 2.9 Hz, 1H), 4.05-3.97 (m, 1H), 3.80-3.70 (in, 1H), 2.77 (s, 3H), 2.19 (m, 1H), 2.12-2.04 (m, 1H), 2.02-1.93 (m, 1H), 1.79-1.70 (m, 1H), 1.62 (m, 2H). m/z (ESI): 263.0 $(M+H)^+$.

Intermediate 93: 5-Methyl-1-(tetrahydro-2H-pyran-2-yl)-1H-pyrazolo[3,4-b]pyridine-4-carbaldehyde The synthesis of Intermediate 93 was done in an analogous manner to Intermediate 92, steps 4-6 using 4-iodo-5-methyl-1H-pyrazolo[3,4-b]pyridine (synthesized according to the procedure described in WO 2009/073300).

Intermediate 94: 2-Chloro-5-hydroxy-3-methylbenzaldehyde

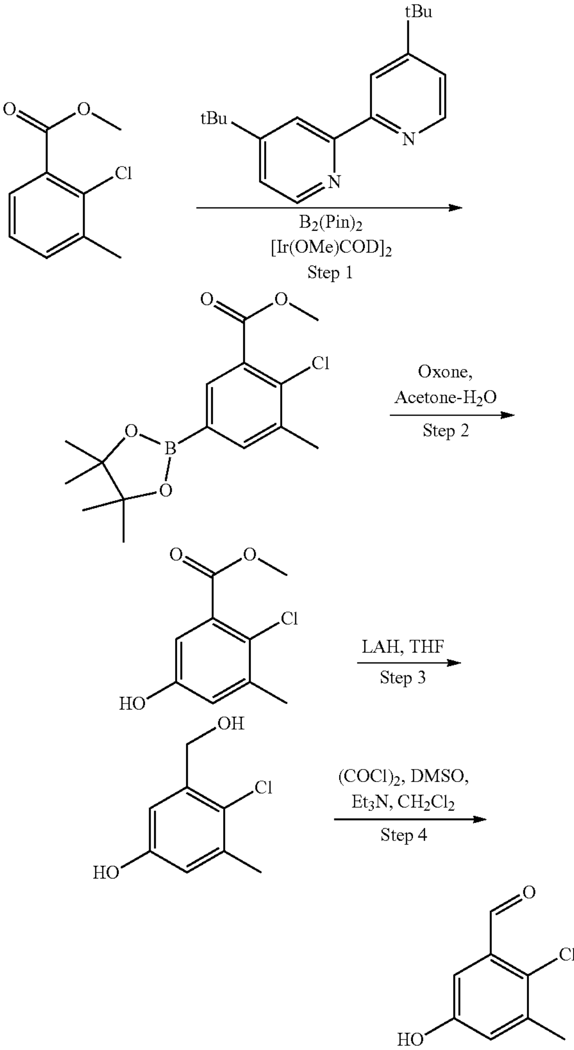

Intermediate 94

Step 1: Methyl 2-chloro-3-methyl-5-(4,4,5,5-tetramethyl-1,3,2-dioxaborolan-2-yl)benzoate A mixture of methyl 2-chloro-3-methylbenzoate (1.1 g, 5.96 mmol, Combi Blocks), 4,4,5,5-tetramethyl-1,3,2-dioxaborolane (1.144 g, 8.94 mmol, Sigma-Aldrich), 4,4'-di-tert-butyl-2,2'-bipyridine (0.032 g, 0.119 mmol, Alfa) and $[Ir(OMe)COD]_2$ (0.039 g, 0.060 mmol, Strem) was heated in a sealed tube at 80° C. for 16 h. The reaction mixture was cooled to room temperature and filtered through a celite pad and washed with DCM. The filtrated was concentrated under reduced pressure to provide methyl 2-chloro-3-methyl-5-(4,4,5,5-tetramethyl-1,3,2-dioxaborolan-2-yl)benzoate (1.65 g) which was taken to the next step without further purification. m/z (ESI): 311.1 $(M)^+$.

Step 2: Methyl 2-chloro-5-hydroxy-3-methylbenzoate

To a solution of methyl 2-chloro-3-methyl-5-(4,4,5,5-tetramethyl-1,3,2-dioxaborolan-2-yl)benzoate (1.65 g) in acetone (10 mL) was added a solution of oxone (4.90 g, 7.97 mmol, Chempure) in water (10 mL). The resulting mixture was stirred at room temperature for 14 h. The reaction mixture was concentrated under reduced pressure and the residue was diluted with water and extracted with EtOAc. The organic extracts were washed with brine, dried over $Na_2SO_4$, filtered, and concentrated under reduced pressure. The residue was purified on a Redi-Sep pre-packed silica gel column (40 g) eluting with a gradient of 0-20% EtOAc in petroleum ether to provide methyl 2-chloro-5-hydroxy-3-methylbenzoate (1.02 g, 96% yield). m/z (ESI): 201.0 $(M)^+$.

Step 3: 4-Chloro-3-(hydroxymethyl)-5-methylphenol

To a solution of methyl 2-chloro-5-hydroxy-3-methylbenzoate (1 g, 4.98 mmol) in THF (15 mL) was added dropwise a solution of $LiAlH_4$ (9.97 mL, 9.97 mmol) in THF (5 mL) at −78° C. The reaction mixture was stirred for 1 h at −78° C. and then slowly warmed to room temperature and stirred for 12 h. The reaction mixture was cooled to 0° C. and quenched with ice-cold 1 M HCl and extracted with EtOAc. The organic extracts were washed with brine, dried over $Na_2SO_4$, and concentrated under reduced pressure to provide 4-chloro-3-(hydroxymethyl)-5-methylphenol (0.8 g, 93% yield) which was used in the next step without further purification. m/z (ESI): 170.9 $(M-H)^-$.

Step 4: 2-Chloro-5-hydroxy-3-methylbenzaldehyde

To a solution of DMSO (0.822 mL, 11.59 mmol) and DCM (10 mL) was added oxalyl chloride (0.609 mL, 6.95 mmol, Spectrochem) at −78° C. and stirred for 30 min. To the reaction mixture was added a solution of 4-chloro-3-(hydroxymethyl)-5-methylphenol (0.8 g, 4.63 mmol) in DCM (10 mL) at −78° C. The reaction mixture stirred for 2 h at −78° C., treated with TEA (3.23 mL, 23.17 mmol) and stirred at −78° C. for 2 h. The reaction mixture was warmed to 0° C. and was quenched with ice-cold water and extracted with DCM. The combined organic layers were washed with brine, dried over $Na_2SO_4$, filtered and concentrated under reduced pressure. The residue was purified on a Redi-Sep pre-packed silica gel column eluting with a gradient of 0-15% EtOAc in petroleum ether to provide 2-chloro-5-hydroxy-3-methylbenzaldehyde (0.35 g, 44.3% yield). m/z (ESI): 168.9 $(M-H)^-$.

Intermediate 95: tert-Butyl 6-(3-cyano-4-(2-fluorophenyl)-5,6,7,8-tetrahydro-1,7-naphthyridin-2-yl)-2,6-diazaspiro[3.4]octane-2-carboxylate

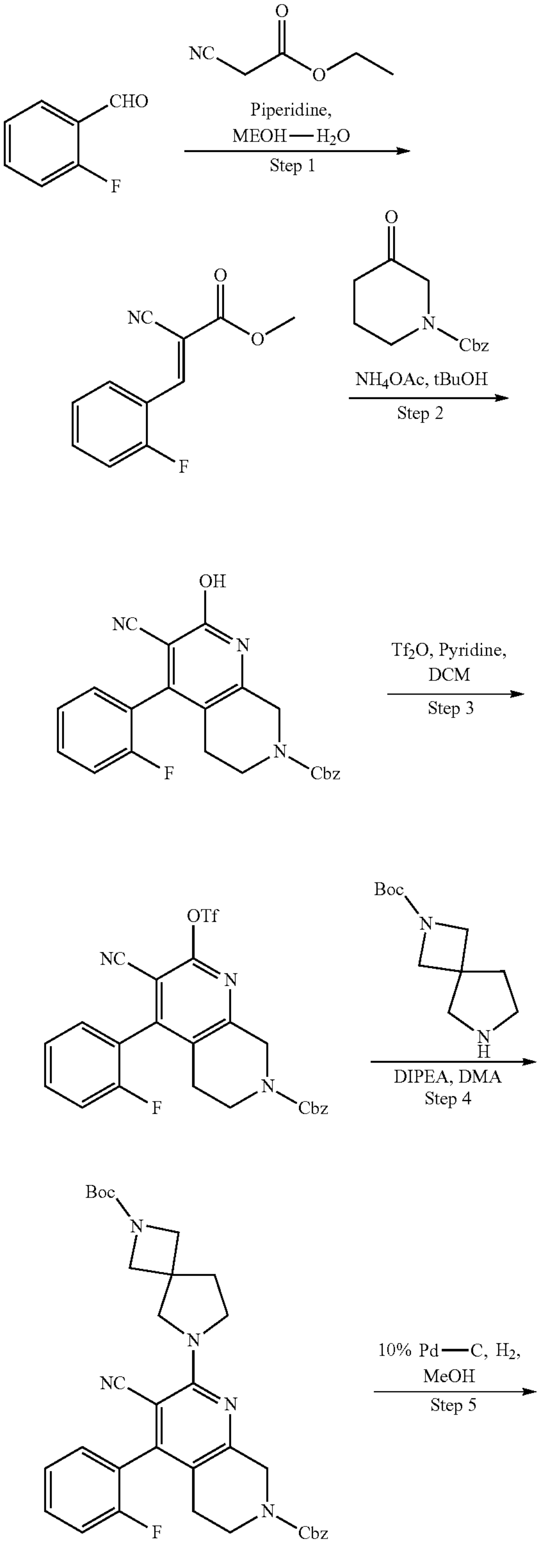

-continued

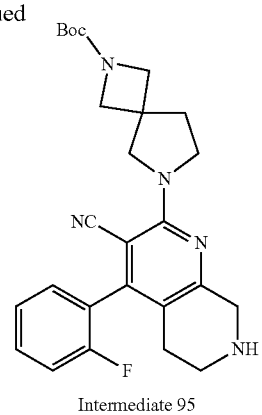

Intermediate 95

Step 1: Methyl (E)-2-cyano-3-(2-fluorophenyl)acrylate

To a mixture of 2-fluorobenzaldehyde (100.0 g, 886 mmol) and ethyl 2-cyanoacetate (100.0 g, 806 mmol) in MeOH (1000 mL) and water (250 mL) was added piperidine (15.95 mL, 161 mmol) at room temperature and the reaction was stirred for 16 h. The reaction mixture was concentrated under reduced pressure and quenched with water (500 mL) and stirred for 30 min. The precipitated solid was filtered, washed with water (100 mL), and dried under vacuum to give methyl (E)-2-cyano-3-(2-fluorophenyl)acrylate (124.0 g, 75% yield) as a pale yellow solid. $^1$H NMR (400 MHz, DMSO-$d_6$) δ 8.42 (s, 1H), 8.19 (td, J=7.7, 1.8 Hz, 1H), 7.70-7.80 (m, 1H), 7.53-7.42 (m, 2H), 3.89 (s, 3H).

Step 2: Benzyl 3-cyano-4-(2-fluorophenyl)-2-hydroxy-5,8-dihydro-1,7-naphthyridine-7(6H)-carboxylate To a solution of methyl (E)-2-cyano-3-(2-fluorophenyl) acrylate (140.0 g, 638.64 mmol) in tert-butanol (100 mL) was added benzyl 3-oxopiperidine-1-carboxylate (113.0 g, 482 mmol) and $NH_4OAc$ (338.0 g, 4386 mmol) at room temperature. The reaction mixture was stirred at 100° C. for 16 h. The reaction mixture was quenched with water (1 L), extracted with EtOAc (2×1 L), and washed with brine (200 mL). The organic layer was dried over $Na_2SO_4$, filtered and concentrated under reduced pressure. The crude residue was purified by column chromatography over silica gel using 50% EtOAc in hexanes as an eluent to give benzyl 3-cyano-4-(2-fluorophenyl)-2-hydroxy-5,8-dihydro-1,7-naphthyridine-7(6H)-carboxylate (55 g, 21% yield with 80% purity) as a pale yellow solid. m/z: 403.8 [M+H]$^+$.

Step 3: Benzyl 3-cyano-4-(2-fluorophenyl)-2-(((trifluoromethyl)sulfonyl)oxy)-5,8-dihydro-1,7-naphthyridine-7(6H)-carboxylate To a stirred solution of benzyl 3-cyano-4-(2-fluorophenyl)-2-hydroxy-5,8-dihydro-1,7-naphthyridine-7(6H)-carboxylate (55.0 g, 136 mmol) in DCM (825 mL) was added pyridine (33.1 mL, 409 mmol) and triflic anhydride (27.6 mL, 164 mmol) at 0° C. and the reaction was stirred for 30 min. The reaction mixture was concentrated under reduced pressure and co-evaporated with toluene to give benzyl 3-cyano-4-(2-fluorophenyl)-2-(((trifluoromethyl)sulfonyl)oxy)-5,8-dihydro-1,7-naphthyridine-7(6H)-carboxylate (74.1 g; crude) as a brown viscous oil. The crude material was taken on without further purification.

Step 4: Benzyl 2-(2-(tert-butoxycarbonyl)-2,6-diazaspiro[3.4]octan-6-yl)-3-cyano-4-(2-fluorophenyl)-5,8-dihydro-1,7-naphthyridine-7(6H)-carboxylate To a solution of benzyl 3-cyano-4-(2-fluorophenyl)-2-(((trifluoromethyl)sulfonyl)oxy)-5,8-dihydro-1,7-naphthyridine-7(6H)-carboxylate (74.0 g, 138 mmol) in DMA (740 mL) was added tert-butyl 2,6-diazaspiro[3.4]octane-2-carboxylate (35.2 g, 166 mmol) and DIPEA (102 mL, 553 mmol) and the reaction mixture was stirred at 80° C. for 4 h. The reaction was concentrated under reduced pressure. The crude residue was quenched with ice-cold water (250 mL) and the yellow solid that precipitated out was filtered, washed with water (100 mL) and dried under vacuum to give benzyl 2-(2-(tert-butoxycarbonyl)-2,6-diazaspiro[3.4]octan-6-yl)-3-cyano-4-(2-fluorophenyl)-5,8-dihydro-1,7-naphthyridine-7(6H)-carboxylate (50.0 g, 29% yield with 50% purity) as a brown solid. The crude was taken on without further purification. m/z (ESI): 597.9 [M+H]$^+$.

Step 5: tert-Butyl 6-(3-cyano-4-(2-fluorophenyl)-5,6,7,8-tetrahydro-1,7-naphthyridin-2-yl)-2,6-diazaspiro[3.4]octane-2-carboxylate To a solution of benzyl 2-(2-(tert-butoxycarbonyl)-2,6-diazaspiro[3.4]octan-6-yl)-3-cyano-4-(2-fluorophenyl)-5,8-dihydro-1,7-naphthyridine-7(6H)-carboxylate (50.0 g, 84 mmol) in MeOH (1 L) was added 10% Pd/C (26.7 g, 25.10 mmol) at room temperature and the reaction mixture was stirred under a hydrogen atmosphere for 3 h. The reaction mixture was filtered through a celite bed and washed with MeOH (200 mL). The filtrate was concentrated under reduced pressure. The crude residue was purified by column chromatography over silica gel using 5% MeOH in DCM as an eluent to give a yellow gummy solid. This solid was triturated with hexanes (150 mL), filtered and dried under vacuum to give tert-butyl 6-(3-cyano-4-(2-fluorophenyl)-5,6,7,8-tetrahydro-1,7-naphthyridin-2-yl)-2,6-diazaspiro[3.4]octane-2-carboxylate (22.1 g, 57% yield) as a pale yellow solid. $^1$H NMR (400 MHz, DMSO-$d_6$) δ 7.55 (m, 1H), 7.47-7.20 (m, 3H), 5.28 (br s, 1H), 3.85-3.74 (m, 8H), 3.70 (t, J=6.8 Hz, 2H), 2.93 (m, 2H), 2.16 (m, 4H), 1.39 (s, 9H). m/z: 463.9 [M+H]$^+$.

TABLE 19

Intermediates 96 to 107 were prepared following the procedure described in Intermediate 95, above as follows:

| Intermediate # | Structure | Name | Reagent |
| --- | --- | --- | --- |
| 96 | 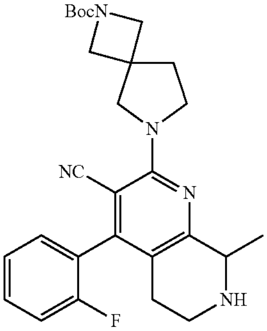 [SMILES: CC1NCCc2c1nc(N1CCC3(CN(C(=O)OC(C)(C)C)C3)C1)c(C#N)c2-c1ccccc1F] | tert-butyl 6-(3-cyano-4-(2-fluorophenyl)-8-methyl-5,6,7,8-tetrahydro-1,7-naphthyridin-2-yl)-2,6-diazaspiro[3.4]octane-2-carboxylate | Step 2: tert-butyl 2-methyl-3-oxopiperidine-1-carboxylate (Combi-Blocks) Additional Steps: After Step 2, Boc was removed with HCl and Cbz group was incorporated. |
| 97 | 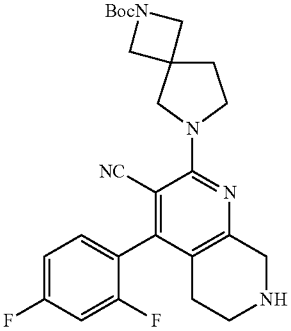 [SMILES: CC(C)(C)OC(=O)N1CC2(CCN(c3nc4c(c(-c5ccc(F)cc5F)c3C#N)CCNC4)C2)C1] | tert-butyl 6-(3-cyano-4-(2,4-difluorophenyl)-5,6,7,8-tetrahydro-1,7-naphthyridin-2-yl)-2,6-diazaspiro[3.4]octane-2-carboxylate | Step 1: 2,4-difluorobenzaldehyde |
| 98 | 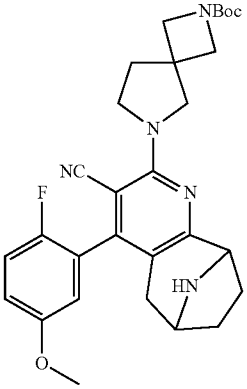 [SMILES: COc1ccc(F)c(-c2c(C#N)c(N3CCC4(CN(C(=O)OC(C)(C)C)C4)C3)nc3c2CC2CCC3N2)c1] | tert-butyl 6-(3-cyano-4-(2-fluoro-5-methoxyphenyl)-6,7,8,9-tetrahydro-5H-6,9-epiminocyclohepta[b]pyridin-2-yl)-2,6-diazaspiro[3.4]octane-2-carboxylate | Step 1: 2-fluoro-5-methoxybenzaldehyde; Step 2: tert-Butyl 2-oxo-8-azabicyclo[3.2.1]octane-8-carboxylate (Combi-Blocks) |
| 99 | 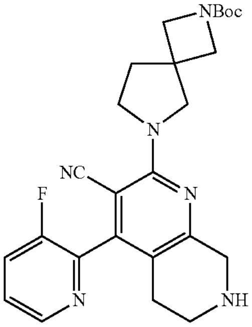 [SMILES: CC(C)(C)OC(=O)N1CC2(CCN(c3nc4c(c(-c5ncccc5F)c3C#N)CCNC4)C2)C1] | tert-butyl 6-(3-cyano-4-(3-fluoropyridin-2-yl)-5,6,7,8-tetrahydro-1,7-naphthyridin-2-yl)-2,6-diazaspiro[3.4]octane-2-carboxylate | Step 1: 3-fluoropicolinaldehyde |

TABLE 19-continued

| Intermediates 96 to 107 were prepared following the procedure described in Intermediate 95, above as follows: | | | |
|---|---|---|---|
| Intermediate # | Structure | Name | Reagent |
| 100 | 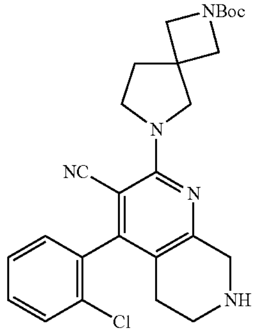 [SMILES: CC(C)(C)OC(=O)N1CC2(CCN(c3nc4c(c(-c5ccccc5Cl)c3C#N)CCNC4)C2)C1] | tert-butyl 6-(4-(2-chlorophenyl)-3-cyano-5,6,7,8-tetrahydro-1,7-naphthyridin-2-yl)-2,6-diazaspiro[3.4]octane-2-carboxylate | Step 1: 2-chlorobenzaldehyde |
| 101 | 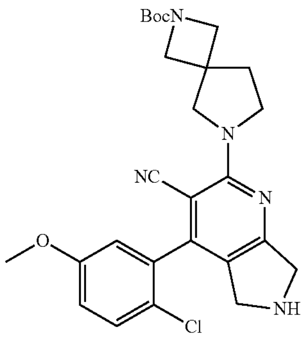 [SMILES: COc1ccc(Cl)c(-c2c(C#N)c(N3CCC4(CN(C(=O)OC(C)(C)C)C4)C3)nc3c2CNC3)c1] | tert-butyl 6-(4-(2-chloro-5-methoxyphenyl)-3-cyano-6,7-dihydro-5H-pyrrolo[3,4-b]pyridin-2-yl)-2,6-diazaspiro[3.4]octane-2-carboxylate | Step 1: 2-chloro-5-methoxybenzaldehyde; Step 2: Benzyl 3-oxopyrrolidine-1-carboxylate (Combi-Blocks) |
| 102 | 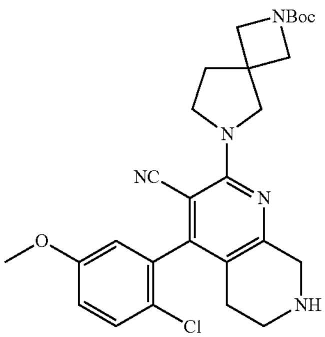 [SMILES: COc1ccc(Cl)c(-c2c(C#N)c(N3CCC4(CN(C(=O)OC(C)(C)C)C4)C3)nc3c2CCNC3)c1] | tert-butyl 6-(4-(2-chloro-5-methoxyphenyl)-3-cyano-5,6,7,8-tetrahydro-1,7-naphthyridin-2-yl)-2,6-diazaspiro[3.4]octane-2-carboxylate | Step 1: 2-chloro-5-methoxybenzaldehyde |
| 103 | 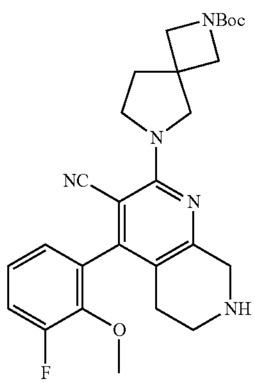 [SMILES: COc1c(F)cccc1-c1c(C#N)c(N2CCC3(CN(C(=O)OC(C)(C)C)C3)C2)nc2c1CCNC2] | tert-butyl 6-(3-cyano-4-(3-fluoro-2-methoxyphenyl)-5,6,7,8-tetrahydro-1,7-naphthyridin-2-yl)-2,6-diazaspiro[3.4]octane-2-carboxylate | Step 1: 3-fluoro-2-methoxybenzaldehyde |

TABLE 19-continued

Intermediates 96 to 107 were prepared following the procedure described in Intermediate 95, above as follows:

| Intermediate # | Structure | Name | Reagent |
|---|---|---|---|
| 104 | 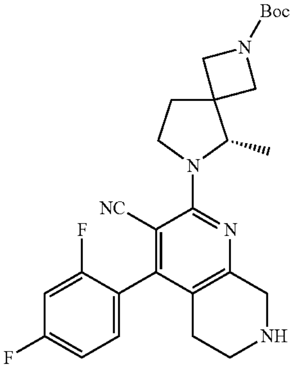 [SMILES: C[C@@H]1N(c2nc3c(c(-c4ccc(F)cc4F)c2C#N)CCNC3)CCC12CN(C(=O)OC(C)(C)C)C2] | tert-butyl (5S)-6-(3-cyano-4-(2,4-difluorophenyl)-5,6,7,8-tetrahydro-1,7-naphthyridin-2-yl)-5-methyl-2,6-diazaspiro[3.4]octane-2-carboxylate | Step 1: 2,4-difluorobenzaldehyde; Step 4: tert-butyl (S)-7-methyl-2,6-diazaspiro[3.4]octane-2-carboxylate |
| 105 | 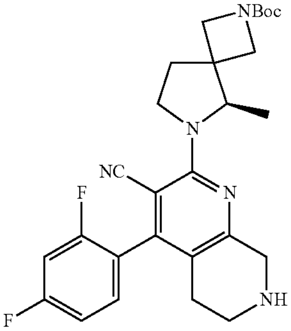 [SMILES: C[C@H]1N(c2nc3c(c(-c4ccc(F)cc4F)c2C#N)CCNC3)CCC12CN(C(=O)OC(C)(C)C)C2] | tert-butyl (5R)-6-(3-cyano-4-(2,4-difluorophenyl)-5,6,7,8-tetrahydro-1,7-naphthyridin-2-yl)-5-methyl-2,6-diazaspiro[3.4]octane-2-carboxylate | Step 1: 2,4-Difluorobenzaldehyde; Step 4: tert-butyl (R)-7-methyl-2,6-diazaspiro[3.4]octane-2-carboxylate |
| 106 | 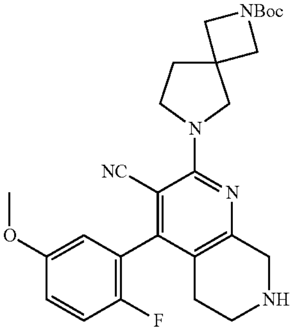 [SMILES: COc1ccc(F)c(-c2c(C#N)c(N3CCC4(CN(C(=O)OC(C)(C)C)C4)C3)nc3c2CCNC3)c1] | tert-butyl 6-(3-cyano-4-(2-fluoro-5-methoxyphenyl)-5,6,7,8-tetrahydro-1,7-naphthyridin-2-yl)-2,6-diazaspiro[3.4]octane-2-carboxylate | Step 1: 2-fluoro-5-methoxybenzaldehyde |
| 107 | 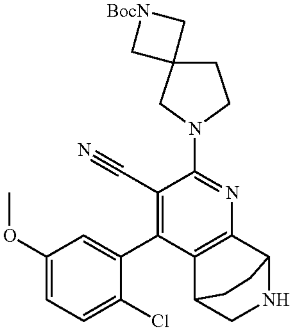 [SMILES: COc1ccc(Cl)c(-c2c(C#N)c(N3CCC4(CN(C(=O)OC(C)(C)C)C4)C3)nc3c2C2CCC3NC2)c1] | tert-butyl 6-(4-(2-chloro-5-methoxyphenyl)-3-cyano-5,6,7,8-tetrahydro-8,5-(epiminomethano)quinolin-2-yl)-2,6-diazaspiro[3.4]octane-2-carboxylate | Step 1: 2-chloro-5-methoxybenzaldehyde; Step 2: tert-Butyl 6-oxo-2-azabicyclo[2.2.2]octane-2-carboxylate (Pharma Block) Additional Steps: After Step 2, Boc was removed with HCl and Ns group was incorporated which was cleaved at Step 5. |

Intermediate 108: (S1-methylpyrrolidin-2-yl)methyl methanesulfonate

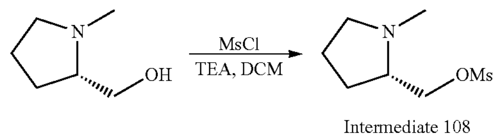

Intermediate 108

To a solution of (S)-(1-methylpyrrolidin-2-yl)methanol (0.8 g, 6.95 mmol, Combi-Blocks) in DCM (8.00 mL) was added TEA (2.90 mL, 20.84 mmol) followed by mesyl-Cl (0.812 mL, 10.42 mmol) at 0° C. The reaction mass was stirred at room temperature for 2 h. The reaction was concentrated in vacuo to provide crude (S)-(1-methylpyrrolidin-2-yl)methyl methanesulfonate, which was carried forward to the next step.

Intermediate 109: methyl 4-(1,4-dimethyl-1H-pyrazol-5-yl)-2-oxocyclohexane-1-carboxylate

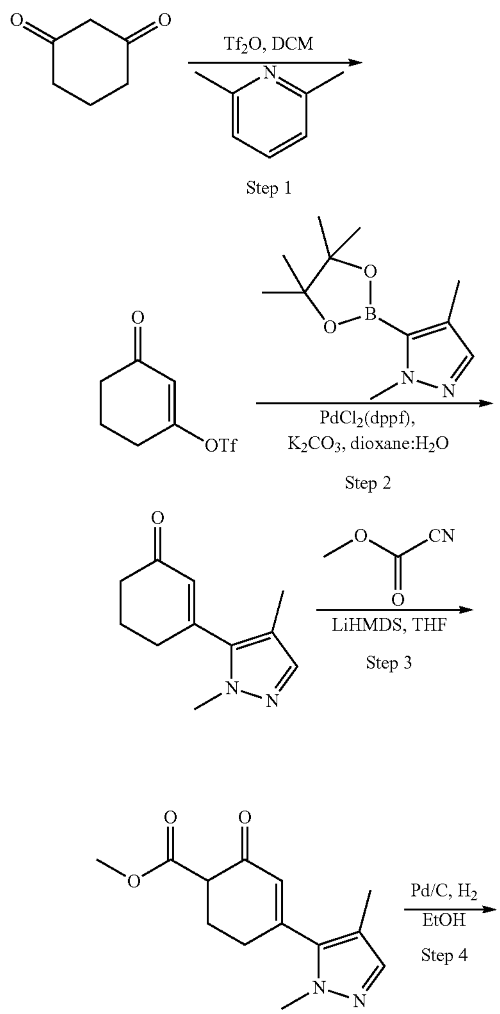

-continued

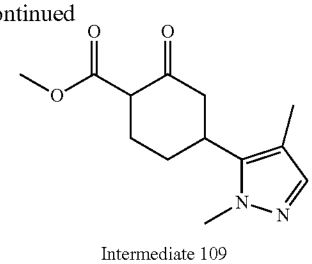

Intermediate 109

Step 1: 3-oxocyclohex-1-en-1-yl trifluoromethanesulfonate

To a 1 L RBF was added cyclohexane-1,3-dione (15 g, 134 mmol), DCM (550 mL) and 2,6-dimethylpyridine (28.7 g, 268 mmol). Triflic anhydride (33.9 mL, 201 mmol) was added dropwise at 0° C. and slowly allowed to warm to room temperature and stirred for 1 h. The reaction mixture was quenched with water and extracted with DCM (2×200 mL). The organic extracts were washed with 1.5 N HCl solution (2×200 mL), water (150 mL), brine (150 mL), and dried over $Na_2SO_4$. The solution was filtered and concentrated in vacuo to give the crude material as a brown oil. The crude material was purified through Biotage®, Isolera eluting with 20% EtOAc in petroleum ether to provide 3-oxocyclohex-1-en-1-yl trifluoromethanesulfonate (30 g, 92% yield) as a pale yellow oil. mz (ESI): 244.9 $(M+H)^+$. $^1H$ NMR (400 MHz, $CDCl_3$) δ ppm 6.08 (t, J=1.4 Hz, 1H), 2.71 (td, J=6.2, 1.4 Hz, 2H), 2.52-2.44 (m, 2H), 2.21-2.10 (m, 2H)

Step 2: 3-(1,4-dimethyl-1H-pyrazol-5-yl)cyclohex-2-en-1-one

To a 500 mL RBF was charged 3-oxocyclohex-1-en-1-yl trifluoromethanesulfonate (21.99 g, 90 mmol), 1,4-dimethyl-5-(4,4,5,5-tetramethyl-1,3,2-dioxaborolan-2-yl)-1H-pyrazole (20 g, 90 mmol), 1,4-dioxane (160 mL) and water (80 mL). $K_2CO_3$ (37.3 g, 270 mmol) was added. The reaction mixture was purged with nitrogen gas for 10 min and $PdCl_2$(dppf)-DCM adduct (7.35 g, 9.01 mmol) was added and the reaction mixture was stirred at 85° C. for 16 h. The reaction was cooled to ambient temperature and quenched with water (300 mL), extracted with EtOAc (3×100 mL). The organic extract was washed with water (100 mL) and brine solution (100 mL), dried over $Na_2SO_4$, and evaporated under reduced pressure. The crude product was purified through Biotage® Isolera using a gradient of 40-45% EtOAc in petroleum ether to afford 3-(1,4-dimethyl-1H-pyrazol-5-yl)cyclohex-2-en-1-one (17 g, 99% yield) as a clear oil. m/z (ESI): 191.1 $(M+H)^+$. $^1H$ NMR (400 MHz $CDCl_3$) δ ppm 7.32 (d, J=0.7 Hz, 1H), 6.05 (t, J=1.6 Hz, 1H), 3.84 (s, 3H), 2.63 (td, J=6.0, 1.6 Hz, 2H), 2.59-2.52 (m, 2H), 2.23-2.15 (m, 2H), 2.07 (d, J=0.6 Hz, 3H).

Step 3: methyl 4-(1,4-dimethyl-1H-pyrazol-5-yl)-2-oxocyclohex-3-ene-1-carboxylate To a stirred solution of 3-(1,4-dimethyl-1H-pyrazol-5-yl) cyclohex-2-en-1-one (10 g, 52.6 mmol) in THF (150 mL) was added LiHMDS (1M in THF, 79 mL, 79 mmol) dropwise at −78° C. The resulting reaction mixture was stirred for 30 min. A solution of methyl carbonocyanidate (5.81 g, 68.3 mmol) in THF (15 mL) was added dropwise at the same temperature. The reaction mixture was stirred at −30° C. to −20° C. for 1.5 h. After complete consumption of starting material, the reaction mixture was quenched with aqueous saturated $NH_4Cl$ (300 mL) and extracted with EtOAc (2×150 mL). The combined organic layers were washed with water (75 mL) and brine (75 mL), dried over $Na_2SO_4$ and concentrated under reduced pressure. The crude product was purified through a Biotage® Isolera using 50% EtOAc in petroleum ether to afford methyl 4-(1,4-dimethyl-1H-pyrazol-5-yl)-2-oxocyclohex-3-ene-1-carboxylate as a clear oil. m/z (ESI): 249.0 $(M+H)^+$. $^1$H NMR (400 MHz, $CDCl_3$) δ ppm 7.34-7.32 (m, 1H), 6.10 (t, J=1.6 Hz, 1H), 3.85 (s, 3H), 3.81 (s, 3H), 2.78 (dddd, J=18.4, 6.2, 4.8, 1.5 Hz, 1H), 2.67 (dddd, J=18.4, 7.9, 4.7, 1.9 Hz, 1H), 2.62-2.49 (m, 2H), 2.38 (ddt, J=13.7, 6.3, 4.8 Hz, 1H), 2.08 (d, J=0.6 Hz, 3H).

Step 4: methyl 4-(1,4-dimethyl-1H-pyrazol-5-yl)-2-oxocyclohexane-1-carboxylate

To a solution of methyl 4-(1,4-dimethyl-1H-pyrazol-5-yl)-2-oxocyclohex-3-ene-1-carboxylate (10 g, 40.3 mmol) in EtOH (100 mL) was added Pd/C (10 wt % on carbon, 3.4 g, 3.19 mmol) and stirred at hydrogen bladder pressure for 16 h. After completion, the reaction was filtered through a celite bed and washed with EtOAc (200 mL). The filtrate was concentrated under reduced pressure and purified through an Biotage® Isolera using 30% EtOAc in petroleum ether to afford methyl 4-(1,4-dimethyl-1H-pyrazol-5-yl)-2-oxocyclohexane-1-carboxylate (6.6 g, 65.5% yield) as a pale yellow syrup. m/z (ESI): 251.1 $(M+H)^+$. $^1$H NMR (400 MHz, DMSO-$d_6$) δ (ppm) 7.17 (s, 1H), 5.75-5.77 (m, 1H), 5.08-5.10 (m, 1H), 4.39-4.41 (m, 1H), 3.67 (s, 3H), 3.60 (s, 3H), 2.67-2.70 (m, 1H), 2.17-2.19 (m, 1H), 1.82-1.99 (m, 6H).

Intermediate 110: tert-butyl 6-(4-chloro-7-(1,4-dimethyl-1H-pyrazol-5-yl)-3-methyl-5,6,7,8-tetrahydroquinolin-2-yl)-2,6-diazaspiro[3.4]octane-2-carboxylate Intermediate 109 can be used to synthesize the title compound using the method described for Intermediate 50. The racemic material was separated by SFC using a Lux Cellulose-3 column with a mobile phase of 80% liquid $CO_2$ and 20% MeOH:ACN (1:1)) at a flow rate of 150 mL/min to provide the R and S isomers of tert-butyl 6-(4-chloro-7-(1,4-dimethyl-1H-pyrazol-5-yl)-3-methyl-5,6,7,8-tetrahydroquinolin-2-yl)-2,6-diazaspiro[3.4]octane-2-carboxylate. The stereochemistry was assigned arbitrarily and is not established. The 1st eluting peak was assigned as the R isomer (Intermediate 110-1) and the 2nd eluting peak assigned as the S isomer (Intermediate 110-2).

Intermediate 110-1 m/z (ESI): 486.1 $(M+H)^+$. $^1$H NMR (400 MHz, DMSO-$d_6$) δ (ppm) 7.11 (s, 1H), 3.87-3.72 (m, 7H), 3.60-3.50 (m, 2H), 3.48-3.35 (m, 2H), 3.20 (t, J=7.4 Hz, 1H), 3.03-2.91 (m, 1H), 2.90-2.75 (m, 2H), 2.69 (dt, J=17.5, 9.0 Hz, 1H), 2.27 (s, 3H), 2.03 (d, J=8.4 Hz, 7H), 1.38 (s, 9H).

Intermediate 110-2 m/z (ESI): 486.1 $(M+H)^+$. $^1$H NMR (400 MHz, DMSO-$d_4$) δ (ppm) 7.11 (s, 1H), 3.76 (s, 7H), 3.60-3.50 (m, 2H), 3.48-3.37 (m, 2H), 3.21 (td, J=13.6, 12.5, 5.3 Hz, 1H), 2.97 (dd, J=16.9, 12.1 Hz, 1H), 2.89-2.75 (m, 2H), 2.74-2.64 (m, 1H), 2.27 (s, 3H), 2.03 (d, J=8.3 Hz, 7H), 1.38 (s, 9H).

Intermediate 111: 6-bromo-8-iodo-3-(pyrrolidin-1-yl)imidazo[1,2-a]pyridine-7-carbonitrile

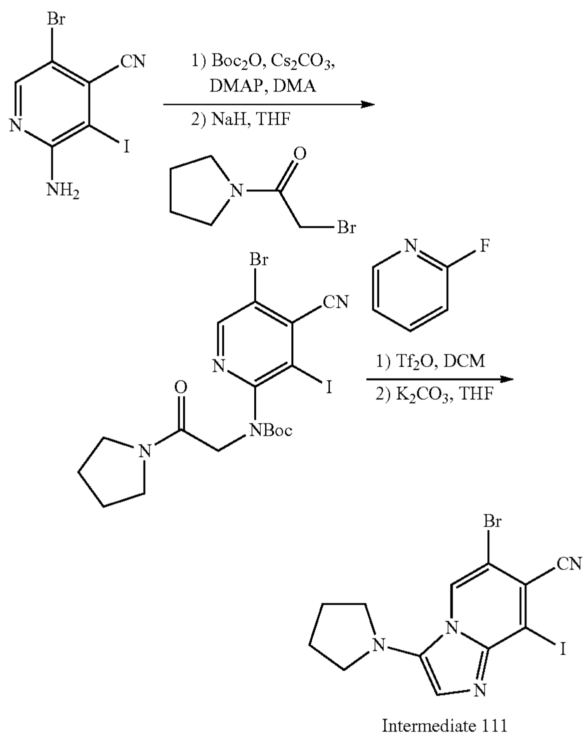

Intermediate 111

Step 1: tert-butyl (5-bromo-4-cyano-3-iodopyridin-2-yl)carbamate

To a RBF was added 2-amino-5-bromo-3-iodoisonicotinonitrile (1 g. 3.09 mmol), $Boc_2O$ (0.876 g, 4.01 mmol, Adamas), $K_2CO_3$ (2.073 g, 15 mmol, Sigma-Aldrich) and DMAP (0.038 g, 0.309 mmol, Adamas) in DMA (10 mL). The reaction was stirred at room temperature for 2 h. The reaction mixture was diluted with aqueous saturated $NH_4Cl$ (20 mL) and extracted with EtOAc (3×20 mL). The organic extract was dried over $Na_2SO_4$ and concentrated in vacuo. The crude material was absorbed onto a plug of silica gel and purified by chromatography through a Redi-Sep pre-packed silica gel column eluting with 0-100% EtOAc in hexane, to provide tert-butyl (5-bromo-4-cyano-3-iodopyridin-2-yl)carbamate (1.31 g, 3.09 mmol) as a yellow solid. m/z (ESI): 367.8 $(M+H-tBu)^+$.

Step 2: tert-butyl (5-bromo-4-cyano-3-iodopyridin-2-yl)(2-oxo-2-(pyrrolidin-1-yn)ethyl)carbamate To a 0° C. solution of NaH (0.370 g, 9.26 mmol, Sigma-Aldrich) and THF (10 mL) was added dropwise a solution of tert-butyl (5-bromo-4-cyano-3-iodopyridin-2-yl)carbamate (1.31 g, 3.09 mmol) in THF (2 mL). The reaction was stirred at 0° C. for 1 h. 2-bromo-1-(pyrrolidin-1-yl)ethan-1-one (0.889 g, 4.63 mmol) was added into the mixture in one portion. The reaction was allowed to warm to room temperature, then stirred overnight. The reaction mixture was diluted with aqueous saturated $NH_4Cl$ (20 mL) and extracted with EtOAc (3×15 mL). The organic extracts were dried over $Na_2SO_4$ and concentrated in vacuo. The crude material was absorbed onto a plug of silica gel and purified by chromatography through a Redi-Sep pre-packed silica gel column eluting with 10-100% EtOAc in hexane, to provide tert-butyl (5-bromo-4-cyano-3-iodopyridin-2-yl)(2-oxo-2-(pyrrolidin-1-yl)ethyl)carbamate (803 mg) as yellow oil. m/z (ESI): 536.9 $(M+H)^+$.

Step 3: 6-bromo-8-iodo-3-(pyrrolidin-1-yl)imidazo[1,2-a]pyridine-7-carbonitrile

To a RBF was added (5-bromo-4-cyano-3-iodopyridin-2-yl)(2-oxo-2-(pyrrolidin-1-yl)ethyl)carbamate (803 mg, 1.5 mmol), 2-fluoropyridine (0.583 g, 6 mmol, Adamas), $Tf_2O$ (0.846 g, 0.505 mL, 3 mmol, TCI) and DCM (5.00 mL). The reaction was stirred at room temperature for 2 h. Then $K_2CO_3$ (2.073 g, 15 mmol, Sigma-Aldrich) and THF (5.00 mL) were added. The reaction was stirred at 50° C. for 1 h. The reaction mixture was diluted with aqueous saturated $NaHCO_3$ (10 mL) and extracted with EtOAc (3×10 mL). The organic extract was dried over $Na_2SO_4$ and concentrated in vacuo. The crude material was absorbed onto a plug of silica gel and purified by chromatography through a Redi-Sep pre-packed silica gel column eluting with 0-100% EtOAc in hexane, to provide 6-bromo-8-iodo-3-(pyrrolidin-1-yl)imidazo[1,2-a]pyridine-7-carbonitrile (390 mg, 30.3% yield) as an orange solid. m/z (ESI): 417.9 $(M+H)^+$.

Intermediate 112: 6-bromo-8-iodo-3-(4-methylpiperazin-1-yl)imidazo[1,2-a]pyridine-7-carbonitrile This intermediate was synthesized in an analogous manner to Intermediate 111 to provide 6-bromo-8-iodo-3-(4-methylpiperazin-1-yl)imidazo[1,2-a]pyridine-7-carbonitrile. m/z (ESI): 445.9 $(M+H)^+$.

Intermediate 113: 6-bromo-8-iodo-2-(thiazol-2-yl)imidazo[1,2-a]pyridine-7-carbonitrile

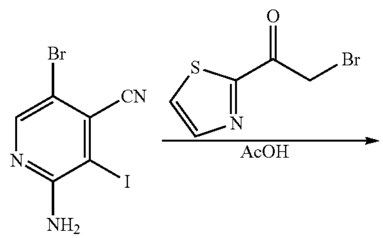

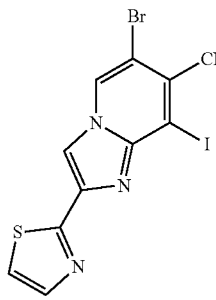

Intermediate 113

To a solution of 2-amino-5-bromo-3-iodoisonicotinonitrile (1 g, 3.09 mmol) in acetic acid (25 mL) was added 2-bromo-1-(thiazol-2-yl)ethan-1-one (1.272 g, 6.17 mmol). The mixture was stirred at 120° C. for 48 h. The reaction was concentrated in vacuo to give 6-bromo-8-iodo-2-(thiazol-2-yl)imidazo[1,2-a]pyridine-7-carbonitrile (780 mg, 58.6% yield) as a brown solid. m/z (ESI): 430.0 $[M+H]^+$.

Intermediate 114: 3-(1-methyl-1H-pyrazol-5-yl)cyclohex-2-en-1-one

This intermediate was synthesized in an analogous manner to Intermediate 109, Steps 1-2 using 4-bromo-1-methyl-1H-pyrazole (Sigma-Aldrich).

Intermediate 115: tert-butyl 6-(7-methyl-8-(((trifluoromethyl)sulfonyl)oxy)isochroman-6-yl)-2,6-diazaspiro[3.4]octane-2-carboxylate

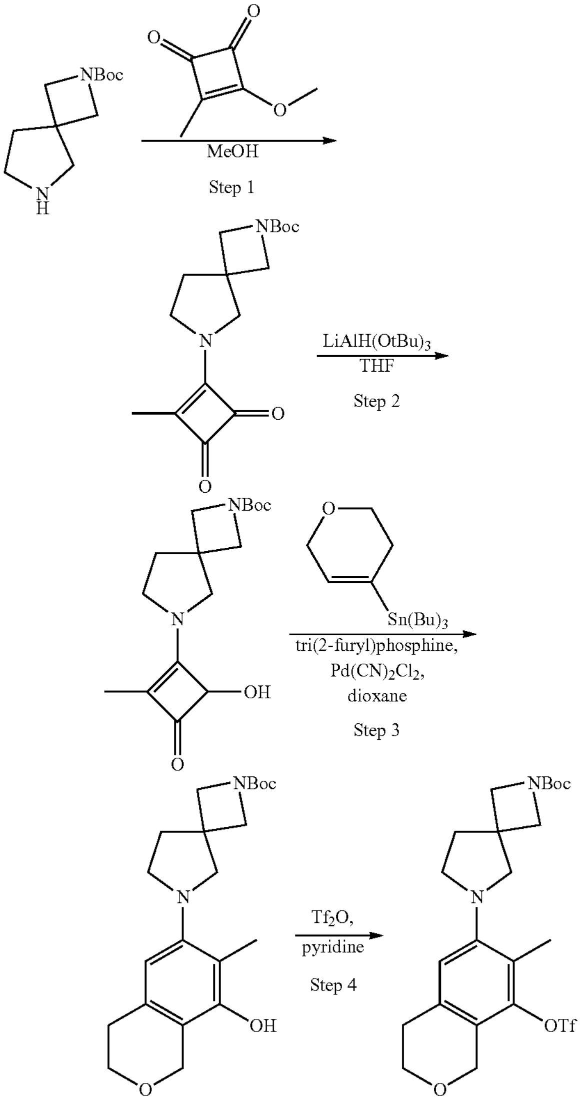

Intermediate 115

Step 1: tert-butyl 6-(2-methyl-3,4-dioxocyclobut-1-en-1-yl)-2,6-diazaspiro[3.4]octane-2-carboxylate To a RBF was added 2-(tert-butoxycarbonyl)-2,6-diazaspiro[3.4]octane (9.68 g, 45.6 mmol, PharmaBlock), 3-methoxy-4-methylcyclobut-3-ene-1,2-dione (5 g, 39.6 mmol, Enovation) and MeOH (198 mL). After 5 min, LC-MS suggests complete conversion. The reaction was concentrated and the crude material was purified using a Biotage Sfar HCD with MeOH in DCM (1-10%) to provide tert-butyl 6-(2-methyl-3,4-dioxocyclobut-1-en-1-yl)-2,6-diazaspiro[3.4]octane-2-carboxylate (10.5 g, 86% yield). m/z (ESI): 307.2 $(M+H)^+$.

Step 2: tert-butyl 6-(4-hydroxy-2-methyl-3-oxocyclobut-1-en-1-yl)-2,6-diazaspiro[3.4]octane-2-carboxylate To a −40° C. solution of tert-butyl 6-(2-methyl-3,4-dioxocyclobut-1-en-1-yl)-2,6-diazaspiro[3.4]octane-2-carboxylate (5.67 g, 18.51 mmol) and THF (61.7 mL) was added $LiAlH(OtBu)_3$ (20.36 mL, 20.36 mmol, Sigma-Aldrich) slowly, and the reaction was continuously stirred at −40° C. for 1 h after the addition. The reaction was quenched with aqueous 30% Rochelle salt (50 mL) and diluted with THF (50 mL). The crude material was extracted with EtOAc (3×50 mL), washed with brine, dried over $Na_2SO_4$, and concentrated in vacuo. The crude material was purified using Biotage Sfar HCD with MeOH in DCM (0-10%) to provide tert-butyl 6-(4-hydroxy-2-methyl-3-oxocyclobut-1-en-1-yl)-2,6-diazaspiro[3.4]octane-2-carboxylate (5.5 g, 96% yield). m/z (ESI): 309.2 $(M+H)^+$.

Step 3: tert-butyl 6-(8-hydroxy-7-methylisochroman-6-yl)-2,6-diazaspiro[3.4]octane-2-carboxylate To a vial with a stir bar was added tri(2-furyl)phosphine (51.6 mg, 0.222 mmol, Sigma-Aldrich), bis(benzonitrile) palladium(II) chloride (42.7 mg, 0.111 mmol, Sigma-Aldrich), tert-butyl 6-(4-chloro-2-methyl-3-oxocyclobut-1-en-1-yl)-2,6-diazaspiro[3.4]octane-2-carboxylate (727 mg, 2.224 mmol), 4-tributylstannyl-3,6-dihydro-2h-pyran (830 μL, 2.224 mmol, Combi-Blocks), and 1,4-dioxane (7.4 mL). The mixture was shaken until all solids were dissolved, then $N_2$ was bubbled through the solution for 30 min. The reaction mixture was heated at 100° C. for 18 h. The reaction was quenched with water (5 mL). The crude material was washed with water (2×5 mL), washed with brine, dried over $Na_2SO_4$, and concentrated in vacuo. The crude was taken up in 8 mL of ACN, and the solution was washed with heptanes (2×8 mL). The ACN solution was concentrated and purified using a Biotage Sfar HCD with EtOAc in heptanes (5-55%) to provide tert-butyl 6-(8-hydroxy-7-methylisochroman-6-yl)-2,6-diazaspiro[3.4]octane-2-carboxylate (320 mg, 38% yield). $^1H$ NMR (400 MHz, $CDCl_3$) δ ppm 6.35 (s, 1H), 5.43 (s, 1H), 4.77 (s, 2H), 3.86-4.00 (m, 6H), 3.25 (s, 2H), 3.08-3.22 (m, 2H), 2.77 (br t, J=5.2 Hz, 2H), 2.06-2.22 (m, 5H), 1.47 (s, 9H). m/z (ESI): 375.2 $(M+H)^+$.

Step 4: tert-butyl 6-(7-methyl-8-(((trifluoromethyl)sulfonyl)oxy)isochroman-6-yl)-2,6-diazaspiro[3.4]octane-2-carboxylate Trifluoromethanesulfonic anhydride (0.234 mL, 0.234 mmol, Sigma-Aldrich) was added to a mixture of tert-butyl 6-(8-hydroxy-7-methylisochroman-6-yl)-2,6-diazaspiro[3.4]octane-2-carboxylate (73 mg, 0.195 mmol) and pyridine (0.032 mL, 0.390 mmol, Sigma-Aldrich) in DCM (1 mL) at 0° C. The reaction mixture was stirred at 0° C. for 30 min. The reaction mixture was concentrated in vacuo to give crude tert-butyl 6-(7-methyl-8-(((trifluoromethyl)sulfonyl)oxy)isochroman-6-yl)-2,6-diazaspiro[3.4]octane-2-carboxylate that was used as is.

Intermediate 116: 6-chloro-5-methyl-7-(4,4,5,5-tetramethyl-1,3,2-dioxaborolan-2-yl)-1H-indazole Synthesized in an analogous manner to Intermediate 38 using 1-Chloro-2,4-dimethyl-5-nitrobenzene (CAS #69383-68-2, WO 2000/044753).

Intermediate 117: tert-butyl 6-((5R,8S)-4-chloro-3-methyl-5,6,7,8-tetrahydro-5,8-methanoquinolin-2-yl)-2,6-diazaspiro[3.4]octane-2-carboxylate 2,4-dichloro-3-methyl-5,6,7,8-tetrahydro-5,8-methanoquinoline was synthesized in an analogous manner to Intermediate 37 starting with bicyclo[2.2.1]heptan-2-one (CAS #497-38-1, Synlett (2007), (1), 47-50).

Intermediate 118: tert-butyl 6-(4-chloro-3-fluoro-7-(oxetan-3-yl)-5,6,7,8-tetrahydro-1,7-naphthyridin-2-yl)-2,6-diazaspiro[3.4]octane-2-carboxylate Synthesized in analogous manner to Intermediate 50 and 51, starting with ethyl 1-benzyl-3-oxopiperidine-4-carboxylate (Suzhou Sibian Chemical Ltd) and oxetan-3-one (Combi-Blocks) in place of acetone in Intermediate 51, step 2.

Intermediate 119: 2,4-dichloro-6,7,8,9-tetrahydro-5H-cyclohepta[b]pyridine-3-carbonitrile This intermediate was synthesized in an analogous manner to Intermediate 1 using 2-oxo-cycloheptanecarboxylic acid ethyl ester (Enamine)

Intermediate 120: 2-(4-Methylthiazol-5-yl)tetrahydro-4H-pyran-4-one

Step 1: 4-methylthiazole-5-carbaldehyde

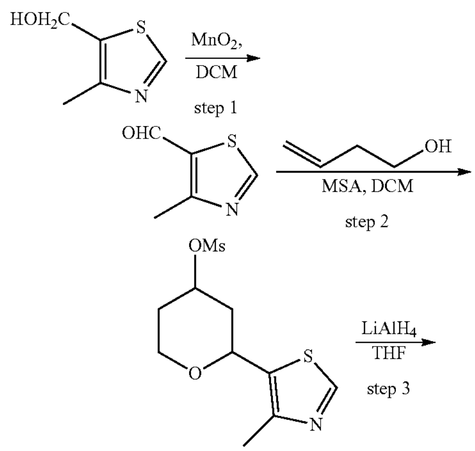

-continued

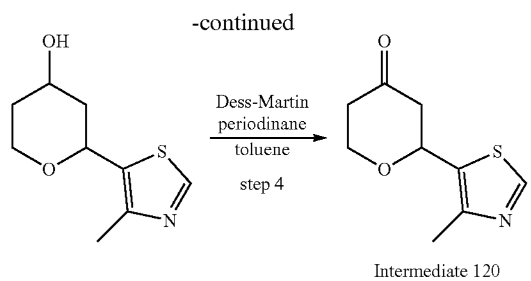

Intermediate 120

Step 1: 4-methylthiazole-5-carbaldehyde

To a RBF was added (4-methylthiazol-5-yl)methanol (9 g, 69.7 mmol, Spectrochem) and $MnO_2$ (60.6 g, 697 mmol) in toluene. The reaction mixture was stirred at 58° C. for 12 h. The reaction was filtered while hot through celite and the filtrate concentrated in vacuo. The crude material was absorbed onto a plug of silica gel and purified by chromatography through a Redi-Sep pre-packed silica gel column eluting with a gradient of 0-50% EtOAc in hexanes, to provide 4-methylthiazole-5-carbaldehyde (4.5 g, 50.8% yield) as a yellow solid. m/z (ESI): 128.3 $(M+H)^+$. $^1$H NMR (401 MHz, $CDCl_3$) δ ppm 10.15 (d, J=0.9 Hz, 1H), 8.98 (s, 1H), 2.80 (s, 3H).

Step 2: 2-(4-methylthiazol-5-yl)tetrahydro-2H-pyran-4-yl methanesulfonate

To a stirred solution of but-3-en-1-ol (2.55 g, 35.4 mmol) and 4-methylthiazole-5-carbaldehyde (4.5 g, 35.4 mmol) in DCM (20 mL) was added methanesulfonic acid (6.89 mL, 106 mmol) dropwise at 0° C. and stirred at room temperature for 16 h. The reaction was cooled to 0° C. and basified to pH 8 with aqueous 10% $NaHCO_3$ and extracted with DCM (2×10 mL). The combined organic layers were dried over $Na_2SO_4$ and concentrated in vacuo. The crude material was absorbed onto a plug of silica gel and purified by chromatography through a Redi-Sep pre-packed silica gel column eluting with a gradient of 0-60% EtOAc in hexanes, to provide 2-(4-methylthiazol-5-yl)tetrahydro-2H-pyran-4-yl methanesulfonate (6.3 g, 64.2% yield) as a yellow oil. m/z (ESI): 278.9 $(M+H)^+$.

Step 3: 2-(4-methylthiazol-5-yl)tetrahydro-2H-pyran-4-ol

To a −78° C. solution of $LiAlH_4$ in THE (33.5 mL, 67.1 mmol) and THF (40 mL) was slowly added a solution of 2-(4-methylthiazol-5-yl)tetrahydro-2H-pyran-4-yl methanesulfonate (6.2 g, 22.35 mmol) in THF. After addition, the reaction was allowed to warm to room temperature and then heated to 70° C. for 1 h. The reaction was quenched with brine at −78° C. and stirred at room temperature for 30 min. The precipitated solid was filtered and the filtrate was concentrated to provide 2-(4-methylthiazol-5-yl)tetrahydro-2H-pyran-4-ol (4.4 g, 99% yield). m/z (ESI): 200.2 $(M+H)^+$.

Step 4: 2-(4-methylthiazol-5-yl)tetrahydro-4H-pyran-4-one

To a 0° C. solution of 2-(4-methylthiazol-5-yl)tetrahydro-2H-pyran-4-ol (5 g, 25.09 mmol) in DCM (50 mL) was slowly added Dess-Martin periodinane (12.77 g, 30.1 mmol). The reaction was stirred for 1 h at 0° C. and warmed to room temperature. The reaction was quenched with saturated aqueous $NaHCO_3$. The reaction was stirred for 30 min and the precipitated solid was filtered and washed with DCM (2×50 mL). The organic extract was washed with water (2×25 mL), dried over $Na_2SO_4$, and concentrated in vacuo. The crude material was absorbed onto a plug of silica gel and purified by chromatography through a Redi-Sep pre-packed silica gel column eluting with a gradient of 0-40% EtOAc in hexanes, to provide 2-(4-methylthiazol-5-yl)tetrahydro-4H-pyran-4-one (3.3 g, 66.7% yield) as a yellow solid. m/z (ESI): 198.1 $(M+H)^+$. $^1$H NMR (401 MHz, $CDCl_3$) δ ppm 8.72 (s, 1H), 4.95 (dd, J=10.4, 3.9 Hz, 1H), 4.42 (ddd, J=11.7, 7.5, 1.5 Hz, 1H), 4.12 (q, J=7.1 Hz, 1H), 3.87 (td, J=12.0, 2.9 Hz, 1H), 2.78 (dd, J=7.4, 0.9 Hz, 1H), 2.75 (ddd, J=7.5, 2.4, 0.9 Hz, 2H), 2.41-2.50 (m, 3H).

Intermediate 121: 3-methyl-3-(4-methylthiazol-5-yl)cyclohexan-1-one

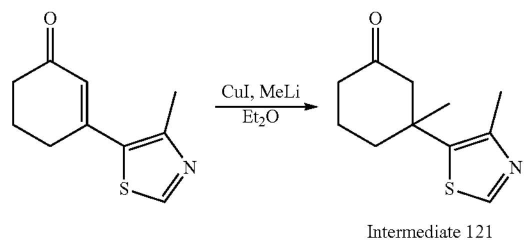

Intermediate 121

To a −78° C. solution of CuI (3.94 g, 20.70 mmol) in diethyl ether (50 mL) was added MeLi (1.6 M in $Et_2O$) (25.9 mL, 41.4 mmol). Following a color change to a clear solution, 3-(4-methylthiazol-5-yl)cyclohex-2-en-1-one (2 g, 10.35 mmol, Example 22-1, step 2) in diethyl ether (50 mL) was added. After addition, the reaction was stirred at −78° C. for 3 h. The reaction was quenched with aqueous saturated $NH_4Cl$, diluted with cold water (100 mL) and extracted with DCM (2×100 mL). The combined organic layers were washed with water (100 mL), brine solution (100 mL), dried over $Na_2SO_4$, and concentrated under reduced pressure. The crude product was purified by HPLC using 20% ACN in water as eluent to provide 3-methyl-3-(4-methylthiazol-5-yl)cyclohexan-1-one (1.6 g, 73.9% yield) as pale yellow liquid. m/z (ESI): 210.3 $(M+H)^+$. $^1$H NMR (401 MHz, DMSO-$d_6$) δ ppm 8.76 (s, 2H), 2.82 (dt, J=14.0, 1.3 Hz, 2H), 2.55 (t, J=1.3 Hz, 1H), 2.46 (s, 7H), 2.44 (s, 1H), 2.33-2.19 (m, 6H), 2.10-1.79 (m, 4H), 1.77-1.63 (m, 2H), 1.32 (s, 6H), 1.07 (s, 1H).

Intermediate 122: 7,7-difluoro-6-(4-methylthiazol-5-yl)bicyclo[4.1.0]heptan-2-one

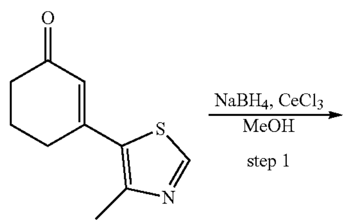

-continued

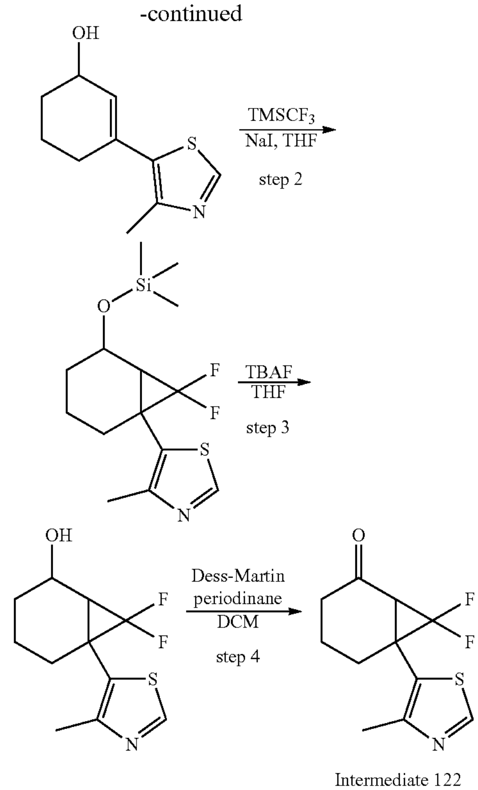

Intermediate 122

Step 1: 3-(4-methylthiazol-5-yl)cyclohex-2-en-1-ol

To a 0° C. solution of 3-(4-methylthiazol-5-yl)cyclohex-2-en-1-one (4.3 g, 22.25 mmol) in MeOH (43 mL) was added cerium (III) chloride heptahydrate (8.29 g, 22.25 mmol) followed by portionwise addition of $NaBH_4$ (0.842 g, 22.25 mmol). The reaction mixture was slowly allowed to warm to room temperature and stirred for 3 h. The reaction was quenched with aqueous saturated $NH_4Cl$ at 0° C. and stirred for 10 min. The precipitates were filtered and washed with DCM. The filtrate was partitioned and the aqueous layer was extracted with DCM (2×20 mL). The combined organic layers were washed with brine (10 mL), dried over $Na_2SO_4$, and concentrated under reduced pressure. The crude material was absorbed onto a plug of silica gel and purified by chromatography through a Redi-Sep pre-packed silica gel column eluting with a gradient of 0-50% EtOAc in hexane, to provide 3-(4-methylthiazol-5-yl)cyclohex-2-en-1-ol (3.5 g, 81% yield) as a pale reddish yellow liquid. m/z (ESI): 196.1 $(M+H)^+$. $^1$H NMR (401 MHz, DMSO-$d_6$): δ (ppm) 8.87 (s, 1H), 5.88 (dt, J=3.5, 1.8 Hz, 1H), 4.85 (d, J=5.6 Hz, 1H), 4.18 (s, 1H), 2.42 (s, 3H), 2.33-2.15 (m, 2H), 1.82 (dt, J=9.8, 5.7 Hz, 2H), 1.61 (dtt, J=10.4, 7.5, 4.9 Hz, 1H), 1.47 (td, J=9.9, 6.9 Hz, 1H).

Step 2: 5-(7,7-difluoro-5-((trimethylsilyl)oxy)bicyclo[4.1.0]heptan-1-yl)-4-methylthiazole To a 20-mL microwave vial was added 3-(4-methylthiazol-5-yl)cyclohex-2-en-1-ol (0.7 g, 3.58 mmol) and THF (10.5 mL). The reaction mixture was cooled to 0° C., before sodium iodide (1.612 g, 10.75 mmol) was slowly added, followed by trimethyl(trifluoromethyl)silane (1.529 g, 10.75 mmol). The reaction mixture was subjected to microwave irradiation for 2 h at 115° C. The reaction mixture was cooled to room temperature, quenched with ice cold water and extracted with EtOAc (2×5 mL). The combined organic layers were washed with brine, dried over $Na_2SO_4$, and concentrated in vacuo. Note: The above procedure was repeated on 2×0.7 g batches. The crude material was absorbed onto a plug of silica gel and purified by chromatography through a Redi-Sep pre-packed silica gel column eluting with a gradient of 0-50% EtOAc in hexanes, to provide 5-(7,7-difluoro-5-((trimethylsilyl)oxy)-bicyclo[4.1.0]heptan-1-yl)-4-methylthiazole (0.9 g) as a pale yellow liquid. m/z (ESI): 246.1 $(M+H-TMS)^+$. $^1$H NMR (401 MHz, DMSO-$d_6$) δ ppm 8.88 (s, 1H), 4.20 (m, J=6.2, 4.1, 1.7 Hz, 1H), 2.50-2.32 (m, 1H), 2.40 (s, 3H), 2.09-1.97 (m, 1H), 1.90-1.69 (m, 2H), 1.64 (dtd, J=12.0, 6.0, 3.1 Hz, 1H), 1.52 (d, J=9.6 Hz, 1H), 1.44 (q. J=6.9 Hz, 1H), 0.15 (s, 9H).

Step 3: 7,7-difluoro-6-(4-methylthiazol-5-yl)bicyclo[4.1.0]heptan-2-ol

To a 0° C. solution of 5-(7,7-difluoro-5-((trimethylsilyl)oxy)bicyclo[4.1.0]heptan-1-yl)-4-methylthiazole (0.9 g, 2.83 mmol) in THF (9 mL) was added TBAF (4.25 mL, 4.25 mmol, 1M in THF). The reaction was stirred at room temperature for 30 min. The reaction mixture was quenched with ice cold water and extracted with EtOAc (2×10 mL). The combined organic layers were dried over $Na_2SO_4$ and evaporated under vacuum to afford crude title compound (0.8 g) as a pale yellow color liquid. The crude material was taken forward to the next step without further purification. m/z (ESI): 246.1 $(M+H)^+$. $^1$H NMR (401 MHz, DMSO-$d_6$) δ ppm 8.87 (s, 1H), 5.29 (d, J=3.8 Hz, 1H), 4.12-3.93 (m, 1H), 2.41 (d, J=13.7 Hz, 4H), 2.10-1.95 (m, 1H), 1.80-1.70 (m, 1H), 1.70-1.45 (m, 2H), 1.31-1.11 (m, 2H).

Step 4: 7,7-difluoro-6-(4-methylthiazol-5-yl)bicyclo[4.1.0]heptan-2-one

To a 0° C. solution of 7,7-difluoro-6-(4-methylthiazol-5-yl)bicyclo[4.1.0]heptan-2-ol (0.8 g, 3.26 mmol) in DCM (16 mL) was added Dess-Martin periodinane (2.075 g, 4.89 mmol) portionwise and the reaction was stirred at room temperature for 1 h. The reaction mixture was quenched with aqueous saturated sodium thiosulphate and aqueous saturated $NaHCO_3$, then extracted with DCM (2×5 mL). The combined organic layers were dried over $Na_2SO_4$ and concentrated in vacuo. The crude material was absorbed onto a plug of silica gel and purified by chromatography through a Redi-Sep pre-packed silica gel column eluting with a gradient of 0-50% EtOAc in hexanes, to provide 7,7-difluoro-6-(4-methylthiazol-5-yl)bicyclo[4.1.0]heptan-2-one (0.4 g, 50.4% yield) as a colorless liquid. m/z (ESI): 244.1 $(M+H)^+$. $^1$H NMR (401 MHz, DMSO-$d_6$) δ ppm 8.95 (s, 1H), 2.94 (d, J=16.2 Hz, 1H), 2.50-2.33 (m, 2H), 2.37 (s, 3H), 2.28 (m, J=17.0, 7.0, 4.5 Hz, 1H), 2.12-1.74 (m, 3H).

Intermediate 123: 5-bromo-1-fluoro-naphthalen-2-ol

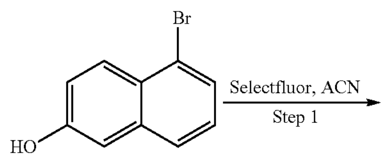

-continued

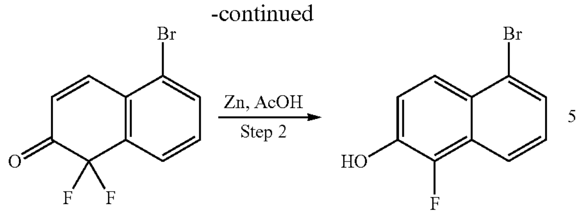

Step 1: 5-bromo-1,1-difluoro-naphthalen-2-one

To a solution of 5-bromonaphthalen-2-ol (5 g, 22.41 mmol, Labter Pharmatech Co., Ltd) in ACN (50 mL) was added Selectfluor (9.53 g, 26.90 mmol). The mixture was stirred at 25° C. for 12 h. The reaction mixture was quenched by $H_2O$ (50 mL) at 25° C., extracted with EtOAc (50 mL×3). The combined organic layers were washed with $H_2O$ (100 mL×2), dried over $Na_2SO_4$, and concentrated under reduced pressure. The residue was purified by column chromatography ($SiO_2$, 5-25% EtOAc in petroleum ether) to provide 5-bromo-1,1-difluoro-naphthalen-2-one (2.2 g, 37.89% yield) as a yellow solid. m/z (ESI): 258.8, 260.8 $(M+H)^+$. $^1H$ NMR (400 MHz, $CDCl_3$) δ ppm 7.87 (d, J=10.4 Hz, 1H), 7.68-7.72 (m, 2H), 7.29-7.33 (m, 1H), 6.22-6.26 (m, 1H).

Step 2: 5-bromo-1-fluoro-naphthalen-2-ol

To a solution of 5-bromo-1,1-difluoro-naphthalen-2-one (4.8 g, 18.53 mmol) in AcOH (50 mL) was added Zn (1.21 g, 18.53 mmol) at 0° C. The mixture was stirred at 25° C. for 0.5 h. The reaction mixture was diluted with $H_2O$ (50 mL) and extracted with EtOAc (50 mL×3). The combined organic layers were washed with sat. $NaHCO_3$ (30 mL), dried over $Na_2SO_4$, and concentrated under reduced pressure. The residue was purified by column chromatography ($SiO_2$, petroleum ether:EtOAc=50:1 to 3:1) to provide 5-bromo-1-fluoro-naphthalen-2-ol (3.30 g, 73.2% yield) as a white solid. m/z (ESI): 238.9, 240.8 $(M+H)^+$. $^1H$ NMR (400 MHz, Methanol-$d_4$) δ ppm 7.95 (d, J=8.40 Hz, 1H), 7.90 (d, J=9.20 Hz, 1H), 7.66 (d, J=7.60 Hz, 1H), 7.30-7.38 (m, 2H).

Intermediate 124: 1,5,6-trimethylindazole-7-carbaldehyde

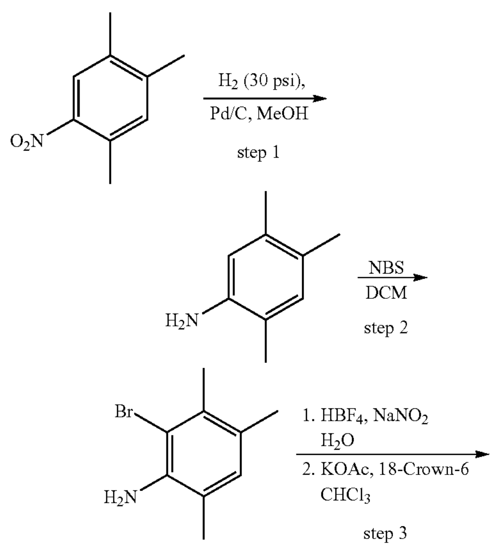

-continued

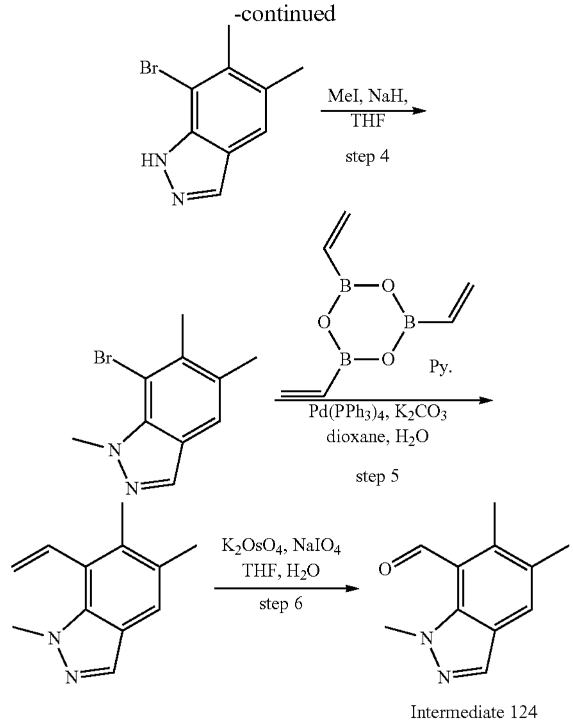

Intermediate 124

Step 1: 2,4,5-trimethylaniline

To a solution of 1,2,4-trimethyl-5-nitro-benzene (80 g, 484.29 mmol, TCASChem) in MeOH (1 L) was added Pd/C (30 g, 10 wt %) under Ar. The suspension was degassed under vacuum and purged with $H_2$ (30 psi) several times. The mixture was stirred under $H_2$ (30 psi) at 30° C. for 12 h. Three reactions with same scale were combined for work-up. The mixture was filtered and concentrated under reduced pressure. The residue was washed with petroleum ether (300 mL) to provide 2,4,5-trimethylaniline (190 g, crude) as a red solid. $^1H$ NMR (400 MHz, $CDCl_3$) δ ppm 6.84 (s, 1H), 6.53 (s, 1H), 3.50 (br s, 2H), 2.12-2.20 (m, 9H).

Step 2: 2-bromo-3,4,6-trimethyl-aniline

To a mixture of 2,4,5-trimethylaniline (63 g, 465.96 mmol) in DCM (600 mL) was added NBS (82.93 g, 465.96 mmol) in one portion at 0° C. under $N_2$. The mixture was stirred at 15° C. for 12 h. The residue was poured into water (1500 mL). The aqueous phase was extracted with DCM (500 mL×3). The combined organic phase was washed with brine (800 mL×2), dried over $Na_2SO_4$, and concentrated in vacuo to provide 2-bromo-3,4,6-trimethyl-aniline (66.7 g, crude) as a brown solid. m/z (ESI): 213.9 $[M+H]^+$. $^1H$ NMR (400 MHz, $CDCl_3$) δ ppm 6.81 (s, 1H), 4.05 (br s, 2H), 2.33 (s, 3H), 2.23 (s, 3H), 2.19 (s, 3H).

Step 3: 7-bromo-5,6-dimethyl-1H-indazole

To a 0° C. solution of 2-bromo-3,4,6-trimethyl-aniline (40 g, 186.83 mmol) and $HBF_4$ (615.22 g, 2.80 mol, 436.32 mL, 40 wt %) was added a solution of $NaNO_2$ (25.78 g, 373.66 mmol) in $H_2O$ (50 mL) dropwise and the reaction stirred at 0° C. for 1 h. The reaction was warmed and stirred at 15° C. for 0.5 h. The resulting precipitate was filtered, washed with $(i\text{-}Pr)_2O$ (40 mL) and concentrated under vacuum to provide the crude diazonium salt. To a mixture of 2-bromo-3,4,6-trimethyl-benzenediazonium in $CHCl_3$ (310 mL) was added KOAc (35.13 g, 357.94 mmol) in portions at 15° C. under $N_2$. The mixture was treated with 18-Crown-6 (2.37 g, 8.95 mmol) in one portion at 15° C. under $N_2$. The mixture was stirred at 35° C. for 0.5 h. The reaction mixture was filtered and concentrated in vacuo. The residue was purified by column chromatography ($SiO_2$, petroleum ether/EtOAc=20/1 to 15/1) to provide 7-bromo-5,6-dimethyl-1H-indazole (16 g, 39.72% yield) as a brown solid. m/z (ESI): 224.9 $[M+H]^+$.

Step 4: 7-bromo-1,5,6-trimethyl-indazole

To a solution of 7-bromo-5,6-dimethyl-1H-indazole (40 g, 177.71 mmol) in THF (400 mL) was added LiHMDS (1 M, 177.71 mL) at 0° C. The mixture was stirred at 0° C. for 0.5 h. MeI (75.67 g, 533.13 mmol, 33.19 mL) was added dropwise to the mixture at 0° C. The mixture was stirred at 35° C. for 11.5 h. The reaction mixture was quenched by addition of aqueous saturated $NH_4Cl$ 500 mL, and extracted with EtOAc (200 mL×3). The combined organic layers were washed with brine (500 mL×2), dried over $Na_2SO_4$, and concentrated under reduced pressure. The residue was purified by column chromatography ($SiO_2$, petroleum ether/EtOAc=10/1 to 1/1) to provide 7-bromo-1,5,6-trimethyl-indazole (30 g, 70.6% yield) as a yellow solid.

Step 5: 1,5,6-trimethyl-7-vinyl-indazole

To a mixture of 7-bromo-1,5,6-trimethyl-indazole (10 g, 41.82 mmol), pyridine: 2,4,6-trivinyl-1,3,5,2,4,6-trioxatriborinane (10.07 g, 41.82 mmol, Labnetwork) and $K_2CO_3$ (17.34 g, 125.46 mmol) in dioxane (100 mL) and $H_2O$ (10 mL) was added $Pd(PPh_3)_4$ (4.83 g, 4.18 mmol) at 15° C. The mixture was stirred at 100° C. for 12 h under $N_2$. The mixture was cooled to 25° C. and filtered. The filter cake was washed with EtOAc (300 mL). The aqueous phase was extracted with EtOAc (200 mL×3). The combined organic phase was washed with brine (300 mL×2), dried over $Na_2SO_4$, and concentrated in vacuo. The residue was purified by flash silica gel chromatography (0-18% EtOAc/petroleum ether) to provide 1,5,6-trimethyl-7-vinyl-indazole (5.5 g, 70.6% yield) as a yellow solid.

Step 6: 1,5,6-trimethylindazole-7-carbaldehyde

To a mixture of 1,5,6-trimethyl-7-vinyl-indazole (5.5 g, 29.53 mmol) and THF (100 mL):$H_2O$ (20 mL) was added $K_2OsO_4.2H_2O$ (870.43 mg, 2.36 mmol) and $NaIO_4$ (17.43 g, 81.50 mmol, 4.52 mL) in portions at 25° C. The mixture was stirred at 70° C. for 12 h. The mixture was cooled to 25° C. To the mixture was added aqueous saturated $Na_2SO_3$ (200 mL). The mixture was stirred at 25° C. for 1 h. The mixture was extracted with EtOAc (200 mL×4). The combined organic phases were washed with brine (100 mL×2), dried over $Na_2SO_4$, and concentrated in vacuo. The residue was purified by flash silica gel chromatography (0-35% EtOAc/petroleum ether) to provide 1,5,6-trimethylindazole-7-carbaldehyde (2.25 g, 40.5% yield) as a yellow solid. m/z (ESI): 189.0 $[M+H]^+$. $^1H$ NMR (400 MHz, $CDCl_3$) δ ppm 10.85 (s, 1H), 7.94 (s, 1H), 7.73 (s, 1H), 4.19 (s, 3H), 2.67 (s, 3H), 2.42 (s, 3H).

Intermediate 125: 3-(4-(methoxymethyl)thiazol-5-yl)cyclohex-2-en-1-one

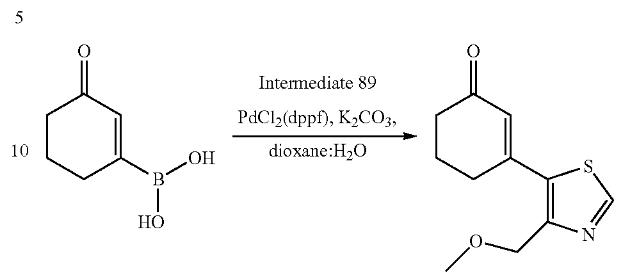

To a RBF charged (3-oxocyclohex-1-en-1-yl)boronic acid (0.673 g, 4.81 mmol), $K_2CO_3$ (1.328 g, 9.61 mmol), 5-bromo-4-(methoxymethyl)thiazole (1 g, 4.81 mmol), 1,4-dioxane (12 mL) and water (2 mL). The mixture was sparged with $N_2$ for 5 min before adding $PdCl_2$(dppf)-DCM adduct (0.220 g, 0.269 mmol). The reaction was heated at 90° C. for 16 h. The reaction mixture was allowed to cool to room temperature, filtered through a celite pad and the celite pad washed with EtOAc. The filtrate was washed with water, dried over $Na_2SO_4$, and concentrated in vacuo. The material was absorbed onto a plug of silica gel and purified by chromatography through a Redi-Sep pre-packed silica gel column, eluting with a gradient of 20-100% EtOAc in hexane, to provide 3-(4-(methoxymethyl)thiazol-5-yl)cyclohex-2-en-1-one (0.6 g, 55.9% yield) as a brown oil. m/z (ESI): 224.1 $(M+H)^+$. $^1H$ NMR (400 MHz, DMSO-$d_6$) δ ppm 9.18 (s, 1H), 6.46-5.86 (m, 1H), 3.93 (s, 2H), 3.31 (s, 3H), 2.72 (td, J=6.0, 1.6 Hz, 2H), 2.48-2.30 (m, 2H), 2.06 (dq, J=8.0, 6.2 Hz, 2H).

Intermediate 126: tert-butyl 6-(4-chloro-3-fluoro-7-(oxetan-3-yl)-5,6,7,8-tetrahydro-1,7-naphthyridin-2-yl)-2,6-diazaspiro[3.4]octane-2-carboxylate

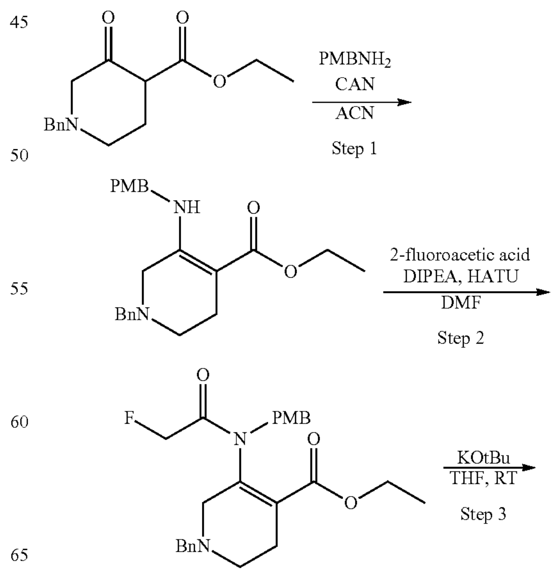

-continued

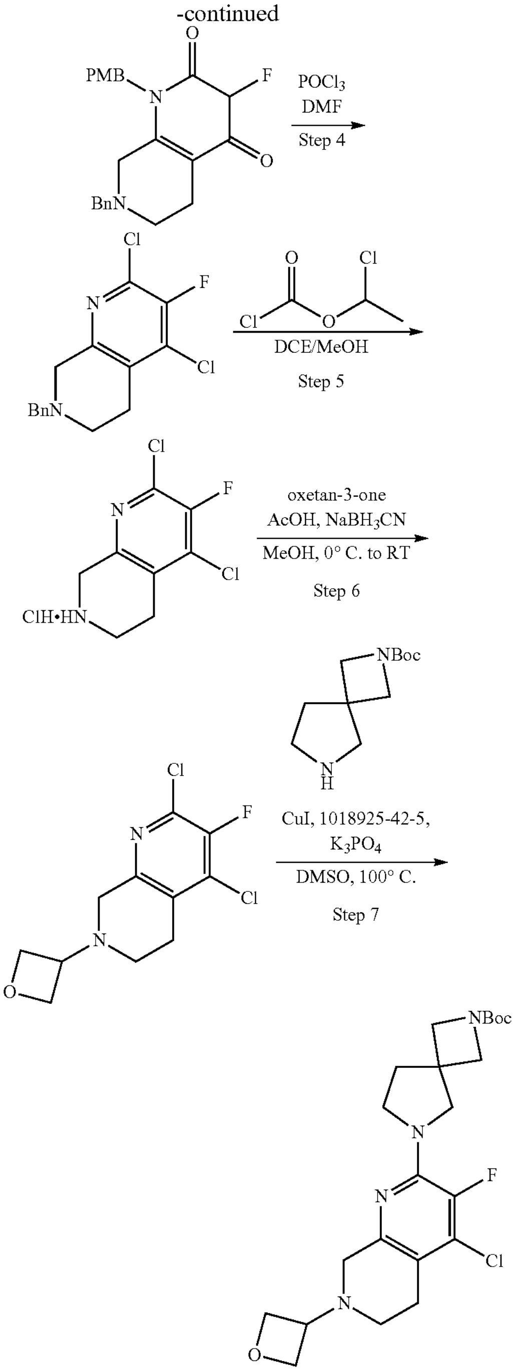

Intermediate 126

Step 1: ethyl 1-benzyl-5-((4-methoxybenzyl) amino)-1,2,3,6-tetrahydropyridine-4-carboxylate To a stirred solution of ethyl 1-benzyl-3-oxopiperidine-4-carboxylate (500 g, 1913 mmol, Suzhou Sibian Chemical) in MeCN (5000 mL) was added (4-methoxyphenyl)methanamine (341 g, 2487 mmol, Chempure) and ceric ammonium nitrate (52.4 g, 96 mmol, Avra) at 0° C., and reaction mixture was stirred at room temperature for 16 h. The reaction mixture was diluted with water (500 mL) and extracted with EtOAc (3×500 mL). The combined organic layers were washed with brine, dried over $Na_2SO_4$, and concentrated under reduced pressure. The resulting residue was purified by silica gel column chromatography eluting with 10% EtOAc in petroleum ether to give ethyl 1-benzyl-5-((4-methoxybenzyl)amino)-1,2,3,6-tetrahydropyridine-4-carboxylate (550 g, 76% yield) as a yellow solid. m/z (ESI): 381.0 $(M+H)^+$.

Step 2: ethyl 1-benzyl-5-(2-fluoro-N-(4-methoxybenzyl)acetamido)-1,2,3,6-tetrahydropyridine-4-carboxylate To a mixture of ethyl 1-benzyl-5-((4-methoxybenzyl) amino)-1,2,3,6-tetrahydropyridine-4-carboxylate (4 g, 10.51 mmol) in DMF (30 mL) at 0° C. under a $N_2$ atmosphere was added 2-fluoroacetic acid (1.231 g, 15.77 mmol, Essen) and DIPEA (7.34 mL, 42.1 mmol). The reaction mixture was stirred at 0° C. for 5 min before HATU (6.00 g, 15.77 mmol) was added. The reaction mixture was heated at 60° C. and stirred for 12 h. The reaction mixture was quenched with ice water and extracted with EtOAc (3×100 mL). The combined organic layers were washed with brine (100 mL), dried over $Na_2SO_4$, and concentrated under reduced pressure. The resulting residue was purified by silica gel column chromatography eluting with 15% EtOAc in hexanes to give ethyl 1-benzyl-5-(2-fluoro-N-(4-methoxybenzyl)acetamido)-1,2,3,6-tetrahydropyridine-4-carboxylate (1.8 g, 38.9% yield) as a brown liquid. m/z (ESI): 441.3 $(M+H)^+$.

Step 3: 7-benzyl-3-fluoro-1-(4-methoxybenzyl)-5,6,7,8-tetrahydro-1,7-naphthyridine-2,4(1H,3H)-dione To a mixture of ethyl 1-benzyl-5-(2-fluoro-N-(4-methoxybenzyl)acetamido)-1,2,3,6-tetrahydropyridine-4-carboxylate (44 g, 100 mmol) in THF (440 mL) at 0° C. was added potassium tert-butoxide (300 mL, 300 mmol). The reaction mixture was stirred at room temperature for 2 h. The reaction mixture was quenched with ice water (350 mL) and washed with EtOAc (2×800 mL). The aqueous layer was acidify with 1.5M HCl to pH 5-6 and concentrated in vacuo. The crude material was washed with 20% MeOH in DCM (800 mL), and the filtrate was concentrated to give 7-benzyl-3-fluoro-1-(4-methoxybenzyl)-5,6,7,8-tetrahydro-1,7-naphthyridine-2,4(1H,3H)-dione (33 g, 84% yield) that was used directly without further purification. m/z (ESI): 392.2 $(M+H)^+$.

Step 4: 7-benzyl-2,4-dichloro-3-fluoro-5,6,7,8-tetrahydro-1,7-naphthyridine

A RBF charged with 7-benzyl-3-fluoro-1-(4-methoxybenzyl)-5,6,7,8-tetrahydro-1,7-naphthyridine-2,4(1H,3H)-dione (21 g, 53.2 mmol), $POCl_3$ (149 mL, 1597 mmol) and DMF (0.412 mL, 5.32 mmol). The reaction mixture was stirred at 80° C. for 16 h. The reaction mixture was allowed to cool to room temperature, concentrated in vacuo, and the resulting residue was quenched with saturated aqueous $NaHCO_3$ (450 mL) at 0° C. and extracted with EtOAc (2×100 mL). The combined organic extracts were washed with brine (50 mL), dried over $Na_2SO_4$, and concentrated in vacuo. The material was purified by silica gel column chromatography eluting with 20% EtOAc in petroleum ether to afford 7-benzyl-2,4-dichloro-3-fluoro-5,6,7,8-tetrahydro-1,7-naphthyridine (0.8 g, 4.8% yield). m/z (ESI): 310.8 $(M+H)^+$.

Step 5: 2,4-dichloro-3-fluoro-5,6,7,8-tetrahydro-1,7-naphthyridine hydrochloride To a mixture of 7-benzyl-2,4-dichloro-3-fluoro-5,6,7,8-tetrahydro-1,7-naphthyridine (1 g, 3.21 mmol) in DCE (15 mL) at 0° C. was added 1-chloroethyl carbonochloridate (3.47 mL, 32.1 mmol, Spectrochem), and the reaction mixture was stirred at room temperature for 16 h. The reaction mixture was concentrated under reduced pressure before being taken up in MeOH (15 mL) and heated at 70° C. for 2 h. The reaction mixture was concentrated under reduced pressure, triturated with EtOAc and filtered. The solids were washed with EtOAc, and dried to afford 2,4-dichloro-3-fluoro-5,6,7,8-tetrahydro-1,7-naphthyridine hydrochloride (0.67 g, 81% yield) as a white solid. m/z (ESI): 222.9 $(M+H)^+$.

Step 6: 2,4-dichloro-3-fluoro-7-(oxetan-3-yl)-5,6,7,8-tetrahydro-1,7-naphthyridine To a 0° C. solution of 2,4-dichloro-3-fluoro-5,6,7,8-tetrahydro-1,7-naphthyridine hydrochloride (0.67 g, 2.60 mmol) and MeOH (10 mL) was added HOAc (0.149 mL, 2.60 mmol) and oxetan-3-one (0.469 g, 6.50 mmol, Combi-Blocks). The reaction mixture was stirred at 0° C. for 30 min before $NaCNBH_3$ (0.654 g, 10.41 mmol) was added, and the mixture was stirred at room temperature for 16 h. The reaction mixture was quenched with cold water and extracted with EtOAc (2×40 mL). The combined organic extracts were washed with water (20 mL), washed with brine (20 mL), dried over $Na_2SO_4$, and concentrated under reduced pressure. The crude product was purified via silica gel column chromatography eluting with 30% EtOAc in petroleum ether to afford 2,4-dichloro-3-fluoro-7-(oxetan-3-yl)-5,6,7,8-tetrahydro-1,7-naphthyridine (0.55 g, 76% yield) as a yellow oil. $^1H$ NMR (400 MHz, DMSO-$d_6$) δ ppm 4.91-4.83 (m, 1H), 4.62 (t, J=6.6 Hz, 2H), 4.57 (d, J=7.4 Hz, 1H), 4.52 (t, J=6.1 Hz, 2H), 3.67 (p, J=6.3 Hz, 1H), 2.82 (t, J=5.9 Hz, 2H), 2.63 (t, J=5.9 Hz, 2H). m/z (ESI): 276.9 $(M+H)^+$.

Step 7: tert-butyl 6-(4-chloro-3-fluoro-7-(oxetan-3-yl)-5,6,7,8-tetrahydro-1,7-naphthyridin-2-yl)-2,6-diazaspiro[3.4]octane-2-carboxylate To a sealable tube containing a mixture of 2,4-dichloro-3-fluoro-7-(oxetan-3-yl)-5,6,7,8-tetrahydro-1,7-naphthyridine (0.55 g, 1.985 mmol) and tert-butyl 2,6-diazaspiro[3.4]octane-2-carboxylate (1.053 g, 4.96 mmol, PharmaBlock) in DMSO (9 mL) was added $K_3PO_4$ (2.106 g, 9.92 mmol). The mixture was purged with $N_2$ for 2 min before CuI (0.076 g, 0.397 mmol) was added followed by 2-((2,6-difluorophenyl)amino)-2-oxoacetic acid (0.160 g, 0.794 mmol, Enamine). The reaction mixture was heated at 100° C. for 16 h. The reaction mixture was cooled, quenched with cold water, and extracted with EtOAc (2×40 mL). The combined organic extracts were washed with water (20 mL), washed with brine (20 mL), dried over $Na_2SO_4$, and concentrated under reduced pressure. The resulting crude residue was purified via silica gel column chromatography eluting with 60% EtOAc in petroleum ether to afford tert-butyl 6-(4-chloro-3-fluoro-7-(oxetan-3-yl)-5,6,7,8-tetrahydro-1,7-naphthyridin-2-yl)-2,6-diazaspiro[3.4]octane-2-carboxylate (0.32 g, 35.6% yield) as a pale yellow gum. m/z (ESI): 452.9 $(M+H)^+$.

Synthesis of Amines

Amine 1: tert-butyl 8-fluoro-2,6-diazaspiro[3.4]octane-2-carboxylate

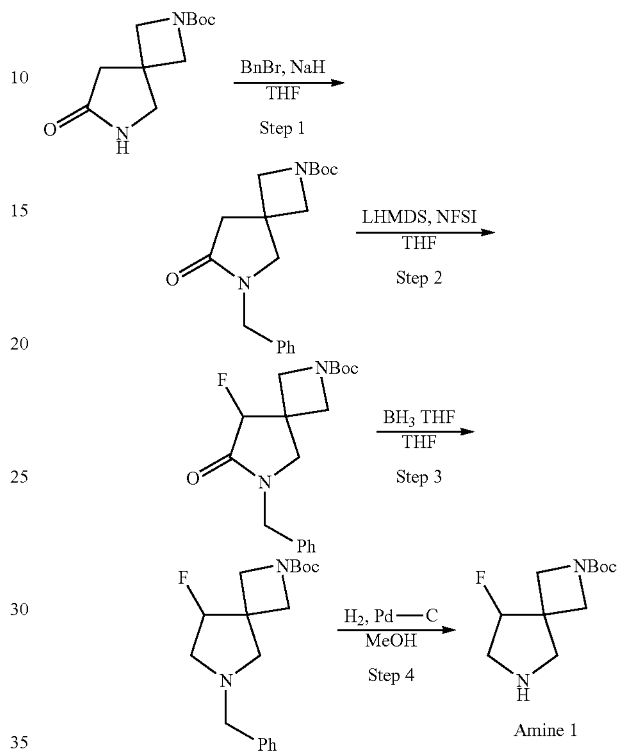

Step 1: tert-Butyl 6-benzyl-7-oxo-2,6-diazaspiro[3.4]octane-2-carboxylate

To a solution of tert-butyl 7-oxo-2,6-diazaspiro[3.4]octane-2-carboxylate (500 mg, 2.21 mmol) and benzyl bromide (397 mg, 2.32 mmol) in THF (10 mL) at 0° C. was added NaH (60% dispersion, 97 mg, 2.43 mmol). The reaction mixture was stirred at 60° C. for 18 h. Upon completion, the reaction mixture was diluted with water and extracted with EtOAc. The combined organic extracts were washed with brine, dried over $Na_2SO_4$, and concentrated under reduced pressure. The residue was stirred in $Et_2O$ (15 mL) and filtered to provide tert-butyl 6-benzyl-7-oxo-2,6-diazaspiro[3.4]octane-2-carboxylate (500 mg, 1.58 mmol, 72% yield) as a white solid. m/z (ESI): 317.0 $(M+H)^+$.

Step 2: tert-butyl 6-benzyl-8-fluoro-7-oxo-2,6-diazaspiro[3.4]octane-2-carboxylate A stirred solution of tert-butyl 6-benzyl-7-oxo-2,6-diazaspiro[3.4]octane-2-carboxylate (500 mg, 1.58 mmol) in THF (15 mL) was cooled to −15° C. and LHMDS (1 M in THF) (2.05 mL, 2.05 mmol) was added dropwise. The reaction mixture was stirred for 45 min at −15° C. After that, a solution of NFSI (997 mg, 3.16 mmol) in THF (5 mL) was added dropwise, and the mixture was stirred at the same temperature for 45 min. The reaction was quenched with aqueous saturated ammonium chloride, extracted with EtOAc (2×50 mL), and dried over $Na_2SO_4$, and concentrated under reduced pressure. The crude residue was purified by column chromatography over silica gel by using 40% of EtOAc in PE as eluent to give tert-butyl 6-benzyl-8-fluoro-7-oxo-2,6-diazaspiro[3.4]octane-2-carboxylate (330 mg, 0.987 mmol, 62% yield) as an opaque solid. m/z (ESI): 235.1 $(M-Boc+H)^+$.

Step 3: tert-butyl 6-benzyl-8-fluoro-2,6-diazaspiro[3.4]octane-2-carboxylate

To a stirred solution of tert-butyl 6-benzyl-8-fluoro-7-oxo-2,6-diazaspiro[3.4]octane-2-carboxylate (100 mg, 0.30 mmol) in THF (6 mL) was added borane THF complex (1.2 mL, 1.2 mmol) dropwise at 0° C. under a $N_2$ atmosphere. After that the reaction mixture was heated at 65° C. and stirred at the same temperature for 4 h. The reaction was quenched with aqueous saturated $NH_4C$ and extracted with EtOAc (2×20 mL). The organic extract was dried over $Na_2SO_4$, and concentrated under reduced pressure. The crude residue was purified by column chromatography over silica gel by using 28% of EtOAc in PE as eluent to give tert-butyl 6-benzyl-8-fluoro-2,6-diazaspiro[3.4]octane-2-carboxylate (25 mg, 0.078 mmol, 26% yield) as an opaque solid. m/z (ESI): 321.3 $(M+H)^+$.

Step 4: tert-butyl 8-fluoro-2,6-diazaspiro[3.4]octane-2-carboxylate

To a solution of tert-butyl 6-benzyl-8-fluoro-2,6-diazaspiro[3.4]octane-2-carboxylate (400 mg, 1.25 mmol) in MeOH (10 mL) was added Pd—C(133 mg, 1.25 mmol). The system was evacuated and backfilled with $H_2$. The reaction was stirred at rt for 2 h. The solution was filtered and concentrated in vacuo to give the crude material tert-butyl 8-fluoro-2,6-diazaspiro[3.4]octane-2-carboxylate (270 mg, 1.17 mmol, 94% yield) as an off-white oil, which was used in the next step as is. m/z (ESI): 231.0 $(M+H)^+$.

Amine 2: tert-butyl 7-(difluoromethyl)-2,6-diazaspiro[3.4]octane-2-carboxylate

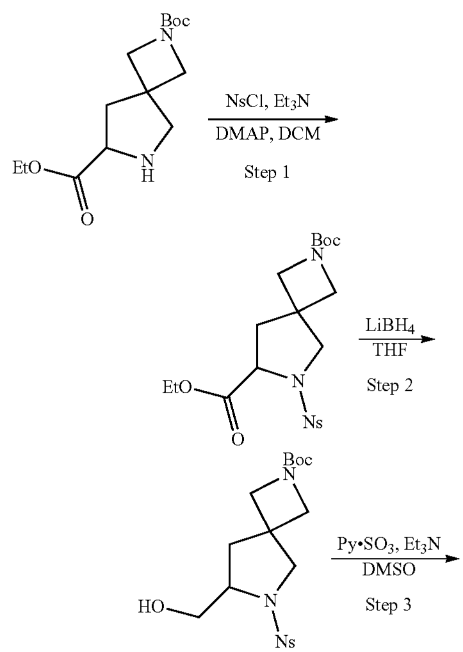

-continued

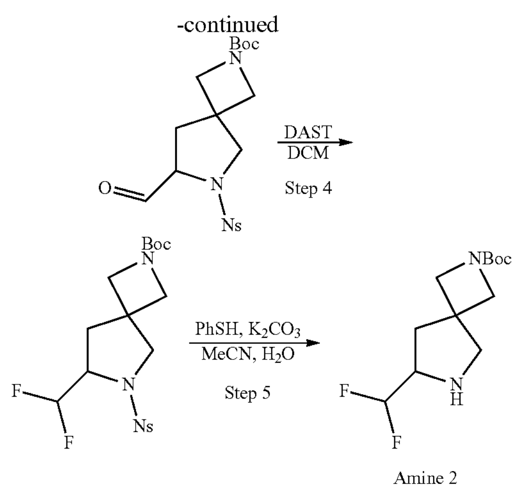

Amine 2

Step 1: 2-(tert-butyl) 7-ethyl 6-((4-nitrophenyl)sulfonyl)-2,6-diazaspiro[3.4]octane-2,7-dicarboxylate To a solution of 2-(tert-butyl) 7-ethyl 2,6-diazaspiro[3.4]octane-2,7-dicarboxylate (1.5 g, 5.28 mmol), $Et_3N$ (2.206 mL, 15.83 mmol) and DMAP (0.064 g, 0.528 mmol) in DCM (20 mL) was added NsCl (1.286 g, 5.80 mmol, Spectrochem) at 0° C. The reaction mixture was stirred at room temperature for 3 h. The reaction mixture was diluted with water and extracted with DCM. The combined organic extracts were washed with brine, dried over $Na_2SO_4$, and concentrated under reduced pressure. The residue was purified on a Redi-Sep pre-packed silica gel column eluting with a gradient of 40-50% EtOAc in PE to provide 2-(tert-butyl) 7-ethyl 6-((4-nitrophenyl)sulfonyl)-2,6-diazaspiro[3.4]octane-2,7-dicarboxylate (2.1 g, 85% yield) as a light yellow liquid. $^1H$ NMR (400 MHz, $CDCl_3$) δ ppm 8.40 (d, J=8.9 Hz, 1H), 8.12 (d, J=8.9 Hz, 1H), 4.54 (dd, J=8.8, 4.3 Hz, 1H), 4.02-4.30 (m, 2H), 3.70-3.89 (m, 4H), 3.56-3.67 (m, 2H), 2.43 (dd, J=13.2, 8.9 Hz, 1H), 2.30 (dd, J=13.2, 4.3 Hz, 1H), 1.43 (s, 9H), 1.29 (t, J=7.1 Hz, 3H). m/z (ESI): 369.9 $(M-Boc+H)^+$.

Step 2: tert-butyl 7-(hydroxymethyl)-6-((4-nitrophenyl)sulfonyl)-2,6-diazaspiro[3.4]octane-2-carboxylate To a solution of 2-(tert-butyl) 7-ethyl 6-((4-nitrophenyl)sulfonyl)-2,6-diazaspiro[3.4]octane-2,7-dicarboxylate (6.0 g, 12.78 mmol) in THF (5 mL) and MeOH (1 mL) was added $LiBH_4$ (9.58 mL, 19.17 mmol, Symax) at −20° C. and stirred for 1 h. Then the reaction mixture was diluted with aqueous saturated $NH_4Cl$ at −78° C. and extracted with EtOAc. The combined organic extracts were washed with brine, dried over $Na_2SO_4$, and concentrated in vacuo. The residue was purified on a Redi-Sep pre-packed silica gel column eluting with a gradient of 10-20% MeOH in DCM to provide tert-butyl 7-(hydroxymethyl)-6-((4-nitrophenyl)sulfonyl)-2,6-diazaspiro[3.4]octane-2-carboxylate (5.2 g, 95% yield) as an off-white solid. $^1H$ NMR (400 MHz, DMSO-$d_6$) δ ppm 8.44 (d, J=8.6 Hz, 2H), 8.12 (d, J=8.3 Hz, 2H), 4.96 (t, J=5.6 Hz, 1H), 3.63-3.89 (m, 4H), 3.45-3.62 (m, 2H), 3.37 (d, J=13.6 Hz, 3H), 2.10 (dd, J=13.0, 4.6 Hz, 1H), 1.85 (dd, J=13.0, 8.4 Hz, 1H), 1.33 (s, 9H). m/z (ESI): 327.9 $(M-Boc+H)^+$.

Step 3: tert-butyl 7-formyl-6-((4-nitrophenyl)sulfonyl)-2,6-diazaspiro[3.4]octane-2-carboxylate To a solution of tert-butyl 7-(hydroxymethyl)-6-((4-nitrophenyl)sulfonyl)-2,6-diazaspiro[3.4]octane-2-carboxylate (2.4 g, 5.61 mmol) and $Et_3N$ (3.91 mL, 28.1 mmol) in DMSO (50 mL) was added pyridinesulfur trioxide (1.79 g, 11.23 mmol, Chempure) at 0° C. The reaction mixture was stirred at rt for 2 h before it was diluted with ice-cold water and extracted with EtOAc. The combined organic extracts were washed with brine, dried over $Na_2SO_4$, and concentrated under reduced pressure to provide tert-butyl 7-formyl-6-((4-nitrophenyl)sulfonyl)-2,6-diazaspiro[3.4]octane-2-carboxylate (2.3 g), which was used in next step without purification.

Step 4: tert-butyl 7-(difluoromethyl)-6-((4-nitrophenyl)sulfonyl)-2,6-diazaspiro[3.4]octane-2-carboxylate To a solution of tert-butyl 7-formyl-6-((4-nitrophenyl)sulfonyl)-2,6-diazaspiro[3.4]octane-2-carboxylate (1.4 g, 3.29 mmol) in DCM (28 mL) was added DAST (1.74 mL, 13.16 mmol, Spectrochem) at −78° C. Then the reaction mixture was stirred at rt for 16 h before it was diluted with 10% aqueous solution of $NaHCO_3$ and extracted with EtOAc. The combined organic extracts were washed with brine, dried over $Na_2SO_4$, and concentrated under reduced pressure. The residue was purified on a Redi-Sep pre-packed silica gel column, eluting with a gradient of 15-30% EtOAc in petroleum ether to provide tert-butyl 7-(difluoromethyl)-6-((4-nitrophenyl)sulfonyl)-2,6-diazaspiro[3.4]octane-2-carboxylate (1.8 g, quantitative yield) as an off-white solid. $^1H$ NMR (400 MHz, DMSO-$d_6$) δ ppm 8.45 (d, J=9.0 Hz, 2H), 8.20 (d, J=8.8 Hz, 2H), 6.18 (t, J=71.7 Hz, 1H), 4.10-4.29 (br m, 1H), 3.73 (br s, 2H), 3.51 (br s, 2H), 1.95-2.27 (m, 2H), 1.32 (s, 9H). m/z (ESI): 446.9 $(M+H)^+$.

Step 5: tert-butyl 7-(difluoromethyl)-2,6-diazaspiro[3.4]octane-2-carboxylate

To a solution of tert-butyl 7-(difluoromethyl)-6-((4-nitrophenyl)sulfonyl)-2,6-diazaspiro[3.4]octane-2-carboxylate (2.4 g, 5.36 mmol) and $K_2CO_3$ (3.71 g, 26.8 mmol, Spectrochem) in water (12 mL) and MeCN (36 mL) was added thiophenol (1.1 mL, 10.73 mmol, Spectrochem) and the resulting mixture was stirred at 55° C. for 16 h. The reaction mixture was cooled to rt, diluted with ice-cold water and extracted with EtOAc. The combined organic extracts were washed with brine, dried over anhydrous $Na_2SO_4$, filtered, and concentrated under reduced pressure. The residue was purified on a Redi-Sep pre-packed silica gel column eluting with a gradient of 40-50% EtOAc in petroleum ether to give tert-butyl 7-(difluoromethyl)-2,6-diazaspiro[3.4]octane-2-carboxylate (0.90 g, 64% yield) as a light yellow solid. $^1H$ NMR (400 MHz, $CDCl_3$) δ ppm 5.57 (td, J=56.5, 4.7 Hz, 1H), 3.76-3.91 (m, 4H), 3.46-3.55 (m, 3H), 3.13 (s, 1H), 2.15 (dd, J=13.6, 8.5 Hz, 1H), 1.99 (dd, J=13.6, 6.4 Hz, 1H), 1.43 (s, 8H). $^{19}F$ NMR (377 MHz, $CDCl_3$) δ ppm −122.63 (d, J=282.7 Hz), −126.09 (d, J=313.3 Hz). m/z (ESI): 263.0 $(M+H)^+$.

Amine 3: tert-butyl (S)-5-methyl-2,6-diazaspiro[3.4]octane-2-carboxylate

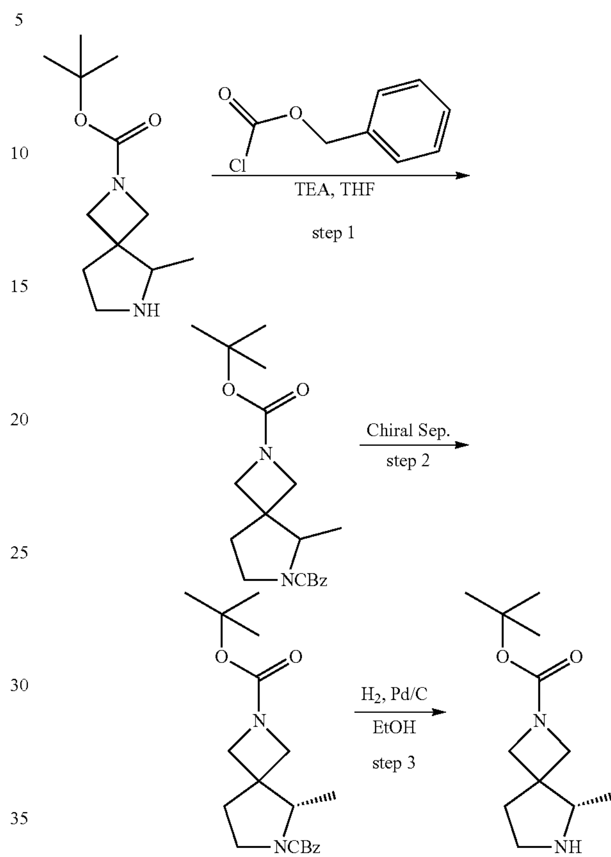

Step 1: 6-benzyl 2-(tert-butyl) 5-methyl-2,6-diazaspiro[3.4]octane-2,6-dicarboxylate Benzyl chloroformate (4.01 mL, 28.2 mmol, TCI America) and TEA (6.34 mL, 45.1 mmol, Sigma-Aldrich) were added to a solution of tert-butyl 5-methyl-2,6-diazaspiro-[3.4]octane-2-carboxylate (5.103 g, 22.55 mmol, Enamine) in THF (96 mL) under argon at 0° C. The mixture was stirred overnight at room temperature, then the resulting suspension was filtered and the filter cake was washed with THF. The filtrate was concentrated and the resulting oil was purified by chromatography through a Redi-Sep pre-packed silica gel column (220 g), eluting with 0-50% EtOAc in heptanes to afford 6-benzyl 2-(tert-butyl) 5-methyl-2,6-diazaspiro[3.4]octane-2,6-dicarboxylate (6.67 g, 82% yield) as colorless oil.

Step 2: 6-benzyl 2-(tert-butyl) (S)-5-methyl-2,6-diazaspiro[3.4]octane-2,6-dicarboxylate The sample was purified by SFC using a (S,S) Whelk-01column (500×21 mm, 5 μm) with a mobile phase of 70% liquid $CO_2$ and 30% MeOH using a flowrate of 80 mL/min to generate 2.62 grams of Peak 1 with ee of >99% and 2.72 grams of peak 2 with ee of >99%. Absolute stereochemistry of peak 1 assigned as the R isomer and peak 2 as the S isomer.

Step 3: tert-butyl (S)-5-methyl-2,6-diazaspiro[3.4]octane-2-carboxylate

A pressure tube was charged with 6-benzyl 2-(tert-butyl) (R)-5-methyl-2,6-diazaspiro[3.4]octane-2,6-dicarboxylate (2.31 g, 6.41 mmol) and Pd/C (10%) (0.341 g, 0.320 mmol, Sigma-Aldrich) and then placed under nitrogen atmosphere using 3 evacuation/backfill cycles. EtOH (40 mL) was added against a positive pressure of nitrogen and then the pressure tube was placed under 40 psi hydrogen. The mixture was stirred for 1 h, at which time the regulator read 25 psi. The tube was charged back to 40 psi and left to stir for 1 h. The mixture was placed under nitrogen atmosphere and then the suspension was filtered through celite while keeping the celite wet. The filtrate was concentrated in vacuo to give tert-butyl (S)-5-methyl-2,6-diazaspiro[3.4]octane-2-carboxylate (1.31 g, 90% yield) as a colorless oil. $^1$H NMR (400 MHz, $CDCl_3$) δ ppm 3.97 (d, J=8.8 Hz, 1H), 3.83 (d, J=8.6 Hz, 1H), 3.73 (d, J=8.4 Hz, 1H), 3.61 (d, J=8.8 Hz, 1H), 2.98-3.07 (m, 2H), 2.85-2.96 (m, 1H), 1.99-2.24 (m, 3H), 1.47 (s, 9H), 1.20 (d, J=6.5 Hz, 3H).

Amine 4: tert-butyl 5-(hydroxymethyl)-2,6-diazaspiro[3.4]octane-2-carboxylate

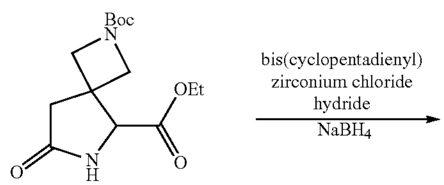

-continued

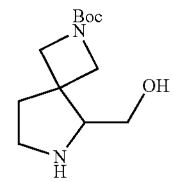

To a RBF was added 2-(tert-butyl) 5-ethyl 7-oxo-2,6-diazaspiro[3.4]octane-2,5-dicarboxylate (500 mg, 1.676 mmol, Enamine) and bis(cyclopentadienyl)zirconium chloride hydride (691 mg, 2.68 mmol, Sigma-Aldrich). The flask was purged with $N_2$ for 5 min and THF (32 mL) was added. The reaction was allowed to stir at room temperature until the mixture became clear (20 min). Then, $NaBH_4$ (190 mg, 5.03 mmol, Sigma-Aldrich) was added in 1 portion at 0° C. The reaction was stirred in the cooling bath as it expired. After 24 h, LC-MS showed a 1:1 mixture of ester and alcohol. The reaction was quenched with 0.5 mL of $H_2O$, filtered, and concentrated. The residue was re-dissolved in EtOH (15 mL), cooled down to 0° C., and $NaBH_4$ (190 mg, 5.03 mmol) was added. After stirring overnight, the reaction was quenched with 0.3 mL of water, concentrated, and chromatographed with 0-100% EtOAc in heptanes to provide tert-butyl 5-(hydroxymethyl)-2,6-diazaspiro[3.4]octane-2-carboxylate (345 mg, 85%). m/z (ESI): 243.3 $(M+H)^+$.

Analytical Data

TABLE 20

Analytical Data for Examples 1-2 to 2-9

| Ex. # | LRMS: (ESI, +ve ion) m/z | NMR |
|---|---|---|
| 1-2 | 448.0 | $^1$H NMR (400 MHz, DMSO-$d_6$) δ ppm 13.19 (s, 1H), 7.86 (d, J = 8.3 Hz, 1H), 7.62 (d, J = 8.6 Hz, 1H), 7.53-7.49 (m, 1H), 7.43 (d, J = 8.6 Hz, 1H), 7.37-7.25 (m, 2 H), 7.18-7.08 (m, 1H), 6.91 (d, J = 8.4 Hz, 1H), 6.33 (dd, J = 17.0, 10.2 Hz, 1H), 6.12 (dd, J = 17.0, 2.3 Hz, 1H), 5.68 (dd, J = 10.3, 2.3 Hz, 1H), 4.30 (d, J = 8.6 Hz, 1H), 4.22 (dd, J = 8.5, 3.8 Hz, 1H), 4.01 (d, J = 10.1 Hz, 1H), 3.94 (dd, J = 10.1, 4.1 Hz, 1H), 3.77 (t, J = 5.9 Hz, 2 H), 3.66 (m, 2 H), 2.26 (m, 2 H), 2.03 (d, J = 5.1 Hz, 3 H). |
| 1-3 | 439.0 | $^1$H NMR (400 MHz, DMSO-$d_6$) δ ppm 13.14 (s, 1 H), 7.59 (s, 1 H), 7.52 (d, J = 8.4 Hz, 1 H), 7.33 (d, J = 8.4 Hz, 1 H), 6.34-6.28 (m, 1 H), 6.11 (dd, J = 16.8, 2 Hz, 1 H), 5.68 (dd, J = 10.4, 2.4 Hz, 1 H), 4.27 (d, J = 8.8 Hz, 1 H), 4.17 (d, J = 8.8 Hz, 1 H), 3.99-3.84 (m, 4 H), 3.76 (t, J = 6.8 Hz, 2 H), 2.91 (t, J = 7.2 Hz, 2 H), 2.30 (t, J = 1.2 Hz, 2 H), 2.19-2.12 (m, 5 H), 2.01-1.93 (m, 2 H). |
| 1-4 | 467.1 | $^1$H NMR (400 MHz, DMSO-$d_6$) δ ppm 13.26 (s, 1 H), 7.67 (d, J = 8.4 Hz, 1 H), 7.57-7.52 (m, 2 H), 7.45 (d, J = 8.4 Hz, 1H), 7.12-7.07 (m, 1H), 6.71 (d, J = 8.4 Hz, 1H), 6.36-6.29 (m, 1H), 6.12 (dd, J = 2.4, 17.2 Hz, 1H), 5.68 (dd, J = 2.4, 10.4 Hz, 1H), 4.34 (d, J = 8.8 Hz, 1H), 4.22-4.22 (m, 1H), 4.05-4.02 (m, 3 H), 3.95-3.90 (m, 3 H), 2.27-2.24 (m, 2 H), 2.09-2.07 (m, 3 H). |
| 1-5 | 438.1 | $^1$H NMR (400 MHz, Methanol-$d_4$) δ ppm 8.29 (s, 1 H), 8.02 (d, J = 1.2 Hz, 1 H), 7.64-7.66 (m, 2 H), 7.47-7.52 (m, 2 H), 6.29-6.38 (m, 2 H), 5.76 (dd, J = 10.0, 2.4 Hz, 1 H), 4.34-4.40 (m, 2 H), 4.11-4.16 (m, 2 H), 3.60-3.80 (m, 4 H), 2.35-2.39 (m, 2 H), 2.24 (s, 3 H), |
| 1-6 | 463.0 | $^1$H NMR (400 MHz, DMSO-$d_6$) δ ppm 13.22 (s, 1 H), 7.64 (d, J = 8.4 Hz, 1 H), 7.57 (d, J = 6.4 Hz, 1 H), 7.49 (s, 1 H), 7.43 (d, J = 8.4 Hz, 1 H), 7.05-7.02 (m, 1H), 6.75 (d, J = 8.4 Hz, 1 H), 6.36-6.29 (m, 1H), 6.16 (dd, J = 17.2, 2.4 Hz, 1H), 5.67 (dd, J = 10.4, 2.4 Hz, 1H), 4.33 (d, J = 8.4 Hz, 1 H), 4.23-4.20 (m, 1H), 4.07-4.00 (m, 3 H), 3.95-3.88 (m, 3 H), 2.61 (s, 3 H), 2.28-2.23 (m, 2 H), 2.06 (d, J = 2.8 Hz, 3 H). |
| 1-7 | 438.9 | $^1$H NMR (400 MHz, DMSO-$d_6$) δ ppm 7.99 (dd, J = 8.2, 1.5 Hz, 1 H), 7.87 (d, J = 8.0 Hz, 1 H), 7.54 (dd, J = 8.2, 7.0 Hz, 1 H), 7.43 (dd, J = 8.2, 7.0 Hz, 1 H), 7.30 (d, J = 7.0 Hz, 1 H), 7.22 (dd, J = 7.0, 1.4 Hz, 1 H), 6.29 (dd, J = 17.0, 10.3 Hz, 1 H), 6.09 (dd, J = 16.9, 2.3 Hz, 1 H), 5.66 (dd, J = 10.3, 2.3 Hz, 1 H), 4.13-4.19 (m, 2 |

TABLE 20-continued

| Ex. # | LRMS: (ESI, +ve ion) m/z | NMR |
|---|---|---|
| | | Analytical Data for Examples 1-2 to 2-9 |
| | | H), 3.87-3.91 (m, 2 H), 3.63-3.68 (m, 2 H), 2.71 (t, J = 6.5 Hz, 2 H), 2.01-2.24 (m, 7 H), 1.94-1.99 (m, 2 H), 1.73-1.78 (m, 2 H), 1.58-1.62 (m, 2 H). |
| 1-8 | 481.2 | $^1$H NMR (400 MHz, DMSO-$d_6$) δ ppm 13.15 (s, 1H), 7.62-7.44 (m, 2 H), 7.35 (d, J = 8.7 Hz, 1 H), 6.34-6.27 (m, 1 H), 6.11 (dd, J = 17.0, 2.3 Hz, 1 H), 5.67 (dd, J = 10.3, 2.3 Hz, 1 H), 4.27 (d, J = 8.6 Hz, 1 H), 4.16 (d, J = 8.5 Hz, 1 H), 3.97 (d, J = 10.1 Hz, 1 H), 3.92-3.76 (m, 3 H), 3.73 (t, J = 6.8 Hz, 2 H), 2.58 (s, 2 H), 2.22-2.13 (m, 2 H), 2.03-1.89 (m, 3 H), 2.02-1.90 (m, 2 H), 1.37 (t, J = 6.7 Hz, 2 H), 0.94 (s, 6 H). |
| 1-9 | 458.9 | $^1$H NMR (400 MHz, DMSO-$d_6$) δ ppm 8.11 (dd, J = 8.4, 1.3 Hz, 1 H), 8.06 (dd, J = 8.3, 1.3 Hz, 1 H), 7.56-7.70 (m, 2 H), 7.45-7.56 (m, 1 H), 7.37 (dd, J = 7.1, 1.3 Hz, 1 H), 6.30 (dd, J = 17.0, 10.3 Hz, 1 H), 6.09 (dd, J = 17.0, 2.3 Hz, 1 H), 5.66 (dd, J = 10.3, 2.3 Hz, 1 H), 4.20 (t, J = 9.2 Hz, 1 H), 4.13 (d, J = 8.5 Hz, 1 H), 3.88-3.91 (m, 2 H), 3.64 (d, J = 10.2 Hz, 2 H), 3.34-3.36 (m, 2 H), 2.69 (d, J = 6.2 Hz, 2 H), 2.14 (td, J = 6.8, 2.8 Hz, 2 H), 2.03 (t, J = 6.3 Hz, 2 H), 1.65-1.80 (m, 2 H), 1.53-1.63 (m, 2 H). |
| 1-10 | 481.2 | $^1$H NMR (400 MHz, DMSO-$d_6$) δ ppm 13.15 (s, 1 H), 7.62-7.44 (m, 2 H), 7.35 (d, J = 8.7 Hz, 1 H), 6.34-6.27 (m, 1 H), 6.11 (dd, J = 17.0, 2.3 Hz, 1 H), 5.67 (dd, J = 10.3, 2.3 Hz, 1 H), 4.27 (d, J = 8.6 Hz, 1 H), 4.16 (d, J = 8.5 Hz, 1 H), 3.97 (d, J = 10.1 Hz, 1 H), 3.92-3.76 (m, 3 H), 3.73 (t, J = 6.8 Hz, 2 H), 2.58 (s, 2 H), 2.22-2.13 (m, 2 H), 2.03-1.89 (m, 3 H), 2.02-1.90 (m, 2 H), 1.37 (t, J = 6.7 Hz, 2 H), 0.94 (s, 6 H). |
| 1-11 | 443.1 | $^1$H NMR (400 MHz, DMSO-$d_6$) δ ppm 1 H 13.07 (d, J = 5.8 Hz, 1 H), 7.51 (dd, J = 19.4, 9.4 Hz, 2 H), 7.28 (dd, J = 8.6, 1.3 Hz, 1 H), 6.30 (dd, J = 17.0, 10.2 Hz, 1 H), 6.09 (dd, J = 17.0, 2.2 Hz, 1 H), 5.66 (dd, J = 10.3, 2.2 Hz, 1 H), 4.25-4.09 (m, 2 H), 3.95-3.82 (m, 2 H), 3.70-3.42 (m, 1 H), 2.81 (d, J = 15.2 Hz, 1 H), 2.41-2.31 (m, 1 H), 2.30-2.08 (m, 6 H), 2.08-1.96 (m, 1 H), 1.87 (s, 1 H), 1.66 (s, 1 H), 1.27-1.14 (m, 1 H), 1.01 (dd, J = 6.6, 2.1 Hz, 3 H). |
| 1-12 | 438.9 | $^1$H NMR (400 MHz, DMSO-$d_6$) δ ppm 7.81-8.06 (m, 2 H), 7.33-7.58 (m, 3 H), 7.18 (d, J = 8.2 Hz, 1 H), 6.29 (dd, J = 16.9, 10.4 Hz, 1 H), 6.09 (dd, J = 16.8, 2.3 Hz, 1 H), 5.65 (dd, J = 10.4, 2.3 Hz, 1 H), 4.09-4.30 (m, 2 H), 3.87 (t, J = 12.0 Hz, 2 H), 3.60-3.69 (m, 4 H), 2.75 (t, J = 6.6 Hz, 2 H), 2.16-2.19 (m, 5 H), 1.93-2.07 (m, 1 H), 1.78-1.90 (m, 1 H), 1.70-1.75 (m, 2 H), 1.56 (d, J = 4.9 Hz, 2 H). |
| 1-13 | 484.9 | $^1$H NMR (400 MHz, DMSO-$d_6$) δ ppm 13.2 (s, 1 H), 7.70-7.66 (m, 1 H), 7.60-7.47 (m, 1 H), 7.45-7.43 (m, 1 H), 7.17-7.12 (m, 1 H), 6.75 (t, J = 8.8 Hz, 1 H), 6.41-6.24 (m, 1 H), 6.14 (dd, J = 16.8, 2.4 Hz, 1 H), 5.61 (t, J = 2 Hz, 1 H), 5.47 (d, J = 7.6 Hz, 1 H), 4.47-4.33 (m, 2 H), 4.27-3.91 (m, 6 H), 3.30 (s, 1 H), 2.10 (d, J = 50.4 Hz, 3 H). $^{19}$F NMR (376 MHz, DMSO-$d_6$) δ ppm −126.90-−126.97 (m, 1 F), −184.53(dd, J = 232.744, 55.2 Hz, 1 F). |
| 1-14 | 465.1 | $^1$H NMR (400 MHz, DMSO-$d_6$) δ ppm 13.25 (s, 1 H), 7.67-7.65 (d, J = 8.4 Hz, 1 H), 7.57-7.52 (m, 2 H), 7.44 (d, J = 8.4 Hz, 1 H), 7.12-7.07 (m, 1 H), 6.72 (d, J = 8.4 Hz, 1 H), 4.447 (s, 1 H), 4.30 (d, J = 8.8 Hz, 1 H), 4.15 (dd, J = 8.8 Hz, 2.8 Hz, 1 H), 4.08-4.00 (m, 3 H), 3.95-3.89 (m, 3 H), 2.27-2.24 (m, 2 H), 2.09-2.07 (m, 3 H). $^{19}$F NMR (376 MHz, DMSO-$d_6$) δ ppm −127.104 (s, 1 F). |
| 1-15 | 443.1 | $^1$H NMR (400 MHz, $CDCl_3$) δ ppm 7.65 (d, J = 4.0 Hz, 1 H), 7.40 (d, J = 8.4 Hz, 1 H), 7.29 (d, J = 8.8 Hz, 1 H), 6.35 (d, J = 16.8 Hz, 1 H), 6.22-6.15 (m, 1 H), 5.68 (d, J = 11.6 Hz, 1 H), 4.23-4.20 (m, 1 H), 4.13-4.01(m, 3 H), 3.83-3.65 (m, 4 H), 2.88-2.85 (m, 1 H), 2.24 (d, J = 4.0 Hz, 3 H), 2.19 (t, J = 7.2 Hz, 2 H), 2.16-2.07 (m, 2 H), 2.03-1.96 (m, 2 H), 1.74-1.67 (m, 2 H), 1.42 (t, J = 6.8 Hz, 3 H). |
| 1-16 | 428.9 | $^1$H NMR (400 MHz, DMSO-$d_6$) δ ppm 8.02 (s, 1 H), 7.68 (d, J = 8.2 Hz, 1 H), 7.05 (d, J = 8.3 Hz, 1 H), 6.30 (dd, J = 17.0, 10.3 Hz, 1 H), 6.10 (dd, J = 17.0, 2.3 Hz, 1 H), 5.67 (dd, J = 10.2, 2.3 Hz, 1 H), 4.17-4.21 (m, 2 H), 3.85-3.99 (m, 2 H), 3.61-3.75 (m, 2 H), 3.49-3.60 (m, 2 H), 2.70-2.76 (m, 2 H), 2.17 (s, 3 H), 1.98-2.20 (m, 4 H), 1.72-1.80 (m, 2 H), 1.52-1.65 (m, 2 H). |
| 1-17 | 429.1 | $^1$H NMR (400 MHz, DMSO-$d_6$) δ ppm 13.06 (s, 1 H), 7.54 (s, 1 H), 7.48 (d, J = 8.7 Hz, 1 H), 7.28 (d, J = 8.7 Hz, 1 H), 6.21-6.35 (m, 1 H), 6.09 (dd, J = 17.0, 2.2 Hz, 1 H), 5.57-5.71 (m, 1 H), 4.08-4.30 (m, 2 H), 3.78-4.00 (m, 2 H), 3.40-3.76 (m, 4 H), 3.33 (s, 5 H), 2.73 (t, J = 6.5 Hz, 2 H), 2.05 (q, J = 5.8 Hz, 2 H), 1.71-1.80 (m, 2 H), 1.58 (dq, J = 11.5, 5.6 Hz, 2 H). |
| 1-18 | 424.8 | $^1$H NMR (400 MHz, DMSO-$d_6$) δ ppm 9.86 (s, 1 H), 7.31 (d, J = 8.7 Hz, 1 H), 6.83 (dd, J = 8.7, 2.9 Hz, 1 H), 6.63 (d, J = 2.9 Hz, 1 H), 6.31 (dd, J = 17.0, 10.3 Hz, 1 H), 6.10 (dd, J = 17.0, 2.3 Hz, 1 H), 5.67 (dd, J = 10.3, 2.3 Hz, 1 H), 4.14-4.22 (m, 2 H), 3.86-3.92 (m, 2 H), 3.63 (d, J = 11.2 Hz, 2 H), 3.48-3.51 (m, 2 H), 2.67-2.69 (m, 2 H), 2.10-2.20 (m, 4 H), 1.64-1.74 (m, 4 H). |
| 1-19 | 518.8 | $^1$H NMR (400 MHz, DMSO-$d_6$) δ ppm 9.94 (s, 1 H), 7.78 (d, J = 8.3 Hz, 1 H), 7.36 7.47 (m, 1 H), 7.15-7.30 (m, 3 H), 7.00 (s, 1 H), 6.37-6.72 (m, 1 H), 6.30 (m, 1 H), 6.08 (d, J = 16.9 Hz, 1 H), 5.65 (d, J = 10.3 Hz, 1 H), 4.31-4.54 (br m, 1 H), 4.20 (br s, 2 H), 3.66-3.99 (m, 4 H), 2.58 (m, 2 H), 2.24-2.45 (m, 2 H), 1.96-2.23 (m, 2 H), 1.31-1.50 (m, 2 H), 0.97 (s, 6 H). $^{19}$F NMR (377 MHz, DMSO-$d_6$) δ ppm −126.33-−112.72 (m), −133.70 (d, J = 281.2 Hz). |
| 1-20 | 429.1 | $^1$H NMR (400 MHz, DMSO-$d_6$) δ ppm 13.01 (s, 1 H), 8.06 (s, 1 H), 7.70 (s, 1 H), 7.55 (d, J = 8.8 Hz, 1 H), 7.32 (d, J = 8.4 Hz, 1 H), 6.35-6.28 (m, 1 H), 6.10 (d, J = 14.8 Hz, 1 H), 5.67 (d, J = 8.4 Hz, 1 H), 4.27 (d, J = 8.8 Hz, 1 H), 4.18 (d, J = 8.4 |

TABLE 20-continued

| Ex. # | LRMS: (ESI, +ve ion) m/z | NMR |
|---|---|---|
| | | Analytical Data for Examples 1-2 to 2-9 |
| | | Hz, 1 H), 3.97 (d, J = 10.4 Hz, 1 H), 3.90 (d, J = 10.4 Hz, 1 H), 3.83-3.77 (m, 2 H), 3.74 (s, 3 H), 3.72-3.62 (m, 2 H), 2.32 (s, 3 H), 2.19-2.12 (m, 2 H). |
| 1-21 | 440.0 | $^1$H NMR (400 MHz, DMSO-$d_6$) δ ppm 9.83 (br s, 1 H), 7.76 (d, J = 8.3 Hz, 1 H), 7.45 (dd, J = 8.3, 7.0 Hz, 1 H), 7.32 (d, J = 9.1 Hz, 1 H), 7.20 (d, J = 2.5 Hz, 1 H), 7.12 (dd, J = 7.0, 1.2 Hz, 1 H), 7.05 (dd, J = 9.1, 2.5 Hz, 1 H), 6.30 (dd, J = 17.0, 10.3 Hz, 1 H), 6.10 (dd, J = 17.0, 2.3 Hz, 1 H), 5.66 (dd, J = 10.3, 2.3 Hz, 1 H), 4.21 (d, J = 8.8 Hz, 1 H), 4.14 (d, J = 8.6 Hz, 1 H), 3.89-3.92 (m, 2 H), 3.45-3.68 (m, 4 H), 2.74 (d, J = 6.8 Hz, 2 H), 2.01-2.23 (m, 4 H), 1.76-1.79 (m, 2 H), 1.57 (d, J = 7.0 Hz, 2 H). |
| 1-22 | 451.8 | $^1$H NMR (400 MHz, DMSO-$d_6$) δ ppm 9.94 (s, 1 H), 8.30 (d, J = 2.0 Hz, 1 H), 7.76-7.84 (m, 2 H), 7.29-7.39 (m, 3 H), 7.14-7.18 (m, 2 H), 6.30 (m, 1 H), 6.12 (m, 1 H), 5.67 (m, 1 H), 4.19-4.24 (m, 2 H), 3.70-3.91 (m, 6 H), 2.45 (s, 3 H), 2.23 (s, 2 H). |
| 1-23 | 446.9 | $^1$H NMR (400 MHz, DMSO-$d_6$) δ ppm 7.67-7.76 (m, 1 H), 7.60 (s, 2 H), 7.04-7.12 (m, 2 H), 6.31 (dd, J = 17.0, 10.3 Hz, 1 H), 6.10 (dd, J = 17.0, 2.3 Hz, 1 H), 5.65 (dd, J = 10.3, 2.3 Hz, 1 H), 4.21 (d, J = 8.6 Hz, 1 H), 4.12 (d, J = 8.6 Hz, 1 H), 3.91 (d, J = 10.1 Hz, 1 H), 3.86 (d, J = 10.1 Hz, 1 H), 3.60-3.64 (m, 2 H), 3.41-3.44 (m, 2 H), 2.68 (d, J = 9.2 Hz, 2 H), 2.01-2.18 (m, 4 H), 1.50-1.80 (m, 4 H). |
| 1-24 | 444.8 | 1H NMR (400 MHz, DMSO-$d_6$,) δ ppm 7.73 (dd, J = 8.0, 1.5 Hz, 1 H), 7.47 (t, J = 7.8 Hz, 1 H), 7.31 (dd, J = 7.8, 1.5 Hz, 1 H), 6.30 (dd, J = 17.0, 10.3 Hz, 1 H), 6.10 (dd, J = 17.0, 2.4 Hz, 1 H), 5.66 (dd, J = 10.3, 2.4 Hz, 1 H), 4.21 (d, J = 7.8 Hz, 1 H), 4.14 (d, J = 7.8 Hz, 1 H), 3.82-3.96 (m, 2 H), 3.56-3.73 (m, 2 H), 3.48-3.52 (m, 2 H), 2.65-2.75 (m, 2 H), 2.05-2.25 (m, 4 H), 1.71-1.85 (m, 2 H), 1.57-1.68 (m, 2 H). |
| 1-25 | 443.0 | $^1$H NMR (400 MHz, DMSO-$d_6$) δ ppm 8.02 (s, 1 H), 7.69 (d, J = 8.3 Hz, 1 H), 7.08 (d, J = 8.2 Hz, 1 H), 6.30 (dd, J = 17.0, 10.3 Hz, 1 H), 6.09 (dd, J = 17.0, 2.3 Hz, 1 H), 5.66 (dd, J = 10.3, 2.3 Hz, 1 H), 4.21 (d, J = 8.7 Hz, 1 H), 4.14 (d, J = 8.5 Hz, 1 H), 3.81-3.98 (m, 2 H), 3.48-3.77 (m, 4 H), 3.45 (s, 3 H), 2.74 (t, J = 6.5 Hz, 2 H), 2.13-2.21 (m, 2 H), 2.13 (s, 3 H), 1.93-2.10 (m, 2 H), 1.72-1.82 (m, 2 H), 1.56-1.68 (m, 2 H). |
| 1-26 | 402.9 | $^1$H NMR (400 MHz, DMSO-$d_6$) δ (ppm) 7.05-7.26 (m, 2 H), 6.92 (d, J = 7.4 Hz, 1 H), 6.31 (dd, J = 17.0, 10.3 Hz, 1 H), 6.10 (dd, J = 17.0, 2.3 Hz, 1 H), 5.66 (dd, J = 10.3, 2.3 Hz, 1 H), 4.05-4.33 (m, 2 H), 3.88-3.92 (m, 2 H), 3.38-3.73 (m, 4 H), 2.57-2.78 (m, 3 H), 2.28 (s, 3 H), 2.01-2.22 (m, 4 H), 1.95 (s, 2 H), 1.67-1.83 (m, 2 H), 1.47-1.68 (m, 2 H). |
| 1-27 | 422.9 | $^1$H NMR(400 MHz, DMSO-$d_6$) δ (ppm) 7.42 (dd, J = 7.6, 1.7, 1 H), 7.32 (t, J = 7.5 Hz, 1 H), 7.12 (dd, J = 7.5, 1.7 Hz, 1 H), 6.31 (dd, J = 17.0, 10.2 Hz, 1 H), 6.10 (dd, J = 17.0, 2.3 Hz, 1 H), 5.66 (dd, J = 10.2, 2.4 Hz, 1 H), 4.08-4.28 (m, 2 H), 3.89-3.94 (m, 2 H), 3.60-3.67 (m, 2 H), 3.44-3.55 (m, 2 H), 2.60-2.76 (m, 2 H), 2.39 (s, 3 H), 2.10-2.23 (m, 4 H), 1.71-1.77 (m, 2 H), 1.60-1.67 (m, 2 H). |
| 1-28 | 455.9 | $^1$H NMR(400 MHz, DMSO-$d_6$) δ ppm 7.93 (dd, J = 8.3, 1.5 Hz, 1 H), 7.83 (d, J = 8.1 Hz, 1 H), 7.48 (dd, J = 8.1, 7.0 Hz, 1 H), 7.39 (dd, J = 8.2, 7.0 Hz, 1 H), 7.22-7.30 (m, 2 H), 6.30 (dd, J = 17.0, 10.3 Hz, 1 H), 6.09 (dd, J = 17.0, 2.3 Hz, 1 H), 5.65 (dd, J = 10.3, 2.3 Hz, 1 H), 4.09-4.22 (m, 2 H), 3.94-3.98 (m, 2 H), 3.86-3.89 (m, 2 H), 3.57-3.59 (m, 2 H), 3.42-3.48 (m, 4 H), 3.13 (s, 3 H), 2.29 (s, 3 H), 2.10-2.14 (m, 2 H), |
| 1-29 | 414.0 | $^1$H NMR (400 MHz, Methanol-$d_4$) δ ppm 8.16-8.66 (m, 1 H), 7.92-8.12 (m, 1 H), 7.66 (d, J = 1.1 Hz, 1 H), 7.18-7.24 (m, 1 H), 6.84-6.91 (m, 1 H), 6.71-6.77 (m, 1 H), 6.31-6.42 (m, 1 H), 6.21-6.29 (m, 1 H), 5.74 (dd, J = 10.2, 2.1 Hz, 1 H), 4.27-4.43 (m, 2 H), 4.01-4.19 (m, 2 H), 3.45-3.70 (m, 4 H), 2.33 (t, J = 7.0 Hz, 2 H), 1.99 (d, J = 1.1 Hz, 3 H). OH not observed. |
| 1-30 | 467.0 | $^1$H NMR (400 MHz, DMSO-$d_6$) δ ppm 7.99 (dd, J = 8.3, 1.4 Hz, 1 H), 7.88 (d, J = 8.2 Hz, 1 H), 7.54 (dd, J = 8.2, 7.0 Hz, 1 H), 7.43 (dd, J = 8.2, 7.0 Hz, 1 H), 7.30 (d, J = 7.0 Hz, 1 H), 7.23 (dd, J = 7.0, 1.4 Hz, 1 H), 6.29 (dd, J = 17.0, 10.3 Hz, 1 H), 6.09 (dd, J = 17.0, 2.3 Hz, 1 H), 5.66 (dd, J = 10.2, 2.3 Hz, 1 H), 4.13-4.19 (m, 2 H), 3.88 (m, 2 H), 3.30-3.63 (m, 6 H), 2.10-2.18 (m, 3 H), 2.07 (s, 3 H), 1.88 2.00 (m, 1 H), 1.40 (m, 2 H), 0.94 (d, J = 15.3 Hz, 6 H). |
| 1-31 | 468.9 | $^1$H NMR (400 MHz, DMSO-$d_6$) δ ppm 9.90 (s, 1 H), 7.77 (d, J-8.3 Hz, 1 H), 7.40 (t, J = 7.4 Hz, 1 H), 7.17-7.28 (m, 3 H), 6.95 (d, J = 2.4 Hz, 1 H), 6.30 (dd, J = 17.0, 10.3 Hz, 1 H), 6.10 (d, J = 16.3 Hz, 1 H), 5.62-5.70 (m, 1 H), 4.21 (m, 1 H), 4.14 (m, 1 H), 3.86-3.91 (m, 2 H), 3.50-3.64 (m, 4 H), 2.05-2.15 (m, 4 H), 1.39 (m, 2 H), 0.96 (s, 6 H). |
| 1-32 | 392.2 | $^1$H NMR (400 MHz, DMSO-$d_6$) δ ppm 7.78 (td, J = 7.5, 1.8 Hz, 1 H), 7.52-7.62 (m, 1 H), 7.31-7.46 (m, 2 H), 7.15 (d, J = 3.6 Hz, 1 H), 6.33 (dd, J = 17.0, 10.3 Hz, 1 H), 6.22 (d, J = 3.6 Hz, 1 H), 6.12 (dd, J = 17.0, 2.3 Hz, 1 H), 5.68 (dd, J = 10.3, 2.3 Hz, 1 H), 4.27 (d, J = 8.6 Hz, 1 H), 4.18 (d, J = 8.6 Hz, 1 H), 3.97 (d, J = 10.1 Hz, 1 H), 3.91 (d, J = 10.1 Hz, 1 H), 3.83 (d, J = 11.2 Hz, 1 H), 3.77 (d, J = 11.2 Hz, 1 H), 3.68 (s, 3 H), 3.60-3.68 (m, 2 H), 2.20 (td, J = 6.9, 2.6 Hz, 2 H). |
| 1-33 | 408.1 | $^1$H NMR (400 MHz, DMSO-$d_6$) δ ppm 7.40-7.50 (m, 1 H), 7.36 (d, J = 7.6, 2.0 Hz, 1 H), 7.20-7.30 (m, 2 H), 6.31 (dd, J = 17.0, 10.3 Hz, 1 H), 6.10 (dd, J = 17.0, 2.3 Hz, 1 H), 5.66 (dd, J = 10.3, 2.3 Hz, 1 H), 4.19 (d, J = 8.6 Hz, 1 H), 4.13 (d, J = 8.6 Hz, 1 H), 3.87-3.91 (m, 2 H), 3.65 (d, J = 11.3 Hz, 1 H), 3.59 (d, J = 11.1 Hz, 1 H), 3.46-3.49 (m, 2 H), 3.09 (s, 3 H), 2.52-2.55 (m, 2 H), 2.28 (t, J = 6.1 |

TABLE 20-continued

| Analytical Data for Examples 1-2 to 2-9 | | |
|---|---|---|
| Ex. # | LRMS: (ESI, +ve ion) m/z | NMR |
| | | Hz, 2 H), 2.11-2.14 (m, 2 H), 1.73-1.77 (m, 2 H). $^{19}$F NMR (376 MHz, DMSO-$d_6$) δ ppm −115.41 (s, 1 F). |
| 1-34 | 434.0 | $^1$H NMR (400 MHz, DMSO-$d_6$) δ ppm 13.20 (s, 1 H), 7.87 (d, J = 8.3 Hz, 1 H), 7.63 (d, J = 8.7 Hz, 1 H), 7.56-7.47 (m, 1 H), 7.43 (d, J = 8.6 Hz, 1 H), 7.29 (s, 1 H), 7.19-7.12 (m, 1 H), 7.10 (s, 1 H), 6.93 (d, J = 8.4 Hz, 1 H), 6.31 (dd, J = 17.0, 10.3 Hz, 1 H), 6.10 (dd, J = 17.0, 2.3 Hz, 1 H), 5.68 (dd, J = 10.4, 2.3 Hz, 1 H), 4.47 (s, 2 H), 4.35 (s, 4 H), 4.17 (s, 2 H), 2.02 (s, 3 H). |
| 1-35 | 456.9 | $^1$H NMR (400 MHz, DMSO-$d_6$) δ ppm 13.08 (s, 1 H), 7.56 (d, J = 8.7 Hz, 1 H), 7.50 (s, 1 H), 7.43 (d, J = 8.8 Hz, 1 H), 6.30 (dd, J = 17.0, 10.3 Hz, 1 H), 6.10 (dd, J-17.0, 2.3 Hz, 1 H), 5.66 (dd, J = 10.3, 2.3 Hz, 1 H), 4.09-4.27 (m, 2 H), 3.80-4.00 (m, 2 H), 3.41-3.73 (m, 4 H), 2.65-2.83 (m, 3 H), 2.07-2.22 (m, 3 H), 1.95-2.05 (m, 1 H), 1.70-1.84 (m, 2 H), 1.46-1.68 (m, 2 H), 1.18 (d, J = 6.9 Hz, 3 H), 1.15 (d, J = 7.0 Hz, 3 H). |
| 1-36 | 443.0 | $^1$H NMR (400 MHz, DMSO-$d_6$) δ ppm 12.63 (s, 1 H), 7.39 (d, J = 8.5 Hz, 1 H), 7.24 (d, J = 8.5 Hz, 1 H), 6.30 (dd, J = 17.0, 10.3 Hz, 1 H), 6.09 (dd, J = 17.0, 2.3 Hz, 1 H), 5.66 (dd, J = 10.3, 2.3 Hz, 1 H), 4.09-4.26 (m, 2 H), 3.82-3.96 (m, 2 H), 3.40-3.74 (br m, 4 H), 2.72 (t, J = 6.4 Hz, 2 H), 2.11-2.21 (m, 2 H), 2.08 (s, 3 H), 1.99-2.05 (m, 1 H), 1.89-1.99 (m, 1 H), 1.85 (s, 3 H), 1.69-1.80 (m, 2 H), 1.53-1.65 (m, 2 H). |
| 1-37 | 452.2 | $^1$H NMR (500 MHz, Methanol-$d_4$) o ppm 7.94 (s, 1 H), 7.86 (br d, J = 0.92 Hz, 1 H), 7.79 (br d, J = 8.54 Hz, 1 H), 7.69 (s, 1 H), 7.57 (br d, J = 8.70 Hz, 1 H), 6.26-6.47 (m, 2 H), 5.79 (br dd, J = 10.30, 1.91 Hz, 1 H), 4.32-4.49 (m, 2 H), 4.08-4.23 (m, 2 H), 3.77-4.01 (m, 4 H), 2.72 (s, 3 H), 2.28-2.35 (m, 3 H), 1.40 (dd, J = 6.64, 4.20 Hz, 2 H). |
| 1-38 | 514.2 | $^1$H NMR (500 MHz, Methanol-$d_4$) δ ppm 8.50 (s, 1 H), 8.39 (s, 1 H), 7.64-7.81 (m, 4 H), 7.55 (d, J = 8.70 Hz, 1 H), 7.46-7.52 (m, 3 H), 6.37-6.47 (m, 1 H), 6.27-6.31 (m, 1 H), 5.78 (dd, J = 10.38, 1.98 Hz, 1 H), 4.35-4.43 (m, 2 H), 4.10-4.19 (m, 2 H), 3.61-3.90 (m, 4 H), 2.40 (t, J = 6.94 Hz, 2 H), 2.35 (s, 3 H), |
| 1-39 | 503.0 | $^1$H NMR (400 MHz, DMSO-$d_6$) δ ppm 13.27 (s, 1 H), 7.89-7.58 (m, 3 H), 7.48-7.44 (d, J = 16.8 Hz 1 H), 7.22-7.17 (m, 1 H), 6.77 (d, J = 8.4 Hz, 1 H), 6.38-6.32 (m, 1 H), 6.15 (dd, J = 17.2, 2.4 Hz, 1 H), 5.73 (dd, J = 10.4, 2.4 Hz, 1 H), 4.46-4.34 (m, 6 H), 4.14 (s, 2 H), 2.09 (s, 3 H). |
| 1-40 | 439.2 | $^1$H NMR (400 MHz, DMSO-$d_6$) δ ppm 12.99-13.32 (m, 1 H), 7.64 (d, J = 8.4 Hz. 1 H), 7.47-7.54 (m, 2 H), 7.40 (d, J = 8.6 Hz, 1 H), 7.10 (br d, J = 8.4 Hz, 1 H), 7.00 (br d, J = 7.9 Hz, 1 H), 6.31 (br dd, J = 16.7, 10.5 Hz, 1 H), 6.03-6.17 (m, 1 H), 5.67 (br d, J = 9.8 Hz, 1 H), 4.24-4.35 (m, 1 H), 4.16-4.22 (m, 1 H), 3.95-4.07 (m, 1 H), 3.91 (br d, J = 9.8 Hz, 2 H), 3.79-3.88 (m, 2 H), 3.70 (br d, J = 7.3 Hz, 3 H), 2.45 (s, 3 H), 2.16 (s, 3 H). |
| 1-41 | 455.2 | $^1$H NMR (400 MHz, DMSO-$d_6$) δ ppm 12.93-13.32 (m, 1 H), 7.63 (d, J = 8.6 Hz, 1 H), 7.52 (s, 1 H), 7.39 (d, J = 8.6 Hz, 1 H), 7.03-7.12 (m, 2 H), 6.77 (br d, J = 8.2 Hz, 1 H), 6.24-6.38 (m, 1 H), 6.05-6.17 (m, 1 H), 5.67 (br dd, J = 10.5, 1.7 Hz, 1 H), 4.28 (br dd, J = 3.4, 1.8 Hz, 1 H), 4.15-4.23 (m, 1 H), 3.92 (8, 6 H), 3.78-3.87 (m, 2 H), 3.62-3.76 (m, 3 H), 2.16 (s, 3 H). |
| 1-42 | 440.9 | $^1$H NMR (400 MHz, DMSO-$d_6$) δ ppm 7.98 (dd, J = 8.3, 1.4 Hz, 1 H), 7.86 (d, J = 8.0 Hz, 1 H), 7.52 (dd, J = 8.2, 7.0 Hz, 1 H), 7.42 (dd, J = 8.2, 7.0 Hz, 1 H), 7.24-7.33 (m, 2 H), 6.30 (dd, J = 17.0, 10.3 Hz, 1 H), 6.09 (dd, J = 17.0, 2.3 Hz, 1 H), 5.66 (dd, J = 10.3, 2.3 Hz, 1 H), 4.10-4.24 (m, 2 H), 3.82-4.01 (m, 4 H), 3.54-3.68 (m, 2 H), 3.41-3.54 (m, 2 H), 2.76-2.84 (m, 2 H), 2.16 (s, 3 H), 2.09-2.16 (m, 2 H), 1.92-2.03 (m, 2 H). |
| 1-43 | 516.8 | $^1$H NMR (400 MHz, DMSO-$d_6$) δ ppm 13.30 (s, 1 H), 7.72-7.67 (m, 2 H), 7.53 (d, J = 3.6 Hz, 1 H), 7.46 (d, J = 8.4 Hz, 1 H), 7.35-7.30 (m, 1 H), 6.88 (d, J = 8.4 Hz, 1 H), 6.35 (q, J = 10.4 Hz, 1 H), 6.15 (dd, J = 16.8, 2.0 Hz, 1 H), 5.72 (dd, J = 10.4, 2.0 Hz, 1 H), 4.40 (d, J = 9.2 Hz, 1 H), 4.14-3.98 (m, 4 H), 3.85-3.65 (m, 3 H), 2.27 (s, 2 H), 2.08 (d, J = 4.0 Hz, 3 H). $^{19}$F NMR (376 MHz, DMSO-$d_6$) δ ppm −114.154-−115.777 (m, 2 F), −126.069 (d, J = 3.76 Hz, 1 F). |
| 1-44 | 480.9 | $^1$H NMR (400 MHz, DMSO-$d_6$) δ ppm 13.3 (s, 1 H), 7.87-7.82 (m, 1 H), 7.72 (d, J = 8.4 Hz, 1 H), 7.60-7.43(m, 3 H), 7.09 (d, J = 8.4 Hz, 1 H), 6.38-6.31 (m, 1 H), 6.14 (dd, J = 16.8, 2 Hz, 1 H), 5.71 (dd, J = 10.4, 2.3 Hz, 1 H), 4.42-4.33 (m, 2 H), 4.25-4.04 (m, 4 H), 2.66-2.58 (m, 2 H), 2.12 (d, J = 1.6 Hz, 3 H). $^{19}$F NMR (376 MHz, DMSO-$d_6$) δ ppm −124.369 (s, 1 F). |
| 1-45 | 478.8 | $^1$H NMR (400 MHz, DMSO-$d_6$) δ ppm 13.23 (s, 1 H), 7.64 (d, J = 8.5 Hz, 1 H), 7.49 (d, J = 4.6 Hz, 1 H), 7.43 (d, J = 8.7 Hz, 1 H), 7.07 (t, J = 1.3 Hz, 1 H), 6.79 (d, J = 1.2 Hz, 2 H), 6.27-6.38 (m, 1 H), 6.12 (dd, J = 17.0, 2.3 Hz, 1 H), 5.65-5.72 (m, 1 H), 4.32 (d, J = 8.7 Hz, 1 H), 4.21 (dd, J = 8.4, 3.4 Hz, 1 H), 3.98-4.05 (m, 3 H), 3.85-3.96 (m, 6 H), 2.19-2.29 (m, 2 H), 2.06-2.11 (m, 3 H). |
| 1-46 | 524.0 | $^1$H NMR (400 MHz, DMSO-$d_6$) δ ppm 13.26 (s, 1 H), 7.66 (d, J = 8.8 Hz, 1 H), 7.57-7.52 (m, 2 H), 7.44 (d, J = 8.4 Hz, 1 H), 7.12-7.07 (m, 1 H), 6.71(d, J = 8.0 Hz, 1 H), 6.62-6.55 (m, 1 H), 6.10 (d, J = 15.6 Hz, 1 H), 4.30 (d, J = 8.4 Hz, 1 H), 4.19 (d, J = 1.6 Hz, 1 H), 4.04-4.00 (m, 3 H), 3.90 (t, J = 6.8 Hz, 3 H), 3.01 (d, J = 6.0 Hz, 2 H), 2.25-2.22 (m, 2 H), 2.138 (s, 6 H), 2.08 (d, J = 2.8 Hz, 3 H). $^{19}$F NMR (376 MHz, DMSO-$d_6$) δ ppm −127.117 (s, 1 F). |
| 1-47 | 518.8 | $^1$H NMR (400 MHz, DMSO-$d_6$) δ ppm 9.96 (s, 1 H), 7.78 (d, J = 8.3 Hz, 1 H), 7.40-7.42 (m, 1 H), 7.19-7.26 (m, 3 H), 7.00 (d, J = 2.4 Hz, 1 H), 6.45 (s, 1 H), 6.08 |

TABLE 20-continued

| Ex. # | LRMS: (ESI, +ve ion) m/z | NMR |
|---|---|---|
| Analytical Data for Examples 1-2 to 2-9 | | |
| | | (d, J = 16.9 Hz, 1 H), 5.65 (d, J = 10.3 Hz, 1 H), 4.45 (m, 1 H), 4.38 (m, 1 H), 4.20 (m, 2 H), 3.91 (m, 2 H), 3.79 (m, 2 H), 2.56-2.61 (m, 2 H), 2.37 (m, 2 H), 2.10 (m, 2 H), 1.40 (m, 2 H), 0.96 (m, 6 H). $^{19}$F NMR (377 MHz, DMSO-$d_6$) δ ppm −123.17 (d, J = 281.4 Hz), −133.70 (d, J = 281.4 Hz). |
| 1-48 | 439.0 | $^1$H NMR (400 MHz, DMSO-$d_6$) δ 13.19 (s, 1 H), 8.66 (s, 1 H), 8.48 (s, 1 H), 7.68-7.58 (m, 2 H), 7.40 (d, J = 8.6 Hz, 1 H), 6.33 (dd, J = 17.0, 10.4 Hz, 1 H), 6.11 (dd, J = 17.0, 2.2 Hz, 1 H), 5.68 (dd, J = 10.3, 2.2 Hz, 1 H), 4.24 (dt, J = 8.7, 6.5 Hz, 2 H), 3.95 (dt, J = 10.1, 7.6 Hz, 2 H), 3.71 (s, 2 H), 3.56 (d, J = 3.7 Hz, 2 H), 2.26 (d, J = 4.2 Hz, 2 H), 2.16 (d, J = 2.8 Hz, 3 H). |
| 1-49 | 499.0 | $^1$H NMR (400 MHz, DMSO-$d_6$) δ ppm 13.27 (s, 1 H), 7.68-7.43 (m, 6 H), 7.15-7.13 (m, 1 H), 6.74 (d, J = 8.4 Hz, 1 H), 6.42-6.26 (m, 1 H), 6.16-6.10 (m, 1 H), 5.70-5.69 (m, 1 H), 5.01-4.89 (m, 3 H), 4.36-4.15 (m, 3 H), 3.97-3.86 (m, 3 H), 4.00-3.86 (m, 3 H), 3.30 (s, 1 H), 2.36-2.35 (m, 2 H), 2.10 (s, 1 H), 2.07(s, 3 H). |
| 1-50 | 452.0 | $^1$H NMR (400 MHz, DMSO-$d_6$) δ ppm 13.15 (s, 1 H), 7.57 (d, J-8.4 Hz, 1 H), 7.49 (d, J = 5.2 Hz, 1H), 7.37 (d, J = 8.4 Hz, 1 H), 7.24 (d, J = 3.6 Hz, 1 H), 6.29-6.36 (m, 1 H), 6.10-6.14 (m, 1H), 5.67-5.72 (m, 2 H), 4.30 (d, J = 8.4 Hz, 1 H), 4.19-4.21 (m, 1H), 3.91-4.01 (m, 4 H), 3.81 (t, J = 6.8 Hz, 2 H), 3.73 (s, 3 H), 2.21-2.23 (m, 2 H), 2.16-2.17 (m, 3H). |
| 1-51 | 545.1 | N/A |
| 1-52 | 507.2 | $^1$H NMR (500 MHz, Methanol-$d_4$) δ ppm 2.10-2.18 (m, 4 H), 2.32 (s, 3 H), 2.40 (t, J = 7.0 Hz, 2H), 3.38-3.47 (m, 4 H), 3.74-3.87 (m, 4 H), 4.09-4.13 (m, 1 H), 4.18 (br dd, J = 10.4, 2.1 Hz, 1 H), 4.35-4.38 (m, 1 H), 4.41-4.44 (m, 1 H), 5.78 (dd, J = 10.2, 2.0 Hz, 1 H), 6.27-6.32 (m, 1 H), 6.37-6.43 (m, 1 H), 7.55 (d, J = 8.5 Hz, 1 H), 7.65-7.72 (m, 2 H), 7.77 (d, J-8.9 Hz, 1 H), 7.80 (s, 1 H). |
| 1-53 | 536.3 | $^1$H NMR (500 MHz, Methanol-$d_4$) δ ppm 2.30 (s, 3 H), 2.41 (br t, J = 7.0 Hz, 2 H), 3.08 (s, 3 H), 3.50-3.68 (m, 6 H), 3.68-3.80 (m, 4 H), 3.80-3.83 (m, 1 H), 3.87 (br dd, J = 9.6, 3.8 Hz, 1 H), 4.10-4.14 (m, 1 H), 4.18 (br dd, J = 10.7, 2.1 Hz, 1 H), 4.35-4.44 (m, 2 H), 5.79 (br dd, J = 10.2, 2.0 Hz, 1 H), 6.27-6.32 (m, 1 H), 6.37-6.44 (m, 1 H), 7.52-7.56 (m, 1 H), 7.61 (s, 1 H), 7.75 (d, J = 8.9 Hz, 1H), 7.81 (s, 1 H), 7.86 (s, 1 H). |
| 1-54 | 521.0 | $^1$H NMR (400 MHz, DMSO-$d_6$) δ ppm 13.18 (s, 1H), 8.59 (s, 1H), 8.37 (s, 1H), 7.89 (d, J = 3.2 Hz, 1H), 7.71-7.63 (m, 3H), 7.43 (d, J = 8.4 Hz, 1H), 6.37-6.30 (dd, J = 17.2, 11.2 Hz, 1H), 6.14-6.09 (dd, J = 16.8, 2 Hz, 1H), 5.69-5.66 (dd, J = 10, 2 Hz, 1H), 4.30-4.19 (m, 2H), 4.02-3.92 (m, 2H), 3.64-3.43 (m, 4H), 2.33-2.26 (m, 2H), 2.19 (d, J = 3.2 Hz, 3H). |
| 2-2 | 449.0 | $^1$H NMR (400 MHz, DMSO-$d_6$) δ ppm 13.08 (s, 1 H), 7.71-7.66 (m, 2 H), 7.55 (s, 1 H), 7.42 (d, J = 4.4 Hz, 1 H), 7.15-7.11 (m, 1 H), 6.90 (d, J = 8.0 Hz, 1 H), 6.36-6.29 (m, 1 H), 6.12 (dd, J = 2.4 Hz, 17.2 Hz, 1 H), 5.68 (dd, J = 2.4 Hz, 10.0 Hz, 1 H), 4.34-4.31 (m, 1 H), 4.22-4.19 (m, 1 H), 4.05-3.87 (m, 6 H), 2.48 (s, 3 H), 2.27-2.21 (m, 2 H), 1.95 (d, J = 3.2 Hz, 3 H). |
| 2-3 | 467.1 | $^1$H NMR (400 MHz, DMSO-$d_6$) δ ppm 7.87 (dd, J = 7.4, 1.6 Hz, 1 H), 7.66 (d, J = 12.3 Hz, 4 H), 7.35-7.11 (m, 3 H), 7.08 (d, J = 8.3 Hz, 1 H), 6.32 (ddd, J = 16.9, 10.3, 4.2 Hz, 1 H), 6.12 (dd, J = 17.0, 2.2 Hz, 1 H), 5.68 (dd, J = 10.3, 2.1 Hz, 1 H), 4.39-4.13 (m, 2 H), 4.11-3.75 (m, 6 H), 2.34-2.13 (m, 2 H). |
| 2-4 | 461.0 | $^1$H NMR (400 MHz, DMSO-$d_6$) δ ppm 10.11 (s, 1 H), 7.85 (d, J = 8 Hz, 1 H), 7.71-7.67 (m, 2 H), 7.46-7.42 (m, 1 H), 7.35 (s, 1 H), 7.18-7.09 (m, 3 H), 7.06-7.04 (m, 1 H), 6.89 (d, J = 8 Hz, 1 H), 6.34-6.29 (m, 1 H), 6.12 (d, J = 16 Hz, 1 H), 5.68 (d, J = 10.8 Hz, 1 H), 4.34-4.29 (m, 1 H), 4.22-4.19 (m, 1 H), 4.04-3.96 (m, 3 H), 3.94-3.88 (m, 3 H), 2.25-2.22 (m, 2 H). |
| 2-5 | 503.1 | $^1$H NMR (400 MHz, DMSO-$d_6$) δ ppm 13.18 (s, 1 H), 7.65-7.44 (m, 2 H), 7.35 (dd, J = 8.7, 1.8 Hz, 1 H), 6.40-6.24 (m, 1 H), 6.13 (dt, J = 21.8, 8.2 Hz, 1 H), 5.72 (dd, J = 10.3, 2.3 Hz, 1 H), 4.50-4.32 (m, 2 H), 4.22-4.03 (m, 6 H), 2.96-2.83 (m, 1 H), 2.48-2.43 (m, 1 H), 2.11 (s, 3 H), 2.07-1.94 (m, 2 H), 1.94-1.81 (m, 1 H), 1.71-1.61 (m, 1 H), 1.25-1.21 (m, 1 H), 1.01 (d, J = 6.8 Hz, 3 H). $^{19}$F NMR (400 MHz, DMSO-$d_6$) δ ppm −115.02-−117.72 (m, 2 F). |
| 2-6 | 463.0 | $^1$H NMR (400 MHz, DMSO-$d_6$) δ ppm 13.08 (s, 1 H), 7.71-7.66 (m, 2 H), 7.55 (s, 1 H), 7.42 (d, J = 4.4 Hz, 1 H), 7.15-7.11 (m, 1 H), 6.90 (d, J = 8.0 Hz, 1 H), 6.36-6.29 (m, 1 H), 6.12 (dd, J = 2.4 Hz, 17.2 Hz, 1 H), 5.68 (dd, J = 2.4 Hz, 10.0 Hz, 1 H), 4.34-4.31 (m, 1 H), 4.22-4.19 (m, 1 H), 4.05-3.87 (m, 6 H), 2.48 (s, 3 H), 2.27-2.21 (m, 2 H), 1.95 (d, J = 3.2 Hz, 3 H). |
| 2-7 | 417.0 | $^1$H NMR (400 MHz, DMSO-$d_6$) δ ppm 7.54 (m, 1 H), 7.40-7.33 (m, 3 H), 6.30 (dd, J = 10.0, 16.8 Hz, 1 H), 6.11 (dd, J = 17.2, 2.4 Hz, 1 H), 6.44 (dd, J = 10.4, 2.0 Hz, 1 H), 4.25 (dd, J = 8.4, 5.6 Hz 1 H), 4.15 (dd, J = 8.8, 2.8 Hz, 1 H), 3.94 (dd, J = 10.0, 3.6 Hz, 1 H), 3.90-3.86 (m, 1 H), 3.85-3.82 (m, 2 H), 3.72 (t, J = 6.8 Hz, 2 H), 2.75 (t, J = 6.4 Hz, 2 H), 2.20-2.14 (m, 4 H), 1.77-1.60 (m, 4 H). $^{19}$F NMR (376 MHz, DMSO-$d_6$) δ ppm −115.392 (d, J = 6.02 Hz). |
| 2-8 | 453.0 | $^1$H NMR (400 MHz, DMSO-$d_6$) δ ppm 13.14 (s, 1 H), 7.51-5.44 (m, 2 H), 7.33 (d, J = 8.4 Hz, 1 H), 6.27-6.29 (m, 1 H), 6.08-6.13 (m, 1 H), 5.66-5.69 (m, 1 H), 4.26 (d, J = 8.4 Hz, 1 H), 4.16 (d, J = 8.4 Hz, 1 H), 3.95-3.98 (m, 1 H), 3.81-3.90 (m, 3 H), 3.71-3.74 (m, 2 H), 2.78-2.80 (m, 2 H), 2.17-2.18 (m, 2 H), 2.11 (s, 3 H), 1.95-1.97 (m, 2 H), 1.74-1.77 (m, 2 H), 1.54-1.57 (m, 2 H). |
| 2-9 | 433.0 | $^1$H NMR (400 MHz, DMSO-$d_6$) δ ppm 9.64 (s, 1 H), 7.18-7.13 (t, J = 8.8 Hz, 1 H), 6.88-6.84 (m, 1 H), 6.62-6.59 (dd, J1 = 6, J2 = 3.2 Hz, 1 H), 6.33-6.27 (dd, |

TABLE 20-continued

| Ex. # | LRMS: (ESI, +ve ion) m/z | NMR |
|---|---|---|
| Analytical Data for Examples 1-2 to 2-9 | | |
| | | J1 = 16, J2 = 10.4 Hz, 1 H), 6.13-6.08 (dd, J1 = 17.2, J2 = 2.4 Hz, 1 H), 5.68-5.65 (dd, J1 = 10.4, J2 = 2.4 Hz, 1 H), 4.26-4.14 (m, 2 H), 3.96-3.78 (m, 4 H), 3.73-3.69 (t, J = 6.8 Hz, 2 H), 2.76-2.72 (t, J = 6.4 Hz, 2 H), 2.26-2.13 (m, 4 H), 1.78-1.72 (m, 2 H), 1.65-1.59 (m, 2 H). $^{19}$F NMR (376 MHz, DMSO-$d_6$) δ ppm −128.607 (d, J = 3.76 Hz, 1 F). |
| 2-10 | 467.2 | $^1$H NMR (400 MHz, DMSO-$d_6$) δ ppm 13.00-13.32 (m, 1 H), 7.52-7.56 (m, 1 H), 7.48-7.52 (m, 1 H), 7.34 (d, J = 8.4 Hz, 1 H), 6.25-6.40 (m, 1 H), 6.11 (dd, J = 17.0, 2.2 Hz, 1 H), 5.61-5.74 (m, 1 H), 4.28 (d, J = 8.6 Hz, 1 H), 4.17 (d, J = 8.4 Hz, 1 H), 3.94-4.00 (m, 1 H), 3.90 (s, 1 H), 3.82-3.89 (m, 2 H), 3.75 (t, J = 6.8 Hz, 2 H), 2.96 (br d, J = 6.1 Hz, 2 H), 2.15-2.26 (m, 4 H), 2.12 (s, 3 H), 1.58-1.78 (m, 4 H), 1.27-1.36 (m, 2 H). |
| 2-11 | 470.2 | $^1$H NMR (500 MHz, DMSO-$d_6$) δ ppm 13.04 (s, 1 H), 7.42-7.49 (m, 1 H), 7.37 (d, J = 6.4 Hz, 1 H), 7.31 (d, J = 8.6 Hz, 1 H), 6.32 (dd, J = 17.0, 10.3 Hz, 1 H), 6.10 (dd, J = 17.0, 2.3 Hz, 1 H), 5.66 (dd, J = 10.3, 1.5 Hz, 1 H), 4.23 (dd, J = 8.4, 3.9 Hz, 1 H), 4.15 (br d, J = 8.4 Hz, 1 H), 3.91-3.97 (m, 1 H), 3.84-3.90 (m, 1 H), 3.57-3.66 (m, 2 H), 3.40-3.53 (m, 2 H), 2.04-2.16 (m, 2 H), 2.00 (d, J = 3.1 Hz, 3 H), 1.83-1.99 (m, 2 H), 1.72 (s, 3 H), 1.26-1.39 (m, 2 H), 0.92 (s, 6 H) |
| 2-12 | 470.2 | $^1$H NMR (500 MHz, DMSO-$d_6$) δ ppm 13.00-13.11 (m, 1 H), 7.42-7.48 (m, 1 H), 7.35-7.40 (m, 1 H), 7.28-7.34 (m, 1 H), 6.27-6.37 (m, 1 H), 6.07-6.14 (m, 1 H), 5.61-5.70 (m, 1 H), 4.20-4.26 (m, 1 H), 4.12-4.18 (m, 1 H), 3.91-3.97 (m, 1 H), 3.85-3.89 (m, 1 H), 3.56-3.66 (m, 2 H), 3.40-3.52 (m, 2 H), 2.51-2.53 (m, 2 H), 2.05-2.15 (m, 2 H), 1.99-2.02 (m, 3 H), 1.83-1.99 (m, 2 H), 1.70-1.74 (m, 3 H), 1.27-1.38 (m, 2 H), 0.89-0.95 (m, 6 H) |
| 2-13 | 482.2 | $^1$H NMR (400 MHz, $CDCl_3$) δ ppm 7.72 (d, J = 8.4 Hz, 1 H), 7.49 (dd, J = 8.3, 7.0 Hz, 1 H), 7.27 (br d, J = 2.1 Hz, 1 H), 7.18 (d, J = 9.0 Hz, 1 H), 7.05-7.14 (m, 1 H), 7.00-7.07 (m, 1 H), 6.48-6.67 (m, 1 H), 6.31-6.43 (m, 1 H), 6.04-6.29 (m, 1 H), 5.68 (ddd, J = 19.5, 10.3, 1.5 Hz, 1 H), 4.00-4.26 (m, 4 H), 3.49-3.81 (m, 4 H), 2.58-2.73 (m, 2 H), 2.10-2.33 (m, 3 H), 1.87-2.03 (m, 1 H), 1.81 (br d, J = 4.6 Hz, 3 H), 1.29-1.41 (m, 2 H), 0.98 (s, 3 H), 0.86 (s, 3 H) |
| 2-14 | 482.2 | $^1$H NMR (500 MHz, DMSO-$d_6$) δ ppm 9.75 (s, 1 H), 7.66-7.74 (m, 1 H), 7.46 (dd, J = 8.2, 7.1 Hz, 1 H), 7.19 (d, J = 2.4 Hz, 1 H), 7.03-7.11 (m, 1 H), 6.94-7.01 (m, 2 H), 6.25-6.37 (m, 1 H), 6.10 (dd, J = 17.0, 2.2 Hz, 1 H), 5.66 (dt, J = 10.3, 2.2 Hz, 1 H), 4.09-4.29 (m, 2 H), 3.83-3.99 (m, 2 H), 3.61-3.67 (m, 1 H), 3.55-3.60 (m, 1 H), 3.36-3.54 (m, 2 H), 2.48-2.53 (m, 2 H), 2.02-2.18 (m, 3 H), 1.74-1.86 (m, 1 H), 1.72 (s, 3 H), 1.19-1.36 (m, 2 H), 0.91 (d, J = 16.4 Hz, 6 H) |
| 2-15 | 482.2 | $^1$H NMR (500 MHz, DMSO-$d_6$) δ ppm 9.75 (s, 1 H), 7.67-7.74 (m, 1 H), 7.46 (dd, J = 8.3, 7.0 Hz, 1 H), 7.18 (d, J = 2.4 Hz, 1 H), 7.03-7.10 (m, 1 H), 6.94-7.02 (m, 2 H), 6.26-6.37 (m, 1 H), 6.10 (dd, J = 17.0, 2.2 Hz, 1 H), 5.66 (dt, J = 10.3, 2.2 Hz, 1 H), 4.11-4.27 (m, 2 H), 3.84-3.97 (m, 2 H), 3.54-3.67 (m, 2 H), 3.35-3.54 (m, 2 H), 2.52 (s, 3 H), 2.02-2.19 (m, 3 H), 1.75-1.84 (m, 1 H), 1.72 (s, 3 H), 1.21-1.37 (m, 2 H), 0.91 (d, J = 16.5 Hz, 6 H) |
| 2-16 | 506.2 | $^1$H NMR (400 MHz, $CDCl_3$) δ ppm 6.90-6.97 (m, 2 H), 6.31-6.40 (m, 1 H), 6.14-6.28 (m, 1 H), 5.58-5.74 (m, 3 H), 4.03-4.27 (m, 4 H), 3.63-3.79 (m, 2 H), 3.48-3.62 (m, 2 H), 2.57-2.68 (m, 2 H), 2.06-2.27 (m, 4 H), 1.86 (s, 3 H), 1.36-1.44 (m, 2 H), 0.92-1.03 (m, 6 H) |
| 2-17 | 506.2 | $^1$H NMR (500 MHz, DMSO-$d_6$) δ ppm 7.83 (s, 2 H), 6.91-7.01 (m, 2 H), 6.32 (ddd, J = 16.9, 10.3, 4.4 Hz, 1 H), 6.10 (dd, J = 16.9, 2.0 Hz, 1 H), 5.66 (dt, J = 10.1, 2.7 Hz, 1 H), 4.08-4.24 (m, 2 H), 3.83-3.95 (m, 2 H), 3.60 (dd, J = 10.5, 5.4 Hz, 1 H), 3.41-3.54 (m, 2 H), 2.44-2.48 (m, 1 H), 2.04-2.17 (m, 3 H), 2.00 (br s, 1 H), 1.75-1.79 (m, 3 H), 1.32 (dt, J = 12.9, 6.6 Hz, 2 H), 0.93 (s, 3 H), 0.91 (s, 3 H) |
| 2-18 | 506.2 | $^1$H NMR (500 MHz, DMSO-$d_6$) δ ppm 7.83 (s, 2 H), 6.91-7.00 (m, 2 H), 6.32 (ddd, J = 17.0, 10.3, 4.3 Hz, 1 H), 6.10 (dd, J = 16.9, 2.1 Hz, 1 H), 5.66 (dt, J = 10.1, 2.7 Hz, 1 H), 4.11-4.23 (m, 2 H), 3.83-3.95 (m, 2 H), 3.60 (dd, J = 10.5, 5.4 Hz, 1 H), 3.51 (dd, J = 10.6, 4.3 Hz, 1 H), 3.41-3.48 (m, 1 H), 2.44-2.48 (m, 1 H), 1.93-2.18 (m, 4 H), 1.75-1.79 (m, 3 H), 1.25-1.38 (m, 2 H), 0.93 (s, 3 H), 0.91 (s, 3 H) |
| 2-19 | 484.2 | $^1$H NMR (400 MHz, $CDCl_3$) δ ppm 7.89-8.01 (m, 1 H), 7.63 (d, J = 8.2 Hz, 1 H), 7.10 (d, J = 8.4 Hz, 1 H), 6.32-6.44 (m, 1 H), 6.19-6.29 (m, 1 H), 5.69 (dd, J = 10.3, 2.0 Hz, 1 H), 4.23-4.31 (m, 1 H), 4.11-4.20 (m, 2 H), 4.02-4.10 (m, 1 H), 3.66-3.77 (m, 2 H), 3.56 (t, J = 6.9 Hz, 2 H), 3.48 (d, J = 2.3 Hz, 3 H), 2.64 (s, 2 H), 2.15-2.24 (m, 2 H), 1.95-2.13 (m, 5 H), 1.86 (s, 3 H), 1.35-1.49 (m, 2 H), 1.00 (d, J = 6.5 Hz, 6 H) |
| 2-20 | 484.4 | $^1$H NMR (500 MHz, DMSO-$d_6$) δ ppm 8.01 (s, 1 H), 7.66 (d, J = 8.2 Hz, 1 H), 7.12 (d, J = 8.3 Hz, 1 H), 6.32 (dd, J = 17.1, 10.3 Hz, 1 H), 6.10 (dd, J = 17.0, 2.2 Hz, 1 H), 5.64-5.68 (m, 1 H), 4.20-4.26 (m, 1 H), 4.13-4.18 (m, 1 H), 3.90-3.96 (m, 1 H), 3.85-3.89 (m, 1 H), 3.40-3.56 (m, 2 H), 3.37 (d, J = 4.9 Hz, 1 H), 3.16 (d, J = 5.3 Hz, 1 H), 2.58 (s, 3 H), 2.04-2.17 (m, 2 H), 2.00 (d, J = 3.9 Hz, 3 H), 1.97-1.97 (m, 1 H), 1.80-1.98 (m, 2 H), 1.78 (d, J = 0.9 Hz, 3 H), 1.37 (t, J = 6.6 Hz, 2 H), 0.92 (d, J = 5.6 Hz, 6 H) |
| 2-21 | 484.4 | $^1$H NMR (500 MHz, DMSO-$d_6$) δ ppm 8.01 (s, 1 H), 7.66 (d, J = 8.2 Hz, 1 H), 7.12 (d, J = 8.3 Hz, 1 H), 6.32 (dd, J = 17.1, 10.3 Hz, 1 H), 6.10 (dd, J = 17.0, 2.2 Hz, 1 H), 5.64-5.68 (m, 1 H), 4.20-4.26 (m, 1 H), 4.13-4.18 (m, 1 H), 3.90-3.96 (m, 1 H), 3.85-3.89 (m, 1 H), 3.40-3.56 (m, 2 H), 3.37 (d, J = 4.9 Hz, 1 H), 3.16 |

TABLE 20-continued

| Ex. # | LRMS: (ESI, +ve ion) m/z | NMR |
|---|---|---|
| Analytical Data for Examples 1-2 to 2-9 | | |
| | | (d, J = 5.3 Hz, 1 H), 2.58 (s, 3 H), 2.04-2.17 (m, 2 H), 2.00 (d, J = 3.9 Hz, 3 H), 1.97-1.97 (m, 1 H), 1.80-1.98 (m, 2 H), 1.78 (d, J = 0.9 Hz, 3 H), 1.37 (t, J = 6.6 Hz, 2 H), 0.92 (d, J = 5.6 Hz, 6 H) |
| 2-22 | 518.2 | $^1$H NMR (400 MHz, $CDCl_3$) δ ppm 8.85-9.10 (m, 1 H), 7.16 (dd, J = 5.1, 3.0 Hz, 1 H), 6.33-6.44 (m, 1 H), 6.06-6.30 (m, 2 H), 5.74 (dd, J = 10.3, 1.4 Hz, 1 H), 4.02-4.31 (m, 4 H), 3.43-3.74 (m, 4 H), 2.52-2.65 (m, 2 H), 2.09-2.24 (m, 4 H), 1.91 (d, J = 3.3 Hz, 3 H), 1.38-1.54 (m, 2 H), 0.98 (d, J = 12.3 Hz, 6 H) |
| 2-23 | 470.2 | $^1$H NMR (400 MHz, $CDCl_3$) δ ppm 0.96-0.99 (m, 3 H) 1.00 (s, 3 H) 1.40 (br t, J = 5.96 Hz, 2 H) 1.84 (s, 3 H) 1.92-2.12 (m, 2 H) 2.15 (s, 3 H) 2.17-2.25 (m, 2 H) 2.65 (s, 2 H) 3.58 (br t, J = 6.79 Hz, 2 H) 3.75 (s, 2 H) 4.04-4.10 (m, 1 H) 4.11-4.23 (m, 2 H) 4.27 (br d, J = 8.57 Hz, 1 H) 5.71 (dd, J = 10.24, 1.46 Hz, 1 H) 6.19-6.28 (m, 1 H) 6.34-6.42 (m, 1 H) 7.16 (d, J = 8.15 Hz, 1 H) 7.63-7.73 (m, 1 H) 8.02-8.14 (m, 1 H) |
| 2-24 | 470.2 | $^1$H NMR (400 MHz, $CDCl_3$) δ ppm 9.32-9.69 (m, 1 H), 8.06 (s, 1 H), 7.68 (d, J = 8.4 Hz, 1 H), 7.16 (d, J = 8.2 Hz, 1 H), 6.32-6.44 (m, 1 H), 6.17-6.29 (m, 1 H), 5.70 (dd, J = 10.2, 1.9 Hz, 1 H), 4.23-4.31 (m, 1 H), 4.10-4.20 (m, 2 H), 4.04-4.09 (m, 1 H), 3.69-3.82 (m, 2 H), 3.58 (br t, J = 6.9 Hz, 2 H), 2.60-2.69 (m, 2 H), 2.19 (br t, J = 6.9 Hz, 2 H), 2.15 (s, 3 H), 2.09-2.13 (m, 1 H), 1.98 (dt, J = 17.4, 6.2 Hz, 1 H), 1.84 (s, 3 H), 1.37-1.43 (m, 2 H), 1.00 (d, J = 5.4 Hz, 6 H) |
| 2-25 | 470.2 | $^1$H NMR (500 MHz, DMSO-$d_6$) δ ppm 12.50 (s, 1 H), 8.01 (d, J = 0.7 Hz, 1 H), 7.64 (d, J = 8.2 Hz, 1 H), 7.09 (d, J = 8.3 Hz, 1 H), 6.28-6.38 (m, 1 H), 6.11 (dd, J-17.0, 2.1 Hz, 1 H), 5.66 (dd, J = 12.2, 1.3 Hz, 1 H), 4.14-4.26 (m, 2 H), 3.84-3.97 (m, 2 H), 3.58-3.66 (m, 2 H), 3.42-3.55 (m, 2 H), 2.48-2.55 (m, 2 H), 2.04-2.19 (m, 2 H), 2.02 (d, J = 1.7 Hz, 3 H), 1.77-2.00 (m, 2 H), 1.73 (s, 3 H), 1.26-1.39 (m, 2 H), 0.94 (d, J = 17.1 Hz, 6 H) |
| 2-26 | 468.2 | $^1$H NMR (400 MHz, DMSO-$d_6$) δ ppm 9.97 (s, 1 H), 6.81 (ddd, J = 12.2, 6.5, 2.8 Hz, 1 H), 6.25-6.39 (m, 2 H), 6.05-6.16 (m, 1 H), 5.62-5.71 (m, 1 H), 4.09-4.26 (m, 2 H), 3.84-3.99 (m, 2 H), 3.53-3.68 (m, 2 H), 3.38-3.52 (m, 2 H), 2.49 (s, 2 H), 2.04-2.19 (m, 4 H), 1.90 (s, 3 H), 1.41 (br t, J = 6.6 Hz, 2 H), 0.94 (d, J = 5.2 Hz, 6 H) |
| 2-27 | 482.4 | $^1$H NMR (400 MHz, DMSO-$d_6$) δ ppm 9.72-9.91 (m, 1 H), 7.76 (d, J = 8.4 Hz, 1 H), 7.33-7.48 (m, 1 H), 7.15-7.20 (m, 2 H), 7.04-7.11 (m, 1 H), 6.80 (d, J = 2.3 Hz, 1 H), 6.28-6.38 (m, 1 H), 6.11 (dd, J = 17.0, 2.2 Hz, 1 H), 5.67 (dt, J = 10.4, 1.8 Hz, 1 H), 4.12-4.31 (m, 2 H), 3.84-4.00 (m, 2 H), 3.57-3.69 (m, 2 H), 3.39-3.55 (m, 2 H), 2.04-2.22 (m, 3 H), 1.76-1.87 (m, 1 H), 1.74 (s, 3 H), 1.23-1.38 (m, 2 H), 0.92 (d, J = 16.3 Hz, 6 H). |
| 2-28 | 470.4 | $^1$H NMR (400 MHz, DMSO-$d_6$) δ ppm 13.05 (s, 1 H), 7.45 (d, J = 8.5 Hz, 1 H), 7.38 (d, J = 4.8 Hz, 1 H), 7.32 (d, J = 8.5 Hz, 1 H), 6.27-6.41 (m, 1 H), 6.10 (dd, J = 16.9, 2.2 Hz, 1 H), 5.66 (br d, J = 12.2 Hz, 1 H), 4.21-4.26 (m, 1 H), 4.12-4.20 (m, 1 H), 3.91-3.98 (m, 1 H), 3.85-3.90 (m, 1 H), 3.61 (s, 2 H), 3.41-3.51 (m, 2 H), 2.07-2.15 (m, 2 H), 1.84-2.04 (m, 7 H), 1.72 (s, 3 H), 1.27-1.36 (m, 2 H), 0.92 (s, 6 H). |
| 2-29 | 458.3 | $^1$H NMR (400 MHz, DMSO-$d_6$) δ ppm 13.47 (br s, 1 H), 7.65-7.84 (m, 2 H), 7.60 (d, J = 8.8 Hz, 1 H), 7.51 (br d, J = 8.6 Hz, 2 H), 7.07 (br s, 1 H), 6.77 (br d, J = 8.4 Hz, 1 H), 6.29-6.38 (m, 1 H), 6.09-6.16 (m, 1 H), 5.65-5.71 (m, 1 H), 4.25-4.36 (m, 1 H), 4.21 (br d, J = 10.0 Hz, 1 H), 3.84-4.02 (m, 4 H), 3.74 (br s, 2 H), 2.13-2.25 (m, 2 H), 2.00-2.13 (m, 3 H) |
| 2-30 | 482.2 | $^1$H NMR (400 MHz, Methanol-$d_4$) δ ppm 7.68 (dd, J = 7.9, 1.0 Hz, 1 H), 7.13-7.17 (m, 2 H), 6.88 (d, J = 7.1 Hz, 1 H), 6.55 (d, J = 3.1 Hz, 1 H), 6.34-6.43 (m, 1 H), 6.25-6.31 (m, 1 H), 5.76 (dt, J = 10.3, 1.6 Hz, 1 H), 4.21-4.38 (m, 3 H), 3.99-4.11 (m, 5 H), 3.88-3.96 (m, 2 H), 3.43 (d, J = 1.3 Hz, 3 H), 2.80 (s, 2 H), 2.26-2.33 (m, 2 H), 1.29 (s, 3 H), 1.28 (s, 3 H) |
| 2-31 | 547.2 | $^1$H NMR (400 MHz, Methanol-$d_4$) δ ppm 7.83 (s, 2 H), 7.71-7.74 (m, 1 H), 6.38 (ddd, J = 17.0, 10.2, 1.7 Hz, 1 H), 6.27 (dd, J = 16.9, 2.1 Hz, 1 H), 5.76 (dd, J = 10.2, 1.9 Hz, 1 H), 4.24-4.40 (m, 2 H), 3.83-4.11 (m, 6 H), 2.90-2.95 (m, 1 H), 2.65-2.77 (m, 1 H), 2.36-2.45 (m, 1 H), 2.29 (t, J = 6.9 Hz, 2 H), 2.12-2.22 (m, 2 H), 1.42 (s, 3 H), 1.32 (d, J = 9.8 Hz, 1 H), 0.73-0.80 (m, 3 H) |
| 2-32 | 506.2 | $^1$H NMR (400 MHz, DMSO-$d_6$) δ ppm 8.13 (s, 1 H), 7.92 (d, J = 1.9 Hz, 1 H), 7.15 (s, 1 H), 6.32 (dd, J = 17.0, 10.3 Hz, 1 H), 6.11 (dd, J = 17.1, 2.3 Hz, 1 H), 5.65-5.69 (m, 1 H), 4.12-4.28 (m, 3 H), 3.84-3.97 (m, 3 H), 3.68 (s, 2 H), 3.45-3.56 (m, 5 H), 2.68 (s, 2 H), 2.07-2.18 (m, 2 H), 1.85 (s, 3 H), 1.23 (s, 3 H), 1.20 (s, 3 H) |
| 2-33 | 506.2 | $^1$H NMR (500 MHz, DMSO-$d_6$) δ ppm 8.12 (s, 1 H), 7.92 (d, J = 2.0 Hz, 1 H), 7.15 (t, J = 2.1 Hz, 1 H), 6.32 (ddd, J = 17.0, 10.3, 2.0 Hz, 1 H), 6.10 (dd, J = 16.9, 2.3 Hz, 1 H), 5.66 (dd, J = 10.3, 2.1 Hz, 1 H), 4.09-4.25 (m, 3 H), 3.83-3.95 (m, 3 H), 3.66 (s, 2 H), 3.46-3.54 (m, 4 H), 3.16 (d, J = 5.3 Hz, 1 H), 2.66 (s, 2 H), 2.06-2.16 (m, 2 H), 1.82-1.85 (m, 3 H), 1.21 (s, 3 H), 1.18 (s, 3 H) |
| 2-34 | 506.2 | $^1$H NMR (500 MHz, DMSO-$d_6$) δ ppm 8.12 (s, 1 H), 7.92 (d, J = 2.0 Hz, 1 H), 7.15 (t, J = 2.1 Hz, 1 H), 6.32 (ddd, J = 17.0, 10.3, 2.0 Hz, 1 H), 6.10 (dd, J = 17.0, 2.2 Hz, 1 H), 5.66 (dd, J = 10.3, 2.1 Hz, 1 H), 4.08-4.23 (m, 3 H), 3.84-3.95 (m, 3 H), 3.66 (s, 2 H), 3.45-3.54 (m, 4 H), 3.16 (d, J = 5.3 Hz, 1 H), 2.66 (s, 2 H), 2.11 (t, J = 7.0 Hz, 2 H), 1.82-1.85 (m, 3 H), 1.21 (s, 3 H), 1.18 (s, 3 H) |
| 2-35 | 468.2 | $^1$H NMR (400 MHz, $CDCl_3$) δ ppm 7.33 (d, J = 8.8 Hz, 1 H), 6.85 (dd, J = 8.7, 3.0 Hz, 1 H), 6.18-6.40 (m, 3 H), 5.71 (dd, J = 10.5, 1.9 Hz, 1 H), 4.02-4.29 (m, 6 |

TABLE 20-continued

| Analytical Data for Examples 1-2 to 2-9 | | |
|---|---|---|
| Ex. # | LRMS: (ESI, +ve ion) m/z | NMR |
| | | H), 3.50-3.75 (m, 4 H), 2.70-2.81 (m, 2 H), 2.17 (br t, J = 6.8 Hz, 2 H), 1.91 (s, 3 H), 1.31 (s, 3 H), 1.28 (s, 3 H) |
| 2-36 | 506.2 | $^{1}$H NMR (400 MHz, Methanol-$d_4$) δ ppm 7.75-7.81 (m, 1 H), 7.50-7.58 (m, 1 H), 6.25-6.42 (m, 2 H), 5.77 (dd, J = 10.0, 2.1 Hz, 1 H), 4.30-4.40 (m, 2 H), 4.02-4.15 (m, 3 H), 3.87-4.01 (m, 3 H), 3.70-3.86 (m, 2 H), 2.86 (s, 2 H), 2.27-2.36 (m, 2 H), 2.19 (s, 3 H), 1.99 (br s, 3 H), 1.30 (s, 3 H), 1.29 (s, 3 H) |
| 2-37 | 441.2 | $^{1}$H NMR (400 MHz, DMSO-$d_6$) δ ppm 9.39 (s, 1 H) 7.13 (t, J = 8.26 Hz, 1 H) 6.73-6.79 (m, 1 H) 6.51 (dd, J = 17.04, 2.61 Hz, 1 H) 6.26-6.36 (m, 1 H) 6.07-6.15 (m, 1 H) 5.64-5.71 (m, 1 H) 4.26 (dd, J = 8.36, 3.55 Hz, 1 H) 4.16 (d, J = 8.57 Hz, 1 H) 3.93-4.00 (m, 1 H) 3.81-3.91 (m, 3 H) 3.70-3.79 (m, 2 H) 3.26 (br s, 1 H) 2.81-2.97 (m, 1 H) 2.13-2.22 (m, 2 H) 2.01 (s, 2 H) 1.96 (d, J = 2.09 Hz, 2 H) 1.68 (br s, 2 H) 1.50 (br d, J = 8.99 Hz, 1 H) 0.95-1.14 (m, 1 H) |
| 2-38 | 477.2 | $^{1}$H NMR (400 MHz, $CDCl_3$) δ ppm 7.73 (d, J = 8.15 Hz, 1 H) 7.30-7.48 (m, 2 H) 7.22-7.27 (m, 2 H) 7.07 (d, J = 2.09 Hz, 1 H) 6.36-6.42 (m, 1 H) 6.18-6.26 (m, 1 H) 5.73 (dd, J = 10.24, 1.67 Hz, 1 H) 4.21-4.28 (m, 1 H) 4.11-4.18 (m, 2 H) 4.06-4.09 (m, 1 H) 4.01 (s, 2 H) 3.89-3.95 (m, 2 H) 3.51 (s, 1 H) 3.34-3.42 (m, 1 H) 2.87-2.99 (m, 4 H) 2.18-2.26 (m, 2 H) 2.08 (s, 1 H) 1.95-2.03 (m, 1 H) 1.80 (br d, J = 8.15 Hz, 1 H) 1.61-1.76 (m, 2 H) 1.47-1.52 (m, 1 H) 1.37 (s, 2 H) |
| 2-39 | 477.2 | $^{1}$H NMR (400 MHz, DMSO-$d_6$) δ ppm 9.91-10.03 (m, 1 H) 7.75-7.84 (m, 1 H) 7.37-7.49 (m, 2 H) 7.14-7.32 (m, 2 H) 6.94-7.04 (m, 1 H) 6.25-6.39 (m, 1 H) 6.06-6.16 (m, 1 H) 5.62-5.73 (m, 1 H) 4.28 (d, J = 8.36 Hz, 1 H) 4.18 (br d, J = 8.36 Hz, 1 H) 3.94-4.02 (m, 1 H) 3.86-3.93 (m, 3 H) 3.69-3.80 (m, 2 H) 2.63-2.71 (m, 1 H) 2.14-2.24 (m, 2 H) 1.89-2.03 (m, 1 H) 1.60-1.82 (m, 2 H) 1.42-1.51 (m, 1 H) 1.29-1.36 (m, 1 H) 0.95-1.14 (m, 1 H) |
| 2-40 | 477.2 | $^{1}$H NMR (400 MHz, $CDCl_3$) δ ppm 7.72 (br d, J = 8.15 Hz, 1 H) 7.35-7.51 (m, 3 H) 7.29-7.35 (m, 1 H) 7.17-7.27 (m, 1 H) 7.06 (br d, J = 3.55 Hz, 1 H) 6.36-6.43 (m, 1 H) 6.18-6.27 (m, 1 H) 5.73 (br d, J = 10.45 Hz, 1 H) 4.20-4.33 (m, 1 H) 4.12-4.18 (m, 2 H) 4.01 (br s, 2 H) 3.90-3.95 (m, 2 H) 3.51 (s, 1 H) 3.38 (br t, J = 7.00 Hz, 4 H) 2.92-3.00 (m, 2 H) 2.83-2.88 (m, 2 H) 2.18-2.25 (m, 2 H) 2.07 (s, 1 H) 1.94-2.02 (m, 1 H) 1.81-1.87 (m, 1 H) 1.44-1.50 (m, 1 H) |
| 2-41 | 506.2 | $^{1}$H NMR (400 MHz, $CDCl_3$) δ ppm 8.69 (d, J = 3.14 Hz, 1 H) 8.41 (d, J = 6.06 Hz, 1 H) 7.54-7.62 (m, 1 H) 7.15-7.25 (m, 2 H) 6.37-6.44 (m, 1 H) 6.18-6.27 (m, 1 H) 5.72-5.77 (m, 1 H) 4.29 (dt, J = 8.05, 3.92 Hz, 1 H) 4.12-4.22 (m, 2 H) 3.87-4.09 (m, 5 H) 3.62-3.79 (m, 1 H) 3.12 (q, J = 7.39 Hz, 1 H) 2.92 (t, J = 5.43 Hz, 1 H) 2.60-2.71 (m, 1 H) 2.34-2.48 (m, 1 H) 2.13-2.27 (m, 4 H) 1.36-1.49 (m, 12 H) 0.71-0.80 (m, 3 H) |
| 2-42 | 506.2 | $^{1}$H NMR (500 MHz, DMSO-$d_6$) δ ppm 8.79 (dd, J = 4.16, 1.59 Hz, 1 H) 7.59 (d, J = 8.31 Hz, 1 H) 7.35 (d, J = 1.96 Hz, 1 H) 7.23-7.32 (m, 1 H) 7.05-7.10 (m, 1 H) 6.30 (ddd, J = 16.99, 10.33, 1.41 Hz, 1 H) 6.10 (dd, J = 16.99, 2.20 Hz, 1 H) 5.67 (dd, J = 10.27, 2.20 Hz, 1 H) 4.26 (d, J = 8.56 Hz, 1 H) 4.16 (dd, J = 8.56, 4.40 Hz, 1 H) 3.83-4.00 (m, 4 H) 3.72-3.80 (m, 2 H) 2.79-2.86 (m, 1 H) 2.61-2.67 (m, 1 H) 2.28-2.39 (m, 1 H) 2.09-2.22 (m, 3 H) 1.93-2.05 (m, 1 H) 1.32-1.42 (m, 3 H) 1.25 (d, J = 9.66 Hz, 1 H) 1.14 (t, J = 7.27 Hz, 1 H) 0.68-0.72 (m, 3 H) |
| 2-43 | 506.2 | $^{1}$H NMR (500 MHz, DMSO-$d_6$) δ ppm 8.54 (dd, J-4.03, 1.59 Hz, 1 H) 8.21 (dd, J = 8.44, 1.71 Hz, 1 H) 7.42 (dd, J = 8.44, 4.16 Hz, 1 H) 7.25 (d, J = 2.57 Hz, 1 H) 7.21 (d, J = 2.69 Hz, 1 H) 6.26-6.34 (m, 1 H) 6.10 (dd, J = 16.99, 2.20 Hz, 1 H) 5.64-5.69 (m, 1 H) 4.23-4.29 (m, 1 H) 4.13-4.19 (m, 1 H) 3.93-3.98 (m, 1 H) 3.71-3.91 (m, 5 H) 2.79 (t, J = 5.50 Hz, 1 H) 2.59-2.64 (m, 1 H) 2.12-2.27 (m, 3 H) 2.01-2.09 (m, 2 H) 1.11-1.35 (m, 5 H) 0.75 (s, 3 H) |
| 2-44 | 506.3 | $^{1}$H NMR (500 MHz, DMSO-$d_6$) δ ppm 8.54 (dd, J = 4.03, 1.59 Hz, 1 H) 8.21 (dd, J = 8.44, 1.71 Hz, 1 H) 7.42 (dd, J = 8.44, 4.16 Hz, 1 H) 7.25 (d, J-2.57 Hz, 1 H) 7.21 (d, J-2.69 Hz, 1 H) 6.26-6.34 (m, 1 H) 6.10 (dd, J = 16.99, 2.20 Hz, 1 H) 5.64-5.69 (m, 1 H) 4.23-4.29 (m, 1 H) 4.13-4.19 (m, 1 H) 3.93-3.98 (m, 1 H) 3.71-3.91 (m, 5 H) 2.79 (t, J = 5.50 Hz, 1 H) 2.59-2.64 (m, 1 H) 2.12-2.27 (m, 3 H) 2.01-2.09 (m, 2 H) 1.11-1.35 (m, 5 H) 0.75 (s, 3 H) |
| 2-45 | 506.3 | $^{1}$H NMR (500 MHz, DMSO-$d_6$) δ ppm 8.60 (dd, J = 4.16, 1.71 Hz, 1 H) 8.22 (dd, J = 8.44, 1.71 Hz, 1 H) 7.43 (dd, J = 8.38, 4.10 Hz, 1 H) 7.25 (d, J = 2.69 Hz, 1 H) 7.18 (d, J = 2.69 Hz, 1 H) 6.30 (dd, J = 16.99, 10.39 Hz, 1 H) 6.10 (dd, J = 16.99, 2.20 Hz, 1 H) 5.64-5.69 (m, 1 H) 4.26 (dd, J = 8.50, 4.83 Hz, 1 H) 4.16 (d, J-8.68 Hz, 1 H) 3.66-3.99 (m, 6 H) 2.80 (t, J = 5.44 Hz, 1 H) 2.59-2.65 (m, 1 H) 2.25-2.31 (m, 1 H) 2.03-2.22 (m, 4 H) 1.22-1.36 (m, 3 H) 1.17 (d, J = 9.41 Hz, 1 H) 0.71 (8, 3 H) |
| 2-46 | 506.3 | $^{1}$H NMR (500 MHz, DMSO-$d_6$) δ ppm 8.79 (dd, J = 4.16, 1.59 Hz, 1 H) 7.59 (d, J = 8.31 Hz, 1 H) 7.35 (d, J = 1.96 Hz, 1 H) 7.23-7.32 (m, 1 H) 7.05-7.10 (m, 1 H) 6.30 (ddd, J = 16.99, 10.33, 1.41 Hz, 1 H) 6.10 (dd, J = 16.99, 2.20 Hz, 1 H) 5.67 (dd, J = 10.27, 2.20 Hz, 1 H) 4.26 (d, J = 8.56 Hz, 1 H) 4.16 (dd, J = 8.56, 4.40 Hz, 1 H) 3.83-4.00 (m, 4 H) 3.72-3.80 (m, 2 H) 2.79-2.86 (m, 1 H) 2.61-2.67 (m, 1 H) 2.28-2.39 (m, 1 H) 2.09-2.22 (m, 3 H) 1.93-2.05 (m, 1 H) 1.32-1.42 (m, 3 H) 1.25 (d, J = 9.66 Hz, 1 H) 1.14 (t, J = 7.27 Hz, 1 H) 0.68-0.72 (m, 3 H) |
| 2-47 | 506.3 | $^{1}$H NMR (500 MHz, DMSO-$d_6$) δ ppm 8.79 (dd, J = 4.16, 1.59 Hz, 1 H) 7.68 (br d, J = 8.31 Hz, 1 H) 7.35 (d, J = 2.20 Hz, 1 H) 7.27 (dd, J = 8.44, 4.28 Hz, 1 H) 7.06 (d, J = 2.32 Hz, 1 H) 6.30 (dd, J = 16.93, 10.33 Hz, 1 H) 6.10 (dd, J = 16.99, 2.20 Hz, 1 H) 5.67 (dd, J = 10.33, 2.26 Hz, 1 H) 4.22-4.30 (m, 1 H) 4.16 (br d, J = 8.56 Hz, 1 |

TABLE 20-continued

| Analytical Data for Examples 1-2 to 2-9 | | |
|---|---|---|
| Ex. # | LRMS: (ESI, +ve ion) m/z | NMR |
| | | H) 3.86-3.99 (m, 4 H) 3.72-3.84 (m, 2 H) 2.83 (t, J = 5.50 Hz, 1 H) 2.61-2.67 (m, 1 H) 2.25-2.37 (m, 1 H) 2.09-2.22 (m, 3 H) 2.03 (dd, J = 16.69, 3.00 Hz, 1 H) 1.35 (s, 3 H) 1.25 (d, J = 9.54 Hz, 1 H) 1.15 (t, J = 7.21 Hz, 1 H) 0.71 (s, 3 H) |
| 2-48 | 468.3 | $^1$H NMR (400 MHz, DMSO-$d_6$) δ ppm 13.10 (s, 1 H), 7.55 (d, J-8.4 Hz, 1 H), 7.21-7.45 (m, 2 H), 7.08 (d, J = 2.5 Hz, 1 H), 6.57-6.74 (m, 2 H), 6.24-6.42 (m, 1 H), 6.11 (dd, J = 17.1, 2.3 Hz, 1 H), 5.60-5.75 (m, 1 H), 4.28 (br d, J = 7.1 Hz, 1 H), 4.20 (br d, J = 7.7 Hz, 1 H), 3.90-4.03 (m, 2 H), 3.82-3.88 (m, 5 H), 3.71 (br t, J = 7.4 Hz, 2 H), 2.10-2.26 (m, 2 H), 1.94-1.99 (m, 6 H) |
| 2-49 | 468.0 | $^1$H NMR (400 MHz, DMSO-$d_6$) δ ppm 12.50 (d, J = 4.8 Hz, 1 H), 8.07 (s, 1 H), 7.76 (d, J = 8.2 Hz, 1H), 7.17 (d, J = 8.2 Hz, 1 H), 7.10 (d, J = 2.4 Hz, 1 H), 6.73-6.64 (m, 2 H), 6.38-6.30 (m, 1 H), 6.14-6.10 (m, 1 H), 5.68 (dd, J = 10.3, 2.2 Hz, 1 H), 4.31-4.21 (m, 2 H), 4.02-3.89 (m, 2 H), 3.86 3.84 (m, 5 H), 3.82-3.69 (m, 2 H), 2.22-2.14 (m, 2 H), 1.98-1.95 (m, 6 H). |
| 2-50 | 482.0 | $^1$H NMR (400 MHz, DMSO-$d_6$) δ ppm 8.05 (s, 1 H), 7.77 (d, J = 8.2 Hz, 1 H), 7.19 (d, J = 8.2 Hz, 1H), 7.10 (d, J = 2.4 Hz, 1 H), 6.74 (dd, J = 9.0, 2.5 Hz, 1 H), 6.60 (dd, J = 9.0, 3.0 Hz, 1 H), 6.37-6.29 (m, 1 H), 6.12 (dd, J = 17.0, 2.3 Hz, 1 H), 5.69-5.66 (m, 1 H), 4.27-4.17 (m, 2 H), 3.99-3.90 (m, 2 H), 3.87-3.85 (m, 5 H), 3.74-3.70 (m, 2 H), 3.15 (d, J = 10.6 Hz, 3 H), 2.17-2.15 (m, 2 H), 2.00-1.97 (m, 6 H). |
| 2-51 | 469.3 | $^1$H NMR (400 MHz, DMSO-$d_6$) δ ppm 12.99 (s, 1 H), 8.12 (d, J = 2.1 Hz, 1 H), 7.49 (d, J = 8.5 Hz, 1 H), 7.42 (d, J = 2.7 Hz, 1 H), 7.30-7.37 (m, 2 H), 6.28-6.40 (m, 1 H), 6.12 (dd, J = 16.8, 2.1 Hz, 1 H), 5.68 (dd, J = 10.4, 2.1 Hz, 1 H), 4.29 (dd, J = 8.5, 5.2 Hz, 1 H), 4.15-4.23 (m, 1 H), 3.89-4.04 (m, 7 H), 3.68-3.83 (m, 2 H), 2.19 (br t, J = 6.9 Hz, 2 H), 1.99 (s, 3 H), 1.93 (d, J = 7.9 Hz, 3 H) |
| 2-52 | 466.1 | $^1$H NMR (400 MHz, DMSO-de) δ ppm 7.73 (d, J-8.4 Hz, 1 H), 7.38 (ddd, J = 8.1, 6.3, 1.7 Hz, 1 H), 7.17-7.24 (m, 2 H), 7.16 (d, J = 2.3 Hz, 1 H), 6.93 (d, J = 2.5 Hz, 1 H), 6.73 (s, 1 H), 6.24-6.36 (m, 1 H), 6.10 (dd, J = 16.9, 2.3 Hz, 1 H), 5.61-5.71 (m, 1 H), 4.20-4.25 (m, 2 H), 4.18 (br d, J = 4.6 Hz, 1 H), 3.85-3.97 (m, 4 H), 3.61 (d, J = 2.3 Hz, 2 H), 3.50 (br t, J = 7.1 Hz, 2 H), 2.82-2.92 (m, 2 H), 2.12-2.23 (m, 2 H), 1.81-1.90 (m, 2 H) |
| 2-53 | 466.2 | $^1$H NMR (500 MHz, DMSO-$d_6$) δ ppm 9.79 (s, 1 H), 7.73 (d, J = 8.3 Hz, 1 H), 7.38 (ddd, J = 8.2, 6.4, 1.6 Hz, 1 H), 7.17-7.23 (m, 2 H), 7.16 (d, J = 2.3 Hz, 1 H), 6.92 (d, J = 2.4 Hz, 1 H), 6.73 (s, 1 H), 6.25-6.35 (m, 1 H), 6.10 (dd, J = 17.0, 2.2 Hz, 1 H), 5.61-5.70 (m, 1 H), 4.19-4.26 (m, 1 H), 4.14-4.19 (m, 1 H), 3.82-3.97 (m, 4 H), 3.58-3.65 (m, 2 H), 3.44-3.55 (m, 2 H), 2.87 (q, J = 6.2 Hz, 2 H), 2.10-2.22 (m, 2 H), 1.81-1.89 (m, 2 H) |
| 2-54 | 466.2 | $^1$H NMR (500 MHz, DMSO-$d_6$) δ ppm 9.79 (s, 1 H), 7.73 (d, J = 8.3 Hz, 1 H), 7.38 (ddd, J = 8.1, 6.4, 1.6 Hz, 1 H), 7.18-7.23 (m, 2 H), 7.16 (d, J = 2.3 Hz, 1 H), 6.92 (d, J = 2.4 Hz, 1 H), 6.73 (s, 1 H), 6.24-6.35 (m, 1 H), 6.10 (dd, J = 17.0, 2.2 Hz, 1 H), 5.63-5.68 (m, 1 H), 4.20-4.26 (m, 1 H), 4.13-4.19 (m, 1 H), 3.80-3.97 (m, 4 H), 3.61 (d, J = 3.5 Hz, 2 H), 3.42-3.55 (m, 2 H), 2.87 (q, J = 6.2 Hz, 2 H), 2.17 (quin, J = 6.5 Hz, 2 H), 1.79-1.90 (m, 2 H) |
| 2-55 | 438.2 | $^1$H NMR (500 MHz, DMSO-$d_6$) δ ppm 7.68 (d, J = 7.8 Hz, 1 H), 7.57 (d, J = 8.6 Hz, 1 H), 7.47 (ddd, J = 8.3, 6.9, 1.4 Hz, 1 H), 7.41 (d, J = 8.6 Hz, 1 H), 7.34 (br d, J = 15.5 Hz, 1 H), 7.00-7.07 (m, 1 H), 6.75 (br d, J = 8.2 Hz, 1 H), 6.28-6.37 (m, 1 H), 6.11 (dd, J = 17.1, 2.3 Hz, 1 H), 5.64-5.70 (m, 1 H), 4.28 (dd, J = 8.5, 4.0 Hz, 1 H), 4.15-4.22 (m, 1 H), 3.98-4.03 (m, 1 H), 3.89-3.95 (m, 1 H), 3.87 (s, 2 H), 3.67-3.78 (m, 2 H), 3.57-3.57 (m, 1 H), 2.11-2.22 (m, 2 H), 1.99 (s, 3 H), 1.96 (d, J = 8.4 Hz, 3 H) |
| 2-56 | 438.2 | $^1$H NMR (500 MHz, DMSO-$d_6$) δ ppm 7.66-7.71 (m, 1 H), 7.57 (d, J = 8.6 Hz, 1 H), 7.47 (ddd, J = 8.3, 7.0, 1.3 Hz, 1 H), 7.41 (d, J = 8.6 Hz, 1 H), 7.34 (br d, J = 15.5 Hz, 1 H), 7.00-7.06 (m, 1 H), 6.94-6.95 (m, 1 H), 6.75 (br d, J = 8.2 Hz, 1 H), 6.27-6.37 (m, 1 H), 6.11 (dd, J = 16.9, 2.3 Hz, 1 H), 5.81-5.81 (m, 1 H), 5.64-5.70 (m, 1 H), 4.28 (dd, J = 8.5, 3.9 Hz, 1 H), 4.15-4.21 (m, 1 H), 3.97-4.02 (m, 1 H), 3.89-3.95 (m, 1 H), 3.87 (s, 2 H), 3.66-3.79 (m, 2 H), 2.12-2.23 (m, 2 H), 1.99 (s, 3 H), 1.96 (d, J = 8.4 Hz, 2 H) |
| 2-57 | 452.3 | $^1$H NMR (400 MHz, DMSO-$d_6$) δ ppm 13.13 (br s, 1 H), 7.73 (dd, J = 8.3, 3.9 Hz, 1 H), 7.58 (d, J = 8.4 Hz, 1 H), 7.50 (br t, J = 7.5 Hz, 1 H), 7.38-7.47 (m, 2 H), 7.04-7.17 (m, 1 H), 6.69-6.89 (m, 1 H), 6.28-6.44 (m, 1 H), 6.13 (br d, J = 17.1 Hz, 1 H), 5.69 (dd, J = 10.2, 2.3 Hz, 1 H), 4.23-4.52 (m, 2 H), 3.68-4.22 (m, 4 H), 3.37-3.48 (m, 1 H), 2.20-2.29 (m, 1 H), 2.05 (d, J = 1.9 Hz, 2 H), 1.84-1.98 (m, 5 H), 1.28-1.34 (m, 3 H) |
| 2-58 | 470.3 | $^1$H NMR (400 MHz, DMSO-$d_6$) δ ppm 13.08-13.21 (m, 1 H), 7.59 (br d, J-8.2 Hz, 1 H), 7.15-7.52 (m, 3 H), 6.91-7.06 (m, 1 H), 6.72-6.88 (m, 1 H), 6.30-6.44 (m, 1 H), 6.07-6.18 (m, 1 H), 5.69 (dd, J = 10.2, 2.3 Hz, 1 H), 4.23-4.51 (m, 2 H), 3.96-4.21 (m, 2 H), 3.76-3.95 (m, 2 H), 3.36-3.52 (m, 2 H), 2.18-2.29 (m, 1 H), 2.01-2.16 (m, 2 H), 1.88-1.97 (m, 4 H), 1.26-1.35 (m, 3 H) |
| 2-59 | 470.3 | $^1$H NMR (400 MHz, DMSO-$d_6$) δ ppm 13.14 (br s, 1 H), 7.58 (d, J = 8.6 Hz, 1 H), 7.14-7.50 (m, 3 H), 6.73-7.03 (m, 2 H), 6.31-6.44 (m, 1 H), 6.08-6.18 (m, 1 H), 5.69 (dd, J = 10.3, 2.4 Hz, 1 H), 4.43-4.52 (m, 1 H), 4.40 (br d, J = 8.8 Hz, 1 H), 3.94-4.22 (m, 2 H), 3.76-3.92 (m, 2 H), 3.42-3.55 (m, 1 H), 2.19-2.30 (m, 1 H), 2.00-2.15 (m, 3 H), 1.93 (dd, J = 10.8, 4.5 Hz, 3 H), 1.89 (s, 1 H), 1.27-1.34 (m, 3 H) |

TABLE 20-continued

| Analytical Data for Examples 1-2 to 2-9 | | |
|---|---|---|
| Ex. # | LRMS: (ESI, +ve ion) m/z | NMR |
| 2-60 | 470.2 | $^1$H NMR (500 MHz, DMSO-$d_6$) δ ppm 13.14 (s, 1 H), 7.64 (br d, J-8.4 Hz, 1 H), 7.58 (d, J = 8.6 Hz, 1 H), 7.37-7.44 (m, 2 H), 7.16 (br d, J = 4.0 Hz, 1 H), 6.90-6.99 (m, 1 H), 6.71-6.80 (m, 1 H), 6.36 (dt, J = 17.0, 9.5 Hz, 1 H), 6.12 (dt, J = 17.0, 2.6 Hz, 1 H), 5.64-5.72 (m, 1 H), 4.39-4.51 (m, 1 H), 4.13-4.29 (m, 1 H), 4.03-4.12 (m, 1 H), 3.82-3.96 (m, 2 H), 3.38-3.48 (m, 1 H), 2.18-2.30 (m, 1 H), 2.05 (d, J-2.8 Hz, 3 H), 1.94 (d, J = 5.7 Hz, 3 H), 1.30 (t, J-6.7 Hz, 3 H), 1.16 (br s, 1 H) |
| 2-61 | 470.2 | $^1$H NMR (500 MHz, DMSO-$d_6$) δ ppm 13.13 (s, 1 H), 7.58 (d, J = 8.6 Hz, 1 H), 7.47 (br d, J = 8.3 Hz, 1 H), 7.35-7.43 (m, 2 H), 6.95-7.02 (m, 1 H), 6.83 (dt, J = 9.0, 5.8 Hz, 1 H), 6.36 (ddd, J = 16.9, 10.5, 6.1 Hz, 1 H), 6.13 (br d, J = 17.0 Hz, 1 H), 5.66-5.71 (m, 1 H), 4.45 (dd, J = 13.8, 6.5 Hz, 1 H), 4.17-4.28 (m, 1 H), 4.03-4.14 (m, 1 H), 3.88-3.97 (m, 1 H), 3.71-3.83 (m, 1 H), 3.43-3.52 (m, 1 H), 2.25 (dt, J = 7.5, 3.8 Hz, 1 H), 2.04-2.13 (m, 1 H), 1.92 (d, J = 5.3 Hz, 3 H), 1.89 (s, 3 H), 1.31 (t, J = 5.7 Hz, 3 H), 1.23 (br s, 1 H) |
| 2-62 | 446.2 | $^1$H NMR (400 MHz, DMSO-$d_6$) δ ppm 9.23 (s, 1 H), 7.10 (d, J-8.4 Hz, 1 H), 6.68 (dd, J = 8.2, 2.7 Hz, 1 H), 6.27-6.38 (m, 2 H), 6.11 (dd, J = 17.1, 2.3 Hz, 1 H), 5.63-5.70 (m, 1 H), 4.11-4.28 (m, 2 H), 3.83-3.97 (m, 2 H), 3.53-3.65 (m, 2 H), 3.36-3.51 (m, 2 H), 2.48 (s, 3 H), 2.04-2.21 (m, 3 H), 1.88-2.01 (m, 1 H), 1.75-1.82 (m, 6 H), 0.93 (d, J = 10.7 Hz, 6 H) |
| 2-63 | 473.2 | $^1$H NMR (400 MHz, $CDCl_3$) δ ppm 7.48-7.58 (m, 1 H), 7.35-7.45 (m, 2 H), 7.18-7.25 (m, 1 H), 6.32-6.41 (m, 1 H), 6.14-6.26 (m, 1 H), 5.64-5.76 (m, 1 H), 4.22-4.29 (m, 1 H), 4.08-4.18 (m, 2 H), 3.83-4.06 (m, 5 H), 2.81-2.95 (m, 1 H), 2.61-2.71 (m, 1 H), 2.41-2.50 (m, 1 H), 2.31-2.40 (m, 1 H), 2.17-2.27 (m, 2 H), 1.38-1.43 (m, 3 H), 1.23-1.36 (m, 2 H), 0.72-0.79 (m, 3 H) |
| 2-64 | 489.2 | $^1$H NMR (400 MHz, $CDCl_3$) δ ppm 7.29-7.38 (m, 1 H), 6.81-6.93 (m, 1 H), 6.62-6.74 (m, 1 H), 6.33-6.44 (m, 1 H), 6.11-6.25 (m, 1 H), 5.69-5.77 (m, 1 H), 3.73-4.32 (m, 8 H), 2.81-2.91 (m, 1 H), 2.62-2.70 (m, 1 H), 2.33-2.56 (m, 2 H), 2.11-2.28 (m, 2 H), 1.37-1.41 (m, 3 H), 1.21-1.33 (m, 2 H), 0.67-0.79 (m, 3 H). The free OH proton is not observed in $CDCl_3$ |
| 2-65 | 502.9 | $^1$H NMR (400 MHz, $CDCl_3$) δ ppm 7.48-7.53 (m, 1 H), 7.36-7.42 (m, 1 H), 7.21-7.25 (m, 1 H), 6.32-6.41 (m, 1 H), 6.15-6.25 (m, 1 H), 5.66-5.74 (m, 1 H), 4.69-4.78 (m, 2 H), 3.83-4.30 (m, 8 H), 2.87 (t, J = 5.5 Hz, 1 H), 2.62-2.71 (m, 1 H), 2.33-2.49 (m, 2 H), 2.18-2.25 (m, 3 H), 1.40 (s, 3 H), 1.26-1.34 (m, 1 H), 0.75 (d, J = 12.8 Hz, 3 H). The OH proton is not observed in $CDCl_3$ |
| 2-66 | 472.9 | $^1$H NMR (400 MHz, $CDCl_3$) δ ppm 7.02-7.11 (m, 1 H), 6.84-6.91 (m, 1 H), 6.63-6.74 (m, 1 H), 6.33-6.42 (m, 1 H), 6.15-6.26 (m, 1 H), 5.69-5.76 (m, 1 H), 3.83-4.29 (m, 8 H), 2.81-2.92 (m, 1 H), 2.62-2.72 (m, 1 H), 2.40-2.57 (m, 2 H), 2.14-2.30 (m, 3 H), 1.38-1.41 (m, 3 H), 1.23-1.33 (m, 1 H), 0.68-0.76 (m, 3 H). The OH proton is not observed in $CDCl_3$ |
| 2-67 | 469.3 | $^1$H NMR (400 MHz, $CDCl_3$) δ ppm 7.14-7.25 (m, 1 H), 6.79-6.92 (m, 1 H), 6.49-6.64 (m, 1 H), 6.30-6.46 (m, 1 H), 6.12-6.27 (m, 1 H), 5.62-5.79 (m, 1 H), 3.84-4.31 (m, 8 H), 2.84-2.95 (m, 1 H), 2.59-2.76 (m, 1 H), 2.42-2.52 (m, 1 H), 2.16-2.34 (m, 4 H), 2.04-2.08 (m, 3 H), 1.37-1.44 (m, 3 H), 1.24-1.32 (m, 1 H), 0.70-0.77 (m, 3 H). The OH proton is not observed in $CDCl_3$ |
| 2-68 | 469.3 | $^1$H NMR (500 MHz, DMSO-$d_6$) δ ppm 7.06-7.23 (m, 1 H), 6.67-6.87 (m, 1 H), 6.47 (d, J = 2.6 Hz, 1 H), 6.25-6.37 (m, 1 H), 6.05-6.16 (m, 1 H), 5.59-5.73 (m, 1 H), 4.26 (dd, J = 8.6, 2.3 Hz, 1 H), 4.12-4.19 (m, 1 H), 3.92-4.00 (m, 1 H), 3.81-3.92 (m, 3 H), 3.68-3.80 (m, 2 H), 2.75-2.81 (m, 1 H), 2.60-2.68 (m, 1 H), 2.30-2.41 (m, 1 H), 2.11-2.23 (m, 4 H), 1.92-1.99 (m, 3 H), 1.31-1.39 (m, 3 H), 1.18-1.23 (m, 1 H), 0.67 (s, 3 H). The OH proton is not observed. |
| 2-69 | 469.3 | $^1$H NMR (500 MHz, DMSO-$d_6$) δ ppm 7.13 (d, J = 8.4 Hz, 1 H), 6.73 (dd, J = 8.2, 2.6 Hz, 1 H), 6.46 (d, J = 2.6 Hz, 1 H), 6.30 (dd, J = 17.0, 10.3 Hz, 1 H), 6.05-6.15 (m, 1 H), 5.63-5.72 (m, 1 H), 4.26 (br d, J = 8.4 Hz, 1 H), 4.15 (br d, J = 8.7 Hz, 1 H), 3.93-3.99 (m, 1 H), 3.79-3.91 (m, 3 H), 3.69-3.77 (m, 2 H), 2.72-2.81 (m, 1 H), 2.60-2.68 (m, 1 H), 2.28-2.36 (m, 1 H), 2.10-2.24 (m, 4 H), 1.93 (d, J = 1.3 Hz, 3 H), 1.36 (s, 3 H), 1.12-1.19 (m, 1 H), 0.59-0.75 (m, 3 H). The OH proton is not observed. |
| 2-70 | 472.9 | $^1$H NMR (400 MHz, $CDCl_3$) δ ppm 7.12-7.21 (m, 1 H), 6.89-7.03 (m, 2 H), 6.33-6.42 (m, 1 H), 6.15-6.29 (m, 1 H), 5.67-5.73 (m, 1 H), 3.83-4.30 (m, 8 H), 2.82-2.94 (m, 1 H), 2.63-2.72 (m, 1 H), 2.50-2.59 (m, 1 H), 2.38-2.49 (m, 1 H), 2.17-2.26 (m, 3 H), 1.39-1.42 (m, 3 H), 1.24-1.34 (m, 1 H), 0.69-0.78 (m, 3 H). The OH proton is not observed in $CDCl_3$ |
| 2-71 | 473.2 | $^1$H NMR (500 MHz, DMSO-$d_6$) δ ppm 7.16-7.35 (m, 1 H), 6.78-7.02 (m, 2 H), 6.25-6.41 (m, 1 H), 6.03-6.19 (m, 1 H), 5.59-5.71 (m, 1 H), 4.22-4.30 (m, 1 H), 4.11-4.21 (m, 1 H), 3.67-4.00 (m, 6 H), 2.71-2.80 (m, 1 H), 2.60-2.69 (m, 1 H), 2.38-2.46 (m, 1 H), 2.27-2.34 (m, 1 H), 2.10-2.22 (m, 3 H), 1.32-1.38 (m, 3 H), 1.16-1.22 (m, 1 H), 0.60-0.68 (m, 3 H). The OH proton is not observed. |
| 2-72 | 473.2 | $^1$H NMR (500 MHz, DMSO-$d_6$) δ ppm 9.82 (s, 1 H), 7.24 (ddd, J = 11.1, 6.0, 3.7 Hz, 1 H), 6.78-6.98 (m, 2 H), 6.22-6.49 (m, 1 H), 6.10 (dd, J = 17.0, 2.2 Hz, 1 H), 5.62-5.71 (m, 1 H), 4.22-4.29 (m, 1 H), 4.12-4.19 (m, 1 H), 3.66-3.99 (m, 6 H), 2.73-2.80 (m, 1 H), 2.57-2.68 (m, 1 H), 2.39-2.47 (m, 1 H), 2.28- |

TABLE 20-continued

| Ex. # | LRMS: (ESI, +ve ion) m/z | NMR |
|---|---|---|
| Analytical Data for Examples 1-2 to 2-9 | | |
| | | 2.38 (m, 1 H), 2.09-2.24 (m, 3 H), 1.30-1.39 (m, 3 H), 1.14-1.22 (m, 1 H), 0.67-0.72 (m, 3 H) |
| 2-73 | 487.0 | $^1$H NMR (400 MHz, $CDCl_3$) δ ppm 7.41-7.50 (m, 2 H), 7.10-7.19 (m, 1 H), 6.31-6.44 (m, 1 H), 6.15-6.28 (m, 1 H), 5.66-5.78 (m, 1 H), 4.40-4.59 (m, 2 H), 4.21-4.31 (m, 1 H), 4.09-4.18 (m, 2 H), 3.84-4.07 (m, 5 H), 2.83-2.95 (m, 1 H), 2.59-2.73 (m, 1 H), 2.39-2.51 (m, 1 H), 2.25-2.36 (m, 1 H), 2.17-2.26 (m, 3 H), 1.39-1.42 (m, 3 H), 1.24-1.30 (m, 1 H), 0.70-0.77 (m, 3 H). The OH proton is not observed in $CDCl_3$ |
| 2-74 | 489.2 | $^1$H NMR (500 MHz, DMSO-$d_6$) δ ppm 7.26-7.48 (m, 1 H), 6.87 (dd, J = 8.8, 2.9 Hz, 1 H), 6.56-6.76 (m, 1 H), 6.23-6.39 (m, 1 H), 5.98-6.17 (m, 1 H), 5.63-5.70 (m, 1 H), 4.26 (dd, J = 8.6, 3.3 Hz, 1 H), 4.15 (d, J = 8.6 Hz, 1 H), 3.69-3.98 (m, 6 H), 2.78 (t, J = 5.5 Hz, 1 H), 2.60-2.70 (m, 1 H), 2.31 (d, J-2.6 Hz, 2 H), 2.10-2.25 (m, 3 H), 1.36 (s, 3 H), 1.10-1.19 (m, 1 H), 0.62-0.71 (m, 3 H). The OH proton is not observed. |
| 2-75 | 489.2 | $^1$H NMR (500 MHz, DMSO-$d_6$) δ ppm 7.38 (d, J = 8.7 Hz, 1 H), 6.87 (dd, J = 8.7, 2.9 Hz, 1 H), 6.63-6.71 (m, 1 H), 6.20-6.39 (m, 1 H), 6.03-6.16 (m, 1 H), 5.64-5.71 (m, 1 H), 4.22-4.31 (m, 1 H), 4.11-4.21 (m, 1 H), 3.64-3.99 (m, 6 H), 2.73-2.82 (m, 1 H), 2.59-2.70 (m, 1 H), 2.24-2.38 (m, 2 H), 2.09-2.25 (m, 3 H), 1.36 (s, 3 H), 1.21 (d, J-9.5 Hz, 1 H), 0.69 (s, 3 H). The OH proton is not observed. |
| 2-76 | 504.0 | $^1$H NMR (400 MHz, $CDCl_3$) δ ppm 7.73 (d, J = 8.2 Hz, 1 H), 7.42 (ddd, J = 8.1, 6.3, 1.7 Hz, 1 H), 7.17-7.27 (m, 3 H), 6.77-6.91 (m, 1 H), 6.33-6.44 (m, 1 H), 6.07-6.27 (m, 1 H), 5.70 (ddd, J = 14.2, 10.4, 1.6 Hz, 1 H), 3.66-4.39 (m, 10 H), 2.77 (s, 2 H), 2.11-2.22 (m, 2 H), 1.25-1.29 (m, 6 H). The OH proton is not observed in $CDCl_3$. |
| 2-77 | 504.2 | $^1$H NMR (400 MHz, $CDCl_3$) δ ppm 7.74 (d, J = 8.4 Hz, 1 H), 7.40-7.49 (m, 1 H), 7.21-7.27 (m, 3 H), 6.84-6.90 (m, 1 H), 6.32-6.41 (m, 1 H), 6.13-6.28 (m, 1 H), 5.64-5.74 (m, 1 H), 3.69-4.33 (m, 10 H), 2.72-2.81 (m, 2 H), 2.13-2.23 (m, 2 H), 1.28 (s, 3 H), 1.25-1.27 (m, 3 H). The OH proton is not observed in $CDCl_3$. |
| 2-78 | 504.2 | $^1$H NMR (400 MHz, $CDCl_3$) δ ppm 7.70-7.80 (m, 1 H), 7.44 (ddd, J = 8.2, 6.3, 1.8 Hz, 1 H), 7.20-7.27 (m, 3 H), 6.78-6.91 (m, 1 H), 6.32-6.41 (m, 1 H), 6.11-6.29 (m, 1 H), 5.62-5.81 (m, 1 H), 3.70-4.34 (m, 10 H), 2.72-2.83 (m, 2 H), 2.12-2.23 (m, 2 H), 1.28 (s, 3 H), 1.25-1.27 (m, 3 H). The OH proton is not observed in $CDCl_3$. |
| 2-79 | 468.0 | $^1$H NMR (400 MHz, $CDCl_3$) δ ppm 7.13-7.18 (m, 1 H), 6.78-6.83 (m, 1 H), 6.41-6.48 (m, 1 H), 6.32-6.40 (m, 1 H), 6.15-6.28 (m, 1 H), 5.66-5.71 (m, 1 H), 3.65-4.38 (m, 10 H), 2.68-2.76 (m, 2 H), 2.10-2.25 (m, 2 H), 1.95 (s, 3 H), 1.28 (d, J = 2.9 Hz, 6 H). The OH proton is not observed in CDCl. |
| 2-80 | 468.2 | $^1$H NMR (500 MHz, DMSO-$d_6$) δ ppm 9.16-9.43 (m, 1 H), 6.99-7.21 (m, 1 H), 6.63-6.82 (m, 1 H), 6.36-6.42 (m, 1 H), 6.25-6.36 (m, 1 H), 6.04-6.13 (m, 1 H), 5.61-5.72 (m, 1 H), 4.23 (dd, J = 8.5, 3.0 Hz, 1 H), 4.09-4.17 (m, 2 H), 3.84-3.97 (m, 3 H), 3.71-3.78 (m, 2 H), 3.55-3.70 (m, 2 H), 2.58-2.70 (m, 2 H), 2.03-2.21 (m, 2 H), 1.81-1.86 (m, 3 H), 1.14-1.23 (m, 6 H) |
| 2-81 | 484.2 | 1H NMR (500 MHz, DMSO-$d_6$) δ ppm 9.34 (s, 1 H), 7.05-7.17 (m, 1 H), 6.72 (s, 1 H), 6.39 (d, J = 2.6 Hz, 1 H), 6.27-6.36 (m, 1 H), 6.07-6.15 (m, 1 H), 5.63-5.69 (m, 1 H), 4.20-4.27 (m, 1 H), 4.09-4.19 (m, 2 H), 3.84-3.96 (m, 3 H), 3.71-3.80 (m, 2 H), 3.57-3.70 (m, 2 H), 2.59-2.69 (m, 2 H), 2.02-2.20 (m, 2 H), 1.78-1.88 (m, 3 H), 1.14-1.24 (m, 6 H) |
| 2-82 | 484.2 | $^1$H NMR (400 MHz, $CDCl_3$) δ ppm 8.28-8.40 (m, 1 H), 7.55 (dd, J = 8.5, 7.0 Hz, 1 H), 7.21-7.26 (m, 1 H), 7.12-7.17 (m, 1 H), 6.87-6.97 (m, 1 H), 6.73-6.83 (m, 1 H), 6.34-6.43 (m, 1 H), 6.10-6.27 (m, 1 H), 5.62 (d, J = 4.0 Hz, 1 H), 3.76-4.36 (m, 10 H), 2.97-3.04 (m, 2 H), 2.28 (br d, J = 6.3 Hz, 2 H), 1.86-1.97 (m, 3 H), 1.24-1.27 (m, 3 H), 1.20-1.23 (m, 3 H). The OH proton is not observed in $CDCl_3$. |
| 2-83 | 492.2 | $^1$H NMR (400 MHz, $CDCl_3$) δ ppm 7.57 (s, 1 H), 7.44-7.49 (m, 1 H), 7.35 (d, J = 8.8 Hz, 1 H), 6.32-6.43 (m, 1 H), 6.15-6.28 (m, 1 H), 5.69 (dd, J = 10.2, 1.9 Hz, 1 H), 3.73-4.30 (m, 10 H), 2.77 (s, 2 H), 2.14-2.23 (m, 5 H), 1.28-1.29 (m, 3 H), 1.26-1.27 (m, 3 H). The indazole NH is not observed in $CDCl_3$. |
| 2-84 | 492.2 | $^1$H NMR (600 MHz, DMSO-$d_6$) δ ppm 12.96-13.28 (m, 1 H), 7.47-7.53 (m, 1 H), 7.38-7.41 (m, 1 H), 7.31-7.34 (m, 1 H), 6.26-6.39 (m, 1 H), 6.05-6.17 (m, 1 H), 5.62-5.71 (m, 1 H), 4.22-4.32 (m, 1 H), 4.12-4.20 (m, 1 H), 3.74-4.01 (m, 6 H), 3.62-3.72 (m, 2 H), 2.63-2.74 (m, 2 H), 2.09-2.17 (m, 2 H), 2.05-2.08 (m, 3 H), 1.19 (d, J = 2.9 Hz, 6 H) |
| 2-85 | 492.2 | IH NMR (600 MHz, DMSO-$d_6$) δ ppm 12.99-13.29 (m, 1 H), 8.23 (s, 1 H), 7.50 (br d, J = 8.1 Hz, 1 H), 7.33 (d, J = 8.7 Hz, 1 H), 6.27-6.38 (m, 1 H), 6.06-6.15 (m, 1 H), 5.60-5.71 (m, 1 H), 4.10-4.32 (m, 2 H), 3.59-3.99 (m, 8 H), 2.65-2.70 (m, 2 H), 2.09-2.18 (m, 2 H), 2.04-2.08 (m, 3 H), 1.17-1.20 (m, 6 H) |
| 2-86 | 506.2 | $^1$H NMR (400 MHz, $CDCl_3$) δ ppm 7.95 (s, 1 H), 7.63-7.70 (m, 1 H), 7.06-7.12 (m, 1 H), 6.33-6.42 (m, 1 H), 6.16-6.28 (m, 1 H), 5.62-5.75 (m, 1 H), 3.77 ~ 4.31 (m, 10 H), 3.55 (s, 3 H), 2.72-2.82 (m, 2 H), 2.17-2.23 (m, 2 H), 2.12-2.16 (m, 3 H), 1.26-1.32 (m, 6 H) |
| 2-87 | 506.2 | $^1$H NMR (400 MHz, $CDCl_3$) δ ppm 7.94 (s, 1 H), 7.63-7.71 (m, 1 H), 7.05-7.16 (m, 1 H), 6.32-6.41 (m, 1 H), 6.13-6.27 (m, 1 H), 5.63-5.74 (m, 1 H), 3.75- |

TABLE 20-continued

| Ex. # | LRMS: (ESI, +ve ion) m/z | NMR |
|---|---|---|
| | | 4.31 (m, 10 H), 3.53-3.64 (m, 3 H), 2.73-2.81 (m, 2 H), 2.17-2.23 (m, 2 H), 2.12-2.16 (m, 3 H), 1.29 (s, 3 H), 1.25-1.28 (m, 3 H |
| 2-88 | 506.2 | $^1$H NMR (400 MHz, $CDCl_3$) δ ppm 7.94 (s, 1 H), 7.66 (d, J = 8.4 Hz, 1 H), 7.09 (d, J = 8.4 Hz, 1 H), 6.33-6.41 (m, 1 H), 6.15-6.30 (m, 1 H), 5.62-5.75 (m, 1 H), 3.76-4.30 (m, 10 H), 3.52-3.63 (m, 3 H), 2.71-2.81 (m, 2 H), 2.20 (t, J = 7.0 Hz, 2 H), 2.13-2.16 (m, 3 H), 1.28-1.30 (m, 3 H), 1.26-1.28 (m, 3 H) |
| 2-89 | 540.0 | $^1$H NMR (400 MHz, $CDCl_3$) δ ppm 7.91 (s, 1 H), 7.76-7.83 (m, 1 H), 6.33-6.45 (m, 1 H), 6.16-6.28 (m, 1 H), 5.64-5.78 (m, 1 H), 3.78-4.28 (m, 10 H), 3.51-3.61 (m, 3 H), 2.71-2.84 (m, 2 H), 2.13-2.25 (m, 5 H), 1.28 (d, J = 3.6 Hz, 6 H) |
| 2-90 | 540.0 | $^1$H NMR (400 MHz, $CDCl_3$) δ ppm 7.91 (s, 1 H), 7.76-7.82 (m, 1 H), 6.32-6.44 (m, 1 H), 6.15-6.27 (m, 1 H), 5.64-5.73 (m, 1 H), 3.78-4.32 (m, 10 H), 3.52-3.61 (m, 3 H), 2.70-2.83 (m, 2 H), 2.16-2.25 (m, 5 H), 1.28-1.30 (m, 3 H), 1.27-1.28 (m, 3 H) |
| 2-91 | 540.0 | 3H NMR (400 MHz, $CDCl_3$) δ ppm 7.91 (s, 1 H), 7.80 (s, 1 H), 6.33-6.42 (m, 1 H), 6.15-6.29 (m, 1 H), 5.63-5.76 (m, 1 H), 3.77-4.30 (m, 10 H), 3.56 (s, 3 H), 2.73-2.84 (m, 2 H), 2.12-2.28 (m, 5 H), 1.29 (s, 3 H), 1.28 (s, 3 H) |
| 2-92 | 526.2 | $^1$H NMR (400 MHz, $CDCl_3$) δ ppm 7.98-8.08 (m, 1 H), 7.83-7.89 (m, 1 H), 6.32-6.40 (m, 1 H), 6.16-6.27 (m, 1 H), 5.66-5.73 (m, 1 H), 3.75-4.32 (m, 10 H), 2.70-2.81 (m, 2 H), 2.23 (s, 3 H), 2.16-2.21 (m, 2 H), 1.27-1.28 (m, 6 H). The indazole NH proton is not observed in $CDCl_3$. |
| 2-93 | 452.2 | $^1$H NMR (400 MHz, Methanol-$d_4$) δ ppm 7.51 (1 H, d, J = 8.57 Hz) 7.45 (1 H, s) 7.39 (1 H, d, J = 8.57 Hz) 6.70 (1 H, s) 6.38 (1 H, dd, J = 17.14, 10.24 Hz) 6.27 (1 H, dd, J = 17.14, 1.88 Hz) 5.75 (1 H, dd, J = 10.24, 2.09 Hz) 4.25-4.38 (2 H, m) 4.02-4.15 (2 H, m) 3.73-3.80 (2 H, m) 3.62-3.73 (2 H, m) 2.89 (2 H, t, J = 6.38 Hz) 2.28 (2 H, t, J = 6.90 Hz) 2.17 (3 H, s) 2.05-2.12 (2 H, m) 1.71-1.81 (2 H, m) 1.59-1.70 (2 H, m) |
| 2-94 | 511.3 | $^1$H NMR (400 MHz, DMSO-$d_6$) δ ppm 13.10 (1 H, s) 7.51 (1 H, d, J = 8.57 Hz) 7.47 (1 H, s) 7.33 (1 H, d, J = 8.57 Hz) 6.71 (1 H, s) 6.59 (1 H, dt, J = 15.47, 6.17 Hz) 6.11 (1 H, d, J = 15.47 Hz) 4.23 (1 H, br d, J = 8.36 Hz) 4.16 (1 H, br d, J = 8.36 Hz) 3.85-4.00 (4 H, m) 3.81 (2 H, t, J = 5.75 Hz) 3.68-3.76 (2 H, m) 3.60 (2 H, br t, J = 6.58 Hz) 3.06 (2 H, br d, J = 5.60 Hz) 2.88 (2 H, br t, J = 5.60 Hz) 2.14-2.22 (8 H, m) 2.11 (3 H, s) |
| 2-95 | 454.2 | $^1$H NMR (400 MHz, DMSO-$d_6$) δ ppm 13.10 (1 H, s) 7.51 (1 H, d, J = 8.57 Hz) 7.47 (1 H, s) 7.33 (1 H, d, J = 8.57 Hz) 6.71 (1 H, s) 6.32 (1 H, dd, J = 16.93, 10.24 Hz) 6.11 (1 H, dd, J = 16.93, 2.30 Hz) 5.68 (1 H, dd, J = 10.45, 2.30 Hz) 4.26 (1 H, d, J = 8.57 Hz) 4.18 (1 H, br d, J = 8.57 Hz) 3.87-4.00 (4 H, m) 3.81 (2 H, t, J = 5.75 Hz) 3.68-3.76 (2 H, m) 3.61 (2 H, br t, J = 6.58 Hz) 2.88 (2 H, t, J = 5.64 Hz) 2.15-2.24 (2 H, m) 2.11 (3 H, s) |
| 2-96 | 468.3 | $^1$H NMR (400 MHz, DMSO-$d_6$) δ ppm 8.04 (1 H, s) 7.72 (1 H, m, J = 8.36 Hz) 7.14 (1 H, m, J = 8.36 Hz) 6.77 (1 H, s) 6.32 (1 H, dd, J = 16.93, 10.24 Hz) 6.11 (1 H, dd, J = 16.93, 2.30 Hz) 5.68 (1 H, dd, J = 10.24, 2.30 Hz) 4.26 (1 H, br d, J = 8.57 Hz) 4.18 (1 H, br d, J = 8.57 Hz) 3.72-3.98 (8 H, m) 3.62 (2 H, br t, J = 6.79 Hz) 3.44 (3 H, d, J = 1.46 Hz) 2.85-2.92 (2 H, m) 2.17-2.25 (2 H, m) 2.13 (3 H, s) |
| 2-97 | 494.2 | $^1$H NMR (400 MHz, DMSO-$d_6$) δ: 8.03 (s, 1 H), 7.69 (d, J-8.2 Hz, 1 H), 7.14 (d, J = 8.3 Hz, 1 H), 6.66 (s, 1 H), 6.32 (ddd, J = 17.0, 10.3, 1.5 Hz, 1 H), 6.11 (dd, J = 17.0, 2.3 Hz, 1 H), 5.68 (dd, J = 10.3, 2.3 Hz, 1 H), 4.17-4.26 (m, 2 H), 3.88-3.96 (m, 2 H), 3.69-3.76 (m, 2 H), 3.59 (t, J = 6.7 Hz, 2 H), 3.41 (d, J = 1.8 Hz, 3 H), 2.60 (s, 2 H), 2.20 (s, 2 H), 2.09 (d, J = 1.3 Hz, 3 H), 2.12-1.82 (m, 2 H), 1.40 (t, J = 6.8 Hz, 2 H), 0.92 (d, J = 5.5 Hz, 6 H). |
| 2-98 | 492.1 | $^1$H NMR(400 MHz, DMSO-$d_6$) δ (ppm) 9.88 (s, 1 H), 7.77 (d, J = 8.3 Hz, 1 H), 7.40 (ddd, J = 8.1, 6.7, 1.3 Hz, 1 H), 7.10-7.32 (m, 2 H), 7.08 (d, J = 8.3 Hz, 1 H), 6.90 (d, J = 2.4 Hz, 1 H), 6.63 (s, 1 H), 6.32 (ddd, J = 17.0, 10.2, 3.7 Hz, 1 H), 6.11 (dd, J = 17.0, 2.4 Hz, 1 H), 5.68 (dd, J = 10.3, 2.3 Hz, 1 H), 4.21 (ddd, J = 29.3, 8.6, 5.7 Hz, 2 H) 3.88-4.08 (m, 2 H), 3.68 (t, J = 4.9 Hz, 2 H), 3.52-3.67 (m, 2 H), 2.59 (s, 2 H), 2.15 (ddt, J = 23.4, 12.1, 5.9 Hz, 3 H), 1.78-2.00 (m, 1 H), 1.32 (q, J = 6.9 Hz, 1 H), 1.24 (s, 1 H), 0.91 (d, J = 13.0 Hz, 6 H). |
| 2-99 | 454.2 | $^1$H NMR (500 MHz, DMSO-$d_6$) δ ppm 7.50 (d, J = 8.68 Hz, 1 H) 7.46 (s, 1 H) 7.32 (d, J = 8.56 Hz, 1 H) 6.70 (s, 1 H) 6.31 (dd, J = 17.06, 10.33 Hz, 1 H) 6.10 (dd, J = 17.06, 2.26 Hz, 1 H) 5.67 (dd, J = 10.27, 2.20 Hz, 1 H) 4.24 (d, J = 8.56 Hz, 1 H) 4.14-4.21 (m, 1 H) 3.85-3.99 (m, 4 H) 3.80 (t, J = 5.81 Hz, 2 H) 3.67-3.76 (m, 2 H) 3.55-3.63 (m, 2 H) 2.87 (t, J = 5.69 Hz, 2 H) 2.14-2.24 (m, 2 H) 2.08-2.12 (m, 3 H) |
| 2-100 | 454.2 | $^1$H NMR (500 MHz, DMSO-$d_6$) δ ppm 13.10 (s, 1 H) 7.50 (d, J = 8.56 Hz, 1 H) 7.46 (s, 1 H) 7.32 (d, J = 8.56 Hz, 1 H) 6.70 (s, 1 H) 6.31 (dd, J = 16.93, 10.33 Hz, 1 H) 6.10 (dd, J = 16.99, 2.20 Hz, 1 H) 5.67 (dd, J = 10.39, 2.08 Hz, 1 H) 4.24 (d, J = 8.68 Hz, 1 H) 4.13-4.21 (m, 1 H) 3.86-3.98 (m, 4 H) 3.80 (t, J = 5.75 Hz, 2 H) 3.67-3.75 (m, 2 H) 3.55-3.64 (m, 2 H) 2.87 (t, J = 5.75 Hz, 2 H) 2.14-2.24 (m, 2 H) 2.08-2.12 (m, 3 H). |
| 2-101 | 468.3 | $^1$H NMR (400 MHz, DMSO-$d_6$) δ ppm 7.99 (1 H, s) 7.66 (1 H, d, J = 8.15 Hz) 7.09 (1 H, d, J = 8.15 Hz) 6.76 (1 H, s) 6.32 (1 H, dd, J = 17.14, 10.24 Hz) 6.11 (1 H, dd, J = 17.04, 2.19 Hz) 5.67 (1 H, dd, J = 10.24, 2.30 Hz) 4.24 (1 H, d, J = 8.36 Hz) 4.17 (1 H, d, J = 8.57 Hz) 3.87-4.03 (4 H, m) 3.61-3.69 (2 H, m) 3.45-3.56 (5 H, m) 2.88 (2 H, t, J = 6.48 Hz) 2.16-2.22 (2 H, m) 2.14 (3 H, s) 1.85-1.92 (2 H, m) |

Analytical Data for Examples 1-2 to 2-9

TABLE 20-continued

Analytical Data for Examples 1-2 to 2-9

| Ex. # | LRMS: (ESI, +ve ion) m/z | NMR |
|---|---|---|
| 2-102 | 477.1 | $^1$H NMR (400 MHz, Methanol-$d_4$) δ ppm 7.91 (1 H, s) 7.63 (1 H, d, J = 8.15 Hz) 7.10 (1 H, d, J = 8.36 Hz) 7.00 (1 H, s) 6.36 (1 H, dd, J = 16.93, 10.24 Hz) 6.25 (1 H, dd, J = 16.90, 2.10 Hz) 5.74 (1 H, dd, J = 10.24, 2.09 Hz) 4.31-4.37 (1 H, m) 4.25-4.31 (1 H, m) 3.99-4.13 (4 H, m) 3.50 (3 H, s) 3.47 (2 H, dd, J = 5.54, 2.82 Hz) 3.35-3.45 (2 H, m) 2.88 (2 H, t, J-6.58 Hz) 2.26 (2 H, t, J-7.11 Hz) 2.13 (3 H, s) 1.92-2.02 (2 H, m) |
| 2-103 | 517.2 | $^1$H NMR (400 MHz, Methanol-$d_4$) δ ppm 7.65-7.75 (2 H, m) 7.57 (1 H, s) 6.98 (1 H, s) 6.36 (1 H, ddd, J = 17.14, 10.24, 1.05 Hz) 6.25 (1 H, dd, J = 17.14, 2.09 Hz) 5.74 (1 H, dd, J = 10.24, 2.09 Hz) 4.30-4.38 (1 H, m) 4.23-4.30 (1 H, m) 4.01-4.14 (2 H, m) 3.94 (2 H, dd, J = 5.64, 4.60 Hz) 3.35-3.53 (4 H, m) 2.86 (2 H, t, J = 6.48 Hz) 2.21-2.31 (2 H, m) 1.92-2.00 (2 H, m) |
| 2-104 | 502.3 | $^1$H NMR (400 MHz, DMSO-$d_6$) δ ppm 8.02 (1 H, s) 7.92 (1 H, s) 6.80 (1 H, s) 6.31 (1 H, dd, J = 16.93, 10.24 Hz) 6.11 (1 H, dd, J = 17.04, 2.19 Hz) 5.67 (1 H, dd, J = 10.24, 2.30 Hz) 4.24 (1 H, br d, J = 8.80 Hz) 4.13-4.20 (1 H, m) 3.86-4.02 (4 H, m) 3.62-3.71 (2 H, m) 3.49-3.57 (2 H, m) 3.48 (3 H, s) 2.89 (2 H, t, J-6.38 Hz) 2.12-2.24 (5 H, m) 1.89 (2 H, quin, J = 5.64 Hz) |
| 2-105 | 516.8 | $^1$H NMR (400 MHz, DMSO-$d_6$) δ 13.18 (s, 1H), 7.54 (d, J = 7.8 Hz, 2H), 7.36 (d, J = 8.6 Hz, 1H), 6.33 (dd, J = 17.0, 10.2 Hz, 1H), 6.14 (dd, J = 17.0, 2.1 Hz, 1H), 5.72 (dd, J = 10.3, 2.1 Hz, 1H), 4.41 (dd, J = 18.7, 9.4 Hz, 2H), 4.27-3.97 (m, 6H), 2.62 (s, 2H), 2.11 (s, 3H), 2.06-1.87 (m, 2H), 1.39 (t, J = 6.7 Hz, 2H), 0.94 (s, 6H). $^{19}$F NMR (376 MHz, DMSO-$d_6$) δ ppm −115.20-−117.49 (m, 2 F) |
| 2-106 | 520.3 | $^1$H NMR (400 MHz, DMSO-$d_6$) δ ppm 7.81 (dd, J = 8.0, 2.0 Hz, 1 H), 7.59 (d, J = 8.2 Hz, 1 H), 7.51 (d, J = 1.9 Hz, 1 H), 7.41 (s, 2 H), 6.25-6.37 (m, 1 H), 6.11 (dd, J = 17.0, 2.2 Hz, 1 H), 5.61-5.75 (m, 1 H), 4.26 (dd, J = 8.5, 4.7 Hz, 1 H), 4.16 (dd, J = 8.4, 4.2 Hz, 1 H), 3.92-4.01 (m, 1 H), 3.80-3.92 (m, 3 H), 3.68-3.79 (m, 2 H), 2.57 (br d, J = 2.1 Hz, 2 H), 2.09-2.20 (m, 6 H), 1.88-2.02 (m, 1 H), 1.45 (br t, J = 6.6 Hz, 2 H), 0.97 (s, 3 H), 0.93 (s, 3 H) |
| 2-107 | 516.2 | $^1$H NMR (400 MHz, DMSO-$d_6$) δ ppm 8.00-8.06 (m, 1 H), 7.92 (s, 1 H), 6.85-6.97 (m, 1 H), 6.24-6.39 (m, 1 H), 6.10 (dd, J = 16.9, 2.1 Hz, 1 H), 5.66 (br d, J = 10.2 Hz, 1 H), 4.33 (br d, J = 9.0 Hz, 1 H), 4.09-4.24 (m, 2 H), 3.92-4.08 (m, 3 H), 3.84 (br d, J = 5.0 Hz, 1 H), 3.65-3.81 (m, 2 H), 3.46 (s, 3 H), 2.84-2.94 (m, 2 H), 2.18-2.35 (m, 2 H), 2.14-2.16 (m, 3 H), 1.84-1.96 (m, 2 H), 1.12 (br d, J = 5.6 Hz, 3 H) |
| 2-108 | 526.2 | $^1$H NMR (500 MHz, DMSO-$d_6$) δ ppm 13.25 (s, 1 H), 7.67-7.81 (m, 1 H), 7.44-7.64 (m, 1 H), 6.24-6.39 (m, 1 H), 6.03-6.18 (m, 1 H), 5.63-5.70 (m, 1 H), 4.22-4.28 (m, 1 H), 4.12-4.19 (m, 1 H), 3.94-4.01 (m, 2 H), 3.83-3.91 (m, 2 H), 3.76-3.81 (m, 2 H), 3.63-3.73 (m, 2 H), 2.66-2.73 (m, 2 H), 2.10-2.18 (m, 2 H), 2.06-2.10 (m, 3 H), 1.19 (d, J = 3.3 Hz, 6 H) |
| 2-109 | 526.2 | $^1$H NMR (500 MHz, DMSO-$d_6$) δ ppm 13.13-13.48 (m, 1 H), 7.69-7.77 (m, 1 H), 7.48-7.62 (m, 1 H), 6.25-6.37 (m, 1 H), 6.04-6.15 (m, 1 H), 5.60-5.71 (m, 1 H), 4.21-4.29 (m, 1 H), 4.11-4.17 (m, 1 H), 3.76-4.00 (m, 6 H), 3.62-3.73 (m, 2 H), 2.66-2.71 (m, 2 H), 2.09-2.17 (m, 2 H), 2.08 (d, J = 2.7 Hz, 3 H), 1.17-1.21 (m, 6 H) |
| 2-110 | 511.1 | $^1$H NMR (400 MHz, Methanol-$d_4$) δ ppm 7.92 (1 H, s) 7.80 (1 H, s) 7.03 (1 H, s) 6.36 (1 H, dd, J = 16.93, 10.24 Hz) 6.25 (1 H, dd, J = 16.93, 2.09 Hz) 5.74 (1 H, dd, J = 10.24, 2.09 Hz) 4.47 (1 H, br s) 4.32-4.36 (1 H, m) 4.26-4.30 (1 H, m) 4.00-4.13 (4 H, m) 3.35-3.51 (6 H, m) 2.88 (2 H, t, J = 6.48 Hz) 2.26 (2 H, t, J = 7.00 Hz) 2.17 (3 H, s) 1.94-2.01 (2 H, m). |
| 2-111 | 482.1 | $^1$H NMR (400 MHz, DMSO-$d_6$) δ ppm 7.95 (s, 1 H), 7.57 (s, 1 H), 6.33 (m, 1 H), 6.11 (dd, J = 17.0, 2.3 Hz, 1 H), 5.67 (dd, J = 10.2, 2.3 Hz, 1 H), 4.24 (dd, J = 13.0, 8.5 Hz, 1 H), 4.17 (dd, J = 8.6, 4.7 Hz, 1 H), 3.95 (t, J-9.1 Hz, 1 H), 3.89 (dd, J = 10.0, 3.2 Hz, 1 H), 3.66 (dd, J = 10.5, 2.7 Hz, 1 H), 3.63-3.51 (m, 1 H), 3.46-3.35 (m, 4 H), 3.26 (d, J = 3.8 Hz, 1H), 2.53 (d, J = 3.3 Hz, 2 H), 2.37 (s, 3 H), 2.18-1.99 (m, 2 H), 1.93-1.83 (m, 4H), 1.80 (s, 3 H), 1.78-1.66 (m, 2H), 1.40 (d, J = 8.7 Hz, 1 H), 1.18-1.25 (m, 1 H), 0.98-1.05 (m, 1 H) |

TABLE 21

Analytical Data for Examples 12-2 to 12-46.

| Ex. # | LRMS: (ESI, +ve ion) m/z | NMR |
|---|---|---|
| 12-2 | 482.1 | $^1$H NMR (400 MHz, Methanol-$d_4$) δ ppm 6.90 (d, J = 2.5 Hz, 1 H), 6.34-6.42 (m, 2 H), 6.23-6.29 (m, 1 H), 5.75 (dd, J = 10.2, 2.1 Hz, 1 H), 4.25-4.35 (m, 3 H), 4.01-4.11 (m, 3 H), 3.67-3.76 (m, 2 H), 3.50-3.64 (m, 2 H), 2.73 (s, 2 H), 2.21 (t, J = 7.0 Hz, 2 H), 1.92 (s, 6 H), 1.29 (s, 3 H), 1.27 (s, 3 H) |
| 12-3 | 486.2 | $^1$H NMR (500 MHz, DMSO-$d_6$) δ ppm 11.28 (br s, 1 H), 7.37 (t, J = 2.7 Hz, 1 H), 6.95-6.99 (m, 1 H), 6.90 (dd, J = 10.3, 7.9 Hz, 1 H), 6.58 (dd, J = 3.1, 1.9 Hz, 1 H), |

TABLE 21-continued

| Analytical Data for Examples 12-2 to 12-46. | | |
|---|---|---|
| Ex. # | LRMS: (ESI, +ve ion) m/z | NMR |
| | | 6.31 (ddd, J = 17.0, 10.3, 0.9 Hz, 1 H), 6.11 (dd, J = 17.0, 2.2 Hz, 1 H), 5.65-5.69 (m, 1 H), 4.15-4.27 (m, 3 H), 3.83-3.97 (m, 5 H), 3.72-3.80 (m, 2 H), 2.71 (s, 2 H), 2.14-2.24 (m, 2 H), 1.22 (s, 3 H), 1.21 (s, 3 H) |
| 12-4 | 494.3 | $^1$H NMR (400 MHz, Methanol-$d_4$) δ ppm 7.69 (d, J = 8.6 Hz, 1 H), 7.43 (dd, J = 8.4, 6.9 Hz, 1 H), 7.08-7.15 (m, 2 H), 6.98-7.04 (m, 2 H), 6.33-6.41 (m, 1 H), 6.24-6.30 (m, 1 H), 5.76 (dd, J = 10.1, 2.0 Hz, 1 H), 4.17-4.37 (m, 3 H), 3.97-4.14 (m, 5 H), 3.90 (t, J = 6.9 Hz, 2 H), 3.37 (s, 2 H), 2.81 (s, 2 H), 2.28 (t, J = 6.8 Hz, 2 H), 1.27 (m, J = 3.6 Hz, 6 H) |
| 12-5 | 516.2 | $^1$H NMR (500 MHz, DMSO-$d_6$) δ ppm 7.46 (d, J = 3.3 Hz, 1 H), 7.21 (d, J = 7.8 Hz, 1 H), 6.92 (d, J = 7.8 Hz, 1 H), 6.57 (d, J = 3.2 Hz, 1 H), 6.30 (dd, J = 17.0, 10.3 Hz, 1 H), 6.10 (dd, J = 17.0, 2.2 Hz, 1 H), 5.65-5.69 (m, 1 H), 4.26 (d, J = 8.7 Hz, 1 H), 4.11-4.20 (m, 2 H), 3.84-4.00 (m, 5 H), 3.76 (br t, J = 6.7 Hz, 2 H), 3.36-3.40 (m, 2 H), 3.30 (s, 1 H), 2.72 (s, 2 H), 2.14-2.23 (m, 2 H), 1.21 (m, J = 4.3 Hz, 6 H) |
| 12-6 | 502.2 | $^1$H NMR (500 MHz, DMSO-$d_6$) δ ppm 11.35 (br s, 1H), 7.45 (t, 1H, J = 2.8 Hz), 7.19 (d, 1H, J = 7.7 Hz), 6.99 (d, 1H, J = 7.7 Hz), 6.56 (dd, 1H, J = 2.0, 3.2 Hz), 6.31 (ddd, 1H, J = 1.3, 10.4, 17.0 Hz), 6.11 (dd, 1H, J = 2.2, 17.0 Hz), 5.7-5.7 (m, 1H), 4.2-4.3 (m, 3H), 3.9-4.0 (m, 3H), 3.8-3.9 (m, 2H), 3.7-3.8 (m, 2H), 2.7-2.8 (m, 2H), 2.1-2.2 (m, 2H), 1.22 (m, 6H) |
| 12-7 | 502.3 | $^1$H NMR (400 MHz, METHANOL-$d_4$) δ ppm 7.67 (d, J = 2.1 Hz, 1 H), 7.31 (d, J = 3.1 Hz, 1 H), 6.99 (d, J = 1.9 Hz, 1 H), 6.55 (d, J = 3.1 Hz, 1 H), 6.25-6.42 (m, 2 H), 5.76 (dd, J = 10.1, 1.1 Hz, 1 H), 4.27-4.38 (m, 3 H), 3.98-4.11 (m, 5 H), 3.85-3.97 (m, 2 H), 2.80 (s, 2 H), 2.29 (t, J = 6.8 Hz, 2 H), 1.30 (m, J = 3.8 Hz, 6 H) |
| 12-8 | 516.3 | $^1$H NMR (400 MHz, DMSO-$d_6$) δ ppm 7.72 (d, J = 2.1 Hz, 1 H), 7.41 (d, J = 3.1 Hz, 1 H), 6.97 (d, J = 1.9 Hz, 1 H), 6.53 (d, J = 3.1 Hz, 1 H), 6.30 (dd, J = 16.9, 10.2 Hz, 1 H), 6.11 (dd, J = 17.1, 2.3 Hz, 1 H), 5.65-5.69 (m, 1 H), 4.22-4.31 (m, 1 H), 4.13-4.20 (m, 2 H), 3.84-4.00 (m, 5 H), 3.77 (t, J = 6.9 Hz, 2 H), 3.35 (s, 3 H), 2.73 (s, 2 H), 2.19 (dt, J = 6.7, 3.3 Hz, 2 H), 1.19-1.24 (m, 6 H). |
| 12-9 | 516.2 | $^1$H NMR (500 MHz, DMSO-$d_6$) δ ppm 7.71 (d, J = 2.0 Hz, 1 H), 7.41 (d, J = 3.2 Hz, 1 H), 6.97 (s, 1 H), 6.53 (d, J = 3.2 Hz, 1 H), 6.30 (ddd, J = 17.0, 10.3, 1.5 Hz, 1 H), 6.10 (dd, J = 17.1, 2.3 Hz, 1 H), 5.75 (s, 1 H), 5.65-5.69 (m, 1 H), 4.26 (dd, J = 8.6, 3.2 Hz, 1 H), 4.13-4.19 (m, 2 H), 3.85-4.00 (m, 5 H), 3.76 (br t, J = 6.8 Hz, 2 H), 3.35 (s, 1 H), 3.17 (d, J = 5.3 Hz, 1 H), 2.72 (s, 2 H), 2.19 (quin, J = 5.9 Hz, 2 H), 1.21 (m, J = 6.1 Hz, 6 H) |
| 12-10 | 516.2 | $^1$H NMR (500 MHz, DMSO-$d_6$) δ ppm 7.71 (d, J = 2.0 Hz, 1 H), 7.41 (d, J = 3.2 Hz, 1 H), 6.97 (s, 1 H), 6.53 (d, J = 3.1 Hz, 1 H), 6.30 (ddd, J = 17.0, 10.3, 1.5 Hz, 1 H), 6.10 (dd, J = 17.0, 2.2 Hz, 1 H), 5.65-5.69 (m, 1 H), 4.26 (dd, J = 8.6, 3.2 Hz, 1 H), 4.13-4.19 (m, 2 H), 3.85-4.00 (m, 5 H), 3.76 (br t, J = 6.9 Hz, 2 H), 3.35 (s, 1 H), 3.17 (d, J = 5.3 Hz, 1 H), 2.72 (s, 2 H), 2.13-2.24 (m, 2 H), 1.21 (m, J = 6.1 Hz, 6 H), 0.07 (s, 1 H |
| 12-11 | 511.3 | $^1$H NMR (400 MHz, DMSO-$d_6$) δ ppm 13.58-13.82 (m, 1 H), 7.57-7.75 (m, 1 H), 7.25 (br s, 1H), 6.25-6.41 (m, 1 H), 6.06-6.21 (m, 1 H), 5.68 (dd, J = 10.5, 2.1 Hz, 1 H), 4.28 (br dd, J = 8.2, 3.6 Hz, 1 H), 4.10-4.24 (m, 1 H), 3.87-4.01 (m, 4 H), 3.74-3.80 (m, 2 H), 2.76-2.87 (m, 1H), 2.66 (br dd, J = 9.8, 4.4 Hz, 1 H), 2.15-2.25 (m, 7 H), 1.28-1.44 (m, 6 H), 0.70 (s, 2 H). |
| 12-12 | 477.2 | $^1$H NMR (400 MHz, DMSO-$d_6$) δ 8.03 (s, 1 H), 7.76 (8, 1 H), 7.18-7.21 (m, 3 H), 6.88 (d, J = 8.4 Hz, 1 H), 6.28-6.31 (m, 1 H), 6.11 (dd, J = 16.8, 2.4 Hz, 1 H), 5.67 (dd, J = 10.0, 2.4 Hz, 1 H), 4.30-4.32 (m, 1 H), 4.20-4.23 (m, 1 H), 4.01-4.07 (m, 3 H), 3.89-3.94 m, 3 H), 3.17 (d, J = 5.2 Hz, 3 H), 2.43 (s, 3 H), 2.25 (m, 2 H), 1.98 (d, dd, J = 3.6 Hz, 3 H). |
| 12-13 | 502.2 | $^1$H NMR (400 MHz, DMSO-$d_6$) δ ppm 11.12 (br s, 1 H), 7.66 (d, J = 8.5 Hz, 1 H), 7.36 (t, J = 2.5 Hz, 1 H), 7.20 (d, J = 8.5 Hz, 1 H), 6.56 (d, J = 1.2 Hz, 1 H), 6.30 (d, J = 10.0 Hz, 1 H), 6.12 (dd, J = 16.9, 2.2 Hz, 1 H), 5.68 (dd, J = 10.5, 2.2 Hz, 1 H), 4.06-4.33 (m, 3 H), 3.88 (s, 5 H), 3.73-3.82 (m, 2 H), 2.74 (s, 2 H), 2.11-2.29 (m, 2 H), 1.22 (d, J = 5.4 Hz, 6 H) |
| 12-14 | 515.8 | $^1$H NMR (400 MHz, DMSO-$d_6$) δ ppm 7.67 (d, J = 8.5 Hz, 1 H), 7.37 (d, J = 2.9 Hz, 1 H), 7.23 (d, J = 8.5 Hz, 1 H), 6.56 (d, J = 3.1 Hz, 1 H), 6.24-6.38 (m, 1 H), 6.11 (dd, J = 17.0, 2.3 Hz, 1 H), 5.60-5.71 (m, 1 H), 4.12-4.33 (m, 2 H), 3.73-4.13 (m, 8 H), 3.29 (s, 3 H), 2.75 (s, 2 H), 2.20 (br t, J = 6.5 Hz, 2 H), 1.22 (d, J = 1.0 Hz, 6 H) |
| 12-15 | 496.0 | $^1$H NMR (400 MHz, DMSO-$d_6$) δ ppm 11.02 (br d, J = 2.3 Hz, 1 H), 7.63 (dd, J = 8.6, 5.2 Hz, 1 H), 7.31 (t, J = 2.6 Hz, 1 H), 7.00 (ddd, J = 10.2, 8.6, 3.1 Hz, 1 H), 6.53 (d, J = 2.3 Hz, 1 H), 6.32 (dd, J = 17.0, 10.3 Hz, 1 H), 6.12 (dd, J = 17.0, 2.2 Hz, 1 H), 5.65-5.72 (m, 1 H), 4.16-4.33 (m, 2 H), 3.89 (br d, J = 3.1 Hz, 4 H), 3.79 (br t, J = 7.0 Hz, 2 H), 2.82 (t, J = 5.5 Hz, 1 H), 2.08-2.24 (m, 4 H), 1.36 (d, J = 4.4 Hz, 3 H), 0.79-0.92 (m, 3 H), 0.71 (d, J = 16.5 Hz, 3 H) |
| 12-16 | 501.8 | $^1$H NMR (400 MHz, DMSO-$d_6$) δ ppm 11.53 (br s, 1 H), 7.53 (dd, J = 8.6, 0.8 Hz, 1 H), 7.46 (t, J = 2.8 Hz, 1 H), 7.27 (d, J = 8.6 Hz, 1 H), 6.26-6.36 (m, 1 H), 6.07-6.15 (m, 1 H), 6.00 (d, J = 1.9 Hz, 1 H), 5.63-5.71 (m, 1 H), 4.28 (s, 2 H), 4.05-4.14 (m, 1 H), 3.94-4.02 (m, 2 H), 3.84-3.94 (m, 3 H), 3.73-3.81 (m, 2 H), 2.74 (s, 2 H), 2.15-2.24 (m, 2 H), 1.21 (s, 6 H) |
| 12-17 | 495.2 | $^1$H NMR (400 MHz, DMSO-$d_6$) δ ppm 8.25 (s, 1 H), 7.61-7.68 (m, 1 H), 7.55 (dd, J = 8.6, 6.9 Hz, 1 H), 7.01 (dd, J = 6.9, 1.0 Hz, 1 H), 6.72 (s, 1 H), 6.24-6.38 (m, 1 H), 6.11 (dd, J = 17.1, 2.3 Hz, 1 H), 6.06 (s, 2 H), 5.61-5.71 (m, 1 H), 4.25- |

TABLE 21-continued

| Analytical Data for Examples 12-2 to 12-46. | | |
|---|---|---|
| Ex. # | LRMS: (ESI, +ve ion) m/z | NMR |
| | | 4.30 (m, 1 H), 4.15-4.23 (m, 2 H), 3.85-4.00 (m, 5 H), 3.77 (s, 2 H), 2.75 (s, 2 H), 2.14-2.25 (m, 2 H), 1.21 (d, J = 7.5 Hz, 6 H) |
| 12-18 | 527.1 | $^1$H NMR (400 MHz, $CDCl_3$) δ ppm 7.62 (s, 1 H), 7.44 (s, 1 H), 6.35-6.45 (m, 1 H), 6.17-6.29 (m, 1 H), 5.72 (dd, J = 10.35, 1.78 Hz, 1 H), 4.29 (br d, J = 8.57 Hz, 1 H), 4.12-4.20 (m, 3 H), 3.91-4.10 (m, 6 H), 2.88-2.98 (m, 1 H), 2.64-2.74 (m, 1 H), 2.59 (d, J = 0.84 Hz, 3 H), 2.41 (ddd, J = 16.62, 8.67, 2.51 Hz, 1 H), 2.20-2.30 (m, 4 H), 2.18 (td, J = 5.59, 2.82 Hz, 1 H), 1.41 (d, J = 1.25 Hz, 4 H), 0.80 (d, J = 7.11 Hz, 3 H) |
| 12-19 | 493.2 | $^1$H NMR (400 MHz, Methanol-$d_4$) δ ppm 8.33-8.38 (m, 1 H), 8.26 (d, J = 7.11 Hz, 1 H), 6.78-6.83 (m, 1 H), 6.73 (d, J = 7.32 Hz, 1 H), 6.33-6.51 (m, 1 H), 6.24-6.31 (m, 1 H), 5.76 (dd, J = 10.24, 2.09 Hz, 1 H), 4.24-4.38 (m, 2 H), 4.01 (s, 3 H), 3.86-3.95 (m, 2 H), 3.25 (q, J = 7.52 Hz, 2 H), 2.87-2.96 (m, 1 H), 2.65-2.81 (m, 1 H), 2.34-2.47 (m, 2 H), 2.29 (s, 2 H), 2.19-2.24 (m, 1 H), 2.09-2.14 (m, 3 H), 1.37-1.43 (m, 11 H), 0.74-0.80 (m, 3 H) |
| 12-20 | 516.1 | $^1$H NMR (400 MHz, DMSO-$d_6$) δ ppm 10.88-11.20 (m, 1 H), 7.47 (br d, J = 7.5 Hz, 1 H), 7.39 (s, 1 H), 7.09-7.17 (m, 1 H), 6.28-6.37 (m, 1 H), 6.04-6.18 (m, 1 H), 5.61-5.73 (m, 1 H), 4.15-4.30 (m, 2 H), 3.76-4.03 (m, 8 H), 2.73 (d, J = 2.1 Hz, 2 H), 2.21 (br d, J = 6.1 Hz, 2 H), 2.14 (s, 3 H), 1.22 (d, J = 5.0 Hz, 6 H) |
| 12-21 | 487.1 | $^1$H NMR (400 MHz, DMSO-$d_6$) δ ppm 8.57 (dd, J = 8.3, 1.0 Hz, 1 H), 7.95 (dd, J = 8.2, 7.2 Hz, 1 H), 7.73 (dd, J = 7.0, 0.8 Hz, 1 H), 6.25-6.38 (m, 1 H), 6.10 (dd, J = 17.0, 2.3 Hz, 1 H), 5.62-5.72 (m, 1 H), 4.15-4.32 (m, 3 H), 3.94-4.01 (m, 2 H), 3.83-3.93 (m, 3 H), 3.77 (br t, J = 6.8 Hz, 2 H), 2.76 (s, 2 H), 2.13-2.27 (m, 2 H), 1.21 (d, J = 12.4 Hz, 6 H) |
| 12-22 | 533.2 | $^1$H NMR (400 MHz, DMSO-$d_6$) δ ppm 8.04 (s, 1 H), 7.93 (s, 1 H), 6.28-6.37 (m, 1 H), 6.11 (dd, J = 17.0, 2.3 Hz, 1 H), 5.63-5.69 (m, 1 H), 4.13-4.26 (m, 2 H), 3.83-3.99 (m, 2 H), 3.64 (s, 2 H), 3.59 (br s, 2 H), 3.44-3.56 (m, 2 H), 3.36 (d, J = 4.1 Hz, 4 H), 2.77-2.89 (m, 1 H), 2.08-2.18 (m, 2 H), 2.06 (d, J = 2.9 Hz, 3 H), 1.99 (s, 2 H), 1.89 (br s, 1 H), 1.80 (s, 3 H), 1.03 (br d, J = 6.2 Hz, 6 H). |
| 12-23 | 533.3 | $^1$H NMR (500 MHz, DMSO-$d_6$) δ ppm 8.03 (s, 1 H), 7.93 (s, 1 H), 6.31 (dd, J = 17.0, 10.3 Hz, 1 H), 6.10 (dd, J = 17.1, 2.3 Hz, 1 H), 5.66 (dd, J = 10.4, 2.1 Hz, 1 H), 4.22 (dd, J = 8.4, 5.1 Hz, 1 H), 4.13-4.17 (m, 1 H), 3.90-3.95 (m, 1 H), 3.84-3.90 (m, 1 H), 3.63 (s, 2 H), 3.58 (s, 2 H), 3.43-3.53 (m, 2 H), 3.35 (d, J = 5.1 Hz, 1 H), 2.77-2.88 (m, 1 H), 2.07-2.18 (m, 3 H), 2.05 (d, J = 3.8 Hz, 3 H), 1.97-2.04 (m, 2 H), 1.82-1.91 (m, 1 H), 1.80 (s, 3 H), 1.50-1.73 (m, 1 H), 1.08-1.37 (m, 1 H), 1.02 (dd, J = 6.5, 1.6 Hz, 6 H) |
| 12-24 | 533.3 | $^1$H NMR (500 MHz, DMSO-$d_6$) δ ppm 8.03 (s, 1 H), 7.93 (s, 1 H), 6.31 (dd, J = 17.0, 10.3 Hz, 1 H), 6.10 (dd, J = 16.9, 2.3 Hz, 1 H), 5.64-5.68 (m, 1 H), 4.22 (dd, J = 8.4, 5.1 Hz, 1 H), 4.13-4.17 (m, 1 H), 3.90-3.96 (m, 1 H), 3.85-3.89 (m, 1 H), 3.63 (s, 2 H), 3.58 (s, 2 H), 3.44-3.55 (m, 2 H), 3.35 (d, J = 5.1 Hz, 1 H), 2.82 (quin, J = 6.5 Hz, 1 H), 2.29 (s, 1 H), 2.08-2.16 (m, 2 H), 1.96-2.07 (m, 4 H), 1.88 (br d, J = 4.5 Hz, 1 H), 1.85 (br t, J = 5.0 Hz, 1 H), 1.80 (s, 3 H), 1.64 (br d, J = 6.0 Hz, 1 H), 1.14-1.35 (m, 1 H), 0.97-1.05 (m, 6 H) |
| 12-25 | 495.4 | $^1$H NMR (400 MHz, $CDCl_3$) δ ppm 7.84 (d, J = 9.1 Hz, 1 H), 7.42 (d, J = 9.1 Hz, 1 H), 6.33-6.43 (m, 1 H), 6.16-6.29 (m, 1 H), 5.71 (d, J = 10.4 Hz, 1 H), 3.85-4.32 (m, 8 H), 2.89-2.97 (m, 1 H), 2.64-2.75 (m, 1 H), 2.33 (s, 5 H), 2.16-2.27 (m, 3 H), 1.42 (d, J = 2.5 Hz, 3 H), 1.29 (d, J = 9.7 Hz, 1 H), 0.73-0.86 (m, 3 H) |
| 12-26 | 546.2 | $^1$H NMR (400 MHz, $CDCl_3$) δ ppm 8.42 (br s, 1 H), 7.78 (d, J = 8.2 Hz, 1 H), 7.21-7.36 (m, 3 H), 7.01-7.05 (m, 1 H), 6.36 (br d, J = 17.1 Hz, 1 H), 6.20 (dd, J = 16.8, 10.3 Hz, 1 H), 5.71 (d, J = 10.5 Hz, 1 H), 4.20-4.28 (m, 1 H), 3.92-4.18 (m, 7 H), 2.90-2.98 (m, 1 H), 2.64-2.75 (m, 1 H), 2.40-2.51 (m, 1 H), 2.17-2.34 (m, 4 H), 1.42 (d, J = 2.3 Hz, 3 H), 1.33 (dd, J = 16.1, 9.8 Hz, 1 H), 0.75 (s, 2 H) |
| 12-27 | 513.2 | $^1$H NMR (400 MHz, $CDCl_3$) δ ppm 8.22-8.38 (m, 1 H), 7.49-7.60 (m, 1 H), 7.39-7.48 (m, 1 H), 7.28-7.32 (m, 1 H), 7.14-7.21 (m, 1 H), 6.31-6.44 (m, 1 H), 6.09-6.28 (m, 1 H), 5.81-5.93 (m, 1 H), 5.59-5.77 (m, 1 H), 3.89-4.28 (m, 10 H), 2.74-2.87 (m, 2 H), 2.19-2.28 (m, 2 H), 1.28 (d, J = 2.5 Hz, 6 H) |
| 12-28 | 513.9 | $^1$H NMR (400 MHz, $CDCl_3$) δ ppm 8.71-8.77 (m, 1 H), 8.61-8.69 (m, 1 H), 8.30-8.41 (m, 1 H), 7.86-8.01 (m, 1 H), 7.45-7.59 (m, 1 H), 6.33-6.45 (m, 1 H), 6.13-6.28 (m, 1 H), 5.71 (dd, J = 10.3, 1.8 Hz, 1 H), 3.83-4.34 (m, 10 H), 2.82 (s, 2 H), 2.25 (br t, J = 6.8 Hz, 2 H), 1.30 (s, 3 H), 1.27 (s, 3 H) |
| 12-29 | 516.1 | $^1$H NMR (400 MHz, DMSO-$d_6$) δ ppm 10.88-11.20 (m, 1 H), 7.47 (br d, J = 7.5 Hz, 1 H), 7.39 (s, 1 H), 7.09-7.17 (m, 1 H), 6.28-6.37 (m, 1 H), 6.04-6.18 (m, 1 H), 5.61-5.73 (m, 1 H), 4.15-4.30 (m, 2 H), 3.76-4.03 (m, 8 H), 2.73 (d, J = 2.1 Hz, 2 H), 2.21 (br d, J = 6.1 Hz, 2 H), 2.14 (s, 3 H), 1.22 (d, J = 5.0 Hz, 6 H) |
| 12-30 | 514.2 | $^1$H NMR (400 MHz, $CDCl_3$) δ ppm 8.72 (s, 1 H), 8.27-8.39 (m, 1 H), 7.79-7.93 (m, 1 H), 7.57-7.70 (m, 2 H), 6.31-6.46 (m, 1 H), 6.14-6.29 (m, 1 H), 5.64-5.79 (m, 1 H), 3.85-4.51 (m, 10 H), 2.69-2.90 (m, 2 H), 2.15-2.32 (m, 2 H), 1.29-1.30 (m, 3 H), 1.28 (s, 3 H) |
| 12-31 | 495.2 | $^1$H NMR (400 MHz, $CDCl_3$) δ ppm 8.29 (d, J = 7.7 Hz, 1 H), 7.42-7.60 (m, 2 H), 7.28-7.33 (m, 1 H), 7.12-7.18 (m, 1 H), 6.87-6.93 (m, 1 H), 6.34-6.43 (m, 1 H), 6.14-6.27 (m, 1 H), 5.67 (s, 1 H), 3.85-4.32 (m, 10 H), 2.73-2.86 (m, 2 H), 2.17-2.29 (m, 2 H), 1.27-1.29 (m, 6 H). The OH proton is not observed in $CDCl_3$. |
| 12-32 | 495.2 | $^1$H NMR (400 MHz, $CDCl_3$) δ ppm 7.80-7.90 (m, 2 H), 7.38-7.45 (m, 1 H), 7.24-7.26 (m, 1 H), 7.11-7.17 (m, 1 H), 6.64-6.71 (m, 1 H), 6.33-6.43 (m, 1 H), |

TABLE 21-continued

| Analytical Data for Examples 12-2 to 12-46. | | |
|---|---|---|
| Ex. # | LRMS: (ESI, +ve ion) m/z | NMR |
| | | 6.14-6.26 (m, 1 H), 5.70-5.74 (m, 1 H), 3.87-4.30 (m, 10 H), 2.70-2.86 (m, 2 H), 2.18-2.28 (m, 2 H), 1.27-1.29 (m, 6 H). The OH proton is not observed in $CDCl_3$. |
| 12-33 | 495.2 | $^1H$ NMR (400 MHz, $CDCl_3$) δ ppm 8.33 (d, J = 8.5 Hz, 1 H), 7.52-7.61 (m, 1 H), 7.32 (dd, J = 6.9, 1.1 Hz, 1 H), 7.23-7.27 (m, 1 H), 6.90-6.96 (m, 1 H), 6.80 (s, 1 H), 6.34-6.45 (m, 1 H), 6.15-6.28 (m, 1 H), 5.69-5.74 (m, 1 H), 3.88-4.29 (m, 10 H), 2.74-2.88 (m, 2 H), 2.23 (s, 2 H), 1.26-1.29 (m, 6 H). The OH proton is not observed in $CDCl_3$. |
| 12-34 | 507.2 | $^1H$ NMR (400 MHz, $CDCl_3$) δ ppm 6.70-6.82 (m, 1 H), 6.48-6.63 (m, 1 H), 6.34-6.43 (m, 1 H), 6.11-6.25 (m, 1 H), 5.62-5.82 (m, 1 H), 3.68-4.45 (m, 8 H), 2.81-2.95 (m, 1 H), 2.60-2.72 (m, 1 H), 2.32-2.59 (m, 2 H), 2.11-2.30 (m, 3 H), 1.37-1.43 (m, 3 H), 1.26-1.29 (m, 1 H), 0.67-0.80 (m, 3 H). The OH proton is not observed in $CDCl_3$ |
| 12-35 | 490.2 | $^1H$ NMR (400 MHz, $CDCl_3$) δ ppm 8.04-8.20 (m, 1 H), 7.14-7.24 (m, 1 H), 6.36-6.46 (m, 1 H), 6.11-6.28 (m, 1 H), 5.77 (dd, J = 10.3, 1.4 Hz, 1 H), 3.69-4.37 (m, 8 H), 2.86 (td, J = 5.2, 2.6 Hz, 1 H), 2.67 (br dd, J = 9.6, 5.6 Hz, 1 H), 2.48-2.60 (m, 1 H), 2.31-2.43 (m, 1 H), 2.13-2.31 (m, 3 H), 1.40 (s, 3 H), 1.29-1.35 (m, 1 H), 0.66-0.80 (m, 3 H). The OH proton is not observed in $CDCl_3$. |
| 12-36 | 501.2 | $^1H$ NMR (400 MHz, $CDCl_3$) δ ppm 7.55-7.61 (m, 1 H), 7.46-7.54 (m, 1 H), 7.07-7.15 (m, 1 H), 6.32-6.42 (m, 1 H), 6.15-6.26 (m, 1 H), 5.68-5.80 (m, 1 H), 4.62-4.85 (m, 1 H), 4.20-4.30 (m, 1 H), 3.78-4.18 (m, 7 H), 2.85-2.92 (m, 1 H), 2.63-2.74 (m, 1 H), 2.51-2.59 (m, 1 H), 2.20-2.27 (m, 4 H), 1.39-1.43 (m, 3 H), 1.31-1.38 (m, 3 H), 1.18-1.24 (m, 1 H), 0.67-0.83 (m, 3 H). The OH proton is not observed in $CDCl_3$ |
| 12-37 | 501.2 | $^1H$ NMR (400 MHz, $CDCl_3$) δ ppm 7.40-7.61 (m, 2 H), 7.06-7.21 (m, 1 H), 6.31-6.47 (m, 1 H), 6.11-6.30 (m, 1 H), 5.70 (dd, J = 10.5, 1.9 Hz, 1 H), 4.55-4.69 (m, 1 H), 4.23-4.29 (m, 1 H), 4.09-4.18 (m, 2 H), 3.85-4.06 (m, 5 H), 2.84-2.93 (m, 1 H), 2.62-2.72 (m, 1 H), 2.35-2.44 (m, 2 H), 2.22 (br t, J = 6.8 Hz, 3 H), 1.53 (dd, J = 10.7, 6.5 Hz, 3 H), 1.38-1.42 (m, 3 H), 1.29-1.32 (m, 1 H), 0.71-0.80 (m, 3 H). The OH proton is not observed in $CDCl_3$ |
| 12-38 | 507.0 | $^1H$ NMR (400 MHz, $CDCl_3$) δ ppm 8.76-8.84 (m, 1 H), 8.62-8.72 (m, 1 H), 7.45-7.53 (m, 1 H), 7.31-7.38 (m, 1 H), 6.34-6.47 (m, 1 H), 6.09-6.29 (m, 1 H), 5.72 (br dd, J = 10.2, 2.5 Hz, 1 H), 4.21-4.29 (m, 1 H), 4.10-4.17 (m, 2 H), 3.86-4.08 (m, 5 H), 2.85-2.99 (m, 1 H), 2.60-2.73 (m, 1 H), 2.34-2.44 (m, 1 H), 2.12-2.25 (m, 4 H), 1.37-1.42 (m, 4 H), 0.68-0.79 (m, 3 H). The OH proton is not observed in $CDCl_3$ |
| 12-39 | 507.0 | $^1H$ NMR (400 MHz, $CDCl_3$) δ ppm 8.72-8.81 (m, 1 H), 8.57-8.65 (m, 1 H), 7.45-7.52 (m, 1 H), 7.35-7.43 (m, 1 H), 6.32-6.46 (m, 1 H), 6.17-6.28 (m, 1 H), 5.63-5.82 (m, 1 H), 4.25 (br dd, J = 8.5, 2.2 Hz, 1 H), 4.10-4.19 (m, 2 H), 3.85-4.09 (m, 5 H), 2.90 (t, J = 5.4 Hz, 1 H), 2.60-2.70 (m, 1 H), 2.30-2.42 (m, 1 H), 2.09-2.23 (m, 4 H), 1.36-1.40 (m, 3 H), 1.28-1.31 (m, 1 H), 0.84 (s, 3 H). The OH proton is not observed in $CDCl_3$ |
| 12-40 | 493.3 | 1H NMR (400 MHz, DMSO-$d_6$) δ ppm 8.12-8.21 (m, 1 H), 7.88 (dd, J = 8.0, 0.9 Hz, 1 H), 7.24-7.31 (m, 1 H), 7.17-7.23 (m, 1 H), 6.26-6.37 (m, 1 H), 6.11 (dd, J = 17.0, 2.3 Hz, 1 H), 5.61-5.71 (m, 1 H), 4.23-4.32 (m, 1 H), 4.14-4.22 (m, 1 H), 3.85-4.01 (m, 4 H), 3.78 (br t, J = 5.6 Hz, 2 H), 3.63-3.73 (m, 3 H), 2.80-2.88 (m, 1 H), 2.63-2.76 (m, 1 H), 2.11-2.31 (m, 5 H), 1.36 (s, 3 H), 1.22-1.31 (m, 1 H), 0.66-0.76 (m, 3 H) |
| 12-41 | 495 | $^1H$ NMR (400 MHz, DMSO-$d_6$) δ ppm 9.89 (s, 1 H), 7.81 (d, J = 8.3 Hz, 1 H), 7.51 (dd, J = 8.3, 7.0 Hz, 1 H), 7.26-7.18 (m, 2 H), 7.16 (dd, J = 7.0, 1.2 Hz, 1 H), 7.09 (dd, J = 9.0, 2.5 Hz, 1 H), 6.32 (m, 1 H), 6.11 (dd, J = 17.0, 2.3 Hz, 1 H), 5.68 (dd, J = 10.3, 2.3 Hz, 1 H), 4.28 (dd, J = 8.7, 5.3 Hz, 1 H), 4.18 (dd, J = 8.7, 2.5 Hz, 1 H), 4.11 (d, J = 15.4 Hz, 1 H), 4.02-3.73 (m, 7 H), 2.74 (d, J = 2.6 Hz, 2 H), 2.19 (m, 2 H), 1.20 (d, J = 2.8 Hz, 6 H). |
| 12-42 | 478.3 | N/A |
| 12-43 | 482.2 | $^1H$ NMR (500 MHz, DMSO-$d_6$) δ ppm 9.85 (br s, 1 H), 6.87 (d, J = 2.4 Hz, 1 H), 6.37 (d, J = 2.4 Hz, 1 H), 6.28-6.35 (m, 1 H), 6.10 (dd, J = 16.9, 2.3 Hz, 1 H), 5.64-5.68 (m, 1 H), 4.18-4.24 (m, 1 H), 4.07-4.18 (m, 2 H), 3.85-3.95 (m, 3 H), 3.62 (d, J = 2.8 Hz, 2 H), 3.47 (br t, J = 7.0 Hz, 2 H), 2.61 (s, 2 H), 2.09 (br t, J = 6.7 Hz, 2 H), 1.83 (d, J = 3.4 Hz, 3 H), 1.81 (s, 3 H), 1.19 (s, 3 H), 1.17 (s, 3 H) |
| 12-44 | 482.2 | $^1H$ NMR (500 MHz, DMSO-$d_6$) δ ppm 9.84 (br s, 1 H), 6.87 (d, J = 2.4 Hz, 1 H), 6.37 (d, J = 2.4 Hz, 1 H), 6.28-6.35 (m, 1 H), 6.10 (dd, J = 17.0, 2.2 Hz, 1 H), 5.64-5.68 (m, 1 H), 4.19-4.23 (m, 1 H), 4.07-4.17 (m, 2 H), 3.85-3.95 (m, 3 H), 3.59-3.65 (m, 2 H), 3.47 (br t, J = 7.1 Hz, 2 H), 2.61 (s, 2 H), 2.10 (br t, J = 6.8 Hz, 2 H), 1.83 (d, J = 3.3 Hz, 3 H), 1.81 (s, 3 H), 1.19 (s, 3 H), 1.17 (s, 3 H) |
| 12-45 | 502.3 | $^1H$ NMR (400 MHz, Methanol-$d_4$) δ ppm 8.02 (d, J = 8.6 Hz, 1 H), 7.59 (dd, J = 8.5, 7.0 Hz, 1 H), 7.08-7.15 (m, 2 H), 6.98 (dd, J = 9.1, 3.2 Hz, 1 H), 6.34-6.42 (m, 1 H), 6.22-6.30 (m, 1 H), 5.73-5.78 (m, 1 H), 4.22-4.37 (m, 3 H), 4.02-4.11 (m, 2 H), 3.90 (d, J = 15.5 Hz, 1 H), 3.54-3.80 (m, 4 H), 2.77 (s, 2 H), 2.19-2.26 (m, 2 H), 1.85 (s, 3 H), 1.28 (s, 3 H), 1.25 (s, 3 H), |

TABLE 22

| Analytical Data for Examples 13-2 to 13-157. | | |
|---|---|---|
| Ex. # | LRMS: (ESI, +ve ion) m/z | NMR |
| 13-2 | 538.2 | $^1$H NMR (400 MHz, DMSO-$d_6$) δ ppm 13.15 (1 H, s), 7.49-7.56 (2 H, m), 7.35 (1 H, d, J = 8.71 Hz), 6.59 (1 H, dt, J = 15.34, 6.22 Hz), 6.11 (1 H, d, J = 15.34 Hz), 4.25 (1 H, d, J = 8.50 Hz), 4.15 (1 H, d, J = 8.30 Hz), 3.95 (1 H, d, J = 10.16 Hz), 3.80-3.91 (3 H, m), 3.74 (2 H, br t, J = 6.74 Hz), 3.06 (2 H, d, J = 6.01 Hz), 2.59 (2 H, s), 2.18 (8 H, s), 2.12 (3 H, s), 1.92-2.04 (2 H, m), 1.38 (2 H, br t, J = 6.63 Hz), 0.95 (6 H, s) |
| 13-3 | 515.2 | $^1$H NMR (400 MHz, DMSO-$d_6$) δ ppm 13.16 (1 H, s), 7.50-7.57 (2 H, m), 7.35 (1 H, d, J = 8.71 Hz), 6.09 (1 H, d, J = 2.49 Hz), 5.96 (1 H, d, J = 2.49 Hz), 4.42 (1 H, br d, J = 8.91 Hz), 4.30 (1 H, br d, J = 9.12 Hz), 3.99-4.06 (1 H, m), 3.82-3.99 (3 H, m), 3.73 (2 H, br t, J = 6.84 Hz), 2.56-2.62 (2 H, m), 2.15-2.25 (2 H, m), 2.12 (3 H, s), 1.92-2.06 (2 H, m), 1.38 (2 H, br t, J = 6.63 Hz), 0.95 (6 H, s) |
| 13-4 | 525.3 | $^1$H NMR (400 MHz, DMSO-$d_6$) δ ppm 13.16 (1 H, br s), 7.50-7.57 (2 H, m), 7.35 (1 H, d, J = 8.71 Hz), 6.66 (1 H, dt, J = 15.45, 4.51 Hz), 6.09-6.16 (1 H, m), 4.26 (1 H, d, J = 8.50 Hz), 4.15 (1 H, br d, J = 8.50 Hz), 4.06 (2 H, dd, J = 4.35, 1.87 Hz), 3.96 (1 H, d, J = 10.16 Hz), 3.81-3.92 (3 H, m), 3.74 (2 H, br t, J = 6.84 Hz), 3.29 (3 H, s), 2.55-2.64 (2 H, m), 2.15-2.21 (2 H, m), 2.12 (3 H, s), 1.91-2.05 (2 H, m), 1.38 (2 H, br t, J = 6.63 Hz), 0.95 (6 H, s) |
| 13-5 | 463.2 | $^1$H NMR (400 MHz, DMSO-$d_6$) δ ppm 7.64-7.67 (1 H, m), 7.50-7.55 (2 H, m), 7.37-7.41 (1 H, m), 6.31 (1 H, ddd, J = 17.04, 10.24, 3.24 Hz), 6.11 (1 H, dd, J = 17.04, 2.19 Hz), 5.68 (1 H, dd, J = 10.24, 2.30 Hz), 4.27 (1 H, dd, J = 8.36, 4.60 Hz), 4.14-4.19 (1 H, m), 4.04-4.14 (2 H, m), 3.93-3.99 (1 H, m), 3.84-3.93 (3 H, m), 3.76 (2 H, t, J = 6.90 Hz), 2.71 (2 H, s), 2.14-2.25 (2 H, m), 1.22 (6 H, d, J = 8.15 Hz). |
| 13-6 | 513.3 | $^1$H NMR (400 MHz, DMSO-$d_6$) δ ppm 13.16 (s, 1 H), 7.50-7.57 (m, 2 H), 7.35 (d, J = 8.71 Hz, 1 H), 6.67-6.80 (m, 1 H), 6.20 (d, J = 15.10 Hz, 1 H), 5.05-5.20 (m, 2 H), 4.29 (d, J = 8.71 Hz, 1 H), 4.18 (d, J = 8.30 Hz, 1 H), 3.98 (d, J = 10.16 Hz, 1 H), 3.81-3.94 (m, 3 H), 3.74 (t, J = 6.70 Hz, 2 H), 2.59 (s, 2 H), 2.15-2.24 (m, 2 H), 2.12 (s, 3 H), 1.91-2.04 (m, 2 H), 1.38 (t, J = 6.60 Hz, 2 H), 0.95 (s, 6 H) |
| 13-7 | 549.3 | $^1$H NMR (400 MHz, DMSO-$d_6$) δ ppm 13.16 (s, 1 H), 7.49-7.57 (m, 2 H), 7.35 (d, J = 8.78 Hz, 1 H), 6.75-6.86 (m, 2 H), 4.38 (d, J = 8.78 Hz, 1 H), 4.28 (br d, J = 8.99 Hz, 1 H), 4.01-4.06 (m, 1 H), 3.93-3.98 (m, 1 H), 3.82-3.91 (m, 2 H), 3.70-3.77 (m, 2 H), 2.59 (s, 2 H), 2.16-2.23 (m, 2 H), 2.12 (d, J = 1.05 Hz, 3 H), 1.94-2.02 (m, 2 H), 1.38 (br t, J = 6.79 Hz, 2 H), 0.95 (s, 6 H). |
| 13-8 | 531.3 | $^1$H NMR (400 MHz, DMSO-$d_6$) δ ppm 13.16 (s, 1 H), 7.50-7.56 (m, 2 H), 7.35 (d, J = 8.78 Hz, 1 H), 6.47-6.78 (m, 3 H), 4.33 (d, J = 8.57 Hz, 1 H), 4.22 (d, J = 8.80 Hz, 1 H), 4.01 (d, J = 10.45 Hz, 1 H), 3.82-3.96 (m, 3 H), 3.74 (br t, J = 6.90 Hz, 2 H), 2.59 (s, 2 H), 2.15-2.23 (m, 2 H), 2.12 (s, 3 H), 1.94-2.02 (m, 2 H), 1.38 (br t, J = 6.79 Hz, 2 H), 0.95 (s, 6 H) |
| 13-9 | 511.2 | $^1$H NMR (400 MHz, DMSO-$d_6$) δ ppm 13.16 (s, 1 H), 7.49-7.56 (m, 2 H), 7.35 (d, J = 8.78 Hz, 1 H), 6.74 (dt, J = 15.36, 3.81 Hz, 1 H), 6.13 (dt, J = 15.36, 1.93 Hz, 1 H), 5.02 (t, J = 5.33 Hz, 1 H), 4.25 (br d, J = 8.36 Hz, 1 H), 4.10-4.16 (m, 3 H), 3.95 (br d, J = 9.80 Hz, 1 H), 3.81-3.90 (m, 3 H), 3.74 (br t, J = 6.79 Hz, 2 H), 2.59 (s, 2 H), 2.17 (br d, J = 7.11 Hz, 2 H), 2.12 (s, 3 H), 1.95-2.02 (m, 2 H), 1.38 (br t, J = 6.69 Hz, 2 H), 0.95 (s, 6 H) |
| 13-10 | 521.3 | $^1$H NMR (400 MHz, DMSO-$d_6$) δ 13.18 (s, 1H), 7.63-7.47 (m, 2H), 7.40-7.28 (m, 1H), 6.36-6.21 (m, 1H), 6.11 (dd, J = 17.0, 2.2 Hz, 1H), 5.67 (dd, J = 10.3, 2.2 Hz, 1H), 4.32-4.21 (m, 1H), 4.17 (d, J = 8.6 Hz, 1H), 4.00-3.81 (m, 4H), 3.74 (t, J = 6.8 Hz, 2H), 3.00 (d, J = 12.7 Hz, 1H), 2.92-2.76 (m, 2H), 2.24-2.08 (m, 6H), 2.08-1.97 (m, 1H), 1.97-1.85 (m, 1H), 1.50 (s, 1H). $^{19}$F NMR (376 MHz, DMSO-$d_6$) δ ppm −72.00 (s, 3F). |
| 13-11 | 479.3 | $^1$H NMR (400 MHz, DMSO-$d_6$) δ ppm 13.03-13.27 (m, 1 H), 7.46-7.68 (m, 2 H), 7.33 (d, J = 8.6 Hz, 1 H), 6.25-6.45 (m, 1 H), 6.11 (dd, J = 17.0, 2.2 Hz, 1 H), 5.57-5.73 (m, 1 H), 4.24-4.34 (m, 1 H), 4.17 (br d, J = 8.2 Hz, 1 H), 3.95-4.01 (m, 1 H), 3.83-3.93 (m, 3 H), 3.74 (br t, J = 6.7 Hz, 2 H), 2.89 (t, J = 6.4 Hz, 2 H), 2.15-2.24 (m, 2 H), 2.10 (s, 3 H), 1.85 (d, J = 3.6 Hz, 1 H), 1.51-1.71 (m, 2 H), 0.34 (s, 2 H), 0.12 (d, J = 8.8 Hz, 2 H). |
| 13-12 | 467.3 | $^1$H NMR (400 MHz, DMSO-$d_6$) δ ppm 13.02-13.27 (m, 1 H), 7.49-7.60 (m, 2 H), 7.30-7.38 (m, 1 H), 6.25-6.39 (m, 1 H), 6.08-6.16 (m, 1 H), 5.60-5.72 (m, 1 H), 4.26-4.32 (m, 1 H), 4.14-4.21 (m, 1 H), 3.96-4.01 (m, 1 H), 3.86-3.93 (m, 3 H), 3.77 (s, 2 H), 2.73-2.77 (m, 2 H), 2.18 (s, 4 H), 2.12 (s, 3 H), 1.06 (d, J = 4.8 Hz, 7 H). |
| 13-13 | 483.3 | $^1$H NMR (400 MHz, DMSO-$d_6$) δ ppm 13.13 (br s, 1 H), 7.78 (s, 1 H), 7.53-7.62 (m, 1 H), 7.31-7.38 (m, 1 H), 6.26-6.37 (m, 1 H), 6.08-6.15 (m, 1 H), 5.68 (dd, J = 10.3, 2.2 Hz, 1 H), 4.41-4.52 (m, 1 H), 4.12-4.35 (m, 2 H), 3.69-4.01 (m, 7 H), 2.68-2.74 (m, 2 H), 2.53-2.57 (m, 1 H), 2.19-2.32 (m, 2 H), 2.12 (s, 2 H), 1.24 (d, J = 6.1 Hz, 3 H), 0.55-0.72 (m, 3 H) |
| 13-14 | 465.2 | $^1$H NMR (400 MHz, DMSO-$d_6$) δ ppm 13.14 (s, 1 H), 7.58-7.66 (m, 1 H), 7.48-7.55 (m, 1 H), 7.29-7.37 (m, 1 H), 6.27-6.36 (m, 1 H), 6.14 (d, J = 2.3 Hz, 1 H), 5.70 (s, 1 H), 4.29 (br d, J = 8.6 Hz, 1 H), 4.18 (br d, J = 8.2 Hz, 1 H), 3.97-4.00 (m, 1 H), 3.87-3.92 (m, 3 H), 3.77 (t, J = 6.9 Hz, 2 H), 2.94 (d, J = 9.0 Hz, 2 H), 2.29 (s, 2 H), 2.19 (s, 5 H), 0.60 (s, 2 H), 0.47 (br d, J = 5.0 Hz, 2 H). |
| 13-15 | 505.2 | $^1$H NMR (400 MHz, DMSO-$d_6$) δ ppm 13.14-13.25 (m, 1 H), 7.55-7.66 (m, 2 H), 7.37 (d, J = 8.8 Hz, 1 H), 6.22-6.37 (m, 1 H), 6.04-6.14 (m, 1 H), 5.61-5.71 |

TABLE 22-continued

| Analytical Data for Examples 13-2 to 13-157. | | |
|---|---|---|
| Ex. # | LRMS: (ESI, +ve ion) m/z | NMR |
| | | (m, 1 H), 4.28-4.33 (m, 1 H), 4.16-4.21 (m, 1 H), 4.09 (br d, J = 3.8 Hz, 2 H), 3.88-4.07 (m, 8 H), 3.82 (br t, J = 7.0 Hz, 2 H), 2.17-2.26 (m, 2 H), 2.14 (s, 3 H) |
| 13-16 | 481.3 | $^1$H NMR (400 MHz, $CDCl_3$) δ ppm 7.98 (s, 1 H), 7.68 (d, J = 8.2 Hz, 1 H), 7.11 (d, J = 8.4 Hz, 1 H), 6.36-6.43 (m, 1 H), 6.17-6.28 (m, 1 H), 5.68-5.76 (m, 1 H), 3.89-4.31 (m, 8 H), 3.64 (s, 3 H), 2.83 (s, 2 H), 2.23-2.31 (m, 2 H), 2.23 (s, 3 H), 1.14 (d, J = 2.9 Hz, 6 H). |
| 13-17 | 481.3 | $^1$H NMR (400 MHz, DMSO-$d_6$) δ ppm 8.06 (s, 1 H), 7.73 (d, J = 8.4 Hz, 1 H), 7.14 (d, J = 8.4 Hz, 1 H), 6.23-6.40 (m, 1 H), 6.11 (dd, J = 17.0, 2.2 Hz, 1 H), 5.59-5.72 (m, 1 H), 4.28 (dd, J = 8.6, 2.9 Hz, 1 H), 4.18 (br d, J = 3.6 Hz, 1 H), 3.85-4.02 (m, 4 H), 3.78 (t, J = 6.8 Hz, 2 H), 2.77 (d, J = 5.2 Hz, 2 H), 2.17-2.24 (m, 2 H), 2.14 (s, 3 H), 1.08 (d, J = 6.3 Hz, 6 H) |
| 13-18 | 481.3 | $^1$H NMR (400 MHz, DMSO-$d_6$) δ ppm 8.03-8.10 (m, 1 H), 7.73 (d, J = 8.2 Hz, 1 H), 7.14 (d, J = 8.4 Hz, 1 H), 6.26-6.38 (m, 1 H), 6.11 (dd, J = 17.0, 2.2 Hz, 1 H), 5.64-5.73 (m, 1 H), 4.28 (dd, J = 8.5, 3.0 Hz, 1 H), 4.17 (dd, J = 8.5, 3.7 Hz, 1 H), 3.86-4.06 (m, 4 H), 3.78 (t, J = 6.8 Hz, 2 H), 2.77 (d, J = 5.0 Hz, 2 H), 2.17-2.24 (m, 2 H), 2.14 (s, 3 H), 1.08 (d, J = 6.1 Hz, 6 H) |
| 13-19 | 513.2 | $^1$H NMR (400 MHz, DMSO-$d_6$) δ ppm 7.62-7.71 (m, 1 H), 7.47-7.59 (m, 2 H), 7.28-7.37 (m, 2 H), 6.26-6.38 (m, 1 H), 6.05-6.16 (m, 2 H), 5.68 (dd, J = 10.5, 2.0 Hz, 1 H), 4.22-4.30 (m, 1 H), 4.17 (dd, J = 8.6, 3.4 Hz, 1 H), 3.83-4.00 (m, 4 H), 3.77-3.81 (m, 3 H), 3.75 (br t, J = 6.6 Hz, 2 H), 3.17-3.23 (m, 1 H), 3.08 (br dd, J = 17.9, 5.1 Hz, 1 H), 2.80-2.93 (m, 1 H), 2.29-2.41 (m, 1 H), 2.11-2.24 (m, 3 H), 1.93-2.05 (m, 1 H), 1.54-1.69 (m, 1 H) |
| 13-20 | 513.3 | $^1$H NMR (400 MHz, DMSO-$d_6$) δ ppm 7.61-7.72 (m, 1 H), 7.47-7.59 (m, 2 H), 7.29-7.39 (m, 2 H), 6.26-6.38 (m, 1 H), 6.05-6.17 (m, 2 H), 5.63-5.75 (m, 1 H), 4.24-4.31 (m, 1 H), 4.18 (dd, J = 8.3, 3.7 Hz, 1 H), 3.83-3.99 (m, 4 H), 3.78-3.81 (m, 3 H), 3.75 (br t, J = 6.9 Hz, 2 H), 3.18-3.26 (m, 1 H), 3.05-3.13 (m, 1 H), 2.80-2.94 (m, 1 H), 2.29-2.41 (m, 1 H), 2.13-2.25 (m, 3 H), 1.94-2.04 (m, 1 H), 1.57-1.70 (m, 1 H) |
| 13-21 | 513.2 | $^1$H NMR (400 MHz, DMSO-$d_6$) δ ppm 7.62-7.71 (m, 1 H), 7.47-7.59 (m, 2 H), 7.28-7.37 (m, 2 H), 6.26-6.38 (m, 1 H), 6.05-6.16 (m, 2 H), 5.68 (dd, J = 10.5, 2.0 Hz, 1 H), 4.22-4.30 (m, 1 H), 4.17 (dd, J = 8.6, 3.4 Hz, 1 H), 3.83-4.00 (m, 4 H), 3.77-3.81 (m, 3 H), 3.75 (br t, J = 6.6 Hz, 2 H), 3.17-3.23 (m, 1 H), 3.08 (br dd, J = 17.9, 5.1 Hz, 1 H), 2.80-2.93 (m, 1 H), 2.29-2.41 (m, 1 H), 2.11-2.24 (m, 3 H), 1.93-2.05 (m, 1 H), 1.54-1.69 (m, 1 H) |
| 13-22 | 468.3 | $^1$H NMR (400 MHz, DMSO-$d_6$) δ ppm 13.17 (s, 1 H), 7.52-7.60 (m, 2 H), 7.32-7.41 (m, 1 H), 6.29 (d, J = 10.5 Hz, 1 H), 6.11 (dd, J = 16.9, 2.3 Hz, 1 H), 5.63-5.71 (m, 1 H), 4.28 (d, J = 8.6 Hz, 1 H), 4.17 (br d, J = 9.0 Hz, 1 H), 3.95-4.00 (m, 1 H), 3.83-3.94 (m, 2 H), 3.75 (br t, J = 7.0 Hz, 2 H), 2.88 (br t, J = 5.9 Hz, 2 H), 2.78 (q, J = 14.7 Hz, 2 H), 2.59-2.66 (m, 2 H), 2.16-2.23 (m, 2 H), 2.14 (s, 3 H), 2.11 (s, 3 H). |
| 13-23 | 447.3 | $^1$H NMR (400 MHz, DMSO-$d_6$) δ ppm 7.59-7.66 (m, 1 H), 7.46-7.54 (m, 2 H), 7.33-7.39 (m, 1 H), 6.27-6.37 (m, 1 H), 6.11 (dd, J = 17.0, 2.2 Hz, 1 H), 5.61-5.72 (m, 1 H), 4.14-4.33 (m, 2 H), 3.81-4.00 (m, 4 H), 3.72-3.80 (m, 2 H), 2.72 (d, J = 3.8 Hz, 2 H), 2.27 (d, J = 4.6 Hz, 2 H), 2.20 (br d, J = 5.9 Hz, 2 H), 1.08 (d, J = 8.2 Hz, 6 H) |
| 13-24 | 447.3 | $^1$H NMR (400 MHz, DMSO-$d_6$) δ ppm 7.57-7.69 (m, 1 H), 7.45-7.57 (m, 2 H), 7.31-7.41 (m, 1 H), 6.25-6.40 (m, 1 H), 6.11 (dd, J = 17.0, 2.2 Hz, 1 H), 5.64-5.72 (m, 1 H), 4.27 (dd, J = 8.6, 2.5 Hz, 1 H), 4.17 (dd, J = 8.5, 3.4 Hz, 1 H), 3.81-4.02 (m, 4 H), 3.76 (t, J = 6.9 Hz, 2 H), 2.72 (d, J = 3.6 Hz, 2 H), 2.27 (d, J = 4.6 Hz, 2 H), 2.12-2.24 (m, 2 H), 1.08 (d, J = 8.2 Hz, 6 H) |
| 13-25 | 447.3 | $^1$H NMR (400 MHz, DMSO-$d_6$) δ ppm 7.60-7.68 (m, 1 H), 7.45-7.56 (m, 2 H), 7.32-7.40 (m, 1 H), 6.25-6.38 (m, 1 H), 6.11 (dd, J = 17.0, 2.2 Hz, 1 H), 5.65-5.72 (m, 1 H), 4.27 (dd, J = 8.6, 2.5 Hz, 1 H), 4.17 (dd, J = 8.6, 3.3 Hz, 1 H), 3.81-4.03 (m, 4 H), 3.76 (t, J = 6.8 Hz, 2 H), 2.73 (s, 2 H), 2.24-2.34 (m, 2 H), 2.19 (br s, 2 H), 1.08 (d, J = 8.2 Hz, 6 H) |
| 13-26 | 497.2 | $^1$H NMR (400 MHz, DMSO-$d_6$) δ ppm 7.53-7.60 (m, 1 H), 7.33-7.44 (m, 3 H), 7.31 (s, 1 H), 6.26-6.37 (m, 1 H), 6.06-6.16 (m, 2 H), 5.68 (dd, J = 10.0, 2.1 Hz, 1 H), 4.22-4.32 (m, 1 H), 4.17 (br dd, J = 8.7, 3.3 Hz, 1 H), 3.81-4.00 (m, 4 H), 3.79 (s, 3 H), 3.75 (br t, J = 6.6 Hz, 2 H), 3.19-3.27 (m, 1 H), 3.08 (br dd, J = 17.8, 4.6 Hz, 1 H), 2.81-2.92 (m, 1 H), 2.41 (ddd, J = 16.2, 11.0, 5.2 Hz, 1 H), 2.16-2.29 (m, 3 H), 1.98 (br s, 1 H), 1.56-1.71 (m, 1 H). |
| 13-27 | 500.2 | $^1$H NMR (400 MHz, CDC1) δ ppm 8.82-8.95 (m, 1 H), 7.43 (t, J = 2.0 Hz, 1 H), 6.33-6.45 (m, 1 H), 6.17-6.28 (m, 1 H), 6.03 (dd, J = 3.3, 1.9 Hz, 1 H), 5.72 (dd, J = 10.3, 1.8 Hz, 1 H), 4.22-4.29 (m, 1 H), 4.19 (br s, 1 H), 4.00-4.12 (m, 2 H), 3.97 (s, 2 H), 3.91 (br s, 2 H), 3.89 (d, J = 2.3 Hz, 3 H), 3.10-3.25 (m, 2 H), 2.95 (td, J = 7.7, 4.1 Hz, 1 H), 2.46-2.58 (m, 1 H), 2.39 (br d, J = 4.2 Hz, 1 H), 2.36 (d, J = 6.3 Hz, 3 H), 2.24 (br t, J = 6.9 Hz, 2 H), 2.09-2.19 (m, 1 H), 1.72-1.87 (m, 1 H). |
| 13-28 | 484.3 | $^1$H NMR (400 MHz, $CDCl_3$) δ ppm 7.58-7.66 (m, 1 H), 7.38-7.50 (m, 1 H), 6.36-6.42 (m, 1 H), 6.28-6.33 (m, 1 H), 6.17-6.28 (m, 1 H), 6.00-6.07 (m, 1 H), 5.72 (dd, J = 10.3, 1.8 Hz, 1 H), 4.23-4.30 (m, 1 H), 4.18 (br d, J = 8.8 Hz, 1 H), 4.02-4.13 (m, 2 H), 3.98 (s, 2 H), 3.91-3.96 (m, 2 H), 3.88-3.90 (m, 3 H), 3.71-3.77 (m, 3 H), 3.12-3.26 (m, 2 H), 2.88-3.03 (m, 1 H), 2.45-2.57 (m, 1 H), 2.21-2.38 (m, 3 H), 2.12 (br d, J = 11.1 Hz, 1 H), 1.72-1.87 (m, 1 H). |
| 13-29 | 484.3 | $^1$H NMR (400 MHz, $CDCl_3$) δ ppm 7.58-7.66 (m, 1 H), 7.38-7.50 (m, 1 H), 6.36-6.42 (m, 1 H), 6.28-6.33 (m, 1 H), 6.17-6.28 (m, 1 H), 6.00-6.07 (m, 1 H), |

TABLE 22-continued

Analytical Data for Examples 13-2 to 13-157.

| Ex. # | LRMS: (ESI, +ve ion) m/z | NMR |
|---|---|---|
| | | 5.72 (dd, J = 10.3, 1.8 Hz, 1 H), 4.23-4.30 (m, 1 H), 4.18 (br d, J = 8.8 Hz, 1 H), 4.02-4.13 (m, 2 H), 3.98 (s, 2 H), 3.91-3.96 (m, 2 H), 3.88-3.90 (m, 3 H), 3.71-3.77 (m, 3 H), 3.12-3.26 (m, 2 H), 2.88-3.03 (m, 1 H), 2.45-2.57 (m, 1 H), 2.21-2.38 (m, 3 H), 2.12 (br d, J = 11.1 Hz, 1 H), 1.72-1.87 (m, 1 H). |
| 13-30 | 493.3 | $^1$H NMR (400 MHz, DMSO-$d_6$) δ ppm 8.06 (s, 1 H), 7.74 (d, J = 8.2 Hz, 1 H), 7.16 (d, J = 8.2 Hz, 1 H), 6.23-6.43 (m, 1 H), 6.04-6.18 (m, 1 H), 5.68 (ddd, J = 10.2, 6.0, 2.2 Hz, 1 H), 4.54-4.67 (m, 1 H), 4.06-4.17 (m, 2 H), 3.89-3.98 (m, 1 H), 3.78-3.87 (m, 1 H), 3.60-3.71 (m, 1 H), 3.56 (s, 3 H), 3.13 (q, J = 5.4 Hz, 1 H), 2.59-2.71 (m, 1 H), 2.18 (m, 7 H), 1.42-1.50 (m, 2 H), 1.24 (d, J = 6.3 Hz, 3 H) |
| 13-31 | 493.3 | $^1$H NMR (500 MHz, DMSO-$d_6$) δ ppm 8.05 (s, 1 H), 7.73 (d, J = 8.2 Hz, 1 H), 7.15 (d, J = 8.3 Hz, 1 H), 6.25-6.37 (m, 1 H), 6.10 (dt, J = 17.0, 2.5 Hz, 1 H), 5.67 (ddd, J = 10.2, 7.8, 2.2 Hz, 1 H), 4.55-4.61 (m, 1 H), 4.37 (d, J = 9.2 Hz, 1 H), 4.02-4.14 (m, 2 H), 3.88-3.95 (m, 1 H), 3.77-3.84 (m, 1 H), 3.59-3.69 (m, 1 H), 3.56 (s, 3 H), 3.12 (q, J = 5.5 Hz, 1 H), 2.61-2.66 (m, 1 H), 2.40-2.55 (m, 2 H), 2.14-2.27 (m, 7 H), 1.42-1.48 (m, 2 H), 1.23 (d, J = 6.4 Hz, 3 H). |
| 13-32 | 493.3 | $^1$H NMR (500 MHz, DMSO-$d_6$) δ ppm 8.05 (s, 1 H), 7.73 (d, J = 8.2 Hz, 1 H), 7.15 (d, J = 8.3 Hz, 1 H), 6.25-6.37 (m, 1 H), 6.10 (dt, J = 17.0, 2.5 Hz, 1 H), 5.67 (ddd, J = 10.2, 7.8, 2.2 Hz, 1 H), 4.55-4.61 (m, 1 H), 4.37 (d, J = 9.2 Hz, 1 H), 4.02-4.14 (m, 2 H), 3.88-3.95 (m, 1 H), 3.77-3.84 (m, 1 H), 3.59-3.69 (m, 1 H), 3.56 (s, 3 H), 3.12 (q, J = 5.5 Hz, 1 H), 2.61-2.66 (m, 1 H), 2.40-2.55 (m, 2 H), 2.14-2.27 (m, 7 H), 1.42-1.48 (m, 2 H), 1.23 (d, J = 6.4 Hz, 3 H). |
| 13-33 | 493.3 | $^1$H NMR (400 MHz, DMSO-$d_6$) δ ppm 7.92-7.97 (m, 1 H), 7.84 (s, 1 H), 7.51-7.58 (m, 1 H), 7.44 (td, J = 7.6, 1.0 Hz, 1 H), 7.26-7.35 (m, 2 H), 6.25-6.38 (m, 1 H), 6.08-6.17 (m, 1 H), 5.63-5.71 (m, 1 H), 4.25-4.32 (m, 1 H), 4.11-4.21 (m, 2 H), 3.87-4.00 (m, 4 H), 3.73-3.81 (m, 3 H), 2.75 (d, J = 2.1 Hz, 2 H), 2.53 (s, 3 H), 2.14-2.24 (m, 2 H), 1.20 (d, J = 6.9 Hz, 6 H). |
| 13-34 | 495.3 | $^1$H NMR (400 MHz, DMSO-$d_6$) δ ppm 9.93-10.05 (m, 1 H), 7.82-7.97 (m, 2 H), 7.25-7.46 (m, 3 H), 7.09 (d, J = 8.4 Hz, 1 H), 6.25-6.39 (m, 1 H), 6.07-6.20 (m, 1 H), 5.63-5.73 (m, 1 H), 4.29 (d, J = 8.6 Hz, 1 H), 4.10-4.22 (m, 2 H), 3.95-4.00 (m, 1 H), 3.81-3.93 (m, 4 H), 3.76 (br t, J = 6.9 Hz, 2 H), 2.74 (d, J = 2.3 Hz, 2 H), 2.14-2.25 (m, 2 H), 1.20 (d, J = 7.1 Hz, 6 H). |
| 13-35 | 477.3 | $^1$H NMR (400 MHz, DMSO-$d_6$) δ ppm 9.77-9.91 (m, 1 H), 7.87 (br d, J = 7.3 Hz, 2 H), 7.27-7.42 (m, 4 H), 7.13 (br s, 1 H), 6.23-6.39 (m, 1 H), 6.06-6.18 (m, 1 H), 5.60-5.71 (m, 1 H), 4.15-4.34 (m, 2 H), 3.84-4.04 (m, 4 H), 3.76 (br s, 2 H), 3.12 (br d, J = 4.4 Hz, 1 H), 2.57-2.63 (m, 1 H), 2.40-2.50 (m, 2 H), 2.33 (br d, J = 1.0 Hz, 1 H), 2.00-2.26 (m, 4 H), 1.42 (br s, 2 H). |
| 13-36 | 477.3 | $^1$H NMR (400 MHz, DMSO-$d_6$) δ ppm 9.83 (s, 1 H), 7.89 (d, J = 3.1 Hz, 1 H), 7.87 (s, 1 H), 7.28-7.41 (m, 3 H), 7.15 (br d, J = 8.2 Hz, 1 H), 6.28-6.33 (m, 1 H), 6.13 (d, J = 2.3 Hz, 1 H), 5.66-5.70 (m, 1 H), 4.28 (d, J = 8.4 Hz, 1 H), 4.18 (br d, J = 8.8 Hz, 1 H), 3.94-3.99 (m, 1 H), 3.83-3.93 (m, 3 H), 3.76 (br t, J = 6.8 Hz, 2 H), 3.12 (q, J = 5.4 Hz, 1 H), 2.57-2.63 (m, 1 H), 2.40-2.50 (m, 2 H), 2.34 (br d, J = 1.9 Hz, 1 H), 2.07-2.25 (m, 3 H), 1.40-1.46 (m, 2 H). |
| 13-37 | 477.3 | $^1$H NMR (400 MHz, DMSO-$d_6$) δ ppm 9.83 (s, 1 H), 7.85-7.91 (m, 2 H), 7.27-7.41 (m, 3 H), 7.15 (br d, J = 8.6 Hz, 1 H), 6.27-6.36 (m, 1 H), 6.08-6.16 (m, 1 H), 5.65-5.71 (m, 1 H), 4.28 (d, J = 8.6 Hz, 1 H), 4.18 (d, J = 8.6 Hz, 1 H), 3.83-4.00 (m, 4 H), 3.71-3.81 (m, 2 H), 3.12 (d, J = 5.4 Hz, 1 H), 2.57-2.63 (m, 1 H), 2.32-2.40 (m, 1 H), 2.09-2.24 (m, 3 H), 1.38-1.47 (m, 2 H). |
| 13-38 | 441.3 | $^1$H NMR (400 MHz, DMSO-$d_6$) δ ppm 9.31-9.39 (m, 1 H), 7.13 (t, J = 7.8 Hz, 1 H), 6.78 (d, J = 8.2 Hz, 2 H), 6.25-6.39 (m, 1 H), 6.13 (d, J = 2.3 Hz, 1 H), 5.61-5.74 (m, 1 H), 4.24-4.31 (m, 1 H), 4.13-4.20 (m, 1 H), 3.95 (s, 1 H), 3.83-3.93 (m, 3 H), 3.74 (s, 2 H), 3.07 (d, J = 5.4 Hz, 1 H), 2.67 (br dd, J = 3.7, 2.0 Hz, 1 H), 2.33-2.50 (m, 3 H), 2.18 (br d, J = 2.9 Hz, 3 H), 1.97 (s, 3 H), 1.33-1.46 (m, 2 H). |
| 13-39 | 441.3 | $^1$H NMR (500 MHz, DMSO-$d_6$) δ ppm 9.34 (s, 1 H), 7.12 (t, J = 7.8 Hz, 1 H), 6.77 (d, J = 7.8 Hz, 2 H), 6.30 (dd, J = 17.0, 10.3 Hz, 1 H), 6.10 (dd, J = 17.0, 2.2 Hz, 1 H), 5.65-5.68 (m, 1 H), 4.26 (br d, J = 8.3 Hz, 1 H), 4.14-4.18 (m, 1 H), 3.93-3.97 (m, 1 H), 3.80-3.88 (m, 2 H), 3.71-3.77 (m, 2 H), 3.06 (q, J = 5.5 Hz, 1 H), 2.64-2.69 (m, 1 H), 2.46-2.55 (m, 2 H), 2.39-2.44 (m, 1 H), 2.36 (d, J = 2.4 Hz, 1 H), 2.14-2.26 (m, 3 H), 1.95-1.98 (m, 3 H), 1.36-1.40 (m, 2 H). |
| 13-40 | 441.3 | $^1$H NMR (500 MHz, DMSO-$d_6$) δ ppm 9.34 (s, 1 H), 7.12 (t, J = 7.8 Hz, 1 H), 6.77 (d, J = 7.8 Hz, 3 H), 6.30 (dd, J = 17.0, 10.3 Hz, 1 H), 6.10 (dd, J = 17.0, 2.3 Hz, 1 H), 5.65-5.68 (m, 1 H), 4.25 (br d, J = 8.4 Hz, 1 H), 4.16 (br d, J = 8.6 Hz, 1 H), 3.90-3.98 (m, 1 H), 3.80-3.88 (m, 3 H), 3.73 (br t, J = 6.7 Hz, 3 H), 3.06 (q, J = 5.4 Hz, 1 H), 2.63-2.69 (m, 1 H), 2.42-2.50 (m, 2 H), 2.35-2.41 (m, 1 H), 2.13-2.26 (m, 4 H), 1.95-1.98 (m, 4 H), 1.36-1.40 (m, 3 H). |
| 13-41 | 495.2 | $^1$H NMR (400 MHz, DMSO-$d_6$) δ ppm 10.12-9.99 (m, 1 H), 7.80 (d, J = 8.4 Hz, 1 H), 7.49-7.41 (m, 1 H), 7.32-7.23 (m, 2 H), 7.22-7.16 (m, 1 H), 6.99 (d, J = 2.3 Hz, 1 H), 6.29 (br dd, J = 10.3, 1.8 Hz, 1 H), 6.11 (dd, J = 16.9, 2.3 Hz, 1 H), 5.62-5.71 (m, 1 H), 4.32-4.16 (m, 2 H), 4.11 (s, 1 H), 4.01-3.95 (m, 1 H), 3.95-3.84 (m, 4 H), 3.77 (t, J = 6.7 Hz, 2 H), 2.75 (d, J = 2.1 Hz, 2 H), 2.20 (br s, 2 H), 1.20 (d, J = 5.4 Hz, 6 H), |
| 13-42 | 495.2 | $^1$H NMR (500 MHz, DMSO-$d_6$) δ ppm 10.02 (s, 1 H), 7.79 (d, J = 8.3 Hz, 1 H), 7.44 (t, J = 7.5 Hz, 1 H), 7.22-7.27 (m, 2 H), 7.18 (d, J = 8.3 Hz, 1 H), 6.98 (d, J = 2.4 Hz, 1 H), 6.30 (ddd, J = 17.0, 10.3, 2.3 Hz, 1 H), 6.11 (dd, J = 17.0, 2.2 Hz, 1 H), 5.65-5.69 (m, 1 H), 4.27 (dd, J = 8.3, 6.1 Hz, 1 H), 4.07-4.20 (m, 2 H), 3.83- |

TABLE 22-continued

| Analytical Data for Examples 13-2 to 13-157. | | |
|---|---|---|
| Ex. # | LRMS: (ESI, +ve ion) m/z | NMR |
| | | 3.99 (m, 5 H), 3.72-3.80 (m, 2 H), 2.68-2.78 (m, 2 H), 2.12-2.24 (m, 2 H), 1.15-1.29 (m, 6 H). |
| 13-43 | 495.2 | $^1$H NMR (500 MHz, DMSO-$d_6$) δ ppm 10.02 (s, 1 H), 7.79 (d, J = 8.3 Hz, 1 H), 7.44 (t, J = 7.5 Hz, 1 H), 7.22-7.27 (m, 2 H), 7.18 (d, J = 8.3 Hz, 1 H), 6.98 (d, J = 2.4 Hz, 1 H), 6.30 (ddd, J = 17.0, 10.3, 2.3 Hz, 1 H), 6.11 (dd, J = 17.0, 2.2 Hz, 1 H), 5.65-5.69 (m, 1 H), 4.27 (dd, J = 8.3, 6.1 Hz, 1 H), 4.07-4.20 (m, 2 H), 3.83-3.99 (m, 5 H), 3.72-3.80 (m, 2 H), 2.68-2.78 (m, 2 H), 2.12-2.24 (m, 2 H), 1.15-1.29 (m, 6 H). |
| 13-44 | 514.1 | $^1$H NMR (400 MHz, $CDCl_3$;) δ ppm 7.62 (br d, J = 6.9 Hz, 1 H), 7.50 (d, J = 8.6 Hz, 1 H), 7.35 (d, J = 8.6 Hz, 1 H), 6.34-6.42 (m, 1 H), 6.14-6.26 (m, 1 H), 5.74 (dd, J = 10.3, 1.8 Hz, 1 H), 4.22-4.30 (m, 1 H), 4.15-4.21 (m, 1 H), 4.03-4.13 (m, 2 H), 3.67-3.89 (m, 5 H), 3.18 (s, 3 H), 2.86 (s, 2 H), 2.16 (br d, J = 5.4 Hz, 3 H), 1.99-2.08 (m, 2 H), 1.43 (br t, J = 6.8 Hz, 2 H), 1.00 (s, 6 H). |
| 13-45 | 508.2 | $^1$H NMR (400 MHz, DMSO-$d_6$) δ ppm 7.48-7.57 (m, 2 H), 7.34 (d, J = 8.8 Hz, 1 H), 6.24-6.48 (m, 2 H), 6.12 (dd, J = 17.0, 2.2 Hz, 1 H), 5.68 (br d, J = 11.1 Hz, 1 H), 4.14-4.32 (m, 3 H), 3.85-3.96 (m, 3 H), 3.72-3.81 (m, 3 H), 3.63 (q, J = 6.3 Hz, 2 H), 2.72 (s, 2 H), 2.13-2.21 (m, 2 H), 2.06 (s, 3 H), 1.19 (d, J = 6.7 Hz, 6 H). |
| 13-46 | 500.3 | $^1$H NMR (400 MHz, DMSO-$d_6$) δ 13.03 (s, 1H), 7.46 (d, J = 8.8 Hz, 1H), 7.33 (d, J = 2.4 Hz, 1H), 7.31 (d, J = 8.4 Hz, 1H), 6.36-6.29 (m, 1H), 6.13 (dd, J = 2, 2.4 Hz, 1H), 5.68-5.65 (m, 1H), 4.25-4.19 (m, 1H), 4.17-4.13 (m, 1H), 3.95-3.86 (m, 3H), 3.78-3.70 (m, 3H), 3.67-3.62 (m, 2H), 3.31-3.33 (m, 3 H, osbcured by water) 2.74 (d, J = 1.6 Hz, 3H), 2.12-2.07 (m, 2H), 2.01 (d, J = 2 Hz, 3H), 1.89-1.79 (m, 2H), 1.32-1.23 (m, 2H), 0.91 (d, J = 4 Hz, 6H). |
| 13-47 | 533.2 | $^1$H NMR (400 MHz, CDCB) δ ppm 8.05 (s, 1 H), 7.75 (d, J = 8.4 Hz, 1 H), 7.16 (d, J = = 8.4 Hz, 1 H), 6.44 (dd, J = 16.9, 1.5 Hz, 1 H), 6.16-6.28 (m, 1 H), 5.83 (dd, J = 10.5, 1.5 Hz, 1 H), 4.43-4.62 (m, 2 H), 4.25 (br d, J = 13.2 Hz, 5 H), 4.13 (s, 2 H), 3.62 (s, 3 H), 2.82 (s, 3 H), 2.22 (s, 3 H), 1.31 (d, J = 1.9 Hz, 6 H). |
| 13-48 | 525.2 | $^1$H NMR (400 MHz, $CDCl_3$) δ ppm 8.05 (s, 1 H), 7.73 (d, J = 8.2 Hz, 1 H), 7.16 (d, J = 8.4 Hz, 1 H), 6.44 (dd, J = 16.9, 1.5 Hz, 1 H), 6.18-6.31 (m, 1 H), 5.75-5.88 (m, 1 H), 4.42 (br d, J = 9.0 Hz, 1 H), 4.21-4.27 (m, 1 H), 4.11 (d, J = 4.4 Hz, 2 H), 3.93-4.02 (m, 4 H), 3.62-3.69 (m, 3 H), 2.84 (s, 2 H), 2.29-2.42 (m, 2 H), 2.25 (br d, J = 3.8 Hz, 2 H), 1.59-1.75 (m, 6 H), 1.32 (d, J = 3.6 Hz, 6 H). |
| 13-49 | 497.3 | $^1$H NMR (400 MHz, $CDCl_3$) δ ppm 7.98 (s, 1 H), 7.70 (d, J = 8.15 Hz, 1 H), 7.12 (d, J = 8.15 Hz, 1 H), 6.40 (dd, J = 17.04, 1.78 Hz, 1 H), 6.22 (dd, J = 17.04, 10.35 Hz, 1 H), 5.73 (dd, J = 10.35, 1.78 Hz, 1 H), 5.32 (s, 1 H), 4.24-4.33 (m, 1 H), 3.92-4.21 (m, 9 H), 3.64 (s, 3 H), 2.82 (s, 2 H), 2.20-2.29 (m, 5 H), 1.63-1.89 (m, 3 H). |
| 13-50 | 525.1 | $^1$H NMR (400 MHz, CDC1) δ ppm 7.45-7.61 (m, 2 H), 7.38 (d, J = 8.57 Hz, 1 H), 6.33-6.45 (m, 1 H), 6.16-6.29 (m, 1 H), 5.73 (dd, J = 10.35, 1.78 Hz, 1 H), 3.85-4.37 (m, 10 H), 3.59-3.78 (m, 4 H), 2.76-2.89 (m, 2 H), 2.16-2.33 (m, 5 H), 1.67-1.79 (m, 4 H). |
| 13-51 | 511.0 | $^1$H NMR (400 MHz, $CDCl_3$) δ ppm 7.50 (s, 2 H), 7.33-7.43 (m, 1 H), 6.34-6.45 (m, 1 H), 6.25 (d, J = 10.24 Hz, 1 H), 5.67-5.78 (m, 1 H), 3.85-4.35 (m, 13 H), 3.57-3.70 (m, 1 H), 2.92-3.08 (m, 2 H), 2.11-2.34 (m, 8 H), 1.87 (dtd, J = 13.04, 8.22, 8.22, 5.02 Hz, 1 H). |
| 13-52 | 481.4 | $^1$H NMR (400 MHz, DMSO-$d_6$) δ ppm 13.14 (s, 1 H), 7.49-7.61 (m, 2 H), 7.34 (d, J = 8.57 Hz, 1 H), 6.24-6.42 (m, 1 H), 6.06-6.18 (m, 1 H), 5.62 (s, 1 H), 4.48-4.65 (m, 1 H), 4.31-4.42 (m, 1 H), 4.07-4.15 (m, 2 H), 3.88-3.98 (m, 1 H), 3.77-3.87 (m, 1 H), 3.56-3.70 (m, 1 H), 2.70-2.80 (m, 2 H), 2.08-2.32 (m, 7 H), 1.25-1.33 (m, 3 H), 1.01-1.10 (m, 6 H). |
| 13-53 | 481.2 | $^1$H NMR (400 MHz, DMSO-$d_6$) δ ppm 13.04-13.23 (m, 1 H), 7.46-7.65 (m, 2 H), 7.28-7.38 (m, 1 H), 6.21-6.46 (m, 1 H), 6.10-6.11 (m, 1 H), 6.05-6.17 (m, 1 H), 5.62-5.72 (m, 1 H), 4.51-4.68 (m, 1 H), 4.01-4.15 (m, 2 H), 3.76-3.99 (m, 3 H), 3.48-3.69 (m, 1 H), 2.72-2.80 (m, 2 H), 1.98-2.30 (m, 8 H), 1.06 (d, J = 14.42 Hz, 6 H). |
| 13-54 | 481.2 | $^1$H NMR (400 MHz, DMSO-$d_6$) δ ppm 13.07-13.20 (m, 1 H), 7.49-7.62 (m, 2 H), 7.35 (s, 1 H), 6.24-6.42 (m, 1 H), 6.06-6.17 (m, 1 H), 5.63-5.72 (m, 1 H), 4.49-4.62 (m, 1 H), 4.11 (s, 2 H), 3.79-3.97 (m, 2 H), 3.60-3.70 (m, 1 H), 2.75 (s, 2 H), 2.08-2.35 (m, 8 H), 1.06 (d, J = 1.05 Hz, 6 H). |
| 13-55 | 483.3 | $^1$H NMR (500 MHz, DMSO-$d_6$) δ ppm 8.06 (s, 1 H), 7.75 (d, J = 8.19 Hz, 1 H), 7.15 (d, J = 8.31 Hz, 1 H), 6.30 (dd, J = 16.93, 10.33 Hz, 1 H), 6.10 (dd, J = 16.93, 2.26 Hz, 1 H), 5.65-5.69 (m, 1 H), 4.44-4.51 (m, 2 H), 4.30 (br d, J = 8.56 Hz, 1 H), 4.18 (br d, J = 8.19 Hz, 1 H), 3.90-4.02 (m, 4 H), 3.77-3.87 (m, 2 H), 3.54 (d, J = 3.18 Hz, 3 H), 2.17-2.26 (m, 5 H), 1.45 (s, 3 H), 1.43 (s, 3 H). |
| 13-56 | 483.2 | $^1$H NMR (500 MHz, DMSO-$d_6$) δ ppm 8.06 (s, 1 H), 7.75 (d, J = 8.19 Hz, 1 H), 7.15 (d, J = 8.44 Hz, 1 H), 6.30 (dd, J = 16.99, 10.27 Hz, 1 H), 6.11 (dd, J = 16.99, 2.20 Hz, 1 H), 5.65-5.69 (m, 1 H), 4.44-4.51 (m, 2 H), 4.30 (br d, J = 8.56 Hz, 1 H), 4.18 (br d, J = 8.56 Hz, 1 H), 3.91-4.08 (m, 4 H), 3.77-3.87 (m, 2 H), 3.54 (d, J = 3.18 Hz, 3 H), 2.17-2.26 (m, 5 H), 1.45 (s, 3 H), 1.43 (s, 3 H). |
| 13-57 | 483.2 | $^1$H NMR (500 MHz, DMSO-$d_6$) δ ppm 8.06 (s, 1 H), 7.75 (d, J = 8.19 Hz, 1 H), 7.15 (d, J = 8.44 Hz, 1 H), 6.30 (dd, J = 16.99, 10.27 Hz, 1 H), 6.11 (dd, J = 16.99, 2.20 Hz, 1 H), 5.65-5.69 (m, 1 H), 4.44-4.51 (m, 2 H), 4.30 (br d, J = 8.56 Hz, 1 H), 4.18 (br d, J = 8.56 Hz, 1 H), 3.91-4.08 (m, 4 H), 3.77-3.87 (m, 2 H), 3.54 (d, J = 3.18 Hz, 3 H), 2.17-2.26 (m, 5 H), 1.45 (s, 3 H), 1.43 (s, 3 H). |

TABLE 22-continued

| Analytical Data for Examples 13-2 to 13-157. | | |
|---|---|---|
| Ex. # | LRMS: (ESI, +ve ion) m/z | NMR |
| 13-58 | 475.0 | $^1$H NMR (400 MHz, DMSO-$d_6$) δ ppm 13.21 (s, 1 H), 7.68 (s, 1 H), 7.58 (d, J = 8.36 Hz, 1 H), 7.38 (d, J = 8.78 Hz, 1 H), 6.26-6.38 (m, 1 H), 6.06-6.17 (m, 1 H), 5.68 (dd, J = 10.24, 2.30 Hz, 1 H), 4.29-4.35 (m, 1 H), 4.19 (br d, J = 8.99 Hz, 1 H), 3.98-4.03 (m, 1 H), 3.88-3.97 (m, 3 H), 3.82 (t, J = 6.79 Hz, 2 H), 2.54-2.64 (m, 2 H), 2.31-2.45 (m, 2 H), 2.16-2.27 (m, 5 H). |
| 13-59 | 497.2 | $^1$H NMR (500 MHz, DMSO-$d_6$) δ ppm 8.07 (s, 1 H), 7.76 (d, J = 8.19 Hz, 1 H), 7.16 (d, J = 8.31 Hz, 1 H), 6.30 (ddd, J = 16.99, 10.27, 2.45 Hz, 1 H), 6.10 (dd, J = 17.06, 2.26 Hz, 1 H), 5.67 (dd, J = 10.27, 2.20 Hz, 1 H), 4.22-4.34 (m, 1 H), 4.16 (dd, J = 8.50, 4.71 Hz, 1 H), 3.84-4.02 (m, 6 H), 3.73-3.81 (m, 2 H), 3.53-3.54 (m, 1 H), 2.76 (s, 2 H), 2.11-2.26 (m, 5 H), 1.21 (d, J = 2.69 Hz, 6 H). 2 H obscured by water peak. |
| 13-60 | 497.2 | $^1$H NMR (500 MHz, DMSO-$d_6$) δ ppm 8.07 (s, 1 H), 7.76 (d, J = 8.31 Hz, 1 H), 7.16 (d, J = 8.31 Hz, 1 H), 6.30 (ddd, J = 17.00, 10.27, 2.45 Hz, 1 H), 6.11 (dd, J = 16.99, 2.20 Hz, 1 H), 5.64-5.69 (m, 1 H), 4.22-4.34 (m, 1 H), 4.17 (dd, J = 8.56, 4.65 Hz, 1 H), 3.86-4.02 (m, 6 H), 3.73-3.82 (m, 2 H), 3.53-3.54 (m, 1 H), 2.76 (s, 2 H), 2.11-2.26 (m, 5 H), 1.21 (d, J = 2.69 Hz, 6 H). 2 H obscured by water peak. |
| 13-61 | 537.2 | $^1$H NMR (400 MHz, DMSO-$d_6$) δ ppm 8.03-8.13 (m, 1 H), 7.74 (dd, J = 8.2, 2.3 Hz, 1 H), 7.16 (d, J = 8.2 Hz, 1 H), 6.07-6.15 (m, 1 H), 5.67 (br s, 1 H), 4.78-4.95 (m, 1 H), 4.62 (br d, J = 4.2 Hz, 2 H), 4.29 (s, 1 H), 4.14 (br s, 1 H), 3.90-4.04 (m, 1 H), 3.71-3.90 (m, 4 H), 3.59-3.69 (m, 3 H), 3.56 (d, J = 2.1 Hz, 1 H), 2.63-2.86 (m, 2 H), 2.30-2.45 (m, 2 H), 2.10-2.24 (m, 7 H), 1.37 (s, 3 H), 0.67-0.80 (m, 3 H). |
| 13-62 | 537.3 | $^1$H NMR (400 MHz, DMSO-$d_6$) δ ppm 8.07 (d, J = 6.3 Hz, 1 H), 7.74 (dd, J = 8.2, 1.5 Hz, 1 H), 7.16 (d, J = 8.4 Hz, 1 H), 6.25-6.40 (m, 1 H), 6.07-6.14 (m, 1 H), 5.67 (ddd, J = 10.1, 7.7, 2.2 Hz, 1 H), 4.81-4.89 (m, 1 H), 4.57-4.66 (m, 1 H), 4.29-4.47 (m, 1 H), 4.14-4.20 (m, 2 1), 3.93-4.04 (m, 1 H), 3.71-3.87 (m, 3 H), 3.55-3.69 (m, 4 H), 2.84 (t, J = 5.3 Hz, 1 H), 2.66-2.74 (m, 1 H), 2.32-2.49 (m, 2 H), 2.07-2.28 (m, 7 H), 1.37 (s, 3 H), 0.69-0.77 (m, 3 H). |
| 13-63 | 509.3 | $^1$H NMR (400 MHz, DMSO-$d_6$) δ ppm 8.00-8.08 (m, 1 H), 7.67-7.78 (m, 1 H), 7.14 (dd, J = 8.15, 2.93 Hz, 1 H), 6.22-6.42 (m, 1 H), 6.05-6.16 (m, 1 H), 5.59-5.73 (m, 1 H), 4.78-4.92 (m, 1 H), 4.57-4.71 (m, 1 H), 4.31-4.41 (m, 1 H), 3.92-4.25 (m, 3 H), 3.72-3.92 (m, 4 H), 3.55-3.67 (m, 1 H), 3.44-3.53 (m, 3 H), 2.34-2.45 (m, 1 H), 2.21-2.30 (m, 1 H), 2.05-2.15 (m, 5 H), 1.93 (br dd, J = 13.48, 7.21 Hz, 2 H), 1.72-1.85 (m, 2 H), 1.45-1.59 (m, 1 H), 1.02-1.20 (m, 2 H). |
| 13-64 | 461.1 | $^1$H NMR (500 MHz, DMSO-$d_6$) δ ppm 10.02-10.07 (m, 1 H), 7.27 (t, J = 8.13 Hz, 1 H), 7.03 (dd, J = 8.07, 0.86 Hz, 1 H), 6.94 (dd, J = 8.31, 0.86 Hz, 1 H), 6.30 (dd, J = 17.06, 10.33 Hz, 1 H), 6.10 (dd, J = 16.99, 2.20 Hz, 1 H), 5.65-5.68 (m, 1 H), 4.26 (d, J = 8.68 Hz, 1 H), 4.16 (d, J = 8.56 Hz, 1 H), 3.94 (s, 1 H), 3.79-3.91 (m, 3 H), 3.74 (t, J = 6.72 Hz, 2 H), 3.07 (q, J = 5.50 Hz, 1 H), 2.63-2.71 (m, 1 H), 2.42-2.48 (m, 1 H), 2.37 (d, J = 1.34 Hz, 2 H), 2.13-2.23 (m, 2 H), 1.34-1.41 (m, 2 H). |
| 13-65 | 479.3 | $^1$H NMR (400 MHz, DMSO-$d_6$) δ ppm 9.97 (s, 1 H), 7.79 (d, J = 8.15 Hz, 1 H), 7.40-7.48 (m, 1 H), 7.22-7.29 (m, 3 H), 6.95-7.01 (m, 1 H), 6.26-6.39 (m, 1 H), 6.12 (dd, J = 16.93, 2.30 Hz, 1 H), 5.63-5.73 (m, 1 H), 4.24-4.32 (m, 1 H), 4.13-4.22 (m, 1 H), 3.89 (s, 4 H), 3.77 (s, 2 H), 3.57-3.69 (m, 1 H), .75 (d, J = 1.46 Hz, 2 H), 2.05-2.26 (m, 4 H), 1.05 (d, J = 2.51 Hz, 6 H). |
| 13-66 | 461.2 | $^1$H NMR (500 MHz, DMSO-$d_6$) δ ppm 7.27 (t, J = 8.13 Hz, 1 H), 7.03 (dd, J = 8.07, 0.86 Hz, 1 H), 6.94 (dd, J = 8.25, 0.79 Hz, 1 H), 6.30 (dd, J = 16.99, 10.27 Hz, 1 H), 6.10 (dd, J = 16.99, 2.32 Hz, 1 H), 5.65-5.68 (m, 1 H), 4.26 (d, J = 8.44 Hz, 1 H), 4.16 (d, J = 8.68 Hz, 1 H), 3.92-3.98 (m, 1 H), 3.87-3.91 (m, 1 H), 3.74 (br t, J = 6.85 Hz, 2 H), 3.07 (q, J = 5.46 Hz, 1 H), 2.69 (br d, J = 5.87 Hz, 1 H), 2.41-2.48 (m, 1 H), 2.35-2.39 (m, 2 H), 2.11-2.22 (m, 2 H), 1.34-1.42 (m, 2 H). 2 H obscured by water peak. |
| 13-67 | 461.2 | $^1$H NMR (500 MHz, DMSO-$d_6$) δ ppm 10.02-10.07 (m, 1 H), 7.27 (t, J = 8.13 Hz, 1 H), 7.03 (dd, J = 8.07, 0.86 Hz, 1 H), 6.94 (dd, J = 8.31, 0.86 Hz, 1 H), 6.30 (dd, J = 17.06, 10.33 Hz, 1 H), 6.10 (dd, J = 16.99, 2.20 Hz, 1 H), 5.65-5.68 (m, 1 H), 4.26 (d, J = 8.68 Hz, 1 H), 4.16 (d, J = 8.56 Hz, 1 H), 3.94 (s, 1 H), 3.79-3.91 (m, 3 H), 3.74 (t, J = 6.72 Hz, 2 H), 3.07 (q, J = 5.50 Hz, 1 H), 2.63-2.71 (m, 1 H), 2.42-2.48 (m, 1 H), 2.37 (d, J = 1.34 Hz, 2 H), 2.13-2.23 (m, 2 H), 1.34-1.41 (m, 2 H). |
| 13-68 | 479.2 | $^1$H NMR (500 MHz, DMSO-$d_6$) δ ppm 7.78 (d, J = 8.44 Hz, 1 H), 7.39-7.47 (m, 1 H), 7.19-7.27 (m, 3 H), 6.97 (d, J = 2.45 Hz, 1 H), 6.31 (ddd, J = 16.96, 10.30, 1.96 Hz, 1 H), 6.11 (dd, J = 16.93, 2.26 Hz, 1 H), 5.65-5.69 (m, 1 H), 4.27 (dd, J = 8.31, 5.99 Hz, 1 H), 4.17 (dd, J = 8.44, 2.93 Hz, 1 H), 3.84-3.99 (m, 4 H), 3.73-3.82 (m, 2 H), 2.74 (d, J = 2.45 Hz, 2 H), 2.13-2.23 (m, 3 H), 2.05 (d, J = 15.41 Hz, 1 H), 1.04 (d, J = 3.55 Hz, 6 H). |
| 13-69 | 479.2 | $^1$H NMR (500 MHz, DMSO-$d_6$) δ ppm 9.87-10.03 (m, 1 H), 7.78 (d, J = 8.44 Hz, 1 H), 7.39-7.46 (m, 1 H), 7.19-7.27 (m, 3 H), 6.97 (d, J = 2.32 Hz, 1 H), 6.31 (ddd, J = 17.03, 10.30, 2.02 Hz, 1 H), 6.11 (dd, J = 17.00, 2.32 Hz, 1 H), 5.65-5.69 (m, 1 H), 4.27 (dd, J = 8.44, 5.99 Hz, 1 H), 4.17 (dd, J = 8.56, 2.81 Hz, 1 H), 3.94-3.99 (m, 1 H), 3.73-3.92 (m, 5 H), 2.74 (d, J = 2.57 Hz, 2 H), 2.13-2.23 (m, 3 H), 2.05 (d, J = 15.41 Hz, 1 H), 1.03 (d, J = 3.55 Hz, 6 H). |
| 13-70 | 497.3 | $^1$H NMR (400 MHz, DMSO-$d_6$) δ ppm 10.35 (br s, 1 H), 7.96-8.04 (m, 1 H), 7.54-7.64 (m, 1 H), 7.36 (br d, J = 15.68 Hz, 2 H), 7.18 (br s, 1 H), 6.26-6.38 (m, 1 H), 6.14 (br s, 1 H), 5.68 (br d, J = 7.11 Hz, 1 H), 4.27 (br s, 1 H), 4.19 (br s, 1 H), 3.95- |

TABLE 22-continued

| Ex. # | LRMS: (ESI, +ve ion) m/z | NMR |
|---|---|---|
| Analytical Data for Examples 13-2 to 13-157. | | |
| | | 4.03 (m, 2 H), 3.85-3.93 (m, 4 H), 3.78 (br d, J = 5.23 Hz, 2 H), 2.75 (br s, 2 H), 2.05-2.25 (m, 4 H), 1.05 (br s, 6 H). |
| 13-71 | 513.2 | $^1$H NMR (500 MHz, DMSO-$d_6$) δ ppm 7.99 (d, J = 8.44 Hz, 1 H), 7.59 (ddd, J = 8.28, 7.06, 0.92 Hz, 1 H), 7.37 (t, J = 7.59 Hz, 1 H), 7.25 (d, J = 8.44 Hz, 1 H), 7.17 (d, J = 8.19 Hz, 1 H), 6.30 (ddd, J = 16.99, 10.27, 1.96 Hz, 1 H), 6.10 (dd, J = 16.99, 2.20 Hz, 1 H), 5.65-5.69 (m, 1 H), 4.27 (dd, J = 8.44, 5.75 Hz, 1 H), 4.11-4.19 (m, 2 H), 3.83-3.99 (m, 5 H), 3.72-3.80 (m, 2 H), 2.69-2.78 (m, 2 H), 2.05-2.24 (m, 4 H), 1.19 (d, J = 6.24 Hz, 6 H). |
| 13-72 | 495.2 | $^1$H NMR (400 MHz, DMSO-$d_6$) δ ppm 10.27-10.34 (m, 1 H), 7.98 (d, J = 8.36 Hz, 1 H), 7.58 (td, J = 7.63, 1.04 Hz, 1 H), 7.32-7.39 (m, 1 H), 7.22 (br d, J = 8.57 Hz, 1 H), 7.06-7.13 (m, 1 H), 6.25-6.37 (m, 1 H), 6.12 (dd, J = 17.04, 2.19 Hz, 1 H), 5.64-5.72 (m, 1 H), 4.23-4.32 (m, 1 H), 4.15-4.22 (m, 1 H), 3.93-3.99 (m, 1 H), 3.90 (br d, J = 6.69 Hz, 3 H), 3.71-3.82 (m, 2 H), 2.05-2.25 (m, 3 H), 1.66-1.91 (m, 4 H), 1.36-1.49 (m, 1 H), 0.99-1.15 (m, 2 H). |
| 13-73 | 495.2 | $^1$H NMR (400 MHz, DMSO-$d_6$) δ ppm 10.27-10.34 (m, 1 H), 7.98 (d, J = 8.36 Hz, 1 H), 7.58 (td, J = 7.63, 1.04 Hz, 1 H), 7.32-7.39 (m, 1 H), 7.22 (br d, J = 8.57 Hz, 1 H), 7.06-7.13 (m, 1 H), 6.25-6.37 (m, 1 H), 6.12 (dd, J = 17.04, 2.19 Hz, 1 H), 5.64-5.72 (m, 1 H), 4.23-4.32 (m, 1 H), 4.15-4.22 (m, 1 H), 3.93-3.99 (m, 1 H), 3.90 (br d, J = 6.69 Hz, 3 H), 3.71-3.82 (m, 2 H), 2.05-2.25 (m, 3 H), 1.66-1.91 (m, 4 H), 1.36-1.49 (m, 1 H), 0.99-1.15 (m, 2 H). |
| 13-74 | 495.2 | $^1$H NMR (400 MHz, DMSO-$d_6$) δ ppm 10.31 (br s, 1 H), 7.94-8.01 (m, 1 H), 7.57 (td, J = 7.63, 1.05 Hz, 1 H), 7.31-7.38 (m, 1 H), 7.17-7.24 (m, 1 H), 7.06-7.13 (m, 1 H), 3.78 (s, 2 H), 3.70 (br dd, J = 6.06, 2.51 Hz, 2 H), 3.59 (s, 2 H), 3.13 (br s, 4 H), 2.65 (br s, 2 H), 2.27-2.36 (m, 2 H), 2.04-2.14 (m, 3 H), 1.84 (br dd, J = 14.84, 7.32 Hz, 2 H), 1.72 (br d, J = 5.64 Hz, 2 H). |
| 13-75 | 495.2 | $^1$H NMR (400 MHz, $CDCl_3$) δ ppm 8.05 (d, J = 8.36 Hz, 1 H), 7.55 (t, J = 7.63 Hz, 1 H), 7.30-7.42 (m, 1 H), 7.22-7.28 (m, 1 H), 7.09 (d, J = 8.15 Hz, 1 H), 6.39 (dd, J = 16.93, 1.46 Hz, 1 H), 6.22 (dd, J = 17.04, 10.35 Hz, 1 H), 5.73 (dd, J = 10.35, 1.78 Hz, 1 H), 4.21-4.32 (m, 1 H), 4.11-4.20 (m, 2 H), 3.98-4.09 (m, 4 H), 3.93 (s, 2 H), 2.14-2.28 (m, 3 H), 1.90-2.02 (m, 3 H), 1.77 (br d, J = 6.27 Hz, 1 H), 1.44-1.51 (m, 1 H), 1.05-1.14 (m, 3 H). |
| 13-76 | 495.2 | $^1$H NMR (400 MHz, $CDCl_3$) δ ppm 8.05 (br d, J = 8.36 Hz, 1 H), 7.54 (br t, J = 7.42 Hz, 1 H), 7.30-7.41 (m, 1 H), 7.29-7.39 (m, 1 H), 7.09 (br d, J = 7.94 Hz, 1 H), 6.39 (br d, J = 16.93 Hz, 1 H), 6.22 (dd, J = 16.93, 10.24 Hz, 1 H), 5.73 (br d, J = 10.45 Hz, 1 H), 4.26 (br d, J = 7.73 Hz, 1 H), 4.11-4.20 (m, 2 H), 4.00-4.09 (m, 4 H), 3.93 (br t, J = 6.58 Hz, 2 H), 2.21 (br d, J = 6.48 Hz, 3 H), 1.94 (br d, J = 6.48 Hz, 3 H), 1.76 (br d, J = 5.85 Hz, 1 H), 1.45-1.51 (m, 1 H), 1.04-1.14 (m, 2 H). |
| 13-77 | 513.2 | $^1$H NMR (500 MHz, DMSO-$d_6$) δ ppm 7.99 (d, J = 8.44 Hz, 1 H), 7.59 (ddd, J = 8.28, 7.06, 0.92 Hz, 1 H), 7.37 (t, J = 7.59 Hz, 1 H), 7.25 (d, J = 8.44 Hz, 1 H), 7.17 (d, J = 8.19 Hz, 1 H), 6.30 (ddd, J = 16.99, 10.27, 1.96 Hz, 1 H), 6.10 (dd, J = 16.99, 2.20 Hz, 1 H), 5.65-5.69 (m, 1 H), 4.27 (dd, J = 8.44, 5.75 Hz, 1 H), 4.11-4.19 (m, 2 H), 3.83-3.99 (m, 5 H), 3.72-3.80 (m, 2 H), 2.69-2.78 (m, 2 H), 2.13-2.24 (m, 2 H), 1.19 (d, J = 6.24 Hz, 6 H). |
| 13-78 | 513.2 | $^1$H NMR (500 MHz, DMSO-$d_6$) δ ppm 7.99 (d, J = 8.31 Hz, 1 H), 7.59 (ddd, J = 8.28, 7.00, 0.98 Hz, 1 H), 7.37 (ddd, J = 8.31, 6.97, 1.10 Hz, 1 H), 7.25 (d, J = 8.44 Hz, 1 H), 7.17 (d, J = 8.19 Hz, 1 H), 6.30 (ddd, J = 17.00, 10.33, 1.90 Hz, 1 H), 6.10 (dd, J = 16.99, 2.20 Hz, 1 H), 5.65-5.69 (m, 1 H), 4.27 (dd, J = 8.50, 5.81 Hz, 1 H), 4.10-4.20 (m, 2 H), 3.83-3.99 (m, 5 H), 3.76 (br t, J = 6.85 Hz, 2 H), 2.69-2.78 (m, 2 H), 2.13-2.24 (m, 2 H), 1.20 (d, J = 6.48 Hz, 6 H). |
| 13-79 | 513.0 | $^1$H NMR (400 MHz, DMSO-$d_6$) δ 13.19 (d, J = 13.4 Hz, 1H), 7.60-7.43 (m, 2H), 7.39-7.32 (m, 1H), 6.42-6.21 (m, 1H), 6.12 (dd, J = 16.9, 2.1 Hz, 1H), 5.77-5.61 (m, 1H), 5.02-4.46 (m, 2.5H), 4.35-4.04 (m, 1.5H), 4.04-3.64 (m, 4H), 3.64-3.53 (m, 1H), 2.75-2.54 (m, 2H), 2.40-2.20 (m, 2H), 2.10 (dd, J = 14.0, 4.6 Hz, 3H), 2.04-1.93 (m, 2H), 1.45-1.33 (m, 2H), 0.94 (d, J = 4.6 Hz, 6H). $^{19}$F NMR (376 MHz, DMSO-$d_6$) δ ppm −228.75 (d, J = 235.5 Hz, 1F). |
| 13-80 | 513.1 | $^1$H NMR (400 MHz, DMSO-$d_6$) δ 13.17 (s, 1H), 7.62-7.45 (m, 2H), 7.35 (d, J = 8.6 Hz, 1H), 6.45-6.24 (m, 1H), 6.18-6.05 (m, 1H), 5.75-5.65 (m, 1H), 4.95-4.75 (m, 3H), 4.57 (d, J = 9.0 Hz, 0.5H), 4.29 (d, J = 9.0 Hz, 0.5H), 4.24-3.78 (m, 4H), 3.70-3.55 (m, 1H), 2.60 (s, 2H), 2.40-2.20 (m, 2H), 2.11 (s, 3H), 2.04-1.92 (m, 2H), 1.45-1.30 (m, 1H), 0.94 (s, 6H). $_{19}$F NMR (376 MHz, DMSO-$d^6$) δ ppm −228.83 (d, J = 218.4 Hz, 1F). |
| 13-81 | 451.0 | $^1$H NMR (400 MHz, DMSO-$d_6$) δ ppm 13.14 (s, 1 H), 7.50-7.61 (m, 2 H), 7.30-7.34 (m, 1 H), 6.28-6.35 (m, 1 H), 6.09-6.13 (m, 1 H ), 5.67-5.69 (m, 1 H), 4.26-4.30 (m, 1 H ), 4.16-4.18 (m, 1 H), 3.96-3.99 (m, 1 H), 3.85-3.90 (m, 3 H ), 3.73-3.78 (m, 2 H), 2.53-2.58 (m, 1 H), 2.40-2.31 (m, 2 H), 2.21-2.25 (m. 1 H), 2.18 (s, 3H), 2.10-2.18 (m, 1 H), 1.92-1.95 (m, 1H), 1.25-1.28 (m, 1 H), 0.19-0.39 (m, 1 H). |
| 13-82 | 450.9 | $^1$H NMR (400 MHz, DMSO-$d_6$) δ ppm 13.16 (s, 1H), 7.66-7.60 (d, J = 24.0Hz, 1H), 7.55-7.53 (d, J = 8.4Hz, 1H), 7.37-7.35 (d, J = 8.4Hz, 1H), 6.32-6.27 (m, 1H), 6.13-6.08 (dd, J = 16.8Hz, 2.4Hz, 1H), 4.28-4.26 (d, J = 8.8Hz, 1H), 4.17-4.15 (d, J = 8.8Hz, 1H), 3.98-3.96 (d, J = 10.4Hz, 1H), 3.89-3.82 (m, 3H), 3.74-3.71(t, J = 6.4Hz, 2H), 3.25-3.18 (m, 1H), 2.92-2.87 (d, J = 18.8Hz, 1H), 2.25-2.15 (m, 5H), 1.75-1.55 (m, 2H), 1.01-0.82 (m, 1H), 0.20-0.07 (m, 1H). |
| 13-83 | 478.9 | $^1$H NMR (400 MHz, DMSO-$d_6$) δ ppm 13.17 (s, 1 H), 7.52-7.59 (m, 2 H), 7.33-7.36 (m, 1 H), 6.27-6.33 (m, 1 H), 6.09-6.13 (m, 1 H ), 5.65-5.69 (m, 1 H), 4.27- |

TABLE 22-continued

| Ex. # | LRMS: (ESI, +ve ion) m/z | NMR |
|---|---|---|
| Analytical Data for Examples 13-2 to 13-157. | | |
| | | 4.29 (m, 1 H ), 4.16-4.18 (m, 1 H), 3.88-3.99 (m, 4 H), 3.76-3.78 (m, 2 H ), 3.01-3.07 (m, 1 H), 2.59-2.79 (m, 2 H), 2.38-2.45 (m, 1 H), 2.11-2.18 (m, 5 H), 1.76-1.82 (m. 1 H), 0.76-0.79 (m, 1 H), 0.30-0.37 (m, 2 H), 0.02-0.10 (m, 2 H). |
| 13-84 | 479.2 | $^1$H NMR (400 MHz, DMSO-$d_6$) δ ppm 13.15 (s, 1H), 7.62-7.48 (m, 2H), 7.37-7.35 (d, J = 8.8Hz, 1H), 6.34-6.27 (m, 1H), 6.13-6.08 (dd, J = 16.4Hz, 2.4Hz, 1H), 5.69-5.66 (dd, J1 = 10.4Hz, 2.0Hz, 1H), 4.28-4.26 (d, J = 8.8Hz, 1H), 4.17-4.15 (d, J = 8.8Hz, 1H), 3.98-3.96 (d, J = 10.0Hz, 1H), 3.89-3.83 (m, 3H), 3.76-3.73(t, J = 6.6Hz, 2H), 3.17-3.10 (m, 1H), 2.78-2.73 (d, J = 18.8Hz, 1H), 2.21-2.17 (m, 5H), 2.03-1.96 (m, 1H), 1.01-0.90-0.77 (m, 4H), 0.68-0.67 (d, J = 2.8Hz, 3H). |
| 13-85 | 534.4 | $^1$H NMR (400 MHz, DMSO-$d_6$) δ ppm 9.96 (1 H, br s), 7.78 (1 H, d, J = 8.15 Hz), 7.40-7.45 (1 H, m), 7.19-7.26 (2 H, m), 7.12-7.17 (1 H, m), 6.90-6.93 (1 H, m), 6.59 (1 H, dt, J = 15.36, 6.22 Hz), 6.10 (1 H, dd, J = 15.47, 1.46 Hz), 4.22-4.28 (1 H, m), 4.12-4.19 (1 H, m), 3.82-3.98 (4 H, m), 3.71-3.82 (2 H, m), 3.01 (2 H, d, J = 5.23 Hz), 2.06-2.23 (9 H, m), 1.67-1.90 (4 H, m), 1.31-1.49 (1 H, m), 0.98-1.15 (2 H, m). |
| 13-86 | 534.3 | $^1$H NMR (400 MHz, DMSO-$d_6$) δ ppm 7.78 (d, J = 8.15 Hz, 1 H), 7.42 (t, J = 7.52 Hz, 1 H), 7.20-7.26 (m, 2 H), 7.10-7.19 (m, 1 H), 6.88-6.93 (m, 1 H), 6.59 (dt, J = 15.42, 6.09 Hz, 1 H), 6.10 (dd, J = 15.47, 1.25 Hz, 1 H), 4.20-4.29 (m, 1 H), 4.16 (br dd, J = 8.15, 4.81 Hz, 1 H), 3.84-3.99 (m, 4 H), 3.72-3.80 (m, 2 H), 3.01 (d, J = 6.69 Hz, 2 H), 2.07-2.23 (m, 9 H), 1.67-1.93 (m, 4 H), 1.34-1.50 (m, 1 H), 1.02-1.14 (m, 2 H). |
| 13-87 | 534.3 | $^1$H NMR (500 MHz, DMSO-$d_6$) δ ppm 7.77 (d, J = 8.19 Hz, 1 H), 7.42 (ddd, J = 8.10, 6.88, 1.04 Hz, 1 H), 7.19-7.24 (m, 2 H), 7.13 (br d, J = 8.31 Hz, 1 H), 6.91 (d, J = 2.45 Hz, 1 H), 6.58 (dt, J = 15.41, 6.11 Hz, 1 H), 6.06-6.11 (m, 1 H), 4.24 (t, J = 8.25 Hz, 1 H), 4.14 (br d, J = 8.31 Hz, 1 H), 3.82-3.97 (m, 4 H), 3.70-3.79 (m, 2 H), 3.00 (d, J = 6.00 Hz, 2 H), 2.06-2.22 (m, 9 H), 1.67-2.00 (m, 1 H), 1.31-1.40 (m, 1 H), 1.07-1.14 (m, 2 H). |
| 13-88 | 534.4 | $^1$H NMR (500 MHz, DMSO-$d_6$) δ ppm 7.77 (d, J = 8.19 Hz, 1 H), 7.41 (ddd, J = 8.13, 6.85, 1.16 Hz, 1 H), 7.19-7.25 (m, 2 H), 7.14 (d, J = 8.44 Hz, 1 H), 6.90 (d, J = 2.08 Hz, 1 H), 6.58 (dt, J = 15.37, 6.13 Hz, 1 H), 6.06-6.12 (m, 1 H), 4.24 (t, J = 7.58 Hz, 1 H), 4.15 (t, J = 7.46 Hz, 1 H), 3.84-3.97 (m, 4 H), 3.71-3.80 (m, 2 H), 3.00 (d, J = 5.99 Hz, 2 H), 2.07-2.21 (m, 9 H), 1.69-1.89 (m, 4 H), 1.38-1.47 (m, 1 H), 1.02-1.13 (m, 2 H). |
| 13-89 | 509.3 | $^1$H NMR (400 MHz, $CDCl_3$) δ ppm 7.89 (s, 1 H), 7.56 (s, 1 H), 6.36-6.40 (m, 1 H), 6.18-6.24 (m, 1 H), 5.71 (d, J = 10.40 Hz, 1 H), 4.23-4.27 (m, 1 H), 4.14-4.18 (m, 2 H), 4.03-4.06 (m, 1 H), 3.91-3.98 (m, 4 H), 3.56 (s, 3 H), 2.65 (s, 2 H), 2.42 (s, 3 H), 2.22-2.24 (s, 2 H), 2.08 (s, 5 H), 1.42-1.46 (m, 2 H), 1.00 (s. 6 H). |
| 13-90 | 511.0 | $^1$H NMR (400 MHz, DMSO-$d_6$) δ ppm 7.99 (1 H, s), 7.65 (1 H, s), 6.31 (1 H, ddd, J = 16.95, 10.31, 2.38 Hz), 6.11 (1 H, dd, J = 17.00, 2.28 Hz), 5.68 (1 H, dd, J = 10.26, 2.18 Hz), 4.29 (1 H, dd, J = 8.50, 3.32 Hz), 4.18 (1 H, dd, J = 8.50, 4.77 Hz), 3.86-4.04 (6 H, m), 3.78 (2 H, br t, J = 6.63 Hz), 3.50 (3 H, s), 2.77 (2 H, s), 2.38 (3 H, s), 2.14-2.27 (2 H, m), 2.03 (3 H, s), 1.22 (3 H, s), 1.21 (3 H, s) |
| 13-91 | 511.2 | $^1$H NMR (500 MHz, DMSO-$d_6$) δ ppm 7.97 (1 H, s), 7.64 (1 H, s), 6.30 (1 H, ddd, J = 17.03, 10.30, 3.24 Hz), 6.10 (1 H, dd, J = 17.06, 2.26 Hz), 5.67 (1 H, dd, J = 10.39, 2.20 Hz), 4.28 (1 H, dd, J = 8.50, 4.34 Hz), 4.17 (1 H, dd, J = 8.25, 6.05 Hz), 3.84-4.03 (6 H, m), 3.77 (2 H, br t, J = 6.60 Hz), 3.49 (3 H, d, J = 1.96 Hz), 2.76 (2 H, s), 2.37 (3 H, s), 2.14-2.25 (2 H, m), 2.02 (3 H, s), 1.21 (3 H, s), 1.20 (3 H, s) |
| 13-92 | 511.4 | $^1$H NMR (500 MHz, DMSO-$d_6$) δ ppm 7.97 (1 H, s), 7.64 (1 H, s), 6.30 (1 H, ddd, J = 16.99, 10.33, 3.24 Hz), 6.10 (1 H, dd, J = 17.06, 2.26 Hz), 5.67 (1 H, dd, J = 10.27, 2.32 Hz), 4.28 (1 H, dd, J = 8.62, 4.34 Hz), 4.17 (1 H, dd, J = 8.38, 6.05 Hz), 3.84-4.03 (6 H, m), 3.77 (2 H, br t, J = 6.60 Hz), 3.49 (3 H, d, J = 1.83 Hz), 2.76 (2 H, s), 2.37 (3 H, s), 2.14-2.27 (2 H, m), 2.02 (3 H, s), 1.21 (3 H, s), 1.20 (3 H, s) |
| 13-93 | 493.3 | $^1$H NMR (400 MHz, DMSO-$d_6$) δ ppm 13.16 (br d, J = 14.4 Hz, 1 H), 7.45-7.57 (m, 1 H), 7.59 (s, 1 H), 7.36 (d, J = 8.6 Hz, 1 H), 6.23-6.40 (m, 1 H), 6.03-6.19 (m, 1 H), 5.68 (dd, J = 10.2, 2.1 Hz, 1 H), 4.28 (br dd, J = 7.9, 2.9 Hz, 1 H), 4.17 (br d, J = 8.4 Hz, 1 H), 3.82-4.03 (m, 4 H), 3.77 (br s, 2 H), 2.83 (br t, J = 5.1 Hz, 1 H), 2.60-2.72 (m, 1 H), 2.10-2.21 (m, 7 H), 1.26-1.46 (m, 4 H), 1.16-1.26 (m, 1 H), 0.72 (d, J = 12.8 Hz, 3 H) |
| 13-94 | 507.3 | $^1$H NMR (400 MHz, DMSO-$d_6$) δ ppm 13.16 (br d, J = 15.5 Hz, 1 H), 7.21-7.78 (m, 3 H), 6.22-6.44 (m, 1 H), 6.05-6.19 (m, 1 H), 5.68 (br dd, J = 9.1, 6.6 Hz, 1 H), 4.47-4.69 (m, 1 H), 4.00-4.11 (m, 2 H), 3.73-3.98 (m, 3 H), 3.56-3.71 (m, 1 H), 2.83 (br s, 1 H), 2.61-2.74 (m, 1 H), 2.07-2.30 (m, 8 H), 1.36 (s, 3 H), 1.18-1.27 (m, 4 H), 0.63-0.78 (m, 3 H) |
| 13-95 | 483.4 | $^1$H NMR (400 MHz, DMSO-$d_6$) δ ppm 13.20 (s, 1 H), 7.59 (s, 1 H), 7.55 (d, J = 8.6 Hz, 1 H), 7.36 (d, J = 8.6 Hz, 1 H), 6.26-6.36 (m, 1 H), 6.11 (dd, J = 16.9, 2.3 Hz, 1 H), 5.68 (dd, J = 10.2, 2.1 Hz, 1 H), 4.29 (d, J = 8.6 Hz, 1 H), 4.18 (br d, J = 8.8 Hz, 1 H), 3.95-4.03 (m, 2 H), 3.83-3.95 (m, 4 H), 3.77 (br t, J = 6.8 Hz, 2 H), 2.75 (s, 2 H), 2.20 (br t, J = 6.9 Hz, 2 H), 2.14 (s, 3 H), 1.21 (s, 6 H) |
| 13-96 | 489.4 | $^1$H NMR (400 MHz, DMSO-$d_6$) δ ppm 13.20 (s, 1 H), 7.64 (s, 1 H), 7.57 (d, J = 8.6 Hz, 1 H), 7.37 (d, J = 8.8 Hz, 1 H), 6.25-6.37 (m, 1 H), 6.11 (dd, J = 16.9, 2.3 Hz, 1 H), 5.64-5.71 (m, 1 H), 4.31 (d, J = 8.8 Hz, 1 H), 4.18 (br d, J = 7.5 Hz, 1 H), 3.97-4.03 (m, 1 H), 3.86-3.97 (m, 3 H), 3.79 (br t, J = 6.8 Hz, 2 H), 2.26-2.40 (m, 2 |

TABLE 22-continued

| Analytical Data for Examples 13-2 to 13-157. | | |
|---|---|---|
| Ex. # | LRMS: (ESI, +ve ion) m/z | NMR |
| | | H), 2.17-2.24 (m, 2 H), 2.14 (s, 3 H), 2.03-2.11 (m, 2 H), 1.65-1.79 (m, 2 H). $^{19}$F NMR (376 MHz, DMSO-$d_6$) δ ppm −93.21-−89.75 (m, 2 F). |
| 13-97 | 467.2 | $^{1}$H NMR (400 MHz, DMSO-$d_6$) δ ppm 13.14 (s, 1 H), 7.58 (br s, 1 H), 7.53 (d, J = 8.6 Hz, 1 H), 7.34 (d, J = 8.6 Hz, 1 H), 6.26-6.38 (m, 1 H), 6.12 (dd, J = 16.9, 2.3 Hz, 1 H), 5.64-5.73 (m, 1 H), 4.30 (br d, J = 8.8 Hz, 1 H), 4.18 (d, J = 8.6 Hz, 1 H), 3.88-4.02 (m, 4 H), 3.79 (t, J = 6.8 Hz, 2 H), 2.16-2.29 (m, 7 H), 1.81-1.88 (m, 2 H), 1.27 (s, 3 H), 1.24 (s, 3 H) |
| 13-98 | 495.3 | $^{1}$H NMR (400 MHz, DMSO-$d_6$) δ ppm 13.20 (s, 1 H), 7.49-7.61 (m, 2 H), 7.36 (d, J = 8.6 Hz, 1 H), 6.26-6.39 (m, 1 H), 6.12 (dd, J = 17.1, 2.3 Hz, 1 H), 5.63-5.73 (m, 1 H), 4.29 (d, J = 8.8 Hz, 1 H), 4.18 (br d, J = 8.6 Hz, 1 H), 3.95-4.04 (m, 2 H), 3.83-3.94 (m, 4 H), 3.77 (br t, J = 6.8 Hz, 2 H), 2.96 (s, 2 H), 2.16-2.25 (m, 2 H), 2.13 (s, 3 H), 1.99-2.11 (m, 2 H), 1.83-1.98 (m, 2 H), 1.69-1.79 (m, 2 H) |
| 13-99 | 523.2 | $^{1}$H NMR (400 MHz, DMSO-de) δ ppm 13.21 (br d, J = 3.3 Hz, 1 H), 7.62 (d, J = 3.8 Hz, 1 H), 7.57 (d, J = 8.4 Hz, 1 H), 7.36 (dd, J = 8.6, 5.6 Hz, 1 H), 6.24-6.38 (m, 1 H), 6.11 (dd, J = 17.1, 2.3 Hz, 1 H), 5.62-5.72 (m, 1 H), 4.60-4.75 (m, 1 H), 4.02-4.38 (m, 4 H), 3.87-4.02 (m, 4 H), 3.78 (br t, J = 6.7 Hz, 2 H), 2.90-3.08 (m, 2 H), 2.17-2.26 (m, 3 H), 2.15 (s, 2 H). $^{19}$F NMR (376 MHz, DMSO-$d_6$) δ ppm −77.52 (s, 3 F), −77.54 (s, 3 F) |
| 13-100 | 469.3 | $^{1}$H NMR (400 MHz, DMSO-$d_6$) δ ppm 13.20 (s, 1 H), 7.66 (s, 1 H), 7.56 (d, J = 8.4 Hz, 1 H), 7.35 (d, J = 8.8 Hz, 1 H), 6.27-6.39 (m, 1 H), 6.12 (dd, J = 17.0, 2.2 Hz, 1 H), 5.65-5.71 (m, 1 H), 4.39-4.49 (m, 2 H), 4.31 (br d, J = 7.9 Hz, 1 H), 4.19 (d, J = 8.8 Hz, 1 H), 3.89-4.02 (m, 4 H), 3.83 (br t, J = 6.8 Hz, 2 H), 2.22 (br d, J = 1.0 Hz, 5 H), 1.45 (d, J = 11.5 Hz, 6 H) |
| 13-101 | 465.3 | $^{1}$H NMR (400 MHz, DMSO-$d_6$) δ ppm 13.14 (s, 1 H), 7.61 (s, 1 H), 7.53 (d, J = 8.8 Hz, 1 H), 7.35 (d, J = 8.6 Hz, 1 H), 6.24-6.38 (m, 1 H), 6.07-6.16 (m, 1 H), 5.62-5.74 (m, 1 H), 4.27 (d, J = 8.6 Hz, 1 H), 4.16 (br d, J = 7.5 Hz, 1 H), 3.94-4.01 (m, 1 H), 3.80-3.92 (m, 3 H), 3.73 (t, J = 6.8 Hz, 2 H), 2.37-2.45 (m, 2 H), 2.15-2.23 (m, 5 H), 2.02-2.14 (m, 2 H), 1.13-1.26 (m, 2 H), 0.96-1.08 (m, 2 H) |
| 13-102 | 481.2 | $^{1}$H NMR (500 MHz, DMSO-$d_6$) δ ppm 8.05 (s, 1 H), 7.73 (d, J = 8.2 Hz, 1 H), 7.14 (d, J = 8.4 Hz, 1 H), 6.30 (dd, J = 17.0, 10.3 Hz, 1 H), 6.10 (dd, J = 17.0, 2.2 Hz, 1 H), 5.63-5.71 (m, 1 H), 4.30 (dd, J = 8.6, 2.1 Hz, 1 H), 4.17 (d, J = 8.6 Hz, 1 H), 3.87-4.01 (m, 4 H), 3.75-3.83 (m, 2 H), 3.49 (d, J = 3.5 Hz, 3 H), 2.25 (br t, J = 7.2 Hz, 2 H), 2.20 (q, J = 6.4 Hz, 2 H), 2.15 (d, J = 2.7 Hz, 3 H), 1.81-1.94 (m, 2 H), 1.24 (d, J = 13.2 Hz, 6 H) |
| 13-103 | 481.2 | $^{1}$H NMR (500 MHz, DMSO-$d_6$) δ ppm 8.05 (s, 1 H), 7.73 (d, J = 8.2 Hz, 1 H), 7.14 (d, J = 8.4 Hz, 1 H), 6.30 (dd, J = 17.0, 10.3 Hz, 1 H), 6.10 (dd, J = 17.0, 2.2 Hz, 1 H), 5.63-5.71 (m, 1 H), 4.30 (dd, J = 8.6, 2.1 Hz, 1 H), 4.17 (d, J = 8.6 Hz, 1 H), 3.87-4.01 (m, 4 H), 3.75-3.83 (m, 2 H), 3.49 (d, J = 3.5 Hz, 3 H), 2.25 (br t, J = 7.2 Hz, 2 H), 2.20 (q, J = 6.4 Hz, 2 H), 2.15 (d, J = 2.7 Hz, 3 H), 1.81-1.94 (m, 2 H), 1.24 (d, J = 13.2 Hz, 6 H) |
| 13-104 | 507.3 | $^{1}$H NMR (400 MHz, DMSO-$d_6$) δ ppm 8.07 (d, J = 6.7 Hz, 1 H), 7.74 (dd, J = 8.3, 2.0 Hz, 1 H), 7.16 (d, J = 8.4 Hz, 1 H), 6.24-6.37 (m, 1 H), 6.11 (dd, J = 16.9, 2.3 Hz, 1 H), 5.63-5.72 (m, 1 H), 4.23-4.34 (m, 1 H), 4.17 (dd, J = 8.4, 5.0 Hz, 1 H), 3.86-4.02 (m, 4 H), 3.74-3.83 (m, 2 H), 3.52-3.66 (m, 3 H), 2.85 (t, J = 5.3 Hz, 1 H), 2.64-2.76 (m, 1 H), 2.10-2.24 (m, 8 H), 1.37 (s, 3 H), 1.14-1.27 (m, 1 H), 0.73 (d, J = 9.8 Hz, 3 H) |
| 13-105 | 507.3 | $^{1}$H NMR (400 MHz, DMSO-$d_6$) δ ppm 8.06 (s, 1 H), 7.74 (br d, J = 8.2 Hz, 1 H), 7.16 (br d, J = 8.4 Hz, 1 H), 6.31 (br dd, J = 16.7, 10.5 Hz, 1 H), 6.03-6.19 (m, 1 H), 5.68 (br d, J = 10.5 Hz, 1 H), 4.29 (br d, J = 8.2 Hz, 1 H), 4.12-4.22 (m, 1 H), 3.72-4.05 (m, 6 H), 3.56 (s, 3 H), 2.85 (br t, J = 5.1 Hz, 1 H), 2.64-2.77 (m, 1 H), 2.07-2.28 (m, 8 H), 1.37 (s, 3 H), 1.23 (br d, J = 9.8 Hz, 1 H), 0.72 (s, 3 H) |
| 13-106 | 507.3 | $^{1}$H NMR (400 MHz, DMSO-$d_6$) δ ppm 8.08 (s, 1 H), 7.75 (d, J = 8.4 Hz, 1 H), 7.16 (d, J = 8.2 Hz, 1 H), 6.24-6.37 (m, 1 H), 6.11 (dd, J = 17.0, 2.2 Hz, 1 H), 5.63-5.72 (m, 1 H), 4.23-4.36 (m, 1 H), 4.17 (dd, J = 8.6, 5.0 Hz, 1 H), 3.72-4.03 (m, 6 H), 3.64 (s, 3 H), 2.85 (t, J = 5.2 Hz, 1 H), 2.65-2.75 (m, 1 H), 2.07-2.26 (m, 8 H), 1.37 (s, 3 H), 1.17 (d, J = 9.6 Hz, 1 H), 0.75 (s, 3 H) |
| 13-107 | 483.1 | $^{1}$H NMR (400 MHz, DMSO-$d_6$) δ ppm 13.22 (s, 1 H), 7.72 (s, 1 H), 7.60 (d, J = 8.6 Hz, 1 H), 7.39 (d, J = 8.6 Hz, 1 H), 6.24-6.40 (m, 1 H), 6.05-6.16 (m, 1 H), 5.68 (dd, J = 10.3, 2.2 Hz, 1 H), 4.94 (s, 2 H), 4.49 (d, J = 7.3 Hz, 1 H), 4.36 (d, J = 6.9 Hz, 1 H), 4.25-4.33 (m, 2 H), 4.18 (dd, J = 8.7, 2.8 Hz, 1 H), 4.09 (d, J = 7.1 Hz, 1 H), 3.94-4.02 (m, 1 H), 3.87-3.94 (m, 3 H), 3.75-3.85 (m, 2 H), 2.19 (s, 5 H) |
| 13-108 | 505.3 | $^{1}$H NMR (400 MHz, DMSO-$d_6$) δ ppm 9.99 (br s, 1 H), 7.74-7.84 (m, 1 H), 7.40-7.47 (m, 1 H), 7.22-7.30 (m, 2 H), 7.15-7.22 (m, 1 H), 6.94-7.00 (m, 1 H), 6.26-6.37 (m, 1 H), 6.11 (dd, J = 16.9, 2.3 Hz, 1 H), 5.63-5.72 (m, 1 H), 4.28 (br d, J = 8.6 Hz, 1 H), 4.17 (dd, J = 8.6, 4.0 Hz, 1 H), 3.95-4.01 (m, 1 H), 3.84-3.95 (m, 3 H), 3.77 (br t, J = 6.7 Hz, 2 H), 2.84 (t, J = 5.5 Hz, 1 H), 2.59-2.72 (m, 1 H), 2.28-2.36 (m, 1 H), 2.14-2.24 (m, 2 H), 2.07-2.14 (m, 1 H), 2.02 (dd, J = 16.6, 2.2 Hz, 1 H), 1.30-1.40 (m, 3 H), 1.24 (d, J = 9.4 Hz, 1 H), 0.67-0.76 (m, 3 H) |
| 13-109 | 454.2 | $^{1}$H NMR (400 MHz, DMSO-$d_6$) δ ppm 8.53 (d, J = 5.0 Hz, 1 H), 8.31 (d, J = 3.6 Hz, 1 H), 7.39-7.47 (m, 1 H), 6.24-6.37 (m, 1 H), 6.11 (dd, J = 16.9, 2.3 Hz, 1 H), 5.60-5.72 (m, 1 H), 4.27 (br d, J = 8.6 Hz, 1 H), 4.17 (dd, J = 8.5, 2.8 Hz, 1 H), 3.92-4.01 (m, 1 H), 3.81-3.92 (m, 3 H), 3.71-3.81 (m, 2 H), 2.77-2.86 (m, 1 H), 2.61-2.72 (m, 1 H), 2.28-2.41 (m, 1 H), 2.07-2.27 (m, 7 H), 1.30-1.42 (m, 3 H), 1.17-1.30 (m, 1 H), 0.70 (d, J = 13.6 Hz, 3 H) |

TABLE 22-continued

| Analytical Data for Examples 13-2 to 13-157. | | |
|---|---|---|
| Ex. # | LRMS: (ESI, +ve ion) m/z | NMR |
| 13-110 | 479.2 | $^1$H NMR (400 MHz, DMSO-$d_6$) δ ppm 8.06 (s, 1 H), 7.74 (d, J = 8.2 Hz, 1 H), 7.16 (d, J = 8.4 Hz, 1 H), 6.25-6.38 (m, 1 H), 6.11 (dd, J = 16.9, 2.1 Hz, 1 H), 5.68 (dd, J = 10.3, 2.2 Hz, 1 H), 4.28 (br d, J = 8.6 Hz, 1 H), 4.17 (br d, J = 8.6 Hz, 1 H), 3.93-3.93 (m, 1 H), 3.85-4.02 (m, 3 H), 3.78 (br t, J = 6.7 Hz, 2 H), 3.56 (d, J = 1.3 Hz, 3 H), 3.10-3.17 (m, 1 H), 2.60-2.73 (m, 1 H), 2.44-2.50 (m, 2 H), 2.13-2.29 (m, 7 H), 1.39-1.53 (m, 2 H) |
| 13-111 | 509.2 | $^1$H NMR (400 MHz, DMSO-$d_6$) δ ppm 8.07 (d, J = 4.6 Hz, 1 H), 7.76 (d, J = 8.4 Hz, 1 H), 7.16 (t, J = 7.8 Hz, 1 H), 6.25-6.38 (m, 1 H), 6.11 (dd, J = 16.9, 2.1 Hz, 1 H), 5.68 (dd, J = 10.2, 2.1 Hz, 1 H), 4.24-4.34 (m, 1 H), 4.18 (br d, J = 8.4 Hz, 1 H), 3.85-4.12 (m, 6 H), 3.78 (br t, J = 6.7 Hz, 2 H), 3.52 (d, J = 11.9 Hz, 3 H), 3.11-3.22 (m, 1 H), 2.75-2.95 (m, 2 H), 2.08-2.26 (m, 5 H), 0.99 (td, J = 7.8, 4.9 Hz, 1 H), 0.40-0.59 (m, 2 H), 0.31 (br d, J = 3.6 Hz, 2 H) |
| 13-112 | 459.3 | $^1$H NMR (400 MHz, DMSO-$d_6$) δ ppm 9.44 (s, 1 H), 7.15 (d, J = 8.6 Hz, 1 H), 6.77 (dd, J = 8.3, 2.6 Hz, 1 H), 6.48 (d, J = 2.7 Hz, 1 H), 6.26-6.37 (m, 1 H), 6.06-6.16 (m, 1 H), 5.62-5.73 (m, 1 H), 4.27 (br d, J = 7.5 Hz, 1 H), 4.12-4.20 (m, 2 H), 3.97 (br d, J = 14.8 Hz, 2 H), 3.81-3.93 (m, 3 H), 3.75 (t, J = 6.8 Hz, 2 H), 2.65-2.73 (m, 2 H), 2.11-2.26 (m, 2 H), 1.91 (s, 3 H), 1.22 (s, 3 H), 1.20 (s, 3 H) |
| 13-113 | 441.3 | $^1$H NMR (400 MHz, DMSO-$d_6$) δ ppm 9.36 (s, 1 H), 7.14 (d, J = 8.4 Hz, 1 H), 6.74 (dd, J = 8.3, 2.6 Hz, 1 H), 6.49 (d, J = 2.5 Hz, 1 H), 6.25-6.37 (m, 1 H), 6.06-6.16 (m, 1 H), 5.62-5.73 (m, 1 H), 4.26 (dd, J = 8.7, 1.8 Hz, 1 H), 4.16 (dd, J = 8.7, 2.6 Hz, 1 H), 3.93-3.99 (m, 1 H), 3.80-3.92 (m, 3 H), 3.74 (br t, J = 6.9 Hz, 2 H), 3.08 (q, J = 5.4 Hz, 1 H), 2.64-2.73 (m, 1 H), 2.39-2.48 (m, 3 H), 2.12-2.27 (m, 3 H), 1.94 (s, 3 H), 1.31-1.54 (m, 2 H). |
| 13-114 | 493.3 | $^1$H NMR (500 MHz, DMSO-$d_6$) δ ppm 13.12 (s, 1 H), 7.58 (s, 1 H), 7.52 (d, J = 8.6 Hz, 1 H), 7.35 (d, J = 8.6 Hz, 1 H), 6.23-6.37 (m, 1 H), 6.10 (dd, J = 16.9, 2.3 Hz, 1 H), 5.62-5.71 (m, 1 H), 4.27 (dd, J = 8.4, 5.4 Hz, 1 H), 4.16 (dd, J = 8.5, 3.7 Hz, 1 H), 3.93-4.01 (m, 1 H), 3.82-3.92 (m, 3 H), 3.70-3.82 (m, 2 H), 2.82 (t, J = 5.4 Hz, 1 H), 2.60-2.68 (m, 1 H), 2.08-2.22 (m, 8 H), 1.35 (s, 3 H), 1.29 (d, J = 9.5 Hz, 1 H), 0.69 (s, 3 H). |
| 13-115 | 493.3 | $^1$H NMR (500 MHz, DMSO-$d_6$) δ ppm 13.16 (s, 1 H), 7.52 (d, J = 8.7 Hz, 1 H), 7.49 (s, 1 H), 7.35 (d, J = 8.6 Hz, 1 H), 6.30 (dd, J = 17.0, 10.3 Hz, 1 H), 6.10 (dd, J = 17.0, 2.2 Hz, 1 H), 5.63-5.69 (m, 1 H), 4.27 (dd, J = 8.6, 3.2 Hz, 1 H), 4.16 (dd, J = 8.6, 2.6 Hz, 1 H), 3.97 (dd, J = 10.1, 3.1 Hz, 1 H), 3.82-3.94 (m, 3 H), 3.76 (br t, J = 6.7 Hz, 2 H), 2.82 (t, J = 5.3 Hz, 1 H), 2.61-2.70 (m, 1 H), 2.05-2.23 (m, 8 H), 1.32-1.38 (m, 3 H), 1.20 (d, J = 9.5 Hz, 1 H), 0.73 (s, 3 H). |
| 13-116 | 479.2 | $^1$H NMR (400 MHz, DMSO-$d_6$) δ ppm 8.04 (d, J = 4.0 Hz, 1 H), 7.73 (dd, J = 8.2, 2.1 Hz, 1 H), 7.14 (dd, J = 8.4, 2.7 Hz, 1 H), 6.25-6.37 (m, 1 H), 6.11 (dd, J = 17.0, 2.2 Hz, 1 H), 5.60-5.73 (m, 1 H), 4.28 (br d, J = 8.6 Hz, 1 H), 4.18 (br d, J = 8.6 Hz, 1 H), 3.85-4.04 (m, 4 H), 3.78 (br t, J = 6.2 Hz, 2 H), 3.48 (dd, J = 6.9, 1.7 Hz, 3 H), 2.15-2.24 (m, 2 H), 2.05-2.15 (m, 4 H), 1.87-2.03 (m, 2 H), 1.69-1.87 (m, 2 H), 1.43-1.58 (m, 1 H), 1.14 (dq, J = 9.5, 4.8 Hz, 1 H), 0.99-1.11 (m, 1 H). |
| 13-117 | 479.2 | $^1$H NMR (500 MHz, DMSO-$d_6$) δ ppm 8.05 (s, 1 H), 7.73 (d, J = 8.2 Hz, 1 H), 7.15 (d, J = 8.4 Hz, 1 H), 6.30 (dd, J = 17.0, 10.3 Hz, 1 H), 6.10 (dd, J = 17.1, 2.3 Hz, 1 H), 5.63-5.70 (m, 1 H), 4.27 (d, J = 8.6 Hz, 1 H), 4.16 (br d, J = 8.4 Hz, 1 H), 3.85-4.01 (m, 4 H), 3.77 (t, J = 6.7 Hz, 2 H), 3.55 (d, J = 2.3 Hz, 3 H), 3.12 (q, J = 5.5 Hz, 1 H), 2.63 (tt, J = 5.6, 3.0 Hz, 1 H), 2.43-2.53 (m, 2 H), 2.14-2.22 (m, 7 H), 1.40-1.48 (m, 2 H) |
| 13-118 | 479.2 | $^1$H NMR (500 MHz, DMSO-$d_6$) δ ppm 8.05 (s, 1 H), 7.73 (d, J = 8.2 Hz, 1 H), 7.15 (d, J = 8.4 Hz, 1 H), 6.30 (dd, J = 17.0, 10.3 Hz, 1 H), 6.10 (dd, J = 17.1, 2.3 Hz, 1 H), 5.63-5.70 (m, 1 H), 4.27 (d, J = 8.6 Hz, 1 H), 4.16 (br d, J = 8.4 Hz, 1 H), 3.85-4.01 (m, 4 H), 3.77 (t, J = 6.7 Hz, 2 H), 3.55 (d, J = 2.3 Hz, 3 H), 3.12 (q, J = 5.5 Hz, 1 H), 2.63 (tt, J = 5.6, 3.0 Hz, 1 H), 2.43-2.53 (m, 2 H), 2.14-2.22 (m, 7 H), 1.40-1.48 (m, 2 H) |
| 13-119 | 509.2 | $^1$H NMR (500 MHz, DMSO-$d_6$) δ ppm 8.05 (s, 1 H), 7.73-7.78 (m, 1 H), 7.15 (d, J = 8.3 Hz, 1 H), 6.30 (dd, J = 17.0, 10.3 Hz, 1 H), 6.10 (dd, J = 17.1, 2.3 Hz, 1 H), 5.67 (dd, J = 10.4, 2.2 Hz, 1 H), 4.27 (dd, J = 8.6, 2.1 Hz, 1 H), 4.17 (dd, J = 8.6, 3.0 Hz, 1 H), 3.86-3.99 (m, 6 H), 3.77 (br t, J = 6.8 Hz, 2 H), 3.50 (d, J = 2.0 Hz, 3 H), 3.08-3.20 (m, 1 H), 2.78-2.86 (m, 2 H), 2.10-2.24 (m, 5 H), 0.94-1.03 (m, 1 H), 0.40-0.52 (m, 2 H), 0.24-0.36 (m, 2 H) |
| 13-120 | 509.2 | $^1$H NMR (500 MHz, DMSO-$d_6$) δ ppm 8.06 (s, 1 H), 7.75 (d, J = 8.2 Hz, 1 H), 7.14 (d, J = 8.4 Hz, 1 H), 6.22-6.38 (m, 1 H), 6.10 (dd, J = 17.1, 2.3 Hz, 1 H), 5.64-5.70 (m, 1 H), 4.27 (t, J = 7.5 Hz, 1 H), 4.17 (dd, J = 8.6, 1.7 Hz, 1 H), 4.03-4.11 (m, 1 H), 3.84-4.01 (m, 5 H), 3.72-3.82 (m, 2 H), 3.52 (d, J = 2.1 Hz, 3 H), 3.15 (td, J = 8.4, 4.9 Hz, 1 H), 2.77-2.92 (m, 2 H), 2.08-2.24 (m, 5 H), 0.95-1.03 (m, 1 H), 0.41-0.52 (m, 2 H), 0.25-0.35 (m, 2 H) |
| 13-121 | 509.2 | $^1$H NMR (500 MHz, DMSO-$d_6$) δ ppm 8.05 (s, 1 H), 7.73-7.78 (m, 1 H), 7.15 (d, J = 8.3 Hz, 1 H), 6.30 (dd, J = 17.0, 10.3 Hz, 1 H), 6.10 (dd, J = 17.1, 2.3 Hz, 1 H), 5.67 (dd, J = 10.4, 2.2 Hz, 1 H), 4.27 (dd, J = 8.6, 2.1 Hz, 1 H), 4.17 (dd, J = 8.6, 3.0 Hz, 1 H), 3.86-3.99 (m, 6 H), 3.77 (br t, J = 6.8 Hz, 2 H), 3.50 (d, J = 2.0 Hz, 3 H), 3.08-3.20 (m, 1 H), 2.78-2.86 (m, 2 H), 2.10-2.24 (m, 5 H), 0.94-1.03 (m, 1 H), 0.40-0.52 (m, 2 H), 0.24-0.36 (m, 2 H) |
| 13-122 | 509.2 | $^1$H NMR (500 MHz, DMSO-$d_6$) δ ppm 8.06 (s, 1 H), 7.75 (d, J = 8.2 Hz, 1 H), 7.14 (d, J = 8.4 Hz, 1 H), 6.22-6.38 (m, 1 H), 6.10 (dd, J = 17.1, 2.3 Hz, 1 H), 5.64-5.70 (m, 1 H), 4.27 (t, J = 7.5 Hz, 1 H), 4.17 (dd, J = 8.6, 1.7 Hz, 1 H), 4.03-4.11 (m, 1 |

TABLE 22-continued

| Analytical Data for Examples 13-2 to 13-157. | | |
|---|---|---|
| Ex. # | LRMS: (ESI, +ve ion) m/z | NMR |
| | | H), 3.84-4.01 (m, 5 H), 3.72-3.82 (m, 2 H), 3.52 (d, J = 2.1 Hz, 3 H), 3.15 (td, J = 8.4, 4.9 Hz, 1 H), 2.77-2.92 (m, 2 H), 2.08-2.24 (m, 5 H), 0.95-1.03 (m, 1 H), 0.41-0.52 (m, 2 H), 0.25-0.35 (m, 2 H) |
| 13-123 | 454.3 | $^1$H NMR (500 MHz, DMSO-$d_6$) δ ppm 8.52 (d, J = 5.0 Hz, 1 H), 8.30 (s, 1 H), 7.42 (d, J = 5.1 Hz, 1 H), 6.30 (dd, J = 17.0, 10.3 Hz, 1 H), 6.10 (dd, J = 17.1, 2.3 Hz, 1 H), 5.63-5.70 (m, 1 H), 4.26 (dd, J = 8.6, 4.0 Hz, 1 H), 4.16 (dd, J = 8.6, 2.6 Hz, 1 H), 3.96 (dd, J = 10.0, 5.1 Hz, 1 H), 3.81-3.93 (m, 3 H), 3.70-3.81 (m, 2 H), 2.79 (t, J = 5.4 Hz, 1 H), 2.60-2.72 (m, 1 H), 2.27-2.34 (m, 1 H), 2.09-2.24 (m, 7 H), 1.36 (s, 3 H), 1.19 (d, J = 9.7 Hz, 1 H), 0.71 (s, 3 H) |
| 13-124 | 454.3 | $^1$H NMR (500 MHz, DMSO-$d_6$) δ ppm 8.52 (d, J = 5.0 Hz, 1 H), 8.30 (s, 1 H), 7.42 (d, J = 5.1 Hz, 1 H), 6.30 (dd, J = 17.0, 10.3 Hz, 1 H), 6.10 (dd, J = 17.1, 2.3 Hz, 1 H), 5.63-5.70 (m, 1 H), 4.26 (dd, J = 8.6, 4.0 Hz, 1 H), 4.16 (dd, J = 8.6, 2.6 Hz, 1 H), 3.96 (dd, J = 10.0, 5.1 Hz, 1 H), 3.81-3.93 (m, 3 H), 3.70-3.81 (m, 2 H), 2.79 (t, J = 5.4 Hz, 1 H), 2.60-2.72 (m, 1 H), 2.27-2.34 (m, 1 H), 2.09-2.24 (m, 7 H), 1.36 (s, 3 H), 1.19 (d, J = 9.7 Hz, 1 H), 0.71 (s, 3 H) |
| 13-125 | 441.2 | $^1$H NMR (500 MHz, DMSO-$d_6$) δ ppm 9.35 (s, 1 H), 7.13 (d, J = 8.4 Hz, 1 H), 6.73 (dd, J = 8.3, 2.6 Hz, 1 H), 6.48 (d, J = 2.6 Hz, 1 H), 6.24-6.36 (m, 1 H), 6.10 (dd, J = 17.1, 2.3 Hz, 1 H), 5.63-5.70 (m, 1 H), 4.25 (dd, J = 8.6, 2.9 Hz, 1 H), 4.15 (dd, J = 8.6, 3.5 Hz, 1 H), 3.92-3.98 (m, 1 H), 3.80-3.91 (m, 3 H), 3.73 (br t, J = 6.9 Hz, 2 H), 3.07 (q, J = 5.5 Hz, 1 H), 2.64-2.72 (m, 1 H), 2.38-2.47 (m, 3 H), 2.10-2.26 (m, 3 H), 1.93 (s, 3 H), 1.39-1.47 (m, 1 H), 1.33-1.39 (m, 1 H) |
| 13-126 | 441.2 | $^1$H NMR (500 MHz, DMSO-$d_6$) δ ppm 9.35 (s, 1 H), 7.13 (d, J = 8.4 Hz, 1 H), 6.73 (dd, J = 8.3, 2.6 Hz, 1 H), 6.48 (d, J = 2.6 Hz, 1 H), 6.24-6.36 (m, 1 H), 6.10 (dd, J = 17.1, 2.3 Hz, 1 H), 5.63-5.70 (m, 1 H), 4.25 (dd, J = 8.6, 2.9 Hz, 1 H), 4.15 (dd, J = 8.6, 3.5 Hz, 1 H), 3.92-3.98 (m, 1 H), 3.80-3.91 (m, 3 H), 3.73 (br t, J = 6.9 Hz, 2 H), 3.07 (q, J = 5.5 Hz, 1 H), 2.64-2.72 (m, 1 H), 2.38-2.47 (m, 3 H), 2.10-2.26 (m, 3 H), 1.93 (s, 3 H), 1.39-1.47 (m, 1 H), 1.33-1.39 (m, 1 H) |
| 13-127 | 459.2 | $^1$H NMR (500 MHz, DMSO-$d_6$) δ ppm 9.42 (s, 1 H), 7.14 (d, J = 8.4 Hz, 1 H), 6.76 (dd, J = 8.3, 2.6 Hz, 1 H), 6.47 (d, J = 2.7 Hz, 1 H), 6.25-6.36 (m, 1 H), 6.10 (dd, J = 17.1, 2.3 Hz, 1 H), 5.60-5.73 (m, 1 H), 4.26 (dd, J = 8.6, 2.4 Hz, 1 H), 4.12-4.20 (m, 2 H), 3.92-4.01 (m, 2 H), 3.80-3.91 (m, 3 H), 3.74 (t, J = 6.8 Hz, 2 H), 2.68 (s, 2 H), 2.09-2.25 (m, 2 H), 1.90 (s, 3 H), 1.21 (s, 3 H), 1.19 (s, 3 H) |
| 13-128 | 459.2 | $^1$H NMR (500 MHz, DMSO-$d_6$) δ ppm 9.42 (s, 1 H), 7.14 (d, J = 8.4 Hz, 1 H), 6.76 (dd, J = 8.3, 2.6 Hz, 1 H), 6.47 (d, J = 2.7 Hz, 1 H), 6.25-6.36 (m, 1 H), 6.10 (dd, J = 17.1, 2.3 Hz, 1 H), 5.60-5.73 (m, 1 H), 4.26 (dd, J = 8.6, 2.4 Hz, 1 H), 4.12-4.20 (m, 2 H), 3.92-4.01 (m, 2 H), 3.80-3.91 (m, 3 H), 3.74 (t, J = 6.8 Hz, 2 H), 2.68 (s, 2 H), 2.09-2.25 (m, 2 H), 1.90 (s, 3 H), 1.21 (s, 3 H), 1.19 (s, 3 H) |
| 13-129 | 505.4 | $^1$H NMR (500 MHz, DMSO-$d_6$) δ ppm 7.78 (d, J = 8.4 Hz, 1 H), 7.43 (ddd, J = 8.2, 5.1, 3.0 Hz, 1 H), 7.19-7.28 (m, 3 H), 6.92-6.99 (m, 1 H), 6.30 (dd, J = 17.0, 10.3 Hz, 1 H), 6.10 (dd, J = 17.1, 2.3 Hz, 1 H), 5.63-5.70 (m, 1 H), 4.27 (dd, J = 8.4, 5.7 Hz, 1 H), 4.16 (br d, J = 8.6 Hz, 1 H), 3.93-4.02 (m, 1 H), 3.81-3.93 (m, 3 H), 3.70-3.81 (m, 2 H), 2.82 (t, J = 5.4 Hz, 1 H), 2.59-2.68 (m, 1 H), 2.28 (br d, J = 16.5 Hz, 1 H), 2.13-2.23 (m, 2 H), 2.01-2.13 (m, 2 H), 1.31-1.38 (m, 3 H), 1.13-1.28 (m, 2 H), 0.66-0.75 (m, 3 H). |
| 13-130 | 505.2 | $^1$H NMR (500 MHz, DMSO-$d_6$) δ ppm 7.79 (d, J = 8.3 Hz, 1 H), 7.43 (ddd, J = 8.2, 6.8, 1.3 Hz, 1 H), 7.21-7.27 (m, 2 H), 7.16-7.21 (m, 1 H), 6.96 (d, J = 2.4 Hz, 1 H), 6.25-6.35 (m, 1 H), 6.10 (dd, J = 17.1, 2.3 Hz, 1 H), 5.64-5.70 (m, 1 H), 4.27 (d, J = 8.7 Hz, 1 H), 4.16 (dd, J = 8.5, 5.6 Hz, 1 H), 3.94-4.00 (m, 1 H), 3.84-3.94 (m, 3 H), 3.77 (br t, J = 6.7 Hz, 2 H), 2.83 (t, J = 5.5 Hz, 1 H), 2.64 (dt, J = 9.6, 5.7 Hz, 1 H), 2.31 (dd, J = 16.6, 2.9 Hz, 1 H), 2.13-2.24 (m, 2 H), 2.10 (tt, J = 5.6, 2.7 Hz, 1 H), 2.01 (dd, J = 16.6, 2.2 Hz, 1 H), 1.34 (s, 3 H), 1.23 (d, J = 9.4 Hz, 1 H), 1.04 (d, J = 6.0 Hz, 1 H), 0.71 (s, 3 H) |
| 13-131 | 479.2 | $^1$H NMR (400 MHz, DMSO-$d_6$) δ ppm 8.05 (s, 1 H), 7.73 (d, J = 8.2 Hz, 1 H), 7.13 (d, J = 8.4 Hz, 1 H), 6.26-6.38 (m, 1 H), 6.08-6.17 (m, 1 H), 5.63-5.72 (m, 1 H), 4.29 (dd, J = 8.6, 3.6 Hz, 1 H), 4.18 (dd, J = 8.6, 4.6 Hz, 1 H), 3.84-4.03 (m, 4 H), 3.78 (t, J = 6.7 Hz, 2 H), 3.54 (d, J = 1.5 Hz, 3 H), 3.10 (br s, 2 H), 2.69-2.83 (m, 1 H), 2.29-2.44 (m, 2 H), 2.13-2.29 (m, 3 H), 2.08 (s, 3 H), 1.31-1.47 (m, 2 H). |
| 13-132 | 479.3 | $^1$H NMR (500 MHz, DMSO-$d_6$) δ ppm 8.04 (s, 1 H), 7.72 (d, J = 8.2 Hz, 1 H), 7.12 (d, J = 8.3 Hz, 1 H), 6.25-6.37 (m, 1 H), 6.11 (dd, J = 17.0, 2.3 Hz, 1 H), 5.63-5.71 (m, 1 H), 4.28 (dd, J = 8.5, 4.6 Hz, 1 H), 4.17 (dd, J = 8.4, 6.1 Hz, 1 H), 3.94-4.02 (m, 1 H), 3.83-3.94 (m, 3 H), 3.77 (t, J = 6.7 Hz, 2 H), 3.53 (d, J = 2.0 Hz, 3 H), 3.09 (br s, 2 H), 2.70-2.79 (m, 1 H), 2.28-2.42 (m, 2 H), 2.13-2.28 (m, 3 H), 2.07 (s, 3 H), 1.37 (quin, J = 8.3 Hz, 2 H) |
| 13-133 | 479.3 | $^1$H NMR (500 MHz, DMSO-$d_6$) δ ppm 8.04 (s, 1 H), 7.72 (d, J = 8.2 Hz, 1 H), 7.12 (d, J = 8.3 Hz, 1 H), 6.25-6.37 (m, 1 H), 6.11 (dd, J = 17.0, 2.3 Hz, 1 H), 5.63-5.71 (m, 1 H), 4.28 (dd, J = 8.5, 4.6 Hz, 1 H), 4.17 (dd, J = 8.4, 6.1 Hz, 1 H), 3.94-4.02 (m, 1 H), 3.83-3.94 (m, 3 H), 3.77 (t, J = 6.7 Hz, 2 H), 3.53 (d, J = 2.0 Hz, 3 H), 3.09 (br s, 2 H), 2.70-2.79 (m, 1 H), 2.28-2.42 (m, 2 H), 2.13-2.28 (m, 3 H), 2.07 (s, 3 H), 1.37 (quin, J = 8.3 Hz, 2 H) |
| 13-134 | 479.3 | $^1$H NMR (500 MHz, DMSO-$d_6$) δ ppm 8.04 (s, 1 H), 7.71 (d, J = 8.2 Hz, 1 H), 7.12 (d, J = 8.3 Hz, 1 H), 6.25-6.36 (m, 1 H), 6.10 (dd, J = 16.9, 2.3 Hz, 1 H), 5.62-5.70 (m, 1 H), 4.27 (br d, J = 8.4 Hz, 1 H), 4.16 (dd, J = 8.4, 4.2 Hz, 1 H), 3.93-4.00 (m, 2 H), 3.87-3.92 (m, 2 H), 3.74-3.81 (m, 2 H), 3.46 (d, J = 2.2 Hz, 3 H), 2.15- |

TABLE 22-continued

| Analytical Data for Examples 13-2 to 13-157. | | |
|---|---|---|
| Ex. # | LRMS: (ESI, +ve ion) m/z | NMR |
| | | 2.23 (m, 2 H), 2.08-2.12 (m, 4 H), 1.87-2.00 (m, 2 H), 1.73-1.85 (m, 2 H), 1.44-1.57 (m, 1 H), 1.11-1.16 (m, 1 H), 1.03-1.07 (m, 1 H). |
| 13-135 | 479.2 | $^1$H NMR (500 MHz, DMSO-$d_6$) δ ppm 8.03 (s, 1 H), 7.72 (d, J = 8.2 Hz, 1 H), 7.13 (d, J = 8.3 Hz, 1 H), 6.30 (dd, J = 17.0, 10.3 Hz, 1 H), 6.10 (dd, J = 17.0, 2.2 Hz, 1 H), 5.61-5.71 (m, 1 H), 4.27 (br d, J = 8.4 Hz, 1 H), 4.17 (d, J = 8.6 Hz, 1 H), 3.92-4.00 (m, 2 H), 3.84-3.92 (m, 2 H), 3.71-3.81 (m, 2 H), 3.48 (d, J = 2.4 Hz, 3 H), 2.13-2.25 (m, 2 H), 2.04-2.13 (m, 4 H), 1.89-1.98 (m, 1 H), 1.79-1.88 (m, 1 H), 1.70-1.79 (m, 2 H), 1.43-1.54 (m, 1 H), 1.11-1.19 (m, 1 H), 1.01-1.07 (m, 1 H). |
| 13-136 | 479.3 | $^1$H NMR (500 MHz, DMSO-$d_6$) δ ppm 8.03 (s, 1 H), 7.72 (d, J = 8.2 Hz, 1 H), 7.13 (d, J = 8.3 Hz, 1 H), 6.30 (dd, J = 17.0, 10.3 Hz, 1 H), 6.10 (dd, J = 17.0, 2.2 Hz, 1 H), 5.61-5.71 (m, 1 H), 4.27 (br d, J = 8.4 Hz, 1 H), 4.17 (d, J = 8.6 Hz, 1 H), 3.92-4.00 (m, 2 H), 3.84-3.92 (m, 2 H), 3.71-3.81 (m, 2 H), 3.48 (d, J = 2.4 Hz, 3 H), 2.13-2.25 (m, 2 H), 2.04-2.13 (m, 4 H), 1.89-1.98 (m, 1 H), 1.79-1.88 (m, 1 H), 1.70-1.79 (m, 2 H), 1.43-1.54 (m, 1 H), 1.11-1.19 (m, 1 H), 1.01-1.07 (m, 1 H). |
| 13-137 | 479.3 | $^1$H NMR (500 MHz, DMSO-$d_6$) δ ppm 8.04 (s, 1 H), 7.71 (d, J = 8.2 Hz, 1 H), 7.12 (d, J = 8.3 Hz, 1 H), 6.25-6.36 (m, 1 H), 6.10 (dd, J = 16.9, 2.3 Hz, 1 H), 5.62-5.70 (m, 1 H), 4.27 (br d, J = 8.4 Hz, 1 H), 4.16 (dd, J = 8.4, 4.2 Hz, 1 H), 3.93-4.00 (m, 2 H), 3.87-3.92 (m, 2 H), 3.74-3.81 (m, 2 H), 3.46 (d, J = 2.2 Hz, 3 H), 2.15-2.23 (m, 2 H), 2.08-2.12 (m, 4 H), 1.87-2.00 (m, 2 H), 1.73-1.85 (m, 2 H), 1.44-1.57 (m, 1 H), 1.11-1.16 (m, 1 H), 1.03-1.07 (m, 1 H). |
| 13-138 | 496.3 | $^1$H NMR (400 MHz, DMSO-$d_6$) δ ppm 9.13-9.60 (m, 1 H), 8.11 (s, 1 H), 7.82 (d, J = 8.1 Hz, 1 H), 7.21 (d, J = 8.5 Hz, 1 H), 6.24-6.38 (m, 1 H), 6.05-6.17 (m, 1 H), 5.63-5.72 (m, 1 H), 4.29 (dd, J = 8.6, 2.2 Hz, 1 H), 4.18 (dd, J = 8.8, 4.0 Hz, 1 H), 3.88-4.01 (m, 4 H), 3.79 (br t, J = 6.4 Hz, 2 H), 3.58 (s, 3 H), 3.42-3.55 (m, 2 H), 2.91-3.08 (m, 2 H), 2.14-2.26 (m, 5 H), 1.36 (s, 3 H), 1.33 (s, 3 H) |
| 13-139 | 483.3 | $^1$H NMR (400 MHz, DMSO-$d_6$) δ ppm 8.03-8.11 (m, 1 H), 7.76 (d, J = 8.4 Hz, 1 H), 7.16 (dd, J = 8.4, 5.0 Hz, 1 H), 6.24-6.37 (m, 1 H), 6.11 (dd, J = 16.9, 2.3 Hz, 1 H), 5.63-5.73 (m, 1 H), 4.25-4.33 (m, 1 H), 4.14-4.22 (m, 1 H), 4.05-4.13 (m, 1 H), 3.82-4.05 (m, 6 H), 3.78 (br t, J = 6.7 Hz, 2 H), 3.53 (d, J = 1.5 Hz, 3 H), 2.77-2.92 (m, 1 H), 2.60-2.75 (m, 1 H), 2.12-2.28 (m, 5 H), 1.25 (dd, J = 6.1, 1.7 Hz, 3 H) |
| 13-140 | 483.3 | $^1$H NMR (400 MHz, DMSO-$d_6$) δ ppm 8.07 (d, J = 2.9 Hz, 1 H), 7.76 (d, J = 8.3 Hz, 1 H), 7.16 (dd, J = 8.2, 5.1 Hz, 1 H), 6.24-6.37 (m, 1 H), 6.03-6.18 (m, 1 H), 5.68 (dd, J = 10.4, 2.3 Hz, 1 H), 4.24-4.33 (m, 1 H), 3.84-4.22 (m, 8 H), 3.78 (br t, J = 6.6 Hz, 2 H), 3.53 (s, 3 H), 2.78-2.91 (m, 1 H), 2.61-2.75 (m, 1 H), 2.10-2.26 (m, 5 H), 1.25 (d, J = 6.0 Hz, 3 H) |
| 13-141 | 483.2 | $^1$H NMR (500 MHz, DMSO-$d_6$) δ ppm 8.06 (s, 1 H), 7.75 (d, J = 8.2 Hz, 1 H), 7.15 (d, J = 8.3 Hz, 1 H), 6.30 (dd, J = 17.0, 10.3 Hz, 1 H), 6.10 (dd, J = 17.1, 2.3 Hz, 1 H), 5.63-5.71 (m, 1 H), 4.27 (d, J = 8.7 Hz, 1 H), 4.17 (dd, J = 8.6, 2.6 Hz, 1 H), 4.01-4.07 (m, 1 H), 3.81-4.00 (m, 6 H), 3.77 (t, J = 6.8 Hz, 2 H), 3.52 (d, J = 2.0 Hz, 3 H), 2.81 (br d, J = 17.6 Hz, 1 H), 2.59-2.71 (m, 1 H), 2.10-2.25 (m, 5 H), 1.23 (d, J = 6.1 Hz, 3 H) |
| 13-142 | 483.2 | $^1$H NMR (500 MHz, DMSO-$d_6$) δ ppm 8.06 (s, 1 H), 7.75 (d, J = 8.2 Hz, 1 H), 7.14 (d, J = 8.3 Hz, 1 H), 6.24-6.36 (m, 1 H), 6.10 (dd, J = 17.0, 2.2 Hz, 1 H), 5.63-5.71 (m, 1 H), 4.27 (dd, J = 8.4, 5.4 Hz, 1 H), 4.09-4.20 (m, 2 H), 3.81-4.01 (m, 6 H), 3.73-3.80 (m, 2 H), 3.52 (d, J = 2.3 Hz, 3 H), 2.83 (br d, J = 17.7 Hz, 1 H), 2.66 (dd, J = 17.9, 10.8 Hz, 1 H), 2.10-2.24 (m, 5 H), 1.24 (d, J = 6.1 Hz, 3 H) |
| 13-143 | 494.9 | $^1$H NMR (400 MHz, DMSO-$d_6$) δ ppm 8.06 (s, 1 H), 7.73 (d, J = 8.2 Hz, 1 H), 7.15 (d, J = 8.3 Hz, 1 H), 6.30 (m, 1 H), 6.10 (dd, J = 17.0, 2.3 Hz, 1 H), 5.67 (dd, J = 10.2, 2.3 Hz, 1 H), 4.27 (dd, J = 8.7, 2.8 Hz, 1 H), 4.16 (dd, J = 8.7, 3.2 Hz, 1 H), 3.81-3.97 (m, 4 H), 3.74 (t, J = 6.7 Hz, 2 H), 3.50 (d, J = 1.9 Hz, 3 H), 2.60 (s, 2 H), 2.17 (m, 2 H), 2.10 (d, J = 1.5 Hz, 3 H), 1.87-2.06 (m, 2 H), 1.37-1.49 (m, 2 H), 0.94 (s, 6 H). |
| 13-144 | 500.9 | $^1$H NMR (400 MHz, DMSO-$d_6$) δ ppm 13.49 (s, 1 H), 7.75-7.66 (m, 2 H), 7.53 (d, J = 8.9 Hz, 1 H), 6.31 (m, 1 H), 6.10 (dd, J = 17.0, 2.3 Hz, 1 H), 5.67 (dd, J = 10.3, 2.4 Hz, 1 H), 4.27 (d, J = 8.6 Hz, 1 H), 4.16 (dd, J = 8.6, 5.7 Hz, 1 H), 3.97-3.79 (m, 4 H), 3.73 (t, J = 6.9 Hz, 2 H), 2.59 (d, J = 1.8 Hz, 2 H), 2.26-2.09 (m, 3 H), 1.95 (m, 1 H), 1.39 (t, J = 6.8 Hz, 2 H), 0.94 (d, J = 7.2 Hz, 6 H). |
| 13-145 | 495.0 | $^1$H NMR (400 MHz, DMSO-$d_6$) δ ppm 8.05 (s, 1 H), 7.73 (d, J = 8.2 Hz, 1 H), 7.15 (d, J = 8.2 Hz, 1 H), 6.30 (dd, J = 17.0, 10.3 Hz, 1 H), 6.10 (dd, J = 17.1, 2.4 Hz, 1 H), 5.71-5.63 (m, 1 H), 4.31-4.24 (m, 1 H), 4.16 (dd, J = 8.6, 3.4 Hz, 1 H), 3.88-3.97 (m, 4 H), 3.74 (t, J = 6.8 Hz, 2 H), 3.49 (s, 3 H), 2.59 (s, 2 H), 2.19 (d, J = 7.4 Hz, 2 H), 2.10 (s, 3 H), 1.97 (m, 2 H), 1.43 (d, J = 6.8 Hz, 2 H), 0.94 (s, 6 H). |
| 13-146 | 499.0 | $^1$H NMR (400 MHz, DMSO-$d_6$) δ ppm 7.66 (dd, J = 3.4, 1.7 Hz, 1 H), 7.25 (d, J = 12.0 Hz, 1 H), 6.30 (dd, J = 17.0, 10.3 Hz, 1 H), 6.10 (dd, J = 17.0, 2.3 Hz, 1 H), 5.67 (dd, J = 10.3, 2.3 Hz, 1 H), 4.27 (d, J = 8.7 Hz, 1 H), 4.16 (d, J = 8.6 Hz, 1 H), 3.96-3.83 (m, 4 H), 3.72 (t, J = 6.9 Hz, 2 H), 2.58 (s, 2 H), 2.17 (m, 2 H), 2.10 (d, J = 1.5 Hz, 3 H), 2.03-1.91 (m, 2 H), 1.38 (t, J = 6.8 Hz, 2 H), 1.16 (t, J = 6.7 Hz, 1 H), 0.94 (d, J = 2.4 Hz, 6 H) |
| 13-147 | 501.1 | $^1$H NMR (400 MHz, DMSO-$d_6$) δ ppm 13.80 (s, 1 H), 7.73 (s, 1 H), 7.27 (d, J = 11.8 Hz, 1 H), 6.31 (dd, J = 17.0, 10.3 Hz, 1 H), 6.11 (dd, J = 17.0, 2.3 Hz, 1 H), 5.68 (dd, J = 10.3, 2.3 Hz, 1 H), 4.28 (d, J = 8.6 Hz, 1 H), 4.18 (d, J = 8.6 Hz, 1 H), 4.08-3.67 (m, 8 H), 2.74 (s, 2 H), 2.27-2.04 (m, 5 H), 1.21 (s, 6 H). |
| 13-148 | 503.0 | $^{1H}$ NMR (400 MHz, DMSO-$d_6$) δ ppm 13.54 (s, 1 H), 7.81 (s, 1 H), 7.75-7.68 (m, 1 H), 7.55 (d, J = 8.9 Hz, 1 H), 6.31 (m, 1 H), 6.11 (dd, J = 17.0, 2.3 Hz, 1 H), 5.68 |

TABLE 22-continued

| Analytical Data for Examples 13-2 to 13-157. | | |
|---|---|---|
| Ex. # | LRMS: (ESI, +ve ion) m/z | NMR |
| | | (dd, J = 10.3, 2.3 Hz, 1 H), 4.29 (d, J = 8.6 Hz, 1 H), 4.18 (dd, J = 8.7, 5.5 Hz, 1 H), 4.12 (d, J = 15.3 Hz, 1 H), 4.02-3.94 (m, 2 H), 3.94-3.85 (m, 3 H), 3.77 (t, J = 6.9 Hz, 2 H), 2.75 (s, 2 H), 2.25-2.15 (m, 2 H), 1.22 (d, J = 2.6 Hz, 6 H). |
| 13-149 | 487.2 | $^1$H NMR (400 MHz, DMSO-$d_6$) δ ppm 13.46 (s, 1 H), 7.86 (s, 1 H), 7.73 (dd, J = 9.3, 3.9 Hz, 1 H), 7.43 (t, J = 9.4 Hz, 1 H), 6.31 (m, 1 H), 6.11 (dd, J = 17.0, 2.3 Hz, 1 H), 5.68 (dd, J = 10.3, 2.3 Hz, 1 H), 4.29 (d, J = 8.9 Hz, 1 H), 4.22-4.13 (m, 2 H), 4.06-3.82 (m, 5 H), 3.77 (t, J = 6.9 Hz, 2 H), 2.75 (s, 2 H), 2.24-2.16 (m, 2 H), 1.22 (d, J = 4.1 Hz, 6 H). |
| 13-150 | 495.9 | $^1$H NMR (400 MHz, DMSO-$d_6$) δ ppm 8.06 (s, 1H), 7.73 (d, J = 8.2 Hz, 1H), 7.15 (d, J = 8.2 Hz, 1H), 6.30 (dd, J = 17.1, 10.3 Hz, 1H), 6.10 (d, J = 16.9 Hz, 1H), 5.67 (d, J = 10.3 Hz, 1H), 4.27 (d, J = 8.3 Hz, 1H), 4.16 (dd, J = 8.7, 3.1 Hz, 1H), 3.97 (d, J = 10.2 Hz, 1H), 3.88 (q, J = 7.8, 6.1 Hz, 3H), 3.74 (t, J = 6.8 Hz, 2H), 3.50 (s, 3H), 2.60 (s, 2H), 2.19 (d, J = 8.3 Hz, 2H), 2.10 (s, 3H), 1.96 (m, 2H), 1.44 (d, J = 7.0 Hz, 2H), 0.94 (s, 6H). |
| 13-151 | 482.0 | $^1$H NMR (400 MHz, DMSO-$d_6$) δ ppm 13.79 (s, 1 H), 8.57 (s, 1 H), 7.75 (d, J = 1.4 Hz, 1 H), 6.43-6.27 (m, 1 H), 6.10 (dd, J = 17.0, 2.3 Hz, 1 H), 5.67 (dd, J = 10.3, 2.3 Hz, 1 H), 4.27 (d, J = 8.6 Hz, 1 H), 4.16 (d, J = 8.6 Hz, 1 H), 3.97-3.82 (m, 4 H), 3.73 (t, J = 6.9 Hz, 2 H), 2.59 (s, 2 H), 2.26-2.12 (m, 5 H), 1.98 (t, J = 6.9 Hz, 2 H), 1.39 (t, J = 6.8 Hz, 2 H), 0.94 (d, J = 2.7 Hz, 6 H). |
| 13-152 | 476.9 | $^1$H NMR (400 MHz, DMSO-$d_6$) δ ppm 7.50 (d, J = 7.6 Hz, 1 H), 7.40 (t, J = 7.6 Hz, 1 H), 7.20 (d, J = 7.5 Hz, 1 H), 6.31 (m, 1 H), 6.11 (dd, J = 17.1, 2.3 Hz, 1 H), 5.68 (dd, J = 10.3, 2.3 Hz, 1 H), 4.27 (dd, J = 8.7, 4.0 Hz, 1 H), 4.21-4.02 (m, 3 H), 3.97-3.79 (m, 4 H), 3.75 (t, J = 6.9 Hz, 2 H), 2.70 (s, 2 H), 2.42 (s, 3 H), 2.19 (m, 2 H), 1.21 (d, J = 9.0 Hz, 6 H). |
| 13-153 | 492.9 | $^1$H NMR (400 MHz, DMSO-$d_6$) δ ppm 9.87 (s, 1 H), 6.87 (dd, J = 2.9, 0.9 Hz, 1 H), 6.54 (d, J = 2.9 Hz, 1 H), 6.31 (m, 1 H), 6.11 (dd, J = 17.0, 2.3 Hz, 1 H), 5.68 (dd, J = 10.3, 2.4 Hz, 1 H), 4.27 (dd, J = 8.7, 3.6 Hz, 1 H), 4.21-4.05 (m, 3 H), 3.97-3.78 (m, 4 H), 3.75 (t, J = 6.9 Hz, 2 H), 2.69 (s, 2 H), 2.32 (s, 3 H), 2.28-2.10 (m, 2 H), 1.21 (d, J = 9.6 Hz, 6 H). |
| 13-154 | 530.1 | $^1$H NMR (400 MHz, DMSO-$d_6$) δ ppm 7.65 (d, J = 7.6 Hz, 1 H), 6.32 (dd, J = 17.0, 10.3 Hz, 1 H), 6.12 (dd, J = 17.0, 2.3 Hz, 1 H), 5.72-5.65 (m, 3 H), 4.29-4.15 (m, 4 H), 3.99-3.83 (m, 4 H), 3.76 (t, J = 6.1 Hz, 2 H), 2.70 (s, 2 H), 2.20 (m, 2 H), 1.22 (d, J = 12.6 Hz, 6H ). |
| 13-155 | 530.0 | $^1$H NMR (400 MHz, DMSO-$d_6$) δ ppm 7.65 (d, J = 7.6 Hz, 1 H), 6.32 (dd, J = 17.0, 10.3 Hz, 1 H), 6.12 (dd, J = 17.0, 2.3 Hz, 1 H), 5.72-5.65 (m, 1 H), 5.66 (s, 2 H), 4.30-4.11 (m, 4 H), 4.00-3.71 (m, 6 H), 2.70 (s, 2 H), 2.21 (m, 2 H), 1.22 (d, J = 12.7 Hz, 6 H). |
| 13-156 | 530.0 | $^1$H NMR (401 MHz, DMSO-$d_6$) δ 7.80 (dd, J = 7.8, 1.8 Hz, 1 H), 6.30 (dd, J = 17.0, 10.3 Hz, 1 H), 6.11 (dd, J = 17.0, 2.1 Hz, 1 H), 5.69-5.66 (m, 3 H), 4.28-4.16 (m, 4 H), 3.99-3.81 (m, 4 H), 3.74 (s, 2 H), 2.69 (s, 2 H), 2.25-2.15 (m, 2 H), 1.24-1.11 (m, 6 H). |
| 13-157 | 462.0 | $^1$H NMR (400 MHz, DMSO-$d_6$) δ ppm 7.13 (m, 1 H), 6.57 (d, J = 8.2 Hz, 1 H), 6.42 (t, J = 8.8 Hz, 1 H), 6.32 (dd, J = 17.0, 10.2 Hz, 1 H), 6.11 (dd, J = 17.0, 2.3 Hz, 1 H), 5.68 (dd, J = 10.3, 2.3 Hz, 1 H), 5.24 (s, 2 H), 4.30-4.10 (m, 4 H), 4.00-3.81 (m, 4 H), 3.75 (t, J = 6.3 Hz, 2 H), 2.68 (s, 2 H), 2.20 (m, 2 H), 1.21 (d, J = 13.0 Hz, 6 H). |

TABLE 23

| Analytical Data for Examples 14-2 to 14-107. | | |
|---|---|---|
| Ex. # | LRMS: (ESI, +ve ion) m/z | NMR |
| 14-2 | 467.2 | $^1$H NMR (400 MHz, $CDCl_3$) δ ppm 7.95 (s, 1 H), 7.61 (t, J = 7.20 Hz, 1 H), 7.37 (s, 1 H), 7.28 (d, J = 8.80 Hz, 1 H), 7.08 (t, J = 6.80 Hz, 1 H), 6.97 (d, J = 7.20 Hz, 1 H), 6.31 (d, J = 16.8 Hz, 1 H), 6.11-6.15 (m, 1 H), 5.65 (d, J = 8.80 Hz, 1 H), 4.23-4.24 (m, 1 H), 4.00-4.14 (m, 7 H), 2.47 (t, J = 6.80 Hz, 2 H), 2.03 (s, 3 H). |
| 14-3 | 483 | $^1$H NMR (400 MHz, $CDCl_3$) δ ppm 10.53 (s, 1 H), 7.77 (d, J = 8.4 Hz, 1 H), 7.64 (t, J = 8.0 Hz, 1 H), 7.53 (d, J = 8.8 Hz, 1 H), 7.45 (d, J = 8.8 Hz, 1 H), 7.11 (t, J = 8.0 Hz, 1 H), 7.00 (d, J = 8.4 Hz, 1 H), 6.39 (d, J = 17.2 Hz, 1 H), 6.26-6.18 (m, 1 H), 5.72 (d, J = 10.4 Hz, 1 H), 4.34-4.28 (m, 1 H), 4.21-4.18 (m, 2 H), 4.16-4.09 (m, 3 H), 4.07-3.99 (m, 2 H), 2.30 (t, J = 6.8 Hz, 2 H), 2.15 (d, J = 3.6 Hz, 3 H). |
| 14-4 | 465.2 | $^1$H NMR (400 MHz, Methanol-$d_4$) δ ppm 7.54-7.60 (m, 2 H), 7.38-7.43 (m, 1 H), 6.38 (dd, J = 17.0, 10.1 Hz, 1 H), 6.27 (dd, J = 17.1, 2.1 Hz, 1 H), 5.76 (dd, J = 10.2, 2.1 Hz, 1 H), 4.26-4.38 (m, 2 H), 3.98-4.12 (m, 5 H), 3.86-3.95 (m, 2 H), 3.35-3.40 (m, 1 H), 2.80 (br d, J = 2.1 Hz, 1 H), 2.24-2.32 (m, 5 H), 1.75-1.91 (m, 2 H), 1.57 (br d, J = 9.0 Hz, 1 H), 1.32-1.42 (m, 1 H), 1.13 (br s, 1 H). |

TABLE 23-continued

| Analytical Data for Examples 14-2 to 14-107. | | |
|---|---|---|
| Ex. # | LRMS: (ESI, +ve ion) m/z | NMR |
| 14-5 | 462.2 | 1H NMR (400 MHz, Methanol-$d_4$) δ ppm 7.54-7.62 (m, 2 H), 7.38-7.44 (m, ( H), 6.34-6.42 (m, 1 H), 6.23-6.31 (m, 1 H), 5.76 (dd, J = 10.0, 2.1 Hz, 1 H), 4.27-4.38 (m, 2 H), 3.97-4.12 (m, 4 H), 3.87-3.94 (m, 2 H), 3.35-3.40 (m, 1 H), 2.80 (br d, J = 2.1 Hz, 1 H), 2.23-2.34 (m, 5 H), 2.03-2.08 (m, 1 H), 1.74-1.91 (m, 2 H), 1.57 (br d, J = 9.2 Hz, 1 H), 1.29-1.40 (m, 1 H), 1.07-1.19 (m, 1 H) |
| 14-6 | 465.2 | $^1$H NMR (500 MHz, DMSO-$d_6$) δ 13.11 (s, 1H), 7.57 (d, 1H, J = 3.7 Hz), 7.53 (d, 1H, J = 8.6 Hz), 7.35 (d, 1H, J = 8.6 Hz), 6.31 (ddd, 1H, J = 2.0, 10.3, 17.0 Hz), 6.11 (dd, 1H, J = 2.2, 17.0 Hz), 5.7-5.7 (m, 1H), 4.28 (dd, 1H, J = 1.7, 8.6 Hz), 4.17 (dd, 1H, J = 3.0, 8.6 Hz), 3.9-4.0 (m, 1H), 3.8-3.9 (m, 3H), 3.76 (t, 2H, J = 6.8 Hz), 2.1-2.2 (m, 5H), 1.9-2.0 (m, 1H), 1.6-1.8 (m, 2H), 1.4-1.5 (m, 1H), 1.3-1.4 (m, 1H), 0.9-1.0 (m, 1H). |
| 14-7 | 465.2 | $^1$H NMR (500 MHz, DMSO-$d_6$) δ 13.11 (s, 1H), 7.58 (s, 1H), 7.53 (d, 1H, J = 8.6 Hz), 7.34 (d, 1H, J = 8.6 Hz), 6.3-6.3 (m, 1H), 6.11 (dd, 1H, J = 2.3, 17.0 Hz), 5.67 (dd, 1H, J = 2.3, 10.3 Hz), 4.27 (t, 1H, J = 8.4 Hz), 4.16 (dd, 1H, J = 2.4, 8.5 Hz), 3.9-4.0 (m, 1H), 3.8-3.9 (m, 3H), 3.7-3.8 (m, 2H), 2.66 (br d, 1H, J = 2.3 Hz), 2.1-2.2 (m, 5H), 1.9-2.0 (m, 1H), 1.84 (br d, 1H, J = 7.7 Hz), 1.7-1.8 (m, 1H), 1.47 (br d, 1H, J = 8.6 Hz), 1.25 (br t, 1H, J = 8.7 Hz), 0.9-1.0 (m, 1H). |
| 14-8 | 465.2 | $^1$H NMR (500 MHz, DMSO-$d_6$) δ ppm 13.14 (s, 1 H), 7.58 (s, 1 H), 7.53 (d, J = 8.6 Hz, 1 H), 7.33 (d, J = 8.7 Hz, 1 H), 6.30 (ddd, J = 17.0, 10.3, 1.8 Hz, 1 H), 6.10 (dd, J = 17.0, 2.2 Hz, 1 H), 5.67 (dd, J = 10.3, 2.2 Hz, 1 H), 4.27 (t, J = 8.4 Hz, 1 H), 4.16 (dd, J = 8.5, 2.1 Hz, 1 H), 3.94-4.01 (m, 1 H), 3.83-3.94 (m, 3 H), 3.75 (br t, J = 6.7 Hz, 2 H), 3.30 (s, 1 H), 2.62-2.69 (m, 1 H), 2.10-2.25 (m, 5 H), 1.90-1.99 (m, 1 H), 1.84 (br d, J = 7.8 Hz, 1 H), 1.73 (tt, J = 11.0, 4.0 Hz, 1 H), 1.47 (br d, J = 8.7 Hz, 1 H), 1.25 (br t, J = 8.6 Hz, 1 H), 0.97 (br t, J = 8.6 Hz, 1 H). |
| 14-9 | 441.2 | $^1$H NMR (400 MHz, METHANOL-$d_4$) δ ppm 7.14 (t, J = 8.8 Hz, 1 H), 6.78 (ddd, J = 8.3, 2.6, 1.0 Hz, 1 H), 6.55 (dd, J = 18.3, 2.6 Hz, 1 H), 6.32-6.40 (m, 1 H), 6.21-6.28 (m, 1 H), 5.74 (dd, J = 10.2, 2.1 Hz, 1 H), 4.25-4.35 (m, 2 H), 3.93-4.08 (m, 4 H), 3.86 (td, J = 6.8, 3.3 Hz, 2 H), 3.32-3.35 (m, 1 H), 2.93-3.09 (m, 1 H), 2.27 (t, J = 6.8 Hz, 2 H), 2.02-2.09 (m, 3 H), 1.89 (s, 1 H), 1.74-1.83 (m, 1 H), 1.57 (d, J = 9.0 Hz, 1 H), 1.38 (dd, J = 6.7, 3.1 Hz, 1 H), 1.27-1.35 (m, 1 H). NMR solvent obscures a peak. |
| 14-10 | 441.2 | $^1$H NMR (500 MHz, DMSO-$d_6$) δ ppm 9.13-9.57 (m, 1 H), 7.13 (d, J = 8.3 Hz, 1 H), 6.74 (dd, J = 8.3, 2.6 Hz, 1 H), 6.48 (d, J = 2.6 Hz, 1 H), 6.30 (dd, J = 16.9, 10.3 Hz, 1 H), 6.10 (dd, J = 17.0, 2.3 Hz, 1 H), 5.64-5.69 (m, 1 H), 4.25 (dd, J = 8.5, 4.0 Hz, 1 H), 4.06-4.19 (m, 1 H), 3.92-3.99 (m, 1 H), 3.80-3.91 (m, 3 H), 3.68-3.78 (m, 2 H), 3.22-3.25 (m, 1 H), 2.84 (br d, J = 2.2 Hz, 1 H), 2.08-2.24 (m, 2 H), 1.90-2.03 (m, 4 H), 1.76-1.88 (m, 1 H), 1.68 (br d, J = 8.9 Hz, 1 H), 1.49 (d, J = 8.9 Hz, 1 H), 1.15-1.27 (m, 1 H), 1.05-1.15 (m, 1 H) |
| 14-11 | 441.4 | $^1$H NMR (500 MHz, DMSO-$d_6$) δ ppm 9.37 (s, 1 H), 7.11 (d, J = 8.4 Hz, 1 H), 6.75 (dd, J = 8.3, 2.6 Hz, 1 H), 6.52 (d, J = 2.7 Hz, 1 H), 6.30 (dd, J = 16.9, 10.3 Hz, 1 H), 6.10 (dd, J = 17.0, 2.2 Hz, 1 H), 5.64-5.69 (m, 1 H), 4.21-4.29 (m, 1 H), 4.15 (d, J = 8.7 Hz, 1 H), 3.90-4.00 (m, 1 H), 3.81-3.90 (m, 3 H), 3.73 (br t, J = 6.8 Hz, 2 H), 3.25 (br d, J = 3.2 Hz, 1 H), 3.17 (d, J = 5.3 Hz, 1 H), 2.93 (br s, 1 H), 2.11-2.21 (m, 2 H), 1.95 (d, J = 2.8 Hz, 4 H), 1.67-1.84 (m, 2 H), 1.49 (d, J = 8.9 Hz, 1 H), 1.21 (br t, J = 9.4 Hz, 1 H), 0.92-1.08 (m, 1 H). |
| 14-12 | 441.2 | $^1$H NMR (400 MHz, DMSO-$d_6$) δ ppm 9.36 (s, 1 H), 7.13 (t, J = 8.3 Hz, 1 H), 6.76 (ddd, J = 8.2, 2.5, 1.3 Hz, 1 H), 6.51 (dd, J = 17.2, 2.6 Hz, 1 H), 6.31 (dd, J = 16.9, 10.2 Hz, 1 H), 6.11 (dd, J = 17.0, 2.2 Hz, 1 H), 5.65-5.70 (m, 1 H), 4.26 (dd, J = 8.6, 3.8 Hz, 1 H), 4.16 (d, J = 8.6 Hz, 1 H), 3.93-3.99 (m, 1 H), 3.81-3.93 (m, 3 H), 3.69-3.79 (m, 2 H), 3.24-3.28 (m, 1 H), 2.83-2.96 (m, 1 H), 2.17 (td, J = 6.6, 2.9 Hz, 2 H), 2.01 (s, 2 H), 1.96 (d, J = 1.5 Hz, 2 H), 1.83 (br s, 2 H), 1.50 (d, J = 9.0 Hz, 1 H), 1.23 (br s, 1 H), 0.95-1.15 (m, 1 H). |
| 14-13 | 441 | $^1$H NMR (500 MHz, DMSO-$d_6$) δ ppm 9.37 (s, 1 H), 7.11 (d, J = 8.3 Hz, 1 H), 6.75 (dd, J = 8.3, 2.6 Hz, 1 H), 6.52 (d, J = 2.6 Hz, 1 H), 6.30 (dd, J = 17.0, 10.3 Hz, 1 H), 6.10 (dd, J = 17.0, 2.3 Hz, 1 H), 5.64-5.69 (m, 1 H), 4.22-4.29 (m, 1 H), 4.15 (d, J = 8.6 Hz, 1 H), 4.07 (d, J = 5.3 Hz, 1 H), 3.90-3.99 (m, 1 H), 3.81-3.88 (m, 2 H), 3.73 (br t, J = 6.9 Hz, 2 H), 3.25 (br d, J = 3.2 Hz, 1 H), 3.17 (d, J = 5.3 Hz, 1 H), 2.93 (br s, 1 H), 2.11-2.21 (m, 2 H), 1.95 (d, J = 2.8 Hz, 3 H), 1.75-1.83 (m, 1 H), 1.72 (br d, J = 8.8 Hz, 1 H), 1.49 (d, J = 8.9 Hz, 1 H), 1.22 (br d, J = 9.7 Hz, 1 H), 1.00 (br s, 1 H). |
| 14-14 | 441 | $^1$H NMR (500 MHz, DMSO-$d_6$) δ ppm 9.37 (s, 1 H), 7.13 (d, J = 8.4 Hz, 1 H), 6.74 (dd, J = 8.3, 2.6 Hz, 1 H), 6.48 (d, J = 2.6 Hz, 1 H), 6.30 (dd, J = 17.1, 10.3 Hz, 1 H), 6.10 (dd, J = 17.0, 2.3 Hz, 1 H), 5.65-5.69 (m, 1 H), 4.25 (dd, J = 8.6, 4.0 Hz, 1 H), 4.13-4.19 (m, 1 H), 3.96 (dd, J = 10.1, 3.9 Hz, 1 H), 3.86-3.90 (m, 2 H), 3.79-3.83 (m, 1 H), 3.69-3.78 (m, 2 H), 3.24 (br d, J = 3.2 Hz, 1 H), 2.84 (br d, J = 2.1 Hz, 1 H), 2.10-2.23 (m, 2 H), 1.89-2.03 (m, 4 H), 1.76-1.88 (m, 1 H), 1.68 (br d, J = 8.9 Hz, 1 H), 1.49 (d, J = 8.8 Hz, 1 H), 1.15-1.30 (m, 1 H), 1.05-1.15 (m, 1 H), |
| 14-15 | 479.3 | $^1$H NMR (400 MHz, METHANOL-$d_4$) δ ppm 8.02 (s, 1 H), 7.75 (d, J = 8.2 Hz, 1 H), 7.16-7.22 (m, 1 H), 6.34-6.42 (m, 1 H), 6.22-6.31 (m, 1 H), 5.76 (dd, J = 10.0, 2.1 Hz, 1 H), 4.28-4.38 (m, 2 H), 3.99-4.12 (m, 4 H), 3.92 (t, J = 6.9 Hz, 2 H), 3.64 (d, J = 1.3 Hz, 2 H), 3.56 (d, J = 2.3 Hz, 1 H), 3.36-3.40 (m, 1 H), |

TABLE 23-continued

| Analytical Data for Examples 14-2 to 14-107. | | |
|---|---|---|
| Ex. # | LRMS: (ESI, +ve ion) m/z | NMR |
| | | 2.77-2.93 (m, 1 H), 2.25-2.32 (m, 3 H), 2.22 (s, 2 H), 2.01-2.13 (m, 2 H), 1.80-1.90 (m, 2 H), 1.60 (d, J = 9.4 Hz, 1 H), 1.38 (br d, J = 7.9 Hz, 1 H), |
| 14-16 | 479.2 | $^1$H NMR (500 MHz, DMSO-$d_6$) δ ppm 8.07 (s, 1 H), 7.74 (d, J = 8.2 Hz, 1 H), 7.14 (d, J = 8.3 Hz, 1 H), 6.30 (ddd, J = 17.0, 10.3, 0.9 Hz, 1 H), 6.10 (dd, J = 17.0, 2.2 Hz, 1 H), 5.65-5.69 (m, 1 H), 4.27 (d, J = 8.7 Hz, 1 H), 4.16 (dd, J = 8.6, 4.4 Hz, 1 H), 3.86-3.99 (m, 4 H), 3.77 (t, J = 6.8 Hz, 2 H), 3.54 (d, J = 2.8 Hz, 3 H), 3.27-3.33 (m, 1 H), 2.65 (br s, 1 H), 2.18 (q, J = 6.0 Hz, 2 H), 2.13 (d, J = 2.0 Hz, 3 H), 1.93-2.01 (m, 1 H), 1.73-1.81 (m, 2 H), 1.50 (d, J = 9.2 Hz, 1 H), 1.24-1.31 (m, 1 H), 1.02-1.11 (m, 1 H). |
| 14-17 | 479.2 | $^1$H NMR (500 MHz, DMSO-$d_6$) δ ppm 8.06 (s, 1 H), 7.74 (d, J = 8.2 Hz, 1 H), 7.16 (d, J = 8.3 Hz, 1 H), 6.30 (ddd, J = 17.0, 10.3, 1.9 Hz, 1 H), 6.10 (dd, J = 17.0, 2.2 Hz, 1 H), 5.75 (s, 1 H), 5.65-5.69 (m, 1 H), 4.27 (dd, J = 8.4, 5.0 Hz, 1 H), 4.16 (dd, J = 8.6, 2.4 Hz, 1 H), 3.90-4.01 (m, 2 H), 3.84-3.91 (m, 2 H), 3.76 (br t, J = 6.7 Hz, 2 H), 3.47 (d, J = 4.4 Hz, 2 H), 3.27-3.33 (m, 1 H), 2.78 (br s, 1 H), 2.17 (d, J = 1.8 Hz, 4 H), 2.13-2.22 (m, 1 H), 1.96-2.05 (m, 1 H), 1.70-1.78 (m, 2 H), 1.53 (br d, J = 8.2 Hz, 1 H), 1.22-1.32 (m, 1 H), 0.96-1.04 (m, 1 H) |
| 14-18 | 482.8 | $^1$H NMR (400 MHz, $CDCl_3$) δ 7.80 (t, J = 14.3 Hz, 1H), 7.76 (s, 1H), 7.71-7.59 (m, 1H), 7.41 (s, 1H), 7.11 (t, J = 7.6 Hz, 1H), 7.01 (d, J = 6.6 Hz, 1H), 6.38 (dd, J = 17.0, 1.8 Hz, 1H), 6.22 (dd, J = 17.0, 10.3 Hz, 1H), 5.72 (dd, J = 10.3, 1.8 Hz, 1H), 4.34-4.27 (m, 1H), 4.24-3.97 (m, 7H), 2.30 (t, J = 6.8 Hz, 2H), 2.20 (d, J = 2.2 Hz, 3H). NH doesn't show in $CDCl_3$. |
| 14-19 | 488.8 | $^1$H NMR (400 MHz, DMSO-$d_6$) δ ppm 13.22 (br s, 1 H), 7.65 (d, J = 8.3 Hz, 1 H), 7.48 (br d, J = 4.4 Hz, 1 H), 7.43 (d, J = 8.7 Hz, 1 H), 7.39 (d, J = 1.5 Hz, 1 H), 6.83-6.89 (m, 1 H), 6.75-6.81 (m, 1 H), 6.33 (dd, J = 17.2, 9.7 Hz, 1 H), 6.12 (dd, J = 17.0, 2.3 Hz, 1 H), 5.65-5.73 (m, 1 H), 4.32 (d, J = 8.5 Hz, 1 H), 4.21 (dd, J = 8.4, 3.0 Hz, 1 H), 3.98-4.05 (m, 3 H), 3.85-3.95 (m, 3 H), 2.19-2.29 (m, 2 H), 2.07 (d, J = 3.3 Hz, 4 H), 1.06 (dd, J = 8.3, 2.3 Hz, 2 H), 0.81 (br dd, J = 4.8, 2.1 Hz, 2 H). |
| 14-20 | 514.8 | $^1$H NMR (400 MHz, DMSO-$d_6$) δ ppm 13.24 (br s, 1 H), 7.66 (d, J = 8.5 Hz, 1 H), 7.53 (s, 1 H), 7.44 (d, J = 8.7 Hz, 1 H), 7.15 (d, J = 2.1 Hz, 1 H), 6.85-6.89 (m, 2 H), 6.35 (dd, J = 16.2, 10.4 Hz, 1 H), 6.12-6.19 (m, 1 H), 5.69-5.76 (m, 1 H), 4.41-4.52 (m, 2 H), 4.30-4.41 (m, 4 H), 4.14 (br d, J = 5.0 Hz, 2 H), 3.93 (s, 3 H), 2.08 (s, 3 H) |
| 14-21 | 492.8 | $^1$H NMR (400 MHz, DMSO-$d_6$) δ ppm 13.05-13.45 (m, 1 H), 7.64 (d, J = 7.9 Hz, 1 H), 7.43 (dd, J = 8.5, 2.8 Hz, 2 H), 7.06 (br s, 1 H), 6.75-6.83 (m, 2 H), 6.26-6.43 (m, 1 H), 6.09-6.18 (m, 1 H), 5.69 (s, 1 H), 4.65-4.78 (m, 1 H), 3.96-4.25 (m, 4 H), 3.79-3.94 (m, 6 H), 2.03-2.15 (m, 4 H), 1.35 (br dd, J = 5.2, 3.1 Hz, 3 H). |
| 14-22 | 478.0 | $^1$H NMR (400 MHz, DMSO-$d_6$) δ ppm 10.74-10.96 (m, 1 H), 7.62 (dd, J = 7.8, 4.3 Hz, 1 H), 7.31 (q, J = 2.4 Hz, 1 H), 7.06-7.16 (m, 1 H), 6.92-6.99 (m, 1 H), 6.49-6.55 (m, 1 H), 6.25-6.38 (m, 1 H), 6.12 (dd, J = 17.0, 2.2 Hz, 1 H), 5.62-5.71 (m, 1 H), 4.15-4.32 (m, 2 H), 3.86-3.99 (m, 4 H), 3.73-3.83 (m, 2 H), 2.81 (t, J = 5.5 Hz, 1 H), 2.19 (br s, 4 H), 1.35 (d, J = 4.0 Hz, 3 H), 0.82-0.90 (m, 1 H), 0.71 (d, J = 19.2 Hz, 3 H) |
| 14-23 | 472.0 | $^1$H NMR (400 MHz, DMSO-$d_6$) δ ppm 13.09 (br s, 1 H), 7.49 (d, J = 8.4 Hz, 1 H), 7.44 (br s, 1 H), 7.33 (d, J = 8.6 Hz, 1 H), 6.28-6.39 (m, 1 H), 6.06-6.15 (m, 1 H), 5.63-5.72 (m, 1 H), 4.11-4.30 (m, 3 H), 3.78-4.01 (m, 5 H), 3.64-3.71 (m, 2 H), 3.49-3.58 (m, 3 H), 2.65-2.69 (m, 3 H), 2.10-2.14 (m, 1 H), 2.04 (s, 3 H), 1.19 (d, J = 4.0 Hz, 6 H) |
| 14-24 | 493.0 | $^1$H NMR (400 MHz, DMSO-$d_6$) δ ppm 7.67-7.82 (m, 2 H), 7.54 (ddd, J = 8.3, 7.2, 0.8 Hz, 1 H), 7.08 (dd, J = 6.7, 5.0 Hz, 1 H), 6.26-6.37 (m, 1 H), 6.11 (dd, J = 16.9, 2.3 Hz, 1 H), 5.64-5.72 (m, 1 H), 4.14-4.31 (m, 2 H), 4.11 (d, J = 1.7 Hz, 3 H), 3.84-4.02 (m, 4 H), 3.77 (br d, J = 4.8 Hz, 2 H), 2.83 (br d, J = 2.7 Hz, 1 H), 2.61-2.67 (m, 1 H), 2.09-2.24 (m, 4 H), 1.20-1.41 (m, 4 H), 0.71 (d, J = 19.2 Hz, 3 H) |
| 14-25 | 478.9 | $^1$H NMR (400 MHz, DMSO-$d_6$) δ ppm 12.98 (s, 1 H), 8.17 (dd, J = 3.0, 1.4 Hz, 1 H), 7.75-7.99 (m, 1 H), 7.15-7.39 (m, 2 H), 6.26-6.37 (m, 1 H), 6.12 (dd, J = 16.9, 2.3 Hz, 1 H), 5.63-5.73 (m, 1 H), 4.13-4.32 (m, 2 H), 3.87-4.01 (m, 4 H), 3.79 (br t, J = 6.7 Hz, 2 H), 2.82 (t, J = 5.4 Hz, 1 H), 2.58-2.67 (m, 1 H), 2.19 (br s, 4 H), 1.36 (d, J = 4.2 Hz, 3 H), 0.82-0.91 (m, 1 H), 0.71 (d, J = 15.3 Hz, 3 H) |
| 14-26 | 484.2 | $^1$H NMR (500 MHz, DMSO-$d_6$) δ ppm 9.88 (s, 1 H), 7.76 (d, J = 8.2 Hz, 1 H), 7.40 (t, J = 7.5 Hz, 1 H), 7.16-7.21 (m, 2 H), 7.09 (t, J = 7.7 Hz, 1 H), 6.83 (d, J = 2.4 Hz, 1 H), 6.32 (ddd, J = 17.0, 10.3, 4.8 Hz, 1 H), 6.10 (dd, J = 16.9, 2.3 Hz, 1 H), 5.66 (dt, J = 10.3, 2.0 Hz, 1 H), 4.24 (dd, J = 13.9, 8.5 Hz, 1 H), 4.11-4.20 (m, 2 H), 3.84-3.99 (m, 2 H), 3.61-3.76 (m, 3 H), 3.44-3.57 (m, 2 H), 2.66 (s, 2 H), 2.11 (br t, J = 7.5 Hz, 2 H), 1.76 (s, 3 H), 1.19 (s, 3 H), 1.15 (s, 3 H) |
| 14-27 | 508.2 | $^1$H NMR (500 MHz, DMSO-$d_6$) δ ppm 7.86 (s, 2 H), 6.97-7.01 (m, 2 H), 6.27-6.39 (m, 1 H), 6.11 (dd, J = 17.0, 2.1 Hz, 1 H), 5.67 (dt, J = 10.2, 2.7 Hz, 1 H), 4.07-4.28 (m, 3 H), 3.85-3.99 (m, 3 H), 3.65 (dd, J = 10.8, 2.1 Hz, 1 H), 3.56 (br d, J = 10.6 Hz, 2 H), 2.61 (s, 2 H), 2.09 (br d, J = 8.0 Hz, 2 H), 1.81 (s, 3 H), 1.18 (d, J = 8.0 Hz, 6 H) |

TABLE 23-continued

| Analytical Data for Examples 14-2 to 14-107. | | |
|---|---|---|
| Ex. # | LRMS: (ESI, +ve ion) m/z | NMR |
| 14-28 | 479.2 | $^1$H NMR (500 MHz, DMSO-$d_6$) δ ppm 12.98 (s, 1 H), 8.17 (d, J = 1.1 Hz, 1 H), 7.86 (dd, J = 5.4, 3.7 Hz, 1 H), 7.22-7.29 (m, 2 H), 6.31 (dd, J = 17.0, 10.3 Hz, 1 H), 6.11 (dd, J = 17.0, 2.3 Hz, 1 H), 5.67 (dd, J = 10.3, 2.2 Hz, 1 H), 4.14-4.30 (m, 2 H), 3.85-3.99 (m, 4 H), 3.66-3.82 (m, 2 H), 2.81 (t, J = 5.6 Hz, 1 H), 2.58-2.65 (m, 1 H), 2.27-2.35 (m, 1 H), 2.07-2.24 (m, 4 H), 1.44 (br d, J = 9.0 Hz, 1 H), 1.35 (s, 3 H), 0.68 (s, 3 H) |
| 14-29 | 479.2 | $^1$H NMR (500 MHz, DMSO-$d_6$) δ ppm 12.97 (s, 1 H), 8.16 (d, J = 1.3 Hz, 1 H), 7.84 (dd, J = 7.2, 1.8 Hz, 1 H), 7.20-7.30 (m, 2 H), 6.31 (dd, J = 17.0, 10.4 Hz, 1 H), 6.11 (dd, J = 17.0, 2.2 Hz, 1 H), 5.53-5.73 (m, 1 H), 4.15-4.34 (m, 2 H), 3.67-4.00 (m, 7 H), 2.81 (t, J = 5.5 Hz, 1 H), 2.60-2.67 (m, 1 H), 2.10-2.23 (m, 4 H), 2.02 (dd, J = 16.8, 2.1 Hz, 1 H), 1.35 (br s, 3 H), 1.25 (d, J = 9.5 Hz, 1 H), 0.72 (s, 3 H) |
| 14-30 | 448 | $^1$H NMR (500 MHz, DMSO-$d_6$) δ ppm 9.30 (s, 1 H), 7.12 (d, J = 8.3 Hz, 1 H), 6.70 (dd, J = 8.2, 2.5 Hz, 1 H), 6.35 (d, J = 2.2 Hz, 1 H), 6.27-6.34 (m, 1 H), 6.11 (dd, J = 17.0, 2.2 Hz, 1 H), 5.65-5.70 (m, 1 H), 4.09-4.26 (m, 3 H), 3.86-3.98 (m, 3 H), 3.62 (d, J = 1.3 Hz, 2 H), 3.48 (br t, J = 6.8 Hz, 2 H), 2.61 (s, 2 H), 2.10 (s, 2 H), 1.82 (s, 3 H), 1.80 (d, J = 3.5 Hz, 3 H), 1.19 (d, J = 8.6 Hz, 6 H) |
| 14-31 | 448.2 | $^1$H NMR (500 MHz, DMSO-$d_6$) δ ppm 9.29 (s, 1 H), 7.11 (d, J = 8.3 Hz, 1 H), 6.69 (dd, J = 8.2, 2.6 Hz, 1 H), 6.34 (d, J = 2.3 Hz, 1 H), 6.27-6.33 (m, 1 H), 6.10 (dd, J = 17.0, 2.2 Hz, 1 H), 5.63-5.68 (m, 1 H), 4.19-4.25 (m, 1 H), 4.08-4.17 (m, 2 H), 3.85-3.96 (m, 3 H), 3.61 (d, J = 1.3 Hz, 2 H), 3.47 (br t, J = 6.8 Hz, 2 H), 2.61 (s, 2 H), 2.10 (br t, J = 6.5 Hz, 2 H), 1.81 (s, 3 H), 1.79 (d, J = 3.3 Hz, 3 H), 1.18 (d, J = 8.6 Hz, 6 H) |
| 14-32 | 448.2 | $^1$H NMR (500 MHz, DMSO-$d_6$) δ ppm 9.29 (s, 1 H), 7.11 (d, J = 8.4 Hz, 1 H), 6.69 (dd, J = 8.3, 2.6 Hz, 1 H), 6.34 (d, J = 2.3 Hz, 1 H), 6.30 (br dd, J = 10.3, 1.7 Hz, 1 H), 6.10 (dd, J = 17.0, 2.2 Hz, 1 H), 5.61-5.69 (m, 1 H), 4.19-4.26 (m, 1 H), 4.04-4.17 (m, 2 H), 3.84-3.96 (m, 3 H), 3.61 (d, J = 1.3 Hz, 2 H), 3.47 (br t, J = 6.8 Hz, 2 H), 2.61 (s, 2 H), 2.10 (br t, J = 6.5 Hz, 2 H), 1.81 (s, 3 H), 1.79 (d, J = 3.3 Hz, 3 H), 1.18 (d, J = 8.7 Hz, 6 H) |
| 14-33 | 472.2 | $^1$H NMR (500 MHz, DMSO-$d_6$) δ ppm 13.08 (s, 1 H), 7.48 (d, J = 8.6 Hz, 1 H), 7.42 (br d, J = 5.1 Hz, 1 H), 7.32 (d, J = 8.6 Hz, 1 H), 6.32 (dd, J = 16.9, 10.3 Hz, 1 H), 6.10 (dd, J = 17.1, 2.3 Hz, 1 H), 5.66 (dd, J = 10.3, 1.2 Hz, 1 H), 4.24 (dd, J = 8.5, 4.8 Hz, 1 H), 4.16 (d, J = 8.6 Hz, 1 H), 3.91-3.98 (m, 2 H), 3.79-3.90 (m, 2 H), 3.65 (d, J = 4.0 Hz, 2 H), 3.51 (br t, J = 6.4 Hz, 2 H), 2.66 (s, 2 H), 2.11 (br d, J = 5.3 Hz, 2 H), 2.03 (d, J = 2.6 Hz, 3 H), 1.75 (s, 3 H), 1.18 (d, J = 4.8 Hz, 6 H) |
| 14-34 | 472.2 | $^1$H NMR (500 MHz, DMSO-$d_6$) δ ppm 13.08 (br s, 1 H), 7.48 (d, J = 8.6 Hz, 1 H), 7.42 (d, J = 5.0 Hz, 1 H), 7.32 (d, J = 8.6 Hz, 1 H), 6.32 (dd, J = 17.0, 10.3 Hz, 1 H), 6.10 (dd, J = 17.0, 2.2 Hz, 1 H), 5.66 (dd, J = 10.3, 1.2 Hz, 1 H), 4.24 (dd, J = 8.4, 4.8 Hz, 1 H), 4.16 (d, J = 8.4 Hz, 1 H), 3.91-3.99 (m, 2 H), 3.79-3.90 (m, 2 H), 3.62-3.70 (m, 2 H), 3.51 (br t, J = 6.4 Hz, 2 H), 2.66 (s, 2 H), 2.12 (br d, J = 5.3 Hz, 2 H), 2.03 (d, J = 2.7 Hz, 3 H), 1.75 (s, 3 H), 1.18 (d, J = 4.6 Hz, 6 H) |
| 14-35 | 484.2 | $^1$H NMR (500 MHz, DMSO-de) δ ppm 9.88 (br s, 1 H), 7.76 (d, J = 8.2 Hz, 1 H), 7.40 (t, J = 7.6 Hz, 1 H), 7.16-7.21 (m, 2 H), 7.09 (t, J = 7.7 Hz, 1 H), 6.83 (d, J = 2.3 Hz, 1 H), 6.32 (ddd, J = 17.0, 10.3, 4.8 Hz, 1 H), 6.10 (dd, J = 17.0, 2.2 Hz, 1 H), 5.66 (dt, J = 10.3, 2.0 Hz, 1 H), 4.07-4.26 (m, 3 H), 3.85-3.98 (m, 2 H), 3.62-3.76 (m, 3 H), 3.44-3.58 (m, 2 H), 2.66 (s, 2 H), 2.11 (br t, J = 7.4 Hz, 2 H), 1.76 (s, 3 H), 1.19 (s, 3 H), 1.15 (s, 3 H) |
| 14-36 | 489.2 | $^1$H NMR (500 MHz, DMSO-$d_6$) δ ppm 8.03 (s, 1 H), 7.70 (d, J = 8.3 Hz, 1 H), 7.14 (d, J = 8.3 Hz, 1 H), 6.33 (dd, J = 17.0, 10.0 Hz, 1 H), 6.11 (dd, J = 17.1, 2.3 Hz, 1 H), 5.67 (dd, J = 10.3, 2.2 Hz, 1 H), 4.14-4.27 (m, 2 H), 3.81-3.98 (m, 4 H), 3.63-3.72 (m, 2 H), 3.45-3.61 (m, 2 H), 2.68 (s, 2 H), 2.10-2.18 (m, 2 H), 2.04 (d, J = 3.4 Hz, 3 H), 1.81 (d, J = 1.7 Hz, 3 H), 1.20 (d, J = 7.1 Hz, 6 H) |
| 14-37 | 486.2 | $^1$H NMR (400 MHz, DMSO-$d_6$) δ ppm 8.03 (s, 1 H), 7.70 (d, J = 8.2 Hz, 1 H), 7.14 (d, J = 8.4 Hz, 1 H), 6.33 (dd, J = 17.0, 10.3 Hz, 1 H), 6.06-6.17 (m, 1 H), 5.67 (dd, J = 10.5, 2.3 Hz, 1 H), 4.14-4.29 (m, 2 H), 3.86-3.98 (m, 4 H), 3.68 (d, J = 4.8 Hz, 2 H), 3.48-3.58 (m, 2 H), 3.42 (d, J = 3.6 Hz, 3 H), 2.69 (s, 2 H), 2.10-2.17 (m, 2 H), 2.04 (d, J = 2.3 Hz, 3 H), 1.82 (s, 3 H), 1.20 (d, J = 5.6 Hz, 6 H) |
| 14-38 | 508 | $^1$H NMR (500 MHz, DMSO-$d_6$) δ ppm 7.84 (s, 2 H), 6.99 (d, J = 2.0 Hz, 1 H), 6.98 (s, 1 H), 6.27-6.37 (m, 1 H), 6.10 (dd, J = 17.0, 2.1 Hz, 1 H), 5.66 (dt, J = 10.1, 2.7 Hz, 1 H), 4.07-4.26 (m, 3 H), 3.83-4.01 (m, 3 H), 3.64 (dd, J = 10.6, 2.0 Hz, 1 H), 3.46-3.58 (m, 2 H), 3.33-3.43 (m, 1 H), 2.60 (s, 2 H), 2.09 (br s, 2 H), 1.80 (d, J = 1.1 Hz, 3 H), 1.17 (d, J = 7.9 Hz, 6 H) |
| 14-39 | 507.8 | $^1$H NMR (500 MHz, DMSO-$d_6$) δ ppm 7.84 (s, 2 H), 6.99 (d, J = 2.1 Hz, 1 H), 6.98 (s, 1 H), 6.28-6.36 (m, 1 H), 6.10 (dd, J = 16.9, 2.1 Hz, 1 H), 5.66 (dt, J = 10.1, 2.7 Hz, 1 H), 4.07-4.26 (m, 3 H), 3.83-4.00 (m, 3 H), 3.64 (dd, J = 10.5, 2.0 Hz, 1 H), 3.46-3.58 (m, 2 H), 3.32-3.42 (m, 1 H), 2.60 (s, 2 H), 2.03-2.16 (m, 2 H), 1.80 (d, J = 1.1 Hz, 3 H), 1.17 (d, J = 7.9 Hz, 6 H) |
| 14-40 | 500.2 | $^1$H NMR (400 MHz, DMSO-$d_6$) δ ppm 7.94 (s, 1 H), 7.58 (s, 1 H), 6.27-6.40 (m, 1 H), 6.11 (dd, J = 16.9, 2.3 Hz, 1 H), 5.62-5.72 (m, 1 H), 4.14-4.29 (m, 2 H), 3.79-4.01 (m, 4 H), 3.68 (d, J = 9.8 Hz, 2 H), 3.37 (d, J = 3.6 Hz, 4 H), 2.65-2.70 (m, 3 H), 2.37 (s, 3 H), 2.13 (br s, 2 H), 1.95 (d, J = 1.9 Hz, 3 H), 1.80 (s, 3 H), 1.19 (d, J = 5.6 Hz, 6 H) |

TABLE 23-continued

Analytical Data for Examples 14-2 to 14-107.

| Ex. # | LRMS: (ESI, +ve ion) m/z | NMR |
|---|---|---|
| 14-41 | 500.0 | $^1$H NMR (500 MHz, DMSO-$d_6$) δ ppm 7.93 (s, 1 H), 7.57 (s, 1 H), 6.24-6.37 (m, 1 H), 6.10 (dd, J = 17.0, 2.2 Hz, 1 H), 5.61-5.70 (m, 1 H), 4.19-4.28 (m, 1 H), 4.12-4.18 (m, 1 H), 3.91-4.00 (m, 2 H), 3.78-3.90 (m, 2 H), 3.62-3.72 (m, 2 H), 3.43-3.61 (m, 2 H), 3.36 (d, J = 4.6 Hz, 1 H), 3.17 (d, J = 5.1 Hz, 1 H), 2.63-2.70 (m, 2 H), 2.47-2.53 (m, 1 H), 2.36 (s, 3 H), 2.12 (br t, J = 6.5 Hz, 2 H), 1.93 (d, J = 2.7 Hz, 3 H), 1.78 (d, J = 1.3 Hz, 3 H), 1.18 (d, J = 7.3 Hz, 6 H) |
| 14-42 | 500.2 | $^1$H NMR (500 MHz, DMSO-$d_6$) δ ppm 7.93 (s, 1 H), 7.57 (s, 1 H), 6.26-6.37 (m, 1 H), 6.25-6.26 (m, 1 H), 6.10 (dd, J = 17.1, 2.3 Hz, 1 H), 5.60-5.71 (m, 1 H), 4.23 (dd, J = 16.2, 8.5 Hz, 1 H), 4.16 (dd, J = 8.5, 4.1 Hz, 1 H), 3.92 (br s, 2 H), 3.78-3.91 (m, 2 H), 3.61-3.73 (m, 2 H), 3.42-3.61 (m, 2 H), 3.37 (s, 1 H), 3.17 (d, J = 5.2 Hz, 1 H), 2.67 (s, 2 H), 2.36 (s, 3 H), 2.12 (br t, J = 6.3 Hz, 2 H), 1.93 (d, J = 2.7 Hz, 3 H), 1.78 (d, J = 1.4 Hz, 3 H), 1.18 (d, J = 7.3 Hz, 6 H) |
| 14-43 | 484.2 | $^1$H NMR (400 MHz, DMSO-$d_6$) δ ppm 9.79 (s, 1 H), 7.74 (d, J = 8.4 Hz, 1 H), 7.48 (dd, J = 8.3, 7.0 Hz, 1 H), 7.21 (d, J = 2.3 Hz, 1 H), 7.07-7.16 (m, 1 H), 6.98-7.05 (m, 2 H), 6.25-6.39 (m, 1 H), 6.11 (dd, J = 16.9, 2.3 Hz, 1 H), 5.67 (br d, J = 10.2 Hz, 1 H), 4.08-4.29 (m, 3 H), 3.85-3.99 (m, 2 H), 3.60-3.77 (m, 3 H), 3.47-3.56 (m, 2 H), 2.66 (s, 2 H), 2.12 (br t, J = 5.7 Hz, 2 H), 1.75 (s, 3 H), 1.18 (d, J = 11.7 Hz, 6 H) |
| 14-44 | 484.2 | $^1$H NMR (500 MHz, DMSO-$d_6$) δ 7.74 (d, 1H, J = 8.3 Hz), 7.47 (dd, 1H, J = 6.8, 8.3 Hz), 7.20 (d, 1H, J = 2.6 Hz), 7.10 (t, 1H, J = 8.0 Hz), 7.01 (t, 2H, J = 7.3 Hz), 6.32 (ddd, 1H, J = 4.8, 10.3, 17.0 Hz), 6.11(dd, 1H, J = 2.2, 17.0 Hz), 5.67 (td, 1H, J = 2.1, 10.4 Hz), 4.24 (dd, 1H, J = 8.5, 14.2 Hz, 2H), 4.10-4.20 (m 1H), 3.9-4.0 (m, 1H), 3.9-3.9 (m, 1H), 3.7-3.7 (m, 1H), 3.7-3.7 (m, 1H), 3.6-3.6 (m, 1H), 3.5-3.6 (m, 1H), 3.4-3.5 (m, 1H), 3.17 (d, 1H, J = 5.1 Hz), 2.6-2.7 (m, 2H), 2.1-2.2 (m, 2H), 1.74 (s, 3H), 1.18 (s, 3H), 1.15 (s, 3H). |
| 14-45 | 484.2 | $^1$H NMR (500 MHz, DMSO-$d_6$) δ 7.74 (d, 1H, J = 8.4 Hz), 7.47 (dd, 1H, J = 7.0, 8.3 Hz), 7.20 (d, 1H, J = 2.4 Hz), 7.10 (t, 1H, J = 8.0 Hz), 7.01 (t, 2H, J = 7.3 Hz), 6.32 (ddd, 1H, J = 4.6, 10.3, 17.0 Hz), 6.11 (dd, 1H, J = 2.3, 17.0 Hz), 5.67 (td, 1H, J = 2.1, 10.3 Hz), 4.24 (dd, 1H, J = 8.6, 14.2 Hz), 4.1-4.2 (m, 1H), 4.12 (dd, 1H, J = 5.6, 15.4 Hz), 3.9-4.0 (m, 2H), 3.71 (d, 1H, J = 15.4 Hz), 3.6-3.7 (m, 2H), 3.4-3.6(m, 2H), 3.17 (d, 1H, J = 5.3 Hz), 2.6-2.7 (m, 2H), 2.1-2.2 (m, 2H), 1.74 (s, 3H), 1.22 (br d, 1H, J = 12.5Hz), 1.17 (d, 6H, J = 14.2 Hz) |
| 14-46 | 537.2 | $^1$H NMR (400 MHz, DMSO-de) δ ppm 7.76 (d, J = 7.7 Hz, 1 H), 7.58-7.68 (m, 2 H), 7.52-7.57 (m, 1 H), 7.47 (d, J = 1.5 Hz, 1 H), 7.20 (dd, J = 8.6, 1.6 Hz, 1 H), 7.04 (d, J = 8.7 Hz, 1 H), 6.26-6.38 (m, 1 H), 6.12 (dd, J = 17.0, 2.3 Hz, 1 H), 5.68 (dd, J = 10.3, 2.2 Hz, 1 H), 4.31 (br d, J = 3.5 Hz, 1 H), 4.21 (br s, 1 H), 3.97-4.04 (m, 3 H), 3.86-3.97 (m, 3 H), 3.73 (s, 3 H), 2.29 (s, 3 H), 2.21-2.28 (m, 2 H), 2.19 (s, 3 H) |
| 14-47 | 479.0 | $^1$H NMR (400 MHz, DMSO-$d_6$) δ ppm 13.23 (s, 1 H), 7.63 (d, J = 14.8 Hz, 1 H), 7.42-7.47 (m, 2H), 7.18 (d, J = 10.8 Hz, 1 H), 7.05 (t, J = 8.4 Hz, 1 H), 6.45 (d, J = 14.8 Hz, 1 H), 6.28-6.33 (m, 1H), 6.09-6.14 (m, 1H ), 5.67-5.70 (m, 1 H ), 4.32 (m, 1H), 4.19-4.21 (m, 1 H), 4.01-4.04 (m, 2 H), 3.95 (s, 3 H), 3.86-3.89 (m, 3 H), 2.22-2.25 (m, 2H), 2.06 (s, 3 H). |
| 14-48 | 493.3 | $^1$H NMR (400 MHz, CDCB) δ ppm 7.99-8.13 (m, 1 H), 7.66-7.78 (m, 1 H), 7.13-7.22 (m, 1 H), 6.31-6.46 (m, 1 H), 6.12-6.25 (m, 1 H), 5.63-5.75 (m, 1 H), 4.20-4.30 (m, 1 H), 4.14-4.19 (m, 1 H), 3.84-4.11 (m, 6 H), 2.93 (br t, J = 4.7 Hz, 1 H), 2.69 (dq, J = 10.0, 5.2 Hz, 1 H), 2.32 (s, 3 H), 2.11-2.30 (m, 6 H), 1.38-1.45 (m, 3 H), 1.33 (br d, J = 9.8 Hz, 1 H), 0.71-0.81 (m, 3 H) |
| 14-49 | 473.4 | $^1$H NMR (400 MHz, $CDCl_3$) δ ppm 7.20 (dd, J = 10.5, 8.4 Hz, 1 H), 6.95 (br d, J = 6.7 Hz, 1 H), 6.75-6.82 (m, 1 H), 6.33-6.45 (m, 1 H), 6.16-6.29 (m, 1 H), 5.72 (dd, J = 10.3, 1.8 Hz, 1 H), 5.40 (br s, 1 H), 4.25 (br d, J = 6.9 Hz, 1 H), 3.87-4.20 (m, 7 H), 2.90 (br s, 1 H), 2.69 (br s, 1 H), 2.51 (br s, 2 H), 2.17-2.30 (m, 3 H), 1.41 (s, 3 H), 0-91-0.95 (m, 1 H), 0.75 (s, 3 H). |
| 14-50 | 462.2 | $^1$H NMR (400 MHz, $CDCl_3$) δ ppm 7.17 (d, J = 8.4 Hz, 1 H), 6.82 (dd, J = 8.4, 2.7 Hz, 1 H), 6.31-6.42 (m, 2 H), 6.09-6.27 (m, 2 H), 5.86-5.99 (m, 1 H), 5.66-5.75 (m, 1 H), 3.65-4.24 (m, 8 H), 2.87 (br s, 1 H), 2.59-2.70 (m, 1 H), 2.37-2.54 (m, 1 H), 2.26 (br dd, J = 16.9, 2.3 Hz, 1 H), 2.10-2.22 (m, 3 H), 2.02-2.09 (m, 3 H), 1.39 (s, 3 H), 0.70-0.76 (m, 3 H) |
| 14-51 | 493.2 | $^1$H NMR (500 MHz, DMSO-$d_6$) δ ppm 12.71 (s, 1 H), 8.03-8.09 (m, 1 H), 7.71 (d, J = 8.3 Hz, 1 H), 7.08-7.15 (m, 1 H), 6.31 (dd, J = 17.0, 10.3 Hz, 1 H), 6.11 (dd, J = 17.0, 2.2 Hz, 1 H), 5.63-5.72 (m, 1 H), 4.23-4.30 (m, 1 H), 4.18 (br d, J = 8.8 Hz, 1 H), 3.73-4.00 (m, 6 H), 2.81 (t, J = 5.5 Hz, 1 H), 2.58-2.71 (m, 1 H), 2.18-2.26 (m, 2 H), 2.16 (s, 4 H), 2.11 (td, J = 5.5, 2.6 Hz, 1 H), 1.94-2.08 (m, 1 H), 1.34 (s, 3 H), 1.17 (d, J = 9.4 Hz, 1 H), 0.75 (s, 3 H) |
| 14-52 | 493.3 | $^1$H NMR (500 MHz, DMSO-$d_6$) δ ppm 12.69 (s, 1 H), 8.02-8.09 (m, 1 H), 7.68-7.75 (m, 1 H), 7.12 (d, J = 8.3 Hz, 1 H), 6.31 (dd, J = 17.0, 10.3 Hz, 1 H), 6.11 (dd, J = 17.0, 2.2 Hz, 1 H), 5.63-5.71 (m, 1 H), 4.26 (dd, J = 8.5, 3.0 Hz, 1 H), 4.18 (dd, J = 8.6, 1.2 Hz, 1 H), 3.71-3.99 (m, 6 H), 2.82 (t, J = 5.4 Hz, 1 H), 2.61 (dt, J = 9.5, 5.7 Hz, 1 H), 2.01-2.26 (m, 8 H), 1.44 (d, J = 9.3 Hz, 1 H), 1.35 (s, 3 H), 0.70 (s, 3 H) |
| 14-53 | 452.2 | $^1$H NMR (400 MHz, $CDCl_3$) δ ppm 7.12-7.20 (m, 1 H), 6.82 (dd, J = 8.4, 2.7 Hz, 1 H), 6.47 (dd, J = 18.3, 2.0 Hz, 1 H), 6.31-6.41 (m, 1 H), 5.99-6.27 (m, 2 |

TABLE 23-continued

| Ex. # | LRMS: (ESI, +ve ion) m/z | NMR |
|---|---|---|
| Analytical Data for Examples 14-2 to 14-107. | | |
| | | H), 5.71 (dd, J = 10.2, 1.7 Hz, 1 H), 4.35 (br d, J = 15.7 Hz, 1 H), 3.98-4.26 (m, 5 H), 3.78-3.92 (m, 2 H), 3.74 (br s, 2 H), 2.74 (br s, 2 H), 2.17 (t, J = 6.9 Hz, 2 H), 2.02 (s, 3 H), 1.28-1.33 (m, 6 H) |
| 14-54 | 476.2 | $^1$H NMR (400 MHz, $CDCl_3$) δ ppm 9.84-11.42 (m, 1 H), 8.08 (s, 1 H), 7.73 (d, J = 8.3 Hz, 1 H), 7.16 (d, J = 8.3 Hz, 1 H), 6.31-6.43 (m, 1 H), 6.11-6.26 (m, 1 H), 5.70 (d, J = 10.4 Hz, 1 H), 3.98-4.21 (m, 6 H), 3.65-3.94 (m, 4 H), 2.77 (br s, 2 H), 2.27 (s, 3 H), 2.17 (br t, J = 6.8 Hz, 2 H), 1.29 (s, 3 H), 1.26 (s, 3 H) |
| 14-55 | 524.2 | $^1$H NMR (400 MHz, $CDCl_3$) δ ppm 7.92 (s, 1 H), 7.81 (s, 1 H), 6.32-6.43 (m, 1 H), 6.15-6.27 (m, 1 H), 5.70 (dd, J = 10.2, 1.9 Hz, 1 H), 4.21-4.29 (m, 1 H), 4.03-4.19 (m, 5 H), 3.82-3.90 (m, 2 H), 3.76 (br t, J = 6.6 Hz, 2 H), 3.62 (s, 3 H), 2.76 (s, 2 H), 2.25 (s, 3 H), 2.22 (t, J = 7.0 Hz, 2 H), 1.30 (d, J = 1.9 Hz, 6 H) |
| 14-56 | 519.2 | $^1$H NMR (400 MHz, $CDCl_3$) δ ppm 7.11-7.19 (m, 1 H), 6.96-7.05 (m, 1 H), 6.34-6.42 (m, 1 H), 6.16-6.28 (m, 1 H), 5.72 (dd, J = 10.2, 1.9 Hz, 1 H), 5.36-5.63 (m, 2 H), 4.33-4.46 (m, 1 H), 4.19-4.29 (m, 2 H), 4.08-4.17 (m, 2 H), 3.87-4.08 (m, 5 H), 2.69-2.91 (m, 2 H), 2.22 (t, J = 6.9 Hz, 2 H), 1.33 (s, 3 H), 1.29 (s, 3 H) |
| 14-57 | 519.2 | $^1$H NMR (500 MHz, DMSO-$d_6$) δ ppm 7.95 (s, 2 H), 7.14-7.20 (m, 1 H), 6.99-7.06 (m, 1 H), 6.24-6.37 (m, 1 H), 6.10 (dd, J = 17.0, 2.2 Hz, 1 H), 5.63-5.70 (m, 1 H), 4.21-4.29 (m, 1 H), 4.06-4.19 (m, 3 H), 3.78-3.98 (m, 4 H), 3.73 (t, J = 6.7 Hz, 2 H), 2.61-2.74 (m, 2 H), 2.08-2.28 (m, 2 H), 1.21 (s, 3 H), 1.18 (s, 3 H) |
| 14-58 | 519.2 | $^1$H NMR (500 MHz, DMSO-$d_6$) δ ppm 7.95 (s, 2 H), 7.16 (dd, J = 8.4, 5.6 Hz, 1 H), 7.03 (t, J = 8.9 Hz, 1 H), 6.23-6.38 (m, 1 H), 6.10 (dd, J = 17.1, 2.3 Hz, 1 H), 5.63-5.72 (m, 1 H), 4.22-4.28 (m, 1 H), 4.06-4.20 (m, 3 H), 3.78-3.98 (m, 4 H), 3.73 (t, J = 6.7 Hz, 2 H), 2.61-2.73 (m, 2 H), 2.11-2.26 (m, 2 H), 1.21 (s, 3 H), 1.18 (s, 3 H) |
| 14-59 | 462.2 | $^1$H NMR (500 MHz, DMSO-$d_6$) δ ppm 9.29 (s, 1 H), 7.07-7.16 (m, 1 H), 6.71 (dd, J = 8.3, 2.6 Hz, 1 H), 6.48 (d, J = 2.6 Hz, 1 H), 6.30 (dd, J = 17.0, 10.3 Hz, 1 H), 6.10 (dd, J = 17.0, 2.2 Hz, 1 H), 5.61-5.70 (m, 1 H), 4.23 (d, J = 8.6 Hz, 1 H), 4.14 (br d, J = 8.6 Hz, 1 H), 3.90-3.97 (m, 1 H), 3.83-3.90 (m, 1 H), 3.63-3.77 (m, 2 H), 3.49-3.62 (m, 2 H), 2.71 (t, J = 5.4 Hz, 1 H), 2.55-2.65 (m, 1 H), 2.33-2.43 (m, 1 H), 2.02-2.23 (m, 4 H), 1.93 (d, J = 0.9 Hz, 3 H), 1.34 (s, 3 H), 1.13 (d, J = 9.3 Hz, 1 H), 0.67 (s, 3 H) |
| 14-60 | 462.2 | $^1$H NMR (500 MHz, DMSO-$d_6$) δ ppm 9.29 (s, 1 H), 7.07-7.16 (m, 1 H), 6.71 (dd, J = 8.3, 2.6 Hz, 1 H), 6.48 (d, J = 2.6 Hz, 1 H), 6.30 (dd, J = 17.0, 10.3 Hz, 1 H), 6.10 (dd, J = 17.0, 2.2 Hz, 1 H), 5.61-5.70 (m, 1 H), 4.23 (d, J = 8.6 Hz, 1 H), 4.14 (br d, J = 8.6 Hz, 1 H), 3.90-3.97 (m, 1 H), 3.83-3.90 (m, 1 H), 3.63-3.77 (m, 2 H), 3.49-3.62 (m, 2 H), 2.71 (t, J = 5.4 Hz, 1 H), 2.55-2.65 (m, 1 H), 2.33-2.43 (m, 1 H), 2.02-2.23 (m, 4 H), 1.93 (d, J = 0.9 Hz, 3 H), 1.34 (s, 3 H), 1.13 (d, J = 9.3 Hz, 1 H), 0.67 (s, 3 H) |
| 14-61 | 452.2 | $^1$H NMR (500 MHz, DMSO-$d_6$) δ ppm 9.34 (s, 1 H), 7.06-7.16 (m, 1 H), 6.73 (dd, J = 8.3, 2.6 Hz, 1 H), 6.48 (d, J = 2.6 Hz, 1 H), 6.30 (dd, J = 17.0, 10.3 Hz, 1 H), 6.10 (dd, J = 17.0, 2.2 Hz, 1 H), 5.57-5.73 (m, 1 H), 4.11-4.27 (m, 3 H), 3.81-3.99 (m, 3 H), 3.65-3.77 (m, 2 H), 3.58 (br t, J = 6.6 Hz, 2 H), 3.17 (d, J = 5.3 Hz, 1 H), 2.59 (s, 1 H), 2.05-2.21 (m, 2 H), 1.90 (s, 3 H), 1.19 (d, J = 8.8 Hz, 6 H) |
| 14-62 | 452.2 | $^1$H NMR (500 MHz, DMSO-$d_6$) δ ppm 9.34 (s, 1 H), 7.12 (d, J = 8.4 Hz, 1 H), 6.73 (dd, J = 8.3, 2.6 Hz, 1 H), 6.48 (d, J = 2.4 Hz, 1 H), 6.30 (dd, J = 17.0, 10.3 Hz, 1 H), 6.10 (dd, J = 17.0, 2.2 Hz, 1 H), 5.59-5.70 (m, 1 H), 4.11-4.28 (m, 3 H), 3.83-4.00 (m, 3 H), 3.64-3.77 (m, 2 H), 3.52-3.66 (m, 2 H), 3.11-3.22 (m, 1 H), 2.59 (s, 1 H), 2.06-2.20 (m, 2 H), 1.90 (s, 3 H), 1.19 (d, J = 8.8 Hz, 6 H) |
| 14-63 | 500.2 | $^1$H NMR (500 MHz, DMSO-$d_6$) δ ppm 8.05 (s, 1 H), 7.72 (d, J = 8.2 Hz, 1 H), 7.14 (d, J = 8.3 Hz, 1 H), 6.26-6.35 (m, 1 H), 6.10 (dd, J = 17.1, 2.3 Hz, 1 H), 5.63-5.70 (m, 1 H), 4.20-4.26 (m, 1 H), 4.14 (dd, J = 8.4, 5.3 Hz, 1 H), 3.90-3.99 (m, 1 H), 3.83-3.89 (m, 1 H), 3.65-3.81 (m, 2 H), 3.57-3.65 (m, 4 H), 2.74-2.82 (m, 1 H), 2.64 (s, 3 H), 2.20-2.27 (m, 1 H), 2.10-2.18 (m, 6 H), 1.35 (s, 3 H), 1.16 (d, J = 9.3 Hz, 1 H), 0.71 (s, 3 H) |
| 14-64 | 500.2 | $^1$H NMR (500 MHz, DMSO-$d_6$) δ ppm 8.03 (s, 1 H), 7.71 (d, J = 8.2 Hz, 1 H), 7.14 (d, J = 8.3 Hz, 1 H), 6.25-6.37 (m, 1 H), 6.10 (dd, J = 17.1, 2.3 Hz, 1 H), 5.60-5.70 (m, 1 H), 4.24 (d, J = 8.6 Hz, 1 H), 4.14 (dd, J = 8.5, 4.2 Hz, 1 H), 3.90-3.98 (m, 1 H), 3.83-3.90 (m, 1 H), 3.67-3.81 (m, 2 H), 3.56-3.66 (m, 2 H), 3.54 (d, J = 2.2 Hz, 2 H), 2.74-2.80 (m, 1 H), 2.61-2.69 (m, 1 H), 2.06-2.22 (m, 8 H), 1.35 (s, 3 H), 1.20 (d, J = 9.4 Hz, 1 H), 0.69 (s, 3 H) |
| 14-65 | 488.2 | $^1$H NMR (400 MHz, CDCB) δ ppm 7.74-7.79 (m, 1 H), 7.46-7.52 (m, 1 H), 7.35-7.41 (m, 1 H), 7.23-7.27 (m, 1 H), 7.12-7.17 (m, 1 H), 7.02-7.08 (m, 1 H), 6.36-6.44 (m, 1 H), 6.16-6.27 (m, 1 H), 5.70-5.76 (m, 1 H), 4.29-4.37 (m, 1 H), 4.22-4.27 (m, 1 H), 4.03-4.19 (m, 4 H), 3.83-3.92 (m, 2 H), 3.72-3.82 (m, 2 H), 2.73-2.87 (m, 2 H), 2.17-2.22 (m, 3 H), 1.31 (s, 3 H), 1.29 (s, 3 H) |
| 14-66 | 488.2 | $^1$H NMR (500 MHz, DMSO-$d_6$) δ ppm 9.94 (s, 1 H), 7.71-7.83 (m, 1 H), 7.42 (dt, J = 8.3, 4.0 Hz, 1 H), 7.23 (dd, J = 7.6, 3.2 Hz, 3 H), 6.98 (d, J = 2.3 Hz, 1 H), 6.30 (dd, J = 17.0, 10.3 Hz, 1 H), 6.10 (dd, J = 17.0, 2.2 Hz, 1 H), 5.60-5.72 (m, 1 H), 4.10-4.31 (m, 3 H), 3.82-3.98 (m, 3 H), 3.68-3.79 (m, 2 H), 3.61 (br s, 2 H), 2.58-2.73 (m, 2 H), 2.04-2.18 (m, 2 H), 1.19 (d, J = 10.0 Hz, 6 H) |

TABLE 23-continued

| Ex. # | LRMS: (ESI, +ve ion) m/z | NMR |
|---|---|---|
| Analytical Data for Examples 14-2 to 14-107. | | |
| 14-67 | 488.2 | $^1H$ NMR (500 MHz, DMSO-$d_6$) δ ppm 9.83 (bs, 1 H), 7.72-7.83 (m, 1 H), 7.47 (dd, J = 8.2, 7.1 Hz, 1 H), 7.25 (br d, J = 9.2 Hz, 1 H), 7.22-7.23 (m, 1 H), 7.21 (d, J = 2.3 Hz, 1 H), 7.15 (dd, J = 7.0, 0.9 Hz, 1 H), 7.07 (dd, J = 9.0, 2.5 Hz, 1 H), 6.30 (dd, J = 17.0, 10.3 Hz, 1 H), 6.10 (dd, J = 17.0, 2.2 Hz, 1 H), 5.62-5.71 (m, 1 H), 4.10-4.30 (m, 3 H), 3.79-3.98 (m, 3 H), 3.68-3.77 (m, 2 H), 3.56-3.65 (m, 2 H), 2.58-2.71 (m, 2 H), 2.06-2.20 (m, 2 H), 1.19 (d, J = 8.2 Hz, 6 H) |
| 14-68 | 488.2 | $^1H$ NMR (400 MHz, $CDCl_3$) δ ppm 7.70-7.76 (m, 1 H), 7.43 (ddd, J = 8.2, 6.8, 1.1 Hz, 1 H), 7.37 (br d, J = 8.2 Hz, 1 H), 7.14-7.28 (m, 3 H), 6.85-6.98 (m, 1 H), 6.40 (br dd, J = 17.0, 3.4 Hz, 1 H), 6.06-6.28 (m, 1 H), 5.62-5.78 (m, 1 H), 4.32 (d, J = 15.7 Hz, 1 H), 4.00-4.25 (m, 5 H), 3.79-3.91 (m, 2 H), 3.68-3.79 (m, 2 H), 2.78 (s, 2 H), 2.14 (t, J = 7.0 Hz, 2 H), 1.26-1.35 (m, 6 H) |
| 14-69 | 488.2 | $^1H$ NMR (500 MHz, DMSO-$d_6$) δ ppm 9.88-9.99 (m, 1 H), 7.77 (d, J = 8.3 Hz, 1 H), 7.42 (dt, J = 8.3, 4.0 Hz, 1 H), 7.23 (dd, J = 7.6, 3.2 Hz, 3 H), 6.98 (d, J = 2.3 Hz, 1 H), 6.30 (dd, J = 17.0, 10.3 Hz, 1 H), 6.10 (dd, J = 17.0, 2.2 Hz, 1 H), 5.64-5.68 (m, 1 H), 4.12-4.26 (m, 3 H), 3.91-3.97 (m, 1 H), 3.82-3.90 (m, 2 H), 3.74 (br d, J = 8.4 Hz, 2 H), 3.55-3.66 (m, 2 H), 2.65 (s, 2 H), 2.09-2.18 (m, 2 H), 1.20 (s, 3 H), 1.18 (s, 3 H) |
| 14-70 | 488.2 | $^1H$ NMR (500 MHz, DMSO-$d_6$) δ ppm 9.94 (br s, 1 H), 7.77 (d, J = 8.2 Hz, 1 H), 7.42 (dt, J = 8.3, 4.0 Hz, 1 H), 7.21-7.25 (m, 3 H), 6.98 (d, J = 2.4 Hz, 1 H), 6.30 (dd, J = 17.0, 10.3 Hz, 1 H), 6.10 (dd, J = 17.0, 2.2 Hz, 1 H), 5.64-5.68 (m, 1 H), 4.12-4.26 (m, 3 H), 3.92-3.96 (m, 1 H), 3.82-3.89 (m, 2 H), 3.69-3.78 (m, 2 H), 3.61 (br s, 2 H), 2.65 (s, 2 H), 2.08-2.18 (m, 2 H), 1.20 (s, 3 H), 1.18 (s, 3 H) |
| 14-71 | 490 | $^1H$ NMR (400 MHz, $CDCl_3$) δ ppm 7.96 (s, 1 H), 7.67 (d, J = 8.2 Hz, 1 H), 7.11 (d, J = 8.4 Hz, 1 H), 6.32-6.44 (m, 1 H), 6.14-6.29 (m, 1 H), 5.70 (dd, J = 10.3, 2.0 Hz, 1 H), 4.04-4.26 (m, 6 H), 3.82-3.93 (m, 2 H), 3.77 (br t, J = 6.7 Hz, 2 H), 3.65 (s, 3 H), 2.77 (s, 2 H), 2.18-2.26 (m, 5 H), 1.30 (d, J = 3.8 Hz, 6 H) |
| 14-72 | 486.2 | $^1H$ NMR (400 MHz, $CDCl_3$) δ ppm 10.4 (br s, 1 H), 7.64-7.70 (m, 1 H), 7.44-7.50 (m, 1 H), 7.37 (d, J = 8.6 Hz, 1 H), 6.34-6.41 (m, 1 H), 6.17-6.28 (m, 1 H), 5.70 (dd, J = 10.3, 1.8 Hz, 1 H), 4.25 (br dd, J = 8.2, 4.2 Hz, 1 H), 4.10-4.19 (m, 2 H), 4.02-4.08 (m, 1 H), 3.69-3.94 (m, 4 H), 2.85-2.97 (m, 1 H), 2.63-2.70 (m, 1 H), 2.11-2.22 (m, 3 H), 2.10-2.40 (m, 5 H), 1.40 (s, 3 H), 1.34 (d, J = 9.6 Hz, 1 H), 0.73-0.84 (m, 3 H) |
| 14-73 | 486.2 | $^1H$ NMR (400 MHz, CDC1) δ ppm 7.68 (s, 1 H), 7.47 (d, J = 8.8 Hz, 1 H), 7.35-7.40 (m, 1 H), 6.34-6.45 (m, 1 H), 6.13-6.28 (m, 1 H), 5.70 (dd, J = 10.2, 1.9 Hz, 1 H), 4.25 (br dd, J = 8.2, 2.9 Hz, 1 H), 4.10-4.19 (m, 2 H), 4.01-4.09 (m, 1 H), 3.81-3.94 (m, 2 H), 3.70-3.80 (m, 2 H), 2.89 (t, J = 5.5 Hz, 1 H), 2.61-2.71 (m, 1 H), 2.27-2.39 (m, 2 H), 2.26 (s, 3 H), 2.19 (t, J = 6.9 Hz, 2 H), 2.14 (dt, J = 5.6, 2.7 Hz, 1 H), 1.40 (s, 3 H), 1.30 (d, J = 9.4 Hz, 1 H), 0.81 (s, 3 H) |
| 14-74 | 486.2 | $^1H$ NMR (500 MHz, DMSO-$d_6$) δ ppm 13.08 (s, 1 H), 7.54-7.60 (m, 1 H), 7.47-7.53 (m, 1 H), 7.30-7.37 (m, 1 H), 6.30 (dd, J = 17.1, 10.3 Hz, 1 H), 6.10 (dd, J = 17.0, 2.2 Hz, 1 H), 5.61-5.69 (m, 1 H), 4.24 (dd, J = 8.5, 3.2 Hz, 1 H), 4.14 (br d, J = 8.3 Hz, 1 H), 3.83-3.98 (m, 2 H), 3.66-3.79 (m, 2 H), 3.52-3.66 (m, 2 H), 2.77 (t, J = 5.6 Hz, 1 H), 2.54-2.66 (m, 1 H), 2.06-2.25 (m, 8 H), 1.34 (s, 3 H), 1.28 (d, J = 9.3 Hz, 1 H), 0.67 (s, 3 H) |
| 14-75 | 500.2 | $^1H$ NMR (400 MHz, $CDCl_3$) δ ppm 7.96 (d, J = 7.5 Hz, 1 H), 7.66 (dd, J = 8.2, 1.7 Hz, 1 H), 7.11 (dd, J = 8.4, 2.1 Hz, 1 H), 6.32-6.41 (m, 1 H), 6.15-6.26 (m, 1 H), 5.69 (dd, J = 10.2, 1.9 Hz, 1 H), 4.21-4.28 (m, 1 H), 4.09-4.15 (m, 2 H), 4.02-4.08 (m, 1 H), 3.80-3.91 (m, 2 H), 3.63-3.78 (m, 5 H), 2.90 (br d, J = 2.5 Hz, 1 H), 2.69 (dtd, J = 9.4, 5.8, 5.8, 3.6 Hz, 1 H), 2.13-2.31 (m, 8 H), 1.40 (s, 3 H), 1.24-1.27 (m, 1 H), 0.77 (d, J = 9.4 Hz, 3 H) |
| 14-76 | 498.2 | 1H NMR (400 MHz, $CDCl_3$) δ ppm 7.76 (d, J = 8.2 Hz, 1 H), 7.37-7.51 (m, 2 H), 7.28-7.30 (m, 1 H), 7.23-7.28 (m, 1 H), 6.61-6.89 (m, 1 H), 6.26-6.44 (m, 1 H), 5.86-6.25 (m, 1 H), 5.57-5.75 (m, 1 H), 3.58-4.25 (m, 8 H), 2.96-3.17 (m, 1 H), 2.60-2.71 (m, 1 H), 2.36-2.51 (m, 1 H), 2.22 (dd, J = 17.0, 2.2 Hz, 1 H), 2.02-2.16 (m, 3 H), 1.39 (s, 3 H), 1.29 (br dd, J = 9.4, 5.4 Hz, 1 H), 0.78 (s, 3 H) |
| 14-77 | 498.2 | $^1H$ NMR (400 MHz, $CDCl_3$) δ ppm 7.72-7.81 (m, 1 H), 7.38-7.50 (m, 2 H), 7.29-7.31 (m, 1 H), 7.24-7.28 (m, 1 H), 6.44-6.80 (m, 1 H), 6.11-6.31 (m, 1 H), 5.64-5.84 (m, 1 H), 5.50-6.41 (m, 1 H), 3.62-4.22 (m, 8 H), 2.93-3.20 (m, 1 H), 2.61-2.73 (m, 1 H), 2.19-2.45 (m, 2 H), 1.97-2.17 (m, 3 H), 1.39 (s, 3 H), 1.32 (d, J = 9.6 Hz, 1 H), 0.75 (s, 3 H) |
| 14-78 | 524.2 | $^1H$ NMR (400 MHz, $CDCl_3$) δ ppm 7.92 (s, 1 H), 7.81 (s, 1 H), 6.32-6.43 (m, 1 H), 6.15-6.27 (m, 1 H), 5.70 (dd, J = 10.2, 1.9 Hz, 1 H), 4.21-4.29 (m, 1 H), 4.03-4.19 (m, 5 H), 3.82-3.90 (m, 2 H), 3.76 (br t, J = 6.6 Hz, 2 H), 3.62 (s, 3 H), 2.76 (s, 2 H), 2.25 (s, 3 H), 2.22 (t, J = 7.0 Hz, 2 H), 1.30 (d, J = 1.9 Hz, 6 H) |
| 14-79 | 524.2 | $^1H$ NMR (400 MHz, $CDCl_3$) δ ppm 7.90-7.96 (m, 1 H), 7.82 (s, 1 H), 6.33-6.43 (m, 1 H), 6.17-6.29 (m, 1 H), 5.71 (dd, J = 10.2, 1.9 Hz, 1 H), 4.21-4.30 (m, 1 H), 4.03-4.20 (m, 5 H), 3.86 (br s, 2 H), 3.76 (br t, J = 6.8 Hz, 2 H), 3.62 (s, 3 H), 2.76 (s, 2 H), 2.25 (s, 3 H), 2.22 (t, J = 7.0 Hz, 2 H), 1.30 (d, J = 2.1 Hz, 6 H) |
| 14-80 | 483.2 | $^1H$ NMR (400 MHz, CDC)3) δ ppm 1.28 (s, 3 H), 1.30 (s, 3 H), 2.24 (br t, J = 6.90 Hz, 2 H), 2.29 (s, 3 H), 2.82 (d, J = 2.51 Hz, 2 H), 3.90-4.29 (m, 7 H), 4.25 (br dd, J = 8.15, 3.14 Hz, 1 H), 5.71 (dd, J = 10.35, 1.78 Hz, 1 H), 6.14- |

TABLE 23-continued

| Analytical Data for Examples 14-2 to 14-107. | | |
|---|---|---|
| Ex. # | LRMS: (ESI, +ve ion) m/z | NMR |
| | | 6.25 (m, 1 H), 6.34-6.41 (m, 1 H), 7.18 (d, J = 8.36 Hz, 1 H), 7.75 (d, J = 8.15 Hz, 1 H), 8.08 (s, 1 H) |
| 14-81 | 483.2 | $^1$H NMR (500 MHz, DMSO-$d_6$) o ppm 1.22 (d, J = 7.70 Hz, 6 H), 2.17 (s, 3 H), 2.20 (br t, J = 6.66 Hz, 2 H), 2.73 (d, J = 3.06 Hz, 2 H), 3.73-3.80 (m, 2 H), 3.83-4.02 (m, 6 H), 4.18 (d, J = 8.56 Hz, 1 H), 4.26 (dd, J = 8.50, 3.85 Hz, 1 H), 5.65-5.69 (m, 1 H), 6.11 (dd, J = 16.99, 2.20 Hz, 1 H), 6.31 (dd, J = 16.99, 10.27 Hz, 1 H), 7.12 (d, J = 8.31 Hz, 1 H), 7.74 (d, J = 8.19 Hz, 1 H), 8.07 (d, J = 1.22 Hz, 1 H), 12.73 (s, 1 H) |
| 14-82 | 483.2 | $^1$H NMR (500 MHz, DMSO-$d_6$) δ ppm 1.22 (d, J = 7.83 Hz, 6 H), 2.12-2.17 (m, 3 H), 2.17-2.25 (m, 2 H), 2.69-2.73 (m, 1 H), 2.73-2.78 (m, 1 H), 3.74-3.80 (m, 2 H), 3.83-4.02 (m, 6 H), 4.14-4.23 (m, 1 H), 4.26 (dd, J = 8.56, 3.91 Hz, 1 H), 5.65-5.69 (m, 1 H), 6.11 (dd, J = 16.99, 2.20 Hz, 1 H), 6.31 (dd, J = 16.99, 10.39 Hz, 1 H), 7.12 (d, J = 8.31 Hz, 1 H), 7.74 (d, J = 8.31 Hz, 1 H), 8.07 (d, J = 1.35 Hz, 1 H), 12.66-12.81 (m, 1 H) |
| 14-83 | 533.2 | $^1$H NMR (400 MHz, $CDCl_3$) δ ppm 8.16 (s, 1 H), 7.78 (d, J = 8.4 Hz, 1 H), 7.34 (d, J = 8.2 Hz, 1 H), 6.94-7.27 (m, 1 H), 6.33-6.48 (m, 1 H), 6.17-6.29 (m, 1 H), 5.72 (dd, J = 10.3, 1.8 Hz, 1 H), 3.79-4.40 (m, 10 H), 2.82 (s, 2 H), 2.20-2.32 (m, 5 H), 1.32 (s, 3 H), 1.27 (s, 3 H) |
| 14-84 | 507.2 | $^1$H NMR (400 MHz, DMSO-$d_6$) δ ppm 10.43 (br s, 1 H), 7.52-7.59 (m, 1 H), 6.89 (d, J = 9.0 Hz, 1 H), 6.25-6.36 (m, 1 H), 6.11 (dd, J = 17.0, 2.2 Hz, 1 H), 5.64-5.70 (m, 1 H), 4.27 (br d, J = 8.8 Hz, 1 H), 4.12-4.20 (m, 1 H), 3.68-4.00 (m, 6 H), 3.26-3.29 (m, 1 H), 2.76-2.83 (m, 1 H), 2.62-2.71 (m, 1 H), 2.27-2.39 (m, 2 H), 2.13-2.25 (m, 3 H), 1.37 (s, 3 H), 0.69 (d, J = 3.1 Hz, 3 H) |
| 14-85 | 510.2 | $^1$H NMR (400 MHz, $CDCl_3$) δ ppm 10.20 (s, 1 H), 8.00-8.12 (m, 1 H), 7.82-7.92 (m, 1 H), 6.30-6.43 (m, 1 H), 6.11-6.27 (m, 1 H), 5.69 (dd, J = 10.2, 1.7 Hz, 1 H), 3.98-4.27 (m, 6 H), 3.64-3.94 (m, 4 H), 2.69-2.87 (m, 2 H), 2.30 (s, 3 H), 2.17 (br t, J = 6.9 Hz, 2 H), 1.29 (s, 3 H), 1.26 (s, 3 H) |
| 14-86 | 513.0 | $^1$H NMR (400 MHz, $CDCl_3$) δ ppm 7.61-7.71 (m, 1 H), 6.95-7.04 (m, 1 H), 6.64-6.76 (m, 1 H), 6.34-6.48 (m, 1 H), 6.12-6.30 (m, 1 H), 5.65-5.83 (m, 1 H), 3.77-4.32 (m, 10 H), 2.63-2.84 (m, 2 H), 2.10-2.27 (m, 2 H), 1.22-1.29 (m, 6 H). The OH proton is not observed in CDCl |
| 14-87 | 520.2 | $^1$H NMR (400 MHz, DMSO-$d_6$) δ ppm 8.06 (1 H, s), 7.96 (1 H, s), 6.32 (1 H, ddd, J = 16.95, 10.21, 1.24 Hz), 6.11 (1 H, dd, J = 17.00, 2.28 Hz), 5.67 (1 H, dd, J = 10.16, 2.28 Hz), 4.12-4.27 (2 H, m), 3.82-4.00 (4 H, m), 3.64-3.73 (2 H, m), 3.45-3.61 (2 H, m), 3.40 (3 H, d, J = 3.73 Hz), 2.69 (2 H, s), 2.04-2.16 (5 H, m), 1.80 (3 H, s), 1.20 (3 H, s), 1.19 (3 H, s) |
| 14-88 | 520.2 | $^1$H NMR (400 MHz, DMSO-$d_6$) δ ppm 8.06 (1 H, s), 7.96 (1 H, s), 6.28-6.36 (1 H, m), 6.11 (1 H, dd, J = 16.93, 2.30 Hz), 5.67 (1 H, dd, J = 10.45, 2.09 Hz), 4.20-4.28 (1 H, m), 4.12-4.20 (1 H, m), 3.82-4.00 (4 H, m), 3.64-3.74 (2 H, m), 3.46-3.62 (2 H, m), 3.40 (3 H, d, J = 3.55 Hz), 2.69 (2 H, s), 2.09-2.16 (2 H, m), 2.08 (3 H, d, J = 2.30 Hz), 1.81 (3 H, s), 1.21 (3 H, s), 1.19 (3 H, s) |
| 14-89 | 520.2 | $^1$H NMR (400 MHz, DMSO-$d_6$) δ ppm 8.06 (1 H, s), 7.96 (1 H, s), 6.28-6.37 (1 H, m), 6.11 (1 H, dd, J = 16.93, 2.30 Hz), 5.67 (1 H, dd, J = 10.45, 2.30 Hz), 4.20-4.28 (1 H, m), 4.12-4.20 (1 H, m), 3.82-4.01 (4 H, m), 3.63-3.74 (2 H, m), 3.46-3.62 (2 H, m), 3.40 (3 H, d, J = 3.55 Hz), 2.69 (2 H, s), 2.10-2.16 (2 H, m), 2.08 (3 H, d, J = 2.30 Hz), 1.81 (3 H, s), 1.21 (3 H, s), 1.19 (3 H, s) |
| 14-90 | 497.1 | $^1$H NMR (400 MHz, DMSO-$d_6$) δ ppm 8.15 (s, 2 H), 7.75 (s, 2 H), 7.20-7.23 (m, 1 H), 6.94 (d, J = 8.40 Hz, 1 H), 6.29-6.31 (m, 1 H), 6.10-6.14 (m, 1 H), 5.66-5.70 (m, 1 H), 4.29-4.31 (m, 1 H), 4.20-4.22 (m, 1 H), 4.01-4.08 (m, 3 H), 3.89-3.93 (m, 3 H), 3.20 (s, 3 H), 2.23-2.26 (m, 2 H), 2.10 (d, J = 3.60 Hz, 3 H). |
| 14-91 | 517.3 | $^1$H NMR (400 MHz, DMSO-$d_6$) δ ppm 12.96 (br s, 1 H), 8.11 (s, 1 H), 8.01 (s, 1 H), 6.32 (dd, J = 16.93, 10.24 Hz, 1 H), 6.12 (dd, J = 16.93, 2.30 Hz, 1 H), 5.68 (dd, J = 10.24, 2.30 Hz, 1 H), 4.27 (dd, J = 8.57, 3.55 Hz, 1 H), 4.19 (d, J = 8.57 Hz, 1 H), 3.83-4.08 (m, 6 H), 3.75-3.82 (m, 2 H), 2.75 (d, J = 2.51 Hz, 2 H), 2.16-2.24 (m, 5 H), 1.23 (d, J = 3.34 Hz, 6 H) |
| 14-92 | 531.3 | $^1$H NMR (400 MHz, DMSO-$d_6$) δ ppm 8.10 (s, 1 H), 8.04 (s, 1 H), 6.31 (ddd, J = 17.04, 10.24, 2.40 Hz, 1 H), 6.11 (dd, J = 16.93, 2.30 Hz, 1 H), 5.68 (dd, J = 10.24, 2.30 Hz, 1 H), 4.29 (dd, J = 8.36, 3.14 Hz, 1 H), 4.17 (dd, J = 8.67, 4.70 Hz, 1 H), 3.95-4.09 (m, 4 H), 3.87-3.94 (m, 2 H), 3.79 (br t, J = 6.58 Hz, 2 H), 3.53 (s, 3 H), 2.78 (s, 2 H), 2.17-2.23 (m, 2 H), 2.16 (s, 3 H), 1.23 (s, 3 H), 1.22 (s, 3 H) |
| 14-93 | 518.3 | $^1$H NMR (400 MHz, DMSO-$d_6$) δ ppm 7.41 (td, J = 9.6, 2.4 Hz, 1 H), 7.33-7.19 (m, 2 H), 7.10 (s, 1 H), 6.35-6.28 (m, 1 H), 6.10 (dd, J = 17.0, 2.3 Hz, 1 H), 5.66 (dd, J = 10.3, 2.3 Hz, 1 H), 4.21 (dd, J = 8.7, 4.7 Hz, 1 H), 4.15 (d, J = 8.4 Hz, 1 H), 3.96-3.85 (m, 2 H), 3.75 (s, 3 H), 3.65-3.56 (m, 2 H), 3.53-3.38 (m, 2 H), 3.25-3.15 (m, 1 H), 2.95-3.08 (m, 1 H), 2.85 (dd, J = 17.0, 5.1 Hz, 1 H), 2.47-2.35 (m, 1 H), 2.07-2.15 (m, 3 H), 1.98 (s, 3 H), 1.94 (dd, J = 11.9, 4.9 Hz, 2 H), 1.89 (s, 3 H). |
| 14-94 | 516.3 | $^1$H NMR (400 MHz, DMSO-$d_6$) δ ppm 9.44 (br s, 1 H), 7.20-7.10 (m, 2 H), 6.72-6.68 (m, 2 H), 6.32 (dd, J = 17.0, 10.2 Hz, 1 H), 6.10 (dd, J = 17.0, 2.3 Hz, 1 H), 5.66 (dd, J = 10.3, 2.3 Hz, 1 H), 4.27-4.12 (m, 2 H), 3.98-3.85 (m, 2 H), 3.75 (s, 3 H), 3.66-3.47 (m, 2 H), 3.42 (t, J = 6.5 Hz, 2 H), 3.18-2.99 (m, 2 H), 2.83 (dd, J = 16.9, 5.1 Hz, 1 H), 2.26-2.10 (m, 4 H), 2.02 (s, 3 H), 1.92-1.90 (m, 2 H), 1.87 (s, 3 H). |

TABLE 23-continued

| Analytical Data for Examples 14-2 to 14-107. | | |
|---|---|---|
| Ex. # | LRMS: (ESI, +ve ion) m/z | NMR |
| 14-95 | 516.3 | $^1$H NMR (400 MHz, DMSO-$d_6$) δ ppm 9.44 (br s, 1 H), 7.23-7.10 (m, 2 H), 6.89-6.87 (m, 1 H), 6.74 (d, J = 7.6 Hz, 1 H), 6.32 (dd, J = 17.0, 10.2 Hz, 1 H), 6.10 (dd, J = 17.0, 2.3 Hz, 1 H), 5.66 (dd, J = 10.3, 2.3 Hz, 1 H), 4.27-4.11 (m, 2 H), 3.98-3.83 (m, 2 H), 3.75 (s, 3 H), 3.67-3.34 (m, 4 H), 3.24-2.94 (m, 2 H), 2.84 (dd, J = 16.9, 5.1 Hz, 1 H), 2.38-2.06 (m, 4 H), 2.01 (s, 3 H), 1.92-1.88 (m, 2 H), 1.87 (s, 3 H) |
| 14-96 | 516.2 | $^1$H NMR (400 MHz, DMSO-$d_6$) δ ppm 7.65-7.58 (m, 1 H), 7.50-7.43 (m, 2 H), 7.24-7.18 (m, 1 H), 7.09 (s, 1 H), 6.37-6.28 (m, 1 H), 6.10 (dd, J = 17.0, 2.3 Hz, 1 H), 5.66 (dd, J = 10.3, 2.3 Hz, 1 H), 4.25-4.13 (m, 2 H), 3.97-3.85 (m, 2 H), 3.79-3.71 (m, 3 H), 3.67-3.35 (m, 4 H), 3.26-3.13 (m, 1 H), 3.08-2.81 (m, 2 H), 2.38-2.04 (m, 4 H), 2.01 (s, 3 H), 1.97-1.80 (m, 5 H). |
| 14-97 | 536.3 | $^1$H NMR (400 MHz, DMSO-$d_6$) δ ppm 12.52 (s, 1 H), 8.04 (d, J = 1.4 Hz, 1 H), 7.67 (d, J = 8.2 Hz, 1 H), 7.17-7.05 (m, 2 H), 6.36-6.29 (m, 1 H), 6.11 (dd, J = 17.0, 2.3 Hz, 1 H), 5.67 (dt, J = 10.6, 1.5 Hz, 1 H), 4.26-4.16 (m, 2 H), 3.92 (m, 2 H), 3.76 (s, 3 H), 3.68-3.61 (m, 2 H), 3.55-3.46 (m, 2 H), 3.25-2.88 (m, 3 H), 2.31-2.12 (m, 4 H), 2.10 (s, 3 H), 2.03 (s, 3 H), 1.95-1.85 (m, 2 H), 1.76 (s, 3 H). |
| 14-98 | 550.2 | $^1$H NMR (400 MHz, DMSO-$d_6$) δ ppm 8.02 (s, 1 H), 7.68 (d, J = 8.2 Hz, 1 H), 7.14 (d, J = 8.3 Hz, 1 H), 7.09 (s, 1 H), 6.33-6.31 (m, 1 H), 6.11 (dd, J = 17.0, 2.3 Hz, 1 H), 5.67 (m, 1 H), 4.23 (dd, J = 8.5, 5.1 Hz, 1 H), 4.16 (dd, J = 8.6, 3.6 Hz, 1 H), 3.98-3.86 (m, 2 H), 3.75 (s, 3 H), 3.70-3.60 (m, 2 H), 3.57-3.447 (m, 5 H), 3.20-2.89 (m, 3 H), 2.11 (m, 3 H), 2.09-2.06 (m, 4 H), 2.02 (s, 3 H), 1.95 (t, J = 11.6 Hz, 2 H), 1.84 (s, 3 H). |
| 14-99 | 486.1 | $^1$H NMR (400 MHz, $CDCl_3$) δ ppm 7.91-8.00 (m, 1 H), 7.64 (d, J = 8.4 Hz, 1 H), 7.05-7.15 (m, 1 H), 6.33-6.43 (m, 1 H), 6.16-6.30 (m, 1 H), 5.70 (dd, J = 10.3, 2.0 Hz, 1 H), 4.23-4.32 (m, 1 H), 3.99-4.21 (m, 5 H), 3.71-3.82 (m, 2 H), 3.54-3.65 (m, 2 H), 3.46-3.54 (m, 3 H), 2.75-2.86 (m, 2 H), 2.17-2.25 (m, 2 H), 2.11 (s, 3 H), 1.89 (s, 3 H), 1.29 (d, J = 7.1 Hz, 6 H) |
| 14-100 | 486.1 | $^1$H NMR (400 MHz, $CDCl_3$) δ ppm 7.91-7.99 (m, 1 H), 7.64 (d, J = 8.2 Hz, 1 H), 7.05-7.13 (m, 1 H), 6.32-6.44 (m, 1 H), 6.17-6.31 (m, 1 H), 5.70 (br d, J = 11.1 Hz, 1 H), 4.27 (br d, J = 7.7 Hz, 1 H), 4.00-4.22 (m, 5 H), 3.75 (br s, 2 H), 3.60 (br s, 2 H), 3.51 (s, 3 H), 2.69-2.87 (m, 2 H), 2.21 (br t, J = 6.0 Hz, 2 H), 2.11 (s, 3 H), 1.86-1.93 (m, 3 H), 1.29 (d, J = 6.9 Hz, 6 H) |
| 14-101 | 490.0 | $^1$H NMR (500 MHz, DMSO-$d_6$) δ ppm 8.01-8.08 (m, 1 H), 7.68-7.78 (m, 1 H), 7.14 (d, J = 8.3 Hz, 1 H), 6.26-6.35 (m, 1 H), 6.10 (dd, J = 17.0, 2.2 Hz, 1 H), 5.63-5.71 (m, 1 H), 4.24 (dd, J = 8.4, 5.0 Hz, 1 H), 4.15 (dd, J = 8.5, 3.5 Hz, 1 H), 3.92-4.03 (m, 3 H), 3.83-3.90 (m, 1 H), 3.69-3.82 (m, 2 H), 3.58-3.68 (m, 2 H), 3.53 (d, J = 2.2 Hz, 3 H), 2.66 (s, 2 H), 2.07-2.22 (m, 5 H), 1.20 (d, J = 4.2 Hz, 6 H) |
| 14-102 | 490.0 | $^1$H NMR (500 MHz, DMSO-$d_6$) δ ppm 8.04 (s, 1 H), 7.73 (d, J = 8.3 Hz, 1 H), 7.14 (d, J = 8.3 Hz, 1 H), 6.25-6.38 (m, 1 H), 6.10 (dd, J = 17.0, 2.2 Hz, 1 H), 5.61-5.71 (m, 1 H), 4.24 (dd, J = 8.5, 5.1 Hz, 1 H), 4.15 (dd, J = 8.6, 3.5 Hz, 1 H), 3.92-4.04 (m, 3 H), 3.84-3.92 (m, 1 H), 3.69-3.82 (m, 2 H), 3.63 (br d, J = 6.6 Hz, 2 H), 3.53 (d, J = 2.2 Hz, 3 H), 2.66 (s, 2 H), 2.05-2.23 (m, 5 H), 1.20 (d, J = 4.2 Hz, 6 H) |
| 14-103 | 484.2 | $^1$H NMR (500 MHz, DMSO-$d_6$) δ ppm 9.88 (s, 1 H), 7.76 (d, J = 8.2 Hz, 1 H), 7.40 (td, J = 7.5, 1.0 Hz, 1 H), 7.17-7.21 (m, 2 H), 7.06-7.12 (m, 1 H), 6.83 (d, J = 2.4 Hz, 1 H), 6.27-6.37 (m, 1 H), 6.10 (dd, J = 16.9, 2.3 Hz, 1 H), 5.66 (d, J = 10.3 Hz, 1 H), 4.09-4.30 (m, 3 H), 3.84-4.01 (m, 2 H), 3.60-3.75 (m, 3 H), 3.42-3.59 (m, 2 H), 2.66 (s, 2 H), 2.11 (br t, J = 7.5 Hz, 2 H), 1.76 (s, 3 H), 1.19 (s, 3 H), 1.15 (s, 3 H) |
| 14-104 | 443.4 | $^1$H NMR (400 MHz, DMSO-$d_6$) δ ppm 12.99 (1 H, s), 7.45 (1 H, d, J = 8.57 Hz), 7.34 (1 H, s), 7.31 (1 H, d, J = 8.57 Hz), 6.81 (1 H, s), 6.32 (1 H, dd, J = 17.04, 10.35 Hz), 6.10 (1 H, dd, J = 16.93, 2.30 Hz), 5.66 (1 H, dd, J = 10.24, 2.30 Hz), 4.16-4.27 (2 H, m), 3.83-3.99 (4 H, m), 3.79 (2 H, t, J = 5.75 Hz), 3.30-3.39 (2 H, m), 3.10-3.25 (2 H, m), 2.78-2.84 (2 H, m), 2.13-2.22 (2 H, m), 2.01 (3 H, s), 1.72 (3 H, s). |
| 14-105 | 520.3 | $^1$H NMR (400 MHz, DMSO-$d_6$) δ ppm 8.07 (1 H, s), 7.81 (1 H, d, J = 0.84 Hz), 6.32 (1 H, ddd, J = 16.98, 10.29, 3.03 Hz), 6.11 (1 H, dd, J = 16.93, 2.30 Hz), 5.67 (1 H, dd, J = 10.24, 2.30 Hz), 4.11-4.35 (2 H, m), 4.01-4.09 (1 H, m), 3.86-3.99 (3 H, m), 3.70-3.75 (1 H, m), 3.56-3.69 (2 H, m), 3.42-3.53 (4 H, m), 2.64-2.75 (2 H, m), 2.46-2.48 (3 H, m), 2.07-2.20 (2 H, m), 1.83 (3 H, s), 1.21 (3 H, s), 1.20 (3 H, s) |
| 14-06 | 532.2 | $^1$H NMR (400 MHz, DMSO-$d_6$) δ ppm 8.00 (2 H, br d, J = 3.11 Hz), 7.00-7.12 (2 H, m), 6.31 (1 H, ddd, J = 16.74, 10.52, 5.70 Hz), 6.10 (1 H, dd, J = 16.90, 1.76 Hz), 5.67 (1 H, dd, J = 10.37, 1.66 Hz), 4.10-4.26 (3 H, m), 3.84-3.98 (3 H, m), 3.66 (1 H, d, J = 10.57 Hz), 3.52-3.61 (2 H, m), 3.36-3.45 (1 H, m), 2.63 (2 H, s), 2.04-2.16 (2 H, m), 1.82 (3 H, s), 1.22 (3 H, s), 1.21 (3 H, s) |
| 14. 107 | 551.1 | $^1$H NMR (400 MHz, DMSO-$d_6$) δ ppm 8.08 (s, 1H), 8.01 (s, 1H), 6.31 (ddd, J = 17.0, 10.3, 2.2 Hz, 1H), 6.11 (dd, J = 17.0, 2.3 Hz, 1H), 5.67 (dd, J = 10.3, 2.3 Hz, 1H), 4.60 (t, J = 6.5 Hz, 2H), 4.49 (td, J = 6.1, 3.7 Hz, 2H), 4.24 (dd, J = 8.6, 4.1 Hz, 1H), 4.15 (dd, J = 8.7, 3.5 Hz, 1H), 3.98-3.85 (m, 2H), 3.81-3.68 (m, |

TABLE 23-continued

| Analytical Data for Examples 14-2 to 14-107. | | |
|---|---|---|
| Ex. # | LRMS: (ESI, +ve ion) m/z | NMR |
| | | 2H), 3.61 (t, J = 6.4 Hz, 3H), 3.51 (d, J = 2.0 Hz, 3H), 3.42 (d, J = 7.4 Hz, 2H), 2.43-2.48 (m, 2H), 2.19-2.09 (m, 6 H), 2.04-1.97 (m, 1H) |

TABLE 24

| Analytical Data for Examples 15-2 to 15-7. | | |
|---|---|---|
| Ex. # | LRMS: (ESI, +ve ion) m/z | NMR |
| 15-2 | 515.1 | $^1$H NMR (400 MHz, Methanol-$d_4$) δ ppm 8.91 (s, 1 H), 7.86 (d, J = 1.7 Hz, 1 H), 7.61-7.67 (m, 1 H), 7.48-7.56 (m, 2 H), 7.30 (dt, J = 4.5, 2.3 Hz, 1 H), 7.25 (dd, J = 8.5, 1.7 Hz, 1 H), 7.04 (d, J = 8.5 Hz, 1 H), 6.38 (dd, J = 17.0, 10.2 Hz, 1 H), 6.23-6.29 (m, 1 H), 5.74 (dd, J = 10.3, 2.0 Hz, 1 H), 4.26-4.38 (m, 2 H), 4.04-4.11 (m, 2 H), 3.94 (s, 2 H), 3.81 (br t, J = 7.0 Hz, 2 H), 2.57 (s, 3 H), 2.27 (t, J = 6.8 Hz, 2 H), 2.16 (s, 3 H) |
| 15-3 | 535.2 | $^1$H NMR (400 MHz, Methanol-$d_4$) δ ppm 8.91 (s, 1 H), 7.91 (d, J = 1.7 Hz, 1 H), 7.61 (d, J = 8.6 Hz, 1 H), 7.48 (d, J = 8.8 Hz, 1 H), 7.37 (d, J = 8.4 Hz, 1 H), 7.18 (dd, J = 8.5, 1.8 Hz, 1 H), 6.94 (d, J = 8.6 Hz, 1 H), 6.39 (dd, J = 17.1, 10.2 Hz, 1 H), 6.26 (dd, J = 17.1, 2.1 Hz, 1 H), 5.75 (dd, J = 10.3, 2.0 Hz, 1 H), 4.29-4.40 (m, 2 H), 4.03-4.17 (m, 2 H), 3.99 (s, 2 H), 3.78-3.93 (m, 2 H), 2.57 (s, 3 H), 2.29 (t, J = 7.0 Hz, 2 H), 2.11 (s, 3 H), 2.08 (d, J = 5.0 Hz, 3 H) |
| 15-4 | 498.2 | $^1$H NMR (400 MHz, DMSO-$d_6$) δ ppm 7.69-7.75 (m, 1 H), 7.56-7.62 (m, 3 H), 7.37 (s, 2 H), 7.18-7.23 (m, 1 H), 6.91-6.99 (m, 2 H), 6.31 (br dd, J = 10.6, 2.1 Hz, 1 H), 6.12 (dd, J = 17.1, 2.2 Hz, 1 H), 5.68 (dd, J = 10.3, 2.0 Hz, 1 H), 4.16-4.31 (m, 2 H), 3.89 (br s, 4 H), 3.75 (br t, J = 6.4 Hz, 2 H), 2.33 (s, 3 H), 2.15-2.22 (m, 2 H), 2.12 (s, 3 H) |
| 15-5 | 511.9 | $^1$H NMR (500 MHz, DMSO-$d_6$) δ ppm 7.69-7.73 (m, 1 H), 7.63-7.66 (m, 1 H), 7.56-7.59 (m, 2 H), 7.42 (dt, J = 6.8, 2.6 Hz, 1 H), 7.37 (s, 1 H), 7.22-7.27 (m, 1 H), 6.98 (dd, J = 8.7, 3.4 Hz, 1 H), 6.93 (d, J = 1.1 Hz, 1 H), 6.36 (ddd, J = 17.0, 10.2, 8.8 Hz, 1 H), 6.08-6.16 (m, 1 H), 5.65-5.72 (m, 1 H), 4.37-4.50 (m, 2 H), 4.03-4.26 (m, 2 H), 3.71-3.95 (m, 3 H), 2.32 (s, 3 H), 2.24 (br dd, J = 7.6, 3.7 Hz, 1 H), 2.05 (d, J = 4.8 Hz, 3 H), 1.31 (dd, J = 7.2, 6.6 Hz, 3 H) |
| 15-6 | 511.9 | $^1$H NMR (500 MHz, DMSO-$d_6$) δ ppm 7.73 (dd, J = 6.4, 1.4 Hz, 1 H), 7.65 (dd, J = 5.9, 2.2 Hz, 1 H), 7.56 (ddd, J = 7.4, 5.4, 1.8 Hz, 2 H), 7.36 (br d, J = 3.9 Hz, 2 H), 7.22-7.28 (m, 1 H), 7.02 (dd, J = 8.7, 4.0 Hz, 1 H), 6.93 (s, 1 H), 6.36 (ddd, J = 17.0, 10.3, 8.9 Hz, 1 H), 6.08-6.16 (m, 1 H), 5.64-5.71 (m, 1 H), 4.36-4.50 (m, 2 H), 4.04-4.27 (m, 2 H), 3.74-3.96 (m, 3 H), 2.33 (s, 3 H), 2.25 (br dd, J = 7.8, 4.2 Hz, 2 H), 2.07 (d, J = 4.4 Hz, 3 H), 1.27 (t, J = 6.3 Hz, 3 H) |
| 15-7 | 509.2 | $^1$H NMR (400 MHz, DMSO-$d_6$) δ ppm 7.93 (d, J = 1.5 Hz, 1 H), 7.77 (d, J = 7.3 Hz, 1 H), 7.60-7.70 (m, 3 H), 7.53-7.58 (m, 1 H), 7.36 (s, 1 H), 7.10 (d, J = 8.7 Hz, 1 H), 7.07 (s, 1 H), 6.31 (br dd, J = 10.4, 3.1 Hz, 1 H), 6.12 (dd, J = 16.9, 2.2 Hz, 1 H), 5.69 (dd, J = 10.4, 2.3 Hz, 1 H), 4.29-4.36 (m, 1 H), 4.18-4.26 (m, 1 H), 4.04 (s, 3 H), 3.88 (s, 7 H), 2.17-2.22 (m, 2 H). |

TABLE 25

| Analytical Data for Examples 16-2 to 16-14. | | |
|---|---|---|
| Ex. # | LRMS: (ESI, +ve ion) m/z | NMR |
| 16-2 | 512.2 | $^1$H NMR (400 MHz, DMSO-$d_6$) δ ppm 7.71 (d, J = 1.9 Hz, 2 H), 7.55-7.60 (m, 2 H), 7.36 (td, J = 4.7, 2.2 Hz, 1 H), 7.27 (dd, J = 8.5, 1.8 Hz, 1 H), 6.93 (d, J = 8.6 Hz, 1 H), 6.29-6.39 (m, 1 H), 6.26 (s, 1 H), 6.12 (dd, J = 17.0, 2.4 Hz, 1 H), 5.64-5.71 (m, 1 H), 4.16-4.32 (m, 2 H), 3.85-4.01 (m, 4 H), 3.82 (s, 3 H), 3.73 (br t, J = 6.8 Hz, 2 H), 2.19 (s, 5 H), 2.11 (s, 3 H) |
| 16-3 | 482.2 | $^1$H NMR (400 MHz, DMSO-$d_6$) δ ppm 7.74 (s, 1 H), 7.50 (d, J = 1.5 Hz, 1 H), 7.34-7.46 (m, 4 H), 7.28-7.33 (m, 1 H), 7.13 (d, J = 8.3 Hz, 1 H), 6.49 (d, J = 2.1 Hz, 1 H), 6.29-6.38 (m, 1 H), 6.08-6.16 (m, 1 H), 5.68 (dd, J = 10.3, 2.0 Hz, 1 H), 4.22 (br d, J = 13.5 Hz, 2 H), 3.85-3.99 (m, 7 H), 3.69-3.78 (m, 2 H), 2.15-2.23 (m, 2 H), 2.11-2.14 (m, 3 H) |
| 16-4 | 482.2 | $^1$H NMR (400 MHz, $CDCl_3$) δ ppm 7.80-7.92 (m, 1 H), 7.56 (d, J = 1.9 Hz, 1 H), 7.48-7.54 (m, 1 H), 7.30-7.38 (m, 2 H), 7.22-7.27 (m, 3 H), 6.32-6.48 (m, 2 |

TABLE 25-continued

| Analytical Data for Examples 16-2 to 16-14. | | |
|---|---|---|
| Ex. # | LRMS: (ESI, +ve ion) m/z | NMR |
| | | H), 6.12-6.31 (m, 1 H), 5.61-5.82 (m, 1 H), 4.07-4.39 (m, 4 H), 3.98-4.02 (m, 3 H), 3.65-3.97 (m, 4 H), 2.25 (br t, J = 6.8 Hz, 2 H), 2.20-2.22 (m, 3 H) |
| 16-5 | 514.2 | $^1$H NMR (400 MHz, DMSO-$d_6$) δ ppm 9.93-10.40 (m, 1 H), 8.00-8.21 (m, 1 H), 7.52-7.55 (m, 1 H), 7.45-7.51 (m, 1 H), 7.37-7.44 (m, 1 H), 7.11-7.19 (m, 1 H), 7.05 (dd, J = 8.2, 5.0 Hz, 2 H), 6.47-6.57 (m, 1 H), 6.25-6.39 (m, 1 H), 6.01-6.20 (m, 1 H), 5.66-5.71 (m, 1 H), 4.19-4.38 (m, 3 H), 4.09-4.19 (m, 3 H), 3.98-4.06 (m, 2 H), 3.94-3.95 (m, 3 H), 2.23-2.30 (m, 5 H) |
| 16-6 | 500.2 | $^1$H NMR (400 MHz, $CDCl_3$) δ ppm 8.36-8.48 (m, 1 H), 7.60 (d, J = 2.1 Hz, 1 H), 7.41-7.52 (m, 1 H), 7.08-7.26 (m, 4 H), 6.47-6.50 (m, 1 H), 6.32-6.43 (m, 1 H), 6.14-6.27 (m, 1 H), 5.77 (dd, J = 10.3, 1.6 Hz, 1 H), 4.11-4.46 (m, 8 H), 3.99-4.04 (m, 3 H), 2.36-2.45 (m, 2 H), 2.33-2.35 (m, 3 H) |
| 16-7 | 516.2 | $^1$H NMR (400 MHz, $CDCl_3$) δ ppm 8.38-8.46 (m, 1 H), 7.58-7.60 (m, 1 H), 7.49-7.56 (m, 1 H), 7.39-7.46 (m, 2 H), 7.11 (d, J = 8.6 Hz, 1 H), 7.01-7.07 (m, 1 H), 6.46-6.49 (m, 1 H), 6.34-6.45 (m, 1 H), 6.16-6.26 (m, 1 H), 5.69-5.81 (m, 1 H), 4.10-4.43 (m, 8 H), 3.98-4.06 (m, 3 H), 2.36-2.46 (m, 2 H), 2.27-2.32 (m, 3 H) |
| 16-8 | 496.2 | $^1$H NMR (400 MHz, $CDCl_3$) δ ppm 8.31-8.56 (m, 1 H), 7.55-7.61 (m, 1 H), 7.46-7.54 (m, 1 H), 7.40-7.45 (m, 1 H), 7.25-7.27 (m, 1 H), 7.09-7.20 (m, 2 H), 6.46-6.49 (m, 1 H), 6.33-6.43 (m, 1 H), 6.09-6.29 (m, 1 H), 5.70-5.80 (m, 1 H), 4.09-4.50 (m, 8 H), 3.99-4.07 (m, 3 H), 2.35-2.43 (m, 2 H), 2.28-2.33 (m, 3 H), 1.97-2.08 (m, 3 H) |
| 16-9 | 514.2 | $^1$H NMR (400 MHz, $CDCl_3$) δ ppm 7.77-7.90 (m, 1 H), 7.51-7.57 (m, 1 H), 7.39-7.46 (m, 1 H), 7.11-7.21 (m, 2 H), 6.92-6.99 (m, 1 H), 6.57-6.64 (m, 1 H), 6.33-6.42 (m, 2 H), 6.14-6.27 (m, 1 H), 5.63-5.77 (m, 1 H), 4.03-4.30 (m, 4 H), 3.93-3.95 (m, 3 H), 3.70-3.93 (m, 4 H), 2.18-2.25 (m, 2 H), 2.11-2.17 (m, 3 H). The OH proton is not observed in $CDCl_3$. |
| 16-10 | 498.2 | $^1$H NMR (400 MHz, $CDCl_3$) δ ppm 7.80-7.90 (m, 1 H), 7.47-7.52 (m, 1 H), 7.35-7.44 (m, 1 H), 7.28-7.32 (m, 1 H), 7.20-7.26 (m, 1 H), 6.90-6.97 (m, 1 H), 6.81-6.89 (m, 1 H), 6.31-6.43 (m, 2 H), 6.13-6.27 (m, 1 H), 5.64-5.76 (m, 1 H), 3.99-4.32 (m, 5 H), 3.92-3.95 (m, 3 H), 3.69-3.90 (m, 3 H), 2.16-2.29 (m, 5 H). The OH proton is not observed in $CDCl_3$. |
| 16-11 | 498.2 | $^1$H NMR (400 MHz, $CDCl_3$) δ ppm 7.77-7.92 (m, 1 H), 7.51-7.60 (m, 1 H), 7.29-7.32 (m, 1 H), 7.09-7.21 (m, 2 H), 6.90-7.03 (m, 1 H), 6.53-6.64 (m, 1 H), 6.32-6.48 (m, 2 H), 6.13-6.32 (m, 1 H), 5.61-5.82 (m, 1 H), 4.03-4.34 (m, 4 H), 3.67-3.98 (m, 7 H), 2.16-2.27 (m, 5 H). The OH proton is not observed in $CDCl_3$. |
| 16-12 | 516.2 | $^1$H NMR (400 MHz, $CDCl_3$) δ ppm 7.81-7.88 (m, 1 H), 7.50-7.60 (m, 1 H), 7.19-7.26 (m, 2 H), 7.03-7.12 (m, 1 H), 6.82-6.92 (m, 1 H), 6.33-6.44 (m, 2 H), 6.15-6.27 (m, 1 H), 5.66-5.75 (m, 1 H), 4.04-4.30 (m, 4 H), 3.97 (s, 3 H), 3.69-3.94 (m, 4 H), 2.17-2.28 (m, 5 H). The OH proton is not observed in $CDCl_3$ |
| 16-13 | 516.3 | $^1$H NMR (400 MHz, $CDCl_3$) δ ppm 7.81-7.88 (m, 1 H), 7.50-7.60 (m, 1 H), 7.19-7.26 (m, 2 H), 7.03-7.12 (m, 1 H), 6.82-6.92 (m, 1 H), 6.33-6.44 (m, 2 H), 6.15-6.27 (m, 1 H), 5.66-5.75 (m, 1 H), 4.04-4.30 (m, 4 H), 3.97 (s, 3 H), 3.69-3.94 (m, 4 H), 2.17-2.28 (m, 5 H) |
| 16-14 | 532.2 | $^1$H NMR (400 MHz, $CDCl_3$) δ ppm 7.80-7.90 (m, 1 H), 7.49-7.60 (m, 1 H), 7.32-7.42 (m, 1 H), 7.18-7.23 (m, 1 H), 7.10-7.16 (m, 1 H), 6.83-6.91 (m, 1 H), 6.33-6.41 (m, 2 H), 6.16-6.27 (m, 1 H), 5.67-5.76 (m, 1 H), 4.04-4.33 (m, 5 H), 3.97 (s, 2 H), 3.95-3.99 (m, 1 H), 3.73-3.95 (m, 3 H), 2.23 (br t, J = 6.9 Hz, 2 H), 2.16 (s, 3 H). The OH proton is not observed in $CDCl_3$. |

TABLE 26

| Analytical Data for Examples 17-2 to 17-10. | | |
|---|---|---|
| Ex. # | LRMS: (ESI, +ve ion) m/z | NMR |
| 17-2 | 545.0 | $^1$H NMR (400 MHz, DMSO-$d_6$) δ ppm 7.87 (s, 1 H), 7.79 (d, J = 7.9 Hz, 1 H), 7.61-7.73 (m, 2 H), 7.50-7.60 (m, 3 H), 7.19 (d, J = 8.5 Hz, 1 H), 6.62 (d, J = 1.7 Hz, 1 H), 6.29-6.42 (m, 1 H), 6.10-6.19 (m, 1 H), 5.70-5.76 (m, 1 H), 4.27-4.51 (m, 6 H), 4.15 (br s, 2 H), 3.96 (s, 3 H) |
| 17-3 | 509.2 | $^1$H NMR (400 MHz, DMSO-$d_6$) δ ppm 7.77 (d, J = 7.9 Hz, 1 H), 7.59-7.71 (m, 3 H), 7.53-7.59 (m, 1 H), 7.45 (d, J = 1.0 Hz, 1 H), 7.34 (dd, J = 8.9, 2.1 Hz, 1 H), 7.15 (d, J = 8.7 Hz, 1 H), 6.97 (d, J = 1.2 Hz, 1 H), 6.25-6.39 (m, 1 H), 6.12 (dd, J = 17.0, 2.1 Hz, 1 H), 5.69 (dd, J = 10.5, 2.2 Hz, 1 H), 4.17-4.36 (m, 2 H), 3.97-4.10 (m, 3 H), 3.87-3.97 (m, 3 H), 2.38 (s, 3 H), 2.27 (br d, J = 6.4 Hz, 2 H) |
| 17-4 | 544.7 | $^1$H NMR (400 MHz, DMSO-$d_6$) δ ppm 8.37 (d, J = 2.7 Hz, 1 H), 8.15 (s, 1 H), 7.73-8.07 (m, 3 H), 7.55-7.70 (m, 3 H), 7.29 (d, J = 2.5 Hz, 1 H), 7.12 (d, J = 8.7 Hz, 1 H), 6.26-6.40 (m, 1 H), 6.06-6.18 (m, 1 H), 5.62-5.73 (m, 1 H), 4.18-4.37 (m, 2 H), 3.99-4.09 (m, 3 H), 3.92 (br s, 3 H), 2.22-2.32 (m, 2 H) |

TABLE 26-continued

| Analytical Data for Examples 17-2 to 17-10. | | |
|---|---|---|
| Ex. # | LRMS: (ESI, +ve ion) m/z | NMR |
| 17-5 | 493.2 | $^1$H NMR (400 MHz, DMSO-$d_6$) δ ppm 7.68-7.76 (m, 1 H), 7.65 (d, J = 2.1 Hz, 1 H), 7.47-7.62 (m, 3 H), 7.44 (s, 1 H), 7.33-7.38 (m, 1 H), 7.26-7.31 (m, 1 H), 6.97 (s, 1 H), 6.32 (dd, J = 16.1, 10.3 Hz, 1 H), 6.09-6.16 (m, 1 H), 5.68 (dd, J = 10.3, 2.0 Hz, 1 H), 4.18-4.34 (m, 2 H), 3.97-4.11 (m, 3 H), 3.91 (s, 3 H), 2.38 (s, 3 H), 2.25 (br s, 2 H) |
| 17-6 | 493.2 | $^1$H NMR (400 MHz, DMSO-$d_6$) δ ppm 8.38 (s, 1 H), 7.83 (d, J = 2.3 Hz, 1 H), 7.67 (s, 2 H), 7.45-7.61 (m, 4 H), 7.24 (d, J = 8.7 Hz, 1 H), 6.33 (dd, J = 16.4, 10.6 Hz, 1 H), 6.07-6.18 (m, 1 H), 5.66-5.72 (m, 1 H), 4.17-4.35 (m, 2 H), 3.87-4.06 (m, 6 H), 2.25 (br d, J = 6.0 Hz, 2 H), 2.18 (s, 3 H) |
| 17-7 | 509.0 | $^1$H NMR (400 MHz, DMSO-$d_6$) δ ppm 8.37 (d, J = 1.2 Hz, 1 H), 7.82 (d, J = 2.3 Hz, 1 H), 7.76 (dd, J = 7.8, 1.1 Hz, 1 H), 7.65 (br s, 3 H), 7.52-7.58 (m, 2 H), 7.09 (d, J = 8.9 Hz, 1 H), 6.27-6.39 (m, 1 H), 6.12 (dd, J = 17.0, 2.3 Hz, 1 H), 5.65-5.71 (m, 1 H), 4.17-4.36 (m, 2 H), 4.03 (m, 6 H), 2.22-2.30 (m, 2 H), 2.18 (d, J = 0.6 Hz, 3 H) |
| 17-8 | 495.0 | $^1$H NMR (400 MHz, DMSO-$d_6$) δ ppm 12.85-13.37 (m, 1 H), 8.07 (s, 1 H), 7.81 (br d, J = 2.1 Hz, 1 H), 7.76 (br d, J = 7.7 Hz, 2 H), 7.59-7.69 (m, 2 H), 7.55 (br d, J = 7.5 Hz, 1 H), 7.06 (d, J = 8.7 Hz, 1 H), 6.94 (d, J = 1.9 Hz, 1 H), 6.27-6.39 (m, 1 H), 6.13 (dd, J = 16.9, 2.0 Hz, 1 H), 5.66-5.71 (m, 1 H), 4.19-4.36 (m, 2 H), 3.88-4.10 (m, 6 H), 2.20-2.31 (m, 2 H) |
| 17-9 | 510.0 | $^1$H NMR (400 MHz, DMSO-$d_6$) δ ppm 8.45 (s, 1 H), 7.82 (s, 1 H), 7.74-7.79 (m, 1 H), 7.59-7.70 (m, 2 H), 7.51-7.57 (m, 2 H), 7.14 (d, J = 8.7 Hz, 1 H), 6.28-6.38 (m, 1 H), 6.12 (dd, J = 16.6, 1.9 Hz, 1 H), 5.66-5.71 (m, 1 H), 4.18-4.37 (m, 2 H), 4.00-4.07 (m, 3 H), 3.91 (s, 3 H), 2.46 (s, 3 H), 2.19-2.30 (m, 2 H) |
| 17-10 | 494.0 | $^1$H NMR (400 MHz, DMSO-$d_6$) δ ppm 8.46 (s, 1 H), 7.82 (s, 1 H), 7.67-7.75 (m, 1 H), 7.55 (s, 4 H), 7.28 (d, J = 8.7 Hz, 1 H), 6.31 (br d, J = 10.6 Hz, 1 H), 6.12 (dd, J = 17.1, 2.2 Hz, 1 H), 5.69 (dd, J = 10.3, 2.0 Hz, 1 H), 4.19-4.36 (m, 2 H), 3.99-4.07 (m, 3 H), 3.92 (s, 3 H), 2.47 (s, 3 H), 2.25 (br s, 2 H) |

TABLE 27

| Analytical Data for Examples 18-2 to 18-22. | | |
|---|---|---|
| Ex. # | LRMS: (ESI, +ve ion) m/z | NMR |
| 18-2 | 485.0 | $^1$H NMR (400 MHz, DMSO-$d_6$) δ ppm 13.06 (s, 1 H), 7.43-7.50 (m, 1 H), 7.40 (d, J = 4.7 Hz, 1 H), 7.32 (d, J = 8.6 Hz, 1 H), 6.33 (dd, J = 17.0, 10.3 Hz, 1 H), 6.11 (dd, J = 17.0, 2.3 Hz, 1 H), 5.67 (dd, J = 10.4, 2.3 Hz, 1 H), 4.28-4.16 (m, 2 H), 3.99-3.85 (m, 2 H), 3.68-3.40 (m, 6 H), 2.88-2.76 (m, 1 H), 2.55-2.45 (m, 2 H), 2.20-1.83 (m, 7 H), 1.74 (s, 3 H), 1.03 (d, J = 6.5 Hz, 6 H). |
| 18-3 | 497.0 | $^1$H NMR (400 MHz, DMSO-$d_6$) δ ppm 9.87 (br s, 1 H), 7.77 (d, J = 8.3 Hz, 1 H), 7.44-7.37 (m, 1 H), 7.22-7.06 (m, 3 H), 6.80 (d, J = 2.5 Hz, 1 H), 6.33 (ddd, J = 17.0, 10.3, 3.6 Hz, 1 H), 6.11 (dd, J = 17.0, 2.3 Hz, 1H), 5.67 (dt, J = 10.3, 1.9 Hz, 1H), 4.28-4.13 (m, 2 H), 4.00-3.85 (m, 2 H), 3.69-3.47 (m, 6 H), 2.85-2.75 (m, 1 H), 2.45-2.40 (m, 2 H), 2.22-2.05 (m, 3 H), 1.89-1.78 (m, 1 H), 1.76 (s, 3 H), 1.02 (d, J = 6.4 Hz, 6 H). |
| 18-4 | 497.0 | $^1$H NMR (400 MHz, DMSO-$d_6$) δ ppm 9.77 (s, 1 H), 7.72 (d, J = 8.3 Hz, 1 H), 7.47 (dd, J = 8.3, 6.9 Hz, 1 H), 7.19 (d, J = 2.5 Hz, 1 H), 7.10 (dd, J = 9.1, 5.2 Hz, 1 H), 7.05-6.94 (m, 2 H), 6.33 (dd, J = 17.0, 10.3 Hz, 1 H), 6.11 (dd, J = 17.0, 2.3 Hz, 1 H), 5.67 (dt, J = 10.3, 1.8 Hz, 1 H), 4.28-4.14 (m, 2 H), 3.98-3.85 (m, 2 H), 3.68-3.37 (m, 6 H), 2.85-2.74 (m, 1 H), 2.48-2.40 (m, 2 H), 2.22-2.05 (m, 3 H), 1.88-1.77 (m, 1 H), 1.75 (s, 3 H), 1.02 (d, J = 6.5 Hz, 6 H). |
| 18-5 | 486.0 | $^1$H NMR (400 MHz, DMSO-$d_6$) δ ppm 6.87 (dd, J = 6.0, 3.0 Hz, 1 H), 6.57-6.48 (m, 2 H), 6.32 (dd, J = 17.0, 10.3 Hz, 1 H), 6.11 (dd, J = 17.0, 2.4 Hz, 1 H), 5.67 (dd, J = 10.3, 2.4 Hz, 1 H), 4.28-4.12 (m, 3 H), 3.97-3.84 (m, 2 H), 3.65-3.37 (m, 6 H), 3.17-3.08 (m, 2 H), 2.88-2.71 (m, 3 H), 2.65-2.47 (m, 2 H), 2.31-2.05 (m, 4 H), 1.86 (s, 3 H), 1.81-1.72 (m, 2 H), 1.04 (d, J = 6.5 Hz, 6H). |
| 18-6 | 469.0 | $^1$H NMR (400 MHz, DMSO-$d_6$) δ ppm 9.78 (s, 1 H), 7.72 (d, J = 8.3 Hz, 1 H), 7.47 (dd, J = 8.3, 6.9 Hz, 1 H), 7.20 (d, J = 2.5 Hz, 1 H), 7.10 (dd, J = 9.1, 5.3 Hz, 1 H), 7.05-6.95 (m, 2 H), 6.37-6.28 (m, 1 H), 6.11 (dd, J = 16.9, 2.3 Hz, 1 H), 5.67 (dt, J = 10.3, 1.9 Hz, 1 H), 4.28-4.12 (m, 2 H), 3.98-3.85 (m, 2 H), 3.68-3.37 (m, 6 H), 2.45-2.05 (m, 8 H), 1.92-1.80 (m, 1 H), 1.75 (s, 3H). |
| 18-7 | 511.0 | $^1$H NMR(400 MHz, DMSO-$d_6$) δ ppm 9.79 (s, 1 H), 7.73 (d, J = 8.3 Hz, 1 H), 7.48 (dd, J = 8.4, 6.9 Hz, 1 H), 7.20 (d, J = 2.4 Hz, 1 H), 7.11 (dd, J = 9.1, 5.4 Hz, 1 H), 7.07-6.96 (m, 2 H), 6.33 (ddd, J = 16.9, 10.3, 3.1 Hz, 1 H), 6.11 (dd, J = 16.9, 2.3 Hz, 1 H), 5.67 (dt, J = 10.3, 1.8 Hz, 1 H), 4.58 (td, J = 6.4, 2.7 Hz, 2 H), 4.47 (dt, J = 9.6, 6.1 Hz, 2 H), 4.29-4.12 (m, 2 H), 3.99-3.85 (m, 2 H), 3.68-3.38 (m, 7 H), 2.41-2.25 (m, 2 H), 2.23-2.05 (m, 3 H), 1.94-1.83 (m, 1 H), 1.76 (s, 3 H). |
| 18-8 | 527.0 | $^1$H NMR (400 MHz, DMSO-$d_6$) δ ppm 9.78 (s, 1 H), 7.72 (d, J = 8.3 Hz, 1 H), 7.47 (dd, J = 8.4, 6.9 Hz, 1 H), 7.19 (d, J = 2.5 Hz, 1 H), 7.10 (dd, J = 9.1, 5.2 Hz, 1 H), 7.05-6.93 (m, 2 H), 6.33 (ddd, J = 17.0, 10.3, 3.1 Hz, 1 H), 6.11 (dd, J = 17.0, 2.3 |

TABLE 27-continued

| Ex. # | LRMS: (ESI, +ve ion) m/z | NMR |
|---|---|---|
| Analytical Data for Examples 18-2 to 18-22. | | |
| | | Hz, 1 H), 5.67 (dt, J = 10.4, 1.9 Hz, 1 H), 4.31-4.10 (m, 2 H), 4.00-3.83 (m, 2 H), 3.68-3.39 (m, 7 H), 3.30-3.19 (m, 5 H), 2.96-2.80 (m, 1 H), 2.21-2.02 (m, 4 H), 1.87-1.68 (m, 4 H), 1.00 (d, J = 6.6 Hz, 3 H). |
| 18-9 | 481.0 | $^1$H NMR (400 MHz, DMSO-$d_6$) δ ppm 9.85 (s, 1 H), 7.35 (d, J = 8.7 Hz, 1 H), 6.81 (dd, J = 8.7, 2.9 Hz, 1 H), 6.51 (d, J = 2.9 Hz, 1 H), 6.32 (ddd, J = 17.0, 10.3, 2.3 Hz, 1 H), 6.11 (dd, J = 17.0, 2.3 Hz, 1 H), 5.67 (dd, J = 10.3, 2.3 Hz, 1 H), 4.28-4.12 (m, 2 H), 3.97-3.82 (m, 2 H), 3.65-3.32 (m, 6 H), 2.88-2.75 (m, 1 H), 2.65-2.48 (m, 2 H), 2.25-2.03 (m, 4 H), 1.85 (s, 3 H), 1.03 (d, J = 6.5 Hz, 6 H). |
| 18-10 | 497.0 | $^1$H NMR (400 MHz, DMSO-$d_6$) δ ppm 9.82 (br s, 1 H), 7.74 (d, J = 8.3 Hz, 1 H), 7.51-7.43 (m, 1 H), 7.21 (d, J = 2.5 Hz, 1 H), 7.17-7.09 (m, 1 H), 7.06-6.94 (m, 2 H), 6.33 (ddd, J = 17.0, 10.3, 2.8 Hz, 1 H), 6.11 (dd, J = 17.0, 2.3 Hz, 1 H), 5.72-5.62 (m, 1 H), 4.60-4.50 (m, 2 H), 4.30-4.13 (m, 2 H), 4.00-3.88 (m, 2 H), 3.70-3.40 (m, 6 H), 2.30-2.05 (m, 5 H), 2.00-1.80 (m, 2 H), 1.77 (s, 3 H). |
| 18-11 | 536.3 | $^1$H NMR (400 MHz, DMSO-$d_6$) δ ppm 10.21 (s, 1 H), 7.34 (d, J = 8.8 Hz, 1 H), 6.81 (dd, J = 8.7, 2.9 Hz, 1 H), 6.50 (d, J = 2.9 Hz, 1 H), 6.32 (ddd, J = 17.0, 10.3, 2.4 Hz, 1 H), 6.11 (dd, J = 17.0, 2.3 Hz, 1 H), 5.67 (dd, J = 10.3, 2.3 Hz, 1 H), 4.26-4.12 (m, 2 H), 3.97-3.84 (m, 2 H), 3.65-3.36 (m, 7 H), 2.92-2.85 (m, 1 H), 2.72-2.60 (m, 3 H), 2.22-2.04 (m, 7 H), 1.90-1.61 (m, 7 H), 1.51-1.38 (m, 1 H), 1.26-1.11 (m, 1 H). |
| 18-12 | 521.8 | $^1$H NMR (400 MHz, DMSO-$d_6$) δ ppm 8.68 (s, 1 H), 7.47-7.19 (m, 3 H), 6.32 (dd, J = 17.0, 10.3 Hz, 1 H), 6.10 (dd, J = 17.0, 2.3 Hz, 1 H), 5.67 (dd, J = 10.3, 2.3 Hz, 1 H), 4.26-4.11 (m, 2 H), 3.99-3.83 (m, 4 H), 3.62 (s, 2 H), 3.53-3.40 (m, 2 H), 3.10-2.97 (m, 2 H), 2.44-2.29 (m, 2 H), 2.27 (s, 3 H), 2.14-2.05 (m, 2 H), 1.92 (s, 3 H). |
| 18-13 | 519.9 | $^1$H NMR (400 MHz, DMSO-$d_6$) δ ppm 9.55 (s, 1 H), 8.68 (s, 1 H), 7.16-7.12 (m, 1 H), 6.84-6.79 (m, 1 H), 6.53-6.51 (m, 1 H), 6.36-6.28 (m, 1 H), 6.13-6.08 (m, 1 H), 5.68-5.65 (m, 1 H), 4.26-4.16 (m, 2 H), 3.96-3.85 (m, 4 H), 3.64-3.58 (m, 2 H), 3.51-3.43 (m, 2 H), 3.06-2.97 (m, 2 H), 2.49-2.30 (m, 2 H), 2.27 (s, 3 H), 2.12-2.09 (m, 2 H), 1.95 (s, 3 H). |
| 18-14 | 499.2 | $^1$H NMR (400 MHz, DMSO-$d_6$) δ ppm 13.07 (s, 1 H), 7.48 (d, J = 8.4 Hz, 1 H), 7.39 (d, J = 3.0 Hz, 1 H), 7.34 (d, J = 8.6 Hz, 1 H), 6.34 (dd, J = 17.0, 10.3 Hz, 1 H), 6.12 (dd, J = 17.0, 2.3 Hz, 1 H), 5.68 (dd, J = 10.4, 2.3 Hz, 1 H), 4.67-4.44 (m, 4 H), 4.27-4.14 (m, 2 H), 3.99-3.85 (m, 2 H), 3.55-3.33 (m, 7 H), 2.45-2.30 (m, 2 H), 2.25-1.90 (m, 7 H), 1.76 (s, 3 H). |
| 18-15 | 489.1 | $^1$H NMR (400 MHz, DMSO-$d_6$) δ ppm 13.32 (s, 1 H), 7.65-7.61 (m, 2 H), 7.40-7.34 (m, 1 H), 6.36-6.28 (m, 1 H), 6.14-6.08 (m, 1 H), 5.69-5.65 (m, 1 H), 4.28-4.12 (m, 2 H), 3.98-3.85 (m, 2 H), 3.68-3.40 (m, 5 H), 2.90-2.75 (m, 1 H), 2.65-2.45 (m, 2 H), 2.30-2.00 (m, 5 H), 1.84 (s, 3 H), 1.22-1.00 (m, 6 H). |
| 18-16 | 483.1 | $^1$H NMR (400 MHz, DMSO-$d_6$) δ ppm 13.06 (s, 1 H), 7.46 (d, J = 8.5 Hz, 1 H), 7.39 (d, J = 4.7 Hz, 1 H), 7.32 (d, J = 8.5 Hz, 1 H), 6.33 (dd, J = 17.0, 10.3 Hz, 1 H), 6.11 (dd, J = 17.0, 2.3 Hz, 1 H), 5.67 (dd, J = 10.3, 2.3 Hz, 1 H), 4.28-4.12 (m, 2 H), 3.99-3.85 (m, 2 H), 3.68-3.60 (m, 4 H), 3.52-3.42 (m, 2 H), 2.70-2.60 (m, 2 H), 2.18-1.83 (m, 8 H), 1.71-1.62 (m, 4 H), 0.50-0.32 (m, 4 H). |
| 18-17 | 495.1 | $^1$H NMR (400 MHz, DMSO-$d_6$) δ ppm 9.79 (s, 1 H), 7.72 (d, J = 8.4 Hz, 1 H), 7.47 (dd, J = 8.4, 6.9 Hz, 1 H), 7.19 (d, J = 2.4 Hz, 1 H), 7.10 (dd, J = 9.1, 5.4 Hz, 1 H), 7.03-6.94 (m, 2 H), 6.33 (dd, J = 16.9, 10.3 Hz, 1 H), 6.11 (dd, J = 16.9, 2.3 Hz, 1 H), 5.67 (dt, J = 10.3, 1.8 Hz, 1 H), 4.28-4.12 (m, 2 H), 3.98-3.85 (m, 2 H), 3.68-3.37 (m, 6 H), 2.67-2.59 (m, 1 H), 2.22-2.05 (m, 4 H), 1.89-1.71 (m, 4 H), 0.50-0.30 (m, 4 H). |
| 18-18 | 568.2 | $^1$H NMR (400 MHz, DMSO-$d_6$) δ ppm 9.78 (s, 1 H), 7.73 (d, J = 8.3 Hz, 1 H), 7.48 (dd, J = 8.3, 6.9 Hz, 1 H), 7.20 (d, J = 2.5 Hz, 1 H), 7.10 (dd, J = 9.2, 5.2 Hz, 1 H), 7.05-6.95 (m, 2 H), 6.33 (ddd, J = 17.0, 10.3, 3.2 Hz, 1 H), 6.21-6.03 (m, 2 H), 5.67 (dt, J = 10.3, 1.8 Hz, 1 H), 4.29-4.11 (m, 3 H), 4.00-3.85 (m, 2 H), 3.71-3.38 (m, 6 H), 2.73-2.52 (m, 4 H), 2.25-2.05 (m, 3 H), 1.93-1.82 (m, 1 H), 1.76 (s, 3 H). |
| 18-19 | 485.3 | $^1$H NMR (400 MHz, DMSO-$d_6$) δ ppm 13.06 (s, 1 H), 7.47 (d, J = 8.5 Hz, 1 H), 7.40 (d, J = 4.6 Hz, 1 H), 7.32 (d, J = 8.6 Hz, 1 H), 6.33 (dd, J = 17.0, 10.3 Hz, 1 H), 6.11 (dd, J = 17.0, 2.3 Hz, 1 H), 5.67 (dd, J = 10.4, 2.3 Hz, 1 H), 4.28-4.16 (m, 2 H), 3.99-3.85 (m, 2 H), 3.68-3.40 (m, 6 H), 2.88-2.76 (m, 1 H), 2.55-2.45 (m, 2 H), 2.20-1.83 (m, 7 H), 1.74 (s, 3 H), 1.03 (d, J = 6.5 Hz, 6 H). |
| 18-20 | 554.3 | $^1$H NMR (400 MHz, DMSO-$d_6$) δ ppm 8.02 (s, 1 H), 7.69 (d, J = 8.2 Hz, 1 H), 7.14 (d, J = 8.3 Hz, 1 H), 6.33 (dd, J = 17.0, 10.3 Hz, 1 H), 6.11 (dd, J = 17.0, 2.3 Hz, 1 H), 5.68 (dd, J = 10.2, 2.3 Hz, 1 H), 4.25-4.12 (m, 2 H), 3.98-3.84 (m, 2 H), 3.79-3.60 (m, 4 H), 3.56-3.36 (m, 8 H), 3.00-2.85 (m, 2 H), 2.82-2.61 (m, 5 H), 2.19-1.75 (m, 13 H), 1.73-1.58 (m, 1 H). |
| 18-21 | 520.2 | $^1$H NMR (400 MHz, DMSO-$d_6$) δ ppm 8.68 (s, 1 H), 7.20-7.10 (m, 1 H), 6.93-6.67 (m, 2 H), 6.32 (ddd, J = 17.0, 10.3, 2.5 Hz, 1 H), 6.10 (dd, J = 17.0, 2.3 Hz, 1 H), 5.67 (dd, J = 10.3, 2.3 Hz, 1 H), 4.26-4.12 (m, 2 H), 3.97-3.84 (m, 4 H), 3.65-3.34 (m, 4 H), 3.05-2.95 (m, 2 H), 2.43-2.31 (m, 2 H), 2.27 (s, 3 H), 2.17-2.02 (m, 2 H), 1.90 (s, 3 H). |
| 18-22 | 485.3 | $^1$H NMR (400 MHz, DMSO-$d_6$) δ ppm 13.06 (s, 1H), 7.46 (d, J = 8.4 Hz, 1H), 7.40 (d, J = 4.8 Hz, 1H), 7.32 (d, J = 8.5 Hz, 1H), 6.33 (dd, J = 16.9, 10.3 Hz, 1H), 6.11 (dd, J = 17.0, 2.3 Hz, 1H), 5.67 (dd, J = 10.6, 2.3 Hz, 1H), 4.24 (d, J = 8.9 Hz, 1H), 4.20-4.13 (m, 1H), 3.99-3.85 (m, 2H), 3.60 (d, J = 17.7 Hz, 4H), 3.47 (q, J = 6.5 Hz, 2H), |

TABLE 27-continued

| Analytical Data for Examples 18-2 to 18-22. | | |
|---|---|---|
| Ex. # | LRMS: (ESI, +ve ion) m/z | NMR |
| | | 2.85-2.78 (m, 1H), 2.11 (s, 2H), 2.02 (d, J = 2.2 Hz, 3H), 1.96-1.91 (m, 2H), 1.74 (s, 3H), 1.03 (d, J = 6.5 Hz, 6H) |

TABLE 28

| Analytical Data for Examples 19-2 to 19-15. | | |
|---|---|---|
| Ex. # | LRMS: (ESI, +ve ion) m/z | NMR |
| 19-2 | 505.8 | $^1$H NMR (400 MHz, DMSO-$d_6$) δ ppm 9.05 (s, 1 H), 7.71 (d, J = 1.8 Hz, 1 H), 7.56-7.45 (m, 2 H), 7.41 (td, J = 7.2, 2.1 Hz, 1 H), 7.34 (dd, J = 8.6, 1.9 Hz, 1 H), 7.26 (d, J = 7.5 Hz, 1 H), 7.07 (d, J = 8.6 Hz, 1 H), 6.32 (m, 1 H), 6.12 (dd, J = 17.0, 2.2 Hz, 1 H), 5.69 (dd, J = 10.3, 2.2 Hz, 1 H), 4.29 (dd, J = 8.9, 3.9 Hz, 1 H), 4.21 (d, J = 8.8 Hz, 1 H), 4.07-3.80 (m, 6 H), 2.53 (s, 3 H), 2.30-2.16 (m, 2 H), 2.02 (d, J = 3.1 Hz, 3 H). |
| 19-3 | 526.1 | $^1$H NMR (400 MHz, DMSO-$d_6$) δ ppm 10.37 (s, 1 H), 9.10 (s, 1 H), 7.71 (d, J = 1.8 Hz, 1 H), 7.46 (td, J = 8.3, 6.9 Hz, 1 H), 7.39 (dd, J = 8.6, 1.9 Hz, 1 H), 7.27 (d, J = 8.5 Hz, 1 H), 7.00-6.84 (m, 2 H), 6.40-6.25 (m, 1 H), 6.12 (dd, J = 17.0, 2.3 Hz, 1 H), 5.68 (dd, J = 10.3, 2.3 Hz, 1 H), 4.32 (d, J = 8.7 Hz, 1 H), 4.21 (dd, J = 8.9, 2.0 Hz, 1 H), 4.10-3.79 (m, 6 H), 2.56 (s, 3 H), 2.26 (m, 2 H). |
| 19-4 | 526.1 | $^1$H NMR (400 MHz, DMSO-$d_6$) δ ppm 10.37 (s, 1 H), 9.10 (s, 1 H), 7.71 (d, J = 1.8 Hz, 1 H), 7.46 (td, J = 8.3, 6.9 Hz, 1 H), 7.39 (dd, J = 8.6, 1.9 Hz, 1 H), 7.27 (d, J = 8.5 Hz, 1 H), 7.00-6.84 (m, 2 H), 6.40-6.25 (m, 1 H), 6.12 (dd, J = 17.0, 2.3 Hz, 1 H), 5.68 (dd, J = 10.3, 2.3 Hz, 1 H), 4.32 (d, J = 8.7 Hz, 1 H), 4.21 (dd, J = 8.9, 2.0 Hz, 1 H), 4.10-3.79 (m, 6 H), 2.56 (s, 3 H), 2.26 (m, 2 H). |
| 19-5 | 529.8 | $^1$H NMR (400 MHz, DMSO-$d_6$) δ ppm 9.17 (s, 1 H), 8.77 (d, J = 2.1 Hz, 1 H), 8.06 (d, J = 2.2 Hz, 1 H), 7.67 (m, 1 H), 7.51 (td, J = 9.7, 2.5 Hz, 1 H), 7.34 (td, J = 8.5, 2.5 Hz, 1 H), 6.32 (m, 1 H), 6.12 (dd, J = 17.0, 2.3 Hz, 1 H), 5.68 (dd, J = 10.3, 2.3 Hz, 1 H), 4.31 (m, 1 H), 4.21 (dd, J = 8.8, 3.4 Hz, 1 H), 4.13-3.85 (m, 6 H), 2.56 (s, 3 H), 2.25 (m, 2 H). |
| 19-6 | 522.9 | $^1$H NMR(400 MHz, DMSO-$d_6$) δ ppm 9.15 (s, 1H), 8.71 (d, J = 2.3 Hz, 1H), 8.02 (d, J = 2.2 Hz, 1H), 7.51 (m, 1H), 7.34-7.27 (m, 1H), 7.21 (d, J = 8.3 Hz, 1H), 7.11 (t, J = 7.4 Hz, 1H), 6.32 (m, 1H), 6.11 (dd, J = 17.0, 2.3 Hz, 1H), 5.68 (dd, J = 10.3, 2.3 Hz, 1H), 4.31 (dd, J = 8.7, 4.8 Hz, 1H), 4.20 (dd, J = 8.7, 5.2 Hz, 1H), 4.11-3.87 (m, 6H), 3.71 (d, J = 1.4 Hz, 3H), 2.56 (s, 3H), 2.29-2.21 (m, 2H) |
| 19-7 | 494.2 | $^1$H NMR (400 MHz, DMSO-$d_6$) δ ppm 8.84 (d, J = 2.2 Hz, 1 H), 8.08 (d, J = 2.2 Hz, 1 H), 7.87 (s, 1 H), 7.68-7.53 (m, 2 H), 7.50-7.35 (m, 3 H), 6.33 (m, 1 H), 6.12 (dd, J = 17.0, 2.3 Hz, 1 H), 5.69 (dd, J = 10.3, 2.3 Hz, 1 H), 4.31 (m, 1 H), 4.22 (dd, J = 8.7, 4.1 Hz, 1 H), 4.14-3.98 (m, 3 H), 3.98-3.89 (m, 3 H), 3.86 (s, 3 H), 2.27 (m, 2 H). |
| 19-8 | 511.1 | $^1$H NMR(400 MHz, DMSO-$d_6$) δ ppm 9.17 (s, 1H), 8.77 (d, J = 2.2 Hz, 1H), 8.05 (d, J = 2.2 Hz, 1H), 7.71-7.61 (m, 2H), 7.47-7.36 (m, 2H), 6.32 (dd, J = 17.0, 10.3 Hz, 1H), 6.12 (dd, J = 17.0, 2.3 Hz, 1H), 5.68 (dd, J = 10.3, 2.3 Hz, 1H), 4.29 (d, J = 8.7 Hz, 1H), 4.21 (d, J = 8.7 Hz, 1H), 4.10-3.96 (m, 3H), 3.96-3.88 (m, 3H), 2.57 (s, 3H), 2.29-2.21 (m, 2H) |
| 19-9 | 556.7 | $^1$H NMR(40 MHz, $CDCl_3$): 8 (ppm) 8.75 (d, J = 2.2 Hz, 1H), 8.04 (d, J = 2.2 Hz, 1H), 7.67-7.62 (m, 1H), 7.58-7.48 (m, 2H), 7.43-7.37 (m, 1H), 6.41 (dd, J = 17.0, 1.9 Hz, 1H), 6.23 (dd, J = 17.0, 10.3 Hz, 1H), 5.74 (dd, J = 10.3, 1.8 Hz, 1H), 4.98 (s, 2H), 4.36-4.29 (m, 1H), 4.27-4.05 (m, 7H), 3.44-3.38 (m, 1H), 2.61 (s, 3H), 2.33 (t, J = 6.9 Hz, 2H) |
| 19-10 | 527.1 | $^1$H NMR (400 MHz, DMSO-$d_6$) δ ppm 9.21 (s, 1 H), 8.80 (d, J = 2.2 Hz, 1 H), 8.25 (d, J = 2.1 Hz, 1 H), 7.71-7.52 (m, 2 H), 7.42 (m, 2 H), 6.32 (dd, J = 16.9, 10.4 Hz, 1 H), 6.11 (dd, J = 17.1, 2.4 Hz, 1 H), 5.68 (dd, J = 10.3, 2.3 Hz, 1 H), 5.58 (s, 1 H), 4.62 (s, 2 H), 4.31 (m, 1 H), 4.21 (dd, J = 8.7, 4.1 Hz, 1 H), 4.15-3.76 (m, 6 H), 2.25 (m, 2 H). |
| 19-11 | 506.2 | $^1$H NMR (400 MHz, DMSO-$d_6$) δ 9.09 (s, 1 H), 7.71 (d, J = 1.9 Hz, 1 H), 7.49 (d, J = 7.1 Hz, 2 H), 7.42 (td, J = 7.1, 2.1 Hz, 1 H), 7.35 (dd, J = 8.6, 1.9 Hz, 1 H), 7.29 (d, J = 7.5 Hz, 1 H), 7.07 (d, J = 8.6 Hz, 1 H), 6.32 (dd, J = 17.0, 10.3 Hz, 1 H), 6.11 (dd, J = 17.0, 2.3 Hz, 1 H), 5.68 (dd, J = 10.3, 2.3 Hz, 1 H), 4.31 (dd, J = 8.9, 3.7 Hz, 1 H), 4.20 (d, J = 8.7 Hz, 1 H), 4.10-3.96 (m, 3 H), 3.96-3.81 (m, 3 H), 2.54 (s, 3 H), 2.23 (m, 2 H), 2.04 (d, J = 3.1 Hz, 3 H). |
| 19-12 | 506.1 | $^1$H NMR (400 MHz, DMSO-$d_6$) δ 9.09 (s, 1 H), 7.71 (d, J = 1.9 Hz, 1 H), 7.49 (d, J = 7.1 Hz, 2 H), 7.42 (td, J = 7.1, 2.1 Hz, 1 H), 7.35 (dd, J = 8.6, 1.9 Hz, 1 H), 7.29 (d, J = 7.5 Hz, 1 H), 7.07 (d, J = 8.6 Hz, 1 H), 6.32 (dd, J = 17.0, 10.3 Hz, 1 H), 6.11 (dd, J = 17.0, 2.3 Hz, 1 H), 5.68 (dd, J = 10.3, 2.3 Hz, 1 H), 4.31 (dd, J = 8.9, 3.7 Hz, 1 H), 4.20 (d, J = 8.7 Hz, 1 H), 4.10-3.96 (m, 3 H), 3.96-3.81 (m, 3 H), 2.54 (s, 3 H), 2.23 (m, 2 H), 2.04 (d, J = 3.1 Hz, 3 H). |
| 19-13 | 520.8 | $^1$H NMR (400 MHz, DMSO-de) δ ppm 9.16 (s, 1 H), 8.72 (d, J = 2.2 Hz, 1 H), 8.04 (d, J = 2.2 Hz, 1 H), 7.31 (d, J = 7.5 Hz, 1 H), 7.23 (t, J = 7.5 Hz, 1 H), 7.10 (d, J = 7.5 |

TABLE 28-continued

| Analytical Data for Examples 19-2 to 19-15. | | |
|---|---|---|
| Ex. # | LRMS: (ESI, +ve ion) m/z | NMR |
| | | Hz, 1 H), 6.32 (m, 1 H), 6.11 (dd, J = 17.0, 2.4 Hz, 1 H), 5.68 (dd, J = 10.3, 2.4 Hz, 1 H), 4.31 (m, 1 H), 4.21 (dd, J = 8.7, 3.7 Hz, 1 H), 4.13-3.97 (m, 3 H), 3.97-3.82 (m, 3 H), 2.56 (s, 3 H), 2.34 (s, 3 H), 2.24 (m, 2 H), 1.90 (d, J = 2.7 Hz, 3 H). |
| 19-14 | 520.8 | $^1$H NMR (400 MHz, DMSO-$d_6$) δ ppm 9.16 (s, 1 H), 8.72 (d, J = 2.2 Hz, 1 H), 8.04 (d, J = 2.2 Hz, 1 H), 7.31 (d, J = 7.5 Hz, 1 H), 7.23 (t, J = 7.5 Hz, 1 H), 7.10 (d, J = 7.5 Hz, 1 H), 6.32 (m, 1 H), 6.11 (dd, J = 17.0, 2.4 Hz, 1 H), 5.68 (dd, J = 10.3, 2.4 Hz, 1 H), 4.31 (m, 1 H), 4.21 (dd, J = 8.7, 3.7 Hz, 1 H), 4.13-3.97 (m, 3 H), 3.97-3.82 (m, 3 H), 2.56 (s, 3 H), 2.34 (s, 3 H), 2.24 (h, J = 4.4 Hz, 2 H), 1.90 (d, J = 2.7 Hz, 3 H). |
| 19-15 | 526.1 | $^1$H NMR(400 MHz, DMSO-$d_6$) δ ppm 10.55 (br s, 1 H), 9.09 (s, 1 H), 7.69 (d, J = 1.8 Hz, 1 H), 7.45-7.34 (m, 2 H), 7.27 (d, J = 8.6 Hz, 1 H), 6.88 (d, J = 8.4 Hz, 1 H), 6.83 (s, 1 H), 6.31 (dd, J = 17.0, 10.3 Hz, 1 H), 6.11 (dd, J = 17.0, 2.3 Hz, 1 H), 5.67 (dd, J = 10.3, 2.3 Hz, 1 H), 4.35-4.28 (m, 1H), 4.20 (d, J = 8.7 Hz, 1 H), 4.07 3.86 (m, 6 H), 2.55 (s, 3 H), 2.24 (td, J = 6.7, 2.8 Hz, 2 H). |

TABLE 29

| Analytical Data for Examples 20-2 to 20-22. | | |
|---|---|---|
| Ex. # | LRMS: (ESI, +ve ion) m/z | NMR |
| 20-2 | 510.1 | $^1$H NMR (401 MHz, DMSO-$d_6$) δ ppm 9.10 (s, 1 H), 7.76-7.65 (m, 2 H), 7.62-7.44 (m, 3 H), 7.40 (dd, J = 8.6, 1.9 Hz, 1 H), 7.24 (dd, J = 8.6, 1.3 Hz, 1 H), 6.32 (m, 1 H), 6.11 (dd, J = 17.0, 2.3 Hz, 1 H), 5.68 (dd, J = 10.3, 2.3 Hz, 1 H), 4.30 (m, 1 H), 4.20 (dd, J = 8.7, 3.1 Hz, 1 H), 4.12-3.76 (m, 6 H), 2.55 (s, 3 H), 2.26 (m, 2 H). |
| 20-3 | 526.0 | $^1$H NMR (400 MHz, DMSO-$d_6$) δ ppm 9.10 (s, 1 H), 7.76 (dd, J = 7.9, 1.5 Hz, 1 H), 7.72 (d, J = 1.8 Hz, 1 H), 7.63 (m, 2 H), 7.55 (dd, J = 7.4, 2.0 Hz, 1 H), 7.38 (dd, J = 8.6, 1.9 Hz, 1 H), 7.10 (d, J = 8.6 Hz, 1 H), 6.32 (m, 1 H), 6.11 (dd, J = 17.0, 2.3 Hz, 1 H), 5.68 (dd, J = 10.3, 2.3 Hz, 1 H), 4.31 (dd, J = 8.7, 5.4 Hz, 1 H), 4.20 (dd, J = 8.7, 4.9 Hz, 1 H), 4.10-3.82 (m, 6 H), 2.55 (s, 3 H), 2.31-2.15 (m, 2 H). |
| 20-4 | 526.1 | $^1$H NMR (400 MHz, DMSO-$d_6$) δ ppm 9.10 (s, 1 H), 7.76 (dd, J = 7.9, 1.5 Hz, 1 H), 7.72 (d, J = 1.8 Hz, 1 H), 7.63 (m, 2 H), 7.55 (dd, J = 7.4, 2.0 Hz, 1 H), 7.38 (dd, J = 8.6, 1.9 Hz, 1 H), 7.10 (d, J = 8.6 Hz, 1 H), 6.32 (m, 1 H), 6.11 (dd, J = 17.0, 2.3 Hz, 1 H), 5.68 (dd, J = 10.3, 2.3 Hz, 1 H), 4.31 (dd, J = 8.7, 5.4 Hz, 1 H), 4.20 (dd, J = 8.7, 4.9 Hz, 1 H), 4.10-3.82 (m, 6 H), 2.55 (s, 3 H), 2.31-2.15 (m, 2 H). |
| 20-5 | 459.1 | $^1$H NMR (400 MHz, DMSO-$d_6$) δ ppm 7.72 (dd, J = 7.8, 1.5 Hz, 1 H), 7.60 (m, 2 H), 7.51-7.42 (m, 1 H), 7.04 (d, J = 2.2 Hz, 1 H), 6.96-6.83 (m, 2 H), 6.32 (m, 1 H), 6.12 (dd, J = 17.0, 2.3 Hz, 1 H), 5.69 (dd, J = 10.3, 2.3 Hz, 1 H), 4.29 (dd, J = 8.7, 5.2 Hz, 1 H), 4.20 (dd, J = 8.7, 6.1 Hz, 1 H), 4.09-3.75 (m, 9 H), 2.24 (m, 2 H). |
| 20-6 | 520.2 | $^1$H NMR (400 MHz, DMSO-$d_6$) δ ppm 9.09 (s, 1 H), 7.70 (d, J = 1.8 Hz, 1 H), 7.45-7.26 (m, 3 H), 7.09 (dd, J = 13.8, 8.1 Hz, 2 H), 6.32 (m, 1 H), 6.11 (dd, J = 17.0, 2.3 Hz, 1 H), 5.68 (dd, J = 10.3, 2.3 Hz, 1 H), 4.31 (dd, J = 8.7, 5.4 Hz, 1 H), 4.20 (dd, J = 8.7, 2.8 Hz, 1 H), 4.11-3.96 (m, 3 H), 3.91 (m, 3 H), 2.54 (s, 3 H), 2.37 (s, 3 H), 2.23 (td, J = 7.1, 3.2 Hz, 2 H), 1.92 (d, J = 2.9 Hz, 3 H). |
| 20-7 | 526.8 | $^1$H NMR (400 MHz, DMSO-$d_6$) δ ppm 9.10 (s, 1 H), 7.76 (dd, J = 7.9, 1.5 Hz, 1 H), 7.72 (d, J = 1.8 Hz, 1 H), 7.63-7.10 (m, 3 H), 6.32 (m, 1 H), 6.11 (dd, J = 17.0, 2.3 Hz, 1 H), 5.68 (dd, J = 10.3, 2.3 Hz, 1 H), 4.31 (dd, J = 8.7, 5.4 Hz, 1 H), 4.20 (dd, J = 8.7, 4.9 Hz, 1 H), 4.10-3.82 (m, 6 H), 2.55 (s, 3 H), 2.31-2.15 (m, 2 H). |
| 20-8 | 527.1 | $^1$H NMR (400 MHz, DMSO-$d_6$) δ ppm 9.17 (s, 1 H), 8.75 (d, J = 2.2 Hz, 1 H), 8.07 (d, J = 2.2 Hz, 1 H), 7.68 (dd, J = 7.4, 1.5 Hz, 1 H), 7.61-7.52 (m, 2 H), 6.33 (m, 1 H), 6.12 (dd, J = 17.0, 2.4 Hz, 1 H), 5.69 (dd, J = 10.3, 2.4 Hz, 1 H), 4.41-4.27 (m, 1 H), 4.22 (dd, J = 8.8, 5.6 Hz, 1 H), 4.14-3.85 (m, 6 H), 2.57 (s, 3 H), 2.28 (m, 2 H). |
| 20-9 | 527.1 | $^1$H NMR (400 MHz, DMSO-$d_6$) δ ppm 9.17 (s, 1 H), 8.75 (d, J = 2.2 Hz, 1 H), 8.07 (d, J = 2.2 Hz, 1 H), 7.68 (dd, J = 7.4, 1.5 Hz, 1 H), 7.61-7.52 (m, 3 H), 6.33 (m, 1 H), 6.12 (dd, J = 17.0, 2.4 Hz, 1 H), 5.69 (dd, J = 10.3, 2.4 Hz, 1 H), 4.41-4.27 (m, 1 H), 4.22 (dd, J = 8.8, 5.6 Hz, 1 H), 4.14-3.85 (m, 6 H), 2.57 (s, 3 H), 2.28 (m, 2 H). |
| 20-10 | 540.2 | $^1$H NMR (400 MHz, DMSO-$d_6$) δ ppm 9.14 (s, 1 H), 7.77 (dd, J = 7.8, 1.4 Hz, 1 H), 7.64 (m, 2 H), 7.59-7.52 (m, 2 H), 7.00-6.92 (m, 1 H), 6.32 (m, 1 H), 6.12 (dd, J = 17.0, 2.3 Hz, 1 H), 5.68 (dd, J = 10.3, 2.3 Hz, 1 H), 4.30 (dd, J = 8.7, 4.7 Hz, 1 H), 4.20 (dd, J = 8.7, 4.6 Hz, 1 H), 4.07-3.80 (m, 6 H), 2.28-2.17 (m, 5 H), 2.09 (d, J = 1.0 Hz, 3 H). |
| 20-11 | 487.2 | $^1$H NMR (400 MHz, DMSO-$d_6$) δ ppm 7.72 (dd, J = 7.8, 1.4 Hz, 1 H), 7.60 (m, 2 H), 7.48 (dd, J = 7.2, 2.0 Hz, 1 H), 7.01 (d, J = 2.5 Hz, 1 H), 6.90 (d, J = 9.1 Hz, 1 H), 6.84 (dd, J = 9.1, 2.4 Hz, 1 H), 6.32 (m, 1 H), 6.12 (dd, J = 17.0, 2.3 Hz, 1 H), 5.68 (dd, J = 10.3, 2.3 Hz, 1 H), 4.82 (m 1 H), 4.30 (dd, J = 8.7, 4.4 Hz, 1 H), 4.20 (dd, J = 8.7, 5.0 Hz, 1 H), 4.07-3.75 (m, 6 H), 2.23 (m, 2 H), 1.33 (dd, J = 6.0, 1.3 Hz, 6 H). |
| 20-12 | 509.1 | $^1$H NMR (400 MHz, DMSO-$d_6$) δ ppm 9.29 (s, 2 H), 9.26 (s, 1 H), 8.10 (d, J = 1.8 Hz, 1 H), 7.74-7.58 (m, 3 H), 7.42 (td, J = 8.5, 2.5 Hz, 1 H), 7.34 (dd, J = 8.7, 1.3 |

TABLE 29-continued

| Analytical Data for Examples 20-2 to 20-22. | | |
|---|---|---|
| Ex. # | LRMS: (ESI, +ve ion) m/z | NMR |
| | | Hz, 1 H), 6.33 (m, 1 H), 6.13 (dd, J = 17.0, 2.3 Hz, 1 H), 5.69 (dd, J = 10.3, 2.3 Hz, 1 H), 4.31 (m, 1 H), 4.22 (dd, J = 8.7, 3.0 Hz, 1 H), 4.11-3.98 (m, 3 H), 3.93 (m, 3 H), 2.31-2.20 (m, 2 H). |
| 20-13 | 528.2 | $^1$H NMR(400 MHz, DMSO-$d_6$) δ (ppm) 9.11 (s, 1H), 7.75-7.57 (m, 3H), 7.41 (m, 2H), 7.28 (dd, J = 8.6, 1.2 Hz, 1H), 6.32 (m, 1H), 6.12 (dd, J = 16.9, 2.3 Hz, 1H), 5.68 (dd, J = 10.3, 2.3 Hz, 1H), 4.31 (t, J = 8.1 Hz, 1H), 4.21 (dd, J = 8.8, 2.4 Hz, 1H), 4.09-3.96 (m, 3H), 3.96-3.87 (m, 3H), 2.56 (s, 3H), 2.25 (m, 2H). |
| 20-14 | 510.8 | $^1$H NMR (400 MHz, DMSO-$d_6$) δ ppm 7.93 (d, J = 1.8 Hz, 1 H), 7.75-7.56 (m, 3 H), 7.47-7.34 (m, 2 H), 7.28 (dd, J = 8.6, 1.2 Hz, 1 H), 7.07 (d, J = 1.1 Hz, 1 H), 6.33 (m, 1 H), 6.12 (dd, J = 17.0, 2.3 Hz, 1 H), 5.68 (dd, J = 10.3, 2.3 Hz, 1 H), 4.31 (m, 1 H), 4.21 (dd, J = 8.8, 2.7 Hz, 1 H), 4.12-3.84 (m, 9 H), 2.25 (m, 2 H). |
| 20-15 | 510.8 | $^1$H NMR (400 MHz, DMSO-$d_6$) δ ppm 9.16 (s, 1 H), 8.76 (d, J = 2.2 Hz, 1 H), 8.06 (d, J = 2.2 Hz, 1 H), 7.69-7.54 (m, 2 H), 7.49-7.36 (m, 2 H), 6.32 (m, 1 H), 6.12 (dd, J = 17.0, 2.3 Hz, 1 H), 5.68 (dd, J = 10.3, 2.3 Hz, 1 H), 4.31 (m, 1 H), 4.21 (dd, J = 8.7, 4.0 Hz, 1 H), 4.13-3.83 (m, 6 H), 2.56 (s, 3 H), 2.26 (m, 2 H). |
| 20-16 | 539.8 | $^1$H NMR (400 MHz, DMSO-$d_6$) δ ppm 9.17 (s, 1 H), 7.84 (d, J = 1.8 Hz, 1 H), 7.71 (m, 1 H), 7.63-7.46 (m, 3 H), 7.43 (dd, J = 8.6, 1.9 Hz, 1 H), 7.27 (dd, J = 8.5, 1.3 Hz, 1 H), 6.32 (m, 1 H), 6.12 (dd, J = 17.0, 2.3 Hz, 1 H), 5.68 (dd, J = 10.3, 2.4 Hz, 1 H), 4.54 (s, 2 H), 4.32 (m, 1 H), 4.21 (dd, J = 8.9, 3.0 Hz, 1 H), 4.13-3.97 (m, 3 H), 3.97-3.85 (m, 3 H), 3.35 (s, 3 H), 2.25 (m, 2 H). |
| 20-17 | 522.9 | $^1$H NMR(400 MHz, DMSO-$d_6$) δ ppm 9.09 (s, 1H), 7.68 (d, J = 1.8 Hz, 1H), 7.59 (m, 1H), 7.32 (m, 3H), 7.23-7.14 (m, 2H), 6.32 (m, 1H), 6.11 (dd, J = 17.0, 2.3 Hz, 1H), 5.68 (dd, J = 10.2, 2.3 Hz, 1H), 4.30 (dd, J = 8.7, 5.9 Hz, 1H), 4.20 (dd, J = 8.7, 5.0 Hz, 1H), 4.08-3.85 (m, 6H), 3.73 (s, 3H), 2.54 (s, 3H), 2.32-2.15 (m, J = 4.9 Hz, 2H). |
| 20-18 | 525.9 | $^1$H NMR (400 MHz, DMSO-$d_6$) δ ppm 9.15 (s, 1 H), 7.92 (d, J = 1.8 Hz, 1 H), 7.71 (m, 1 H), 7.63-7.42 (m, 4 H), 7.25 (dd, J = 8.6, 1.3 Hz, 1 H), 6.32 (m, 1 H), 6.12 (dd, J = 17.0, 2.3 Hz, 1 H), 5.68 (dd, J = 10.3, 2.3 Hz, 1 H), 5.49 (t, J = 5.4 Hz, 1 H), 4.61 (d, J = 5.4 Hz, 2 H), 4.32 (m, 1 H), 4.21 (dd, J = 8.7, 3.0 Hz, 1 H), 4.13-3.98 (m, 3 H), 3.92 (m, 3 H), 2.26 (m, 2 H). |
| 20-19 | 496.0 | $^1$H NMR (400 MHz, DMSO-$d_6$) δ ppm 9.20 (s, 1 H), 8.56 (s, 1 H), 7.90 (d, J = 1.8 Hz, 1 H), 7.71 (m, 1 H), 7.66-7.42 (m, 4 H), 7.22 (dd, J = 8.8, 1.3 Hz, 1 H), 6.32 (m, 1 H), 6.12 (dd, J = 17.0, 2.4 Hz, 1 H), 5.68 (dd, J = 10.3, 2.3 Hz, 1 H), 4.30 (m, 1 H), 4.21 (dd, J = 8.7, 3.4 Hz, 1 H), 4.11-3.96 (m, 3 H), 3.96-3.83 (m, 3 H), 2.31-2.12 (m, 2 H). |
| 20-20 | 507.9 | $^1$H NMR (400 MHz, DMSO-$d_6$) δ ppm 9.83 (d, J = 6.5 Hz, 1 H), 9.09 (s, 1 H), 7.69 (d, J = 1.9 Hz, 1 H), 7.46-7.32 (m, 2 H), 7.31-7.18 (m, 2 H), 7.12-6.95 (m, 2 H), 6.32 (m, 1 H), 6.11 (dd, J = 17.0, 2.3 Hz, 1 H), 5.68 (dd, J = 10.3, 2.3 Hz, 1 H), 4.30 (dd, J = 8.7, 4.8 Hz, 1 H), 4.20 (dd, J = 8.7, 6.0 Hz, 1 H), 4.09-3.82 (m, 6 H), 2.54 (s, 3 H), 2.24 (m, 2 H). |
| 20-21 | 508.8 | $^1$H NMR (400 MHz, DMSO-$d_6$) δ ppm 9.66 (s, 1 H), 9.16 (s, 1 H), 8.76 (d, J = 2.3 Hz, 1 H), 8.03 (d, J = 2.2 Hz, 1 H), 7.40-7.27 (m, 1 H), 7.00-6.86 (m, 3 H), 6.32 (dd, J = 17.0, 10.3 Hz, 1 H), 6.12 (dd, J = 17.0, 2.3 Hz, 1 H), 5.68 (dd, J = 10.3, 2.3 Hz, 1 H), 4.30 (d, J = 8.7 Hz, 1 H), 4.20 (d, J = 8.7 Hz, 1 H), 4.11-3.97 (m, 3 H), 3.97-3.83 (m, 3 H), 2.57 (s, 3 H), 2.25 (m, 2 H). |
| 20-22 | 526.8 | $^1$H NMR (400 MHz, DMSO-$d_6$) δ ppm 10.12 (s, 1 H), 9.16 (s, 1 H), 8.77 (d, J = 2.2 Hz, 1 H), 8.03 (d, J = 2.2 Hz, 1 H), 7.32 (dd, J = 11.3, 8.4 Hz, 1 H), 7.13 (dd, J = 8.5, 2.1 Hz, 1 H), 6.99 (m, 1 H), 6.32 (dd, J = 17.0, 10.3 Hz, 1 H), 6.12 (dd, J = 17.0, 2.3 Hz, 1 H), 5.68 (dd, J = 10.3, 2.3 Hz, 1 H), 4.29 (d, J = 8.7 Hz, 1 H), 4.21 (d, J = 8.7 Hz, 1 H), 4.10-3.97 (m, 3 H), 3.97-3.83 (m, 3 H), 2.57 (s, 3 H), 2.25 (m, 2 H). |

TABLE 30

| Analytical Data for Examples 21-2 to 21-37. | | |
|---|---|---|
| Ex. # | LRMS: (ESI, +ve ion) m/z | NMR |
| 21-2 | 498.9 | $^1$H NMR (400 MHz, DMSO-$d_6$) δ ppm 7.65-7.54 (m, 1 H), 7.47-7.36 (m, 3 H), 7.29 (d, J = 1.9 Hz, 1 H), 6.31 (m, 1 H), 6.11 (dd, J = 17.0, 2.3 Hz, 1 H), 5.92 (d, J = 2.0 Hz, 1 H), 5.68 (dd, J = 10.3, 2.3 Hz, 1 H), 4.26 (dd, J = 8.7, 5.3 Hz, 1 H), 4.17 (dd, J = 8.7, 2.7 Hz, 1 H), 4.05 (s, 2 H), 3.96 (dd, J = 10.2, 3.6 Hz, 1 H), 3.94-3.84 (m, 3 H), 3.75 (t, J = 6.8 Hz, 2 H), 3.64 (s, 3 H), 3.09 (t, J = 5.9 Hz, 2 H), 2.42 (s, 1 H), 2.37 (d, J = 6.3 Hz, 1 H), 2.25-2.14 (m, 2 H) |
| 21-3 | 533.1 | $^1$H NMR (400 MHz, DMSO-$d_6$) δ ppm 8.71 (s, 1 H), 7.45-7.56 (m, 2 H), 7.30 (m, 1 H), 6.26-6.35 (m, 1 H), 6.11 (dd, J = 17.0, 2.3 Hz, 1 H), 5.67 (dd, J = 10.3, 2.3 Hz, 1 H), 4.13-4.30 (m, 2 H), 4.00 (s, 2 H), 3.80-3.99 (m, 4 H), 3.75 (t, J = 6.8 Hz, 2 H), 3.07 (t, J = 5.8 Hz, 2 H), 2.45 (d, J = 1.8 Hz, 1 H), 2.39 (t, J = 5.8 Hz, 1 H), 2.27 (s, 3 H), 2.20 (m, 2 H). |

TABLE 30-continued

| Analytical Data for Examples 21-2 to 21-37. | | |
|---|---|---|
| Ex. # | LRMS: (ESI, +ve ion) m/z | NMR |
| 21-4 | 529.2 | $^1$H NMR (400 MHz, DMSO-$d_6$) δ ppm 8.79 (d, J = 5.1 Hz, 1 H), 7.58 (m, 1 H), 7.50-7.35 (m, 3 H), 6.39-6.23 (m, 1 H), 6.11 (dd, J = 17.0, 2.3 Hz, 1 H), 5.67 (dd, J = 10.3, 2.3 Hz, 1 H), 4.27 (m, 1 H), 4.18 (d, J = 7.6 Hz, 1 H), 4.04-3.82 (m, 5 H), 3.76 (m, 2 H), 3.23-3.11 (m, 2 H), 2.94 (m, 1 H), 2.27 (d, J = 1.0 Hz, 3 H), 2.20 (dd, J = 8.6, 6.0 Hz, 2 H), 1.36 (dd, J = 6.6, 5.2 Hz, 3 H). |
| 21-5 | 529.0 | $^1$H NMR (400 MHz, DMSO-$d_6$) δ ppm 8.80 (d, J = 5.2 Hz, 1 H), 7.57 (m, 1 H), 7.33 7.48 (m, 3 H), 6.25-6.37 (m, 1 H), 6.11 (dd, J = 17.0, 2.3 Hz, 1 H), 5.68 (dd, J = 10.3, 2.3 Hz, 1 H), 4.23-4.32 (m, 1 H), 4.18 (s, 1 H), 3.81-4.02 (m, 5 H), 3.76 (s, 2 H), 3.16 (dd, J = 11.7, 6.1 Hz, 1 H), 2.87-3.00 (m, 1 H), 2.27 (s, 3 H), 2.21 (m, 3 H), 1.31-1.43 (m, 3 H). |
| 21-6 | 529.2 | $^1$H NMR (400 MHz, DMSO-$d_6$) δ ppm 8.80 (d, J = 5.3 Hz, 1 H), 7.58 (d, J = 7.3 Hz, 1 H), 7.35-7.48 (m, 3 H), 6.24-6.37 (m, 1 H), 6.11 (dd, J = 17.1, 2.3 Hz, 1 H), 5.68 (dd, J = 10.2, 2.4 Hz, 1 H), 4.22 (d, J = 33.3 Hz, 2 H), 3.83-4.01 (m, 5 H), 3.76 (s, 2 H), 3.16 (s, 1 H), 2.94 (s, 1 H), 2.24-2.31 (m, 3 H), 2.21 (m, 3 H), 1.36 (t, J = 6.0 Hz, 3 H). |
| 21-7 | 542.8 | $^1$H NMR (400 MHz, $CDCl_3$) δ ppm 7.20-7.26 (m, 1 H), 6.95-7.09 (m, 4 H), 6.85-6.95 (m, 2 H), 6.39 (dd, J = 17.0, 1.9 Hz, 1 H), 6.22 (dd, J = 17.0, 10.3 Hz, 1 H), 5.73 (dd, J = 10.4, 1.9 Hz, 1 H), 4.26 (m, 2 H), 4.03-4.22 (m, 4 H), 3.87-4.02 (m, 4 H), 3.81 (s, 3 H), 3.36 (m, 2 H), 2.54 (m, 2 H), 2.25 (t, J = 6.8 Hz, 2 H) |
| 21-8 | 502.2 | $^1$H NMR (400 MHz, DMSO-$d_6$) δ ppm 9.67 (s, 1 H), 7.10-7.24 (m, 1 H), 6.87 (s, 1 H), 6.63 (d, J = 20.1 Hz, 1 H), 6.31 (m, 1 H), 6.11 (dd, J = 17.0, 2.3 Hz, 1 H), 5.68 (dd, J = 10.2, 2.3 Hz, 1 H), 4.12-4.34 (m, 2 H), 3.94-4.05 (m, 1 H), 3.80-3.93 (m, 3 H), 3.76 (m, 2 H), 3.64 (m, 2 H), 2.18 (m, 4 H), 1.77 (d, J = 44.3 Hz, 3 H), 1.37 (s, 2 H), 1.02 (d, J = 22.4 Hz, 6 H). |
| 21-9 | 493.2 | $^1$H NMR (400 MHz, DMSO-$d_6$) δ ppm 9.99 (s, 1 H), 7.35-7.44 (m, 1 H), 6.88 (dd, J = 8.8, 2.9 Hz, 1 H), 6.65 (d, J = 2.9 Hz, 1 H), 6.31 (m, 1 H), 6.11 (dd, J = 17.0, 2.3 Hz, 1 H), 5.68 (dd, J = 10.3, 2.3 Hz, 1 H), 4.26 (dd, J = 8.6, 4.3 Hz, 1 H), 4.17 (dd, J = 8.6, 5.4 Hz, 1 H), 3.76-4.00 (m, 4 H), 3.72 (t, J = 6.8 Hz, 2 H), 3.58 (d, J = 3.1 Hz, 2 H), 2.86 (m, 1 H), 2.58 (m, 2 H), 2.03-2.27 (m, 4 H), 1.03 (d, J = 6.5 Hz, 6 H). |
| 21-10 | 516.8 | $^1$H NMR (400 MHz, DMSO-$d_6$) δ ppm 8.71 (s, 1 H), 8.64 (dt, J = 4.7, 1.6 Hz, 1 H), 8.00 (m, 1 H), 7.68 (dt, J = 8.7, 4.5 Hz, 1 H), 6.31 (m, 1 H), 6.11 (dd, J = 17.0, 2.3 Hz, 1 H), 5.67 (dd, J = 10.3, 2.3 Hz, 1 H), 4.27 (dd, J = 8.9, 2.9 Hz, 1 H), 4.17 (d, J = 8.7 Hz, 1 H), 4.03 (s, 2 H), 3.96 (d, J = 10.0 Hz, 1 H), 3.82-3.92 (m, 3 H), 3.75 (t, J = 6.8 Hz, 2 H), 3.07 (t, J = 5.9 Hz, 2 H), 2.31 (s, 1 H), 2.27 (s, 3 H), 2.21 (d, J = 8.1 Hz, 2 H). |
| 21-11 | 532 | $^1$H NMR (400 MHz, DMSO-$d_6$) δ ppm 8.70 (s, 1 H), 7.63-7.70 (m, 1 H), 7.49 7.58 (m, 2 H), 7.35-7.43 (m, 1 H), 6.31 (m, 1 H), 6.11 (dd, J = 17.0, 2.3 Hz, 1 H), 5.68 (dd, J = 10.3, 2.3 Hz, 1 H), 4.26 (dd, J = 8.6, 4.2 Hz, 1 H), 4.17 (dd, J = 8.7, 4.3 Hz, 1 H), 4.01 (s, 2 H), 3.96 (d, J = 9.8 Hz, 1 H), 3.79-3.92 (m, 3 H), 3.75 (t, J = 6.9 Hz, 2 H), 3.07 (t, J = 6.0 Hz, 2 H), 2.31 (d, J = 6.2 Hz, 2 H), 2.26 (s, 3 H), 2.20 (q, J = 6.0 Hz, 2 H). |
| 21-12 | 546.8 | $^1$H NMR(400 MHz, DMSO-$d_6$) δ (ppm) 8.70 (s, 1H), 7.39 (d, J = 8.8 Hz, 1H), 6.88 (dd, J = 8.8, 2.9 Hz, 1H), 6.68 (d, J = 3.0 Hz, 1H), 6.31 (ddd, J = 16.9, 10.3, 3.4 Hz, 1H), 6.11 (dd, J = 17.0, 2.4 Hz, 1H), 5.67 (dd, J = 10.2, 2.4 Hz, 1H), 4.26 (dd, J = 8.7, 3.8 Hz, 1H), 4.17 (dd, J = 8.5, 5.5 Hz, 1H), 3.97 (d, J = 21.0 Hz, 3H), 3.87 (dt, J = 21.5, 8.3 Hz, 3H), 3.74 (t, J = 6.9 Hz, 2H), 3.07 (t, J = 6.1 Hz, 2H), 2.35 (d, J = 4.9 Hz, 2H), 2.26 (s, 3H), 2.20 (q, J = 6.1 Hz, 2H) |
| 21-13 | 546.8 | $^1$H NMR (400 MHz, DMSO-$d_6$) δ ppm 10.04 (s, 1 H), 8.70 (s, 1 H), 7.42 (d, J = 8.8 Hz, 1 H), 6.90 (dd, J = 8.8, 2.9 Hz, 1 H), 6.70 (d, J = 2.9 Hz, 1 H), 6.31 (ddd, J = 17.0, 10.3, 3.2 Hz, 1 H), 6.11 (dd, J = 17.0, 2.3 Hz, 1 H), 5.68 (dd, J = 10.2, 2.3 Hz, 1 H), 4.26 (dd, J = 8.7, 4.1 Hz, 1 H), 4.17 (dd, J = 8.7, 5.3 Hz, 1 H), 4.00 (s, 2 H), 3.96 (d, J = 10.0 Hz, 1 H), 3.77-3.93 (m, 3 H), 3.74 (t, J = 6.9 Hz, 2 H), 3.07 (t, J = 6.1 Hz, 2 H), 2.35 (d, J = 4.2 Hz, 2 H), 2.26 (s, 3 H), 2.20 (m, 2 H). |
| 21-14 | 531 | $^1$H NMR (400 MHz, DMSO-$d_6$) δ ppm 9.94 (s, 1 H), 8.71 (s, 1 H), 7.24-7.34 (m, 1 H), 6.90-6.98 (m, 2 H), 6.31 (m, 1 H), 6.11 (dd, J = 17.0, 2.3 Hz, 1 H), 5.68 (dd, J = 10.3, 2.3 Hz, 1 H), 4.25 (dd, J = 8.9, 4.1 Hz, 1 H), 4.17 (dd, J = 8.7, 4.9 Hz, 1 H), 3.98 (d, J = 4.6 Hz, 2 H), 3.94 (d, J = 2.3 Hz, 1 H), 3.78-3.92 (m, 3 H), 3.73 (t, J = 6.9 Hz, 2 H), 2.97-3.12 (m, 2 H), 2.39 (m, 2 H), 2.27 (s, 3 H), 2.18 (dd, J = 7.5, 3.8 Hz, 2 H). |
| 21-15 | 476 | $^1$H NMR (400 MHz, DMSO-$d_6$) δ ppm 9.67 (s, 1 H), 7.17 (t, J = 9.1 Hz, 1 H), 6.81-6.92 (m, 1 H), 6.64 (dd, J = 5.9, 3.0 Hz, 1 H), 6.31 (m, 1 H), 6.11 (dd, J = 17.0, 2.3 Hz, 1 H), 5.68 (dd, J = 10.3, 2.3 Hz, 1 H), 4.26 (dd, J = 8.8, 5.3 Hz, 1 H), 4.16 (dd, J = 8.9, 3.7 Hz, 1 H), 3.95 (dd, J = 10.2, 3.4 Hz, 1 H), 3.77-3.91 (m, 3 H), 3.72 (t, J = 6.9 Hz, 2 H), 3.58 (s, 2 H), 2.81-2.93 (m, 1 H), 2.60 (s, 2 H), 2.12-2.31 (m, 4 H), 1.03 (d, J = 6.5 Hz, 6 H) |
| 21-16 | 546.9 | $^1$H NMR (400 MHz, DMSO-$d_6$) δ ppm 8.72 (s, 1 H), 7.46-7.60 (m, 2 H), 7.30 (dd, J = 9.6, 7.2 Hz, 1 H), 6.21-6.45 (m, 1 H), 6.11 (m, 1 H), 5.68 (m, 1 H), 4.44-4.59 (m, 1 H), 4.37 (d, J = 9.3 Hz, 1 H), 3.97-4.16 (m, 3 H), 3.91 (d, J = 7.6 Hz, 1 H), 3.80 (dd, J = 21.3, 8.2 Hz, 3 H), 3.64 (d, J = 9.5 Hz, 1 H), 3.06 (m, 2 H), 2.27 (m, 6 H), 1.21 (td, J = 6.1, 1.6 Hz, 3 H). |
| 21-17 | 546.9 | $^1$H NMR (400 MHz, DMSO-$d_6$) δ ppm 8.72 (s, 1 H), 7.53 (m, 2 H), 7.30 (dd, J = 9.6, 7.3 Hz, 1 H), 6.23-6.40 (m, 1 H), 6.11 (m, 1 H), 5.68 (m, 1 H), 4.44-4.58 (m, 1 H), 4.37 (m, 1 H), 3.97-4.17 (m, 4 H), 3.91 (d, J = 7.6 Hz, 1 H), 3.80 (dd, |

TABLE 30-continued

| Analytical Data for Examples 21-2 to 21-37. | | |
|---|---|---|
| Ex. # | LRMS: (ESI, +ve ion) m/z | NMR |
| | | J = 21.4, 8.2 Hz, 2 H), 3.65 (d, J = 10.2 Hz, 1 H), 3.06 (m, 2 H), 2.27 (m, 6 H), 1.21 (td, J = 6.1, 1.6 Hz, 3 H) |
| 21-18 | 491.9 | $^1$H NMR (400 MHz, DMSO-$d_6$) δ ppm 7.43-7.54 (m, 2 H), 7.27 (m, 1 H), 6.24-6.40 (m, 1 H), 6.11 (dt, J = 17.0, 2.5 Hz, 1 H), 5.68 (m, 1 H), 4.50 (m, 1 H), 4.37 (d, J = 9.4 Hz, 1 H), 4.02-4.17 (m, 2 H), 3.89 (d, J = 7.6 Hz, 1 H), 3.72-3.85 (m, 2 H), 3.54-3.69 (m, 3 H), 2.87 (p, J = 6.5 Hz, 1 H), 2.62 (s, 1 H), 2.09-2.31 (m, 4 H), 1.21 (m, 3 H), 1.03 (d, J = 6.5 Hz, 6 H) |
| 21-19 | 530.8 | $^1$H NMR (400 MHz, DMSO-$d_6$) δ ppm 9.71 (s, 1 H), 8.71 (s, 1 H), 7.20 (t, J = 9.1 Hz, 1 H), 6.84-6.93 (m, 1 H), 6.68 (dd, J = 5.9, 3.0 Hz, 1 H), 6.31 (m, 1 H), 6.11 (dd, J = 17.0, 2.4 Hz, 1 H), 5.68 (dd, J = 10.3, 2.3 Hz, 1 H), 4.26 (dd, J = 8.7, 5.0 Hz, 1 H), 4.17 (dd, J = 8.6, 3.4 Hz, 1 H), 3.99 (s, 2 H), 3.94-3.79 (m, 4 H), 3.74 (t, J = 6.9 Hz, 2 H), 3.07 (t, J = 5.9 Hz, 2 H), 2.27 (s, 3 H), 2.19 (m, 2 H). |
| 21-20 | 515.1 | $^1$H NMR (400 MHz, DMSO-$d_6$) δ ppm 7.58 (m, 1 H), 7.32-7.48 (m, 3 H), 6.85 (m, 1 H), 6.25-6.38 (m, 1 H), 6.11 (dd, J = 17.0, 2.3 Hz, 1 H), 5.67 (dd, J = 10.3, 2.3 Hz, 1 H), 4.50 (s, 2 H), 4.26 (dd, J = 8.6, 5.3 Hz, 1 H), 4.17 (dd, J = 8.4, 2.6 Hz, 1 H), 3.80-4.02 (m, 4 H), 3.76 (t, J = 6.8 Hz, 2 H), 3.59 (t, J = 5.8 Hz, 2 H), 2.43 (m, 2 H), 2.26 (s, 3 H), 2.12-2.24 (m, 2 H). |
| 21-21 | 508.9 | $^1$H NMR (400 MHz, DMSO-$d_6$) δ ppm 8.47 (d, J = 7.5 Hz, 2 H), 7.55-7.64 (m, 1 H), 7.37-7.48 (m, 3 H), 7.31 (d, J = 7.0 Hz, 1 H), 6.32 (dd, J = 17.0, 10.3 Hz, 1 H), 6.12 (dd, J = 17.0, 2.3 Hz, 1 H), 5.68 (dd, J = 10.3, 2.3 Hz, 1 H), 4.57-4.74 (m, 1 H), 4.22-4.38 (m, 3 H), 4.18 (dd, J = 8.6, 2.7 Hz, 1 H), 3.83-4.01 (m, 4 H), 3.77 (t, J = 6.9 Hz, 2 H), 3.69 (t, J = 6.0 Hz, 2 H), 2.37 (m, 4 H), 2.20 (m, 2 H). |
| 21-22 | 531.2 | $^1$H NMR(400 MHz, DMSO-$d_6$) δ (ppm) 8.70 (s, 1H), 7.70-7.63 (m, 1H), 7.59-7.48 (m, 2H), 7.43-7.36 (m, 1H), 6.31-6.30 (m, 1H), 6.11-6.10 (m, 1H), 5.68 (m, 1H), 4.26 (dd, J = 8.6, 4.2 Hz, 1H), 4.17 (dd, J = 8.7, 4.3 Hz, 1H), 3.96-3.79 (m, 4H), 3.75 (t, J = 6.9 Hz, 2H), 3.07 (t, J = 6.0 Hz, 2H), 2.56-2.46 (m, 2H), 2.39-2.28 (m, 2H), 2.26 (s, 3H), 2.21-2.20 (m, 2H). |
| 21-23 | 531.2 | $^1$H NMR(400 MHz, DMSO-$d_6$) ? (ppm) 8.70 (s, 1H), 7.70-7.63 (m, 1H), 7.59 7.48 (m, 2H), 7.43-7.36 (m, 1H), 6.31-6.30 (m, 1H), 6.11-6.10 (m, 1H), 5.68 (m, 1H), 4.26 (dd, J = 8.6, 4.2 Hz, 1H), 4.17 (dd, J = 8.7, 4.3 Hz, 1H), 3.96-3.79 (m, 4H), 3.75 (t, J = 6.9 Hz, 2H), 3.07 (t, J = 6.0 Hz, 2H), 2.56-2.46 (m, 2H), 2.39 2.28 (m, 2H), 2.26 (s, 3H), 2.21-2.20 (m, 2H). |
| 21-24 | 546.8 | $^1$H NMR(400 MHz, DMSO-$d_6$) δ (ppm) 10.12 (s, 1H), 8.70 (s, 1H), 7.41 (d, J = 8.8 Hz, 1H), 6.90 (dd, J = 8.8, 2.9 Hz, 1H), 6.70 (d, J = 2.9 Hz, 1H), 6.31 (ddd, J = 17.1, 10.3, 3.1 Hz, 1H), 6.11 (dd, J = 17.0, 2.3 Hz, 1H), 5.67 (dd, J = 10.2, 2.3 Hz, 1H), 4.26 (dd, J = 8.8, 4.0 Hz, 1H), 4.17 (dd, J = 8.5, 5.3 Hz, 1H), 3.97 (d, J = 21.8 Hz, 3H), 3.92-3.82 (m, 3H), 3.74 (t, J = 6.9 Hz, 2H), 3.07 (t, J = 6.1 Hz, 2H), 2.35 (d, J = 4.8 Hz, 2H), 2.26 (s, 3H), 2.20 (q, J = 6.1 Hz, 2H). |
| 21-25 | 546.8 | $^1$H NMR(400 MHz, DMSO-$d_6$) δ (ppm) 8.70 (s, 1H), 7.39 (d, J = 8.8 Hz, 1H), 6.88 (dd, J = 8.8, 2.9 Hz, 1H), 6.68 (d, J = 3.0 Hz, 1H), 6.31 (ddd, J = 16.9, 10.3, 3.4 Hz, 1H), 6.11 (dd, J = 17.0, 2.4 Hz, 1H), 5.67 (dd, J = 10.2, 2.4 Hz, 1H), 4.26 (dd, J = 8.7, 3.8 Hz, 1H), 4.17 (dd, J = 8.5, 5.5 Hz, 1H), 3.97 (d, J = 21.0 Hz, 3H), 3.87 (dt, J = 21.5, 8.3 Hz, 3H), 3.74 (t, J = 6.9 Hz, 2H), 3.07 (t, J = 6.1 Hz, 2H), 2.35 (d, J = 4.9 Hz, 2H), 2.26 (s, 3H), 2.20 (q, J = 6.1 Hz, 2H) |
| 21-26 | 516.2 | $^1$H NMR(400 MHz, DMSO-$d_6$) δ (ppm) 9.99 (s, 1H), 7.40 (d, J = 8.8 Hz, 1H), 6.89 (dd, J = 8.8, 2.9 Hz, 1H), 6.70 (t, J = 2.6 Hz, 1H), 6.38-6.25 (m, 1H), 6.11 (dd, J = 17.0, 2.3 Hz, 1H), 5.68 (dd, J = 10.3, 2.3 Hz, 1H), 4.29 (t, J = 7.5 Hz, 1H), 4.17 (t, J = 7.0 Hz, 1H), 4.00-3.89 (m, 1H), 3.88 (s, 3H), 3.92-3.81 (m, 1H), 3.76 (d, J = 7.1 Hz, 3H), 2.97 (t, J = 7.7 Hz, 1H), 2.20 (s, 1H), 2.05 (s, 1H), 1.63 (s, 1H), 1.47 (s, 1H), 1.24 (s, 1H), 1.15 (s, 1H), 0.95 (dd, J = 12.7, 6.4 Hz, 3H), 0.81 (dd, J = 9.1, 6.2 Hz, 3H) |
| 21-27 | 478.1 | $^1$H NMR (400 MHz, DMSO-$d_6$) δ ppm 7.41-7.55 (m, 2 H), 7.28 (m, 1 H), 6.31 (m, 1 H), 6.11 (dd, J = 17.0, 2.3 Hz, 1 H), 5.68 (dd, J = 10.2, 2.3 Hz, 1 H), 4.22-4.31 (m, 1 H), 4.17 (dd, J = 8.7, 2.5 Hz, 1 H), 3.79-4.02 (m, 4 H), 3.73 (t, J = 6.8 Hz, 2 H), 3.59 (s, 2 H), 2.86 (m, 1 H), 2.60 (m, 2 H), 2.10-2.32 (m, 4 H), 1.03 (d, J = 6.5 Hz, 6 H), |
| 21-28 | 546.9 | $^1$H NMR (400 MHz, DMSO-de) δ ppm 10.03 (br s, 1 H), 7.39 (d, J = 8.8 Hz, 1 H), 6.88 (dd, J = 8.8, 3.0 Hz, 1 H), 6.66 (d, J = 3.0 Hz, 1 H), 6.31 (m, 1 H), 6.11 (dd, J = 17.0, 2.3 Hz, 1 H), 5.68 (dd, J = 10.3, 2.4 Hz, 1 H), 4.25 (m, 1 H), 4.17 (m, 1 H), 3.77-4.00 (m, 4 H), 3.73 (m, 2 H), 3.55 (s, 2 H), 2.91 (m, 1 H), 2.27 (s, 3 H), 2.19 (d, J = 6.8 Hz, 4 H), 1.88-1.79 (m, 1 H), 1.61-1.59 (m, 2 H), 1.52 (s, 1 H), 1.24 (s, 1 H). (4 protons obscured by NMR solvent peak) |
| 21-29 | 515.3 | $^1$H NMR (400 MHz, DMSO-$d_6$) δ ppm 7.56 (m, 1 H), 7.31-7.45 (m, 3 H), 6.31 (m, 1 H), 6.11 (dd, J = 17.0, 2.3 Hz, 1 H), 5.68 (dd, J = 10.2, 2.3 Hz, 1 H), 4.26 (dd, J = 8.7, 5.4 Hz, 1 H), 4.17 (dd, J = 8.6, 2.8 Hz, 1 H), 3.79-4.01 (m, 4 H), 3.73 (t, J = 6.8 Hz, 2 H), 3.56 (s, 2 H), 2.91 (m, 1 H), 2.60 (m, 2 H), 2.37 (m, 2 H), 2.28 (m, 4 H), 2.01-2.24 (m, 4 H), 1.88 (m, 1 H), 1.61 (m, 2 H), 1.51 (m, 1 H), 1.21 (m, 1 H). |
| 21-30 | 515.0 | $^1$H NMR (400 MHz, DMSO-$d_6$) δ ppm 7.51-7.60 (m, 1 H), 7.32-7.44 (m, 3 H), 6.31 (m, 1 H), 6.11 (dd, J = 17.0, 2.3 Hz, 1 H), 5.68 (dd, J = 10.3, 2.3 Hz, 1 H), 4.25 (dd, J = 8.7, 5.2 Hz, 1 H), 4.17 (dd, J = 8.6, 2.8 Hz, 1 H), 3.77-4.01 (m, 4 H), 3.63-3.77 (m, 4 H), 2.87 (d, J = 10.5 Hz, 1 H), 2.64 (m, 4 H), 2.09-2.30 (m, 7 H), 1.60-1.88 (m, 4 H), 1.46 (m, 1 H), 1.17 (m, 1 H) |
| 21-31 | 572.0 | $^1$H NMR (400 MHz, DMSO-$d_6$) δ ppm 8.71 (s, 1 H), 7.53-7.63 (m, 1 H), 7.35-7.46 (m, 3 H), 6.58 (m, 1 H), 6.12 (m, 1 H), 4.24 (dd, J = 8.5, 5.5 Hz, 1 H), 4.15 (dd, |

TABLE 30-continued

| Analytical Data for Examples 21-2 to 21-37. | | |
|---|---|---|
| Ex. # | LRMS: (ESI, +ve ion) m/z | NMR |
| | | J = 8.4, 2.7 Hz, 1 H), 4.00 (s, 2 H), 3.80-3.97 (m, 4 H), 3.75 (t, J = 6.9 Hz, 2 H), 3.08 (m, 3 H), 2.39 (m, 2 H), 2.27 (s, 3 H), 2.17-2.24 (m, 6 H). (3 proton missing) |
| 21-32 | 533.2 | $^1$H NMR (400 MHz, DMSO-$d_6$) δ ppm 7.43-7.51 (m, 2 H), 7.27 (m, 1 H), 6.31 (m, 1 H), 6.11 (dd, J = 17.0, 2.3 Hz, 1 H), 5.68 (dd, J = 10.3, 2.3 Hz, 1 H), 4.13-4.29 (m, 2 H), 3.78-3.98 (m, 4 H), 3.64-3.76 (m, 4 H), 2.83-2.91 (m, 1 H), 2.67 (m, 3 H), 2.12-2.35 (m, 8 H), 1.74 (m, 4 H), 1.38-1.52 (m, 1 H), 1.17 (m, 1 H). |
| 21-33 | 515.0 | $^1$H NMR (400 MHz, DMSO-$d_6$) δ ppm 7.66-7.51 (m, 2 H), 7.46-7.30 (m, 3 H), 6.39-6.26 (m, 1 H), 6.11 (dd, J = 17.0, 2.3 Hz, 1 H), 5.68 (dd, J = 10.3, 2.3 Hz, 1 H), 4.25 (dd, J = 8.7, 5.4 Hz, 1 H), 4.22-4.10 (m, 1 H), 4.02-3.80 (m, 4 H), 3.73 (m, 3 H), 3.65-3.50 (m, 2 H), 2.62 (m, 2 H), 2.43 (m, 2 H), 2.27 (m, 2 H), 2.24-2.02 (m, 5 H), 1.76-1.65 (m, 1 H). |
| 21-34 | 529.0 | $^1$H NMR (400 MHz, DMSO-$d_6$) δ ppm 7.64-7.52 (m, 1 H), 7.39 (m, 3 H), 6.31 (dd, J = 16.9, 10.3 Hz, 1 H), 6.11 (dd, J = 17.0, 2.3 Hz, 1 H), 5.68 (dd, J = 10.3, 2.4 Hz, 1 H), 4.83 (m, 1 H), 4.72-4.44 (m, 2 H), 4.26 (dd, J = 8.7, 5.3 Hz, 1 H), 4.17 (dd, J = 8.7, 2.6 Hz, 1 H), 4.02-3.82 (m, 3 H), 3.80-3.56 (m, 4 H), 3.18 (m, 1 H), 2.96 (m, 1 H), 2.20 (m, 8 H), 2.08 (m, 1 H), 1.72 (m, 3 H), |
| 21-35 | 518.8 | $^1$H NMR (400 MHz, DMSO-$d_6$) δ ppm 8.71 (s, 1 H), 8.64 (m, 1 H), 8.00 (m, 1 H), 7.68 (m, 1 H), 4.27 (d, J = 8.9 Hz, 1 H), 4.17 (d, J = 8.6 Hz, 1 H), 4.03 (s, 2 H), 3.96 (d, J = 10.0 Hz, 2 H), 3.94-3.82 (m, 4 H), 3.76 (t, J = 6.8 Hz, 2 H), 3.08 (t, J = 5.8 Hz, 2 H), 2.27 (s, 3 H), 2.20 (m, 2 H). |
| 21-36 | 546.9 | $^1$H NMR (400 MHz, DMSO-$d_6$) δ ppm 7.38 (d, J = 8.8 Hz, 1 H), 6.87 (dd, J = 8.8, 2.9 Hz, 1 H), 6.64 (d, J = 2.9 Hz, 1 H), 6.31 (m, 1 H), 6.11 (dd, J = 17.0, 2.3 Hz, 1 H), 5.68 (dd, J = 10.3, 2.3 Hz, 1 H), 4.26 (dd, J = 8.7, 3.9 Hz, 1 H), 4.16 (dd, J = 8.7, 5.4 Hz, 1 H), 3.95 (m, 1 H), 3.92-3.79 (m, 3 H), 3.77-3.60 (m, 4 H), 2.87 (d, J = 10.5 Hz, 1 H), 2.80-2.61 (m, 4 H), 2.17 (m, 7 H), 1.88-1.60 (m, 4 H), 1.44 (m, 1 H), 1.29-1.08 (m, 1 H). |
| 21-37 | 458.0 | $^1$H NMR (400 MHz, DMSO-$d_6$) δ ppm 7.61-7.50 (m, 1 H), 7.43-7.33 (m, 3 H), 6.31 (m, 1 H), 6.11 (dd, J = 17.0, 2.3 Hz, 1 H), 5.68 (dd, J = 10.3, 2.3 Hz, 1 H), 4.21 (m, 2 H), 4.01-3.78 (m, 4 H), 3.78-3.63 (m, 4 H), 2.75 (t, J = 6.0 Hz, 2 H), 2.34-2.10 (m, 3 H), 1.81 (m, 1 H), 0.48 (m, 2 H), 0.38 (m, 2 H). |
| 21-38 | 503.1 | $^1$H NMR (400 MHz, Methanol-$d_4$) δ ppm 7.54 (m, 1 H), 7.41-7.24 (m, 3 H), 6.38 (m, 1 H), 6.28 (dd, J = 17.0, 2.1 Hz, 1 H), 5.81-5.75 (m, 1 H), 4.31 (m, 3 H), 4.09-4.04 (m, 2 H), 3.97 (d, J = 3.3 Hz, 2 H), 3.92-3.79 (m, 4 H), 3.75 (m, 2 H), 3.24 (m, 1 H), 3.07 (m, 1 H), 2.89 (m, 2 H), 2.83-2.72 (m, 2 H), 2.49-2.40 (m, 3 H), 2.34-2.23 (m, 3 H), 1.11 (dd, J = 6.6, 1.4 Hz, 3 H). |

TABLE 31

| Analytical Data for Examples 22-3 to 22-4. | | |
|---|---|---|
| Ex. # | LRMS: (ESI, +ve ion) m/z | NMR |
| 22-3 | 485.9 | $^1$H NMR (400 MHz, DMSO-$d_6$) δ ppm 7.74 (d, J = 3.3 Hz, 1 H), 7.64 (d, J = 3.3 Hz, 1 H), 7.23-7.18 (m, 1 H), 7.15 (t, J = 7.5 Hz, 1 H), 6.98-6.86 (m, 1 H), 6.31 (dd, J = 17.0, 10.2 Hz, 1 H), 6.10 (dd, J = 17.0, 2.3 Hz, 1 H), 5.67 (dd, J = 10.3, 2.3 Hz, 1 H), 4.22 (d, J = 8.3 Hz, 1 H), 4.15 (d, J = 8.5 Hz, 1 H), 3.90 (m, 2 H), 3.65 (d, J = 10.6 Hz, 2 H), 3.54 (m, 4 H), 3.17 (dd, J = 17.7, 5.4 Hz, 1 H), 3.11-3.01 (m, 2 H), 2.55 (s, 3 H), 2.28 (s, 3 H), 2.16 (dt, J = 9.6, 4.6 Hz, 2 H), 1.93-1.90 (m, 2 H). |
| 22-4 | 522.2 | $^1$H NMR (400 MHz, DMSO-$d_6$) δ ppm 9.93 (br s, 1 H), 8.84 (s, 1 H), 7.31 (d, J = 8.7 Hz, 1 H), 6.84 (dd, J = 8.7, 2.9 Hz, 1 H), 6.65 (m, 1 H), 6.30 (dd, J = 17.0, 10.3 Hz, 1 H), 6.09 (dd, J = 17.0, 2.4 Hz, 1 H), 5.66 (dd, J = 10.3, 2.3 Hz, 1 H), 4.21 (d, J = 8.7 Hz, 1 H), 4.14 (d, J = 8.6 Hz, 1 H), 3.92-3.87 (m, 2 H), 3.64 (d, J = 9.8 Hz, 2 H), 3.57-3.38 (m, 4 H), 3.03 (dd, J = 17.8, 5.1 Hz, 1 H), 2.36 (s, 3 H), 2.28-2.6 (m, 2 H), 2.15 (m, 2 H), 2.00 (m, 2 H). |

TABLE 32

| Analytical Data for Examples 23-2 to 23-61. | | |
|---|---|---|
| Ex. # | LRMS: (ESI, +ve ion) m/z | NMR |
| 23-2 | 510.1 | $^1$H NMR (400 MHz, DMSO-$d_6$) δ ppm 8.84 (d, J = 1.3 Hz, 1 H), 7.39-7.34 (m, 2 H), 7.34-7.29 (m, 1 H), 7.10-7.03 (m, 1 H), 6.30 (m, 1 H), 6.10 (dd, J = 17.0, 2.3 |

TABLE 32-continued

| Analytical Data for Examples 23-2 to 23-61. | | |
|---|---|---|
| Ex. # | LRMS: (ESI, +ve ion) m/z | NMR |
| | | Hz, 1 H), 5.67 (dd, J = 10.3, 2.3 Hz, 1 H), 4.24 (d, J = 8.3 Hz, 1 H), 4.16 (d, J = 8.6 Hz, 1 H), 3.97-3.79 (m, 4 H), 3.72 (t, J = 6.9 Hz, 2 H), 3.45-3.08 (m, 2 H), 2.78-2.76 (m, 2 H), 2.35 (s, 3 H), 2.19 (dt, J = 17.4, 5.5 Hz, 2 H), 2.10 (s, 3 H), 1.98-1.90 (m, 1 H), 1.62-1.71 (m, 1 H). |
| 23-3 | 510.2 | $^1$H NMR (400 MHz, DMSO-$d_6$) δ ppm 8.84 (s, 1 H), 7.36-7.32 (m, 3 H), 7.09-7.03 (m, 1 H), 6.36-6.26 (m, 1 H), 6.10 (dd, J = 17.0, 2.3 Hz, 1 H), 5.67 (dd, J = 10.3, 2.3 Hz, 1 H), 4.25 (d, J = 8.6 Hz, 1 H), 4.16 (d, J = 8.7 Hz, 1 H), 3.94-3.82 (m, 4 H), 3.72 (m, 2 H), 3.38-3.42 (m, 1 H), 3.08 (dd, J = 18.2, 5.0 Hz, 1 H), 2.78-2.82 (m, 1 H), 2.35 (s, 3 H), 2.24-2.16 (m, 4 H), 2.08 (s, 3 H), 1.96 (d, J = 12.8 Hz, 1 H), 1.60-1.40 (m, 1 H). |
| 23-4 | 510.2 | $^1$H NMR (400 MHz, DMSO-$d_6$) δ ppm 8.83 (s, 1 H), 7.36-7.32 (m, 3 H), 7.08 (d, J = 7.3 Hz, 1 H), 6.30 (dd, J = 16.9, 10.2 Hz, 1 H), 6.10 (dd, J = 16.8, 2.3 Hz, 1 H), 5.67 (dd, J = 10.2, 2.3 Hz, 1 H), 4.24 (d, J = 8.6 Hz, 1 H), 4.16 (d, J = 9.1 Hz, 1 H), 3.94-3.85 (m, 4 H), 3.72 (m, 2 H), 3.08 (dd, J = 18.2, 5.0 Hz, 1 H), 2.78-2.82 (m, 1 H), 2.34 (s, 3 H), 2.28-2.17 (m, 4 H), 2.04 (s, 3 H), 1.95-1.90 (m, 1 H), 1.71-1.62 (m, 1 H). |
| 23-5 | 510.2 | $^1$H NMR (400 MHz, DMSO-$d_6$) δ ppm 8.84 (s, 1 H), 7.36-7.31 (m, 3 H), 7.09-7.03 (m, 1 H), 6.30 (m, 1 H), 6.10 (dd, J = 17.0, 2.3 Hz, 1 H), 5.67 (dd, J = 10.2, 2.3 Hz, 1 H), 4.25 (d, J = 8.6 Hz, 1 H), 4.16 (d, J = 8.6 Hz, 1 H), 3.94-3.80 (m, 4 H), 3.72 (m, 2 H), 3.38-3.42 (m, 1 H), 3.08 (dd, J = 17.8, 5.0 Hz, 1 H), 2.78-2.82 (m, 1 H), 2.35 (s, 3 H), 2.21-2.13 (m, 4 H), 2.08 (s, 3 H), 1.95-1.90 (m, 1 H), 1.71-1.62 (m, 1 H). |
| 23-6 | 510.2 | $^1$H NMR (400 MHz DMSO-$d_6$) δ ppm 8.83 (s, 1 H), 7.36-7.30 (m, 3 H), 7.08 (m, 1 H), 6.30 (dd, J = 17.0, 10.2 Hz, 1 H), 6.10 (dd, J = 17.0, 2.3 Hz, 1 H), 5.67 (dd, J = 10.2, 2.3 Hz, 1 H), 4.27 (d, J = 8.6 Hz, 1 H), 4.16 (d, J = 9.1 Hz, 1 H), 3.95-3.80 (m, 4 H), 3.73-3.70 (m, 2 H), 3.38-3.42 (m, 1 H), 3.08 (dd, J = 17.8, 5.0 Hz, 1 H), 2.35 (s, 3 H), 2.29-2.14 (m, 4 H), 2.04 (s, 3 H), 1.97-1.94 (m, 1 H), 1.68-1.60 (m, 1 H). |
| 23-7 | 512.2 | $^1$H NMR (400 MHz, DMSO-$d_6$) δ ppm 9.03 (s, 1 H), 7.62-7.55 (m, 1 H), 7.48 7.35 (m, 3 H), 6.67 (d, J = 1.5 Hz, 1 H), 6.31 (dd, J = 16.9, 10.3 Hz, 1 H), 6.11 (dd, J = 17.0, 2.3 Hz, 1 H), 5.68 (dd, J = 10.3, 2.3 Hz, 1 H), 4.27 (dd, J = 8.7, 4.8 Hz, 1 H), 4.17 (dd, J = 8.8, 2.6 Hz, 1 H), 3.99-3.84 (m, 4 H), 3.77 (t, J = 6.8 Hz, 2 H), 2.68-2.64 (m, 2 H), 2.56 (s, 3 H), 2.50-2.44 (m, 2 H), 2.20-2.17 (m, 2 H). |
| 23-8 | 516.1 | $^1$H NMR (400 MHz, DMSO-$d_6$) δ ppm 8.96 (s, 1 H), 7.62-7.57 (m, 1 H), 7.44-7.34 (m, 3 H), 6.34-6.26 (m, 1 H), 6.11 (dd, J = 17.0, 2.3 Hz, 1 H), 5.68 (dd, J = 10.3, 2.3 Hz, 1 H), 5.27-5.24 (m, 1 H), 4.53-4.35 (m, 2 H), 4.30-4.15 (m, 2 H), 3.99-3.84 (m, 4 H), 3.77 (t, J = 6.7 Hz, 2 H), 3.15-2.95 (m, 2 H), 2.36 (s, 3 H), 2.28-2.15 (m, 2 H). |
| 23-9 | 525.2 | $^1$H NMR (400 MHz, DMSO-$d_6$) δ ppm 8.67 (s, 1 H), 8.50 (d, J = 4.8 Hz, 1 H), 7.73 (d, J = 7.8 Hz, 1 H), 7.36 (dd, J = 7.8, 4.8 Hz, 1 H), 6.35-6.25 (m, 1 H), 6.11 (dd, J = 17.0, 2.3 Hz, 1 H), 5.67 (dd, J = 10.3, 2.3 Hz, 1 H), 4.28 (dd, J = 8.7, 4.9 Hz, 1 H), 4.17 (dd, J = 8.8, 2.6 Hz, 1 H), 3.97-3.81 (m, 4 H), 3.80-3.67 (m, 2 H), 3.24-3.03 (m, 2 H), 2.40 (s, 3 H), 2.27-2.10 (m, 4 H), 1.85-1.75 (m, 2 H), 1.69 (s, 3 H), 1.40 (s, 3 H). |
| 23-10 | 525.2 | $^1$H NMR (400 MHz, DMSO-$d_6$) δ ppm 8.70 (s, 1 H), 8.46 (dd, J = 4.7, 1.6 Hz, 1 H), 7.79 (d, J = 7.7 Hz, 1 H), 7.37 (dd, J = 7.8, 4.8 Hz, 1 H), 6.35-6.25 (m, 1 H), 6.11 (dd, J = 17.0, 2.3 Hz, 1 H), 5.67 (dd, J = 10.2, 2.3 Hz, 1 H), 4.28 (dd, J = 8.7, 5.0 Hz, 1 H), 4.17 (dd, J = 8.8, 2.6 Hz, 1 H), 3.97-3.83 (m, 4 H), 3.75-3.67 (m, 2 H), 3.24-3.04 (m, 2 H), 2.42 (s, 3 H), 2.25-2.14 (m, 4 H), 2.08 (s, 3 H), 1.98-1.85 (m, 2 H), 1.37 (s, 3 H). |
| 23-11 | 508.2 | $^1$H NMR (400 MHz, DMSO-$d_6$) δ ppm 9.01 (s, 1 H), 7.37-7.31 (m, 3 H), 7.13 (d, J = 7.3 Hz, 1 H), 6.66 (s, 1 H), 6.30 (dd, J = 16.9, 10.4 Hz, 1 H), 6.10 (dd, J = 17.0, 2.4 Hz, 1 H), 5.67 (dd, J = 10.2, 2.4 Hz, 1 H), 4.26 (dd, J = 8.7, 2.8 Hz, 1 H), 4.16 (dd, J = 8.7, 4.0 Hz, 1 H), 3.96-3.83 (m, 4 H), 3.75 (t, J = 6.9 Hz, 2 H), 2.63 (t, J = 8.0 Hz, 2 H), 2.55 (s, 3 H), 2.37-2.32 (m, 2 H), 2.18-2.10 (m, 2 H), 2.10 (s, 3 H). |
| 23-12 | 528.2 | $^1$H NMR (400 MHz, DMSO-$d_6$) δ ppm 8.70 (s, 1 H), 7.58-7.48 (m, 1 H), 7.42 7.11 (m, 3 H), 6.31 (dd, J = 17.0, 10.3 Hz, 1 H), 6.11 (dd, J = 17.0, 2.3 Hz, 1 H), 5.67 (dd, J = 10.2, 2.3 Hz, 1 H), 4.26 (dd, J = 8.7, 2.8 Hz, 1 H), 4.17 (dd, J = 8.7, 4.0 Hz, 1 H), 3.97-3.88 (m, 4 H), 3.75 (t, J = 7.0 Hz, 2 H), 3.21-3.06 (m, 2 H), 2.43 (s, 3 H), 2.27-2.31 (m, 4 H), 2.09-1.96 (m, 1 H), 1.93-1.80 (m, 1 H), 1.39 (d, J = 7.9 Hz, 3 H). |
| 23-13 | 528.2 | $^1$H NMR (400 MHz, DMSO-$d_6$) δ ppm 8.70 (s, 1 H), 7.57-7.49 (m, 1 H), 7.42-7.11 (m, 3 H), 6.31 (dd, J = 17.0, 10.3 Hz, 1 H), 6.11 (dd, J = 17.0, 2.3 Hz, 1 H), 5.67 (dd, J = 10.3, 2.3 Hz, 1 H), 4.27 (dd, J = 8.6, 6.0 Hz, 1 H), 4.17 (dd, J = 8.3, 4.4 Hz, 1 H), 3.97-3.82 (m, 4 H), 3.75 (t, J = 6.9 Hz, 2 H), 3.21-3.04 (m, 2 H), 2.43 (s, 3 H), 2.21-2.28 (m, 4 H), 2.09-1.86 (m, 1 H), 1.93-1.80 (m, 1 H), 1.38 (d, J = 7.9 Hz, 3 H). |
| 23-14 | 513.2 | $^1$H NMR (400 MHz, DMSO-$d_6$) δ 8.96 (s, 1 H), 8.53 (td, J = 4.6, 1.6 Hz, 1 H), 7.84 (d, J = 7.9 Hz, 1 H), 7.44-7.39 (m, 1 H), 6.31 (dd, J = 17.0, 10.3 Hz, 1 H), 6.11 (dd, J = 17.0, 2.3 Hz, 1 H), 5.68 (dd, J = 10.3, 2.3 Hz, 1 H), 5.30-5.20 (m, 1 H), 4.51 (d, J = 14.9 Hz, 1 H), 4.36 (d, J = 14.6 Hz, 1 H), 4.31-4.14 (m, 2 H), 4.08-3.91 (m, 2 H), 3.94-3.82 (m, 2 H), 3.81-3.73 (m, 2 H), 3.09-2.90 (m, 2 H), 2.39 (s, 3 H), 2.20-2.16 (m, 2 H), 2.15 (s, 3 H). |

TABLE 32-continued

| Analytical Data for Examples 23-2 to 23-61. | | |
|---|---|---|
| Ex. # | LRMS: (ESI, +ve ion) m/z | NMR |
| 23-15 | 532.0 | $^1$H NMR (400 MHz, DMSO-$d_6$) δ ppm 8.96 (s, 1 H), 7.67 (dt, J = 7.2, 2.3 Hz, 1 H), 7.62-7.48 (m, 2 H), 7.44-7.31 (m, 1 H), 6.30-6.27 (m, 1 H), 6.11 (dd, J = 17.0, 2.3 Hz, 1 H), 5.68 (dd, J = 10.3, 2.3 Hz, 1 H), 5.30-5.20 (m, 1 H), 4.47-4.23 (m, 4 H), 4.00-3.81 (m, 4 H), 3.77 (t, J = 6.9 Hz, 2 H), 3.17-2.95 (m, 2 H), 2.39 (s, 3 H), 2.29-2.18 (m, 2 H), |
| 23-16 | 511.2 | $^1$H NMR (400 MHz, DMSO-$d_6$) δ ppm 7.74-7.81 (m, 2 H), 7.51-7.69 (m, 4 H), 7.42 (dd, J = 8.6, 1.7 Hz, 1 H), 7.11 (d, J = 8.6 Hz, 1 H), 6.59 (d, J = 1.9 Hz, 1 H), 6.28-6.39 (m, 1 H), 6.09-6.16 (m, 1 H), 5.68 (dd, J = 10.2, 2.3 Hz, 1 H), 4.32 (dd, J = 8.6, 5.4 Hz, 1 H), 4.21 (dd, J = 8.6, 4.8 Hz, 1 H), 3.90-4.09 (m, 8 H), 3.81-3.88 (m, 1 H), 2.19-2.33 (m, 2 H) |
| 23-17 | 534.2 | $^1$H NMR (400 MHz, DMSO-$d_6$) δ ppm 8.96 (s, 1 H), 7.58-7.38 (m, 2 H), 7.29 (td, J = 8.5, 2.5 Hz, 1 H), 6.30 (dd, J = 17.0, 10.3 Hz, 1 H), 6.10 (dd, J = 17.0, 2.3 Hz, 1 H), 5.67 (dd, J = 10.3, 2.3 Hz, 1 H), 5.35-5.10 (m, 1 H), 4.69-4.37 (m, 2 H), 4.32-4.08 (m, 2 H), 4.05-3.80 (m, 4 H), 3.75 (m, 2 H), 3.07-2.92 (m, 2 H), 2.49 (s, 3 H), 2.28-2.04 (m, 2 H). |
| 23-18 | 546.1 | $^1$H NMR (400 MHz, DMSO-$d_6$) δ ppm 9.03 (s, 1 H), 7.71 (dd, J = 8.8, 2.5 Hz, 1 H), 7.54-7.39 (m, 2 H), 6.67 (d, J = 1.5 Hz, 1 H), 6.31 (dd, J = 17.0, 10.3, 2.5 Hz, 1 H), 6.11 (dd, J = 17.0, 2.3 Hz, 1 H), 5.68 (dd, J = 10.3, 2.3 Hz, 1 H), 4.27 (dd, J = 8.7, 5.0 Hz, 1 H), 4.18 (dd, J = 8.7, 4.0 Hz, 1 H), 4.01-3.81 (m, 4 H), 3.77 (t, J = 6.8 Hz, 2 H), 2.67 (t, J = 8.0 Hz, 2 H), 2.56 (s, 3 H), 2.45-2.45 (m, 2 H), 2.28-2.11 (m, 2 H) |
| 23-19 | 528.1 | $^1$H NMR (400 MHz, DMSO-$d_6$) δ ppm 9.03 (s, 1 H), 7.70-7.64 (m, 1 H), 7.58-7.49 (m, 2 H), 7.44-7.38 (m, 1 H), 6.67 (d, J = 1.5 Hz, 1 H), 6.31 (dd, J = 17.0, 10.3, 2.5 Hz, 1 H), 6.11 (dd, J = 17.0, 2.3 Hz, 1 H), 5.68 (dd, J = 10.3, 2.4 Hz, 1 H), 4.27 (dd, J = 8.8, 4.3 Hz, 1 H), 4.18 (dd, J = 8.8, 4.3 Hz, 1 H), 4.00-3.83 (m, 4 H), 3.77 (t, J = 6.8 Hz, 2 H), 2.68-2.64 (m, 2 H), 2.56 (s, 3 H), 2.43 (m, 2 H), 2.21-2.18 (m, 2 H). |
| 23-20 | 550.2 | $^1$H NMR (400 MHz, DMSO-$d_6$) δ ppm 8.92 (s, 1 H), 7.66 (dd, J = 8.7, 2.5 Hz, 1 H), 7.50-7.35 (m, 2 H), 6.30 (dd, J = 17.0, 10.3 Hz, 1 H), 6.11 (dd, J = 17.0, 2.1 Hz, 1 H), 5.68 (dd, J = 10.3, 2.1 Hz, 1 H), 5.25-5.15 (m, 1 H), 4.45-4.05 (m, 4 H), 3.98-3.79 (m, 4 H), 3.78-3.65 (m, 2 H), 3.09-2.86 (m, 2 H), 2.36 (s, 3 H), 2.25-2.15 (m, 2 H). |
| 23-21 | 530.1 | $^1$H NMR (400 MHz, DMSO-$d_6$) δ ppm 9.03 (s, 1 H), 7.52-7.47 (m, 2 H), 7.30 (td, J = 8.5, 2.6 Hz, 1 H), 6.67 (d, J = 1.5 Hz, 1 H), 6.31 (dd, J = 17.0, 10.3 Hz, 1 H), 6.11 (dd, J = 17.0, 2.4 Hz, 1 H), 5.68 (dd, J = 10.3, 2.4 Hz, 1 H), 4.27 (dd, J = 8.7, 5.5 Hz, 1 H), 4.17 (dd, J = 8.8, 4.3 Hz, 1 H), 4.01-3.83 (m, 4 H), 3.77 (t, J = 6.8 Hz, 2 H), 2.72-2.63 (m, 2 H), 2.56 (s, 3 H), 2.48-2.43 (m, 2 H), 2.21-2.18 (m, 2 H). |
| 23-22 | 546.1 | $^1$H NMR (400 MHz, DMSO-$d_6$) δ ppm 9.04 (s, 1 H), 7.63-7.56 (m, 2 H), 7.49 7.47 (m, 1 H), 6.68 (d, J = 1.5 Hz, 1 H), 6.31 (dd, J = 17.0, 10.3 Hz, 1 H), 6.11 (dd, J = 17.0, 2.3 Hz, 1 H), 5.68 (dd, J = 10.2, 2.3 Hz, 1 H), 4.29 (dd, J = 8.7, 5.5 Hz, 1 H), 4.17 (dd, J = 8.8, 4.3 Hz, 1 H), 4.01-3.86 (m, 4 H), 3.78 (t, J = 6.8 Hz, 2 H), 2.73-2.65 (m, 2 H), 2.57 (s, 3 H), 2.48-2.43 (m, 2 H), 2.21-2.18 (m, 2 H). |
| 23-23 | 508.1 | $^1$H NMR (400 MHz, DMSO-$d_6$) δ ppm 9.02 (s, 1 H), 7.42-7.33 (m, 3 H), 7.11 (dd, J = 24.2, 8.0 Hz, 1 H), 6.67 (s, 1 H), 6.38-6.26 (m, 1 H), 6.11-6.09 (m, 1 H), 5.68 (dd, J = .3, 2.4 Hz, 1 H), 4.35-4.17 (m, 2 H), 4.06-3.83 (m, 4 H), 3.76 (t, J = 6.9 Hz, 2 H), 2.69-2.60 (m, 2 H), 2.56 (d, J = 2.0 Hz, 2 H), 2.38 (s, 3 H), 2.27 2.13 (m, 2 H), 2.11 (s, 3 H). |
| 23-24 | 508.1 | $^1$H NMR (400 MHz, DMSO-$d_6$) δ ppm 9.02 (s, 1 H), 7.42-7.31 (m, 3 H), 7.14 (d, J = 7.3 Hz, 1 H), 6.67 (d, J = 1.5 Hz, 1 H), 6.31-6.29 (m, 1 H), 6.11-6.09 (m, 1 H), 5.68-5.66 (m, 1 H), 4.27-4.17 (m, 2 H), 3.97-3.83 (m, 4 H), 3.76 (t, J = 6.9 Hz, 2 H), 2.69-2.60 (m, 2 H), 2.56 (d, J = 2.0 Hz, 2 H), 2.38 (s, 3 H), 2.19-2.16 (m, 2 H), 2.11 (s, 3 H). |
| 23-25 | 509.2 | $^1$H NMR (400 MHz, DMSO-$d_6$) δ ppm 9.02 (s, 1 H), 8.54 (dd, J = 4.9, 1.6 Hz, 1 H), 7.84 (d, J = 7.8 Hz, 1 H),, 7.43 (dd, J = 7.8, 4.8 Hz, 1 H), 6.68 (d, J = 1.5 Hz, 1 H), 6.31 (dd, J = 17.0, 10.3 Hz, 1 H), 6.11 (dd, J = 17.0, 2.4 Hz, 1 H), 5.68 (dd, J = 10.3, 2.4 Hz, 1 H), 4.28 (dd, J = 8.6, 3.6 Hz, 1 H), 4.17 (dd, J = 8.8, 4.3 Hz, 1 H), 4.02 3.84 (m, 4 H), 3.81-3.73 (m, 2 H), 2.65 (t, J = 8.1 Hz, 2 H), 2.56 (s, 3 H), 2.45-2.28 (m, 2 H), 2.23-2.17 (m, 2 H), 2.15 (s, 3 H). |
| 23-26 | 509.2 | $^1$H NMR (400 MHz, DMSO-$d_6$) δ ppm 9.03 (s, 1 H), 8.55 (dd, J = 4.8, 1.6 Hz, 1 H), 7.84 (d, J = 7.8 Hz, 1 H), 7.43 (dd, J = 7.8, 4.8 Hz, 1 H), 6.68 (d, J = 1.5 Hz, 1 H), 6.31 (dd, J = 17.0, 10.3 Hz, 1 H), 6.11 (dd, J = 17.1, 2.3 Hz, 1 H), 5.68 (dd, J = 10.3, 2.3 Hz, 1 H), 4.28 (dd, J = 8.6, 3.6 Hz, 1 H), 4.17 (dd, J = 8.8, 4.3 Hz, 1 H), 4.00-3.86 (m, 4 H), 3.80-3.73 (m, 2 H), 2.65 (t, J = 8.3 Hz, 2 H), 2.56 (s, 3 H), 2.45 2.29 (m, 2 H), 2.23-2.17 (m, 2 H), 2.15 (s, 3 H). |
| 23-27 | 551.0 | $^1$H NMR (400 MHz, DMSO-$d_6$) δ ppm 8.96 (s, 1 H), 7.71 (dd, J = 8.8, 2.5 Hz, 1 H), 7.50 (dd, J = 8.6, 6.1 Hz, 1 H), 7.42 (td, J = 8.4, 2.5 Hz, 1 H), 6.33-6.26 (m, 1 H), 6.10 (dd, J = 17.0, 2.3 Hz, 1 H), 5.67 (dd, J = 10.3, 2.3 Hz, 1 H), 5.23-5.21 (m, 1 H), 4.43 (d, J = 14.7 Hz, 1 H), 4.34-4.23 (m, 2 H), 4.17 (dd, J = 8.9, 2.0 Hz, 1 H), 4.00-3.82 (m, 4 H), 3.76 (t, J = 6.9 Hz, 2 H), 3.11 (dd, J = 17.5, 3.5 Hz, 1 H), 2.92 (dd, J = 17.5, 10.6 Hz, 1 H), 2.38 (s, 3 H), 2.22-2.18 (m, 2 H). |
| 23-28 | 551.1 | $^1$H NMR (400 MHz, DMSO-$d_6$) δ ppm 8.96 (s, 1 H), 7.71 (dt, J = 8.9, 2.3 Hz, 1 H), 7.55-7.39 (m, 2 H), 6.34-6.26 (m, 1 H), 6.10 (dd, J = 17.0, 2.3 Hz, 1 H), 5.67 (dd, J = 10.3, 2.3 Hz, 1 H), 5.21-5.19 (m, 1 H), 4.47 (dd, J = 27.2, 14.8 Hz, 1 H), 4.33-4.09 (m, 3 H), 4.01-3.82 (m, 4 H), 3.76 (t, J = 6.8 Hz, 2 H), 3.15-2.94 (m, 2 H), 2.38 (s, 3 H), 2.21-2.19 (m, 2 H). |

TABLE 32-continued

| Analytical Data for Examples 23-2 to 23-61. | | |
|---|---|---|
| Ex. # | LRMS: (ESI, +ve ion) m/z | NMR |
| 23-29 | 529.1 | $^1$H NMR (400 MHz, DMSO-$d_6$) δ ppm 10.21 (br s, 1 H), 9.02 (s, 1 H), 7.32 (td, J = 8.3, 6.9 Hz, 1 H), 6.87-6.73 (m, 2 H), 6.65 (d, J = 1.5 Hz, 1 H), 6.30 (dd, J = 17.0, 10.3 Hz, 1 H), 6.10 (dd, J = 17.0, 2.3 Hz, 1 H), 5.67 (dd, J = 10.3, 2.3 Hz, 1 H), 4.27 (dd, J = 8.8, 5.0 Hz, 1 H), 4.17 (dd, J = 8.7, 4.0 Hz, 1 H), 3.99-3.82 (m, 4 H), 3.75 (t, J = 6.8 Hz, 2 H), 2.63 (d, J = 7.9 Hz, 2 H), 2.55 (s, 3 H), 2.53-2.52 (m, 2 H), 2.23-2.13 (m, 2 H). |
| 23-30 | 512.2 | $^1$H NMR (400 MHz, DMSO-$d_6$) δ ppm 9.02 (s, 1 H), 7.44 (m, 2 H), 7.41-7.34 (m, 2 H), 6.66 (d, J = 1.5 Hz, 1 H), 6.31 (dd, J = 17.0, 10.3 Hz, 1 H), 6.11 (dd, J = 17.0, 2.3 Hz, 1 H), 5.67 (dd, J = 10.3, 2.3 Hz, 1 H), 4.25 (dd, J = 8.8, 5.0 Hz, 1 H), 4.17 (dd, J = 8.7, 4.0 Hz, 1 H), 4.00-3.83 (m, 4 H), 3.75 (t, J = 6.8 Hz, 2 H), 2.64 (dd, J = 8.1, 1.9 Hz, 2 H), 2.55 (s, 3 H), 2.53-2.52 (m, 2 H), 2.23-2.14 (m, 2 H). |
| 23-31 | 559.1 | $^1$H NMR (400 MHz, DMSO-$d_6$) δ ppm 9.02 (s, 1 H), 7.55 (d, J = 8.9 Hz, 1 H), 7.10 (dd, J = 8.9, 3.1 Hz, 1 H), 6.97 (d, J = 3.0 Hz, 1 H), 6.66 (d, J = 1.5 Hz, 1 H), 6.34-6.27 (m, 1 H), 6.11 (dd, J = 17.0, 2.3 Hz, 1 H), 5.67 (dd, J = 10.3, 2.3 Hz, 1 H), 4.26 (dd, J = 8.7, 4.1 Hz, 1 H), 4.17 (dd, J = 8.7, 4.0 Hz, 1 H), 3.98-3.84 (m, 4 H), 3.79 (s, 3 H), 3.78-3.74 (m, 2 H), 2.66 (td, J = 7.9, 2.5 Hz, 2 H), 2.55 (s, 3 H), 2.48 2.38 (m, 2 H), 2.21-2.15 (m, 2 H). |
| 23-32 | 547.1 | $^1$H NMR (400 MHz, DMSO-$d_6$) δ ppm 9.02 (s, 1 H), 7.70 (dd, J = 8.9, 2.5 Hz, 1 H), 7.53-7.38 (m, 2 H), 6.67 (d, J = 1.5 Hz, 1 H), 6.34-6.26 (m, 1 H), 6.10 (dd, J = 17.0, 2.3 Hz, 1 H), 5.67 (dd, J = 10.3, 2.3 Hz, 1 H), 4.26 (dd, J = 8.8, 5.0 Hz, 1 H), 4.17 (dd, J = 8.7, 4.0 Hz, 1 H), 3.96-3.81 (m, 4 H), 3.76 (t, J = 6.8 Hz, 2 H), 2.66 (t, J = 7.9 Hz, 2 H), 2.55 (s, 3 H), 2.43 (m, 2 H), 2.22-2.17 (m, 2 H). |
| 23-33 | 547.1 | $^1$H NMR (400 MHz, DMSO-$d_6$) δ ppm 9.02 (s, 1 H), 7.70 (dd, J = 8.9, 2.5 Hz, 1 H), 7.53-7.38 (m, 2 H), 6.66 (d, J = 1.5 Hz, 1 H), 6.34-6.26 (m, 1 H), 6.10 (dd, J = 17.0, 2.3 Hz, 1 H), 5.67 (dd, J = 10.3, 2.3 Hz, 1 H), 4.26 (dd, J = 8.7, 5.0 Hz, 1 H), 4.17 (dd, J = 8.7, 4.0 Hz, 1 H), 3.96-3.81 (m, 4 H), 3.76 (t, J = 6.9 Hz, 2 H), 2.69 2.62 (m, 2 H), 2.55 (s, 3 H), 2.44-2.40 (m, 2 H), 2.22-2.17 (m, 2 H). |
| 23-34 | 545.1 | $^1$H NMR (400 MHz, DMSO-$d_6$) δ ppm 10.19 (br s, 1 H), 9.02 (s, 1 H), 7.30 (t, J = 8.1 Hz, 1 H), 7.04 (d, J = 8.0 Hz, 1 H), 6.95 (d, J = 8.2 Hz, 1 H), 6.66 (d, J = 1.5 Hz, 1 H), 6.31 (dd, J = 17.0, 10.3 Hz, 1 H), 6.11 (dd, J = 17.0, 2.3 Hz, 1 H), 5.68 (dd, J = 10.3, 2.3 Hz, 1 H), 4.28 (dd, J = 8.7, 5.0 Hz, 1 H), 4.18 (dd, J = 8.6, 2.6 Hz, 1 H), 3.97-3.83 (m, 4 H), 3.76 (t, J = 6.8 Hz, 2 H), 2.69-2.61 (m, 2 H), 2.56 (s, 3 H), 2.44 (t, J = 8.0 Hz, 2 H), 2.21 (d, J = 7.3 Hz, 2 H). |
| 23-35 | 549.1 | $^1$H NMR (400 MHz, DMSO-$d_6$) δ ppm 10.35 (br s, 1 H), 8.96 (s, 1 H), 7.32 (t, J = 8.2 Hz, 1 H), 7.03 (dd, J = 19.7, 8.1 Hz, 2 H), 6.31 (dd, J = 17.0, 10.3 Hz, 1 H), 6.11 (dd, J = 17.0, 2.3 Hz, 1 H), 5.68 (dd, J = 10.3, 2.3 Hz, 1 H), 5.20-5.18 (m, 1 H), 4.43 (d, J = 14.5 Hz, 1 H), 4.31-4.22 (m, 2 H), 4.18 (dd, J = 8.9, 3.6 Hz, 1 H),, 3.97-3.88 (m, 4 H), 3.76-3.51 (m, 2 H), 3.10-2.89 (m, 2 H), 2.39 (s, 3 H), 2.20 (d, J = 3.0 Hz, 2 H). |
| 23-36 | 551.1 | $^1$H NMR (400 MHz, DMSO-$d_6$) δ ppm 8.97 (s, 1 H), 7.68-7.55 (m, 2 H), 7.49 7.45 (m, 1 H), 6.31 (dd, J = 17.0, 10.3 Hz, 1 H), 6.11 (dd, J = 17.0, 2.3 Hz, 1 H), 5.68 (dd, J = 10.3, 2.3 Hz, 1 H), 5.28-5.24 (m, 1 H), 4.48 (dd, J = 14.7, 5.1 Hz, 1 H), 4.32-4.23 (m, 2 H), 4.18 (dd, J = 8.9, 3.6 Hz, 1 H), 3.97-3.89 (m, 4 H), 3.78 (m, 2 H), 3.18-2.97 (m, 2 H), 2.39 (s, 3 H), 2.22-2.19 (m, 2 H). |
| 23-37 | 562.1 | $^1$H NMR (400 MHz, DMSO-$d_6$) δ ppm 8.97 (s, 1 H), 7.58 (m, 1 H), 7.49-7.35 (m, 3 H), 6.34-6.27 (m, 1 H), 6.11 (dd, J = 17.0, 2.3 Hz, 1 H), 5.67 (dd, J = 10.2, 2.3 Hz, 1 H), 4.28 (dd, J = 8.7, 4.3 Hz, 1 H), 4.18 (dd, J = 8.9, 3.6 Hz, 1 H), 4.02-3.87 (m, 4 H), 3.81 (t, J = 6.9 Hz, 2 H), 3.19 (d, J = 14.0 Hz, 1 H), 2.34 (s, 3 H), 2.32-2.30 (m, 3 H), 2.22-2.19 (m, 2 H), 1.71-1.80 (m, 1 H). |
| 23-38 | 542.2 | $^1$H NMR (400 MHz, DMSO-$d_6$) δ ppm 9.03 (s, 1 H), 7.34 (t, J = 9.1 Hz, 1 H), 7.10 (dt, J = 9.1, 3.6 Hz, 1 H), 6.96 (dd, J = 5.8, 3.1 Hz, 1 H), 6.67 (d, J = 1.5 Hz, 1 H), 6.38-6.26 (m, 1 H), 6.11 (dd, J = 17.0, 2.3 Hz, 1 H), 5.68 (dd, J = 10.3, 2.4 Hz, 1 H), 4.27 (dd, J = 8.7, 5.0 Hz, 1 H), 4.18 (dd, J = 8.6, 2.6 Hz, 1 H), 3.99-3.83 (m, 4 H), 3.79 (s, 3 H), 3.76 (m, 2 H), 2.71-2.63 (m, 2 H), 2.56 (s, 3 H), 2.20-2.17 (m, 2 H). 2 protons obscured by NMR solvent. |
| 23-39 | 523.8 | $^1$H NMR (400 MHz, DMSO-$d_6$) δ ppm 9.02 (s, 1 H), 7.48 (m, 1 H), 7.23-7.17 (m, 2 H), 7.09 (td, J = 7.2, 2.6 Hz, 1 H), 6.65 (d, J = 1.4 Hz, 1 H), 6.35-6.27 (m, 1 H), 6.11 (dd, J = 17.0, 2.3 Hz, 1 H), 5.68 (dd, J = 10.3, 2.3 Hz, 1 H), 4.27 (dd, J = 8.7, 4.3 Hz, 1 H), 4.17 (dd, J = 8.7, 5.0 Hz, 1 H), 3.96-3.82 (m, 4 H), 3.78 (s, 3 H), 3.75 (t, J = 6.9 Hz, 2 H), 2.64-2.60 (m, 2 H), 2.56 (s, 3 H), 2.45 (t, J = 7.9 Hz, 2 H), 2.21-2.17 (m, 2 H). |
| 23-40 | 510.1 | $^1$H NMR (400 MHz, DMSO-$d_6$) δ ppm 9.72 (br s, 1 H), 9.02 (s, 1 H), 7.29 (t, J = 7.8 Hz, 1 H), 7.12 (dd, J = 7.6, 1.8 Hz, 1 H), 7.01-6.87 (m, 2 H), 6.65 (d, J = 1.6 Hz, 1 H), 6.38-6.26 (m, 1 H), 6.11 (dd, J = 16.9, 2.3 Hz, 1 H), 5.68 (dd, J = 10.2, 2.3 Hz, 1 H), 4.26 (dd, J = 8.7, 4.3 Hz, 1 H), 4.18 (dd, J = 8.8, 4.4 Hz, 1 H), 4.00-3.81 (m, 4 H), 3.75 (t, J = 6.9 Hz, 2 H), 2.62-5.58 (m, 4 H), 2.56 (s, 3 H), 2.20-2.17 (m, 2 H) |
| 23-41 | 529.1 | $^1$H NMR (400 MHz, DMSO-$d_6$) δ ppm 9.03 (s, 1 H), 7.70-7.65 (m, 1 H), 7.57-7.51 (m, 2 H), 7.44-7.39 (m, 1 H), 6.67 (d, J = 1.6 Hz, 1 H), 6.35-6.27 (m, 1 H), 6.11 (dd, J = 17.0, 2.3 Hz, 1 H), 5.68 (dd, J = 10.3, 2.3 Hz, 1 H), 4.27 (dd, J = 8.8, 4.4 Hz, 1 H), 4.18 (dd, J = 8.8, 4.4 Hz, 1 H), 4.01-3.84 (m, 4 H), 3.77 (t, J = 6.8 Hz, 2 H), 2.68-2.64 (m, 2 H), 2.56 (s, 3 H), 2.44-2.40 (m, 2 H), 2.22-2.18 (m, 2 H). |
| 23-42 | 529.1 | $^1$H NMR (400 MHz, DMSO-$d_6$) δ ppm 9.02 (s, 1 H), 7.69-7.63 (m, 1 H), 7.56-7.49 (m, 2 H), 7.42-7.38 (m, 1 H), 6.66 (d, J = 1.6 Hz, 1 H), 6.34-6.26 (m, 1 H), 6.10 (dd, J = 17.0, 2.3 Hz, 1 H), 5.67 (dd, J = 10.3, 2.3 Hz, 1 H), 4.26 (dd, J = 8.7, 4.3 |

TABLE 32-continued

| Analytical Data for Examples 23-2 to 23-61. | | |
|---|---|---|
| Ex. # | LRMS: (ESI, +ve ion) m/z | NMR |
| | | Hz, 1 H), 4.17 (dd, J = 8.7, 4.4 Hz, 1 H), 4.00-3.83 (m, 4 H), 3.76 (t, J = 6.8 Hz, 2 H), 2.71-2.62 (m, 2 H), 2.55 (s, 3 H), 2.44-2.40 (m, 2 H), 2.25-2.15 (m, 2 H) |
| 23-43 | 528.2 | $^1$H NMR (400 MHz, DMSO-$d_6$) δ ppm 10.23 (br s, 1 H), 9.03 (s, 1 H), 7.17-7.04 (m, 2 H), 6.78-6.71 (m, 1 H), 6.66 (s, 1 H), 6.34-6.28 (m, 1 H), 6.11 (dd, J = 17.0, 2.4 Hz, 1 H), 5.68 (dd, J = 10.3, 2.4 Hz, 1 H), 4.27 (dd, J = 8.8, 4.8 Hz, 1 H), 4.17 (dd, J = 8.7, 3.4 Hz, 1 H), 4.00-3.83 (m, 4 H), 3.76 (t, J = 6.8 Hz, 2 H), 2.65 (d, J = 7.8 Hz, 2 H), 2.56 (s, 3 H), 2.23-2.15 (m, 2 H). 2 protons obscured by NMR solvent. |
| 23-44 | 542.1 | $^1$H NMR (400 MHz, DMSO-$d_6$) δ ppm 9.02 (s, 1 H), 7.30 (dd, J = 5.9, 3.7 Hz, 2 H), 6.95-6.88 (m, 1 H), 6.66 (s, 1 H), 6.34-6.26 (m, 1 H), 6.10 (dd, J = 17.0, 2.3 Hz, 1 H), 5.67 (dd, J = 10.3, 2.3 Hz, 1 H), 4.26 (dd, J = 8.7, 5.4 Hz, 1 H), 4.16 (dd, J = 8.7, 3.2 Hz, 1 H), 3.97-3.94 (m, 1 H), 3.90 (s, 3 H), 3.90-3.83 (m, 3 H), 3.76 (t, J = 6.8 Hz, 2 H), 2.70-2.62 (m, 2 H), 2.55 (s, 3 H), 2.45-2.43 (m, 2 H), 2.18 (dd, J = 8.1, 4.5 Hz, 2 H). |
| 23-45 | 545.1 | $^1$H NMR (400 MHz, DMSO-$d_6$) δ ppm 10.12 (br s, 1 H), 9.03 (s, 1 H), 7.40 (d, J = 8.8 Hz, 1 H), 6.89 (dd, J = 8.7, 2.9 Hz, 1 H), 6.72 (d, J = 2.9 Hz, 1 H), 6.66 (d, J = 1.5 Hz, 1 H), 6.35-6.27 (m, 1 H), 6.11 (dd, J = 17.0, 2.3 Hz, 1 H), 5.68 (dd, J = 10.2, 2.3 Hz, 1 H), 4.27 (dd, J = 8.9, 4.4 Hz, 1 H), 4.17 (dd, J = 8.6, 5.5 Hz, 1 H), 4.01-3.82 (m, 4 H), 3.76 (t, J = 6.8 Hz, 2 H), 2.67-2.64 (m, 2 H), 2.56 (s, 3 H), 2.45-2.17 (m, 4 H). |
| 23-46 | 530.2 | $^1$H NMR (400 MHz,, DMSO-$d_6$) δ ppm 9.04 (s, 1 H), 7.63-7.65 (m, 1 H), 7.55-7.36 (m, 1 H), 7.27-7.30 (m, 1 H), 6.68 (d, J = 1.4 Hz, 1 H), 6.34-6.27 (dd, J = 16.9, 10.3 Hz, 1 H), 6.11 (dd, J = 17.0, 2.3 Hz, 1 H), 5.68 (dd, J = 10.3, 2.4 Hz, 1 H), 4.27 (dd, J = 8.7, 4.6 Hz, 1 H), 4.18 (d, J = 8.6 Hz, 1 H), 4.10-3.82 (m, 4 H), 3.77 (t, J = 6.8 Hz, 2 H), 2.74-2.63 (m, 2 H), 2.57 (s, 3 H), 2.54-2.53 (m, 2 H), 2.22-2.18 (m, 2 H). |
| 23-47 | 528.1 | $^1$H NMR (400 MHz, DMSO-$d_6$) δ ppm 9.70 (br s, 1 H), 9.03 (s, 1 H), 7.19 (t, J = 9.1 Hz, 1 H), 6.90-6.89 (m, 1 H), 6.70 (dd, J = 6.0, 3.0 Hz, 1 H), 6.66 (d, J = 1.5 Hz, 1 H), 6.41-6.35 (m, 1 H), 6.11 (dd, J = 17.0, 2.3 Hz, 1 H), 5.68 (dd, J = 10.3, 2.4 Hz, 1 H), 4.27 (dd, J = 8.7, 4.7 Hz, 1 H), 4.17 (dd, J = 8.7, 3.5 Hz, 1 H), 4.02-3.83 (m, 4 H), 3.76 (t, J = 6.8 Hz, 2 H), 2.72-2.63 (m, 2 H), 2.56 (s, 3 H), 2.54 (d, J = 2.3 Hz, 2 H), 2.20-2.10 (m, 2 H). |
| 23-48 | 526.2 | $^1$H NMR (400 MHz, DMSO-$d_6$) δ ppm 9.02 (s, 1 H), 7.44 (td, J = 8.0, 6.0 Hz, 1 H), 7.26-7.18 (m, 2 H), 6.67 (s, 1 H), 6.30 (dd, J = 17.0, 10.3 Hz, 1 H), 6.10 (dd, J = 17.0, 2.3 Hz, 1 H), 5.67 (dd, J = 10.3, 2.3 Hz, 1 H), 4.28 (dd, J = 8.6, 4.3 Hz, 1 H), 4.16 (dd, J = 8.6, 2.7 Hz, 1 H), 3.96-3.82 (m, 4 H), 3.76 (t, J = 6.9 Hz, 2 H), 2.73 2.59 (m, 2 H), 2.56 (s, 3 H), 2.44-2.33 (m, 2 H), 2.18-2.17 (m, 2 H), 2.12 (s, 3 H). |
| 23-49 | 512.8 | $^1$H NMR (400 MHz, DMSO-$d_6$) δ ppm 9.03 (s, 1 H), 8.64 (dt, J = 4.7, 1.6 Hz, 1 H), 8.01-7.96 (m, 1 H), 7.68 (dt, J = 8.7, 4.4 Hz, 1 H), 6.69 (d, J = 1.5 Hz, 1 H), 6.30 6.27 (m, 1 H), 6.11 (dd, J = 17.0, 2.3 Hz, 1 H), 5.68 (dd, J = 10.3, 2.3 Hz, 1 H), 4.28 (dd, J = 8.6, 4.3 Hz, 1 H), 4.17 (d, J = 8.5 Hz, 1 H), 4.01-3.85 (m, 4 H), 3.77 (t, J = 6.9 Hz, 2 H), 2.71-2.64 (m, 2 H), 2.57 (s, 3 H), 2.49-2.40 (m, 2 H), 2.25-2.17 (m, 2 H). |
| 23-50 | 527.8 | $^1$H NMR (400 MHz, DMSO-$d_6$) δ ppm 10.55 (br s, 1 H), 9.01 (s, 1 H), 7.26-7.24 (m, 1 H), 6.77 (d, J = 8.3 Hz, 1 H), 6.73-6.63 (m, 2 H), 6.31 (dd, J = 17.0, 10.3 Hz, 1 H), 6.11 (dd, J = 17.0, 2.3 Hz, 1 H), 5.67 (dd, J = 10.3, 2.3 Hz, 1 H), 4.26-4.15 (m, 2 H), 3.96-3.82 (m, 4 H), 3.75 (t, J = 6.8 Hz, 2 H), 2.68-2.63 (m, 2 H), 2.55 (s, 3 H), 2.53-2.51 (m, 2 H), 2.25-2.15 (m, 2 H). |
| 23-51 | 527.8 | $^1$H NMR(400 MHz, DMSO-$d_6$) δ ppm 9.00 (s, 1H), 7.09 (d, J = 8.3 Hz, 1H), 6.62 (s, 1H), 6.59 (d, J = 7.9 Hz, 1H), 6.41 (s, 1H), 6.31 (dd, J = 17.0, 10.3 Hz, 1H), 6.11 (dd, J = 17.0, 2.3 Hz, 1H), 5.67 (dd, J = 10.3, 2.3 Hz, 1H), 4.25 (t, J = 8.1 Hz, 1H), 4.16 (d, J = 8.7 Hz, 1H), 3.95 (d, J = 10.1 Hz, 1H), 3.92-3.78 (m, 3H), 3.74 (t, J = 6.8 Hz, 2H), 2.64-2.57 (m, 4H), 2.54 (s, 3H), 2.17 (d, J = 5.4 Hz, 2H). |
| 23-52 | 541.8 | $^1$H NMR (400 MHz, DMSO-$d_6$) δ ppm 9.09 (s, 1 H), 7.64-7.55 (m, 1 H), 7.48 7.36 (m, 3 H), 6.86-6.81 (m, 1 H), 6.34-6.27 (m, 1 H), 6.11 (dd, J = 17.0, 2.3 Hz, 1 H), 5.68 (dd, J = 10.3, 2.3 Hz, 1 H), 4.54 (s, 2 H), 4.27 (dd, J = 8.7, 5.3 Hz, 1 H), 4.18 (dd, J = 8.6, 2.7 Hz, 1 H), 4.01-3.84 (m, 4 H), 3.77 (t, J = 6.8 Hz, 2 H), 3.35 (s, 3 H), 2.72-2.64 (m, 2 H), 2.54 (d, J = 6.8 Hz, 2 H), 2.24-2.15 (m, 2 H). |
| 23-53 | 542.3 | $^1$H NMR (400 MHz, DMSO-$d_6$) δ ppm 9.02 (s, 1 H), 7.44-7.39 (m, 1 H), 7.27 7.21 (m, 1 H), 7.06 (dd, J = 7.7, 1.5 Hz, 1 H), 6.66 (d, J = 1.5 Hz, 1 H), 6.34-6.27 (m, 1 H), 6.11 (dd, J = 17.0, 2.4 Hz, 1 H), 5.67 (dd, J = 10.3, 2.3 Hz, 1 H), 4.26 (dd, J = 8.5, 3.4 Hz, 1 H), 4.17 (dd, J = 8.7, 3.4 Hz, 1 H), 3.96-3.81 (m, 4 H), 3.78 (s, 3 H) 3.77-3.73 (m, 2 H), 2.64 (t, J = 8.1 Hz, 2 H), 2.55 (s, 3 H), 2.48-2.44 (m, 2 H), 2.24-2.14 (m, 2 H). |
| 23-54 | 527.8 | $^1$H NMR (400 MHz, DMSO-$d_6$) δ ppm 9.90 (br s, 1 H), 9.02 (s, 1 H), 7.31-7.25 (m, 1 H), 7.01-6.89 (m, 2 H), 6.66 (d, J = 1.4 Hz, 1 H), 6.35-6.27 (m, 1 H), 6.11 (dd, J = 17.0, 2.3 Hz, 1 H), 5.68 (dd, J = 10.3, 2.3 Hz, 1 H), 4.26 (dd, J = 8.7, 4.1 Hz, 1 H), 4.18 (dd, J = 8.7, 5.2 Hz, 1 H), 4.00-3.80 (m, 4 H), 3.76 (t, J = 6.8 Hz, 2 H), 2.69-2.60 (m, 2 H), 2.56 (s, 3 H), 2.49-2.46 (m, 2 H), 2.20-1.83 (m, 2 H). |
| 23-55 | 509.9 | $^1$H NMR (400 MHz, DMSO-$d_6$,) δ ppm 9.69 (br s, 1 H), 9.01 (s, 1 H), 7.31 (t, J = 7.9 Hz, 1 H), 6.87-6.85 (m, 1 H), 6.77-6.68 (m, 2 H), 6.65 (d, J = 1.4 Hz, 1 H), 6.31 (dd, J = 17.0, 10.2 Hz, 1 H), 6.11 (dd, J = 17.0, 2.3 Hz, 1 H), 5.67 (dd, J = 10.3, 2.3 Hz, 1 H), 4.25 (d, J = 8.6 Hz, 1 H), 4.16 (d, J = 8.7 Hz, 1 H), 3.95-3.85 (m, 4 H), |

TABLE 32-continued

| Analytical Data for Examples 23-2 to 23-61. | | |
|---|---|---|
| Ex. # | LRMS: (ESI, +ve ion) m/z | NMR |
| | | 3.74 (t, J = 6.8 Hz, 2 H), 2.63 (d, J = 7.8 Hz, 2 H), 2.60-2.56 (m, 2 H), 2.55 (s, 3 H), 2.19-2.15 (m, 2 H). |
| 23-56 | 527.8 | $^1$H NMR (400 MHz, DMSO-$d_6$) δ ppm 9.07 (s, 1 H), 7.63-7.54 (m, 1 H), 7.48-7.34 (m, 3 H), 6.94 (d, J = 1.4 Hz, 1 H), 6.37-6.26 (m, 1 H), 6.11 (dd, J = 17.0, 2.4 Hz, 1 H), 5.68 (dd, J = 10.2, 2.4 Hz, 1 H), 5.45 (t, J = 5.4 Hz, 1 H), 4.62 (d, J = 5.5 Hz, 2 H), 4.27-4.14 (m, 2 H), 4.05-3.83 (m, 4 H), 3.77 (t, J = 6.8 Hz, 2 H), 2.67-2.65 (m, 2 H), 2.26-2.13 (m, 2 H). $^{19}$F NMR (377 MHz, DMSO-$d_6$): δ ppm −114.90 (s, 1 F). 2 Protons obscured by NMR solvent. |
| 23-57 | 515.1 | $^1$H NMR (400 MHz, DMSO-$d_6$) δ ppm 8.85 (d, J = 1.4 Hz, 1 H), 8.62-8.61 (m, 1 H), 8.03-7.93 (m, 1 H), 7.68-7.64 (m, 1 H), 6.31 (dd, J = 17.0, 10.2 Hz, 1 H), 6.11 (dd, J = 17.0, 2.3 Hz, 1 H), 5.67 (dd, J = 10.2, 2.3 Hz, 1 H), 4.26 (dd, J = 8.7, 4.4 Hz, 1 H), 4.17 (d, J = 8.7 Hz, 1 H), 4.00-3.81 (m, 4 H), 3.74 (t, J = 6.9 Hz, 2 H), 3.55-3.45 (m, 1 H), 3.11 (dd, J = 17.8, 4.9 Hz, 1 H), 2.86-2.83 (m, 1 H), 2.36 (s, 3 H), 2.23-2.15 (m, 2 H), 2.01-1.95 (m, 1 H), 1.79-1.61 (m, 1 H). $^{19}$F NMR (377 MHz, DMSO-$d_6$) δ ppm −122.60. 2 proton obscured by NMR solvent. |
| 23-58 | 510.1 | $^1$H NMR (400 MHz, DMSO-$d_6$) δ ppm 8.64 (dt, J = 4.6, 1.6 Hz, 1 H), 8.01-7.96 (m, 1 H), 7.68 (dt, J = 8.6, 4.4 Hz, 1 H), 7.29 (s, 1 H), 6.51 (d, J = 1.4 Hz, 1 H), 6.34-6.27 (m, 1 H), 6.11 (dd, J = 17.0, 2.3 Hz, 1 H), 5.68 (dt, J = 10.3, 2.6 Hz, 1 H), 4.27 (dd, J = 8.7, 3.6 Hz, 1 H), 4.17 (d, J = 8.7 Hz, 1 H), 4.00-3.85 (m, 4 H), 3.79 (s, 3 H), 3.76 (d, J = 6.9 Hz, 2 H), 2.56-2.54 (m, 2 H), 2.49-2.43 (m, 2 H), 2.22-2.18 (m, 2 H), 2.03 (s, 3 H). |
| 23-59 | 514.9 | $^1$H NMR (500 MHz, DMSO-$d_6$) δ ppm 8.83 (d, J = 1.6 Hz, 1 H), 8.59-8.62 (m, 1 H), 7.93-7.99 (m, 1 H), 7.65 (dtd, 1 H), 6.29 (dd, J = 16.9, 10.5 Hz, 1 H), 6.10 (dd, J = 17.0, 2.2 Hz, 1 H), 5.64-5.68 (m, 1 H), 4.22-4.29 (m, 1 H), 4.16 (d, J = 8.4 Hz, 1 H), 3.82-3.97 (m, 4 H), 3.74 (br t, J = 6.7 Hz, 2 H), 3.44-3.50 (m, 1 H), 3.11 (br dd, J = 17.8, 3.7 Hz, 1 H), 2.82 (br dd, J = 18.2, 10.9 Hz, 1 H), 2.34-2.36 (m, 4 H), 2.10-2.23 (m, 2 H), 1.95-2.03 (m, 1 H), 1.62-1.74 (m, 1 H) |
| 23-60 | 515 | $^1$H NMR (500 MHz, DMSO-$d_6$) δ ppm 8.83 (d, J = 1.6 Hz, 1 H), 8.61 (dq, J = 4.6, 1.5 Hz, 1 H), 7.96 (t, J = 8.7 Hz, 1 H), 7.65 (dtd, 1 H), 6.29 (dd, J = 17.0, 10.4 Hz, 1 H), 6.10 (dd, J = 17.1, 2.3 Hz, 1 H), 5.75 (s, 1 H), 5.66 (dd, J = 10.3, 2.2 Hz, 1 H), 4.21-4.30 (m, 1 H), 4.16 (d, J = 8.7 Hz, 1 H), 3.90-3.99 (m, 1 H), 3.82-3.88 (m, 2 H), 3.74 (br t, J = 6.8 Hz, 2 H), 3.44-3.50 (m, 1 H), 3.11 (br dd, J = 17.2, 3.4 Hz, 1 H), 2.82 (br dd, J = 17.2, 10.6 Hz, 1 H), 2.32-2.39 (m, 4 H), 2.10-2.23 (m, 3 H), 1.96-2.02 (m, 1 H), 1.68 (br dd, J = 12.0, 5.3 Hz, 1 H) |
| 23-61 | 580.3 | $^1$H NMR (400 MHz, DMSO-$d_6$) δ ppm 8.71 (s, 1 H), 7.85 (d, J = 8.4 Hz, 1 H), 7.75 (dt, J = 8.5, 1.3 Hz, 1 H), 7.63 (8, 1 H), 7.13 (t, J = 55.5 Hz, 1 H), 6.31 (ddd, J = 17.0, 10.3, 4.2 Hz, 1 H), 6.11 (dd, J = 17.0, 2.3 Hz, 1 H), 5.68 (dd, J = 10.3, 2.3 Hz, 1 H), 4.22-4.31 (m, 1 H), 4.17 (dd, J = 8.7, 6.0 Hz, 1 H), 4.02 (m, 2 H), 3.80-3.99 (m, 4 H), 3.75 (t, J = 6.9 Hz, 2 H), 3.07 (m, 2 H), 2.29-2.40 (m, 2 H), 2.26 (s, 3 H), 2.20 (m, 2 H). |

Biological Evaluation

Provided in this section is the biological evaluation of the specific examples provided herein. See Table 33.

Coupled Nucleotide Exchange Assay:

Purified GDP-bound KRAS protein (aa 1-169), containing both G12C and C118A amino acid substitutions and an N-terminal His-tag, was pre-incubated in assay buffer (25 mM HEPES pH 7.4, 10 mM $MgCl_2$, and 0.01% Triton X-100) with serially diluted compound for either 2 h or 20 h. For all subsequent steps, DTT was added to the reaction buffer at a final concentration of 1 mM. Following compound pre-incubation, purified SOS protein (aa 564-1049) and GTP (Roche 10106399001) were added to the assay wells and incubated for an additional 30 min. To determine the extent of inhibition of SOS-mediated nucleotide exchange, purified GST-tagged cRAF (aa 1-149), nickel chelate AlphaLISA acceptor beads (PerkinElmer AL108R), and AlphaScreen glutathione donor beads (PerkinElmer 6765302) were added to the assay wells and incubated for 5 min. The assay plates were then read on a plate reader measuring luminescence signal. Signal intensity of compound-containing wells were normalized to DMSO control, and data were analyzed using a 4-parameter logistic model to calculate $IC_{50}$ values.

Cell Viability Assay:

MIA PaCa-2 (human pancreatic carcinoma; ATCC CRL-1420) or A549 (human lung carcinoma; ATCC CCL-185) cells were cultured in RPMI 1640 medium containing 10% fetal bovine serum and 1× penicillin/streptomycin/L-glutamine. Cells were seeded in 384-well plates at a density of 1.67E+04 cells/mL and incubated at 37° C., 5% $CO_2$, overnight. Serially-diluted compound or DMSO was added to the cells, and plates were incubated at 37° C., 5% $CO_2$ for 72 h. Cell viability was measured using a CellTiter-Glo® Luminescent Cell Viability Assay kit (Promega) according to the manufacturer's protocol. The luminescence signal of treated samples was normalized to DMSO control, and data were analyzed using a 4-parameter logistic model to calculate $IC_{50}$ values.

TABLE 33

| Biochemical and cellular activity of examples | | | |
|---|---|---|---|
| Ex.# | Avg 2 h Coupled exchange $IC_{50}$ (μM) | MIA PaCa-2, $IC_{50}$ (μM) | A549, $IC_{50}$ (μM) |
| 1-1 | 0.431 | >5.0 | >5.0 |
| 1-2 | 0.158 | 0.58 | 3.71 |
| 1-3 | 0.154 | 0.847 | 7.42 |

TABLE 33-continued

Biochemical and cellular activity of examples

| Ex.# | Avg 2 h Coupled exchange $IC_{50}$ (μM) | MIA PaCa-2, $IC_{50}$ (μM) | A549, $IC_{50}$ (μM) |
|---|---|---|---|
| 1-4 | 0.29 | 1.393 | 4.94 |
| 1-5 | 0.52 | 1.63 | 50.0 |
| 1-6 | 1.89 | 1.14 | 6.44 |
| 1-7 | 0.997 | >5.0 | >5.0 |
| 1-8 | 0.014 | 0.0364 | >5.0 |
| 1-9 | 4.58 | 18.1 | >25.0 |
| 1-10 | 6.7 | 2.5 | 2.91 |
| 1-11 | 3.09 | >5.0 | >5.0 |
| 1-12 | 2.59 | 5.39 | 7.23 |
| 1-13 | 0.601 | 1.88 | 3.12 |
| 1-14 | 0.327 | 0.069 | 1.09 |
| 1-15 | 9.06 | >5.0 | >5.0 |
| 1-16 | 6.72 | 10.3 | >25.0 |
| 1-17 | 5.76 | >5.0 | >5.0 |
| 1-18 | 8.46 | 8.67 | 9.46 |
| 1-19 | 5.23 | >5.0 | 14.2 |
| 1-20 | 4.65** | >5.0 | >5.0 |
| 1-21 | 0.435 | >5.0 | >5.0 |
| 1-22 | 1.14 | 4.26 | >25.0 |
| 1-23 | 1.216 | 5.27 | 10.5 |
| 1-24 | 4.245 | 8.29 | 10.6 |
| 1-25 | 2.6 | 8.86 | 20.3 |
| 1-26 | 3.98 | 9.82 | 13.8 |
| 1-27 | 5.17 | 11.8 | 20.8 |
| 1-28 | 2.98 | 9.36 | 11.5 |
| 1-29 | 3.53 | NT | NT |
| 1-30 | 3.46 | >5.0 | 10.3 |
| 1-31 | 0.075 | >5.0 | >5.0 |
| 1-32 | 250 | 17.1 | 12.1 |
| 1-33 | 174 | 13.4 | 13.45 |
| 1-34 | 0.823 | NT | NT |
| 1-35 | 1.55 | 2.37 | 7.12 |
| 1-36 | 1.66 | 3.38 | 15.9 |
| 1-37 | 0.402 | 2.28 | >25.0 |
| 1-38 | 0.103 | 0.294 | 6.25 |
| 1-39 | 0.757 | 2.745 | 6.25 |
| 1-40 | 9.01 | NT | NT |
| 1-41 | 0.882 | >5.0 | >5.0 |
| 1-42 | 0.456 | 5.92 | 22.8 |
| 1-43 | 0.858 | 2.16 | 6.25 |
| 1-44 | 6.83 | 6.4 | 12.5 |
| 1-45 | 0.032 | 0.332 | >5.0 |
| 1-46 | 1.53 | 2.02 | 6.25 |
| 1-47 | 0.47 | 4.46 | 7.23 |
| 1-48 | 0.554 | >5 | >5 |
| 1-49 | 0.124 | 24.6 | 13.4 |
| 1-50 | 0.498 | >5 | >5 |
| 1-51 | 0.791 | NT | NT |
| 1-52 | 0.244 | 1.89 | 39 |
| 1-53 | 0.099 | 13.4 | >50 |
| 1-54 | 0.122 | 0.976 | >5 |
| 2-1 | 0.042 | 0.43 | 3.105 |
| 2-2 | 0.694 | 1.73 | 6.25 |
| 2-3 | 0.537 | 0.693 | 3.12 |
| 2-4 | 0.173 | 2.055 | 6.25 |
| 2-5 | 0.042 | 0.943 | 6.25 |
| 2-6 | 0.056 | 0.237 | 6.25 |
| 2-7 | 2.02 | NT | NT |
| 2-8 | 0.059 | 0.554 | 3.64 |
| 2-9 | 0.41 | 2.97 | 6.125 |
| 2-10 | 0.044 | 0.452 | >5.0 |
| 2-11 | 0.027 | 0.053 | 6.75 |
| 2-12 | 1.11 | NT | NT |
| 2-13 | 0.15 | 0.403 | >5.0 |
| 2-14 | 2.9 | NT | NT |
| 2-15 | 0.066 | 0.106 | >5.0 |
| 2-16 | 0.122 | 0.176 | >5.0 |
| 2-17 | 0.064 | 0.155 | >5.0 |
| 2-18 | 5.24 | NT | NT |
| 2-19 | 0.104 | 0.392 | >5.0 |
| 2-20 | 10.5 | NT | NT |
| 2-21 | 0.161 | 0.441 | >5.0 |
| 2-22 | 0.846 | NT | NT |

TABLE 33-continued

Biochemical and cellular activity of examples

| Ex.# | Avg 2 h Coupled exchange $IC_{50}$ (μM) | MIA PaCa-2, $IC_{50}$ (μM) | A549, $IC_{50}$ (μM) |
|---|---|---|---|
| 2-23 | 0.735 | NT | NT |
| 2-24 | 0.119 | NT | NT |
| 2-25 | 6.88 | NT | NT |
| 2-26 | 0.234 | NT | NT |
| 2-27 | 0.102 | 0.214 | >5.0 |
| 2-28 | 0.067 | 0.187 | >5.0 |
| 2-29 | 0.903 | NT | NT |
| 2-30 | 0.75 | NT | NT |
| 2-31 | 0.053 | 0.054 | 2.78 |
| 2-32 | 0.808 | NT | NT |
| 2-33 | 17.4 | NT | NT |
| 2-34 | 0.427 | NT | NT |
| 2-35 | 0.186 | NT | NT |
| 2-36 | 0.02 | 0.013 | >5.0 |
| 2-37 | 0.298 | NT | NT |
| 2-38 | 0.067 | 0.157 | 3.42 |
| 2-39 | 0.009 | 0.068 | >5.0 |
| 2-40 | 0.046 | 0.529 | 2 |
| 2-41 | 0.113 | NT | NT |
| 2-42 | 0.028 | 0.175 | >5.0 |
| 2-43 | 0.193 | NT | NT |
| 2-44 | 131 | NT | NT |
| 2-45 | 0.077 | >5.0 | >5.0 |
| 2-46 | 0.006 | 0.135 | >5.0 |
| 2-47 | 0.181 | NT | NT |
| 2-48 | 0.109 | 0.885 | >5.0 |
| 2-49 | 0.323 | 1.21 | >5.0 |
| 2-50 | 0.466 | 2.61 | >5.0 |
| 2-51 | 0.267 | NT | NT |
| 2-52 | 0.026 | 0.061 | >5.0 |
| 2-53 | 7.11 | NT | NT |
| 2-54 | 0.028 | 0.056 | >5.0 |
| 2-55 | 0.419 | NT | NT |
| 2-56 | 43.6 | NT | NT |
| 2-57 | 0.106 | 0.921 | >5.0 |
| 2-58 | 0.282 | 2.08 | >5.0 |
| 2-59 | 14.9 | NT | NT |
| 2-60 | 4.67 | NT | NT |
| 2-61 | 0.134 | 1.32 | >5.0 |
| 2-62 | 0.186 | 1.27 | >5.0 |
| 2-63 | 0.793 | NT | NT |
| 2-64 | 0.039 | 0.432 | >5.0 |
| 2-65 | 0.735 | NT | NT |
| 2-66 | 0.089 | 0.735 | >5.0 |
| 2-67 | 0.038 | 0.381 | >5.0 |
| 2-68 | 16 | NT | NT |
| 2-69 | 0.015 | 0.221 | >5.0 |
| 2-70 | 1.34 | NT | NT |
| 2-71 | 20.3 | NT | NT |
| 2-72 | 0.651 | NT | NT |
| 2-73 | 0.228 | 1.94 | >5.0 |
| 2-74 | 0.021 | 0.202 | >5.0 |
| 2-75 | 0.454 | NT | NT |
| 2-76 | 0.031 | 0.026 | >5.0 |
| 2-77 | 3.895 | NT | NT |
| 2-78 | 0.018 | 0.014 | >5.0 |
| 2-79 | 0.071 | 0.159 | >5.0 |
| 2-80 | 20.1 | NT | NT |
| 2-81 | 0.053 | 0.058 | >5.0 |
| 2-82 | 0.641 | NT | NT |
| 2-83 | 0.033 | 0.017 | 12.2 |
| 2-84 | 0.808 | NT | NT |
| 2-85 | 12.6 | NT | NT |
| 2-86 | 6.15 | NT | NT |
| 2-87 | 0.115 | NT | NT |
| 2-88 | 4.73 | NT | NT |
| 2-89 | 0.024 | NT | NT |
| 2-90 | 0.005 | NT | NT |
| 2-91 | 2.89 | NT | NT |
| 2-92 | 0.021 | NT | NT |
| 2-93 | 0.019 | 0.07 | 2.04 |
| 2-94 | 0.61 | NT | NT |
| 2-95 | 0.088 | 0.792 | >5.0 |

TABLE 33-continued

Biochemical and cellular activity of examples

| Ex.# | Avg 2 h Coupled exchange $IC_{50}$ (μM) | MIA PaCa-2, $IC_{50}$ (μM) | A549, $IC_{50}$ (μM) |
|---|---|---|---|
| 2-96 | 0.232 | 0.246 | >5.0 |
| 2-97 | 0.082 | 0.207 | >5.0 |
| 2-98 | 0.055 | 0.11 | >5.0 |
| 2-99 | 4.39 | NT | NT |
| 2-100 | 0.033 | 0.025 | >5.0 |
| 2-101 | 0.028 | 0.037 | 13.4 |
| 2-102 | 0.07 | NT | NT |
| 2-103 | 0.294 | 0.118 | >5.0 |
| 2-104 | 0.018 | 0.003 | >5.0 |
| 2-105 | 0.091 | 0.425 | 3.42 |
| 2-106 | 0.288 | NT | NT |
| 2-107 | 0.017 | 0.007 | >5.0 |
| 2-108 | 14.1 | NT | NT |
| 2-109 | 0.023 | 0.003 | >5.0 |
| 2-110 | 0.053 | 0.02 | >5.0 |
| 2-111 | 0.003 | 0.21 | 10.9 |
| 3 | 1.38** | NT | NT |
| 4 | 1.05 | NT | NT |
| 5 | 181.0 | 12.9 | >25.0 |
| 6 | 3.505 | NT | NT |
| 7 | 0.879 | 3.42 | >5.0 |
| 8 | 1.27 | NT | NT |
| 9 | 0.691 | 1.69 | >5.0 |
| 10 | 1.68 | 3.24 | >5.0 |
| 11 | 1.94 | 1.16 | 12.6 |
| 12-1 | 0.094 | 0.088 | >5.0 |
| 12-2 | 0.041 | 0.038 | >5.0 |
| 12-3 | 0.623 | NT | NT |
| 12-4 | 0.818 | NT | NT |
| 12-5 | 0.463 | NT | NT |
| 12-6 | 0.213 | NT | NT |
| 12-7 | 0.435 | NT | NT |
| 12-8 | 0.399 | NT | NT |
| 12-9 | 0.443 | NT | NT |
| 12-10 | 7.42 | NT | NT |
| 12-11 | 0.036 | 0.02 | 3.78 |
| 12-13 | 0.252 | NT | NT |
| 12-14 | 0.246 | NT | NT |
| 12-15 | 0.464 | NT | NT |
| 12-16 | 0.242 | NT | NT |
| 12-17 | 0.132 | NT | NT |
| 12-18 | 0.988 | NT | NT |
| 12-19 | 0.037 | 0.018 | 3.745 |
| 12-20 | 0.105 | 2.57 | >5.0 |
| 12-21 | 0.601 | NT | NT |
| 12-22 | 0.037 | 0.044 | >5.0 |
| 12-23 | 18.7 | NT | NT |
| 12-24 | 0.05 | NT | NT |
| 12-25 | 0.141 | NT | NT |
| 12-26 | 0.687 | NT | NT |
| 12-27 | 0.476 | NT | NT |
| 12-28 | 0.263 | NT | NT |
| 12-29 | 0.816 | NT | NT |
| 12-30 | 0.438 | NT | NT |
| 12-31 | 0.189 | NT | NT |
| 12-32 | 0.515 | NT | NT |
| 12-33 | 0.527 | NT | NT |
| 12-34 | 0.02 | 0.092 | >5.0 |
| 12-35 | 0.044 | 1.09 | >5.0 |
| 12-36 | 0.441 | NT | NT |
| 12-37 | 1.44 | NT | NT |
| 12-38 | 0.137 | >5.0 | >5.0 |
| 12-39 | 3.9 | NT | NT |
| 12-40 | 0.344 | NT | NT |
| 12-41 | 0.11 | 0.502 | >5.0 |
| 12-42 | 0.878 | NT | NT |
| 12-43 | 0.026 | 0.082 | >5.0 |
| 12-44 | 11 | NT | NT |
| 12-45 | 0.76 | >5.0 | >5.0 |
| 13-1 | 0.036 | 0.065 | 4.89 |
| 13-2 | 0.061 | 0.366 | 3.7 |
| 13-3 | 0.166 | 0.625 | 1.25 |
| 13-4 | 0.357 | 1.62 | >5.0 |

TABLE 33-continued

Biochemical and cellular activity of examples

| Ex.# | Avg 2 h Coupled exchange $IC_{50}$ (μM) | MIA PaCa-2, $IC_{50}$ (μM) | A549, $IC_{50}$ (μM) |
|---|---|---|---|
| 13-5 | 0.973 | >5.0 | >5.0 |
| 13-6 | 0.169 | NT | NT |
| 13-7 | 0.229 | NT | NT |
| 13-8 | 0.044 | 0.218 | 3.37 |
| 13-9 | 0.324 | NT | NT |
| 13-10 | 0.071 | 0.246 | >5.0 |
| 13-11 | 0.067 | 0.537 | 4.24 |
| 13-12 | 0.029 | 0.157 | >5.0 |
| 13-13 | 0.093 | 0.462 | >5.0 |
| 13-14 | 0.034 | 0.517 | >5.0 |
| 13-15 | 0.163 | 1.17 | >5.0 |
| 13-16 | 0.082 | 0.393 | >5.0 |
| 13-17 | 19.9 | NT | NT |
| 13-18 | 0.026 | 0.18 | >5.0 |
| 13-19 | 0.064 | 0.338 | >5.0 |
| 13-20 | 0.012 | 0.224 | 3.0 |
| 13-21 | 0.062 | 0.615 | >5.0 |
| 13-22 | 0.259 | NT | NT |
| 13-23 | 0.769 | NT | NT |
| 13-24 | 1.8 | NT | NT |
| 13-25 | 0.337 | NT | NT |
| 13-26 | 0.035 | 0.28 | >5.0 |
| 13-27 | 0.231 | NT | NT |
| 13-28 | 0.266 | NT | NT |
| 13-29 | 0.217 | NT | NT |
| 13-30 | 0.715 | NT | NT |
| 13-31 | 0.652 | NT | NT |
| 13-32 | 64.9 | NT | NT |
| 13-33 | 0.676 | NT | NT |
| 13-34 | 0.946 | NT | NT |
| 13-35 | 1.78 | NT | NT |
| 13-36 | 0.991 | NT | NT |
| 13-37 | 31.7 | NT | NT |
| 13-38 | 1.42 | NT | NT |
| 13-39 | 0.639 | NT | NT |
| 13-40 | 34.1 | NT | NT |
| 13-41 | 0.033 | 0.19 | >5.0 |
| 13-42 | 23.335 | NT | NT |
| 13-43 | 0.016 | 0.143 | >5.0 |
| 13-44 | 0.589 | 1.44 | >5.0 |
| 13-45 | 0.148 | 0.421 | >5.0 |
| 13-46 | 0.685 | NT | NT |
| 13-47 | 0.298 | NT | NT |
| 13-48 | 0.664 | NT | NT |
| 13-49 | 0.123 | 0.442 | >5.0 |
| 13-50 | 0.076 | 0.198 | >5.0 |
| 13-51 | 0.095 | 0.287 | >5.0 |
| 13-52 | 0.043 | 0.231 | >5.0 |
| 13-53 | 0.657 | NT | NT |
| 13-54 | 0.017 | 0.058 | >5.0 |
| 13-55 | 0.877 | NT | NT |
| 13-56 | 141 | NT | NT |
| 13-57 | 0.361 | NT | NT |
| 13-58 | 0.514 | NT | NT |
| 13-59 | 32.2 | NT | NT |
| 13-60 | 0.063 | 0.146 | >5.0 |
| 13-61 | 0.332 | NT | NT |
| 13-62 | 0.334 | NT | NT |
| 13-63 | 0.145 | NT | NT |
| 13-64 | 1.08 | NT | NT |
| 13-65 | 0.074 | 0.472 | >5.0 |
| 13-66 | 76 | NT | NT |
| 13-67 | 0.506 | NT | NT |
| 13-68 | 27 | NT | NT |
| 13-69 | 0.027 | 0.217 | 3.23 |
| 13-70 | 0.291 | NT | NT |
| 13-71 | 0.366 | NT | NT |
| 13-72 | 0.564 | NT | NT |
| 13-73 | 19.3 | NT | NT |
| 13-74 | 0.076 | >5.0 | >5.0 |
| 13-75 | 17 | NT | NT |
| 13-76 | 0.04 | 1.188 | 3.26 |
| 13-77 | 35.6 | NT | NT |

TABLE 33-continued

Biochemical and cellular activity of examples

| Ex.# | Avg 2 h Coupled exchange $IC_{50}$ (μM) | MIA PaCa-2, $IC_{50}$ (μM) | A549, $IC_{50}$ (μM) |
|---|---|---|---|
| 13-78 | 0.076 | 0.842 | >5.0 |
| 13-79 | 0.433 | 8.235 | 7.45 |
| 13-80 | 0.045 | 0.952 | >5.0 |
| 13-81 | 0.098 | 0.319 | >5.0 |
| 13-82 | 0.066 | 0.462 | >5.0 |
| 13-83 | 0.086 | >5.0 | >5.0 |
| 13-84 | 0.108 | 0.479 | >5.0 |
| 13-85 | 0.316 | NT | NT |
| 13-86 | 20.4 | NT | NT |
| 13-87 | 0.13 | NT | NT |
| 13-88 | 0.143 | NT | NT |
| 13-89 | 0.035 | 0.101 | >5.0 |
| 13-90 | 0.027 | 0.024 | >5.0 |
| 13-91 | 9.27 | NT | NT |
| 13-92 | 0.013 | 0.009 | >5.0 |
| 13-93 | 0.053 | 0.013 | >5.0 |
| 13-94 | 0.051 | 0.042 | >5.0 |
| 13-95 | 0.034 | 0.092 | >5.0 |
| 13-96 | 0.325 | >5.0 | >5.0 |
| 13-97 | 0.046 | 0.423 | >5.0 |
| 13-98 | 0.051 | 0.103 | >5.0 |
| 13-99 | 0.18 | 1.43 | >5.0 |
| 13-100 | 0.124 | 0.947 | >5.0 |
| 13-101 | 0.102 | 1.37 | >5.0 |
| 13-102 | 140 | NT | NT |
| 13-103 | 0.283 | NT | NT |
| 13-104 | 0.097 | 1.34 | >5.0 |
| 13-105 | 14.7 | NT | NT |
| 13-106 | 0.078 | 0.831 | >5.0 |
| 13-107 | 0.702 | NT | NT |
| 13-108 | 0.024 | 0.063 | 2.91 |
| 13-109 | 1.11 | NT | NT |
| 13-110 | 0.073 | 0.524 | >5.0 |
| 13-111 | 0.294 | NT | NT |
| 13-112 | 0.117 | >5.0 | >5.0 |
| 13-113 | 0.071 | >5.0 | >5.0 |
| 13-114 | 1.38 | NT | NT |
| 13-115 | 0.012 | 0.009 | >5.0 |
| 13-116 | 0.03 | 0.775 | >5.0 |
| 13-117 | 15.8 | NT | NT |
| 13-118 | 0.072 | 0.279 | >5.0 |
| 13-119 | 6.7 | NT | NT |
| 13-120 | 9.19 | NT | NT |
| 13-121 | 0.849 | NT | NT |
| 13-122 | 0.299 | 1.08 | >5.0 |
| 13-123 | 0.856 | NT | NT |
| 13-124 | 45.5 | NT | NT |
| 13-125 | 12.6 | NT | NT |
| 13-126 | 0.029 | >5.0 | >5.0 |
| 13-127 | 153 | NT | NT |
| 13-128 | 0.091 | >5.0 | >5.0 |
| 13-129 | 0.013 | 0.021 | >5.0 |
| 13-130 | 13.1 | NT | NT |
| 13-131 | 0.101 | NT | NT |
| 13-132 | 24.4 | NT | NT |
| 13-133 | 0.064 | 0.2 | >5.0 |
| 13-134 | 39.3 | NT | NT |
| 13-135 | 62.5 | NT | NT |
| 13-136 | 0.078 | 0.401 | >5.0 |
| 13-137 | 0.072 | 0.468 | >5.0 |
| 13-138 | 0.641 | NT | NT |
| 13-139 | 0.388 | 1.87 | >5.0 |
| 13-140 | 167 | NT | NT |
| 13-141 | 0.842 | NT | NT |
| 13-142 | 0.62 | NT | NT |
| 13-143 | 0.033 | 0.602 | >5.0 |
| 13-144 | 0.041 | 0.172 | 3.80 |
| 13-145 | 0.031 | 0.208 | >5.0 |
| 13-146 | 0.029 | 0.071 | >5.0 |
| 13-147 | 0.098 | 0.176 | >5.0 |
| 13-148 | 0.026 | 0.103 | >5.0 |
| 13-149 | 0.276 | 0.616 | 11.198 |
| 13-150 | 2.895 | 4.02 | 6.73 |

TABLE 33-continued

Biochemical and cellular activity of examples

| Ex.# | Avg 2 h Coupled exchange $IC_{50}$ (μM) | MIA PaCa-2, $IC_{50}$ (μM) | A549, $IC_{50}$ (μM) |
|---|---|---|---|
| 13-151 | 0.149 | 1.19 | 9.34 |
| 13-152 | 0.787 | 1.93 | 9.05 |
| 13-153 | 0.064 | 0.058 | >5.0 |
| 13-154 | 0.081 | 0.776 | >5.0 |
| 13-155 | 0.111 | 0.093 | >5.0 |
| 13-156 | 139.9 | 5.92 | 8.16 |
| 13-157 | 0.555 | 0.357 | 16.2 |
| 14-1 | 0.018 | 0.039 | >5.0 |
| 14-2 | 0.087 | 0.458 | >5.0 |
| 14-3 | 0.588 | NT | NT |
| 14-4 | 0.017 | 0.009 | >5.0 |
| 14-5 | 0.129 | NT | NT |
| 14-6 | 1.42 | NT | NT |
| 14-7 | 0.014 | 0.006 | 5.57 |
| 14-8 | 2.57 | NT | NT |
| 14-9 | 0.091 | 0.569 | 10.4 |
| 14-10 | 1.14 | NT | NT |
| 14-11 | 0.038 | 0.149 | >5.0 |
| 14-12 | 0.422 | NT | NT |
| 14-13 | 2.84 | NT | NT |
| 14-14 | 0.108 | NT | NT |
| 14-15 | 0.049 | 0.068 | >5.0 |
| 14-16 | 250 | NT | NT |
| 14-17 | 0.022 | 0.051 | >5.0 |
| 14-18 | 0.043 | 0.324 | >5.0 |
| 14-19 | 0.13 | 1.69 | >5.0 |
| 14-20 | 0.031 | 2.55 | >5.0 |
| 14-21 | 0.111 | 0.447 | >5.0 |
| 14-22 | 0.606 | NT | NT |
| 14-23 | 0.102 | 0.018 | >5.0 |
| 14-24 | 0.506 | NT | NT |
| 14-25 | 0.11 | 0.669 | >5.0 |
| 14-26 | 0.067 | 0.076 | >5.0 |
| 14-27 | 0.164 | NT | NT |
| 14-28 | 0.886 | NT | NT |
| 14-29 | 0.058 | 0.143 | >5.0 |
| 14-30 | 0.215 | NT | NT |
| 14-31 | 0.106 | 0.105 | >5.0 |
| 14-32 | 3.04 | NT | NT |
| 14-33 | 0.044 | 0.032 | >5.0 |
| 14-34 | 7.59 | NT | NT |
| 14-35 | 5.617 | NT | NT |
| 14-36 | 0.226 | NT | NT |
| 14-37 | 0.478 | NT | NT |
| 14-38 | 0.063 | 0.123 | >5.0 |
| 14-39 | 1.77 | NT | NT |
| 14-40 | 0.11 | 0.502 | >5.0 |
| 14-41 | 0.066 | 0.408 | >5.0 |
| 14-42 | 7.815 | NT | NT |
| 14-43 | 0.11 | 0.136 | >5.0 |
| 14-44 | 0.071 | 0.044 | >5.0 |
| 14-45 | 7.485 | NT | NT |
| 14-46 | 0.113 | 0.459 | 2.38 |
| 14-47 | 0.482 | >5.0 | >5.0 |
| 14-48 | 0.061 | 0.053 | >5.0 |
| 14-49 | 0.776 | NT | NT |
| 14-50 | 0.065 | 1.61 | >5.0 |
| 14-51 | 0.011 | 0.018 | >5.0 |
| 14-52 | 1.02 | NT | NT |
| 14-53 | 0.36 | NT | NT |
| 14-54 | 0.349 | NT | NT |
| 14-55 | 0.209 | NT | NT |
| 14-56 | 0.093 | 0.135 | >5.0 |
| 14-57 | 0.04 | 0.071 | >5.0 |
| 14-58 | 0.357 | NT | NT |
| 14-59 | 0.025 | 0.293 | >5.0 |
| 14-60 | 3.35 | NT | NT |
| 14-61 | 76.85 | NT | NT |
| 14-62 | 0.696 | NT | NT |
| 14-63 | 0.364 | NT | NT |
| 14-64 | 11.8 | NT | NT |
| 14-65 | 0.367 | NT | NT |
| 14-66 | 33.5 | NT | NT |

TABLE 33-continued

Biochemical and cellular activity of examples

| Ex.# | Avg 2 h Coupled exchange $IC_{50}$ (μM) | MIA PaCa-2, $IC_{50}$ (μM) | A549, $IC_{50}$ (μM) |
|---|---|---|---|
| 14-67 | 0.64 | NT | NT |
| 14-68 | 0.05 | 0.091 | >5.0 |
| 14-69 | 17.033 | NT | NT |
| 14-70 | 0.068 | 0.082 | >5.0 |
| 14-71 | 0.781 | NT | NT |
| 14-72 | 0.03 | 0.024 | >5.0 |
| 14-73 | 0.01 | 0.011 | >5.0 |
| 14-74 | 1.56 | NT | NT |
| 14-75 | 0.726 | NT | NT |
| 14-76 | 3.945 | NT | NT |
| 14-77 | 0.013 | 0.023 | >5.0 |
| 14-78 | 0.023 | NT | NT |
| 14-79 | 9.6 | NT | NT |
| 14-80 | 0.089 | 1.19 | >5.0 |
| 14-81 | 0.045 | 0.092 | >5.0 |
| 14-82 | 5.76 | NT | NT |
| 14-83 | 0.432 | NT | NT |
| 14-84 | 0.144 | 2.15 | >5.0 |
| 14-85 | 0.056 | NT | NT |
| 14-86 | 0.108 | 0.418 | >5.0 |
| 14-87 | 0.039 | 0.068 | >5.0 |
| 14-88 | 10.4 | NT | NT |
| 14-89 | 0.081 | 0.08 | 1.80 |
| 14-90 | 0.148 | NT | NT |
| 14-91 | 0.016 | 0.02 | >5.0 |
| 14-92 | 0.028 | 0.009 | >5.0 |
| 14-93 | 0.134 | 0.352 | 12.4 |
| 14-94 | 0.228 | 0.118 | 14.4 |
| 14-95 | 0.687 | 3.35 | 15.4 |
| 14-96 | 0.546 | 0.852 | 13.4 |
| 14-97 | 0.208 | 0.254 | 10 |
| 14-98 | 0.071 | 0.08 | >5.0 |
| 14-99 | 0.071 | 0.08 | >5.0 |
| 14-100 | 0.602 | NT | NT |
| 14-101 | 0.301 | NT | NT |
| 14-102 | 55.6 | NT | NT |
| 14-103 | 0.045 | 0.032 | 7.62 |
| 14-104 | 0.242 | 0.21 | >5.0 |
| 14-105 | 0.054 | NT | NT |
| 14-106 | 0.046 | NT | NT |
| 14-107 | 0.013 | 0.03 | 15.3 |
| 15-1 | 0.031 | 0.144 | 3.31 |
| 15-2 | 0.478 | NT | NT |
| 15-3 | 0.062 | 1.12 | >5.0 |
| 15-4 | 0.28 | NT | NT |
| 15-5 | 0.779 | NT | NT |
| 15-6 | 3.58 | NT | NT |
| 15-7 | 0.115 | 0.966 | 4.14 |
| 16-1 | 0.28 | >5.0 | >5.0 |
| 16-2 | 0.648 | NT | NT |
| 16-3 | 0.519 | NT | NT |
| 16-4 | 0.644 | NT | NT |
| 16-5 | 0.39 | NT | NT |
| 16-6 | 0.708 | NT | NT |
| 16-7 | 0.716 | NT | NT |
| 16-8 | 0.702 | NT | NT |
| 16-9 | 0.06 | 1.33 | >5.0 |
| 16-10 | 0.26 | NT | NT |
| 16-11 | 0.347 | NT | NT |
| 16-12 | 0.488 | NT | NT |
| 16-13 | 0.368 | NT | NT |
| 16-14 | 0.373 | NT | NT |
| 17-1 | 0.293 | NT | NT |
| 17-2 | 0.098 | 1.88 | 3.02 |
| 17-3 | 0.036 | 0.684 | 1.88 |
| 17-4 | 0.521 | NT | NT |
| 17-5 | 0.07 | 1.27 | 4.43 |
| 17-6 | 0.149 | 2.19 | 4.37 |
| 17-7 | 0.126 | 1.8 | 3.10 |
| 17-8 | 0.571 | NT | NT |
| 17-9 | 0.722 | NT | NT |
| 17-10 | 0.57 | NT | NT |
| 18-1 | 0.037 | 0.023 | >5.0 |
| 18-2 | 0.268 | 0.093 | >5.0 |
| 18-3 | 0.229 | 0.137 | >5.0 |
| 18-4 | 0.017 | 0.012 | >5.0 |
| 18-5 | 0.99 | 0.546 | 15.3 |
| 18-6 | 0.08 | 0.07 | >5.0 |
| 18-7 | 0.071 | 0.064 | >5.0 |
| 18-8 | 0.047 | 0.17 | >5.0 |
| 18-9 | 0.419 | 0.316 | >5.0 |
| 18-10 | 0.26 | 0.381 | >5.0 |
| 18-11 | 0.167 | 0.174 | >5.0 |
| 18-12 | 0.172 | 0.335 | 12.5 |
| 18-13 | 0.086 | 0.089 | >5.0 |
| 18-14 | 0.376 | 0.167 | >25 |
| 18-15 | 0.72 | 0.23 | >25 |
| 18-16 | 0.355 | 0.188 | >5.0 |
| 18-17 | 0.079 | 0.133 | >5.0 |
| 18-18 | 0.106 | 0.402 | >5.0 |
| 18-19 | 0.131 | 0.056 | >25 |
| 18-20 | 0.374 | 0.135 | >25 |
| 18-21 | 0.8 | 3.37 | >25 |
| 18-22 | 6.88 | 0.804 | >20 |
| 19-1 | 0.074 | 0.374 | >5.0 |
| 19-2 | 0.126 | 1.45 | >5.0 |
| 19-3 | 0.058 | 0.717 | 4.18 |
| 19-4 | 0.038 | 0.695 | >5.0 |
| 19-5 | 0.096 | 0.452 | >5.0 |
| 19-6 | 0.363 | 1.13 | >5.0 |
| 19-7 | 0.789 | 0.495 | 14.1 |
| 19-8 | 0.28 | 0.32 | 11.2 |
| 19-9 | 0.056 | 0.204 | >5.0 |
| 19-10 | 0.113 | 1.13 | 15.3 |
| 19-11 | 0.068 | 1.35 | >5.0 |
| 19-12 | 0.074 | 1.4 | 3.79 |
| 19-13 | 0.067 | 0.671 | >5.0 |
| 19-14 | 0.038 | 0.366 | >5.0 |
| 19-15 | 2.955 | 4.56 | 7.6 |
| 20-1 | 0.149 | 1.56 | >5.0 |
| 20-2 | 0.146 | 1.44 | >5.0 |
| 20-3 | 0.277 | 2.18 | >5.0 |
| 20-4 | 0.069 | 1.006 | >5.0 |
| 20-5 | 0.572 | 5.51 | 9.11 |
| 20-6 | 0.124 | 1.55 | >5.0 |
| 20-7 | 0.131 | 0.534 | >5.0 |
| 20-8 | 0.139 | 0.974 | >5.0 |
| 20-9 | 0.042 | 0.2 | 3.19 |
| 20-10 | 0.89 | 5.38 | 6.78 |
| 20-11 | 0.834 | 3.1 | 8.81 |
| 20-12 | 0.245 | 2.06 | >25 |
| 20-13 | 0.104 | 1.07 | 5.98 |
| 20-14 | 0.243 | 1.35 | 9.15 |
| 20-15 | 0.116 | 0.649 | >5.0 |
| 20-16 | 0.124 | 0.817 | 9.15 |
| 20-17 | 0.431 | 1.82 | 7.58 |
| 20-18 | 0.095 | 0.651 | >5.0 |
| 20-19 | 0.325 | 2.07 | 4.77 |
| 20-20 | 0.162 | 1.75 | 6.85 |
| 20-21 | 0.958 | 4.97 | 10.8 |
| 20-22 | 0.371 | 7.48 | 12.1 |
| 21-1 | 0.041 | 0.327 | >5.0 |
| 21-2 | 0.189 | 0.805 | >5.0 |
| 21-3 | 0.025 | 0.19 | >5.0 |
| 21-4 | 0.085 | 1.61 | 10.1 |
| 21-5 | 0.057 | 0.454 | 3.98 |
| 21-6 | 0.93 | 4.57 | 11.2 |
| 21-7 | 0.094 | 0.749 | 6.02 |
| 21-8 | 0.933 | 5.56 | >25 |
| 21-9 | 0.264 | >5.0 | >5.0 |
| 21-10 | 0.189 | 0.716 | >5.0 |
| 21-11 | 0.033 | 0.633 | 4.41 |
| 21-12 | 0.393 | 5.405 | >25 |
| 21-13 | 0.014 | 1.074 | >5.0 |
| 21-14 | 0.035 | >5.0 | >5.0 |
| 21-15 | 0.22 | >5.0 | >5.0 |

TABLE 33-continued

| Biochemical and cellular activity of examples | | | |
|---|---|---|---|
| Ex.# | Avg 2 h Coupled exchange $IC_{50}$ (μM) | MIA PaCa-2, $IC_{50}$ (μM) | A549, $IC_{50}$ (μM) |
| 21-16 | 0.108 | 0.931 | 5.11 |
| 21-17 | 0.136 | 0.337 | 9.84 |
| 21-18 | 0.853 | 2.82 | 10.2 |
| 21-19 | 0.035 | 1.173 | >5 |
| 21-20 | 0.973 | 5.25 | 9.88 |
| 21-21 | 0.442 | >5.0 | >5.0 |
| 21-22 | 0.034 | 0.17 | >5.0 |
| 21-23 | 0.114 | 0.619 | >5.0 |
| 21-24 | 0.018 | 0.297 | >5.0 |
| 21-25 | 3.265 | 7.40 | 13.4 |
| 21-26 | 0.334 | 0.337 | 18.35 |
| 21-27 | 0.918 | 2.99 | 16.5 |
| 21-28 | 0.473 | 0.314 | >25 |
| 21-29 | 0.822 | 4.41 | >25 |
| 21-30 | 0.211 | 2.09 | 15.4 |
| 21-31 | 0.641 | 0.738 | >5.0 |
| 21-32 | 0.355 | 1.45 | 8.22 |
| 21-33 | 0.957 | 5.52 | 16.1 |
| 21-34 | 0.911 | 6.29 | >25 |
| 21-35 | 0.119 | 0.104 | >5.0 |
| 21-36 | 0.167 | 0.174 | >5.0 |
| 21-37 | 0.09 | 0.461 | >5.0 |
| 21-38 | 0.178 | 0.196 | >5.0 |
| 21-39 | 1.12 | 7.18 | 17.6 |
| 22-1 | 0.038 | 0.585 | >5.0 |
| 22-2 | 0.701 | 5.27 | >25 |
| 22-3 | 0.281 | 3.31 | >5.0 |
| 22-4 | 0.222 | >5.0 | >5.0 |
| 23-1 | 0.178 | 0.507 | >5.0 |
| 23-2 | 0.026 | 0.164 | 12.6 |
| 23-3 | 0.107 | 2.52 | >5.0 |
| 23-4 | 0.019 | 0.184 | 11.0 |
| 23-5 | 0.008 | 0.107 | 3.795 |
| 23-6 | 0.128 | 3.42 | 13.0 |
| 23-7 | 0.072 | 0.918 | 3.69 |
| 23-8 | 0.169 | 2.24 | >5.0 |
| 23-9 | 0.531 | 0.916 | 16.2 |
| 23-10 | 0.2 | 0.478 | >5.0 |
| 23-11 | 0.053 | 0.637 | >5.0 |
| 23-12 | 0.108 | 0.754 | 4.07 |
| 23-13 | 0.039 | 0.911 | >5.0 |
| 23-14 | 0.802 | 1.31 | >25 |
| 23-15 | 0.196 | 0.972 | >5.0 |
| 23-16 | 0.149 | 1.03 | 3.16 |
| 23-17 | 0.098 | 0.707 | >5.0 |
| 23-18 | 0.104 | 0.591 | 2.88 |
| 23-19 | 0.087 | 0.537 | 3.29 |
| 23-20 | 0.227 | 1.15 | 8.25 |
| 23-21 | 0.074 | 0.714 | 3.78 |
| 23-22 | 0.182 | 0.725 | >5.0 |
| 23-23 | 0.092 | 1.08 | 3.37 |
| 23-24 | 0.071 | 0.705 | >5.0 |
| 23-25 | 0.196 | 0.48 | >5.0 |
| 23-26 | 0.551 | 1.69 | 13.0 |
| 23-27 | 0.097 | 0.776 | >5.0 |
| 23-28 | 0.415 | 1.4 | 5.68 |
| 23-29 | 0.048 | 1.32 | >5.0 |
| 23-30 | 0.132 | 1.95 | 8.39 |
| 23-31 | 0.168 | 2.24 | 6.72 |
| 23-32 | 0.282 | 1.95 | 5.5 |
| 23-33 | 0.101 | 0.606 | >5.0 |
| 23-34 | 0.097 | 1.09 | >5.0 |
| 23-35 | 0.84 | 2.4 | 21 |
| 23-36 | 0.272 | 1.53 | 9.32 |
| 23-37 | 0.179 | 3.12 | 14.6 |
| 23-38 | 0.135 | 1.54 | 8.01 |
| 23-39 | 0.394 | 2.37 | 7.69 |
| 23-40 | 0.136 | 2.28 | 7.26 |
| 23-41 | 0.325 | 2.39 | 5.77 |
| 23-42 | 0.066 | 0.561 | >5.0 |
| 23-43 | 0.299 | 4.56 | 8.38 |
| 23-44 | 0.687 | 3.1 | 5.86 |
| 23-45 | 0.033 | 1.07 | >5.0 |
| 23-46 | 0.114 | 1.5 | 5.37 |
| 23-47 | 0.044 | >5.0 | >5.0 |
| 23-48 | 0.112 | 0.761 | 3.43 |
| 23-49 | 0.197 | 0.67 | >5.0 |
| 23-50 | 0.038 | 1.19 | >5.0 |
| 23-51 | 127.14 | 6.22 | 9.64 |
| 23-52 | 0.109 | 0.779 | 3.41 |
| 23-53 | 0.391 | 1.23 | 8.87 |
| 23-54 | 0.112 | 2.11 | >5.0 |
| 23-55 | 0.120 | 2.12 | >5.0 |
| 23-56 | 0.128 | 0.487 | >5.0 |
| 23-57 | 0.085 | 0.299 | >5.0 |
| 23-58 | 0.841 | 2.06 | 10.7 |
| 23-59 | 0.164 | NT | NT |
| 23-60 | 0.024 | 0.047 | 14 |
| 23-61 | 0.103 | 1.91 | 12.4 |
| 24-1 | 0.062 | 1.12 | >5.0 |
| 25-1 | 0.45 | NT | NT |
| 26-1 | 0.14 | 0.919 | >5.0 |
| 26-2 | 34.6 | NT | NT |
| 27-1 | 0.134 | 0.996 | >5.0 |
| 27-2 | 0.121 | 2.64 | >5.0 |
| 28-1 | 0.655 | NT | NT |
| 29-1 | 0.648 | NT | NT |
| 30-1 | 0.487 | NT | NT |
| 31-1 | 0.076 | 0.034 | >5.0 |
| 32-1 | 0.599 | NT | NT |
| 33-1 | 0.619 | NT | NT |
| 33-2 | 0.659 | NT | NT |
| 34-1 | 0.814 | 3.51 | 14.1 |
| 35-1 | 0.067 | >5.0 | >5.0 |
| 36-1 | 0.589 | 0.335 | 14.6 |
| 36-2 | 0.087 | 0.028 | 25 |
| 36-3 | 65.3 | 11 | 18.8 |
| 37-1 | 0.214 | 0.096 | >25 |
| 38-1 | 0.407 | 0.348 | 12.7 |

**Avg 20 h Coupled Exchange IC50 (μM)

NT = not tested

[1] The P atropisomer had an $IC_{50}$ of 27.4 μM in the 2 h Coupled Exchange assay.

The results presented in Table 33 have been generated with the in vitro assays described above. These assays may be used to test any of the compounds described herein to assess and characterize a compound's biological activity.

Furthermore, the Examples in Table 34 have been made using the methods provided herein or methods known in the art. The Examples of Table 34 have been evaluated in the Avg 2 h Coupled Exchange Assay and have shown no activity. The Examples of Table 34, however, have not been evaluated in the Avg 20 h Coupled Exchange Assay.

TABLE 34
| Ex.# | Chemical Structure | Name | LRMS: (ESI, +ve ion) m/z |
| --- | --- | --- | --- |
| I-1 | 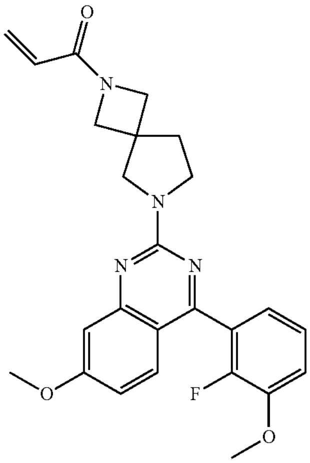 [SMILES: C=CC(=O)N1CC2(CCN(c3nc(-c4cccc(OC)c4F)c4ccc(OC)cc4n3)C2)C1] | 1-(6-(4-(2-fluoro-3-methoxyphenyl)-7-methoxy-2-quinazolinyl)-2,6-diazaspiro[3.4]octan-2-yl)-2-propen-1-one | 448.8 |
| I-2 | 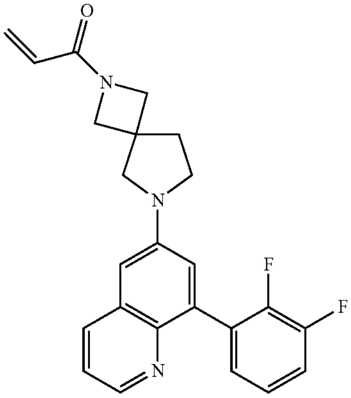 [SMILES: C=CC(=O)N1CC2(CCN(c3cc(-c4cccc(F)c4F)c4ncccc4c3)C2)C1] | 1-(6-(8-(2,3-difluorophenyl)-6-quinolinyl)-2,6-diazaspiro[3.4]octan-2-yl)-2-propen-1-one | 405.9 |
| I-3 | 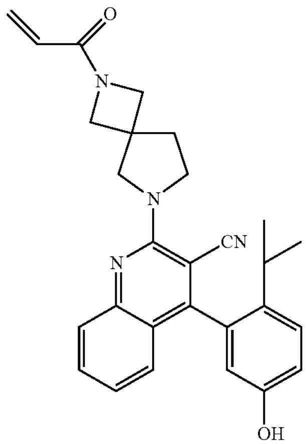 [SMILES: C=CC(=O)N1CC2(CCN(c3nc4ccccc4c(-c4cc(O)ccc4C(C)C)c3C#N)C2)C1] | 4-(5-hydroxy-2-(2-propanyl)phenyl)-2-(2-(2-propenoyl)-2,6-diazaspiro[3.4]octan-6-yl)-3-quinolinecarbonitrile | 453.0 |

TABLE 34-continued
| Ex.# | Chemical Structure | Name | LRMS: (ESI, +ve ion) m/z |
|---|---|---|---|
| I-4 | 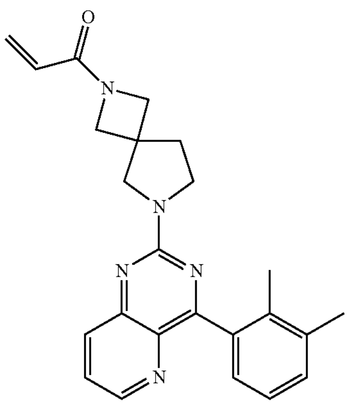 [SMILES: C=CC(=O)N1CC2(CCN(c3nc(-c4cccc(C)c4C)c4ncccc4n3)C2)C1] | 1-(6-(4-(2,3-dimethylphenyl)pyrido[3,2-d]pyrimidin-2-yl)-2,6-diazaspiro[3.4]octan-2-yl)-2-propen-1-one | 400.0 |
| I-5 | 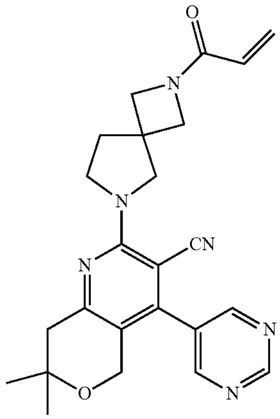 [SMILES: C=CC(=O)N1CC2(CCN(c3nc4c(c(-c5cncnc5)c3C#N)COC(C)(C)C4)C2)C1] | 7,7-dimethyl-2-(2-(2-propenoyl)-2,6-diazaspiro[3.4]octan-6-yl)-4-(5-pyrimidinyl)-7,8-dihydro-5H-pyrano[4,3-b]pyridine-3-carbonitrile | 432.0 |
| I-6 | 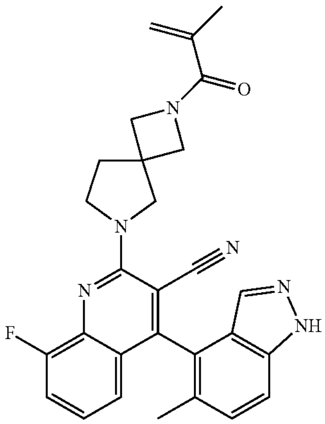 [SMILES: C=C(C)C(=O)N1CC2(CCN(c3nc4c(F)cccc4c(-c4c(C)ccc5[nH]ncc45)c3C#N)C2)C1] | 8-fluoro-4-(5-methyl-1H-indazol-4-yl)-2-(2-(2-methyl-2-propenoyl)-2,6-diazaspiro[3.4]octan-6-yl)-3-quinolinecarbonitrile | 482.2 |

TABLE 34-continued
| Ex.# | Chemical Structure | Name | LRMS: (ESI, +ve ion) m/z |
|---|---|---|---|
| I-7 | 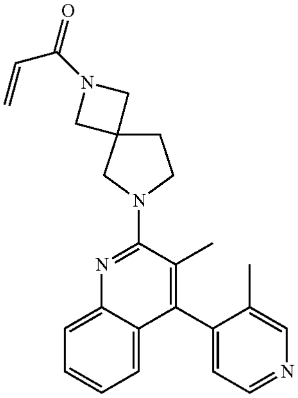 [SMILES: C=CC(=O)N1CC2(CCN(c3nc4ccccc4c(-c4ccncc4C)c3C)C2)C1] | 1-(6-(3-methyl-4-(3-methyl-4-pyridinyl)-2-quinolinyl)-2,6-diazaspiro[3.4]octan-2-yl)-2-propen-1-one | 399.2 |
| I-8 | 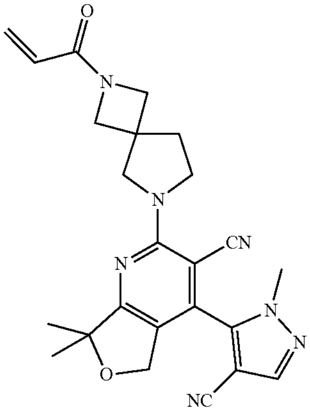 [SMILES: C=CC(=O)N1CC2(CCN(c3nc4c(c(-c5c(C#N)cnn5C)c3C#N)COC4(C)C)C2)C1] | 4-(4-cyano-1-methyl-1H-pyrazol-5-yl)-7,7-dimethyl-2-(2-(2-propenoyl)-2,6-diazaspiro[3.4]octan-6-yl)-5,7-dihydrofuro[3,4-b]pyridine-3-carbonitrile | 444.3 |
| I-9 | 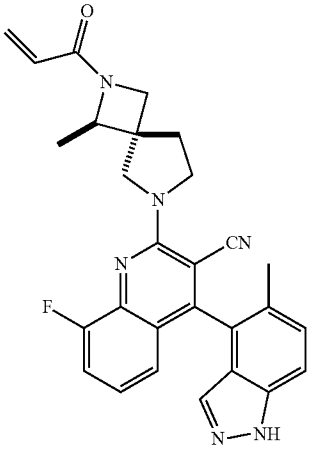 | 8-fluoro-4-(5-methyl-1H-indazol-4-yl)-2-((1R,4R)-1-methyl-2-(2-propenoyl)-2,6-diazaspiro[3.4]octan-6-yl)-3-quinolinecarbonitrile | 481.0 |

TABLE 34-continued
| Ex.# | Chemical Structure | Name | LRMS: (ESI, +ve ion) m/z |
| --- | --- | --- | --- |
| I-10 | 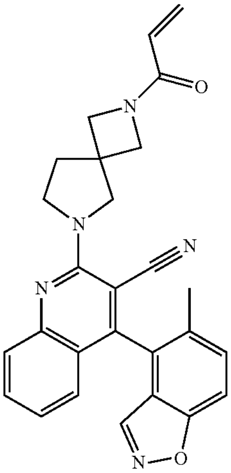 [SMILES: C=CC(=O)N1CC2(CCN(c3nc4ccccc4c(-c4c(C)ccc5oncc45)c3C#N)C2)C1] | 4-(5-methyl-1,2-benzoxazol-4-yl)-2-(2-(2-propenoyl)-2,6-diazaspiro[3.4]octan-6-yl)-3-quinolinecarbonitrile | 450.0 |
| I-11 | 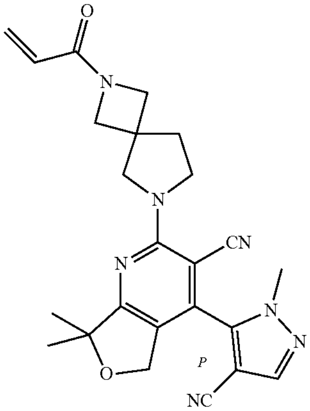 | (P)-4-(4-cyano-1-methyl-1H-pyrazol-5-yl)-7,7-dimethyl-2-(2-(2-propenoyl)-2,6-diazaspiro[3.4]octan-6-yl)-5,7-dihydrofuro[3,4-b]pyridine-3-carbonitrile | 444.3 |
| I-12 | 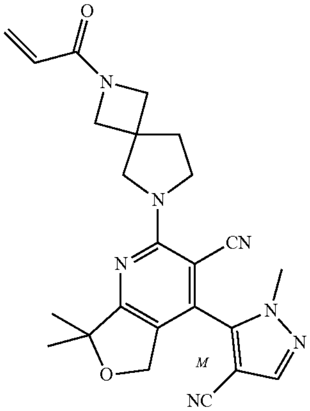 | (M)-4-(4-cyano-1-methyl-1H-pyrazol-5-yl)-7,7-dimethyl-2-(2-(2-propenoyl)-2,6-diazaspiro[3.4]octan-6-yl)-5,7-dihydrofuro[3,4-b]pyridine-3-carbonitrile | 444.3 |

TABLE 34-continued

| Ex.# | Chemical Structure | Name | LRMS: (ESI, +ve ion) m/z |
|---|---|---|---|
| I-13 | 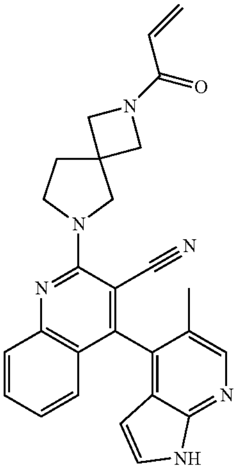 [SMILES: C=CC(=O)N1CC2(CCN(c3nc4ccccc4c(-c4c(C)cnc5[nH]ccc45)c3C#N)C2)C1] | 4-(5-methyl-1H-pyrrolo[2,3-b]pyridin-4-yl)-2-(2-(2-propenoyl)-2,6-diazaspiro[3.4]octan-6-yl)-3-quinolinecarbonitrile | 449.2 |
| I-14 | 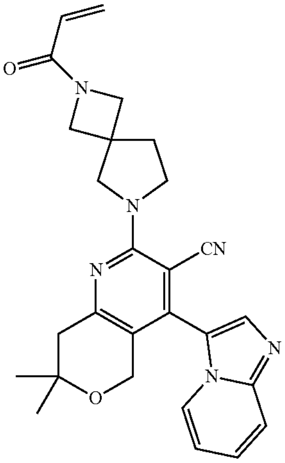 [SMILES: C=CC(=O)N1CC2(CCN(c3nc4c(c(-c5cnc6ccccn56)c3C#N)COC(C)(C)C4)C2)C1] | 4-(imidazo[1,2-a]pyridin-3-yl)-7,7-dimethyl-2-(2-(2-propenoyl)-2,6-diazaspiro[3.4]octan-6-yl)-7,8-dihydro-5H-pyrano[4,3-b]pyridine-3-carbonitrile | 469.3 |
| I-15 | 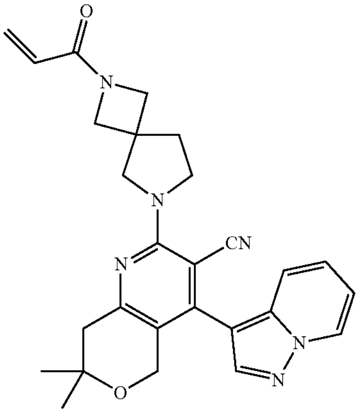 [SMILES: C=CC(=O)N1CC2(CCN(c3nc4c(c(-c5cnn6ccccc56)c3C#N)COC(C)(C)C4)C2)C1] | 7,7-dimethyl-2-(2-(2-propenoyl)-2,6-diazaspiro[3.4]octan-6-yl)-4-(pyrazolo[1,5-a]pyridin-3-yl)-7,8-dihydro-5H-pyrano[4,3-b]pyridine-3-carbonitrile | 469.2 |

TABLE 34-continued

| Ex.# | Chemical Structure | Name | LRMS: (ESI, +ve ion) m/z |
|---|---|---|---|
| I-16 | 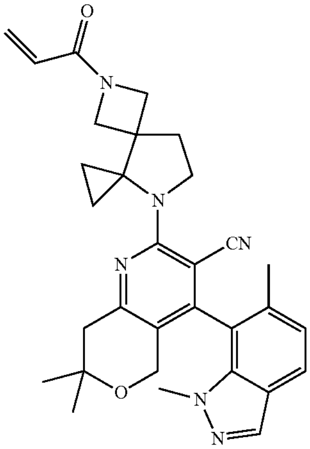 [SMILES: C=CC(=O)N1CC2(CCN(c3nc4c(c(-c5c(C)ccc6cnn(C)c56)c3C#N)COC(C)(C)C4)C23CC3)C1] | 4-(1,6-dimethyl-1H-indazol-7-yl)-7,7-dimethyl-2-(6-(2-propenoyl)-6,10-diazadispiro[2.0.3$^4$,3$^3$]decan-10-yl)-7,8-dihydro-5H-pyrano[4,3-b]pyridine-3-carbonitrile | 523.3 |
| I-17 | 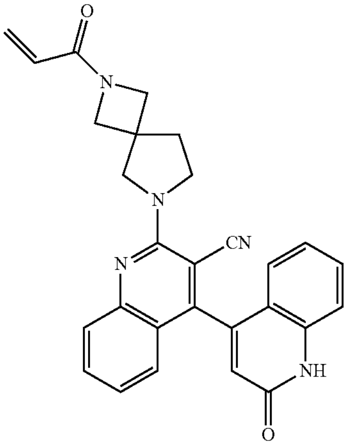 [SMILES: C=CC(=O)N1CC2(CCN(c3nc4ccccc4c(-c4cc(=O)[nH]c5ccccc45)c3C#N)C2)C1] | 2'-oxo-2-(2-(2-propenoyl)-2,6-diazaspiro[3.4]octan-6-yl)-1',2'-dihydro[4,4'-biquinoline]-3-carbonitrile | 462.2 |
| I-18 | 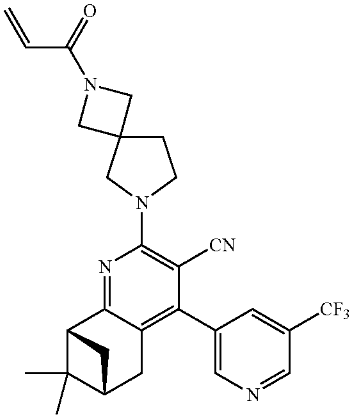 [SMILES: C=CC(=O)N1CC2(CCN(c3nc4c(c(-c5cncc(C(F)(F)F)c5)c3C#N)C[C@H]3C[C@@H]4C3(C)C)C2)C1] | (1R,9R)-10,10-dimethyl-4-(2-(2-propenoyl)-2,6-diazaspiro[3.4]octan-6-yl)-6-(5-(trifluoromethyl)-3-pyridinyl)-3-azatricyclo[7.1.1.0$^{2,7}$]undeca-2,4,6-triene-5-carbonitrile | 508.3 |

TABLE 34-continued

| Ex.# | Chemical Structure | Name | LRMS: (ESI, +ve ion) m/z |
|---|---|---|---|
| I-19 | 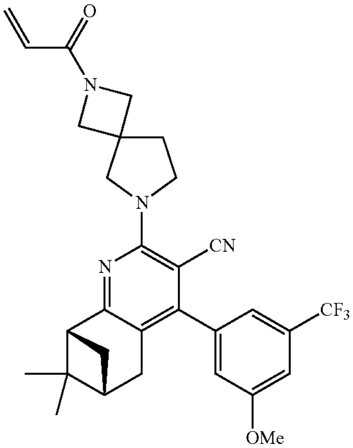 [SMILES: C=CC(=O)N1CC2(CCN(c3nc4c(c(-c5cc(OC)cc(C(F)(F)F)c5)c3C#N)C[C@H]3C[C@@H]4C3(C)C)C2)C1] | (1R,9R)-6-(3-methoxy-5-(trifluoromethyl)phenyl)-10,10-dimethyl-4-(2-(2-propenoyl)-2,6-diazaspiro[3.4]octan-6-yl)-3-azatricyclo[7.1.1.0$^{2,7}$]undeca-2,4,6-triene-5-carbonitrile | 537.2 |
| I-20 | 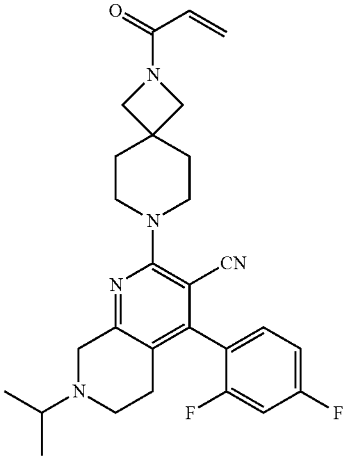 [SMILES: C=CC(=O)N1CC2(CCN(c3nc4c(c(-c5ccc(F)cc5F)c3C#N)CCN(C(C)C)C4)CC2)C1] | 4-(2,4-difluorophenyl)-7-(2-propanyl)-2-(2-(2-propenoyl)-2,7-diazaspiro[3.5]nonan-7-yl)-5,6,7,8-tetrahydro-1,7-naphthyridine-3-carbonitrile | 492.3 |
| I-21 | 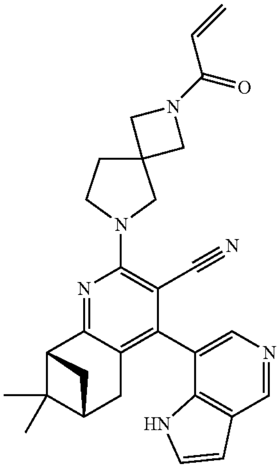 [SMILES: C=CC(=O)N1CC2(CCN(c3nc4c(c(-c5cncc6cc[nH]c56)c3C#N)C[C@H]3C[C@@H]4C3(C)C)C2)C1] | (1R,9R)-10,10-dimethyl-4-(2-(2-propenoyl)-2,6-diazaspiro[3.4]octan-6-yl)-6-(1H-pyrrolo[3,2-c]pyridin-7-yl)-3-azatricyclo[7.1.1.0$^{2,7}$]undeca-2,4,6-triene-5-carbonitrile | 479.4 |

TABLE 34-continued

| Ex.# | Chemical Structure | Name | LRMS: (ESI, +ve ion) m/z |
|---|---|---|---|
| I-22 | 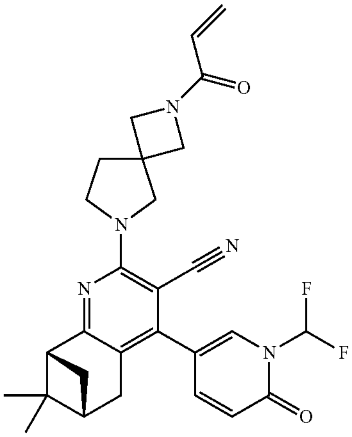 [SMILES: C=CC(=O)N1CC2(CCN(c3nc4c(c(-c5ccc(=O)n(C(F)F)c5)c3C#N)C[C@H]3C[C@@H]4C3(C)C)C2)C1] | (1R,9R)-6-(1-(difluoromethyl)-6-oxo-1,6-dihydro-3-pyridinyl)-10,10-dimethyl-4-(2-(2-propenoyl)-2,6-diazaspiro[3.4]octan-6-yl)-3-azatricyclo[7.1.1.0$^{2,7}$]undeca-2,4,6-triene-5-carbonitrile | 506.2 |
| I-23 | 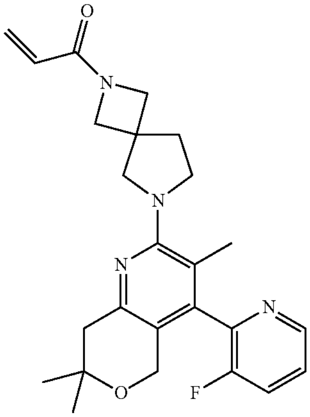 [SMILES: C=CC(=O)N1CC2(CCN(c3nc4c(c(-c5ncccc5F)c3C)COC(C)(C)C4)C2)C1] | 1-(6-(4-(3-fluoro-2-pyridinyl)-3,7,7-trimethyl-7,8-dihydro-5H-pyrano[4,3-b]pyridin-2-yl)-2,6-diazaspiro[3.4]octan-2-yl)-2-propen-1-one | 437.2 |
| I-24 | 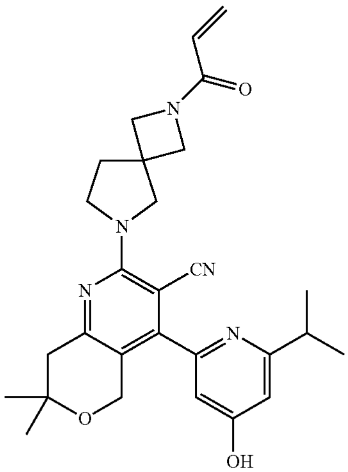 [SMILES: C=CC(=O)N1CC2(CCN(c3nc4c(c(-c5cc(O)cc(C(C)C)n5)c3C#N)COC(C)(C)C4)C2)C1] | 7,7-dimethyl-4-(4-oxo-6-(2-propanyl)-1,4-dihydro-2-pyridinyl)-2-(2-(2-propenoyl)-2,6-diazaspiro[3.4]octan-6-yl)-7,8-dihydro-5H-pyrano[4,3-b]pyridine-3-carbonitrile | 488.3 |

Compounds showing activity in the coupled exchange assay are useful in the methods provided herein (see Section “METHODS OF USE”). See, e.g., Laninan et al., 2020; Hong el al., 2020. The inhibitory effect on tumor growth of the compounds provided herein can be shown, for example, using the following animal model:

Tumor cells are cultured, harvested and implanted subcutaneously into the right flank of female athymic nude mice. When tumors reach about 200 mm$^3$, mice are randomized into treatment groups (n=10/group) and treatment is initiated (on days indicated on graphs). Tumor sizes and body weights are measured 2 to 3 times per week. Tumor volume is measured by digital calipers, calculated as L×W×H and expressed in mm$^3$. Statistical significance of observed differences between growth curves can be evaluated by repeated measures analysis of covariance (RMANOVA) of the log transformed tumor volume data with Dunnett adjusted multiple comparisons comparing the control group to the treatment group. For combination studies, RMANOVA can be run with the combination group compared one to one with each single agent treatment group.

REFERENCES

Caunt, C. J.; Sale, M. J.; Smith, P. D.; Cook, S. *J. Nat. Rev. Cancer* 2015, 15, 577.

Cerami, E.; Gao, J.; Dogrusoz, U.; Gross, B. E.; Sumer, S. O.; Aksoy, B. A.; Jacobsen, A.; Byrne, C. J.; Heuer, M. L.; Larsson, E.; Antipin, Y.; Reva, B.; Goldberg, A. P.; Sander, C.; Schultz N. *Cancer Discov.* 2012, 2(5), 401.

Canon, J.; Rex, K.; Saiki, A. Y.; Mohr, C.; Cooke, K; Bagal, D.; Gaida, K.; Holt, T.; Knutson, C. G.; Koppada, N.; Lamnan, B. A.; Weiner, J.; Rapaport, A. S.; San Miguel, T.; Ortiz, R.; Osgood, T.; Sun, J. R.; Zhu, X.; McCarter, J. D.; Volak, L. P.; Houk, B. E.; Fakih, M. G.; ONeil, B. H.; Price. T. J.; Falchook, G. S.; Desai, J.; Kuo, J.; Govindan. R.; Hong, D. S.; Ouyang, W.; Henary, H.; Arvedson, T.; Cee, V. J.; Lipford, J. R. *Nature* 2019, 575(7781), 217.

Cox, A. D.; Fesik, S. W.; Kimmelman, A. C.; Luo, J.; Der, C. *J. Nat. Rev. Drug Discov.* 2014, 13, 828.

Der, C. J.; Krontiris, T. G.; Cooper, G. M. Proc. Natl. *Acad. Sci.* USA 1982, 79, 3637.

Gao, J.; Aksoy, B. A.; Dogrusoz, U.; Dresdner, G.; Gross, B.; Sumer, S. O.; Sun, Y.; Jacobsen, A.; Sinha, R.; Larsson, E.; Cerami, E.; Sander, C.; Schultz. N. *Science Signaling* 2013, 6(269), p 11.

Holderfield, M.; Deuker, M. M.; McCormick, F.; McMahon, M. *Nat. Rev. Cancer* 2014, 14, 455.

Hong, D. S.; Fakih, M. G.; Strickler, J. H.; Desai, J.; Durm, G. A.; Shapiro, G. I.; Falchook, G. S.; Price, T. J.; Sacher, A.; Denlinger, C. S.; Bang, Y.-J.; Dy, G. K.; Krauss, J. C.; Kuboki, Y.; Kuo, J. C.; Coveler, A. L.; Park, K.; Kim, T. W.; Barlesi, F.; Munster, P. N.; Ramalingam, S. S.; Burns, T. F., Meric-Bernstam, F.; Henary, H.; Ngang, J.; Ngann-chamnanrith, G.; Kim, J.; Houk, B.; Canon, J.; Lipford, J. R.; Friberg, G.; Lito, P.; Govindan, R.; Bob T. Li, B. T. *N. Engl. J. Med.* 2020, 383, 1207.

Lanman, B. A.; Allen, J. R.; Allen, J. G.; Amegadzie, A. K.; Ashton, K. S.; Booker, S. K.; Chen, J. J.; Chen, N.; Frohn, M.; Goodman, G.; Kopecky, D. J.; Liu, L.; Lopez, P.; Low, J. D.; Ma, V.; Minatti, E.; Nguyen, T. T.; Nishimura, N.; Pickrell, A. J.; Reed, A. B.; Shin, Y.; Siegmund, A. C.; Tamayo, N. A.; Tegley, C. M.; Walton, M. C.; Wang, H.-L.; Wurz, R. P.; Xue, M.; Yang, K. C.; Achanta, P.; Bartberger, M. D.; Canon, J.; Hollis, L. S.; McCarter, J. D.; Mohr, C.; Rex. K.; Saiki A. Y.; San Miguel. T.; Volak, L. P.; Wang, K. H.; Whittington, D. A.; Zech, S. G.; Lipford, J. R.; Cee, V. J. *J. Med. Chem.* 2020, 63, 52.

Malumbres, M.; Barbacid, M. *Nat. Rev. Cancer* 2003, 3, 459.

O'Bryan, J. P. *Pharmacol. Res.* 2019, 139, 503.

Ostrem, J. M.; Peters. U.; Sos, M. L.; Wells, J. A.; Shokat, K. M. *Nature* 2013, 503, 548.

Simanshu, D. K.; Nissley, D. V.; McCormick, F. *Cell* 2017, 170, 17.

Sridhar, S. S.; Seymour, L.; Shepherd, F. A. *Lancet Oncol.* 2003, 4, 397.

Vojtek, A. B.; Der, C. *J. J. Biol. Chem.* 1998, 273, 19925.

All references, for example, a scientific publication or patent application publication, cited herein are incorporated herein by reference in their entirety and for all purposes to the same extent as if each reference was specifically and individually indicated to be incorporated by reference in its entirety for all purposes.

What is claimed is:

1. A compound of Formula I (I)

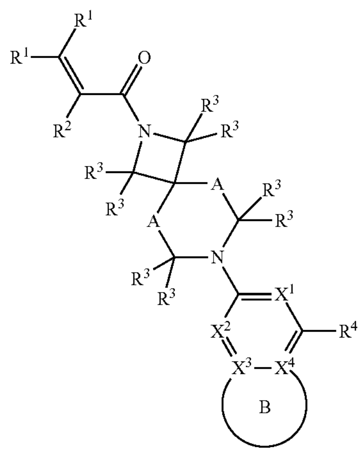

or a pharmaceutically acceptable salt thereof, wherein $R^1$ at each occurrence independently is H, $^2H$, $C_{1-4}$haloalkyl, $C_{1-4}$alkoxy, —$CH_2OH$, —$(CH_2)O(C_{1-4}alkyl)$, —$(CH_2)O(C_{1-4}haloalkyl)$, —$(CH_2)$-$C_{1-4}$dialkylamino, aziridin-1-yl-methyl, azetidin-1-yl-methyl, pyrrolidine-1-yl-methyl, piperidin-1-yl-methyl, or morpholin-1-yl-methyl;

$R^2$ is H, $^2H$, halogen, —CN, $C_{1-4}$alkyl, $C_{1-4}$haloalkyl, —$CH_2CN$, —$CH_2OH$, $C_{1-4}$alkoxy, or $C_{1-4}$haloalkoxy;

wherein, optionally, one $R^1$ and $R^2$ together with the carbon atoms to which they are attached form a

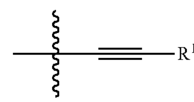

group;

$R^3$ at each occurrence independently is H, halogen, CN, OH, $C_{1-4}$alkyl, $C_{1-4}$haloalkyl, —$CH_2CN$, —$CH_2OH$, $C_{1-4}$alkoxy, or $C_{1-4}$haloalkoxy, wherein two substituents $R^3$ attached to the same carbon atom optionally form together with said carbon atom a $C_{3-6}$cycloalkyl or a carbonyl group;

A at each occurrence independently is $CR^3R^3$ or absent;

$R^4$ is 1,2,3,4-tetrahydro-8-quinolinyl, 6 or 10 membered aryl, or 5 to 10 membered heteroaryl, wherein the aryl or heteroaryl is optionally substituted with 1 to 5 substituents independently selected from OH, halogen, —CN, $NH_2$, $C_{1-4}$alkyl, $C_{1-4}$deuteroalkyl, $C_{1-4}$haloalkyl, $C_{1-4}$alkoxy, $C_{1-4}$haloalkoxy, —$SO_2NH_2$, and —$NHSO_2CH_3$, wherein the $C_{1-4}$alkyl is optionally substituted with OH;

$X^1$ is $CR^5$ or N;

$X^2$ is CH, CF, or N;

$X^3$ is C or N;

$X^4$ is C or N;

$R^5$ is H, halogen, CN, —$COO(C_{1-4}alkyl)$, $C_{1-4}$alkyl, $C_{2-4}$alkenyl, $C_{1-4}$haloalkyl, —$(CH_2)_m(C_{1-4}alkoxy)$, —$(CH_2)_m(C_{1-4}$haloalkoxy), $C_{3-5}$cycloalkyl, $C_{3-5}$cyclohaloalkyl, or $C_{3-5}$heterocycloalkyl;

B together with the atoms to which it is attached forms a 4 to 7 membered fully saturated, fully unsaturated, or partially unsaturated carbocyclic or heterocyclic ring system, wherein the heterocyclic ring system comprises 1 to 5 heteroatoms independently selected from N, O, and S, wherein the ring system is optionally substituted with 1 to 5 substituents $R^6$;

$R^6$ at each occurrence independently is halogen, OH, —CN, —$NH_2$, $C_{1-6}$alkyl, $C_{1-6}$haloalkyl, $C_{1-4}$alkoxy, $C_{1-4}$haloalkoxy, —C(=O)$C_{1-6}$alkyl, —$R^7$-($C_{3-5}$cycloalkyl), —$R^7$-($C_{3-5}$cyclohaloalkyl), —$R^7$-($C_{3-6}$heterocycloalkyl), —$R^7$-(phenyl), or —$R^7$-(5 to 6 membered heteroaryl), wherein the $C_{1-6}$alkyl is optionally substituted with $C_{1-4}$alkoxy, $C_{1-4}$alkylamino, $C_{1-4}$dialkylamino, —CO($C_{1-4}$alkylamino) or —CO($C_{1-4}$dialkylamino), wherein the $C_{1-6}$haloalkyl is optionally substituted with a OH, wherein the $C_{3-6}$heterocycloalkyl is optionally substituted with 1 to 3 substituents independently selected from (=O) and $C_{1-6}$alkyl, wherein the phenyl is optionally substituted with 1 to 3 substituents independently selected from halogen and $C_{1-4}$alkoxy, wherein the heteroaryl is optionally substituted with 1 to 3 substituents independently selected from halogen, —$(CH_2)_{1-3}$OH, $(CH_2)_{1-3O}$ ($C_{1-4}$alkyl), —$(CH_2)_{1-3O}$ ($C_{1-4}$haloalkyl), $C_{1-4}$alkyl, and $C_{1-4}$haloalkyl, wherein two substituents $R^6$ together optionally form a —$(CH_2)_n$— group creating a ring together with the ring atom or ring atoms to which the two substituents $R^6$ are attached, wherein the —$(CH_2)_n$— group optionally has one —$CH_2$— group substituted with one heteroatom selected from N, O, and S, and wherein the —$(CH_2)_n$— group is optionally substituted with 1 to 3 substituents independently selected from halogen and $C_{1-6}$alkyl;

$R^7$ is $(CH_2)$ m or CO;

n is 1, 2, 3, 4, 5 or 6; and m is 0 or 1.

2. The compound according to claim 1 or a pharmaceutically acceptable salt thereof, wherein (a) $R^1$ at each occurrence independently is H, $^2$H, $C_{1-4}$haloalkyl, —$CH_2$OH, —$(CH_2)$O($C_{1-4}$alkyl), —$(CH_2)$O ($C_{1-4}$haloalkyl), or —$(CH_2)$-$C_{1-4}$dialkylamino; or (b) $R^2$ is H or halogen; or (c) both (a) and (b).

3. The compound according to claim 1 or a pharmaceutically acceptable salt thereof, wherein one $R^1$ and $R^2$ together with the carbon atoms to which they are attached form

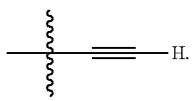

4. The compound according to claim 1 or a pharmaceutically acceptable salt thereof, wherein $R^3$ at each occurrence independently is H, halogen, $C_{1-4}$alkyl, $C_{1-4}$haloalkyl, or —$CH_2$OH.

5. The compound according to claim 1 or a pharmaceutically acceptable salt thereof, wherein (a) one A is absent and the other A is $CR^3R^3$; or (b) both A are absent.

6. The compound according to claim 1 or a pharmaceutically acceptable salt thereof, wherein

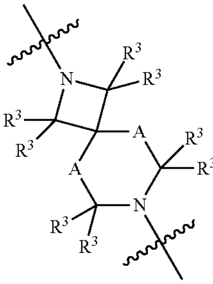

is

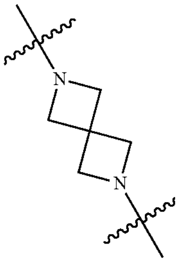

,

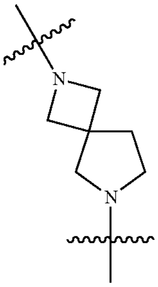

,

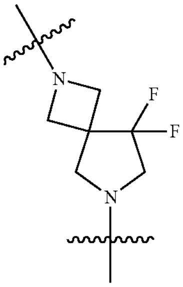

,

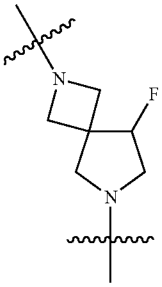

,

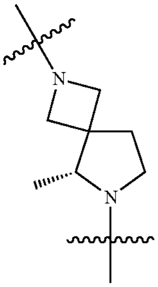

,

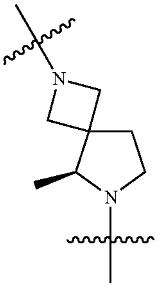

,

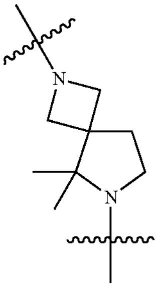

,

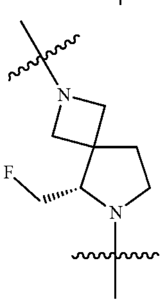

,

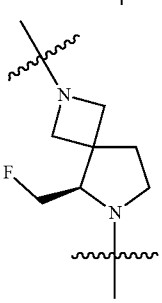

,

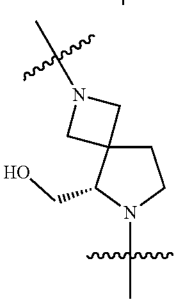

,

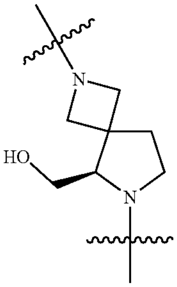

,

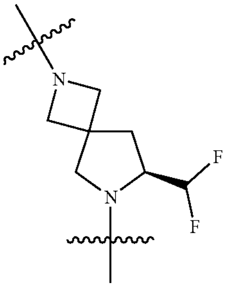

,

-continued

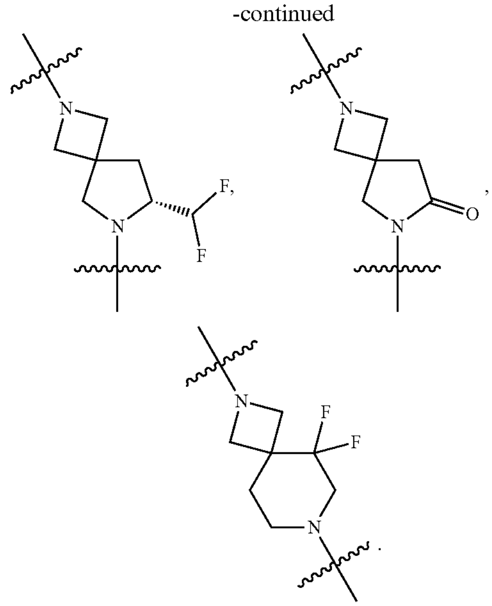

7. The compound according to claim 1 or a pharmaceutically acceptable salt thereof, wherein $R^4$ is 6 or 10 membered aryl or 5 to 10 membered heteroaryl, wherein the aryl or heteroaryl is optionally substituted with 1 to 5 substituents independently selected from OH, halogen, —CN, $NH_2$, $C_{1-4}$alkyl, $C_{1-4}$deuteroalkyl, $C_{1-4}$haloalkyl, $C_{1-4}$alkoxy, —$SO_2NH_2$, and —$NHSO_2CH_3$, wherein the $C_{1-4}$alkyl is optionally substituted with OH.

8. The compound according to claim 1 or a pharmaceutically acceptable salt thereof, wherein the 6 or 10 membered aryl is: (a) phenyl; or (b) naphthalenyl; and the 5 to 10 membered heteroaryl is 1,3-thiazolyl, pyrazolyl, pyridyl, benzothiophenyl, indolyl, indazolyl, 1,3-benzothiazolyl, 1,2,3-benzothiadiazolyl, 2,1,3-benzoxadiazolyl, quinolinyl, isoquinolinyl, quinoxalinyl, imidazo[1,5-a]pyridinyl, or pyrazolo[3,4-b]pyridinyl.

9. The compound according to claim 1 or a pharmaceutically acceptable salt thereof, wherein $R^4$ is

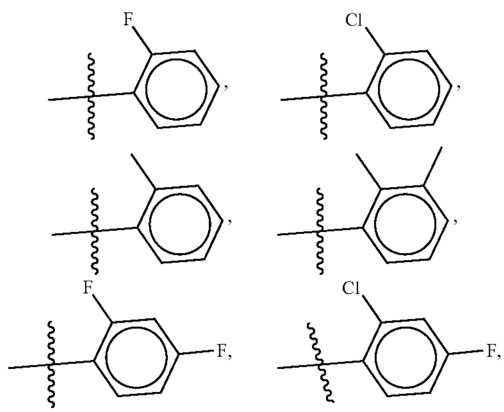

-continued

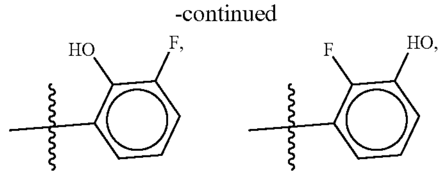

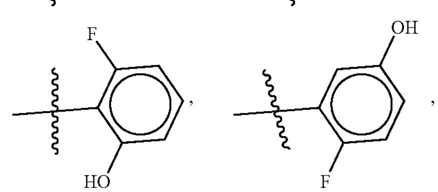

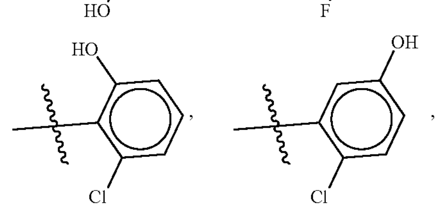

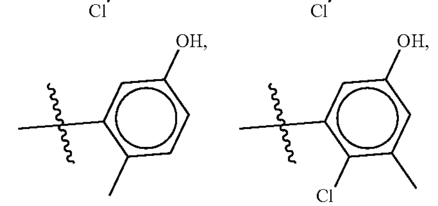

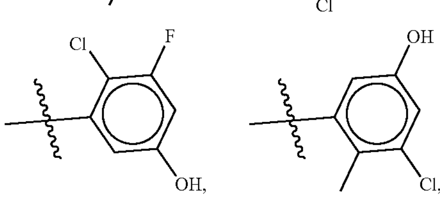

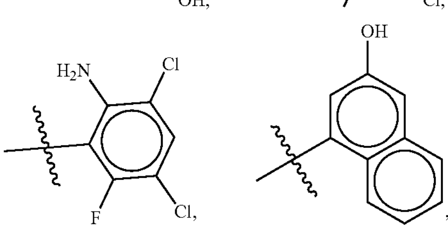

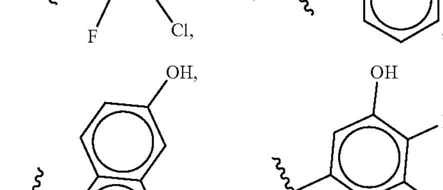

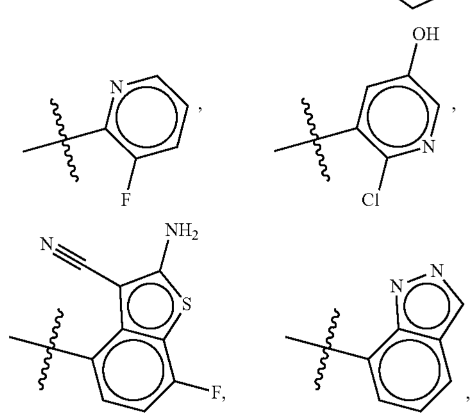

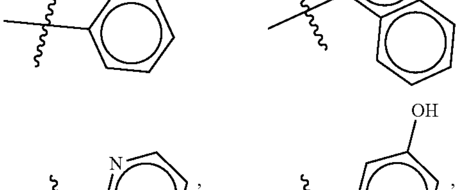

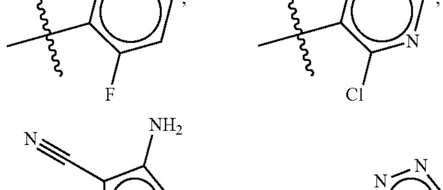

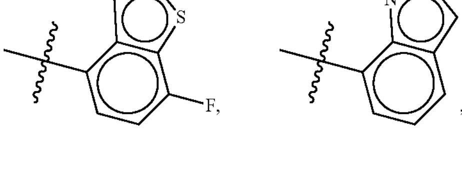

-continued

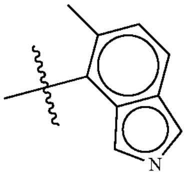, 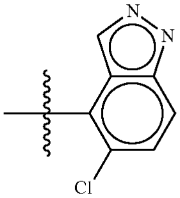, 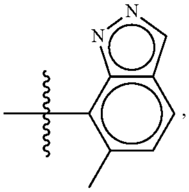, 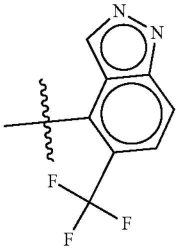, 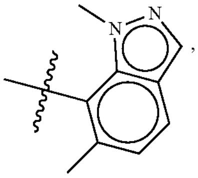, 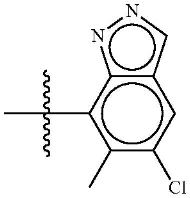, 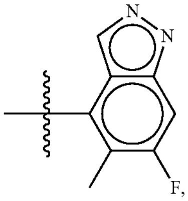, 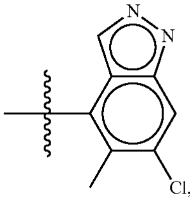, 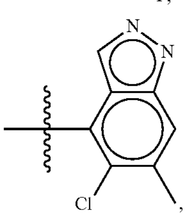, 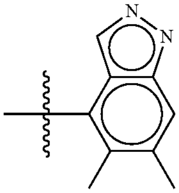, 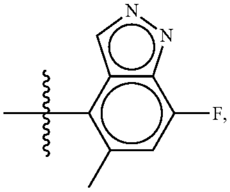, 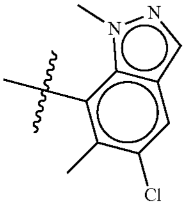, 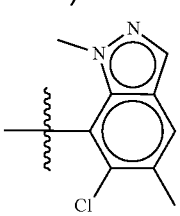, 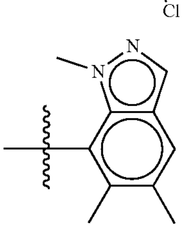, 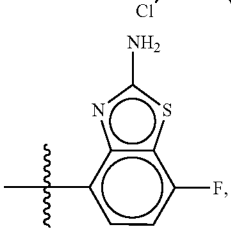, 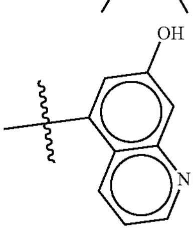, or -continued

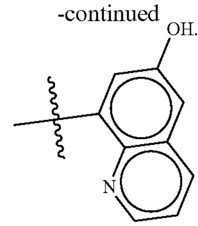.

10. The compound according to claim 1 or a pharmaceutically acceptable salt thereof, wherein $X^1$ is N, $X^2$ is N, $X^3$ is C, and $X^4$ is C; or $X^1$ is $CR^5$, $X^2$ is N, $X^3$ is C, and $X^4$ is C; or $X^1$ is $CR^5$, $X^2$ is CH, $X^3$ is C, and $X^4$ is C; or $X^1$ is $CR^5$, $X^2$ is CH, $X^3$ is N, and $X^4$ is C; or $X^1$ is $CR^5$, $X^2$ is CH, $X^3$ is C, and $X^4$ is N.

11. The compound according to claim 1 or a pharmaceutically acceptable salt thereof, wherein $R^5$ is H, halogen, CN, $-COO(C_{1-4}alkyl)$, $C_{1-4}alkyl$, $C_{2-4}alkenyl$, $C_{1-4}haloalkyl$, $-(CH_2)_m(C_{1-4}alkoxy)$, or, $C_{3-5}cycloalkyl$.

12. The compound according to claim 11 or a pharmaceutically acceptable salt thereof, wherein $R^5$ is F, CI, or methyl.

13. The compound according to claim 1 or a pharmaceutically acceptable salt thereof, wherein B together with the atoms to which it is attached forms a ring system selected from

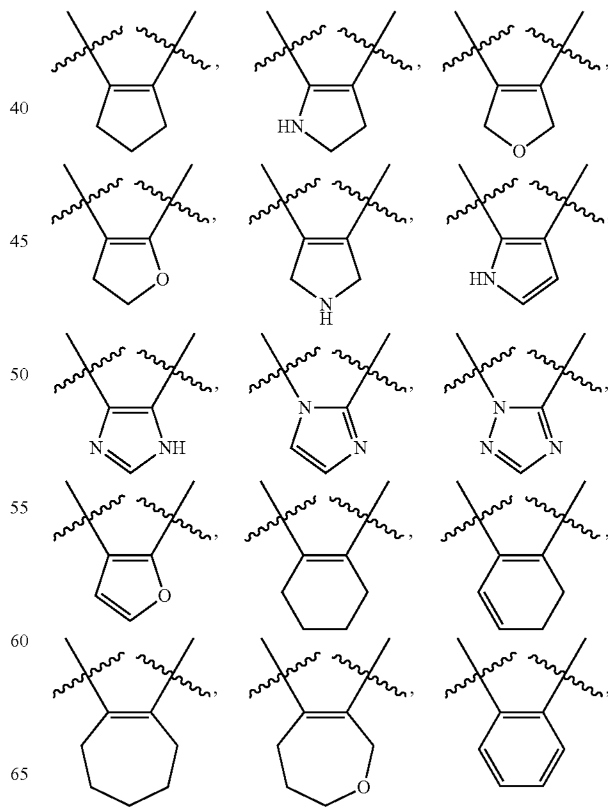

-continued

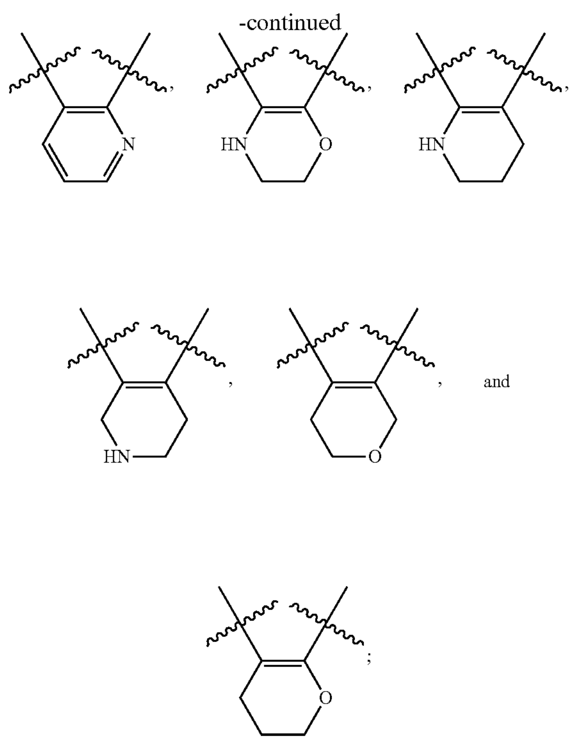

wherein the ring system is optionally substituted with 1 to 5 substituents $R^6$.

14. The compound according to claim 1 or a pharmaceutically acceptable salt thereof, wherein B together with the atoms to which it is attached forms a ring system selected from

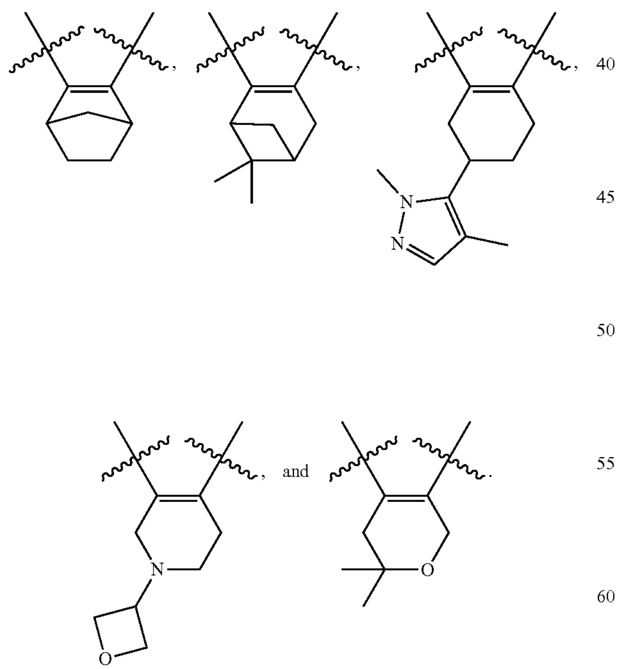

15. The compound according to claim 1 or a pharmaceutically acceptable salt thereof, wherein the compound is a compound of:

(a) Formula II

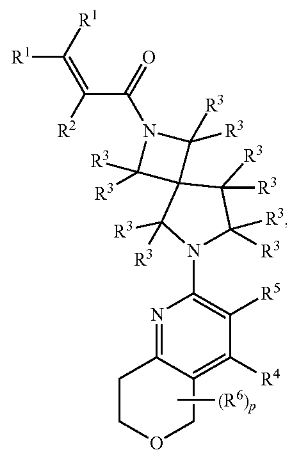

wherein $R^1$ at each occurrence independently, $R^2$, $R^3$ at each occurrence independently, $R^4$, $R^5$, and $R^6$ at each occurrence independently are defined as in claim 1; and p is 0 to 5; or (b) Formula III

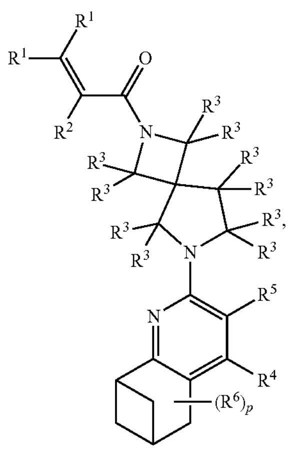

wherein $R^1$ at each occurrence independently, $R^2$, $R^3$ at each occurrence independently, $R^4$, $R^5$, and $R^6$ at each occurrence independently are defined as in claim 1; and p is 0 to 3; or (c) Formula IV (IV)

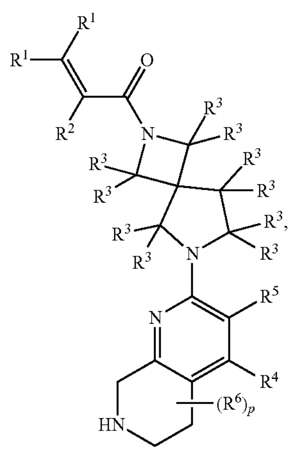

wherein $R^1$ at each occurrence independently, $R^2$, $R^3$ at each occurrence independently, $R^4$, $R^5$, and $R^6$ at each occurrence independently are defined as in claim 1; and p is 0 to 5; or (d) Formula V (V)

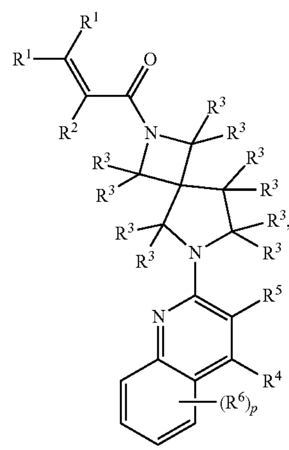

wherein $R^1$ at each occurrence independently, $R^2$, $R^3$ at each occurrence independently, $R^4$, $R^5$, and $R^6$ at each occurrence independently are defined as in claim 1; and p is 0 to 4; or (e) Formula VI (VI)

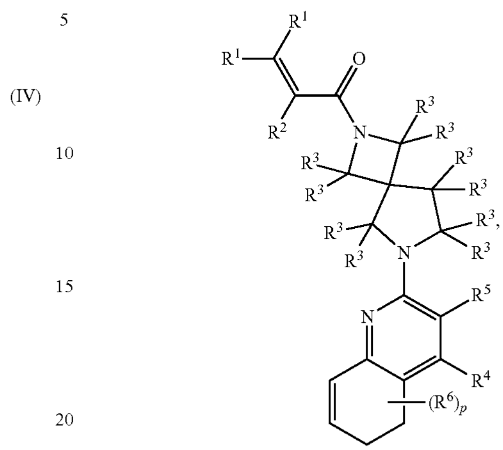

wherein $R^1$ at each occurrence independently, $R^2$, $R^3$ at each occurrence independently, $R^4$, $R^5$, and $R^6$ at each occurrence independently are defined as in claim 1; and p is 0 to 5; or (f) Formula VII (VII)

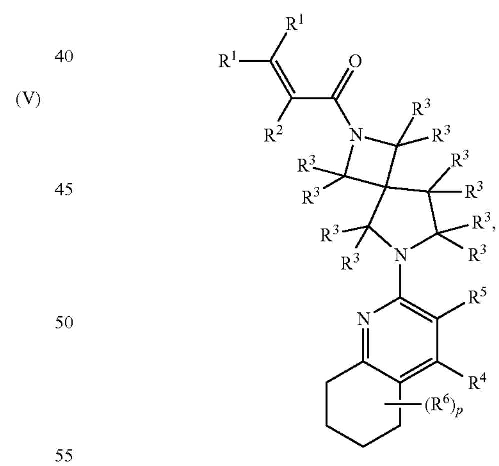

wherein $R^1$ at each occurrence independently, $R^2$, $R^3$ at each occurrence independently, $R^4$, $R^5$, and $R^6$ at each occurrence independently are defined as in claim 1; and p is 0 to 5; or (g) Formula VIII (VIII)

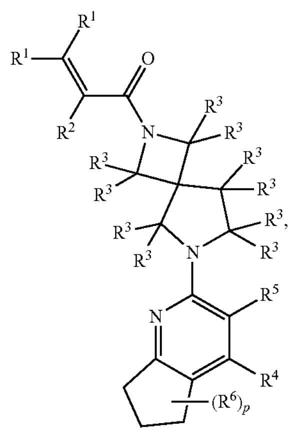

wherein $R^1$ at each occurrence independently, $R^2$, $R^3$ at each occurrence independently, $R^4$, $R^5$, and $R^6$ at each occurrence independently are defined as in claim 1; and p is 0 to 5; or (h) Formula IX (IX)

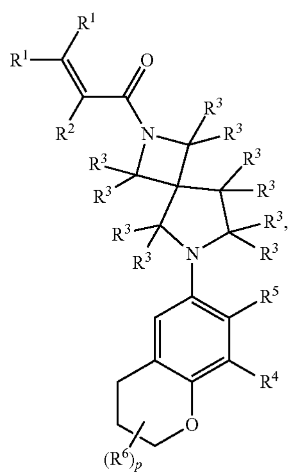

wherein $R^1$ at each occurrence independently, $R^2$, $R^3$ at each occurrence independently, $R^4$, $R^5$, and $R^6$ at each occurrence independently are defined as in claim 1; and p is 0 to 5; or (i) Formula X (X)

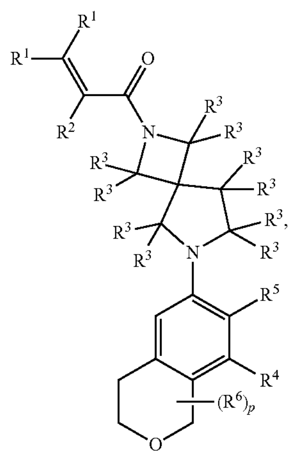

wherein $R^1$ at each occurrence independently, $R^2$, $R^3$ at each occurrence independently, $R^4$, $R^5$, and $R^6$ at each occurrence independently are defined as in claim 1; and p is 0 to 5; or (j) Formula XI (XI)

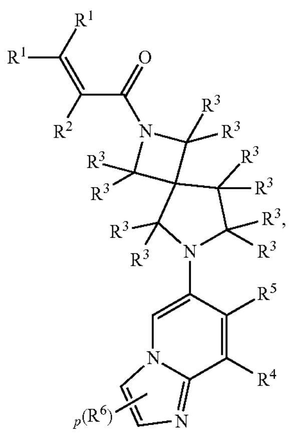

wherein $R^1$ at each occurrence independently, $R^2$, $R^3$ at each occurrence independently, $R^4$, $R^5$, and $R^6$ at each occurrence independently are defined as in claim 1; and p is 0 to 2; or (k) Formula XII (XII)

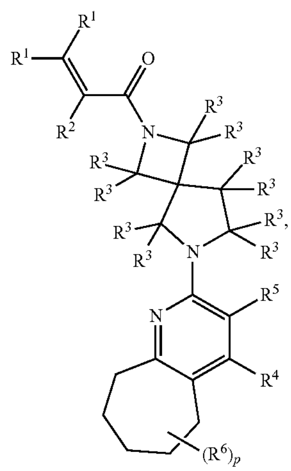

wherein $R^1$ at each occurrence independently, $R^2$, $R^3$ at each occurrence independently, $R^4$, $R^5$, and $R^6$ at each occurrence independently are defined as in claim 1; and p is 0 to 5; or (l) Formula XIII (XIII)

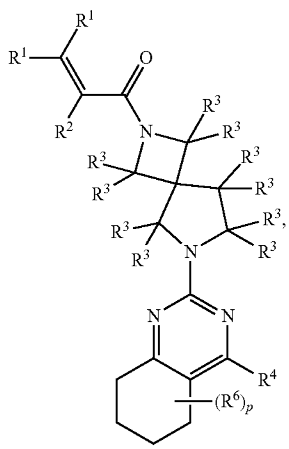

wherein $R^1$ at each occurrence independently, $R^2$, $R^3$ at each occurrence independently, $R^4$, $R^5$, and $R^6$ at each occurrence independently are defined as in claim 1; and p is 0 to 5; or (m) Formula XIV (XIV)

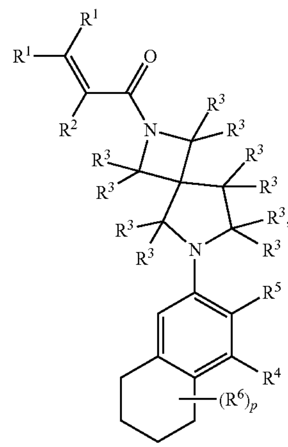

wherein $R^1$ at each occurrence independently, $R^2$, $R^3$ at each occurrence independently, $R^4$, $R^5$, and $R^6$ at each occurrence independently are defined as in claim 1; and p is 0 to 5; or (n) Formula XV (XV)

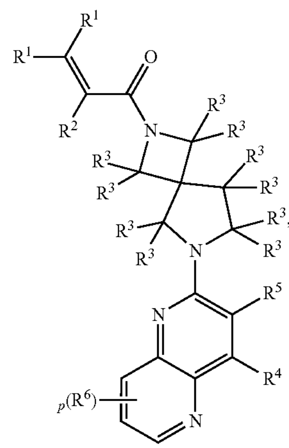

wherein $R^1$ at each occurrence independently, $R^2$, $R^3$ at each occurrence independently, $R^4$, $R^5$, and $R^6$ at each occurrence independently are defined as in claim 1; and p is 0 to 3.

16. The compound according to claim 1 or a pharmaceutically acceptable salt thereof, wherein $R^6$ at each occurrence independently is $C_{1-6}$alkyl, $C_{1-6}$haloalkyl, $C_{1-4}$alkoxy, —$R^7$—($C_{3-5}$cycloalkyl), —$R^7$—($C_{3-6}$heterocycloalkyl), —$R^7$-(phenyl), or —$R^7$-(5 to 6 membered heteroaryl), wherein the $C_{1-6}$alkyl is optionally substituted with $C_{1-4}$alkoxy, wherein the $C_{3-6}$heterocycloalkyl is optionally substituted with $C_{1-6}$alkyl, wherein the phenyl is optionally substituted with $C_{1-4}$alkoxy, wherein the heteroaryl is optionally substituted with 1 to 3 substituents independently selected from halogen, $-(CH_2)_{1-3}OH$ and $C_{1-4}$alkyl, and wherein two substituents $R^6$ together optionally form a $-(CH_2)_n-$ group creating a ring together with the ring atom or ring atoms to which the two substituents $R^6$ are attached, and the $-(CH_2)_n-$ group optionally has one $-CH_2-$ group substituted with an —O— atom.

17. The compound according to claim 1 or a pharmaceutically acceptable salt thereof, wherein $R^6$ at each occurrence independently is methyl, oxetan-3-yl, or 1,4-dimethyl-1H-pyrazol-5-yl, wherein two substituents $R^6$ together optionally form a $-(CH_2)_n-$ group creating a ring together with the ring atom or ring atoms to which the two substituents $R^6$ are attached.

18. The compound according to claim 1 or a pharmaceutically acceptable salt thereof, wherein:

(a) $R^7$ is $(CH_2)_m$; or (b) n is 1; or (c) m is 0; or (d) any combination of (a), (b), and (c).

19. The compound according to claim 1 or a pharmaceutically acceptable salt thereof, wherein the compound is 8-fluoro-2-(5-(fluoromethyl)-2-(2-propenoyl)-2,6-diazaspiro[3.4]octan-6-yl)-4-(5-methyl-1H-indazol-4-yl)-3-quinolinecarbonitrile;

8-(5-methyl-1H-indazol-4-yl)-3-(4-methyl-1-piperazinyl)-6-(2-(2-propenoyl)-2,6-diazaspiro[3.4]octan-6-yl) imidazo[1,2-a]pyridine-7-carbonitrile;

8-(5-methyl-1H-indazol-4-yl)-6-(2-(2-propenoyl)-2,6-diazaspiro[3.4]octan-6-yl)-2-(1,3-thiazol-2-yl)imidazo [1,2-a]pyridine-7-carbonitrile;

4-(5-methyl-1H-indazol-4-yl)-2-(2-(2-propenoyl)-2,6-diazaspiro[3.4]octan-6-yl)-6,7,8,9-tetrahydro-5H-cyclohepta[b]pyridine-3-carbonitrile;

(P)-1-(6-(3,7,7-trimethyl-4-(5-methyl-1H-indazol-4-yl)-5,6,7,8-tetrahydro-2-quinolinyl)-2,6-diazaspiro[3.4] octan-2-yl)-2-propen-1-one;

1-(6-(4-(6-hydroxy-1-naphthalenyl)-3,7,7-trimethyl-5,6,7,8-tetrahydro-2-quinolinyl)-2,6-diazaspiro[3.4]octan-2-yl)-2-propen-1-one;

(P)-1-(6-(4-(6-hydroxy-1-naphthalenyl)-3,7,7-trimethyl-5,6,7,8-tetrahydro-2-quinolinyl)-2,6-diazaspiro[3.4] octan-2-yl)-2-propen-1-one;

1-(6-(4-(2-amino-7-fluoro-1,3-benzothiazol-4-yl)-3,7,7-trimethyl-5,6,7,8-tetrahydro-2-quinolinyl)-2,6-diazaspiro[3.4]octan-2-yl)-2-propen-1-one;

(P)-1-(6-(4-(2-amino-7-fluoro-1,3-benzothiazol-4-yl)-3,7,7-trimethyl-5,6,7,8-tetrahydro-2-quinolinyl)-2,6-diazaspiro[3.4]octan-2-yl)-2-propen-1-one;

1-(6-(4-(1,6-dimethyl-1H-indazol-7-yl)-3,7,7-trimethyl-5,6,7,8-tetrahydro-2-quinolinyl)-2,6-diazaspiro[3.4] octan-2-yl)-2-propen-1-one;

(P)-1-(6-(3,7,7-trimethyl-4-(6-methyl-1H-indazol-7-yl)-5,6,7,8-tetrahydro-2-quinolinyl)-2,6-diazaspiro[3.4] octan-2-yl)-2-propen-1-one;

1-(6-(4-(3-hydroxy-1-naphthalenyl)-3,7,7-trimethyl-5,6,7,8-tetrahydro-2-quinolinyl)-2,6-diazaspiro[3.4]octan-2-yl)-2-propen-1-one;

1-(6-(3,7,7-trimethyl-4-(5-methyl-1H-indazol-4-yl)-5,6,7,8-tetrahydro-2-quinolinyl)-2,6-diazaspiro[3.4]octan-2-yl)-2-propen-1-one;

(1R,9R)-10, 10-dimethyl-4-(2-(2-propenoyl)-2,6-diazaspiro[3.4]octan-6-yl)-6-(5-(trifluoromethyl)-1H-indazol-4-yl)-3-azatricyclo [7.1.1.02,7] undeca-2,4,6-triene-5-carbonitrile;

1-(6-(4-(6-chloro-5-methyl-1H-indazol-4-yl)-3,7,7-trimethyl-7,8-dihydro-5H-pyrano [4,3-b]pyridin-2-yl)-2,6-diazaspiro[3.4]octan-2-yl)-2-propen-1-one;

(P)-(1R,8S)-6-(3-hydroxy-1-naphthalenyl)-4-(2-(2-propenoyl)-2,6-diazaspiro[3.4]octan-6-yl)-3-azatricyclo [6.2.1.02,7] undeca-2,4,6-triene-5-carbonitrile;

(1R,8S)-6-(3-hydroxy-1-naphthalenyl)-4-(2-(2-propenoyl)-2,6-diazaspiro[3.4]octan-6-yl)-3-azatricyclo [6.2.1.02,7] undeca-2,4,6-triene-5-carbonitrile or (1S, 8R)-6-(3-hydroxy-1-naphthalenyl)-4-(2-(2-propenoyl)-2,6-diazaspiro[3.4]octan-6-yl)-3-azatricyclo [6.2.1.02,7] undeca-2,4,6-triene-5-carbonitrile;

(M)-(1R,8S)-6-(3-hydroxy-1-naphthalenyl)-4-(2-(2-propenoyl)-2,6-diazaspiro[3.4]octan-6-yl)-3-azatricyclo [6.2.1.02,7] undeca-2,4,6-triene-5-carbonitrile;

(1R,9R)-6-(6-hydroxy-8-isoquinolinyl)-10, 10-dimethyl-4-(2-(2-propenoyl)-2,6-diazaspiro[3.4]octan-6-yl)-3-azatricyclo [7.1.1.02,7] undeca-2,4,6-triene-5-carbonitrile;

(1R,9R)-6-(7-hydroxy-5-quinolinyl)-10,10-dimethyl-4-(2-(2-propenoyl)-2,6-diazaspiro[3.4]octan-6-yl)-3-azatricyclo [7.1.1.02,7] undeca-2,4,6-triene-5-carbonitrile;

(P)-(1R,9R)-6-(6-hydroxy-8-quinolinyl)-10,10-dimethyl-4-(2-(2-propenoyl)-2,6-diazaspiro[3.4]octan-6-yl)-3-azatricyclo [7.1.1.02,7] undeca-2,4,6-triene-5-carbonitrile;

(P)-(1R,9R)-6-(7-hydroxy-5-quinolinyl)-10,10-dimethyl-4-(2-(2-propenoyl)-2,6-diazaspiro[3.4]octan-6-yl)-3-azatricyclo [7.1.1.02,7] undeca-2,4,6-triene-5-carbonitrile;

1-(6-(7-methoxy-3-methyl-4-(5-methyl-1H-indazol-4-yl)-2-quinolinyl)-2,6-diazaspiro[3.4]octan-2-yl)-2-propen-1-one;

8-(3-hydroxy-1-naphthalenyl)-6-(2-(2-propenoyl)-2,6-diazaspiro[3.4]octan-6-yl)-3,4-dihydro-2H-chromene-7-carbonitrile;

(M)-8-(3-hydroxy-1-naphthalenyl)-6-(2-(2-propenoyl)-2,6-diazaspiro[3.4]octan-6-yl)-3,4-dihydro-2H-chromene-7-carbonitrile;

1-((5S)-5-methyl-6-(3-methyl-4-(5-methyl-1H-indazol-4-yl)-2-quinolinyl)-2,6-diazaspiro[3.4]octan-2-yl)-2-propen-1-one;

(P)-1-((5S)-6-(7-fluoro-3-methyl-4-(5-methyl-1H-indazol-4-yl)-2-quinolinyl)-5-methyl-2,6-diazaspiro[3.4] octan-2-yl)-2-propen-1-one;

(1R,9R)-6-(2-chloro-5-hydroxyphenyl)-10, 10-dimethyl-4-(2-(2-propenoyl)-2,6-diazaspiro[3.4]octan-6-yl)-3-azatricyclo[7.1.1.$0^{2,7}$]undeca-2,4,6-triene-5-carbonitrile;

(1R,9R)-6-(2-fluoro-5-hydroxyphenyl)-10, 10-dimethyl-4-(2-(2-propenoyl)-2,6-diazaspiro[3.4]octan-6-yl)-3-azatricyclo[7.1.1.$0^{2,7}$]undeca-2,4,6-triene-5-carbonitrile;

(1R,9R)-6-(5-hydroxy-2-methylphenyl)-10, 10-dimethyl-4-(2-(2-propenoyl)-2,6-diazaspiro[3.4]octan-6-yl)-3-azatricyclo[7.1.1.$0^{2,7}$]undeca-2,4,6-triene-5-carbonitrile;

(P)-(1R,9R)-6-(5-hydroxy-2-methylphenyl)-10,10-dimethyl-4-(2-(2-propenoyl)-2,6-diazaspiro[3.4]octan-6-yl)-3-azatricyclo[7.1.1.$0^{2,7}$]undeca-2,4,6-triene-5-carbonitrile;

(P)-(1R,9R)-6-(2-chloro-5-hydroxyphenyl)-10,10-dimethyl-4-(2-(2-propenoyl)-2,6-diazaspiro[3.4]octan-6-yl)-3-azatricyclo[7.1.1.0$^{2,7}$]undeca-2,4,6-triene-5-carbonitrile;

1-(6-(3-chloro-4-(3-hydroxy-1-naphthalenyl)-7,7-dimethyl-7,8-dihydro-5H-pyrano[4,3-b]pyridin-2-yl)-2,6-diazaspiro[3.4]octan-2-yl)-2-propen-1-one;

(P)-1-(6-(3-chloro-4-(3-hydroxy-1-naphthalenyl)-7,7-dimethyl-7,8-dihydro-5H-pyrano[4,3-b]pyridin-2-yl)-2,6-diazaspiro[3.4]octan-2-yl)-2-propen-1-one;

1-(6-(3-chloro-4-(5-hydroxy-2-methylphenyl)-7,7-dimethyl-7,8-dihydro-5H-pyrano[4,3-b]pyridin-2-yl)-2,6-diazaspiro[3.4]octan-2-yl)-2-propen-1-one;

(P)-1-(6-(3-chloro-4-(5-hydroxy-2-methylphenyl)-7,7-dimethyl-7,8-dihydro-5H-pyrano[4,3-b]pyridin-2-yl)-2,6-diazaspiro[3.4]octan-2-yl)-2-propen-1-one;

1-(6-(3-chloro-7,7-dimethyl-4-(5-methyl-1H-indazol-4-yl)-7,8-dihydro-5H-pyrano[4,3-b]pyridin-2-yl)-2,6-diazaspiro[3.4]octan-2-yl)-2-propen-1-one;

(M)-1-(6-(3-chloro-4-(1,6-dimethyl-1H-indazol-7-yl)-7,7-dimethyl-7,8-dihydro-5H-pyrano[4,3-b]pyridin-2-yl)-2,6-diazaspiro[3.4]octan-2-yl)-2-propen-1-one;

1-(6-(3-chloro-4-(5-chloro-1,6-dimethyl-1H-indazol-7-yl)-7,7-dimethyl-7,8-dihydro-5H-pyrano[4,3-b]pyridin-2-yl)-2,6-diazaspiro[3.4]octan-2-yl)-2-propen-1-one;

(M)-1-(6-(3-chloro-4-(5-chloro-1,6-dimethyl-1H-indazol-7-yl)-7,7-dimethyl-7,8-dihydro-5H-pyrano[4,3-b]pyridin-2-yl)-2,6-diazaspiro[3.4]octan-2-yl)-2-propen-1-one;

1-(6-(3-chloro-4-(6-chloro-5-methyl-1H-indazol-4-yl)-7,7-dimethyl-7,8-dihydro-5H-pyrano[4,3-b]pyridin-2-yl)-2,6-diazaspiro[3.4]octan-2-yl)-2-propen-1-one;

1-(5-methyl-1H-indazol-4-yl)-3-(2-(2-propenoyl)-2,6-diazaspiro[3.4]octan-6-yl)-5,6,7,8-tetrahydro-2-naphthalenecarbonitrile;

8-(5-methyl-1H-indazol-4-yl)-6-(2-(2-propenoyl)-2,6-diazaspiro[3.4]octan-6-yl)-3,4-dihydro-1H-2-benzopyran-7-carbonitrile;

1-(1,6-dimethyl-1H-indazol-7-yl)-6,6-dimethyl-3-(2-(2-propenoyl)-2,6-diazaspiro[3.4]octan-6-yl)-5,6,7,8-tetrahydro-2-naphthalenecarbonitrile;

3'-hydroxy-6,6-dimethyl-3-(2-(2-propenoyl)-2,6-diazaspiro[3.4]octan-6-yl)-5,6,7,8-tetrahydro [1,1'-binaphthalene]-2-carbonitrile;

(P)-8-(5-methyl-1H-indazol-4-yl)-6-(2-(2-propenoyl)-2,6-diazaspiro[3.4]octan-6-yl)-3,4-dihydro-1H-2-benzopyran-7-carbonitrile;

8-(1,6-dimethyl-1H-indazol-7-yl)-6-(2-(2-propenoyl)-2,6-diazaspiro[3.4]octan-6-yl)-3,4-dihydro-2H-chromene-7-carbonitrile;

1-(6-(7-chloro-8-(1,6-dimethyl-1H-indazol-7-yl)-3,4-dihydro-2H-chromen-6-yl)-2,6-diazaspiro[3.4]octan-2-yl)-2-propen-1-one;

8-(5-chloro-1,6-dimethyl-1H-indazol-7-yl)-6-(2-(2-propenoyl)-2,6-diazaspiro[3.4]octan-6-yl)-3,4-dihydro-2H-chromene-7-carbonitrile;

2-(8,8-difluoro-2-(2-propenoyl)-2,6-diazaspiro[3.4]octan-6-yl)-7,7-dimethyl-4-(5-methyl-1H-indazol-4-yl)-5,6,7,8-tetrahydro-3-quinolinecarbonitrile;

8-(5-chloro-1,6-dimethyl-1H-indazol-7-yl)-6-((5S)-5-methyl-2-(2-propenoyl)-2,6-diazaspiro[3.4]octan-6-yl)-3,4-dihydro-2H-chromene-7-carbonitrile;

(P)-1-(6-(3-chloro-4-(6-chloro-5-methyl-1H-indazol-4-yl)-7,7-dimethyl-7,8-dihydro-5H-pyrano[4,3-b]pyridin-2-yl)-2,6-diazaspiro[3.4]octan-2-yl)-2-propen-1-one;

1-(6-(7-chloro-8-(5-chloro-1,6-dimethyl-1H-indazol-7-yl)-3,4-dihydro-2H-chromen-6-yl)-2,6-diazaspiro[3.4]octan-2-yl)-2-propen-1-one;

(M)-1-(6-((1S,8R)-5-methyl-6-(1,5,6-trimethyl-1H-indazol-7-yl)-3-azatricyclo[6.2.1.02, 7]undeca-2,4,6-trien-4-yl)-2,6-diazaspiro[3.4]octan-2-yl)-2-propen-1-one;

1-(6-(4-(3-chloro-5-hydroxy-2-methylphenyl)-3,7,7-trimethyl-7,8-dihydro-5H-pyrano[4,3-b]pyridin-2-yl)-2,6-diazaspiro[3.4]octan-2-yl)-2-propen-1-one;

(1R,9R)-6-(7-fluoro-5-methyl-1H-indazol-4-yl)-10,10-dimethyl-4-(2-(2-propenoyl)-2,6-diazaspiro[3.4]octan-6-yl)-3-azatricyclo[7.1.1.0$^{2,7}$]undeca-2,4,6-triene-5-carbonitrile;

4-(5-chloro-1H-indol-4-yl)-7,7-dimethyl-2-(2-(2-propenoyl)-2,6-diazaspiro[3.4]octan-6-yl)-7,8-dihydro-5H-pyrano[4,3-b]pyridine-3-carbonitrile;

(1R,9R)-6-(5-chloro-6-methyl-1H-indazol-4-yl)-10,10-dimethyl-4-(2-(2-propenoyl)-2,6-diazaspiro[3.4]octan-6-yl)-3-azatricyclo[7.1.1.0$^{2,7}$]undeca-2,4,6-triene-5-carbonitrile;

(1R,9R)-10, 10-dimethyl-6-(7-methylimidazo[1,5-a]pyridin-8-yl)-4-(2-(2-propenoyl)-2,6-diazaspiro[3.4]octan-6-yl)-3-azatricyclo[7.1.1.0$^{2,7}$]undeca-2,4,6-triene-5-carbonitrile;

4-(3-chloro-6-methyl-1H-indol-7-yl)-7,7-dimethyl-2-(2-(2-propenoyl)-2,6-diazaspiro[3.4]octan-6-yl)-7,8-dihydro-5H-pyrano[4,3-b]pyridine-3-carbonitrile;

1-(6-(4-(5-chloro-1,6-dimethyl-1H-indazol-7-yl)-3-methyl-7-(2-propanyl)-5,6,7,8-tetrahydro-1,7-naphthyridin-2-yl)-2,6-diazaspiro[3.4]octan-2-yl)-2-propen-1-one;

(M)-1-(6-(4-(5-chloro-1,6-dimethyl-1H-indazol-7-yl)-3-methyl-7-(2-propanyl)-5,6,7,8-tetrahydro-1,7-naphthyridin-2-yl)-2,6-diazaspiro[3.4]octan-2-yl)-2-propen-1-one;

1-(6-(3-methyl-7-(2-propanyl)-4-(1,5,6-trimethyl-1H-indazol-7-yl)-5,6,7,8-tetrahydro-1,7-naphthyridin-2-yl)-2,6-diazaspiro[3.4]octan-2-yl)-2-propen-1-one;

(1R,9R)-6-(2-chloro-3-fluoro-5-hydroxyphenyl)-10,10-dimethyl-4-(2-(2-propenoyl)-2,6-diazaspiro[3.4]octan-6-yl)-3-azatricyclo[7.1.1.0$^{2,7}$]undeca-2,4,6-triene-5-carbonitrile;

(1R,9R)-6-(2-chloro-5-hydroxy-3-pyridinyl)-10, 10-dimethyl-4-(2-(2-propenoyl)-2,6-diazaspiro[3.4]octan-6-yl)-3-azatricyclo[7.1.1.0$^{2,7}$]undeca-2,4,6-triene-5-carbonitrile;

(P)-(1R,9R)-6-(7-hydroxy-5-quinoxalinyl)-10,10-dimethyl-4-(2-(2-propenoyl)-2,6-diazaspiro[3.4]octan-6-yl)-3-azatricyclo[7.1.1.0$^{2,7}$]undeca-2,4,6-triene-5-carbonitrile;

4-(6-hydroxy-1-naphthalenyl)-7,7-dimethyl-2-(2-(2-propenoyl)-2,6-diazaspiro[3.4]octan-6-yl)-7,8-dihydro-5H-pyrano[4,3-b]pyridine-3-carbonitrile;

(M)-1-(6-(4-(3-chloro-5-hydroxy-2-methylphenyl)-3,7,7-trimethyl-7,8-dihydro-5H-pyrano[4,3-b]pyridin-2-yl)-2,6-diazaspiro[3.4]octan-2-yl)-2-propen-1-one;

1-(6-(4-(2-chloro-5-hydroxy-3-methylphenyl)-3,7,7-trimethyl-7,8-dihydro-5H-pyrano[4,3-b]pyridin-2-yl)-2,6-diazaspiro[3.4]octan-2-yl)-2-propen-1-one;

7,7-dimethyl-4-(5-methyl-1H-indazol-4-yl)-2-(2-((2H3)-2-propenoyl)-2,6-diazaspiro[3.4]octan-6-yl)-5,6,7,8-tetrahydro-3-quinolinecarbonitrile;

2-(2-((2E)-4-(dimethylamino)-2-butenoyl)-2,6-diazaspiro[3.4]octan-6-yl)-7,7-dimethyl-4-(5-methyl-1H-indazol-4-yl)-5,6,7,8-tetrahydro-3-quinolinecarbonitrile;

2-(2-((2E)-4,4-difluoro-2-butenoyl)-2,6-diazaspiro[3.4]octan-6-yl)-7,7-dimethyl-4-(5-methyl-1H-indazol-4-yl)-5,6,7,8-tetrahydro-3-quinolinecarbonitrile;

(7R)-4-(5-methyl-1H-indazol-4-yl)-2-(2-(2-propenoyl)-2,6-diazaspiro[3.4]octan-6-yl)-7-(trifluoromethyl)-5,6,7,8-tetrahydro-3-quinolinecarbonitrile or (7S)-4-(5-methyl-1H-indazol-4-yl)-2-(2-(2-propenoyl)-2,6-diazaspiro[3.4]octan-6-yl)-7-(trifluoromethyl)-5,6,7,8-tetrahydro-3-quinolinecarbonitrile;

4'-(5-methyl-1H-indazol-4-yl)-2'-(2-(2-propenoyl)-2,6-diazaspiro[3.4]octan-6-yl)-7',8'-dihydro-5'H-spiro[cyclopropane-1,6'-quinoline]-3'-carbonitrile;

6,6-dimethyl-4-(5-methyl-1H-indazol-4-yl)-2-(2-(2-propenoyl)-2,6-diazaspiro[3.4]octan-6-yl)-6,7-dihydro-5H-cyclopenta [b]pyridine-3-carbonitrile;

(5R,7S)-5,7-dimethyl-4-(5-methyl-1H-indazol-4-yl)-2-(2-(2-propenoyl)-2,6-diazaspiro[3.4]octan-6-yl)-7,8-dihydro-5H-pyrano[4,3-b]pyridine-3-carbonitrile or (5S,7R)-5,7-dimethyl-4-(5-methyl-1H-indazol-4-yl)-2-(2-(2-propenoyl)-2,6-diazaspiro[3.4]octan-6-yl)-7,8-dihydro-5H-pyrano[4,3-b]pyridine-3-carbonitrile;

4-(5-methyl-1H-indazol-4-yl)-2-(2-(2-propenoyl)-2,6-diazaspiro[3.4]octan-6-yl)-5,7-dihydrospiro[cyclopenta [b]pyridine-6, 1'-cyclopropane]-3-carbonitrile;

4-(1,6-dimethyl-1H-indazol-7-yl)-6,6-dimethyl-2-(2-(2-propenoyl)-2,6-diazaspiro[3.4]octan-6-yl)-6,7-dihydro-5H-cyclopenta [b]pyridine-3-carbonitrile;

(P)-4-(1,6-dimethyl-1H-indazol-7-yl)-6,6-dimethyl-2-(2-(2-propenoyl)-2,6-diazaspiro[3.4]octan-6-yl)-6,7-dihydro-5H-cyclopenta [b]pyridine-3-carbonitrile;

(7R)-4-(2-chlorophenyl)-7-(1-methyl-1H-pyrazol-5-yl)-2-(2-(2-propenoyl)-2,6-diazaspiro[3.4]octan-6-yl)-5,6,7,8-tetrahydro-3-quinolinecarbonitrile or (7S)-4-(2-chlorophenyl)-7-(1-methyl-1H-pyrazol-5-yl)-2-(2-(2-propenoyl)-2,6-diazaspiro[3.4]octan-6-yl)-5,6,7,8-tetrahydro-3-quinolinecarbonitrile;

(7R)-4-(2-chlorophenyl)-7-(1-methyl-1H-pyrazol-5-yl)-2-(2-(2-propenoyl)-2,6-diazaspiro[3.4]octan-6-yl)-5,6,7,8-tetrahydro-3-quinolinecarbonitrile;

(7S)-4-(2-chlorophenyl)-7-(1-methyl-1H-pyrazol-5-yl)-2-(2-(2-propenoyl)-2,6-diazaspiro[3.4]octan-6-yl)-5,6,7,8-tetrahydro-3-quinolinecarbonitrile;

(7R)-4-(2-fluorophenyl)-7-(1-methyl-1H-pyrazol-5-yl)-2-(2-(2-propenoyl)-2,6-diazaspiro[3.4]octan-6-yl)-5,6,7,8-tetrahydro-3-quinolinecarbonitrile or (7S)-4-(2-fluorophenyl)-7-(1-methyl-1H-pyrazol-5-yl)-2-(2-(2-propenoyl)-2,6-diazaspiro[3.4]octan-6-yl)-5,6,7,8-tetrahydro-3-quinolinecarbonitrile;

4-(3-hydroxy-1-naphthalenyl)-7,7-dimethyl-2-(2-(2-propenoyl)-2,6-diazaspiro[3.4]octan-6-yl)-7,8-dihydro-5H-pyrano[4,3-b]pyridine-3-carbonitrile;

(P)-4-(3-hydroxy-1-naphthalenyl)-7,7-dimethyl-2-(2-(2-propenoyl)-2,6-diazaspiro[3.4]octan-6-yl)-7,8-dihydro-5H-pyrano[4,3-b]pyridine-3-carbonitrile;

1-(6-(3-(difluoromethyl)-7,7-dimethyl-4-(5-methyl-1H-indazol-4-yl)-7,8-dihydro-5H-pyrano[4,3-b]pyridin-2-yl)-2,6-diazaspiro[3.4]octan-2-yl)-2-propen-1-one;

4-(1,6-dimethyl-1H-indazol-7-yl)-7,7-dimethyl-2-(2-(2-propenoyl)-2,6-diazaspiro[3.4]octan-6-yl)-7,8-dihydro-5H-pyrano[4,3-b]pyridine-3-carbonitrile;

4'-(5-methyl-1H-indazol-4-yl)-2'-(2-(2-propenoyl)-2,6-diazaspiro[3.4]octan-6-yl)-2,3,5,5',6,8'-hexahydrospiro [pyran-4,7'-pyrano[4,3-b]pyridine]-3'-carbonitrile;

(3R)-4'-(5-methyl-1H-indazol-4-yl)-2'-(2-(2-propenoyl)-2,6-diazaspiro[3.4]octan-6-yl)-4,5,5',8'-tetrahydrospiro [furan-3,7'-pyrano[4,3-b]pyridine]-3'-carbonitrile or (3S)-4'-(5-methyl-1H-indazol-4-yl)-2'-(2-(2-propenoyl)-2,6-diazaspiro[3.4]octan-6-yl)-4,5,5',8'-tetrahydrospiro[furan-3,7'-pyrano[4,3-b]pyridine]-3'-carbonitrile;

6,6-dimethyl-4-(5-methyl-1H-indazol-4-yl)-2-((5R)-5-methyl-2-(2-propenoyl)-2,6-diazaspiro[3.4]octan-6-yl)-6,7-dihydro-5H-cyclopenta [b]pyridine-3-carbonitrile or 6,6-dimethyl-4-(5-methyl-1H-indazol-4-yl)-2-((5S)-5-methyl-2-(2-propenoyl)-2,6-diazaspiro[3.4]octan-6-yl)-6,7-dihydro-5H-cyclopenta [b]pyridine-3-carbonitrile;

(P)-6,6-dimethyl-4-(5-methyl-1H-indazol-4-yl)-2-((5R)-5-methyl-2-(2-propenoyl)-2,6-diazaspiro[3.4]octan-6-yl)-6,7-dihydro-5H-cyclopenta [b]pyridine-3-carbonitrile;

(P)-4-(1,6-dimethyl-1H-indazol-7-yl)-7,7-dimethyl-2-(2-(2-propenoyl)-2,6-diazaspiro[3.4]octan-6-yl)-7,8-dihydro-5H-pyrano[4,3-b]pyridine-3-carbonitrile;

(6aR,7aR)-4-(1,6-dimethyl-1H-indazol-7-yl)-2-((5R)-5-(hydroxymethyl)-2-(2-propenoyl)-2,6-diazaspiro[3.4]octan-6-yl)-6,6a,7,7a-tetrahydro-5H-cyclopropa[h]quinoline-3-carbonitrile or (6aR,7aR)-4-(1,6-dimethyl-1H-indazol-7-yl)-2-((5S)-5-(hydroxymethyl)-2-(2-propenoyl)-2,6-diazaspiro[3.4]octan-6-yl)-6,6a,7,7a-tetrahydro-5H-cyclopropa[h]quinoline-3-carbonitrile or (6aR,7aS)-4-(1,6-dimethyl-1H-indazol-7-yl)-2-((5R)-5-(hydroxymethyl)-2-(2-propenoyl)-2,6-diazaspiro[3.4]octan-6-yl)-6,6a,7,7a-tetrahydro-5H-cyclopropa[h]quinoline-3-carbonitrile or (6aR,7aS)-4-(1,6-dimethyl-1H-indazol-7-yl)-2-((5S)-5-(hydroxymethyl)-2-(2-propenoyl)-2,6-diazaspiro[3.4]octan-6-yl)-6,6a,7,7a-tetrahydro-5H-cyclopropa[h]quinoline-3-carbonitrile or (6aS,7aR)-4-(1,6-dimethyl-1H-indazol-7-yl)-2-((5R)-5-(hydroxymethyl)-2-(2-propenoyl)-2,6-diazaspiro[3.4]octan-6-yl)-6,6a,7,7a-tetrahydro-5H-cyclopropa[h]quinoline-3-carbonitrile or (6aS,7aR)-4-(1,6-dimethyl-1H-indazol-7-yl)-2-((5S)-5-(hydroxymethyl)-2-(2-propenoyl)-2,6-diazaspiro[3.4]octan-6-yl)-6,6a,7,7a-tetrahydro-5H-cyclopropa[h]quinoline-3-carbonitrile or (6aS,7aS)-4-(1,6-dimethyl-1H-indazol-7-yl)-2-((5R)-5-(hydroxymethyl)-2-(2-propenoyl)-2,6-diazaspiro[3.4]octan-6-yl)-6,6a,7,7a-tetrahydro-5H-cyclopropa[h]quinoline-3-carbonitrile or (6aS,7aS)-4-(1,6-dimethyl-1H-indazol-7-yl)-2-((5S)-5-(hydroxymethyl)-2-(2-propenoyl)-2,6-diazaspiro[3.4]octan-6-yl)-6,6a, 7,7a-tetrahydro-5H-cyclopropa[h]quinoline-3-carbonitrile;

4-(3-hydroxy-1-naphthalenyl)-6,6-dimethyl-2-(2-(2-propenoyl)-2,6-diazaspiro[3.4]octan-6-yl)-6,7-dihydro-5H-cyclopenta [b]pyridine-3-carbonitrile;

(P)-4-(3-hydroxy-1-naphthalenyl)-6,6-dimethyl-2-(2-(2-propenoyl)-2,6-diazaspiro[3.4]octan-6-yl)-6,7-dihydro-5H-cyclopenta [b]pyridine-3-carbonitrile;

(P)-(6aR,7aS)-4-(4-fluoro-3-hydroxy-1-naphthalenyl)-2-(2-(2-propenoyl)-2,6-diazaspiro[3.4]octan-6-yl)-6,6a,7,7a-tetrahydro-5H-cyclopropa[h]quinoline-3-carbonitrile;

(M)-(6aR,7aS)-4-(4-fluoro-3-hydroxy-1-naphthalenyl)-2-(2-(2-propenoyl)-2,6-diazaspiro[3.4]octan-6-yl)-6,6a, 7,7a-tetrahydro-5H-cyclopropa[h]quinoline-3-carbonitrile;

(P)-4-(4-fluoro-3-hydroxy-1-naphthalenyl)-7,7-dimethyl-2-(2-(2-propenoyl)-2,6-diazaspiro[3.4]octan-6-yl)-7,8-dihydro-5H-pyrano[4,3-b]pyridine-3-carbonitrile;

(M)-2-((5S)-5-(fluoromethyl)-2-(2-propenoyl)-2,6-diazaspiro[3.4]octan-6-yl)-7,7-dimethyl-4-(5-methyl-1H-indazol-4-yl)-5,6,7,8-tetrahydro-3-quinolinecarbonitrile and (P)-2-((5R)-5-(fluoromethyl)-2-(2- propenoyl)-2,6-diazaspiro[3.4]octan-6-yl)-7,7-dimethyl-4-(5-methyl-1H-indazol-4-yl)-5,6,7,8-tetrahydro-3-quinolinecarbonitrile;

(5aR,6aR)-4-(5-methyl-1H-indazol-4-yl)-2-(2-(2-propenoyl)-2,6-diazaspiro[3.4]octan-6-yl)-5,5a,6,6a-tetrahydrocyclopropa[4,5]cyclopenta[1,2-b]pyridine-3-carbonitrile or (5aR,6aS)-4-(5-methyl-1H-indazol-4-yl)-2-(2-(2-propenoyl)-2,6-diazaspiro[3.4]octan-6-yl)-5,5a,6,6a-tetrahydrocyclopropa[4,5]cyclopenta[1,2-b]pyridine-3-carbonitrile or (5aS,6aR)-4-(5-methyl-1H-indazol-4-yl)-2-(2-(2-propenoyl)-2,6-diazaspiro[3.4]octan-6-yl)-5,5a,6,6a-tetrahydrocyclopropa[4,5]cyclopenta[1,2-b]pyridine-3-carbonitrile or (5aS,6aS)-4-(5-methyl-1H-indazol-4-yl)-2-(2-(2-propenoyl)-2,6-diazaspiro[3.4]octan-6-yl)-5,5a,6,6a-tetrahydrocyclopropa[4,5]cyclopenta[1,2-b]pyridine-3-carbonitrile;

(4bR,5aR)-4-(5-methyl-1H-indazol-4-yl)-2-(2-(2-propenoyl)-2,6-diazaspiro[3.4]octan-6-yl)-4b,5,5a,6-tetrahydrocyclopropa[3,4]cyclopenta[1,2-b]pyridine-3-carbonitrile or (4bR,5aS)-4-(5-methyl-1H-indazol-4-yl)-2-(2-(2-propenoyl)-2,6-diazaspiro[3.4]octan-6-yl)-4b,5,5a,6-tetrahydrocyclopropa[3,4]cyclopenta[1,2-b]pyridine-3-carbonitrile or (4bS,5aR)-4-(5-methyl-1H-indazol-4-yl)-2-(2-(2-propenoyl)-2,6-diazaspiro[3.4]octan-6-yl)-4b,5,5a,6-tetrahydrocyclopropa[3,4]cyclopenta[1,2-b]pyridine-3-carbonitrile or (4bS,5aS)-4-(5-methyl-1H-indazol-4-yl)-2-(2-(2-propenoyl)-2,6-diazaspiro[3.4]octan-6-yl)-4b, 5,5a,6-tetrahydrocyclopropa[3,4]cyclopenta[1,2-b]pyridine-3-carbonitrile;

(6R)-6-cyclopropyl-4-(5-methyl-1H-indazol-4-yl)-2-(2-(2-propenoyl)-2,6-diazaspiro[3.4]octan-6-yl)-6,7-dihydro-5H-cyclopenta[b]pyridine-3-carbonitrile or (6S)-6-cyclopropyl-4-(5-methyl-1H-indazol-4-yl)-2-(2-(2-propenoyl)-2,6-diazaspiro[3.4]octan-6-yl)-6,7-dihydro-5H-cyclopenta[b]pyridine-3-carbonitrile;

(4bR,5aR)-5,5-dimethyl-4-(5-methyl-1H-indazol-4-yl)-2-(2-(2-propenoyl)-2,6-diazaspiro[3.4]octan-6-yl)-4b,5,5a,6-tetrahydrocyclopropa[3,4]cyclopenta[1,2-b]pyridine-3-carbonitrile or (4bR,5aS)-5,5-dimethyl-4-(5-methyl-1H-indazol-4-yl)-2-(2-(2-propenoyl)-2,6-diazaspiro[3.4]octan-6-yl)-4b, 5,5a,6-tetrahydrocyclopropa[3,4]cyclopenta[1,2-b]pyridine-3-carbonitrile or (4bS,5aR)-5,5-dimethyl-4-(5-methyl-1H-indazol-4-yl)-2-(2-(2-propenoyl)-2,6-diazaspiro[3.4]octan-6-yl)-4b,5,5a,6-tetrahydrocyclopropa[3,4]cyclopenta[1,2-b]pyridine-3-carbonitrile or (4bS,5aS)-5,5-dimethyl-4-(5-methyl-1H-indazol-4-yl)-2-(2-(2-propenoyl)-2,6-diazaspiro[3.4]octan-6-yl)-4b,5,5a,6-tetrahydrocyclopropa[3,4]cyclopenta[1,2-b]pyridine-3-carbonitrile;

(P)-(6aR,7aS)-2-(2-((2E)-4-(dimethylamino)-2-butenoyl)-2,6-diazaspiro[3.4]octan-6-yl)-4-(3-hydroxy-1-naphthalenyl)-6,6a,7,7a-tetrahydro-5H-cyclopropa[h]quinoline-3-carbonitrile ($3^{rd}$ eluting isomer);

(P)-(6aS,7aR)-2-(2-((2E)-4-(dimethylamino)-2-butenoyl)-2,6-diazaspiro[3.4]octan-6-yl)-4-(3-hydroxy-1-naphthalenyl)-6,6a,7,7a-tetrahydro-5H-cyclopropa[h]quinoline-3-carbonitrile;

7,7-dimethyl-2-(2-(2-propenoyl)-2,6-diazaspiro[3.4]octan-6-yl)-4-(1,5,6-trimethyl-1H-indazol-7-yl)-5,6,7,8-tetrahydro-3-quinolinecarbonitrile;

7,7-dimethyl-2-(2-(2-propenoyl)-2,6-diazaspiro[3.4]octan-6-yl)-4-(1,5,6-trimethyl-1H-indazol-7-yl)-7,8-dihydro-5H-pyrano[4,3-b]pyridine-3-carbonitrile;

(P)-7,7-dimethyl-2-(2-(2-propenoyl)-2,6-diazaspiro[3.4]octan-6-yl)-4-(1,5,6-trimethyl-1H-indazol-7-yl)-7,8-dihydro-5H-pyrano[4,3-b]pyridine-3-carbonitrile;

(1R,9R)-10, 10-dimethyl-6-(5-methyl-1H-indazol-4-yl)-4-(2-(2-propenoyl)-2,6-diazaspiro[3.4]octan-6-yl)-3-azatricyclo[$7.1.1.0^{2,7}$]undeca-2,4,6-triene-5-carbonitrile;

(1R,9R)-10, 10-dimethyl-6-(5-methyl-1H-indazol-4-yl)-4-((5R)-5-methyl-2-(2-propenoyl)-2,6-diazaspiro[3.4]octan-6-yl)-3-azatricyclo[$7.1.1.0^{2,7}$]undeca-2,4,6-triene-5-carbonitrile or (1R,9R)-10, 10-dimethyl-6-(5-methyl-1H-indazol-4-yl)-4-((5S)-5-methyl-2-(2-propenoyl)-2,6-diazaspiro[3.4]octan-6-yl)-3-azatricyclo[$7.1.1.0^{2,7}$]undeca-2,4,6-triene-5-carbonitrile;

7,7-dimethyl-4-(5-methyl-1H-indazol-4-yl)-2-(2-(2-propenoyl)-2,6-diazaspiro[3.4]octan-6-yl)-7,8-dihydro-5H-pyrano[4,3-b]pyridine-3-carbonitrile;

7,7-dimethyl-4-(5-methyl-1H-indazol-4-yl)-2-(2-(2-propenoyl)-2,6-diazaspiro[3.4]octan-6-yl)-6,7-dihydro-5H-cyclopenta[b]pyridine-3-carbonitrile;

4'-(5-methyl-1H-indazol-4-yl)-2'-(2-(2-propenoyl)-2,6-diazaspiro[3.4]octan-6-yl)-5',8'-dihydrospiro[cyclobutane-1,7'-pyrano[4,3-b]pyridine]-3'-carbonitrile;

7,7-dimethyl-4-(5-methyl-1H-indazol-4-yl)-2-(2-(2-propenoyl)-2,6-diazaspiro[3.4]octan-6-yl)-5,7-dihydrofuro [3,4-b]pyridine-3-carbonitrile;

4-(5-methyl-1H-indazol-4-yl)-2-(2-(2-propenoyl)-2,6-diazaspiro[3.4]octan-6-yl)-5,6-dihydrospiro[cyclopenta[b]pyridine-7,1'-cyclopropane]-3-carbonitrile;

(1R,9R)-6-(1,6-dimethyl-1H-indazol-7-yl)-10, 10-dimethyl-4-(2-(2-propenoyl)-2,6-diazaspiro[3.4]octan-6-yl)-3-azatricyclo[$7.1.1.0^{2,7}$]undeca-2,4,6-triene-5-carbonitrile;

(M)-(1R,9R)-6-(1,6-dimethyl-1H-indazol-7-yl)-10,10-dimethyl-4-(2-(2-propenoyl)-2,6-diazaspiro[3.4]octan-6-yl)-3-azatricyclo[$7.1.1.0^{2,7}$]undeca-2,4,6-triene-5-carbonitrile;

(1R,9R)-6-(3-hydroxy-1-naphthalenyl)-10, 10-dimethyl-4-(2-(2-propenoyl)-2,6-diazaspiro[3.4]octan-6-yl)-3-azatricyclo[$7.1.1.0^{2,7}$]undeca-2,4,6-triene-5-carbonitrile;

(1s,9s)-6-(1,6-dimethyl-1H-indazol-7-yl)-4-(2-(2-propenoyl)-2,6-diazaspiro[3.4]octan-6-yl)-3-azatricyclo [$7.1.1.0^{2,7}$]undeca-2,4,6-triene-5-carbonitrile;

4-(5-hydroxy-2-methylphenyl)-7,7-dimethyl-2-(2-(2-propenoyl)-2,6-diazaspiro[3.4]octan-6-yl)-7,8-dihydro-5H-pyrano[4,3-b]pyridine-3-carbonitrile;

(1s,9s)-6-(5-hydroxy-2-methylphenyl)-4-(2-(2-propenoyl)-2,6-diazaspiro[3.4]octan-6-yl)-3-azatricyclo [$7.1.1.0^{2,7}$]undeca-2,4,6-triene-5-carbonitrile;

(M)-(1R,9R)-10,10-dimethyl-6-(5-methyl-1H-indazol-4-yl)-4-(2-(2-propenoyl)-2,6-diazaspiro[3.4]octan-6-yl)-3-azatricyclo[$7.1.1.0^{2,7}$]undeca-2,4,6-triene-5-carbonitrile;

(6aR,7aS)-4-(1,6-dimethyl-1H-indazol-7-yl)-2-(2-(2-propenoyl)-2,6-diazaspiro[3.4]octan-6-yl)-6,6a,7,7a-tetrahydro-5H-cyclopropa[h]quinoline-3-carbonitrile or (6aS,7aR)-4-(1,6-dimethyl-1H-indazol-7-yl)-2-(2-(2-propenoyl)-2,6-diazaspiro[3.4]octan-6-yl)-6,6a,7,7a-tetrahydro-5H-cyclopropa[h]quinoline-3-carbonitrile;

(M)-(1s,9s)-6-(1,6-dimethyl-1H-indazol-7-yl)-4-(2-(2-propenoyl)-2,6-diazaspiro[3.4]octan-6-yl)-3-azatricyclo[$7.1.1.0^{2,7}$]undeca-2,4,6-triene-5-carbonitrile;

(P)-(1s,9s)-6-(5-hydroxy-2-methylphenyl)-4-(2-(2-propenoyl)-2,6-diazaspiro[3.4]octan-6-yl)-3-azatricyclo [$7.1.1.0^{2,7}$]undeca-2,4,6-triene-5-carbonitrile;

(P)-4-(5-hydroxy-2-methylphenyl)-7,7-dimethyl-2-(2-(2-propenoyl)-2,6-diazaspiro[3.4]octan-6-yl)-7,8-dihydro-5H-pyrano[4,3-b]pyridine-3-carbonitrile;

(P)-(1R,9R)-6-(3-hydroxy-1-naphthalenyl)-10,10-dimethyl-4-(2-(2-propenoyl)-2,6-diazaspiro[3.4]octan-6-yl)-3-azatricyclo[7.1.1.$0^{2,7}$]undeca-2,4,6-triene-5-carbonitrile;

(1s,9s)-3-(1,6-dimethyl-1H-indazol-7-yl)-5-(2-(2-propenoyl)-2,6-diazaspiro[3.4]octan-6-yl)-6-azatricyclo[7.1.1.$0^{2,7}$]undeca-2,4,6-triene-4-carbonitrile;

(M)-(1s,9s)-3-(1,6-dimethyl-1H-indazol-7-yl)-5-(2-(2-propenoyl)-2,6-diazaspiro[3.4]octan-6-yl)-6-azatricyclo[7.1.1.$0^{2,7}$]undeca-2,4,6-triene-4-carbonitrile;

(M)-(6aR,7aS)-4-(1,6-dimethyl-1H-indazol-7-yl)-2-(2-(2-propenoyl)-2,6-diazaspiro[3.4]octan-6-yl)-6,6a,7,7a-tetrahydro-5H-cyclopropa[h]quinoline-3-carbonitrile;

(M)-(6aS,7aR)-4-(1,6-dimethyl-1H-indazol-7-yl)-2-(2-(2-propenoyl)-2,6-diazaspiro[3.4]octan-6-yl)-6,6a,7,7a-tetrahydro-5H-cyclopropa[h]quinoline-3-carbonitrile;

4-(1,6-dimethyl-1H-indazol-7-yl)-7,7-dimethyl-2-(2-(2-propenoyl)-2,6-diazaspiro[3.4]octan-6-yl)-5,6,7,8-tetrahydro-3-quinolinecarbonitrile;

4-(5-chloro-1H-indazol-4-yl)-7,7-dimethyl-2-(2-(2-propenoyl)-2,6-diazaspiro[3.4]octan-6-yl)-5,6,7,8-tetrahydro-3-quinolinecarbonitrile;

(P)-4-(1,6-dimethyl-1H-indazol-7-yl)-7,7-dimethyl-2-(2-(2-propenoyl)-2,6-diazaspiro[3.4]octan-6-yl)-5,6,7,8-tetrahydro-3-quinolinecarbonitrile;

4-(7-fluoro-5-methyl-1H-indazol-4-yl)-7,7-dimethyl-2-(2-(2-propenoyl)-2,6-diazaspiro[3.4]octan-6-yl)-5,6,7,8-tetrahydro-3-quinolinecarbonitrile;

4-(7-fluoro-5-methyl-1H-indazol-4-yl)-7,7-dimethyl-2-(2-(2-propenoyl)-2,6-diazaspiro[3.4]octan-6-yl)-7,8-dihydro-5H-pyrano[4,3-b]pyridine-3-carbonitrile;

4-(5-chloro-1H-indazol-4-yl)-7,7-dimethyl-2-(2-(2-propenoyl)-2,6-diazaspiro[3.4]octan-6-yl)-7,8-dihydro-5H-pyrano[4,3-b]pyridine-3-carbonitrile;

7,7-dimethyl-4-(5-methyl-1H-pyrazolo [3,4-b]pyridin-4-yl)-2-(2-(2-propenoyl)-2,6-diazaspiro[3.4]octan-6-yl)-5,6,7,8-tetrahydro-3-quinolinecarbonitrile;

4-(2-chloro-5-hydroxy-3-methylphenyl)-7,7-dimethyl-2-(2-(2-propenoyl)-2,6-diazaspiro[3.4]octan-6-yl)-7,8-dihydro-5H-pyrano[4,3-b]pyridine-3-carbonitrile;

4-(2-amino-3,5-dichloro-6-fluorophenyl)-7,7-dimethyl-2-(2-(2-propenoyl)-2,6-diazaspiro[3.4]octan-6-yl)-7,8-dihydro-5H-pyrano[4,3-b]pyridine-3-carbonitrile;

(P)-4-(2-amino-3,5-dichloro-6-fluorophenyl)-7,7-dimethyl-2-(2-(2-propenoyl)-2,6-diazaspiro[3.4]octan-6-yl)-7,8-dihydro-5H-pyrano[4,3-b]pyridine-3-carbonitrile;

1-(6-((1R,9R)-5-fluoro-6-(3-hydroxy-1-naphthalenyl)-10, 10-dimethyl-3-azatricyclo[7.1.1.$0^{2,7}$]undeca-2,4,6-trien-4-yl)-2,6-diazaspiro[3.4]octan-2-yl)-2-propen-1-one;

4-(6-fluoro-5-methyl-1H-indazol-4-yl)-2-(2-(2-propenoyl)-2,6-diazaspiro[3.4]octan-6-yl)-3-quinolinecarbonitrile;

(1S,8R)-6-(5-methyl-1H-indazol-4-yl)-4-(2-(2-propenoyl)-2,6-diazaspiro[3.4]octan-6-yl)-3-azatricyclo[6.2.1.02,7]undeca-2,4,6-triene-5-carbonitrile;

(1R,8S)-6-(5-methyl-1H-indazol-4-yl)-4-(2-(2-propenoyl)-2,6-diazaspiro[3.4]octan-6-yl)-3-azatricyclo[6.2.1.02,7]undeca-2,4,6-triene-5-carbonitrile;

(P)-(1S,8R)-6-(5-methyl-1H-indazol-4-yl)-4-(2-(2-propenoyl)-2,6-diazaspiro[3.4]octan-6-yl)-3-azatricyclo[6.2.1.02,7]undeca-2,4,6-triene-5-carbonitrile;

(1R,8S)-6-(5-hydroxy-2-methylphenyl)-4-(2-(2-propenoyl)-2,6-diazaspiro[3.4]octan-6-yl)-3-azatricyclo[6.2.1.02,7]undeca-2,4,6-triene-5-carbonitrile;

(P)-(1S,8R)-6-(5-hydroxy-2-methylphenyl)-4-(2-(2-propenoyl)-2,6-diazaspiro[3.4]octan-6-yl)-3-azatricyclo[6.2.1.02,7]undeca-2,4,6-triene-5-carbonitrile;

(P)-(1R,8S)-6-(5-hydroxy-2-methylphenyl)-4-(2-(2-propenoyl)-2,6-diazaspiro[3.4]octan-6-yl)-3-azatricyclo[6.2.1.02,7]undeca-2,4,6-triene-5-carbonitrile;

(1S,8R)-6-(1,6-dimethyl-1H-indazol-7-yl)-4-(2-(2-propenoyl)-2,6-diazaspiro[3.4]octan-6-yl)-3-azatricyclo[6.2.1.02,7]undeca-2,4,6-triene-5-carbonitrile;

(P)-(1S,8R)-6-(1,6-dimethyl-1H-indazol-7-yl)-4-(2-(2-propenoyl)-2,6-diazaspiro[3.4]octan-6-yl)-3-azatricyclo[6.2.1.02,7]undeca-2,4,6-triene-5-carbonitrile;

4-(6-chloro-5-methyl-1H-indazol-4-yl)-2-(2-(2-propenoyl)-2,6-diazaspiro[3.4]octan-6-yl)-3-quinolinecarbonitrile;

7-cyclopropyl-4-(5-methyl-1H-indazol-4-yl)-2-(2-(2-propenoyl)-2,6-diazaspiro[3.4]octan-6-yl)-3-quinolinecarbonitrile;

2-(8,8-difluoro-2-(2-propenoyl)-2,6-diazaspiro[3.4]octan-6-yl)-7-methoxy-4-(5-methyl-1H-indazol-4-yl)-3-quinolinecarbonitrile;

7-methoxy-4-(5-methyl-1H-indazol-4-yl)-2-((5R)-5-methyl-2-(2-propenoyl)-2,6-diazaspiro[3.4]octan-6-yl)-3-quinolinecarbonitrile or 7-methoxy-4-(5-methyl-1H-indazol-4-yl)-2-((5S)-5-methyl-2-(2-propenoyl)-2,6-diazaspiro[3.4]octan-6-yl)-3-quinolinecarbonitrile;

1-(6-(3,7,7-trimethyl-4-(5-methyl-1H-indazol-4-yl)-7,8-dihydro-5H-pyrano[4,3-b]pyridin-2-yl)-2,6-diazaspiro[3.4]octan-2-yl)-2-propen-1-one;

(1R,9R)-6-(1H-indazol-7-yl)-10,10-dimethyl-4-(2-(2-propenoyl)-2,6-diazaspiro[3.4]octan-6-yl)-3-azatricyclo[7.1.1.$0^{2,7}$]undeca-2,4,6-triene-5-carbonitrile;

1-(6-(4-(3-hydroxy-1-naphthalenyl)-3,7,7-trimethyl-7,8-dihydro-5H-pyrano[4,3-b]pyridin-2-yl)-2,6-diazaspiro[3.4]octan-2-yl)-2-propen-1-one;

(P)-(1R,9R)-6-(1H-indazol-7-yl)-10,10-dimethyl-4-(2-(2-propenoyl)-2,6-diazaspiro[3.4]octan-6-yl)-3-azatricyclo[7.1.1.$0^{2,7}$]undeca-2,4,6-triene-5-carbonitrile;

(M)-1-(6-(4-(5-hydroxy-2-methylphenyl)-3,7,7-trimethyl-7,8-dihydro-5H-pyrano[4,3-b]pyridin-2-yl)-2,6-diazaspiro[3.4]octan-2-yl)-2-propen-1-one;

(P)-1-(6-(3,7,7-trimethyl-4-(5-methyl-1H-indazol-4-yl)-7,8-dihydro-5H-pyrano[4,3-b]pyridin-2-yl)-2,6-diazaspiro[3.4]octan-2-yl)-2-propen-1-one;

(P)-1-(6-(4-(2-amino-7-fluoro-1,3-benzothiazol-4-yl)-3,7,7-trimethyl-7,8-dihydro-5H-pyrano[4,3-b]pyridin-2-yl)-2,6-diazaspiro[3.4]octan-2-yl)-2-propen-1-one;

1-(6-(3,7,7-trimethyl-4-(1,5,6-trimethyl-1H-indazol-7-yl)-7,8-dihydro-5H-pyrano[4,3-b]pyridin-2-yl)-2,6-diazaspiro[3.4]octan-2-yl)-2-propen-1-one;

(P)-1-(6-(3,7,7-trimethyl-4-(1,5,6-trimethyl-1H-indazol-7-yl)-7,8-dihydro-5H-pyrano[4,3-b]pyridin-2-yl)-2,6-diazaspiro[3.4]octan-2-yl)-2-propen-1-one;

1-(6-(4-(6-hydroxy-1-naphthalenyl)-3,7,7-trimethyl-7,8-dihydro-5H-pyrano[4,3-b]pyridin-2-yl)-2,6-diazaspiro[3.4]octan-2-yl)-2-propen-1-one;

(P)-1-(6-(4-(6-hydroxy-1-naphthalenyl)-3,7,7-trimethyl-7,8-dihydro-5H-pyrano[4,3-b]pyridin-2-yl)-2,6-diazaspiro[3.4]octan-2-yl)-2-propen-1-one;

4-(2-chlorophenyl)-2-(2-(2-propenoyl)-2,6-diazaspiro[3.4]octan-6-yl)-7-(1,3,5-trimethyl-1H-pyrazol-4-yl)-3-quinolinecarbonitrile;

(1R,9R)-10, 10-dimethyl-6-(6-methyl-1H-indazol-7-yl)-4-(2-(2-propenoyl)-2,6-diazaspiro[3.4]octan-6-yl)-3-azatricyclo[7.1.1.0$^{2,7}$]undeca-2,4,6-triene-5-carbonitrile;

1-(6-((1R,9R)-5-fluoro-6-(5-hydroxy-2-methylphenyl)-10, 10-dimethyl-3-azatricyclo[7.1.1.0$^{2,7}$]undeca-2,4,6-trien-4-yl)-2,6-diazaspiro[3.4]octan-2-yl)-2-propen-1-one;

(M)-(1R,9R)-10,10-dimethyl-6-(6-methyl-1H-indazol-7-yl)-4-(2-(2-propenoyl)-2,6-diazaspiro[3.4]octan-6-yl)-3-azatricyclo[7.1.1.0$^{2,7}$]undeca-2,4,6-triene-5-carbonitrile;

4-(2-amino-7-fluoro-1,3-benzothiazol-4-yl)-7,7-dimethyl-2-(2-(2-propenoyl)-2,6-diazaspiro[3.4]octan-6-yl)-7,8-dihydro-5H-pyrano[4,3-b]pyridine-3-carbonitrile;

(P)-4-(2-amino-7-fluoro-1,3-benzothiazol-4-yl)-7,7-dimethyl-2-(2-(2-propenoyl)-2,6-diazaspiro[3.4]octan-6-yl)-7,8-dihydro-5H-pyrano[4,3-b]pyridine-3-carbonitrile;

(P)-1-(6-((1R,9R)-5-fluoro-6-(5-hydroxy-2-methylphenyl)-10,10-dimethyl-3-azatricyclo[7.1.1.0$^{2,7}$]undeca-2,4,6-trien-4-yl)-2,6-diazaspiro[3.4]octan-2-yl)-2-propen-1-one;

1-(6-(3-fluoro-4-(3-hydroxy-1-naphthalenyl)-7,7-dimethyl-7,8-dihydro-5H-pyrano[4,3-b]pyridin-2-yl)-2,6-diazaspiro[3.4]octan-2-yl)-2-propen-1-one;

(P)-1-(6-(3-fluoro-4-(3-hydroxy-1-naphthalenyl)-7,7-dimethyl-7,8-dihydro-5H-pyrano[4,3-b]pyridin-2-yl)-2,6-diazaspiro[3.4]octan-2-yl)-2-propen-1-one;

1-(6-((1R,9R)-5-fluoro-10, 10-dimethyl-6-(5-methyl-1H-indazol-4-yl)-3-azatricyclo[7.1.1.0$^{2,7}$]undeca-2,4,6-trien-4-yl)-2,6-diazaspiro[3.4]octan-2-yl)-2-propen-1-one;

(M)-1-(6-((1R,9R)-5-fluoro-10,10-dimethyl-6-(5-methyl-1H-indazol-4-yl)-3-azatricyclo[7.1.1.0$^{2,7}$]undeca-2,4,6-trien-4-yl)-2,6-diazaspiro[3.4]octan-2-yl)-2-propen-1-one;

(P)-1-(6-((1R,9R)-5-fluoro-6-(3-hydroxy-1-naphthalenyl)-10,10-dimethyl-3-azatricyclo[7.1.1.0$^{2,7}$]undeca-2,4,6-trien-4-yl)-2,6-diazaspiro[3.4]octan-2-yl)-2-propen-1-one;

(M)-1-(6-(4-(5-chloro-1,6-dimethyl-1H-indazol-7-yl)-3-fluoro-7,7-dimethyl-7,8-dihydro-5H-pyrano[4,3-b]pyridin-2-yl)-2,6-diazaspiro[3.4]octan-2-yl)-2-propen-1-one;

7,7-dimethyl-4-(6-methyl-1H-indazol-7-yl)-2-(2-(2-propenoyl)-2,6-diazaspiro[3.4]octan-6-yl)-7,8-dihydro-5H-pyrano[4,3-b]pyridine-3-carbonitrile;

(P)-7,7-dimethyl-4-(6-methyl-1H-indazol-7-yl)-2-(2-(2-propenoyl)-2,6-diazaspiro[3.4]octan-6-yl)-7,8-dihydro-5H-pyrano[4,3-b]pyridine-3-carbonitrile;

(1R,9R)-6-(2-chloro-4-fluoro-5-hydroxyphenyl)-10, 10-dimethyl-4-(2-(2-propenoyl)-2,6-diazaspiro[3.4]octan-6-yl)-3-azatricyclo[7.1.1.0$^{2,7}$]undeca-2,4,6-triene-5-carbonitrile;

1-(6-(4-(5-chloro-6-methyl-1H-indazol-7-yl)-3-fluoro-7,7-dimethyl-7,8-dihydro-5H-pyrano[4,3-b]pyridin-2-yl)-2,6-diazaspiro[3.4]octan-2-yl)-2-propen-1-one;

4-(5-hydroxy-2-(trifluoromethyl) phenyl)-7,7-dimethyl-2-(2-(2-propenoyl)-2,6-diazaspiro[3.4]octan-6-yl)-7,8-dihydro-5H-pyrano[4,3-b]pyridine-3-carbonitrile;

1-(6-(4-(5-chloro-1,6-dimethyl-1H-indazol-7-yl)-3,7,7-trimethyl-7,8-dihydro-5H-pyrano[4,3-b]pyridin-2-yl)-2,6-diazaspiro[3.4]octan-2-yl)-2-propen-1-one;

(P)-1-(6-(4-(5-chloro-1,6-dimethyl-1H-indazol-7-yl)-3,7,7-trimethyl-7,8-dihydro-5H-pyrano[4,3-b]pyridin-2-yl)-2,6-diazaspiro[3.4]octan-2-yl)-2-propen-1-one;

4-(5-chloro-1,6-dimethyl-1H-indazol-7-yl)-2-(2-(2-propenoyl)-2,6-diazaspiro[3.4]octan-6-yl)-3-quinolinecarbonitrile;

4-(5-chloro-6-methyl-1H-indazol-7-yl)-7,7-dimethyl-2-(2-(2-propenoyl)-2,6-diazaspiro[3.4]octan-6-yl)-7,8-dihydro-5H-pyrano[4,3-b]pyridine-3-carbonitrile;

4-(5-chloro-1,6-dimethyl-1H-indazol-7-yl)-7,7-dimethyl-2-(2-(2-propenoyl)-2,6-diazaspiro[3.4]octan-6-yl)-7,8-dihydro-5H-pyrano[4,3-b]pyridine-3-carbonitrile;

1-(6-((7R)-4-(2,4-difluorophenyl)-7-(1,4-dimethyl-1H-pyrazol-5-yl)-3-methyl-5,6,7,8-tetrahydro-2-quinolinyl)-2,6-diazaspiro[3.4]octan-2-yl)-2-propen-1-one;

(P)-1-(6-((7R)-4-(1,6-dimethyl-1H-indazol-7-yl)-7-(1,4-dimethyl-1H-pyrazol-5-yl)-3-methyl-5,6,7,8-tetrahydro-2-quinolinyl)-2,6-diazaspiro[3.4]octan-2-yl)-2-propen-1-one;

(M)-1-(6-(4-(3-hydroxy-1-naphthalenyl)-3,7,7-trimethyl-7,8-dihydro-5H-pyrano[4,3-b]pyridin-2-yl)-2,6-diazaspiro[3.4]octan-2-yl)-2-propen-1-one;

1-(6-(4-(6-chloro-1,5-dimethyl-1H-indazol-7-yl)-3,7,7-trimethyl-7,8-dihydro-5H-pyrano[4,3-b]pyridin-2-yl)-2,6-diazaspiro[3.4]octan-2-yl)-2-propen-1-one;

2-amino-7-fluoro-4-(3,7,7-trimethyl-2-(2-(2-propenoyl)-2,6-diazaspiro[3.4]octan-6-yl)-7,8-dihydro-5H-pyrano[4,3-b]pyridin-4-yl)-1-benzothiophene-3-carbonitrile;

(M)-1-(6-(4-(5-chloro-1,6-dimethyl-1H-indazol-7-yl)-3-fluoro-7-(3-oxetanyl)-5,6,7,8-tetrahydro-1,7-naphthyridin-2-yl)-2,6-diazaspiro[3.4]octan-2-yl)-2-propen-1-one;

(P)-1-(6-(4-(1,6-dimethyl-1H-indazol-7-yl)-3,7,7-trimethyl-7,8-dihydro-5H-pyrano[4,3-b]pyridin-2-yl)-2,6-diazaspiro[3.4]octan-2-yl)-2-propen-1-one;

4-(5-methyl-1H-indazol-4-yl)-7-(1-methyl-1H-pyrazol-5-yl)-2-(2-(2-propenoyl)-2,6-diazaspiro[3.4]octan-6-yl)-3-quinolinecarbonitrile;

1-(6-(3-methyl-4-(5-methyl-1H-indazol-4-yl)-7-(4-methyl-1,3-thiazol-5-yl)-2-quinolinyl)-2,6-diazaspiro[3.4]octan-2-yl)-2-propen-1-one;

4-(2-chlorophenyl)-7-(1-methyl-1H-imidazol-2-yl)-2-(2-(2-propenoyl)-2,6-diazaspiro[3.4]octan-6-yl)-3-quinolinecarbonitrile;

1-(6-(4-(2-chloro-5-hydroxyphenyl)-3-methyl-7-(1-methyl-1H-pyrazol-5-yl)-2-quinolinyl)-2,6-diazaspiro[3.4]octan-2-yl)-2-propen-1-one;

4-(2-chlorophenyl)-2-(8,8-difluoro-2-(2-propenoyl)-2,6-diazaspiro[3.4]octan-6-yl)-7-(1-methyl-1H-pyrazol-5-yl)-3-quinolinecarbonitrile;

4-(2-chlorophenyl)-7-(2-methyl-1H-imidazol-1-yl)-2-(2-(2-propenoyl)-2,6-diazaspiro[3.4]octan-6-yl)-3-quinolinecarbonitrile;

4-(2-fluorophenyl)-7-(2-methyl-1H-imidazol-1-yl)-2-(2-(2-propenoyl)-2,6-diazaspiro[3.4]octan-6-yl)-3-quinolinecarbonitrile;

4-(2-fluorophenyl)-7-(5-methyl-1H-imidazol-1-yl)-2-(2-(2-propenoyl)-2,6-diazaspiro[3.4]octan-6-yl)-3-quinolinecarbonitrile;

4-(2-chlorophenyl)-7-(5-methyl-1H-imidazol-1-yl)-2-(2-(2-propenoyl)-2,6-diazaspiro[3.4]octan-6-yl)-3-quinolinecarbonitrile;

1-(6-(4-(6-hydroxy-1-naphthalenyl)-3-methyl-7-(2-propanyl)-5,6,7,8-tetrahydro-1,7-naphthyridin-2-yl)-2,6-diazaspiro[3.4]octan-2-yl)-2-propen-1-one;

(P)-1-(6-(4-(6-hydroxy-1-naphthalenyl)-3-methyl-7-(2-propanyl)-5,6,7,8-tetrahydro-1,7-naphthyridin-2-yl)-2,6-diazaspiro[3.4]octan-2-yl)-2-propen-1-one;

1-(6-(4-(6-hydroxy-1-naphthalenyl)-3,7-dimethyl-5,6,7,8-tetrahydro-1,7-naphthyridin-2-yl)-2,6-diazaspiro[3.4]octan-2-yl)-2-propen-1-one;

1-(6-(4-(6-hydroxy-1-naphthalenyl)-3-methyl-7-(3-oxetanyl)-5,6,7,8-tetrahydro-1,7-naphthyridin-2-yl)-2,6-diazaspiro[3.4]octan-2-yl)-2-propen-1-one;

1-(6-(4-(6-hydroxy-1-naphthalenyl)-7-((2R)-1-methoxy-2-propanyl)-3-methyl-5,6,7,8-tetrahydro-1,7-naphthyridin-2-yl)-2,6-diazaspiro[3.4]octan-2-yl)-2-propen-1-one or 1-(6-(4-(6-hydroxy-1-naphthalenyl)-7-((2S)-1-methoxy-2-propanyl)-3-methyl-5,6,7,8-tetrahydro-1,7-naphthyridin-2-yl)-2,6-diazaspiro[3.4]octan-2-yl)-2-propen-1-one;

1-(6-(4-(2-fluoro-5-hydroxyphenyl)-3-methyl-7-(4-methyl-1,3-thiazol-5-yl)-5,6,7,8-tetrahydro-1,7-naphthyridin-2-yl)-2,6-diazaspiro[3.4]octan-2-yl)-2-propen-1-one;

1-(6-(7-cyclopropyl-4-(6-hydroxy-1-naphthalenyl)-3-methyl-5,6,7,8-tetrahydro-1,7-naphthyridin-2-yl)-2,6-diazaspiro[3.4]octan-2-yl)-2-propen-1-one;

1-(6-(4-(6-hydroxy-1-naphthalenyl)-3-methyl-7-((2R)-3,3,3-trifluoro-2-hydroxypropyl)-5,6,7,8-tetrahydro-1,7-naphthyridin-2-yl)-2,6-diazaspiro[3.4]octan-2-yl)-2-propen-1-one or 1-(6-(4-(6-hydroxy-1-naphthalenyl)-3-methyl-7-((2S)-3,3,3-trifluoro-2-hydroxypropyl)-5,6,7,8-tetrahydro-1,7-naphthyridin-2-yl)-2,6-diazaspiro[3.4]octan-2-yl)-2-propen-1-one;

1-(6-(3-methyl-4-(5-methyl-1H-indazol-4-yl)-7-(2-propanyl)-5,6,7,8-tetrahydro-1,7-naphthyridin-2-yl)-2,6-diazaspiro[3.4]octan-2-yl)-2-propen-1-one;

4-(2,3-dimethylphenyl)-7-(4-methyl-1,3-thiazol-5-yl)-2-(2-(2-propenoyl)-2,6-diazaspiro[3.4]octan-6-yl)-1,5-naphthyridine-3-carbonitrile;

4-(2-methylphenyl)-7-(4-methyl-1,3-thiazol-5-yl)-2-(2-(2-propenoyl)-2,6-diazaspiro[3.4]octan-6-yl)-3-quinolinecarbonitrile;

4-(2-fluoro-6-hydroxyphenyl)-7-(4-methyl-1,3-thiazol-5-yl)-2-(2-(2-propenoyl)-2,6-diazaspiro[3.4]octan-6-yl)-3-quinolinecarbonitrile;

(P)-4-(2-fluoro-6-hydroxyphenyl)-7-(4-methyl-1,3-thiazol-5-yl)-2-(2-(2-propenoyl)-2,6-diazaspiro[3.4]octan-6-yl)-3-quinolinecarbonitrile;

4-(2,4-difluorophenyl)-7-(4-methyl-1,3-thiazol-5-yl)-2-(2-(2-propenoyl)-2,6-diazaspiro[3.4]octan-6-yl)-1,5-naphthyridine-3-carbonitrile;

4-(2-chlorophenyl)-7-(2-(hydroxymethyl)-4-methyl-1,3-thiazol-5-yl)-2-(2-(2-propenoyl)-2,6-diazaspiro[3.4]octan-6-yl)-1,5-naphthyridine-3-carbonitrile;

4-(2-fluorophenyl)-7-(4-(hydroxymethyl)-1,3-thiazol-5-yl)-2-(2-(2-propenoyl)-2,6-diazaspiro[3.4]octan-6-yl)-1,5-naphthyridine-3-carbonitrile;

(P)-4-(2-methylphenyl)-7-(4-methyl-1,3-thiazol-5-yl)-2-(2-(2-propenoyl)-2,6-diazaspiro[3.4]octan-6-yl)-3-quinolinecarbonitrile;

(M)-4-(2-methylphenyl)-7-(4-methyl-1,3-thiazol-5-yl)-2-(2-(2-propenoyl)-2,6-diazaspiro[3.4]octan-6-yl)-3-quinolinecarbonitrile;

(M)-4-(2,3-dimethylphenyl)-7-(4-methyl-1,3-thiazol-5-yl)-2-(2-(2-propenoyl)-2,6-diazaspiro[3.4]octan-6-yl)-1,5-naphthyridine-3-carbonitrile;

(P)-4-(2,3-dimethylphenyl)-7-(4-methyl-1,3-thiazol-5-yl)-2-(2-(2-propenoyl)-2,6-diazaspiro[3.4]octan-6-yl)-1,5-naphthyridine-3-carbonitrile;

4-(2-chlorophenyl)-7-(4-methyl-1,3-thiazol-5-yl)-2-(2-(2-propenoyl)-2,6-diazaspiro[3.4]octan-6-yl)-3-quinolinecarbonitrile;

4-(2-fluorophenyl)-7-(4-methyl-1,3-thiazol-5-yl)-2-(2-(2-propenoyl)-2,6-diazaspiro[3.4]octan-6-yl)-3-quinolinecarbonitrile;

(P)-4-(2-chlorophenyl)-7-(4-methyl-1,3-thiazol-5-yl)-2-(2-(2-propenoyl)-2,6-diazaspiro[3.4]octan-6-yl)-3-quinolinecarbonitrile;

4-(2,3-dimethylphenyl)-7-(4-methyl-1,3-thiazol-5-yl)-2-(2-(2-propenoyl)-2,6-diazaspiro[3.4]octan-6-yl)-3-quinolinecarbonitrile;

4-(2-chlorophenyl)-7-(4-methyl-1,3-thiazol-5-yl)-2-(2-(2-propenoyl)-2,6-diazaspiro[3.4]octan-6-yl)-1,5-naphthyridine-3-carbonitrile;

(M)-4-(2-chlorophenyl)-7-(4-methyl-1,3-thiazol-5-yl)-2-(2-(2-propenoyl)-2,6-diazaspiro[3.4]octan-6-yl)-1,5-naphthyridine-3-carbonitrile;

(P)-4-(2-chlorophenyl)-7-(4-methyl-1,3-thiazol-5-yl)-2-(2-(2-propenoyl)-2,6-diazaspiro[3.4]octan-6-yl)-1,5-naphthyridine-3-carbonitrile;

4-(2,4-difluorophenyl)-7-(4-methyl-1,3-thiazol-5-yl)-2-(2-(2-propenoyl)-2,6-diazaspiro[3.4]octan-6-yl)-3-quinolinecarbonitrile;

4-(2-fluorophenyl)-7-(4-methyl-1,3-thiazol-5-yl)-2-(2-(2-propenoyl)-2,6-diazaspiro[3.4]octan-6-yl)-1,5-naphthyridine-3-carbonitrile;

4-(2-fluorophenyl)-7-(4-(methoxymethyl)-1,3-thiazol-5-yl)-2-(2-(2-propenoyl)-2,6-diazaspiro[3.4]octan-6-yl)-3-quinolinecarbonitrile;

4-(2-fluorophenyl)-7-(4-(hydroxymethyl)-1,3-thiazol-5-yl)-2-(2-(2-propenoyl)-2,6-diazaspiro[3.4]octan-6-yl)-3-quinolinecarbonitrile;

4-(2-fluorophenyl)-7-(4-methyl-1,3-thiazol-5-yl)-2-(2-(2-propenoyl)-2,6-diazaspiro[3.4]octan-6-yl)-5,6,7,8-tetrahydro-1,7-naphthyridine-3-carbonitrile;

4-(2,4-difluorophenyl)-7-(4-methyl-1,3-thiazol-5-yl)-2-(2-(2-propenoyl)-2,6-diazaspiro[3.4]octan-6-yl)-5,6,7,8-tetrahydro-1,7-naphthyridine-3-carbonitrile;

(8R)-4-(2-fluorophenyl)-8-methyl-7-(4-methyl-1,3-thiazol-5-yl)-2-(2-(2-propenoyl)-2,6-diazaspiro[3.4]octan-6-yl)-5,6,7,8-tetrahydro-1,7-naphthyridine-3-carbonitrile or (8S)-4-(2-fluorophenyl)-8-methyl-7-(4-methyl-1,3-thiazol-5-yl)-2-(2-(2-propenoyl)-2,6-diazaspiro[3.4]octan-6-yl)-5,6,7,8-tetrahydro-1,7-naphthyridine-3-carbonitrile;

(8R)-4-(2-fluorophenyl)-8-methyl-7-(4-methyl-1,3-thiazol-5-yl)-2-(2-(2-propenoyl)-2,6-diazaspiro[3.4]octan-6-yl)-5,6,7,8-tetrahydro-1,7-naphthyridine-3-carbonitrile;

4-(2,4-difluorophenyl)-7-(4-methoxyphenyl)-2-(2-(2-propenoyl)-2,6-diazaspiro[3.4]octan-6-yl)-5,6,7,8-tetrahydro-1,7-naphthyridine-3-carbonitrile;

4-(2-chlorophenyl)-7-(4-methyl-1,3-thiazol-5-yl)-2-(2-(2-propenoyl)-2,6-diazaspiro[3.4]octan-6-yl)-5,6,7,8-tetrahydro-1,7-naphthyridine-3-carbonitrile;

4-(2-chloro-5-hydroxyphenyl)-7-(4-methyl-1,3-thiazol-5-yl)-2-(2-(2-propenoyl)-2,6-diazaspiro[3.4]octan-6-yl)-5,6,7,8-tetrahydro-1,7-naphthyridine-3-carbonitrile;

4-(3-fluoro-2-hydroxyphenyl)-7-(4-methyl-1,3-thiazol-5-yl)-2-(2-(2-propenoyl)-2,6-diazaspiro[3.4]octan-6-yl)-5,6,7,8-tetrahydro-1,7-naphthyridine-3-carbonitrile;

4-(2,4-difluorophenyl)-2-((5S)-5-methyl-2-(2-propenoyl)-2,6-diazaspiro[3.4]octan-6-yl)-7-(4-methyl-1,3-thiazol-5-yl)-5,6,7,8-tetrahydro-1,7-naphthyridine-3-carbonitrile;

4-(2,4-difluorophenyl)-2-((5R)-5-methyl-2-(2-propenoyl)-2,6-diazaspiro[3.4]octan-6-yl)-7-(4-methyl-1,3-thiazol-5-yl)-5,6,7,8-tetrahydro-1,7-naphthyridine-3-carbonitrile;

4-(2-fluoro-5-hydroxyphenyl)-7-(4-methyl-1,3-thiazol-5-yl)-2-(2-(2-propenoyl)-2,6-diazaspiro[3.4]octan-6-yl)-5,6,7,8-tetrahydro-1,7-naphthyridine-3-carbonitrile;

(P)-4-(2-chlorophenyl)-7-(4-methyl-1,3-thiazol-5-yl)-2-(2-(2-propenoyl)-2,6-diazaspiro[3.4]octan-6-yl)-5,6,7,8-tetrahydro-1,7-naphthyridine-3-carbonitrile;

(M)-4-(2-chlorophenyl)-7-(4-methyl-1,3-thiazol-5-yl)-2-(2-(2-propenoyl)-2,6-diazaspiro[3.4]octan-6-yl)-5,6,7,8-tetrahydro-1,7-naphthyridine-3-carbonitrile;

(P)-4-(2-chloro-5-hydroxyphenyl)-7-(4-methyl-1,3-thiazol-5-yl)-2-(2-(2-propenoyl)-2,6-diazaspiro[3.4]octan-6-yl)-5,6,7,8-tetrahydro-1,7-naphthyridine-3-carbonitrile;

4-(3-fluoro-2-pyridinyl)-7-(4-methyl-1,3-thiazol-5-yl)-2-(2-((2H3)-2-propenoyl)-2,6-diazaspiro[3.4]octan-6-yl)-5,6,7,8-tetrahydro-1,7-naphthyridine-3-carbonitrile;

7-cyclopropyl-4-(2-fluorophenyl)-2-(2-(2-propenoyl)-2,6-diazaspiro[3.4]octan-6-yl)-5,6,7,8-tetrahydro-1,7-naphthyridine-3-carbonitrile;

1-(6-((7R)-4-(2,3-dimethylphenyl)-7-(4-methyl-1,3-thiazol-5-yl)-5,6,7,8-tetrahydro-2-quinazolinyl)-2,6-diazaspiro[3.4]octan-2-yl)-2-propen-1-one;

(7R)-4-(2-methylphenyl)-7-(4-methyl-1,3-thiazol-5-yl)-2-(2-(2-propenoyl)-2,6-diazaspiro[3.4]octan-6-yl)-5,6,7,8-tetrahydro-3-quinolinecarbonitrile or (7S)-4-(2-methylphenyl)-7-(4-methyl-1,3-thiazol-5-yl)-2-(2-(2-propenoyl)-2,6-diazaspiro[3.4]octan-6-yl)-5,6,7,8-tetrahydro-3-quinolinecarbonitrile;

(M)-(7R)-4-(2-methylphenyl)-7-(4-methyl-1,3-thiazol-5-yl)-2-(2-(2-propenoyl)-2,6-diazaspiro[3.4]octan-6-yl)-5,6,7,8-tetrahydro-3-quinolinecarbonitrile;

(P)-(7S)-4-(2-methylphenyl)-7-(4-methyl-1,3-thiazol-5-yl)-2-(2-(2-propenoyl)-2,6-diazaspiro[3.4]octan-6-yl)-5,6,7,8-tetrahydro-3-quinolinecarbonitrile;

(P)-(7R)-4-(2-methylphenyl)-7-(4-methyl-1,3-thiazol-5-yl)-2-(2-(2-propenoyl)-2,6-diazaspiro[3.4]octan-6-yl)-5,6, 7,8-tetrahydro-3-quinolinecarbonitrile;

(M)-(7S)-4-(2-methylphenyl)-7-(4-methyl-1,3-thiazol-5-yl)-2-(2-(2-propenoyl)-2,6-diazaspiro[3.4]octan-6-yl)-5,6,7,8-tetrahydro-3-quinolinecarbonitrile;

4-(2-fluorophenyl)-7-(4-methyl-1,3-thiazol-5-yl)-2-(2-(2-propenoyl)-2,6-diazaspiro[3.4]octan-6-yl)-5,6-dihydro-3-quinolinecarbonitrile;

4-(2-methylphenyl)-7-(4-methyl-1,3-thiazol-5-yl)-2-(2-(2-propenoyl)-2,6-diazaspiro[3.4]octan-6-yl)-5,6-dihydro-3-quinolinecarbonitrile;

(7S)-4-(2-fluorophenyl)-7-methyl-7-(4-methyl-1,3-thiazol-5-yl)-2-(2-(2-propenoyl)-2,6-diazaspiro[3.4]octan-6-yl)-5,6, 7,8-tetrahydro-3-quinolinecarbonitrile;

(7R)-4-(2-fluorophenyl)-7-methyl-7-(4-methyl-1,3-thiazol-5-yl)-2-(2-(2-propenoyl)-2,6-diazaspiro[3.4]octan-6-yl)-5,6,7,8-tetrahydro-3-quinolinecarbonitrile;

4-(2-chlorophenyl)-7-(1-methyl-1H-pyrazol-5-yl)-2-(2-(2-propenoyl)-2,6-diazaspiro[3.4]octan-6-yl)-3-quinolinecarbonitrile;

(7R)-4-(2,4-difluorophenyl)-7-(4-methyl-1,3-thiazol-5-yl)-2-(2-(2-propenoyl)-2,6-diazaspiro[3.4]octan-6-yl)-7,8-dihydro-5H-pyrano[4,3-b]pyridine-3-carbonitrile or (7S)-4-(2,4-difluorophenyl)-7-(4-methyl-1,3-thiazol-5-yl)-2-(2-(2-propenoyl)-2,6-diazaspiro[3.4]octan-6-yl)-7,8-dihydro-5H-pyrano[4,3-b]pyridine-3-carbonitrile;

4-(2-chloro-4-fluorophenyl)-7-(4-methyl-1,3-thiazol-5-yl)-2-(2-(2-propenoyl)-2,6-diazaspiro[3.4]octan-6-yl)-5,6-dihydro-3-quinolinecarbonitrile;

4-(2-chlorophenyl)-7-(4-methyl-1,3-thiazol-5-yl)-2-(2-(2-propenoyl)-2,6-diazaspiro[3.4]octan-6-yl)-5,6-dihydro-3-quinolinecarbonitrile;

4-(2,4-difluorophenyl)-7-(4-methyl-1,3-thiazol-5-yl)-2-(2-(2-propenoyl)-2,6-diazaspiro[3.4]octan-6-yl)-5,6-dihydro-3-quinolinecarbonitrile;

(M)-4-(2-methylphenyl)-7-(4-methyl-1,3-thiazol-5-yl)-2-(2-(2-propenoyl)-2,6-diazaspiro[3.4]octan-6-yl)-5,6-dihydro-3-quinolinecarbonitrile;

(P)-4-(2-methylphenyl)-7-(4-methyl-1,3-thiazol-5-yl)-2-(2-(2-propenoyl)-2,6-diazaspiro[3.4]octan-6-yl)-5,6-dihydro-3-quinolinecarbonitrile;

(7R)-4-(2-chloro-4-fluorophenyl)-7-(4-methyl-1,3-thiazol-5-yl)-2-(2-(2-propenoyl)-2,6-diazaspiro[3.4]octan-6-yl)-7,8-dihydro-5H-pyrano[4,3-b]pyridine-3-carbonitrile;

4-(2-fluoro-6-hydroxyphenyl)-7-(4-methyl-1,3-thiazol-5-yl)-2-(2-(2-propenoyl)-2,6-diazaspiro[3.4]octan-6-yl)-5,6-dihydro-3-quinolinecarbonitrile;

4-(4-fluorophenyl)-7-(4-methyl-1,3-thiazol-5-yl)-2-(2-(2-propenoyl)-2,6-diazaspiro[3.4]octan-6-yl)-5,6-dihydro-3-quinolinecarbonitrile;

(P)-4-(2-chloro-4-fluorophenyl)-7-(4-methyl-1,3-thiazol-5-yl)-2-(2-(2-propenoyl)-2,6-diazaspiro[3.4]octan-6-yl)-5,6-dihydro-3-quinolinecarbonitrile;

4-(2-chloro-6-hydroxyphenyl)-7-(4-methyl-1,3-thiazol-5-yl)-2-(2-(2-propenoyl)-2,6-diazaspiro[3.4]octan-6-yl)-5,6-dihydro-3-quinolinecarbonitrile;

4-(2-fluoro-5-methoxyphenyl)-7-(4-methyl-1,3-thiazol-5-yl)-2-(2-(2-propenoyl)-2,6-diazaspiro[3.4]octan-6-yl)-5,6-dihydro-3-quinolinecarbonitrile;

4-(2-hydroxyphenyl)-7-(4-methyl-1,3-thiazol-5-yl)-2-(2-(2-propenoyl)-2,6-diazaspiro[3.4]octan-6-yl)-5,6-dihydro-3-quinolinecarbonitrile;

(P)-4-(2-chlorophenyl)-7-(4-methyl-1,3-thiazol-5-yl)-2-(2-(2-propenoyl)-2,6-diazaspiro[3.4]octan-6-yl)-5,6-dihydro-3-quinolinecarbonitrile;

4-(2-chloro-5-hydroxyphenyl)-7-(4-methyl-1,3-thiazol-5-yl)-2-(2-(2-propenoyl)-2,6-diazaspiro[3.4]octan-6-yl)-5,6-dihydro-3-quinolinecarbonitrile;

4-(2,3-difluorophenyl)-7-(4-methyl-1,3-thiazol-5-yl)-2-(2-(2-propenoyl)-2,6-diazaspiro[3.4]octan-6-yl)-5,6-dihydro-3-quinolinecarbonitrile;

4-(2-fluoro-5-hydroxyphenyl)-7-(4-methyl-1,3-thiazol-5-yl)-2-(2-(2-propenoyl)-2,6-diazaspiro[3.4]octan-6-yl)-5,6-dihydro-3-quinolinecarbonitrile;

4-(2-fluoro-6-methylphenyl)-7-(4-methyl-1,3-thiazol-5-yl)-2-(2-(2-propenoyl)-2,6-diazaspiro[3.4]octan-6-yl)-5,6-dihydro-3-quinolinecarbonitrile;

(P)-4-(2-fluoro-6-hydroxyphenyl)-7-(4-methyl-1,3-thiazol-5-yl)-2-(2-(2-propenoyl)-2,6-diazaspiro[3.4]octan-6-yl)-5,6-dihydro-3-quinolinecarbonitrile;

4-(2-fluorophenyl)-7-(4-(methoxymethyl)-1,3-thiazol-5-yl)-2-(2-(2-propenoyl)-2,6-diazaspiro[3.4]octan-6-yl)-5,6-dihydro-3-quinolinecarbonitrile;

4-(3-fluoro-2-hydroxyphenyl)-7-(4-methyl-1,3-thiazol-5-yl)-2-(2-(2-propenoyl)-2,6-diazaspiro[3.4]octan-6-yl)-5,6-dihydro-3-quinolinecarbonitrile;

4-(3-hydroxyphenyl)-7-(4-methyl-1,3-thiazol-5-yl)-2-(2-(2-propenoyl)-2,6-diazaspiro[3.4]octan-6-yl)-5,6-dihydro-3-quinolinecarbonitrile;

4-(2-fluorophenyl)-7-(4-(hydroxymethyl)-1,3-thiazol-5-yl)-2-(2-(2-propenoyl)-2,6-diazaspiro[3.4]octan-6-yl)-5,6-dihydro-3-quinolinecarbonitrile;

(7R)-4-(3-fluoro-2-pyridinyl)-7-(4-methyl-1,3-thiazol-5-yl)-2-(2-(2-propenoyl)-2,6-diazaspiro[3.4]octan-6-yl)-5,6,7,8-tetrahydro-3-quinolinecarbonitrile or (7S)-4-(3-fluoro-2-pyridinyl)-7-(4-methyl-1,3-thiazol-5-yl)-2-(2-(2-propenoyl)-2,6-diazaspiro[3.4]octan-6-yl)-5,6,7,8-tetrahydro-3-quinolinecarbonitrile;

(7S)-4-(3-fluoro-2-pyridinyl)-7-(4-methyl-1,3-thiazol-5-yl)-2-(2-(2-propenoyl)-2,6-diazaspiro[3.4]octan-6-yl)-5,6, 7,8-tetrahydro-3-quinolinecarbonitrile;

4-(2-chloro-5-(difluoromethyl) phenyl)-7-(4-methyl-1,3-thiazol-5-yl)-2-(2-(2-propenoyl)-2,6-diazaspiro[3.4]octan-6-yl)-5,6,7,8-tetrahydro-1,7-naphthyridine-3-carbonitrile;

(6R)-4-(5-methyl-1H-indazol-4-yl)-6-(2-propanyl)-2-(2-(2-propenoyl)-2,6-diazaspiro[3.4]octan-6-yl)-6,7-dihydro-5H-cyclopenta[b]pyridine-3-carbonitrile or (6S)-4-(5-methyl-1H-indazol-4-yl)-6-(2-propanyl)-2-(2-(2-propenoyl)-2,6-diazaspiro[3.4]octan-6-yl)-6,7-dihydro-5H-cyclopenta[b]pyridine-3-carbonitrile;

(P)-1-(6-(3-ethenyl-4-(5-methyl-1H-indazol-4-yl)-2-quinolinyl)-2,6-diazaspiro[3.4]octan-2-yl)-2-propen-1-one;

1-(6-(3-fluoro-7-methoxy-4-(5-methyl-1H-indazol-4-yl)-2-quinolinyl)-2,6-diazaspiro[3.4]octan-2-yl)-2-propen-1-one;

1-(6-(3-chloro-4-(5-methyl-1H-indazol-4-yl)-2-quinolinyl)-2,6-diazaspiro[3.4]octan-2-yl)-2-propen-1-one;

1-(6-(7-chloro-8-(5-methyl-1H-indazol-4-yl)-3,4-dihydro-2H-chromen-6-yl)-2,6-diazaspiro[3.4]octan-2-yl)-2-propen-1-one;

4-(2-fluoro-3-hydroxyphenyl)-7-(4-methyl-1,3-thiazol-5-yl)-2-(2-(2-propenoyl)-2,6-diazaspiro[3.4]octan-6-yl)-5,6,7,8-tetrahydro-1,7-naphthyridine-3-carbonitrile;

(P)-1-(6-(4-(1,6-dimethyl-1H-indazol-7-yl)-3-methyl-7-(3-methyl-3-oxetanyl)-5,6,7,8-tetrahydro-1,7-naphthyridin-2-yl)-2,6-diazaspiro[3.4]octan-2-yl)-2-propen-1-one;

(P)-7,7-dimethyl-4-(5-methyl-1H-indazol-4-yl)-2-(2-(2-propenoyl)-2,6-diazaspiro[3.4]octan-6-yl)-5,6,7,8-tetrahydro-3-quinolinecarbonitrile;

1-(6-(4-(3-hydroxy-1-naphthalenyl)-7,7-dimethyl-5,6,7,8-tetrahydro-2-quinazolinyl)-2,6-diazaspiro[3.4]octan-2-yl)-2-propen-1-one;

8-(5-methyl-1H-indazol-4-yl)-2-phenyl-6-(2-(2-propenoyl)-2,6-diazaspiro[3.4]octan-6-yl)imidazo[1,2-a]pyridine-7-carbonitrile;

7-methoxy-4-(5-methyl-1H-indazol-4-yl)-2-(2-(2-propenoyl)-2,6-diazaspiro[3.4]octan-6-yl)-3-quinolinecarbonitrile;

2-(2-acryloyl-2,6-diazaspiro[3.4]octan-6-yl)-7-methyl-4-(5-methyl-1H-indazol-4-yl)-5,6,7,8-tetrahydroquinoline-3-carbonitrile;

(7)-2-(8,8-difluoro-2-(2-propenoyl)-2,6-diazaspiro[3.4]octan-6-yl)-7-methyl-4-(5-methyl-1H-indazol-4-yl)-5,6,7,8-tetrahydro-3-quinolinecarbonitrile;

4-(5,6-dimethyl-1H-indazol-4-yl)-2-(2-(2-propenoyl)-2,6-diazaspiro[3.4]octan-6-yl)-3-quinolinecarbonitrile; or 4-(5-methyl-1H-indazol-4-yl)-2-(2-(2-propenoyl)-2,6-diazaspiro[3.4]octan-6-yl)-5,6,7,8-tetrahydro-3-quinolinecarbonitrile.

20. The compound according to claim 1 or a pharmaceutically acceptable salt thereof, wherein:

(a) the compound is 1-(6-(4-(3-hydroxy-1-naphthalenyl)-3,7,7-trimethyl-7,8-dihydro-5H-pyrano[4,3-b]pyridin-2-yl)-2,6-diazaspiro[3.4]octan-2-yl)-2-propen-1-one;

1-(6-(5-fluoro-6-(3-hydroxy-1-naphthalenyl)-10,10-dimethyl-3-azatricyclo[7.1.1.0$^{2,7}$]undeca-2,4,6-trien-4-yl)-2,6-diazaspiro[3.4]octan-2-yl)-2-propen-1-one;

1-(6-(3-chloro-4-(3-hydroxy-1-naphthalenyl)-7,7-dimethyl-7,8-dihydro-5H-pyrano[4,3-b]pyridin-2-yl)-2,6-diazaspiro[3.4]octan-2-yl)-2-propen-1-one;

1-(6-(4-(3-chloro-5-hydroxy-2-methylphenyl)-3,7,7-trimethyl-7,8-dihydro-5H-pyrano[4,3-b]pyridin-2-yl)-2,6-diazaspiro[3.4]octan-2-yl)-2-propen-1-one;

1-(6-(5-methyl-6-(1,5,6-trimethyl-1H-indazol-7-yl)-3-azatricyclo[6.2.1.02,7]undeca-2,4,6-trien-4-yl)-2,6-diazaspiro[3.4]octan-2-yl)-2-propen-1-one;

1-(6-(4-(5-chloro-1,6-dimethyl-1H-indazol-7-yl)-3,7,7-trimethyl-7,8-dihydro-5H-pyrano[4,3-b]pyridin-2-yl)-2,6-diazaspiro[3.4]octan-2-yl)-2-propen-1-one;

1-(6-(5-fluoro-10, 10-dimethyl-6-(5-methyl-1H-indazol-4-yl)-3-azatricyclo[7.1.1.0$^{2,7}$]undeca-2,4,6-trien-4-yl)-2,6-diazaspiro[3.4]octan-2-yl)-2-propen-1-one;

1-(6-(3-fluoro-4-(3-hydroxy-1-naphthalenyl)-7,7-dimethyl-7,8-dihydro-5H-pyrano[4,3-b]pyridin-2-yl)-2,6-diazaspiro[3.4]octan-2-yl)-2-propen-1-one;

1-(6-(4-(5-chloro-1,6-dimethyl-1H-indazol-7-yl)-3-fluoro-7-(3-oxetanyl)-5,6,7,8-tetrahydro-1,7-naphthyridin-2-yl)-2,6-diazaspiro[3.4]octan-2-yl)-2-propen-1-one; or 1-(6-(4-(2,4-difluorophenyl)-7-(1,4-dimethyl-1H-pyrazol-5-yl)-3-methyl-5,6,7,8-tetrahydro-2-quinolinyl)-2,6-diazaspiro[3.4]octan-2-yl)-2-propen-1-one; or (b) the compound is (M)-1-(6-(4-(3-hydroxy-1-naphthalenyl)-3,7,7-trimethyl-7,8-dihydro-5H-pyrano[4,3-b]pyridin-2-yl)-2,6-diazaspiro[3.4]octan-2-yl)-2-propen-1-one;

(P)-1-(6-((1R,9R)-5-fluoro-6-(3-hydroxy-1-naphthalenyl)-10,10-dimethyl-3-azatricyclo[7.1.1.0$^{2,7}$]undeca-2,4,6-trien-4-yl)-2,6-diazaspiro[3.4]octan-2-yl)-2-propen-1-one;

(P)-1-(6-(3-chloro-4-(3-hydroxy-1-naphthalenyl)-7,7-dimethyl-7,8-dihydro-5H-pyrano[4,3-b]pyridin-2-yl)-2,6-diazaspiro[3.4]octan-2-yl)-2-propen-1-one;

(M)-1-(6-(4-(3-chloro-5-hydroxy-2-methylphenyl)-3,7,7-trimethyl-7,8-dihydro-5H-pyrano[4,3-b]pyridin-2-yl)-2,6-diazaspiro[3.4]octan-2-yl)-2-propen-1-one;

(M)-1-(6-((1S,8R)-5-methyl-6-(1,5,6-trimethyl-1H-indazol-7-yl)-3-azatricyclo[6.2.1.02,7]undeca-2,4,6-trien-4-yl)-2,6-diazaspiro[3.4]octan-2-yl)-2-propen-1-one;

(P)-1-(6-(4-(5-chloro-1,6-dimethyl-1H-indazol-7-yl)-3,7,7-trimethyl-7,8-dihydro-5H-pyrano[4,3-b]pyridin-2-yl)-2,6-diazaspiro[3.4]octan-2-yl)-2-propen-1-one;

(M)-1-(6-((1R,9R)-5-fluoro-10,10-dimethyl-6-(5-methyl-1H-indazol-4-yl)-3-azatricyclo[7.1.1.0$^{2,7}$]undeca-2,4,6-trien-4-yl)-2,6-diazaspiro[3.4]octan-2-yl)-2-propen-1-one;

(P)-1-(6-(3-fluoro-4-(3-hydroxy-1-naphthalenyl)-7,7-dimethyl-7,8-dihydro-5H-pyrano[4,3-b]pyridin-2-yl)-2,6-diazaspiro[3.4]octan-2-yl)-2-propen-1-one;

(M)-1-(6-(4-(5-chloro-1,6-dimethyl-1H-indazol-7-yl)-3-fluoro-7-(3-oxetanyl)-5,6,7,8-tetrahydro-1,7-naphthyridin-2-yl)-2,6-diazaspiro[3.4]octan-2-yl)-2-propen-1-one; or 1-(6-((7R)-4-(2,4-difluorophenyl)-7-(1,4-dimethyl-1H-pyrazol-5-yl)-3-methyl-5,6,7,8-tetrahydro-2-quinolinyl)-2,6-diazaspiro[3.4]octan-2-yl)-2-propen-1-one; or (c) the compound is (P)-1-(6-(4-(3-hydroxy-1-naphthalenyl)-3,7,7-trimethyl-7,8-dihydro-5H-pyrano[4,3-b]pyridin-2-yl)-2,6-diazaspiro[3.4]octan-2-yl)-2-propen-1-one;

(M)-1-(6-((1R,9R)-5-fluoro-6-(3-hydroxy-1-naphthalenyl)-10,10-dimethyl-3-azatricyclo[7.1.1.0$^{2,7}$]undeca-2,4,6-trien-4-yl)-2,6-diazaspiro[3.4]octan-2-yl)-2-propen-1-one;

(P)-1-(6-((1S,9S)-5-fluoro-6-(3-hydroxy-1-naphthalenyl)-10,10-dimethyl-3-azatricyclo[7.1.1.0$^{2,7}$]undeca-2,4,6-trien-4-yl)-2,6-diazaspiro[3.4]octan-2-yl)-2-propen-1-one;

(M)-1-(6-((1S,9S)-5-fluoro-6-(3-hydroxy-1-naphthalenyl)-10,10-dimethyl-3-azatricyclo[7.1.1.0$^{2,7}$]undeca-2,4,6-trien-4-yl)-2,6-diazaspiro[3.4]octan-2-yl)-2-propen-1-one;

(M)-1-(6-(3-chloro-4-(3-hydroxy-1-naphthalenyl)-7,7-dimethyl-7,8-dihydro-5H-pyrano[4,3-b]pyridin-2-yl)-2,6-diazaspiro[3.4]octan-2-yl)-2-propen-1-one;

(P)-1-(6-(4-(3-chloro-5-hydroxy-2-methylphenyl)-3,7,7-trimethyl-7,8-dihydro-5H-pyrano[4,3-b]pyridin-2-yl)-2,6-diazaspiro[3.4]octan-2-yl)-2-propen-1-one;

(P)-1-(6-((1S,8R)-5-methyl-6-(1,5,6-trimethyl-1H-indazol-7-yl)-3-azatricyclo[6.2.1.02,7]undeca-2,4,6-trien-4-yl)-2,6-diazaspiro[3.4]octan-2-yl)-2-propen-1-one;

(M)-1-(6-((1R,8S)-5-methyl-6-(1,5,6-trimethyl-1H-indazol-7-yl)-3-azatricyclo[6.2.1.02,7]undeca-2,4,6-trien-4-yl)-2,6-diazaspiro[3.4]octan-2-yl)-2-propen-1-one;

(P)-1-(6-((1R,8S)-5-methyl-6-(1,5,6-trimethyl-1H-indazol-7-yl)-3-azatricyclo[6.2.1.02,7]undeca-2,4,6-trien-4-yl)-2,6-diazaspiro[3.4]octan-2-yl)-2-propen-1-one;

(M)-1-(6-(4-(5-chloro-1,6-dimethyl-1H-indazol-7-yl)-3,7,7-trimethyl-7,8-dihydro-5H-pyrano[4,3-b]pyridin-2-yl)-2,6-diazaspiro[3.4]octan-2-yl)-2-propen-1-one;

(P)-1-(6-((1R,9R)-5-fluoro-10,10-dimethyl-6-(5-methyl-1H-indazol-4-yl)-3-azatricyclo[7.1.1.0$^{2,7}$]undeca-2,4,6-trien-4-yl)-2,6-diazaspiro[3.4]octan-2-yl)-2-propen-1-one;

(M)-1-(6-((1S,9S)-5-fluoro-10, 10-dimethyl-6-(5-methyl-1H-indazol-4-yl)-3-azatricyclo[7.1.1.0$^{2,7}$]undeca-2,4,6-trien-4-yl)-2,6-diazaspiro[3.4]octan-2-yl)-2-propen-1-one;

(P)-1-(6-((1S,9S)-5-fluoro-10,10-dimethyl-6-(5-methyl-1H-indazol-4-yl)-3-azatricyclo[7.1.1.0$^{2,7}$]undeca-2,4,6-trien-4-yl)-2,6-diazaspiro[3.4]octan-2-yl)-2-propen-1-one;

(M)-1-(6-(3-fluoro-4-(3-hydroxy-1-naphthalenyl)-7,7-dimethyl-7,8-dihydro-5H-pyrano[4,3-b]pyridin-2-yl)-2,6-diazaspiro[3.4]octan-2-yl)-2-propen-1-one;

(P)-1-(6-(4-(5-chloro-1,6-dimethyl-1H-indazol-7-yl)-3-fluoro-7-(3-oxetanyl)-5,6,7,8-tetrahydro-1,7-naphthyridin-2-yl)-2,6-diazaspiro[3.4]octan-2-yl)-2-propen-1-one; or 1-(6-((7S)-4-(2,4-difluorophenyl)-7-(1,4-dimethyl-1H-pyrazol-5-yl)-3-methyl-5,6,7,8-tetrahydro-2-quinolinyl)-2,6-diazaspiro[3.4]octan-2-yl)-2-propen-1-one.

21. A pharmaceutical composition comprising the compound according to claim 1 or a pharmaceutically acceptable salt thereof, and a pharmaceutically acceptable excipient.

22. A method of treating cancer in a subject in need of treatment, the method comprising administering to the subject a therapeutically effective amount of the compound according to claim 1.

23. The method according to claim 22, wherein one or more cells express KRAS G12C mutant protein.

24. The method of claim 22, wherein the cancer is non-small cell lung cancer, small bowel cancer, appendiceal cancer, colorectal cancer, cancer of unknown primary, endometrial cancer, mixed cancer types, pancreatic cancer, hepatobiliary cancer, small cell lung cancer, cervical cancer, germ cell cancer, ovarian cancer, gastrointestinal neuroendocrine cancer, bladder cancer, myelodysplastic/myeloproliferative neoplasms, head and neck cancer, esophagogastric cancer, soft tissue sarcoma, mesothelioma, thyroid cancer, leukemia, or melanoma.

25. The method according to claim 22, wherein the subject has a cancer that was determined to have one or more cells expressing the KRAS G12C mutant protein prior to administration of the compound or a pharmaceutically acceptable salt thereof.

26. The method according to claim 22, which further comprises simultaneous, separate, or sequential administration of an effective amount of a second compound, wherein the second compound is an Aurora kinase A inhibitor, AKT inhibitor, arginase inhibitor, CDK4/6 inhibitor, ErbB family inhibitor, ERK inhibitor, FAK inhibitor, FGFR inhibitor, glutaminase inhibitor, IGF-1R inhibitor, KIF18A inhibitor, MCL-1 inhibitor, MEK inhibitor, mTOR inhibitor, PD-1 inhibitor, PD-L1 inhibitor, PI3K inhibitor, Raf kinase inhibitor, SHP2 inhibitor, SOS1 inhibitor, Src kinase inhibitor, or one or more chemotherapeutic agent.

* * * * *